US012686684B2

(12) United States Patent
Hu et al.

(10) Patent No.: US 12,686,684 B2
(45) Date of Patent: *Jul. 21, 2026

(54) BTK DEGRADER AND USE THEREOF

(71) Applicants: Ascentage Pharma (Suzhou) Co., Ltd., Suzhou (CN); Ascentage Pharma Group Corp Limited, Hong Kong (CN)

(72) Inventors: Jiantao Hu, Suzhou (CN); Jianyong Chen, Suzhou (CN)

(73) Assignees: Ascentage Pharma (Suzhou) Co., Ltd., Suzhou (CN); Ascentage Pharma Group Corp Limited, Hong Kong (CN)

( * ) Notice: Subject to any disclaimer, the term of this patent is extended or adjusted under 35 U.S.C. 154(b) by 0 days.

This patent is subject to a terminal disclaimer.

(21) Appl. No.: 19/344,450

(22) Filed: Sep. 29, 2025

(65) Prior Publication Data

US 2026/0028346 A1 Jan. 29, 2026

Related U.S. Application Data

(63) Continuation of application No. 19/292,469, filed on Aug. 6, 2025, which is a continuation of application No. PCT/CN2025/110582, filed on Jul. 25, 2025.

(30) Foreign Application Priority Data

Jul. 26, 2024 (WO) ................ PCT/CN2024/107865
Dec. 4, 2024 (WO) ................ PCT/CN2024/136848
Mar. 7, 2025 (WO) ................ PCT/CN2025/081389

(51) Int. Cl.

| | |
|---|---|
| *C07D 487/04* | (2006.01) |
| *A61K 31/513* | (2006.01) |
| *A61K 31/519* | (2006.01) |
| *A61P 35/00* | (2006.01) |
| *C07D 413/14* | (2006.01) |
| *C07D 471/04* | (2006.01) |

(52) U.S. Cl.

CPC .......... *C07D 487/04* (2013.01); *A61K 31/513* (2013.01); *A61K 31/519* (2013.01); *A61P 35/00* (2018.01); *C07D 413/14* (2013.01); *C07D 471/04* (2013.01)

(58) Field of Classification Search

CPC .. C07D 487/04; C07D 413/14; C07D 471/04; A61P 35/00; A61K 31/513; A61K 31/519
USPC .......................................................... 514/249
See application file for complete search history.

(56) References Cited

U.S. PATENT DOCUMENTS

2025/0041429 A1 2/2025 Lee et al.
2026/0028345 A1* 1/2026 Hu ....................... C07D 487/04 514/249

FOREIGN PATENT DOCUMENTS

| | | | |
|---|---|---|---|
| CN | 119060070 | A | 12/2024 |
| CN | 120208992 | A | 6/2025 |
| WO | 2019/186358 | A1 | 10/2019 |
| WO | 2021/053495 | A1 | 3/2021 |
| WO | 2021/180103 | A1 | 9/2021 |
| WO | 2021/219070 | A1 | 11/2021 |
| WO | 2022/235945 | A1 | 11/2022 |
| WO | 2022/268052 | A1 | 12/2022 |
| WO | 2023/125908 | A1 | 7/2023 |
| WO | 2023/183811 | A1 | 9/2023 |

OTHER PUBLICATIONS

PCT/CN2025/110582 International Search Report and Written Opinion mailed Oct. 21, 2025, 15 pages.

* cited by examiner

*Primary Examiner* — Kristin A Vajda
(74) *Attorney, Agent, or Firm* — Goodwin Procter LLP

(57) ABSTRACT

The present disclosure relates to compounds that function as degraders or inhibitors of BTK. The present disclosure further relates to pharmaceutical compositions comprising them, and to their use in the treatment of diseases mediated by BTK, such as cancer.

26 Claims, No Drawings

BTK DEGRADER AND USE THEREOF

CROSS-REFERENCE TO RELATED APPLICATIONS

This application is a continuation of U.S. application Ser. No. 19/292,469, filed Aug. 6, 2025, which is a continuation of PCT/CN2025/110582, filed Jul. 25, 2025, which claims priority to International Application Nos. PCT/CN2025/081389, filed Mar. 7, 2025, PCT/CN2024/136848, filed Dec. 4, 2024, and PCT/CN2024/107865, filed Jul. 26, 2024, each of which is incorporated herein by reference in its entirety.

TECHNICAL FIELD

The present disclosure relates to compounds that function as degraders or inhibitors of BTK. The present disclosure further relates to pharmaceutical compositions comprising them, and to their use in the treatment of diseases mediated by BTK, such as cancer.

BACKGROUND

Bruton's tyrosine kinase (BTK) belongs to the Tec tyrosine kinase family (Vetrie et al., Nature 361:226-233, 1993; Bradshaw, Cell Signal. 22:1175-84, 2010). Btk is primarily expressed in most hematopoietic cells such as B cells, mast cells and macrophages (Smith et al., J. Immunol. 152:557-565, 1994) and is localized in bone marrow, spleen and lymph node tissue. Btk plays an important role in B-cell receptor (BCR) and FcR signaling pathways, which involve in B-cell development, differentiation (Khan, Immunol. Res. 23:147, 2001). Btk is activated by upstream Src-family kinases. Once activated, Btk, in turn, phosphorylates PLC-gamma, leading to effects on B-cell function and survival (Humphries et al., J. Biol. Chem. 279:37651, 2004). These signaling pathways must be precisely regulated. Mutations in the gene encoding Btk cause an inherited B-cell specific immunodeficiency disease in humans, known as X-linked agammaglobulinemia (XLA) (Conley et al., Annu. Rev. Immunol. 27:199-227, 2009). Aberrant BCR-mediated signaling may result in dysregulated B-cell activation leading to a number of autoimmune and inflammatory diseases. Preclinical studies show that Btk deficient mice are resistant to developing collagen-induced arthritis. Moreover, clinical studies of Rituxan, a CD20 antibody to deplete mature B-cells, reveal the key role of B-cells in a number of inflammatory diseases such as rheumatoid arthritis, systemic lupus erythematosus and multiple sclerosis (Gurcan et al., Int. Immunopharmacol. 9:10-25, 2009). Therefore, Btk inhibitors can be used to treat autoimmune and/or inflammatory diseases.

Inhibition of BTK has been shown to affect cancer development (B cell malignancies) and cell viability, and improve autoimmune diseases (e.g., rheumatoid arthritis and lupus). Inhibition of BTK has also been reported via alternative strategies, such as through degradation of BTK (Alexandru D. et al., Biochemistry 2018, 57, 26, 3564-3575; Adelajda Z. et al., PNAS 2018 115 (31); Dennis D., et al., Blood, 2019, 133:952-961; Yonghui S. et al., Cell Research, 2018, 28, 779-781; Yonghui S. et al., Leukemia, 2019, Degradation of Bruton's tyrosine kinase mutants by PROTACs for the potential treatment of ibrutinib-resistant non-Hodgkin lymphomas) and has been disclosed or discussed in patent publications, e.g. US20190276459, WO2019186343, WO2019186358, WO2019148150, WO2019177902, and WO2019127008.

PROTAC (Proteolytic Targeting Chimera) is a small bivalent molecule containing ligands that recognize target proteins linked to E3 ligands. Such a molecule can bind the target protein to E3 ligase and cause the target protein to degrade. Bifunctional compounds composed of a target protein-binding moiety and an E3 ubiquitin ligase-binding moiety have been shown to induce proteasome-mediated degradation of selected proteins. These drug-like molecules offer the possibility of temporal control over protein expression and could be useful as biochemical reagents for the treatment of diseases. In recent years, this newly developed method has been widely used in antitumor studies There is a need of new BTK inhibitors or degraders which are more potent than known inhibitors of BTK and inhibit BTK via alternative strategies, such as through degradation of BTK. The present application addresses the need.

SUMMARY

Without wishing to be bound by theory, one technical problem to be solved by the present disclosure involves providing a degrader or inhibitor of BTK which has good inhibitory effect on BTK.

The present disclosure solves the above technical problem through the following technical solutions.

In some aspects, the present disclosure provides compounds represented by Formula I below, and the pharmaceutically acceptable salts and solvates, e.g., hydrates, thereof, collectively referred to as "compounds of the disclosure." Compounds of the disclosure are BTK degradation agents and are thus useful in treating or preventing diseases or conditions associated with BTK such as cancers.

In some aspects, the present disclosure provides pharmaceutical compositions comprising the compound of the disclosure, and a pharmaceutically acceptable carrier.

In some aspects, the present disclosure provides methods for inhibiting and/or degrading BTK, comprising administrating an effective amount of a compound of the disclosure; or a pharmaceutical composition of the disclosure.

In some aspects, the present disclosure provides methods for treating or preventing a disease mediated by BTK comprising administering to a patient in need thereof a therapeutically effective amount of a compound of the disclosure; or a pharmaceutical composition of the disclosure. Preferably, the disease is cancer.

In some aspects, the present disclosure provides compounds of the disclosure for use in treating or preventing a disease mediated by BTK.

In some aspects, the present disclosure provides compounds of the disclosure for use in treating cancer.

In some aspects, the present disclosure provides compounds of the disclosure for use in inhibiting and/or degrading BTK protein.

In some aspects, the present disclosure provides the use of compounds of the disclosure in the manufacture of a medicament for treating or preventing a disease mediated by BTK.

In some aspects, the present disclosure provides the use of compounds of the disclosure in the manufacture of a medicament for treating cancer.

In some aspects, the present disclosure provides the use of compounds of the disclosure in the manufacture of a medicament for inhibiting and/or degrading BTK.

Additional embodiments and advantages of the disclosure will be set forth, in part, in the description that follows, and will flow from the description, or can be learned by practice of the disclosure. The embodiments and advantages of the disclosure will be realized and attained by means of the elements and combinations particularly pointed out in the appended claims.

It is to be understood that both the foregoing summary and the following detailed description are exemplary and explanatory only, and are not restrictive of the invention as claimed or disclosed.

DETAILED DESCRIPTION

Without wishing to be bound by theory, the present disclosure relates to PROTAC compounds that function as degradants or inhibitors of BTK. In some aspects, the present disclosure relates to compounds that inhibit the activity of BTK, pharmaceutical compositions comprising the compounds and methods of use therefor.

Unless otherwise defined below, all technical and scientific terms used herein have the same meanings as commonly understood by one of ordinary skill in the art. References to techniques used herein are intended to refer to techniques that are generally understood in the art, including those obvious changes or equivalent replacements of the techniques for those skilled in the art. While it is believed that the following terms are well understood by those skilled in the art, the following definitions are set forth to better explain the disclosure.

I. Definitions

As used herein, the terms "including", "comprising", "having", "containing" or "comprising", and other variants thereof, are inclusive or open, and do not exclude other unlisted elements or method steps.

The use of the terms "a", "an", "the", and similar referents in the context of describing the disclosure (especially in the context of the claims) are to be construed to cover both the singular and the plural, unless otherwise indicated. Recitation of ranges of values herein merely are intended to serve as a shorthand method of referring individually to each separate value falling within the range, unless otherwise indicated herein, and each separate value is incorporated into the specification as if it were individually recited herein. The use of any and all examples, or exemplary language (e.g., "such as") provided herein, is intended to better illustrate the disclosure and is not a limitation on the scope of the disclosure unless otherwise claimed. No language in the specification should be construed as indicating any non-claimed element as essential to the practice of the disclosure.

The term "BTK" as used herein refers to Bruton's tyrosine kinase.

As used herein, the term "degrader" or "degradation agents" is defined as a heterobifunctional compound that binds to and/or inhibits BTK and an E3 ligase with measurable affinity resulting in the ubiquitination and subsequent degradation of the BTK protein.

The term "PROTAC" as used herein refers to proteolytic targeting chimera, wherein a small molecule ligand that can bind to the targeting protein is connected with the ligand of E3 ubiquitin ligase through a bridge fragment to form a bifunctional compound.

As used herein, the term "subject," "individual," or "patient," used interchangeably, refers to any animal, including mammals such as mice, rats, other rodents, rabbits, dogs, cats, swine, cattle, sheep, horses, primates, and humans. In some embodiments, the patient is a human. In some embodiments, the subject has experienced and/or exhibited at least one symptom of the disease or disorder to be treated and/or prevented. In some embodiments, the subject has been identified or diagnosed as having a cancer.

As used herein, the terms "treat," "treating," "treatment," and the like refer to eliminating, reducing, or ameliorating a disease or condition, and/or symptoms associated therewith. Although not precluded, treating a disease or condition does not require that the disease, condition, or symptoms associated therewith be completely eliminated. The term "treat" and synonyms contemplate administering a therapeutically effective amount of a compound of the disclosure to a subject in need of such treatment. The treatment can be orientated symptomatically, for example, to suppress symptoms. It can be effected over a short period, be oriented over a medium term, or can be a long-term treatment, for example within the context of a maintenance therapy.

As used herein, the terms "prevent," "preventing," and "prevention" refer to a method of preventing the onset of a disease or condition and/or its attendant symptoms or barring a subject from acquiring a disease. As used herein, "prevent," "preventing," and "prevention" also include delaying the onset of a disease and/or its attendant symptoms and reducing a subject's risk of acquiring a disease. The terms "prevent," "preventing" and "prevention" may include "prophylactic treatment," which refers to reducing the probability of redeveloping a disease or condition, or of a recurrence of a previously-controlled disease or condition, in a subject who does not have, but is at risk of or is susceptible to, redeveloping a disease or condition or a recurrence of the disease or condition.

The term "therapeutically effective amount" or "effective dose" as used herein refers to an amount of the active ingredient(s) that is (are) sufficient, when administered by a method of the disclosure, to efficaciously deliver the active ingredient(s) for the treatment of condition or disease of interest to a subject in need thereof. In the case of a cancer or other proliferation disorder, the therapeutically effective amount of the agent may reduce (i.e., retard to some extent or stop) unwanted cellular proliferation; reduce the number of cancer cells; reduce the tumor size; inhibit (i.e., retard to some extent or stop) cancer cell infiltration into peripheral organs; inhibit (i.e., retard to some extent or stop) tumor metastasis; inhibit, to some extent, tumor growth; and/or relieve, to some extent, one or more of the symptoms associated with the cancer. To the extent the administered compound or composition prevents growth and/or kills existing cancer cells, it may be cytostatic and/or cytotoxic.

The term "halo" or "halogen" as used herein by itself or as part of another group refers to —Cl, —F, —Br, or —I.

The term "cyano" as used herein by itself or as part of another group refers to —CN.

The term "hydroxy" as herein used by itself or as part of another group refers to —OH.

The term "alkyl" as used herein by itself or as part of another group refers to a straight- or branched-chain aliphatic hydrocarbon containing one to twelve carbon atoms, i.e., a $C_1$-$C_{12}$ alkyl, or the number of carbon atoms designated, e.g., a $C_1$ alkyl such as methyl, a $C_2$ alkyl such as ethyl, etc. In one embodiment, the alkyl is a $C_1$-$C_{10}$ alkyl. In another embodiment, the alkyl is a $C_1$-$C_6$ alkyl. In another embodiment, the alkyl is a $C_1$-$C_4$ alkyl. In another embodiment, the alkyl is a $C_1$-$C_3$ alkyl, i.e., methyl, ethyl, propyl, or isopropyl. Non-limiting exemplary $C_1$-$C_{12}$ alkyl groups include methyl, ethyl, propyl, isopropyl, butyl, sec-butyl, tert-butyl, iso-butyl, 3-pentyl, hexyl, heptyl, octyl, nonyl, and decyl. In another embodiment, one or more of the hydrogen atoms of the alkyl group are replaced by deuterium atoms, i.e., the alkyl group is isotopically-labeled with deuterium. A non-limiting exemplarily deuterated alkyl group is —$CD_3$. In another embodiment, none of the hydrogen atoms of the alkyl group are replaced by deuterium atoms, i.e., the alkyl group is isotopically-labeled with deuterium.

The term "haloalkyl" as used herein by itself or as part of another group refers to an alkyl group substituted by one or more fluorine, chlorine, bromine, and/or iodine atoms. In one embodiment, the alkyl is substituted by one, two, or three fluorine and/or chlorine atoms. In another embodiment, the alkyl is substituted by one, two, or three fluorine atoms. In another embodiment, the alkyl is a $C_1$-$C_6$ alkyl. In another embodiment, the alkyl is a $C_1$-$C_4$ alkyl. In another embodiment, the alkyl group is a $C_1$ or $C_2$ or $C_3$ alkyl. Non-limiting exemplary haloalkyl groups include fluoromethyl, difluoromethyl, trifluoromethyl, pentafluoroethyl, 1,1-difluoroethyl, 2,2-difluoroethyl, 2,2,2-trifluoroethyl, 3,3,3-trifluoropropyl, 4,4,4-trifluorobutyl, and trichloromethyl groups.

The term "alkoxy" as used herein by itself or as part of another group refers to an alkyl group attached to a terminal oxygen atom. In one embodiment, the alkyl is a $C_1$-$C_6$ alkyl and resulting alkoxy is thus referred to as a "$C_1$-$C_6$ alkoxy." In another embodiment, the alkyl is a $C_1$-$C_4$ alkyl group and resulting alkoxy is thus referred to as a $C_1$-$C_4$ alkoxy. Non-limiting exemplary alkoxy groups include methoxy, ethoxy, and tert-butoxy.

The term "carbocyclic" or "carbocycle" as used herein by itself or as part of another group refers to saturated and partially unsaturated, e.g., containing one or two double bonds, monocyclic, bicyclic, or tricyclic aliphatic hydrocarbons containing three to twelve carbon atoms, i.e., a $C_{3-12}$ carbocyclic. For example, a $C_5$ carbocyclic or a $C_6$ carbocyclic. When the aliphatic hydrocarbons are saturated, carbocyclic may also be called as cycloalkyl, e.g., a $C_3$ cycloalkyl such a cyclopropyl, a $C_4$ cycloalkyl such as cyclobutyl, etc. In one embodiment, the carbocyclic is cycloalkyl. In one embodiment, the cycloalkyl is bicyclic, i.e., it has two rings. In another embodiment, the cycloalkyl is monocyclic, i.e., it has one ring. In another embodiment, the cycloalkyl is a $C_{3-8}$ cycloalkyl. In another embodiment, the cycloalkyl is a $C_{3-6}$ cycloalkyl, i.e., cyclopropyl, cyclobutyl, cyclopentyl, or cyclohexyl. In another embodiment, the cycloalkyl is a $C_5$ cycloalkyl, i.e., cyclopentyl. In another embodiment, the cycloalkyl is a $C_6$ cycloalkyl, i.e., cyclohexyl. Non-limiting exemplary $C_{3-12}$ cycloalkyl groups include cyclopropyl, cyclobutyl, cyclopentyl, cyclohexyl, cycloheptyl, cyclooctyl, norbornyl, decalin, adamantyl, cyclohexenyl, and spiro[3.3]heptane.

The term "heterocyclo", heterocyclyl or "heterocyclic" as used herein by itself or as part of another group refers to saturated and partially unsaturated, e.g., containing one, two or three double bonds, monocyclic, bicyclic, or tricyclic groups containing three to fourteen ring members, i.e., a 3- to 14-membered heterocyclo, comprising one, two, three, or four heteroatoms, for example 5-membered, 6-membered, 7-membered, 8-membered, 9-membered, 10-membered heterocyclo. Each heteroatom is independently oxygen, sulfur, or nitrogen. Each sulfur atom is independently oxidized to give a sulfoxide, i.e., S(=O), or sulfone, i.e., $S(=O)_2$.

The term heterocyclo includes groups wherein one or more —$CH_2$— groups is replaced with one or more —C(=O)— (oxo) groups, including cyclic ureido groups such as imidazolidinyl-2-one, cyclic amide groups such as pyrrolidin-2-one or piperidin-2-one, and cyclic carbamate groups such as oxazolidinyl-2-one.

The term heterocyclo also includes groups having fused optionally substituted aryl or optionally substituted heteroaryl groups such as indoline, indolin-2-one, 2,3-dihydro-1H-pyrrolo[2,3-c]pyridine, 2,3,4,5-tetrahydro-1H-benzo[d]azepine, or 1,3,4,5-tetrahydro-2H-benzo[d]azepin-2-one.

In one embodiment, the heterocyclo group is a 4- to 8-membered cyclic group containing one ring and one or two oxygen atoms, e.g., tetrahydrofuran or tetrahydropyran, or one or two nitrogen atoms, e.g., pyrrolidine, piperidine, or piperazine, or one oxygen and one nitrogen atom, e.g., morpholine, and, optionally, one —$CH_2$— group is replaced with one —C(=O)— group, e.g., pyrrolidin-2-one or piperazin-2-one. In another embodiment, the heterocyclo group is a 5- to 8-membered cyclic group containing one ring and one or two nitrogen atoms and, optionally, one —$CH_2$— group is replaced with one —C(=O)— group. In another embodiment, the heterocyclo group is a 5- or 6-membered cyclic group containing one ring and one or two nitrogen atoms and, optionally, one —$CH_2$— group is replaced with one —C(=O)— group. In another embodiment, the heterocyclo group is a 8- to 12-membered cyclic group containing two rings and one or two nitrogen atoms. The heterocyclo can be linked to the rest of the molecule through any available carbon or nitrogen atom. Non-limiting exemplary heterocyclo groups include:

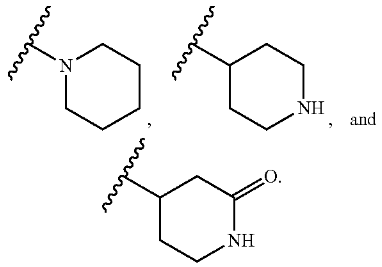

The term "aryl" as used herein by itself or as part of another group refers to an aromatic ring system having six to fourteen carbon atoms, i.e., $C_6$-$C_{14}$ aryl, $C_9$-$C_{10}$ aryl. Non-limiting exemplary aryl groups include phenyl (abbreviated as "Ph"), naphthyl, phenanthryl, anthracyl, indenyl, azulenyl, biphenyl, biphenylenyl, and fluorenyl groups. In one embodiment, the aryl group is phenyl or naphthyl. In another embodiment, the aryl group is phenyl.

The term "heteroaryl" as used herein by itself or as part of another group refers to monocyclic and bicyclic aromatic ring systems having five to 14 fourteen ring members, i.e., a 5- to 14-membered heteroaryl, a 5- to 6-membered-heteroaryl, a 9- to 10-membered comprising one, two, three, or four heteroatoms. Each heteroatom is independently oxygen, sulfur, or nitrogen. In one embodiment, the heteroaryl has three heteroatoms. In another embodiment, the heteroaryl has two heteroatoms. In another embodiment, the heteroaryl has one heteroatom. In another embodiment, the heteroaryl is a 5- to 10-membered heteroaryl. In another embodiment, the heteroaryl has 5 ring atoms, e.g., thienyl, a 5-membered heteroaryl having four carbon atoms and one sulfur atom. In another embodiment, the heteroaryl has 6 ring atoms, e.g., pyridyl, a 6-membered heteroaryl having five carbon atoms and one nitrogen atom. Non-limiting exemplary heteroaryl groups include thienyl, benzo[b]thienyl, naphtho[2,3-b]thienyl, thianthrenyl, furyl, benzofuryl, pyranyl, isobenzofuranyl, benzooxazonyl, chromenyl, xanthenyl, 2H-pyrrolyl, pyrrolyl, imidazolyl, pyrazolyl, pyridyl, pyrazinyl, pyrimidinyl, pyridazinyl, isoindolyl, 3H-indolyl, indolyl, indazolyl, purinyl, isoquinolyl, quinolyl, phthalazinyl, naphthyridinyl, cinnolinyl, quinazolinyl, pteridinyl, 4aH-carbazolyl, carbazolyl, β-carbolinyl, phenanthridinyl, acridinyl, pyrimidinyl, phenanthrolinyl, phenazinyl, thiazolyl, isothiazolyl, phenothiazolyl, isoxazolyl, furazanyl, and phenoxazinyl. In one embodiment, the heteroaryl is chosen from thienyl (e.g., thien-2-yl and thien-3-yl), furyl (e.g., 2-furyl and 3-furyl), pyrrolyl (e.g., 1H-pyrrol-2-yl and 1H-pyrrol-3-yl), imidazolyl (e.g., 2H-imidazol-2-yl and 2H-imidazol-4-yl), pyrazolyl (e.g., 1H-pyrazol-3-yl, 1H-pyrazol-4-yl, and 1H-pyrazol-5-yl), pyridyl (e.g., pyridin-2-yl, pyridin-3-yl, and pyridin-4-yl), pyrimidinyl (e.g., pyrimidin-2-yl, pyrimidin-4-yl, and pyrimidin-5-yl), thiazolyl (e.g., thiazol-2-yl, thiazol-4-yl, and thiazol-5-yl), isothiazolyl (e.g., isothiazol-3-yl, isothiazol-4-yl, and isothiazol-5-yl), oxazolyl (e.g., oxazol-2-yl, oxazol-4-yl, and oxazol-5-yl) and isoxazolyl (e.g., isoxazol-3-yl, isoxazol-4-yl, and isoxazol-5-yl). The term heteroaryl also includes N-oxides. A non-limiting exemplary N-oxide is pyridyl N-oxide.

The term "cycloalkyl" as used herein by itself or as part of another group refers to a cyclic aliphatic hydrocarbon containing three to twelve carbon atoms, i.e., a $C_3$-$C_{12}$ cycloalkyl, or the number of carbon atoms designated, e.g., a $C_3$ cycloalkyl such as cyclopropyl, a $C_4$ cycloalkyl such as cyclobutyl, etc. In one embodiment, the cycloalkyl is $C_3$-$C_6$ cycloalkyl.

The term "carboxy" as used by itself or as part of another group refers to a radical of the formula —C(═O)OH.

The term "amino" as used by itself or as part of another group refers to $—NH_2$.

As used herein, the wavy line ∿∿ represents the site of attachment to the rest of the compound. For divalent groups linked by two wavy lines, the order/direction of linking is arbitrary. For example,

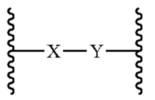

linking A and B moieties can present both A-X-Y-B and A-Y-X-B.

It is understood that, when a bond is shown as pointing to the center of one ring of a polycyclic (e.g., bicyclic or tricyclic) ring system, the bond can be attached to any one of the rings in the polycyclic (e.g., bicyclic or tricyclic) ring system. For example, when a ring system is shown as

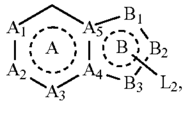

variable $L_2$ can be attached to Ring A or Ring B. Further, when the bond is shown as pointing to the center of one ring that can be absent, and when such ring is absent, then the bond is attached to one of the other rings in the polycyclic (e.g., bicyclic or tricyclic) ring system. For example, when ring system is shown as

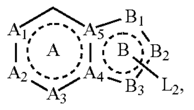

and when Ring B is absent, then variable $L_2$ is attached to Ring A.

The present disclosure encompasses any of the Compounds of the Disclosure being isotopically-labelled (i.e., radiolabeled) by having one or more atoms replaced by an atom having a different atomic mass or mass number. Examples of isotopes that can be incorporated into the disclosed compounds include isotopes of hydrogen, carbon, nitrogen, oxygen, phosphorous, fluorine and chlorine, such as $^2H$ (or deuterium (D)), $^3H$, $^{11}C$, $^{13}C$, $^{14}C$, $^{15}N$, $^{18}O$, $^{17}O$, $^{31}P$, $^{32}P$, $^{35}S$, $^{18}F$, and $^{36}Cl$, respectively, e.g., $^3H$, $^{11}C$, and $^{14}C$. In one embodiment, provided is a compound wherein substantially all of the atoms at a position within the Compound of the Disclosure are replaced by an atom having a different atomic mass or mass number. In another embodiment, provided is a compound wherein substantially all of the atoms at a position within the Compound of the Disclosure are replaced by deuterium atoms, e.g., all of the hydrogen atoms of a $—CH_3$ group are replaced by deuterium atoms to give a $—CD_3$ group. In another embodiment, provided is a compound wherein a portion of the atoms at a position within the Compound of the disclosure are replaced, i.e., the Compound of the Disclosure is enriched at a position with an atom having a different atomic mass or mass number. In another embodiment, provided is a compound wherein none of the atoms of the Compound of the Disclosure are replaced by an atom having a different atomic mass or mass number. Isotopically-labelled Compounds of the Disclosure can be prepared by methods known in the art.

Compounds of the Disclosure contain one or more asymmetric centers and may thus give rise to enantiomers, diastereomers, and other stereoisomeric forms. The present disclosure encompasses the use of all such possible forms, as well as their racemic and resolved forms and mixtures thereof. The individual enantiomers can be separated according to methods known in the art in view of the present disclosure. When the compounds described herein contain olefinic double bonds or other centers of geometric asymmetry, and unless specified otherwise, it is intended that they include both E and Z geometric isomers. All tautomers are also encompassed by the present disclosure.

As used herein, the term "stereoisomers" is a general term for all isomers of individual molecules that differ only in the orientation of their atoms in space. It includes enantiomers and isomers of compounds with more than one chiral center that are not mirror images of one another (diastereomers).

The term "chiral center" or "asymmetric carbon atom" refers to a carbon atom to which four different groups are attached.

The terms "enantiomer" and "enantiomeric" refer to a molecule that cannot be superimposed on its mirror image and hence is optically active wherein the enantiomer rotates the plane of polarized light in one direction and its mirror image compound rotates the plane of polarized light in the opposite direction.

The term "racemic" refers to a mixture of equal parts of enantiomers and which mixture is optically inactive. In one embodiment, Compounds of the Disclosure are racemic.

The term "absolute configuration" refers to the spatial arrangement of the atoms of a chiral molecular entity (or group) and its stereochemical description, e.g., R or S.

The stereochemical terms and conventions used in the specification are meant to be consistent with those described in *Pure & Appl. Chem* 68:2193 (1996), unless otherwise indicated.

The term "enantiomeric excess" or "ee" refers to a measure for how much of one enantiomer is present compared to the other. For a mixture of R and S enantiomers, the percent enantiomeric excess is defined as |R−S|*100, where R and S are the respective mole or weight fractions of enantiomers in a mixture such that R+S=1. With knowledge of the optical rotation of a chiral substance, the percent enantiomeric excess is defined as $([\alpha]_{obs}/[\alpha]_{max})$*100, where $[\alpha]_{obs}$ is the optical rotation of the mixture of enantiomers and $[\alpha]_{max}$ is the optical rotation of the pure enantiomer. Determination of enantiomeric excess is possible using a variety of analytical techniques, including NMR spectroscopy, chiral column chromatography or optical polarimetry.

The term "about," as used herein, includes the recited number ±10%. Thus, "about 10" means 9 to 11.

II. Compounds of the Disclosure

In some aspects, the present disclosure provides a compound of Formula I:

(I)

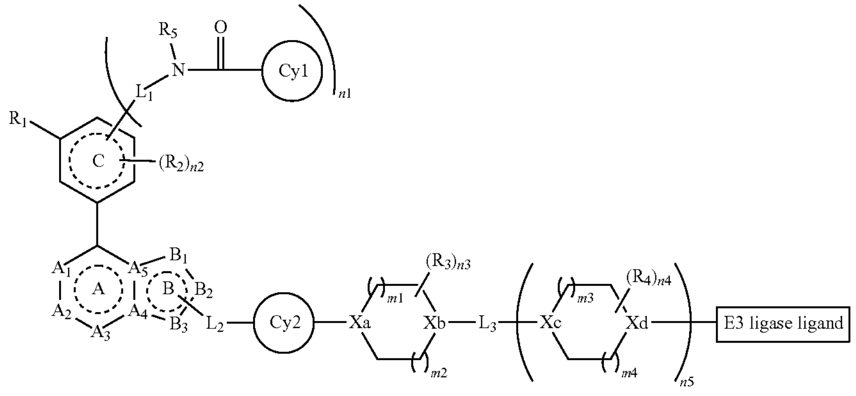

or a pharmaceutically acceptable salt or solvate thereof, wherein:

ring A is a 6-membered aromatic or non-aromatic ring; ring B is an optionally present 5-membered aromatic or non-aromatic ring; wherein when ring B is present, $L_2$ is connected to one of ring A or ring B; and when ring B is absent, $L_2$ is connected to ring A;

$A_1$, $A_2$, $A_3$, $A_4$, $A_5$, $B_1$, $B_2$ and $B_3$ are each independently selected from $CR_a$, $CR_aR_b$, N and $NR_a$;

$R_a$ and $R_b$ are each independently selected from the group consisting of H, D, $C_1$-$C_6$ alkyl, deuterated $C_1$-$C_6$ alkyl, $C_1$-$C_6$ haloalkyl, $C_1$-$C_6$ alkoxy, $C_3$-$C_6$ cycloalkyl, amino, OH, CN, or halogen; or $R_a$ and $R_b$ together with the C atom to which they are attached form an oxo (—C(═O)—);

ring C is a 6-membered aromatic or non-aromatic ring;

$R_1$ is selected from the group consisting of H, $C_1$-$C_6$ alkyl, $C_1$-$C_6$ haloalkyl, $C_1$-$C_6$ hydroxyalkyl, $C_1$-$C_6$ alkoxy, $C_3$-$C_6$ cycloalkyl, amino, OH, CN, or halogen;

$R_2$ is selected from the group consisting of H, $C_1$-$C_6$ alkyl, $C_1$-$C_6$ haloalkyl, $C_1$-$C_6$ hydroxyalkyl, $C_1$-$C_6$ alkoxy, $C_3$-$C_6$ cycloalkyl, amino, OH, CN, halogen, or a 5-6 membered heterocyclyl or heteroaryl optionally substituted with one or more groups selected from $C_1$-$C_6$ alkyl, $C_1$-$C_6$ haloalkyl, $C_1$-$C_6$ hydroxyalkyl, $C_1$-$C_6$ alkoxy, $C_3$-$C_6$ cycloalkyl, amino, oxo, OH, CN, halogen; or when $R_1$ and $R_2$ are on the same carbon atom, they can form a $C_3$-$C_6$ cycloalkyl together with the carbon atom to which they are connected.

n1 is 0 or 1; n2 is 0, 1, 2 or 3;

$L_1$ is a bond or $CR_cR_d$, wherein $R_c$ is H, and $R_d$ is selected from the group consisting of H, $C_1$-$C_6$ alkyl, $C_1$-$C_6$ haloalkyl, $C_1$-$C_6$ alkoxy, or $C_3$-$C_6$ cycloalkyl; or $R_d$ and $R_1$ or $R_2$ together form a $—(CR_eR_f)_{n6}—$ moiety, wherein $R_e$ and $R_f$ are each independently selected from the group consisting of H, $C_1$-$C_6$ alkyl, $C_1$-$C_6$ haloalkyl, $C_1$-$C_6$ alkoxy, $C_3$-$C_6$ cycloalkyl, amino, OH, CN, or halogen; and n6 is 2, 3, 4 or 5; optionally, one of the $CR_eR_f$ can be replaced by $NR_e$;

$R_5$ is selected from the group consisting of H, $C_1$-$C_6$ alkyl, $C_1$-$C_6$ haloalkyl, $C_1$-$C_6$ alkoxy, or $C_3$-$C_6$ cycloalkyl; or $R_5$ and one $R_2$ may together form a $—(CH_2)_{1-3}—$ moiety;

Cy1 is a 6-10 membered aryl, 5-10 membered heteroaryl or 5-10 membered heterocyclyl optionally substituted with one or more $R_6$ group, wherein each $R_6$ group is independently selected from the group consisting of H, $C_1$-$C_6$ alkyl, $C_1$-$C_6$ haloalkyl, $C_1$-$C_6$ hydroxyalkyl, $C_1$-$C_6$ alkoxy, $C_3$-$C_6$ cycloalkyl, $C_3$-$C_6$ cycloalkyl substituted with $C_1$-$C_6$ haloalkyl, $C_3$-$C_6$ cycloalkyl substituted with $C_1$-$C_6$ alkyl, amino, OH, CN, and halogen; optionally, $R_6$ and $R_5$ together form a $—(CH_2)_{n7}—$ or $—(CH{=}CH)_{n7}—$ moiety, and n7 is 1, 2, 3, 4 or 5;

$L_2$ is a bond, —O— or —NH—;

Cy2 is a 6-10 membered aryl, 5-10 membered heteroaryl or 5-10 membered heterocyclyl optionally substituted with one or more $R_7$ group, wherein each $R_7$ group is independently selected from the group consisting of H, $C_1$-$C_6$ alkyl, $C_1$-$C_6$ haloalkyl, $C_1$-$C_6$ hydroxyalkyl, $C_1$-$C_6$ alkoxy, $C_3$-$C_6$ cycloalkyl, amino, OH, CN, and halogen;

Xa is selected from CH or N;

Xb is selected from CH, N or

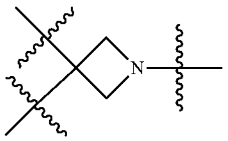

;

Xc is selected from CH or N;

Xd is selected from =C, CH, N,

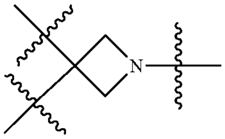

or

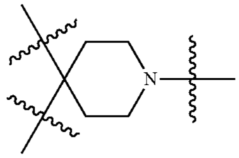

;

m1, m2, m3 and m4 are each independently selected from 0, 1 or 2;

$R_3$ is each independently selected from the group consisting of H, $C_1$-$C_6$ alkyl, $C_1$-$C_6$ haloalkyl, $C_1$-$C_6$ hydroxyalkyl, $C_1$-$C_6$ alkoxy, $C_3$-$C_6$ cycloalkyl, amino, OH, CN, or halogen; or two $R_3$ on different carbon atoms may together form a bond or $-(CH_2)_{1-3}-$ moiety, preferably a $-(CH_2)_2-$ moiety;

$R_4$ is each independently selected from the group consisting of H, $C_1$-$C_6$ alkyl, $C_1$-$C_6$ haloalkyl, $C_1$-$C_6$ hydroxyalkyl, $C_1$-$C_6$ alkoxy, $C_3$-$C_6$ cycloalkyl, amino, OH, CN, or halogen;

n3 is 0, 1 or 2; n4 is 0, 1 or 2; and n5 is 0 or 1;

$L_3$ is $-(CR_gR_h)_{n7}-$ moiety, wherein $R_g$ and $R_h$ are each independently selected from the group consisting of H, $C_1$-$C_6$ alkyl, $C_1$-$C_6$ haloalkyl, $C_1$-$C_6$ alkoxy, $C_3$-$C_6$ cycloalkyl, amino, OH, CN, or halogen; and n7 is 0, 1, 2, 3, 4 or 5; and E3 ligase ligand is a small molecule ligand that targets E3 ubiquitin ligase.

In some aspects, the present disclosure provides a compound of Formula I:

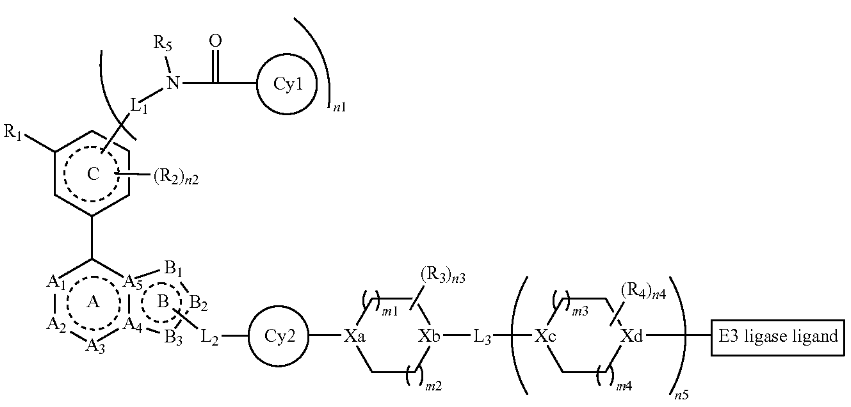

(I)

or a pharmaceutically acceptable salt or solvate thereof, wherein:

ring A is a 6-membered aromatic or non-aromatic ring; ring B is an optionally present 5-membered aromatic or non-aromatic ring; wherein when ring B is present, $L_2$ is connected to one of ring A or ring B; and when ring B is absent, $L_2$ is connected to ring A;

$A_1$, $A_2$, $A_3$, $A_4$, $A_5$, $B_1$, $B_2$ and $B_3$ are each independently selected from $CR_a$, $CR_aR_b$, N and $NR_a$;

$R_a$ and $R_b$ are each independently selected from the group consisting of H, D, $C_1$-$C_6$ alkyl, deuterated $C_1$-$C_6$ alkyl, $C_1$-$C_6$ haloalkyl, $C_1$-$C_6$ alkoxy, $C_3$-$C_6$ cycloalkyl, amino, OH, CN, or halogen; or $R_a$ and $R_b$ together with the C atom to which they are attached form an oxo ($-C(=O)-$);

ring C is a 6-membered aromatic or non-aromatic ring;

$R_1$ is selected from the group consisting of H, $C_1$-$C_6$ alkyl, $C_1$-$C_6$ haloalkyl, $C_1$-$C_6$ hydroxyalkyl, $C_1$-$C_6$ alkoxy, $C_3$-$C_6$ cycloalkyl, amino, OH, CN, or halogen;

$R_2$ is selected from the group consisting of H, $C_1$-$C_6$ alkyl, $C_1$-$C_6$ haloalkyl, $C_1$-$C_6$ hydroxyalkyl, $C_1$-$C_6$ alkoxy, $C_3$-$C_6$ cycloalkyl, amino, OH, CN, halogen, or a 5-6 membered heterocyclyl or heteroaryl optionally substituted with one or more groups selected from $C_1$-$C_6$ alkyl, $C_1$-$C_6$ haloalkyl, $C_1$-$C_6$ hydroxyalkyl, $C_1$-$C_6$ alkoxy, $C_3$-$C_6$ cycloalkyl, amino, oxo, OH, CN, halogen;

n1 is 0 or 1; n2 is 0, 1, 2 or 3;

$L_1$ is a bond or $CR_cR_d$, wherein $R_c$ is H, and $R_d$ is selected from the group consisting of H, $C_1$-$C_6$ alkyl, $C_1$-$C_6$ haloalkyl, $C_1$-$C_6$ alkoxy, or $C_3$-$C_6$ cycloalkyl; or $R_d$ and $R_1$ together form a $-(CR_eR_f)_{n6}-$ moiety, wherein $R_e$ and $R_f$ are each independently selected from the group consisting of H, $C_1$-$C_6$ alkyl, $C_1$-$C_6$ haloalkyl, $C_1$-$C_6$ alkoxy, $C_3$-$C_6$ cycloalkyl, amino, OH, CN, or halogen; and n6 is 2, 3, 4 or 5; optionally, one of the $CR_eR_f$ can be replaced by $NR_e$;

$R_5$ is selected from the group consisting of H, $C_1$-$C_6$ alkyl, $C_1$-$C_6$ haloalkyl, $C_1$-$C_6$ alkoxy, or $C_3$-$C_6$ cycloalkyl;

Cy1 is a 6-10 membered aryl, 5-10 membered heteroaryl or 5-10 membered heterocyclyl optionally substituted with one or more $R_6$ group, wherein each $R_6$ group is independently selected from the group consisting of H, $C_1$-$C_6$ alkyl, $C_1$-$C_6$ haloalkyl, $C_1$-$C_6$ hydroxyalkyl, $C_1$-$C_6$ alkoxy, $C_3$-$C_6$ cycloalkyl, amino, OH, CN, and halogen; optionally, $R_6$ and $R_5$ together form a $-(CH_2)_{n7}-$ or $-(CH{=}CH)_{n7}-$ moiety, and n7 is 1, 2, 3, 4 or 5;

$L_2$ is a bond, —O— or —NH—;

Cy2 is a 6-10 membered aryl, 5-10 membered heteroaryl or 5-10 membered heterocyclyl optionally substituted with one or more $R_7$ group, wherein each $R_7$ group is independently selected from the group consisting of H, $C_1$-$C_6$ alkyl, $C_1$-$C_6$ haloalkyl, $C_1$-$C_6$ hydroxyalkyl, $C_1$-$C_6$ alkoxy, $C_3$-$C_6$ cycloalkyl, amino, OH, CN, and halogen;

Xa, Xb, Xc, and Xd are each independently selected from CH or N;

m1, m2, m3 and m4 are each independently selected from 0 or 1;

$R_3$ and $R_4$ are each independently selected from the group consisting of H, $C_1$-$C_6$ alkyl, $C_1$-$C_6$ haloalkyl, $C_1$-$C_6$ hydroxyalkyl, $C_1$-$C_6$ alkoxy, $C_3$-$C_6$ cycloalkyl, amino, OH, CN, or halogen;

n3 is 0, 1 or 2; n4 is 0, 1 or 2; and n5 is 0 or 1;

$L_3$ is $-(CR_gR_h)_{n7}-$ moiety, wherein $R_g$ and $R_h$ are each independently selected from the group consisting of H, $C_1$-$C_6$ alkyl, $C_1$-$C_6$ haloalkyl, $C_1$-$C_6$ alkoxy, $C_3$-$C_6$ cycloalkyl, amino, OH, CN, or halogen; and n7 is 0, 1, 2, 3, 4 or 5; and E3 ligase ligand is a small molecule ligand that targets E3 ubiquitin ligase.

In some embodiments, ring B is absent and ring A is

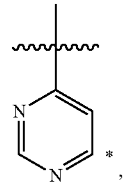 [SMILES: *c1ccncn1]

the wavy line represents the site of attachment to ring C, and the * represents the site of attachment to $L_2$.

In some embodiments, ring B is present; and preferably both ring A and ring B are aromatic rings.

In some embodiments, ring A and ring B together form one of the following modules optionally substituted with one or more of D, $C_1$-$C_6$ alkyl, deuterated $C_1$-$C_6$ alkyl, $C_1$-$C_6$ haloalkyl, $C_1$-$C_6$ alkoxy, $C_3$-$C_6$ cycloalkyl, amino, OH, CN, oxo, or halogen:

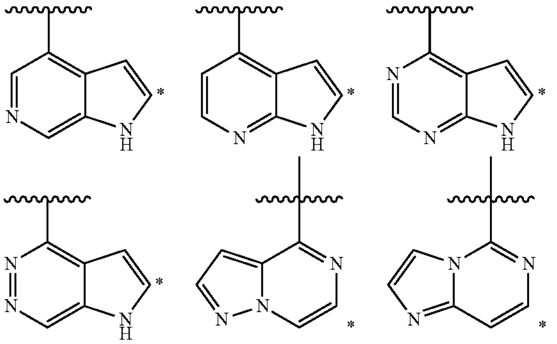

-continued

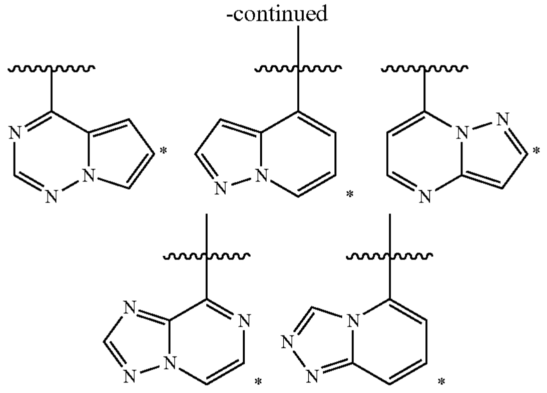

the wavy line represents the site of attachment to ring C, and the * represents the site of attachment to $L_2$.

In some embodiments, ring A and ring B together form one of the following modules optionally substituted with one or more of $C_1$-$C_6$ alkyl, deuterated $C_1$-$C_6$ alkyl, $C_1$-$C_6$ haloalkyl, $C_1$-$C_6$ alkoxy, $C_3$-$C_6$ cycloalkyl, amino, OH, CN, oxo, or halogen:

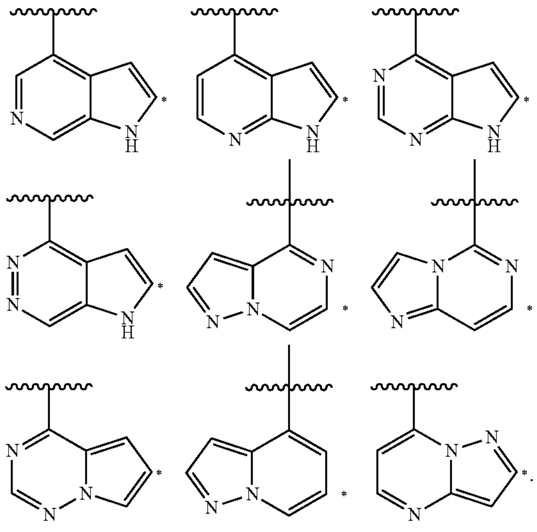

the wavy line represents the site of attachment to ring C, and the * represents the site of attachment to $L_2$.

In some embodiments, ring C is one of the following modules substituted with $R_1$ and $R_2$:

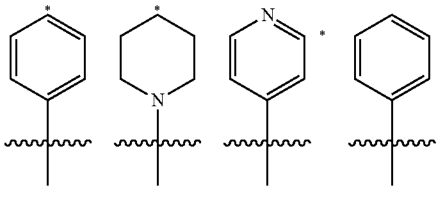

the wavy line represents the site of attachment to ring A, and the * represents the site of attachment to $L_1$.

In some embodiments, $R_1$ is selected from the group consisting of H, methyl, F, difluoromethyl and hydroxymethyl.

In some embodiments, $R_2$ is selected from the group consisting of H, methyl, F, hydroxymethyl and

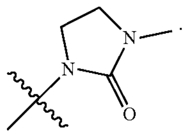 [SMILES: *N1CCN(C)C1=O]

In some embodiments, $L_1$ is $CR_cR_d$, $R_c$ is H, and $R_d$ is $C_1$-$C_6$ alkyl.

In some embodiments, $L_1$ is $CR_cR_d$, $R_c$ is H, and $R_d$ is and $R_1$ together form a —$(CR_eR_f)_{n6}$— moiety, optionally one of the $CR_eR_f$ is replaced by $NR_e$.

In some embodiments, n6 is 4.

In some embodiments, $R_5$ is H.

In some embodiments, Cy1 is a phenyl optionally substituted with one or more $R_6$ group.

In some embodiments, Cy1 is a 5-6 membered heteroaryl optionally substituted with one or more $R_6$ group.

In some embodiments, the 5-6 membered heteroaryl is selected from:

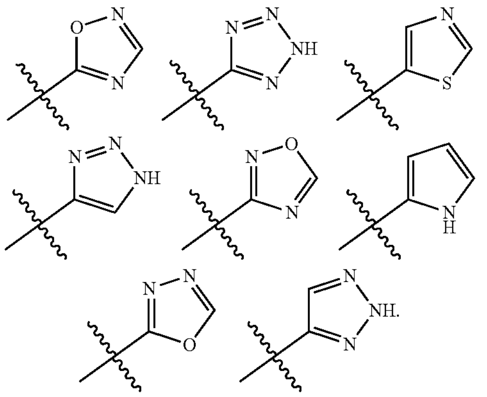

In some embodiments, Cy1 is a 5-6 membered heteroaryl optionally substituted with one or more $R_6$ group, wherein the 5-6 membered heteroaryl is selected from:

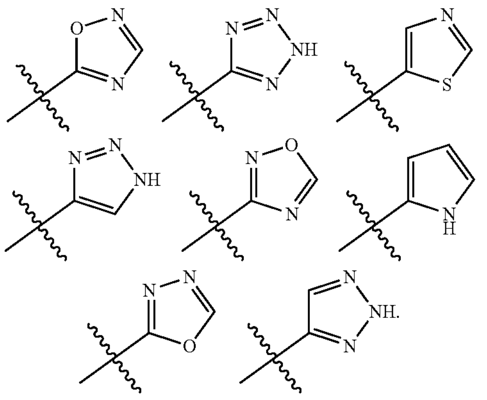

In some embodiments, $R_6$ is selected from $C_1$-$C_6$ alkyl and $C_3$-$C_6$ cycloalkyl, preferably tert-butyl.

In some embodiments, Cy2 is a phenyl, 5-6 membered heteroaryl or 5-6 membered heterocyclyl optionally substituted with one or more $R_6$ group.

In some embodiments, the 5-6 membered heteroaryl or 5-6 membered heterocyclyl is selected from:

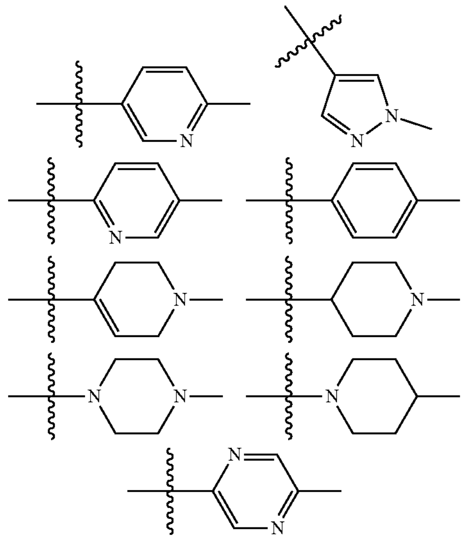

the wavy line represents the site of attachment to $L_2$.

In some embodiments, the 5-6 membered heteroaryl or 5-6 membered heterocyclyl is selected from:

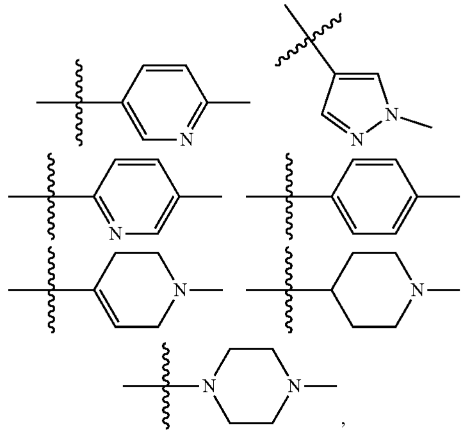

, the wavy line represents the site of attachment to $L_2$.

In some embodiments, the cyclic group containing Xa and Xb is selected from the following moieties optionally substituted with $R_3$:

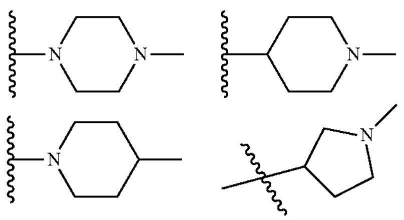

-continued

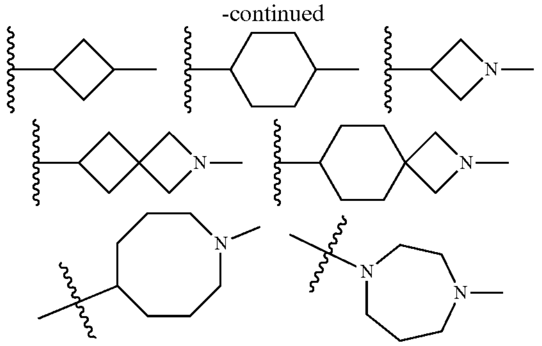

the wavy line ∿∿∿ represents the site of attachment to Cy2.

In some embodiments, the cyclic group containing Xa and Xb is selected from the following moieties optionally substituted with $R_3$:

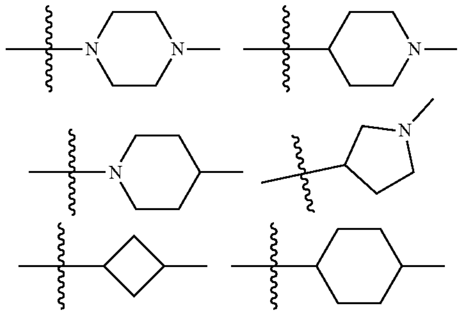

the wavy line ∿∿∿ represents the site of attachment to Cy2.

In some embodiments, $L_3$ is $—CH_2—$ or $—CH_2CH_2—$.

In some embodiments, the cyclic group containing Xc and Xd is selected from the following moieties optionally substituted with $R_4$:

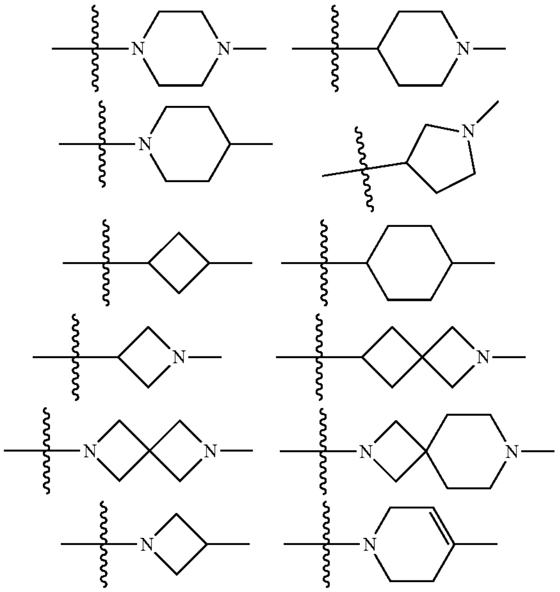

In some embodiments, the cyclic group containing Xc and Xd is selected from the following moieties optionally substituted with $R_4$:

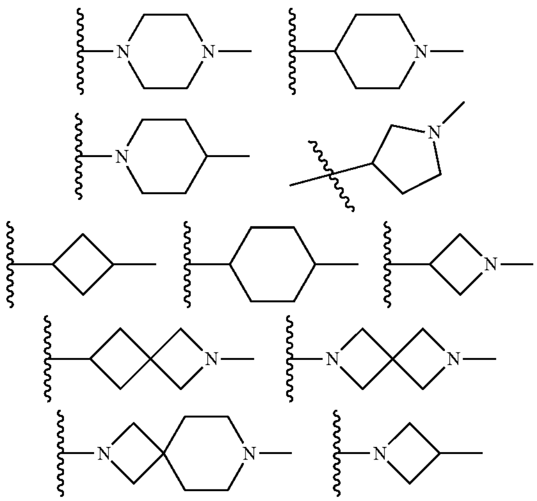

the wavy line ∿∿∿ represents the site of attachment to $L_3$.

In some embodiments, the cyclic group containing Xc and Xd is selected from the following moieties optionally substituted with $R_4$:

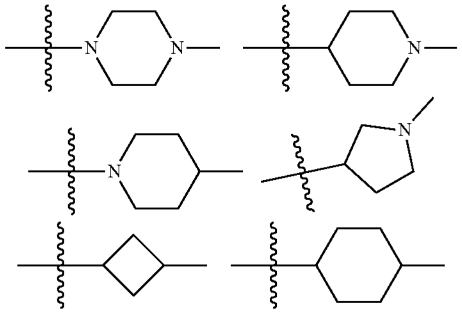

the wavy line ∿∿∿ represents the site of attachment to $L_3$.

In some embodiments, the E3 ligase ligand is:

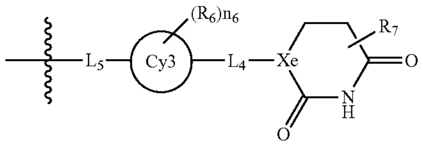

wherein:

Cy3 is a 6-10 membered aryl, 5-10 membered heteroaryl or 5-12 membered heterocyclyl;

$R_6$ is selected from the group consisting of H, $C_1$-$C_6$ alkyl, $C_1$-$C_6$ haloalkyl, $C_1$-$C_6$ hydroxyalkyl, $C_1$-$C_6$ alkoxy, $C_3$-$C_6$ cycloalkyl, amino, oxo, OH, CN, or halogen; or $R_6$ and one $R_4$ may together form a bond or $—(CH_2)_{1-3}—$ moiety, preferably a $—(CH_2)_2—$ moiety;

n6 is 0, 1, 2 or 3;

$L_4$ is a bond, —NH—, —O—, —CO—NH— or —NH—CO—;

$L_5$ is a bond, —NH—, —O—, —$(CH_2)$—O—, —CO—NH— or —NH—CO—;

Xe is CH or N;

$R_7$ is selected from the group consisting of H, $C_1$-$C_6$ alkyl, $C_1$-$C_6$ haloalkyl, $C_1$-$C_6$ hydroxyalkyl, $C_1$-$C_6$ alkoxy, $C_3$-$C_6$ cycloalkyl, amino, OH, CN, or halogen; and the wavy line represents the site of attachment to Xd.

In some embodiments, one —$CH_2$— in the —$(CH_2)_{1-3}$— moiety may be replaced with —O—.

In some embodiments, the E3 ligase ligand is:

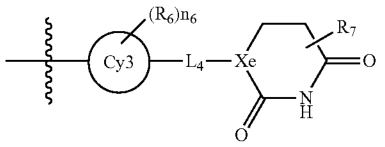

Wherein Cy3 is a 6-10 membered aryl, 5-10 membered heteroaryl or 5-12 membered heterocyclyl;

$R_6$ is selected from the group consisting of H, $C_1$-$C_6$ alkyl, $C_1$-$C_6$ haloalkyl, $C_1$-$C_6$ hydroxyalkyl, $C_1$-$C_6$ alkoxy, $C_3$-$C_6$ cycloalkyl, amino, oxo, OH, CN, or halogen;

n6 is 0, 1, 2 or 3;

$L_4$ is a bond, —NH—, —O—, —CO—NH— or —NH—CO—;

Xe is CH or N;

$R_7$ is selected from the group consisting of H, $C_1$-$C_6$ alkyl, $C_1$-$C_6$ haloalkyl, $C_1$-$C_6$ hydroxyalkyl, $C_1$-$C_6$ alkoxy, $C_3$-$C_6$ cycloalkyl, amino, OH, CN, or halogen; and the wavy line represents the site of attachment to Xd.

In some embodiments, Cy3 is a phenyl or pyridyl.

In some embodiments, Cy3 is selected from the following moieties:

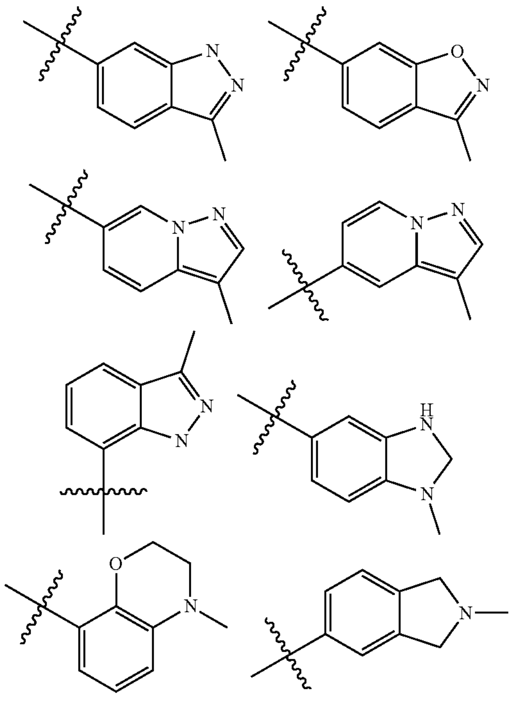

the wavy line now represents the site of attachment to Xd.

In some embodiments, $L_4$ is a bond.

In some embodiments, Xe is N.

EXEMPLARY EMBODIMENTS OF VARIABLES

In some embodiments, ring A is a 6-membered aromatic ring. In some embodiments, ring A is a 6-membered aryl. In some embodiments, ring A is a 6-membered heteroaryl. In some embodiments, ring A is a 6-membered non-aromatic ring. In some embodiments, ring A is a 6-membered cycloalkyl. In some embodiments, ring A is a 6-membered heterocyclo.

In some embodiments, ring B is an optionally present 5-membered aromatic ring. In some embodiments, ring B is a 5-membered aryl. In some embodiments, ring A is a 5-membered heteroaryl. In some embodiments, ring B is an optionally present 5-membered non-aromatic ring. In some embodiments, ring B is a 5-membered cycloalkyl. In some embodiments, ring B is a 5-membered heterocyclo.

In some embodiments, ring B is present, $L_2$ is connected to one of ring A or ring B.

In some embodiments, ring B is 5-membered aromatic ring, $L_2$ is connected to one of ring A or ring B. In some embodiments, ring B is a 5-membered aryl, $L_2$ is connected to one of ring A or ring B. In some embodiments, ring A is a 5-membered heteroaryl, $L_2$ is connected to one of ring A or ring B.

In some embodiments, ring B is a 5-membered non-aromatic ring, $L_2$ is connected to one of ring A or ring B. In some embodiments, ring B is a 5-membered cycloalkyl, $L_2$ is connected to one of ring A or ring B. In some embodiments, ring B is a 5-membered heterocyclo, $L_2$ is connected to one of ring A or ring B.

In some embodiments, ring B is absent and $L_2$ is connected to ring A.

In some embodiments, $A_1$ is $CR_a$. In some embodiments, $A_1$ is $CR_aR_b$. In some embodiments, $A_1$ is N. In some embodiments, $A_1$ is $NR_a$. In some embodiments, $A_2$ is $CR_a$. In some embodiments, $A_2$ is $CR_aR_b$. In some embodiments, $A_2$ is N. In some embodiments, $A_2$ is $NR_a$. In some embodiments, $A_3$ is $CR_a$. In some embodiments, $A_3$ is $CR_aR_b$. In some embodiments, $A_3$ is N. In some embodiments, $A_3$ is $NR_a$. In some embodiments, $A_4$ is $CR_a$. In some embodiments, $A_4$ is $CR_aR_b$. In some embodiments, $A_4$ is N. In some embodiments, $A_4$ is $NR_a$. In some embodiments, $A_5$ is $CR_a$. In some embodiments, $A_5$ is $CR_aR_b$. In some embodiments, $A_5$ is N. In some embodiments, $A_5$ is $NR_a$.

In some embodiments, $B_1$ is $CR_a$. In some embodiments, $B_1$ is $CR_aR_b$. In some embodiments, $B_1$ is N. In some embodiments, $B_1$ is $NR_a$. In some embodiments, $B_2$ is $CR_a$. In some embodiments, $B_2$ is $CR_aR_b$. In some embodiments, $B_2$ is N. In some embodiments, $B_2$ is $NR_a$. In some embodiments, $B_3$ is $CR_a$. In some embodiments, $B_3$ is $CR_aR_b$. In some embodiments, $B_3$ is N. In some embodiments, $B_3$ is $NR_a$.

In some embodiments, $R_a$ is H. In some embodiments, $R_a$ is D. In some embodiments, $R_a$ is $C_1$-$C_6$ alkyl. In some embodiments, $R_a$ is deuterated $C_1$-$C_6$ alkyl. In some embodiments, $R_a$ is $C_1$-$C_6$ haloalkyl. In some embodiments, $R_a$ is $C_1$-$C_6$ alkoxy. In some embodiments, $R_a$ is $C_3$-$C_6$ cycloalkyl. In some embodiments, $R_a$ is amino. In some embodiments, $R_a$ is OH. In some embodiments, $R_a$ is CN. In some embodiments, $R_a$ is or halogen. In some embodiments, $R_b$ is H. In some embodiments, $R_b$ is D. In some embodiments, $R_b$ is $C_1$-$C_6$ alkyl. In some embodiments, $R_b$ is deuterated $C_1$-$C_6$ alkyl. In some embodiments, $R_b$ is $C_1$-$C_6$ haloalkyl. In some embodiments, $R_b$ is $C_1$-$C_6$ alkoxy. In some embodiments, $R_b$ is $C_3$-$C_6$ cycloalkyl. In some embodiments, $R_b$ is amino. In some embodiments, $R_b$ is OH. In some embodiments, $R_b$ is CN. In some embodiments, $R_b$ is or halogen. In some embodiments, $R_a$ and $R_b$ together with the C atom to which they are attached form an oxo (—C(═O)—).

In some embodiments, ring C is a 6-membered aromatic ring. In some embodiments, ring C is a 6-membered aryl. In some embodiments, ring C is a 6-membered heteroaryl.

In some embodiments, ring C is 6-membered non-aromatic ring. In some embodiments, ring C is a 6-membered cycloalkyl. In some embodiments, ring C is a 6-membered heterocyclo.

In some embodiments, $R_1$ is H. In some embodiments, $R_1$ is $C_1$-$C_6$ alkyl. In some embodiments, $R_1$ is $C_1$-$C_6$ haloalkyl. In some embodiments, $R_1$ is $C_1$-$C_6$ hydroxyalkyl. In some embodiments, $R_1$ is $C_1$-$C_6$ alkoxy. In some embodiments, $R_1$ is $C_3$-$C_6$ cycloalkyl. In some embodiments, $R_1$ is amino. In some embodiments, $R_1$ is OH. In some embodiments, $R_1$ is CN. In some embodiments, $R_1$ is halogen.

In some embodiments, $R_2$ is H. In some embodiments, $R_2$ is $C_1$-$C_6$ alkyl. In some embodiments, $R_2$ is $C_1$-$C_6$ haloalkyl. In some embodiments, $R_2$ is $C_1$-$C_6$ hydroxyalkyl. In some embodiments, $R_2$ is $C_1$-$C_6$ alkoxy. In some embodiments, $R_2$ is $C_3$-$C_6$ cycloalkyl. In some embodiments, $R_2$ is amino. In some embodiments, $R_2$ is OH. In some embodiments, $R_2$ is CN. In some embodiments, $R_2$ is halogen. In some embodiments, $R_2$ is a 5-6 membered heterocyclyl optionally substituted with one or more groups selected from $C_1$-$C_6$ alkyl, $C_1$-$C_6$ haloalkyl, $C_1$-$C_6$ hydroxyalkyl, $C_1$-$C_6$ alkoxy, $C_3$-$C_6$ cycloalkyl, amino, oxo, OH, CN, halogen. In some embodiments, $R_2$ is a 5-6 membered heteroaryl optionally substituted with one or more groups selected from $C_1$-$C_6$ alkyl, $C_1$-$C_6$ haloalkyl, $C_1$-$C_6$ hydroxyalkyl, $C_1$-$C_6$ alkoxy, $C_3$-$C_6$ cycloalkyl, amino, oxo, OH, CN, halogen. In some embodiments, $R_1$ and $R_2$ are on the same carbon atom, they can form a $C_3$-$C_6$ cycloalkyl together with the carbon atom to which they are connected.

In some embodiments, n1 is 0. In some embodiments, n1 is 1. In some embodiments, n2 is 0. In some embodiments, n2 is 1. In some embodiments, n2 is 2. In some embodiments, n2 is 3.

In some embodiments, Li is a bond. In some embodiments, Li is $CR_cR_d$, wherein $R_e$ is H, and $R_d$ is selected from the group consisting of H, $C_1$-$C_6$ alkyl, $C_1$-$C_6$ haloalkyl, $C_1$-$C_6$ alkoxy, or $C_3$-$C_6$ cycloalkyl; or $R_d$ and $R_1$ or $R_2$ together form a $—(CR_eR_f)_{n6}—$ moiety, wherein $R_e$ and $R_f$ are each independently selected from the group consisting of H, $C_1$-$C_6$ alkyl, $C_1$-$C_6$ haloalkyl, $C_1$-$C_6$ alkoxy, $C_3$-$C_6$ cycloalkyl, amino, OH, CN, or halogen; and n6 is 2, 3, 4 or 5; optionally, one of the $CR_eR_f$ can be replaced by $NR_e$.

In some embodiments, $R_5$ is H. In some embodiments, $R_5$ is $C_1$-$C_6$ alkyl. In some embodiments, $R_5$ is $C_1$-$C_6$ haloalkyl. In some embodiments, $R_5$ is $C_1$-$C_6$ alkoxy. In some embodiments, $R_5$ is $C_3$-$C_6$ cycloalkyl. In some embodiments, one $R_5$ and one $R_2$ may together form a $—(CH_2)_{1\text{-}3}—$ moiety.

In some embodiments, Cy1 is a 6-10 membered aryl optionally substituted with one or more $R_6$ group, wherein each $R_6$ group is independently selected from the group consisting of H, $C_1$-$C_6$ alkyl, $C_1$-$C_6$ haloalkyl, $C_1$-$C_6$ hydroxyalkyl, $C_1$-$C_6$ alkoxy, $C_3$-$C_6$ cycloalkyl, $C_3$-$C_6$ cycloalkyl substituted with $C_1$-$C_6$ haloalkyl, $C_3$-$C_6$ cycloalkyl substituted with $C_1$-$C_6$ alkyl, amino, OH, CN, and halogen; optionally, $R_6$ and $R_5$ together form a $—(CH_2)_{n7}—$ or $—(CH═CH)_{n7}—$ moiety, and n7 is 1, 2, 3, 4 or 5.

In some embodiments, Cy1 is a 5-10 membered heteroaryl optionally substituted with one or more $R_6$ group, wherein each $R_6$ group is independently selected from the group consisting of H, $C_1$-$C_6$ alkyl, $C_1$-$C_6$ haloalkyl, $C_1$-$C_6$ hydroxyalkyl, $C_1$-$C_6$ alkoxy, $C_3$-$C_6$ cycloalkyl, $C_3$-$C_6$ cycloalkyl substituted with $C_1$-$C_6$ haloalkyl, $C_3$-$C_6$ cycloalkyl substituted with $C_1$-$C_6$ alkyl, amino, OH, CN, and halogen; optionally, $R_6$ and $R_5$ together form a $—(CH_2)_{n7}—$ or $—(CH═CH)_{n7}—$ moiety, and n7 is 1, 2, 3, 4 or 5.

In some embodiments, Cy1 is a 5-10 membered heterocyclyl optionally substituted with one or more $R_6$ group, wherein each $R_6$ group is independently selected from the group consisting of H, $C_1$-$C_6$ alkyl, $C_1$-$C_6$ haloalkyl, $C_1$-$C_6$ hydroxyalkyl, $C_1$-$C_6$ alkoxy, $C_3$-$C_6$ cycloalkyl, $C_3$-$C_6$ cycloalkyl substituted with $C_1$-$C_6$ haloalkyl, $C_3$-$C_6$ cycloalkyl substituted with $C_1$-$C_6$ alkyl, amino, OH, CN, and halogen; optionally, $R_6$ and $R_5$ together form a $—(CH_2)_{n7}—$ or $—(CH═CH)_{n7}—$ moiety, and n7 is 1, 2, 3, 4 or 5.

In some embodiments, $L_2$ is a bond. In some embodiments, $L_2$ is —O—. In some embodiments, $L_2$ is —NH—.

In some embodiments, Cy2 is a 6-10 membered aryl optionally substituted with one or more $R_7$ group, wherein each $R_7$ group is independently selected from the group consisting of H, $C_1$-$C_6$ alkyl, $C_1$-$C_6$ haloalkyl, $C_1$-$C_6$ hydroxyalkyl, $C_1$-$C_6$ alkoxy, $C_3$-$C_6$ cycloalkyl, amino, OH, CN, and halogen.

In some embodiments, Cy2 is a 5-10 membered heteroaryl optionally substituted with one or more $R_7$ group, wherein each $R_7$ group is independently selected from the group consisting of H, $C_1$-$C_6$ alkyl, $C_1$-$C_6$ haloalkyl, $C_1$-$C_6$ hydroxyalkyl, $C_1$-$C_6$ alkoxy, $C_3$-$C_6$ cycloalkyl, amino, OH, CN, and halogen.

In some embodiments, Cy2 is a 5-10 membered heterocyclyl optionally substituted with one or more $R_7$ group, wherein each $R_7$ group is independently selected from the group consisting of H, $C_1$-$C_6$ alkyl, $C_1$-$C_6$ haloalkyl, $C_1$-$C_6$ hydroxyalkyl, $C_1$-$C_6$ alkoxy, $C_3$-$C_6$ cycloalkyl, amino, OH, CN, and halogen.

In some embodiments, Xa is CH. In some embodiments, Xa is N.

In some embodiments, Xb is CH. In some embodiments, Xb is N. In some embodiments, Xb is

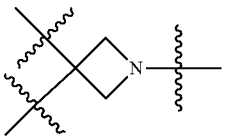

.

In some embodiments, Xc is CH. In some embodiments, Xc is N.

In some embodiments, Xd is ═C. In some embodiments, Xd is CH. In some embodiments, Xd is N. In some embodiments, Xd is

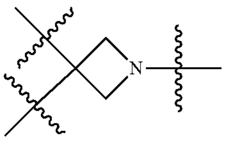

.

In some embodiments, Xd is

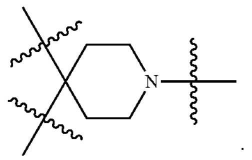 [SMILES: *N1CCC(*)(*)CC1]

In some embodiments, m1 is 0. In some embodiments, m1 is 1. In some embodiments, m1 is 2. In some embodiments, m2 is 0. In some embodiments, m2 is 1. In some embodiments, m2 is 2. In some embodiments, m3 is 0. In some embodiments, m3 is 1. In some embodiments, m3 is 2. In some embodiments, m4 is 0. In some embodiments, m4 is 1. In some embodiments, m4 is 2.

In some embodiments, $R_3$ is H. In some embodiments, $R_3$ is $C_1$-$C_6$ alkyl. In some embodiments, $R_3$ is $C_1$-$C_6$ haloalkyl. In some embodiments, $R_3$ is $C_1$-$C_6$ hydroxyalkyl. In some embodiments, $R_3$ is $C_1$-$C_6$ alkoxy. In some embodiments, $R_3$ is $C_3$-$C_6$ cycloalkyl. In some embodiments, $R_3$ is amino. In some embodiments, $R_3$ is OH. In some embodiments, $R_3$ is CN. In some embodiments, $R_3$ is halogen. In some embodiments, two $R_3$ on different carbon atoms may together form a bond or $-(CH_2)_{1-3}-$ moiety. In some embodiments, two $R_3$ on different carbon atoms may together form preferably a $-(CH_2)_2-$ moiety.

In some embodiments, $R_4$ is H. In some embodiments, $R_4$ is $C_1$-$C_6$ alkyl. In some embodiments, $R_4$ is $C_1$-$C_6$ haloalkyl. In some embodiments, $R_4$ is $C_1$-$C_6$ hydroxyalkyl. In some embodiments, $R_4$ is $C_1$-$C_6$ alkoxy. In some embodiments, $R_4$ is $C_3$-$C_6$ cycloalkyl. In some embodiments, $R_4$ is amino. In some embodiments, $R_4$ is OH. In some embodiments, $R_4$ is CN. In some embodiments, $R_4$ is halogen.

In some embodiments, n3 is 0. In some embodiments, n3 is 1. In some embodiments, n3 is 2. In some embodiments, n4 is 0. In some embodiments, n4 is 1. In some embodiments, n4 is 2. In some embodiments, n5 is 0. In some embodiments, n5 is 1;

In some embodiments, $L_3$ is $-(CR_gR_h)_{n7}-$ moiety, wherein $R_g$ and $R_h$ are each independently selected from the group consisting of H, $C_1$-$C_6$ alkyl, $C_1$-$C_6$ haloalkyl, $C_1$-$C_6$ alkoxy, $C_3$-$C_6$ cycloalkyl, amino, OH, CN, or halogen; and n7 is 0, 1, 2, 3, 4 or 5. In some embodiments, $R_g$ is H. In some embodiments, $R_g$ is $C_1$-$C_6$ alkyl. In some embodiments, $R_g$ is $C_1$-$C_6$ haloalkyl. In some embodiments, $R_g$ is $C_1$-$C_6$ alkoxy. In some embodiments, $R_g$ is $C_3$-$C_6$ cycloalkyl. In some embodiments, $R_g$ is amino. In some embodiments, $R_g$ is OH. In some embodiments, $R_g$ is CN. In some embodiments, $R_g$ is halogen. In some embodiments, $R_h$ is H. In some embodiments, $R_h$ is $C_1$-$C_6$ alkyl. In some embodiments, $R_h$ is $C_1$-$C_6$ haloalkyl. In some embodiments, $R_h$ is $C_1$-$C_6$ alkoxy. In some embodiments, $R_h$ is $C_3$-$C_6$ cycloalkyl. In some embodiments, Rn is amino. In some embodiments, $R_h$ is OH. In some embodiments, $R_h$ is CN. In some embodiments, $R_h$ is halogen. In some embodiments, n7 is 0. In some embodiments, n7 is 1. In some embodiments, n7 is 2. In some embodiments, n7 is 3. In some embodiments, n7 is 4. In some embodiments, n7 is 5.

In some embodiments, E3 ligase ligand is a small molecule ligand that targets E3 ubiquitin ligase.

In some embodiments, ring B is absent and ring A is

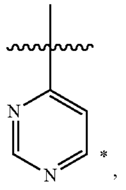 [SMILES: *c1ccncn1]

wherein the wavy line ∿∿∿ represents the site of attachment to ring C, and the * represents the site of attachment to $L_2$.

In some embodiments, ring B is present. In some embodiments, both ring A and ring B are preferably aromatic rings.

In some embodiments, ring A and ring B together form one of the following modules optionally substituted with one or more of D, $C_1$-$C_6$ alkyl, deuterated $C_1$-$C_6$ alkyl, $C_1$-$C_6$ haloalkyl, $C_1$-$C_6$ alkoxy, $C_3$-$C_6$ cycloalkyl, amino, OH, CN, oxo, or halogen, wherein the wavy line ∿∿∿ represents the site of attachment to ring C, and the * represents the site of attachment to $L_2$. In some embodiments, ring A and ring B together form

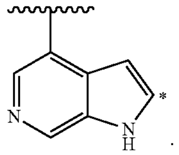 [SMILES: *c1cncc2[nH]ccc12]

In some embodiments, ring A and ring B together form

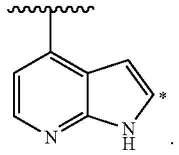 [SMILES: *c1ccnc2[nH]ccc12]

In some embodiments, ring A and ring B together form

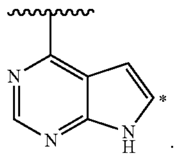 [SMILES: *c1ncnc2[nH]ccc12]

In some embodiments, ring A and ring B together form

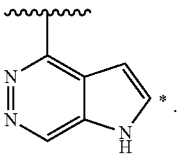 [SMILES: *c1nncc2[nH]ccc12]

In some embodiments, ring A and ring B together form

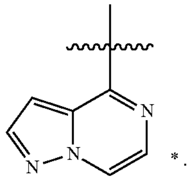 [SMILES: *c1nccn2nccc12]

In some embodiments, ring A and ring B together form

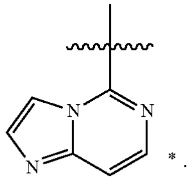 [SMILES: *c1nccc2nccn12]

In some embodiments, ring A and ring B together form

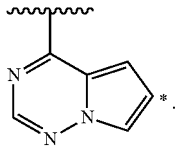 [SMILES: *c1ncnn2cccc12]

In some embodiments, ring A and ring B together form

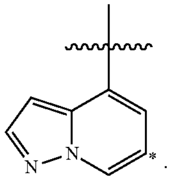 [SMILES: *c1cccn2nccc12]

In some embodiments, ring A and ring B together form

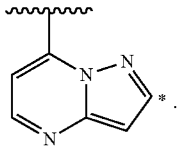 [SMILES: *c1ccnc2ccnn12]

In some embodiments, ring A and ring B together form

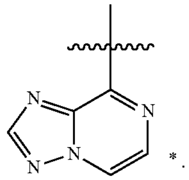 [SMILES: *c1nccn2ncnc12]

In some embodiments, ring A and ring B together form

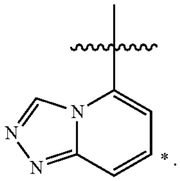 [SMILES: *c1cccc2nncn12]

In some embodiments, ring A and ring B together form one of the following modules optionally substituted with one or more of $C_1$-$C_6$ alkyl, deuterated $C_1$-$C_6$ alkyl, $C_1$-$C_6$ haloalkyl, $C_1$-$C_6$ alkoxy, $C_3$-$C_6$ cycloalkyl, amino, OH, CN, oxo, or halogen, wherein the wavy line ∿∿∿ represents the site of attachment to ring C, and the * represents the site of attachment to $L_2$. In some embodiments, ring A and ring B together form

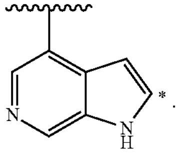 [SMILES: *c1cncc2[nH]ccc12]

In some embodiments, ring A and ring B together form

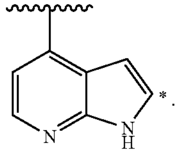 [SMILES: *c1ccnc2[nH]ccc12]

In some embodiments, ring A and ring B together form

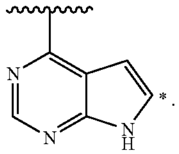 [SMILES: *c1ncnc2[nH]ccc12]

In some embodiments, ring A and ring B together form

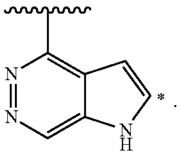 [SMILES: *c1nncc2[nH]ccc12]

In some embodiments, ring A and ring B together form

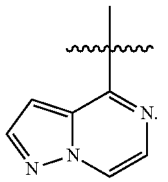 [SMILES: *c1nccn2nccc12]

In some embodiments, ring A and ring B together form

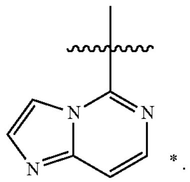 [SMILES: *c1nccc2nccn12]

In some embodiments, ring A and ring B together form

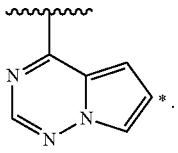 [SMILES: *c1ncnn2cccc12]

In some embodiments, ring A and ring B together form

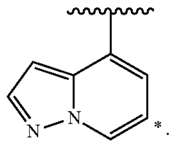 [SMILES: *c1cccn2nccc12]

In some embodiments, ring A and ring B together form

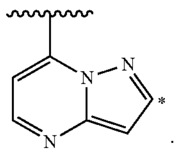 [SMILES: *c1ccnc2ccnn12]

In some embodiments, ring C is

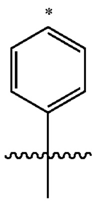 [SMILES: *c1ccccc1]

substituted with $R_1$ and $R_2$, wherein the wavy line represents the site of attachment to ring A, and the * represents the site of attachment to $L_1$. In some embodiments, ring C is

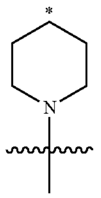

substituted with $R_1$ and $R_2$, wherein the wavy line represents the site of attachment to ring A, and the * represents the site of attachment to $L_1$. In some embodiments, ring C is

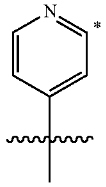 [SMILES: *c1ccncc1]

substituted with $R_1$ and $R_2$, wherein the wavy line represents the site of attachment to ring A, and the * represents the site of attachment to $L_1$. In some embodiments, ring C is

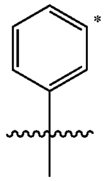 [SMILES: *c1ccccc1]

substituted with $R_1$ and $R_2$, wherein the wavy line represents the site of attachment to ring A, and the * represents the site of attachment to $L_1$.

In some embodiments, $R_1$ is H. In some embodiments, $R_1$ is methyl. In some embodiments, $R_1$ is F. In some embodiments, $R_1$ is difluoromethyl. In some embodiments, $R_1$ is hydroxymethyl.

In some embodiments, $R_2$ is H. In some embodiments, $R_2$ is methyl. In some embodiments, $R_2$ is F. In some embodiments, $R_2$ is hydroxymethyl. In some embodiments, $R_2$ is

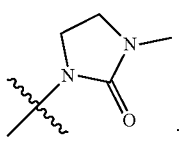 [SMILES: *N1CCN(C)C1=O]

In some embodiments, $L_1$ is $CR_cR_d$, $R_c$ is H, and $R_d$ is $C_1$-$C_6$ alkyl.

In some embodiments, $L_1$ is $CR_cR_d$, $R_c$ is H, and $R_d$ and $R_1$ together form a —$(CR_eR_f)_{n6}$— moiety. In some embodiments, $L_1$ is $CR_cR_d$, $R_c$ is H, and $R_d$ and $R_1$ together form a —$(CR_eR_f)_{n6}$— moiety, wherein one of the $CR_eR_f$ is replaced by $NR_e$.

In some embodiments, n6 is 4.

In some embodiments, $R_5$ is H.

In some embodiments, Cy1 is a phenyl optionally substituted with one $R_6$ group. In some embodiments, Cy1 is a phenyl optionally substituted with more than one $R_6$ groups.

In some embodiments, Cy1 is a 5-6 membered heteroaryl optionally substituted with one $R_6$ group. In some embodiments, Cy1 is a 5-6 membered heteroaryl optionally substituted with more than one $R_6$ groups. In some embodiments, the 5-6 membered heteroaryl is

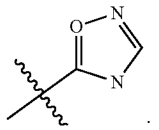

In some embodiments, the 5-6 membered heteroaryl is

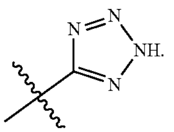 [SMILES: *c1nn[nH]n1]

In some embodiments, the 5-6 membered heteroaryl is

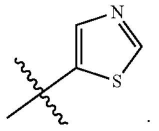 [SMILES: *c1cncs1]

In some embodiments, the 5-6 membered heteroaryl is

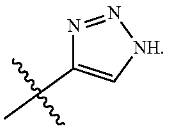 [SMILES: *c1c[nH]nn1]

In some embodiments, the 5-6 membered heteroaryl is

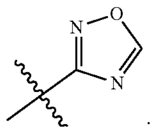 [SMILES: *c1ncon1]

In some embodiments, the 5-6 membered heteroaryl is

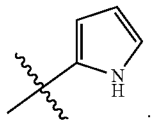 [SMILES: *c1ccc[nH]1]

In some embodiments, the 5-6 membered heteroaryl is

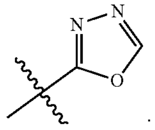 [SMILES: *c1nnco1]

In some embodiments, the 5-6 membered heteroaryl is

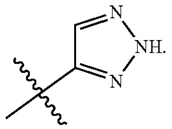 [SMILES: *c1cn[nH]n1]

In some embodiments, $R_6$ is $C_1$-$C_6$ alkyl. In some embodiments, $R_6$ is $C_3$-$C_6$ cycloalkyl. In some embodiments, $R_6$ is preferably tert-butyl.

In some embodiments, Cy2 is a phenyl. In some embodiments, Cy2 is a 5-6 membered heteroaryl. In some embodiments, Cy2 is a 5-6 membered heterocyclyl optionally substituted with one $R_6$ group. In some embodiments, Cy2 is a 5-6 membered heterocyclyl optionally substituted with more than one $R_6$ groups.

In some embodiments, the 5-6 membered heteroaryl or 5-6 membered heterocyclyl is

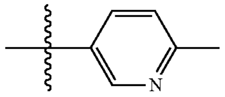 [SMILES: *c1ccc(C)nc1]

wherein the wavy line ∿∿∿ represents the site of attachment to $L_2$. In some embodiments, the 5-6 membered heteroaryl or 5-6 membered heterocyclyl is

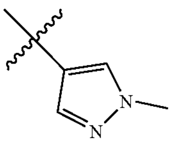 [SMILES: *c1cnn(C)c1]

wherein the wavy line ∿∿∿ represents the site of attachment to $L_2$. In some embodiments, the 5-6 membered heteroaryl or 5-6 membered heterocyclyl is

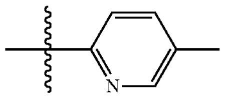 [SMILES: *c1ccc(C)cn1]

wherein the wavy line ∿∿∿ represents the site of attachment to $L_2$. In some embodiments, the 5-6 membered heteroaryl or 5-6 membered heterocyclyl is

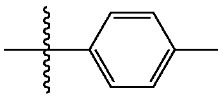 [SMILES: *c1ccc(C)cc1]

wherein the wavy line ∿∿∿ represents the site of attachment to $L_2$. In some embodiments, the 5-6 membered heteroaryl or 5-membered heterocyclyl is

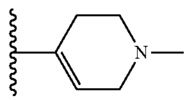

wherein the wavy line ∿∿∿ represents the site of attachment to $L_2$. In some embodiments, the 5-6 membered heteroaryl or 5-6 membered heterocyclyl is

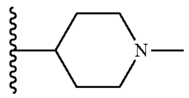

wherein the wavy line ∿∿∿ represents the site of attachment to $L_2$. In some embodiments, the 5-6 membered heteroaryl or 5-6 membered heterocyclyl is

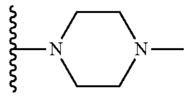

wherein the wavy line ∿∿∿ represents the site of attachment to $L_2$. In some embodiments, the 5-6 membered heteroaryl or 5-6 membered heterocyclyl is

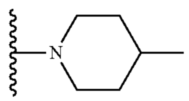 [SMILES: *N1CCC(C)CC1]

wherein the wavy line ∿∿∿ represents the site of attachment to $L_2$. In some embodiments, the 5-6 membered heteroaryl or 5-6 membered heterocyclyl is

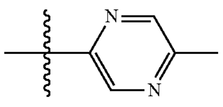 [SMILES: *c1cnc(C)cn1]

wherein the wavy line ∿∿∿ represents the site of attachment to $L_2$.

In some embodiments, the cyclic group containing Xa and Xb is

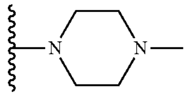

optionally substituted with $R_3$, wherein the wavy line ∿∿∿ represents the site of attachment to Cy2. In some embodiments, the cyclic group containing Xa and Xb is

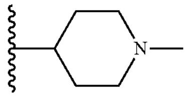 [SMILES: *C1CCN(C)CC1]

optionally substituted with $R_3$, wherein the wavy line ∿∿∿ represents the site of attachment to Cy2. In some embodiments, the cyclic group containing Xa and Xb is

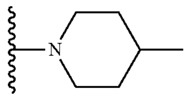

optionally substituted with $R_3$, wherein the wavy line ∿∿∿ represents the site of attachment to Cy2. In some embodiments, the cyclic group containing Xa and Xb is

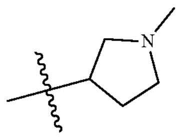 [SMILES: *C1CCN(C)C1]

optionally substituted with $R_3$, wherein the wavy line ∿∿∿ represents the site of attachment to Cy2. In some embodiments, the cyclic group containing Xa and Xb is

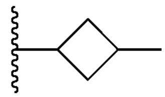 [SMILES: *C1CC(C)C1]

optionally substituted with $R_3$, wherein the wavy line ∿∿∿ represents the site of attachment to Cy2. In some embodiments, the cyclic group containing Xa and Xb is

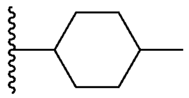

optionally substituted with $R_3$, wherein the wavy line represents the site of attachment to Cy2. In some embodiments, the cyclic group containing Xa and Xb is

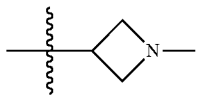 [SMILES: *C1CN(C)C1]

optionally substituted with $R_3$, wherein the wavy line represents the site of attachment to Cy2. In some embodiments, the cyclic group containing Xa and Xb is

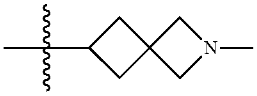 [SMILES: *C1CC2(C1)CN(C)C2]

optionally substituted with $R_3$, wherein the wavy line represents the site of attachment to Cy2. In some embodiments, the cyclic group containing Xa and Xb is

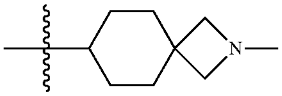 [SMILES: *C1CCC2(CC1)CN(C)C2]

optionally substituted with $R_3$, wherein the wavy line represents the site of attachment to Cy2. In some embodiments, the cyclic group containing Xa and Xb is

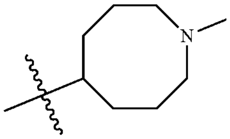 [SMILES: *C1CCCN(C)CCC1]

optionally substituted with $R_3$, wherein the wavy line represents the site of attachment to Cy2. In some embodiments, the cyclic group containing Xa and Xb is

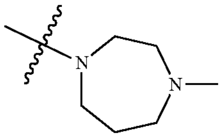 [SMILES: *N1CCCN(C)CC1]

optionally substituted with $R_3$, wherein the wavy line represents the site of attachment to Cy2.

In some embodiments, $L_3$ is $—CH_2—$. In some embodiments, $L_3$ is $—CH_2CH_2—$.

In some embodiments, the cyclic group containing Xc and Xd is

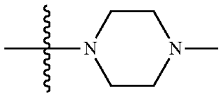 [SMILES: *N1CCN(C)CC1]

optionally substituted with $R_4$, wherein the wavy line represents the site of attachment to $L_3$. In some embodiments, the cyclic group containing Xc and Xd is

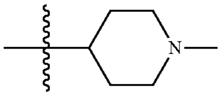 [SMILES: *C1CCN(C)CC1]

optionally substituted with $R_4$, wherein the wavy line represents the site of attachment to $L_3$. In some embodiments, the cyclic group containing Xc and Xd is

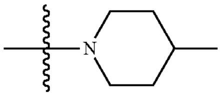 [SMILES: *N1CCC(C)CC1]

optionally substituted with $R_4$, wherein the wavy line represents the site of attachment to $L_3$. In some embodiments, the cyclic group containing Xc and Xd is

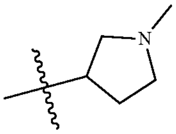 [SMILES: *C1CCN(C)C1]

optionally substituted with $R_4$, wherein the wavy line represents the site of attachment to $L_3$. In some embodiments, the cyclic group containing Xc and Xd is

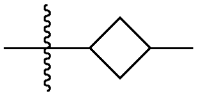 [SMILES: *C1CC(C)C1]

optionally substituted with $R_4$, wherein the wavy line represents the site of attachment to $L_3$. In some embodiments, the cyclic group containing Xc and Xd is

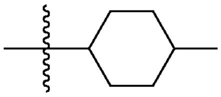 [SMILES: *C1CCC(C)CC1]

optionally substituted with $R_4$, wherein the wavy line represents the site of attachment to $L_3$. In some embodiments, the cyclic group containing Xc and Xd is

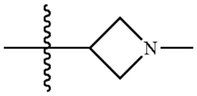

optionally substituted with $R_4$, wherein the wavy line represents the site of attachment to $L_3$. In some embodiments, the cyclic group containing Xc and Xd is

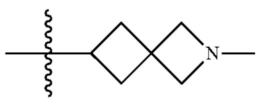 [SMILES: *C1CC2(C1)CN(C)C2]

optionally substituted with $R_4$, wherein the wavy line ∿∿∿ represents the site of attachment to $L_3$. In some embodiments, the cyclic group containing Xc and Xd is

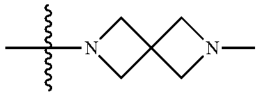 [SMILES: *N1CC2(C1)CN(C)C2]

optionally substituted with $R_4$, wherein the wavy line ∿∿∿ represents the site of attachment to $L_3$. In some embodiments, the cyclic group containing Xc and Xd is

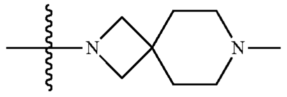 [SMILES: *N1CC2(CCN(C)CC2)C1]

optionally substituted with $R_4$, wherein the wavy line ∿∿∿ represents the site of attachment to $L_3$. In some embodiments, the cyclic group containing Xc and Xd is

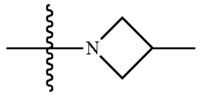 [SMILES: *N1CC(C)C1]

optionally substituted with $R_4$, wherein the wavy line ∿∿∿ represents the site of attachment to $L_3$. In some embodiments, the cyclic group containing Xc and Xd is

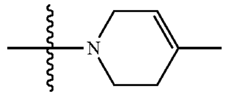 [SMILES: *N1CC=C(C)CC1]

optionally substituted with $R_4$, wherein the wavy line ∿∿∿ represents the site of attachment to $L_3$.

In some embodiments, the E3 ligase ligand is:

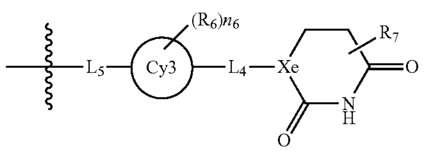

wherein:

Cy3 is a 6-10 membered aryl, 5-10 membered heteroaryl or 5-12 membered heterocyclyl;

$R_6$ is selected from the group consisting of H, $C_1$-$C_6$ alkyl, $C_1$-$C_6$ haloalkyl, $C_1$-$C_6$ hydroxyalkyl, $C_1$-$C_6$ alkoxy, $C_3$-$C_6$ cycloalkyl, amino, oxo, OH, CN, or halogen; or $R_6$ and one $R_4$ may together form a bond or $-(CH_2)_{1-3}-$ moiety, preferably a $-(CH_2)_2$-moiety;

n6 is 0, 1, 2 or 3;

$L_4$ is a bond, —NH—, —O—, —CO—NH— or —NH—CO—;

$L_5$ is a bond, —NH—, —O—, $-(CH_2)-O-$, —CO—NH— or —NH—CO—;

Xe is CH or N;

$R_7$ is selected from the group consisting of H, $C_1$-$C_6$ alkyl, $C_1$-$C_6$ haloalkyl, $C_1$-$C_6$ hydroxyalkyl, $C_1$-$C_6$ alkoxy, $C_3$-$C_6$ cycloalkyl, amino, OH, CN, or halogen; and the wavy line ∿∿∿ represents the site of attachment to Xd.

In some embodiments, one $-CH_2-$ in the $-(CH_2)_{1-3}-$ moiety may be replaced with —O—.

In some embodiments, Cy3 is a 6-10 membered aryl. In some embodiments, Cy3 is a 5-10 membered heteroaryl. In some embodiments, Cy3 is a 5-12 membered heterocyclyl.

In some embodiments, $R_6$ is H. In some embodiments, $R_6$ is $C_1$-$C_6$ alkyl. In some embodiments, $R_6$ is $C_1$-$C_6$ haloalkyl. In some embodiments, $R_6$ is $C_1$-$C_6$ hydroxyalkyl. In some embodiments, $R_6$ is $C_1$-$C_6$ alkoxy. In some embodiments, $R_6$ is $C_3$-$C_6$ cycloalkyl. In some embodiments, $R_6$ is amino. In some embodiments, $R_6$ is oxo. In some embodiments, $R_6$ is OH. In some embodiments, $R_6$ is CN. In some embodiments, $R_6$ is halogen. In some embodiments, one $R_6$ and one $R_4$ may together form a bond. In some embodiments, one $R_6$ and one $R_4$ may together form $-(CH_2)_{1-3}-$ moiety. In some embodiments, one $R_6$ and one $R_4$ may together form preferably a $-(CH_2)_2-$ moiety.

In some embodiments, n6 is 0. In some embodiments, n6 is 1. In some embodiments, n6 is 2. In some embodiments, n6 is 3.

In some embodiments, $L_4$ is a bond. In some embodiments, $L_4$ is —NH—. In some embodiments, $L_4$ is —O—. In some embodiments, $L_4$ is —CO—NH—. In some embodiments, $L_4$ is —NH—CO—;

In some embodiments, $L_5$ is a bond. In some embodiments, $L_5$ is —NH—. In some embodiments, $L_5$ is —O—. In some embodiments, $L_5$ is $-(CH_2)-O-$. In some embodiments, $L_5$ is —CO—NH—. In some embodiments, $L_5$ is —NH—CO—.

In some embodiments, Xe is CH. In some embodiments, Xe is N.

In some embodiments, $R_7$ is H. In some embodiments, $R_7$ is $C_1$-$C_6$ alkyl. In some embodiments, $R_7$ is $C_1$-$C_6$ haloalkyl. In some embodiments, $R_7$ is $C_1$-$C_6$ hydroxyalkyl. In some embodiments, $R_7$ is $C_1$-$C_6$ alkoxy. In some embodiments, $R_7$ is $C_3$-$C_6$ cycloalkyl. In some embodiments, $R_7$ is amino. In some embodiments, $R_7$ is OH. In some embodiments, $R_7$ is CN. In some embodiments, $R_7$ is halogen.

In some embodiments, the E3 ligase ligand is:

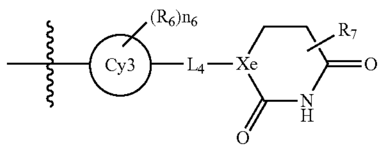

wherein: Cy3 is a 6-10 membered aryl, 5-10 membered heteroaryl or 5-12 membered heterocyclyl; $R_6$ is selected from the group consisting of H, $C_1$-$C_6$ alkyl, $C_1$-$C_6$ haloalkyl, $C_1$-$C_6$ hydroxyalkyl, $C_1$-$C_6$ alkoxy, $C_3$-$C_6$ cycloalkyl, amino, oxo, OH, CN, or halogen; n6 is 0, 1, 2 or 3; $L_4$ is a bond, —NH—, —O—, —CO—NH— or —NH—CO—; Xe is CH or N; $R_7$ is selected from the group consisting of H, $C_1$-$C_6$ alkyl, $C_1$-$C_6$ haloalkyl, $C_1$-$C_6$ hydroxyalkyl, $C_1$-$C_6$ alkoxy, $C_3$-$C_6$ cycloalkyl, amino, OH, CN, or halogen; and the wavy line ∿∿∿ represents the site of attachment to Xd.

In some embodiments, Cy3 is a 6-10 membered aryl. In some embodiments, Cy3 is a 5-10 membered heteroaryl. In some embodiments, Cy3 is a 5-12 membered heterocyclyl.

In some embodiments, $R_6$ is H. In some embodiments, $R_6$ is $C_1$-$C_6$ alkyl. In some embodiments, $R_6$ is $C_1$-$C_6$ haloalkyl. In some embodiments, $R_6$ is $C_1$-$C_6$ hydroxyalkyl. In some embodiments, $R_6$ is $C_1$-$C_6$ alkoxy. In some embodiments, $R_6$ is $C_3$-$C_6$ cycloalkyl. In some embodiments, $R_6$ is amino. In some embodiments, $R_6$ is oxo. In some embodiments, $R_6$ is OH. In some embodiments, $R_6$ is CN. In some embodiments, $R_6$ is halogen.

In some embodiments, n6 is 0. In some embodiments, n6 is 1. In some embodiments, n6 is 2. In some embodiments, n6 is 3.

In some embodiments, $L_4$ is a bond. In some embodiments, $L_4$ is —NH—. In some embodiments, $L_4$ is —O—. In some embodiments, $L_4$ is —CO—NH—. In some embodiments, $L_4$ is —NH—CO—.

In some embodiments, Xe is CH. In some embodiments, Xe is N.

In some embodiments, $R_7$ is H. In some embodiments, $R_7$ is $C_1$-$C_6$ alkyl. In some embodiments, $R_7$ is $C_1$-$C_6$ haloalkyl. In some embodiments, $R_7$ is $C_1$-$C_6$ hydroxyalkyl. In some embodiments, $R_7$ is $C_1$-$C_6$ alkoxy. In some embodiments, $R_7$ is $C_3$-$C_6$ cycloalkyl. In some embodiments, $R_7$ is amino. In some embodiments, $R_7$ is OH. In some embodiments, $R_7$ is CN. In some embodiments, $R_7$ is halogen.

In some embodiments, Cy3 is a phenyl. In some embodiments, Cy3 is a pyridyl.

In some embodiments, Cy3 is

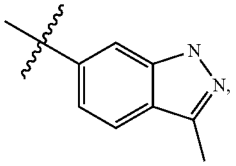 [SMILES: *c1ccc2c(C)n[nH]c2c1]

wherein he wavy line represents the site of attachment to Xd. In some embodiments, Cy3 is

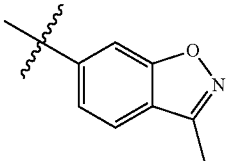 [SMILES: *c1ccc2c(C)noc2c1]

wherein he wavy line represents the site of attachment to Xd. In some embodiments, Cy3 is

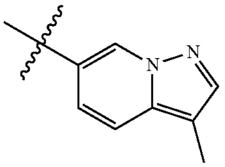 [SMILES: *c1ccc2c(C)cnn2c1]

wherein he wavy line represents the site of attachment to Xd. In some embodiments, Cy3 is

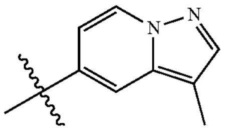 [SMILES: *c1ccn2ncc(C)c2c1]

wherein he wavy line represents the site of attachment to Xd. In some embodiments, Cy3 is

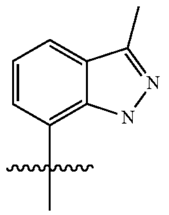 [SMILES: *c1cccc2c(C)n[nH]c12]

wherein he wavy line represents the site of attachment to Xd. In some embodiments, Cy3 is

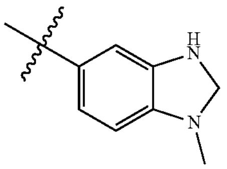 [SMILES: *c1ccc2c(c1)NCN2C]

wherein he wavy line represents the site of attachment to Xd. In some embodiments, Cy3 is

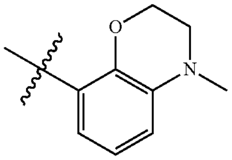 [SMILES: *c1cccc2c1OCCN2C]

wherein he wavy line represents the site of attachment to Xd. In some embodiments, Cy3 is

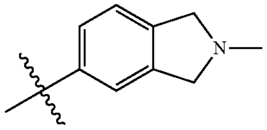 [SMILES: *c1ccc2c(c1)CN(C)C2]

wherein he wavy line represents the site of attachment to Xd

In some embodiments, La is a bond. In some embodiments, Xe is N.

EXEMPLARY EMBODIMENTS OF THE COMPOUNDS
In some embodiments, the compound is of Formula (II-A), (II-B), (II-C), or (II-D):
(II-A)
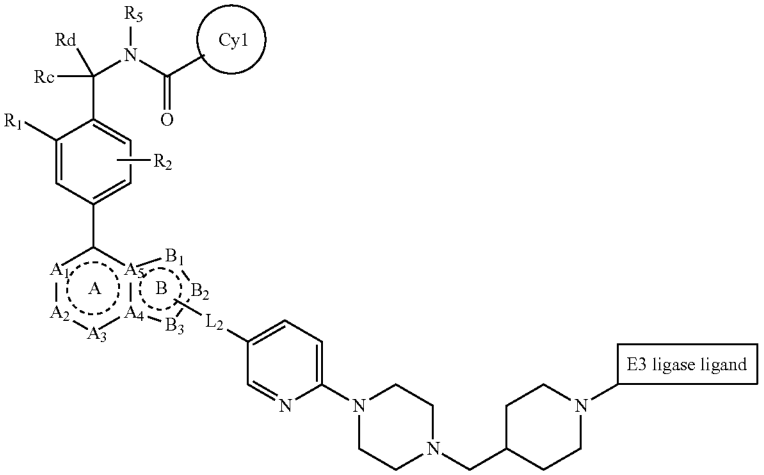
(II-B)
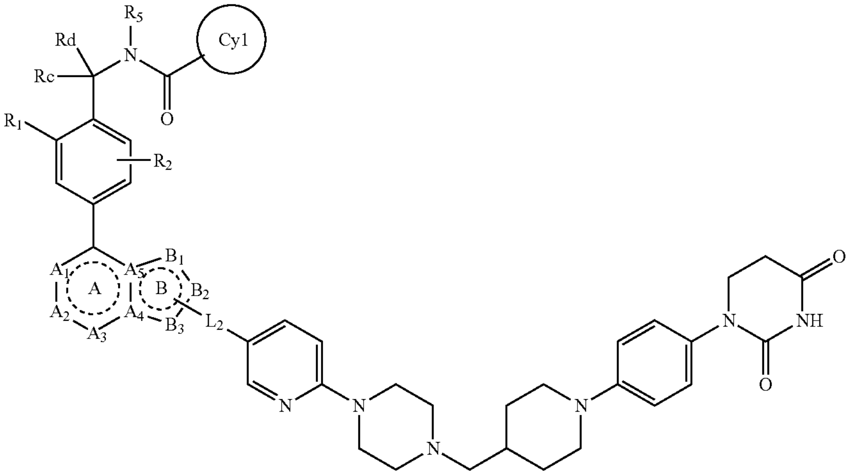
(II-C)
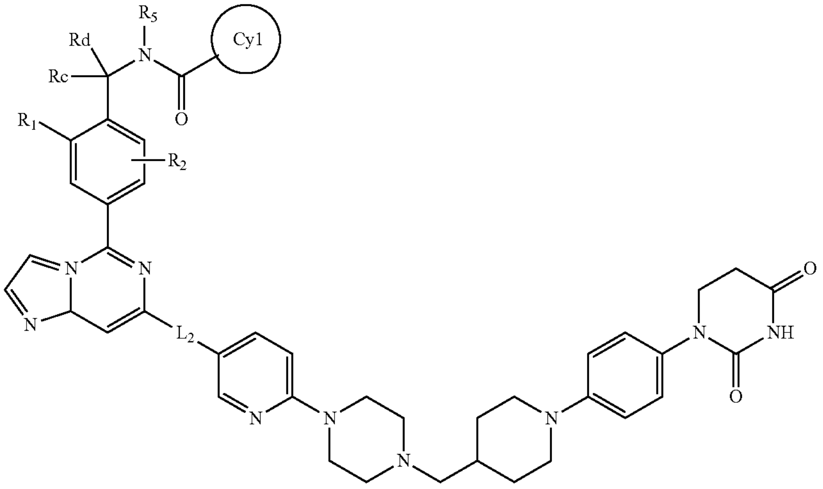

-continued
(II-D)
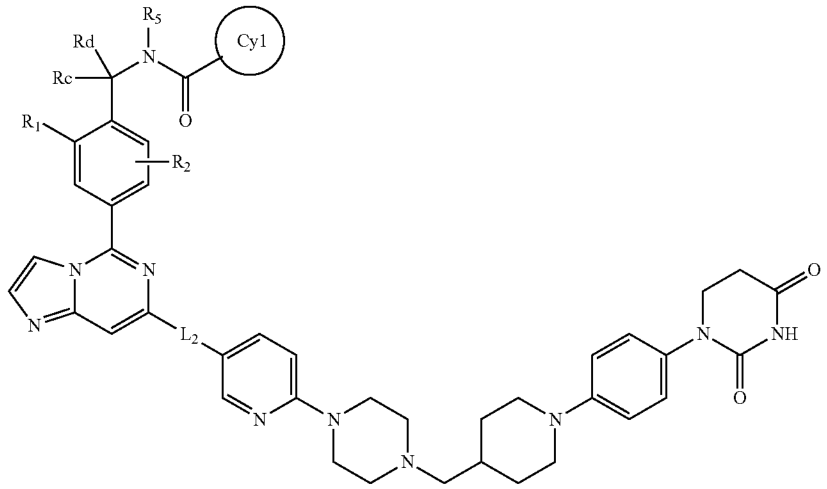
or a pharmaceutically acceptable salt or solvate thereof.
In some embodiments, the compound is of Formula (III-A), (III-B), (III-C), or (III-D):
(III-A)
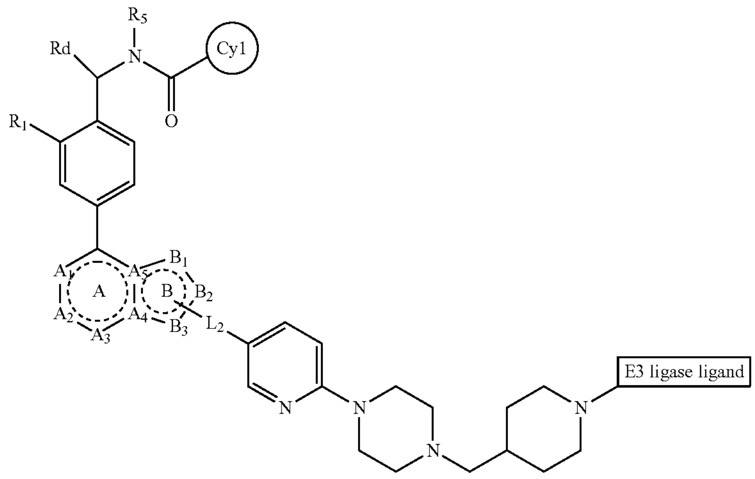
(III-B)
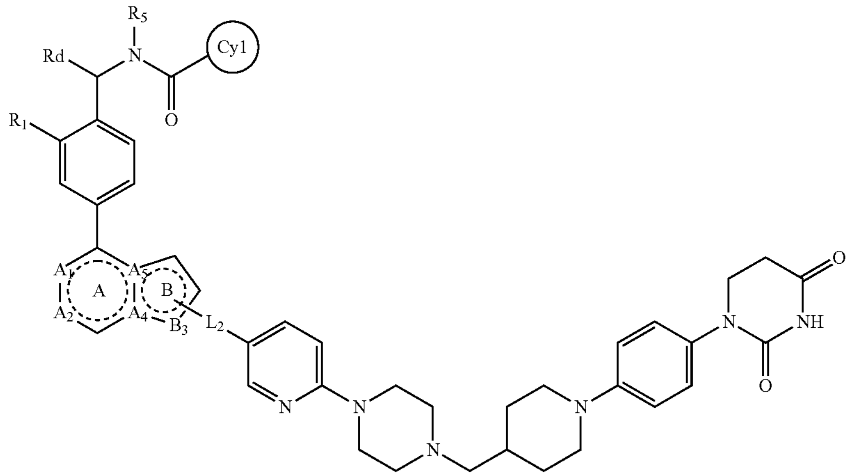

-continued
(III-C)
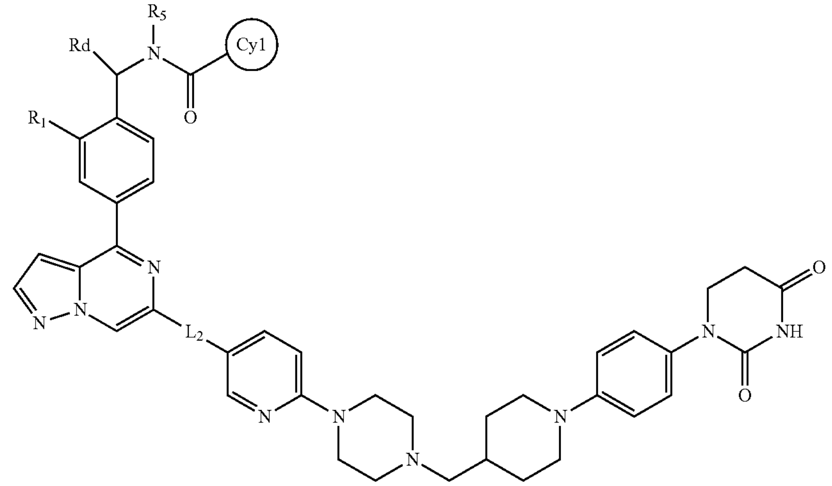
(III-D)
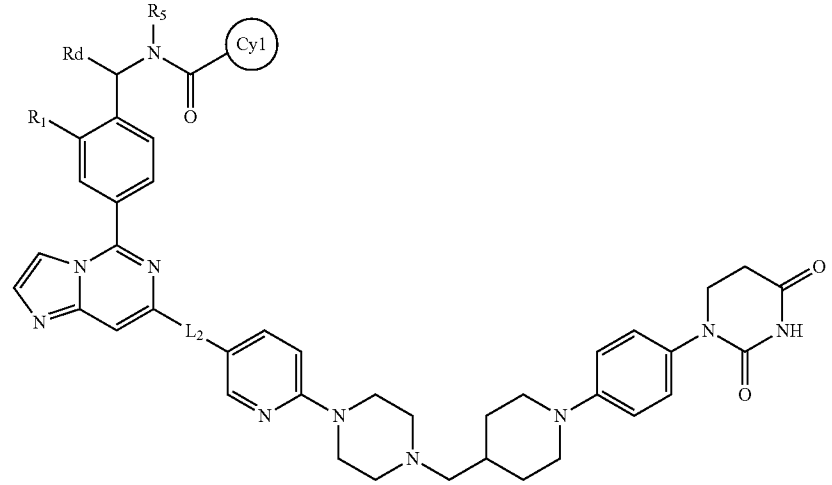
or a pharmaceutically acceptable salt or solvate thereof.
In some embodiments, the compound is of Formula (IV-A), (IV-B), (IV-C), of (IV-D):
(IV-A)
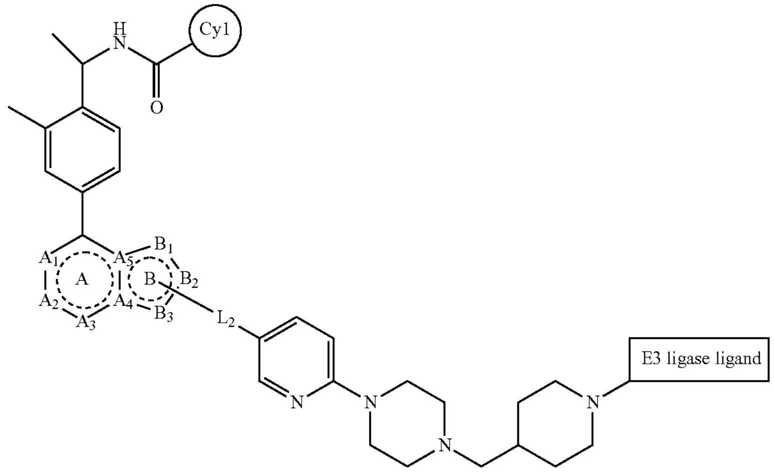

-continued (IV-B)

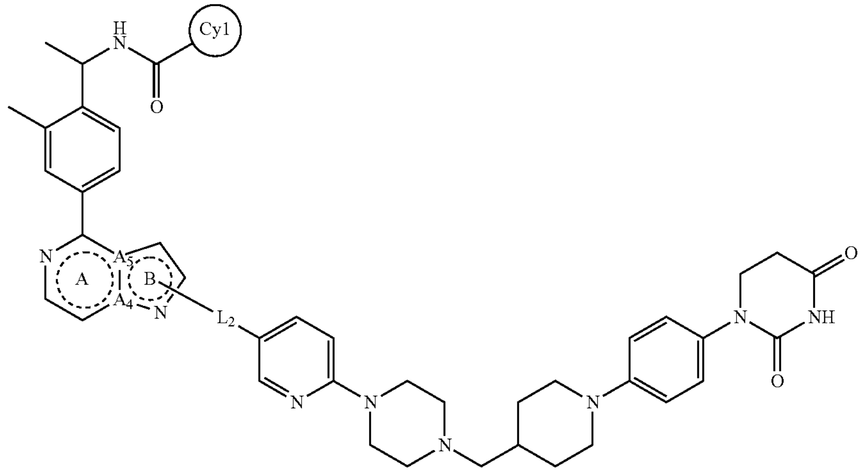

(IV-C)

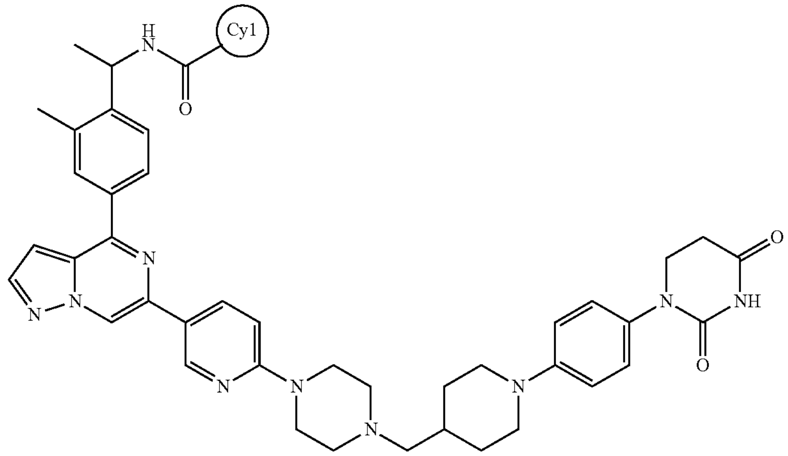

(IV-D)

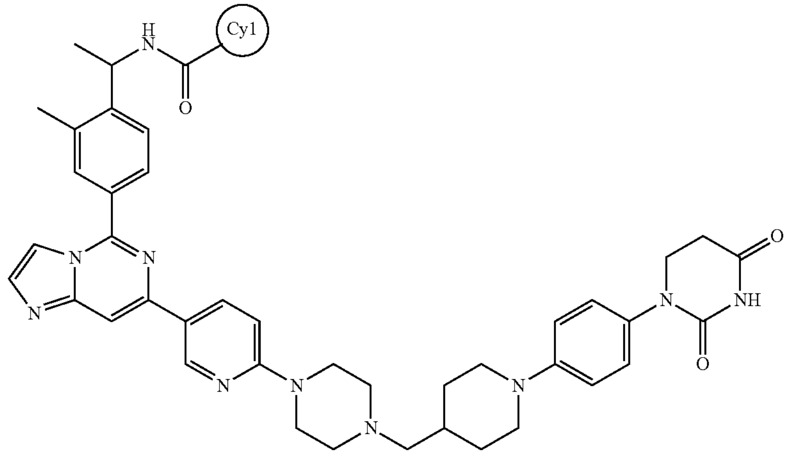

or a pharmaceutically acceptable salt or solvate thereof.

In some embodiments, the compound is selected from the compounds described in Tables 1-3, and pharmaceutically acceptable salts and solvates thereof.

In some embodiments, the compound is selected from the compounds described in Tables 1-3 In some embodiments, the compound is selected from the compounds described in Tables 1-2, and pharmaceutically acceptable salts and solvates thereof.

In some embodiments, the compound is selected from the compounds described in Tables 1-2.

In some embodiments, the compound is selected from the compounds described in Table 1, and pharmaceutically acceptable salts and solvates thereof.

In some embodiments, the compound is selected from the compounds described in Table 1.

In some embodiments, the compound is selected from the compounds described in Table 2, and pharmaceutically acceptable salts and solvates thereof.

In some embodiments, the compound is selected from the compounds described in Table 2.

In some embodiments, the compound is selected from the compounds described in Table 3, and pharmaceutically acceptable salts and solvates thereof.

In some embodiments, the compound is selected from the compounds described in Table 3.

In some embodiments, the compound is selected from the following Table 1:

TABLE 1

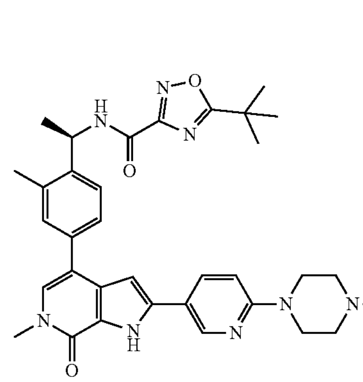

1

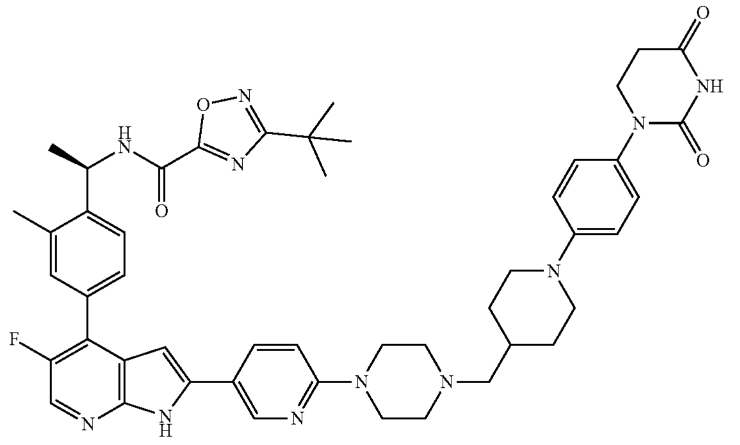 [SMILES: Cc1cc(-c2c(F)cnc3[nH]c(-c4ccc(N5CCN(CC6CCN(c7ccc(N8CCC(=O)NC8=O)cc7)CC6)CC5)nc4)cc23)ccc1[C@@H](C)NC(=O)c1nc(C(C)(C)C)no1]

2

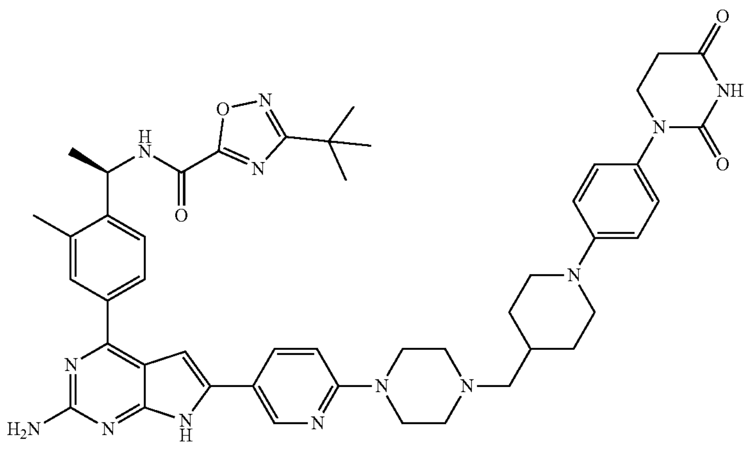 [SMILES: Cc1cc(-c2nc(N)nc3[nH]c(-c4ccc(N5CCN(CC6CCN(c7ccc(N8CCC(=O)NC8=O)cc7)CC6)CC5)nc4)cc23)ccc1[C@@H](C)NC(=O)c1nc(C(C)(C)C)no1]

3

TABLE 1-continued
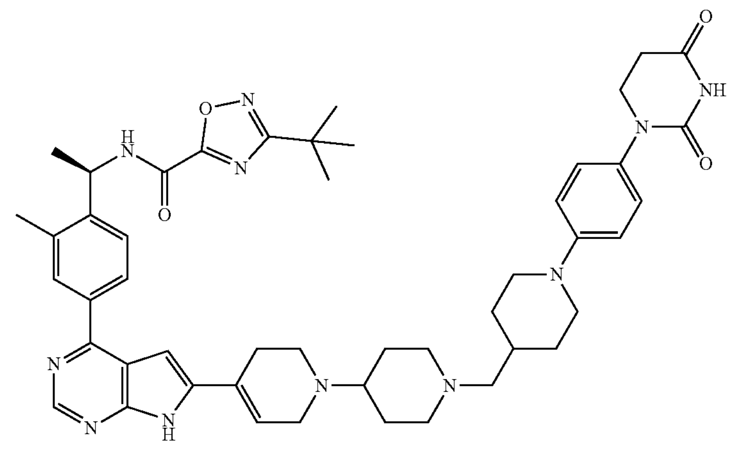 [SMILES: Cc1cc(-c2ncnc3[nH]c(C4=CCN(C5CCN(CC6CCN(c7ccc(N8CCC(=O)NC8=O)cc7)CC6)CC5)CC4)cc23)ccc1[C@@H](C)NC(=O)c1nc(C(C)(C)C)no1]
4
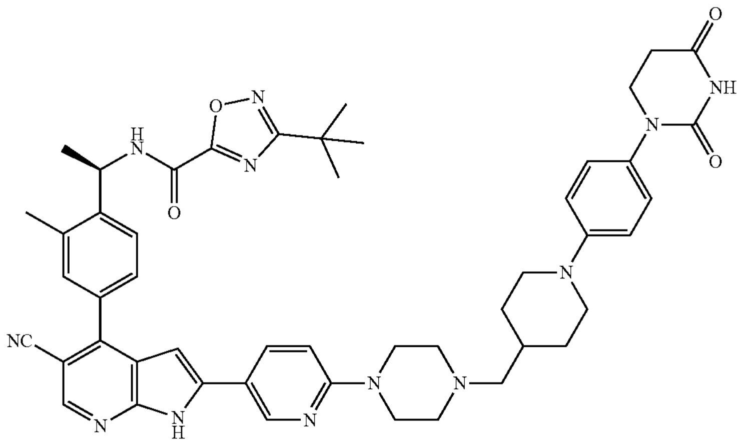 [SMILES: Cc1cc(-c2c(C#N)cnc3[nH]c(-c4ccc(N5CCN(CC6CCN(c7ccc(N8CCC(=O)NC8=O)cc7)CC6)CC5)nc4)cc23)ccc1[C@@H](C)NC(=O)c1nc(C(C)(C)C)no1]
5
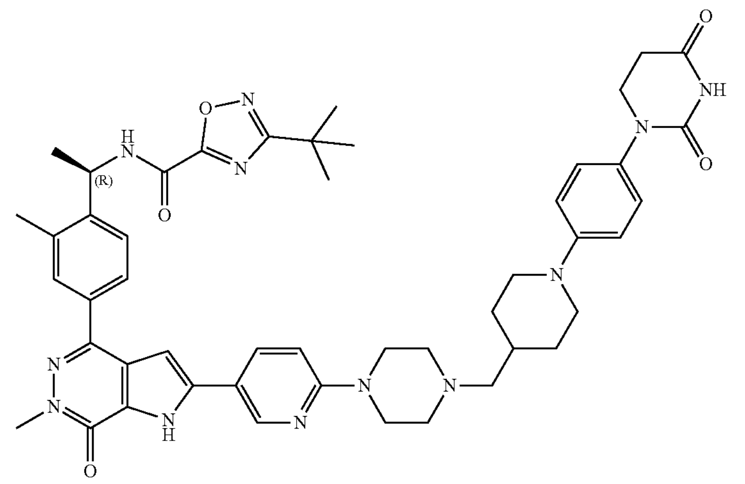
6

TABLE 1-continued
7
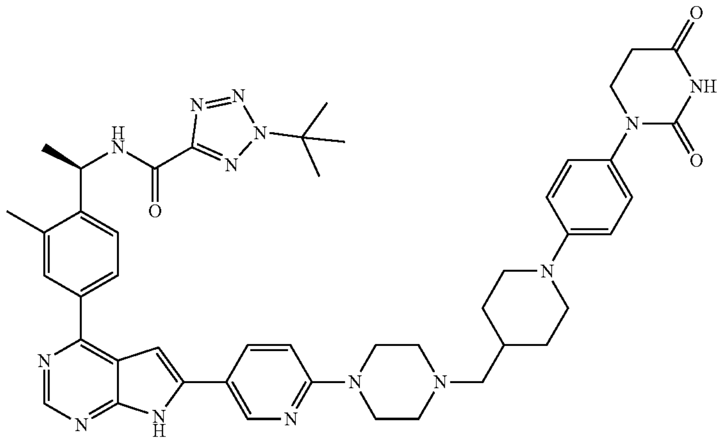 [SMILES: Cc1cc(-c2ncnc3[nH]c(-c4ccc(N5CCN(CC6CCN(c7ccc(N8CCC(=O)NC8=O)cc7)CC6)CC5)nc4)cc23)ccc1[C@@H](C)NC(=O)c1nnn(C(C)(C)C)n1]
8
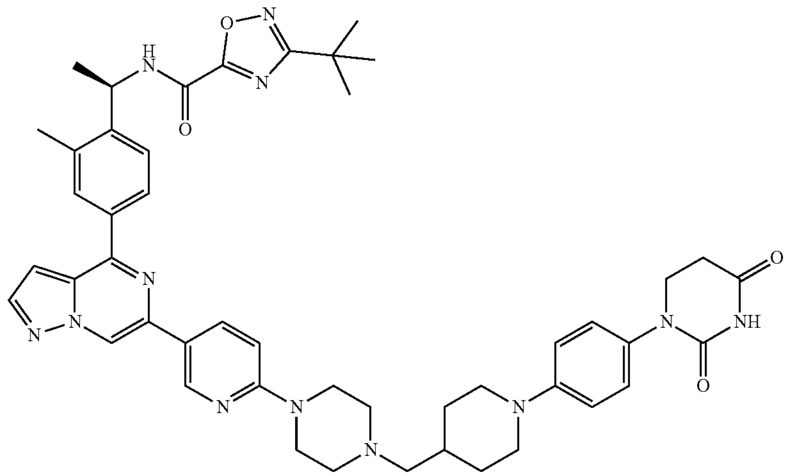
9
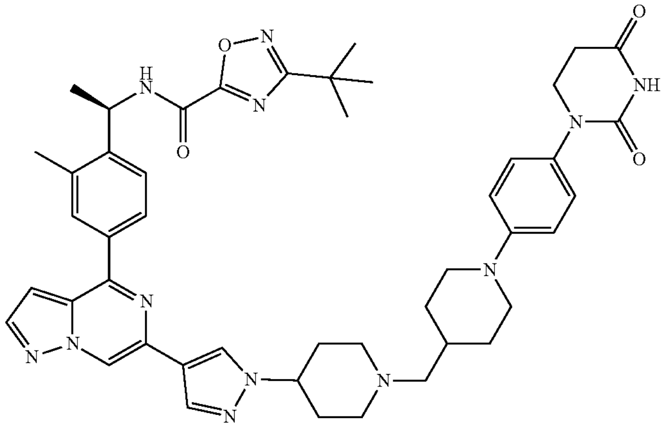 [SMILES: Cc1cc(-c2nc(-c3cnn(C4CCN(CC5CCN(c6ccc(N7CCC(=O)NC7=O)cc6)CC5)CC4)c3)cn3nccc23)ccc1[C@@H](C)NC(=O)c1nc(C(C)(C)C)no1]

TABLE 1-continued
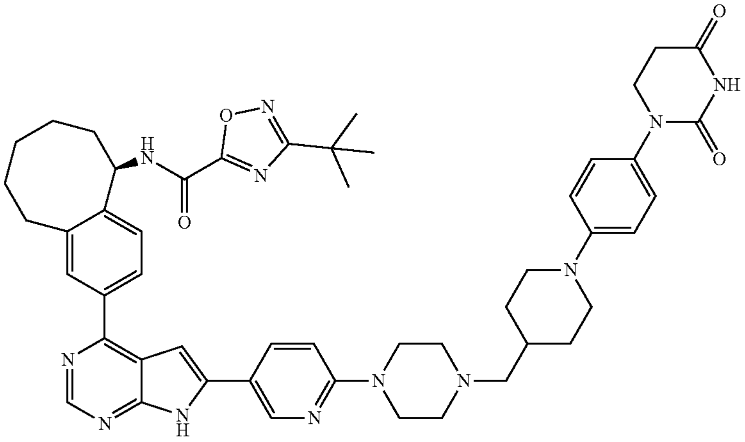
10
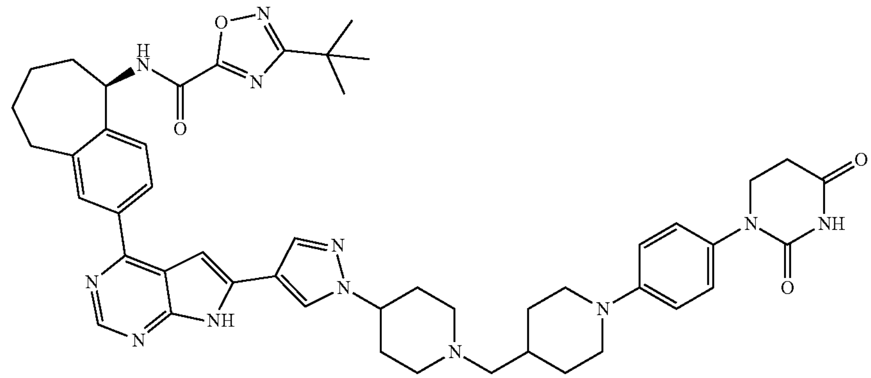 [SMILES: CC(C)(C)c1noc(C(=O)N[C@@H]2CCCCc3cc(-c4ncnc5[nH]c(-c6cnn(C7CCN(CC8CCN(c9ccc(N%10CCC(=O)NC%10=O)cc9)CC8)CC7)c6)cc45)ccc32)n1]
11
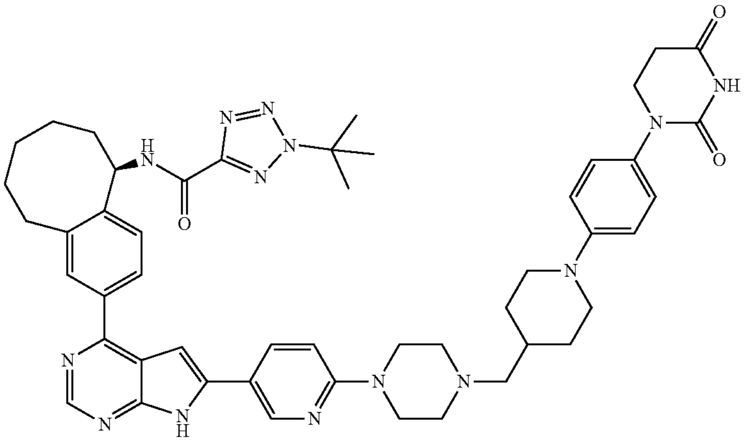 [SMILES: CC(C)(C)n1nnc(C(=O)N[C@@H]2CCCCCc3cc(-c4ncnc5[nH]c(-c6ccc(N7CCN(CC8CCN(c9ccc(N%10CCC(=O)NC%10=O)cc9)CC8)CC7)nc6)cc45)ccc32)n1]
12

TABLE 1-continued
13
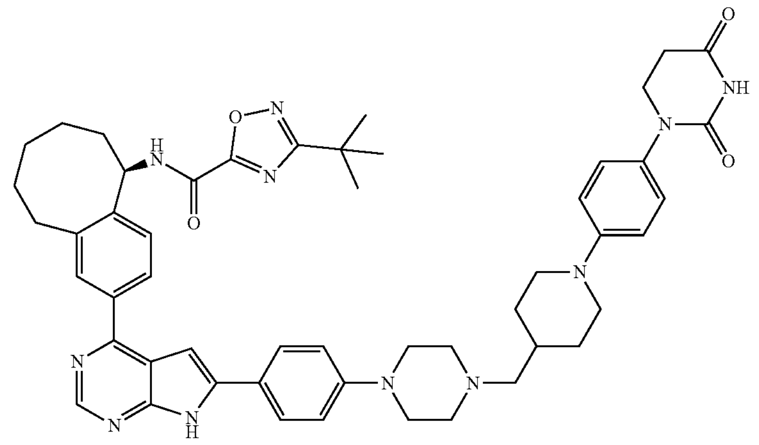 [SMILES: CC(C)(C)c1noc(C(=O)N[C@@H]2CCCCCc3cc(-c4ncnc5[nH]c(-c6ccc(N7CCN(CC8CCN(c9ccc(N%10CCC(=O)NC%10=O)cc9)CC8)CC7)cc6)cc45)ccc32)n1]
14
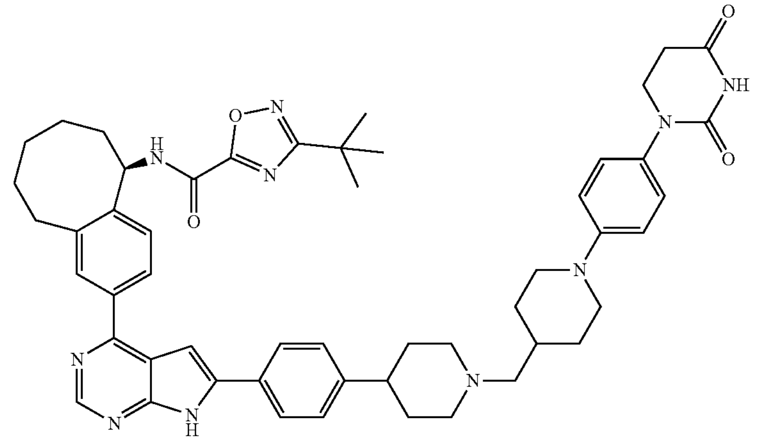 [SMILES: CC(C)(C)c1noc(C(=O)N[C@@H]2CCCCCc3cc(-c4ncnc5[nH]c(-c6ccc(C7CCN(CC8CCN(c9ccc(N%10CCC(=O)NC%10=O)cc9)CC8)CC7)cc6)cc45)ccc32)n1]
15
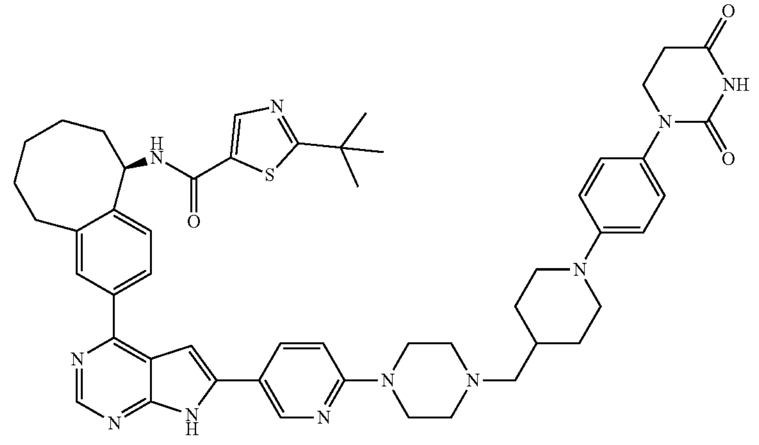 [SMILES: CC(C)(C)c1ncc(C(=O)N[C@@H]2CCCCCc3cc(-c4ncnc5[nH]c(-c6ccc(N7CCN(CC8CCN(c9ccc(N%10CCC(=O)NC%10=O)cc9)CC8)CC7)nc6)cc45)ccc32)s1]

TABLE 1-continued
16
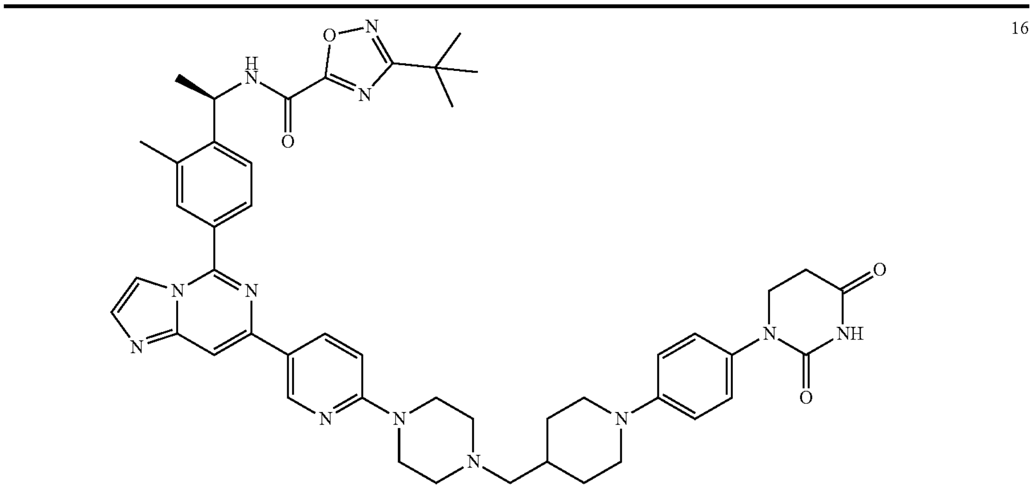
17
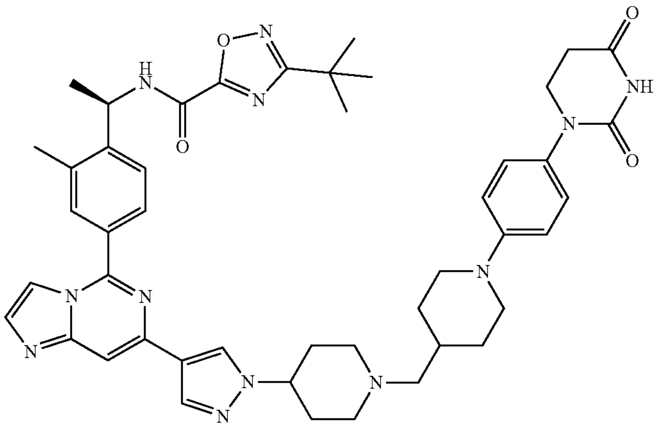 [SMILES: Cc1cc(-c2nc(-c3cnn(C4CCN(CC5CCN(c6ccc(N7CCC(=O)NC7=O)cc6)CC5)CC4)c3)cc3nccn23)ccc1[C@@H](C)NC(=O)c1nc(C(C)(C)C)no1]
18
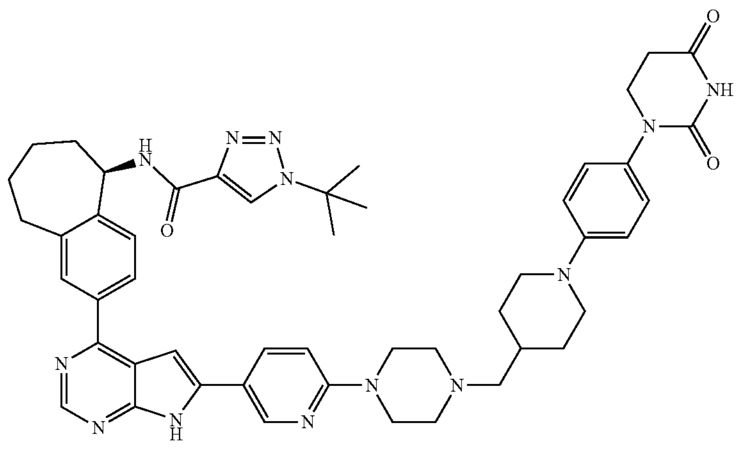 [SMILES: CC(C)(C)n1cc(C(=O)N[C@@H]2CCCCc3cc(-c4ncnc5[nH]c(-c6ccc(N7CCN(CC8CCN(c9ccc(N%10CCC(=O)NC%10=O)cc9)CC8)CC7)nc6)cc45)ccc32)nn1]

TABLE 1-continued
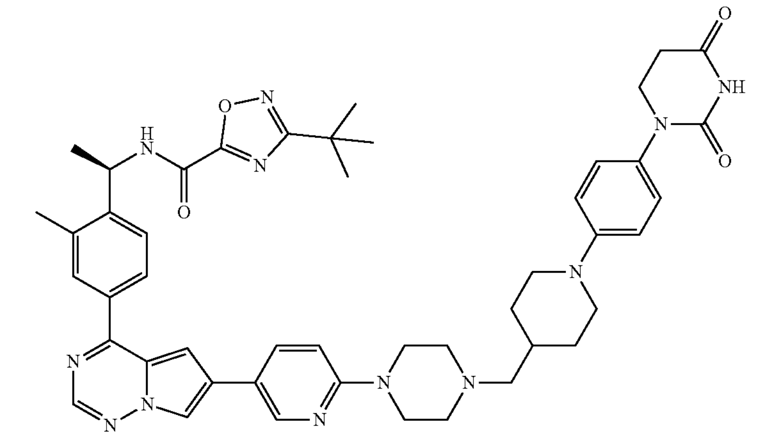 [SMILES: Cc1cc(-c2ncnn3cc(-c4ccc(N5CCN(CC6CCN(c7ccc(N8CCC(=O)NC8=O)cc7)CC6)CC5)nc4)cc23)ccc1[C@@H](C)NC(=O)c1nc(C(C)(C)C)no1]
19
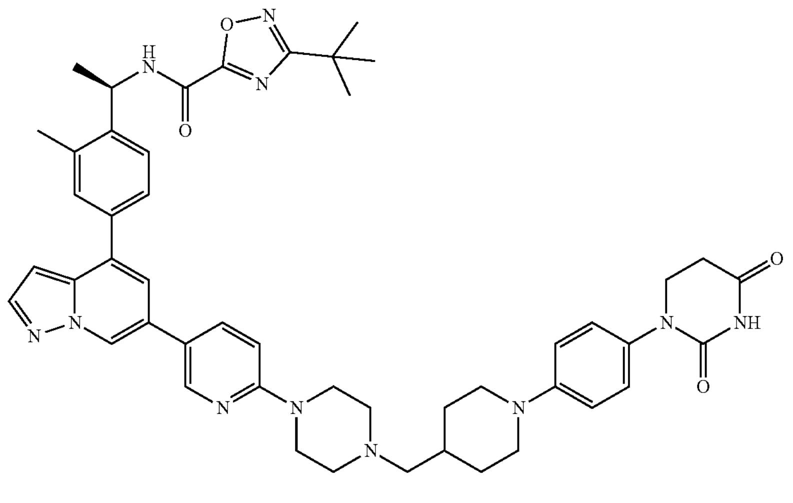
20
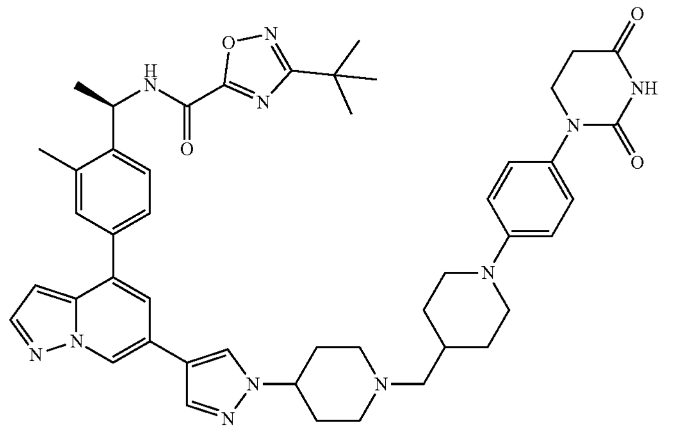 [SMILES: Cc1cc(-c2cc(-c3cnn(C4CCN(CC5CCN(c6ccc(N7CCC(=O)NC7=O)cc6)CC5)CC4)c3)cn3nccc23)ccc1[C@@H](C)NC(=O)c1nc(C(C)(C)C)no1]
21

TABLE 1-continued
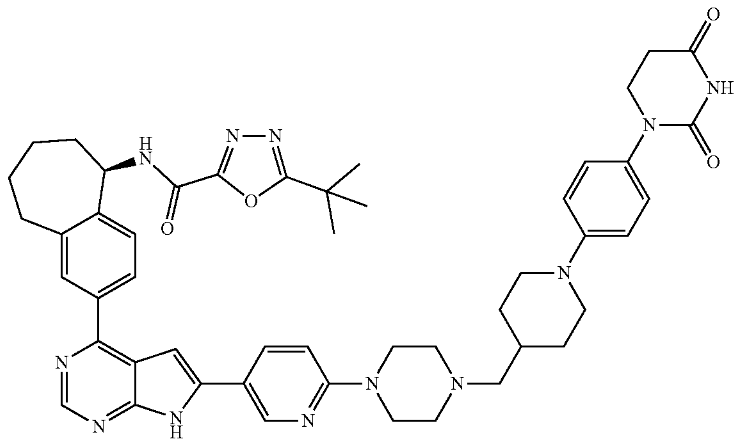 [SMILES: CC(C)(C)c1nnc(C(=O)N[C@@H]2CCCCc3cc(-c4ncnc5[nH]c(-c6ccc(N7CCN(CC8CCN(c9ccc(N%10CCC(=O)NC%10=O)cc9)CC8)CC7)nc6)cc45)ccc32)o1]
22
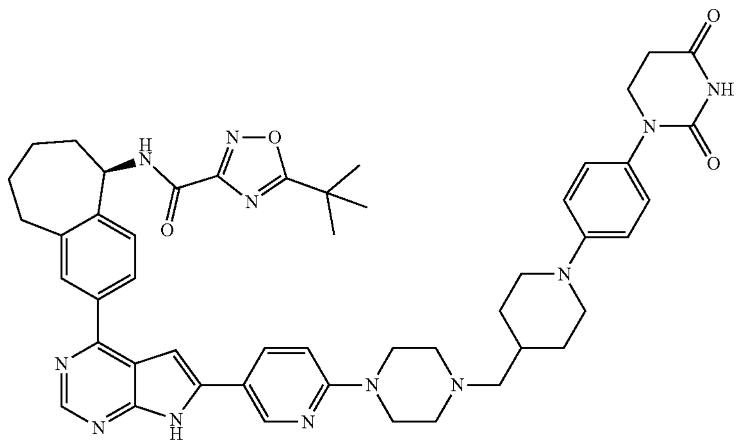 [SMILES: CC(C)(C)c1nc(C(=O)N[C@@H]2CCCCc3cc(-c4ncnc5[nH]c(-c6ccc(N7CCN(CC8CCN(c9ccc(N%10CCC(=O)NC%10=O)cc9)CC8)CC7)nc6)cc45)ccc32)no1]
23
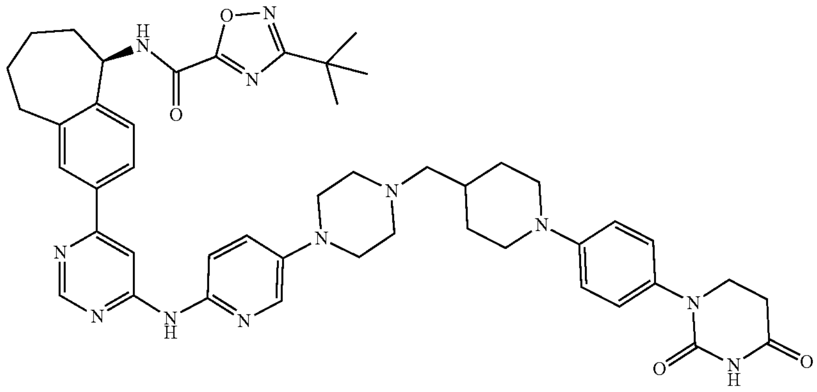 [SMILES: CC(C)(C)c1noc(C(=O)N[C@@H]2CCCCc3cc(-c4cc(Nc5ccc(N6CCN(CC7CCN(c8ccc(N9CCC(=O)NC9=O)cc8)CC7)CC6)cn5)ncn4)ccc32)n1]
24

TABLE 1-continued
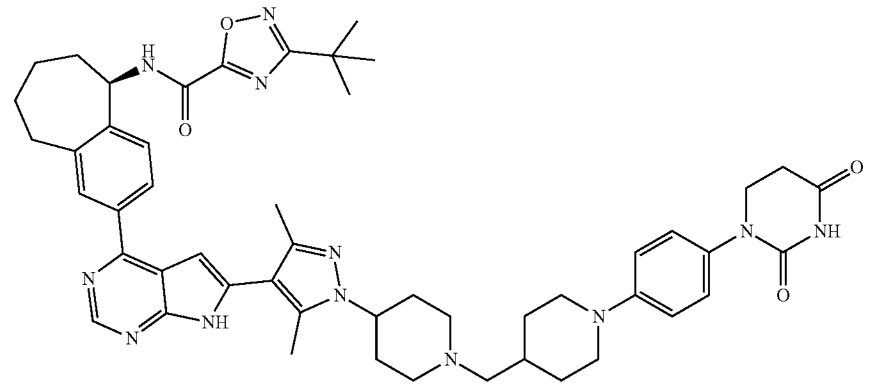 [SMILES: Cc1nn(C2CCN(CC3CCN(c4ccc(N5CCC(=O)NC5=O)cc4)CC3)CC2)c(C)c1-c1cc2c(-c3ccc4c(c3)CCCC[C@H]4NC(=O)c3nc(C(C)(C)C)no3)ncnc2[nH]1]
25
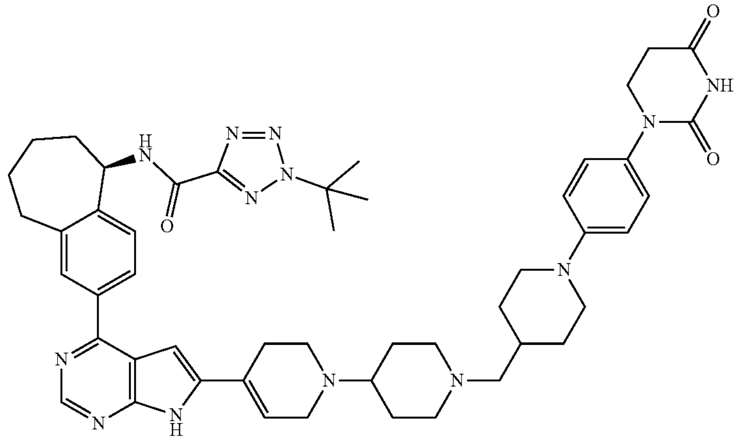 [SMILES: CC(C)(C)n1nnc(C(=O)N[C@@H]2CCCCc3cc(-c4ncnc5[nH]c(C6=CCN(C7CCN(CC8CCN(c9ccc(N%10CCC(=O)NC%10=O)cc9)CC8)CC7)CC6)cc45)ccc32)n1]
26
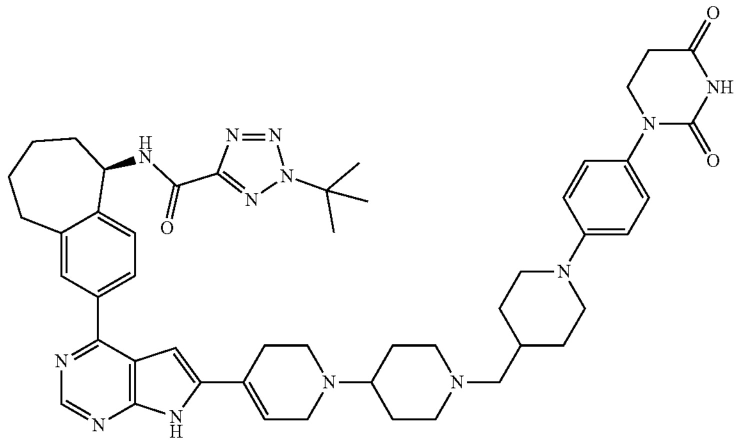 [SMILES: CC(C)(C)n1nnc(C(=O)N[C@@H]2CCCCc3cc(-c4ncnc5[nH]c(C6=CCN(C7CCN(CC8CCN(c9ccc(N%10CCC(=O)NC%10=O)cc9)CC8)CC7)CC6)cc45)ccc32)n1]
27

TABLE 1-continued
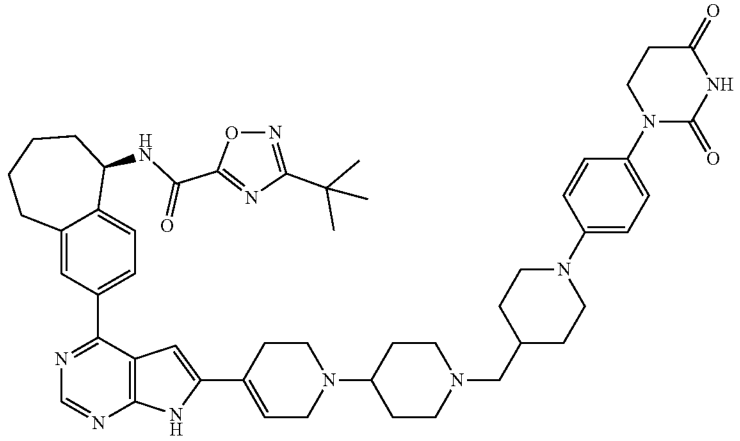 [SMILES: CC(C)(C)c1noc(C(=O)N[C@@H]2CCCCc3cc(-c4ncnc5[nH]c(C6=CCN(C7CCN(CC8CCN(c9ccc(N%10CCC(=O)NC%10=O)cc9)CC8)CC7)CC6)cc45)ccc32)n1]
28
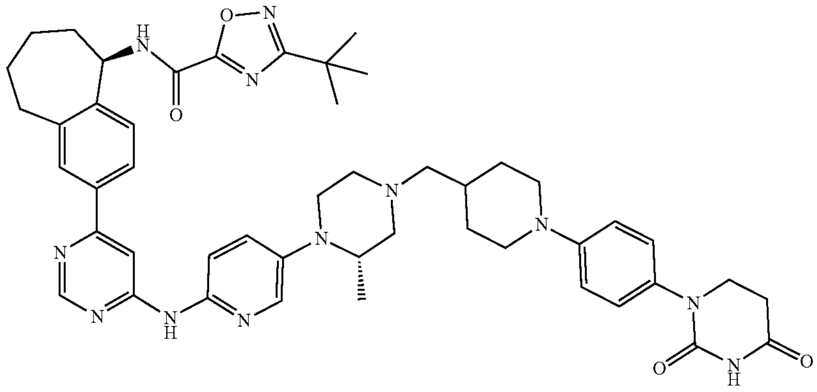 [SMILES: C[C@H]1CN(CC2CCN(c3ccc(N4CCC(=O)NC4=O)cc3)CC2)CCN1c1ccc(Nc2cc(-c3ccc4c(c3)CCCC[C@H]4NC(=O)c3nc(C(C)(C)C)no3)ncn2)nc1]
29
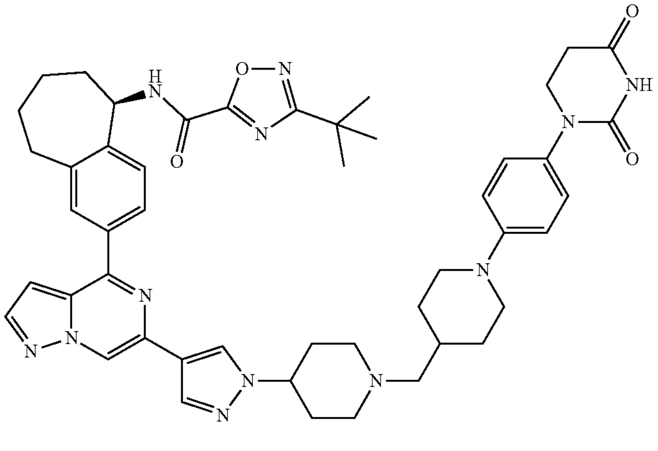 [SMILES: CC(C)(C)c1noc(C(=O)N[C@@H]2CCCCc3cc(-c4nc(-c5cnn(C6CCN(CC7CCN(c8ccc(N9CCC(=O)NC9=O)cc8)CC7)CC6)c5)cn5nccc45)ccc32)n1]
30

TABLE 1-continued
31
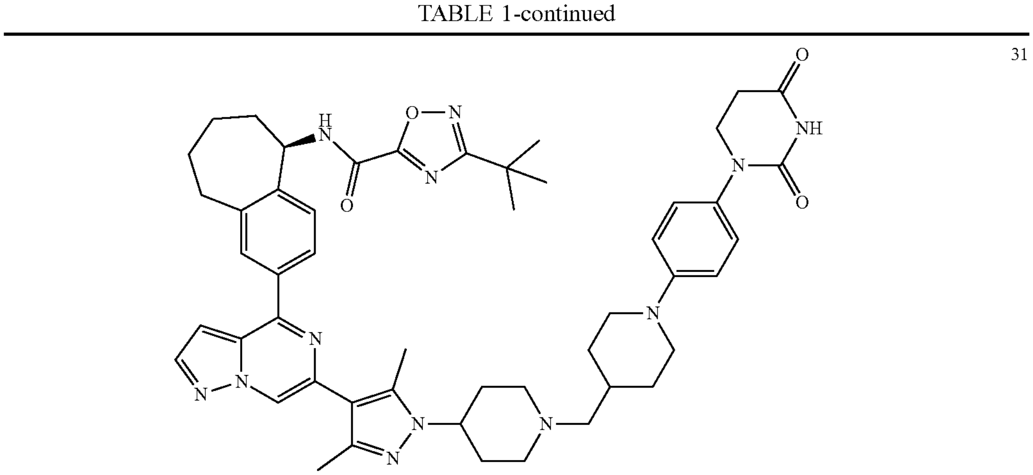
32
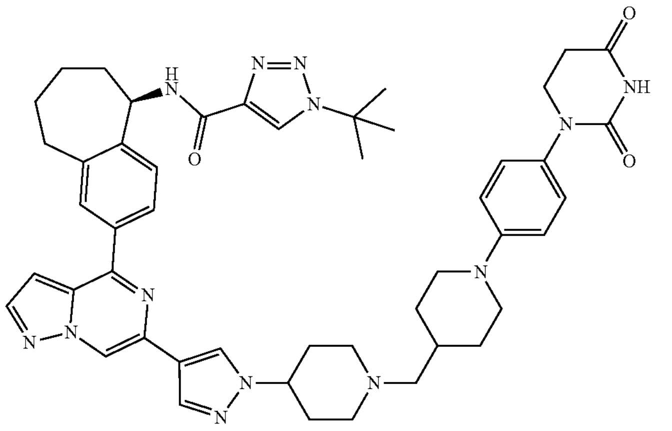 [SMILES: CC(C)(C)n1cc(C(=O)N[C@@H]2CCCCc3cc(-c4nc(-c5cnn(C6CCN(CC7CCN(c8ccc(N9CCC(=O)NC9=O)cc8)CC7)CC6)c5)cn5nccc45)ccc32)nn1]
33
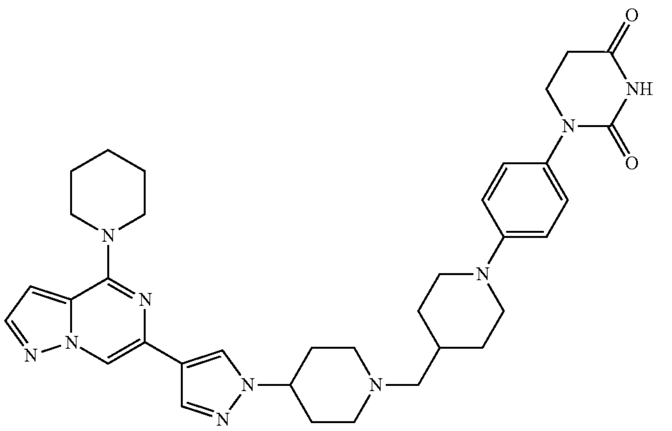 [SMILES: O=C1CCN(c2ccc(N3CCC(CN4CCC(n5cc(-c6cn7nccc7c(N7CCCCC7)n6)cn5)CC4)CC3)cc2)C(=O)N1]

TABLE 1-continued
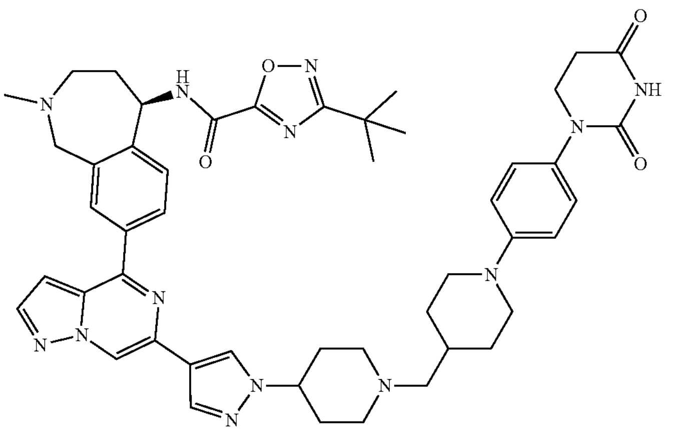 [SMILES: CN1CC[C@@H](NC(=O)c2nc(C(C)(C)C)no2)c2ccc(-c3nc(-c4cnn(C5CCN(CC6CCN(c7ccc(N8CCC(=O)NC8=O)cc7)CC6)CC5)c4)cn4nccc34)cc2C1]
34
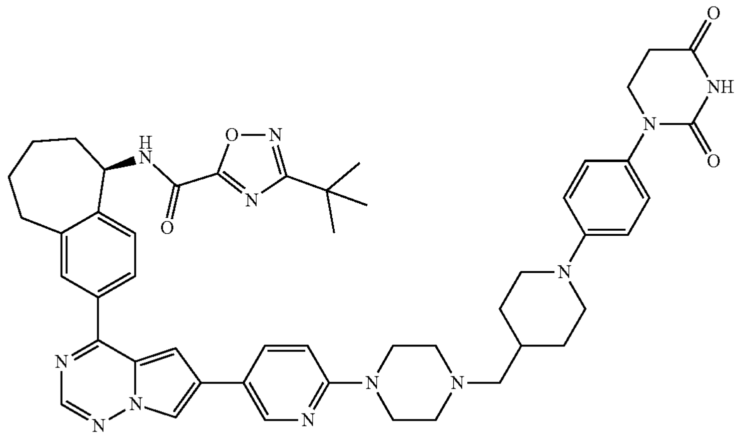 [SMILES: CC(C)(C)c1noc(C(=O)N[C@@H]2CCCCc3cc(-c4ncnn5cc(-c6ccc(N7CCN(CC8CCN(c9ccc(N%10CCC(=O)NC%10=O)cc9)CC8)CC7)nc6)cc45)ccc32)n1]
35
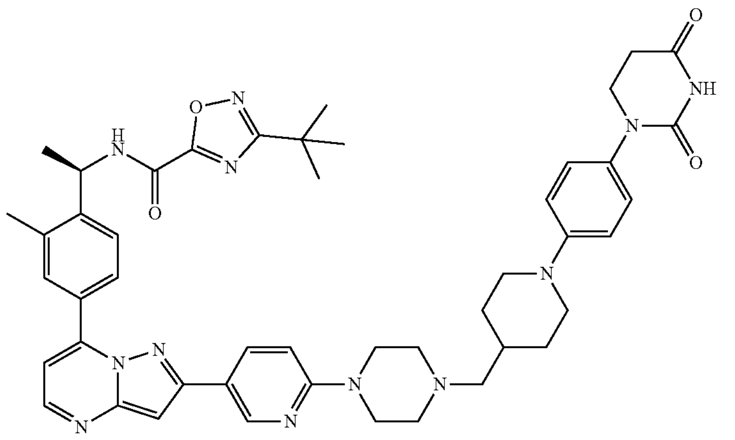 [SMILES: Cc1cc(-c2ccnc3cc(-c4ccc(N5CCN(CC6CCN(c7ccc(N8CCC(=O)NC8=O)cc7)CC6)CC5)nc4)nn23)ccc1[C@@H](C)NC(=O)c1nc(C(C)(C)C)no1]
36

TABLE 1-continued
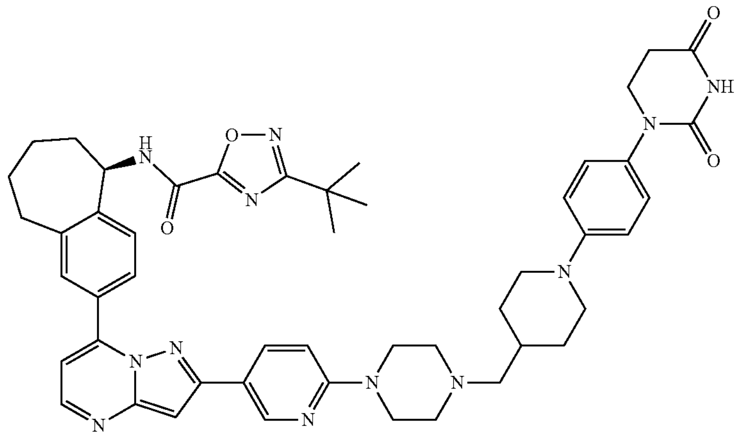 [SMILES: CC(C)(C)c1noc(C(=O)N[C@@H]2CCCCc3cc(-c4ccnc5cc(-c6ccc(N7CCN(CC8CCN(c9ccc(N%10CCC(=O)NC%10=O)cc9)CC8)CC7)nc6)nn45)ccc32)n1]
37
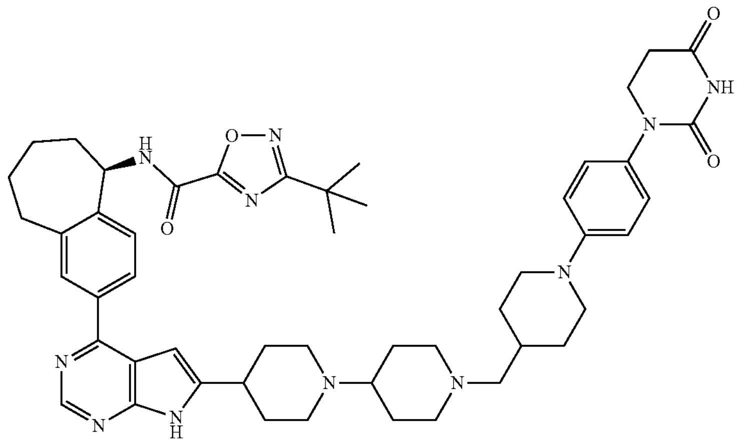 [SMILES: CC(C)(C)c1noc(C(=O)N[C@@H]2CCCCc3cc(-c4ncnc5[nH]c(C6CCN(C7CCN(CC8CCN(c9ccc(N%10CCC(=O)NC%10=O)cc9)CC8)CC7)CC6)cc45)ccc32)n1]
38
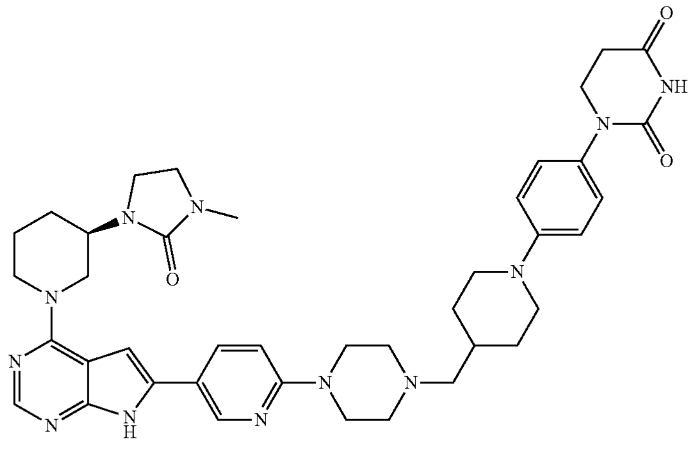 [SMILES: CN1CCN([C@@H]2CCCN(c3ncnc4[nH]c(-c5ccc(N6CCN(CC7CCN(c8ccc(N9CCC(=O)NC9=O)cc8)CC7)CC6)nc5)cc34)C2)C1=O]
39

TABLE 1-continued
40
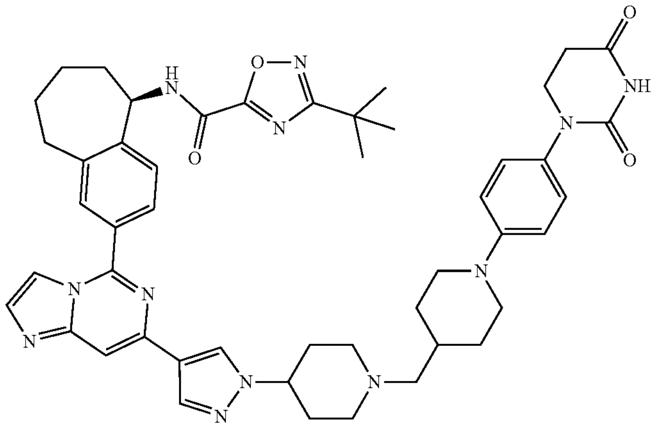 [SMILES: CC(C)(C)c1noc(C(=O)N[C@@H]2CCCCc3cc(-c4nc(-c5cnn(C6CCN(CC7CCN(c8ccc(N9CCC(=O)NC9=O)cc8)CC7)CC6)c5)cc5nccn45)ccc32)n1]
41
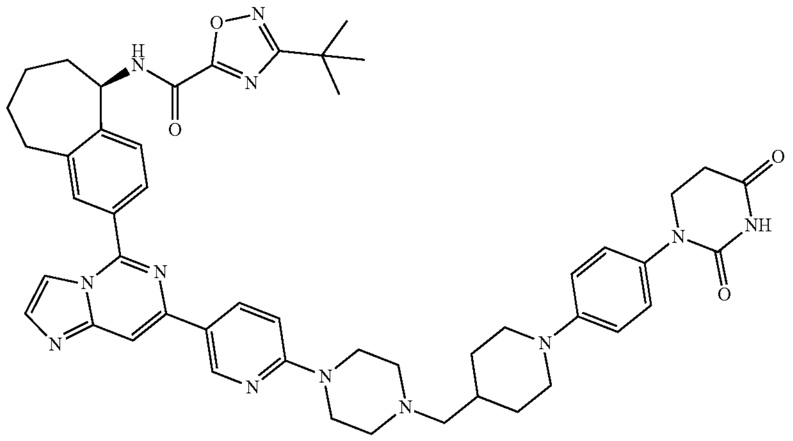 [SMILES: CC(C)(C)c1noc(C(=O)N[C@@H]2CCCCc3cc(-c4nc(-c5ccc(N6CCN(CC7CCN(c8ccc(N9CCC(=O)NC9=O)cc8)CC7)CC6)nc5)cc5nccn45)ccc32)n1]
42
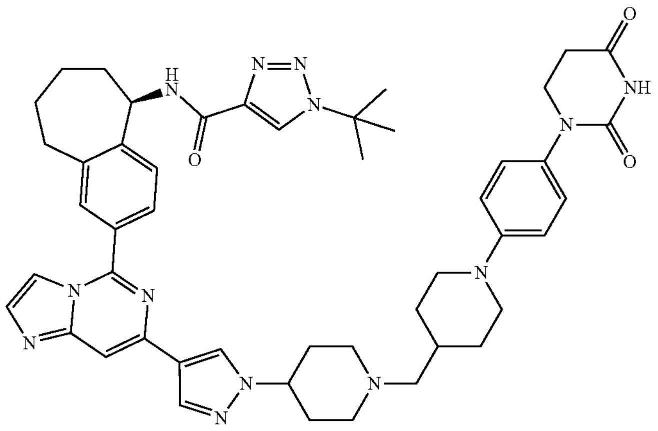 [SMILES: CC(C)(C)n1cc(C(=O)N[C@@H]2CCCCc3cc(-c4nc(-c5cnn(C6CCN(CC7CCN(c8ccc(N9CCC(=O)NC9=O)cc8)CC7)CC6)c5)cc5nccn45)ccc32)nn1]

TABLE 1-continued
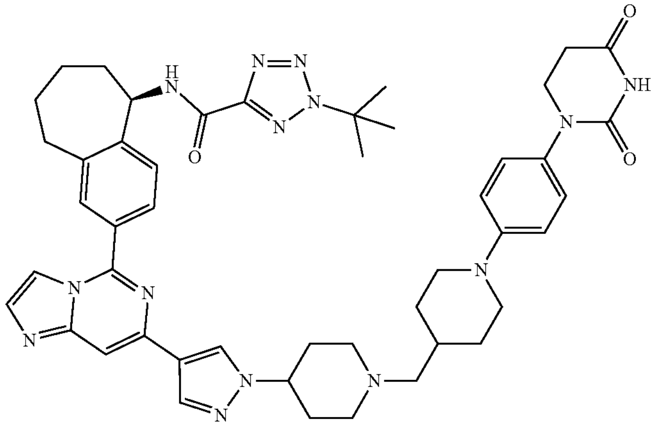 [SMILES: CC(C)(C)n1nnc(C(=O)N[C@@H]2CCCCc3cc(-c4nc(-c5cnn(C6CCN(CC7CCN(c8ccc(N9CCC(=O)NC9=O)cc8)CC7)CC6)c5)cc5nccn45)ccc32)n1]
43
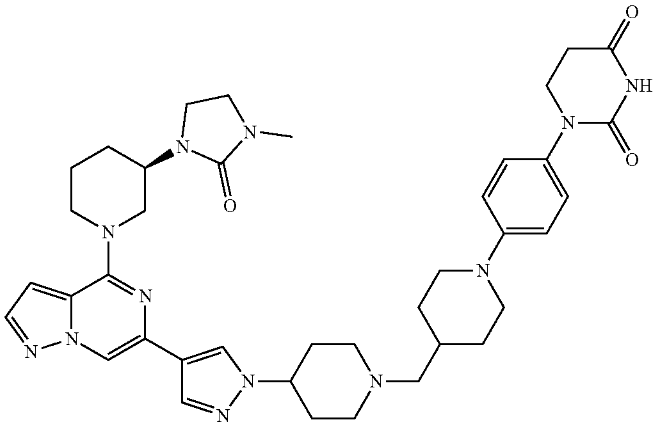 [SMILES: CN1CCN([C@@H]2CCCN(c3nc(-c4cnn(C5CCN(CC6CCN(c7ccc(N8CCC(=O)NC8=O)cc7)CC6)CC5)c4)cn4nccc34)C2)C1=O]
44
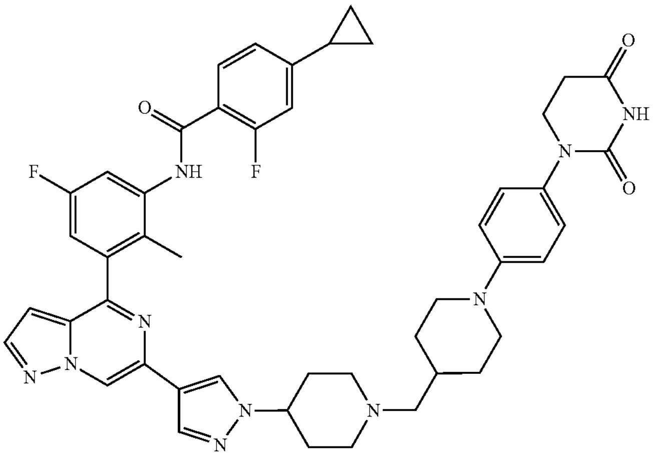 [SMILES: Cc1c(NC(=O)c2ccc(C3CC3)cc2F)cc(F)cc1-c1nc(-c2cnn(C3CCN(CC4CCN(c5ccc(N6CCC(=O)NC6=O)cc5)CC4)CC3)c2)cn2nccc12]
45

TABLE 1-continued
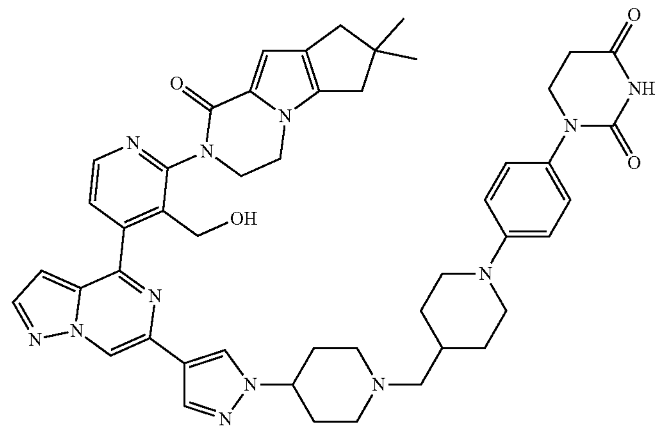 [SMILES: CC1(C)Cc2cc3n(c2C1)CCN(c1nccc(-c2nc(-c4cnn(C5CCN(CC6CCN(c7ccc(N8CCC(=O)NC8=O)cc7)CC6)CC5)c4)cn4nccc24)c1CO)C3=O]
46
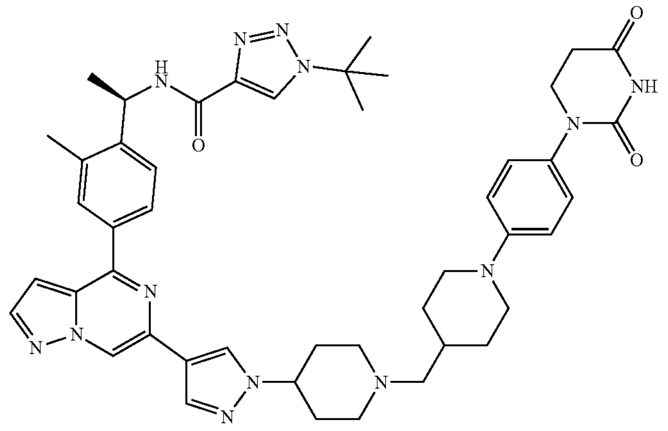
47
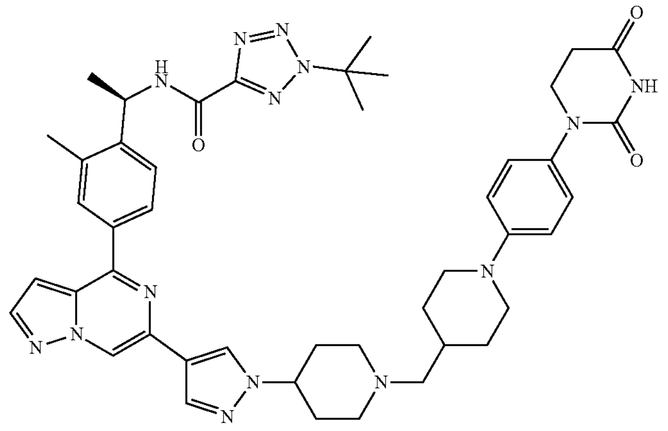 [SMILES: Cc1cc(-c2nc(-c3cnn(C4CCN(CC5CCN(c6ccc(N7CCC(=O)NC7=O)cc6)CC5)CC4)c3)cn3nccc23)ccc1[C@@H](C)NC(=O)c1nnn(C(C)(C)C)n1]
48

TABLE 1-continued
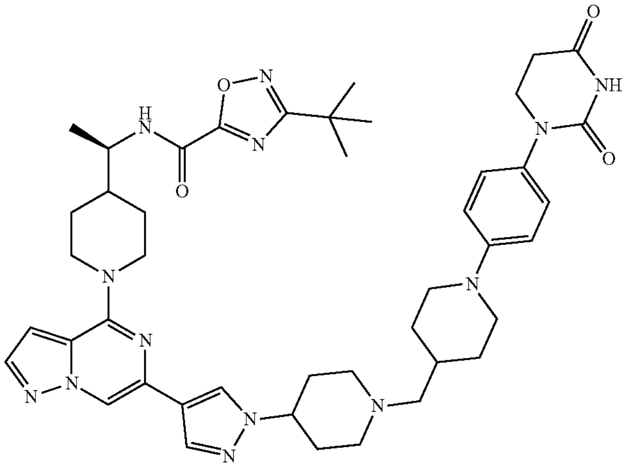 [SMILES: C[C@@H](NC(=O)c1nc(C(C)(C)C)no1)C1CCN(c2nc(-c3cnn(C4CCN(CC5CCN(c6ccc(N7CCC(=O)NC7=O)cc6)CC5)CC4)c3)cn3nccc23)CC1]
49
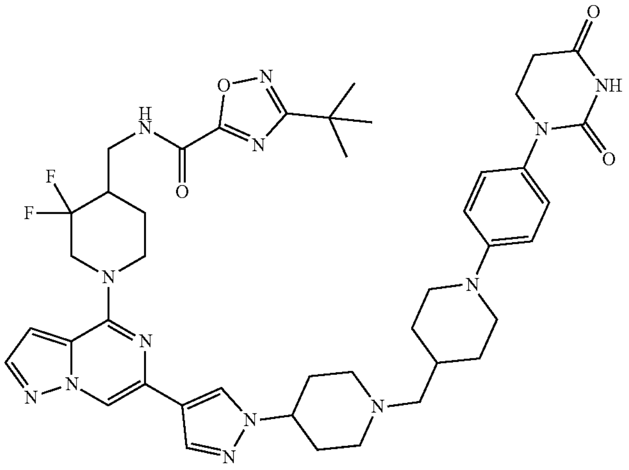 [SMILES: CC(C)(C)c1noc(C(=O)NCC2CCN(c3nc(-c4cnn(C5CCN(CC6CCN(c7ccc(N8CCC(=O)NC8=O)cc7)CC6)CC5)c4)cn4nccc34)CC2(F)F)n1]
50
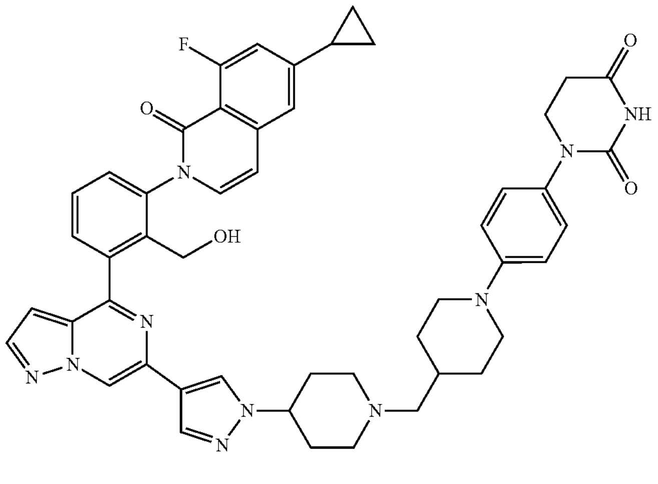 [SMILES: O=C1CCN(c2ccc(N3CCC(CN4CCC(n5cc(-c6cn7nccc7c(-c7cccc(-n8ccc9cc(C%10CC%10)cc(F)c9c8=O)c7CO)n6)cn5)CC4)CC3)cc2)C(=O)N1]
51

TABLE 1-continued
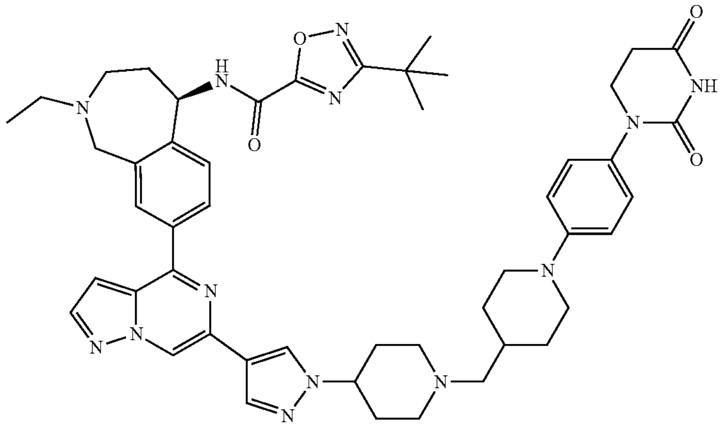 [SMILES: CCN1CC[C@@H](NC(=O)c2nc(C(C)(C)C)no2)c2ccc(-c3nc(-c4cnn(C5CCN(CC6CCN(c7ccc(N8CCC(=O)NC8=O)cc7)CC6)CC5)c4)cn4nccc34)cc2C1]
52
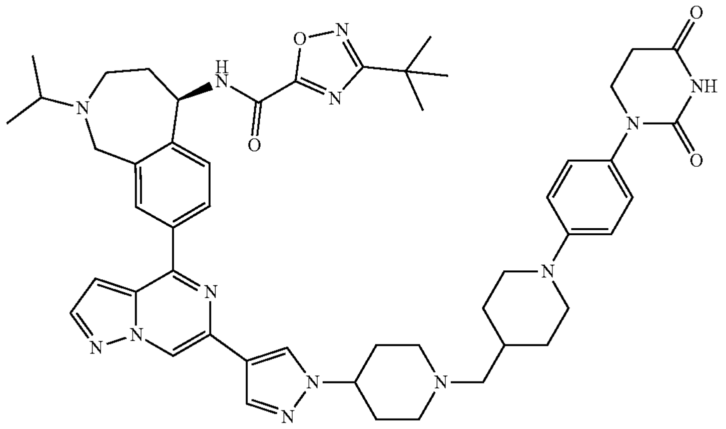 [SMILES: CC(C)N1CC[C@@H](NC(=O)c2nc(C(C)(C)C)no2)c2ccc(-c3nc(-c4cnn(C5CCN(CC6CCN(c7ccc(N8CCC(=O)NC8=O)cc7)CC6)CC5)c4)cn4nccc34)cc2C1]
53
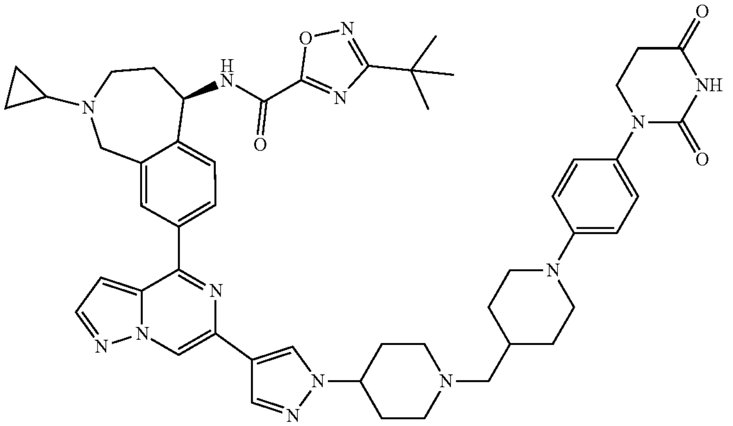 [SMILES: CC(C)(C)c1noc(C(=O)N[C@@H]2CCN(C3CC3)Cc3cc(-c4nc(-c5cnn(C6CCN(CC7CCN(c8ccc(N9CCC(=O)NC9=O)cc8)CC7)CC6)c5)cn5nccc45)ccc32)n1]
54

TABLE 1-continued
55
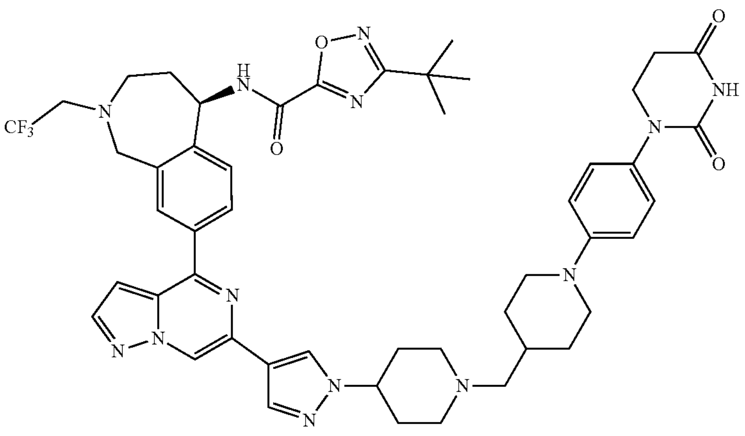 [SMILES: CC(C)(C)c1noc(C(=O)N[C@@H]2CCN(CC(F)(F)F)Cc3cc(-c4nc(-c5cnn(C6CCN(CC7CCN(c8ccc(N9CCC(=O)NC9=O)cc8)CC7)CC6)c5)cn5nccc45)ccc32)n1]
56
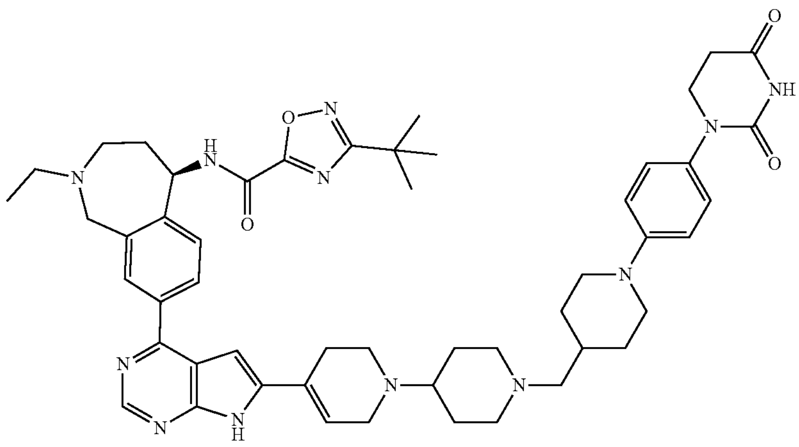 [SMILES: CCN1CC[C@@H](NC(=O)c2nc(C(C)(C)C)no2)c2ccc(-c3ncnc4[nH]c(C5=CCN(C6CCN(CC7CCN(c8ccc(N9CCC(=O)NC9=O)cc8)CC7)CC6)CC5)cc34)cc2C1]
57
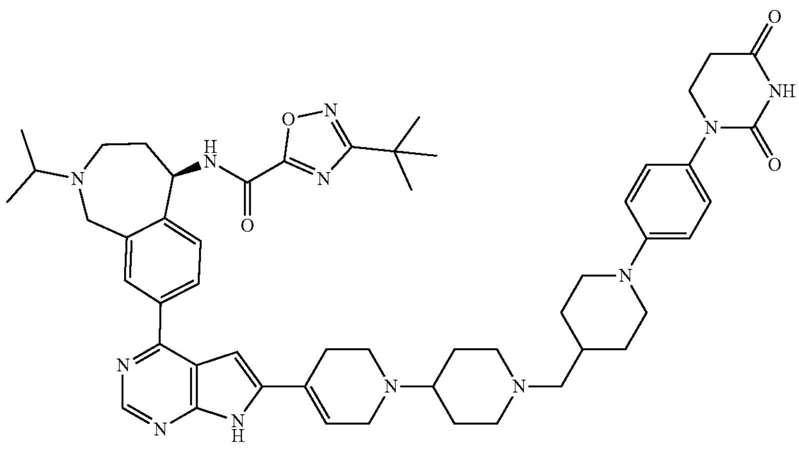 [SMILES: CC(C)N1CC[C@@H](NC(=O)c2nc(C(C)(C)C)no2)c2ccc(-c3ncnc4[nH]c(C5=CCN(C6CCN(CC7CCN(c8ccc(N9CCC(=O)NC9=O)cc8)CC7)CC6)CC5)cc34)cc2C1]

TABLE 1-continued
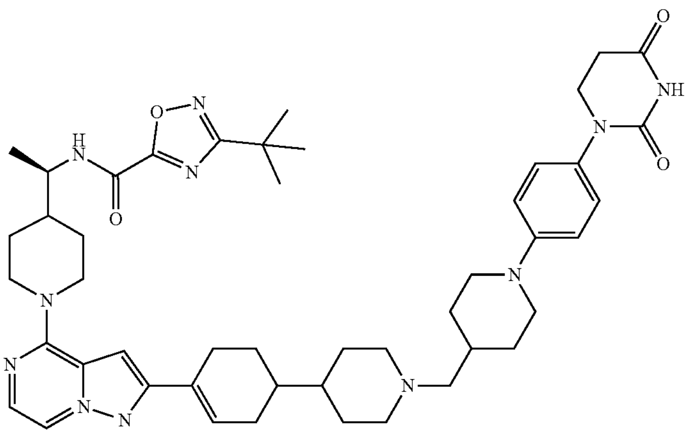
58
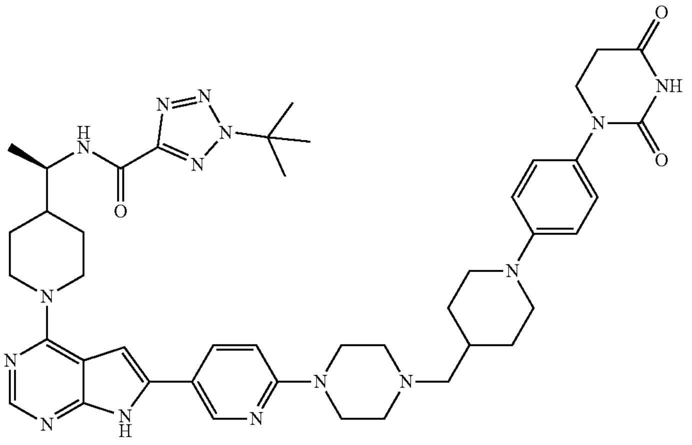 [SMILES: C[C@@H](NC(=O)c1nnn(C(C)(C)C)n1)C1CCN(c2ncnc3[nH]c(-c4ccc(N5CCN(CC6CCN(c7ccc(N8CCC(=O)NC8=O)cc7)CC6)CC5)nc4)cc23)CC1]
59
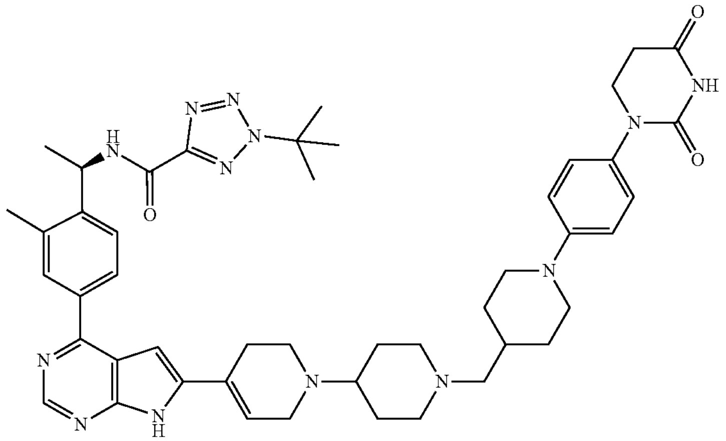 [SMILES: Cc1cc(-c2ncnc3[nH]c(C4=CCN(C5CCN(CC6CCN(c7ccc(N8CCC(=O)NC8=O)cc7)CC6)CC5)CC4)cc23)ccc1[C@@H](C)NC(=O)c1nnn(C(C)(C)C)n1]
60

TABLE 1-continued
61
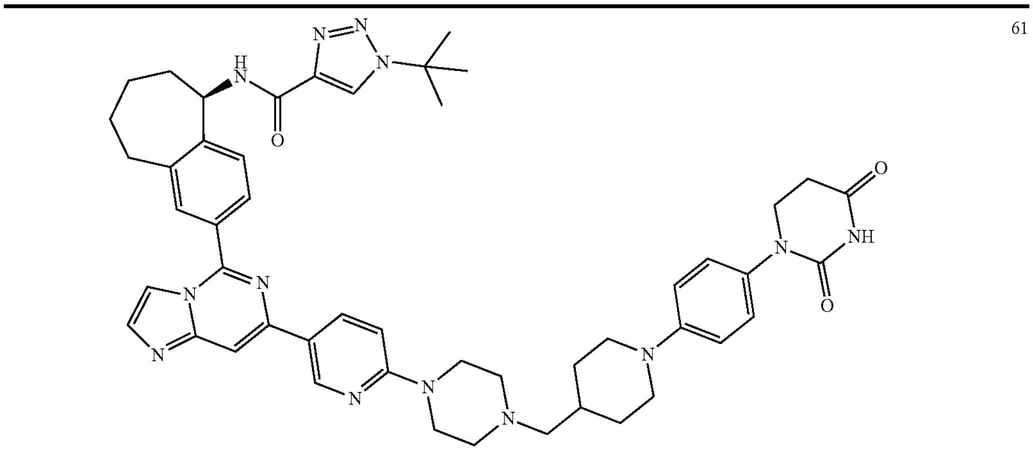
62
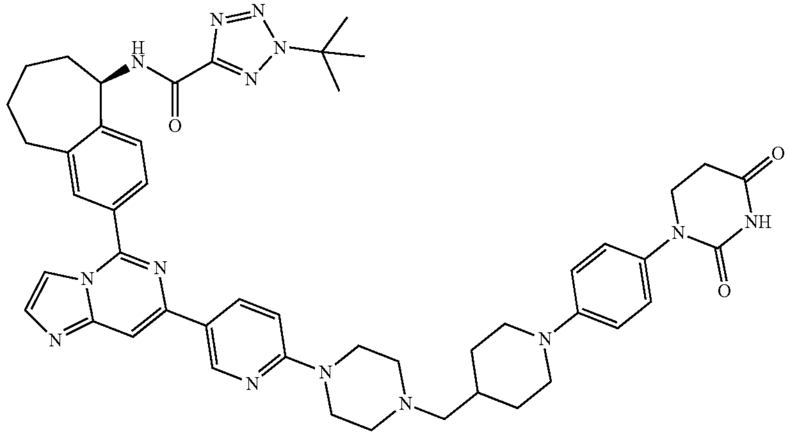 [SMILES: CC(C)(C)n1nnc(C(=O)N[C@@H]2CCCCc3cc(-c4nc(-c5ccc(N6CCN(CC7CCN(c8ccc(N9CCC(=O)NC9=O)cc8)CC7)CC6)nc5)cc5nccn45)ccc32)n1]
63
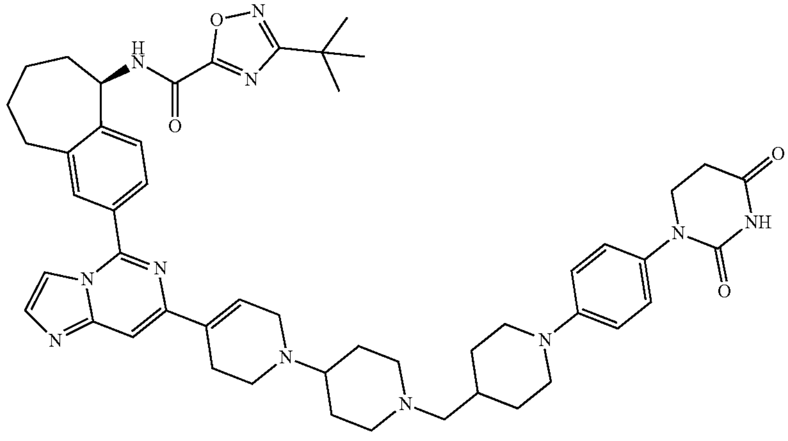 [SMILES: CC(C)(C)c1noc(C(=O)N[C@@H]2CCCCc3cc(-c4nc(C5=CCN(C6CCN(CC7CCN(c8ccc(N9CCC(=O)NC9=O)cc8)CC7)CC6)CC5)cc5nccn45)ccc32)n1]

TABLE 1-continued
64
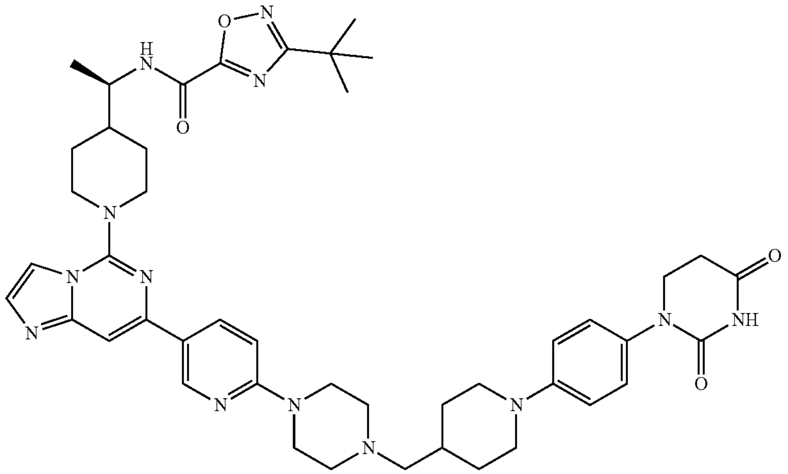 [SMILES: C[C@@H](NC(=O)c1nc(C(C)(C)C)no1)C1CCN(c2nc(-c3ccc(N4CCN(CC5CCN(c6ccc(N7CCC(=O)NC7=O)cc6)CC5)CC4)nc3)cc3nccn23)CC1]
65
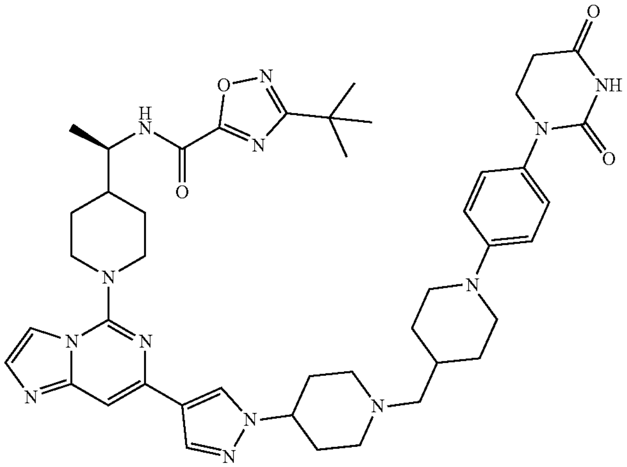 [SMILES: C[C@@H](NC(=O)c1nc(C(C)(C)C)no1)C1CCN(c2nc(-c3cnn(C4CCN(CC5CCN(c6ccc(N7CCC(=O)NC7=O)cc6)CC5)CC4)c3)cc3nccn23)CC1]
66
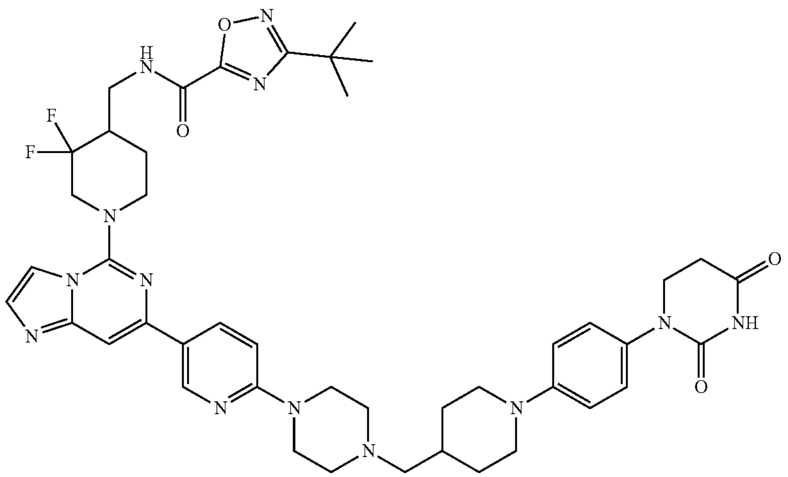 [SMILES: CC(C)(C)c1noc(C(=O)NCC2CCN(c3nc(-c4ccc(N5CCN(CC6CCN(c7ccc(N8CCC(=O)NC8=O)cc7)CC6)CC5)nc4)cc4nccn34)CC2(F)F)n1]

TABLE 1-continued
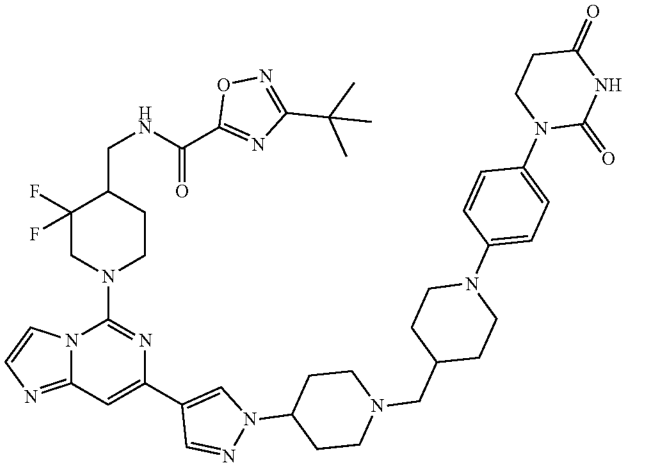 [SMILES: CC(C)(C)c1noc(C(=O)NCC2CCN(c3nc(-c4cnn(C5CCN(CC6CCN(c7ccc(N8CCC(=O)NC8=O)cc7)CC6)CC5)c4)cc4nccn34)CC2(F)F)n1]
67
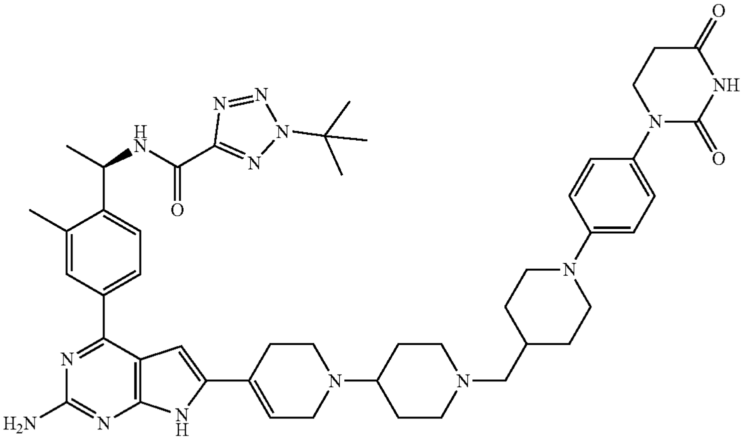 [SMILES: Cc1cc(-c2nc(N)nc3[nH]c(C4=CCN(C5CCN(CC6CCN(c7ccc(N8CCC(=O)NC8=O)cc7)CC6)CC5)CC4)cc23)ccc1[C@@H](C)NC(=O)c1nnn(C(C)(C)C)n1]
68
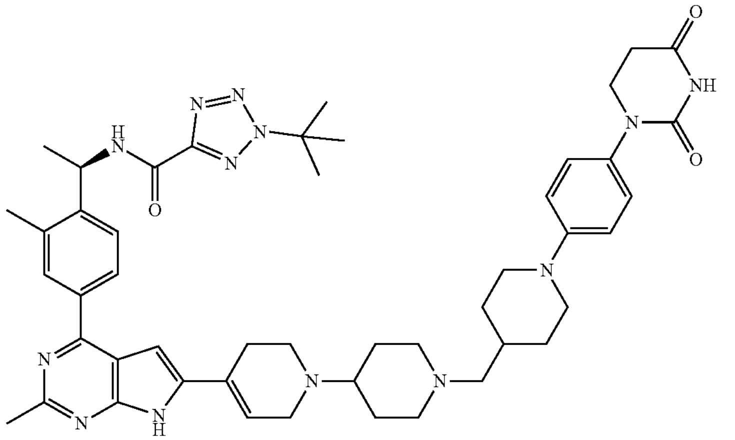 [SMILES: Cc1nc(-c2ccc([C@@H](C)NC(=O)c3nnn(C(C)(C)C)n3)c(C)c2)c2cc(C3=CCN(C4CCN(CC5CCN(c6ccc(N7CCC(=O)NC7=O)cc6)CC5)CC4)CC3)[nH]c2n1]
69

TABLE 1-continued
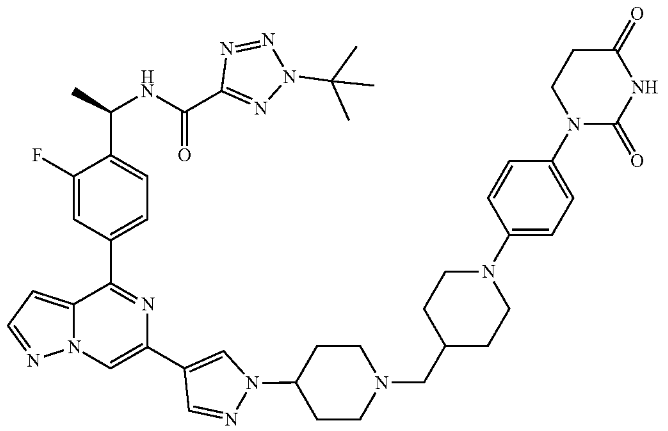 [SMILES: C[C@@H](NC(=O)c1nnn(C(C)(C)C)n1)c1ccc(-c2nc(-c3cnn(C4CCN(CC5CCN(c6ccc(N7CCC(=O)NC7=O)cc6)CC5)CC4)c3)cn3nccc23)cc1F]
70
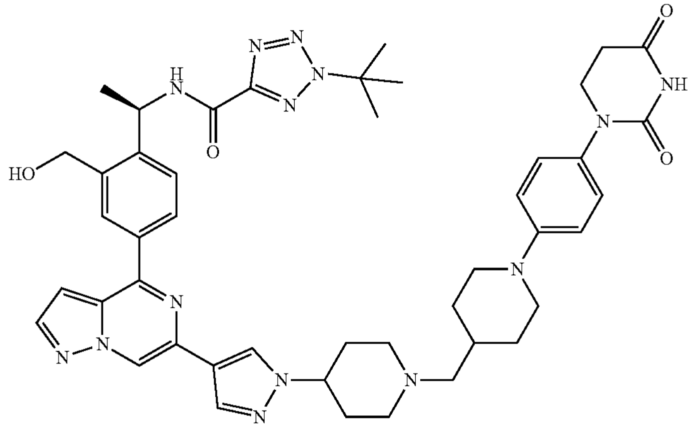 [SMILES: C[C@@H](NC(=O)c1nnn(C(C)(C)C)n1)c1ccc(-c2nc(-c3cnn(C4CCN(CC5CCN(c6ccc(N7CCC(=O)NC7=O)cc6)CC5)CC4)c3)cn3nccc23)cc1CO]
71
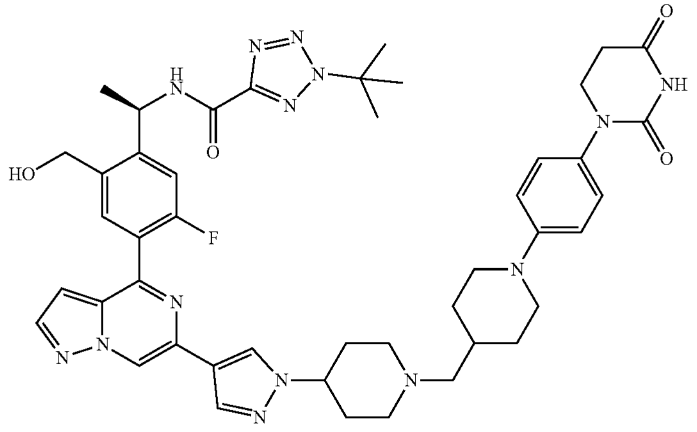 [SMILES: C[C@@H](NC(=O)c1nnn(C(C)(C)C)n1)c1cc(F)c(-c2nc(-c3cnn(C4CCN(CC5CCN(c6ccc(N7CCC(=O)NC7=O)cc6)CC5)CC4)c3)cn3nccc23)cc1CO]
72

TABLE 1-continued
73
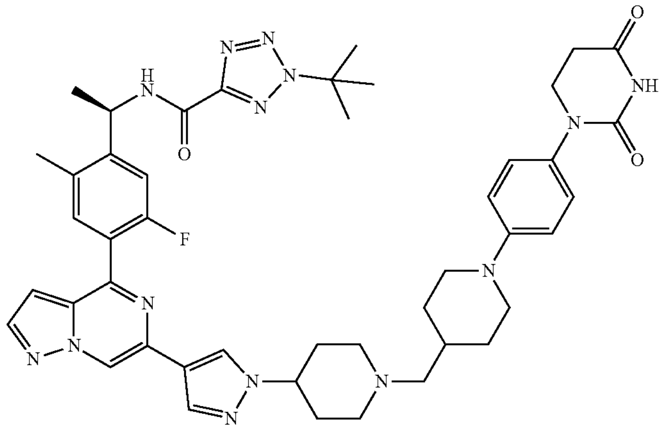 [SMILES: Cc1cc(-c2nc(-c3cnn(C4CCN(CC5CCN(c6ccc(N7CCC(=O)NC7=O)cc6)CC5)CC4)c3)cn3nccc23)c(F)cc1[C@@H](C)NC(=O)c1nnn(C(C)(C)C)n1]
74
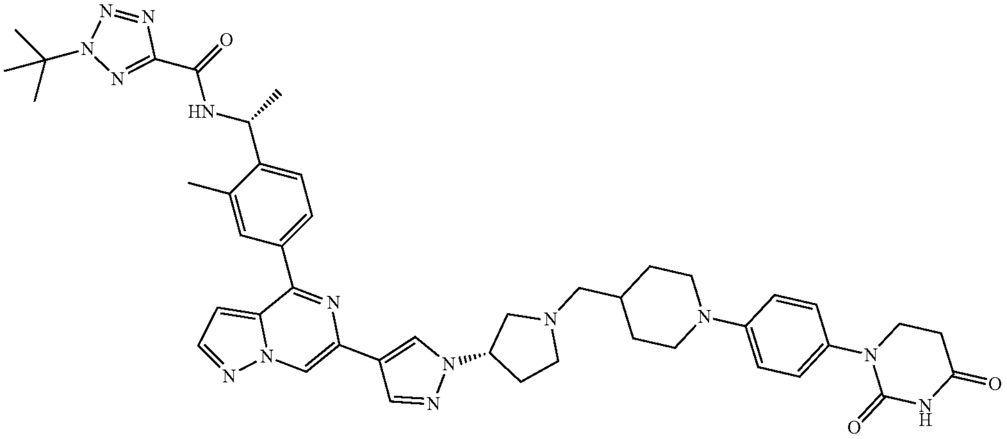 [SMILES: Cc1cc(-c2nc(-c3cnn([C@H]4CCN(CC5CCN(c6ccc(N7CCC(=O)NC7=O)cc6)CC5)C4)c3)cn3nccc23)ccc1[C@@H](C)NC(=O)c1nnn(C(C)(C)C)n1]
75
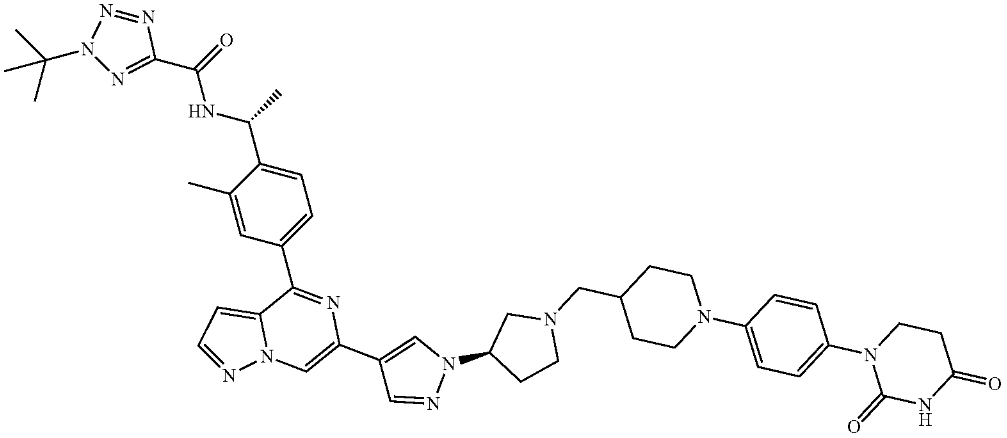 [SMILES: Cc1cc(-c2nc(-c3cnn([C@@H]4CCN(CC5CCN(c6ccc(N7CCC(=O)NC7=O)cc6)CC5)C4)c3)cn3nccc23)ccc1[C@@H](C)NC(=O)c1nnn(C(C)(C)C)n1]

TABLE 1-continued
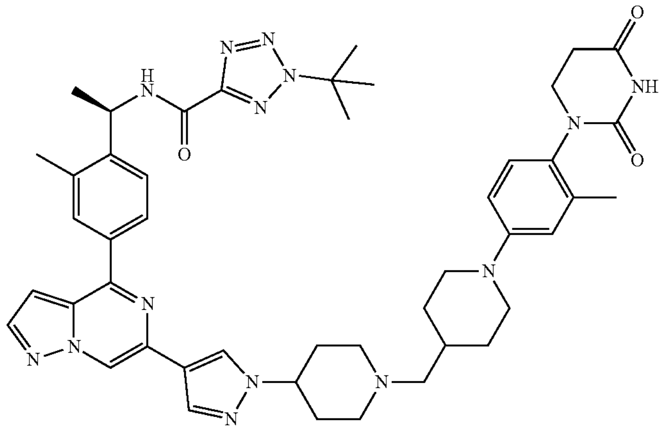
76
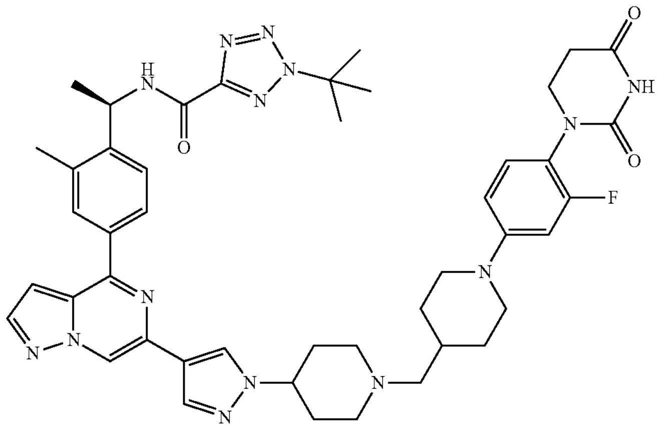 [SMILES: Cc1cc(-c2nc(-c3cnn(C4CCN(CC5CCN(c6ccc(N7CCC(=O)NC7=O)c(F)c6)CC5)CC4)c3)cn3nccc23)ccc1[C@@H](C)NC(=O)c1nnn(C(C)(C)C)n1]
77
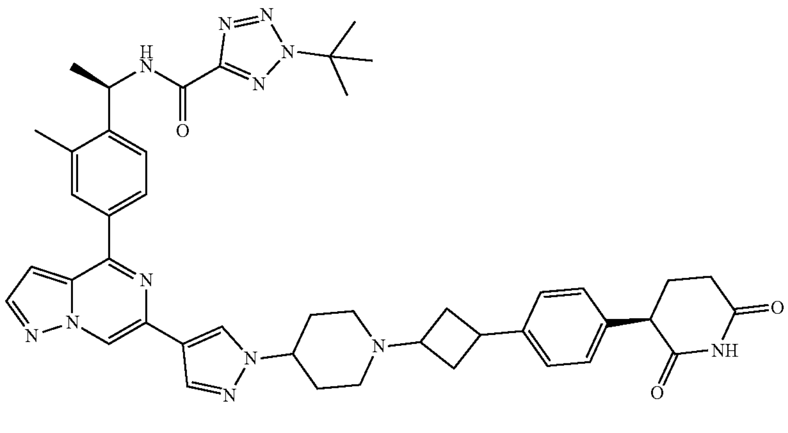 [SMILES: Cc1cc(-c2nc(-c3cnn(C4CCN(C5CC(c6ccc([C@H]7CCC(=O)NC7=O)cc6)C5)CC4)c3)cn3nccc23)ccc1[C@@H](C)NC(=O)c1nnn(C(C)(C)C)n1]
78

TABLE 1-continued
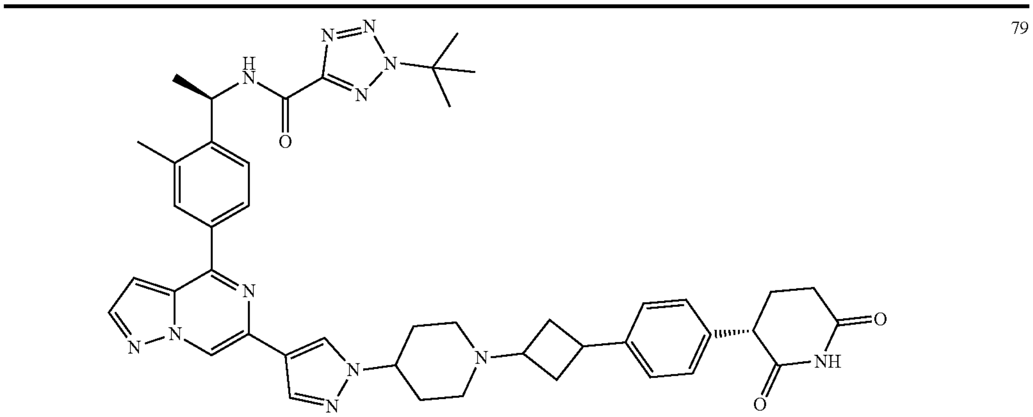
79
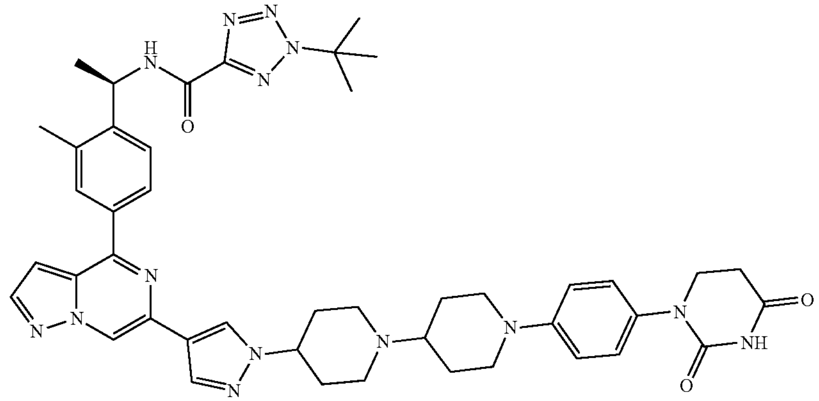 [SMILES: Cc1cc(-c2nc(-c3cnn(C4CCN(C5CCN(c6ccc(N7CCC(=O)NC7=O)cc6)CC5)CC4)c3)cn3nccc23)ccc1[C@@H](C)NC(=O)c1nnn(C(C)(C)C)n1]
80
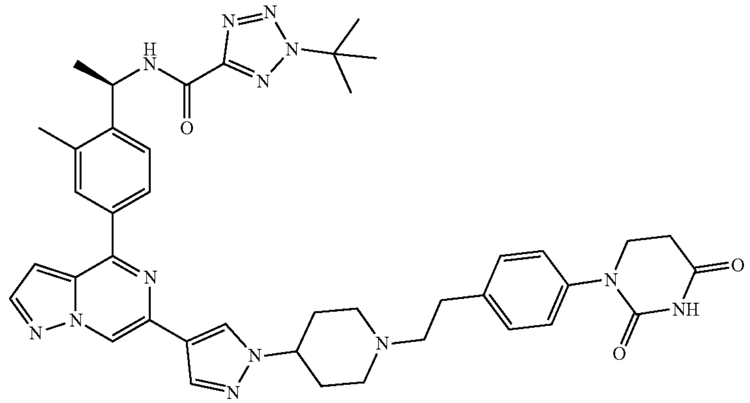 [SMILES: Cc1cc(-c2nc(-c3cnn(C4CCN(CCc5ccc(N6CCC(=O)NC6=O)cc5)CC4)c3)cn3nccc23)ccc1[C@@H](C)NC(=O)c1nnn(C(C)(C)C)n1]
81
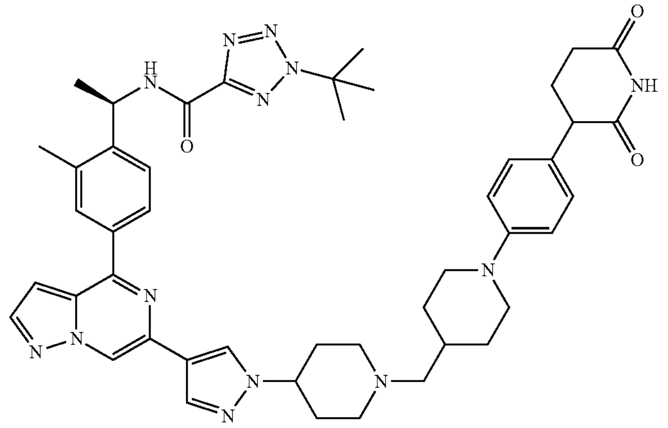 [SMILES: Cc1cc(-c2nc(-c3cnn(C4CCN(CC5CCN(c6ccc(C7CCC(=O)NC7=O)cc6)CC5)CC4)c3)cn3nccc23)ccc1[C@@H](C)NC(=O)c1nnn(C(C)(C)C)n1]
82

TABLE 1-continued
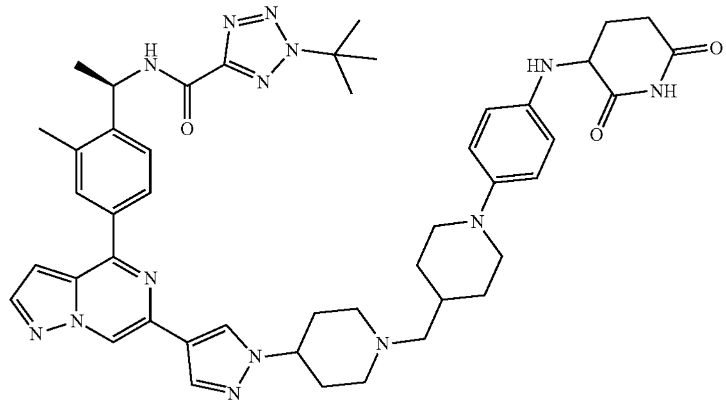
83
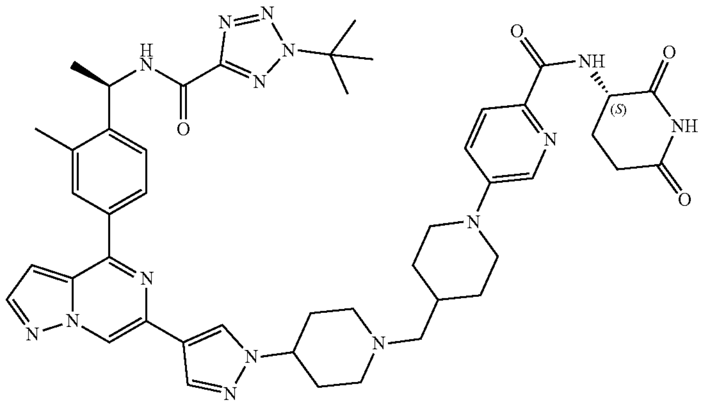
84
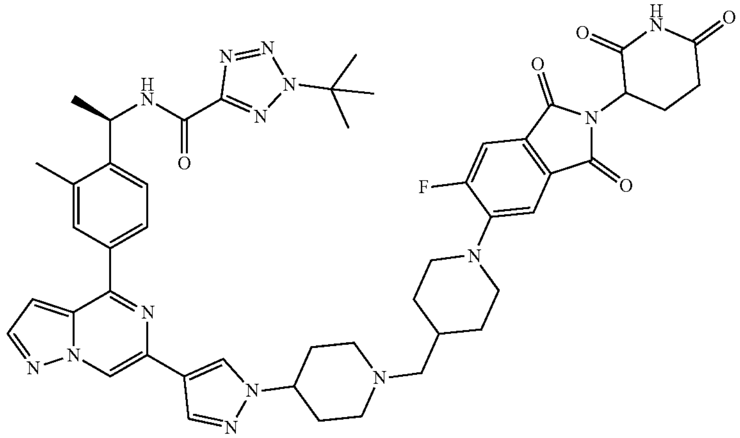 [SMILES: Cc1cc(-c2nc(-c3cnn(C4CCN(CC5CCN(c6cc7c(cc6F)C(=O)N(C6CCC(=O)NC6=O)C7=O)CC5)CC4)c3)cn3nccc23)ccc1[C@@H](C)NC(=O)c1nnn(C(C)(C)C)n1]
85

TABLE 1-continued
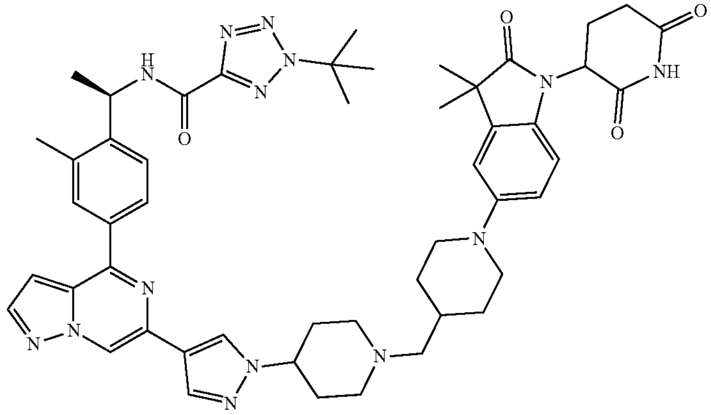 [SMILES: Cc1cc(-c2nc(-c3cnn(C4CCN(CC5CCN(c6ccc7c(c6)C(C)(C)C(=O)N7C6CCC(=O)NC6=O)CC5)CC4)c3)cn3nccc23)ccc1[C@@H](C)NC(=O)c1nnn(C(C)(C)C)n1]
86
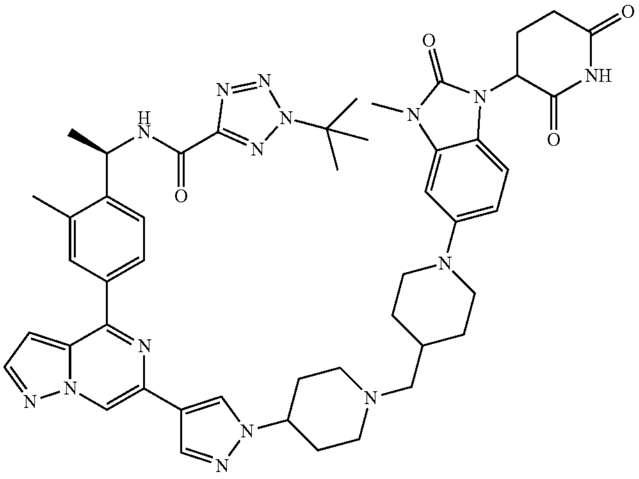 [SMILES: Cc1cc(-c2nc(-c3cnn(C4CCN(CC5CCN(c6ccc7c(c6)n(C)c(=O)n7C6CCC(=O)NC6=O)CC5)CC4)c3)cn3nccc23)ccc1[C@@H](C)NC(=O)c1nnn(C(C)(C)C)n1]
87
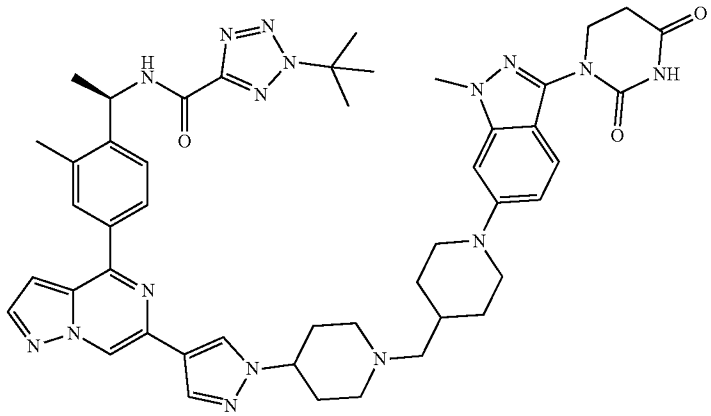 [SMILES: Cc1cc(-c2nc(-c3cnn(C4CCN(CC5CCN(c6ccc7c(N8CCC(=O)NC8=O)nn(C)c7c6)CC5)CC4)c3)cn3nccc23)ccc1[C@@H](C)NC(=O)c1nnn(C(C)(C)C)n1]
88

TABLE 1-continued
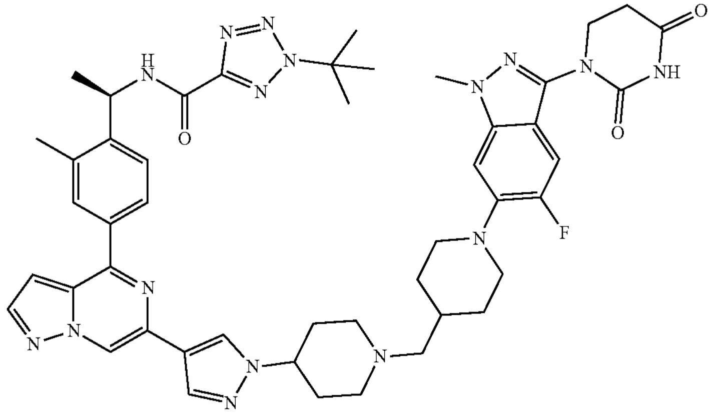 [SMILES: Cc1cc(-c2nc(-c3cnn(C4CCN(CC5CCN(c6cc7c(cc6F)c(N6CCC(=O)NC6=O)nn7C)CC5)CC4)c3)cn3nccc23)ccc1[C@@H](C)NC(=O)c1nnn(C(C)(C)C)n1]
89
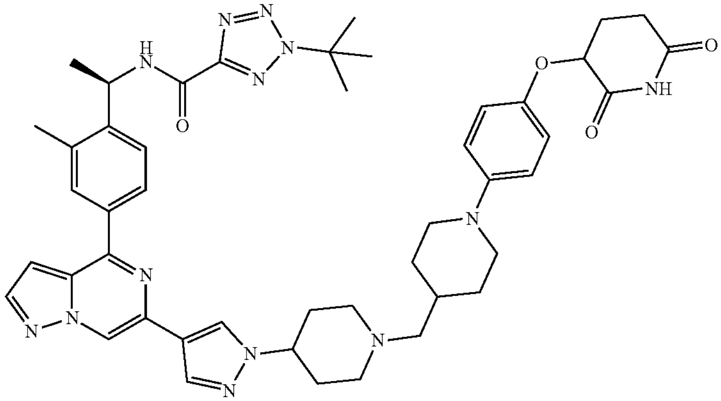
90
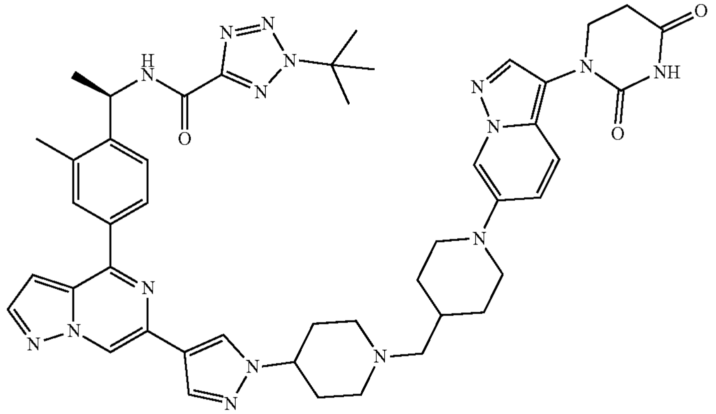 [SMILES: Cc1cc(-c2nc(-c3cnn(C4CCN(CC5CCN(c6ccc7c(N8CCC(=O)NC8=O)cnn7c6)CC5)CC4)c3)cn3nccc23)ccc1[C@@H](C)NC(=O)c1nnn(C(C)(C)C)n1]
91
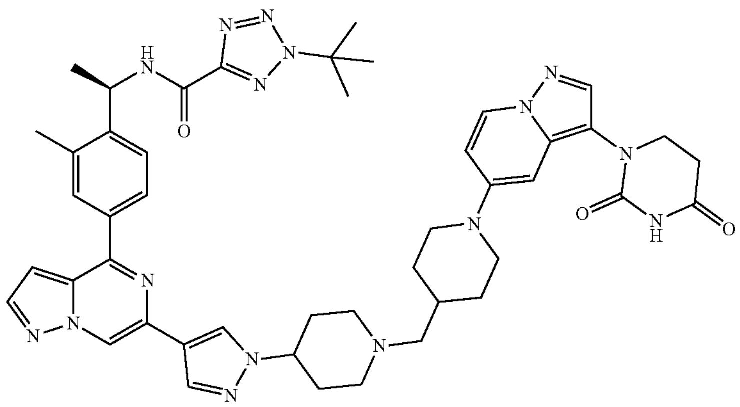 [SMILES: Cc1cc(-c2nc(-c3cnn(C4CCN(CC5CCN(c6ccn7ncc(N8CCC(=O)NC8=O)c7c6)CC5)CC4)c3)cn3nccc23)ccc1[C@@H](C)NC(=O)c1nnn(C(C)(C)C)n1]
92

TABLE 1-continued
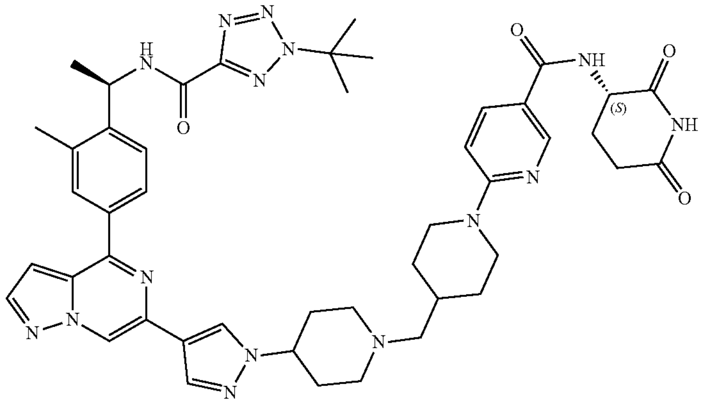
93
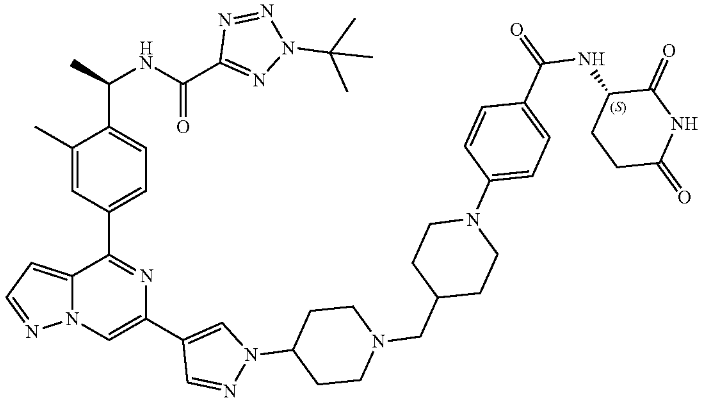
94
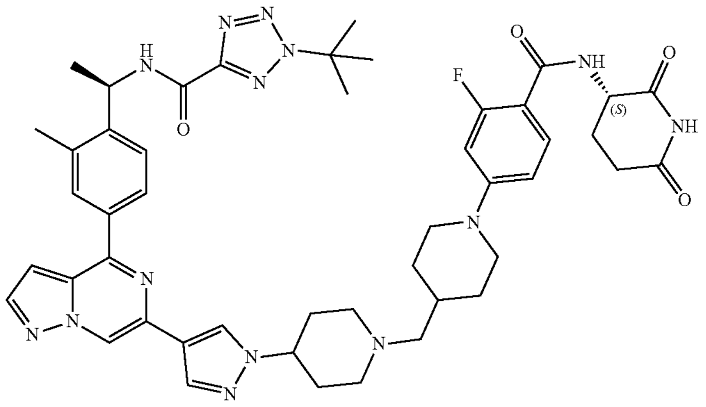
95

TABLE 1-continued
96
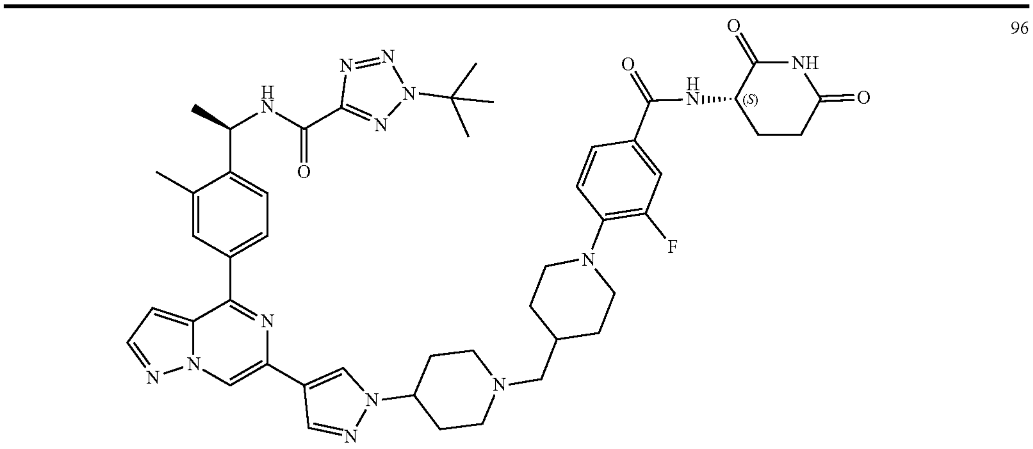
97
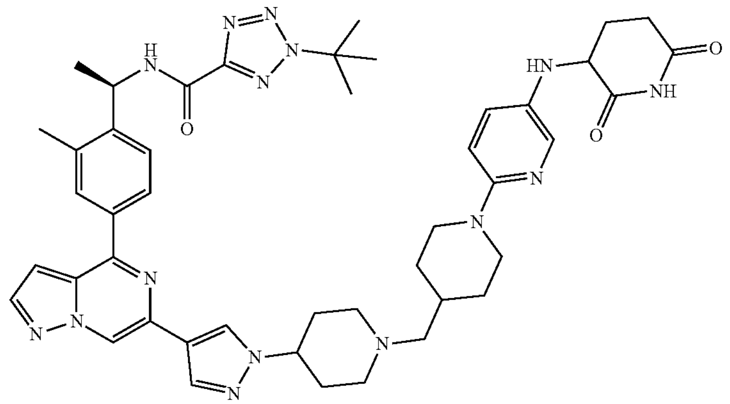
98
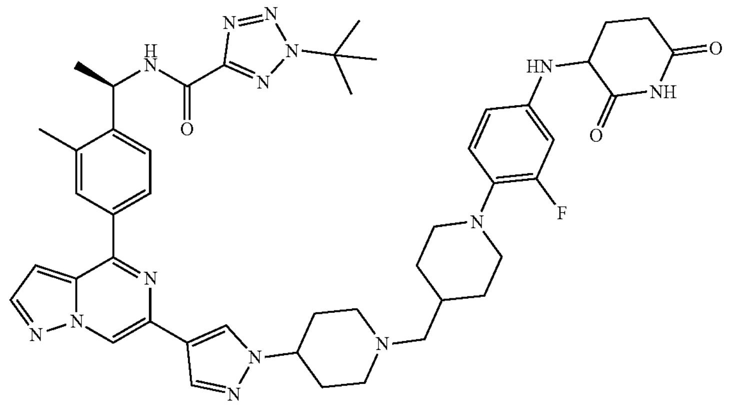
99
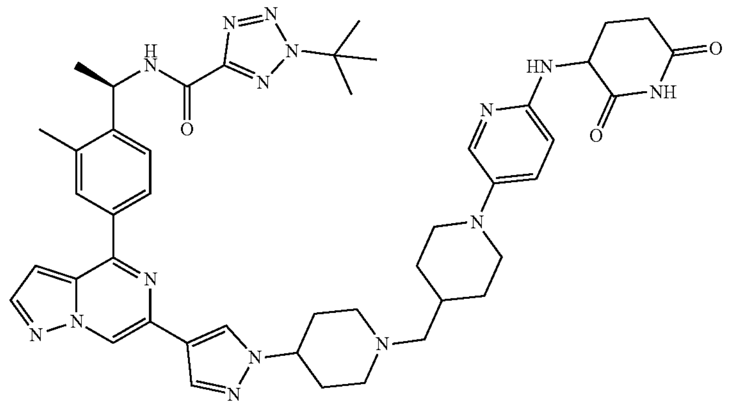

TABLE 1-continued
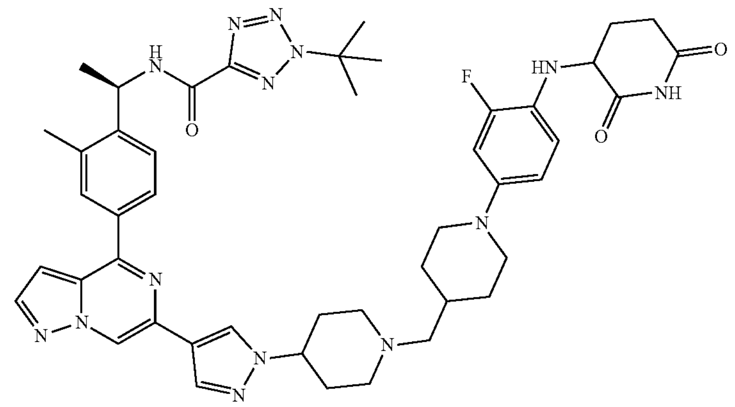
100
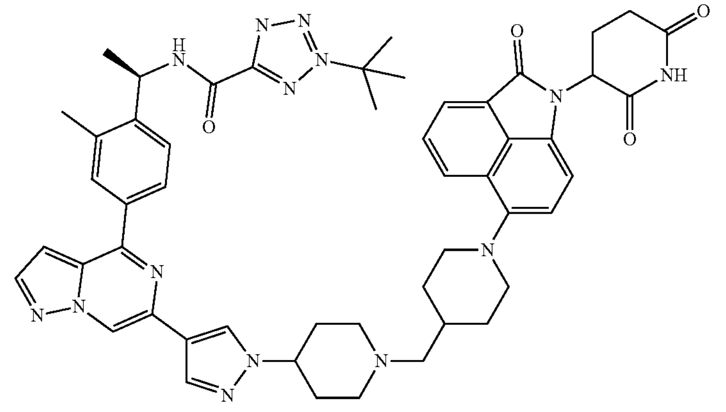
101
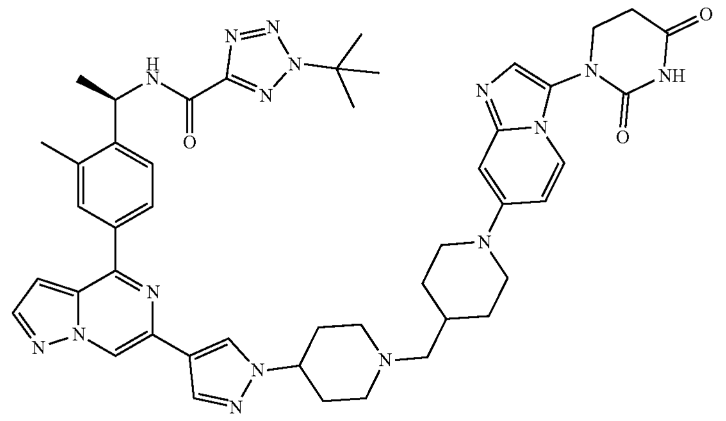 [SMILES: Cc1cc(-c2nc(-c3cnn(C4CCN(CC5CCN(c6ccn7c(N8CCC(=O)NC8=O)cnc7c6)CC5)CC4)c3)cn3nccc23)ccc1[C@@H](C)NC(=O)c1nnn(C(C)(C)C)n1]
102
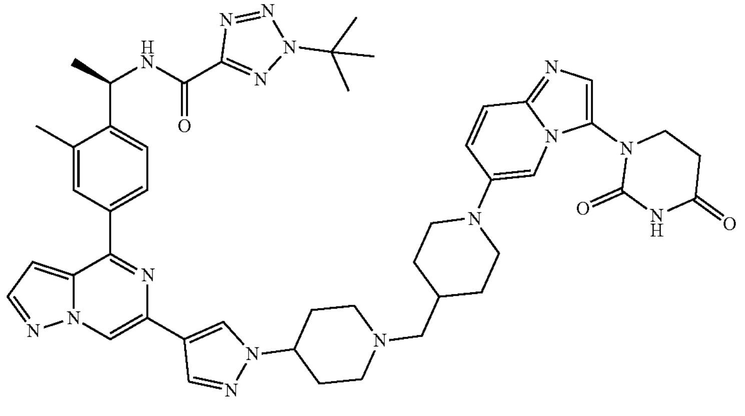 [SMILES: Cc1cc(-c2nc(-c3cnn(C4CCN(CC5CCN(c6ccc7ncc(N8CCC(=O)NC8=O)n7c6)CC5)CC4)c3)cn3nccc23)ccc1[C@@H](C)NC(=O)c1nnn(C(C)(C)C)n1]
103

TABLE 1-continued
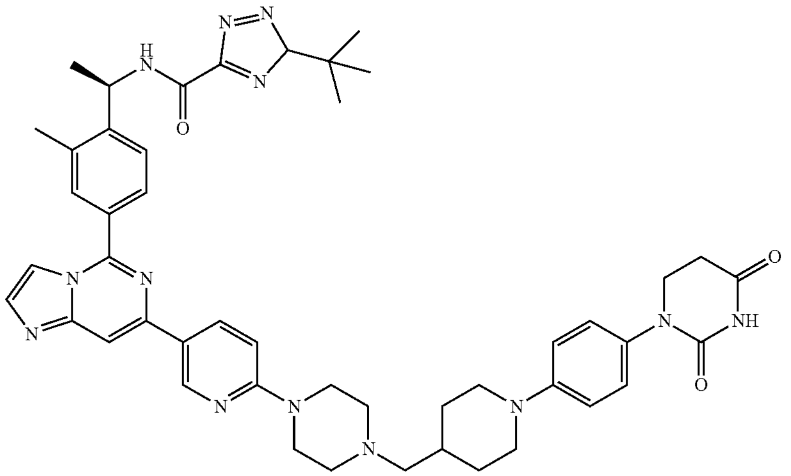 [SMILES: Cc1cc(-c2nc(-c3ccc(N4CCN(CC5CCN(c6ccc(N7CCC(=O)NC7=O)cc6)CC5)CC4)nc3)cc3nccn23)ccc1[C@@H](C)NC(=O)C1=NC(C(C)(C)C)N=N1]
104
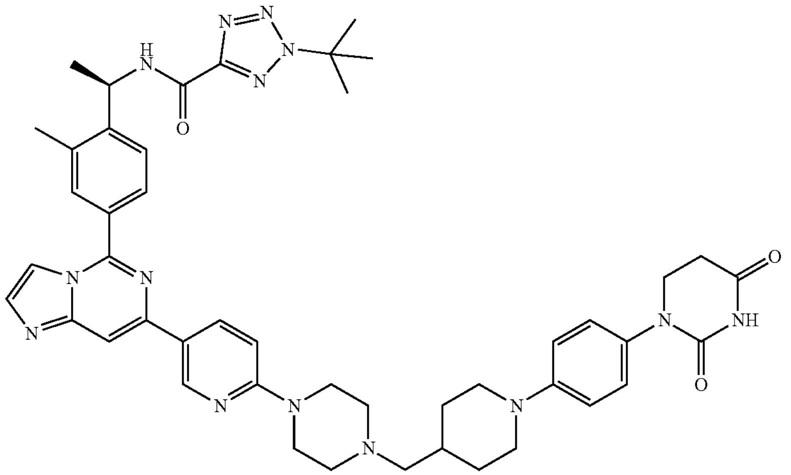
105
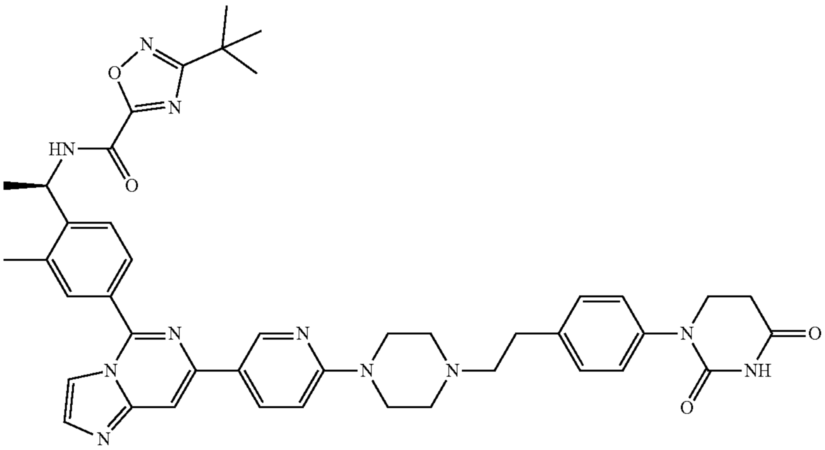 [SMILES: Cc1cc(-c2nc(-c3ccc(N4CCN(CCc5ccc(N6CCC(=O)NC6=O)cc5)CC4)nc3)cc3nccn23)ccc1[C@@H](C)NC(=O)c1nc(C(C)(C)C)no1]
106

TABLE 1-continued
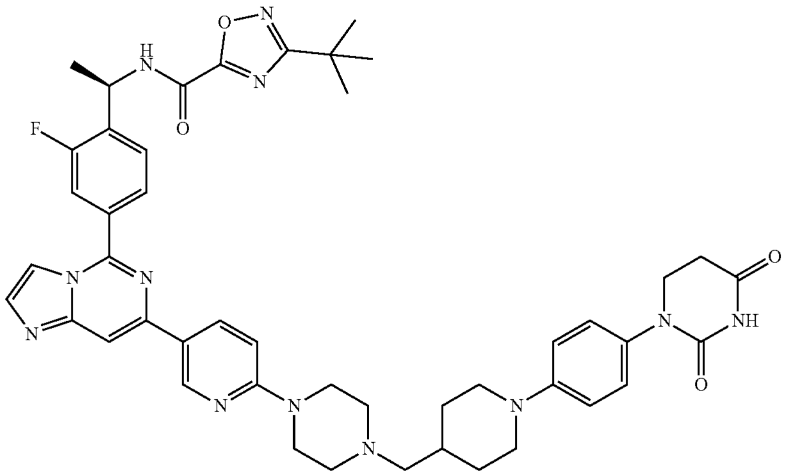
107
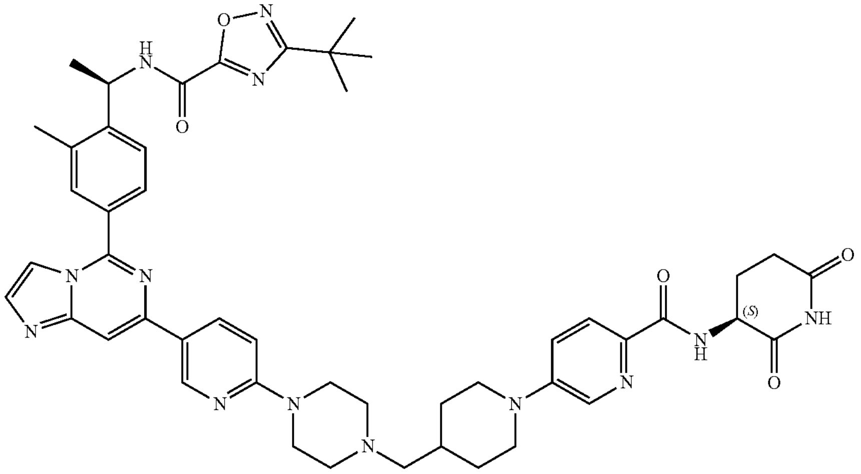
108
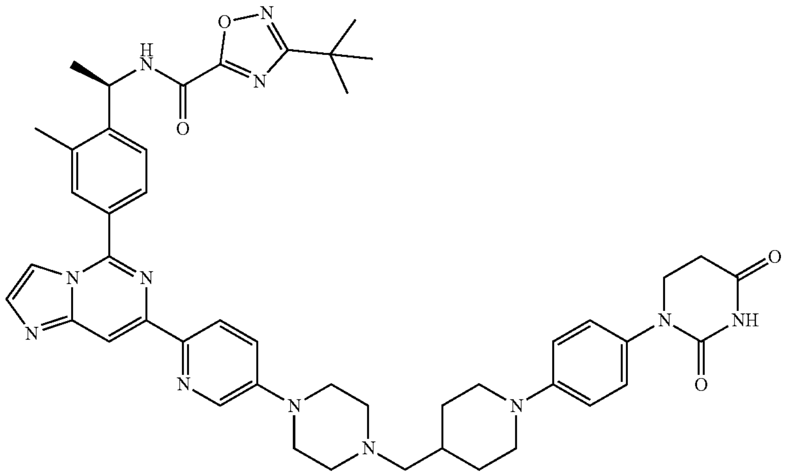
109

TABLE 1-continued
110
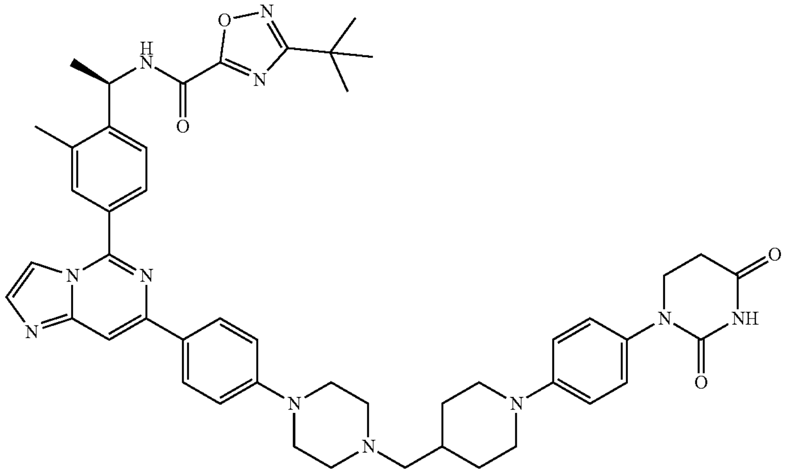
111
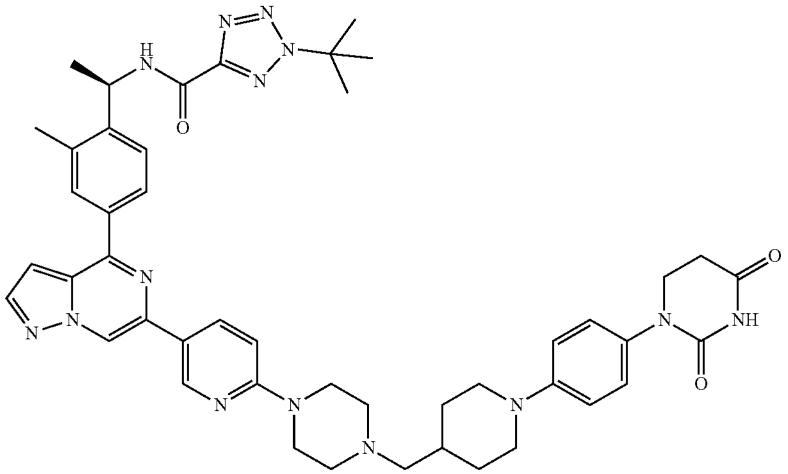
112
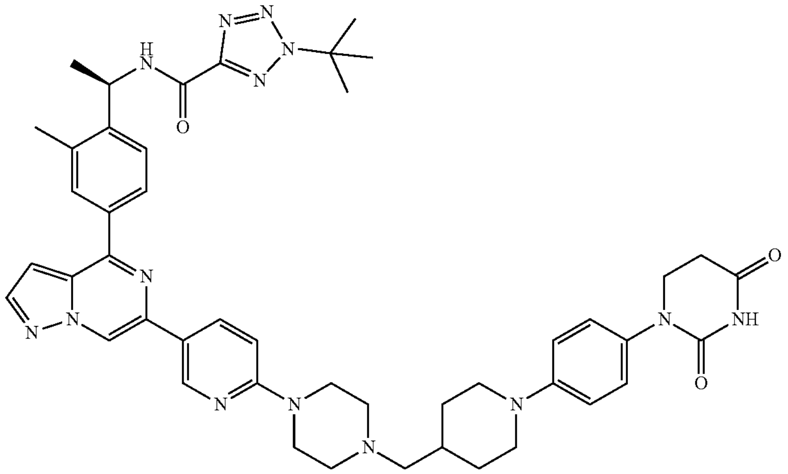

TABLE 1-continued
113
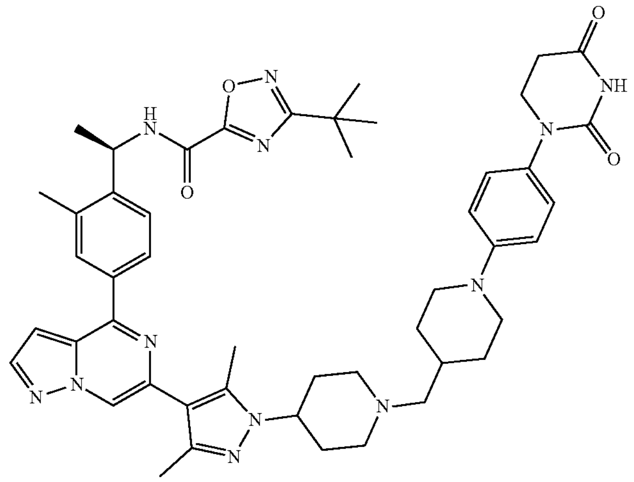 [SMILES: Cc1cc(-c2nc(-c3c(C)nn(C4CCN(CC5CCN(c6ccc(N7CCC(=O)NC7=O)cc6)CC5)CC4)c3C)cn3nccc23)ccc1[C@@H](C)NC(=O)c1nc(C(C)(C)C)no1]
114
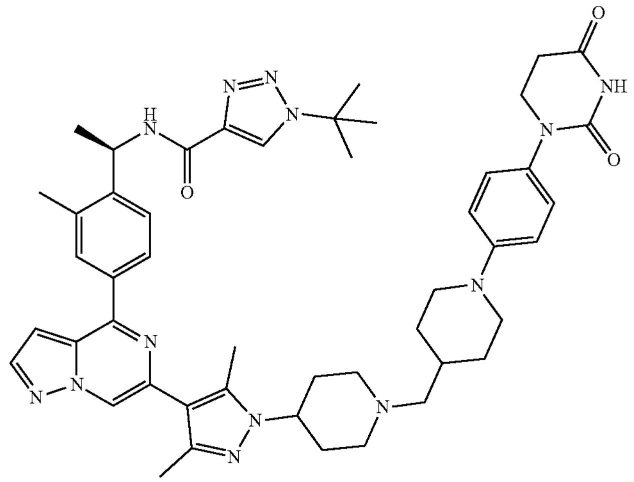
115
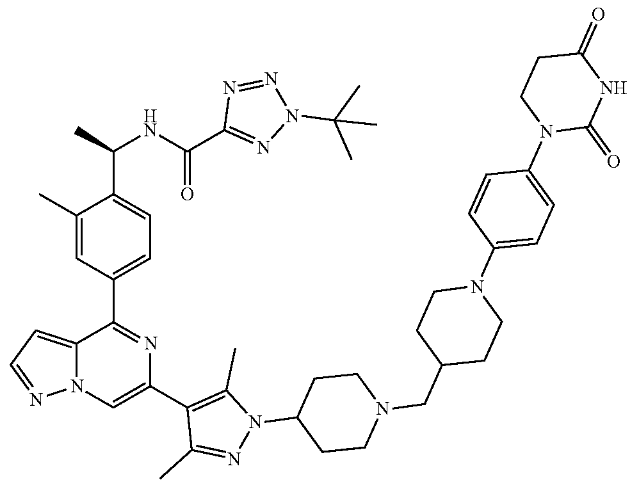

TABLE 1-continued
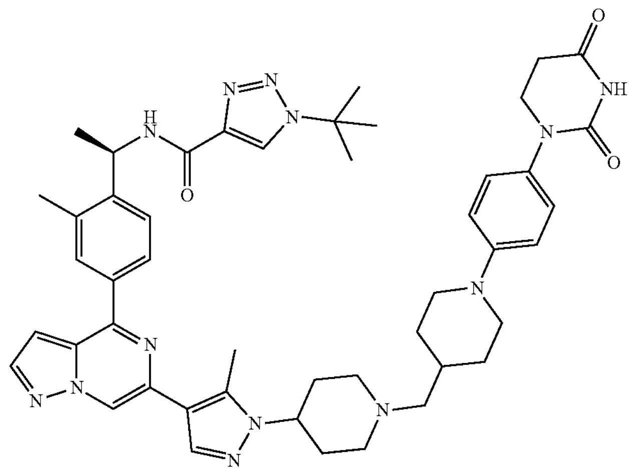 [SMILES: Cc1cc(-c2nc(-c3cnn(C4CCN(CC5CCN(c6ccc(N7CCC(=O)NC7=O)cc6)CC5)CC4)c3C)cn3nccc23)ccc1[C@@H](C)NC(=O)c1cn(C(C)(C)C)nn1]
116
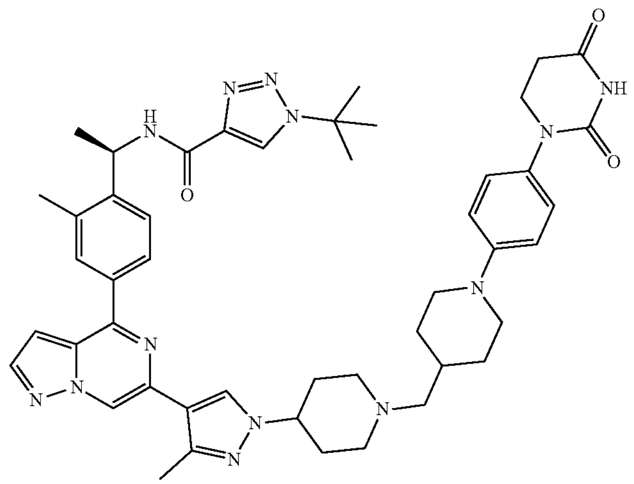 [SMILES: Cc1cc(-c2nc(-c3cn(C4CCN(CC5CCN(c6ccc(N7CCC(=O)NC7=O)cc6)CC5)CC4)nc3C)cn3nccc23)ccc1[C@@H](C)NC(=O)c1cn(C(C)(C)C)nn1]
117
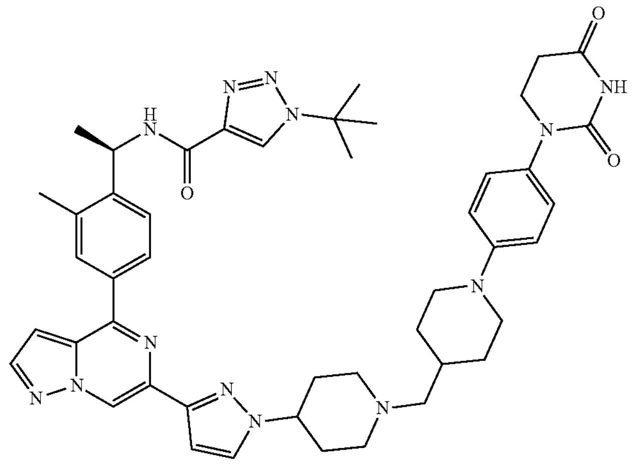 [SMILES: Cc1cc(-c2nc(-c3ccn(C4CCN(CC5CCN(c6ccc(N7CCC(=O)NC7=O)cc6)CC5)CC4)n3)cn3nccc23)ccc1[C@@H](C)NC(=O)c1cn(C(C)(C)C)nn1]
118

TABLE 1-continued
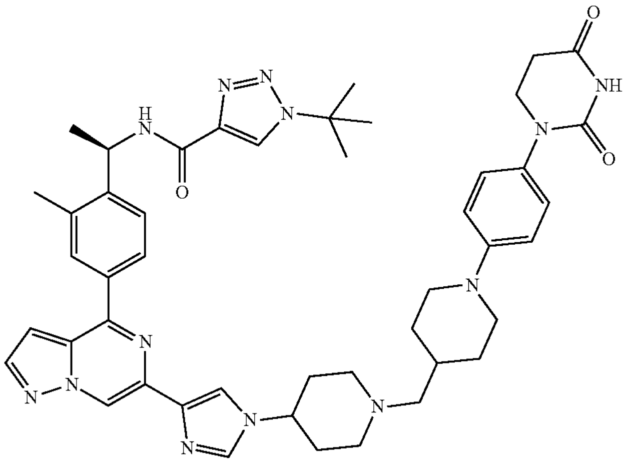
119
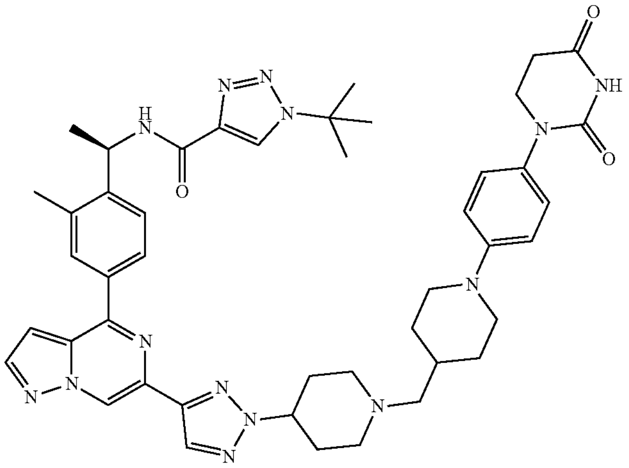 [SMILES: Cc1cc(-c2nc(-c3cnn(C4CCN(CC5CCN(c6ccc(N7CCC(=O)NC7=O)cc6)CC5)CC4)n3)cn3nccc23)ccc1[C@@H](C)NC(=O)c1cn(C(C)(C)C)nn1]
120
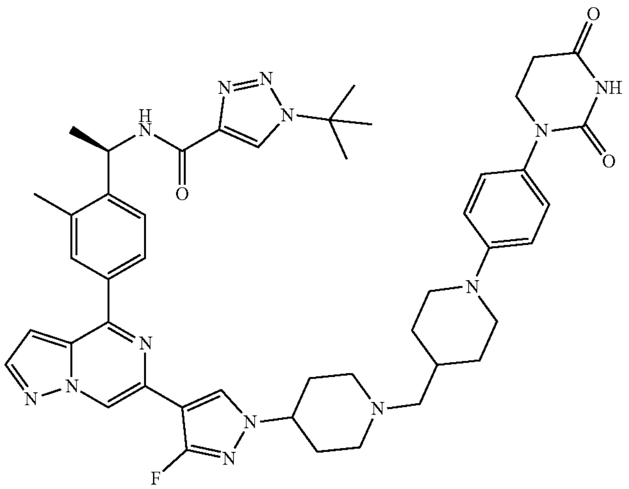 [SMILES: Cc1cc(-c2nc(-c3cn(C4CCN(CC5CCN(c6ccc(N7CCC(=O)NC7=O)cc6)CC5)CC4)nc3F)cn3nccc23)ccc1[C@@H](C)NC(=O)c1cn(C(C)(C)C)nn1]
121

TABLE 1-continued
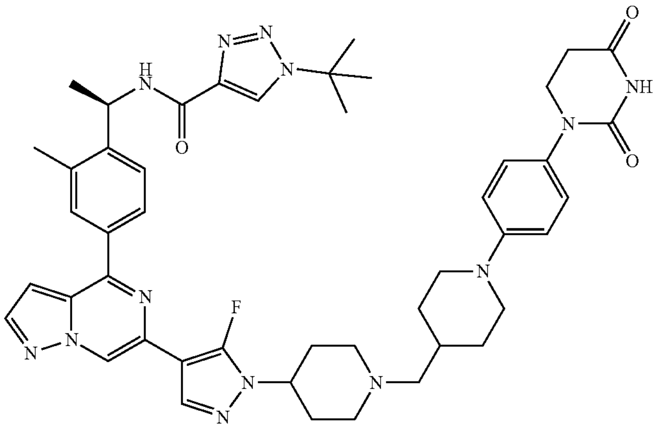 [SMILES: Cc1cc(-c2nc(-c3cnn(C4CCN(CC5CCN(c6ccc(N7CCC(=O)NC7=O)cc6)CC5)CC4)c3F)cn3nccc23)ccc1[C@@H](C)NC(=O)c1cn(C(C)(C)C)nn1]
122
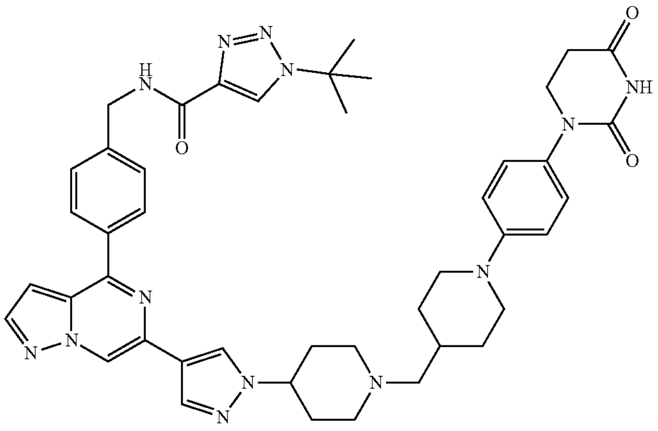
123
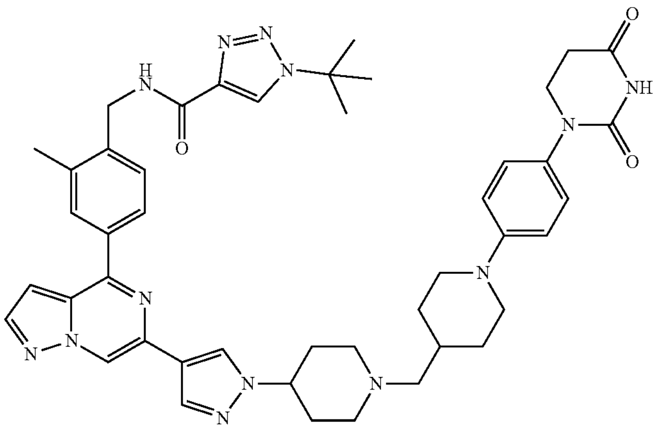
124

TABLE 1-continued
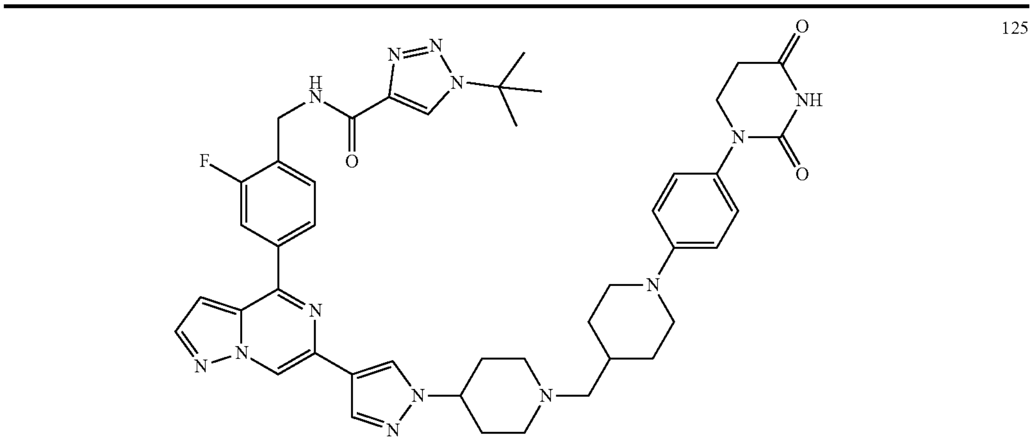
125
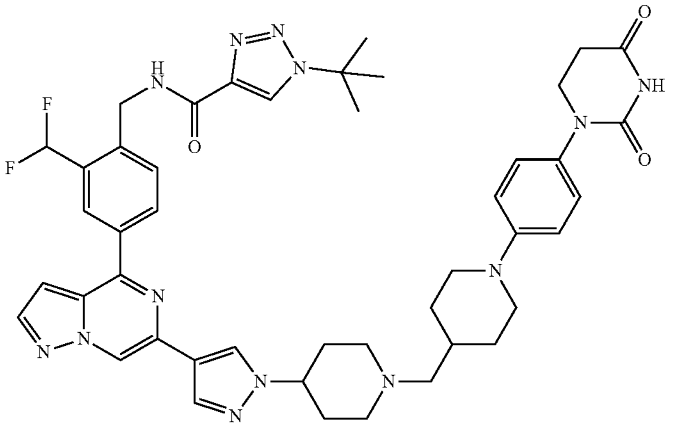 [SMILES: CC(C)(C)n1cc(C(=O)NCc2ccc(-c3nc(-c4cnn(C5CCN(CC6CCN(c7ccc(N8CCC(=O)NC8=O)cc7)CC6)CC5)c4)cn4nccc34)cc2C(F)F)nn1]
126
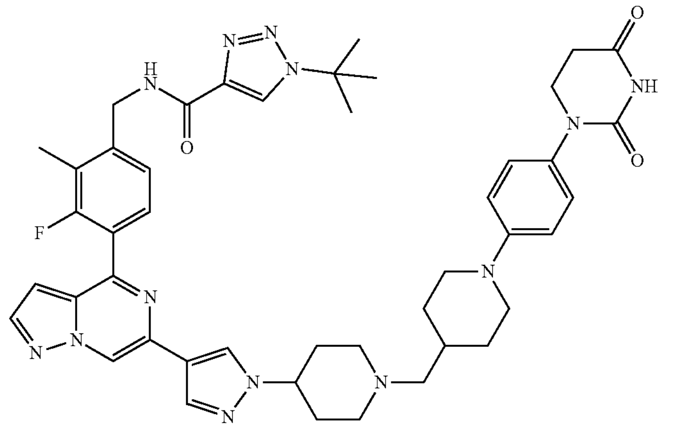 [SMILES: Cc1c(CNC(=O)c2cn(C(C)(C)C)nn2)ccc(-c2nc(-c3cnn(C4CCN(CC5CCN(c6ccc(N7CCC(=O)NC7=O)cc6)CC5)CC4)c3)cn3nccc23)c1F]
127

TABLE 1-continued
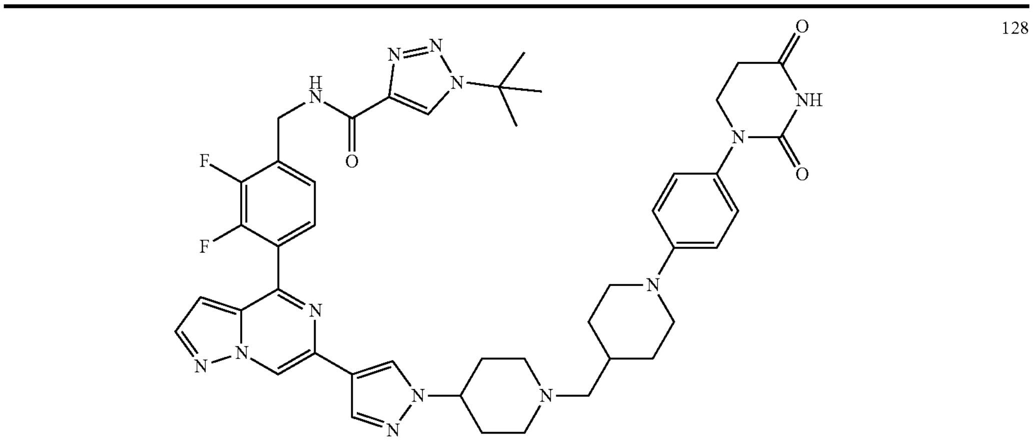
128
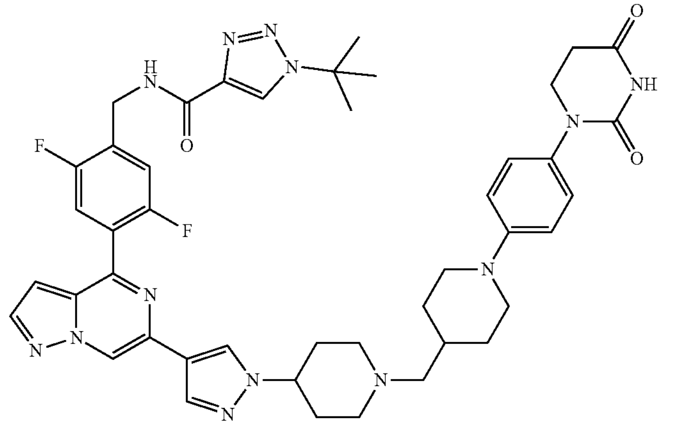 [SMILES: CC(C)(C)n1cc(C(=O)NCc2cc(F)c(-c3nc(-c4cnn(C5CCN(CC6CCN(c7ccc(N8CCC(=O)NC8=O)cc7)CC6)CC5)c4)cn4nccc34)cc2F)nn1]
129
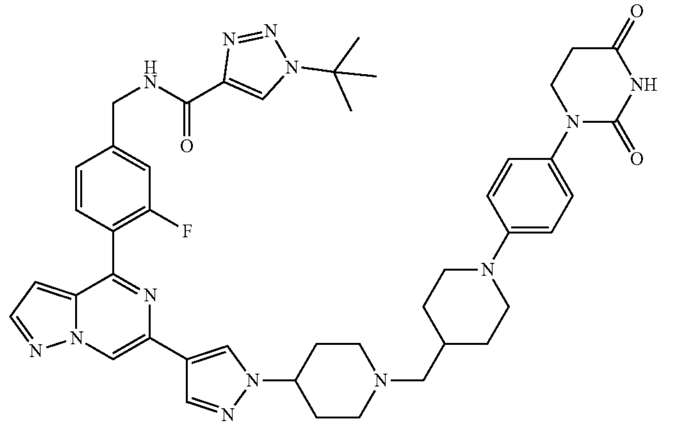 [SMILES: CC(C)(C)n1cc(C(=O)NCc2ccc(-c3nc(-c4cnn(C5CCN(CC6CCN(c7ccc(N8CCC(=O)NC8=O)cc7)CC6)CC5)c4)cn4nccc34)c(F)c2)nn1]
130

TABLE 1-continued
131
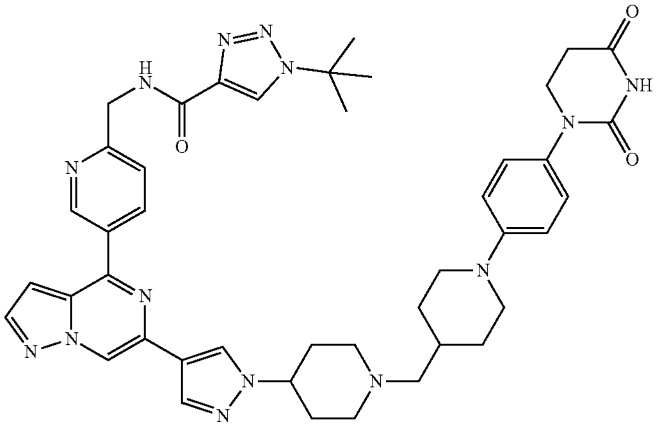 [SMILES: CC(C)(C)n1cc(C(=O)NCc2ccc(-c3nc(-c4cnn(C5CCN(CC6CCN(c7ccc(N8CCC(=O)NC8=O)cc7)CC6)CC5)c4)cn4nccc34)cn2)nn1]
132
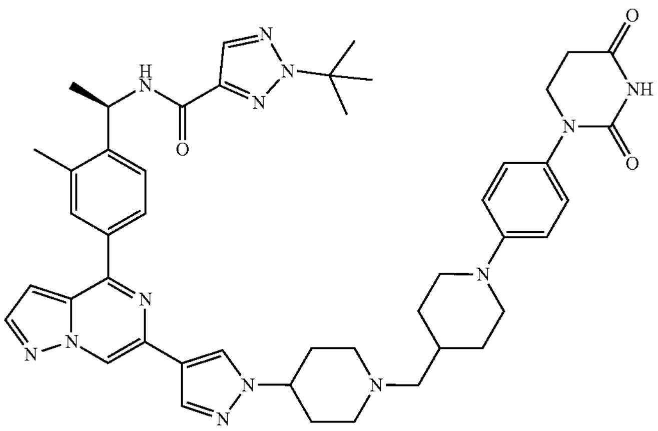 [SMILES: Cc1cc(-c2nc(-c3cnn(C4CCN(CC5CCN(c6ccc(N7CCC(=O)NC7=O)cc6)CC5)CC4)c3)cn3nccc23)ccc1[C@@H](C)NC(=O)c1cnn(C(C)(C)C)n1]
133
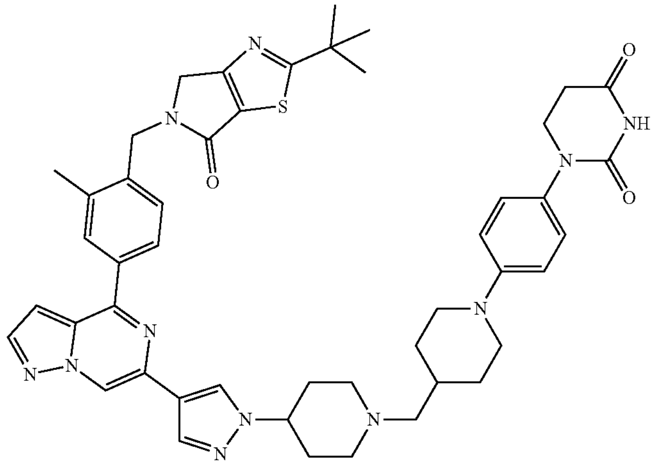 [SMILES: Cc1cc(-c2nc(-c3cnn(C4CCN(CC5CCN(c6ccc(N7CCC(=O)NC7=O)cc6)CC5)CC4)c3)cn3nccc23)ccc1CN1Cc2nc(C(C)(C)C)sc2C1=O]

TABLE 1-continued
134
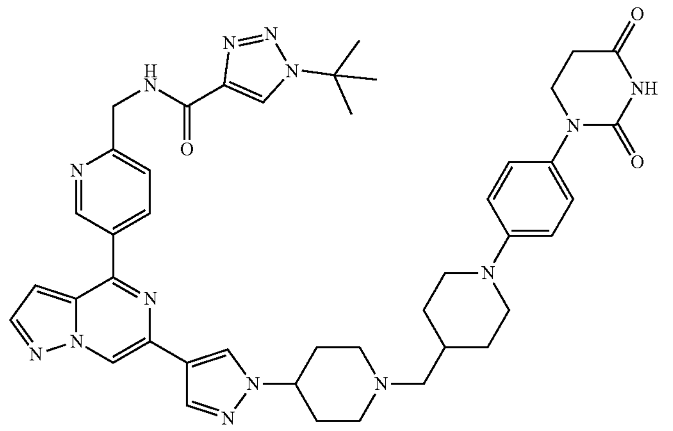 [SMILES: CC(C)(C)n1cc(C(=O)NCc2ccc(-c3nc(-c4cnn(C5CCN(CC6CCN(c7ccc(N8CCC(=O)NC8=O)cc7)CC6)CC5)c4)cn4nccc34)cn2)nn1]
135
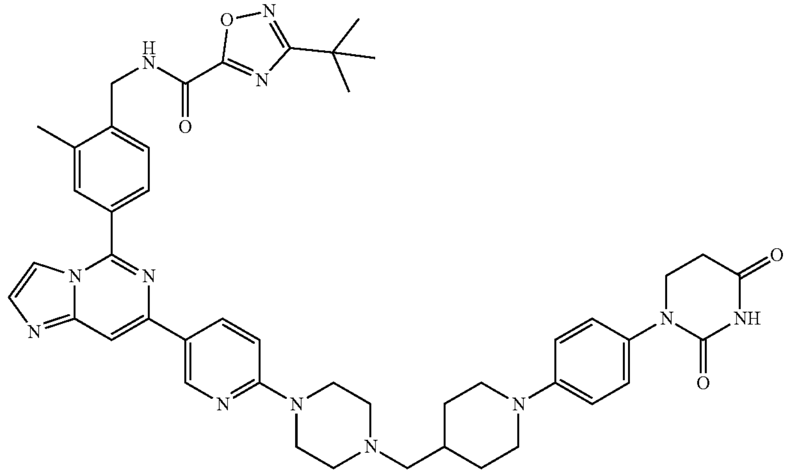
136
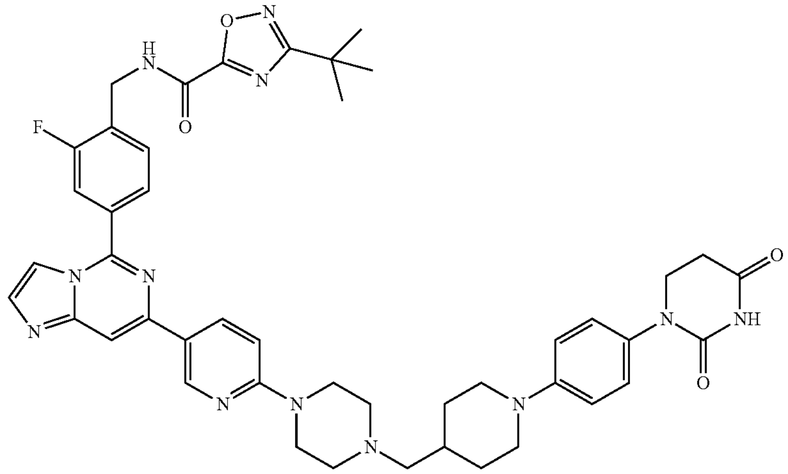 [SMILES: CC(C)(C)c1noc(C(=O)NCc2ccc(-c3nc(-c4ccc(N5CCN(CC6CCN(c7ccc(N8CCC(=O)NC8=O)cc7)CC6)CC5)nc4)cc4nccn34)cc2F)n1]

TABLE 1-continued
137
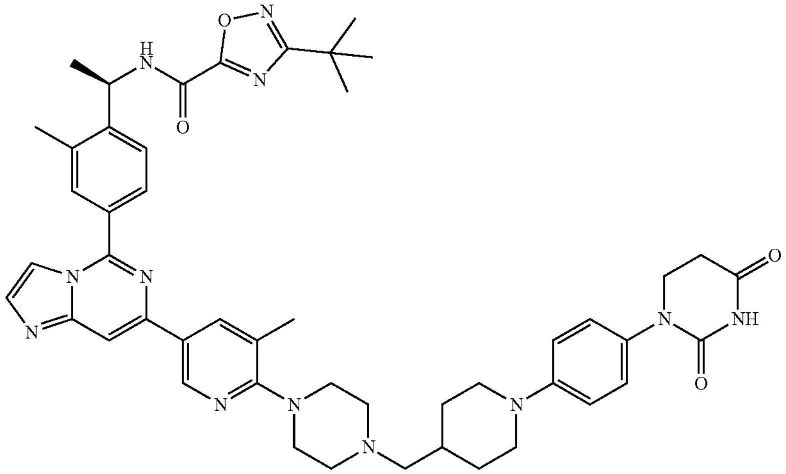
138
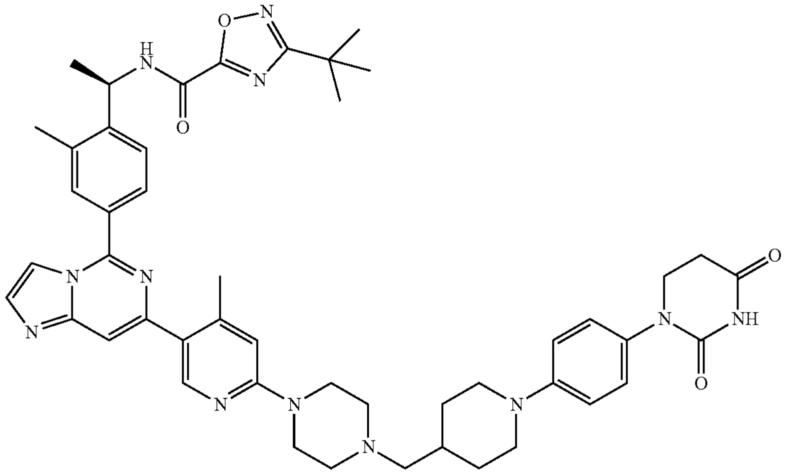
139
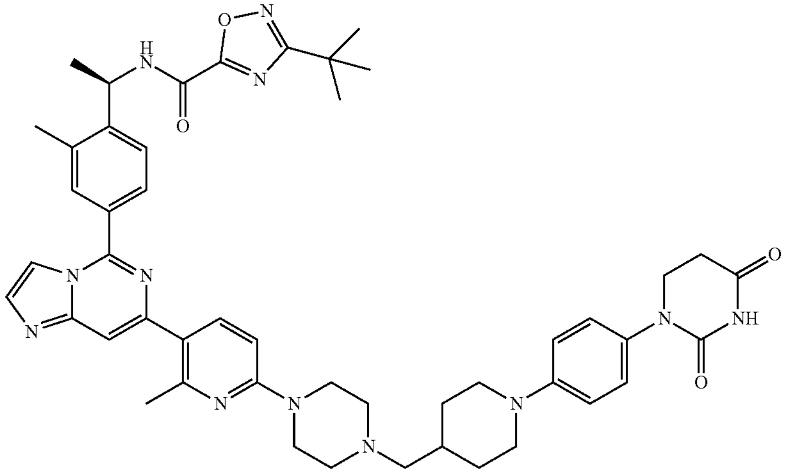 [SMILES: Cc1cc(-c2nc(-c3ccc(N4CCN(CC5CCN(c6ccc(N7CCC(=O)NC7=O)cc6)CC5)CC4)nc3C)cc3nccn23)ccc1[C@@H](C)NC(=O)c1nc(C(C)(C)C)no1]

TABLE 1-continued
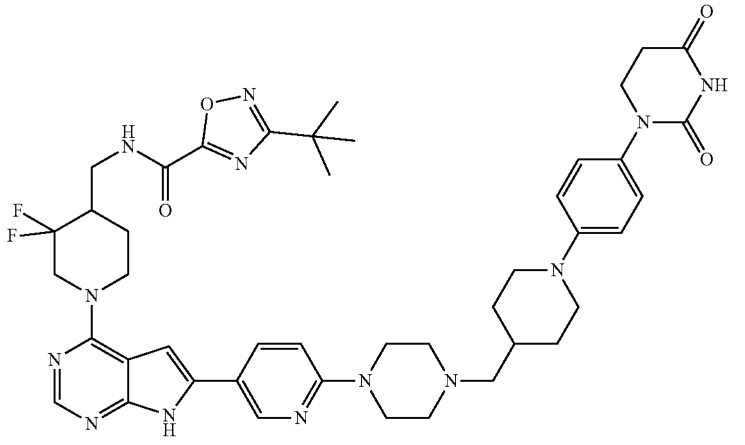 [SMILES: CC(C)(C)c1noc(C(=O)NCC2CCN(c3ncnc4[nH]c(-c5ccc(N6CCN(CC7CCN(c8ccc(N9CCC(=O)NC9=O)cc8)CC7)CC6)nc5)cc34)CC2(F)F)n1]
140
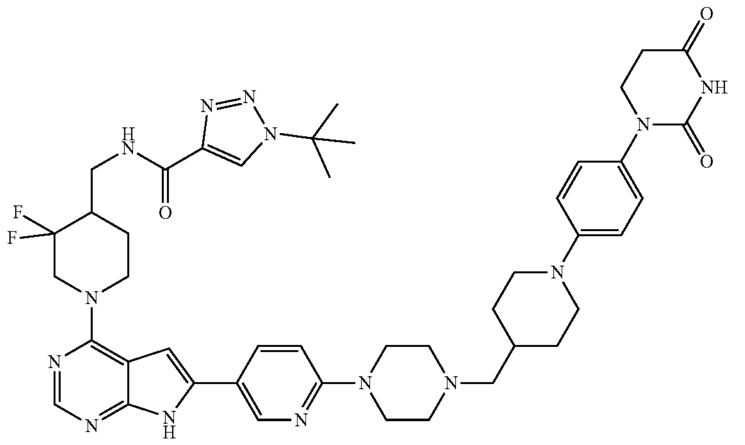 [SMILES: CC(C)(C)n1cc(C(=O)NCC2CCN(c3ncnc4[nH]c(-c5ccc(N6CCN(CC7CCN(c8ccc(N9CCC(=O)NC9=O)cc8)CC7)CC6)nc5)cc34)CC2(F)F)nn1]
141
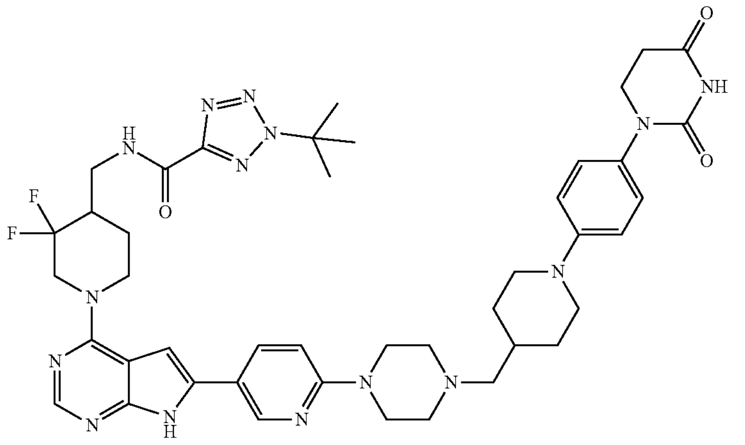 [SMILES: CC(C)(C)n1nnc(C(=O)NCC2CCN(c3ncnc4[nH]c(-c5ccc(N6CCN(CC7CCN(c8ccc(N9CCC(=O)NC9=O)cc8)CC7)CC6)nc5)cc34)CC2(F)F)n1]
142

TABLE 1-continued
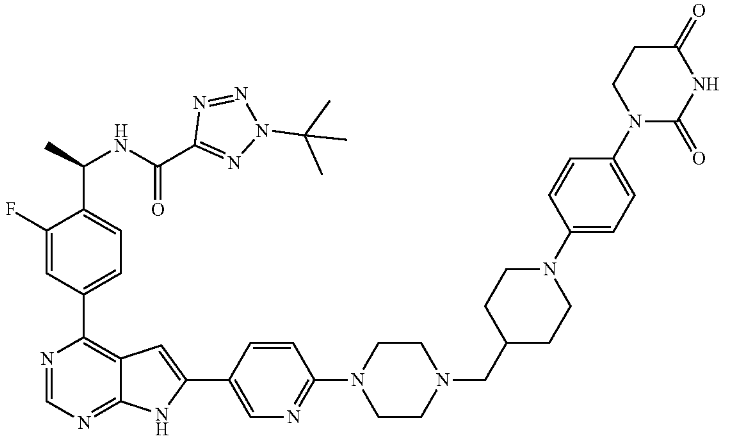 [SMILES: C[C@@H](NC(=O)c1nnn(C(C)(C)C)n1)c1ccc(-c2ncnc3[nH]c(-c4ccc(N5CCN(CC6CCN(c7ccc(N8CCC(=O)NC8=O)cc7)CC6)CC5)nc4)cc23)cc1F]
143
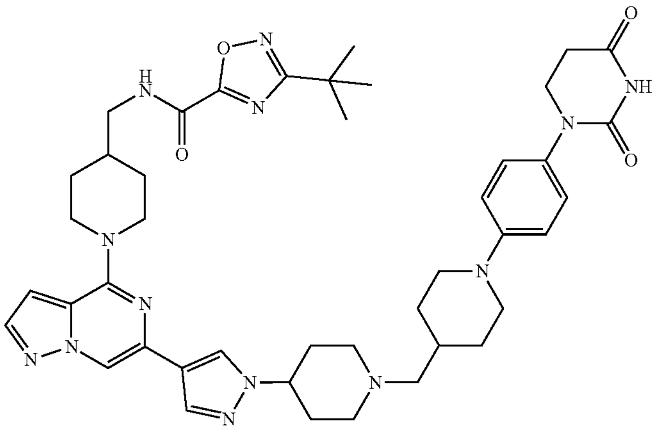 [SMILES: CC(C)(C)c1noc(C(=O)NCC2CCN(c3nc(-c4cnn(C5CCN(CC6CCN(c7ccc(N8CCC(=O)NC8=O)cc7)CC6)CC5)c4)cn4nccc34)CC2)n1]
144
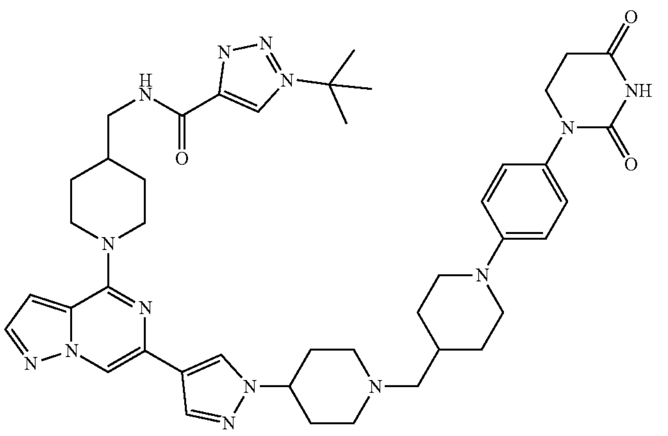
145

TABLE 1-continued
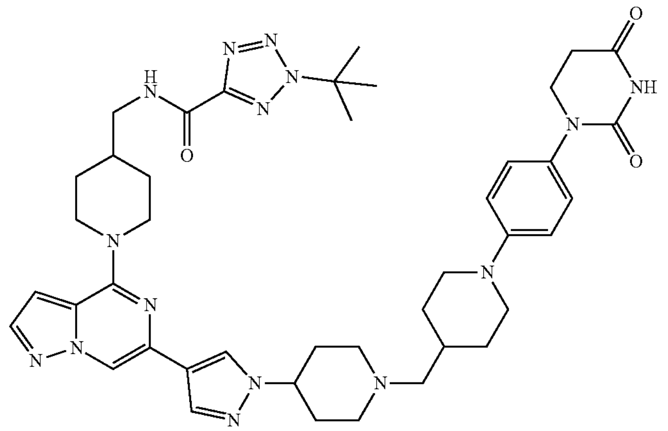 [SMILES: CC(C)(C)n1nnc(C(=O)NCC2CCN(c3nc(-c4cnn(C5CCN(CC6CCN(c7ccc(N8CCC(=O)NC8=O)cc7)CC6)CC5)c4)cn4nccc34)CC2)n1]
146
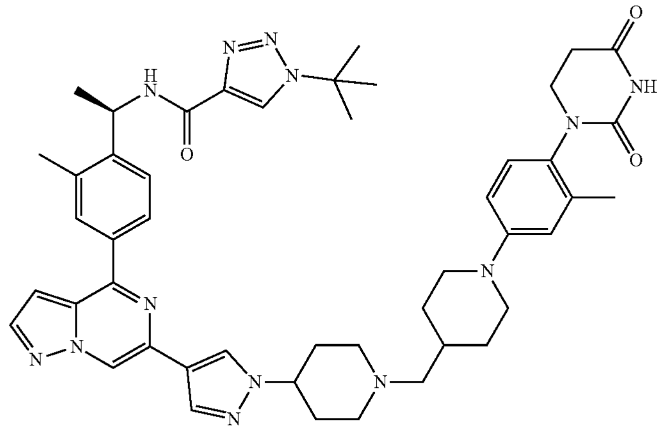 [SMILES: Cc1cc(-c2nc(-c3cnn(C4CCN(CC5CCN(c6ccc(N7CCC(=O)NC7=O)c(C)c6)CC5)CC4)c3)cn3nccc23)ccc1[C@@H](C)NC(=O)c1cn(C(C)(C)C)nn1]
147
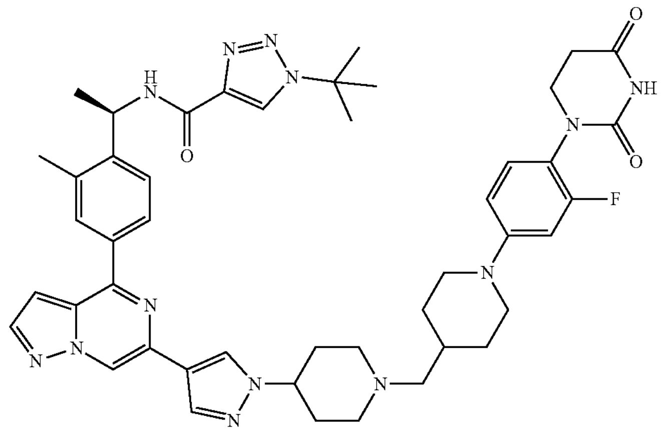
148

TABLE 1-continued
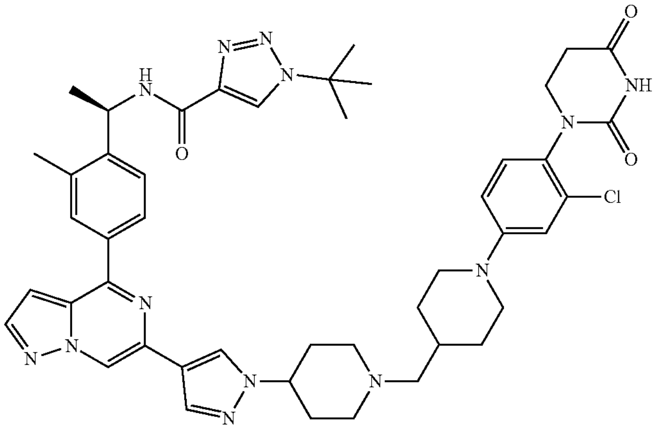 [SMILES: Cc1cc(-c2nc(-c3cnn(C4CCN(CC5CCN(c6ccc(N7CCC(=O)NC7=O)c(Cl)c6)CC5)CC4)c3)cn3nccc23)ccc1[C@@H](C)NC(=O)c1cn(C(C)(C)C)nn1]
149
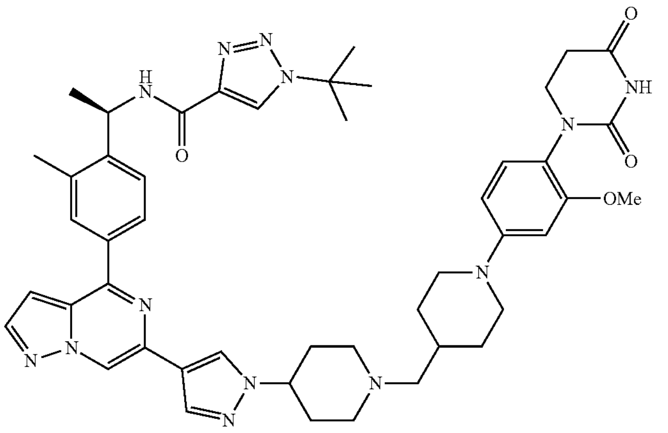
150
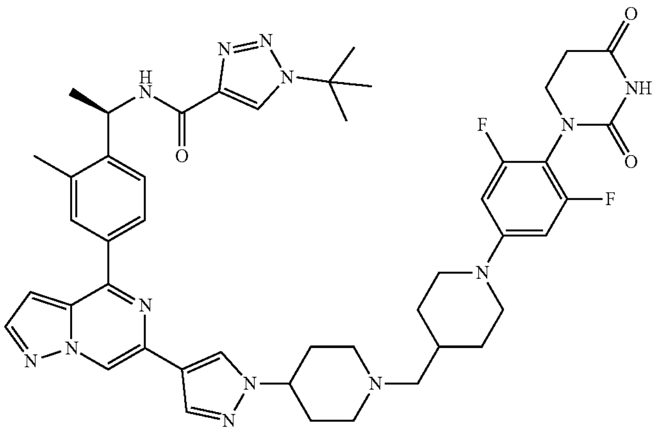
151

TABLE 1-continued
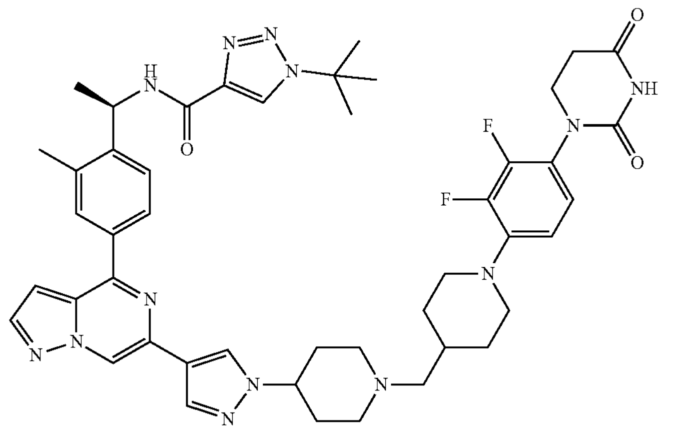 [SMILES: Cc1cc(-c2nc(-c3cnn(C4CCN(CC5CCN(c6ccc(N7CCC(=O)NC7=O)c(F)c6F)CC5)CC4)c3)cn3nccc23)ccc1[C@@H](C)NC(=O)c1cn(C(C)(C)C)nn1]
152
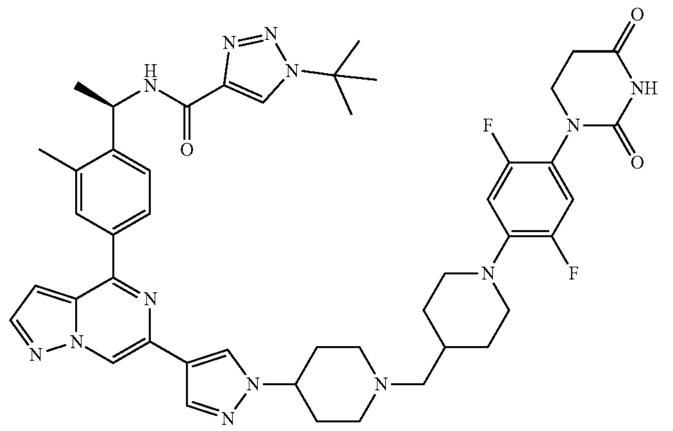
153
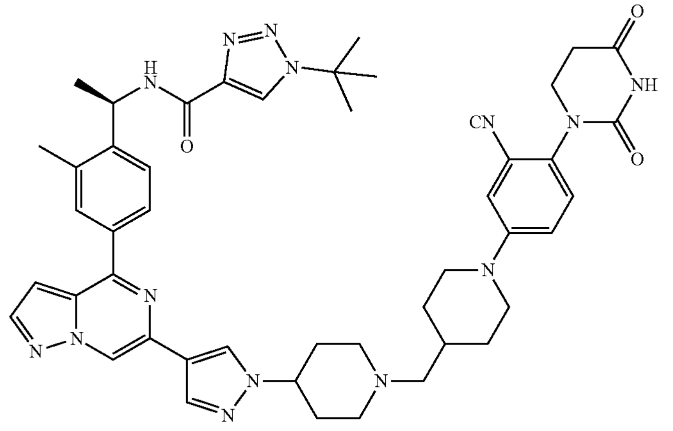
154

TABLE 1-continued
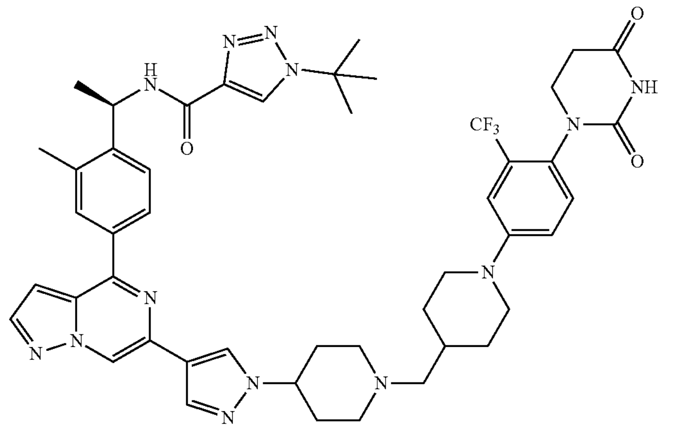
155
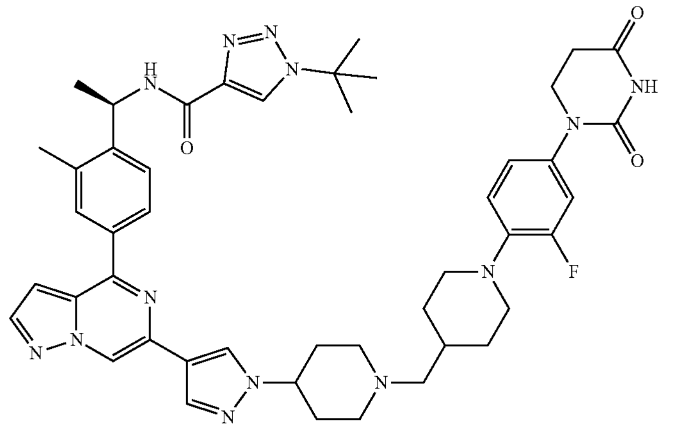 [SMILES: Cc1cc(-c2nc(-c3cnn(C4CCN(CC5CCN(c6ccc(N7CCC(=O)NC7=O)cc6F)CC5)CC4)c3)cn3nccc23)ccc1[C@@H](C)NC(=O)c1cn(C(C)(C)C)nn1]
156
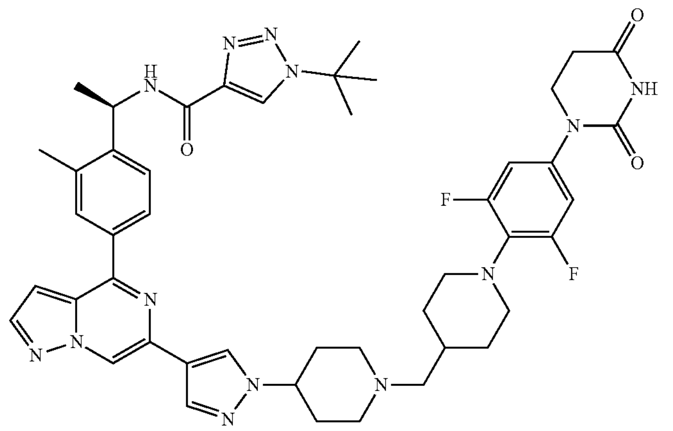 [SMILES: Cc1cc(-c2nc(-c3cnn(C4CCN(CC5CCN(c6c(F)cc(N7CCC(=O)NC7=O)cc6F)CC5)CC4)c3)cn3nccc23)ccc1[C@@H](C)NC(=O)c1cn(C(C)(C)C)nn1]
157

TABLE 1-continued
158
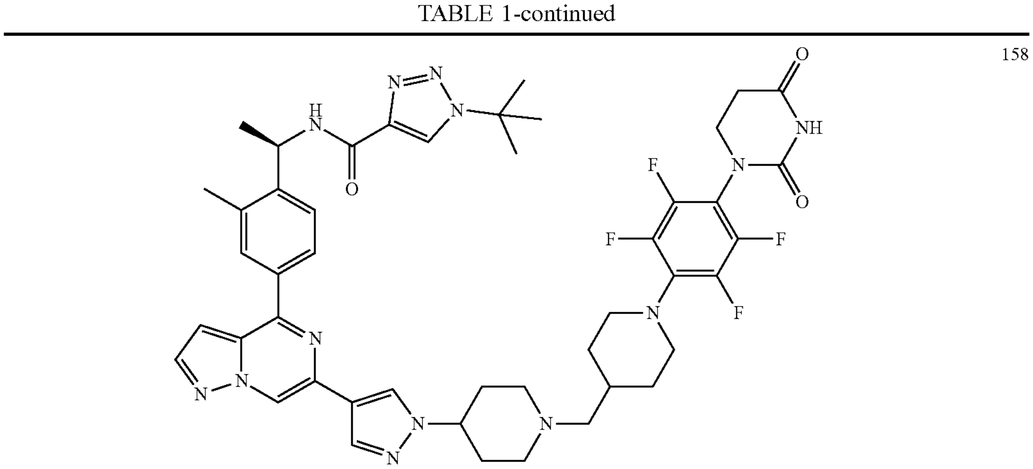
159
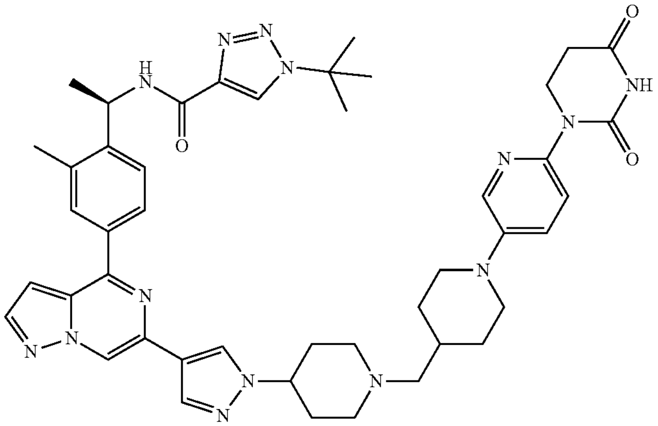 [SMILES: Cc1cc(-c2nc(-c3cnn(C4CCN(CC5CCN(c6ccc(N7CCC(=O)NC7=O)nc6)CC5)CC4)c3)cn3nccc23)ccc1[C@@H](C)NC(=O)c1cn(C(C)(C)C)nn1]
160
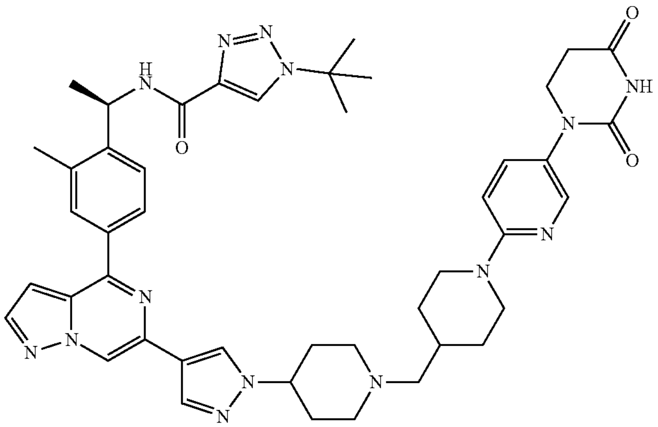 [SMILES: Cc1cc(-c2nc(-c3cnn(C4CCN(CC5CCN(c6ccc(N7CCC(=O)NC7=O)cn6)CC5)CC4)c3)cn3nccc23)ccc1[C@@H](C)NC(=O)c1cn(C(C)(C)C)nn1]
or a pharmaceutically acceptable salt or solvate thereof.
In some embodiments, the compound is selected from the following Table 2:

TABLE 2
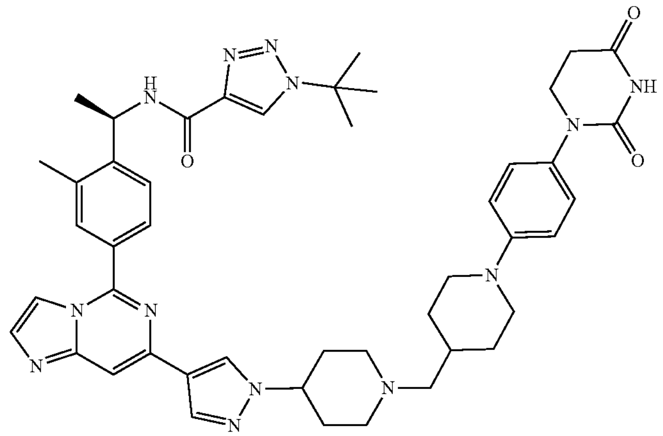 [SMILES: Cc1cc(-c2nc(-c3cnn(C4CCN(CC5CCN(c6ccc(N7CCC(=O)NC7=O)cc6)CC5)CC4)c3)cc3nccn23)ccc1[C@@H](C)NC(=O)c1cn(C(C)(C)C)nn1]
161
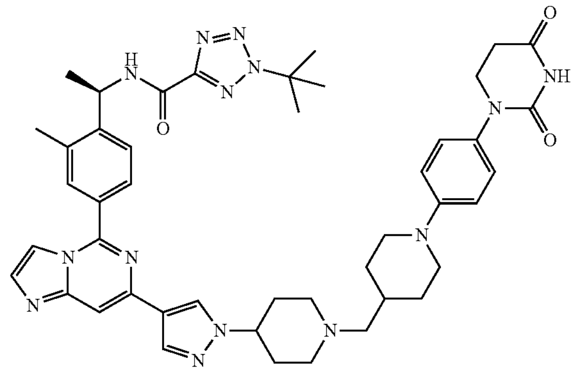 [SMILES: Cc1cc(-c2nc(-c3cnn(C4CCN(CC5CCN(c6ccc(N7CCC(=O)NC7=O)cc6)CC5)CC4)c3)cc3nccn23)ccc1[C@@H](C)NC(=O)c1nnn(C(C)(C)C)n1]
162
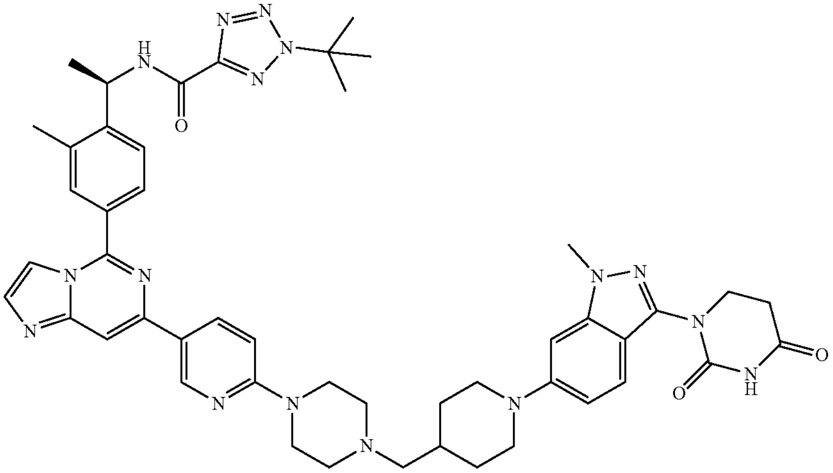
163

TABLE 2-continued
164
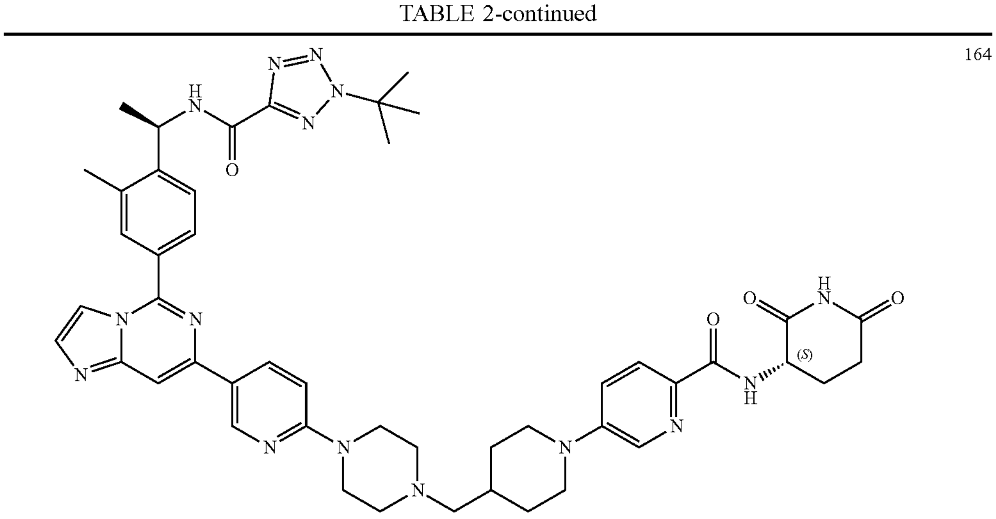
165
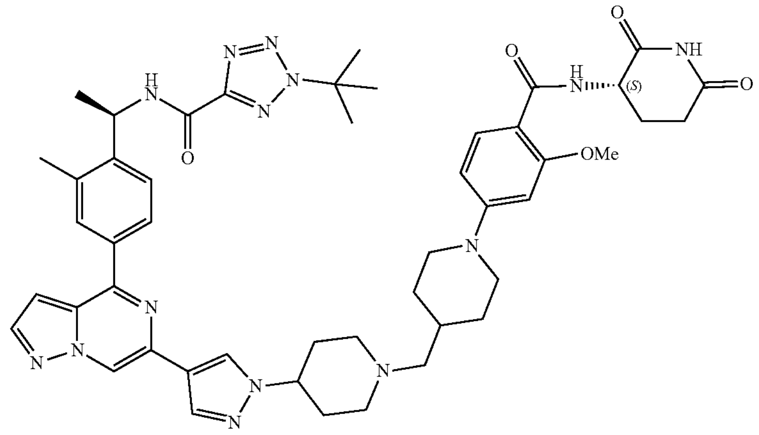
166
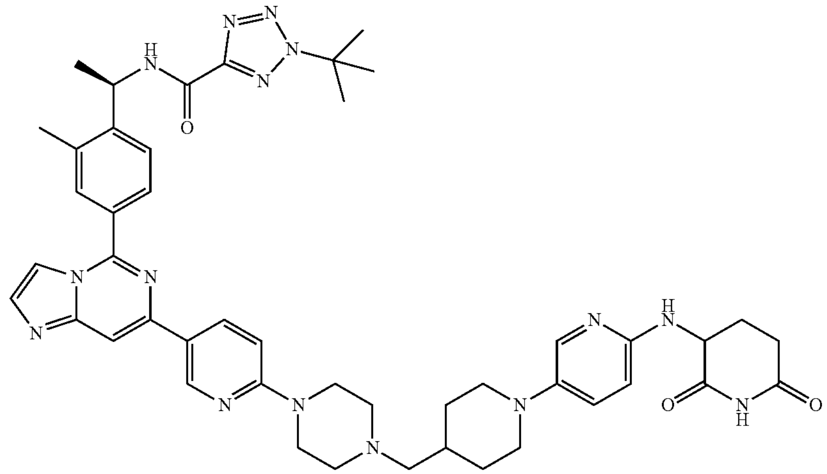

TABLE 2-continued
167
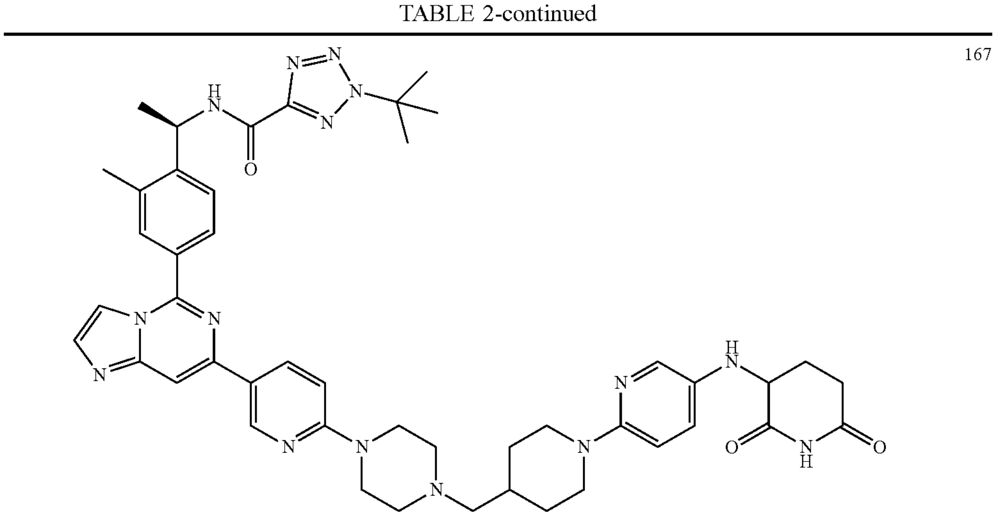
168
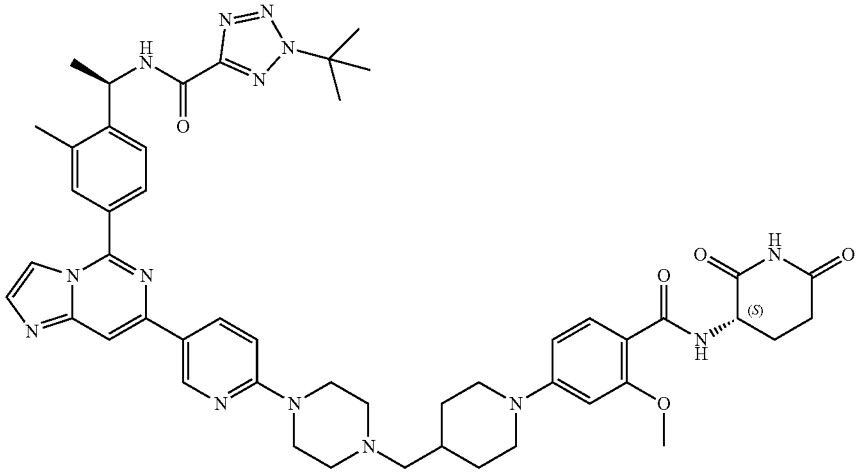
169
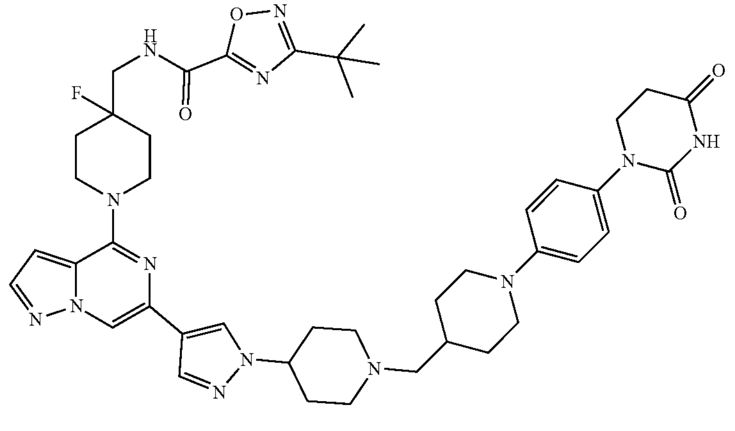 [SMILES: CC(C)(C)c1noc(C(=O)NCC2(F)CCN(c3nc(-c4cnn(C5CCN(CC6CCN(c7ccc(N8CCC(=O)NC8=O)cc7)CC6)CC5)c4)cn4nccc34)CC2)n1]

TABLE 2-continued
170
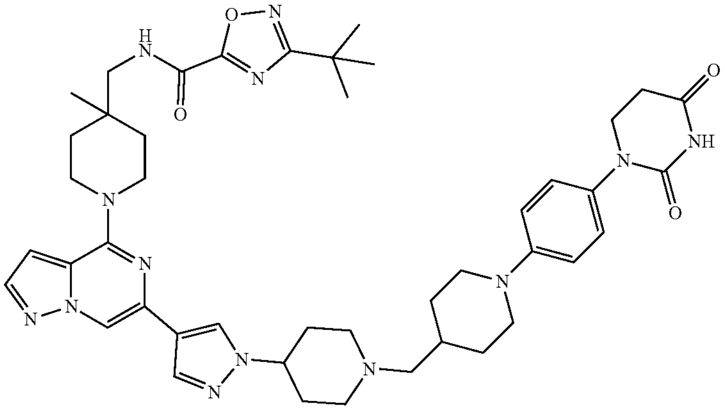 [SMILES: CC1(CNC(=O)c2nc(C(C)(C)C)no2)CCN(c2nc(-c3cnn(C4CCN(CC5CCN(c6ccc(N7CCC(=O)NC7=O)cc6)CC5)CC4)c3)cn3nccc23)CC1]
171
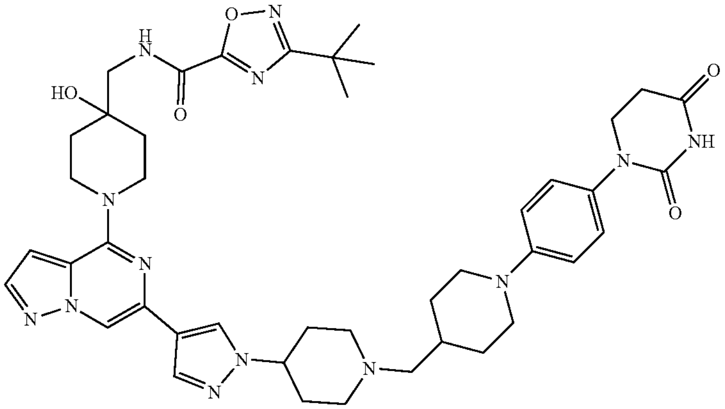 [SMILES: CC(C)(C)c1noc(C(=O)NCC2(O)CCN(c3nc(-c4cnn(C5CCN(CC6CCN(c7ccc(N8CCC(=O)NC8=O)cc7)CC6)CC5)c4)cn4nccc34)CC2)n1]
172
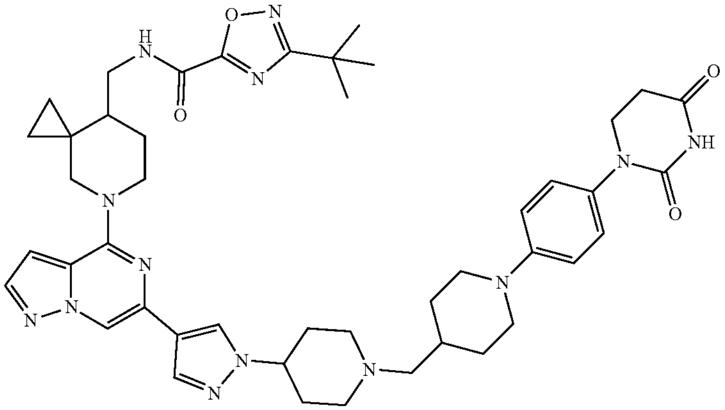 [SMILES: CC(C)(C)c1noc(C(=O)NCC2CCN(c3nc(-c4cnn(C5CCN(CC6CCN(c7ccc(N8CCC(=O)NC8=O)cc7)CC6)CC5)c4)cn4nccc34)CC23CC3)n1]

TABLE 2-continued
173
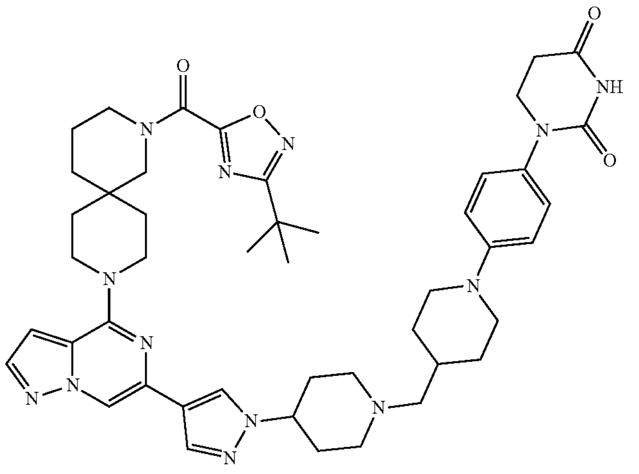 [SMILES: CC(C)(C)c1noc(C(=O)N2CCCC3(CCN(c4nc(-c5cnn(C6CCN(CC7CCN(c8ccc(N9CCC(=O)NC9=O)cc8)CC7)CC6)c5)cn5nccc45)CC3)C2)n1]
174
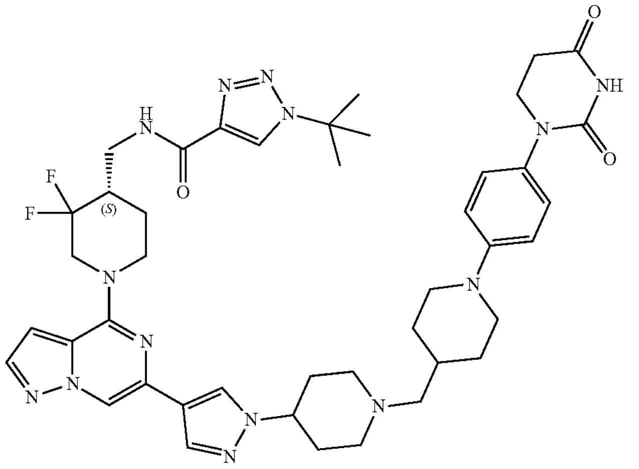
175
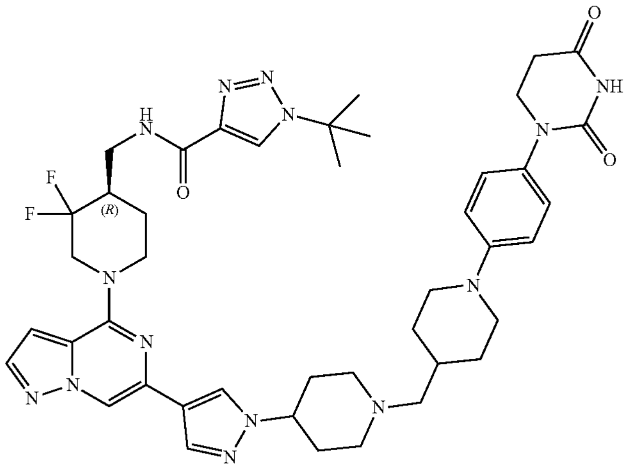

TABLE 2-continued
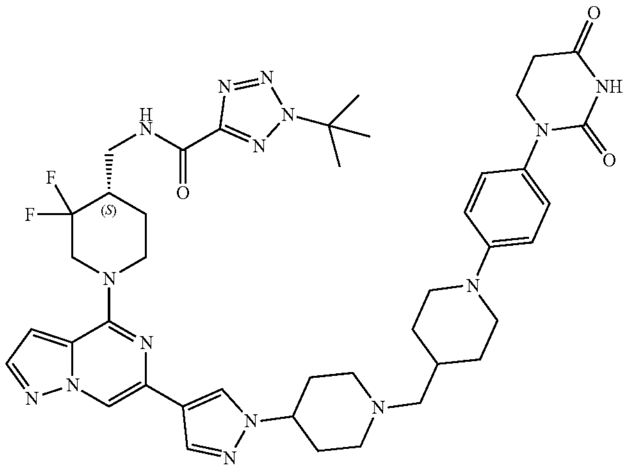
176
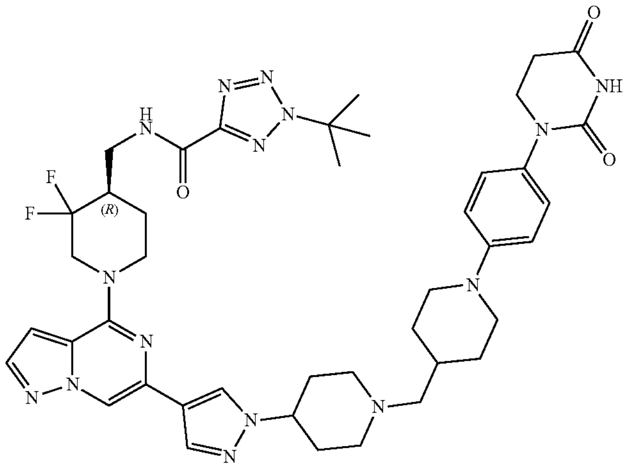
177
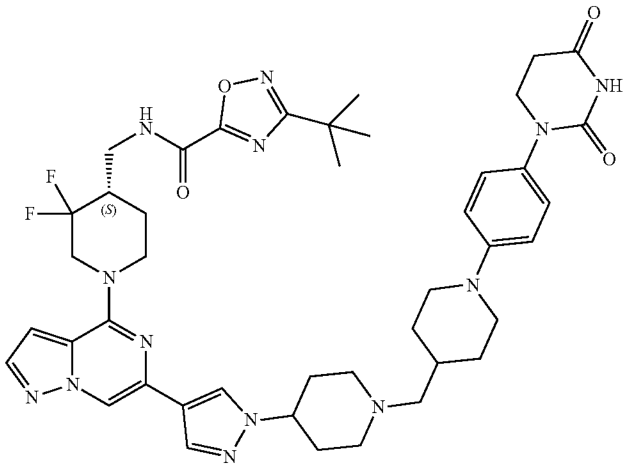
178

TABLE 2-continued
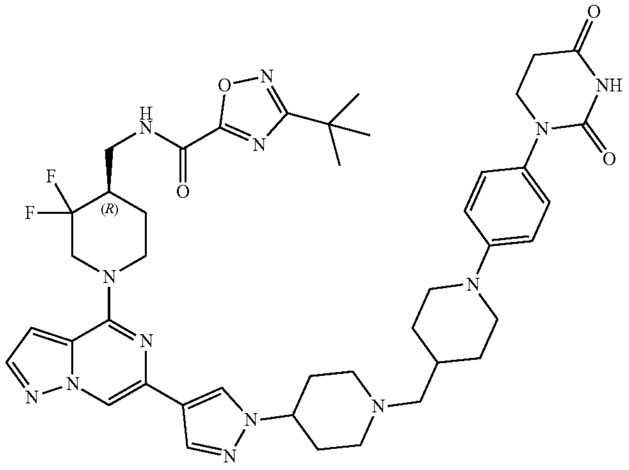
179
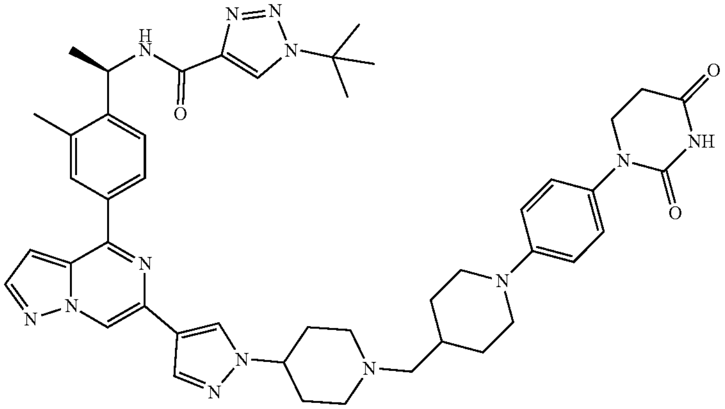 [SMILES: Cc1cc(-c2nc(-c3cnn(C4CCN(CC5CCN(c6ccc(N7CCC(=O)NC7=O)cc6)CC5)CC4)c3)cn3nccc23)ccc1[C@@H](C)NC(=O)c1cn(C(C)(C)C)nn1]
180
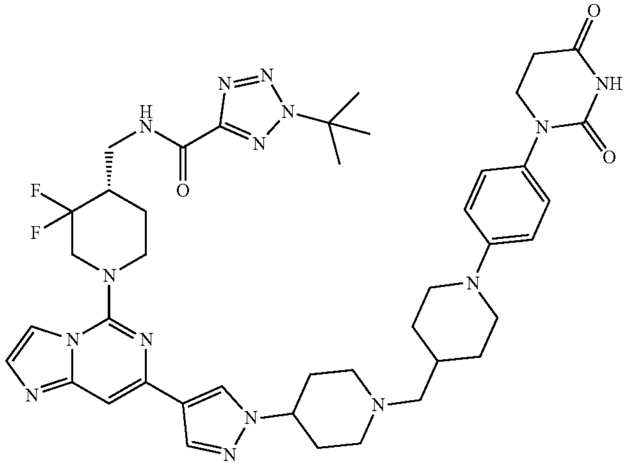
181

TABLE 2-continued
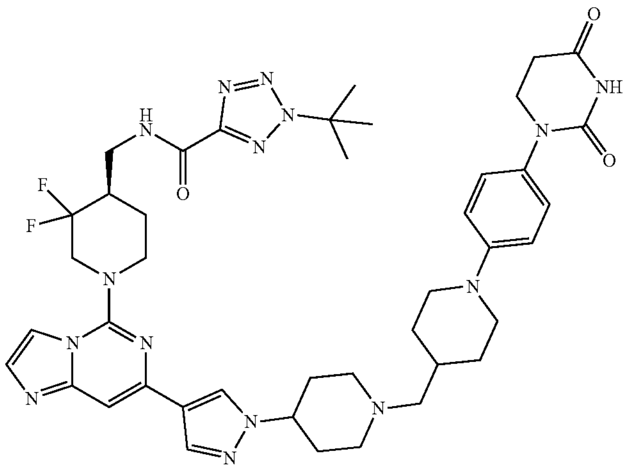 [SMILES: CC(C)(C)n1nnc(C(=O)NC[C@H]2CCN(c3nc(-c4cnn(C5CCN(CC6CCN(c7ccc(N8CCC(=O)NC8=O)cc7)CC6)CC5)c4)cc4nccn34)CC2(F)F)n1]
182
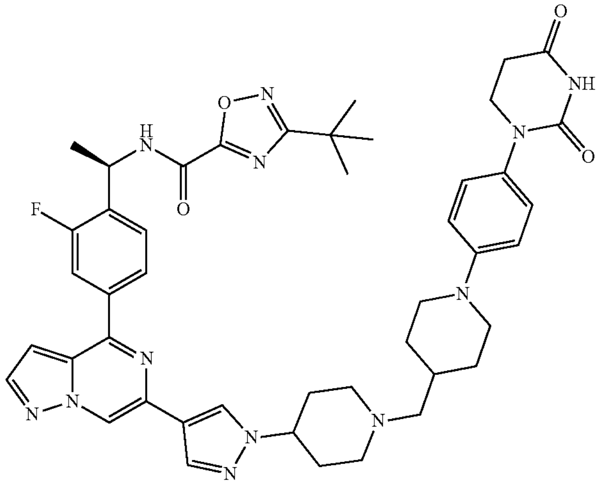 [SMILES: C[C@@H](NC(=O)c1nc(C(C)(C)C)no1)c1ccc(-c2nc(-c3cnn(C4CCN(CC5CCN(c6ccc(N7CCC(=O)NC7=O)cc6)CC5)CC4)c3)cn3nccc23)cc1F]
183
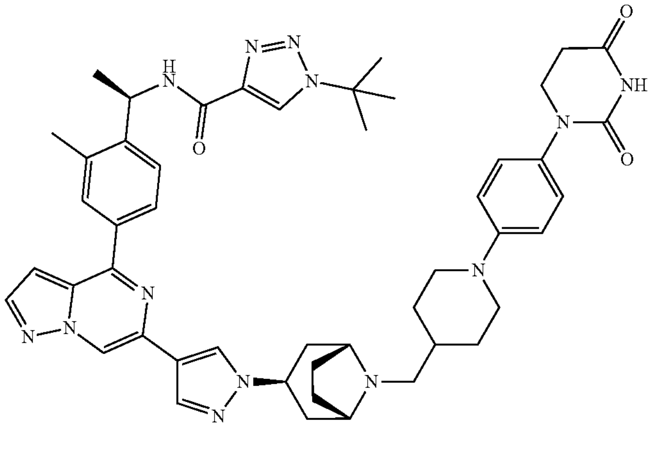 [SMILES: Cc1cc(-c2nc(-c3cnn([C@H]4C[C@H]5CC[C@@H](C4)N5CC4CCN(c5ccc(N6CCC(=O)NC6=O)cc5)CC4)c3)cn3nccc23)ccc1[C@@H](C)NC(=O)c1cn(C(C)(C)C)nn1]
184

TABLE 2-continued
185
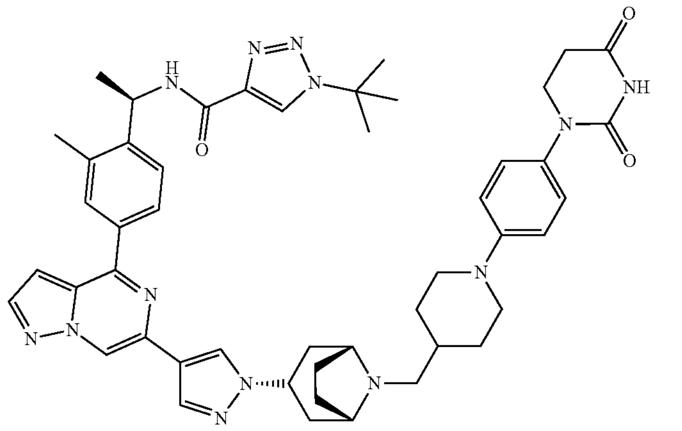
186
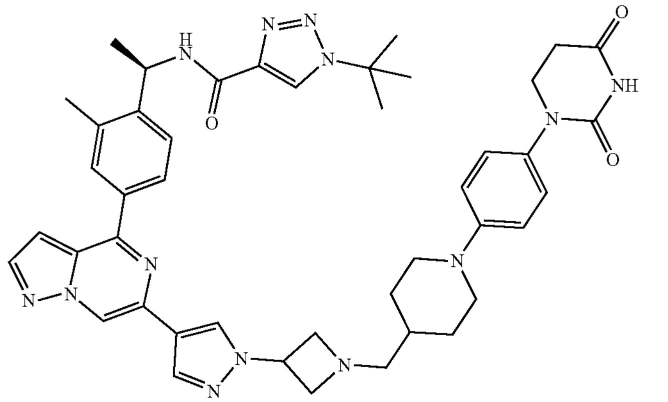 [SMILES: Cc1cc(-c2nc(-c3cnn(C4CN(CC5CCN(c6ccc(N7CCC(=O)NC7=O)cc6)CC5)C4)c3)cn3nccc23)ccc1[C@@H](C)NC(=O)c1cn(C(C)(C)C)nn1]
187
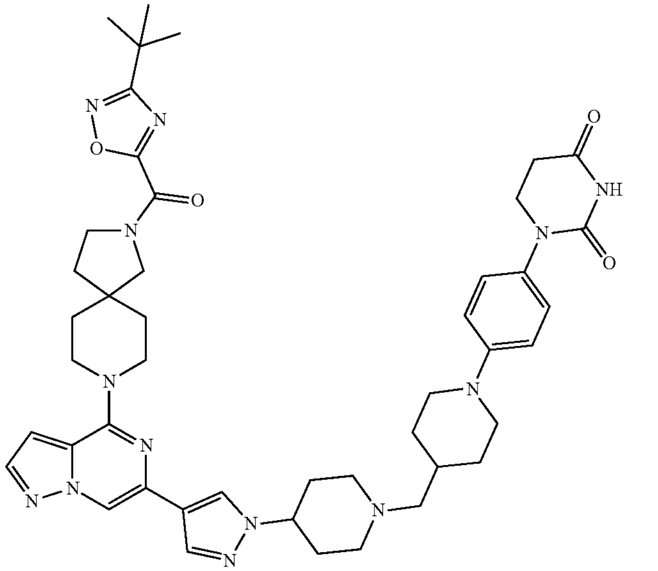 [SMILES: CC(C)(C)c1noc(C(=O)N2CCC3(CCN(c4nc(-c5cnn(C6CCN(CC7CCN(c8ccc(N9CCC(=O)NC9=O)cc8)CC7)CC6)c5)cn5nccc45)CC3)C2)n1]

TABLE 2-continued
188
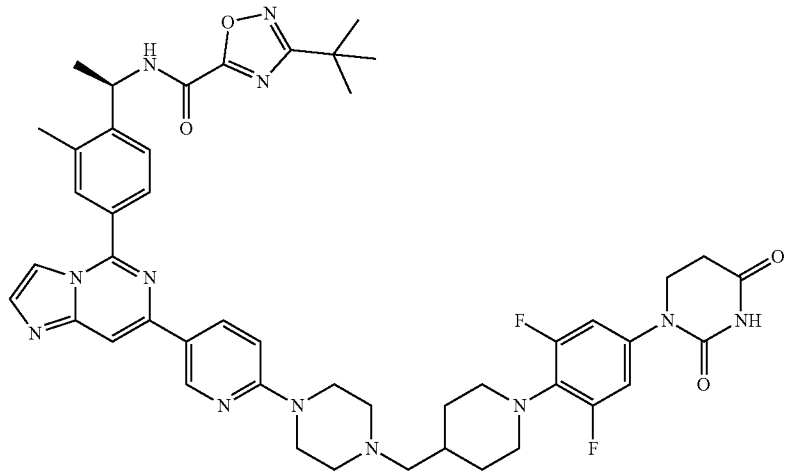 [SMILES: Cc1cc(-c2nc(-c3ccc(N4CCN(CC5CCN(c6c(F)cc(N7CCC(=O)NC7=O)cc6F)CC5)CC4)nc3)cc3nccn23)ccc1[C@@H](C)NC(=O)c1nc(C(C)(C)C)no1]
189
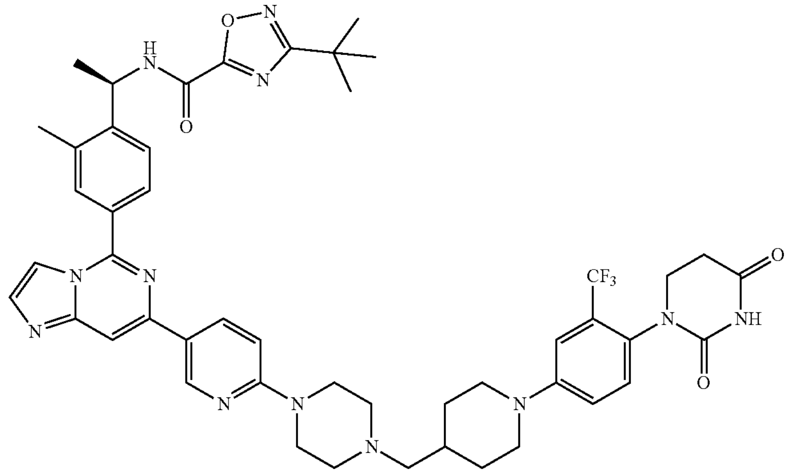 [SMILES: Cc1cc(-c2nc(-c3ccc(N4CCN(CC5CCN(c6ccc(N7CCC(=O)NC7=O)c(C(F)(F)F)c6)CC5)CC4)nc3)cc3nccn23)ccc1[C@@H](C)NC(=O)c1nc(C(C)(C)C)no1]
190
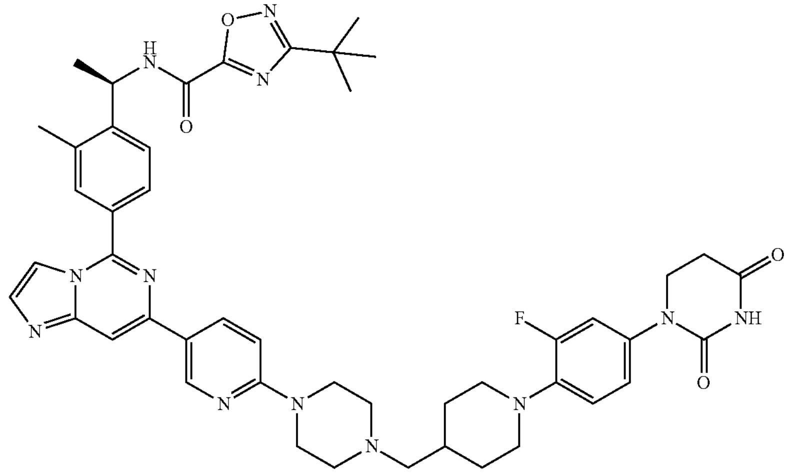 [SMILES: Cc1cc(-c2nc(-c3ccc(N4CCN(CC5CCN(c6ccc(N7CCC(=O)NC7=O)cc6F)CC5)CC4)nc3)cc3nccn23)ccc1[C@@H](C)NC(=O)c1nc(C(C)(C)C)no1]

TABLE 2-continued
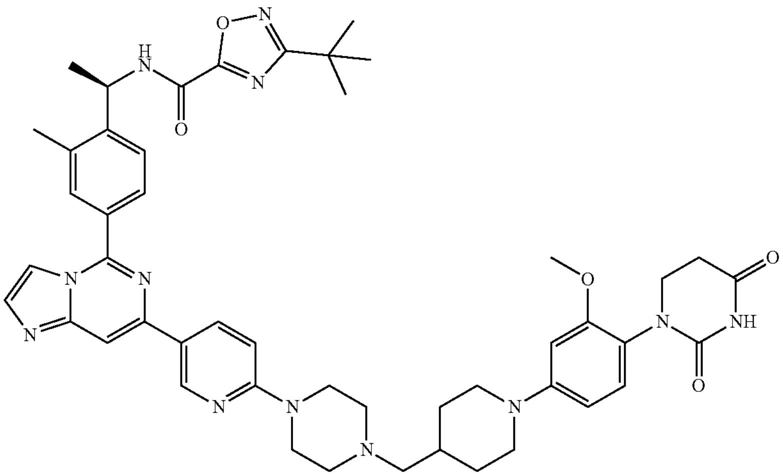 [SMILES: COc1cc(N2CCC(CN3CCN(c4ccc(-c5cc6nccn6c(-c6ccc([C@@H](C)NC(=O)c7nc(C(C)(C)C)no7)c(C)c6)n5)cn4)CC3)CC2)ccc1N1CCC(=O)NC1=O]
191
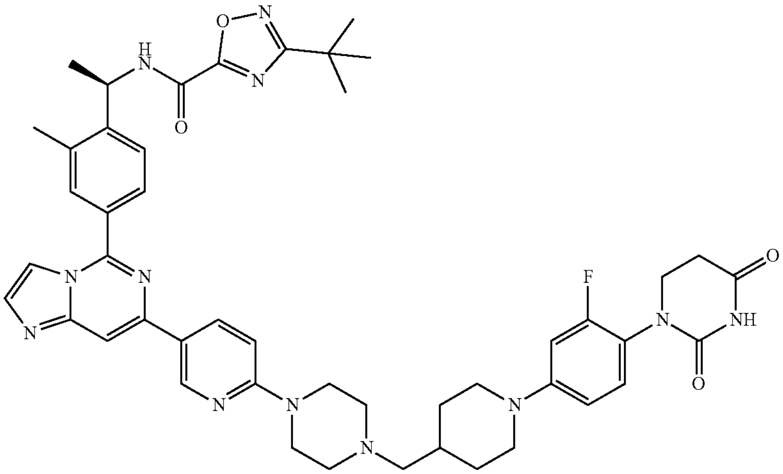 [SMILES: Cc1cc(-c2nc(-c3ccc(N4CCN(CC5CCN(c6ccc(N7CCC(=O)NC7=O)c(C)c6)CC5)CC4)nc3)cc3nccn23)ccc1[C@@H](C)NC(=O)c1nc(C(C)(C)C)no1]
192
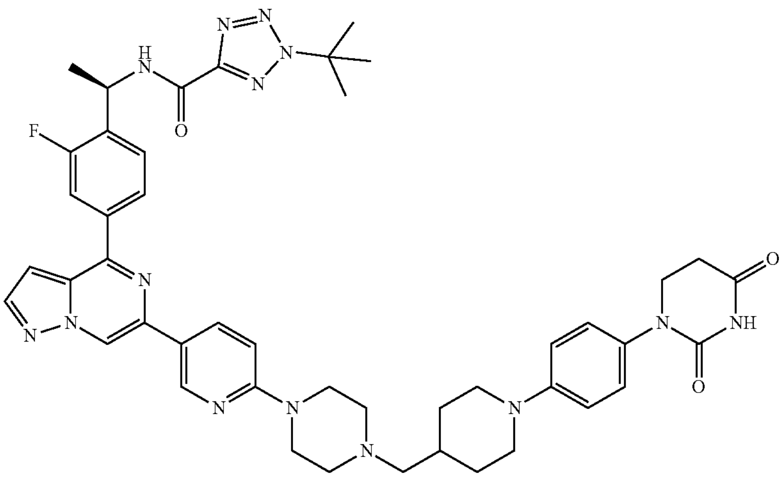
193

TABLE 2-continued
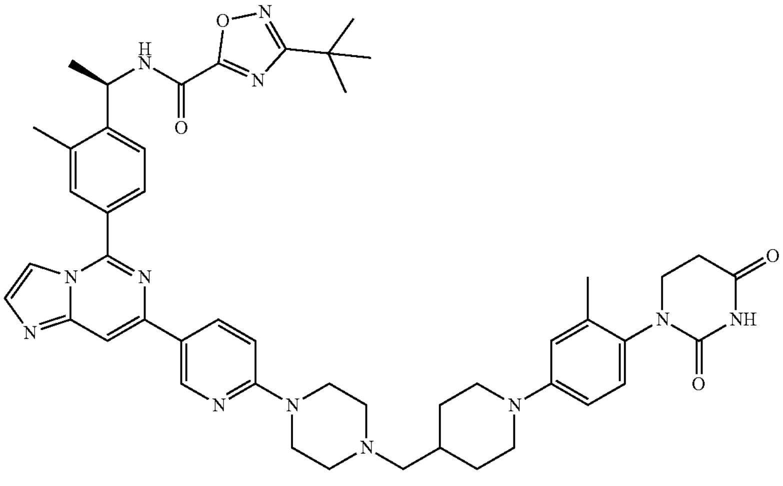
194
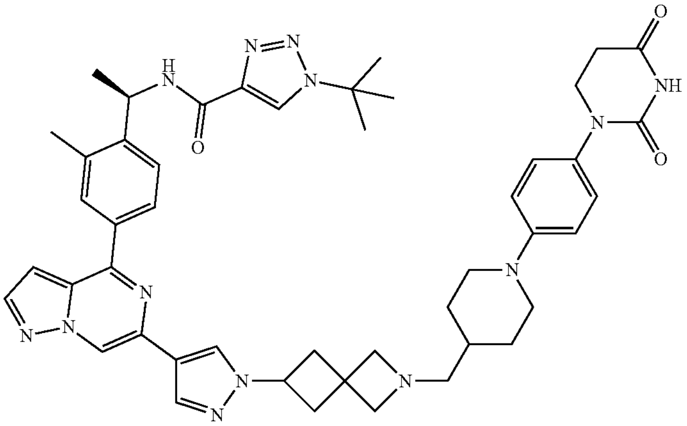 [SMILES: Cc1cc(-c2nc(-c3cnn(C4CC5(C4)CN(CC4CCN(c6ccc(N7CCC(=O)NC7=O)cc6)CC4)C5)c3)cn3nccc23)ccc1[C@@H](C)NC(=O)c1cn(C(C)(C)C)nn1]
195
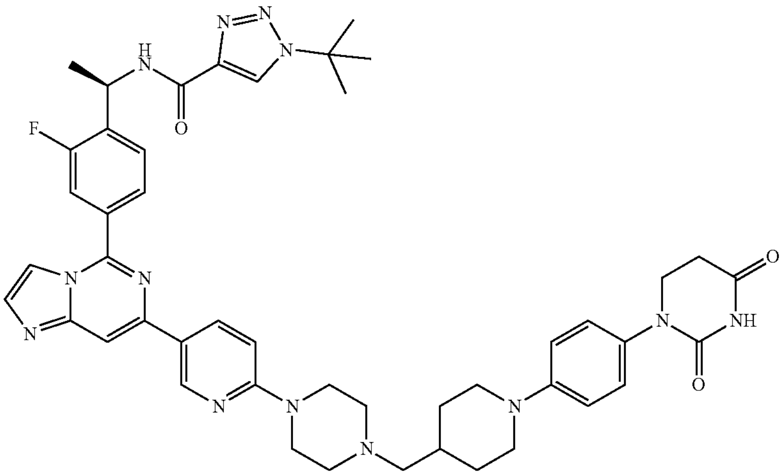 [SMILES: C[C@@H](NC(=O)c1cn(C(C)(C)C)nn1)c1ccc(-c2nc(-c3ccc(N4CCN(CC5CCN(c6ccc(N7CCC(=O)NC7=O)cc6)CC5)CC4)nc3)cc3nccn23)cc1F]
196

TABLE 2-continued
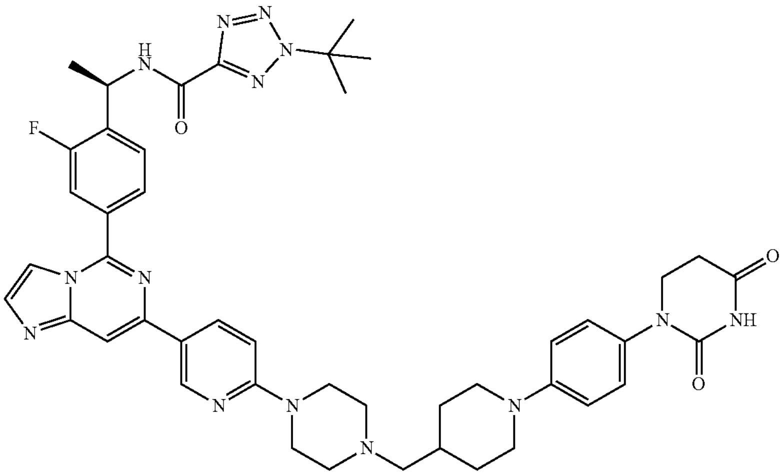 [SMILES: C[C@@H](NC(=O)c1nnn(C(C)(C)C)n1)c1ccc(-c2nc(-c3ccc(N4CCN(CC5CCN(c6ccc(N7CCC(=O)NC7=O)cc6)CC5)CC4)nc3)cc3nccn23)cc1F]
197
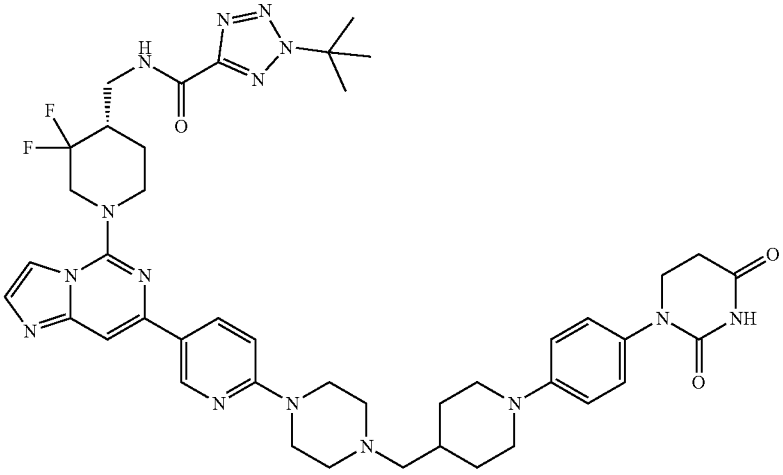 [SMILES: CC(C)(C)n1nnc(C(=O)NC[C@@H]2CCN(c3nc(-c4ccc(N5CCN(CC6CCN(c7ccc(N8CCC(=O)NC8=O)cc7)CC6)CC5)nc4)cc4nccn34)CC2(F)F)n1]
198
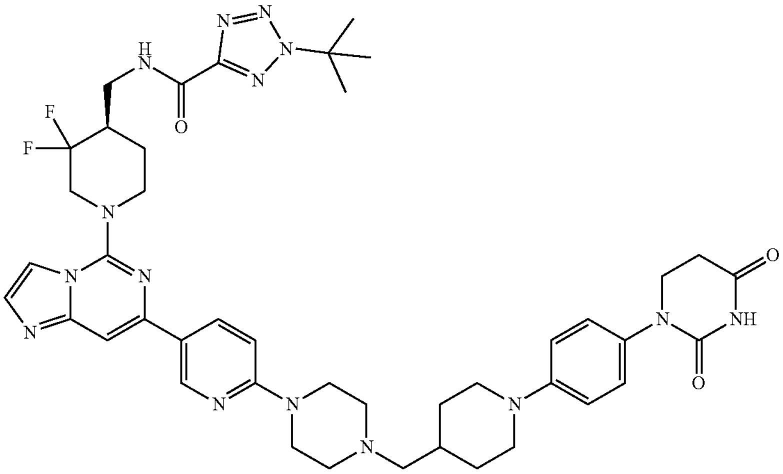 [SMILES: CC(C)(C)n1nnc(C(=O)NC[C@H]2CCN(c3nc(-c4ccc(N5CCN(CC6CCN(c7ccc(N8CCC(=O)NC8=O)cc7)CC6)CC5)nc4)cc4nccn34)CC2(F)F)n1]
199

TABLE 2-continued
200
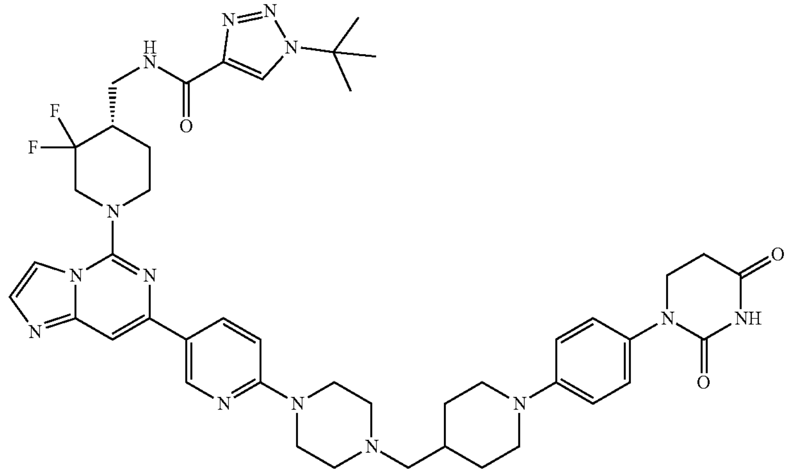 [SMILES: CC(C)(C)n1cc(C(=O)NC[C@@H]2CCN(c3nc(-c4ccc(N5CCN(CC6CCN(c7ccc(N8CCC(=O)NC8=O)cc7)CC6)CC5)nc4)cc4nccn34)CC2(F)F)nn1]
201
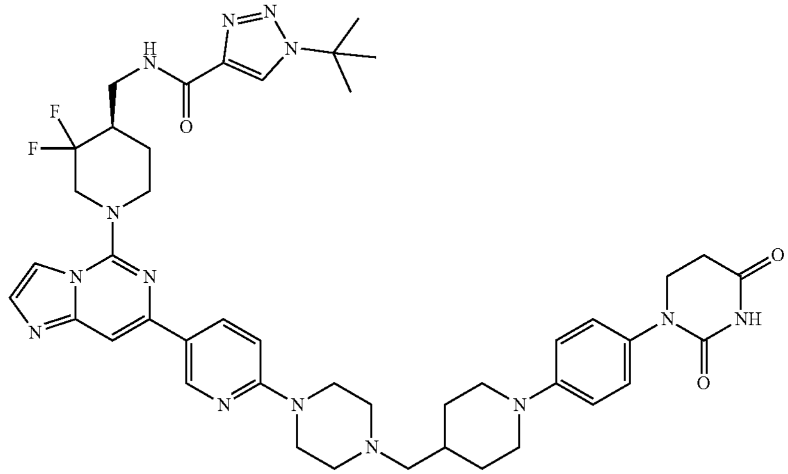 [SMILES: CC(C)(C)n1cc(C(=O)NC[C@H]2CCN(c3nc(-c4ccc(N5CCN(CC6CCN(c7ccc(N8CCC(=O)NC8=O)cc7)CC6)CC5)nc4)cc4nccn34)CC2(F)F)nn1]
202
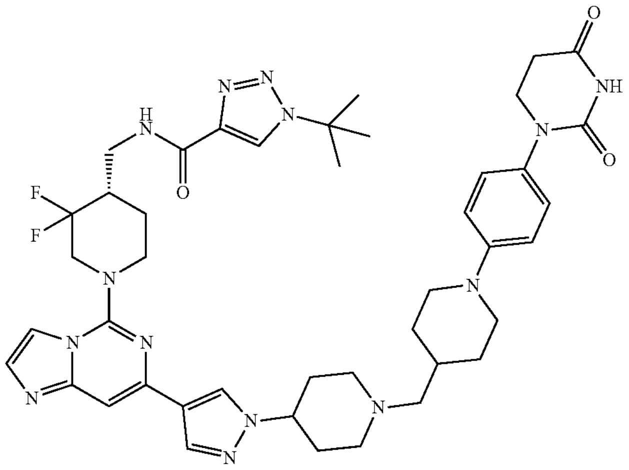 [SMILES: CC(C)(C)n1cc(C(=O)NC[C@@H]2CCN(c3nc(-c4cnn(C5CCN(CC6CCN(c7ccc(N8CCC(=O)NC8=O)cc7)CC6)CC5)c4)cc4nccn34)CC2(F)F)nn1]

TABLE 2-continued
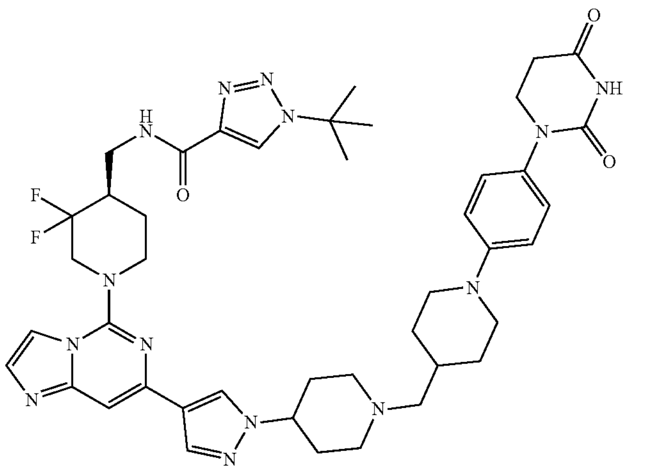 [SMILES: CC(C)(C)n1cc(C(=O)NC[C@H]2CCN(c3nc(-c4cnn(C5CCN(CC6CCN(c7ccc(N8CCC(=O)NC8=O)cc7)CC6)CC5)c4)cc4nccn34)CC2(F)F)nn1]
203
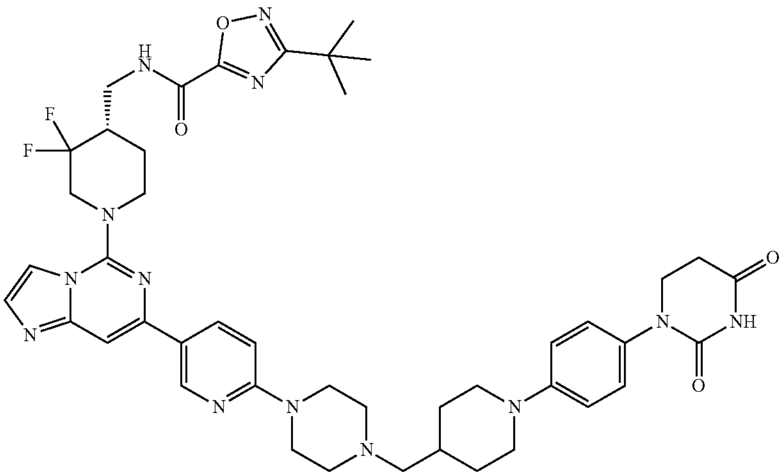 [SMILES: CC(C)(C)c1noc(C(=O)NC[C@@H]2CCN(c3nc(-c4ccc(N5CCN(CC6CCN(c7ccc(N8CCC(=O)NC8=O)cc7)CC6)CC5)nc4)cc4nccn34)CC2(F)F)n1]
204
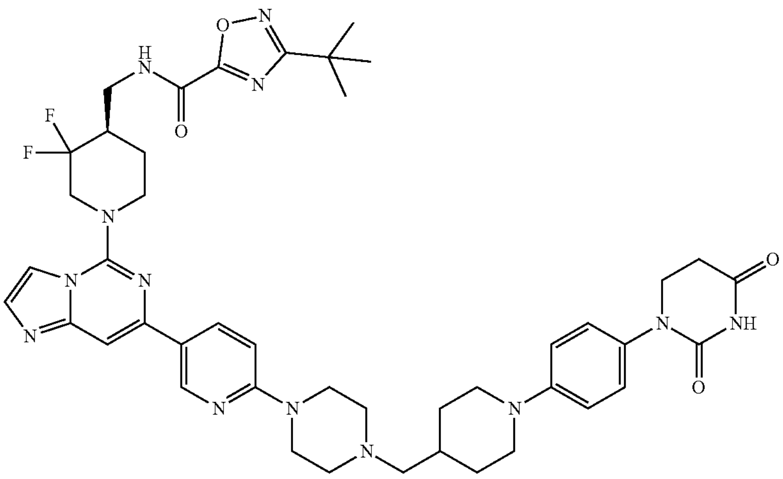 [SMILES: CC(C)(C)c1noc(C(=O)NC[C@H]2CCN(c3nc(-c4ccc(N5CCN(CC6CCN(c7ccc(N8CCC(=O)NC8=O)cc7)CC6)CC5)nc4)cc4nccn34)CC2(F)F)n1]
205

TABLE 2-continued
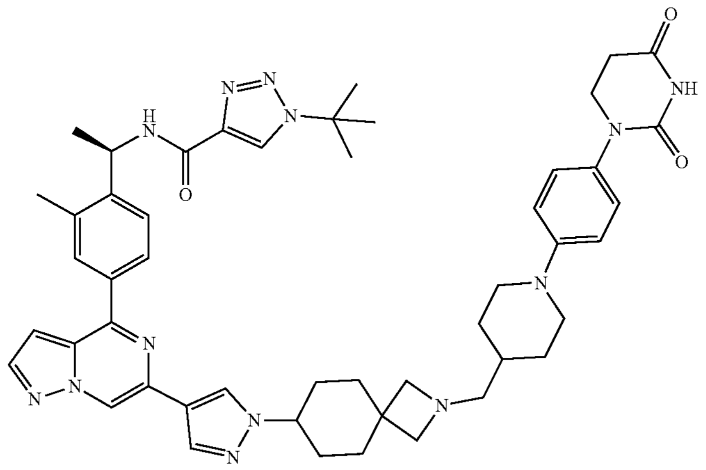 [SMILES: Cc1cc(-c2nc(-c3cnn(C4CCC5(CC4)CN(CC4CCN(c6ccc(N7CCC(=O)NC7=O)cc6)CC4)C5)c3)cn3nccc23)ccc1[C@@H](C)NC(=O)c1cn(C(C)(C)C)nn1]
206
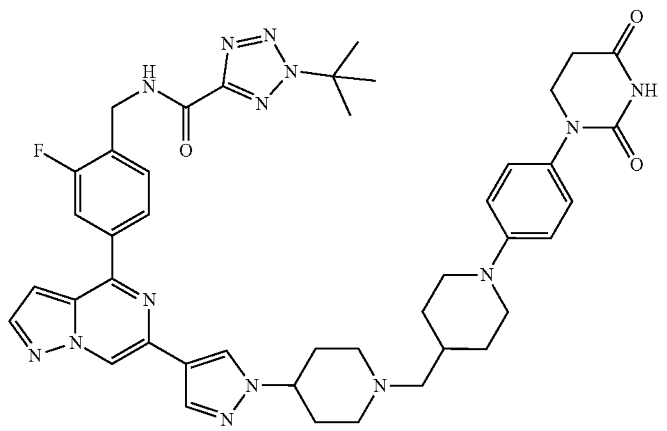 [SMILES: Cc1cc(-c2nc(-c3cnn(C4CCN(CC5CCN(c6ccc(N7CCC(=O)NC7=O)cc6)CC5)CC4)c3)cn3nccc23)ccc1CNC(=O)c1nnn(C(C)(C)C)n1]
207
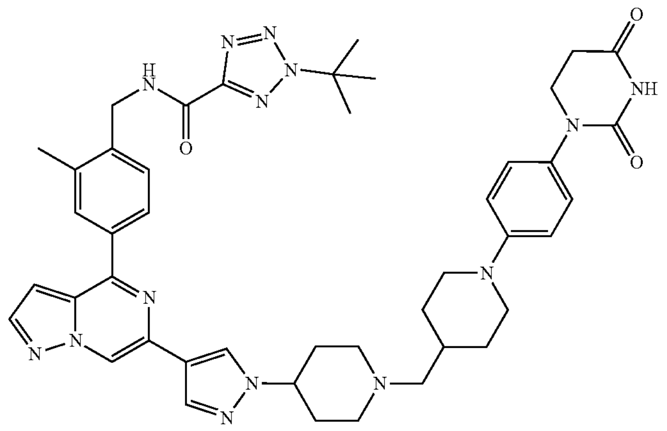
208

TABLE 2-continued
209
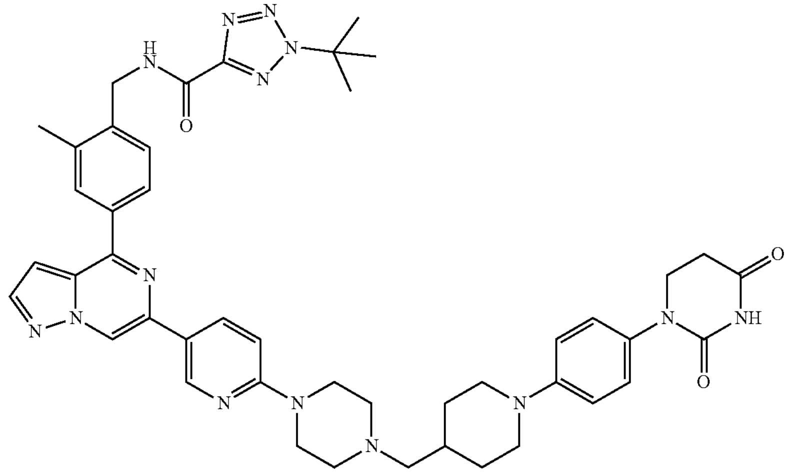
210
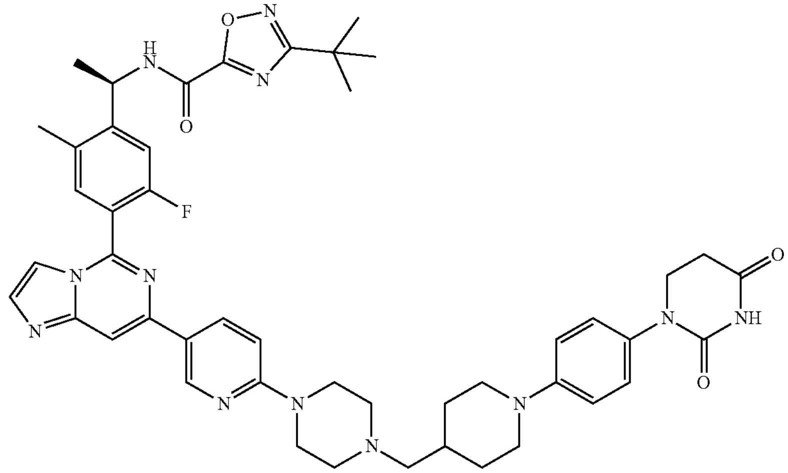 [SMILES: Cc1cc(-c2nc(-c3ccc(N4CCN(CC5CCN(c6ccc(N7CCC(=O)NC7=O)cc6)CC5)CC4)nc3)cc3nccn23)c(F)cc1[C@@H](C)NC(=O)c1nc(C(C)(C)C)no1]
211
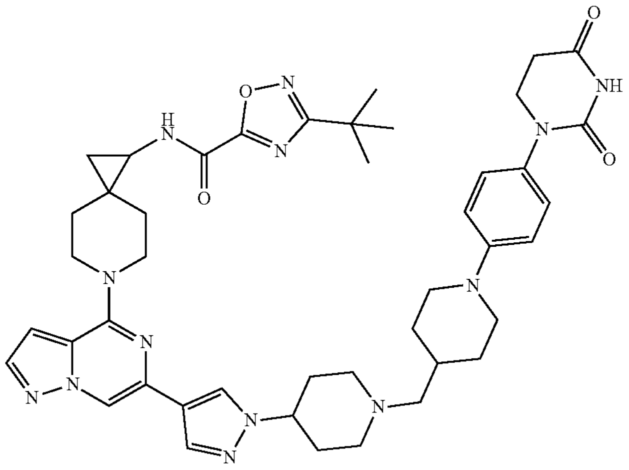 [SMILES: CC(C)(C)c1noc(C(=O)NC2CC23CCN(c2nc(-c4cnn(C5CCN(CC6CCN(c7ccc(N8CCC(=O)NC8=O)cc7)CC6)CC5)c4)cn4nccc24)CC3)n1]

TABLE 2-continued
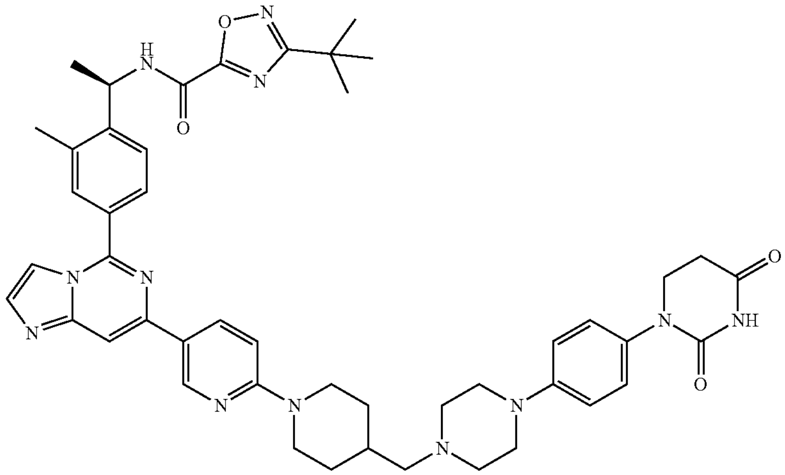
212
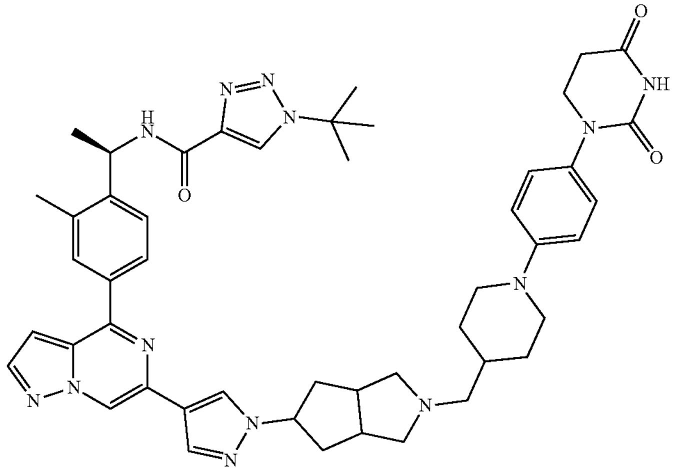 [SMILES: Cc1cc(-c2nc(-c3cnn(C4CC5CN(CC6CCN(c7ccc(N8CCC(=O)NC8=O)cc7)CC6)CC5C4)c3)cn3nccc23)ccc1[C@@H](C)NC(=O)c1cn(C(C)(C)C)nn1]
213
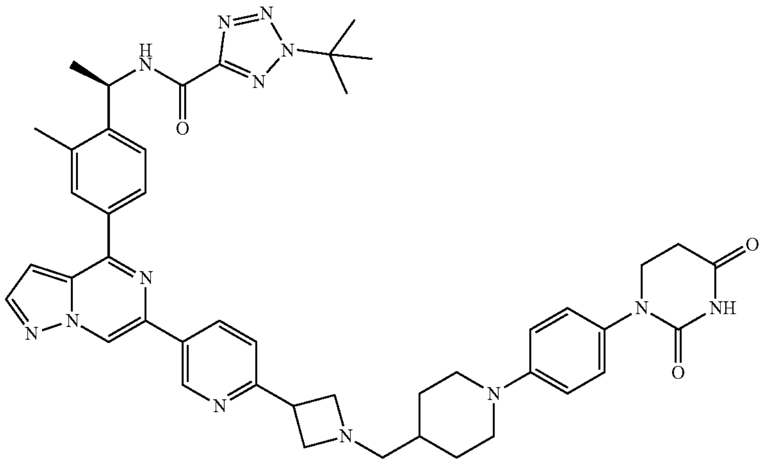 [SMILES: Cc1cc(-c2nc(-c3ccc(C4CN(CC5CCN(c6ccc(N7CCC(=O)NC7=O)cc6)CC5)C4)nc3)cn3nccc23)ccc1[C@@H](C)NC(=O)c1nnn(C(C)(C)C)n1]
214

TABLE 2-continued
215
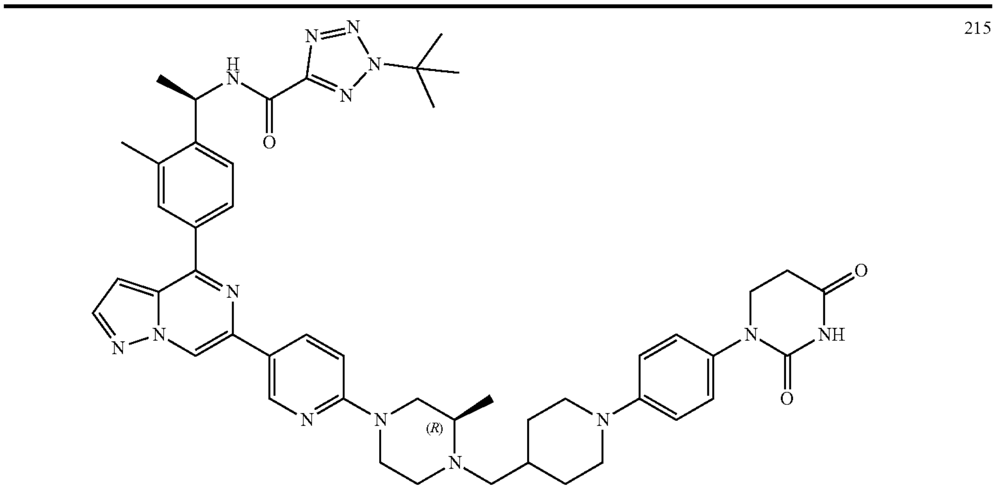
216
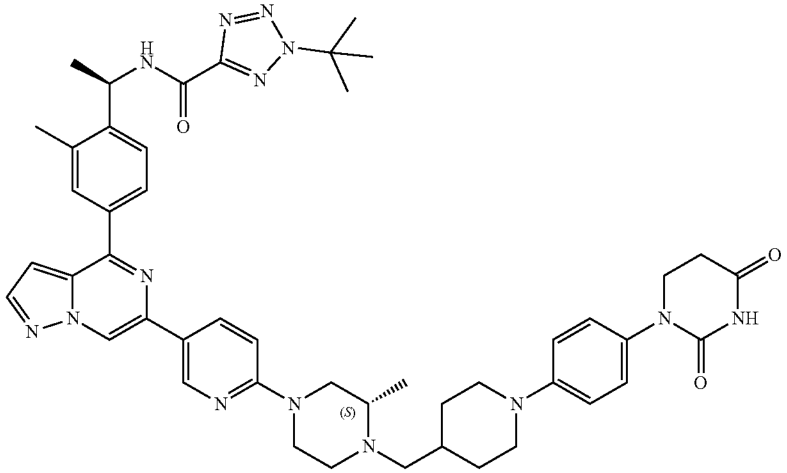
217
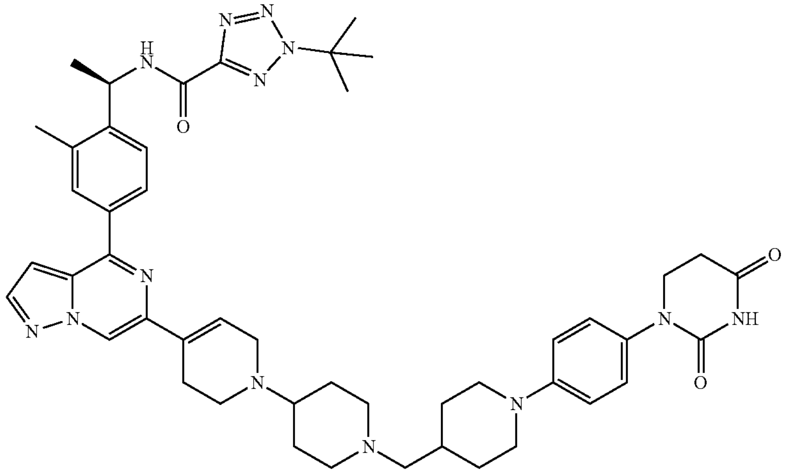

TABLE 2-continued
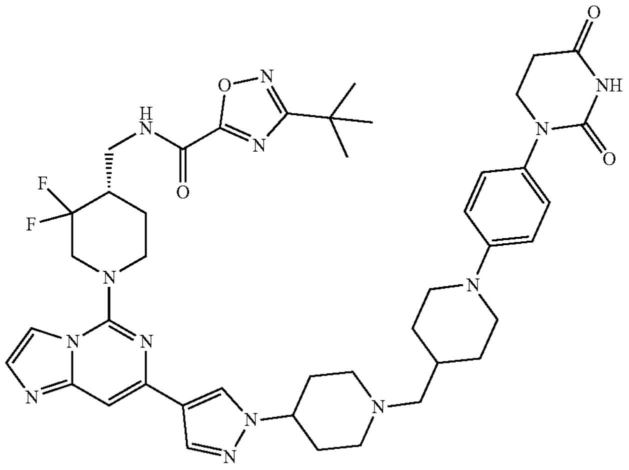 [SMILES: CC(C)(C)c1noc(C(=O)NC[C@@H]2CCN(c3nc(-c4cnn(C5CCN(CC6CCN(c7ccc(N8CCC(=O)NC8=O)cc7)CC6)CC5)c4)cc4nccn34)CC2(F)F)n1]
218
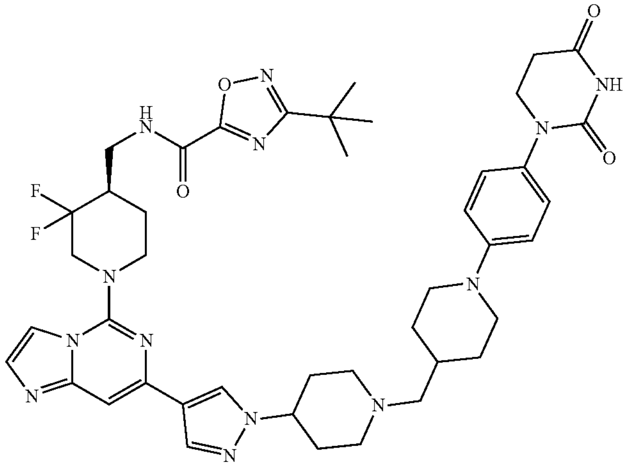 [SMILES: CC(C)(C)c1noc(C(=O)NC[C@H]2CCN(c3nc(-c4cnn(C5CCN(CC6CCN(c7ccc(N8CCC(=O)NC8=O)cc7)CC6)CC5)c4)cc4nccn34)CC2(F)F)n1]
219
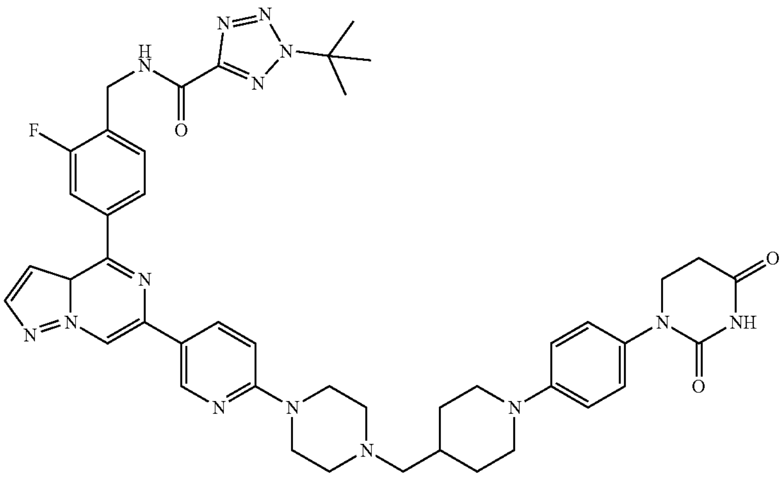
220

TABLE 2-continued
221
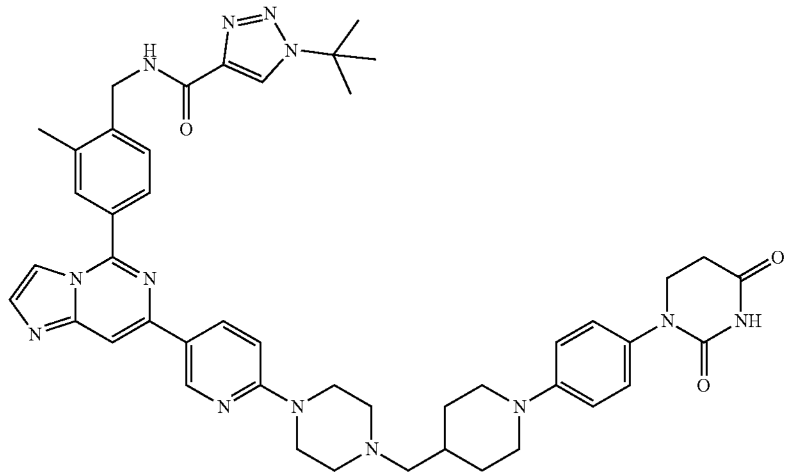
222
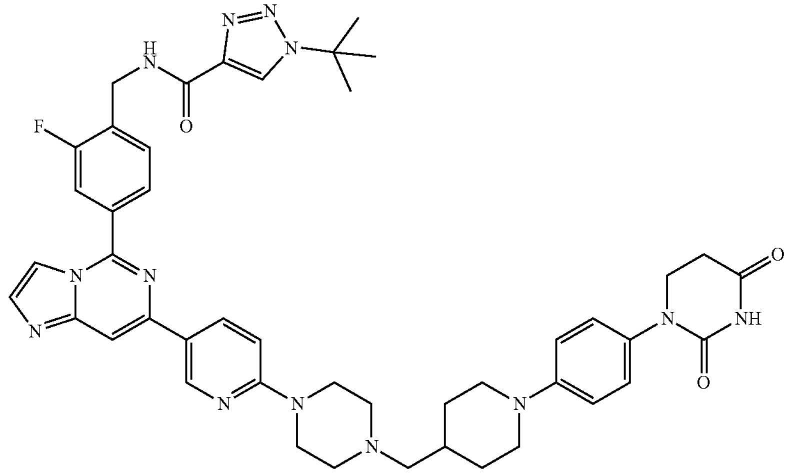
223
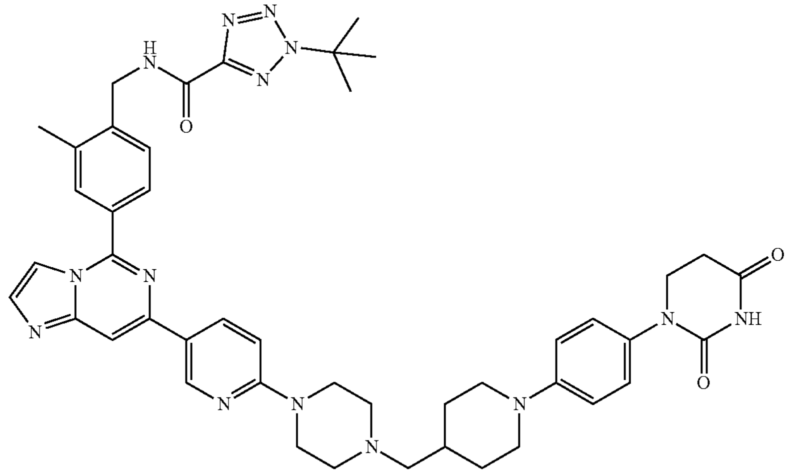

TABLE 2-continued
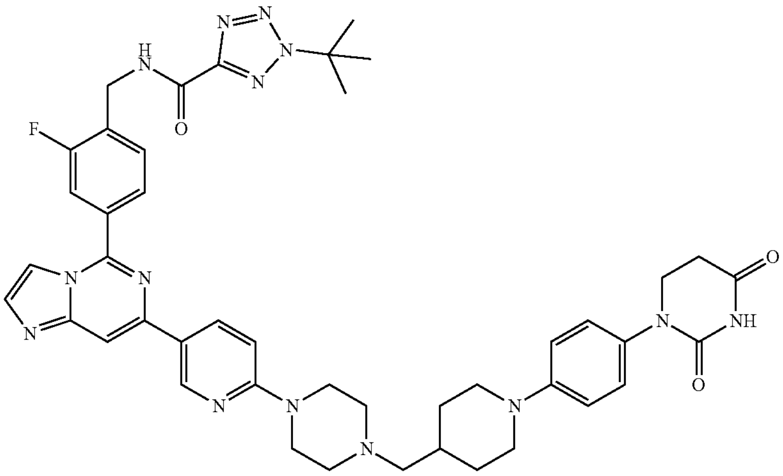
224
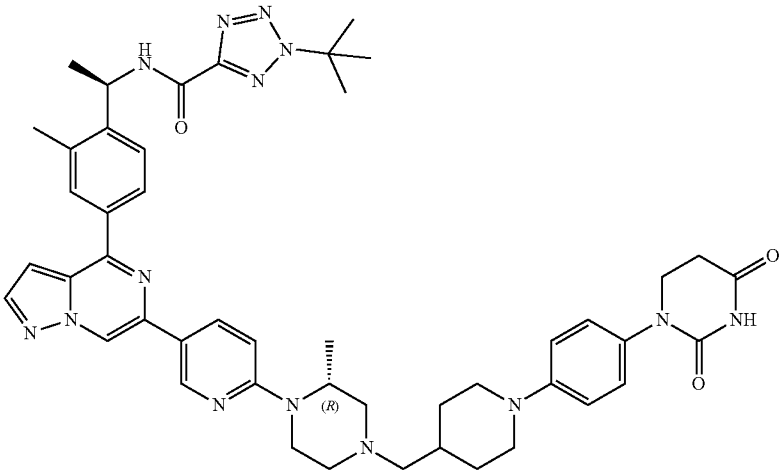
225
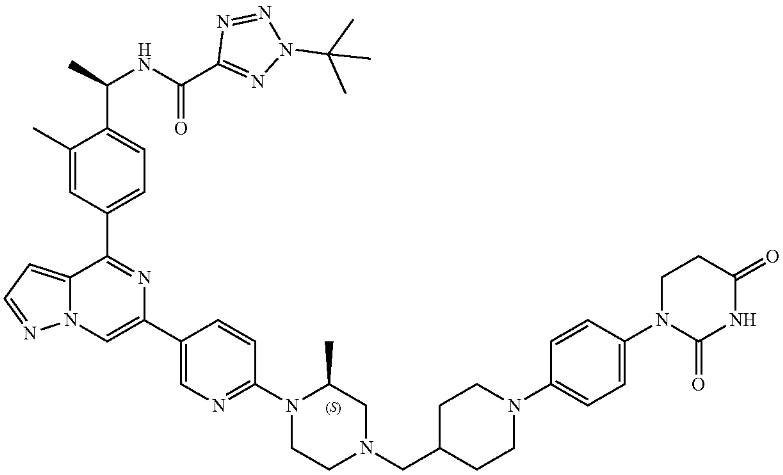
226

TABLE 2-continued
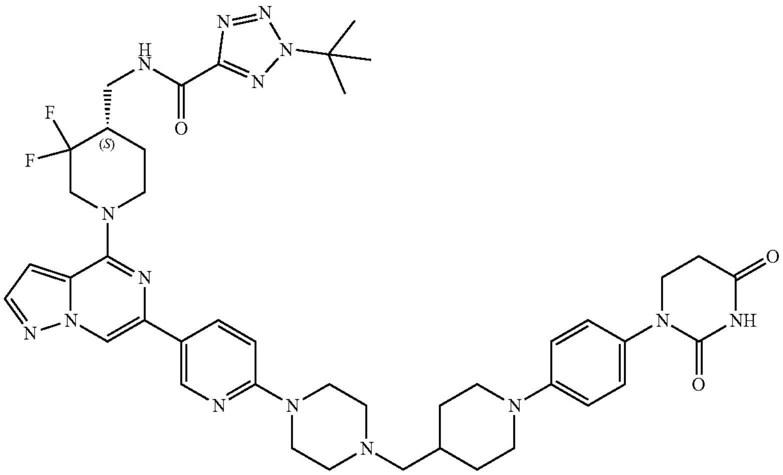
227
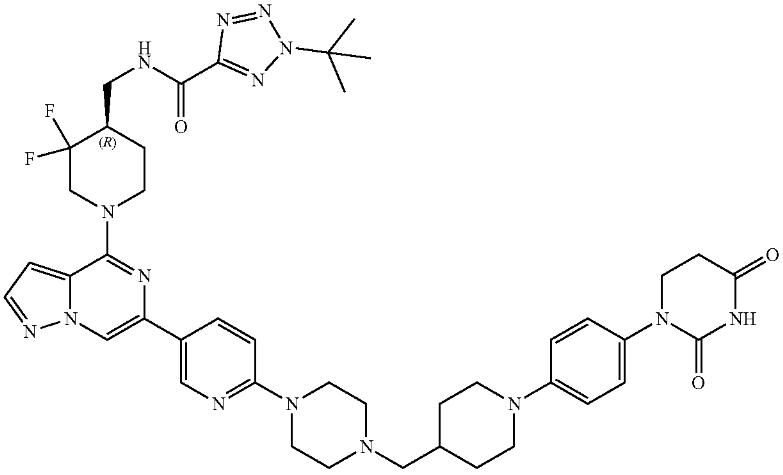
228
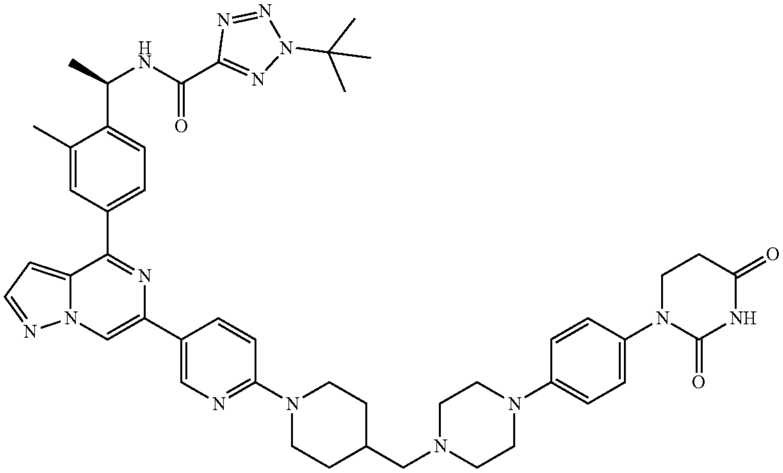
229

TABLE 2-continued
230
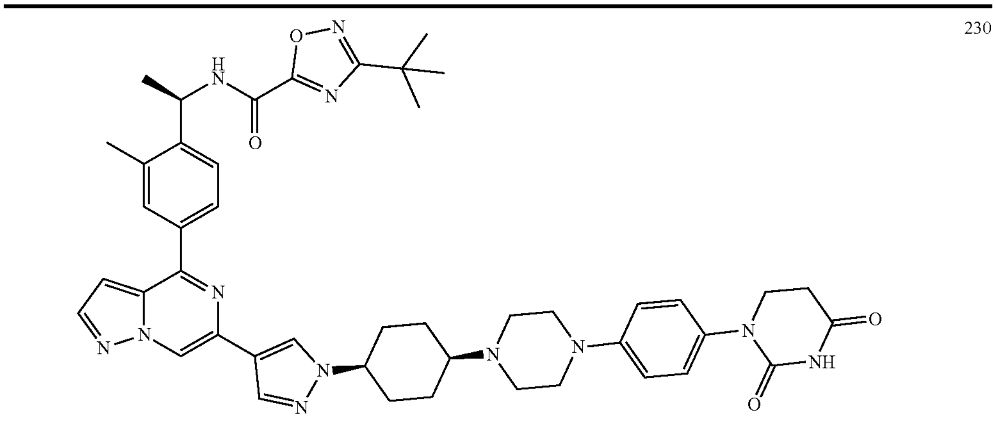
231
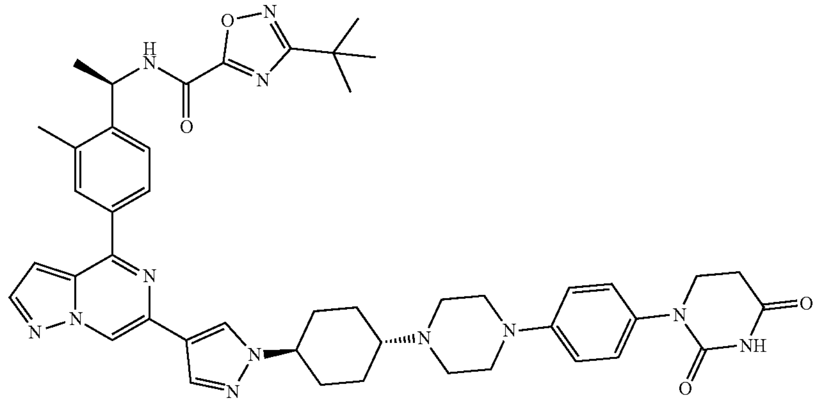 [SMILES: Cc1cc(-c2nc(-c3cnn([C@H]4CC[C@H](N5CCN(c6ccc(N7CCC(=O)NC7=O)cc6)CC5)CC4)c3)cn3nccc23)ccc1[C@@H](C)NC(=O)c1nc(C(C)(C)C)no1]
232
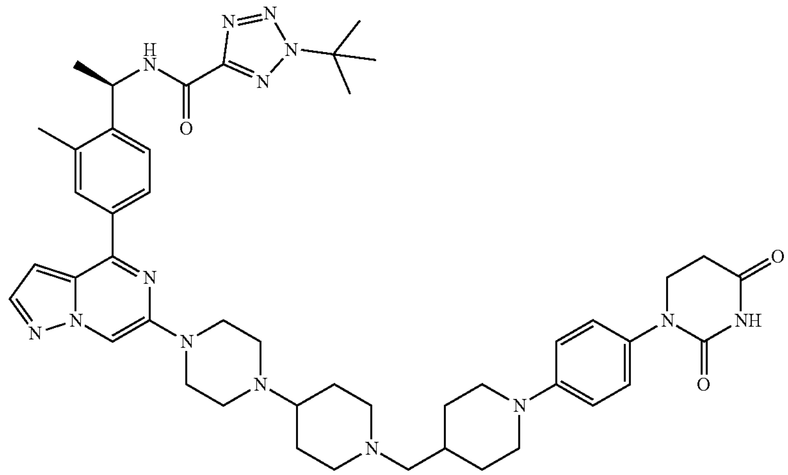

TABLE 2-continued
233
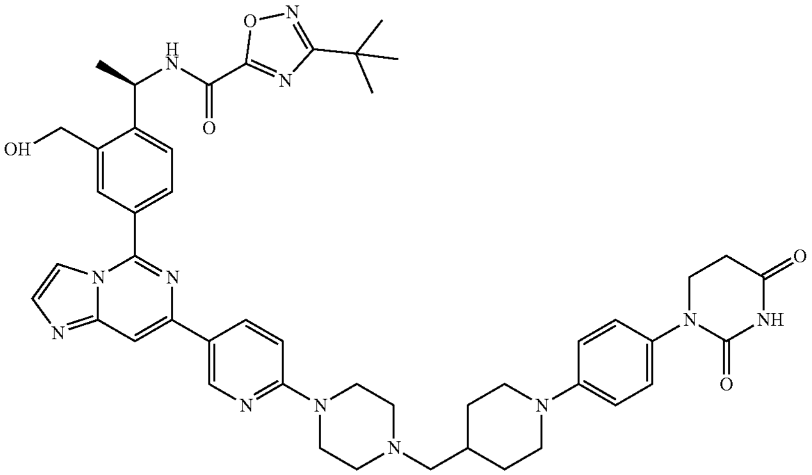 [SMILES: C[C@@H](NC(=O)c1nc(C(C)(C)C)no1)c1ccc(-c2nc(-c3ccc(N4CCN(CC5CCN(c6ccc(N7CCC(=O)NC7=O)cc6)CC5)CC4)nc3)cc3nccn23)cc1CO]
234
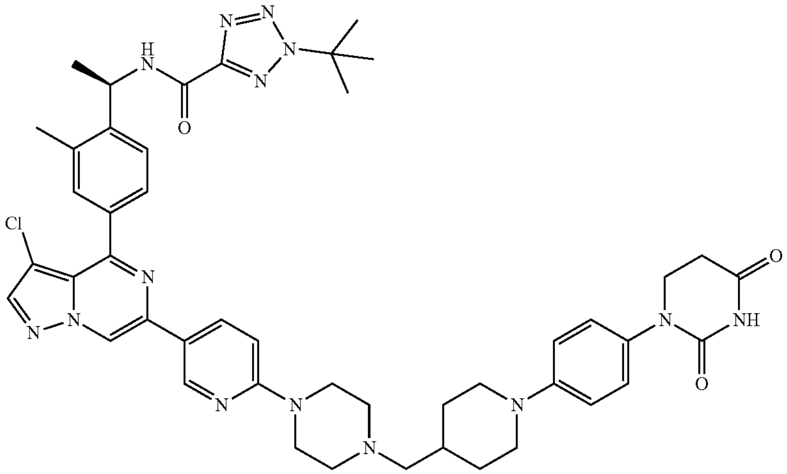 [SMILES: Cc1cc(-c2nc(-c3ccc(N4CCN(CC5CCN(c6ccc(N7CCC(=O)NC7=O)cc6)CC5)CC4)nc3)cn3ncc(Cl)c23)ccc1[C@@H](C)NC(=O)c1nnn(C(C)(C)C)n1]
235
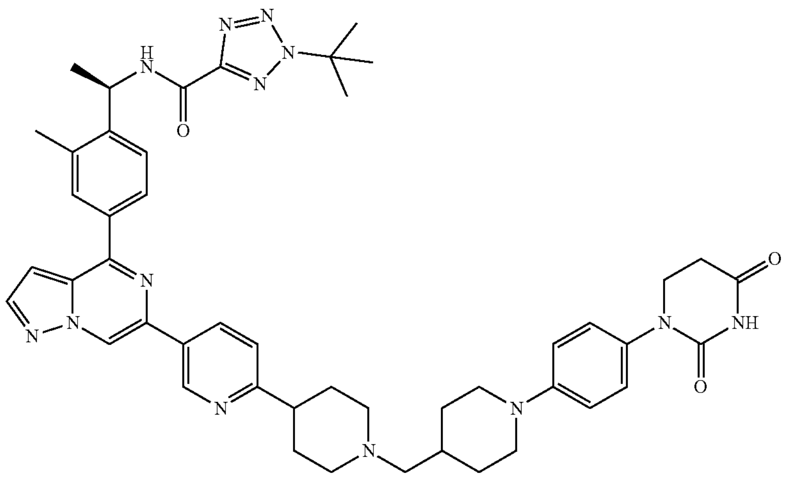

TABLE 2-continued
236
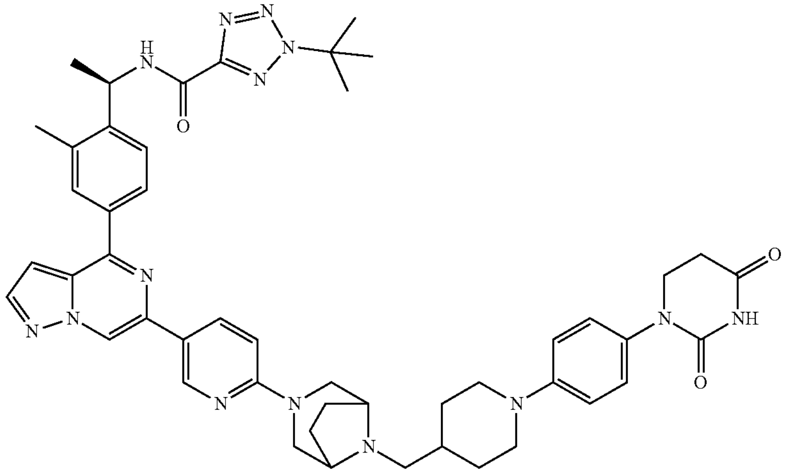 [SMILES: Cc1cc(-c2nc(-c3ccc(N4CC5CCC(C4)N5CC4CCN(c5ccc(N6CCC(=O)NC6=O)cc5)CC4)nc3)cn3nccc23)ccc1[C@@H](C)NC(=O)c1nnn(C(C)(C)C)n1]
237
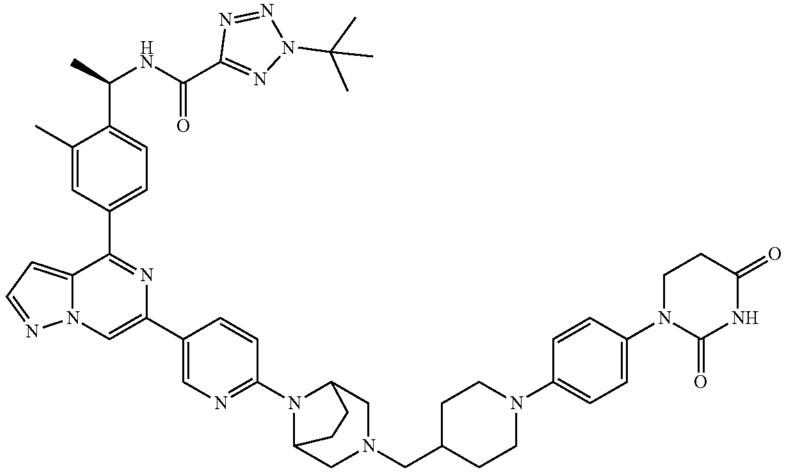 [SMILES: Cc1cc(-c2nc(-c3ccc(N4C5CCC4CN(CC4CCN(c6ccc(N7CCC(=O)NC7=O)cc6)CC4)C5)nc3)cn3nccc23)ccc1[C@@H](C)NC(=O)c1nnn(C(C)(C)C)n1]
238
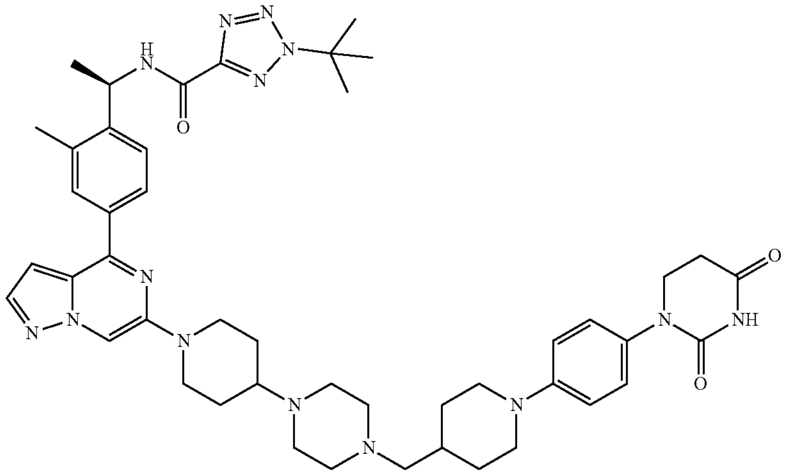

TABLE 2-continued
239
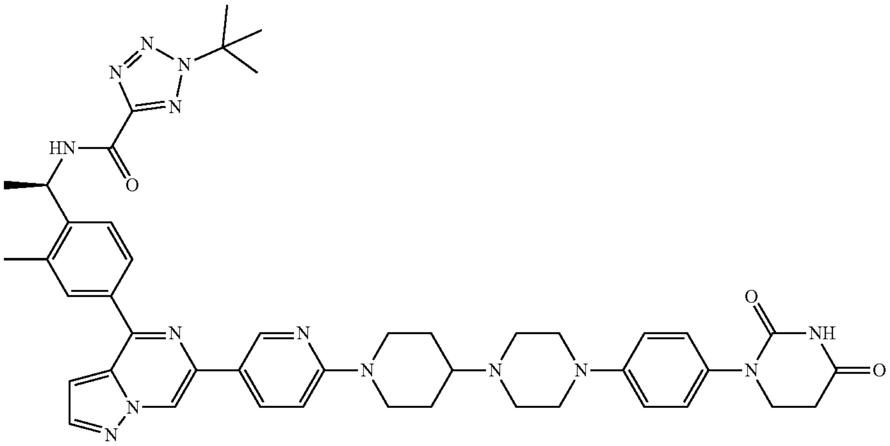 [SMILES: Cc1cc(-c2nc(-c3ccc(N4CCC(N5CCN(c6ccc(N7CCC(=O)NC7=O)cc6)CC5)CC4)nc3)cn3nccc23)ccc1[C@@H](C)NC(=O)c1nnn(C(C)(C)C)n1]
240
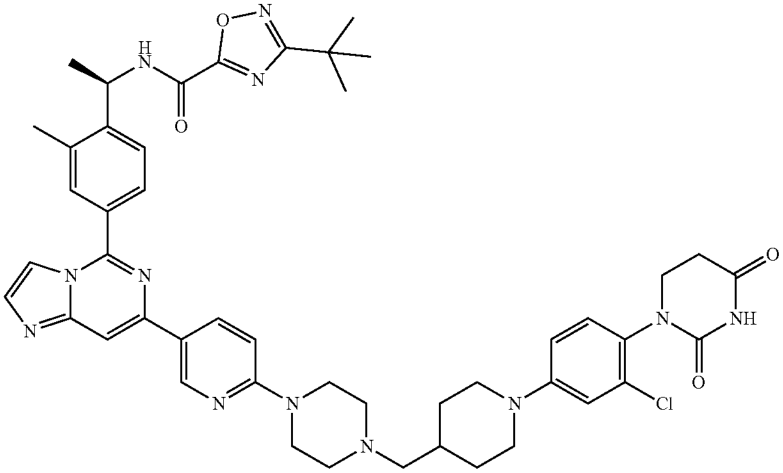
241
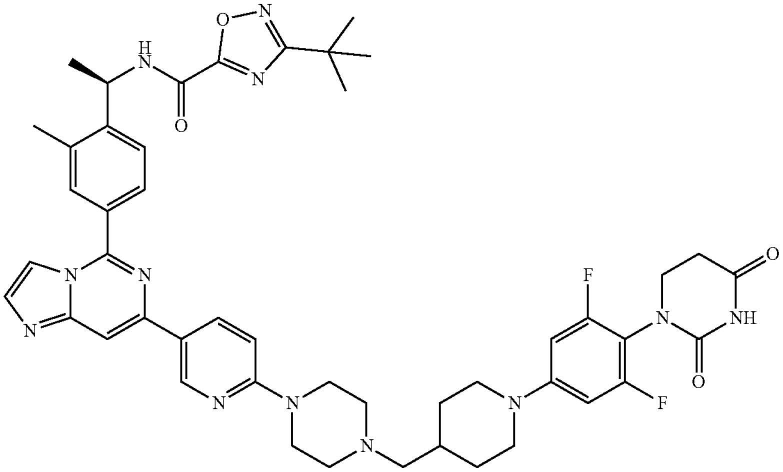

TABLE 2-continued
242
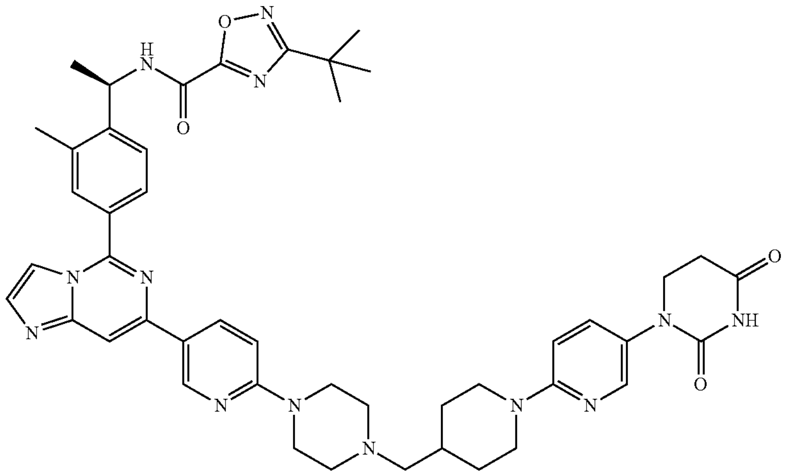
243
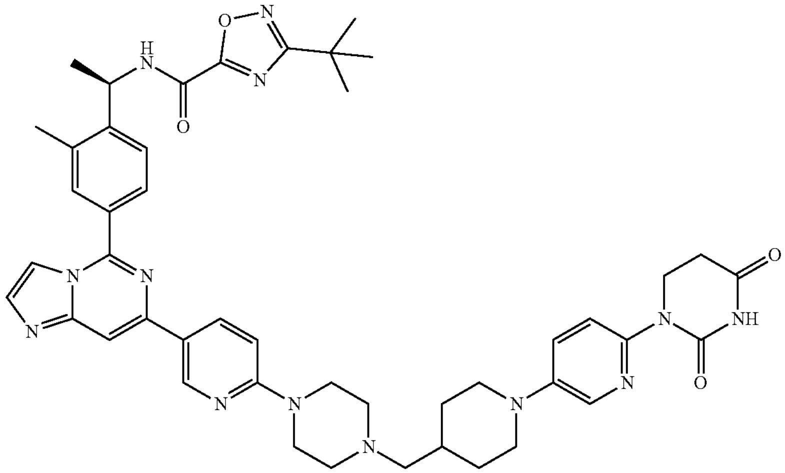
244
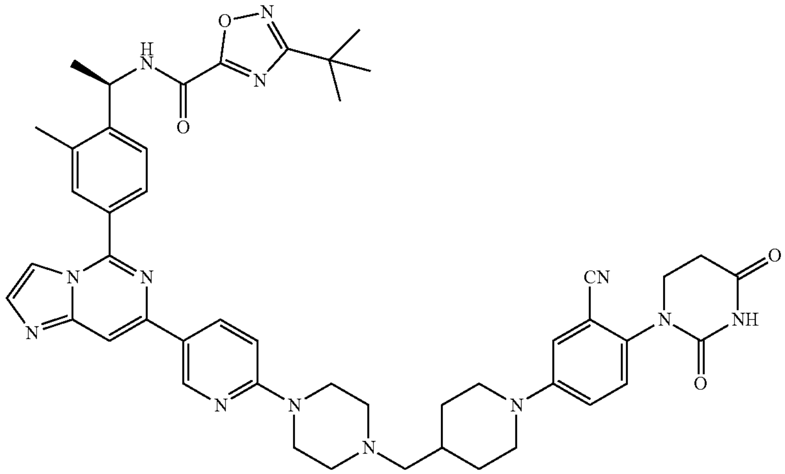 [SMILES: Cc1cc(-c2nc(-c3ccc(N4CCN(CC5CCN(c6ccc(N7CCC(=O)NC7=O)c(C#N)c6)CC5)CC4)nc3)cc3nccn23)ccc1[C@@H](C)NC(=O)c1nc(C(C)(C)C)no1]

TABLE 2-continued
245
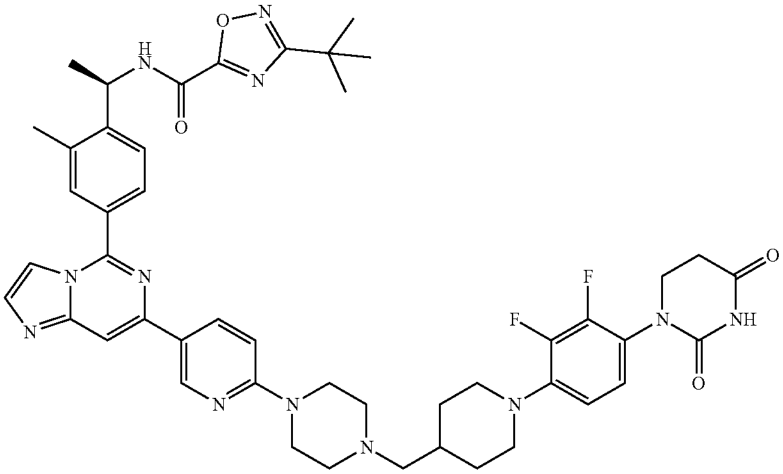
246
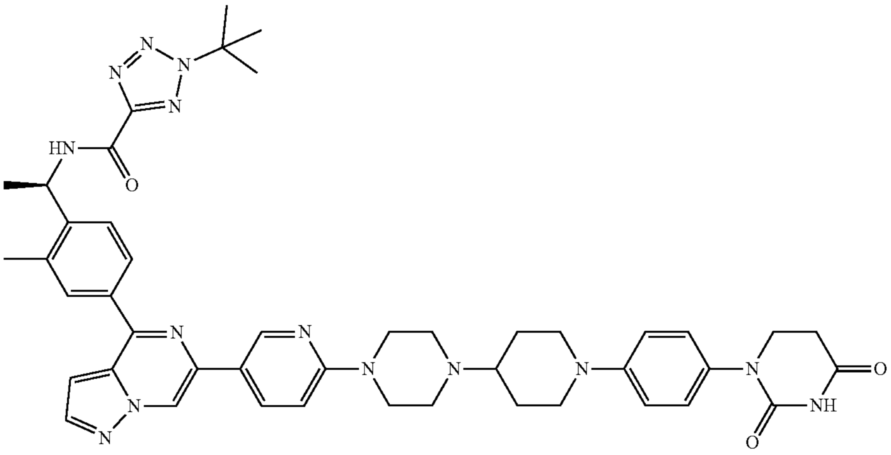 [SMILES: Cc1cc(-c2nc(-c3ccc(N4CCN(C5CCN(c6ccc(N7CCC(=O)NC7=O)cc6)CC5)CC4)nc3)cn3nccc23)ccc1[C@@H](C)NC(=O)c1nnn(C(C)(C)C)n1]
247
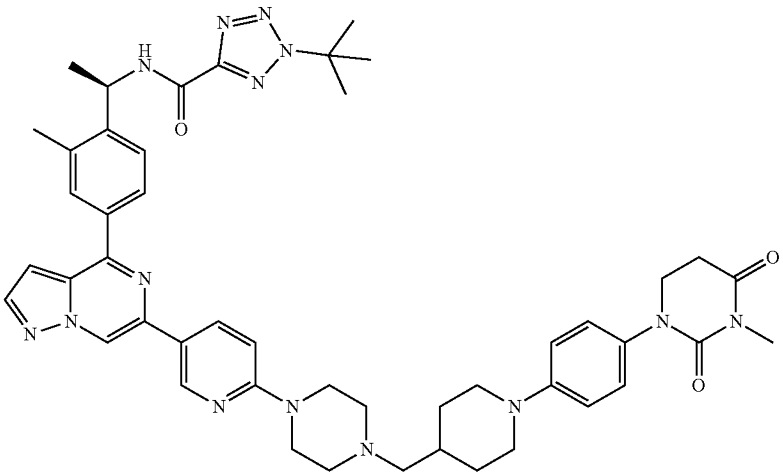

TABLE 2-continued
248
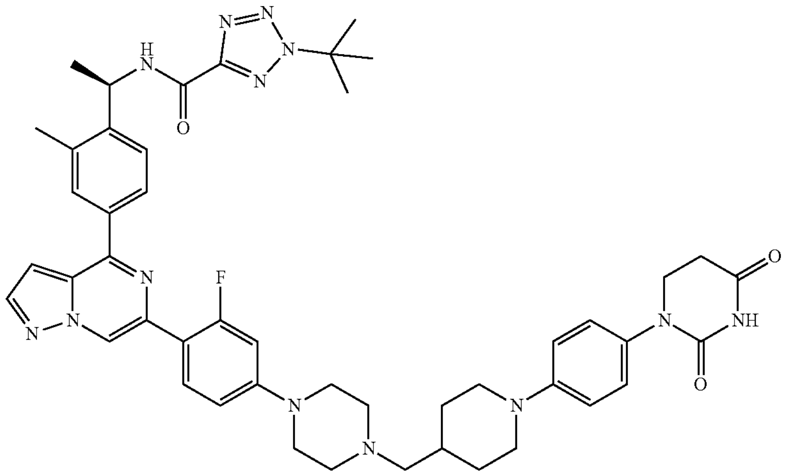
249
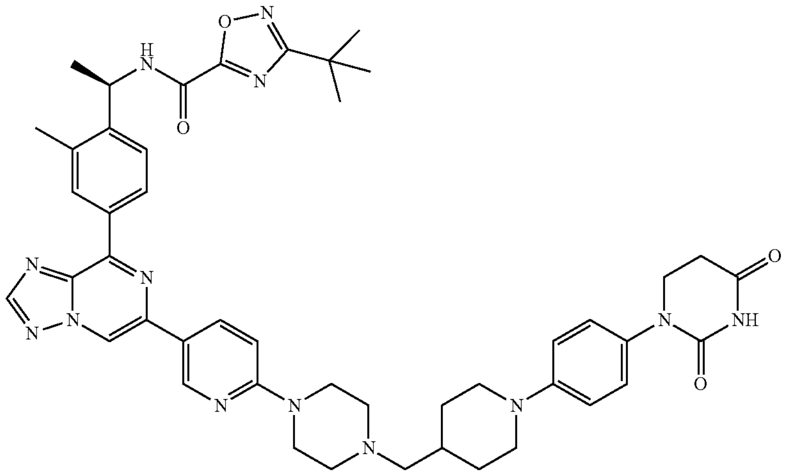 [SMILES: Cc1cc(-c2nc(-c3ccc(N4CCN(CC5CCN(c6ccc(N7CCC(=O)NC7=O)cc6)CC5)CC4)nc3)cn3ncnc23)ccc1[C@@H](C)NC(=O)c1nc(C(C)(C)C)no1]
250
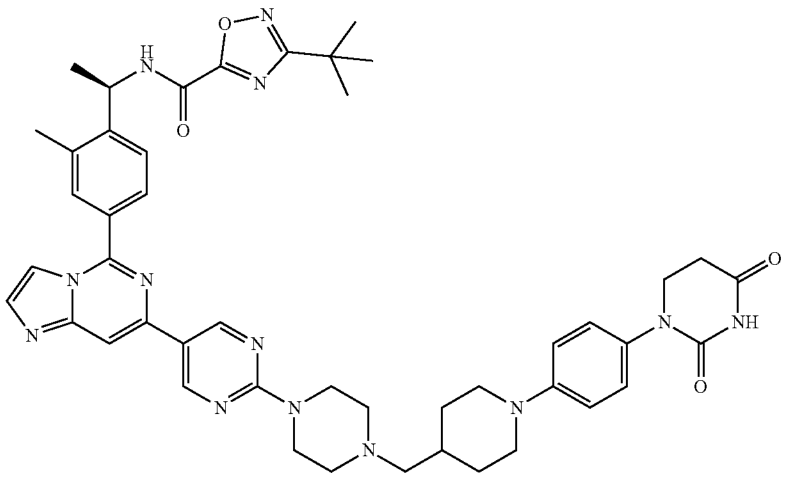

TABLE 2-continued
251
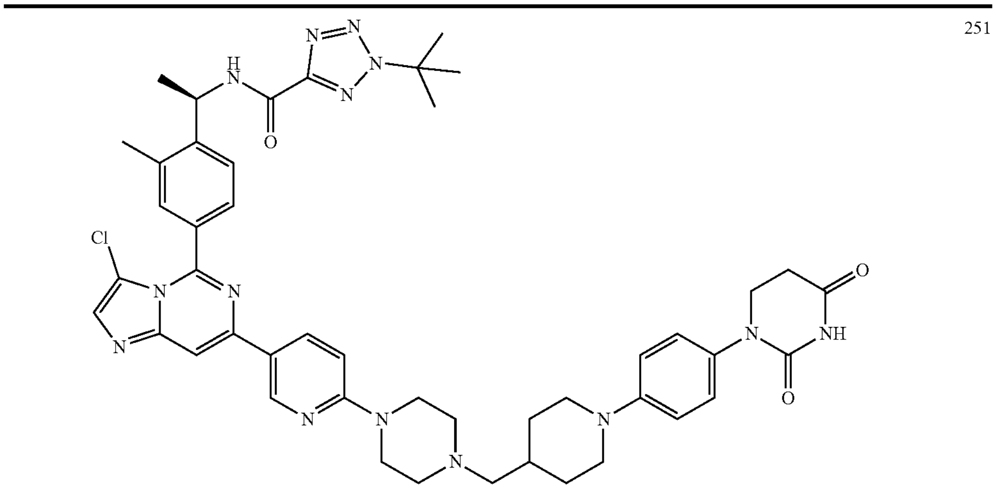
252
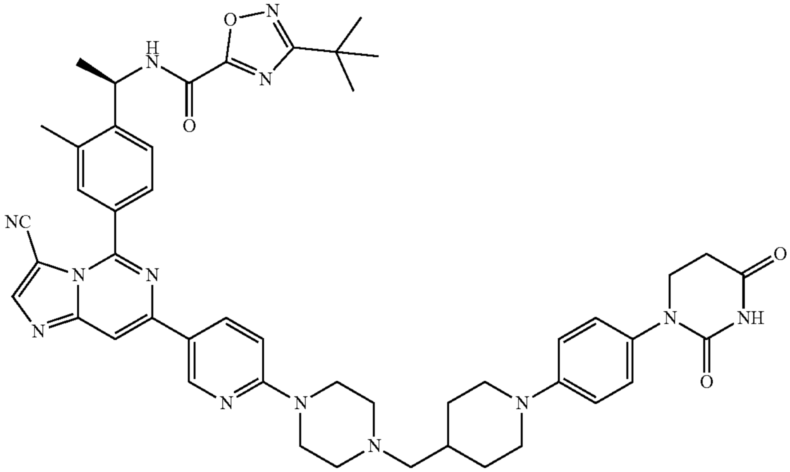
253
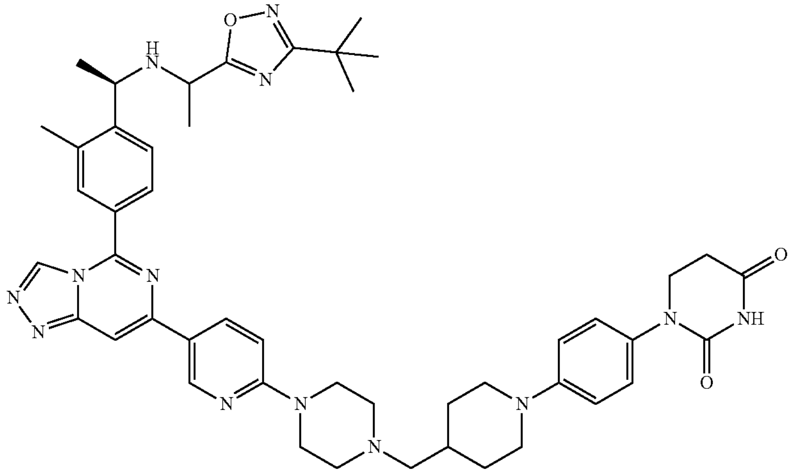

TABLE 2-continued
254
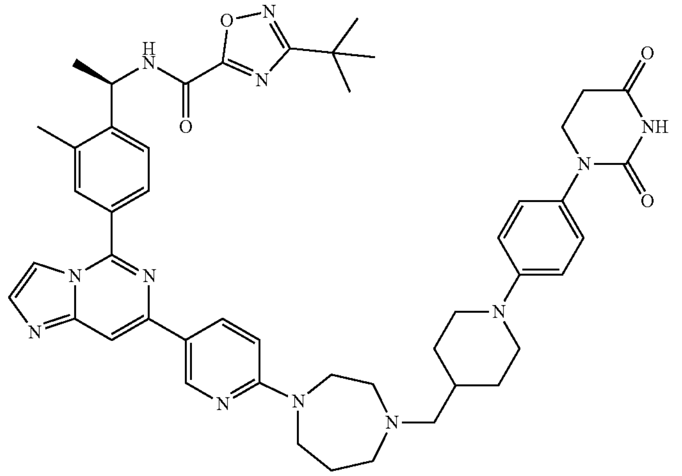 [SMILES: Cc1cc(-c2nc(-c3ccc(N4CCCN(CC5CCN(c6ccc(N7CCC(=O)NC7=O)cc6)CC5)CC4)nc3)cc3nccn23)ccc1[C@@H](C)NC(=O)c1nc(C(C)(C)C)no1]
255
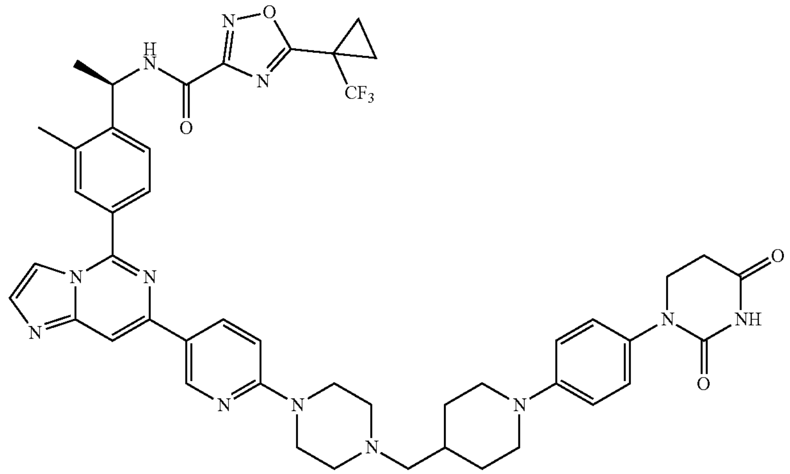
256
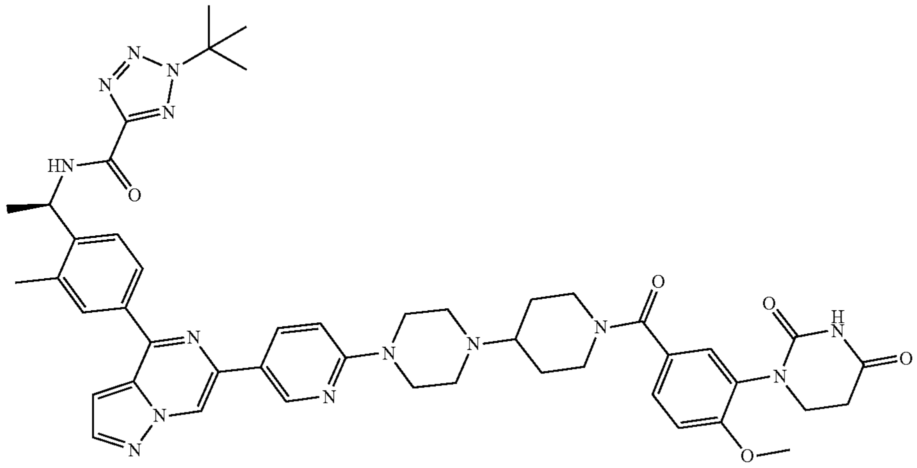 [SMILES: COc1ccc(C(=O)N2CCC(N3CCN(c4ccc(-c5cn6nccc6c(-c6ccc([C@@H](C)NC(=O)c7nnn(C(C)(C)C)n7)c(C)c6)n5)cn4)CC3)CC2)cc1N1CCC(=O)NC1=O]

TABLE 2-continued
257
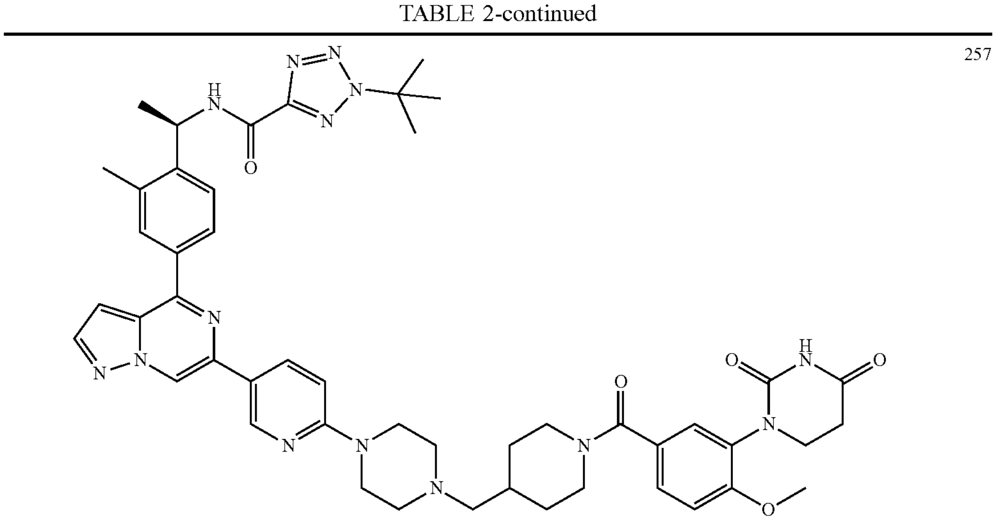
258
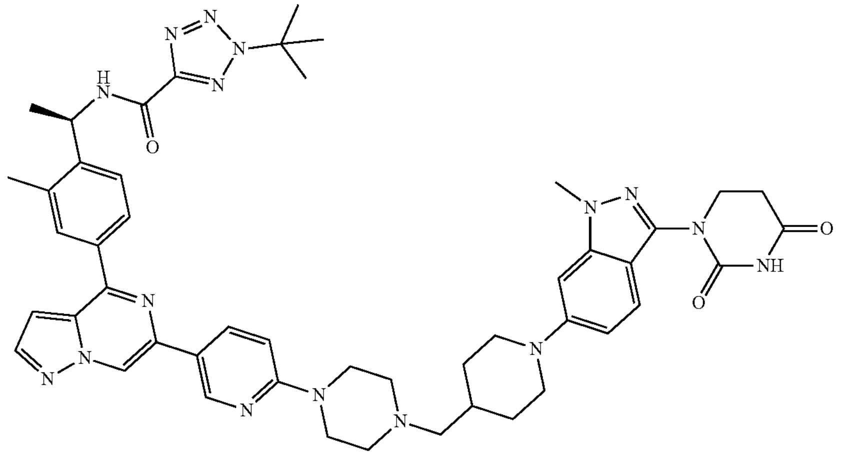 [SMILES: Cc1cc(-c2nc(-c3ccc(N4CCN(CC5CCN(c6ccc7c(N8CCC(=O)NC8=O)nn(C)c7c6)CC5)CC4)nc3)cn3nccc23)ccc1[C@@H](C)NC(=O)c1nnn(C(C)(C)C)n1]
259
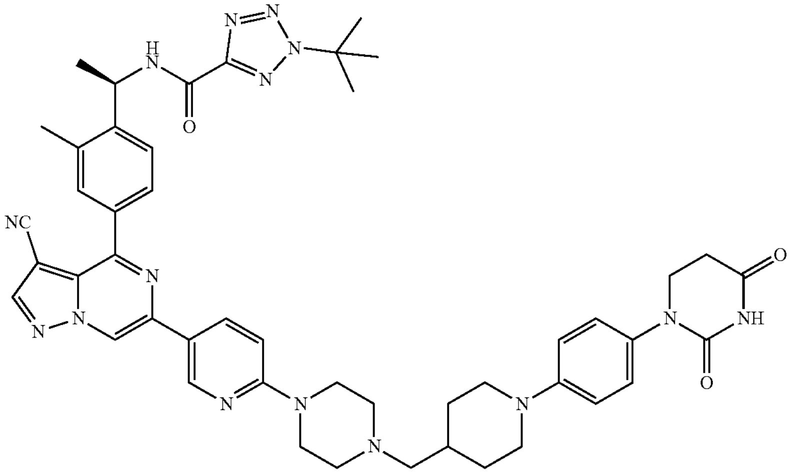 [SMILES: Cc1cc(-c2nc(-c3ccc(N4CCN(CC5CCN(c6ccc(N7CCC(=O)NC7=O)cc6)CC5)CC4)nc3)cn3ncc(C#N)c23)ccc1[C@@H](C)NC(=O)c1nnn(C(C)(C)C)n1]

TABLE 2-continued
260
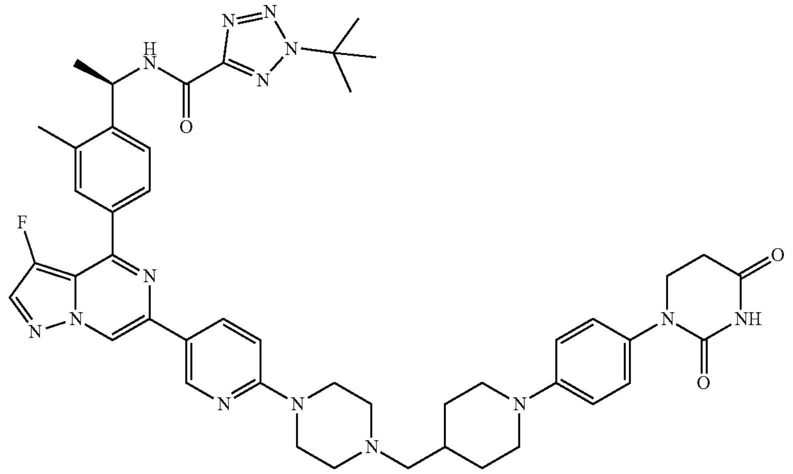
261
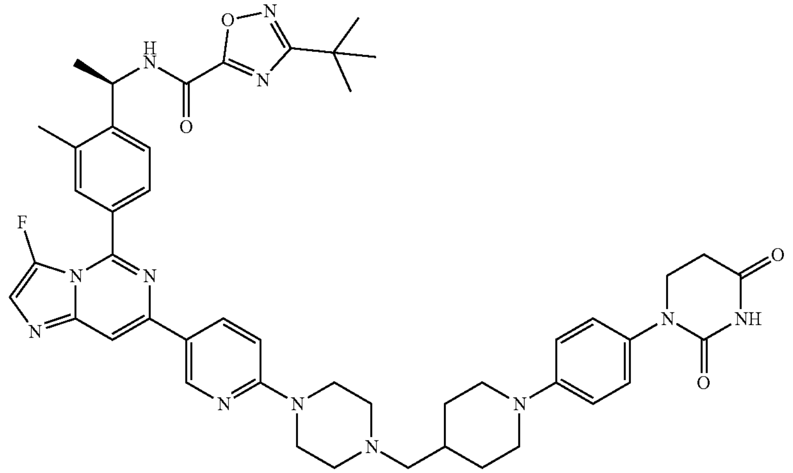
262
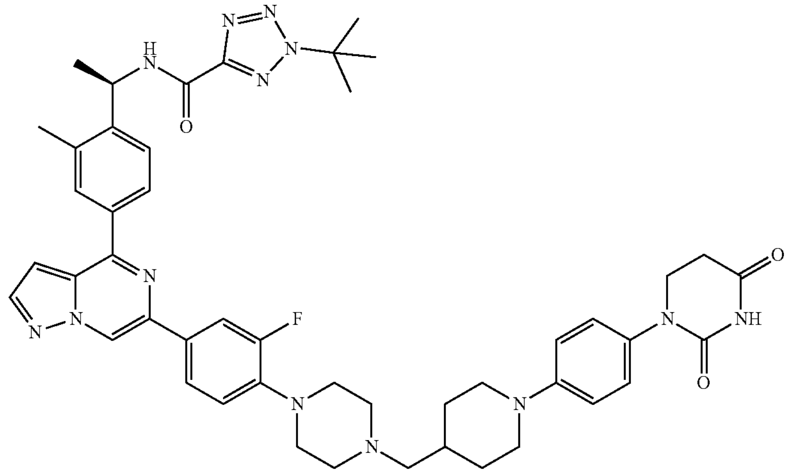

TABLE 2-continued
263
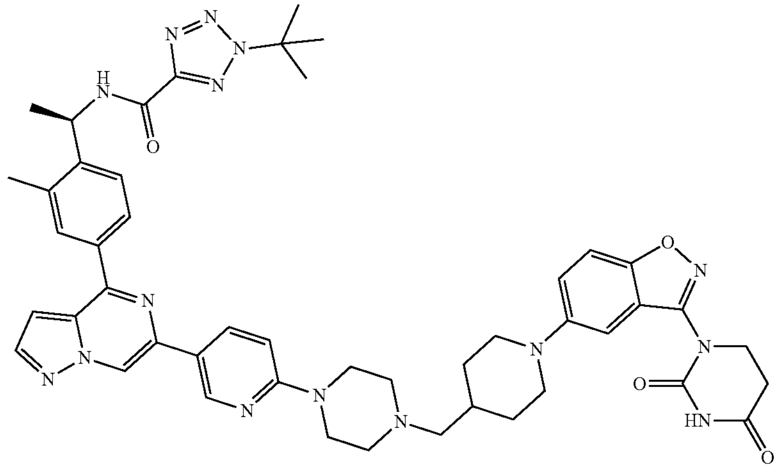 [SMILES: Cc1cc(-c2nc(-c3ccc(N4CCN(CC5CCN(c6ccc7onc(N8CCC(=O)NC8=O)c7c6)CC5)CC4)nc3)cn3nccc23)ccc1[C@@H](C)NC(=O)c1nnn(C(C)(C)C)n1]
264
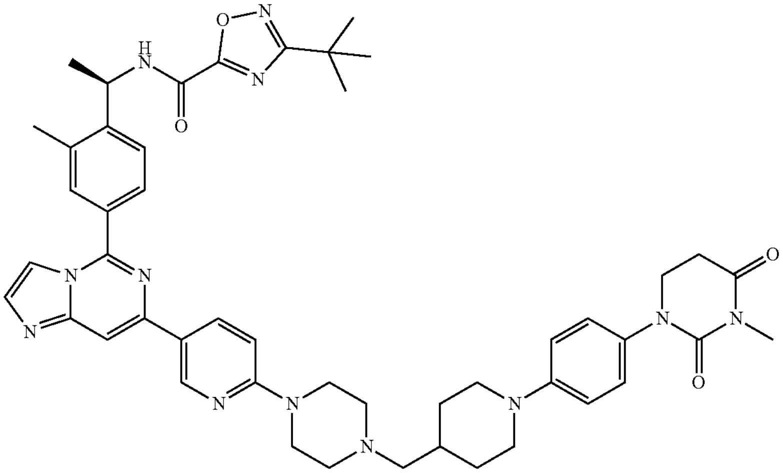
265
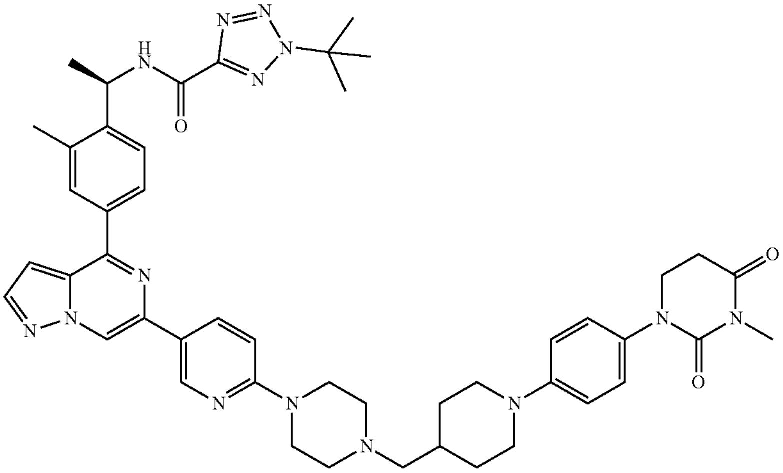

TABLE 2-continued
266
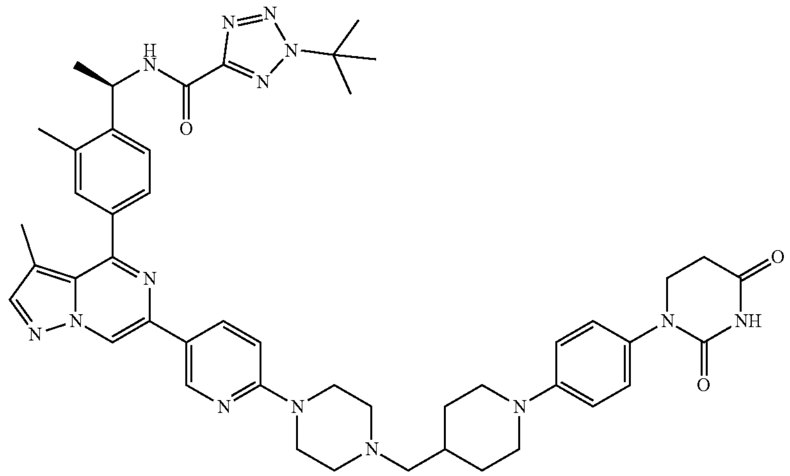
267
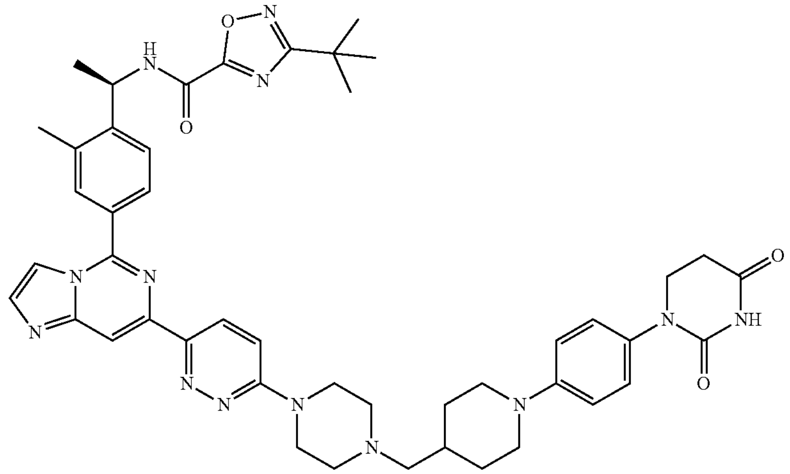
268
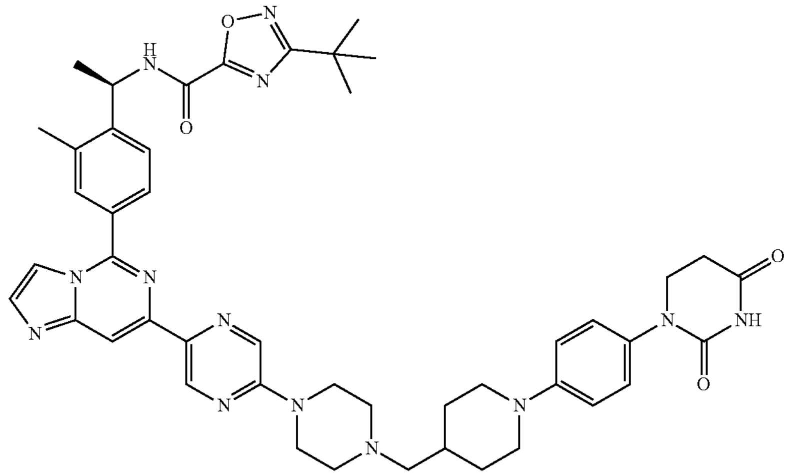

TABLE 2-continued
269
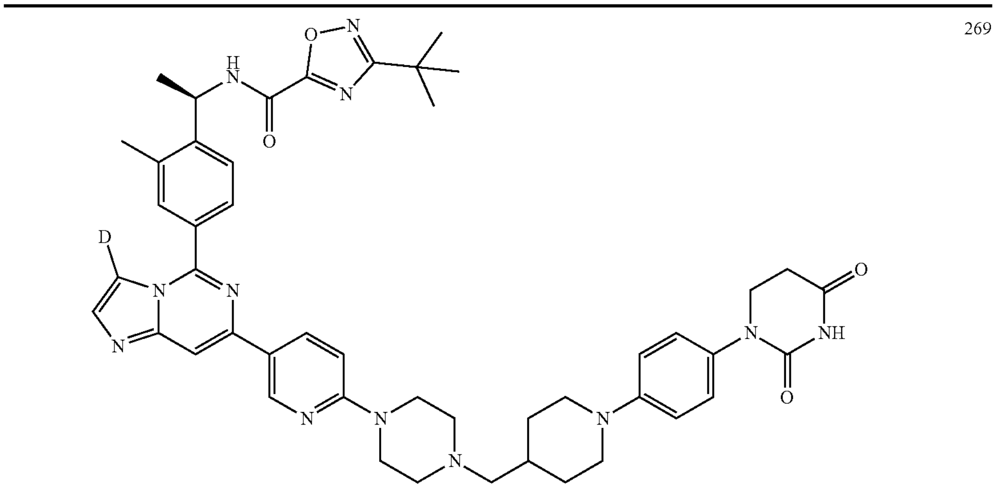
270
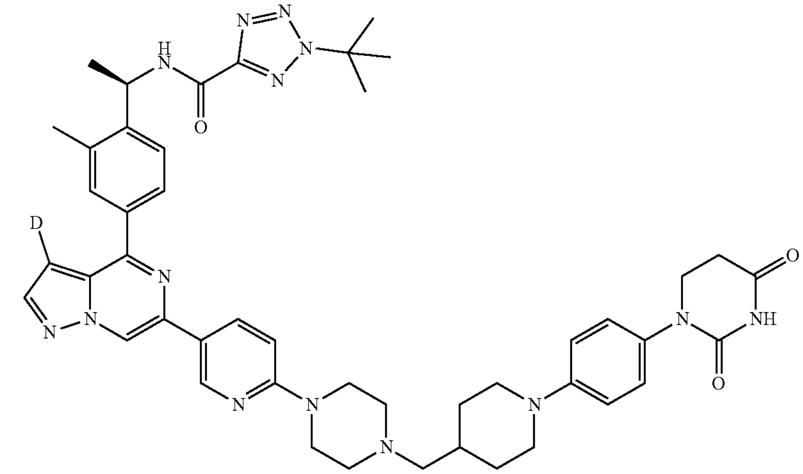
271
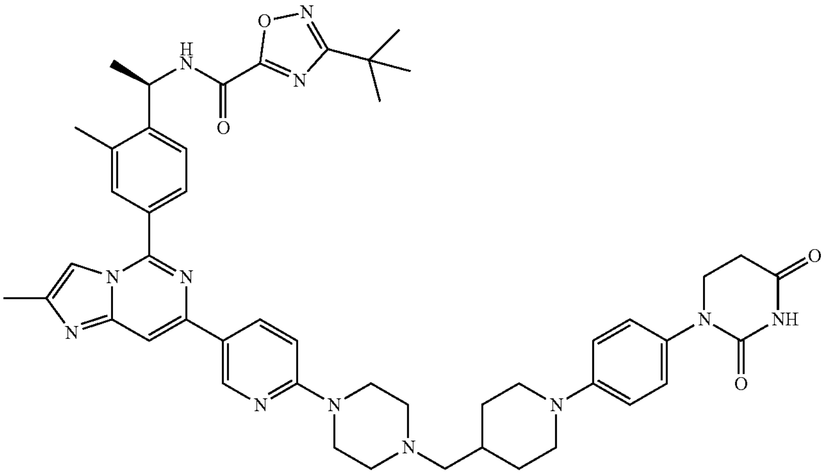 [SMILES: Cc1cn2c(-c3ccc([C@@H](C)NC(=O)c4nc(C(C)(C)C)no4)c(C)c3)nc(-c3ccc(N4CCN(CC5CCN(c6ccc(N7CCC(=O)NC7=O)cc6)CC5)CC4)nc3)cc2n1]

TABLE 2-continued
272
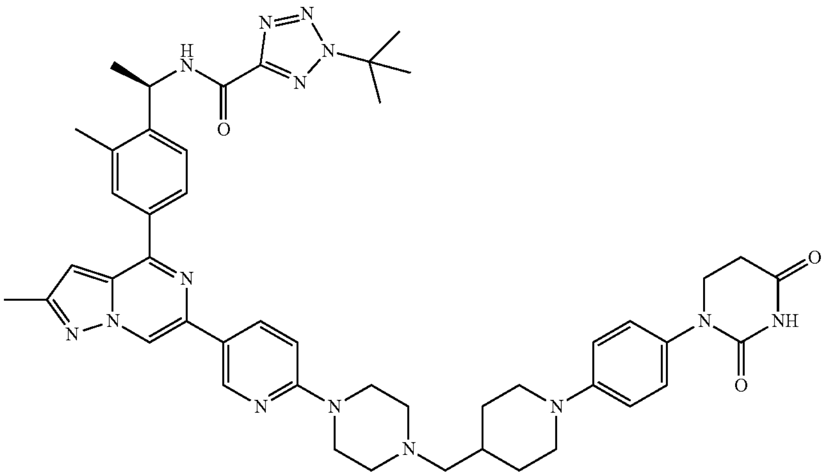 [SMILES: Cc1cc2c(-c3ccc([C@@H](C)NC(=O)c4nnn(C(C)(C)C)n4)c(C)c3)nc(-c3ccc(N4CCN(CC5CCN(c6ccc(N7CCC(=O)NC7=O)cc6)CC5)CC4)nc3)cn2n1]
273
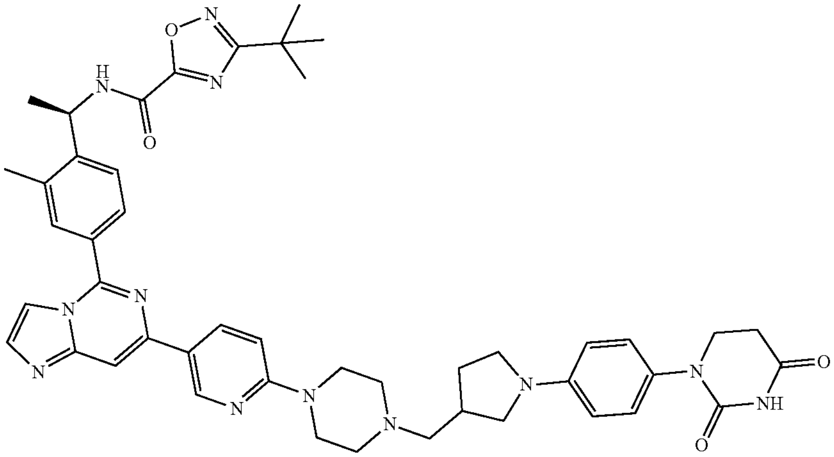 [SMILES: Cc1cc(-c2nc(-c3ccc(N4CCN(CC5CCN(c6ccc(N7CCC(=O)NC7=O)cc6)C5)CC4)nc3)cc3nccn23)ccc1[C@@H](C)NC(=O)c1nc(C(C)(C)C)no1]
274
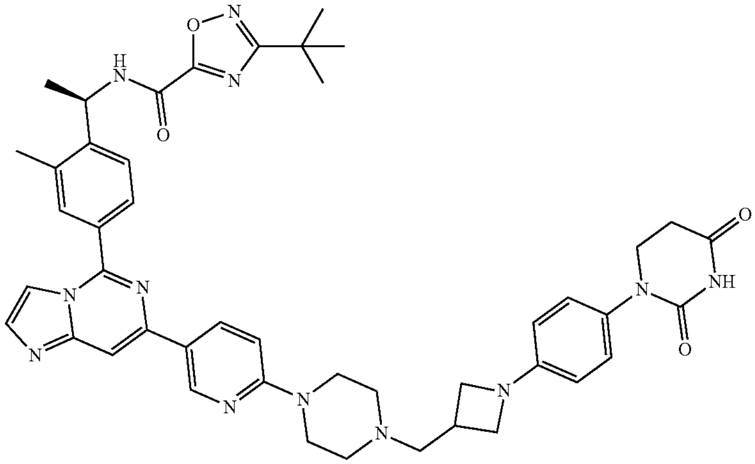 [SMILES: Cc1cc(-c2nc(-c3ccc(N4CCN(CC5CN(c6ccc(N7CCC(=O)NC7=O)cc6)C5)CC4)nc3)cc3nccn23)ccc1[C@@H](C)NC(=O)c1nc(C(C)(C)C)no1]

TABLE 2-continued
275
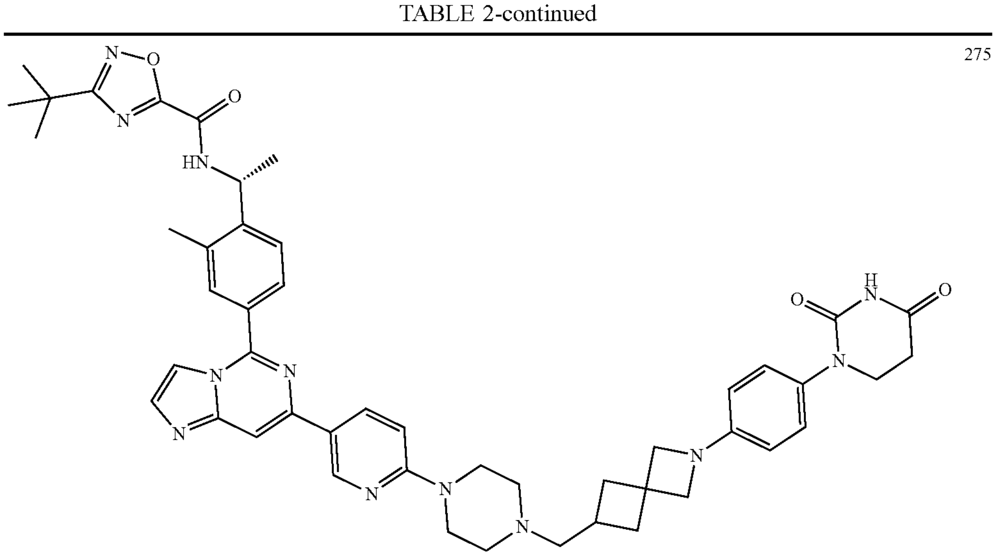
276
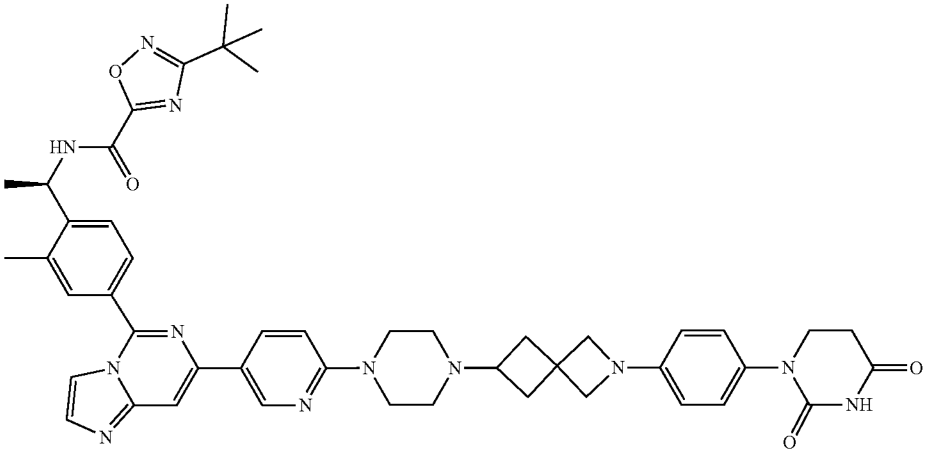 [SMILES: Cc1cc(-c2nc(-c3ccc(N4CCN(C5CC6(C5)CN(c5ccc(N7CCC(=O)NC7=O)cc5)C6)CC4)nc3)cc3nccn23)ccc1[C@@H](C)NC(=O)c1nc(C(C)(C)C)no1]
277
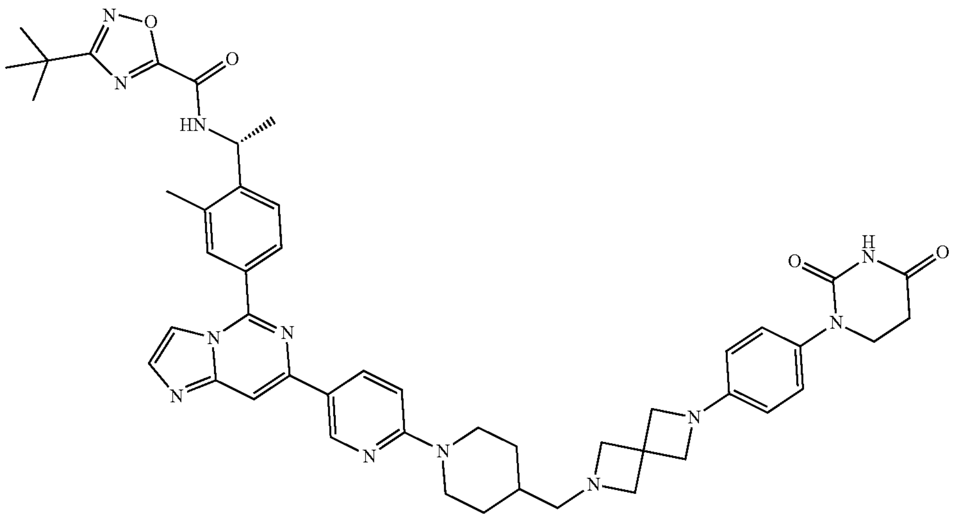 [SMILES: Cc1cc(-c2nc(-c3ccc(N4CCC(CN5CC6(C5)CN(c5ccc(N7CCC(=O)NC7=O)cc5)C6)CC4)nc3)cc3nccn23)ccc1[C@@H](C)NC(=O)c1nc(C(C)(C)C)no1]

TABLE 2-continued
278
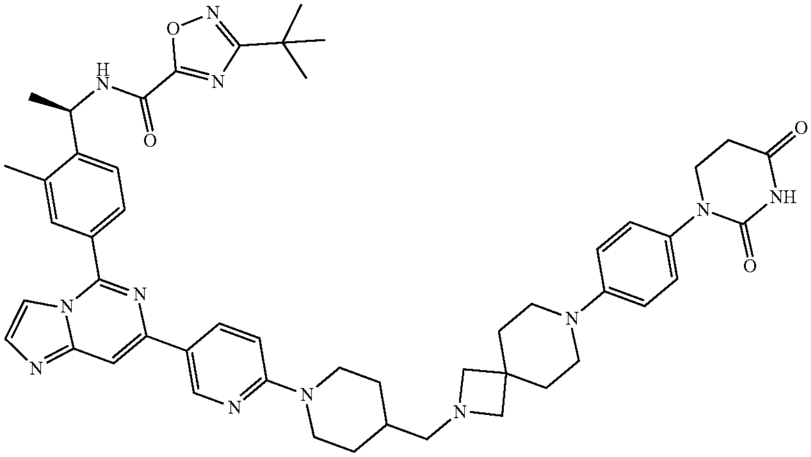 [SMILES: Cc1cc(-c2nc(-c3ccc(N4CCC(CN5CC6(CCN(c7ccc(N8CCC(=O)NC8=O)cc7)CC6)C5)CC4)nc3)cc3nccn23)ccc1[C@@H](C)NC(=O)c1nc(C(C)(C)C)no1]
279
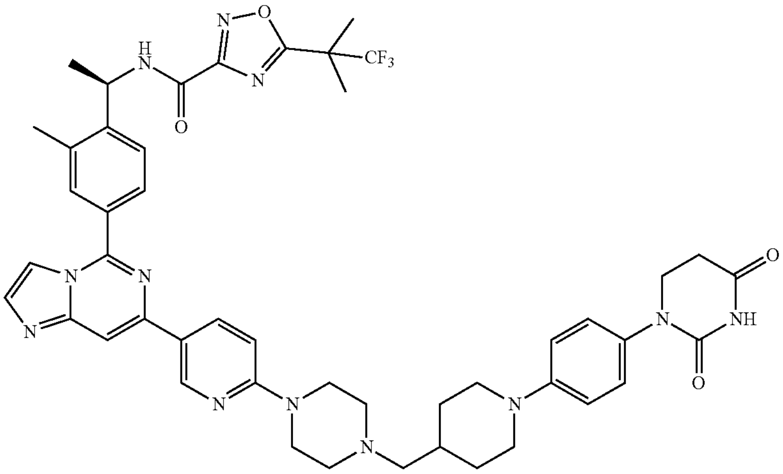
280
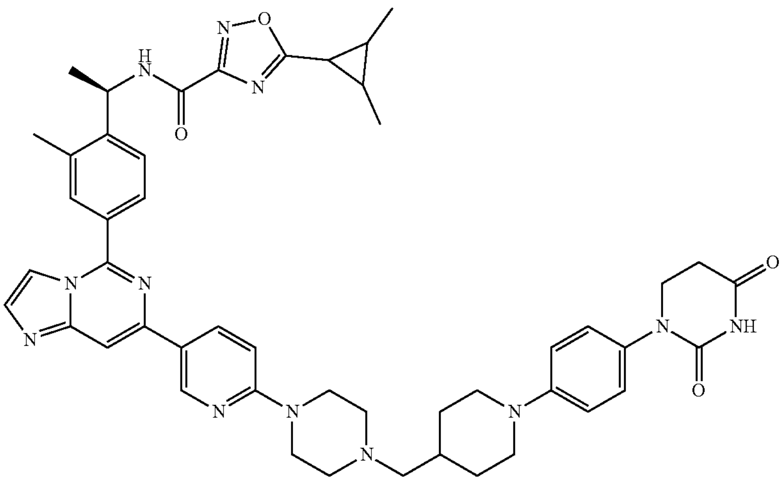 [SMILES: Cc1cc(-c2nc(-c3ccc(N4CCN(CC5CCN(c6ccc(N7CCC(=O)NC7=O)cc6)CC5)CC4)nc3)cc3nccn23)ccc1[C@@H](C)NC(=O)c1noc(C2C(C)C2C)n1]

TABLE 2-continued
281
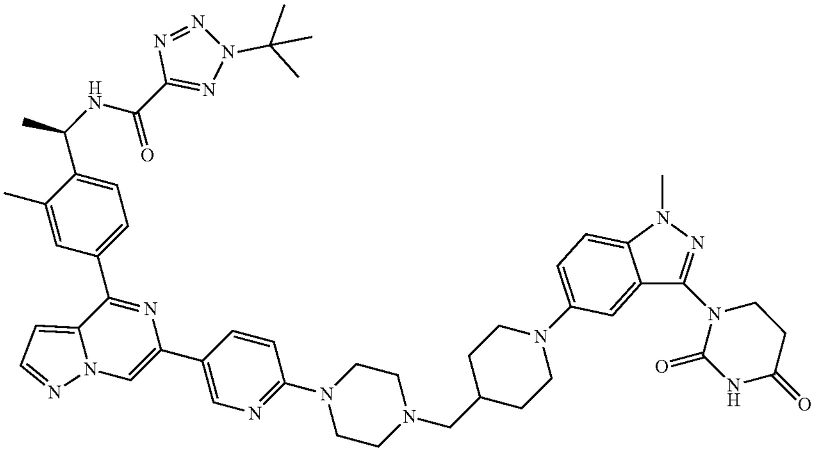 [SMILES: Cc1cc(-c2nc(-c3ccc(N4CCN(CC5CCN(c6ccc7c(c6)c(N6CCC(=O)NC6=O)nn7C)CC5)CC4)nc3)cn3nccc23)ccc1[C@@H](C)NC(=O)c1nnn(C(C)(C)C)n1]
282
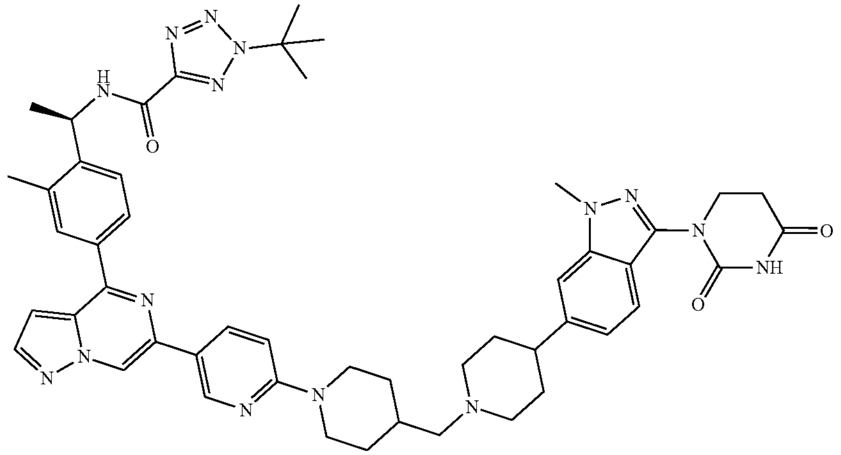 [SMILES: Cc1cc(-c2nc(-c3ccc(N4CCC(CN5CCC(c6ccc7c(N8CCC(=O)NC8=O)nn(C)c7c6)CC5)CC4)nc3)cn3nccc23)ccc1[C@@H](C)NC(=O)c1nnn(C(C)(C)C)n1]
283
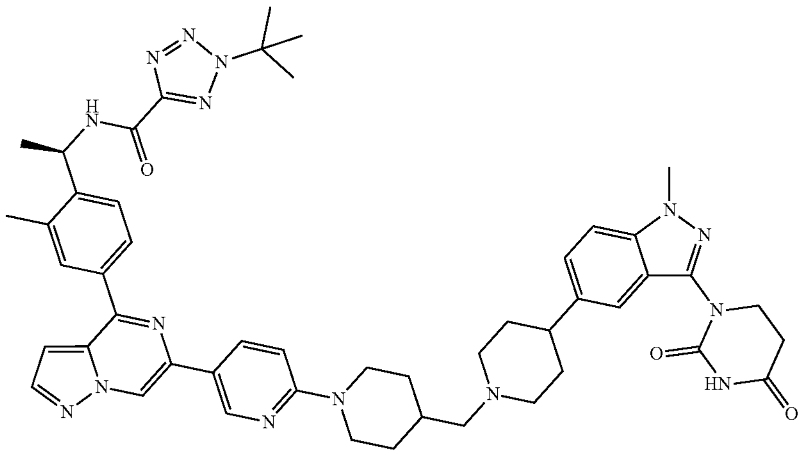 [SMILES: Cc1cc(-c2nc(-c3ccc(N4CCC(CN5CCC(c6ccc7c(c6)c(N6CCC(=O)NC6=O)nn7C)CC5)CC4)nc3)cn3nccc23)ccc1[C@@H](C)NC(=O)c1nnn(C(C)(C)C)n1]

TABLE 2-continued
284
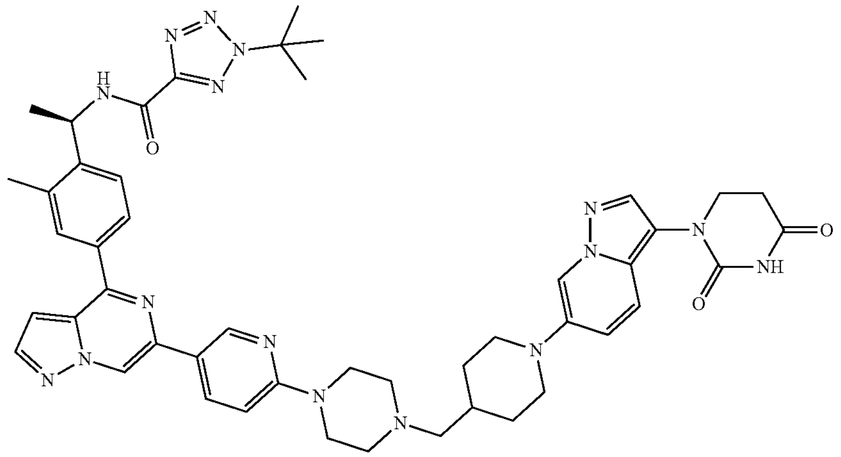 [SMILES: Cc1cc(-c2nc(-c3ccc(N4CCN(CC5CCN(c6ccc7c(N8CCC(=O)NC8=O)cnn7c6)CC5)CC4)nc3)cn3nccc23)ccc1[C@@H](C)NC(=O)c1nnn(C(C)(C)C)n1]
285
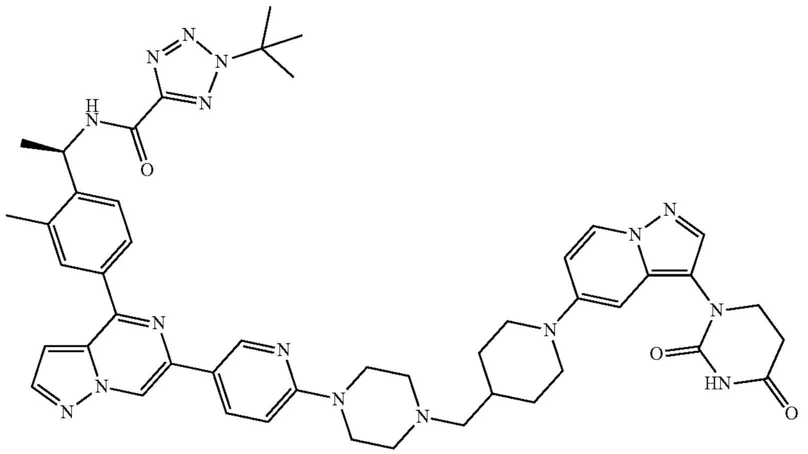 [SMILES: Cc1cc(-c2nc(-c3ccc(N4CCN(CC5CCN(c6ccn7ncc(N8CCC(=O)NC8=O)c7c6)CC5)CC4)nc3)cn3nccc23)ccc1[C@@H](C)NC(=O)c1nnn(C(C)(C)C)n1]
286
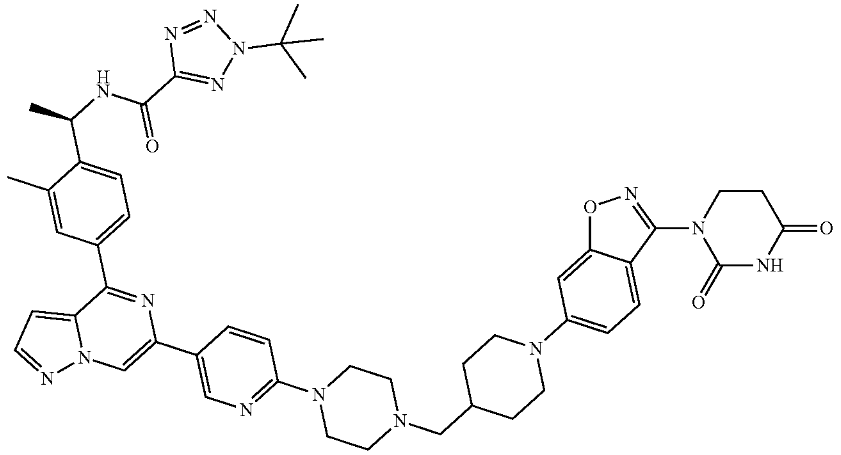 [SMILES: Cc1cc(-c2nc(-c3ccc(N4CCN(CC5CCN(c6ccc7c(N8CCC(=O)NC8=O)noc7c6)CC5)CC4)nc3)cn3nccc23)ccc1[C@@H](C)NC(=O)c1nnn(C(C)(C)C)n1]

TABLE 2-continued
287
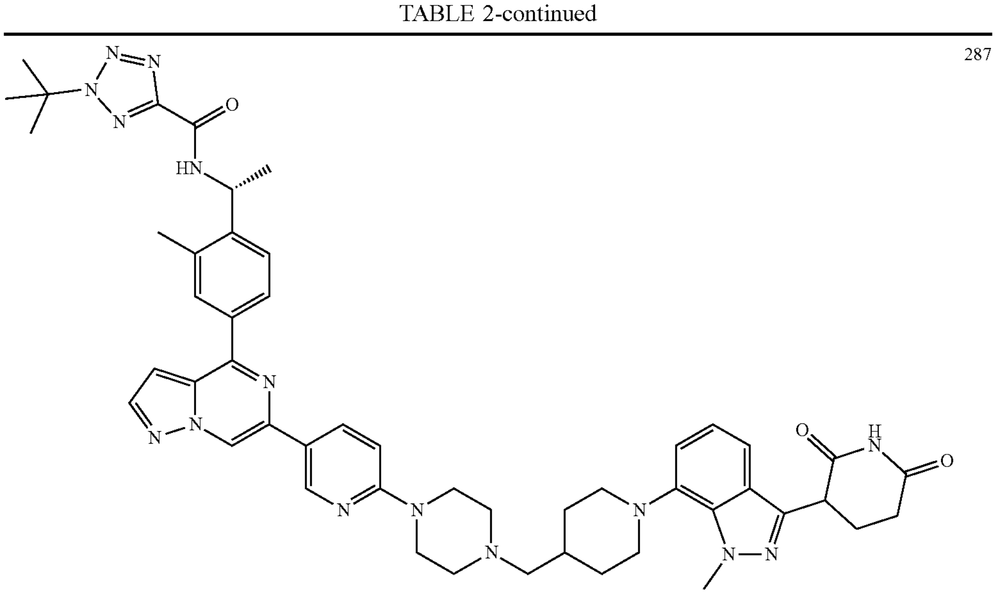
288
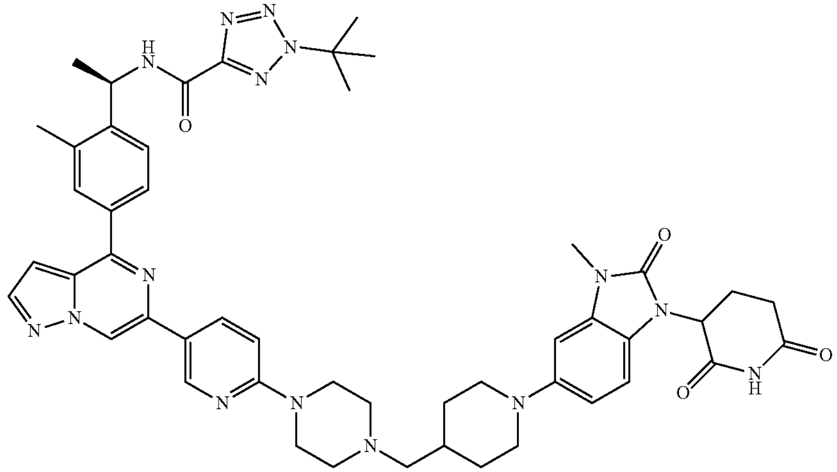 [SMILES: Cc1cc(-c2nc(-c3ccc(N4CCN(CC5CCN(c6ccc7c(c6)n(C)c(=O)n7C6CCC(=O)NC6=O)CC5)CC4)nc3)cn3nccc23)ccc1[C@@H](C)NC(=O)c1nnn(C(C)(C)C)n1]
289
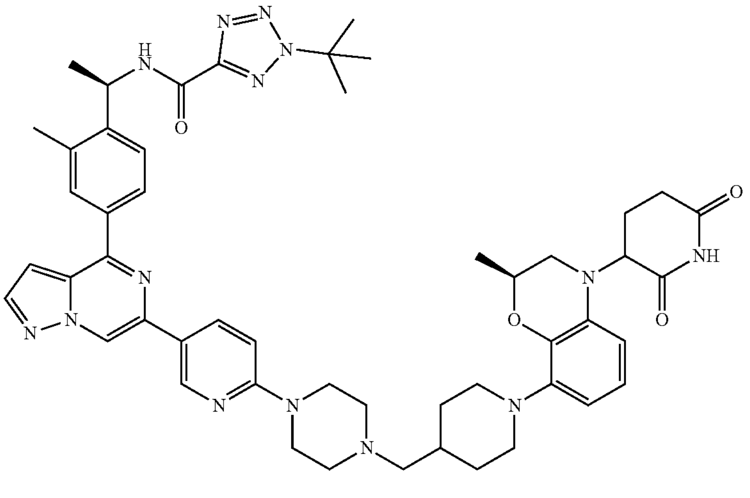 [SMILES: Cc1cc(-c2nc(-c3ccc(N4CCN(CC5CCN(c6cccc7c6O[C@@H](C)CN7C6CCC(=O)NC6=O)CC5)CC4)nc3)cn3nccc23)ccc1[C@@H](C)NC(=O)c1nnn(C(C)(C)C)n1]

TABLE 2-continued
290
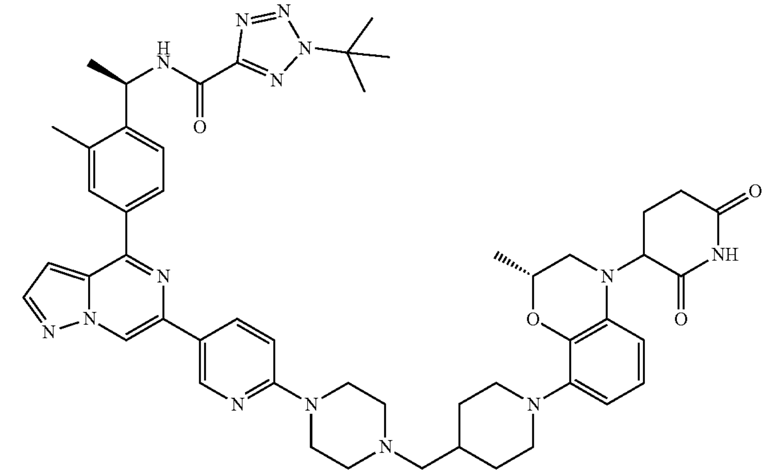 [SMILES: Cc1cc(-c2nc(-c3ccc(N4CCN(CC5CCN(c6cccc7c6O[C@H](C)CN7C6CCC(=O)NC6=O)CC5)CC4)nc3)cn3nccc23)ccc1[C@@H](C)NC(=O)c1nnn(C(C)(C)C)n1]
291
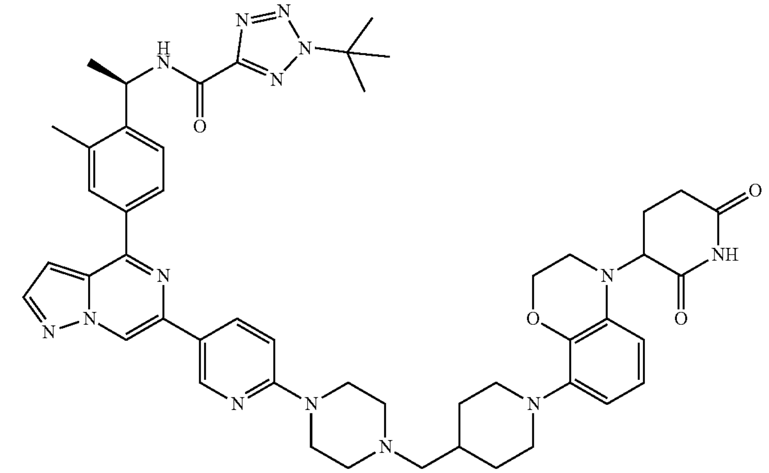 [SMILES: Cc1cc(-c2nc(-c3ccc(N4CCN(CC5CCN(c6cccc7c6OCCN7C6CCC(=O)NC6=O)CC5)CC4)nc3)cn3nccc23)ccc1[C@@H](C)NC(=O)c1nnn(C(C)(C)C)n1]
292
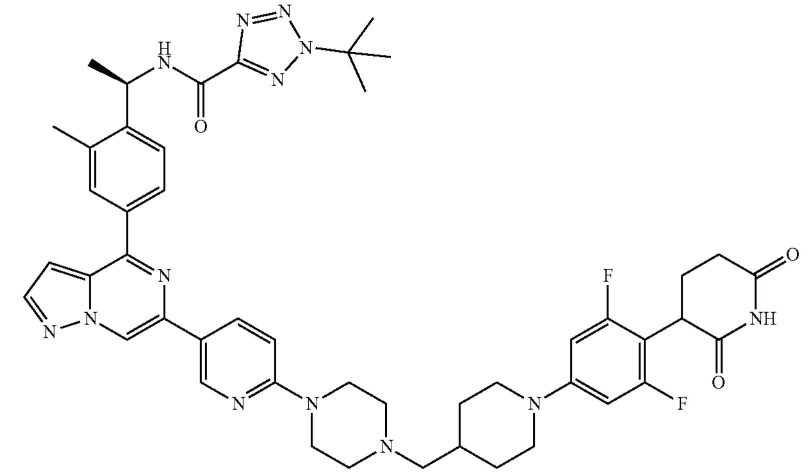 [SMILES: Cc1cc(-c2nc(-c3ccc(N4CCN(CC5CCN(c6cc(F)c(C7CCC(=O)NC7=O)c(F)c6)CC5)CC4)nc3)cn3nccc23)ccc1[C@@H](C)NC(=O)c1nnn(C(C)(C)C)n1]

TABLE 2-continued
293
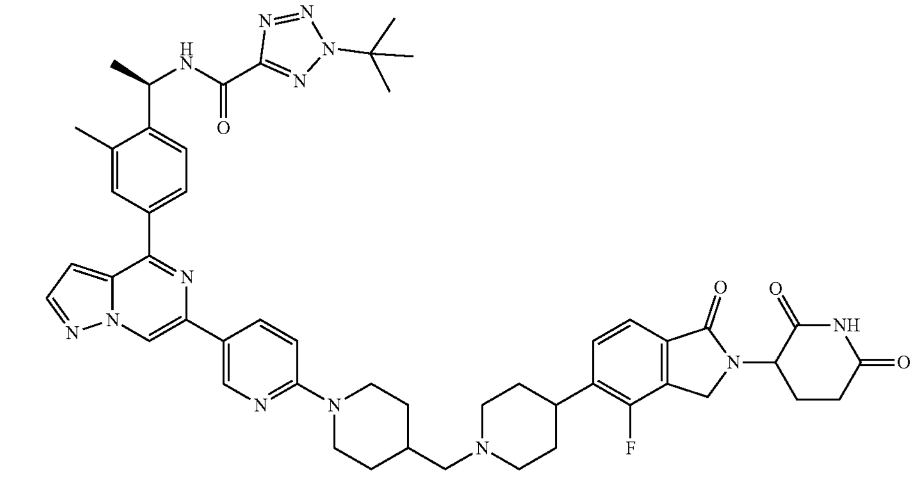 [SMILES: Cc1cc(-c2nc(-c3ccc(N4CCC(CN5CCC(c6ccc7c(c6F)CN(C6CCC(=O)NC6=O)C7=O)CC5)CC4)nc3)cn3nccc23)ccc1[C@@H](C)NC(=O)c1nnn(C(C)(C)C)n1]
294
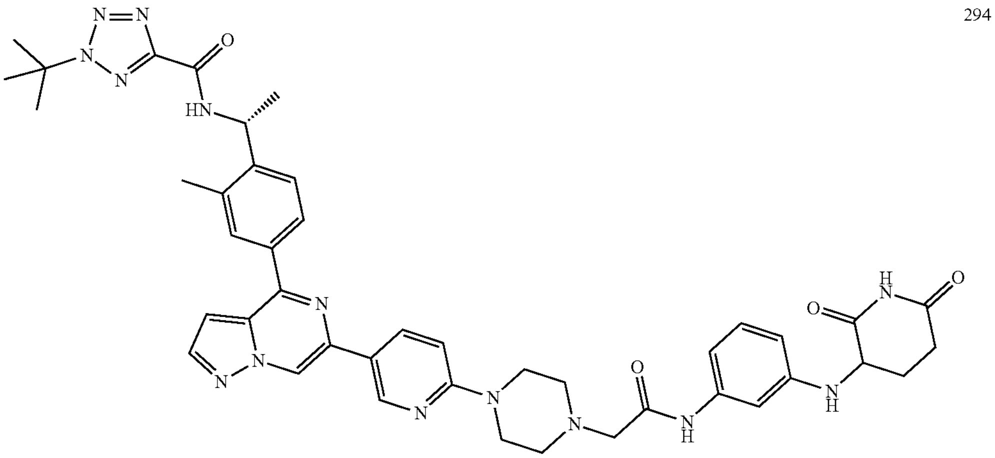
295
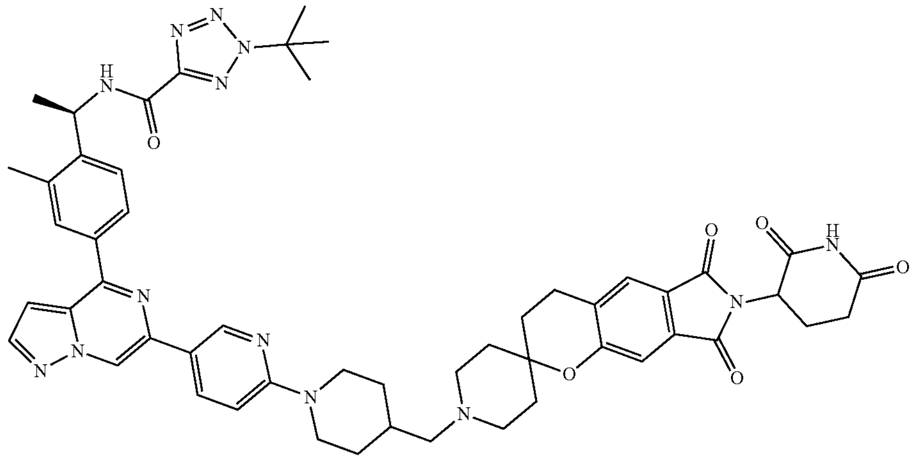 [SMILES: Cc1cc(-c2nc(-c3ccc(N4CCC(CN5CCC6(CCc7cc8c(cc7O6)C(=O)N(C6CCC(=O)NC6=O)C8=O)CC5)CC4)nc3)cn3nccc23)ccc1[C@@H](C)NC(=O)c1nnn(C(C)(C)C)n1]

TABLE 2-continued
296
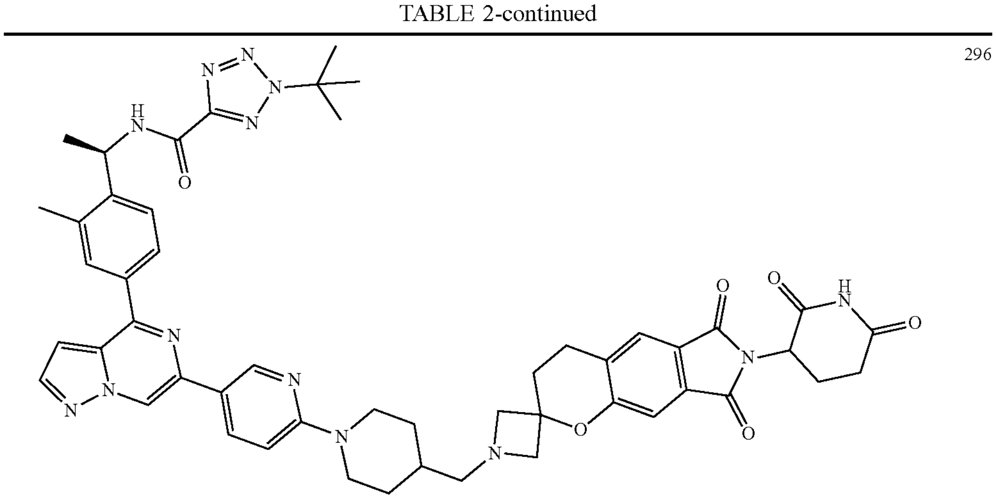
297
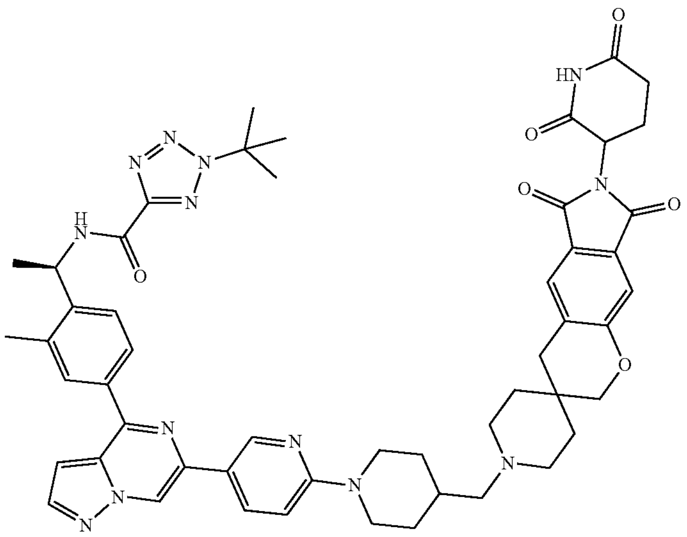 [SMILES: Cc1cc(-c2nc(-c3ccc(N4CCC(CN5CCC6(CC5)COc5cc7c(cc5C6)C(=O)N(C5CCC(=O)NC5=O)C7=O)CC4)nc3)cn3nccc23)ccc1[C@@H](C)NC(=O)c1nnn(C(C)(C)C)n1]
298
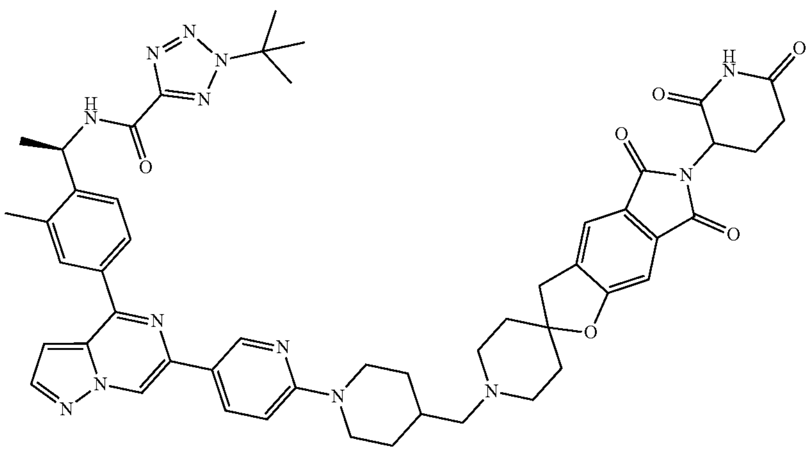 [SMILES: Cc1cc(-c2nc(-c3ccc(N4CCC(CN5CCC6(CC5)Cc5cc7c(cc5O6)C(=O)N(C5CCC(=O)NC5=O)C7=O)CC4)nc3)cn3nccc23)ccc1[C@@H](C)NC(=O)c1nnn(C(C)(C)C)n1]

TABLE 2-continued
299
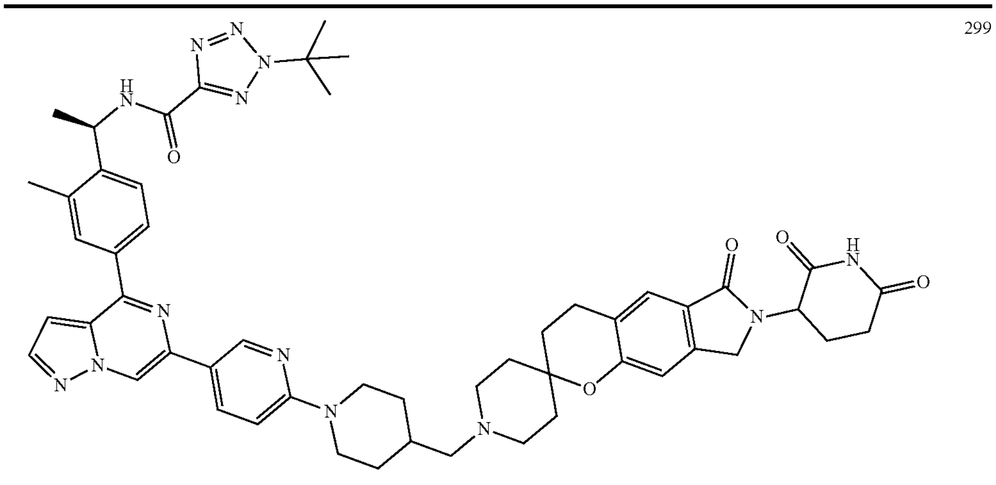
300
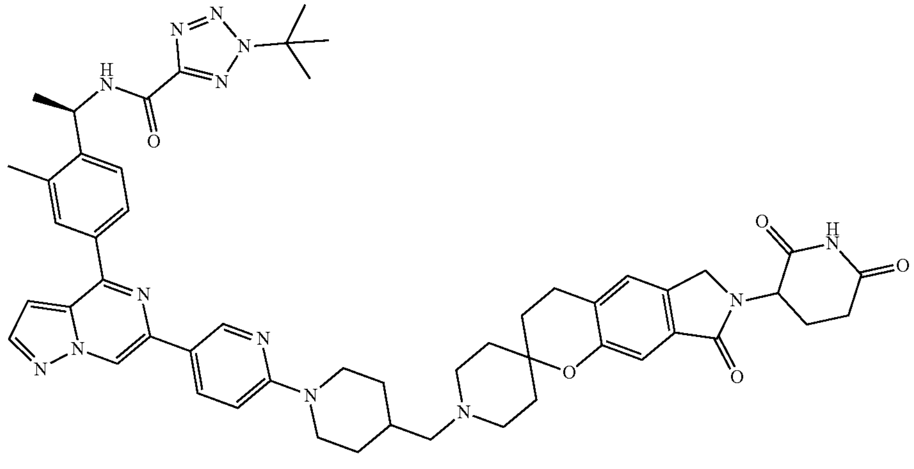 [SMILES: Cc1cc(-c2nc(-c3ccc(N4CCC(CN5CCC6(CCc7cc8c(cc7O6)C(=O)N(C6CCC(=O)NC6=O)C8)CC5)CC4)nc3)cn3nccc23)ccc1[C@@H](C)NC(=O)c1nnn(C(C)(C)C)n1]
301
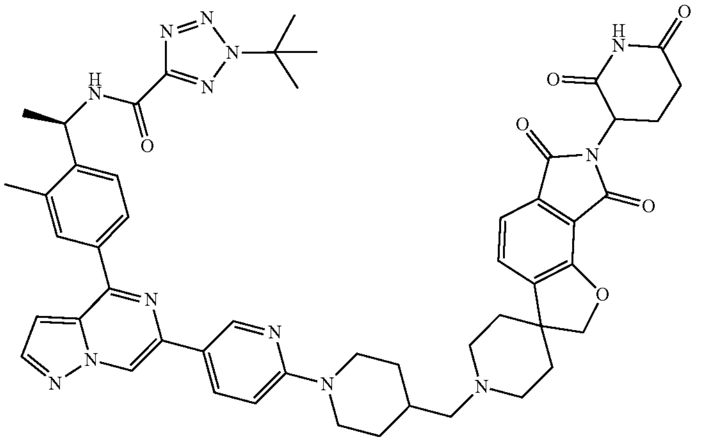 [SMILES: Cc1cc(-c2nc(-c3ccc(N4CCC(CN5CCC6(CC5)COc5c6ccc6c5C(=O)N(C5CCC(=O)NC5=O)C6=O)CC4)nc3)cn3nccc23)ccc1[C@@H](C)NC(=O)c1nnn(C(C)(C)C)n1]

In some embodiments, the compound is selected from the following Table 3:
TABLE 3
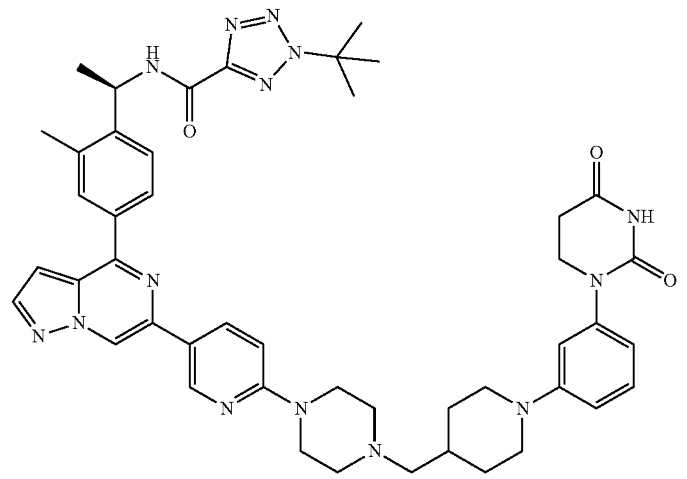 [SMILES: Cc1cc(-c2nc(-c3ccc(N4CCN(CC5CCN(c6cccc(N7CCC(=O)NC7=O)c6)CC5)CC4)nc3)cn3nccc23)ccc1[C@@H](C)NC(=O)c1nnn(C(C)(C)C)n1]
302
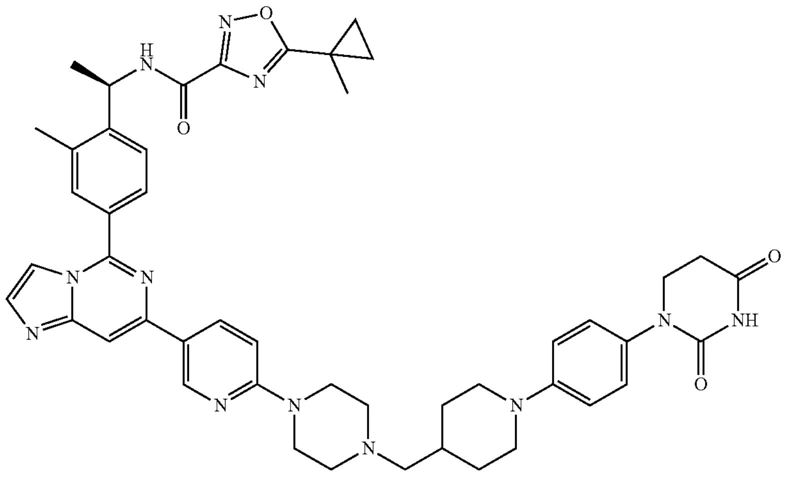 [SMILES: Cc1cc(-c2nc(-c3ccc(N4CCN(CC5CCN(c6ccc(N7CCC(=O)NC7=O)cc6)CC5)CC4)nc3)cc3nccn23)ccc1[C@@H](C)NC(=O)c1noc(C2(C)CC2)n1]
303
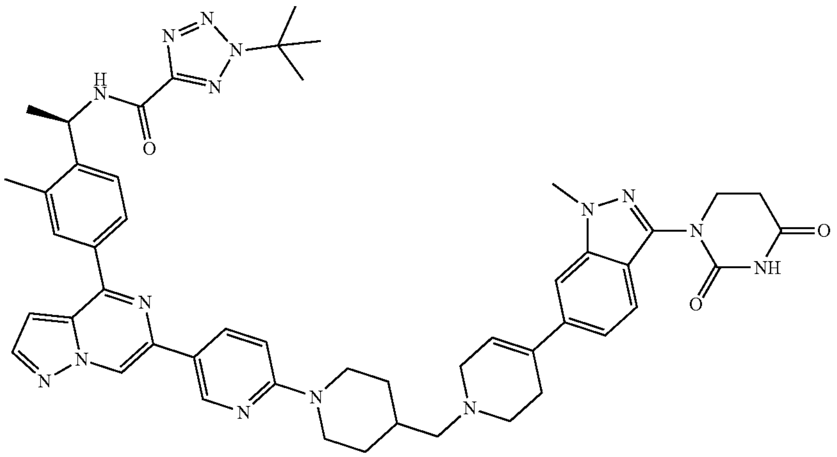 [SMILES: Cc1cc(-c2nc(-c3ccc(N4CCC(CN5CC=C(c6ccc7c(N8CCC(=O)NC8=O)nn(C)c7c6)CC5)CC4)nc3)cn3nccc23)ccc1[C@@H](C)NC(=O)c1nnn(C(C)(C)C)n1]
304

TABLE 3-continued
305
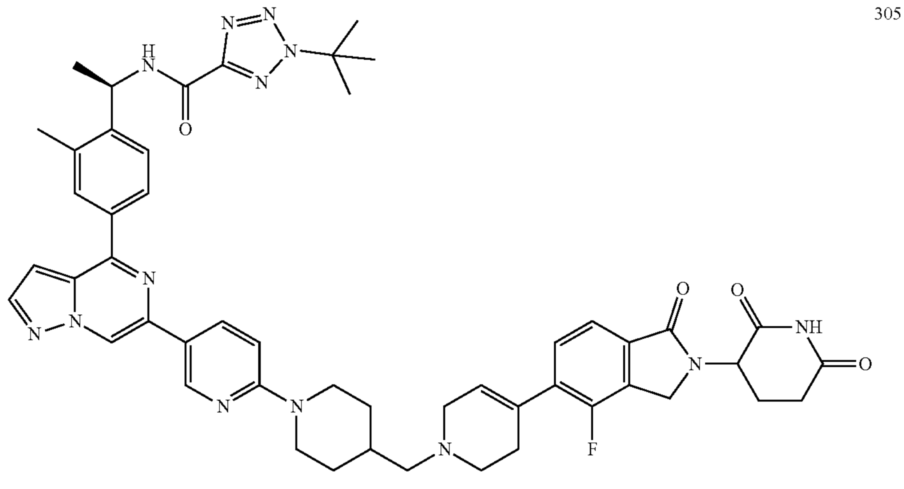
306
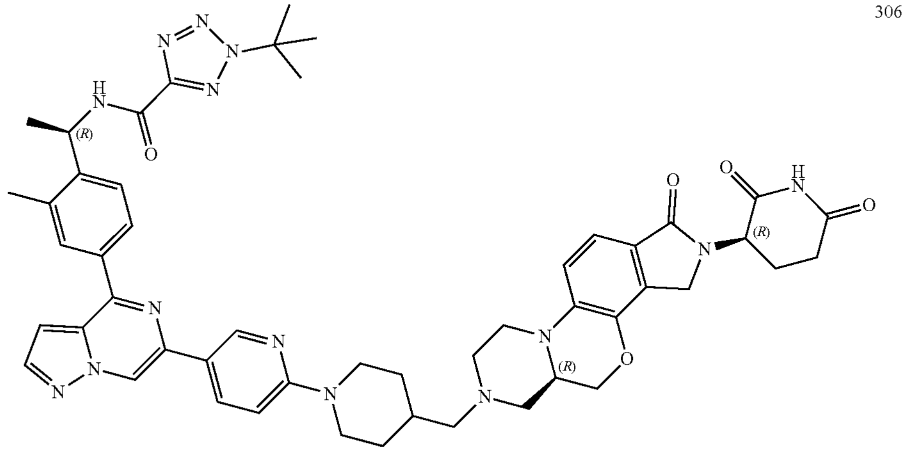
307
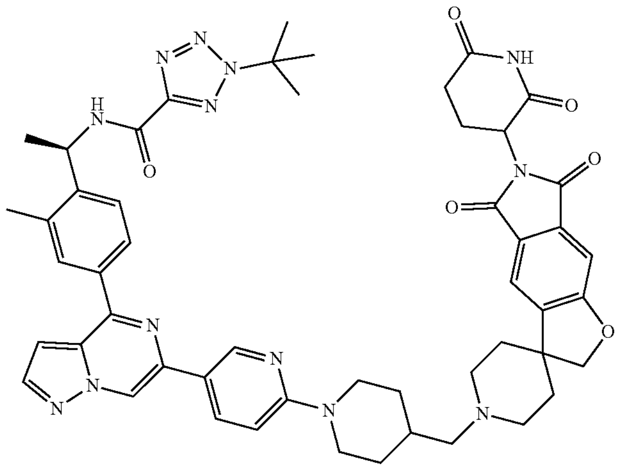 [SMILES: Cc1cc(-c2nc(-c3ccc(N4CCC(CN5CCC6(CC5)COc5cc7c(cc56)C(=O)N(C5CCC(=O)NC5=O)C7=O)CC4)nc3)cn3nccc23)ccc1[C@@H](C)NC(=O)c1nnn(C(C)(C)C)n1]

TABLE 3-continued
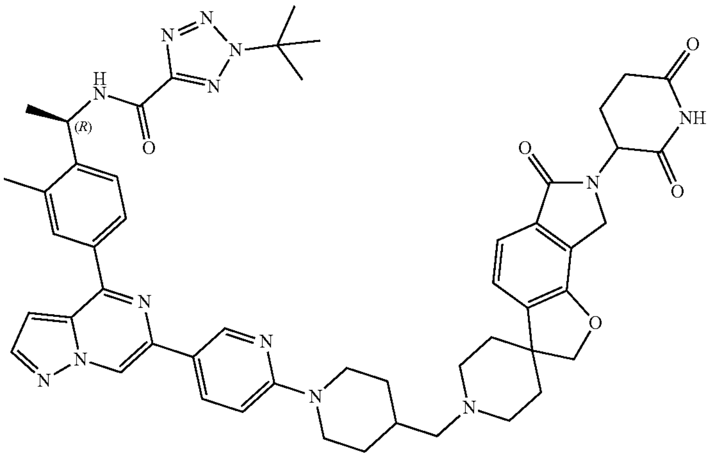
308
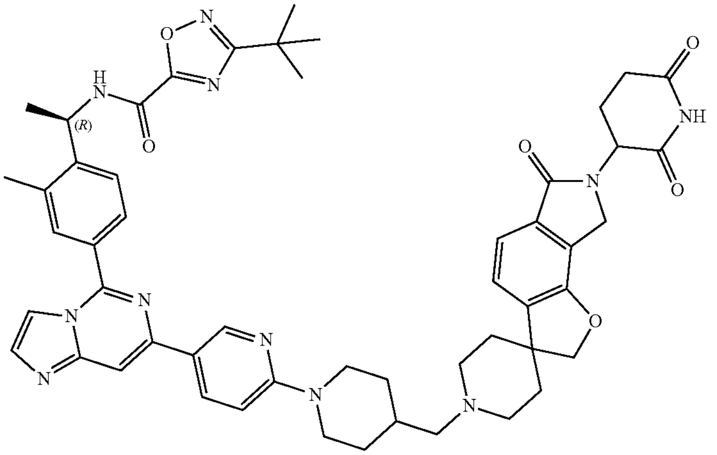
309
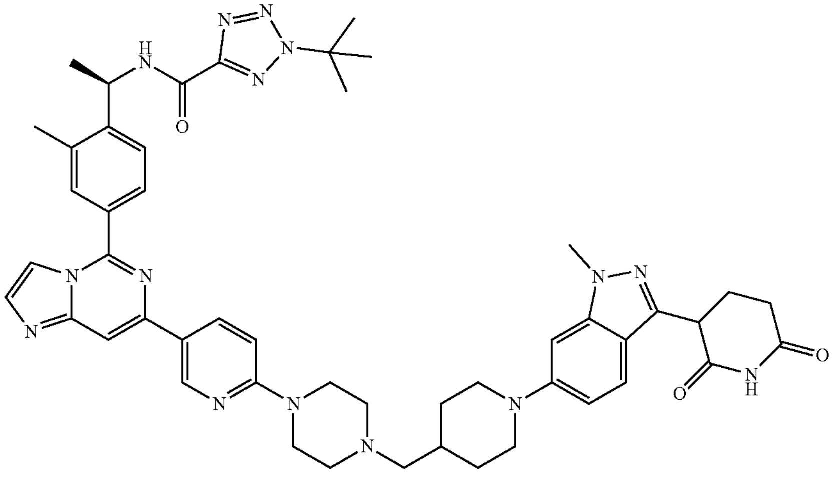 [SMILES: Cc1cc(-c2nc(-c3ccc(N4CCN(CC5CCN(c6ccc7c(C8CCC(=O)NC8=O)nn(C)c7c6)CC5)CC4)nc3)cc3nccn23)ccc1[C@@H](C)NC(=O)c1nnn(C(C)(C)C)n1]
310

TABLE 3-continued
311
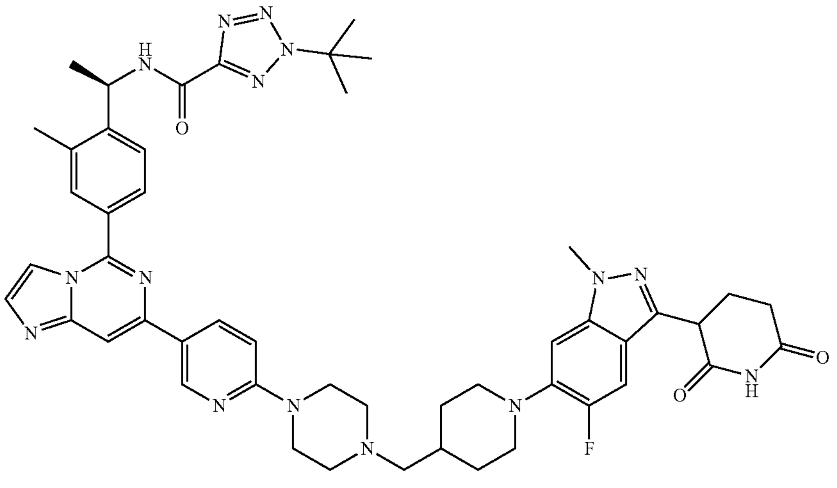 [SMILES: Cc1cc(-c2nc(-c3ccc(N4CCN(CC5CCN(c6cc7c(cc6F)c(C6CCC(=O)NC6=O)nn7C)CC5)CC4)nc3)cc3nccn23)ccc1[C@@H](C)NC(=O)c1nnn(C(C)(C)C)n1]
312
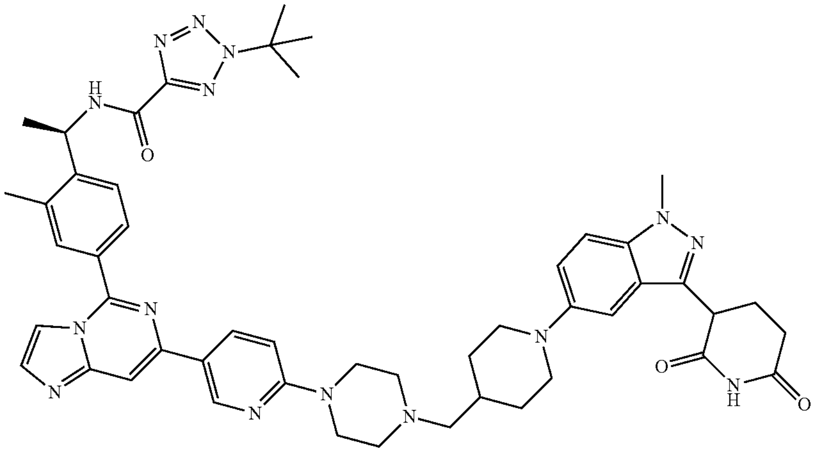 [SMILES: Cc1cc(-c2nc(-c3ccc(N4CCN(CC5CCN(c6ccc7c(c6)c(C6CCC(=O)NC6=O)nn7C)CC5)CC4)nc3)cc3nccn23)ccc1[C@@H](C)NC(=O)c1nnn(C(C)(C)C)n1]
313
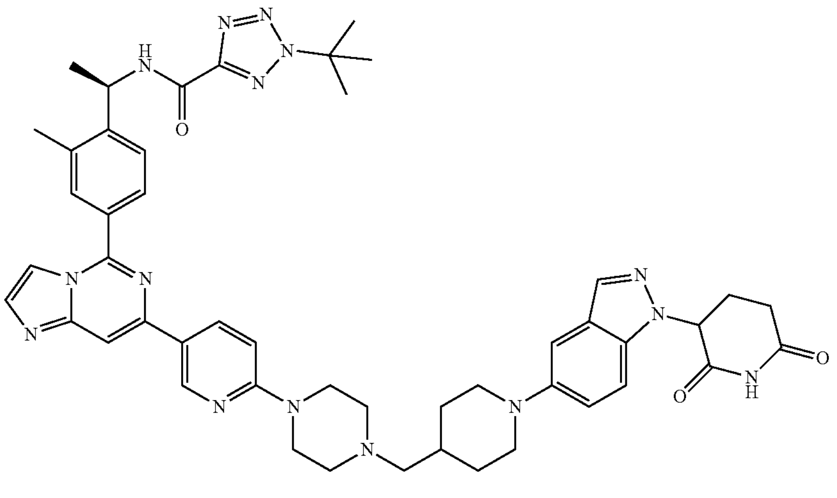 [SMILES: Cc1cc(-c2nc(-c3ccc(N4CCN(CC5CCN(c6ccc7c(cnn7C7CCC(=O)NC7=O)c6)CC5)CC4)nc3)cc3nccn23)ccc1[C@@H](C)NC(=O)c1nnn(C(C)(C)C)n1]

TABLE 3-continued

| | |
|---|---|
| 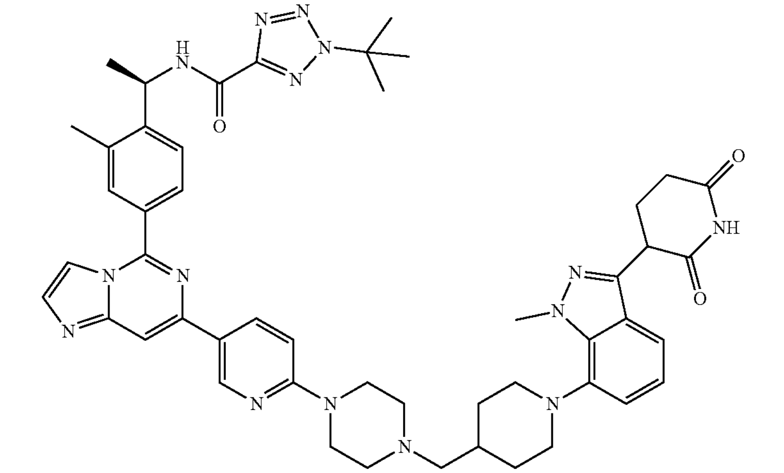 [SMILES: Cc1cc(-c2nc(-c3ccc(N4CCN(CC5CCN(c6cccc7c(C8CCC(=O)NC8=O)nn(C)c67)CC5)CC4)nc3)cc3nccn23)ccc1[C@@H](C)NC(=O)c1nnn(C(C)(C)C)n1] | 314 |
| 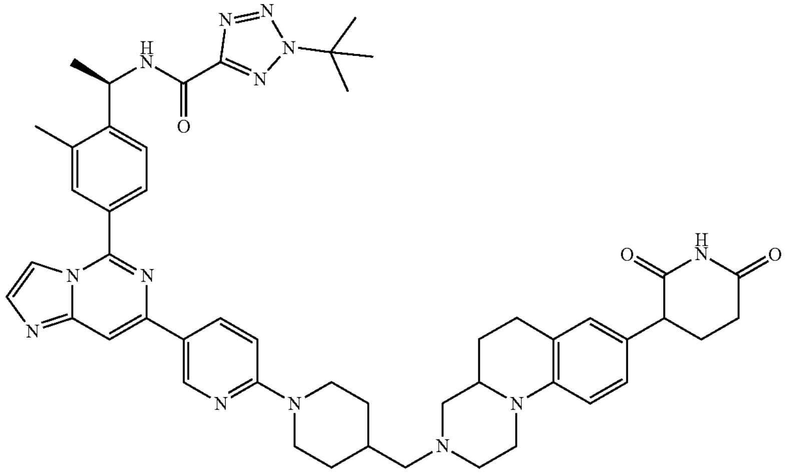 [SMILES: Cc1cc(-c2nc(-c3ccc(N4CCC(CN5CCN6c7ccc(C8CCC(=O)NC8=O)cc7CCC6C5)CC4)nc3)cc3nccn23)ccc1[C@@H](C)NC(=O)c1nnn(C(C)(C)C)n1] | 315 |
| 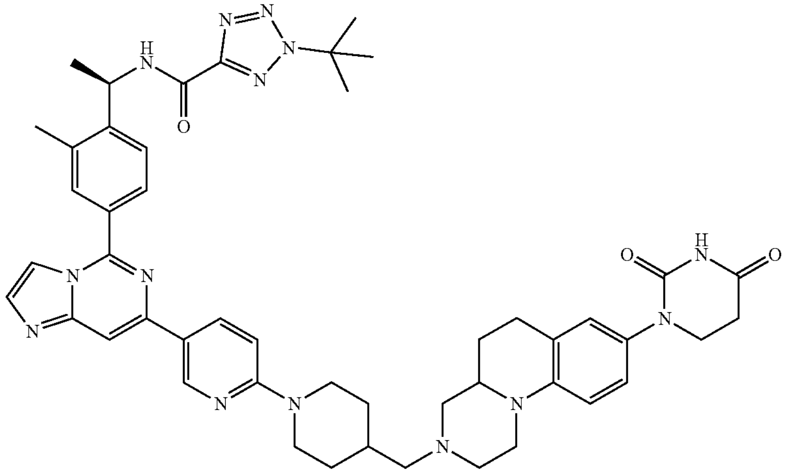 [SMILES: Cc1cc(-c2nc(-c3ccc(N4CCC(CN5CCN6c7ccc(N8CCC(=O)NC8=O)cc7CCC6C5)CC4)nc3)cc3nccn23)ccc1[C@@H](C)NC(=O)c1nnn(C(C)(C)C)n1] | 316 |

or a pharmaceutically acceptable salt or solvate thereof.

The present disclosure encompasses the preparation and use of salts of Compounds of the Disclosure. As used herein, the term "pharmaceutically acceptable salt" refers to salts or zwitterionic forms of Compounds of the Disclosure that are suitable for administration to a subject, e.g., a human. Salts of Compounds of the Disclosure can be prepared during the final isolation and purification of the compounds or separately by reacting the compound with a suitable acid. The pharmaceutically acceptable salts of Compounds of the Disclosure can be acid addition salts formed with pharmaceutically acceptable acids. Examples of acids which can be employed to form pharmaceutically acceptable salts include inorganic acids such as nitric, boric, hydrochloric, hydrobromic, sulfuric, and phosphoric, and organic acids such as oxalic, maleic, succinic, and citric. Non-limiting examples of salts of Compounds of the Disclosure include, but are not limited to, the hydrochloride, hydrobromide, hydroiodide, sulfate, bisulfate, 2-hydroxyethansulfonate, phosphate, hydrogen phosphate, acetate, adipate, alginate, aspartate, benzoate, bisulfate, butyrate, camphorate, camphorsulfonate, digluconate, glycerolphsphate, hemisulfate, heptanoate, hexanoate, formate, succinate, fumarate, maleate, ascorbate, isethionate, salicylate, methanesulfonate, mesitylenesulfonate, naphthylenesulfonate, nicotinate, 2-naphthalenesulfonate, oxalate, pamoate, pectinate, persulfate, 3-phenylproprionate, picrate, pivalate, propionate, trichloroacetate, trifluoroacetate, phosphate, glutamate, bicarbonate, paratoluenesulfonate, undecanoate, lactate, citrate, tartrate, gluconate, methanesulfonate, ethanedisulfonate, benzene sulfonate, and p-toluenesulfonate salts. In addition, available amino groups present in the compounds of the disclosure can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. In light of the foregoing, any reference Compounds of the Disclosure appearing herein is intended to include compounds of Compounds of the Disclosure as well as pharmaceutically acceptable salts, hydrates, or solvates thereof.

The present disclosure encompasses the preparation and use of solvates of Compounds of the Disclosure. Solvates typically do not significantly alter the physiological activity or toxicity of the compounds, and as such may function as pharmacological equivalents. The term "solvate" as used herein is a combination, physical association and/or solvation of a compound of the present disclosure with a solvent molecule such as, e.g. a disolvate, monosolvate or hemisolvate, where the ratio of solvent molecule to compound of the present disclosure is about 2:1, about 1:1 or about 1:2, respectively. This physical association involves varying degrees of ionic and covalent bonding, including hydrogen bonding. In certain instances, the solvate can be isolated, such as when one or more solvent molecules are incorporated into the crystal lattice of a crystalline solid. Thus, "solvate" encompasses both solution-phase and isolatable solvates. Compounds of the Disclosure can be present as solvated forms with a pharmaceutically acceptable solvent, such as water, methanol, and ethanol, and it is intended that the disclosure includes both solvated and unsolvated forms of Compounds of the Disclosure. One type of solvate is a hydrate. A "hydrate" relates to a particular subgroup of solvates where the solvent molecule is water. Solvates typically can function as pharmacological equivalents. Preparation of solvates is known in the art. See, for example, M. Caira et al, *J. Pharmaceut. Sci.,* 93 (3): 601-611 (2004), which describes the preparation of solvates of fluconazole with ethyl acetate and with water. Similar preparation of solvates, hemisolvates, hydrates, and the like are described by E. C. van Tonder et al., *AAPS Pharm. Sci. Tech.,* 5 (1): Article 12 (2004), and A. L. Bingham et al., *Chem. Commun.* 603-604 (2001). A typical, non-limiting, process of preparing a solvate would involve dissolving a Compound of the Disclosure in a desired solvent (organic, water, or a mixture thereof) at temperatures above 20° C. to about 25° C., then cooling the solution at a rate sufficient to form crystals, and isolating the crystals by known methods, e.g., filtration. Analytical techniques such as infrared spectroscopy can be used to confirm the presence of the solvate in a crystal of the solvate.

III. Compositions

In some aspects, the present disclosure provides compositions comprising the compound of the disclosure, or a pharmaceutically acceptable salt or solvate thereof, and a pharmaceutically acceptable carrier.

Pharmaceutical compositions for use in accordance with the present disclosure are formulated in a conventional manner using one or more physiologically acceptable carriers comprising excipients and/or auxiliaries that facilitate processing of Compound of the Disclosure.

These pharmaceutical compositions can be manufactured, for example, by conventional mixing, dissolving, granulating, dragee-making, emulsifying, encapsulating, entrapping, or lyophilizing processes. Proper formulation is dependent upon the route of administration chosen.

When a therapeutically effective amount of the Compound of the Disclosure is administered orally, the composition typically is in the form of a tablet, capsule, powder, solution, or elixir. When administered in tablet form, the composition additionally can contain a solid carrier, such as a gelatin or an adjuvant. The tablet, capsule, and powder contain about 0.01% to about 95%, and preferably from about 1% to about 50%, of a Compound of the Disclosure. When administered in liquid form, a liquid carrier, such as water, petroleum, or oils of animal or plant origin, can be added. The liquid form of the composition can further contain physiological saline solution, dextrose or other saccharide solutions, or glycols. When administered in liquid form, the composition contains about 0.1% to about 90%, and preferably about 1% to about 50%, by weight, of a Compound of the Disclosure.

When a therapeutically effective amount of a Compound of the Disclosure is administered by intravenous, cutaneous, or subcutaneous injection, the composition is in the form of a pyrogen-free, parenterally acceptable aqueous solution. The preparation of such parenterally acceptable solutions, having due regard to pH, isotonicity, stability, and the like, is within the skill in the art. A preferred composition for intravenous, cutaneous, or subcutaneous injection typically contains, an isotonic vehicle.

Compounds of the Disclosure can be readily combined with pharmaceutically acceptable carriers well-known in the art. Standard pharmaceutical carriers are described in Remington's Pharmaceutical Sciences, Mack Publishing Co., Easton, PA, 19th ed. 1995. Such carriers enable the active agents to be formulated as tablets, pills, dragees, capsules, liquids, gels, syrups, slurries, suspensions and the like, for oral ingestion by a subject to be treated. Pharmaceutical preparations for oral use can be obtained by adding the Compound of the Disclosure to a solid excipient, optionally grinding the resulting mixture, and processing the mixture of granules, after adding suitable auxiliaries, if desired, to obtain tablets or dragee cores. Suitable excipients include, for example, fillers and cellulose preparations. If desired, disintegrating agents can be added.

Compound of the Disclosure can be formulated for parenteral administration by injection, e.g., by bolus injection or continuous infusion. Formulations for injection can be presented in unit dosage form, e.g., in ampules or in multidose containers, with an added preservative. The compositions can take such forms as suspensions, solutions, or emulsions in oily or aqueous vehicles, and can contain formulatory agents such as suspending, stabilizing, and/or dispersing agents.

Pharmaceutical compositions for parenteral administration include aqueous solutions of the active agent in water-soluble form. Additionally, suspensions of a Compound of the Disclosure can be prepared as appropriate oily injection suspensions. Suitable lipophilic solvents or vehicles include fatty oils or synthetic fatty acid esters. Aqueous injection suspensions can contain substances which increase the viscosity of the suspension. Optionally, the suspension also can contain suitable stabilizers or agents that increase the solubility of the compounds and allow for the preparation of highly concentrated solutions. Alternatively, a present composition can be in powder form for constitution with a suitable vehicle, e.g., sterile pyrogen-free water, before use.

Compounds of the Disclosure also can be formulated in rectal compositions, such as suppositories or retention enemas, e.g., containing conventional suppository bases. In addition to the formulations described previously, the Compound of the Disclosure also can be formulated as a depot preparation. Such long-acting formulations can be administered by implantation (for example, subcutaneously or intramuscularly) or by intramuscular injection. Thus, for example, the Compound of the Disclosure can be formulated with suitable polymeric or hydrophobic materials (for example, as an emulsion in an acceptable oil) or ion exchange resins.

In particular, the Compounds of the Disclosure can be administered orally, buccally, or sublingually in the form of tablets containing excipients, such as starch or lactose, or in capsules or ovules, either alone or in admixture with excipients, or in the form of elixirs or suspensions containing flavoring or coloring agents. Such liquid preparations can be prepared with pharmaceutically acceptable additives, such as suspending agents. Compound of the Disclosure also can be injected parenterally, for example, intravenously, intramuscularly, subcutaneously, or intracoronarily. For parenteral administration, the Compound of the Disclosure are typically used in the form of a sterile aqueous solution which can contain other substances, for example, salts or monosaccharides, such as mannitol or glucose, to make the solution isotonic with blood.

IV. Methods and Uses

In some aspects, the present disclosure provides a method for treating or preventing a disease mediated by BTK, comprising administrating an effective amount of a compound of the disclosure, or a pharmaceutically acceptable salt or solvate thereof; or the pharmaceutical composition of the disclosure.

Diseases mediated by BTK as described above can be cancers.

Cancers as described above include, but are not limited to:

(1) cancer including bladder cancer (including accelerated and metastatic bladder cancer), breast cancer, colon cancer (including colorectal cancer), kidney cancer, liver cancer, lung cancer (including small cell and non-small cell lung cancer and lung adenocarcinoma), ovarian cancer, prostate cancer, testicular cancer, urogenital tract cancer, lymphatic system cancer, rectal cancer, larynx cancer, pancreatic cancer (including exocrine pancreatic cancer), esophageal cancer, and stomach cancer Carcinoma, gallbladder, cervix, thyroid, kidney and skin cancer (including squamous cell carcinoma);

(2) lymphoid hematopoietic tumors, including chronic lymphocytic leukemia acute lymphoblastic leukemia, acute lymphoblastic leukemia, B-cell lymphoma, T-cell lymphoma, Hodgkin's lymphoma, non-Hodgkin's lymphoma, hair cell lymphoma, histiocytic lymphoma, and Burkitt's lymphoma;

(3) hematopoietic tumors of the bone marrow line, including acute and chronic myelogenous leukemia, myelodysplastic syndrome, myelocytic leukemia, and promyelocytic leukemia;

(4) tumors of the central and peripheral nervous systems, including astrocytoma, neuroblastoma, glioma, and schwannoma;

(5) tumors of mesenchymal origin, including fibrosarcoma, rhabdomyosarcoma and osteosarcoma; and (6) other tumors, including melanoma, xenoderma pigmentosum, keratoactanthoma, seminoblastoma, thyroid follicular carcinoma, teratoma, renal cell carcinoma (RCC), pancreatic cancer, myeloma, lymphoblastic leukemia, and glioblastoma.

In some aspects, the present disclosure provides a method for inhibiting and/or degrading BTK comprising administering to a patient in need thereof a therapeutically effective amount of a compound of the disclosure, or a pharmaceutically acceptable salt or solvate thereof; or a pharmaceutical composition of the disclosure.

A therapeutically effective amount of a Compound of the Disclosure required for use in therapy varies with the nature of the condition being treated, the length of time that activity is desired, and the age and the condition of the subject, and ultimately is determined by the attendant physician. Dosage amounts and intervals can be adjusted individually to provide plasma levels of the Compound of the Disclosure that are sufficient to maintain the desired therapeutic effects. The desired dose can be administered in a single dose, or as multiple doses administered at appropriate intervals, for example as one, two, three, four or more subdoses per day. Multiple doses often are desired, or required. For example, a Compound of the Disclosure can be administered at a frequency of: four doses delivered as one dose per day at four-day intervals (q4d×4); four doses delivered as one dose per day at three-day intervals (q3d×4); one dose delivered per day at five-day intervals (qd×5); one dose per week for three weeks (qwk3); five daily doses, with two days rest, and another five daily doses (5/2/5); or, any dose regimen determined to be appropriate for the circumstance.

A Compound of the Disclosure used in a method of the present disclosure can be administered in an amount of about 0.005 to about 500 milligrams per dose, about 0.05 to about 250 milligrams per dose, or about 0.5 to about 100 milligrams per dose. For example, a Compound of the Disclosure can be administered, per dose, in an amount of about 0.005, about 0.05, about 0.5, about 5, about 10, about 20, about 30, about 40, about 50, about 100, about 150, about 200, about 250, about 300, about 350, about 400, about 450, or about 500 milligrams, including all doses between 0.005 and 500 milligrams.

The dosage of a composition containing a Compound of the Disclosure, or a composition containing the same, can be from about 1 ng/kg to about 200 mg/kg, about 1 μg/kg to about 100 mg/kg, or about 1 mg/kg to about 50 mg/kg. The dosage of a composition can be at any dosage including, but not limited to, about 1 μg/kg. The dosage of a composition may be at any dosage including, but not limited to, about 1 μg/kg, about 10 μg/kg, about 25 μg/kg, about 50 μg/kg, about 75 μg/kg, about 100 μg/kg, about 125 μg/kg, about 150 μg/kg, about 175 μg/kg, about 200 μg/kg, about 225 μg/kg, about 250 μg/kg, about 275 μg/kg, about 300 μg/kg, about 325 μg/kg, about 350 μg/kg, about 375 μg/kg, about 400 μg/kg, about 425 μg/kg, about 450 μg/kg, about 475 μg/kg, about 500 μg/kg, about 525 μg/kg, about 550 μg/kg, about 575 μg/kg, about 600 μg/kg, about 625 μg/kg, about 650 μg/kg, about 675 μg/kg, about 700 μg/kg, about 725 μg/kg, about 750 μg/kg, about 775 μg/kg, about 800 μg/kg, about 825 μg/kg, about 850 μg/kg, about 875 μg/kg, about 900 μg/kg, about 925 μg/kg, about 950 μg/kg, about 975 μg/kg, about 1 mg/kg, about 5 mg/kg, about 10 mg/kg, about 15 mg/kg, about 20 mg/kg, about 25 mg/kg, about 30 mg/kg, about 35 mg/kg, about 40 mg/kg, about 45 mg/kg, about 50 mg/kg, about 60 mg/kg, about 70 mg/kg, about 80 mg/kg, about 90 mg/kg, about 100 mg/kg, about 125 mg/kg, about 150 mg/kg, about 175 mg/kg, about 200 mg/kg, or more. The above dosages are exemplary of the average case, but there can be individual instances in which higher or lower dosages are merited, and such are within the scope of this disclosure. In practice, the physician determines the actual dosing regimen that is most suitable for an individual subject, which can vary with the age, weight, and response of the particular subject.

In certain embodiments, the therapeutically effective amount of the compound is between about 0.01 to 100 mg/kg per day.

In some aspects, the present disclosure provides compound of the disclosure, or a pharmaceutically acceptable salt or solvate thereof, for use in treating or preventing a disease mediated by BTK.

In some aspects, the present disclosure provides compound of the disclosure, or a pharmaceutically acceptable salt or solvate thereof, for use in treating cancer.

In some aspects, the present disclosure provides compound of the disclosure, or a pharmaceutically acceptable salt or solvate thereof, for use in inhibiting and/or degrading BTK.

In some aspects, the present disclosure provides the use of the compound of the disclosure, or a pharmaceutically acceptable salt or solvate thereof, or the pharmaceutical composition of the disclosure, in the manufacture of a medicament for treating or preventing a disease mediated by BTK.

In some aspects, the present disclosure provides the use of the compound of the disclosure, or a pharmaceutically acceptable salt or solvate thereof, or the pharmaceutical composition of the disclosure, in the manufacture of a medicament for inhibiting and/or degrading BTK.

EXAMPLES

In order to make the objects and technical solutions of the present disclosure clearer, the present disclosure will be further described below in conjunction with specific example. It should be understood that the examples are not intended to limit the scope of the invention. Further, specific experimental methods not mentioned in the following examples were carried out in accordance with a conventional experimental method.

I: Compound Synthesis

The invention is further described by means of embodiments below but does not therefore limit the invention to the scope of the embodiments. Experimental methods not specified in the following embodiments shall be selected in accordance with the conventional methods and conditions or in accordance with the commodity specification.

General Information for Chemistry.

Unless otherwise noted, all commercial materials were used as received. NMR spectra were recorded on a Bruker Ascend 400 MHz spectrometer and calibrated using residual solvent peaks as an internal reference. In reported spectral data, the format (δ) chemical shift (multiplicity, J values in Hz, integration) was used with the following abbreviations: s=singlet, d=doublet, t=triplet, q=quartet, hept=heptet, dd=doublet of doublets and m=multiplet. Low-resolution mass spectrometric (MS) analysis was carried out with a Waters UPLC ACQUITY QDa mass spectrometer. High-resolution mass experiments were operated on an Agilent Technologies 6230 TOF LC/MS instrument with APCI ionization. Flash column chromatography was performed by Teledyne CombiFlash RF+ using RediSep Rf silica gel flash column. The final compounds were all purified by a C18 reverse phase preparative HPLC column (SunFire Prep C18 OBD 5 μm, 50×100 mm). The purity of all the final compounds was measured and confirmed to be >95% by UPLCMS analysis (10-100% MeCN in H2O containing 0.1% formic acid in 5 min, 1.0 mL/min flow rate) with a C18 column (ACQUITY UPLC BEH C18 1.7 μm, 2.1×50 mm).

Example 1: (R)-2-(tert-butyl)-N-(1-(4-(6-(6-(4-((1-(4-(2,4-dioxotetrahydropyrimidin-1(2H)-yl)phenyl)piperidin-4-yl)methyl)piperazin-1-yl)pyridin-3-yl)-7H-pyrrolo[2,3-d]pyrimidin-4-yl)-2-methylphenyl)ethyl)-2H-tetrazole-5-carboxamide (Compound No. 7)

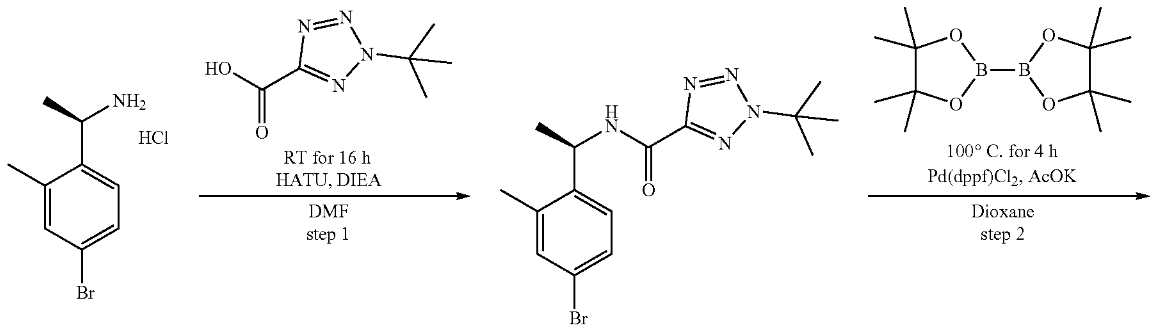

-continued
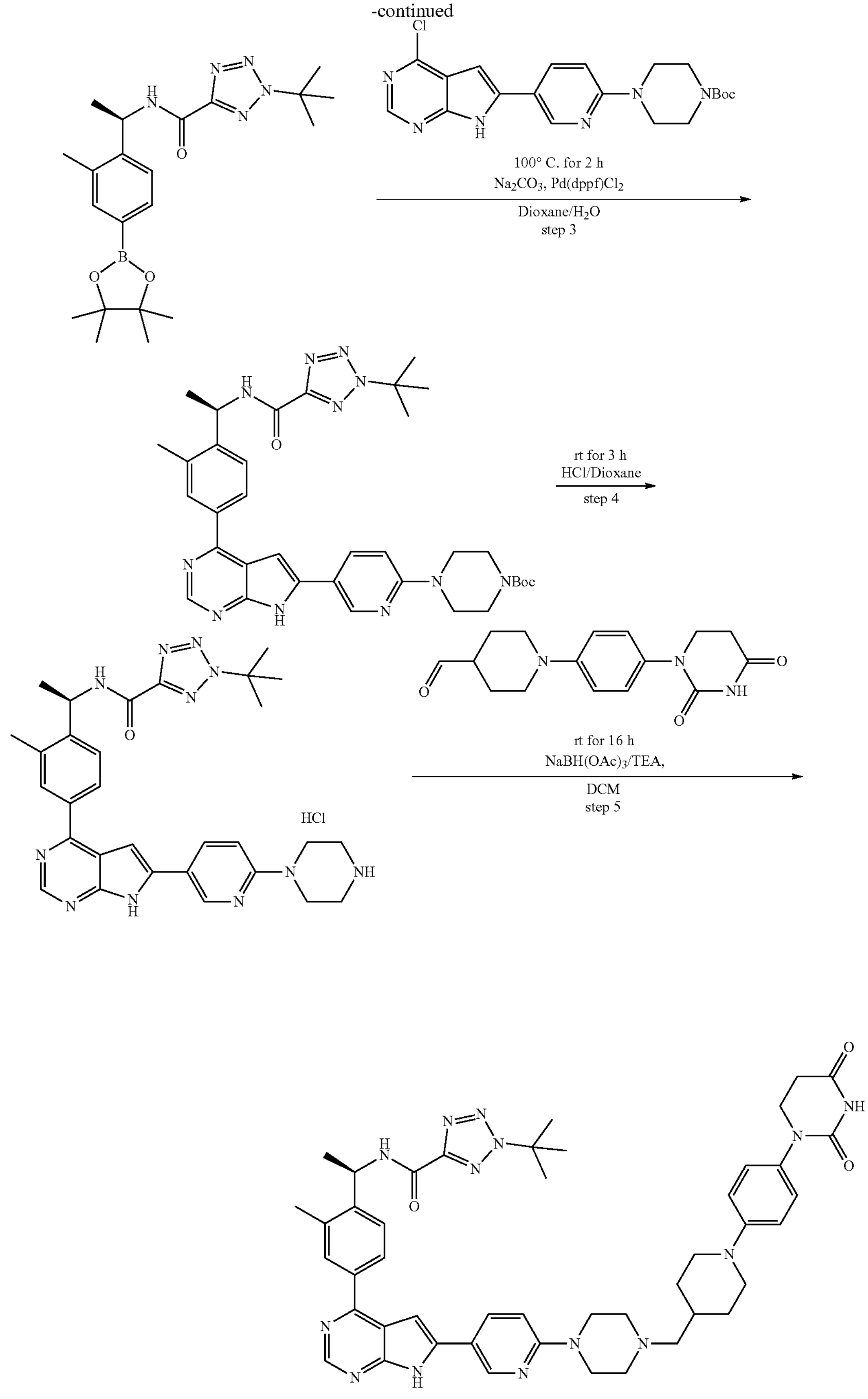

Step 1: (R)—N-(1-(4-bromo-2-methylphenyl)ethyl)-2-(tert-butyl)-2H-tetrazole-5-carboxamide

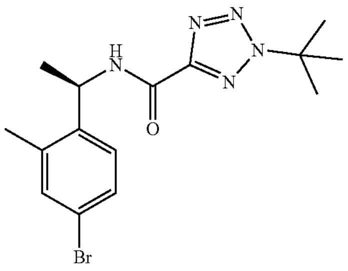 [SMILES: Cc1cc(Br)ccc1[C@@H](C)NC(=O)c1nnn(C(C)(C)C)n1]

To a mixture of 2-(tert-butyl)-2H-tetrazole-5-carboxylic acid (205 mg, 1.2 mmol, 1.0 eq), (R)-1-(4-bromo-2-methylphenyl) ethan-1-amine hydrochloride (300 mg, 1.2 mmol, 1.0 eq) and DIEA (465 mg, 3.6 mmol, 3.0 eq) in dry DMF (6 ml) was added HATU (683 mg, 1.8 mmol, 1.5 eq). The reaction mixture was stirred at rt under Ar for 16 h. The solution was diluted with ethyl acetate, washed with brine, dried over anhydrous $Na_2SO_4$ and concentrated in vacuo. The residue was purified by flash chromatography eluted with Hex/EA=2:1 to give the title compound (350 mg, 80%) as a white solid. LC-MS: 366.3 (M+H$^+$).

Step 2: (R)-2-(tert-butyl)-N-(1-(2-methyl-4-(4,4,5,5-tetramethyl-1,3,2-dioxaborolan-2-yl)phenyl)ethyl)-2H-tetrazole-5-carboxamide

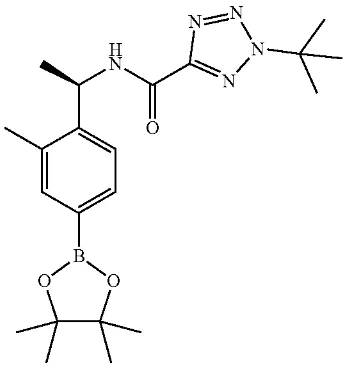 [SMILES: Cc1cc(B2OC(C)(C)C(C)(C)O2)ccc1[C@@H](C)NC(=O)c1nnn(C(C)(C)C)n1]

A mixture of 4,4,4',4',5,5,5',5'-octamethyl-2,2'-bi (1,3,2-dioxaborolane) (267 mg, 1.051 mmol, 1.1 eq), potassium acetate (281 mg, 2.87 mmol, 3.0 eq), Pd(dppf)$Cl_2$ (70 mg, 0.096 mmol, 0.1 eq) and above obtained intermediate (350 mg, 0.956 mmol, 1.0 eq) in dry dioxane (10 ml) was stirred at 100° C. under Ar for 3 h. Water was added and the solution was extracted with ethyl acetate for 3 times. The combined organic layers were washed with brine, dried over anhydrous $Na_2SO_4$. After concentration in vacuo, the residue was purified by flash chromatography eluted with Hex/EA=6:1 to give the title compound (380 mg, 96%) as a white solid. LC-MS: 414.4 (M+H$^+$).

Step 3: tert-butyl (R)-4-(5-(4-(4-(1-(2-(tert-butyl)-2H-tetrazole-5-carboxamido)ethyl)-3-methylphenyl)-7H-pyrrolo[2,3-d]pyrimidin-6-yl)pyridin-2-yl) piperazine-1-carboxylate

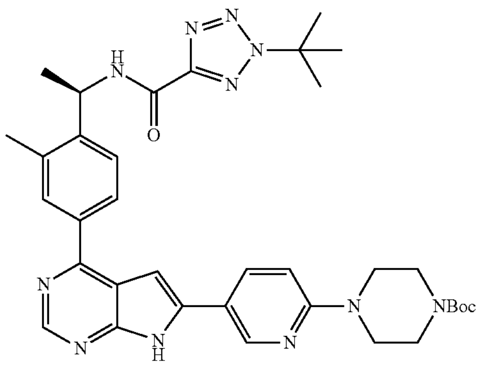 [SMILES: Cc1cc(-c2ncnc3[nH]c(-c4ccc(N5CCN(C(=O)OC(C)(C)C)CC5)nc4)cc23)ccc1[C@@H](C)NC(=O)c1nnn(C(C)(C)C)n1]

A mixture of tert-butyl 4-(5-(4-chloro-7H-pyrrolo[2,3-d] pyrimidin-6-yl)pyridin-2-yl)piperazine-1-carboxylate (100 mg, 0.241 mmol, 1.0 eq), $Na_2CO_3$ (77 mg, 0.723 mmol, 3.0 eq), Pd(dppf)$Cl_2$ (17.6 mg, 0.024 mmol, 0.1 eq) and above obtained intermediate (120 mg, 0.289 mmol, 1.2 eq) in dioxane (4 ml) and water (1 ml) was stirred at 100° C. under Ar for 2 h. The solution was diluted with water, extracted with ethyl acetate for 3 times. The combined organic layers were washed with brine, dried over anhydrous $Na_2SO_4$. After concentration in vacuo. The residue was purified by flash chromatography eluted with Hex/EA=2:1 to give the title compound (100 mg, 62%) as a yellow solid. LC-MS: 666.4 (M+H$^+$).

Step 4: (R)-2-(tert-butyl)-N-(1-(2-methyl-4-(6-(6-(piperazin-1-yl)pyridin-3-yl)-7H-pyrrolo[2,3-d]pyrimidin-4-yl)phenyl)ethyl)-2H-tetrazole-5-carboxamide hydrochloride

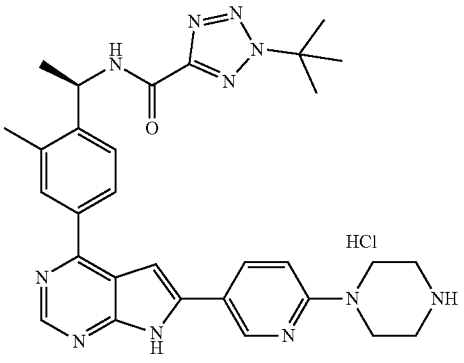 [SMILES: Cc1cc(-c2ncnc3[nH]c(-c4ccc(N5CCNCC5)nc4)cc23)ccc1[C@@H](C)NC(=O)c1nnn(C(C)(C)C)n1 ; Cl]

To a solution of above obtained intermediate (100 mg, 0.15 mmol, 1.0 eq) in dry DCM (2 ml) was added 4 M HCl/Dioxane (1 ml). The reaction mixture was stirred at rt under Ar for 2 h. The reaction mixture was concentrated in vacuo to give the title compound (90 mg, 100%) as a yellow solid. LC-MS: 566.3 (M+H$^+$).

Step 5: (R)-2-(tert-butyl)-N-(1-(4-(6-(6-(4-((1-(4-(2,4-dioxotetrahydropyrimidin-1(2H)-yl)phenyl)piperidin-4-yl)methyl)piperazin-1-yl)pyridin-3-yl)-7H-pyrrolo[2,3-d]pyrimidin-4-yl)-2-methylphenyl)ethyl)-2H-tetrazole-5-carboxamide

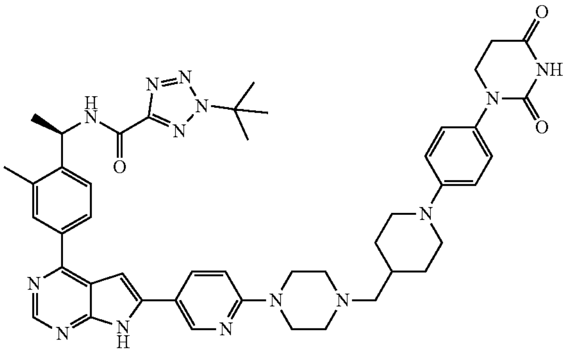 [SMILES: Cc1cc(-c2ncnc3[nH]c(-c4ccc(N5CCN(CC6CCN(c7ccc(N8CCC(=O)NC8=O)cc7)CC6)CC5)nc4)cc23)ccc1[C@@H](C)NC(=O)c1nnn(C(C)(C)C)n1]

To a mixture of above obtained intermediate (90 mg, 0.15 mmol, 1.0 eq), 1-(4-(2,4-dioxotetrahydropyrimidin-1(2H)-yl)phenyl)piperidine-4-carbaldehyde (68 mg, 0.225 mmol, 1.5 eq) and TEA (76 mg, 0.75 mmol, 5.0 eq) in dry DCM (5 ml) was added NaBH(OAc) 3 (64 mg, 0.30 mmol, 2.0 eq) in portions. The reaction was stirred at rt under Ar for 16 h. The reaction was quenched with water and extracted with DCM for 3 times. The organic layers were washed with brine, dried over anhydrous $Na_2SO_4$. After concentration in vacuo. The residue was purified by pre-HPLC to give the title compound (56 mg, 43%) as a yellow solid. LC-MS: 851.5 ($M+H^+$). $^1H$ NMR (400 MHz, DMSO-$d^6$) δ (ppm) 12.49 (s, 1H), 10.16 (s, 1H), 9.46 (d, J=8.0 Hz, 1H), 8.73 (d, J=2.0 Hz, 1H), 8.69 (s, 1H), 8.15-8.05 (m, 1H), 8.01-7.96 (m, 2H), 7.61 (d, J=8.0 Hz, 1H), 7.21 (s, 1H), 7.10-7.00 (m, 2H), 6.90-6.80 (m, 3H), 5.45-5.30 (m, 1H), 3.70-3.45 (m, 8H), 2.65-2.55 (m, 4H), 2.48 (s, 3H), 2.45-2.35 (m, 4H), 2.15 (d, J=7.2 Hz, 2H), 1.80-1.70 (m, 2H), 1.66 (s, 9H), 1.65-1.60 (m, 1H), 1.48 (d, J=7.2 Hz, 3H), 1.25-1.10 (m, 2H).

Following the synthesis of EXAMPLE 1, the following compounds were synthesized and obtained in a similar manner.

| Compd No. | Structure Observed MS $[M + 1]^+$ |
| --- | --- |
| 5 | 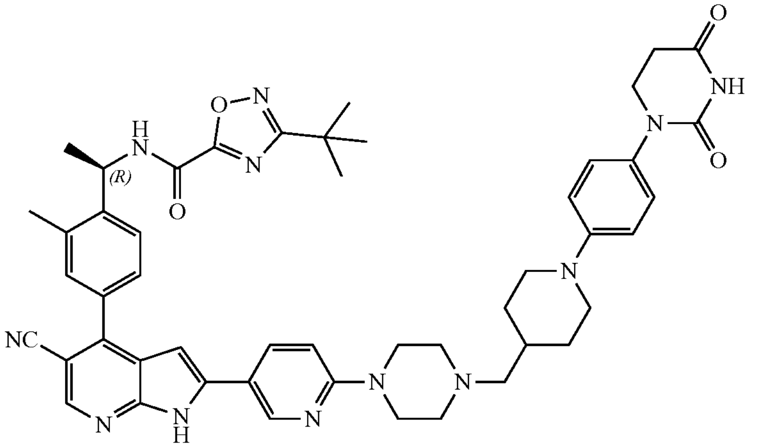 875.5 |
| 10 | 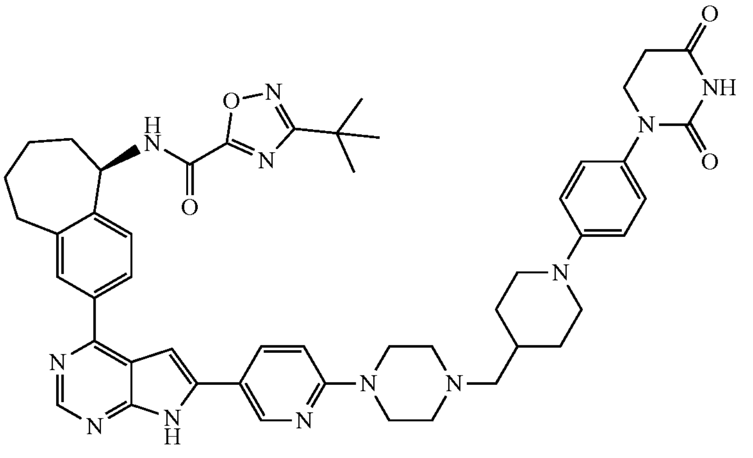 877.5 |

-continued
11
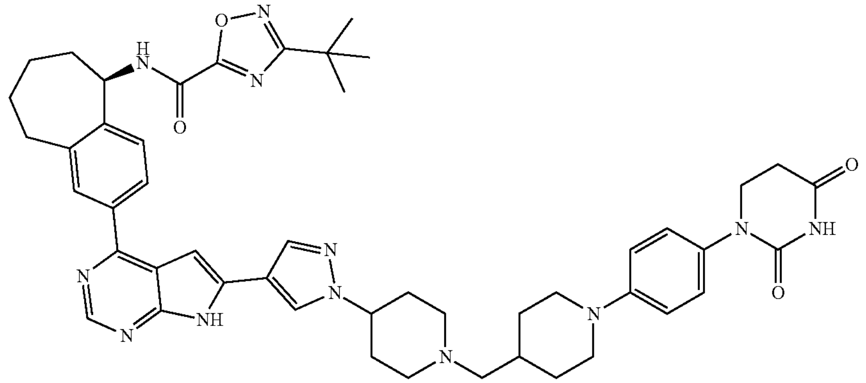 [SMILES: CC(C)(C)c1noc(C(=O)N[C@@H]2CCCCc3cc(-c4ncnc5[nH]c(-c6cnn(C7CCN(CC8CCN(c9ccc(N%10CCC(=O)NC%10=O)cc9)CC8)CC7)c6)cc45)ccc32)n1]
865.6
13
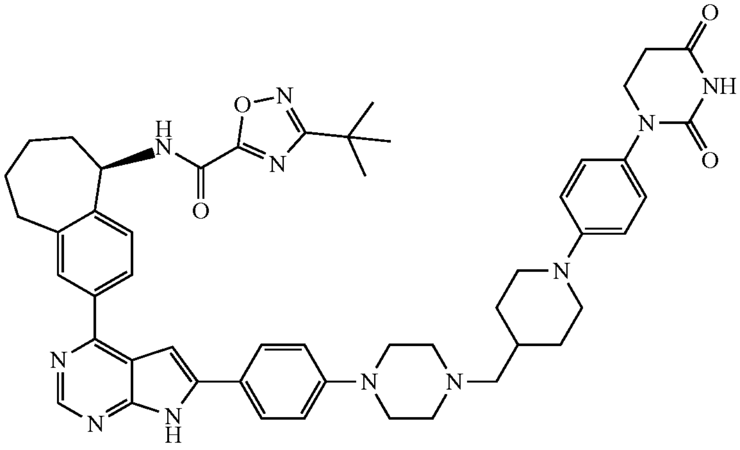
876.6
14
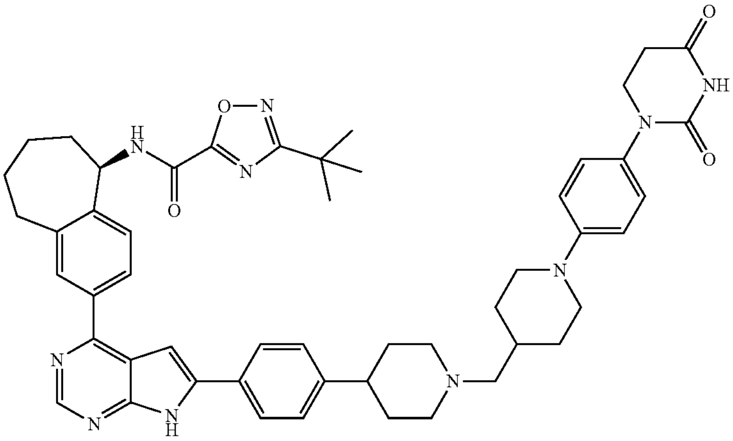 [SMILES: CC(C)(C)c1noc(C(=O)N[C@@H]2CCCCc3cc(-c4ncnc5[nH]c(-c6ccc(C7CCN(CC8CCN(c9ccc(N%10CCC(=O)NC%10=O)cc9)CC8)CC7)cc6)cc45)ccc32)n1]
875.4

-continued
| | | |
|---|---|---|
| 25 | 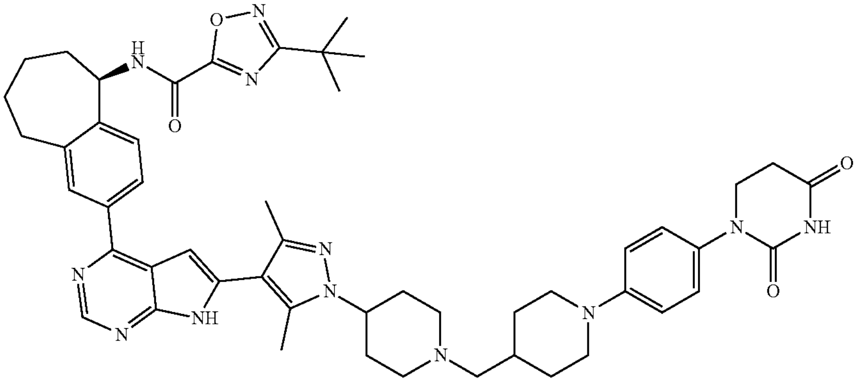 [SMILES: Cc1nn(C2CCN(CC3CCN(c4ccc(N5CCC(=O)NC5=O)cc4)CC3)CC2)c(C)c1-c1cc2c(-c3ccc4c(c3)CCCC[C@H]4NC(=O)c3nc(C(C)(C)C)no3)ncnc2[nH]1] | 893.2 |
| 143 | 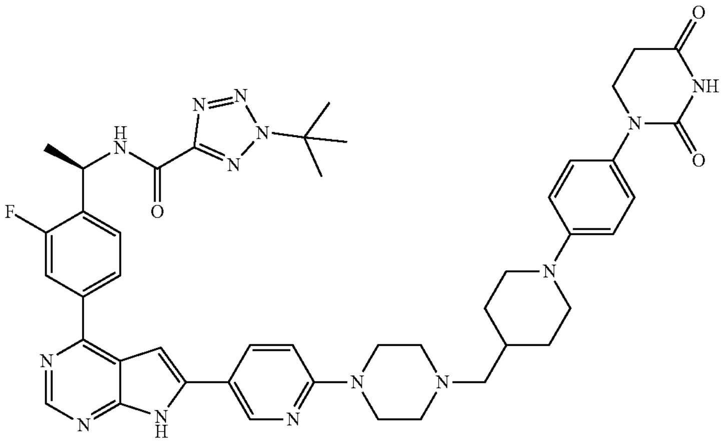 [SMILES: C[C@@H](NC(=O)c1nnn(C(C)(C)C)n1)c1ccc(-c2ncnc3[nH]c(-c4ccc(N5CCN(CC6CCN(c7ccc(N8CCC(=O)NC8=O)cc7)CC6)CC5)nc4)cc23)cc1F] | 855.7 |
| Compd No. | $^1$H NMR (400 MHz, DMSO-$d^6$) δ (ppm) |
|---|---|
| 5 | 12.74 (s, 1H), 10.23 (s, 1H), 9.95 (d, J = 8.0 Hz, 1H), 8.72 (s, 1H), 8.59 (s, 1H), 8.16 - 8.01 (m, 1H), 7.69 (d, J = 8.0 Hz, 1H), 7.61 - 7.46 (m, 2H), 7.11 (d, J = 8.9 Hz, 2H), 6.98 - 6.78 (m, 4H), 5.52 - 5.32 (m, 1H), 3.76 - 3.62 (m, 4H), 3.61 - 3.48 (m, 4H), 2.78 - 2.58 (m, 4H), 2.48 - 2.38 (m, 7H), 2.24 - 2.14 (m, 2H), 1.85 - 1.75 (m, 2H), 1.74 - 1.63 (m, 1H), 1.55 (d, J = 7.0 Hz, 3H), 1.37 (s, 9H), 1.22 - 1.15 (m, 2H). |
| 10 | 12.57 (s, 1H), 10.25 (s, 1H), 10.03 (d, J = 8.0 Hz, 1H), 8.80 (d, J = 2.4 Hz, 1H), 8.76 (s, 1H), 8.20 - 8.15 (m, 1H), 8.09 - 8.03 (m, 2H), 7.41 (d, J = 8.0 Hz, 1H), 7.29 (s, 1H), 7.16 - 7.09 (m, 2H), 6.97 - 6.88 (m, 3H), 5.34 - 5.26 (m, 1H), 3.72 - 3.55 (m, 8H), 3.11 - 2.92 (m, 2H), 2.73 - 2.62 (m, 4H), 2.49 - 2.44 (m, 4H), 2.21 (d, J = 7.2 Hz, 2H), 2.08 - 1.65 (m, 8H), 1.41 (s, 9H), 1.35 - 1.20 (m, 3H). |
| 11 | 12.46 (s, 1H), 10.25 (s, 1H), 10.02 (d, J = 8.0 Hz, 1H), 8.73 (s, 1H), 8.44 (s, 1H), 8.10 (s, 1H), 8.03 - 7.97 (m, 2H), 7.41 (d, J = 7.6 Hz, 1H), 7.16 - 7.07 (m, 3H), 6.92 (d, J = 8.8 Hz, 2H), 5.34 - 5.26 (m, 1H), 4.25 - 4.02 (m, 1H), 3.75 - 3.65 (m, 4H), 3.10 - 2.90 (m, 4H), 2.73 - 2.62 (m, 4H), 2.25 - 1.60 (m, 16H), 1.41 (s, 9H), 1.35 - 1.20 (m, 3H). |
| 13 | 12.50 (s, 1H), 10.25 (s, 1H), 10.02 (d, J = 8.0 Hz, 1H), 8.75 (s, 1H), 8.10 - 8.01 (m, 2H), 7.91 (d, J = 8.8 Hz, 2H), 7.41 (d, J = 8.0 Hz, 1H), 7.22 (s, 1H), 7.13 (d, J = 8.8 Hz, 2H), 7.02 (d, J = 8.8 Hz, 2H), 6.92 (d, J = 8.8 Hz, 2H), 5.34 - 5.26 (m, 1H), 3.75 - 3.65 (m, 4H), 3.28 - 3.20 (m, 4H), 3.10 - 2.92 (m, 2H), 2.73 - 2.62 (m, 4H), 2.56 -2.52 (m, 4H), 2.22 (d, J = 7.2 Hz, 2H), 2.07 - 1.65 (m, 8H), 1.41 (s, 9H), 1.38 - 1.18 (m, 3H). |

-continued
| | |
|---|---|
| 14 | 12.65 (s, 1H), 10.25 (s, 1H), 10.02 (d, J = 8.0 Hz, 1H), 8.80 (s, 1H), 8.11 - 8.02 (m, 2H), 7.98 (d, J = 8.4 Hz, 2H), 7.42 (d, J = 8.0 Hz, 1H), 7.40 - 7.35 (m, 3H), 7.13 (d, J = 8.8 Hz, 2H), 6.93 (d, J = 8.8 Hz, 2H), 5.34 - 5.26 (m, 1H), 3.75 - 3.65 (m, 4H), 3.10 - 2.92 (m, 4H), 2.73 - 2.62 (m, 4H), 2.58 - 2.52 (m, 1H), 2.22 (d, J = 6.8 Hz, 2H), 2.07 - 1.65 (m, 14H), 1.41 (s, 9H), 1.38 - 1.18 (m, 3H). |
| 143 | 12.65 (s, 1H), 10.24 (s, 1H), 9.62 (d, J = 7.9 Hz, 1H), 8.86 - 8.72 (m, 2H), 8.19 (dd, J = 8.9, 2.2 Hz, 1H), 8.14 - 8.07 (m, 1H), 8.02 - 7.94 (m, 1H), 7.71 (t, J = 8.0 Hz, 1H), 7.34 (s, 1H), 7.13 (d, J = 8.9 Hz, 2H), 6.93 (t, J = 10.4 Hz, 3H), 5.59 - 5.46 (m, 1H), 3.74 - 3.52 (m, 8H), 2.74 - 2.60 (m, 4H), 2.46 (s, 4H), 2.21 (s, 2H), 1.81 (d, J = 12.7 Hz, 2H), 1.74 (s, 10H), 1.59 (d, J = 7.0 Hz, 3H), 1.30 - 1.13 (m, 2H). |
Example 2: (R)-3-(tert-butyl)-N-(1-(4-(6-(1-(1-((1-(4-(2,4-dioxotetrahydropyrimidin-1(2H)-yl)phenyl)piperidin-4-yl)methyl)piperidin-4-yl)-1H-pyrazol-4-yl)pyrazolo[1,5-a]pyrazin-4-yl)-2-methylphenyl)ethyl)-1,2,4-oxadiazole-5-carboxamide (Compound No. 9)
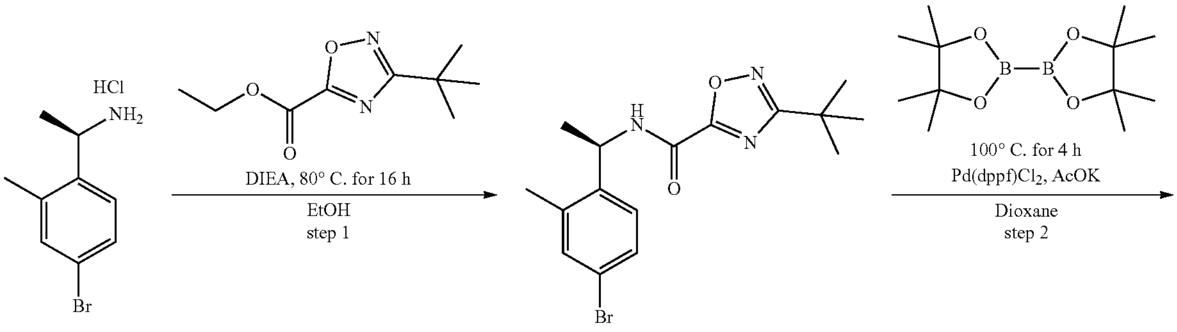
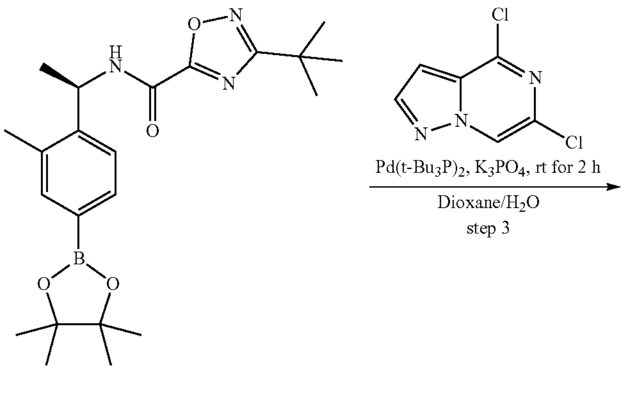

-continued
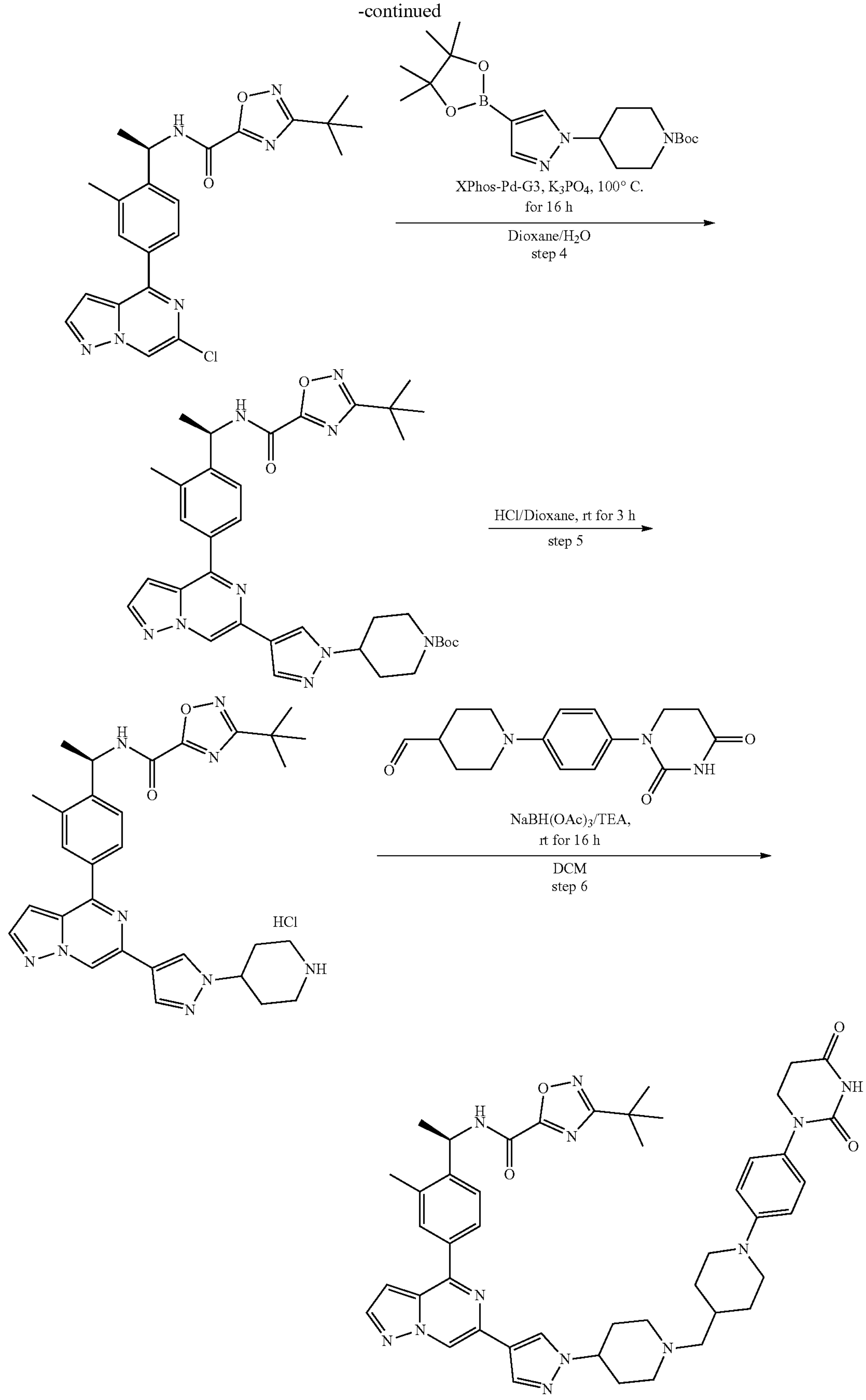

Step 1: (R)—N-(1-(4-bromo-2-methylphenyl)ethyl)-3-(tert-butyl)-1,2,4-oxadiazole-5-carboxamide

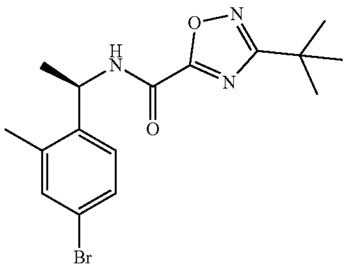 [SMILES: Cc1cc(Br)ccc1[C@@H](C)NC(=O)c1nc(C(C)(C)C)no1]

A solution of (R)-1-(4-bromo-2-methylphenyl) ethan-1-amine hydrochloride (1.0 g, 3.99 mmol, 1.0 eq), ethyl 3-(tert-butyl)-1,2,4-oxadiazole-5-carboxylate (950 mg, 4.79 mmol, 1.2 eq) and TEA (1.62 g, 15.96 mmol, 4.0 eq) in EtOH (20 ml) was stirred at 80° C. for 16 h. Concentrated in vacuo and the residue was purified by flash chromatography eluted with Hex/EA=6:1 to give the title compound (1.1 g, 75%) as a white solid. LC-MS: 366.3 ($M+H^+$).

Step 2 (R)-3-(tert-butyl)-N-(1-(2-methyl-4-(4,4,5,5-tetramethyl-1,3,2-dioxaborolan-2-yl)phenyl)ethyl)-1,2,4-oxadiazole-5-carboxamide

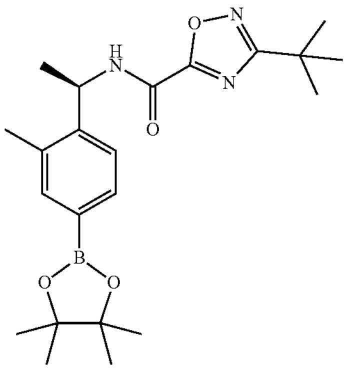 [SMILES: Cc1cc(B2OC(C)(C)C(C)(C)O2)ccc1[C@@H](C)NC(=O)c1nc(C(C)(C)C)no1]

A mixture of 4,4,4',4',5,5,5',5'-octamethyl-2,2'-bi (1,3,2-dioxaborolane) (1.07 g, 4.2 mmol, 1.4 eq), potassium acetate (882 mg, 9.0 mmol, 3.0 eq), Pd(dppf)$Cl_2$ (220 mg, 0.3 mmol, 0.1 eq) and above obtained intermediate (1.1 g, 3.0 mmol, 1.0 eq) in dry dioxane (15 ml) was stirred at 100° C. under Ar for 2 h. Water was added and the solution was extracted with ethyl acetate for 3 times. The combined organic layers were washed with brine, dried over anhydrous $Na_2SO_4$ and concentrated in vacuo. The residue was purified by flash chromatography eluted with Hex/EA=5:1 to give the title compound (900 mg, 72.5%) as a white solid. LC-MS: 414.3 ($M+H^+$).

Step 3: (R)-3-(tert-butyl)-N-(1-(4-(6-chloropyrazolo[1,5-a]pyrazin-4-yl)-2-methylphenyl)ethyl)-1,2,4-oxadiazole-5-carboxamide

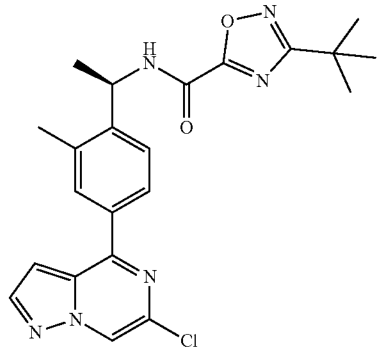 [SMILES: Cc1cc(-c2nc(Cl)cn3nccc23)ccc1[C@@H](C)NC(=O)c1nc(C(C)(C)C)no1]

A mixture of above obtained intermediate (660 mg, 1.60 mmol, 1.2 eq), 4,6-dichloropyrazolo[1,5-a]pyrazine (250 mg, 1.33 mmol, 1.0 eq), $K_3PO_4$ (847 mg, 3.99 mmol, 3.0 eq) and Pd(t-$Bu_3$P)$_2$ (680 mg, 0.13 mmol, 0.1 eq) in THF (10 ml) and water (2 ml) was stirred at rt under Ar for 16 h. The solution was diluted with water, extracted with ethyl acetate for 3 times. The combined organic layers were washed with brine, dried over anhydrous $Na_2SO_4$ and concentrated in vacuo. The residue was purified by flash chromatography eluted with Hex/EA=2:1 to give the title compound (360 mg, 61.7%) as yellow oil. LC-MS: 439.5 ($M+H^+$).

Step 4: tert-butyl (R)-4-(4-(4-(4-(1-(3-(tert-butyl)-1,2,4-oxadiazole-5-carboxamido)ethyl)-3-methylphenyl)pyrazolo[1,5-a]pyrazin-6-yl)-1H-pyrazol-1-yl)piperidine-1-carboxylate

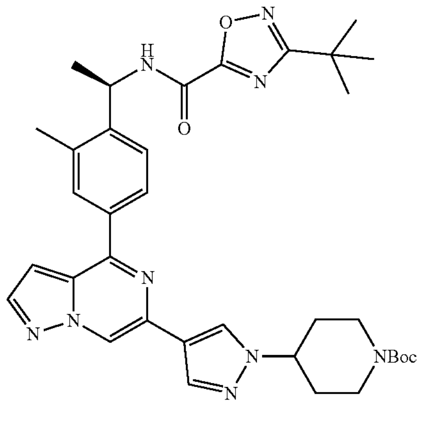 [SMILES: Cc1cc(-c2nc(-c3cnn(C4CCN(C(=O)OC(C)(C)C)CC4)c3)cn3nccc23)ccc1[C@@H](C)NC(=O)c1nc(C(C)(C)C)no1]

A mixture of tert-butyl 4-(4-(4,4,5,5-tetramethyl-1,3,2-dioxaborolan-2-yl)-1H-pyrazol-1-yl)piperidine-1-carboxylate (232 mg, 0.615 mmol, 1.5 eq), above obtained intermediate (180 mg, 0.41 mmol, 1.0 eq), $K_3PO_4$ (261 mg, 1.23 mmol, 3.0 eq) and XPhos-Pd-G3 (35 mg, 0.04 mmol, 0.1 eq) in dioxane (4 ml) and water (1 ml) was stirred at 100° C. under Ar for 16 h. The solution was diluted with water, extracted with ethyl acetate for 3 times. The combined organic layers were washed with brine, dried over anhydrous $Na_2SO_4$ and concentrated in vacuo. The residue was purified by flash chromatography eluted with Hex/EA=1:1 to give the title compound (90 mg, 33.6%) as yellow oil. LC-MS: 654.7 (M+H$^+$).

Step 5: (R)-3-(tert-butyl)-N-(1-(2-methyl-4-(6-(1-(piperidin-4-yl)-1H-pyrazol-4-yl)pyrazolo[1,5-a]pyrazin-4-yl)phenyl)ethyl)-1,2,4-oxadiazole-5-carboxamide hydrochloride

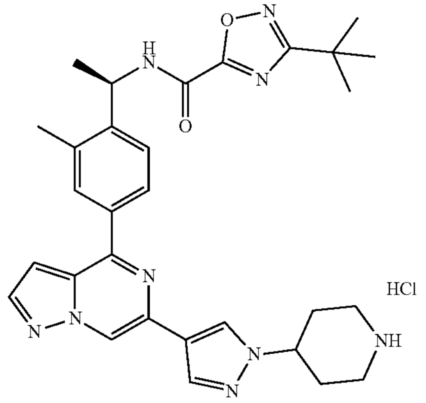 [SMILES: Cc1cc(-c2nc(-c3cnn(C4CCNCC4)c3)cn3nccc23)ccc1[C@@H](C)NC(=O)c1nc(C(C)(C)C)no1 ; Cl]

A mixture of above obtained intermediate (90 mg, 0.138 mmol, 1.0 eq) in DCM (2 ml) and HCl/Dioxane (1 ml, 4 M in dioxane) was stirred at rt for 2 h. After concentration in vacuo, the residue was used in next step without further purification (80 mg, 98%) as a yellow solid. LC-MS: 554.5 (M+H$^+$).

Step 6 (R)-3-(tert-butyl)-N-(1-(4-(6-(1-(1-((1-(4-(2,4-dioxotetrahydropyrimidin-1(2H)-yl)phenyl)piperidin-4-yl)methyl)piperidin-4-yl)-1H-pyrazol-4-yl)pyrazolo[1,5-a]pyrazin-4-yl)-2-methylphenyl)ethyl)-1,2,4-oxadiazole-5-carboxamide

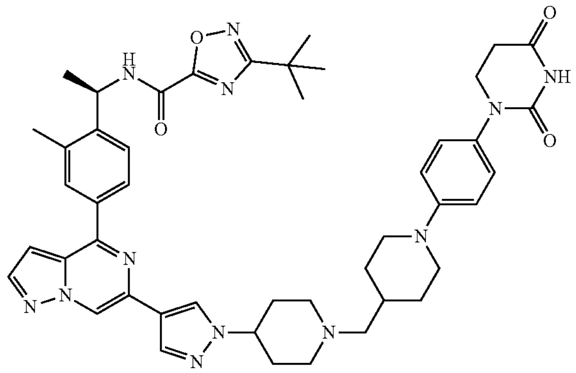 [SMILES: Cc1cc(-c2nc(-c3cnn(C4CCN(CC5CCN(c6ccc(N7CCC(=O)NC7=O)cc6)CC5)CC4)c3)cn3nccc23)ccc1[C@@H](C)NC(=O)c1nc(C(C)(C)C)no1]

To a solution of above obtained intermediate (80 mg, 0.136 mmol, 1.0 eq), 1-(4-(2,4-dioxotetrahydropyrimidin-1(2H)-yl)phenyl)piperidine-4-carbaldehyde (53 mg, 0.176 mmol, 1.3 eq) and TEA (69 mg, 0.68 mmol, 5.0 eq) in dry DCM (3 ml) was added $NaBH(OAc)_3$ (58 mg, 0.272 mmol, 2.0 eq) in portions. The reaction was stirred at rt for 4 h. The solution was quenched with water and extracted with DCM for 3 times. The combined organic layers were washed with brine, dried over anhydrous $Na_2SO_4$ and concentrated in vacuo. The residue was purified by pre-HPLC to give the title compound (22 mg, 19%) as a white solid. LC-MS: 839.4 (M+H$^+$). $^1$H NMR (400 MHz, DMSO-d$^6$) δ (ppm) 10.23 (s, 1H), 9.94 (d, J=8.0 Hz, 1H), 9.10 (s, 1H), 8.43 (s, 1H), 8.17 (d, J=2.8 Hz, 1H), 8.13 (s, 1H), 7.99-7.90 (m, 2H), 7.68 (d, J=8.0 Hz, 1H), 7.17-7.10 (m, 3H), 6.94-6.91 (m, 2H), 5.40-5.35 (m, 1H), 4.25-4.15 (m, 1H), 3.72-3.60 (m, 4H), 3.00-2.90 (m, 2H), 2.70-2.63 (m, 4H), 2.53 (s, 3H), 2.25-2.20 (m, 2H), 2.11-1.98 (m, 6H), 1.85-1.75 (m, 2H), 1.72-1.63 (m, 1H), 1.55 (d, J=6.8 Hz, 3H), 1.37 (s, 9H), 1.25-1.20 (m, 2H).

Following the synthesis of EXAMPLE 2, the following compounds were synthesized and obtained in a similar manner.

| Compd No. | Structure Observed MS $[M + 1]^+$ |
|---|---|
| 8 | 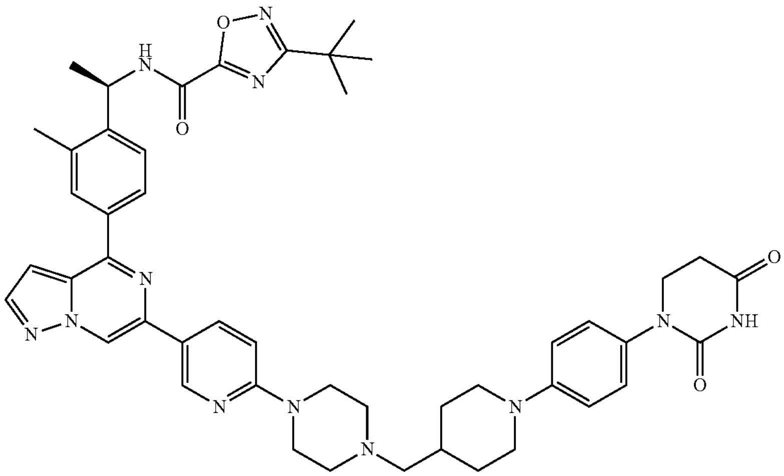 [SMILES: Cc1cc(-c2nc(-c3ccc(N4CCN(CC5CCN(c6ccc(N7CCC(=O)NC7=O)cc6)CC5)CC4)nc3)cn3nccc23)ccc1[C@@H](C)NC(=O)c1nc(C(C)(C)C)no1] 851.5 |
| 30 | 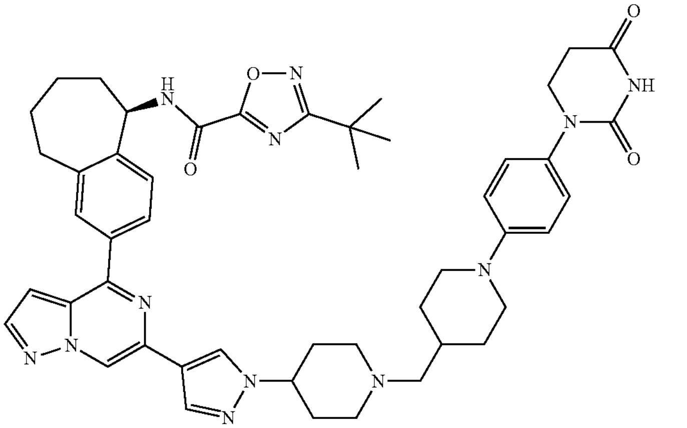 [SMILES: CC(C)(C)c1noc(C(=O)N[C@@H]2CCCCc3cc(-c4nc(-c5cnn(C6CCN(CC7CCN(c8ccc(N9CCC(=O)NC9=O)cc8)CC7)CC6)c5)cn5nccc45)ccc32)n1] 865.5 |
| 31 | 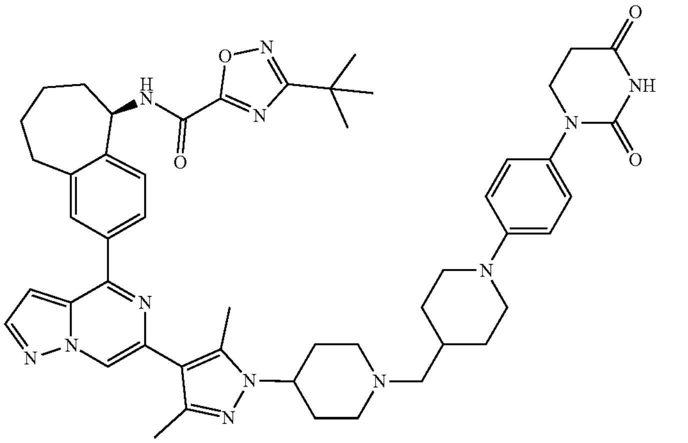 [SMILES: Cc1nn(C2CCN(CC3CCN(c4ccc(N5CCC(=O)NC5=O)cc4)CC3)CC2)c(C)c1-c1cn2nccc2c(-c2ccc3c(c2)CCCC[C@H]3NC(=O)c2nc(C(C)(C)C)no2)n1] 893.6 |

-continued
32
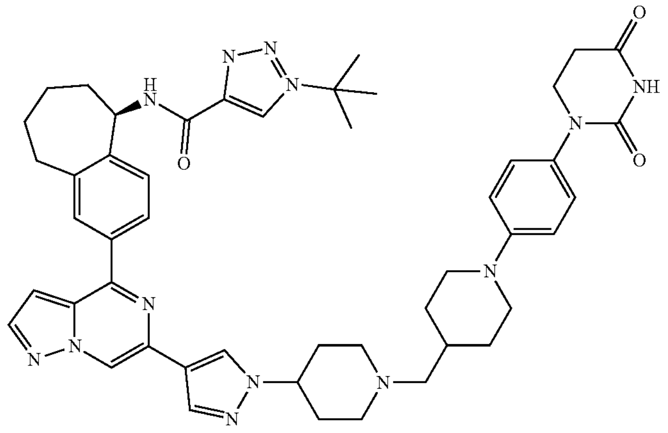
864.6
45
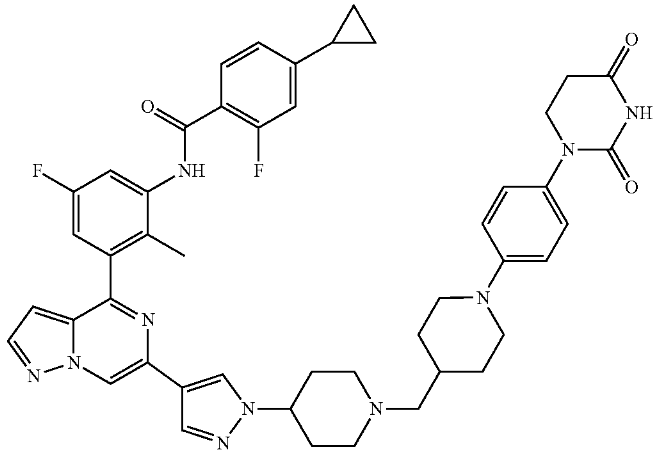 [SMILES: Cc1c(NC(=O)c2ccc(C3CC3)cc2F)cc(F)cc1-c1nc(-c2cnn(C3CCN(CC4CCN(c5ccc(N6CCC(=O)NC6=O)cc5)CC4)CC3)c2)cn2nccc12]
839.3
47
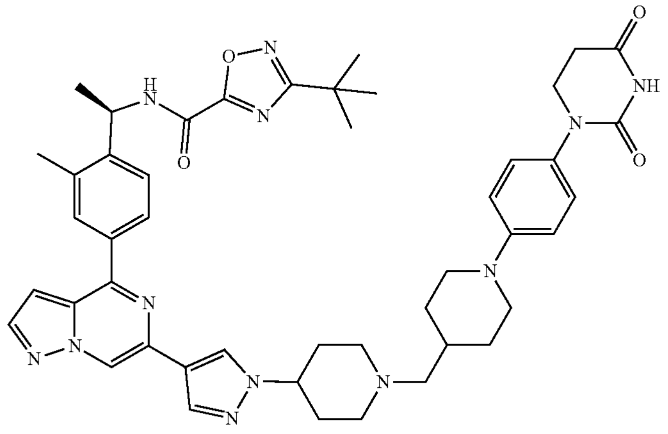 [SMILES: Cc1cc(-c2nc(-c3cnn(C4CCN(CC5CCN(c6ccc(N7CCC(=O)NC7=O)cc6)CC5)CC4)c3)cn3nccc23)ccc1[C@@H](C)NC(=O)c1nc(C(C)(C)C)no1]
839.3

-continued
48
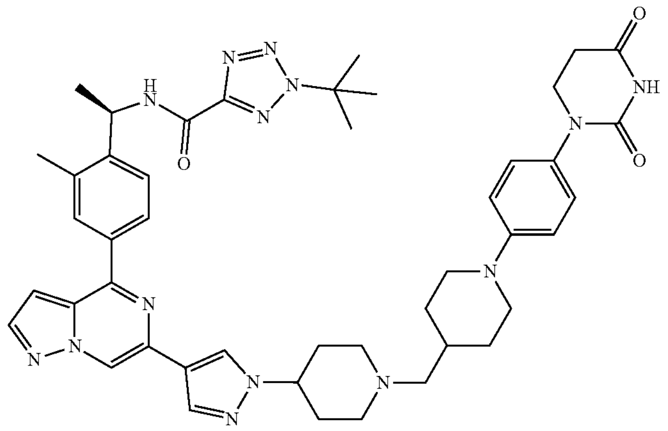 [SMILES: Cc1cc(-c2nc(-c3cnn(C4CCN(CC5CCN(c6ccc(N7CCC(=O)NC7=O)cc6)CC5)CC4)c3)cn3nccc23)ccc1[C@@H](C)NC(=O)c1nnn(C(C)(C)C)n1]
840.3
70
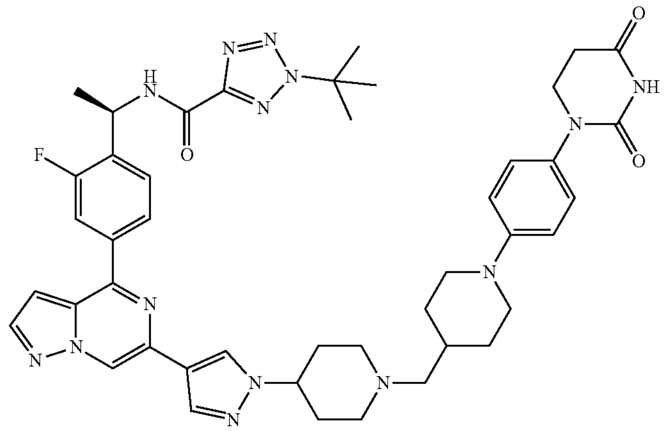 [SMILES: C[C@@H](NC(=O)c1nnn(C(C)(C)C)n1)c1ccc(-c2nc(-c3cnn(C4CCN(CC5CCN(c6ccc(N7CCC(=O)NC7=O)cc6)CC5)CC4)c3)cn3nccc23)cc1F]
843.5
74/75
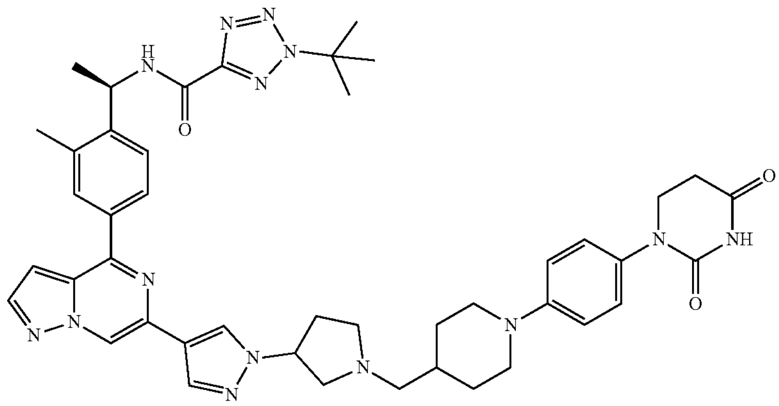 [SMILES: Cc1cc(-c2nc(-c3cnn(C4CCN(CC5CCN(c6ccc(N7CCC(=O)NC7=O)cc6)CC5)C4)c3)cn3nccc23)ccc1[C@@H](C)NC(=O)c1nnn(C(C)(C)C)n1]
825.5

-continued
76
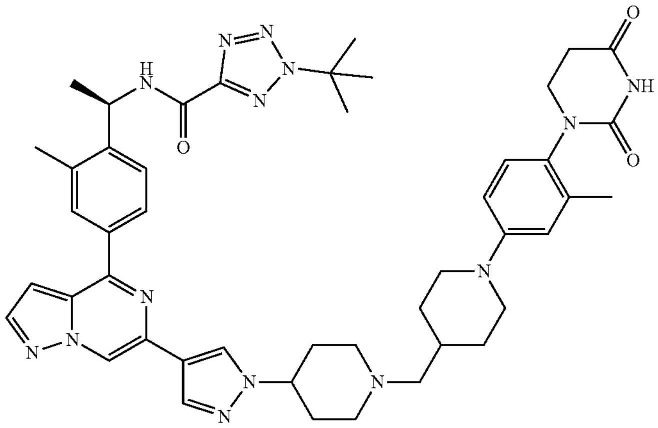 [SMILES: Cc1cc(-c2nc(-c3cnn(C4CCN(CC5CCN(c6ccc(N7CCC(=O)NC7=O)c(C)c6)CC5)CC4)c3)cn3nccc23)ccc1[C@@H](C)NC(=O)c1nnn(C(C)(C)C)n1]
853.4
77
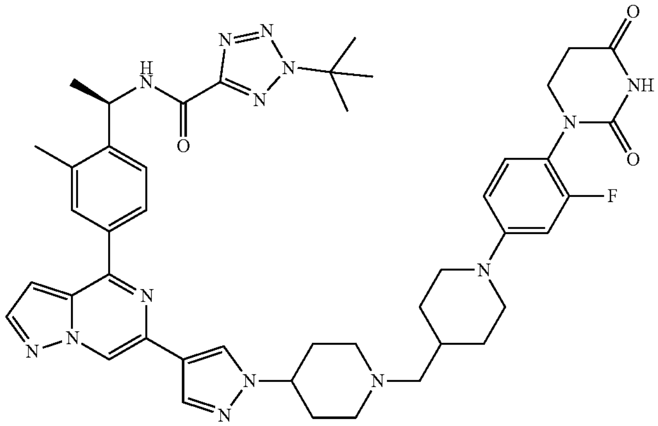 [SMILES: Cc1cc(-c2nc(-c3cnn(C4CCN(CC5CCN(c6ccc(N7CCC(=O)NC7=O)c(F)c6)CC5)CC4)c3)cn3nccc23)ccc1[C@@H](C)NC(=O)c1nnn(C(C)(C)C)n1]
857.7
84
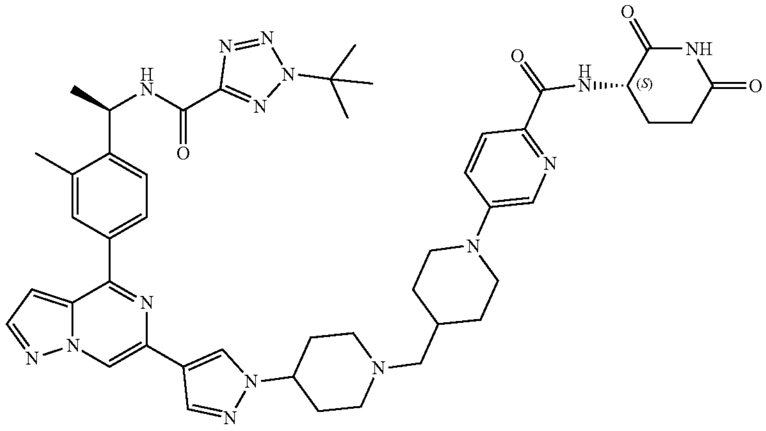
882.5

-continued
111
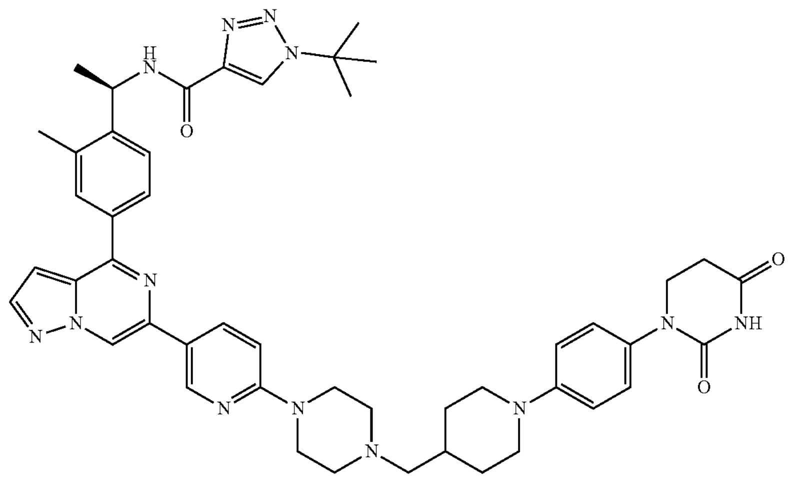
850.6
112
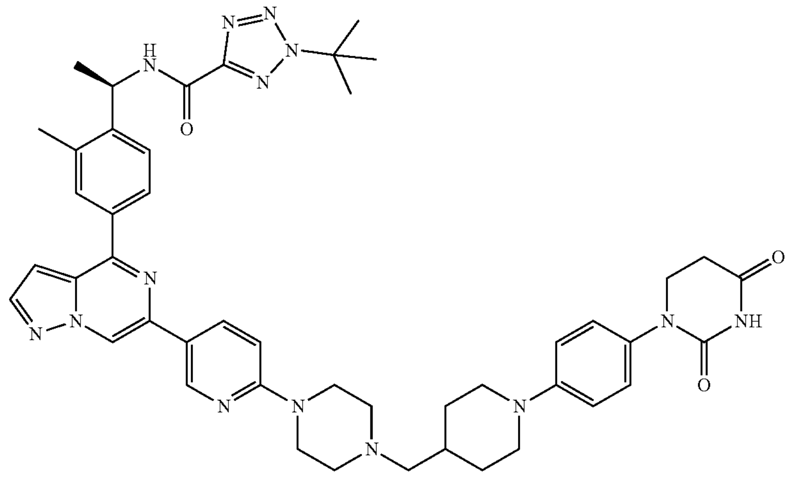
851.1
113
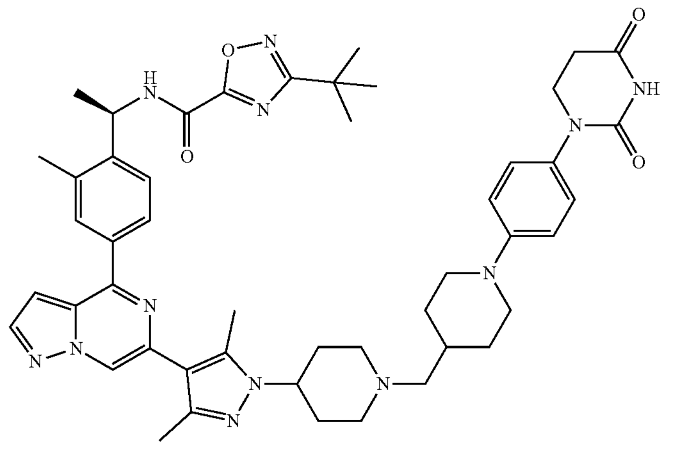 [SMILES: Cc1cc(-c2nc(-c3c(C)nn(C4CCN(CC5CCN(c6ccc(N7CCC(=O)NC7=O)cc6)CC5)CC4)c3C)cn3nccc23)ccc1[C@@H](C)NC(=O)c1nc(C(C)(C)C)no1]
867.4

-continued
114
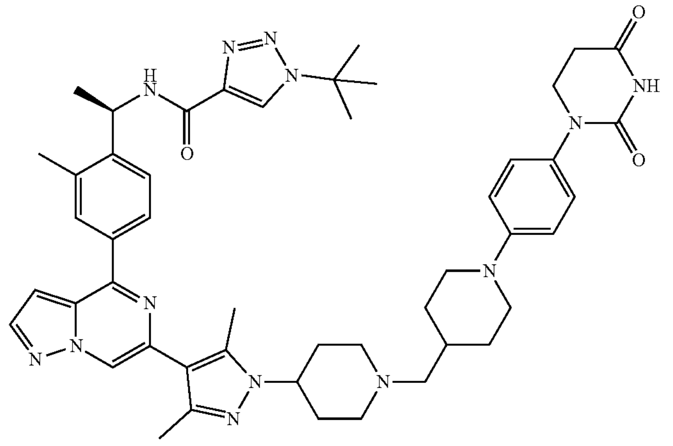 [SMILES: Cc1cc(-c2nc(-c3c(C)nn(C4CCN(CC5CCN(c6ccc(N7CCC(=O)NC7=O)cc6)CC5)CC4)c3C)cn3nccc23)ccc1[C@@H](C)NC(=O)c1cn(C(C)(C)C)nn1]
866.3
115
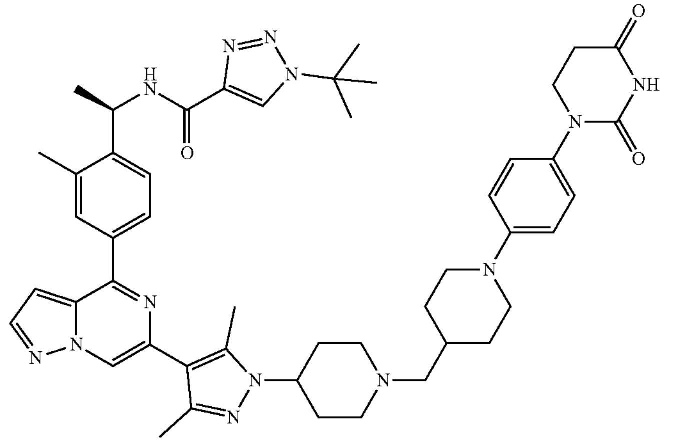 [SMILES: Cc1cc(-c2nc(-c3c(C)nn(C4CCN(CC5CCN(c6ccc(N7CCC(=O)NC7=O)cc6)CC5)CC4)c3C)cn3nccc23)ccc1[C@@H](C)NC(=O)c1cn(C(C)(C)C)nn1]
867.1
117
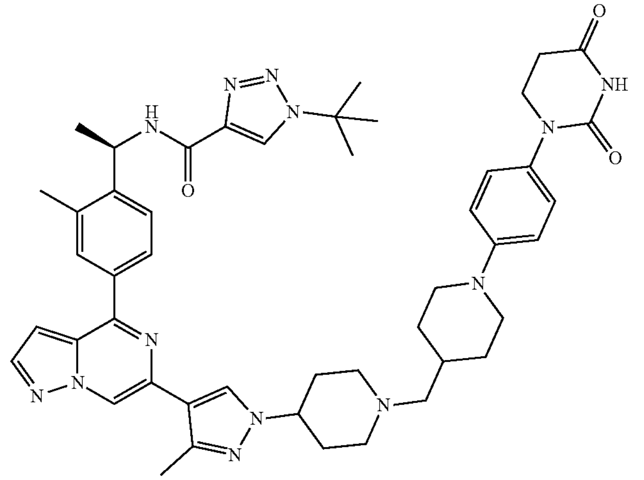 [SMILES: Cc1cc(-c2nc(-c3cn(C4CCN(CC5CCN(c6ccc(N7CCC(=O)NC7=O)cc6)CC5)CC4)nc3C)cn3nccc23)ccc1[C@@H](C)NC(=O)c1cn(C(C)(C)C)nn1]
852.6

-continued
118
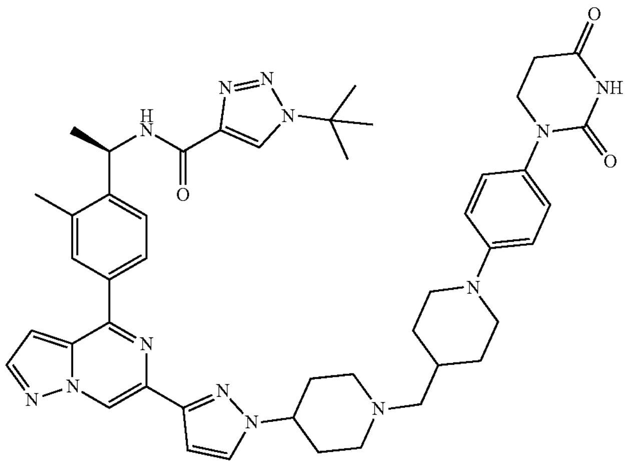 [SMILES: Cc1cc(-c2nc(-c3ccn(C4CCN(CC5CCN(c6ccc(N7CCC(=O)NC7=O)cc6)CC5)CC4)n3)cn3nccc23)ccc1[C@@H](C)NC(=O)c1cn(C(C)(C)C)nn1]
838.1
123
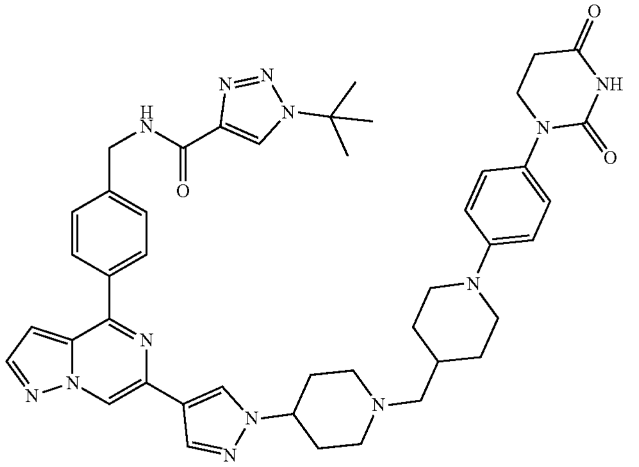 [SMILES: CC(C)(C)n1cc(C(=O)NCc2ccc(-c3nc(-c4cnn(C5CCN(CC6CCN(c7ccc(N8CCC(=O)NC8=O)cc7)CC6)CC5)c4)cn4nccc34)cc2)nn1]
810.4
124
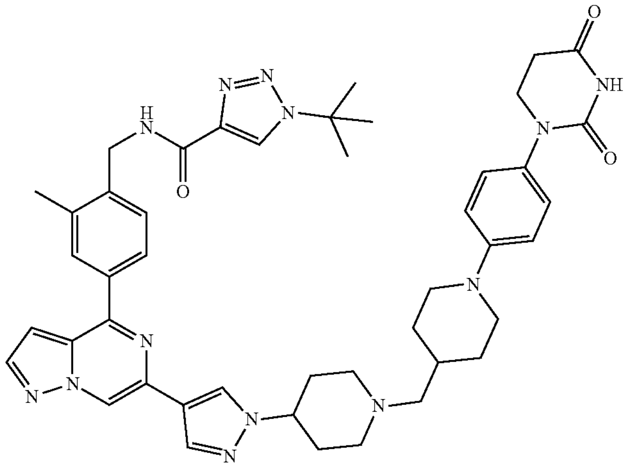 [SMILES: Cc1cc(-c2nc(-c3cnn(C4CCN(CC5CCN(c6ccc(N7CCC(=O)NC7=O)cc6)CC5)CC4)c3)cn3nccc23)ccc1CNC(=O)c1cn(C(C)(C)C)nn1]
824.3

-continued
125
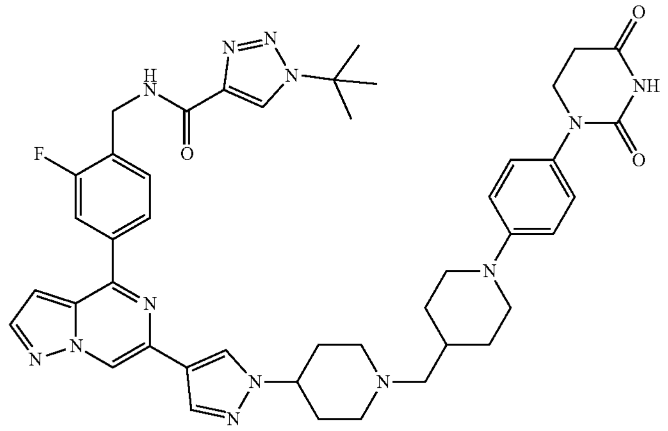 [SMILES: CC(C)(C)n1cc(C(=O)NCc2ccc(-c3nc(-c4cnn(C5CCN(CC6CCN(c7ccc(N8CCC(=O)NC8=O)cc7)CC6)CC5)c4)cn4nccc34)cc2F)nn1]
828.3
130
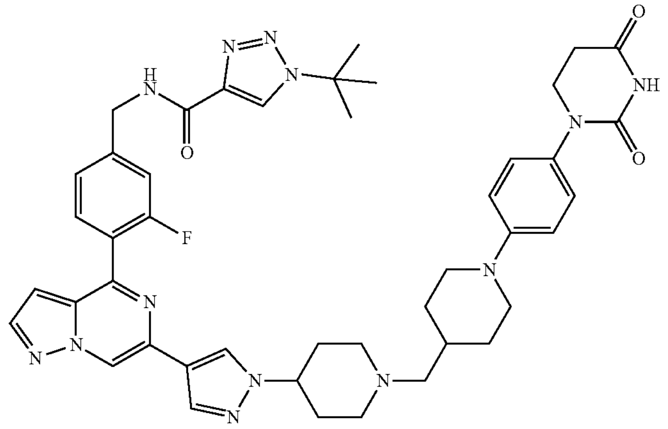 [SMILES: CC(C)(C)n1cc(C(=O)NCc2ccc(-c3nc(-c4cnn(C5CCN(CC6CCN(c7ccc(N8CCC(=O)NC8=O)cc7)CC6)CC5)c4)cn4nccc34)c(F)c2)nn1]
828.9
131
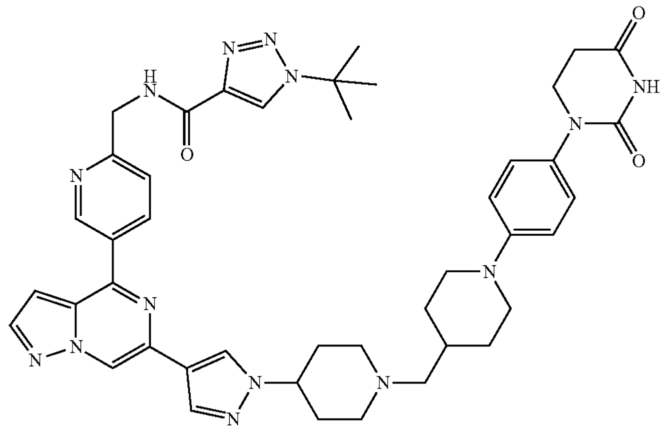 [SMILES: CC(C)(C)n1cc(C(=O)NCc2ccc(-c3nc(-c4cnn(C5CCN(CC6CCN(c7ccc(N8CCC(=O)NC8=O)cc7)CC6)CC5)c4)cn4nccc34)cn2)nn1]
811.6

-continued
180
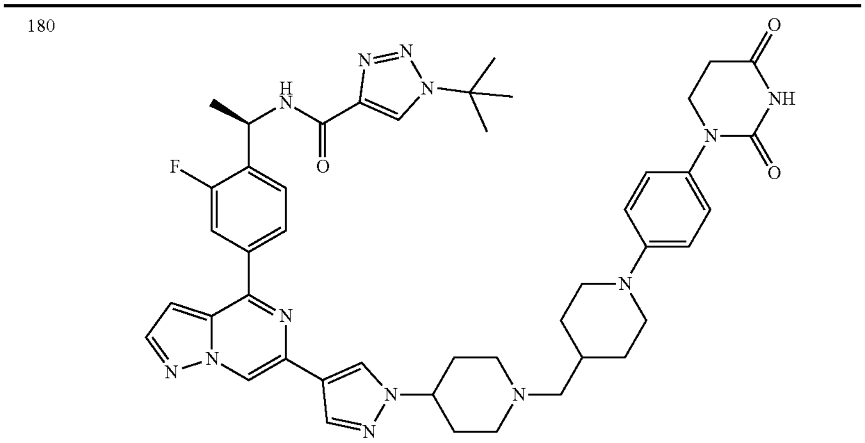
842.6
183
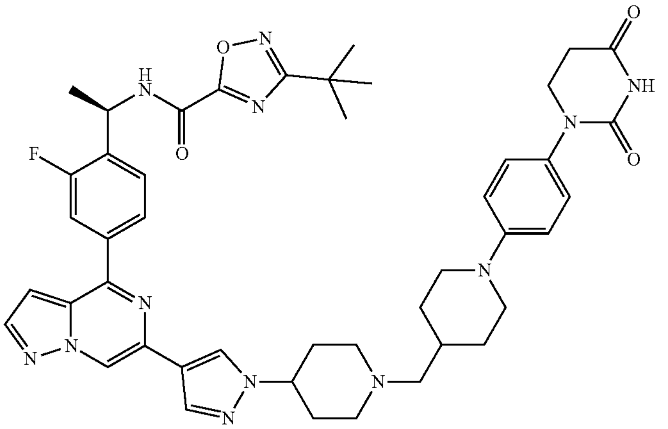 [SMILES: C[C@@H](NC(=O)c1nc(C(C)(C)C)no1)c1ccc(-c2nc(-c3cnn(C4CCN(CC5CCN(c6ccc(N7CCC(=O)NC7=O)cc6)CC5)CC4)c3)cn3nccc23)cc1F]
843.5
193
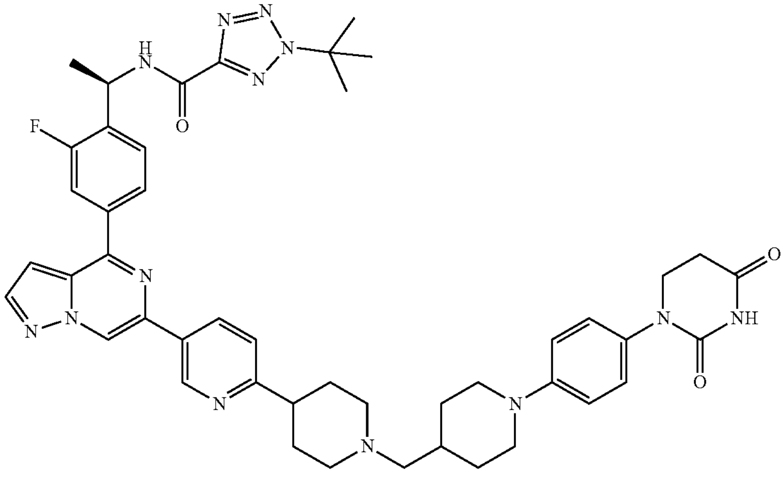
855.5

-continued
207
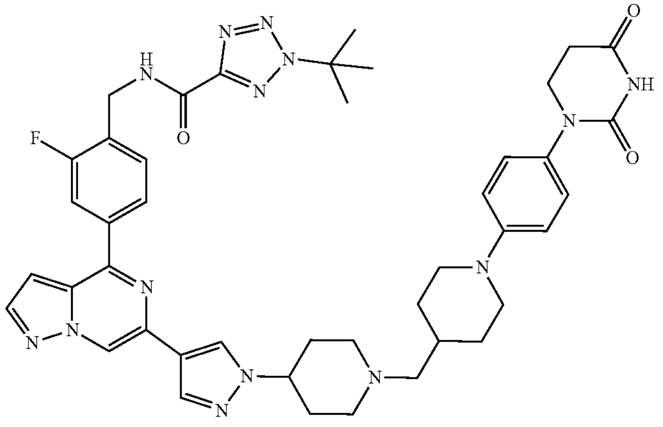 [SMILES: CC(C)(C)n1nnc(C(=O)NCc2ccc(-c3nc(-c4cnn(C5CCN(CC6CCN(c7ccc(N8CCC(=O)NC8=O)cc7)CC6)CC5)c4)cn4nccc34)cc2F)n1]
829.3
208
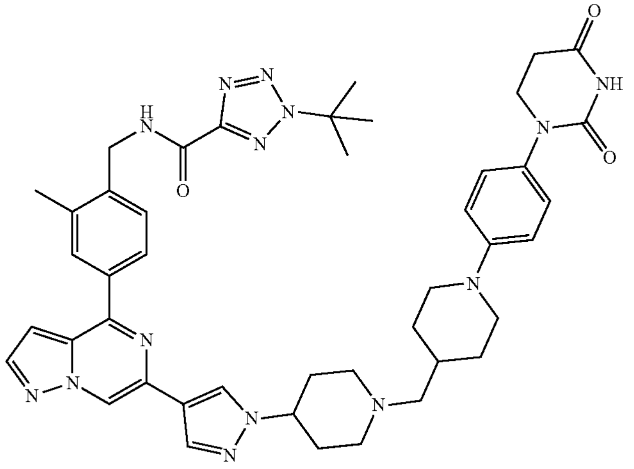
825.3
209
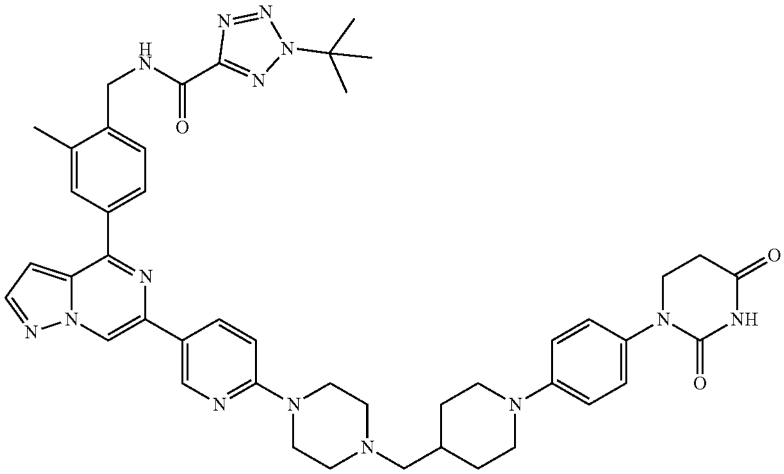 [SMILES: Cc1cc(-c2nc(-c3ccc(N4CCN(CC5CCN(c6ccc(N7CCC(=O)NC7=O)cc6)CC5)CC4)nc3)cn3nccc23)ccc1CNC(=O)c1nnn(C(C)(C)C)n1]
837.7

-continued
214
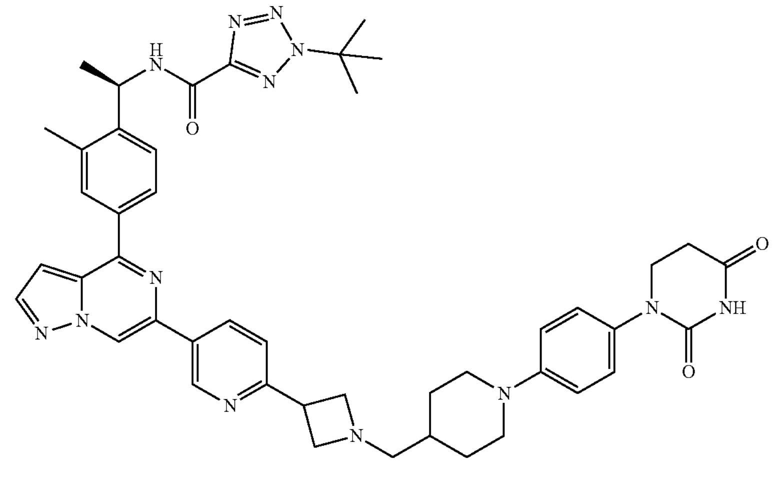 [SMILES: Cc1cc(-c2nc(-c3ccc(C4CN(CC5CCN(c6ccc(N7CCC(=O)NC7=O)cc6)CC5)C4)nc3)cn3nccc23)ccc1[C@@H](C)NC(=O)c1nnn(C(C)(C)C)n1]
821.99
215
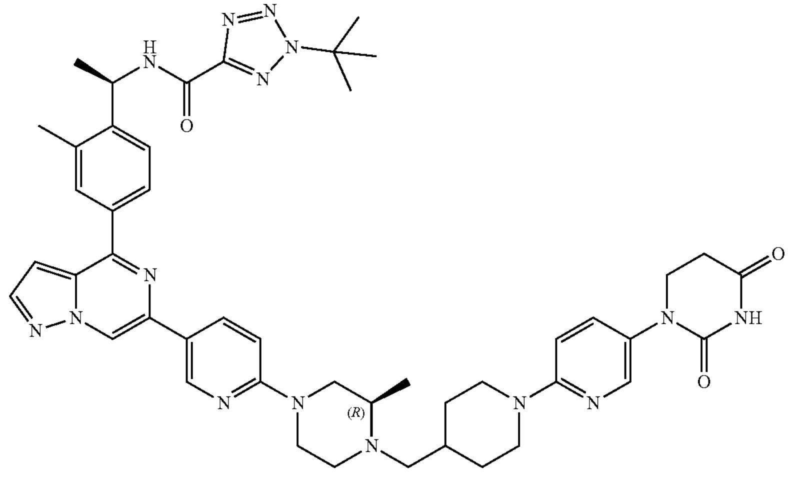
865.75
216
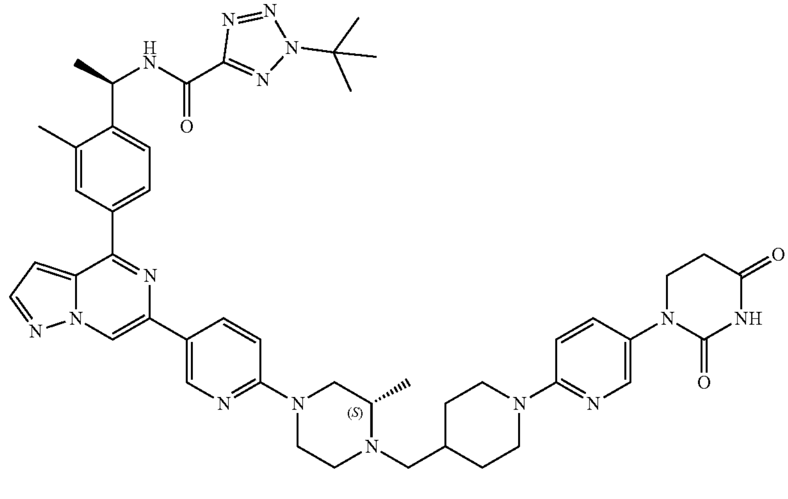
865.79

-continued
220
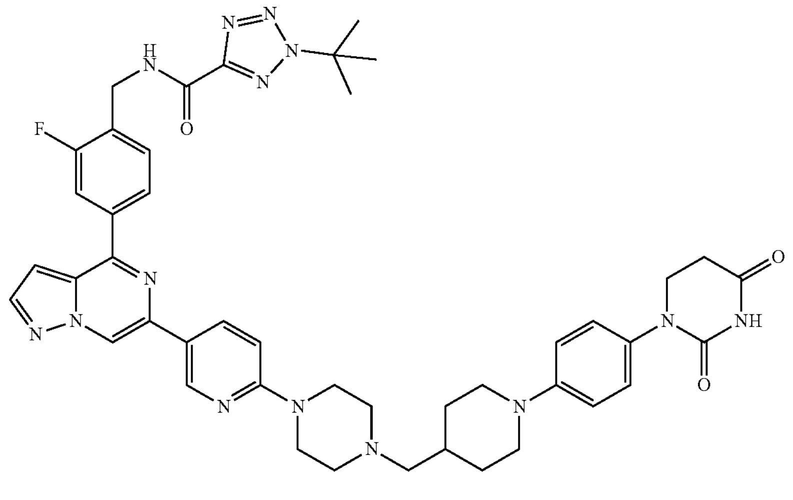 [SMILES: CC(C)(C)n1nnc(C(=O)NCc2ccc(-c3nc(-c4ccc(N5CCN(CC6CCN(c7ccc(N8CCC(=O)NC8=O)cc7)CC6)CC5)nc4)cn4nccc34)cc2F)n1]
841.8
225
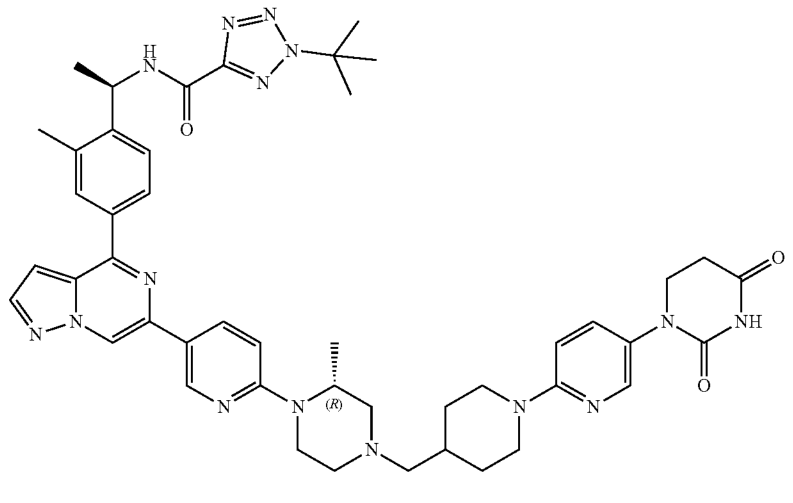
865.79
226
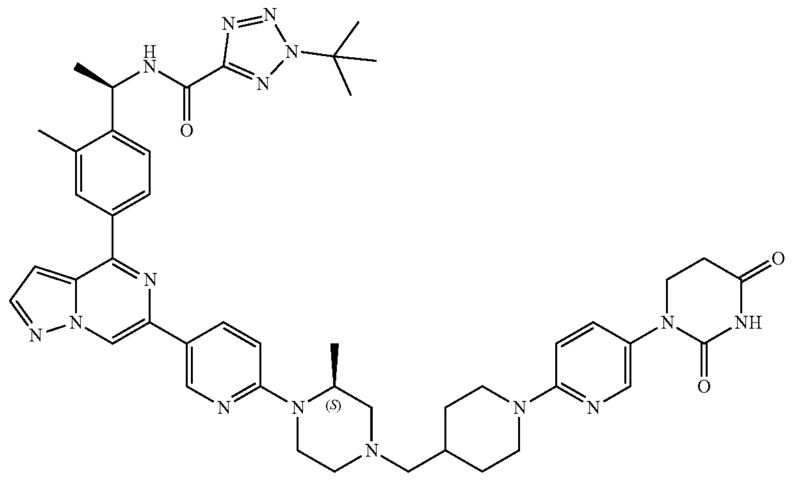
865.75

-continued
229
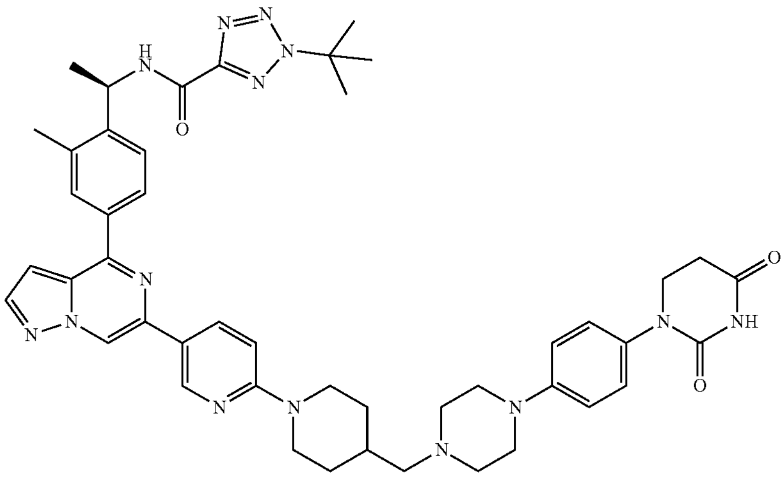 [SMILES: Cc1cc(-c2nc(-c3ccc(N4CCC(CN5CCN(c6ccc(N7CCC(=O)NC7=O)cc6)CC5)CC4)nc3)cn3nccc23)ccc1[C@@H](C)NC(=O)c1nnn(C(C)(C)C)n1]
851.6
235
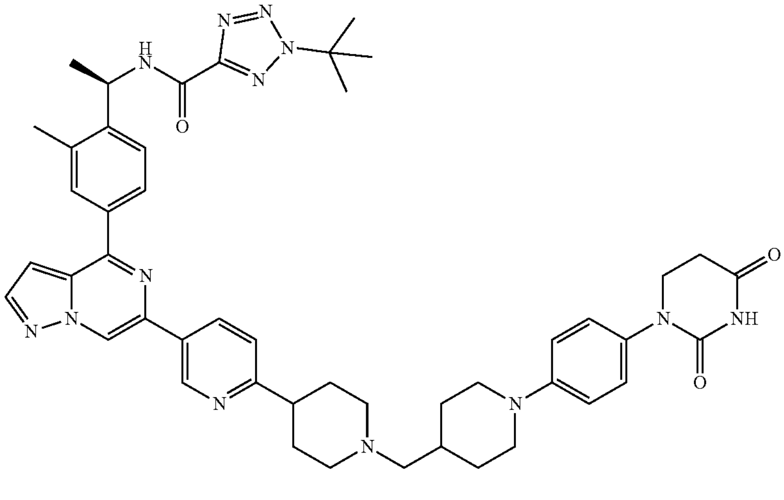 [SMILES: Cc1cc(-c2nc(-c3ccc(C4CCN(CC5CCN(c6ccc(N7CCC(=O)NC7=O)cc6)CC5)CC4)nc3)cn3nccc23)ccc1[C@@H](C)NC(=O)c1nnn(C(C)(C)C)n1]
850.46
236
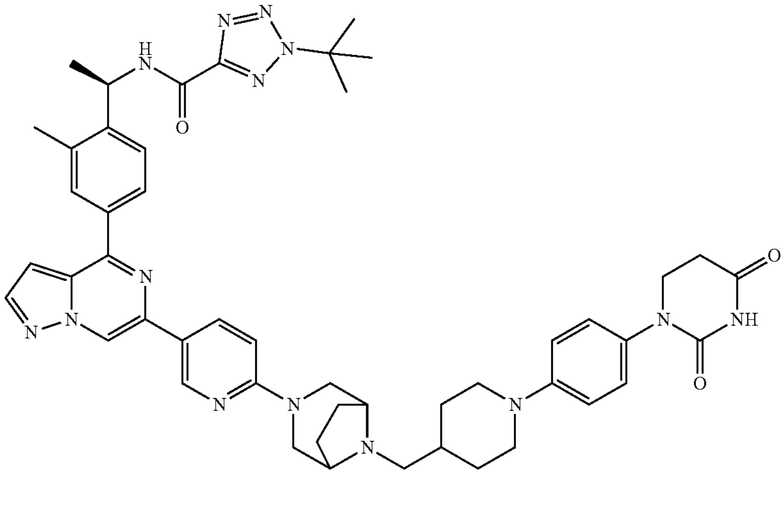 [SMILES: Cc1cc(-c2nc(-c3ccc(N4CC5CCC(C4)N5CC4CCN(c5ccc(N6CCC(=O)NC6=O)cc5)CC4)nc3)cn3nccc23)ccc1[C@@H](C)NC(=O)c1nnn(C(C)(C)C)n1]
877.49

-continued
237
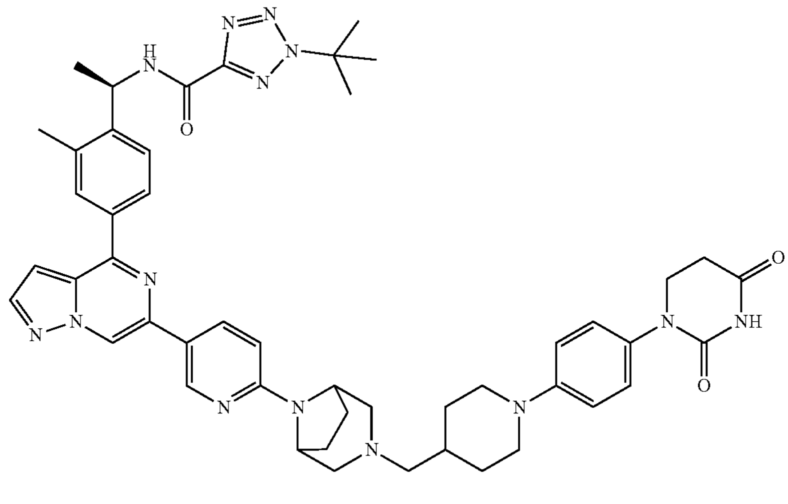 [SMILES: Cc1cc(-c2nc(-c3ccc(N4C5CCC4CN(CC4CCN(c6ccc(N7CCC(=O)NC7=O)cc6)CC4)C5)nc3)cn3nccc23)ccc1[C@@H](C)NC(=O)c1nnn(C(C)(C)C)n1]
877.54
248
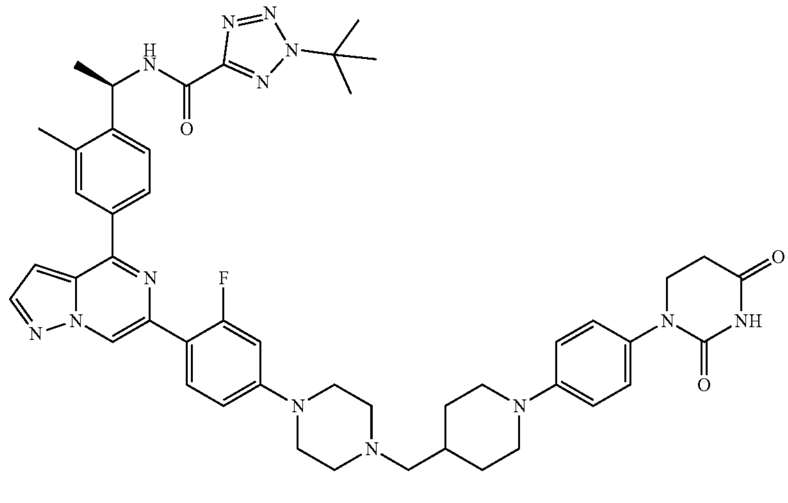 [SMILES: Cc1cc(-c2nc(-c3ccc(N4CCN(CC5CCN(c6ccc(N7CCC(=O)NC7=O)cc6)CC5)CC4)cc3F)cn3nccc23)ccc1[C@@H](C)NC(=O)c1nnn(C(C)(C)C)n1]
868.6
249
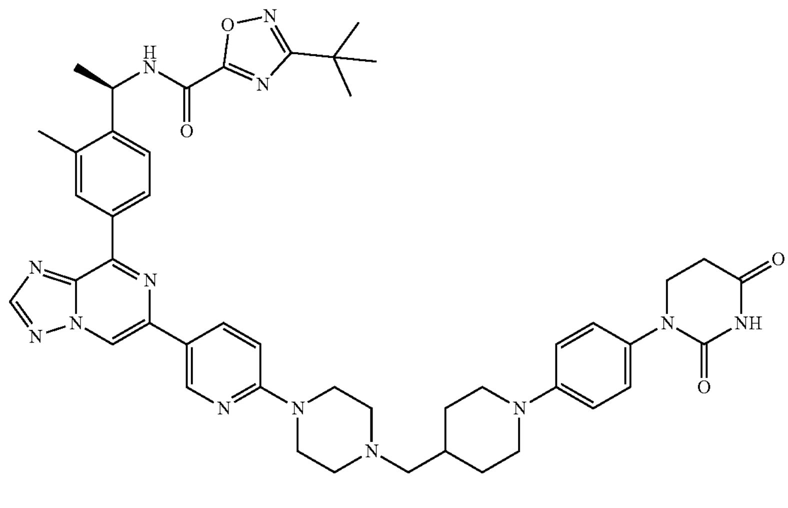 [SMILES: Cc1cc(-c2nc(-c3ccc(N4CCN(CC5CCN(c6ccc(N7CCC(=O)NC7=O)cc6)CC5)CC4)nc3)cn3ncnc23)ccc1[C@@H](C)NC(=O)c1nc(C(C)(C)C)no1]
852.64

-continued

| Compd No. | $^1$H NMR (400 MHz, DMSO-$d^6$) δ (ppm) |
|---|---|
| 8 | 10.23 (s, 1H), 9.94 (d, J = 7.6 Hz, 1H), 9.28 (s, 1H), 8.95 (d, J = 2.4 Hz, 1H), 8.35 - 8.20 (m, 1H), 8.21 (d, J = 2.4 Hz, 1H), 8.00 (d, J = 8.4 Hz, 1H), 7.96 (s, 1H), 7.69 (d, J = 8.0 Hz, 1H), 7.20 (d, J = 2.4 Hz, 1H), 7.13 (d, J = 8.4 Hz, 2H), 6.98 - 6.91 (m, 3H), 5.42 - 5.35 (m, 1H), 3.73 - 3.67 (m, 4H), 3.65 - 3.55 (m, 4H), 2.75 - 2.62 (m, 4H), 2.53 (s, 3H), 2.49 - 2.45 (m, 4H), 2.22 (d, J = 7.2 Hz, 2H), 1.88 - 1.66 (m, 3H), 1.55 (d, J = 6.8 Hz, 3H), 1.37 (s, 9H), 1.28 - 1.20 (m, 2H). |
| 30 | |
| 31 | 10.25 (s, 1H), 10.03 (d, J = 8.0 Hz, 1H), 8.68 (s, 1H), 8.21 (d, J = 2.4 Hz, 1H), 7.95 - 7.88 (m, 2H), 7.42 (d, J = 8.0 Hz, 1H), 7.19 (d, J = 2.4 Hz, 1H), 7.13 (d, J = 8.8 Hz, 2H), 6.93 (d, J = 8.8 Hz, 2H), 5.35 - 5.25 (m, 1H), 4.20 - 4.09 (m, 1H), 3.73 - 3.65 (m, 4H), 3.05 - 2.92 (m, 4H), 2.73 - 2.62 (m, 4H), 2.45 (s, 3H), 2.32 (s, 3H), 2.22 (d, J = 6.4 Hz, 2H), 2.15 - 1.75 (m, 14H), 1.40 (s, 9H), 1.38 - 1.20 (m, 3H). |
| 32 | 10.25 (s, 1H), 9.11 (s, 1H), 9.04 (d, J = 8.4 Hz, 1H), 8.75 (s, 1H), 8.44 (s, 1H), 8.17 (d, J = 2.4 Hz, 1H), 8.14 (s, 1H), 7.97 - 7.90 (m, 2H), 7.43 (d, J = 8.8 Hz, 1H), 7.16 (d, J = 2.4 Hz, 1H), 7.13 (d, J = 9.2 Hz, 2H), 6.93 (d, J = 9.2 Hz, 2H), 5.40 - 5.28 (m, 1H), 4.28 - 4.15 (m, 1H), 3.75 - 3.65 (m, 4H), 3.10 - 2.92 (m, 4H), 2.72 - 2.62 (m, 4H), 2.22 (d, J = 6.8 Hz, 2H), 2.13 - 1.77 (m, 13H), 1.75 - 1.68 (m, 1H), 1.66 (s, 9H), 1.42 - 1.32 (m, 1H), 1.28 - 1.20 (m, 2H). |
| 45 | 10.24 (s, 1H), 9.88 (s, 1H), 9.20 (s, 1H), 8.38 (s, 1H), 8.14 (d, J = 2.4 Hz, 1H), 8.09 (s, 1H), 7.72 - 7.62 (m, 2H), 7.32 - 7.28 (m, 2H), 7.15 - 7.05 (m, 4H), 6.92 (d, J = 9.2 Hz, 1H), 6.63 (s, 1H), 4.25 - 4.13 (m, 1H), 3.75 - 3.65 (m, 4H), 3.00 - 2.90 (m, 2H), 2.72 - 2.60 (m, 4H), 2.21 (d, J = 7.2 Hz, 2H), 2.12 (s, 3H), 2.10 - 1.95 (m, 7H), 1.85 - 1.75 (m, 2H), 1.73 - 1.62 (m, 1H), 1.28 - 1.15 (m, 2H), 1.08 - 1.02 (m, 2H), 0.82 - 0.75 (m, 2H). |
| 47 | 10.24 (s, 1H), 9.10 (s, 1H), 8.97 (d, J = 7.6 Hz, 1H), 8.64 (s, 1H), 8.43 (s, 1H), 8.17 (d, J = 2.4 Hz, 1H), 8.13 (s, 1H), 7.94 (d, J = 8.0 Hz, 1H), 7.90 (s, 1H), 7.69 (d, J = 8.0 Hz, 1H), 7.20 - 7.10 (m, 3H), 6.93 (d, J = 8.8 Hz, 2H), 5.45 - 5.38 (m, 1H), 4.25 - 4.15 (m, 1H), 3.75 - 3.65 (m, 4H), 3.03 - 2.92 (m, 2H), 2.72 - 2.62 (m, 4H), 2.54 (s, 3H), 2.22 (d, J = 6.8 Hz, 2H), 2.13 - 1.95 (m, 6H), 1.85 - 1.75 (m, 2H), 1.73 - 1.65 (m, 1H), 1.63 (s, 9H), 1.53 (d, J = 6.8 Hz, 3H), 1.28 - 1.15 (m, 2H). |
| 48 | 10.25 (s, 1H), 9.56 (d, J = 8.0 Hz, 1H), 9.11 (s, 1H), 8.44 (s, 1H), 8.17 (d, J = 2.4 Hz, 1H), 8.13 (s, 1H), 7.96 (d, J = 8.4 Hz, 1H), 7.92 (s, 1H), 7.69 (d, J = 8.0 Hz, 1H), 7.20 - 7.10 (m, 3H), 6.92 (d, J = 9.2 Hz, 2H), 5.50 - 5.38 (m, 1H), 4.25 - 4.15 (m, 1H), 3.75 - 3.65 (m, 4H), 3.00 - 2.90 (m, 2H), 2.72 - 2.62 (m, 4H), 2.55 (s, 3H), 2.22 (d, J = 7.2 Hz, 2H), 2.13 - 1.95 (m, 6H), 1.83 - 1.77 (m, 2H), 1.73 (s, 9H), 1.68 - 1.60 (m, 1H), 1.55 (d, J = 6.8 Hz, 3H), 1.28 - 1.15 (m, 2H). |
| 70 | |
| 74/75 | 10.25 (s, 1H), 9.54 (d, J = 7.6 Hz, 1H), 9.14 (s, 1H), 8.45 (s, 1H), 8.17 (d, J = 2.4 Hz, 1H), 8.13 (s, 1H), 7.98 - 7.90 (m, 2H), 7.69 (d, J = 8.4 Hz, 1H), 7.18 - 7.08 (m, 3H), 6.89 (d, J = 8.8 Hz, 2H), 5.48 - 5.36 (m, 1H), 5.00 - 4.90 (m, 1H), 3.73 - 3.60 (m, 4H), 2.95 - 2.80 (m, 3H), 2.70 - 2.53 (m, 8H), 2.45 - 2.32 (m, 3H), 2.18 - 2.08 (m, 1H), 1.90 - 1.80 (m, 2H), 1.72 (s, 9H), 1.68 - 1.60 (m, 1H), 1.53 (d, J = 6.8 Hz, 3H), 1.30 - 1.15 (m, 2H). |
| 76 | 10.23 (s, 1H), 9.57 (d, J = 8.0 Hz, 1H), 9.11 (s, 1H), 8.44 (s, 1H), 8.17 (d, J = 2.4 Hz, 1H), 8.13 (s, 1H), 8.00 - 7.90 (m, 2H), 7.69 (d, J = 8.0 Hz, 1H), 7.22 - 7.10 (m, 1H), 7.03 (d, J = 8.8 Hz, 1H), 6.83 - 6.75 (m, 2H), 5.48 - 5.38 (m, 1H), 4.25 - 4.15 (m, 1H), 3.73 - 3.60 (m, 3H), 3.50 - 3.42 (m, 1H), 3.00 - 2.90 (m, 2H), 2.75 - 2.60 (m, 4H), 2.55 (s, 3H), 2.25 - 2.15 (m, 2H), 2.12 (s, 3H), 2.10 - 1.95 (m, 6H), 1.85 - 1.75 (m, 2H), 1.73 (s, 9H), 1.69 - 1.61 (m, 1H), 1.55 (d, J = 6.8 Hz, 3H), 1.25 - 1.15 (m, 2H). |
| 77 | 10.37 (s, 1H), 9.57 (d, J = 8.0 Hz, 1H), 9.11 (s, 1H), 8.44 (s, 1H), 8.17 (d, J = 2.4 Hz, 1H), 8.13 (s, 1H), 8.00 - 7.90 (m, 2H), 7.79 (d, J = 8.4 Hz, 1H), 7.22 - 7.15 (m, 2H), 6.85 - 6.72 (m, 2H), 5.48 - 5.38 (m, 1H), 4.25 - 4.15 (m, 1H), 3.80 - 3.70 (m, 2H), 3.65 - 3.58 (m, 2H), 3.00 - 2.90 (m, 2H), 2.78 - 2.65 (m, 4H), 2.55 (s, 3H), 2.25 - 1.95 (m, 8H), 1.85 - 1.74 (m, 3H), 1.72 (s, 9H), 1.54 (d, J = 7.2 Hz, 3H), 1.25 - 1.15 (m, 2H). |
| 84 | |
| 111 | 10.25 (s, 1H), 9.28 (s, 1H), 9.05 - 8.95 (m, 2H), 8.64 (s, 1H), 8.35 - 8.28 (m, 1H), 8.20 (d, J = 2.4 Hz, 1H), 7.98 - 7.92 (m, 2H), 7.71 (d, J = 2.4 Hz, 1H), 7.19 (d, J = 2.0 Hz, 1H), 7.13 (d, |

-continued

| | |
|---|---|
| | J = 8.8 Hz, 2H), 6.98 − 6.90 (m, 3H), 5.45 − 5.36 (m, 1H), 3.75 − 3.55 (m, 8H), 2.73 − 2.62 (m, 4H), 2.54 (s, 3H), 2.48 − 2.45 (m, 4H), 2.22 (d, J = 7.2 Hz, 2H), 1.87 − 1.66 (m, 3H), 1.63 (s, 9H), 1.53 (d, J = 7.2 Hz, 3H), 1.30 − 1.20 (m, 2H). |
| 112 | 10.24 (s, 1H), 9.55 (d, J = 8.8 Hz, 1H), 9.27 (s, 1H), 8.95 (d, J = 2.4 Hz, 1H), 8.35 − 8.28 (m, 1H), 8.20 (d, J = 2.4 Hz, 1H), 8.00 − 7.93 (m, 2H), 7.71 (d, J = 8.0 Hz, 1H), 7.19 (d, J = 2.0 Hz, 1H), 7.13 (d, J = 8.8 Hz, 2H), 6.98 − 6.90 (m, 3H), 5.45 − 5.40 (m, 1H), 3.75 − 3.53 (m, 8H), 2.73 − 2.62 (m, 4H), 2.55 (s, 3H), 2.48 − 2.45 (m, 4H), 2.22 (d, J = 6.8 Hz, 2H), 1.87 − 1.66 (m, 3H), 1.73 (s, 9H), 1.55 (d, J = 7.2 Hz, 3H), 1.28 − 1.18 (m, 2H). |
| 113 | |
| 114 | 10.25 (s, 1H), 8.96 (d, J = 7.6 Hz, 1H), 8.67 (s, 1H), 8.64 (s, 1H), 8.20 (d, J = 2.0 Hz, 1H), 7.95 − 7.86 (m, 2H), 7.69 (d, J = 8.0 Hz, 1H), 7.18 (d, J = 2.4 Hz, 1H), 7.13 (d, J = 8.8 Hz, 2H), 6.93 (d, J = 8.8 Hz, 2H), 5.45 − 5.36 (m, 1H), 4.20 − 4.08 (m, 1H), 3.73 − 3.60 (m, 4H), 2.98 − 2.90 (m, 2H), 2.70 − 2.60 (m, 4H), 2.52 (s, 3H), 2.44 (s, 3H), 2.32 (s, 3H), 2.21 (d, J = 7.2 Hz, 2H), 2.15 − 2.05 (m, 4H), 1.85 − 1.65 (m, 5H), 1.62 (s, 9H), 1.52 (d, J = 6.8 Hz, 3H), 1.28 − 1.15 (m, 2H). |
| 115 | 10.25 (s, 1H), 9.56 (d, J = 8.0 Hz, 1H), 8.67 (s, 1H), 8.20 (d, J = 2.0 Hz, 1H), 7.94 (d, J = 8.4 Hz, 1H), 7.89 (s, 1H), 7.69 (d, J = 8.0 Hz, 1H), 7.19 (d, J = 2.0 Hz, 1H), 7.13 (d, J = 8.8 Hz, 2H), 6.93 (d, J = 8.8 Hz, 2H), 5.48 − 5.38 (m, 1H), 4.20 − 4.08 (m, 1H), 3.75 − 3.65 (m, 4H), 2.90 − 2.80 (m, 2H), 2.72 − 2.62 (m, 4H), 2.52 (s, 3H), 2.44 (s, 3H), 2.32 (s, 3H), 2.22 (d, J = 6.8 Hz, 2H), 2.15 − 2.02 (m, 4H), 1.85 − 1.77 (m, 4H), 1.72 (s, 9H), 1.70 − 1.62 (m, 1H), 1.54 (d, J = 6.8 Hz, 3H), 1.28 − 1.18 (m, 2H). |
| 117 | 10.25 (s, 1H), 8.96 (d, J = 8.0 Hz, 1H), 8.84 (s, 1H), 8.63 (s, 1H), 8.33 (s, 1H), 8.17 (d, J = 2.4 Hz, 1H), 7.98 − 7.87 (m, 2H), 7.69 (d, J = 8.0 Hz, 1H), 7.18 − 7.10 (m, 3H), 6.92 (d, J = 8.0 Hz, 2H), 5.45 − 5.35 (m, 1H), 4.15 − 4.02 (m, 1H), 3.75 − 3.65 (m, 4H), 3.00 − 2.90 (m, 2H), 2.75 − 2.60 (m, 4H), 2.52 (s, 3H), 2.48 (s, 3H), 2.22 (d, J = 6.8 Hz, 2H), 2.15 − 1.90 (m, 6H), 1.85 − 1.65 (m, 3H), 1.62 (s, 9H), 1.52 (d, J = 7.2 Hz, 3H), 1.28 − 1.15 (m, 2H). |
| 118 | 10.25 (s, 1H), 9.00 − 8.95 (m, 2H), 8.64 (s, 1H), 8.22 (d, J = 2.4 Hz, 1H), 7.97 − 7.87 (m, 3H), 7.71 (d, J = 8.0 Hz, 1H), 7.19 (d, J = 2.0 Hz, 1H), 7.13 (d, J = 8.8 Hz, 2H), 6.95 − 6.85 (m, 3H), 5.45 − 5.35 (m, 1H), 4.30 − 4.20 (m, 1H), 3.73 − 3.65 (m, 4H), 3.03 − 2.92 (m, 2H), 2.70 − 2.62 (m, 4H), 2.54 (s, 3H), 2.22 (d, J = 6.8 Hz, 2H), 2.15 − 2.00 (m, 6H), 1.85 − 1.65 (m, 3H), 1.63 (s, 9H), 1.53 (d, J = 7.2 Hz, 3H), 1.28 − 1.18 (m, 2H). |
| 123 | 10.26 (s, 1H), 9.20 − 9.15 (m, 1H), 9.12 (s, 1H), 8.71 (s, 1H), 8.44 (s, 1H), 8.20 − 8.10 (m, 4H), 7.54 (d, J = 8.0 Hz, 2H), 7.19 − 7.10 (m, 3H), 6.91 (d, J = 8.8 Hz, 2H), 4.63 − 4.55 (m, 2H), 4.22 − 4.12 (m, 1H), 3.73 − 3.63 (m, 4H), 3.00 − 2.90 (m, 2H), 2.71 − 2.60 (m, 4H), 2.25 − 1.95 (m, 8H), 1.85 − 1.65 (m, 3H), 1.63 (s, 9H), 1.25 − 1.18 (m, 2H). |
| 124 | 10.25 (s, 1H), 9.11 (s, 1H), 9.08 − 9.02 (m, 1H), 8.72 (s, 1H), 8.44 (s, 1H), 8.17 (d, J = 2.4 Hz, 1H), 8.13 (s, 1H), 7.98 − 7.92 (m, 2H), 7.44 (d, J = 8.8 Hz, 1H), 7.17 − 7.10 (m, 3H), 6.92 (d, J = 8.8 Hz, 2H), 4.55 (d, J = 6.0 Hz, 2H), 4.25 − 4.15 (m, 1H), 3.73 − 3.63 (m, 4H), 3.00 − 2.90 (m, 2H), 2.72 − 2.62 (m, 4H), 2.48 (s, 3H), 2.21 (d, J = 6.8 Hz, 2H), 2.15 − 1.95 (m, 6H), 1.85 − 1.66 (m, 3H), 1.64 (s, 9H), 1.28 − 1.15 (m, 2H). |
| 125 | 10.25 (s, 1H), 9.20 − 9.10 (m, 2H), 8.72 (s, 1H), 8.48 (s, 1H), 8.20 (d, J = 2.4 Hz, 1H), 8.15 (s, 1H), 8.03 − 7.92 (m, 2H), 7.58 − 7.52 (m, 1H), 7.21 (d, J = 2.0 Hz, 1H), 7.13 (d, J = 8.8 Hz, 2H), 6.92 (d, J = 8.8 Hz, 2H), 4.62 (d, J = 6.0 Hz, 2H), 4.25 − 4.15 (m, 1H), 3.73 − 3.62 (m, 4H), 3.00 − 2.90 (m, 2H), 2.72 − 2.62 (m, 4H), 2.21 (d, J = 7.2 Hz, 2H), 2.13 − 1.95 (m, 6H), 1.85 − 1.66 (m, 3H), 1.64 (s, 9H), 1.28 − 1.15 (m, 2H). |
| 130 | |
| 131 | 10.25 (s, 1H), 9.29 (d, J = 2.0 Hz, 1H), 9.23 − 9.15 (m, 2H), 8.74 (s, 1H), 8.55 − 8.45 (m, 2H), 8.21 (d, J = 2.4 Hz, 1H), 8.15 (s, 1H), 7.54 (d, J = 8.4 Hz, 1H), 7.24 (d, J = 2.4 Hz, 1H), 7.13 (d, J = 8.8 Hz, 2H), 6.92 (d, J = 8.8 Hz, 2H), 4.70 (d, J = 6.0 Hz, 2H), 4.25 − 4.15 (m, 1H), 3.73 − 3.63 (m, 4H), 3.00 − 2.90 (m, 2H), 2.72 − 2.60 (m, 4H), 2.25 − 1.95 (m, 8H), 1.85 − 1.66 (m, 3H), 1.65 (s, 9H), 1.25 − 1.15 (m, 2H). |
| 180 | 10.27 (s, 1H), 9.63 (d, J = 7.6 Hz, 1H), 9.00 (d, J = 2.4 Hz, 1H), 8.38 − 8.30 (m, 1H), 8.07 (s, 1H), 8.03 (s, 1H), 7.93 − 7.85 (m, 2H), 7.77 (d, J = 8.0 Hz, 1H), 7.69 (d, J = 5.6 Hz, 1H), 7.16 (d, J = 9.2 Hz, 2H), 6.95 (d, J = 9.2 Hz, 3H), 5.53 − 5.43 (m, 1H), |

-continued

| | |
|---|---|
| | 3.73 − 3.55 (m, 8H), 2.75 − 2.65 (m, 4H), 2.57 (s, 3H), 2.49 − 2.45 (m, 2H), 2.22 (d, J = 2.8 Hz, 2H), 1.88 − 1.80 (m, 2H), 1.76 (s, 9H), 1.75 − 1.70 (m, 1H), 1.59 (d, J = 6.8 Hz, 3H), 1.32 − 1.20 (m, 2H). |
| 183 | 10.25 (s, 1H), 10.00 (d, J = 7.6 Hz, 1H), 9.16 (s, 1H), 8.48 (s, 1H), 8.20 (d, J = 2.8 Hz, 1H), 8.14 (s, 1H), 8.05 − 7.93 (m, 2H), 7.75 − 7.70 (m, 2H), 7.25 − 7.20 (m, 2H), 7.12 (d, J = 8.8 Hz, 2H), 6.92 (d, J = 8.8 Hz, 2H), 5.50 − 5.40 (m, 1H), 4.25 − 4.15 (m, 1H), 3.75 − 3.65 (m, 2H), 3.02 − 2.92 (m, 2H), 2.70 − 2.60 (m, 4H), 2.21 (d, J = 7.2 Hz, 2H), 2.15 − 1.95 (m, 6H), 1.85 − 1.65 (m, 3H), 1.59 (d, J = 6.8 Hz, 3H), 1.37 (s, 9H), 1.30 − 1.15 (m, 2H). |
| 193 | 10.25 (s, 1H), 9.64 (d, J = 8.0 Hz, 1H), 9.34 (s, 1H), 8.95 (d, J = 2.4 Hz, 1H), 8.35 − 8.30 (m, 1H), 8.24 (d, J = 2.8 Hz, 1H), 8.05 − 7.92 (m, 2H), 7.78 − 7.72 (m, 1H), 7.25 (d, J = 2.4 Hz, 1H), 7.13 (d, J = 8.8 Hz, 2H), 6.98 − 6.90 (m, 3H), 5.58 − 5.48 (m, 1H), 3.73 − 3.55 (m, 8H), 2.72 − 2.62 (m, 4H), 2.49 − 2.45 (m, 4H), 2.22 (d, J = 6.8 Hz, 2H), 1.88 − 1.78 (m, 2H), 1.74 (s, 9H), 1.70 − 1.65 (m, 1H), 1.59 (d, J = 6.8 Hz, 3H), 1.30 − 1.18 (m, 2H). |
| 207 | 10.25 (s, 1H), 9.68 − 9.62 (m, 1H), 9.17 (s, 1H), 8.48 (s, 1H), 8.20 (d, J = 2.8 Hz, 1H), 8.15 (s, 1H), 8.03 − 7.95 (m, 2H), 7.63 − 7.55 (m, 1H), 7.24 − 7.20 (m, 1H), 7.13 (d, J = 8.8 Hz, 2H), 6.92 (d, J = 8.8 Hz, 2H), 4.65 (d, J = 6.0 Hz, 2H), 4.25 − 4.15 (m, 1H), 3.73 − 3.62 (m, 4H), 3.00 − 2.90 (m, 2H), 2.72 − 2.62 (m, 4H), 2.21 (d, J = 6.8 Hz, 2H), 2.13 − 1.95 (m, 6H), 1.85 − 1.77 (m, 2H), 1.74 (s, 9H), 1.70 − 1.60 (m, 1H), 1.28 − 1.15 (m, 2H). |
| 208 | 10.25 (s, 1H), 9.60 − 9.52 (m, 1H), 9.11 (s, 1H), 8.44 (s, 1H), 8.17 (d, J = 2.8 Hz, 1H), 8.14 (s, 1H), 7.98 − 7.92 (m, 2H), 7.47 (d, J = 8.4 Hz, 2H), 7.18 − 7.10 (m, 2H), 6.92 (d, J = 9.2 Hz, 2H), 4.58 (d, J = 6.0 Hz, 2H), 4.25 − 4.15 (m, 1H), 3.73 − 3.62 (m, 4H), 3.00 − 2.90 (m, 2H), 2.72 − 2.60 (m, 4H), 2.49 (s, 3H), 2.22 (d, J = 6.4 Hz, 2H), 2.13 − 1.95 (m, 6H), 1.85 − 1.77 (m, 2H), 1.74 (s, 9H), 1.70 − 1.60 (m, 1H), 1.28 − 1.15 (m, 2H). |
| 209 | 10.25 (s, 1H), 9.60 − 9.52 (m, 1H), 9.26 (s, 1H), 8.95 (d, J = 2.4 Hz, 1H), 8.35 − 8.25 (m, 1H), 8.20 (d, J = 2.4 Hz, 1H), 7.99 − 7.92 (m, 2H), 7.48 (d, J = 8.4 Hz, 1H), 7.18 − 7.16 (m, 1H), 7.12 (d, J = 8.8 Hz, 2H), 6.97 − 6.88 (m, 2H), 4.59 (d, J = 6.0 Hz, 2H), 4.25 − 4.15 (m, 1H), 3.73 − 3.52 (m, 8H), 2.70 − 2.60 (m, 4H), 2.49 (s, 3H), 2.46 − 2.40 (m, 4H), 2.22 (d, J = 6.8 Hz, 2H), 1.85 − 1.77 (m, 2H), 1.74 (s, 9H), 1.73 − 1.65 (m, 1H), 1.28 − 1.15 (m, 2H). |
| 214 | 10.25 (s, 1H), 9.58 (d, J = 7.9 Hz, 1H), 9.49 (s, 1H), 9.35 (d, J = 2.3 Hz, 1H), 8.51 (dd, J = 8.2, 2.4 Hz, 1H), 8.28 (d, J = 2.4 Hz, 1H), 8.04 − 7.95 (m, 2H), 7.72 (d, J = 8.1 Hz, 1H), 7.51 (d, J = 8.2 Hz, 1H), 7.26 (dd, J = 2.5, 1.0 Hz, 1H), 7.16 − 7.08 (m, 2H), 6.95 − 6.89 (m, 2H), 5.44 (p, J = 7.0 Hz, 1H), 3.83 (q, J = 7.4 Hz, 1H), 3.69 (t, J = 6.7 Hz, 5H), 3.65 (s, 1H), 2.71 − 2.58 (m, 4H), 2.56 (s, 3H), 2.39 (d, J = 6.7 Hz, 2H), 1.79 (d, J = 12.5 Hz, 2H), 1.73 (s, 9H), 1.55 (d, J = 7.0 Hz, 3H), 1.30 − 1.19 (m, 2H). |
| 215 | 10.24 (s, 1H), 9.56 (d, J = 7.9 Hz, 1H), 9.25 (d, J = 1.0 Hz, 1H), 8.93 (d, J = 2.4 Hz, 1H), 8.29 (dd, J = 9.0, 2.5 Hz, 1H), 8.20 (d, J = 2.4 Hz, 1H), 8.01 − 7.92 (m, 2H), 7.70 (d, J = 8.1 Hz, 1H), 7.19 (dd, J = 2.6, 1.0 Hz, 1H), 7.17 − 7.08 (m, 2H), 6.99 − 6.88 (m, 3H), 5.43 (p, J = 7.1 Hz, 1H), 4.04 − 3.93 (m, 2H), 3.69 (t, J = 6.7 Hz, 4H), 2.74 − 2.59 (m, 4H), 2.54 (s, 4H), 2.43 − 2.39 (m, 1H), 2.20 (t, J = 10.2 Hz, 1H), 2.05 − 1.96 (m, 1H), 1.96 − 1.86 (m, 1H), 1.72 (s, 9H), 1.55 (d, J = 7.0 Hz, 3H), 1.26 − 1.16 (m, 2H), 1.05 (d, J = 6.1 Hz, 3H). |
| 216 | 10.24 (s, 1H), 9.57 (d, J = 7.9 Hz, 1H), 9.26 (d, J = 1.0 Hz, 1H), 8.93 (d, J = 2.5 Hz, 1H), 8.30 (dd, J = 8.9, 2.5 Hz, 1H), 8.20 (d, J = 2.5 Hz, 1H), 8.01 − 7.92 (m, 2H), 7.71 (d, J = 8.1 Hz, 1H), 7.19 (dd, J = 2.5, 1.0 Hz, 1H), 7.17 − 7.09 (m, 2H), 6.94 (dd, J = 13.2, 9.1 Hz, 4H), 4.02 − 3.95 (m, 2H), 3.73 − 3.64 (m, 5H), 2.96 − 2.87 (m, 2H), 2.74 − 2.60 (m, 5H), 2.55 (s, 5H), 2.41 (s, 1H), 2.21 (t, J = 10.3 Hz, 1H), 2.09 − 1.96 (m, 1H), 1.91 (d, J = 14.5 Hz, 1H), 1.73 (s, 9H), 1.55 (d, J = 7.0 Hz, 4H), 1.25 − 1.19 (m, 2H), 1.05 (d, J = 6.0 Hz, 3H). |
| 220 | 10.26 (s, 1H), 9.70 − 9.62 (m, 1H), 9.34 (s, 1H), 8.95 (d, J = 2.8 Hz, 1H), 8.35 − 8.30 (m, 1H), 8.24 (d, J = 2.4 Hz, 1H), 8.03 − 7.92 (m, 2H), 7.65 − 7.56 (m, 1H), 7.23 (d, J = 2.0 Hz, 1H), 7.13 (d, J = 9.2 Hz, 2H), 6.98 − 6.90 (m, 3H), 4.65 (d, J = 6.0 Hz, 2H), 3.73 − 3.55 (m, 8H), 2.70 − 2.60 (m, 4H), 2.48 − 2.40 (m, 4H), 2.22 (d, J = 7.2 Hz, 2H), 1.85 − 1.77 (m, 2H), 1.74 (s, 9H), 1.73 − 1.65 (m, 1H), 1.28 − 1.16 (m, 2H). |
| 225 | 10.25 (s, 1H), 9.57 (d, J = 7.9 Hz, 1H), 9.26 (d, J = 0.9 Hz, 1H), 8.95 (d, J = 2.5 Hz, 1H), 8.30 (dd, J = 8.9, 2.6 Hz, 1H), 8.20 (d, |

-continued

| | |
|---|---|
| | J = 2.4 Hz, 1H), 8.01 - 7.92 (m, 2H), 7.71 (d, J = 8.1 Hz, 1H), 7.19 (dd, J = 2.5, 0.9 Hz, 1H), 7.13 (d, J = 8.9 Hz, 2H), 6.91 (dd, J = 19.4, 9.1 Hz, 3H), 4.57 (s, 1H), 4.10 (d, J = 12.5 Hz, 1H), 3.75 - 3.65 (m, 5H), 2.97 - 2.89 (m, 1H), 2.86 - 2.78 (m, 1H), 2.69 (d, J = 6.6 Hz, 4H), 2.55 (s, 4H), 2.28 - 2.12 (m, 3H), 2.02 (m, 2H), 1.93 - 1.79 (m, 2H), 1.73 (s, 9H), 1.55 (d, J = 7.0 Hz, 3H), 1.29 - 1.22 (m, 2H), 1.20 (d, J = 6.5 Hz, 3H). |
| 226 | 10.25 (s, 1H), 9.57 (d, J = 7.9 Hz, 1H), 9.26 (d, J = 1.0 Hz, 1H), 8.95 (d, J = 2.4 Hz, 1H), 8.30 (dd, J = 8.9, 2.6 Hz, 1H), 8.20 (d, J = 2.4 Hz, 1H), 8.01 - 7.93 (m, 2H), 7.71 (d, J = 8.1 Hz, 1H), 7.19 (dd, J = 2.5, 0.9 Hz, 1H), 7.13 (d, J = 8.9 Hz, 2H), 6.93 (d, J = 9.1 Hz, 2H), 6.89 (d, J = 9.1 Hz, 1H), 4.17 - 4.03 (m, 1H), 3.76 - 3.64 (m, 4H), 3.05 (m, 1H), 2.97 - 2.90 (m, 1H), 2.87 - 2.78 (m, 1H), 2.74 - 2.62 (m, 4H), 2.55 (s, 3H), 2.25 - 2.22 (m, 1H), 2.18 (m, 2H), 2.09 - 2.00 (m, 2H), 1.98 (m, 2H), 1.84 (s, 1H), 1.73 (s, 9H), 1.55 (d, J = 7.0 Hz, 3H), 1.27 - 1.20 (m, 1H), 1.20 (d, J = 6.5 Hz, 3H). |
| 229 | 10.26 (s, 1H), 9.57 (d, J = 8.0 Hz, 1H), 9.26 (s, 1H), 8.93 (d, J = 2.4 Hz, 1H), 8.30 - 8.25 (m, 1H), 8.20 (d, J = 2.0 Hz, 1H), 8.02 - 7.92 (m, 2H), 7.70 (d, J = 8.0 Hz, 1H), 7.20 - 7.12 (m, 3H), 6.98 - 6.90 (m, 3H), 5.50 - 5.40 (m, 1H), 4.39 (d, J = 9.2 Hz, 2H), 3.73 - 3.65 (m, 2H), 3.20 - 3.10 (m, 4H), 2.95 - 2.85 (m, 2H), 2.72 - 2.65 (m, 2H), 2.55 (s, 3H), 2.54 - 2.51 (m, 4H), 2.22 (d, J = 6.8 Hz, 2H), 1.90 - 1.77 (m, 3H), 1.73 (s, 9H), 1.55 (d, J = 6.8 Hz, 3H), 1.20 - 1.08 (m, 2H). |
| 235 | 10.24 (s, 1H), 9.57 (d, J = 7.9 Hz, 1H), 9.46 (d, J = 1.0 Hz, 1H), 9.32 - 9.27 (m, 1H), 8.48 (dd, J = 8.2, 2.4 Hz, 1H), 8.27 (d, J = 2.4 Hz, 1H), 8.04 - 7.94 (m, 2H), 7.72 (d, J = 8.1 Hz, 1H), 7.43 (d, J = 8.2 Hz, 1H), 7.25 (dd, J = 2.5, 1.0 Hz, 1H), 7.16 - 7.09 (m, 2H), 6.93 (d, J = 9.1 Hz, 2H), 5.44 (m, 1H), 3.69 (t, J = 6.7 Hz, 4H), 3.01 - 2.96 (m, 2H), 2.79 - 2.61 (m, 6H), 2.55 (s, 3H), 2.22 (s, 1H), 2.00 (m, 3H), 1.91 - 1.77 (m, 6H), 1.73 (s, 9H), 1.70 (s, 1H), 1.55 (d, J = 7.0 Hz, 3H), 1.23 (s, 2H). |
| 236 | 10.24 (s, 1H), 9.56 (d, J = 7.9 Hz, 1H), 9.24 (d, J = 1.0 Hz, 1H), 8.92 (d, J = 2.5 Hz, 1H), 8.27 (dd, J = 8.9, 2.5 Hz, 1H), 8.19 (d, J = 2.4 Hz, 1H), 8.01 - 7.92 (m, 2H), 7.71 (d, J = 8.1 Hz, 1H), 7.18 (dd, J = 2.5, 1.0 Hz, 1H), 7.16 - 7.08 (m, 2H), 6.96 - 6.87 (m, 2H), 6.79 (d, J = 9.1 Hz, 1H), 5.44 (m, 1H), 3.88 (d, J = 11.5 Hz, 2H), 3.69 (dd, J = 8.5, 5.0 Hz, 4H), 3.30 (d, J = 4.1 Hz, 3H), 3.01 (d, J = 11.3 Hz, 2H), 2.68 (d, J = 6.4 Hz, 2H), 2.67 - 2.60 (m, 2H), 2.54 (s, 3H), 2.26 (d, J = 6.9 Hz, 2H), 1.92 - 1.84 (m, 4H), 1.72 (s, 9H), 1.55 (d, J = 7.1 Hz, 4H), 1.28 - 1.18 (m, 2H). |
| 237 | 10.24 (s, 1H), 9.57 (d, J = 7.9 Hz, 1H), 9.25 (d, J = 0.9 Hz, 1H), 8.93 (d, J = 2.4 Hz, 1H), 8.27 (dd, J = 8.8, 2.5 Hz, 1H), 8.20 (d, J = 2.4 Hz, 1H), 8.02 - 7.93 (m, 2H), 7.71 (d, J = 8.1 Hz, 1H), 7.19 (dd, J = 2.5, 1.0 Hz, 1H), 7.16 - 7.08 (m, 2H), 6.91 (d, J = 9.0 Hz, 2H), 6.86 (d, J = 8.9 Hz, 1H), 5.44 (m, 1H), 4.60 (s, 2H), 3.68 (m, 4H), 2.71 - 2.59 (m, 6H), 2.55 (s, 3H), 2.28 (d, J = 10.3 Hz, 2H), 2.09 (d, J = 7.2 Hz, 2H), 1.95 (d, J = 7.0 Hz, 2H), 1.87 (t, J = 6.4 Hz, 2H), 1.77 (d, J = 12.3 Hz, 2H), 1.73 (s, 9H), 1.55 (d, J = 7.0 Hz, 3H), 1.24 - 1.15 (m, 2H). |
| 248 | 10.25 (s, 1H), 9.57 (d, J = 7.6 Hz, 1H), 8.87 (s, 1H), 8.22 (d, J = 2.4 Hz, 1H), 8.14 - 8.05 (m, 1H), 7.96 (d, J = 8.0 Hz, 1H), 7.92 (s, 1H), 7.71 (d, J = 8.0 Hz, 1H), 7.19 (d, J = 1.6 Hz, 1H), 7.12 (d, J = 9.2 Hz, 2H), 6.95 - 6.85 (m, 4H), 5.50 - 5.40 (m, 1H), 3.74 - 3.60 (m, 4H), 3.30 - 3.20 (m, 4H), 2.70 - 2.60 (m, 4H), 2.54 (s, 3H), 2.48 - 2.42 (m, 4H), 2.20 (d, J = 6.8 Hz, 2H), 1.85 - 1.75 (m, 2H), 1.72 (s, 9H), 1.70 - 1.63 (m, 1H), 1.55 (d, J = 6.8 Hz, 3H), 1.30 - 1.15 (m, 2H). |
| 249 | 10.27 (s, 1H), 9.96 (d, J = 7.7 Hz, 1H), 9.55 (d, J = 3.4 Hz, 1H), 9.03 (t, J = 2.3 Hz, 1H), 8.80 (d, J = 1.6 Hz, 1H), 8.69 (d, J = 8.3 Hz, 1H), 8.64 (d, J = 2.0 Hz, 1H), 8.38 (dd, J = 9.2, 2.6 Hz, 1H), 7.73 (d, J = 8.3 Hz, 1H), 7.19 - 7.13 (m, 2H), 7.00 (d, J = 9.1 Hz, 1H), 6.95 (d, J = 8.4 Hz, 2H), 5.40 (m, 1H), 3.71 (m, 4H), 3.64 (s, 4H), 2.75 - 2.64 (m, 4H), 2.56 (s, 4H), 2.50 (d, J = 5.8 Hz, 6H), 2.25 (d, J = 6.9 Hz, 2H), 1.85 (d, J = 12.7 Hz, 2H), 1.75 (s, 1H), 1.58 (d, J = 6.9 Hz, 3H), 1.39 (s, 9H), 1.30 - 1.23 (m, 2H). |

Example 3: (R)-3-(tert-butyl)-N-(1-(4-(7-(6-(4-((1-(4-(2,4-dioxotetrahydropyrimidin-1(2H)-yl)phenyl)piperidin-4-yl)methyl)piperazin-1-yl)pyridin-3-yl)imidazo[1,2-c]pyrimidin-5-yl)-2-methylphenyl)ethyl)-1,2,4-oxadiazole-5-carboxamide (Compound No. 16)
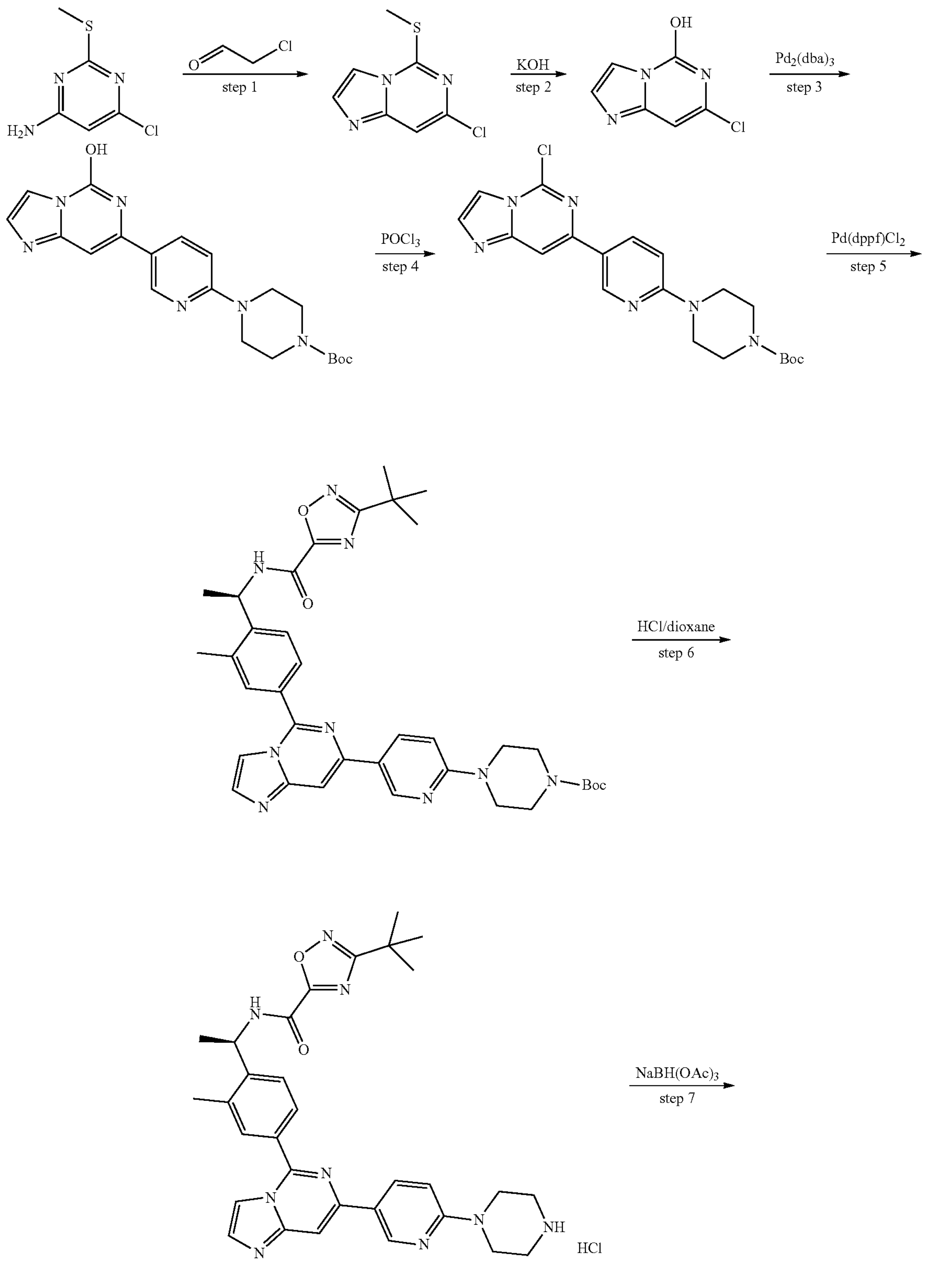

-continued

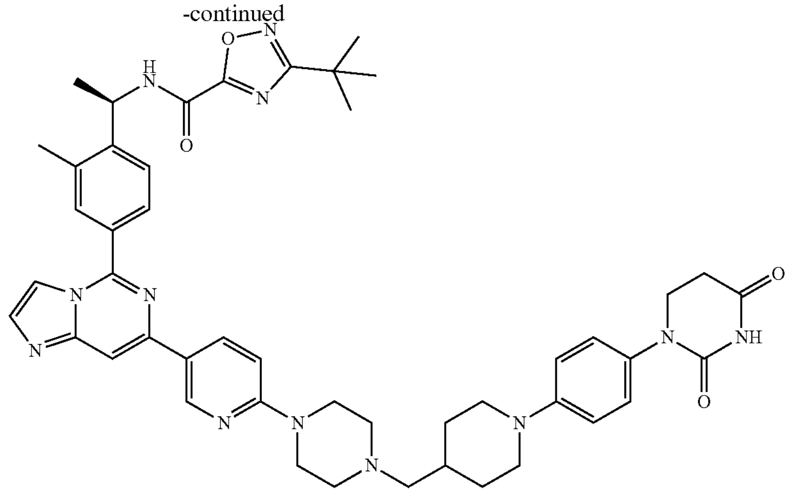

Step 1: 7-chloro-5-(methylthio)imidazo[1,2-c]pyrimidine

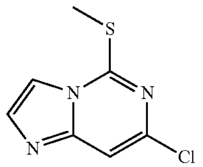

In a 250 ml round-bottomed flask, 6-chloro-2-(methylthio)pyrimidin-4-amine (5 g, 28.5 mmol, 1.0 eq) and 2-chloroacetaldehyde (3.35 g, 42.7 mmol, 1.5 eq) were dissolved in dioxane (50 ml). The reaction was stirred for 5 h at 100° C. The suspension was cooled to 0° C. and the solid was filtered off to give the title compound (5 g, 88%) as a yellow solid. MS (ESI) m/z 200.0 $[M+H]^+$.

Step 2: 7-chloroimidazo[1,2-c]pyrimidin-5-ol

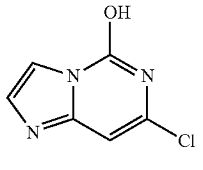 [SMILES: Oc1nc(Cl)cc2nccn12]

In a 100 ml round-bottomed flask, above obtained intermediate (5 g, 25.04 mmol, 1.0 eq) and KOH (4.22 g, 75 mmol, 3.0 eq) were dissolved in MeOH (20 ml) and water (20 ml). The reaction was stirred for 3 h at 100° C. The suspension was cooled to rt. The aqueous layer was adjusted to pH=6 with 6 N HCl aqueous. The solid was filtered off to give the title compound (4 g, 94%) as an off-white solid. MS (ESI) m/z 170.0 $[M+H]^+$.

Step 3: tert-butyl 4-(5-(5-hydroxyimidazo[1,2-c]pyrimidin-7-yl)pyridin-2-yl)piperazine-1-carboxylate

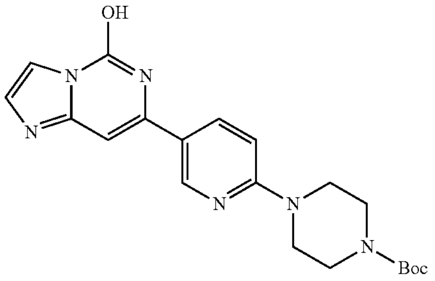 [SMILES: CC(C)(C)OC(=O)N1CCN(c2ccc(-c3cc4nccn4c(O)n3)cn2)CC1]

In a 100 ml round-bottomed flask, above obtained intermediate (300 mg, 1.769 mmol, 1.0 eq), tert-butyl 4-(5-(4,4,5,5-tetramethyl-1,3,2-dioxaborolan-2-yl)pyridin-2-yl)piperazine-1-carboxylate (1033 mg, 2.65 mmol, 1.5 eq), $Pd_2(dba)_3$ (162 mg, 0.177 mmol, 0.1 eq), potassium phosphate (1128 mg, 5.307 mmol, 3.0 eq) and dicyclohexyl(2',4',6'-triisopropyl-[1,1'-biphenyl]-2-yl)phosphane (169 mg, 0.354 mmol, 0.2 eq) were dissolved in 2-propanol (15 ml) and water (5 ml) under argon. The reaction mixture was stirred at 100° C. for 12 h. Water was added to the reaction mixture followed by extraction with DCM. The combined organic layers were dried over $Na_2SO_4$, filtered and concentrated. The crude product was purified by silica gel flash column chromatography eluted with methanol/dichloromethane from 0% to 4% to give the title compound (450 mg, 64.2%) as a yellow solid. MS (ESI) m/z 397.4 $[M+H]^+$.

Step 4: tert-butyl 4-(5-(5-chloroimidazo[1,2-c]pyrimidin-7-yl)pyridin-2-yl)piperazine-1-carboxylate

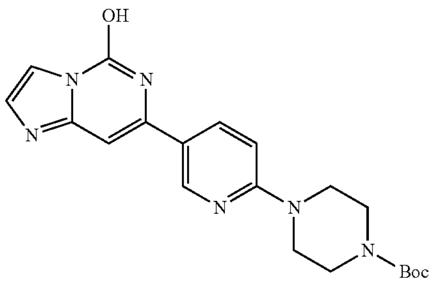 [SMILES: CC(C)(C)OC(=O)N1CCN(c2ccc(-c3cc4nccn4c(O)n3)cn2)CC1]

In a 100 ml round-bottomed flask, above obtained intermediate (450 mg, 1.135 mmol, 1.0 eq), DIPEA (734 mg, 5.68 mmol, 5.0 eq) and $POCl_3$ (522 mg, 3.41 mmol, 3.0 eq) were dissolved in DCM (5 ml). The reaction mixture was stirred for 12 h. Saturated $NaHCO_3$ was added to the reaction mixture followed by extraction with DCM. The combined organic layers were dried over $Na_2SO_4$, filtered and concentrated. The crude product was purified by silica gel column chromatography eluted with methanol/dichloromethane from 0% to 2% to give the title compound (80 mg, 17.0%) as a yellow solid. MS (ESI) m/z 415.3 $[M+H]^+$.

Step 5: tert-butyl 4-(5-(5-chloroimidazo[1,2-c]pyrimidin-7-yl)pyridin-2-yl)piperazine-1-carboxylate

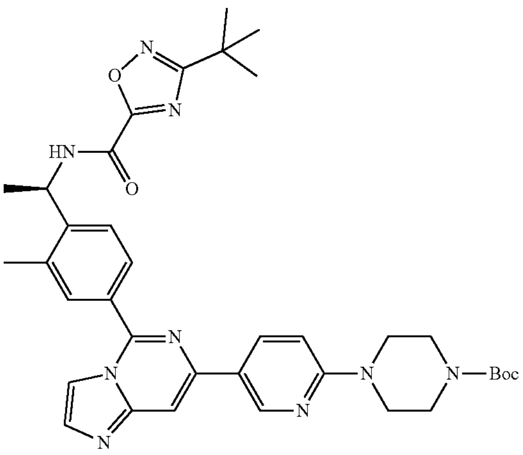 [SMILES: Cc1cc(-c2nc(-c3ccc(N4CCN(C(=O)OC(C)(C)C)CC4)nc3)cc3nccn23)ccc1[C@@H](C)NC(=O)c1nc(C(C)(C)C)no1]

In a 100 ml round-bottomed flask, above obtained intermediate (80 mg, 0.193 mmol, 1.0 eq), (R)-3-(tert-butyl)-N-(1-(2-methyl-4-(4,4,5,5-tetramethyl-1,3,2-dioxaborolan-2-yl)phenyl)ethyl)-1,2,4-oxadiazole-5-carboxamide (96 mg, 0.231 mmol, 1.2 eq), $K_2CO_3$ (53.3 mg, 0.386 mmol, 2.0 eq) and $Pd(dppf)Cl_2$ (14.1 mg, 0.019 mmol, 0.1 eq) were dissolved in dioxane (5 ml) and water (0.5 ml) under nitrogen. The mixture was stirred at 100° C. for 16 h. Water was added to the reaction mixture followed by extraction with DCM. The combined organic layers were dried over $Na_2SO_4$, filtered and concentrated. The crude product was purified by silica gel column chromatography eluted with MeOH/DCM 0~3% to give the title compound (100 mg, 78%) as a yellow solid. MS (ESI) m/z 666.6 $[M+H]^+$.

Step 6: tert-butyl 4-(5-(5-chloroimidazo[1,2-c]pyrimidin-7-yl)pyridin-2-yl)piperazine-1-carboxylate

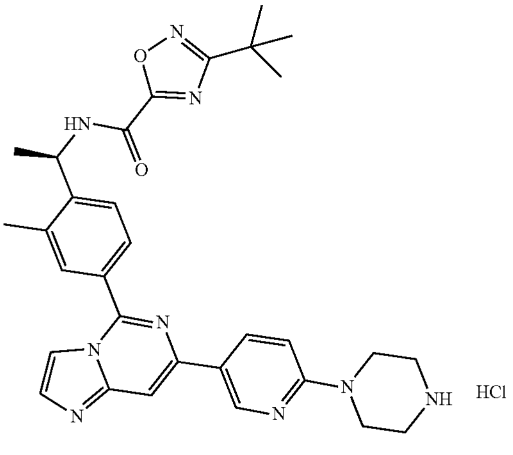 [SMILES: Cc1cc(-c2nc(-c3ccc(N4CCNCC4)nc3)cc3nccn23)ccc1[C@@H](C)NC(=O)c1nc(C(C)(C)C)no1 ; Cl]

In a 100 ml round-bottomed flask, above obtained intermediate (100 mg, 0.150 mmol, 1.0 eq) was dissolved in DCM (10 ml) and 4 M HCl in dioxane (2 ml). The reaction mixture was stirred for 3 h and concentrated to give the title compound (90 mg, 100%) as a yellow solid, which was used in next step without further purification. MS (ESI) m/z 566.6 $[M-HCl+H]^+$.

Step 7: (R)-3-(tert-butyl)-N-(1-(4-(7-(6-(4-((1-(4-(2,4-dioxotetrahydropyrimidin-1(2H)-yl)phenyl)piperidin-4-yl)methyl)piperazin-1-yl)pyridin-3-yl)imidazo[1,2-c]pyrimidin-5-yl)-2-methylphenyl)ethyl)-1,2,4-oxadiazole-5-carboxamide

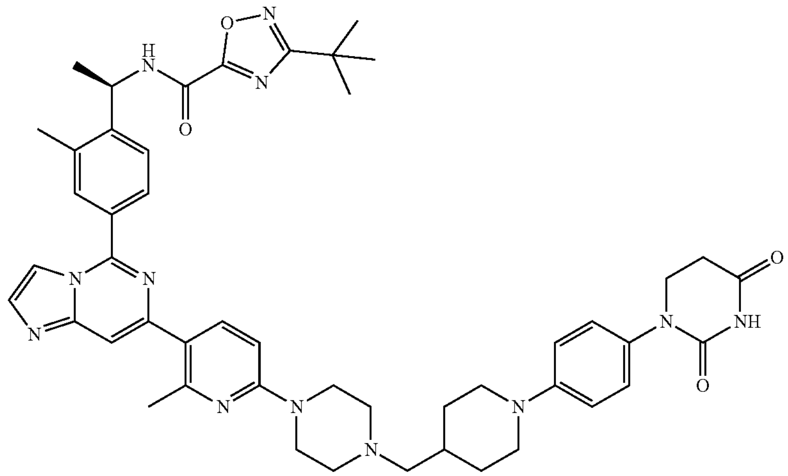 [SMILES: Cc1cc(-c2nc(-c3ccc(N4CCN(CC5CCN(c6ccc(N7CCC(=O)NC7=O)cc6)CC5)CC4)nc3C)cc3nccn23)ccc1[C@@H](C)NC(=O)c1nc(C(C)(C)C)no1]

In a 100 ml round-bottomed flask, above obtained intermediate (90 mg, 0.149 mmol, 1.0 eq), triethylamine (45.4 mg, 0.448 mmol, 3.0 eq), 1-(4-(2,4-dioxotetrahydropyrimidin-1(2H)-yl)phenyl)piperidine-4-carbaldehyde (49.5 mg, 0.164 mmol, 1.1 eq) and NaBH(OAc) 3 (47.5 mg, 0.224 mmol, 1.5 eq) were dissolved in DCM (10 ml). The mixture was stirred for 16 h. Water was added to the reaction mixture followed by extraction with DCM. The combined organic layers were dried over $Na_2SO_4$, filtered and concentrated. The crude product was purified by prep-HPLC to give the title compound (53 mg, 41.7%) as a light-yellow solid. MS (ESI) m/z 851.6 $[M+H]^+$. $^1H$ NMR (400 MHz, DMSO-$d^6$) δ (ppm) 10.27 (s, 1H), 10.01 (d, J=7.7 Hz, 1H), 9.00 (d, J=2.5 Hz, 1H), 8.34 (dd, J=9.0, 2.6 Hz, 1H), 8.05 (d, J=16.6 Hz, 2H), 7.91 (d, J=8.5 Hz, 1H), 7.88-7.84 (m, 1H), 7.75 (d, J=8.1 Hz, 1H), 7.69 (d, J=1.4 Hz, 1H), 7.16 (d, J=8.9 Hz, 2H), 6.95 (d, J=9.1 Hz, 3H), 5.42 (p, J=7.0 Hz, 1H), 3.76-3.68 (m, 3H), 3.66-3.59 (m, 4H), 3.34-3.28 (m, 5H), 2.74-2.65 (m, 3H), 2.55 (s, 3H), 2.51-2.46 (m, 1H), 2.25 (d, J=7.1 Hz, 2H), 1.85 (d, J=12.6 Hz, 2H), 1.75 (s, 1H), 1.59 (d, J=6.9 Hz, 3H), 1.40 (s, 9H), 1.32-1.19 (m, 2H).

Following the synthesis of EXAMPLE 3, the following compounds were synthesized and obtained in a similar manner.

| Compd No. | Structure Observed MS $[M + 1]^+$ | $^1H$ NMR (400 MHz, DMSO-$d^6$) δ (ppm) |
|---|---|---|
| 17 | 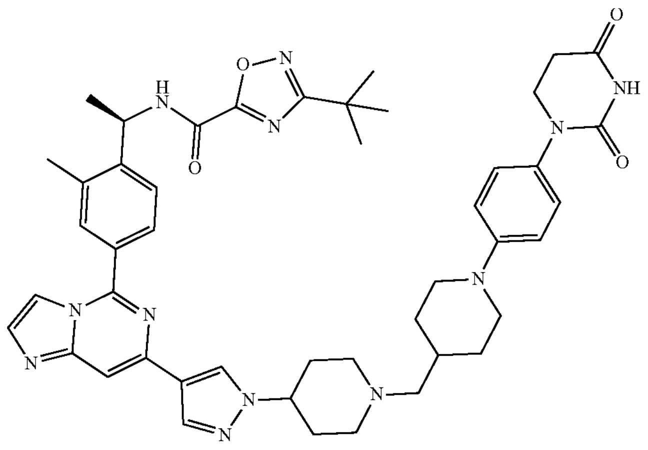 [SMILES: Cc1cc(-c2nc(-c3cnn(C4CCN(CC5CCN(c6ccc(N7CCC(=O)NC7=O)cc6)CC5)CC4)c3)cc3nccn23)ccc1[C@@H](C)NC(=O)c1nc(C(C)(C)C)no1] 839.6 | 10.28 (s, 1H), 10.02 (d, J = 7.7 Hz, 1H), 8.46 (s, 1H), 8.15 (s, 1H), 7.98 (d, J = 1.4 Hz, 1H), 7.88 (d, J = 7.7 Hz, 2H), 7.83 (s, 1H), 7.74 (d, J = 8.1 Hz, 1H), 7.65 (d, J = 1.5 Hz, 1H), 7.16 (d, J = 8.9 Hz, 2H), 6.96 (d, J = 8.9 Hz, 2H), 5.42 (p, J = 7.2 Hz, 1H), 4.27-4.16 (m, 1H), 3.72 (t, J = 6.7 Hz, 3H), 2.99 (d, J = 10.1 Hz, 2H), 2.72 (d, J = 6.5 Hz, 2H), 2.68 (d, J = 12.4 Hz, 2H), 2.55 (s, 3H), 2.24 (d, J = 7.2 Hz, 2H), 2.15-1.96 (m, 6H), 1.84 (d, J = 12.6 Hz, 2H), 1.76-1.66 (m, 1H), 1.59 (d, J = 7.0 Hz, 3H), 1.41 (s, 9H), 1.31-1.18 (m, 2H). |
| 40 | 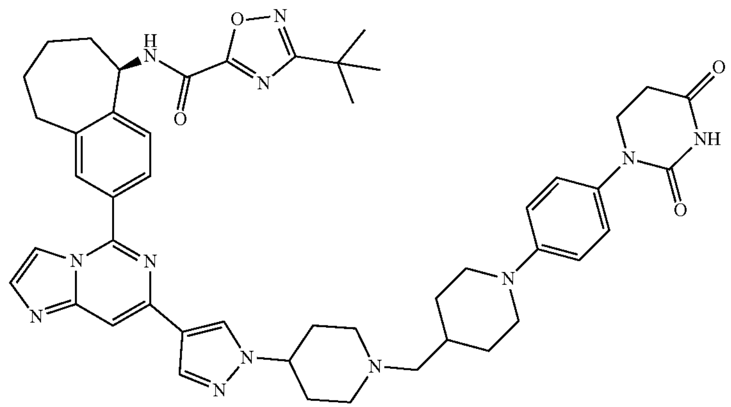 [SMILES: CC(C)(C)c1noc(C(=O)N[C@@H]2CCCCc3cc(-c4nc(-c5cnn(C6CCN(CC7CCN(c8ccc(N9CCC(=O)NC9=O)cc8)CC7)CC6)c5)cc5nccn45)ccc32)n1] 865.7 | 10.28 (s, 1H), 10.09 (d, J = 7.9 Hz, 1H), 8.46 (s, 1H), 8.15 (s, 1H), 8.00-7.95 (m, 1H), 7.89-7.80 (m, 3H), 7.65 (d, J = 1.5 Hz, 1H), 7.48 (d, J = 7.9 Hz, 1H), 7.19-7.13 (m, 2H), 6.95 (d, J = 9.1 Hz, 2H), 5.34 (t, J = 8.7 Hz, 1H), 4.23 (s, 1H), 3.76-3.67 (m, 4H), 3.05-2.89 (m, 4H), 2.74-2.64 (m, 4H), 2.24 (d, J = 7.1 Hz, 2H), 2.15-1.96 (m, 4H), 1.92-1.80 (m, 3H), 1.71 (s, 1H), 1.43 (s, 9H), 1.31-1.16 (m, 2H). |

-continued
| Compd No. | Structure Observed MS $[M + 1]^+$ | $^1H$ NMR (400 MHz, DMSO-$d^6$) δ (ppm) |
|---|---|---|
| 41 | 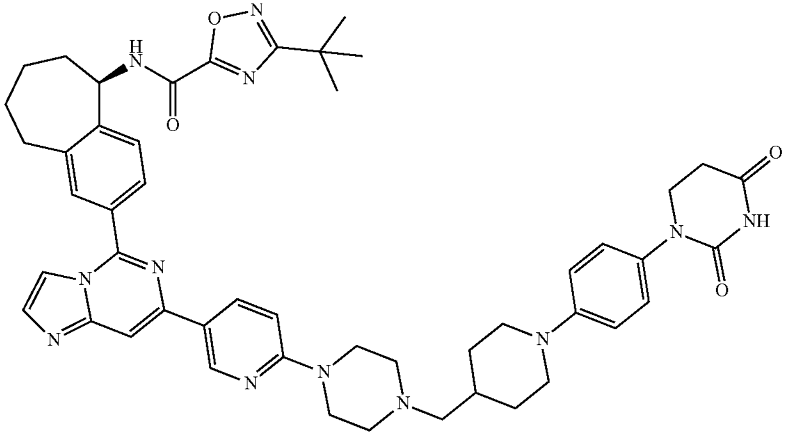 [SMILES: CC(C)(C)c1noc(C(=O)N[C@@H]2CCCCc3cc(-c4nc(-c5ccc(N6CCN(CC7CCN(c8ccc(N9CCC(=O)NC9=O)cc8)CC7)CC6)nc5)cc5nccn45)ccc32)n1] 877.8 | 10.27 (s, 1H), 10.09 (d, J = 7.9 Hz, 1H), 9.00 (d, J = 2.5 Hz, 1H), 8.34 (dd, J = 9.0, 2.5 Hz, 1H), 8.09-8.01 (m, 2H), 7.91-7.84 (m, 2H), 7.69 (d, J = 1.4 Hz, 1H), 7.49 (d, J = 7.9 Hz, 1H), 7.19-7.12 (m, 2H), 6.99-6.92 (m, 3H), 5.35 (t, J = 8.6 Hz, 1H), 3.75-3.67 (m, 4H), 3.61-3.57 (m, 5H), 3.10-2.96 (m, 2H), 2.74-2.64 (m, 4H), 2.51-2.45 (m, 3H), 2.25 (d, J = 7.0 Hz, 2H), 2.09-1.96 (m, 4H), 1.92-1.72 (m, 5H), 1.43 (s, 9H), 1.31-1.22 (m, 2H). |
| 42 | 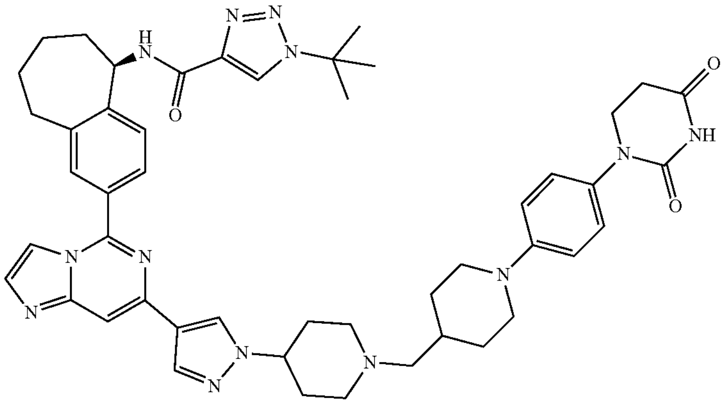 [SMILES: CC(C)(C)n1cc(C(=O)N[C@@H]2CCCCc3cc(-c4nc(-c5cnn(C6CCN(CC7CCN(c8ccc(N9CCC(=O)NC9=O)cc8)CC7)CC6)c5)cc5nccn45)ccc32)nn1] 864.8 | 10.28 (s, 1H), 9.12 (d, J = 8.2 Hz, 1H), 8.77 (s, 1H), 8.45 (s, 1H), 8.15 (s, 1H), 7.97 (s, 1H), 7.88-7.78 (m, 3H), 7.65 (d, J = 1.5 Hz, 1H), 7.49 (d, J = 8.4 Hz, 1H), 7.16 (d, J = 8.7 Hz, 2H), 6.96 (d, J = 8.7 Hz, 2H), 5.36 (d, J = 8.9 Hz, 1H), 4.22 (s, 1H), 3.75-3.67 (m, 4H), 3.06-2.95 (m, 4H), 2.75-2.64 (m, 4H), 2.24 (d, J = 7.1 Hz, 2H), 2.13-1.95 (m, 10H), 1.91-1.80 (m, 4H), 1.69 (s, 9H), 1.41 (s, 1H), 1.28-1.20 (m, 2H). |

-continued
| Compd No. | Structure Observed MS $[M + 1]^+$ | $^1H$ NMR (400 MHz, DMSO-$d^6$) δ (ppm) |
|---|---|---|
| 43 | 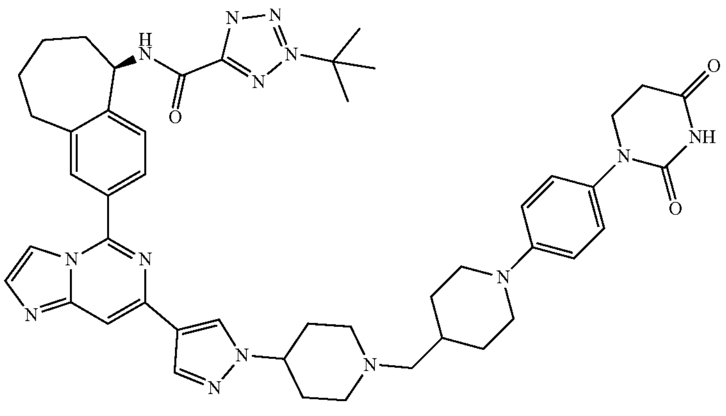 865.8 | 10.27 (s, 1H), 9.71 (d, J = 8.1 Hz, 1H), 8.45 (s, 1H), 8.15 (s, 1H), 7.97 (d, J = 1.6 Hz, 1H), 7.86 (s, 1H), 7.84-7.80 (m, 2H), 7.65 (d, J = 1.4 Hz, 1H), 7.49 (d, J = 8.4 Hz, 1H), 7.16 (d, J = 8.8 Hz, 2H), 6.95 (d, J = 8.5 Hz, 2H), 5.39 (q, J = 11.7, 10.2 Hz, 1H), 4.36-4.13 (m, 1H), 3.76-3.66 (m, 4H), 3.14-2.92 (m, 4H), 2.80-2.58 (m, 4H), 2.31-2.18 (m, 2H), 2.18-1.97 (m, 10H), 1.94-1.81 (m, 4H), 1.69 (s, 9H), 1.94-1.81 (m, 3H). |
| 61 | 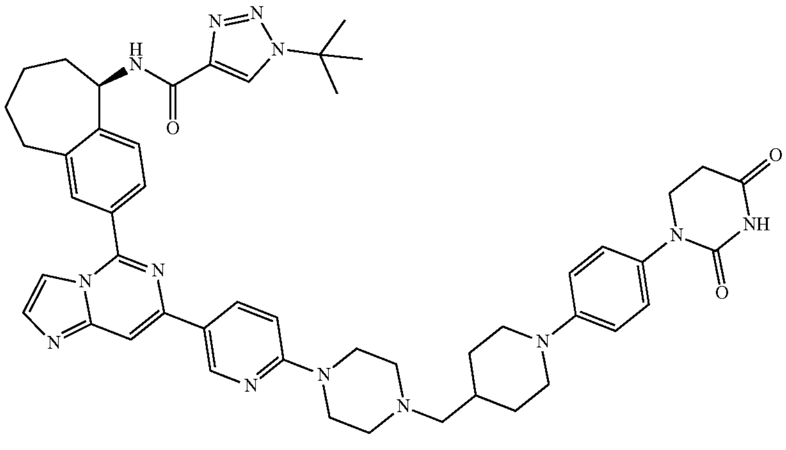 [SMILES: CC(C)(C)n1cc(C(=O)N[C@@H]2CCCCc3cc(-c4nc(-c5ccc(N6CCN(CC7CCN(c8ccc(N9CCC(=O)NC9=O)cc8)CC7)CC6)nc5)cc5nccn45)ccc32)nn1] 876.7 | 10.28 (s, 1H), 9.14 (d, J = 8.2 Hz, 1H), 9.01 (d, J = 2.4 Hz, 1H), 8.77 (s, 1H), 8.35 (dd, J = 9.0, 2.5 Hz, 1H), 8.07 (s, 1H), 8.03 (d, J = 1.4 Hz, 1H), 7.88-7.82 (m, 2H), 7.69 (d, J = 1.5 Hz, 1H), 7.50 (d, J = 8.5 Hz, 1H), 7.16 (d, J = 8.8 Hz, 2H), 6.96 (d, J = 8.9 Hz, 3H), 5.38 (t, J = 8.7 Hz, 1H), 3.76-3.67 (m, 4H), 3.63 (s, 4H), 3.05 (s, 2H), 2.75-2.65 (m, 3H), 2.57 (s, 3H), 2.50 (s, 3H), 2.30-2.21(m, 2H), 2.08-1.96 (m, 2H), 1.93-1.80 (m, 4H), 1.69 (s, 9H), 1.42 (s, 1H), 1.33-1.21 (m, 3H). |

-continued
| Compd No. | Structure Observed MS [M + 1]+ | $^1$H NMR (400 MHz, DMSO-$d^6$) δ (ppm) |
|---|---|---|
| 62 | 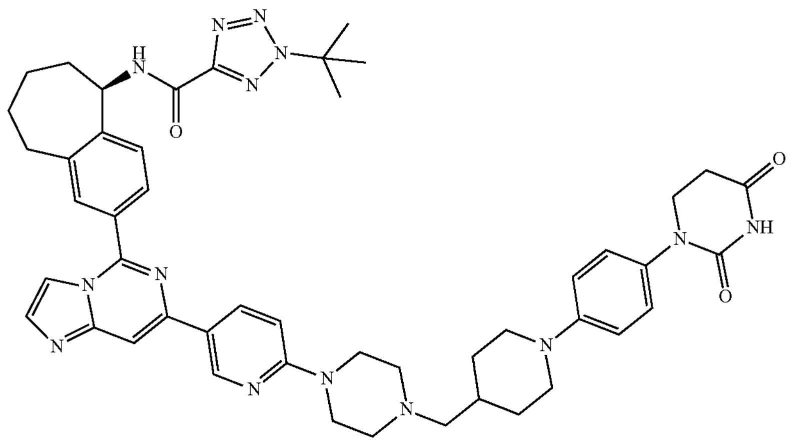 877.8. | 10.28 (s, 1H), 9.73 (d, J = 8.1 Hz, 1H), 9.00 (d, J = 2.4 Hz, 1H), 8.34 (dd, J = 9.0, 2.5 Hz, 1H), 8.05 (d, J = 15.4 Hz, 2H), 7.86 (d, J = 7.1 Hz, 2H), 7.69 (d, J = 1.4 Hz, 1H), 7.50 (d, J = 8.5 Hz, 1H), 7.15 (d, J = 8.9 Hz, 2H), 6.95 (d, J = 8.5 Hz, 3H), 5.41 (t, J = 8.6 Hz, 1H), 3.72 (t, J = 6.7 Hz, 3H), 3.62 (s, 4H), 3.05 (s, 2H), 2.74-2.64 (m, 4H), 2.51-2.44 (m, 4H), 2.24 (d, J = 7.1 Hz, 2H), 2.10-1.94 (m, 5H), 1.90-1.80 (m, 4H), 1.79 (s, 9H), 1.46-1.35 (m, 1H), 1.31-1.20 (m, 2H). |
| 104 | 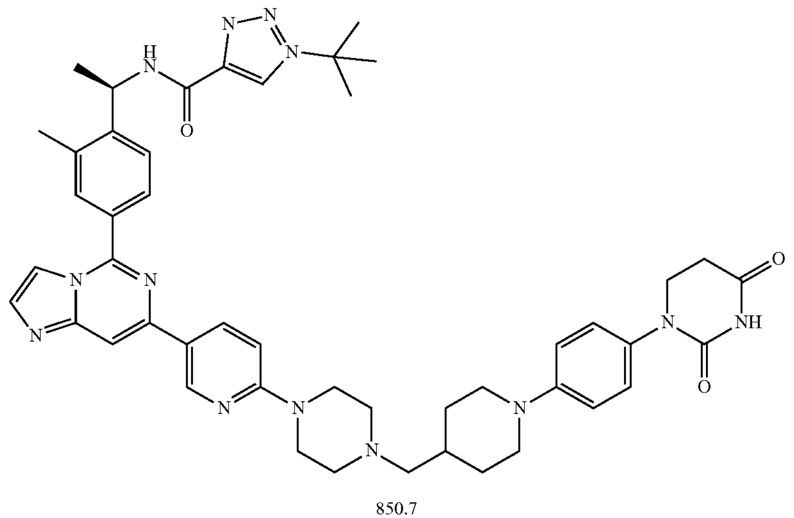 850.7 | 10.28 (s, 1H), 9.06 (d, J = 8.0 Hz, 1H), 9.00 (d, J = 2.4 Hz, 1H), 8.68 (s, 1H), 8.35 (dd, J = 8.9, 2.5 Hz, 1H), 8.07 (s, 1H), 8.04 (s, 1H), 7.91-7.82 (m, 2H), 7.78 (d, J = 8.1 Hz, 1H), 7.69 (d, J = 1.4 Hz, 1H), 7.16 (d, J = 8.8 Hz, 2H), 6.96 (d, J = 8.9 Hz, 3H), 5.46 (p, J = 7.2 Hz, 1H), 3.75-3.67 (m, 4H), 3.64-3.55 (m, 4H), 3.33 (s, 1H), 2.75-2.65 (m, 4H), 2.57 (s, 3H), 2.50 (s, 3H), 2.25 (d, J = 7.1 Hz, 2H), 1.85 (d, J = 12.8 Hz, 2H), 1.78-1.72 (m, 1H), 1.66 (s, 9H), 1.57 (d, J = 6.9 Hz, 3H), 1.32-1.19 (m, 2H). |

-continued
| Compd No. | Structure Observed MS [M + 1]+ | $^1$H NMR (400 MHz, DMSO-d$^6$) δ (ppm) |
|---|---|---|
| 105 | 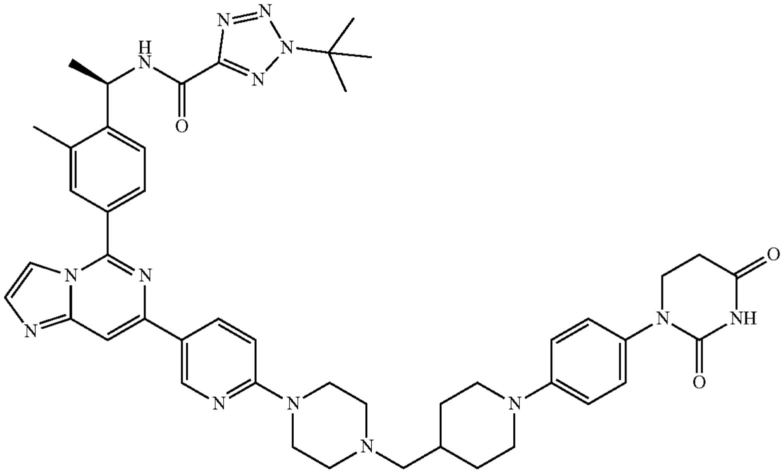 [SMILES: Cc1cc(-c2nc(-c3ccc(N4CCN(CC5CCN(c6ccc(N7CCC(=O)NC7=O)cc6)CC5)CC4)nc3)cc3nccn23)ccc1[C@@H](C)NC(=O)c1nnn(C(C)(C)C)n1] 851.7 | 10.28 (s, 1H), 9.64 (d, J = 7.9 Hz, 1H), 9.00 (d, J = 2.4 Hz, 1H), 8.34 (dd, J = 9.0, 2.5 Hz, 1H), 8.09-8.01 (m, 2H), 7.93-7.83 (m, 2H), 7.77 (d, J = 8.1 Hz, 1H), 7.69 (d, J = 1.4 Hz, 1H), 7.16 (d, J = 8.8 Hz, 2H), 6.96 (d, J = 8.9 Hz, 3H), 5.50-5.42 (m, 1H), 3.76-3.67 (m, 4H), 3.71-3.59 (m, 4H), 2.75-2.65 (m, 4H), 2.57 (s, 3H), 2.25 (d, J = 6.9 Hz, 2H), 1.85 (d, J = 12.8 Hz, 2H), 1.76 (s, 9H), 1.59 (d, J = 7.0 Hz, 3H), 1.33-1.19 (m, 2H). |
| 106 | 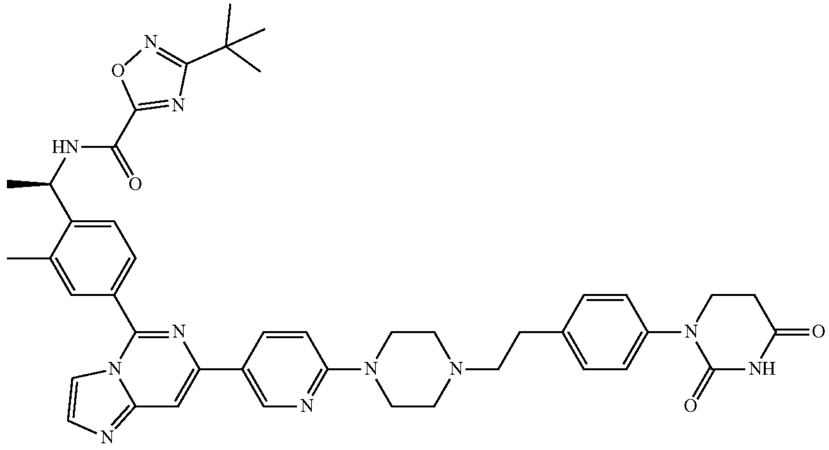 [SMILES: Cc1cc(-c2nc(-c3ccc(N4CCN(CCc5ccc(N6CCC(=O)NC6=O)cc5)CC4)nc3)cc3nccn23)ccc1[C@@H](C)NC(=O)c1nc(C(C)(C)C)no1] 782.6 | 10.36 (s, 1H), 10.02 (d, J = 7.8 Hz, 1H), 9.00 (d, J = 2.6 Hz, 1H), 8.34 (dd, J = 9.0, 2.5 Hz, 1H), 8.07 (s, 1H), 8.03 (d, J = 1.3 Hz, 1H), 7.91 (dd, J = 7.9, 1.9 Hz, 1H), 7.86 (d, J = 1.9 Hz, 1H), 7.75 (d, J = 8.1 Hz, 1H), 7.69 (d, J = 1.4 Hz, 1H), 7.30 (d, J = 8.7 Hz, 2H), 7.26 (d, J = 8.6 Hz, 2H), 6.97 (d, J = 9.1 Hz, 1H), 5.42 (p, J = 7.1 Hz, 1H), 3.78 (t, J = 6.7 Hz, 2H), 3.67-3.54 (m, 4H), 2.82 (t, J = 7.7 Hz, 2H), 2.72 (t, J = 6.7 Hz, 2H), 2.64-2.56 (m, 6H), 2.55 (s, 3H), 1.59 (d, J = 7.0 Hz, 3H), 1.40 (s, 9H). |

-continued
| Compd No. | Structure Observed MS $[M + 1]^+$ | $^1H$ NMR (400 MHz, DMSO-$d^6$) δ (ppm) |
|---|---|---|
| 107 | 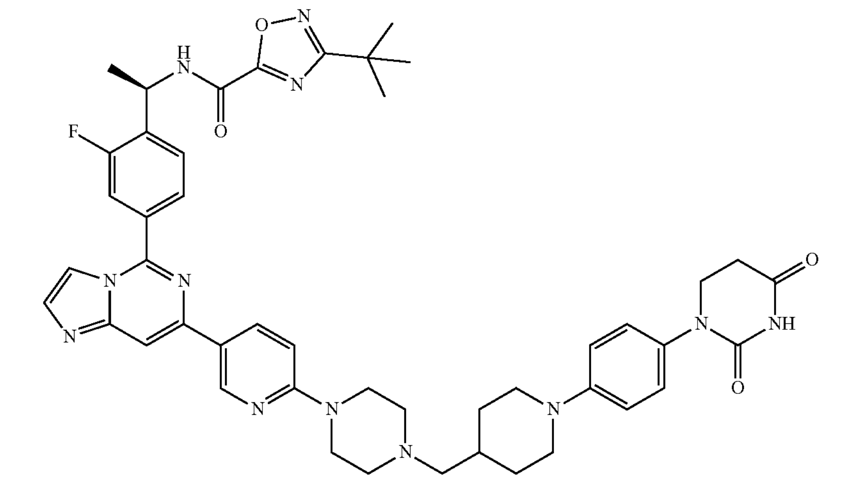 [SMILES: C[C@@H](NC(=O)c1nc(C(C)(C)C)no1)c1ccc(-c2nc(-c3ccc(N4CCN(CC5CCN(c6ccc(N7CCC(=O)NC7=O)cc6)CC5)CC4)nc3)cc3nccn23)cc1F] 855.7 | 10.26 (s, 1H), 10.04 (d, J = 7.7 Hz, 1H), 9.01 (d, J = 2.5 Hz, 1H), 8.35 (dd, J = 9.0, 2.5 Hz, 1H), 8.13-8.05 (m, 2H), 7.98-7.88 (m, 2H), 7.81 (t, J = 7.9 Hz, 1H), 7.72 (d, J = 1.5 Hz, 1H), 7.17 (d, J = 8.9 Hz, 2H), 6.96 (d, J = 9.0 Hz, 3H), 5.54-5.46 (m, 1H), 3.77-3.68 (m, 4H), 3.68-3.59 (m, 4H), 2.76-2.66 (m, 4H), 2.53-2.47 (m, 4H), 2.26 (d, J = 7.1 Hz, 2H), 1.86 (d, J = 12.8 Hz, 2H), 1.79-1.70 (m, 1H), 1.64 (d, J = 7.1 Hz, 3H), 1.42 (s, 9H), 1.35-1.21 (m, 2H). |
| 108 | 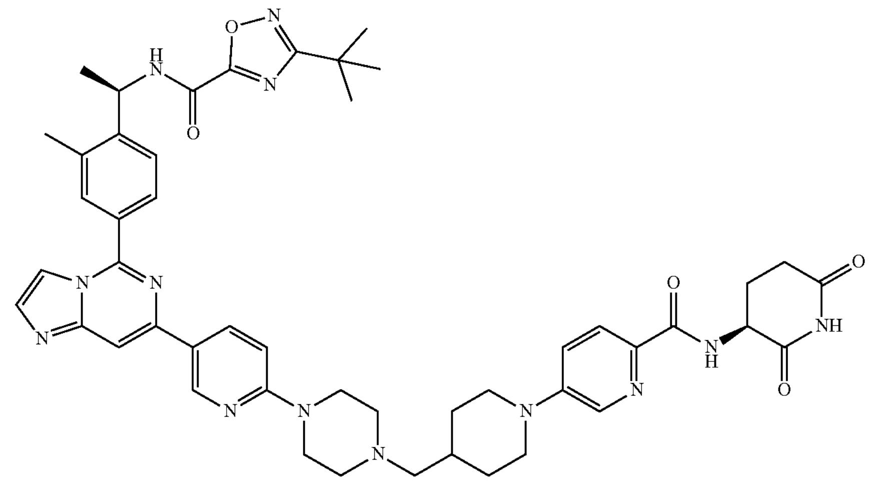 [SMILES: Cc1cc(-c2nc(-c3ccc(N4CCN(CC5CCN(c6ccc(C(=O)N[C@H]7CCC(=O)NC7=O)nc6)CC5)CC4)nc3)cc3nccn23)ccc1[C@@H](C)NC(=O)c1nc(C(C)(C)C)no1] 894.7 | 10.87 (s, 1H), 10.02 (d, J = 7.7 Hz, 1H), 9.00 (d, J = 2.5 Hz, 1H), 8.73 (d, J = 8.3 Hz, 1H), 8.35 (dd, J = 8.4, 2.6 Hz, 2H), 8.08 (s, 1H), 8.04-8.03 (m, 1H), 7.94-7.85 (m, 3H), 7.75 (d, J = 8.0 Hz, 1H), 7.69 (d, J = 1.4 Hz, 1H), 7.43 (dd, J = 8.9, 2.9 Hz, 1H), 6.96 (d, J = 9.1 Hz, 1H), 5.42 (p, J = 7.1 Hz, 1H), 4.85-4.70 (m, 1H), 3.98 (d, J = 12.6 Hz, 2H), 3.63 (s, 4H), 2.91 (t, J = 12.2 Hz, 2H), 2.86-2.75 (m, 1H), 2.56 (s, 3H), 2.52-2.46 (m, 5H), 2.28-2.13 (m, 3H), 2.07-2.00 (m, 1H), 1.87 (d, J = 11.9 Hz, 3H), 1.59 (d, J = 7.0 Hz, 3H), 1.40 (s, 9H), 1.28-1.17 (m, 3H). |

-continued
| Compd No. | Structure Observed MS $[M + 1]^+$ | $^1H$ NMR (400 MHz, DMSO-$d^6$) δ (ppm) |
|---|---|---|
| 110 | 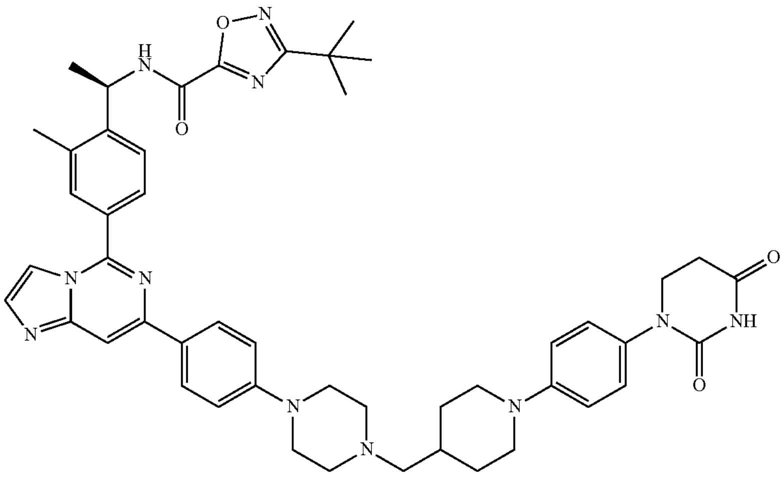 [SMILES: Cc1cc(-c2nc(-c3ccc(N4CCN(CC5CCN(c6ccc(N7CCC(=O)NC7=O)cc6)CC5)CC4)cc3)cc3nccn23)ccc1[C@@H](C)NC(=O)c1nc(C(C)(C)C)no1] 850.7 | |
| 135 | 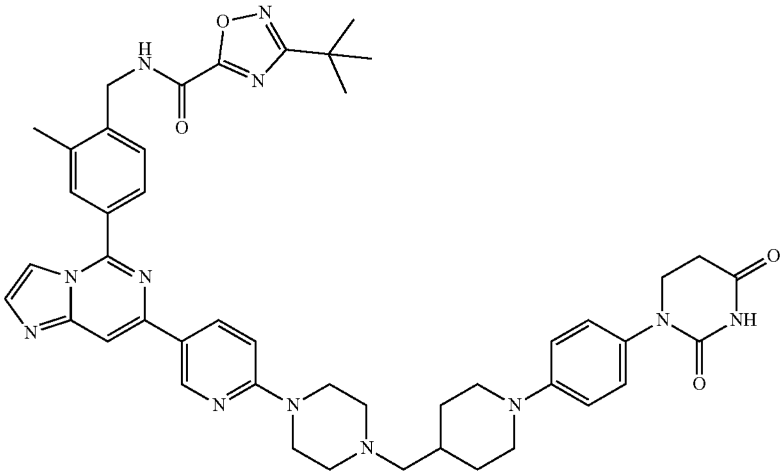 [SMILES: Cc1cc(-c2nc(-c3ccc(N4CCN(CC5CCN(c6ccc(N7CCC(=O)NC7=O)cc6)CC5)CC4)nc3)cc3nccn23)ccc1CNC(=O)c1nc(C(C)(C)C)no1] | 10.27 (s, 1H), 9.95 (t, J = 6.0 Hz, 1H), 9.01 (d, J = 2.5 Hz, 1H), 8.35 (dd, J = 8.9, 2.5 Hz, 1H), 8.08 (s, 1H), 8.01 (d, J = 1.2 Hz, 1H), 7.88 (d, J = 6.7 Hz, 2H), 7.70 (d, J = 1.4 Hz, 1H), 7.56 (d, J = 8.5 Hz, 1H), 7.16 (d, J = 8.9 Hz, 2H), 6.99-6.93 (m, 3H), 4.61 (d, J = 5.9 Hz, 2H), 3.73 (t, J = 6.7 Hz, 4H), 3.64-3.55 (m, 4H), 3.34-3.29 (m, 2H), 2.75-2.65 (m, 3H), 2.56-2.53 (m, 3H), 2.51 (s, 3H), 2.26 (d, J = 7.0 Hz, 2H), 1.86 (d, J = 12.7 Hz, 2H), 1.81-1.69 (m, 1H), 1.41 (s, 9H), 1.33-1.21 (m, 2H). |

-continued
| Compd No. | Structure Observed MS [M + 1]+ | $^1$H NMR (400 MHz, DMSO-d$^6$) δ (ppm) |
|---|---|---|
| 136 | 837.7 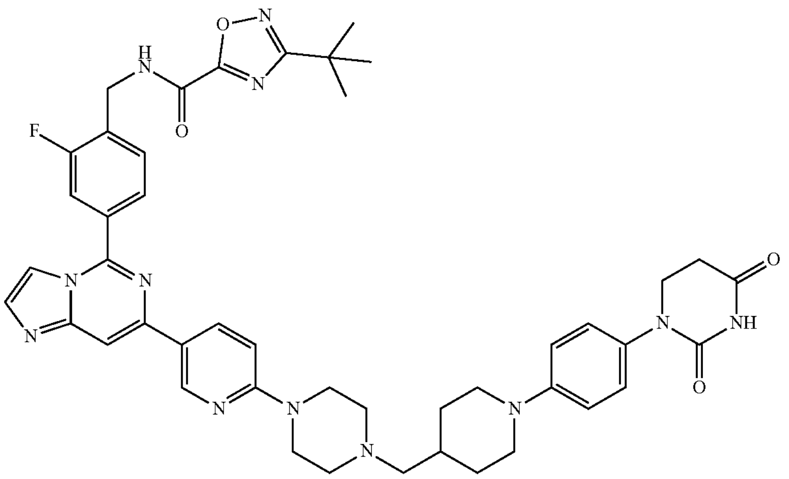 | 10.27 (s, 1H), 10.00 (t, J = 6.0 Hz, 1H), 9.01 (d, J = 2.5 Hz, 1H), 8.35 (dd, J = 9.0, 2.5 Hz, 1H), 8.12 (s, 1H), 8.05 (d, J = 1.2 Hz, 1H), 7.96-7.87 (m, 2H), 7.75-7.66 (m, 2H), 7.16 (d, J = 8.8 Hz, 2H), 6.96 (d, J = 9.0 Hz, 3H), 4.67 (d, J = 5.9 Hz, 2H), 3.77-3.66 (m, 4H), 3.64-3.55 (m, 4H), 3.33-3.30 (m, 2H), 2.76-2.64 (m, 3H), 2.51-2.45 (m, 3H), 2.26 (d, J = 6.9 Hz, 2H), 1.86 (d, J = 13.0 Hz, 2H), 1.80-1.70 (m, 1H), 1.41 (s, 9H), 1.33-1.20 (m, 2H). |
| 137 | 841.7 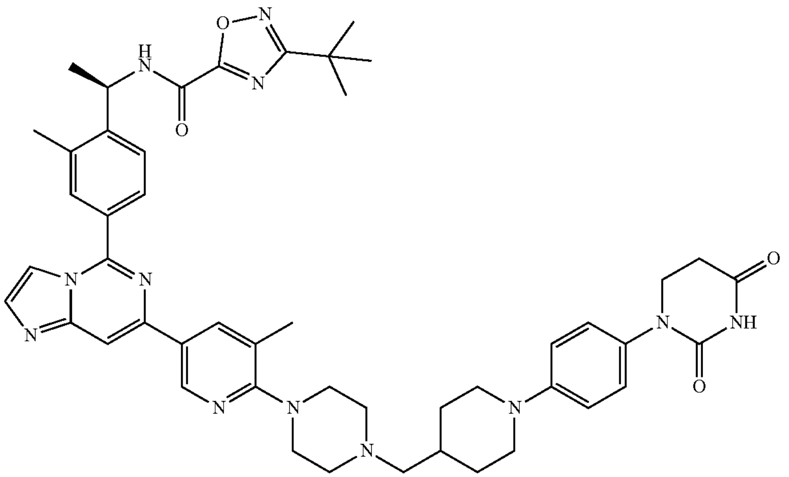 [SMILES: Cc1cc(-c2nc(-c3cnc(N4CCN(CC5CCN(c6ccc(N7CCC(=O)NC7=O)cc6)CC5)CC4)c(C)c3)cc3nccn23)ccc1[C@@H](C)NC(=O)c1nc(C(C)(C)C)no1] | 10.24 (s, 1H), 9.98 (d, J = 7.6 Hz, 1H), 8.93 (d, J = 2.0 Hz, 1H), 8.27 (d, J = 2.0 Hz, 1H), 8.14 (s, 1H), 8.04 (s, 1H), 7.90-7.85 (m, 2H), 7.74-7.70 (m, 2H), 7.13 (d, J = 8.8 Hz, 2H), 6.93 (d, J = 8.8 Hz, 2H), 5.43-5.36 (m, 1H), 3.71-3.67 (m, 4H), 3.20-3.14 (m, 4H), 2.75-2.61 (m, 4H), 2.56-2.51 (m, 7H), 2.32 (s, 3H), 2.24 (d, J = 6.8 Hz, 2H), 1.88-1.67 (m, 3H), 1.56 (d, J = 6.8 Hz, 3H), 1.37 (s, 9H), 1.27-1.19 (m, 2H). |

-continued
| Compd No. | Structure Observed MS $[M + 1]^+$ | $^1H$ NMR (400 MHz, DMSO-$d^6$) δ (ppm) |
|---|---|---|
| 138 | 865.75 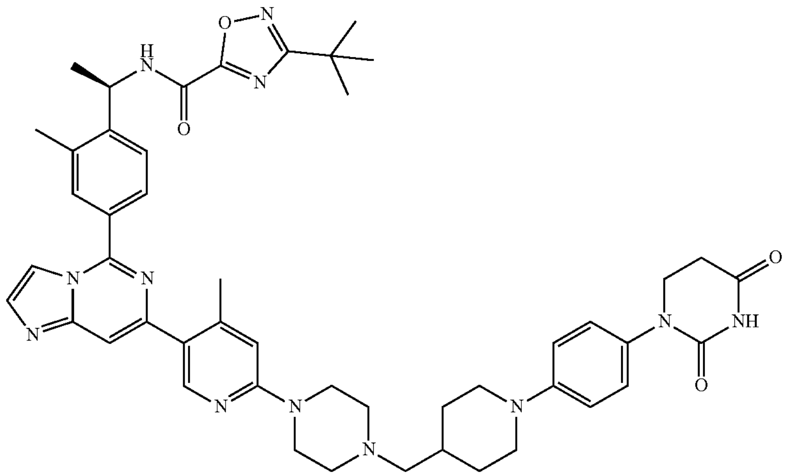 865.75 | 10.25 (s, 1H), 9.97 (d, J = 8.0 Hz, 1H), 8.33 (s, 1H), 8.04 (s, 1H), 8.01 (s, 1H), 7.84 (d, J = 8.4 Hz, 1H), 7.79 (s, 1H), 7.72-7.67 (m, 3H), 7.13 (d, J = 8.8 Hz, 2H), 6.92 (d, J = 8.8 Hz, 2H), 6.78 (s, 1H), 5.42-5.35 (m, 1H), 3.71-3.67 (m, 4H), 3.58-3.54 (m, 4H), 3.32-3.29 (m, 1H), 2.69-2.64 (m, 4H), 2.50 (s, 3H), 2.49-2.44 (m, 5H), 2.21 (d, J = 6.8 Hz, 2H), 1.83-1.71 (m, 3H), 1.54 (d, J = 7.2 Hz, 3H), 1.37 (s, 9H), 1.28-1.19 (m, 2H). |

-continued
| Compd No. | Structure Observed MS $[M + 1]^+$ | $^1H$ NMR (400 MHz, DMSO-$d^6$) δ (ppm) |
|---|---|---|
| 139 | 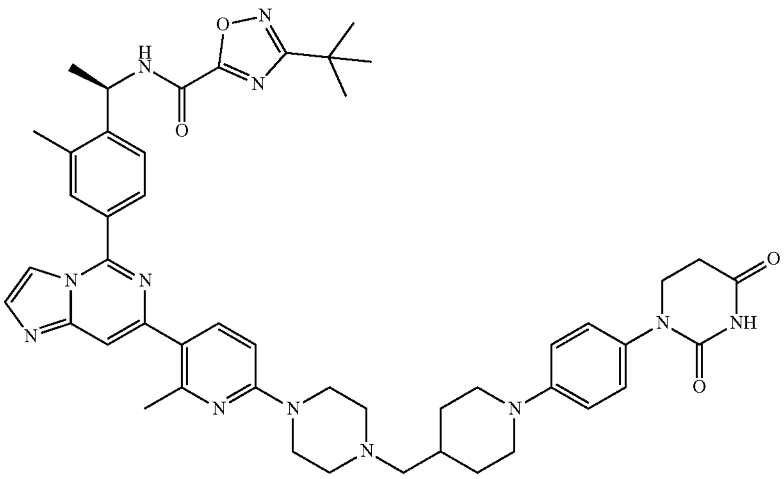 [SMILES: Cc1cc(-c2nc(-c3ccc(N4CCN(CC5CCN(c6ccc(N7CCC(=O)NC7=O)cc6)CC5)CC4)nc3C)cc3nccn23)ccc1[C@@H](C)NC(=O)c1nc(C(C)(C)C)no1] 865.71 | |
| 161 | 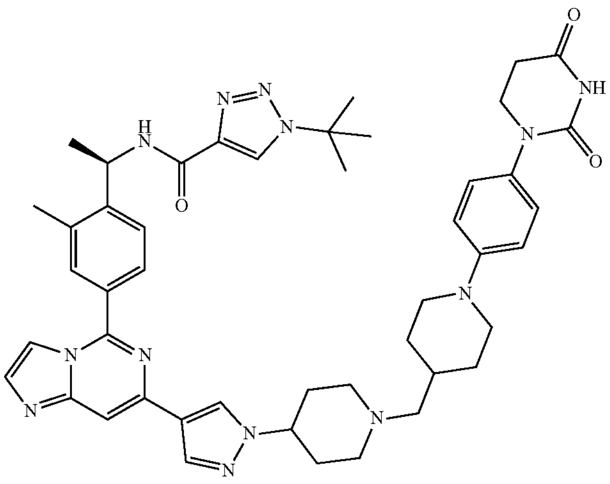 [SMILES: Cc1cc(-c2nc(-c3cnn(C4CCN(CC5CCN(c6ccc(N7CCC(=O)NC7=O)cc6)CC5)CC4)c3)cc3nccn23)ccc1[C@@H](C)NC(=O)c1cn(C(C)(C)C)nn1] | 10.28 (s, 1H), 9.06 (d, J = 8.0 Hz, 1H), 8.67 (s, 1H), 8.46 (s, 1H), 8.15 (s, 1H), 7.98 (s, 1H), 7.88-7.73 (m, 4H), 7.64 (d, J = 1.4 Hz, 1H), 7.16 (d, J = 8.9 Hz, 2H), 6.96 (d, J = 8.9 Hz, 2H), 5.48-5.39 (m, 1H), 4.26-4.15 (m, 1H), 3.72 (t, J = 6.7 Hz, 3H), 3.33 (s, 2H), 2.98 (d, J = 10.0 Hz, 2H), 2.75-2.64 (m, 4H), 2.56 (s, 3H), 2.24 (d, J = 7.1 Hz, 2H), 2.14-1.98 (m, 6H), 1.84 (d, J = 12.8 Hz, 2H), 1.66 (s, 9H), 1.56 (d, J = 7.0 Hz, 3H), 1.31-1.17 (m, 2H). |

-continued
| Compd No. | Structure Observed MS $[M + 1]^+$ | $^1H$ NMR (400 MHz, DMSO-$d^6$) δ (ppm) |
|---|---|---|
| | 838.7 | |
| 162 | 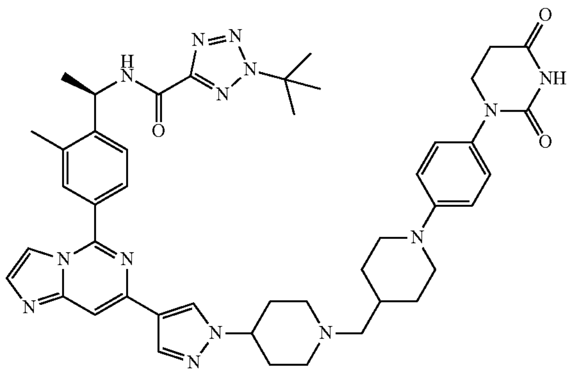 [SMILES: Cc1cc(-c2nc(-c3cnn(C4CCN(CC5CCN(c6ccc(N7CCC(=O)NC7=O)cc6)CC5)CC4)c3)cc3nccn23)ccc1[C@@H](C)NC(=O)c1nnn(C(C)(C)C)n1] 839.7 | 10.16 (s, 1H), 9.52 (d, J = 7.9 Hz, 1H), 8.34 (s, 1H), 8.03 (s, 1H), 7.86 (s, 1H), 7.76-7.68 (m, 3H), 7.63 (d, J = 8.1 Hz, 1H), 7.53 (d, J = 1.4 Hz, 1H), 7.07-7.00 (m, 2H), 6.84 (d, J = 9.0 Hz, 2H), 5.35 (p, J = 7.2 Hz, 1H), 4.10 (s, 1H), 3.64-3.55 (m, 4H), 3.22 (d, J = 11.7 Hz, 2H), 2.86 (d, J = 10.1 Hz, 2H), 2.63-2.52 (m, 4H), 2.45 (s, 3H), 2.12 (d, J = 7.1 Hz, 2H), 2.04-1.84 (m, 5H), 1.71 (d, J = 12.7 Hz, 2H), 1.64 (s, 9H), 1.47 (d, J = 7.0 Hz, 3H), 1.18-1.06 (m, 2H). |
| 163 | 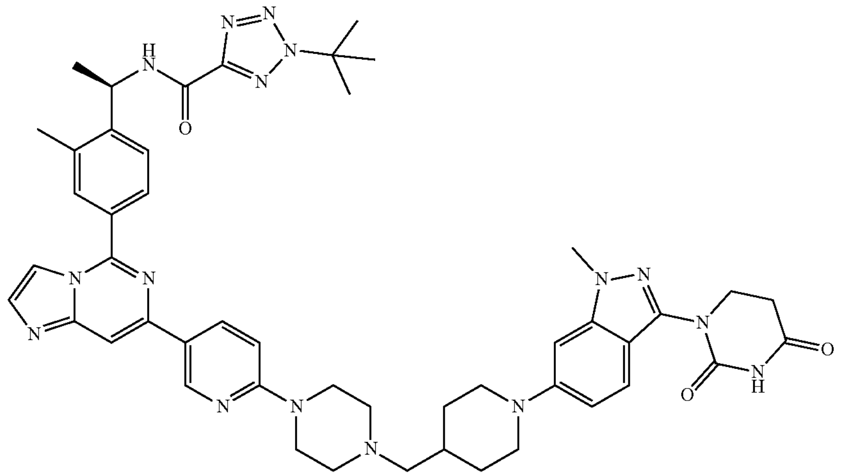 [SMILES: Cc1cc(-c2nc(-c3ccc(N4CCN(CC5CCN(c6ccc7c(N8CCC(=O)NC8=O)nn(C)c7c6)CC5)CC4)nc3)cc3nccn23)ccc1[C@@H](C)NC(=O)c1nnn(C(C)(C)C)n1] 905.7 | 10.53 (s, 1H), 9.65 (d, J = 7.9 Hz, 1H), 9.01 (d, J = 2.5 Hz, 1H), 8.35 (dd, J = 9.0, 2.5 Hz, 1H), 8.10-8.01 (m, 2H), 7.90 (dd, J = 7.9, 1.9 Hz, 1H), 7.86 (d, J = 1.9 Hz, 1H), 7.77 (d, J = 8.1 Hz, 1H), 7.69 (d, J = 1.5 Hz, 1H), 7.46 (d, J = 9.1 Hz, 1H), 6.99-6.90 (m, 2H), 6.84 (d, J = 1.9 Hz, 1H), 5.48 (p, J = 7.1 Hz, 1H), 3.92 (t, J = 6.7 Hz, 2H), 3.91 (s, 3H), 3.84 (d, J = 12.3 Hz, 2H), 3.64-3.55 (m, 4H), 3.36 (s, 1H), 3.36-3.35 (m, 1H), 2.84-2.73 (m, 3H), 2.57 (s, 3H), 2.51 (s, 2H), 2.26 (d, J = 6.9 Hz, 2H), 2.07-1.96 (m, 1H), 1.91-1.80 (m, 3H), 1.76 (s, 9H), 1.59 (d, J = 7.0 Hz, 3H), 1.34-1.24 (m, 2H). |

-continued
| Compd No. | Structure Observed MS $[M + 1]^+$ | $^1H$ NMR (400 MHz, DMSO-$d^6$) δ (ppm) |
|---|---|---|
| 164 | 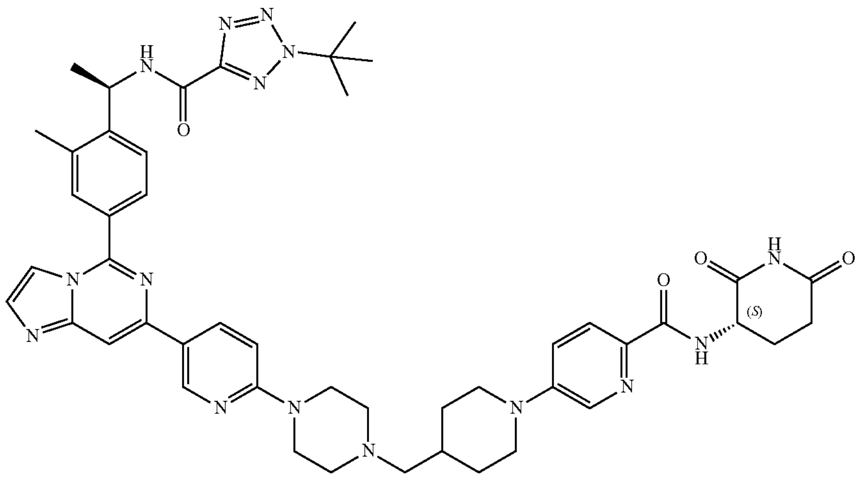 894.7 | 10.87 (s, 1H), 9.65 (d, J = 7.9 Hz, 1H), 9.01 (d, J = 2.4 Hz, 1H), 8.73 (d, J = 8.2 Hz, 1H), 8.38-8.32 (m, 2H), 8.08 (s, 1H), 8.04 (s, 1H), 7.93-7.84 (m, 3H), 7.77 (d, J = 8.1 Hz, 1H), 7.69 (d, J = 1.4 Hz, 1H), 7.44 (dd, J = 8.9, 2.8 Hz, 1H), 6.96 (d, J = 9.1 Hz, 1H), 5.48 (p, J = 7.1 Hz, 1H), 4.85-4.71 (m, 1H), 3.98 (d, J = 12.4 Hz, 2H), 3.64-3.55 (m, 4H), 3.34-3.31 (m, 2H), 2.91 (t, J = 12.2 Hz, 2H), 2.87-2.75 (m, 1H), 2.58 (s, 3H), 2.51-2.45 (m, 2H), 2.30-2.14 (m, 2H), 2.11-1.98 (m, 1H), 1.96-1.83 (m, 3H), 1.76 (s, 9H), 1.59 (d, J = 7.0 Hz, 3H), 1.31-1.16 (m, 2H). |
| 165 | 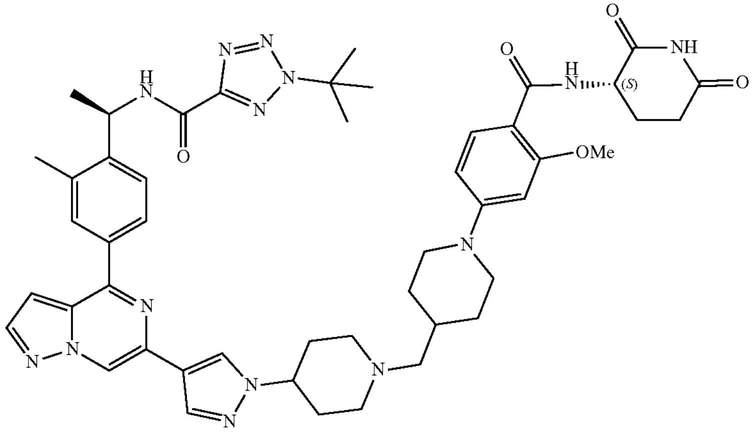 911.2 | |

-continued
| Compd No. | Structure Observed MS $[M + 1]^+$ | $^1H$ NMR (400 MHz, DMSO-$d^6$) δ (ppm) |
|---|---|---|
| 168 | 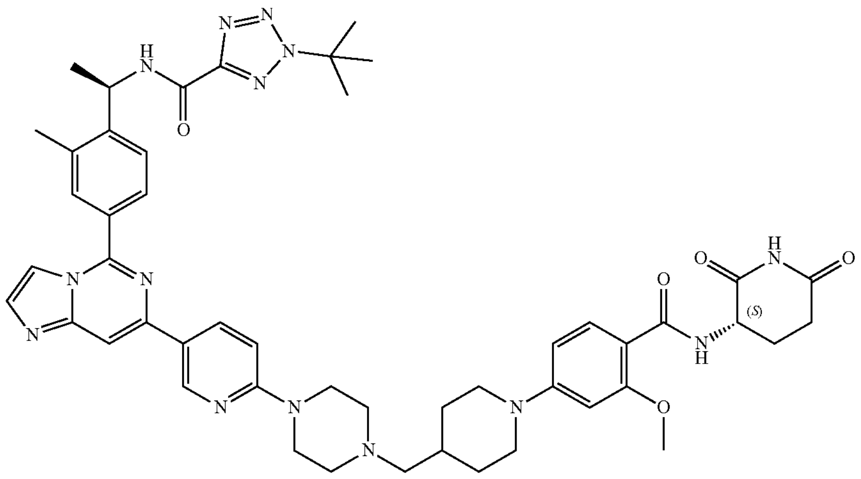 923.7 | |
| 188 | 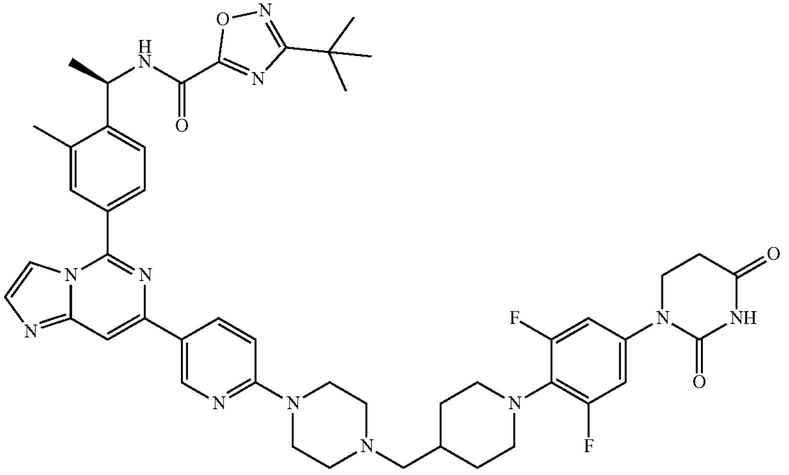 [SMILES: Cc1cc(-c2nc(-c3ccc(N4CCN(CC5CCN(c6c(F)cc(N7CCC(=O)NC7=O)cc6F)CC5)CC4)nc3)cc3nccn23)ccc1[C@@H](C)NC(=O)c1nc(C(C)(C)C)no1] 887.71 | 10.45 (s, 1H), 9.99 (d, J = 7.6 Hz, 1H), 8.97 (d, J = 2.0 Hz, 1H), 8.33-8.30 (m, 1H), 8.05-8.01 (m, 2H), 7.89-7.84 (m, 2H), 7.73-7.66 (m, 2H), 7.11-7.04 (m, 2H), 6.92 (d, J = 9.2 Hz, 1H), 5.44-5.36 (m, 1H), 3.76 (t, J = 6.4 Hz, 2H), 3.72-3.57 (m, 4H), 3.17-3.04 (m, 4H), 2.68 (t, J = 6.4 Hz, 2H), 2.53 (s, 3H), 2.49-2.45 (m, 4H), 2.24-2.22 (m, 2H), 1.81-1.71 (m, 3H), 1.56 (d, J = 7.2 Hz, 3H), 1.37 (s, 9H), 1.29-1.21 (m, 2H). |

-continued
| Compd No. | Structure Observed MS [M + 1]+ | $^1H$ NMR (400 MHz, DMSO-$d^6$) δ (ppm) |
|---|---|---|
| 189 | 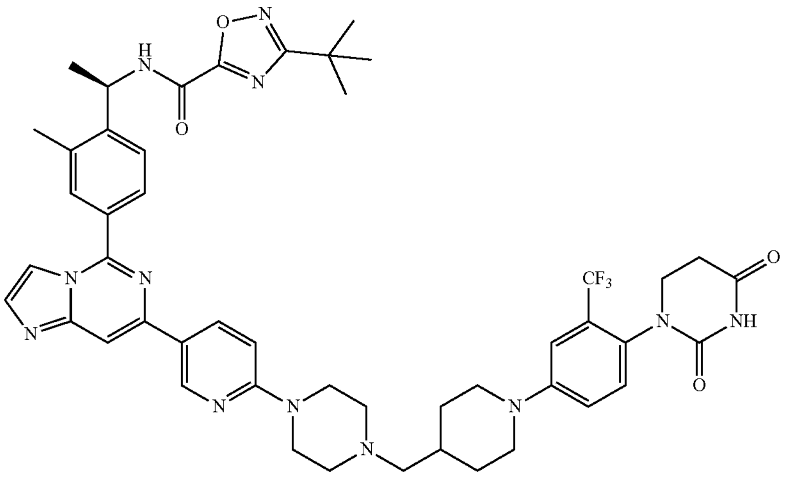 919.74 | 10.38 (s,1H), 9.99 (d, J = 7.6 Hz,1H), 8.97 (d, J = 1.6 Hz,1H), 8.33-8.30 (m, 1H), 8.05-8.01 (m, 2H), 7.89-7.83 (m, 2H), 7.73-7.66 (m, 2H), 7.36 (d, J = 8.8 Hz,1H), 7.25-7.22 (dd, J = 8.8 Hz, 2.4 Hz, 1H), 7.15 (d, J = 2.8 Hz, 1H), 6.92 (d, J = 8.8 Hz, 1H), 5.43-5.34 (m, 1H), 3.83-3.74 (m, 3H), 3.61-3.57 (m, 4H), 338-3.26 (m, 1H), 2.82-2.77 (m, 2H), 2.66-2.63 (m, 2H), 2.53 (s, 3H), 2.49-2.45 (m, 4H), 2.23-2.21 (m, 2H), 1.85-1.76 (m, 3H), 1.56 (d, J = 7.8 Hz, 3H), 1.37 (s, 9H), 1.26-1.20 (m, 2H). |
| 190 | 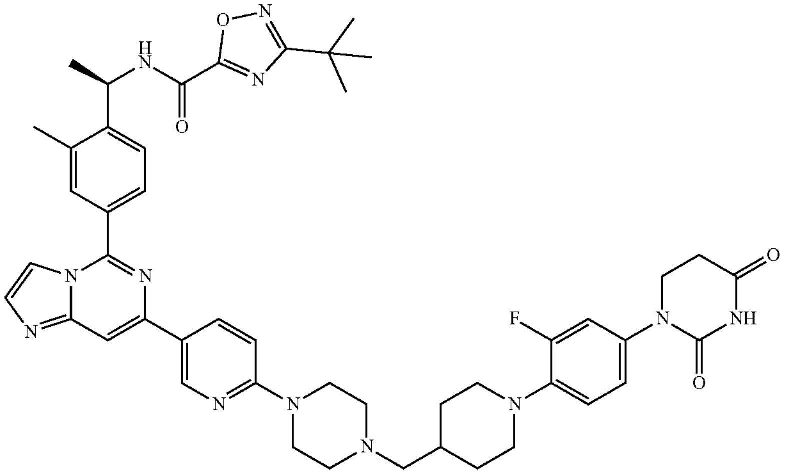 [SMILES: Cc1cc(-c2nc(-c3ccc(N4CCN(CC5CCN(c6ccc(N7CCC(=O)NC7=O)cc6F)CC5)CC4)nc3)cc3nccn23)ccc1[C@@H](C)NC(=O)c1nc(C(C)(C)C)no1] | 10.36 (s, 1H), 9.99 (d, J = 7.6 Hz, 1H), 8.97 (d, J = 1.6 Hz, 1H), 8.33-8.30 (dd, J = 8.8, 2.4 Hz, 1H), 8.05 (s, 1H), 8.01 (s, 1H), 7.88 (d, J = 8.4 Hz, 1H), 7.83 (s, 1H), 7.72 (d, J = 8.0 Hz, 1H), 7.66 (d, J = 1.2 Hz, 1H), 7.18-7.14 (m, 1H), 7.07-7.01 (m, 2H), 6.93 (d, J = 9.2 Hz, 1H), 5.43-5.36 (m, 1H), 3.74 (t, J = 6.4 Hz, 2H), 3.62-3.57 (m, 4H), 3.36-3.29 (m, 2H), 2.70-2.64 (m, 4H), 2.53 (s, 3H), 2.49-2.46 (m, 4H), 2.24 (d, J = 7.2 Hz, 2H), 1.83 (d, J = 7.2 Hz, 2H), 1.74-1.66 (m, 1H), 1.56 (d, J = 6.8 Hz, 3H), 1.37 (s, 9H), 1.34-1.26 (m, 2H). |

-continued
| Compd No. | Structure Observed MS $[M + 1]^+$ | $^1H$ NMR (400 MHz, DMSO-$d^6$) δ (ppm) |
|---|---|---|
| 191 | 869.73 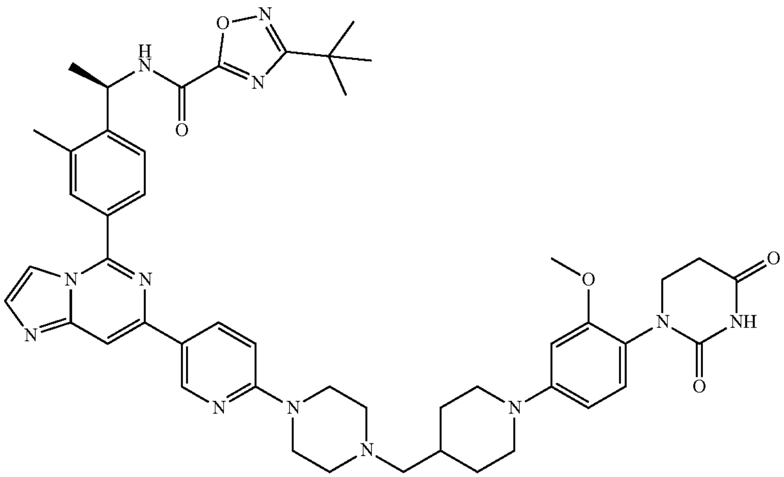 [SMILES: COc1cc(N2CCC(CN3CCN(c4ccc(-c5cc6nccn6c(-c6ccc([C@@H](C)NC(=O)c7nc(C(C)(C)C)no7)c(C)c6)n5)cn4)CC3)CC2)ccc1N1CCC(=O)NC1=O] | 10.19 (s,1H), 9.99 (d, J = 7.6 Hz, 1H), 8.97 (d, J = 1.6 Hz, 1H), 8.33-8.30 (dd, J = 9.2, 2.4 Hz, 1H), 8.05 (s, 1H), 8.01 (s, 1H), 7.88 (d, J = 8.0 Hz, 1H), 7.84 (s, 1H), 7.72 (d, J = 8.0 Hz, 1H), 7.66 (d, J = 1.6 Hz, 1H), 7.01 (d, J = 8.8 Hz, 1H), 6.92 (d, J = 8.8 Hz, 1H), 6.58 (d, J = 2.0 Hz, 1H), 6.49-6.47 (dd, J = 8.8, 2.0 Hz, 1H), 5.43-5.36 (m, 1H), 3.77-3.72 (m, 5H), 3.62-3.57 (m, 4H), 3.50 (t, J = 6.4 Hz, 2H), 2.74-2.62 (m, 4H), 2.53 (s, 3H), 2.49-2.45 (m, 4H), 2.22 (d, J = 6.8 Hz, 2H), 1.82 (d, J = 6.8 Hz, 2H), 1.77-1.72 (m, 1H), 1.56 (d, J = 7.2 Hz, 3H), 1.37 (s, 9H), 1.27-1.19 (m, 2H). |
| 192 | 881.75 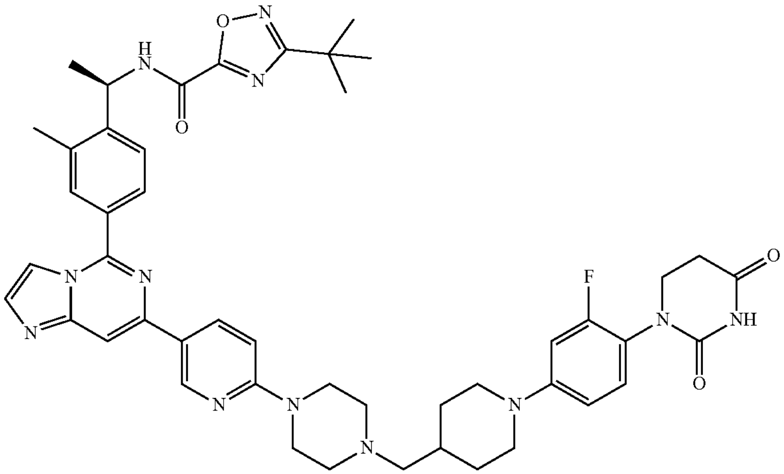 | 10.36 (s,1H), 9.99 (d, J = 8.0 Hz,1H), 8.97 (d, J = 1.6 Hz, 1H), 8.33-8.30 (dd, J = 9.2, 2.4 Hz, 1H), 8.05 (s, 1H), 8.01 (s, 1H), 7.90-7.87 (dd, J = 8.0, 1.6 Hz, 1H), 7.84 (s, 1H), 7.72 (d, J = 8.0 Hz, 1H), 7.66 (d, J = 1.2 Hz, 1H), 7.18 (t, J = 8.8 Hz, 1H), 6.92 (d, J = 8.8 Hz, 1H), 6.82-6.74 (m, 2H), 5.43-5.36 (m, 1H), 3.76-3.73 (m, 2H), 3.64-3.60 (m, 6H), 2.76-2.60 (m, 4H), 2.53 (s, 3H), 2.49-2.45 (m, 4H), 2.21 (d, J = 6.4 Hz, 2H), 1.82-1.74 (m, 3H), 1.56 (d, J = 6.8 Hz, 3H), 1.37 (s, 9H), 1.23-1.16 (m, 2H). |

-continued
| Compd No. | Structure Observed MS $[M + 1]^+$ | $^1H$ NMR (400 MHz, DMSO-$d^6$) δ (ppm) |
|---|---|---|
| | 869.69 | |
| 194 | 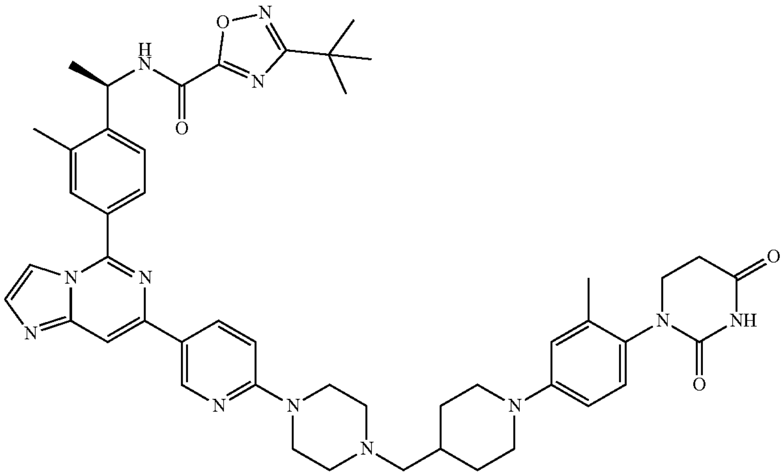 865.75 | 10.23 (s, 1H), 9.98 (d, J = 8.0 Hz, 1H), 8.97 (d, J = 2.0 Hz, 1H), 8.33-8.30 (dd, J = 9.2, 2.4 Hz, 1H), 8.05 (s, 1H), 8.01 (s, 1H), 7.88 (d, J = 8.0 Hz, 1H), 7.84 (s, 1H), 7.72 (d, J = 8.0 Hz, 1H), 7.66 (d, J = 1.2 Hz, 1H), 7.03 (d, J = 8.8 Hz, 1H), 6.92 (d, J = 9.2 Hz, 1H), 6.81-6.75 (m, 2H), 5.43-5.36 (m, 1H), 3.71-3.60 (m, 7H), 3.49-3.43 (m, 1H), 2.72-2.64 (m, 4H), 2.53 (s, 3H), 2.49-2.45 (m, 4H), 2.21 (d, J = 6.8 Hz, 2H), 2.12 (s, 3H), 1.83-1.72 (m, 3H), 1.56 (d, J = 7.2 Hz, 3H), 1.37 (s, 9H), 1.27-1.18 (m, 2H). |

-continued
| Compd No. | Structure Observed MS $[M + 1]^+$ | $^1H$ NMR (400 MHz, DMSO-$d^6$) δ (ppm) |
|---|---|---|
| 196 | 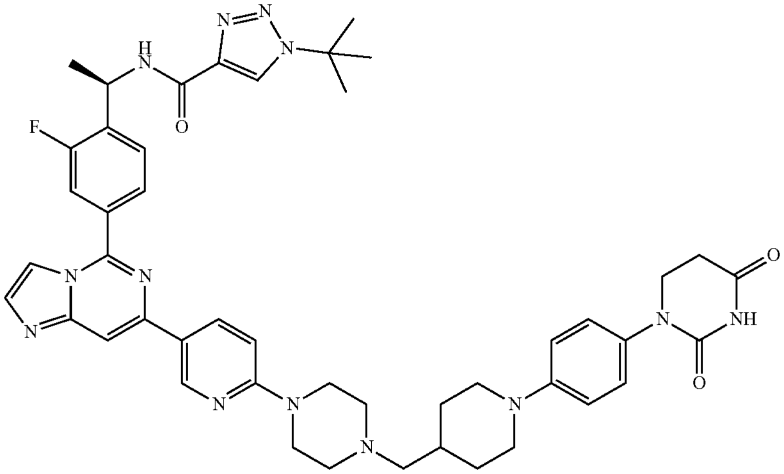 854.8 | 10.27 (s, 1H), 9.13 (d, J = 8.1 Hz, 1H), 9.00 (d, J = 2.5 Hz, 1H), 8.71 (s, 1H), 8.35 (dd, J = 9.0, 2.6 Hz, 1H), 8.13-8.05 (m, 2H), 7.94-7.85 (m, 2H), 7.80 (t, J = 8.0 Hz, 1H), 7.70 (d, J = 1.5 Hz, 1H), 7.19-7.12 (m, 2H), 6.95 (dd, J = 9.1, 1.8 Hz, 3H), 5.54 (p, J = 7.2 Hz, 1H), 3.74-3.68 (m, 4H), 3.64-3.55 (m, 4H), 2.76-2.64 (m, 4H), 2.51-2.47 (m, 4H), 2.25 (d, J = 7.1 Hz, 2H), 1.85 (d, J = 13.0 Hz, 2H), 1.79-1.71 (m, 1H), 1.67 (s, 9H), 1.61 (d, J = 7.1 Hz, 3H), 1.31-1.20 (m, 2H). |
| 197 | 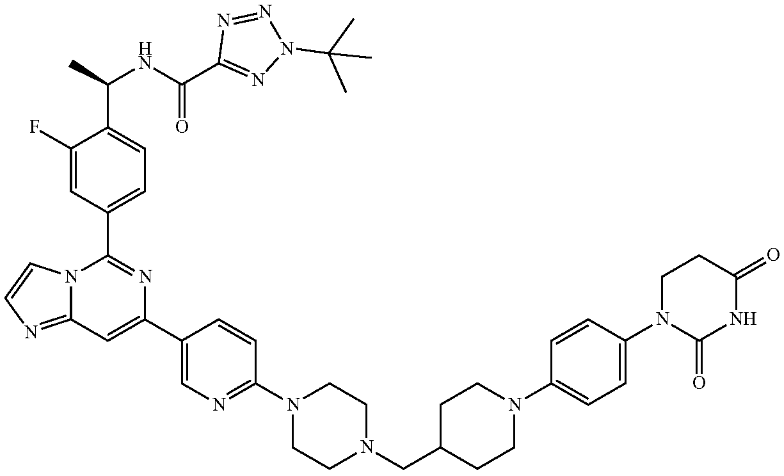 [SMILES: C[C@@H](NC(=O)c1nnn(C(C)(C)C)n1)c1ccc(-c2nc(-c3ccc(N4CCN(CC5CCN(c6ccc(N7CCC(=O)NC7=O)cc6)CC5)CC4)nc3)cc3nccn23)cc1F] 855.8 | 10.28 (s, 1H), 9.70 (d, J = 7.9 Hz, 1H), 9.00 (d, J = 2.5 Hz, 1H), 8.35 (dd, J = 9.0, 2.5 Hz, 1H), 8.14-8.05 (m, 2H), 7.92 (ddd, J = 9.5, 6.6, 1.7 Hz, 2H), 7.80 (t, J = 7.9 Hz, 1H), 7.71 (d, J = 1.5 Hz, 1H), 7.19-7.12 (m, 2H), 6.99-6.92 (m, 3H), 5.61-5.52 (m, 1H), 3.76-3.67 (m, 3H), 3.65-3.59 (m, 4H), 3.35-3.29 (m, 2H), 2.75-2.64 (m, 4H), 2.51-2.46 (m, 4H), 2.25 (d, J = 7.1 Hz, 2H), 1.85 (d, J = 12.5 Hz, 2H), 1.77 (s, 9H), 1.63 (d, J = 7.1 Hz, 3H), 1.32-1.19 (m, 2H). |

-continued
| Compd No. | Structure Observed MS [M + 1]+ | $^1H$ NMR (400 MHz, DMSO-$d^6$) δ (ppm) |
|---|---|---|
| 210 | 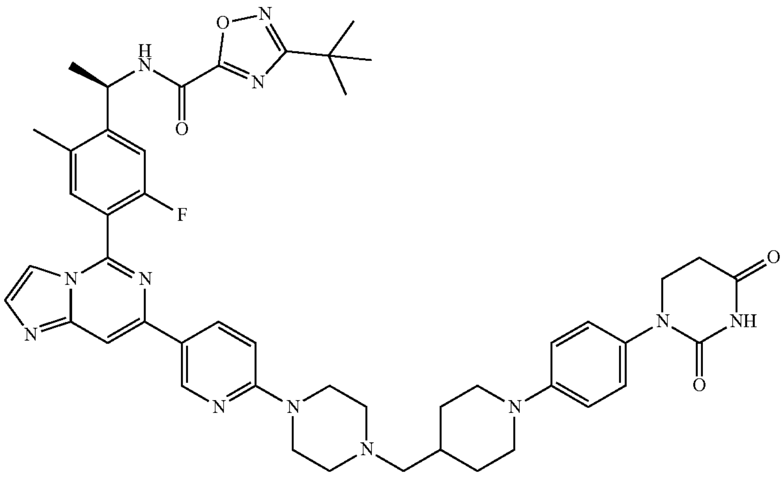 [SMILES: Cc1cc(-c2nc(-c3ccc(N4CCN(CC5CCN(c6ccc(N7CCC(=O)NC7=O)cc6)CC5)CC4)nc3)cc3nccn23)c(F)cc1[C@@H](C)NC(=O)c1nc(C(C)(C)C)no1] 869.69 | 10.25 (s, 1H), 9.95 (d, J = 8.0 Hz, 1H), 8.93 (d, J = 2.4 Hz, 1H), 8.28 (dd, J = 8.8, 2.4 Hz, 1H), 8.13 (s, 1H), 7.71 (d, J = 6.8 Hz, 1H), 7.66-7.58 (m, 3H), 7.13 (d, J = 8.8 Hz, 2H), 6.94-6.91 (m, 3H), 5.41-5.34 (m, 1H), 3.71-3.60 (m, 8H), 3.32-3.29 (m, 1H), 2.69-2.64 (m, 4H), 2.49-2.45 (m, 6H), 2.21 (d, J = 6.8 Hz, 2H), 1.83-1.72 (m, 3H), 1.56 (d, J = 7.2 Hz, 3H), 1.38 (s, 9H), 1.27-1.18 (m, 2H). |
| 212 | 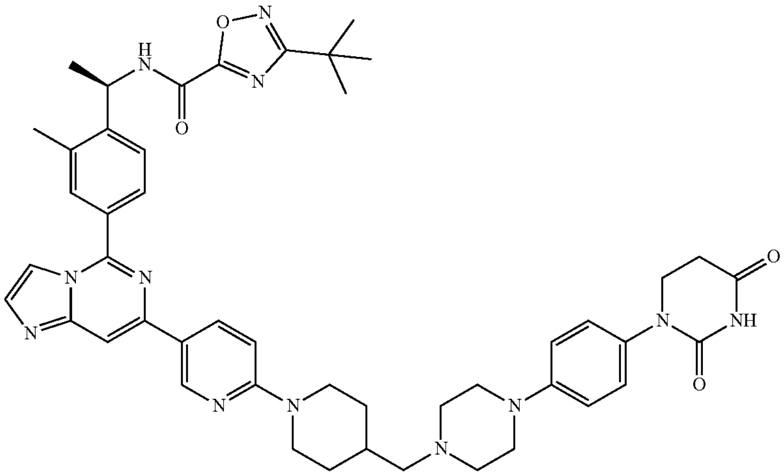 | 10.24 (s, 1H), 9.98 (d, J = 3.6 Hz, 1H, 8.95 (d, J = 2.4 Hz, 1H), 8.28 (dd, J = 9.2, 2.4 Hz, 1H), 8.02 (s, 1H), 8.00 (s, 1H), 7.88 (dd, J = 8.0, 1.6 Hz, 1H), 7.84 (s, 1H), 7.72 (d, J = 8.4 Hz, 1H), 7.65 (d, J = 1.2 Hz, 1H), 5.43-5.36 (m, 1H), 4.42-4.38 (m, 2H), 3.70 (t, J = 6.8 Hz, 2H), 3.15-3.12 (m, 4H), 2.92-2.86 (m, 2H), 2.68 (t, J = 6.8 Hz, 2H), 2.53 (s, 3H), 2.52-2.49 (m, 4H), 2.21 (d, J = 6.4 Hz, 2H), 1.86-1.80 (m, 3H), 1.56 (d, J = 6.8 Hz, 3H), 1.37 (s, 9H), 1.17-1.08 (m, 2H). |

-continued
| Compd No. | Structure Observed MS [M + 1]$^+$ | $^1$H NMR (400 MHz, DMSO-d$^6$) δ (ppm) |
| --- | --- | --- |
| 221 | 851.71 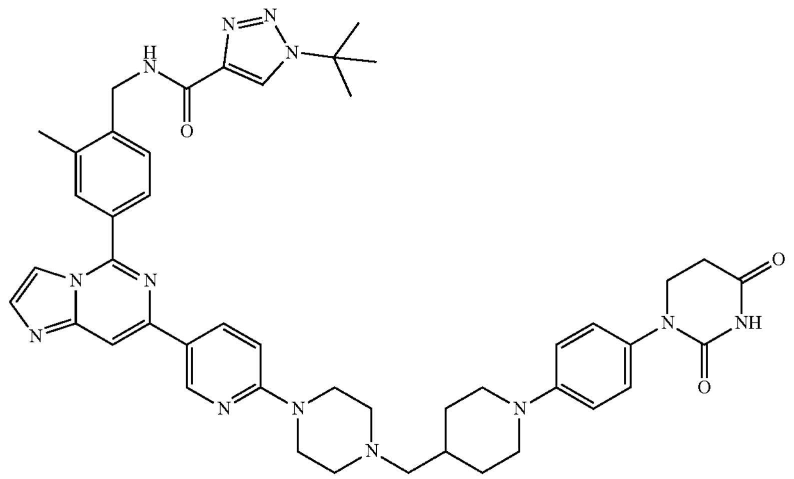 [SMILES: Cc1cc(-c2nc(-c3ccc(N4CCN(CC5CCN(c6ccc(N7CCC(=O)NC7=O)cc6)CC5)CC4)nc3)cc3nccn23)ccc1CNC(=O)c1cn(C(C)(C)C)nn1] | 10.27 (s, 1H), 9.12 (t, J = 6.1 Hz, 1H), 9.00 (d, J = 2.5 Hz, 1H), 8.75 (s, 1H), 8.34 (dd, J = 9.0, 2.5 Hz, 1H), 8.07 (s, 1H), 8.00 (t, J = 1.1 Hz, 1H), 7.85 (d, J = 6.6 Hz, 2H), 7.69 (d, J = 1.4 Hz, 1H), 7.51 (d, J = 8.4 Hz, 1H), 7.20-7.12 (m, 2H), 6.96 (d, J = 9.0 Hz, 3H), 4.60 (d, J = 6.1 Hz, 2H), 3.76-3.67 (m, 4H), 3.63 (s, 4H), 2.75-2.65 (m, 4H), 2.56-2.53 (m, 4H), 2.50 (s, 3H), 2.25 (d, J = 7.1 Hz, 2H), 1.85 (d, J = 12.5 Hz, 2H), 1.80-1.71 (m, 1H), 1.68 (s, 9H), 1.33-1.18 (m, 2H). |
| 222 | 836.8 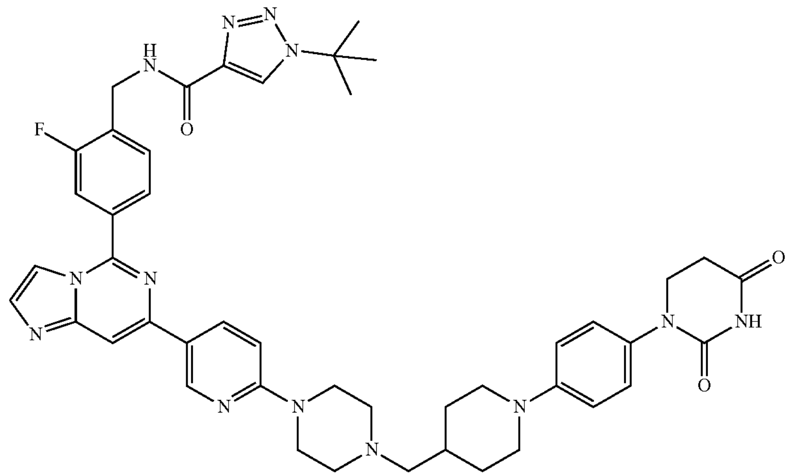 [SMILES: CC(C)(C)n1cc(C(=O)NCc2ccc(-c3nc(-c4ccc(N5CCN(CC6CCN(c7ccc(N8CCC(=O)NC8=O)cc7)CC6)CC5)nc4)cc4nccn34)cc2F)nn1] | 10.27 (s, 1H), 9.21 (t, J = 6.1 Hz, 1H), 9.00 (d, J = 2.5 Hz, 1H), 8.75 (s, 1H), 8.35 (dd, J = 9.0, 2.6 Hz, 1H), 8.11 (s, 1H), 8.05 (t, J = 1.1 Hz, 1H), 7.93-7.85 (m, 2H), 7.71 (d, J = 1.5 Hz, 1H), 7.62 (t, J = 7.9 Hz, 1H), 7.20-7.12 (m, 2H), 6.96 (d, J = 9.1 Hz, 3H), 4.66 (d, J = 6.1 Hz, 2H), 3.75-3.65 (m, 3H), 3.63 (s, 4H), 3.34-3.23 (m, 1H), 2.75-2.65 (m, 4H), 2.52-2.46 (m, 4H), 2.25 (d, J = 7.1 Hz, 2H), 1.85 (d, J = 12.7 Hz, 2H), 1.79-1.70 (m, 1H), 1.68 (s, 9H), 1.32-1.17 (m, 2H). |

-continued
| Compd No. | Structure Observed MS $[M+1]^+$ | $^1H$ NMR (400 MHz, DMSO-$d^6$) δ (ppm) |
|---|---|---|
| | 840.8 | |
| 223 | 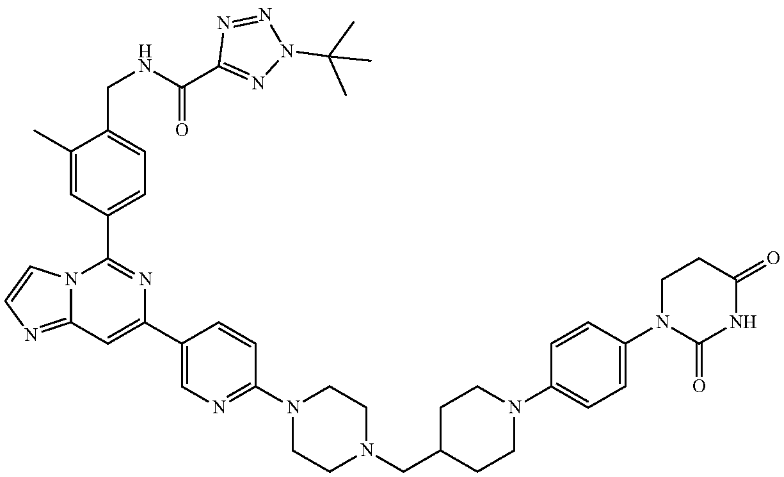 [SMILES: Cc1cc(-c2nc(-c3ccc(N4CCN(CC5CCN(c6ccc(N7CCC(=O)NC7=O)cc6)CC5)CC4)nc3)cc3nccn23)ccc1CNC(=O)c1nnn(C(C)(C)C)n1] 837.7 | 10.28 (s, 1H), 9.64 (t, J = 6.0 Hz, 1H), 9.01 (d, J = 2.5 Hz, 1H), 8.35 (dd, J = 9.0, 2.5 Hz, 1H), 8.08 (s, 1H), 8.01 (d, J = 1.2 Hz, 1H), 7.87 (d, J = 6.8 Hz, 2H), 7.70 (d, J = 1.4 Hz, 1H), 7.54 (d, J = 8.4 Hz, 1H), 7.20-7.12 (m, 2H), 6.96 (d, J = 9.1 Hz, 3H), 4.64 (d, J = 6.0 Hz, 2H), 3.77-3.67 (m, 3H), 3.63 (s, 4H), 3.34-3.31 (m, 1H), 2.75-2.65 (m, 4H), 2.52 (s, 3H), 2.50-2.47 (m, 4H), 2.26 (d, J = 7.1 Hz, 2H), 1.86 (d, J = 12.7 Hz, 2H), 1.83-1.79 (m, 1H), 1.78 (s, 9H), 1.33-1.19 (m, 2H). |

-continued
| Compd No. | Structure Observed MS $[M + 1]^+$ | $^1$H NMR (400 MHz, DMSO-$d^6$) δ (ppm) |
|---|---|---|
| 224 | 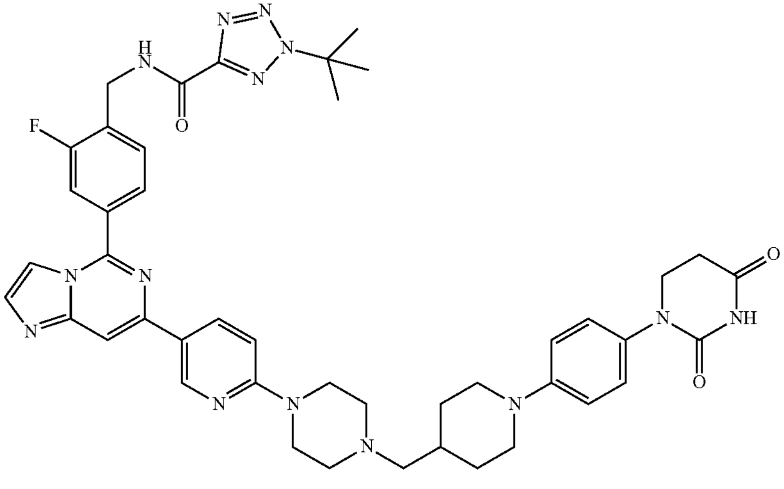 [SMILES: CC(C)(C)n1nnc(C(=O)NCc2ccc(-c3nc(-c4ccc(N5CCN(CC6CCN(c7ccc(N8CCC(=O)NC8=O)cc7)CC6)CC5)nc4)cc4nccn34)cc2F)n1] 841.7 | 10.27 (s, 1H), 9.70 (t, J = 6.0 Hz, 1H), 9.00 (d, J = 2.4 Hz, 1H), 8.35 (dd, J = 9.0, 2.5 Hz, 1H), 8.12 (s, 1H), 8.05 (t, J = 1.2 Hz, 1H), 7.95-7.87 (m, 2H), 7.71 (d, J = 1.5 Hz, 1H), 7.66 (t, J = 7.9 Hz, 1H), 7.20-7.13 (m, 2H), 6.96 (d, J = 9.0 Hz, 3H), 4.70 (d, J = 6.0 Hz, 2H), 3.75-3.68 (m, 3H), 3.66-3.59 (m, 4H), 3.33-3.30 (m, 1H), 2.75-2.65 (m, 4H), 2.52-2.48 (m, 3H), 2.25 (d, J = 7.0 Hz, 2H), 1.85 (d, J = 12.9 Hz, 2H), 1.78 (s, 9H), 1.75-1.71 (m, 1H), 1.52-1.19 (m, 2H). |
| 240 | 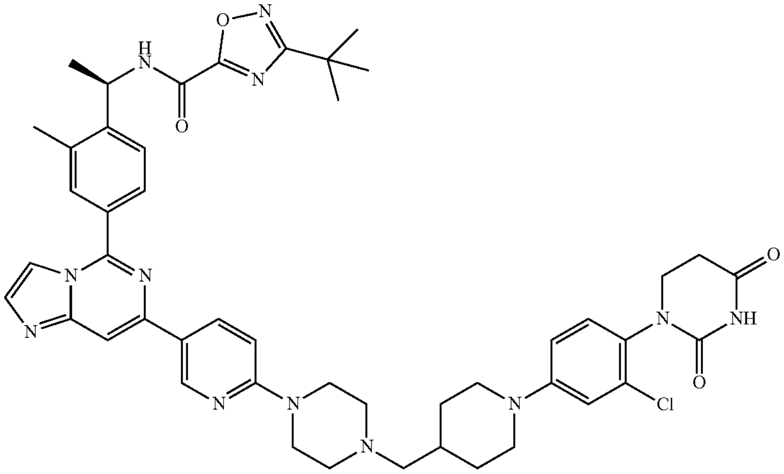 [SMILES: Cc1cc(-c2nc(-c3ccc(N4CCN(CC5CCN(c6ccc(N7CCC(=O)NC7=O)c(Cl)c6)CC5)CC4)nc3)cc3nccn23)ccc1[C@@H](C)NC(=O)c1nc(C(C)(C)C)no1] 866.2 | 10.37 (s, 1H), 10.01 (d, J = 7.8 Hz, 1H), 9.00 (d, J = 2.5 Hz, 1H), 8.34 (dd, J = 9.0, 2.5 Hz, 1H), 8.06 (d, J = 16.3 Hz, 2H), 7.91 (d, J = 8.1 Hz, 1H), 7.86 (d, J = 1.9 Hz, 1H), 7.75 (d, J = 8.1 Hz, 1H), 7.69 (d, J = 1.5 Hz, 1H), 7.26 (d, J = 8.8 Hz, 1H), 7.04 (d, J = 2.7 Hz, 1H), 6.99-6.92 (m, 2H), 5.45-5.38 (m, 1H), 3.79 (d, J = 12.2 Hz, 2H), 3.66-3.53 (m, 5H), 3.33-3.29 (m, 1H), 2.83-2.68 (m, 4H), 2.55 (s, 3H), 2.52-2.45 (m, 4H), 2.28-2.21 (m, 2H), 1.87-1.78 (m, 3H), 1.59 (d, J = 6.9 Hz, 3H), 1.40 (s, 9H), 1.29-1.17 (m, 2H). |

-continued
| Compd No. | Structure Observed MS $[M + 1]^+$ | $^1H$ NMR (400 MHz, DMSO-$d^6$) δ (ppm) |
|---|---|---|
| 241 | 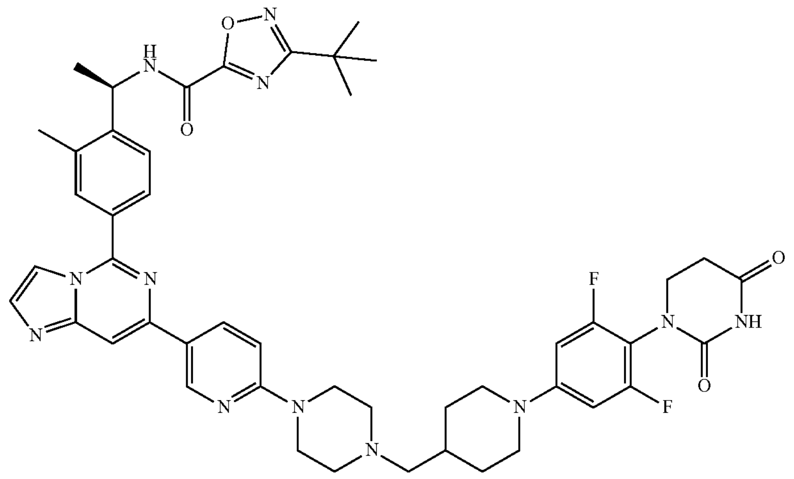 [SMILES: Cc1cc(-c2nc(-c3ccc(N4CCN(CC5CCN(c6cc(F)c(N7CCC(=O)NC7=O)c(F)c6)CC5)CC4)nc3)cc3nccn23)ccc1[C@@H](C)NC(=O)c1nc(C(C)(C)C)no1] 887.7 | 10.52 (s, 1H), 10.01 (d, J = 7.7 Hz, 1H), 9.01 (s, 1H), 8.35 (d, J = 8.9 Hz, 1H), 8.08 (s, 1H), 8.04 (s, 1H), 7.92 (d, J = 8.5 Hz, 1H), 7.87 (d, J = 1.9 Hz, 1H), 7.75 (d, J = 8.1 Hz, 1H), 7.70 (d, J = 1.4 Hz, 1H), 6.96 (d, J = 9.1 Hz, 1H), 6.74 (d, J = 12.3 Hz, 2H), 5.45-5.38 (m, 1H), 3.83 (d, J = 12.5 Hz, 2H), 3.66-3.53 (m, 5H), 3.33-3.29 (m, 1H), 2.82 (t, J = 12.3 Hz, 2H), 2.72 (t, J = 6.6 Hz, 2H), 2.56 (s, 3H), 2.52-2.45 (m, 4H), 2.28-2.21 (m, 2H), 1.87-1.78 (m, 3H), 1.59 (d, J = 7.0 Hz, 3H), 1.40 (s, 9H), 1.29-1.17 (m, 2H). |
| 242 | 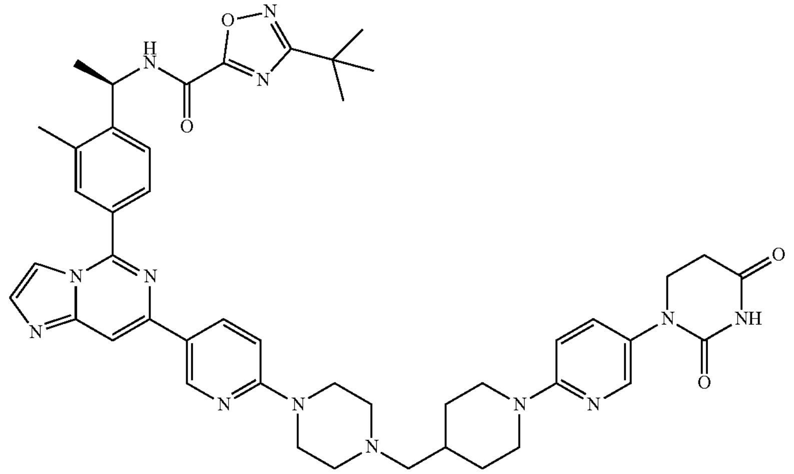 [SMILES: Cc1cc(-c2nc(-c3ccc(N4CCN(CC5CCN(c6ccc(N7CCC(=O)NC7=O)cn6)CC5)CC4)nc3)cc3nccn23)ccc1[C@@H](C)NC(=O)c1nc(C(C)(C)C)no1] | 10.35 (s, 1H), 10.01 (d, J = 7.8 Hz, 1H), 9.00 (d, J = 2.5 Hz, 1H), 8.34 (dd, J = 9.0, 2.5 Hz, 1H), 8.10-8.01 (m, 3H), 7.95-7.88 (m, 1H), 7.88-7.84 (m, 1H), 7.75 (d, J = 8.1 Hz, 1H), 7.69 (d, J = 1.5 Hz, 1H), 7.50 (dd, J = 9.0, 2.7 Hz, 1H), 6.95 (d, J = 9.1 Hz, 1H), 6.86 (d, J = 9.1 Hz, 1H), 5.45-5.38 (m, 1H), 4.30 (d, J = 12.8 Hz, 2H), 3.72 (t, J = 6.7 Hz, 2H), 3.65-3.58 (m, 4H), 3.34-3.29 (m, 1H), 2.84 (t, J = 12.4 Hz, 2H), 2.72 (t, J = 6.7 Hz, 2H), 2.55 (s, 3H), 2.52-2.45 (m, 3H), 2.25-2.20 (m, 2H), 1.91-1.78 (m, 3H), 1.59 (d, J = 7.0 Hz, 3H), 1.40 (s, 9H), 1.22-1.08 (m, 2H). |

-continued
| Compd No. | Structure Observed MS $[M + 1]^+$ | $^1H$ NMR (400 MHz, DMSO-$d^6$) δ (ppm) |
|---|---|---|
| 243 | 852.7 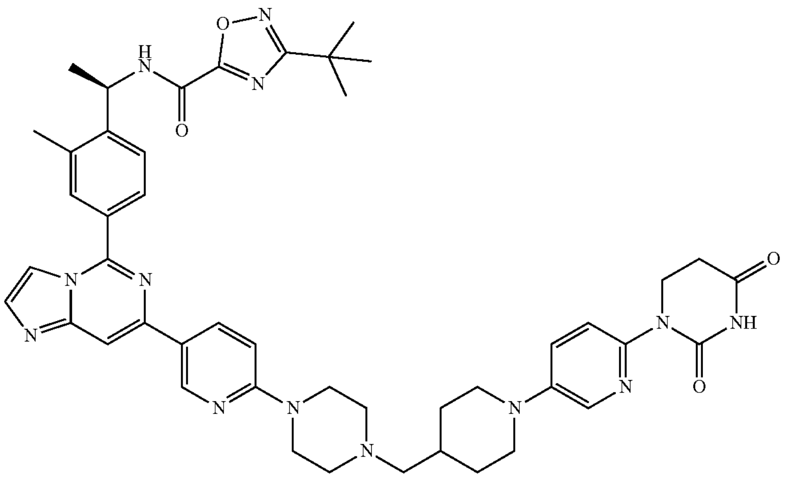 | 10.41 (s, 1H), 10.01 (d, J = 7.8 Hz, 1H), 9.01 (d, J = 2.5 Hz, 1H), 8.35 (dd, J = 9.0, 2.5 Hz, 1H), 8.12-8.06 (m, 2H), 8.04 (d, J = 1.4 Hz, 1H), 7.92 (d, J = 8.2 Hz, 1H), 7.87 (d, J = 1.9 Hz, 1H), 7.75 (d, J = 8.1 Hz, 1H), 7.69 (d, J = 1.4 Hz, 1H), 7.53 (d, J = 9.0 Hz, 1H), 7.45 (dd, J = 9.1, 3.0 Hz, 1H), 6.96 (d, J = 9.1 Hz, 1H), 5.45-5.38 (m, 1H), 3.96 (t, J = 6.6 Hz, 2H), 3.74 (d, J = 12.2 Hz, 2H), 3.66-3.59 (m, 4H), 3.34-3.29 (m, 1H), 2.79-2.65 (m, 4H), 2.56 (s, 3H), 2.52-2.45 (m, 3H), 2.25-2.20 (m, 2H), 1.93-1.70 (m, 3H), 1.59 (d, J = 7.0 Hz, 3H), 1.40 (s, 9H), 1.31-1.20 (m, 2H). |
| 244 | 852.7 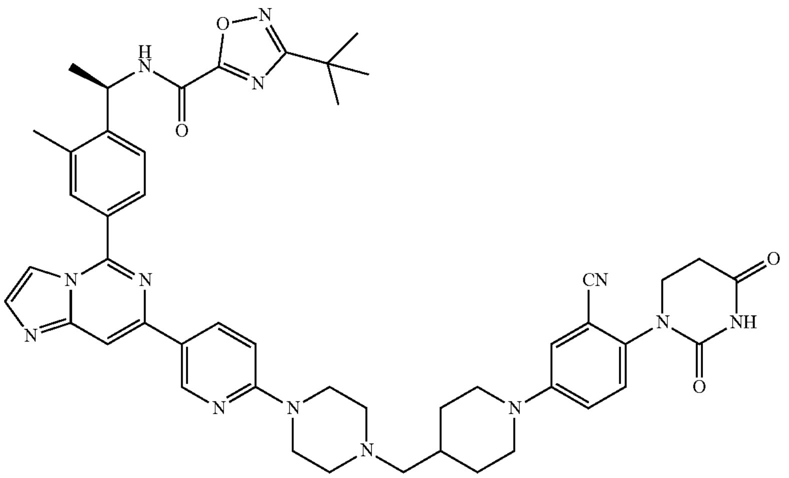 [SMILES: Cc1cc(-c2nc(-c3ccc(N4CCN(CC5CCN(c6ccc(N7CCC(=O)NC7=O)c(C#N)c6)CC5)CC4)nc3)cc3nccn23)ccc1[C@@H](C)NC(=O)c1nc(C(C)(C)C)no1] | 10.54 (s, 1H), 10.01 (d, J = 7.8 Hz, 1H), 9.01 (d, J = 2.5 Hz, 1H), 8.35 (dd, J = 9.0, 2.5 Hz, 1H), 8.08 (s, 1H), 8.04 (d, J = 1.4 Hz, 1H), 7.92 (d, J = 8.1 Hz, 1H), 7.87 (s, 1H), 7.76 (d, J = 8.1 Hz, 1H), 7.70 (d, J = 1.5 Hz, 1H), 7.38 (dd, J = 5.9, 3.1 Hz, 2H), 7.32 (dd, J = 9.1, 2.8 Hz, 1H), 6.96 (d, J = 9.1 Hz, 1H), 5.48-5.36 (m, 1H), 3.85 (d, J = 12.3 Hz, 2H), 3.77-3.69 (m, 2H), 3.67-3.59 (m, 4H), 3.34-3.29 (m, 1H), 2.86-2.71 (m, 4H), 2.56 (s, 3H), 2.52-2.45 (m, 3H), 2.29-2.19 (m, 2H), 1.88-1.76 (m, 3H), 1.59 (d, J = 7.0 Hz, 3H), 1.40 (s, 9H), 1.29-1.19 (m, 2H). |

-continued
| Compd No. | Structure Observed MS [M + 1]+ | $^1$H NMR (400 MHz, DMSO-d$^6$) δ (ppm) |
|---|---|---|
| | 876.7 | |
| 245 | 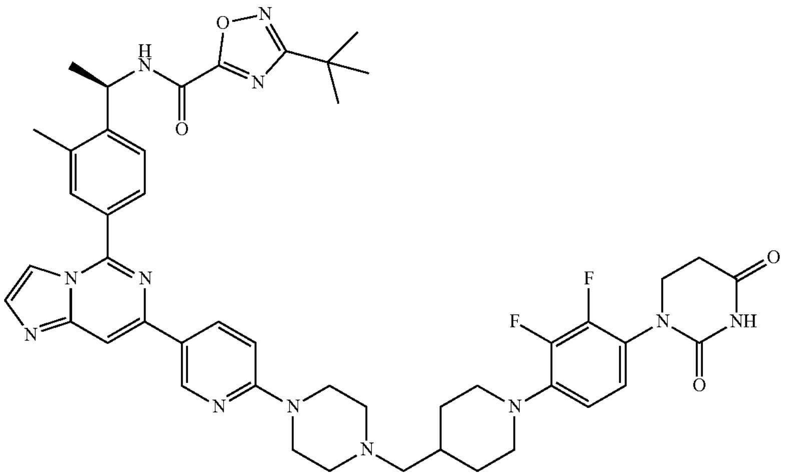 [SMILES: Cc1cc(-c2nc(-c3ccc(N4CCN(CC5CCN(c6ccc(N7CCC(=O)NC7=O)c(F)c6F)CC5)CC4)nc3)cc3nccn23)ccc1[C@@H](C)NC(=O)c1nc(C(C)(C)C)no1] 872.7 | 10.51 (s, 1H), 10.01 (d, J = 7.8 Hz, 1H), 9.00 (d, J = 2.5 Hz, 1H), 8.35 (dd, J = 9.0, 2.5 Hz, 1H), 8.08 (s, 1H), 8.04 (s, 1H), 7.95-7.85 (m, 2H), 7.75 (d, J = 8.1 Hz, 1H), 7.69 (d, J = 1.4 Hz, 1H), 7.17 (t, J = 8.3 Hz, 1H), 6.99-6.87 (m, 2H), 5.46-5.39 (m, 1H), 3.72 (t, J = 6.7 Hz, 2H), 3.67-3.59 (m, 4H), 3.48-3.42 (m, 1H), 3.34-3.29 (m, 1H), 2.82-2.70 (m, 5H), 2.55 (s, 3H), 2.52-2.45 (m, 3H), 2.29-2.19 (m, 2H), 1.91-1.18 (m, 2H), 1.81-1.72 (m, 1H), 1.59 (d, J = 7.0 Hz, 3H), 1.40 (s, 9H), 1.36-1.23 (m, 2H). |

-continued
| Compd No. | Structure Observed MS $[M + 1]^+$ | $^1H$ NMR (400 MHz, DMSO-$d^6$) δ (ppm) |
|---|---|---|
| 250 | 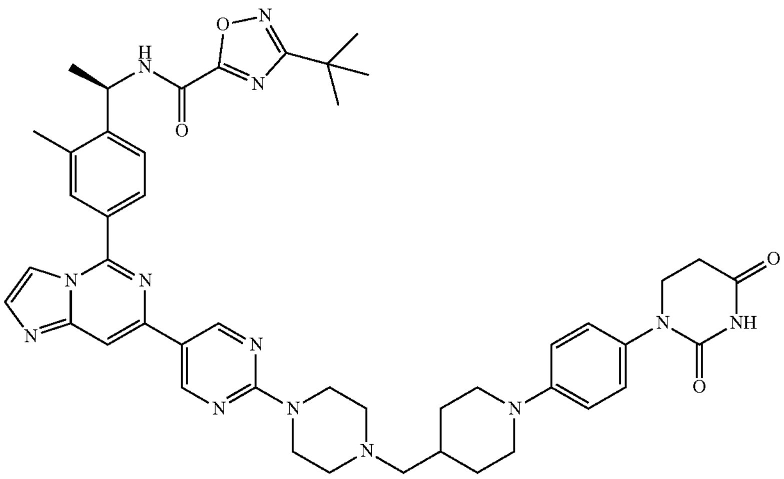 [SMILES: Cc1cc(-c2nc(-c3cnc(N4CCN(CC5CCN(c6ccc(N7CCC(=O)NC7=O)cc6)CC5)CC4)nc3)cc3nccn23)ccc1[C@@H](C)NC(=O)c1nc(C(C)(C)C)no1] | 10.35 (s, 1H), 9.97 (d, J = 7.6Hz, 1H), 8.97 (d, J = 2.4 Hz, 1H), 8.31 (dd, J = 8.8, 2.4 Hz, 1H), 8.04 (s, 1H), 8.00 (s, 1H), 7.89-7.87 (m, 1H), 7.84 (s, 1H), 7.72 (d, J = 8.0 Hz, 1H), 7.66 (d, J = 1.2 Hz, 1H), 7.18 (t, J = 8.8 Hz, 1H), 6.92 (d, J = 9.2 Hz, 1H), 6.82-6.74 (m, 2H), 5.43-5.36 (m, 1H), 3.76-3.73 (m, 2H), 3.63-3.60 (m, 6H), 2.76-2.67 (m, 4H), 2.53 (m, 3H), 2.48-2.45 (m, 4H), 2.21 (d, J = 6.8 Hz, 2H), 1.82-1.72 (m, 3H), 1.56 (d, J = 6.8 Hz, 3H), 1.37 (s, 9H), 1.23-1.56 (m, 2H). |

-continued
| Compd No. | Structure Observed MS [M + 1]$^+$ | $^1$H NMR (400 MHz, DMSO-$d^6$) δ (ppm) |
|---|---|---|
| | 852.72 | |
| 254 | 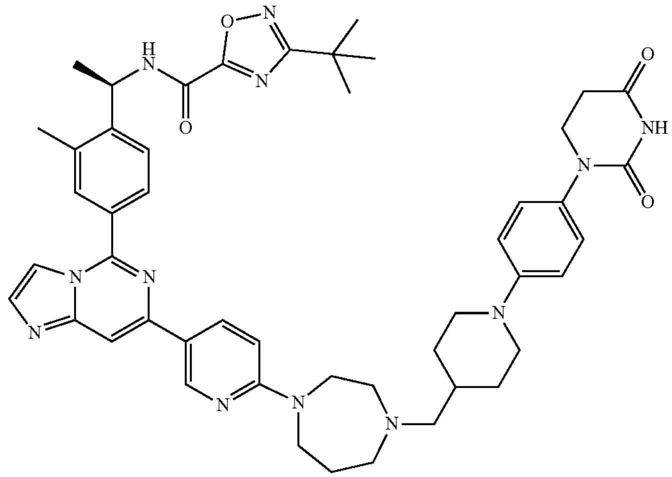 [SMILES: Cc1cc(-c2nc(-c3ccc(N4CCCN(CC5CCN(c6ccc(N7CCC(=O)NC7=O)cc6)CC5)CC4)nc3)cc3nccn23)ccc1[C@@H](C)NC(=O)c1nc(C(C)(C)C)no1] 865.4 | 10.26 (s, 1H), 10.16-9.97 (d, J = 7.6 Hz, 1H), 8.98 (s, 1H), 8.31 (d, J = 8.8 Hz, 1H), 8.02 (s, 2H), 7.92 (d, J = 8.0 Hz, 1H), 7.86 (s, 1H), 7.76 (d, J = 8.4 Hz, 1H), 7.68 (s, 1H), 7.12-7.09 (d, J = 8.8 Hz, 2H), 6.90-6.88 (d, J = 8.8 Hz, 2H), 6.77-6.75 (d, J = 8.8 Hz, 1H), 5.45 (m, 1H), 3.80 (m, 2H), 3.71-3.63 (m, 6H), 2.76 (s, 2H), 2.71 (m, 3H), 2.60 (m, 4H), 2.55 (s, 2H), 2.34 (m, 2H), 1.88 (s, 2H), 1.76-1.75 (m, 2H), 1.59 (d, J = 7.6 Hz, 4H), 1.40 (m, 9H), 1.18-1.16 (d, J = 10 Hz, 2H). |

Example 4: (R)-3-(tert-butyl)-N-(1-(4-(2-(6-(4-((1-(4-(2,4-dioxotetrahydropyrimidin-1(2H)-yl)phenyl)piperidin-4-yl)methyl)piperazin-1-yl)pyridin-3-yl)-6-methyl-7-oxo-6,7-dihydro-1H-pyrrolo[2,3-c]pyridin-4-yl)-2-methylphenyl)ethyl)-1,2,4-oxadiazole-5-carboxamide (Compound No. 1)

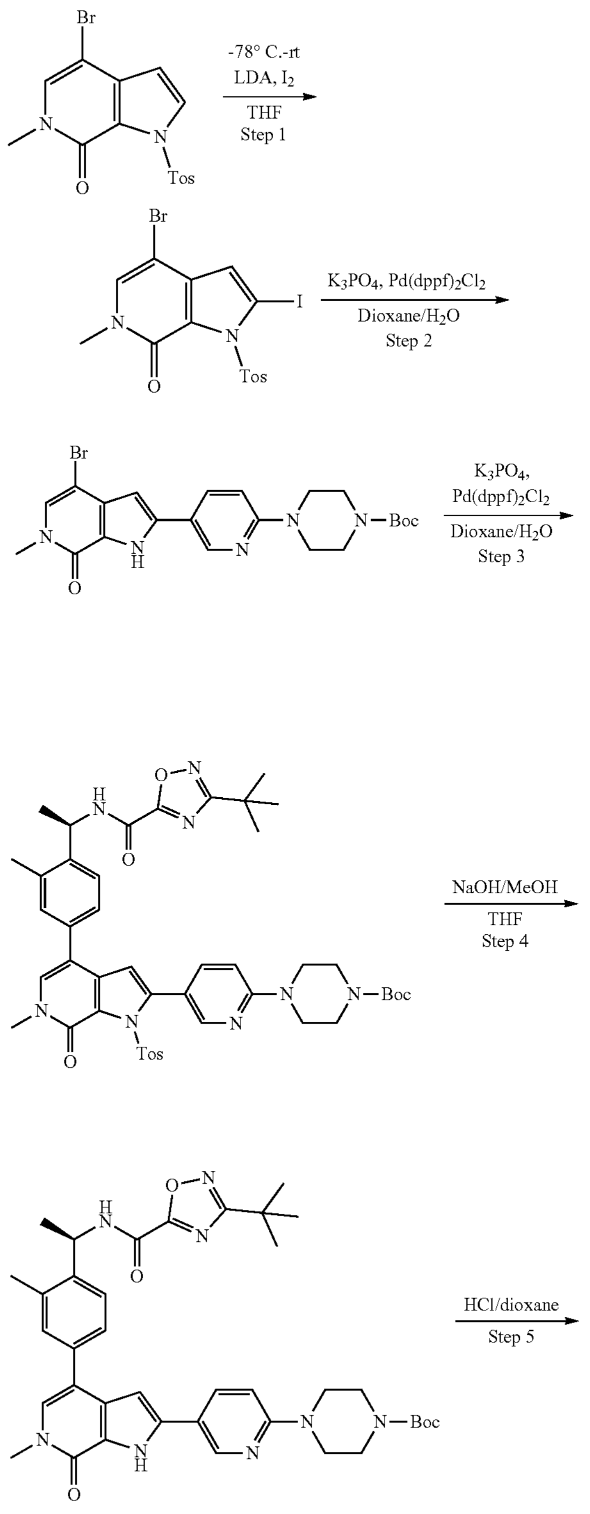

-continued

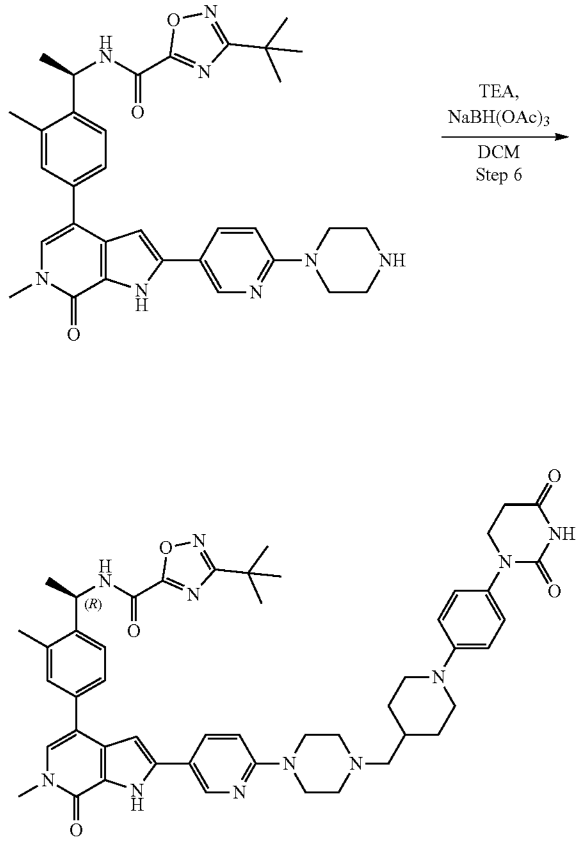

Step 1: 4-bromo-2-iodo-6-methyl-1-tosyl-1,6-dihydro-7H-pyrrolo[2,3-c]pyridin-7-one

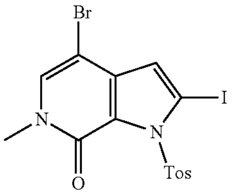

To a solution of 4-bromo-6-methyl-1-tosyl-1,6-dihydro-7H-pyrrolo[2,3-c]pyridin-7-one (500 mg, 1.311 mmol, 1.0 eq) in dry THF (10 ml) was added LDA (0.77 ml, 1.574 mmol, 1.2 eq, 2 M in THF) at −78° C. under $N_2$ and stirred at −78° C. for 1 h. $I_2$ (350 mg, 1.377 mmol, 1.05 eq) in dry THF (4 ml) was added at −78° C. The reaction mixture was stirred at rt for 1 h. Quenched with $NH_4Cl$ aqueous and extracted with EA for 3 times. The combined organic layers were washed with brine, dried over anhydrous $Na_2SO_4$ and concentrated in vacuo. The residue was purified by flash chromatography eluted with Hex/EA=2:1 to give the title compound (385 mg, 57.9%) as a white solid. MS (ESI) m/z 506.7 [M+H$^+$].

Step 2: tert-butyl 4-(5-(4-bromo-6-methyl-7-oxo-1-tosyl-6,7-dihydro-1H-pyrrolo[2,3-c]pyridin-2-yl)pyridin-2-yl)piperazine-1-carboxylate

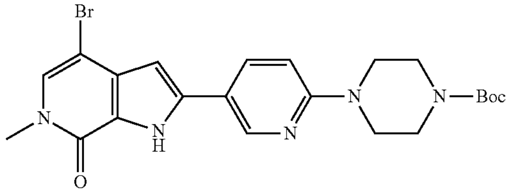 [SMILES: Cn1cc(Br)c2cc(-c3ccc(N4CCN(C(=O)OC(C)(C)C)CC4)nc3)[nH]c2c1=O]

A mixture of tert-butyl 4-(5-(4,4,5,5-tetramethyl-1,3,2-dioxaborolan-2-yl)pyridin-2-yl)piperazine-1-carboxylate (691 mg, 1.775 mmol, 1.5 eq), above obtained intermediate (600 mg, 1.183 mmol, 1.0 eq), $Na_2CO_3$ (251 mg, 2.366 mmol, 2.0 eq) and $PdCl_2$ (dppf) (87 mg, 0.118 mmol, 0.1 eq) in Dioxane (5 ml) and Water (1 ml) was stirred at 80° C. under Ar for 2 h. Water was added to the reaction mixture followed by extraction with EA for 3 times. The combined organic layers were washed with brine, dried over anhydrous $Na_2SO_4$ and concentrated in vacuo. The residue was purified by flash chromatography eluted with Hex/EA=3:1 to give the title compound (380 mg, 50.0%) as a yellow solid. MS (ESI) m/z 488.2 [M+H$^+$].

Step 3: tert-butyl (R)-4-(5-(4-(4-(1-(3-(tert-butyl)-1,2,4-oxadiazole-5-carboxamido)ethyl)-3-methylphenyl)-6-methyl-7-oxo-1-tosyl-6,7-dihydro-1H-pyrrolo[2,3-c]pyridin-2-yl)pyridin-2-yl)piperazine-1-carboxylate

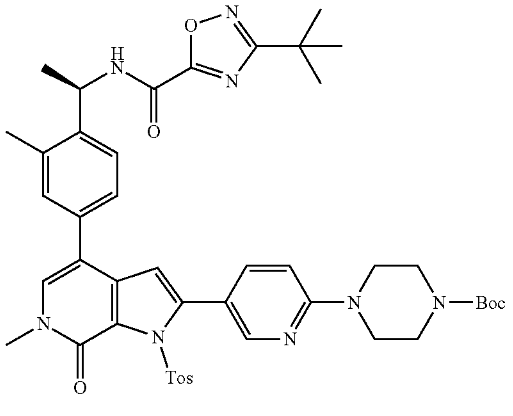

A mixture of (R)-3-(tert-butyl)-N-(1-(2-methyl-4-(4,4,5,5-tetramethyl-1,3,2-dioxaborolan-2-yl)phenyl)ethyl)-1,2,4-oxadiazole-5-carboxamide (193 mg, 0.467 mmol, 1.5 eq), above obtained intermediate (200 mg, 0.311 mmol, 1.0 eq), $Na_2CO_3$ (33 mg, 0.31 mmol, 1.0 eq) and $PdCl_2$ (dppf) (22.8 mg, 0.031 mmol, 0.1 eq) in Dioxane (5 ml) and Water (1.0 ml) was stirred at 100° C. under Ar for 16 h. Water was added to the reaction mixture followed by extraction with EA for 3 times. The combined organic layers were washed with brine, dried over anhydrous $Na_2SO_4$ and concentrated in vacuo. The residue was purified by flash chromatography eluted with Hex/EA=3:1 to give the title compound (90 mg, 34.1%) as a yellow solid. MS (ESI) m/z 489.4 [M+H$^+$].

Step 4: tert-butyl (R)-4-(5-(4-(4-(1-(3-(tert-butyl)-1,2,4-oxadiazole-5-carboxamido)ethyl)-3-methylphenyl)-6-methyl-7-oxo-6,7-dihydro-1H-pyrrolo[2,3-c]pyridin-2-yl)pyridin-2-yl)piperazine-1-carboxylate

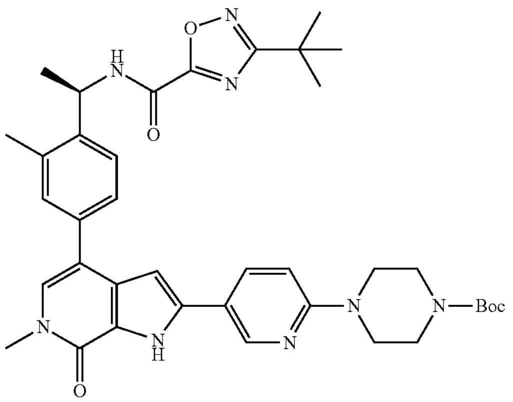 [SMILES: Cc1cc(-c2cn(C)c(=O)c3[nH]c(-c4ccc(N5CCN(C(=O)OC(C)(C)C)CC5)nc4)cc23)ccc1[C@@H](C)NC(=O)c1nc(C(C)(C)C)no1]

To a solution of above obtained intermediate (90 mg, 0.106 mmol, 1.0 eq) in THF (10 ml) was added a solution of sodium hydroxide (8.5 mg, 0.212 mmol, 2.0 eq) in MeOH (3 ml). The reaction mixture was stirred at rt for 2 h. Concentrated in vacuo, the residue was purified by flash chromatography eluted with DCM/MeOH=20:1 to give the title compound (65 mg, 88%) as a yellow solid. MS (ESI) m/z 695.4 [M+H$^+$].

Step 5: (R)-3-(tert-butyl)-N-(1-(2-methyl-4-(6-methyl-7-oxo-2-(6-(piperazin-1-yl)pyridin-3-yl)-6,7-dihydro-1H-pyrrolo[2,3-c]pyridin-4-yl)phenyl)ethyl)-1,2,4-oxadiazole-5-carboxamide

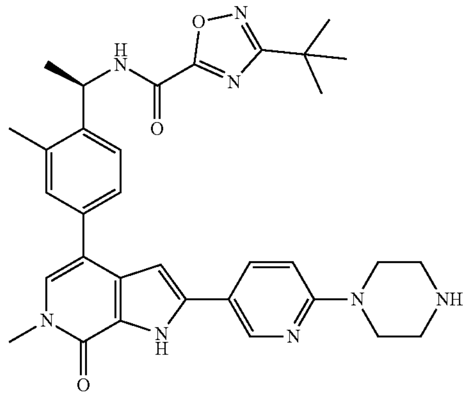 [SMILES: Cc1cc(-c2cn(C)c(=O)c3[nH]c(-c4ccc(N5CCNCC5)nc4)cc23)ccc1[C@@H](C)NC(=O)c1nc(C(C)(C)C)no1]

A mixture of above obtained intermediate (65 mg, 0.094 mmol, 1.0 eq) in HCl/Dioxane (5 ml) was stirred at rt for 2 h. Concentrated in vacuo to give the title compound (55 mg, 99%) as a yellow solid. MS (ESI) m/z 595.3 [M+H$^+$].

Step 6: (R)-3-(tert-butyl)-N-(1-(4-(2-(6-(4-((1-(4-(2,4-dioxotetrahydropyrimidin-1(2H)-yl)phenyl)piperidin-4-yl)methyl)piperazin-1-yl)pyridin-3-yl)-6-methyl-7-oxo-6,7-dihydro-1H-pyrrolo[2,3-c]pyridin-4-yl)-2-methylphenyl)ethyl)-1,2,4-oxadiazole-5-carboxamide

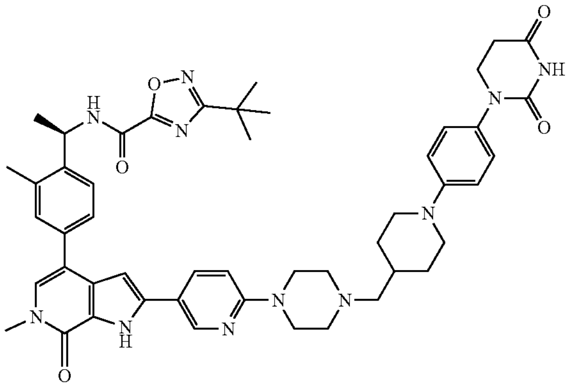 [SMILES: Cc1cc(-c2cn(C)c(=O)c3[nH]c(-c4ccc(N5CCN(CC6CCN(c7ccc(N8CCC(=O)NC8=O)cc7)CC6)CC5)nc4)cc23)ccc1[C@@H](C)NC(=O)c1nc(C(C)(C)C)no1]

To a mixture of above obtained intermediate (55 mg, 0.092 mmol, 1.0 eq), triethylamine (28.1 mg, 0.277 mmol, 3.0 eq) and 1-(4-(2,4-dioxotetrahydropyrimidin-1(2H)-yl)phenyl)piperidine-4-carbaldehyde (27.9 mg, 0.092 mmol, 1.0 eq) in DCM (25 ml) was added $NaBH(OAc)_3$ (29.4 mg, 0.139 mmol, 1.5 eq). The reaction mixture was stirred at rt for 16 h. Water was added to the reaction mixture followed by extraction with DCM for 3 times. The combined organic layers were washed with brine, dried over anhydrous $Na_2SO_4$ and concentrated in vacuo. The crude product was purified by pre-HPLC to give the title compound (22 mg, 27.0%) as a white solid. MS (ESI) m/z 880.5 [M+H$^+$]. $^1$H NMR (400 MHz, DMSO-d$^6$) δ (ppm): 12.27 (s, 1H), 10.24 (s, 1H), 9.86 (d, J=7.9 Hz, 1H), 8.78-8.66 (m, 1H), 8.17-8.06 (m, 1H), 7.56 (d, J=8.1 Hz, 1H), 7.48 (d, J=8.2 Hz, 1H), 7.42 (s, 1H), 7.35 (s, 1H), 7.13 (d, J=8.9 Hz, 2H), 6.92 (d, J=9.1 Hz, 2H), 6.86 (d, J=9.0 Hz, 1H), 6.79 (s, 1H), 5.41-5.25 (m, 1H), 3.73-3.63 (m, 4H), 3.58 (s, 3H), 3.57-3.49 (m, 4H), 2.73-2.62 (m, 4H), 2.48-2.40 (m, 7H), 2.21 (d, J=7.2 Hz, 2H), 1.86-1.77 (m, 2H), 1.76-1.64 (m, 1H), 1.52 (d, J=6.9 Hz, 3H), 1.37 (s, 9H), 1.24-1.17 (m, 2H).

Example 5: (R)-3-(tert-butyl)-N-(1-(4-(2-(6-(4-((1-(4-(2,4-dioxotetrahydropyrimidin-1(2H)-yl)phenyl)piperidin-4-yl)methyl)piperazin-1-yl)pyridin-3-yl)-5-fluoro-1H-pyrrolo[2,3-b]pyridin-4-yl)-2-methylphenyl)ethyl)-1,2,4-oxadiazole-5-carboxamide (Compound No. 2)

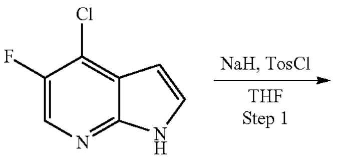

-continued

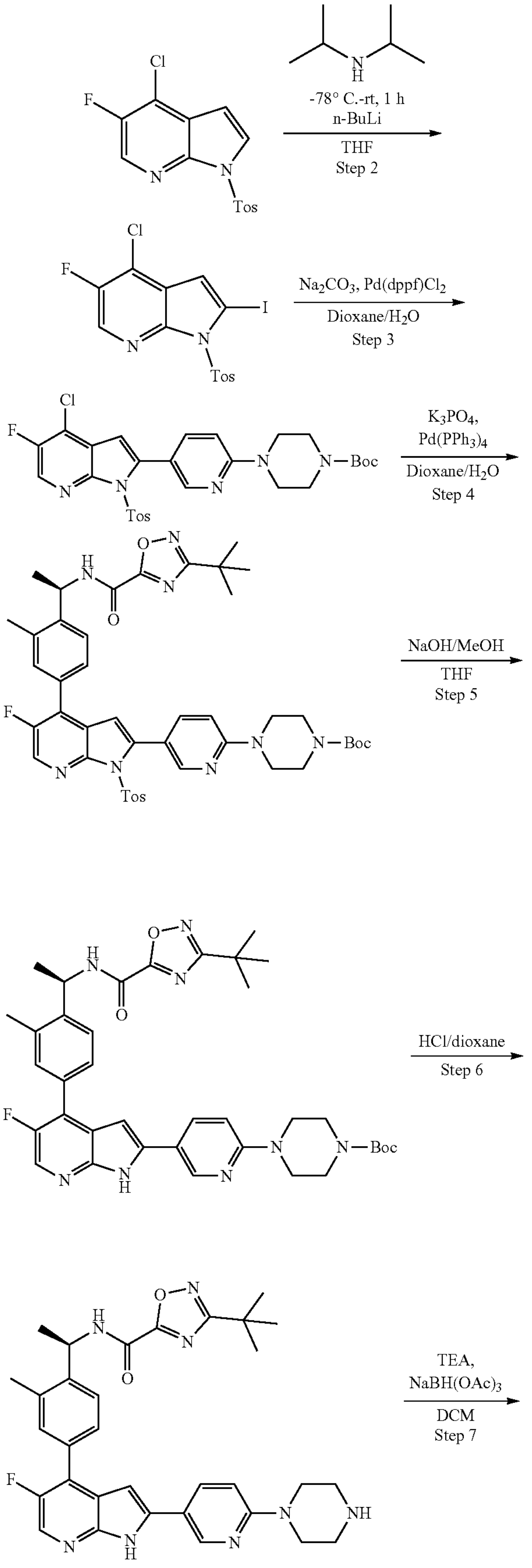

-continued

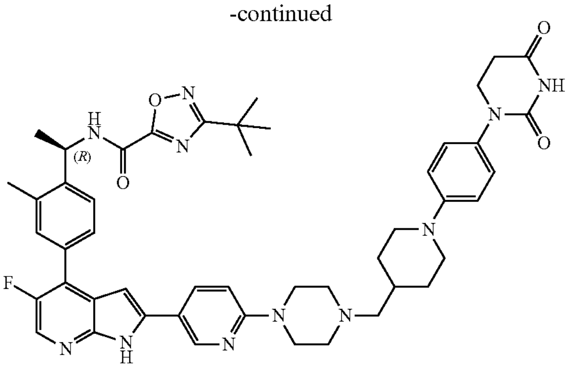

Step 1: 4-chloro-5-fluoro-1-tosyl-1H-pyrrolo[2,3-b]pyridine

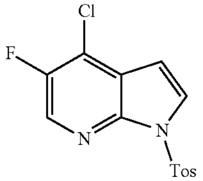

A suspension of 4-chloro-5-fluoro-1H-pyrrolo[2,3-b]pyridine (1 g, 5.86 mmol, 1.0 eq) and sodium hydride (0.281 g, 11.73 mmol, 2.0 eq) in dry THF (25 ml) was stirred at 0° C. for 1 h, then 4-methylbenzenesulfonyl chloride (1.676 g, 8.79 mmol, 1.5 eq) was added and stirred at 0° C. for 1 h. Quenched with $NH_4Cl$ aqueous and extracted with EA for 3 times. The combined organic layers were washed with brine, dried over anhydrous $Na_2SO_4$ and concentrated in vacuo. the residue was purified by flash chromatography eluted with Hex/EA=3:1 to give the title compound (1.8 g, 95%) as a white solid. MS (ESI) m/z 325.1 [M+H$^+$].

Step 2: 4-chloro-5-fluoro-2-iodo-1-tosyl-1H-pyrrolo[2,3-b]pyridine

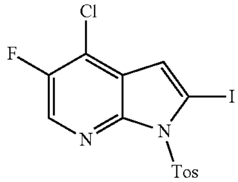

To a solution of diisopropylamine (312 mg, 3.08 mmol, 2.0 eq) in dry THF (10 ml) was added butyllithium (197 mg, 3.08 mmol, 2.0 eq) at −78° C. under Ar, the mixture was stirred at −78° C. for 1 h. The above solution was added to a solution of 4-chloro-5-fluoro-1-tosyl-1H-pyrrolo[2,3-b]pyridine (500 mg, 1.540 mmol, 1.0 eq) in THF (10 ml) at −78° C. under Ar. After stirred at −78° C. for 1 h, 12 (410 mg, 1.617 mmol, 1.05 eq) was added at −78° C. and the reaction mixture was stirred at rt for 1 h. Quenched with $NH_4Cl$ aqueous and extracted with EA for 3 times. The combined organic layers were washed with brine, dried over anhydrous $Na_2SO_4$ and concentrated in vacuo. The residue was purified by flash chromatography eluted with Hex/EA=2:1 to give the title compound (343 mg, 49.4%) as a yellow solid. MS (ESI) m/z 450.9 [M+H$^+$].

Step 3: tert-butyl 4-(5-(4-chloro-5-fluoro-1-tosyl-1H-pyrrolo[2,3-b]pyridin-2-yl)pyridin-2-yl)piperazine-1-carboxylate

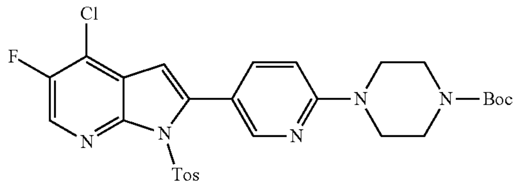

A mixture of tert-butyl 4-(5-(4,4,5,5-tetramethyl-1,3,2-dioxaborolan-2-yl)pyridin-2-yl)piperazine-1-carboxylate (713 mg, 1.831 mmol, 1.5 eq), above obtained intermediate (550 mg, 1.220 mmol, 1.0 eq), $Na_2CO_3$ (259 mg, 2.441 mmol, 2.0 eq) and $PdCl_2$ (dppf) (89 mg, 0.122 mmol, 0.1 eq) in Dioxane (5 ml) and Water (1 ml) was stirred at 80° C. under Ar for 2 h. Water was added to the reaction mixture followed by extraction with EA for 3 times. The combined organic layers were dried over anhydrous $Na_2SO_4$ and concentrated in vacuo. The residue was purified by flash chromatography eluted with Hex/EA=3:1 to give the title compound (700 mg, 98%) as a yellow solid. MS (ESI) m/z 586.2 [M+H$^+$].

Step 4: tert-butyl (R)-4-(5-(4-(4-(1-(3-(tert-butyl)-1,2,4-oxadiazole-5-carboxamido)ethyl)-3-methylphenyl)-5-fluoro-1-tosyl-1H-pyrrolo[2,3-b]pyridin-2-yl)pyridin-2-yl)piperazine-1-carboxylate

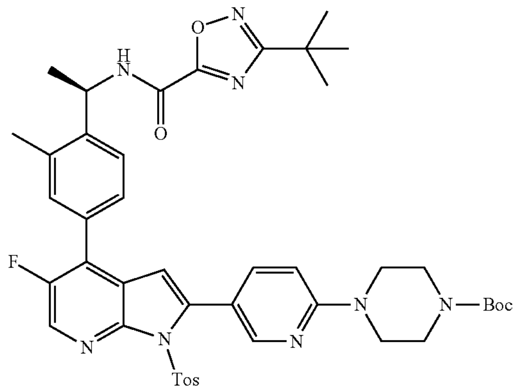

A mixture of (R)-3-(tert-butyl)-N-(1-(2-methyl-4-(4,4,5,5-tetramethyl-1,3,2-dioxaborolan-2-yl)phenyl)ethyl)-1,2,4-oxadiazole-5-carboxamide (317 mg, 0.768 mmol, 1.5 eq), above obtained intermediate (300 mg, 0.512 mmol, 1.0 eq), $K_3PO_4$ (109 mg, 0.512 mmol, 1.0 eq) and $Pd(PPh_3)_4$ (59 mg, 0.051 mmol, 0.1 eq) in Dioxane (5 ml) and Water (1 ml) was stirred at 80° C. for 30 min under MW. Water was added to the reaction mixture followed by extraction with EA for 3 times. The combined organic layers were washed with brine, dried over anhydrous $Na_2SO_4$ and concentrated in vacuo. The crude product was purified by flash chromatography eluted with Hex/EA=3:1 to give the title compound (200 mg, 46.7%) as a yellow solid. MS (ESI) m/z 836.4 [M+H+].

Steps 5-7: (R)-3-(tert-butyl)-N-(1-(4-(2-(6-(4-((1-(4-(2,4-dioxotetrahydropyrimidin-1(2H)-yl)phenyl)piperidin-4-yl)methyl)piperazin-1-yl)pyridin-3-yl)-5-fluoro-1H-pyrrolo[2,3-b]pyridin-4-yl)-2-methylphenyl)ethyl)-1,2,4-oxadiazole-5-carboxamide

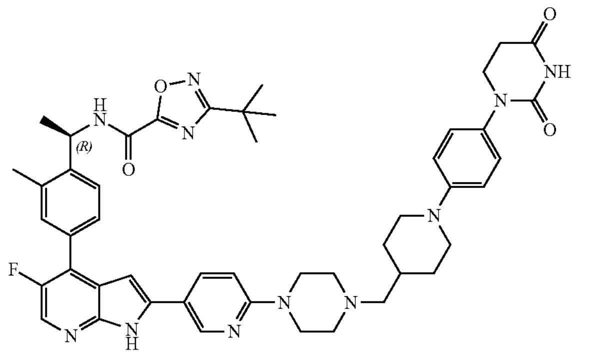

Following the synthesis of EXAMPLE 1, the title compound was obtained (35.9 mg) as a yellow solid. MS (ESI) m/z 868.5 [M+H+]. $^1$H NMR (400 MHz, DMSO-d$^6$) δ (ppm): 12.23 (s, 1H), 10.25 (s, 1H), 9.94 (d, J=7.9 Hz, 1H), 8.73 (d, J=2.4 Hz, 1H), 8.21 (d, J=3.1 Hz, 1H), 8.18-8.00 (m, 1H), 7.67 (d, J=8.1 Hz, 1H), 7.62-7.46 (m, 2H), 7.15 (d, J=8.9 Hz, 2H), 7.00-6.86 (m, 3H), 6.82 (s, 1H), 5.52-5.28 (m, 1H), 3.80-3.64 (m, 4H), 3.63-3.50 (m, 4H), 2.74-2.60 (m, 4H), 2.50-2.41 (m, 7H), 2.23 (d, J=7.2 Hz, 2H), 1.87-1.64 (m, 3H), 1.61-1.51 (m, 3H), 1.39 (s, 9H), 1.25-1.17 (m, 2H).

Example 6: (R)—N-(1-(4-(2-amino-6-(6-(4-((1-(4-(2,4-dioxotetrahydropyrimidin-1(2H)-yl)phenyl)piperidin-4-yl)methyl)piperazin-1-yl)pyridin-3-yl)-7H-pyrrolo[2,3-d]pyrimidin-4-yl)-2-methylphenyl)ethyl)-3-(tert-butyl)-1,2,4-oxadiazole-5-carboxamide (Compound No. 3)

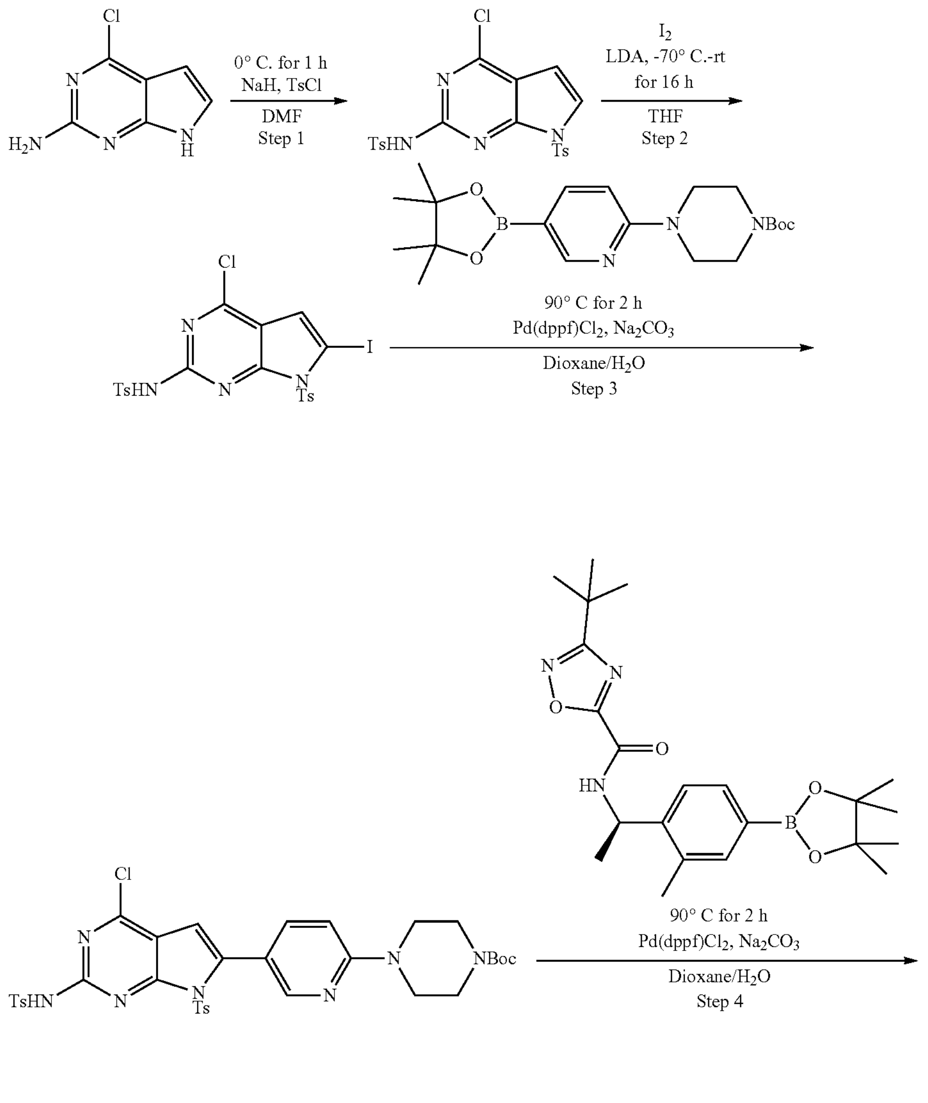

-continued
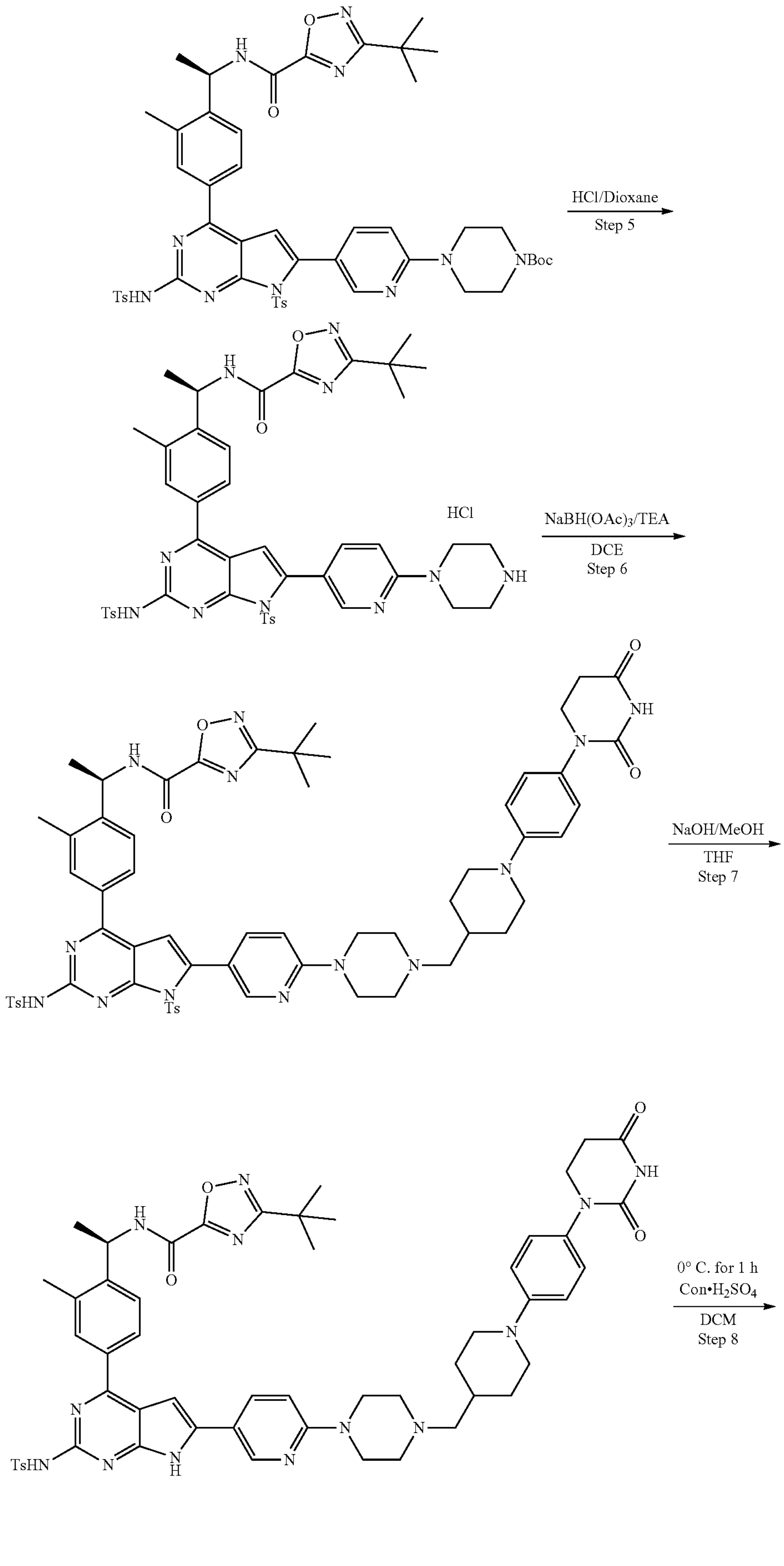

-continued

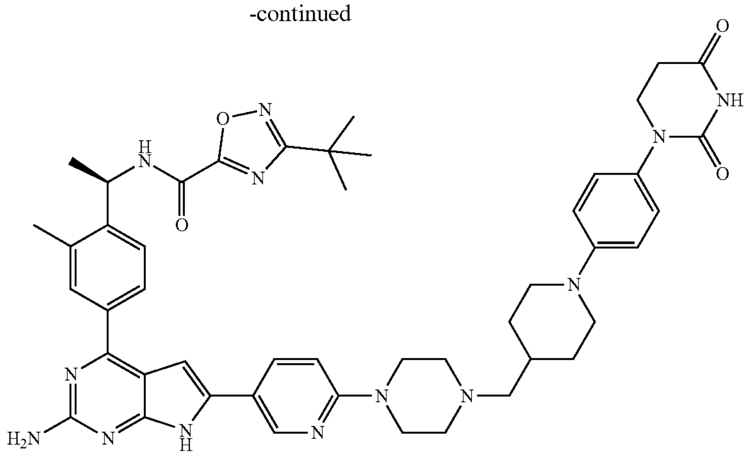

Step 1: N-(4-chloro-7-tosyl-7H-pyrrolo[2,3-d]pyrimidin-2-yl)-4-methylbenzenesulfonamide

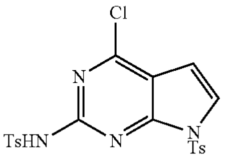

To a suspension of NaH (1.71 g, 71.2 mmol, 3.0 eq) and 4-chloro-7H-pyrrolo[2,3-d]pyrimidin-2-amine (4.0 g, 23.73 mmol, 1.0 eq) in dry DMF (60 ml) was added 4-methylbenzenesulfonyl chloride (9.5 g, 49.8 mmol, 2.1 eq) in portions at 0° C. and stirred at 0° C. for 2 h. The reaction mixture was poured into $NH_4Cl$ aqueous and extracted with EA for 3 times. The combined organic layers were washed with brine, dried over anhydrous $Na_2SO_4$ and concentrated in vacuo. The residue was purified by flash chromatography eluted with Hex/EA=3:1-2:1 to give the title compound (9.5 g, 84%) as a white solid. LC-MS: 477.2 (M+H$^+$).

Step 2: N-(4-chloro-6-iodo-7-tosyl-7H-pyrrolo[2,3-d]pyrimidin-2-yl)-4-methylbenzenesulfonamide

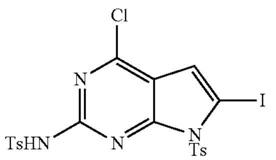

To a solution of N-(4-chloro-7-tosyl-7H-pyrrolo[2,3-d]pyrimidin-2-yl)-4-methylbenzenesulfonamide (3.0 g, 6.29 mmol, 1.0 eq) in dry THF (60 ml) was added LDA (7.55 ml, 18.87 mmol, 3.0 eq) at −70° C., the reaction mixture was stirred at −70° C. for 30 min. A solution of 12 (2.4 g, 9.43 mmol, 1.5 eq) in dry THF (10 ml) was added and the reaction mixture was stirred at 0° C. for 3 h. Quenched with $NH_4Cl$ aqueous, extracted with EA for 3 times. The combined organic layers were washed with brine, dried over anhydrous $Na_2SO_4$ and concentrated in vacuo. The residue was purified by flash chromatography eluted with Hex/EA=2:1 to give the title compound (1.5 g, 39.6%) as a yellow solid. LC-MS: 603.3 (M+H$^+$).

Step 3: tert-butyl 4-(5-(4-chloro-2-((4-methylphenyl)sulfonamido)-7-tosyl-7H-pyrrolo[2,3-d]pyrimidin-6-yl)pyridin-2-yl)piperazine-1-carboxylate

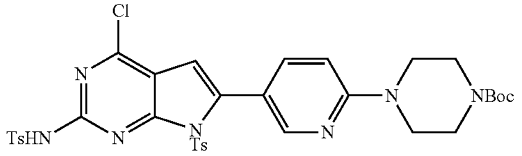

A mixture of $PdCl_2$ (dppf) (182 mg, 0.249 mmol, 1.0 eq), $Na_2CO_3$ (791 mg, 7.46 mmol, 3.0 eq), tert-butyl 4-(5-(4,4,5,5-tetramethyl-1,3,2-dioxaborolan-2-yl)pyridin-2-yl)piperazine-1-carboxylate (1.26 g, 3.23 mmol, 1.3 eq) and N-(4-chloro-6-iodo-7-tosyl-7H-pyrrolo[2,3-d]pyrimidin-2-yl)-4-methylbenzenesulfonamide (1.5 g, 2.49 mmol, 1.0 eq) in Dioxane/$H_2O$ (20 ml/4 ml) was stirred at 85° C. under Ar for 2 h. Diluted with EA, washed with water, brine, dried over anhydrous $Na_2SO_4$ and concentrated in vacuo. The residue was purified by flash chromatography eluted with Hex/EA=3:1 to give the title compound (800 mg, 43.5%) as a yellow solid. LC-MS: 738.4 (M+H$^+$).

Step 4: tert-butyl (R)-4-(5-(4-(4-(1-(3-(tert-butyl)-1,2,4-oxadiazole-5-carboxamido)ethyl)-3-methylphenyl)-2-((4-methylphenyl)sulfonamido)-7-tosyl-7H-pyrrolo[2,3-d]pyrimidin-6-yl)pyridin-2-yl)piperazine-1-carboxylate

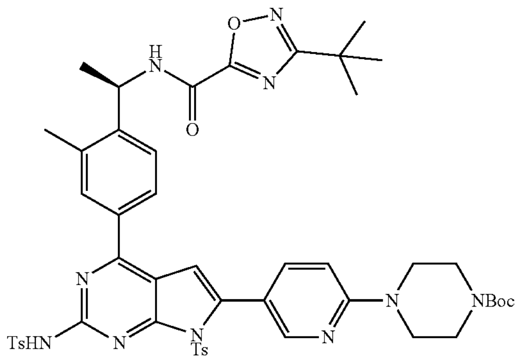

A mixture of (R)-3-(tert-butyl)-N-(1-(2-methyl-4-(4,4,5,5-tetramethyl-1,3,2-dioxaborolan-2-yl)phenyl)ethyl)-1,2,4-oxadiazole-5-carboxamide (235 mg, 0.569 mmol, 1.2 eq), tert-butyl 4-(5-(4-chloro-2-((4-methylphenyl)sulfonamido)-7-tosyl-7H-pyrrolo[2,3-d]pyrimidin-6-yl)pyridin-2-yl)piperazine-1-carboxylate (350 mg, 0.474 mmol, 1.0 eq), $PdCl_2$(dppf) (35 mg, 0.048 mmol, 0.1 eq) and $K_2CO_3$ (197 mg, 1.42 mmol, 3.0 eq) in Dioxane/$H_2O$ (8 ml/2 ml) was stirred at 100° C. under Ar for 2 h. Diluted with water, extracted with EA for 3 times. The combined EA layers were washed with brine, dried over anhydrous $Na_2SO_4$ and concentrated in vacuo. The residue was purified by flash chromatography eluted with Hex/EA=1:1 to give the title compound (220 mg, 46.9%) as a yellow solid. LC-MS: 989.6 ($M+H^+$).

Step 5: (R)-3-(tert-butyl)-N-(1-(2-methyl-4-(2-((4-methylphenyl)sulfonamido)-6-(6-(piperazin-1-yl)pyridin-3-yl)-7-tosyl-7H-pyrrolo[2,3-d]pyrimidin-4-yl)phenyl)ethyl)-1,2,4-oxadiazole-5-carboxamide hydrochloride

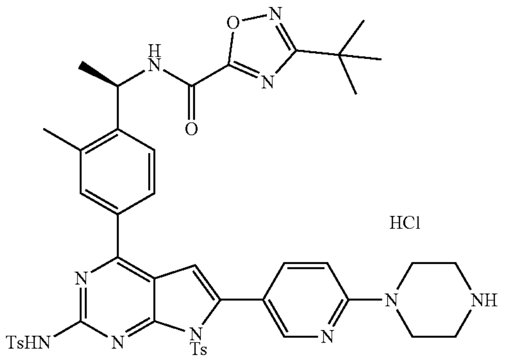

A mixture of above obtained intermediate (220 mg, 0.222 mmol, 1.0 eq) in 4M HCl/Dioxane (1 ml) and dry DCM (4 ml) was stirred at rt for 2 h. Concentrated in vacuo to give the title compound (195 mg, 100%) as a yellow solid. LC-MS: 889.4 ($M+H^+$).

Step 6: (R)-3-(tert-butyl)-N-(1-(2-methyl-4-(2-((4-methylphenyl)sulfonamido)-6-(6-(piperazin-1-yl)pyridin-3-yl)-7-tosyl-7H-pyrrolo[2,3-d]pyrimidin-4-yl)phenyl)ethyl)-1,2,4-oxadiazole-5-carboxamide hydrochloride

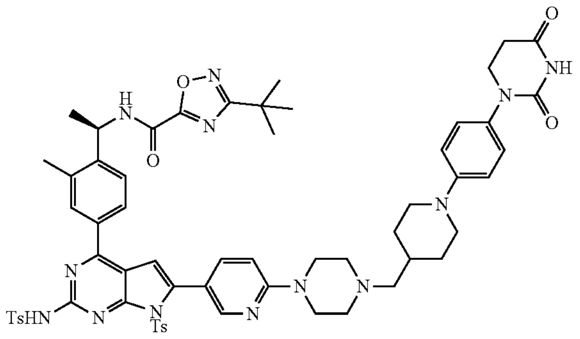

To a solution of above obtained intermediate (195 mg, 0.222 mmol, 1.0 eq), 1-(4-(2,4-dioxotetrahydropyrimidin-1(2H)-yl)phenyl)piperidine-4-carbaldehyde (220 mg, 0.222 mmol, 1.0 eq) and TEA (114 mg, 1.125 mmol, 5.0 eq) in DCE (4 ml) was added NaBH(OAc) 3 (95 mg, 0.45 mmol, 2.0 eq). The reaction was stirred at rt for 2 h. Diluted with water, extracted with DCM for 3 times. The combined DCM layers were washed with brine, dried over anhydrous $Na_2SO_4$ and concentrated in vacuo. The residue was purified by flash chromatography eluted with DCM/MeOH=20:1 to give the title compound (200 mg, 78%) as a yellow solid. LC-MS: 1174.5 ($M+H^+$).

Step 7: (R)-3-(tert-butyl)-N-(1-(4-(6-(6-(4-((1-(4-(2,4-dioxotetrahydropyrimidin-1(2H)-yl)phenyl)piperidin-4-yl)methyl)piperazin-1-yl)pyridin-3-yl)-2-((4-methylphenyl)sulfonamido)-7H-pyrrolo[2,3-d]pyrimidin-4-yl)-2-methylphenyl)ethyl)-1,2,4-oxadiazole-5-carboxamide

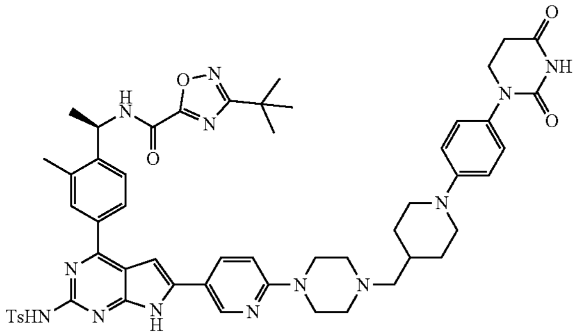

A mixture of above obtained intermediate (200 mg, 0.17 mmol, 1.0 eq) and NaOH (200 mg, 5.0 mmol, 29.4 eq) in MeOH/THF (5 ml/5 ml) was stirred at 0° C. for 3 h. Quenched with $NH_4Cl$ aqueous, extracted with DCM for 3 times. The combined DCM layers were washed with brine, dried over anhydrous $Na_2SO_4$ and concentrated in vacuo. The residue was purified by flash chromatography eluted with DCM/MeOH=20:1 to give the title compound (150 mg, 86%) as a yellow solid. LC-MS: 1020.3 ($M+H^+$).

Step 8: (R)—N-(1-(4-(2-amino-6-(6-(4-((1-(4-(2,4-dioxotetrahydropyrimidin-1(2H)-yl)phenyl)piperidin-4-yl)methyl)piperazin-1-yl)pyridin-3-yl)-7H-pyrrolo[2,3-d]pyrimidin-4-yl)-2-methylphenyl)ethyl)-3-(tert-butyl)-1,2,4-oxadiazole-5-carboxamide

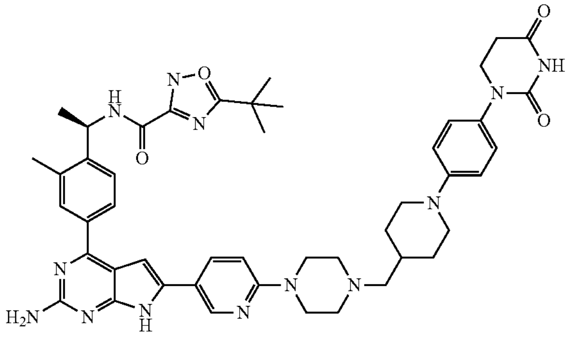

To a solution of above obtained intermediate (150 mg, 0.147 mmol, 1.0 eq) in dry DCM (5 ml) was added Con. $H_2SO_4$ (1.44 g, 14.7 mmol, 100 eq) at 0° C. The reaction mixture was stirred at 0° C. for 3 h. Quenched with $NH_3$/MeOH and concentrated in vacuo. The residue was purified by pre-HPLC to give the title compound (42.3 mg, 33.2%) as a yellow solid. LC-MS: 866.6 ($M+H^+$).

$^1H$ NMR (400 MHz, DMSO-$d^6$) δ (ppm) 11.69 (s, 1H), 10.27 (s, 1H), 9.93 (d, J=7.6 Hz, 1H), 8.68 (s, 1H), 8.10-7.90 (m, 3H), 7.64 (d, J=8.4 Hz, 1H), 7.15 (d, J=8.8 Hz, 2H), 7.00-6.85 (m, 4H), 6.12 (s, 2H), 5.45-5.30 (m, 1H), 3.75-3.65 (m, 4H), 3.61-3.53 (m, 4H), 2.75-2.65 (m, 4H), 2.50-2.45 (m, 6H), 2.28-2.20 (m, 2H), 1.88-1.71 (m, 3H), 1.56 (d, J=6.8 Hz, 3H), 1.39 (s, 9H), 1.30-1.20 (m, 3H).

Example 7: (R)-3-(tert-butyl)-N-(1-(4-(6-(1-(1-((1-(4-(2,4-dioxotetrahydropyrimidin-1(2H)-yl)phenyl)piperidin-4-yl)methyl)piperidin-4-yl)-1,2,3,6-tetrahydropyridin-4-yl)-7H-pyrrolo[2,3-d]pyrimidin-4-yl)-2-methylphenyl)ethyl)-1,2,4-oxadiazole-5-carboxamide (Compound No. 4)

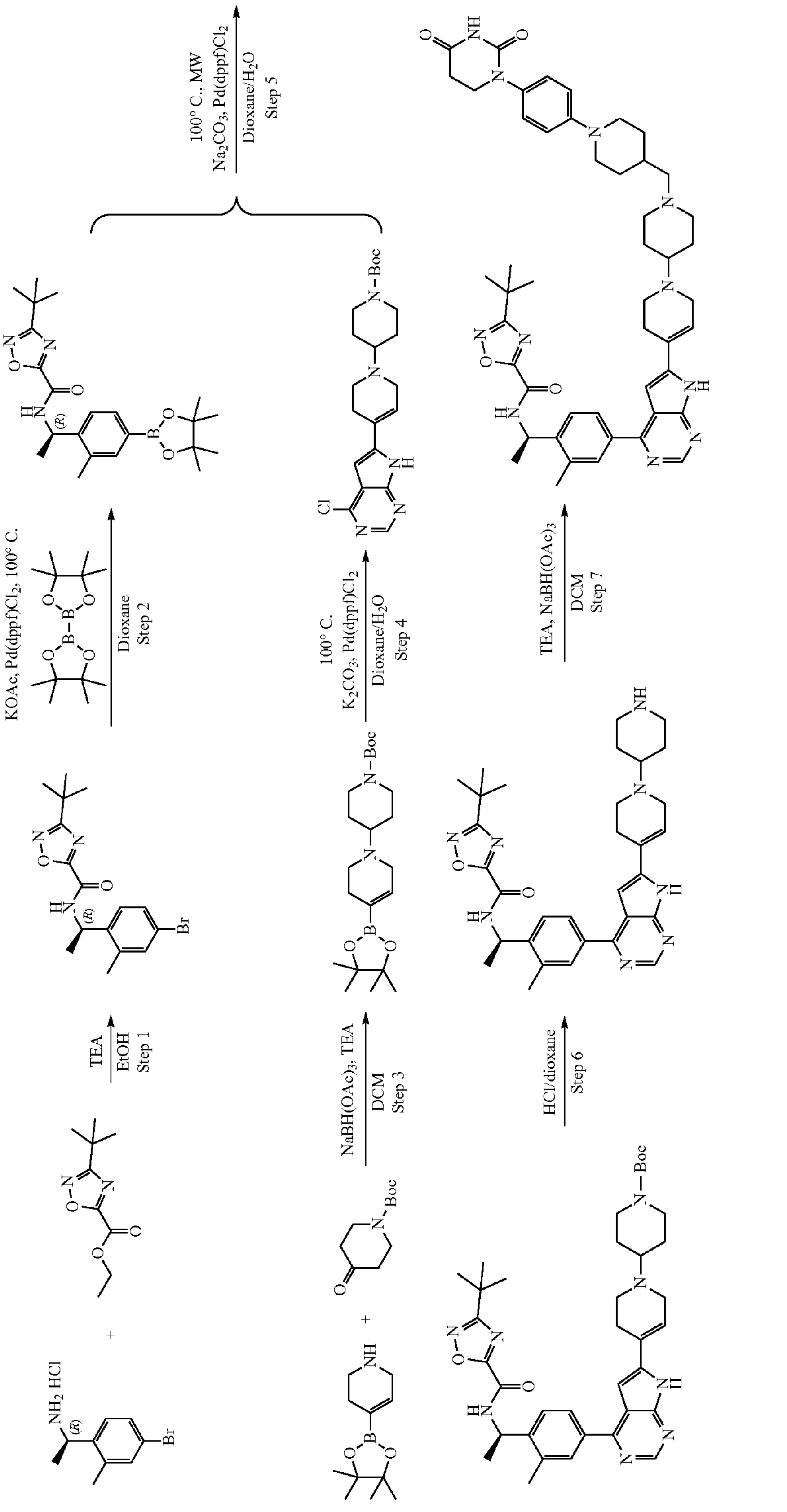
TEA
EtOH
Step 1
KOAc, $Pd(dppf)Cl_2$, 100° C.
Dioxane
Step 2
$NaBH(OAc)_3$, TEA
DCM
Step 3
100° C.
$K_2CO_3$, $Pd(dppf)Cl_2$
Dioxane/$H_2O$
Step 4
100° C., MW
$Na_2CO_3$, $Pd(dppf)Cl_2$
Dioxane/$H_2O$
Step 5
HCl/dioxane
Step 6
TEA, $NaBH(OAc)_3$
DCM
Step 7

Step 1: (R)—N-(1-(4-bromo-2-methylphenyl)ethyl)-3-(tert-butyl)-1,2,4-oxadiazole-5-carboxamide

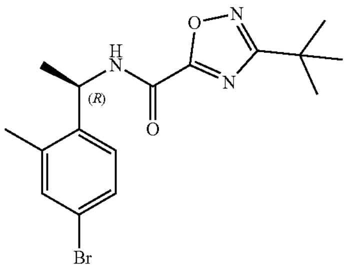

A solution of (R)-1-(4-bromo-2-methylphenyl) ethan-1-amine hydrochloride (4.6 g, 18.36 mmol, 1.0 eq), ethyl 3-(tert-butyl)-1,2,4-oxadiazole-5-carboxylate (4.00 g, 20.19 mmol, 1.1 eq) and triethylamine (5.57 g, 55.1 mmol, 3.0 eq) in THF (25 ml) was stirred at 85° C. under Ar for 16 h. Concentrated in vacuo, the crude product was purified by flash chromatography eluted with Hex/EA=3:1 to give the title compound (4.75 g, 70.6%) as a white solid. MS (ESI) m/z 366.1 [M+H$^+$].

Step 2: (R)-3-(tert-butyl)-N-(1-(2-methyl-4-(4,4,5,5-tetramethyl-1,3,2-dioxaborolan-2-yl)phenyl)ethyl)-1,2,4-oxadiazole-5-carboxamide

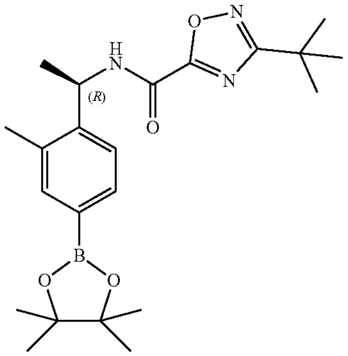

A mixture of (R)—N-(1-(4-bromo-2-methylphenyl)ethyl)-3-(tert-butyl)-1,2,4-oxadiazole-5-carboxamide (4.57 g, 12.48 mmol, 1.0 eq), 4,4,4',4',5,5,5',5'-octamethyl-2,2'-bi(1,3,2-dioxaborolane) (4.75 g, 18.72 mmol, 1.5 eq), KOAc (3.67 g, 37.4 mmol, 3.0 eq) and $PdCl_2$ (dppf) (0.913 g, 1.248 mmol, 0.1 eq) in Dioxane (25 ml) was stirred at 100° C. for 6 h. Water was added to the reaction mixture followed by extraction with EA for 3 times. The combined organic layers were washed with brine, dried over anhydrous $Na_2SO_4$ and concentrated in vacuo. The crude product was purified by flash chromatography eluted with Hex/EA=3:1 to give the title compound (2.7 g, 52.4%) as a white solid. MS (ESI) m/z 414.3 [M+H$^+$].

Step 3: tert-butyl 4-(4-(4,4,5,5-tetramethyl-1,3,2-dioxaborolan-2-yl)-3,6-dihydropyridin-1(2H)-yl)piperidine-1-carboxylate

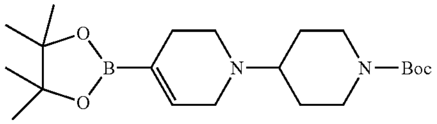 [SMILES: CC(C)(C)OC(=O)N1CCC(N2CC=C(B3OC(C)(C)C(C)(C)O3)CC2)CC1]

To a mixture of 4-(4,4,5,5-tetramethyl-1,3,2-dioxaborolan-2-yl)-1,2,3,6-tetrahydropyridine hydrochloride (1.0 g, 4.07 mmol, 1.0 eq), triethylamine (1.236 g, 12.22 mmol, 3.0 eq) and tert-butyl 4-oxopiperidine-1-carboxylate (0.811 g, 4.07 mmol, 1.0 eq) in DCM (25 ml) was added NaBH(OAc)3 (1.295 g, 6.11 mmol, 1.5 eq) in portions. The reaction mixture was stirred at rt under Ar for 16 h. Water was added to the reaction mixture followed by extraction with DCM for 3 times. The combined organic layers were washed with brine, dried over anhydrous $Na_2SO_4$ and concentrated in vacuo. The crude product was purified by flash chromatography eluted with DCM/MeOH=20:1 to give the title compound (1.0 g, 62.6%) as yellow oil.

Step 4: tert-butyl 4-(4-(4-chloro-7H-pyrrolo[2,3-d]pyrimidin-6-yl)-3,6-dihydropyridin-1(2H)-yl)piperidine-1-carboxylate

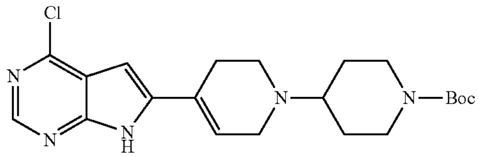 [SMILES: CC(C)(C)OC(=O)N1CCC(N2CC=C(c3cc4c(Cl)ncnc4[nH]3)CC2)CC1]

A mixture of tert-butyl 4-(4-(4,4,5,5-tetramethyl-1,3,2-dioxaborolan-2-yl)-3,6-dihydropyridin-1(2H)-yl)piperidine-1-carboxylate (1004 mg, 2.56 mmol, 1.3 eq), 4-chloro-6-iodo-7H-pyrrolo[2,3-d]pyrimidine (550 mg, 1.968 mmol, 1.0 eq), $Na_2CO_3$ (417 mg, 3.94 mmol, 2.0 eq) and $PdCl_2$ (dppf) (144 mg, 0.197 mmol, 0.1 eq) in Dioxane (5 ml) and Water (1 ml) was stirred at 80° C. for 2 h under Ar. Water was added to the reaction mixture followed by extraction with EA for 3 times. The combined organic layers were washed with brine, dried over anhydrous $Na_2SO_4$ and concentrated. The residue was purified by flash chromatography eluted with Hex/EA=3:1 to give the title compound (333 mg, 40.5%) as a yellow solid. MS (ESI) m/z 418.2 [M+H$^+$].

Step 5: tert-butyl (R)-4-(4-(4-(4-(1-(3-(tert-butyl)-1,2,4-oxadiazole-5-carboxamido)ethyl)-3-methylphenyl)-7H-pyrrolo[2,3-d]pyrimidin-6-yl)-3,6-dihydropyridin-1(2H)-yl)piperidine-1-carboxylate

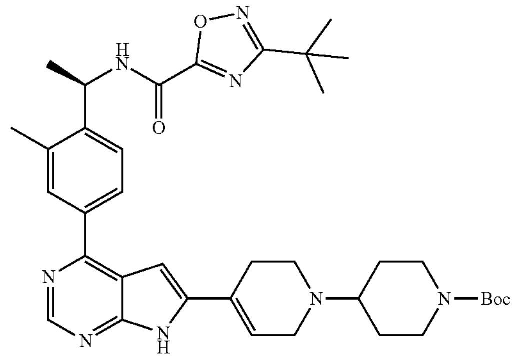 [SMILES: Cc1cc(-c2ncnc3[nH]c(C4=CCN(C5CCN(C(=O)OC(C)(C)C)CC5)CC4)cc23)ccc1[C@@H](C)NC(=O)c1nc(C(C)(C)C)no1]

A mixture of (R)-3-(tert-butyl)-N-(1-(2-methyl-4-(4,4,5,5-tetramethyl-1,3,2-dioxaborolan-2-yl)phenyl)ethyl)-1,2,4-oxadiazole-5-carboxamide (223 mg, 0.538 mmol, 1.5 eq), above obtained intermediate (150 mg, 0.359 mmol, 1.0 eq), $Na_2CO_3$ (38 mg, 0.359 mmol, 1.0 eq) and $PdCl_2$ (dppf) (26.3 mg, 0.036 mmol, 0.1 eq) in Dioxane (5 ml) and Water (1 ml) was stirred at 100° C. for 1 h under MW. Water was added to the reaction mixture followed by extraction with EA for 3 times. The combined organic layers were washed with brine, dried over anhydrous $Na_2SO_4$ and concentrated in vacuo. The residue was purified by flash chromatography eluted with Hex/EA=3:1 to give the title compound (100 mg, 41.7%) as a yellow solid. MS (ESI) m/z 669.4 [M+H$^+$].

Steps 6-7: (R)-3-(tert-butyl)-N-(1-(4-(6-(1-(1-((1-(4-(2,4-dioxotetrahydropyrimidin-1(2H)-yl)phenyl)piperidin-4-yl)methyl)piperidin-4-yl)-1,2,3,6-tetrahydropyridin-4-yl)-7H-pyrrolo[2,3-d]pyrimidin-4-yl)-2-methylphenyl)ethyl)-1,2,4-oxadiazole-5-carboxamide

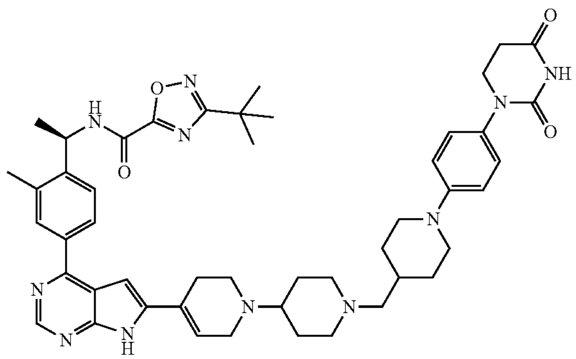 [SMILES: Cc1cc(-c2ncnc3[nH]c(C4=CCN(C5CCN(CC6CCN(c7ccc(N8CCC(=O)NC8=O)cc7)CC6)CC5)CC4)cc23)ccc1[C@@H](C)NC(=O)c1nc(C(C)(C)C)no1]

Following the synthesis of EXAMPLE 1, the title compound was obtained (51.1 mg) as a yellow solid. MS (ESI) m/z 854.5 [M+H$^+$]. $^1$H NMR (400 MHz, DMSO-d$^6$) δ (ppm): 12.28 (s, 1H), 10.23 (s, 1H), 9.92 (d, J=7.8 Hz, 1H), 8.78 (s, 1H), 8.11-7.92 (m, 2H), 7.66 (d, J=8.0 Hz, 1H), 7.23-7.06 (m, 2H), 7.02-6.88 (m, 2H), 6.82 (s, 1H), 6.60 (s, 1H), 5.48-5.27 (m, 1H), 3.76-3.62 (m, 4H), 3.32-3.23 (m, 4H), 2.99-2.85 (m, 2H), 2.78-2.61 (m, 6H), 2.59-2.53 (m, 3H), 2.39-2.23 (m, 1H), 2.15 (d, J=7.0 Hz, 2H), 1.96-1.74 (m, 6H), 1.72-1.61 (m, 1H), 1.58-1.53 (m, 3H), 1.53-1.43 (m, 2H), 1.38 (s, 9H), 1.25-1.11 (m, 2H).

Following the synthesis of EXAMPLE 7, the following compounds were synthesized and obtained in a similar manner.

| Compd No. | Structure Observed MS $[M + 1]^+$ | $^1H$ NMR (400 MHz, DMSO-$d^6$) δ (ppm) |
|---|---|---|
| 26 | 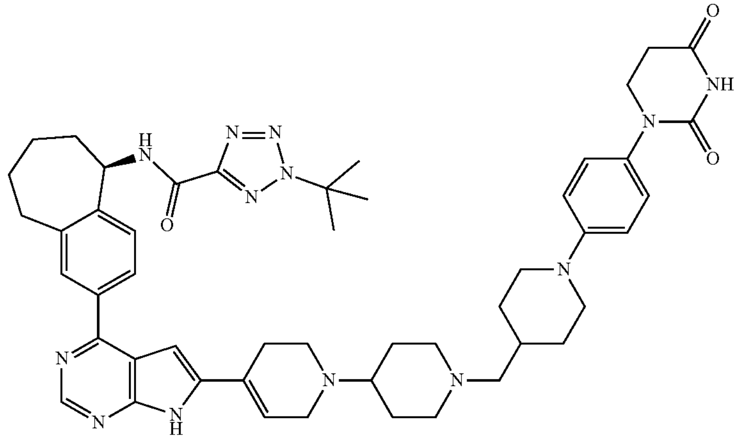 880.5 | 12.24 (s, 1H), 10.22 (s, 1H), 9.59 (d, J = 7.9 Hz, 1H), 8.74 (s, 1H), 8.06-7.87 (m, 2H), 7.39 (d, J = 8.4 Hz, 1H), 7.11 (d, J = 8.7 Hz, 2H), 6.90 (d, J = 8.8 Hz, 2H), 6.79 (s, 1H), 6.55 (s, 1H), 5.42-5.17 (m, 1H), 3.75-3.59 (m, 4H), 3.28-3.20 (m, 2H), 3.09-2.93 (m, 2H), 2.91-2.80 (m, 2H), 2.74-2.57 (m, 6H), 2.55-2.49 (m, 3H), 2.36-2.18 (m, 1H), 2.17-2.06 (m, 2H), 2.05-1.90 (m, 3H), 1.89-1.70 (m, 16H), 1.65-1.55 (m, 1H), 1.53-1.40 (m, 2H), 1.39-1.28 (m, 1H), 1.21-1.09 (m, 2H). |
| 27 | 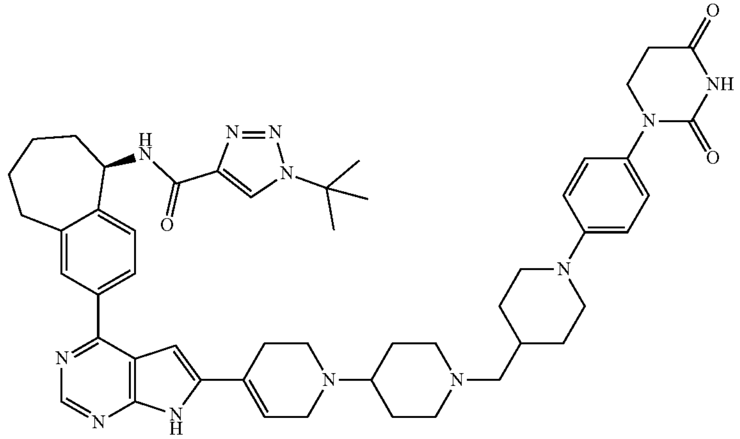 879.5 | 12.24 (s, 1H), 10.23 (s, 1H), 8.99 (d, J = 8.2 Hz, 1H), 8.73 (d, J = 5.5 Hz, 2H), 7.95 (s, 2H), 7.40 (d, J = 8.5 Hz, 1H), 7.12 (d, J = 8.9 Hz, 2H), 6.91 (d, J = 9.0 Hz, 2H), 6.79 (s, 1H), 6.56 (s, 1H), 5.33-5.29 (m, 1H), 3.76-3.58 (m, 4H), 3.28-3.20 (m, 3H), 3.09-2.93 (m, 2H), 2.94-2.81 (m, 1H), 2.76-2.59 (m, 6H), 2.57-2.51 (m, 3H), 2.40-2.23 (m, 1H), 2.23-2.08 (m, 2H), 2.02-1.94 (m, 5H), 1.87-1.75 (m, 5H), 1.66 (s, 9H), 1.52-1.39 (m, 2H), 1.22-1.09 (m, 4H). |

-continued
| Compd No. | Structure Observed MS $[M + 1]^+$ | $^1H$ NMR (400 MHz, DMSO-$d^6$) δ (ppm) |
|---|---|---|
| 28 | 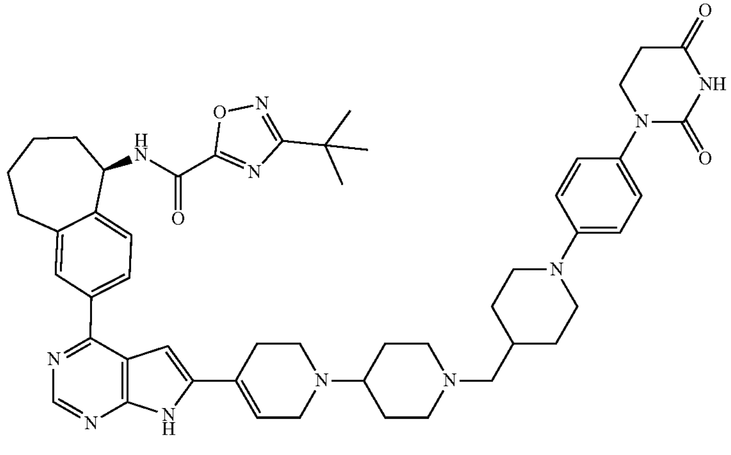 [SMILES: CC(C)(C)c1noc(C(=O)N[C@@H]2CCCCc3cc(-c4ncnc5[nH]c(C6=CCN(C7CCN(CC8CCN(c9ccc(N%10CCC(=O)NC%10=O)cc9)CC8)CC7)CC6)cc45)ccc32)n1] 880.5 | 12.25 (s, 1H), 10.21 (s, 1H), 10.00 (d, J = 8.0 Hz, 1H), 8.74 (s, 1H), 8.04-7.90 (m, 2H), 7.37 (d, J = 7.9 Hz, 1H), 7.11 (d, J = 8.9 Hz, 2H), 6.97-6.85 (m, 2H), 6.79 (s, 1H), 6.56 (s, 1H), 5.35-5.21 (m, 1H), 3.75-3.57 (m, 4H), 3.26-3.19 (m, 2H), 3.07-2.80 (m, 4H), 2.77-2.56 (m, 6H), 2.55-2.49 (m, 3H), 2.38-2.19 (m, 1H), 2.16-2.06 (m, 2H), 2.02-1.90 (m, 4H), 1.85-1.80 (m, 2H), 1.78-1.74 (m, 2H), 1.67-1.57 (m, 1H), 1.50-1.45 (m, 1H), 1.41-1.37 (m, 9H), 1.23-1.09 (m, 6H). |
| 38 | 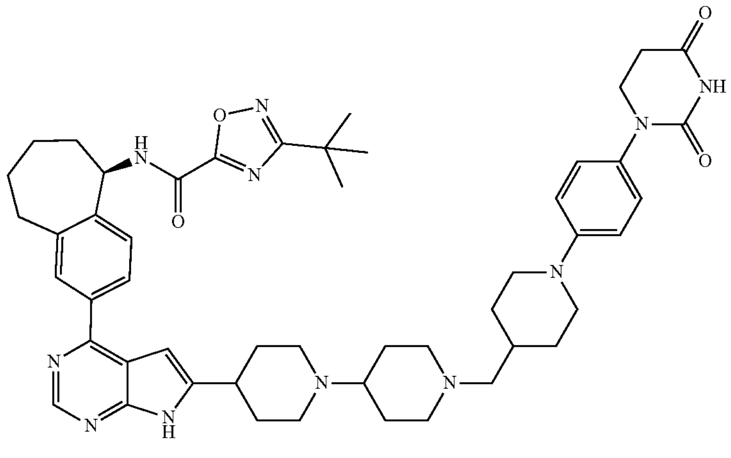 [SMILES: CC(C)(C)c1noc(C(=O)N[C@@H]2CCCCc3cc(-c4ncnc5[nH]c(C6CCN(C7CCN(CC8CCN(c9ccc(N%10CCC(=O)NC%10=O)cc9)CC8)CC7)CC6)cc45)ccc32)n1] 882.5 | 12.03 (s, 1H), 10.21 (s, 1H), 9.97 (d, J = 7.9 Hz, 1H), 8.68 (s, 1H), 8.03-7.83 (m, 2H), 7.34 (d, J = 8.5 Hz, 1H), 7.08 (d, J = 8.9 Hz, 2H), 6.87 (d, J = 9.0 Hz, 2H), 6.57 (s, 1H), 5.36-5.12 (m, 1H), 3.70-3.57 (m, 4H), 3.04-2.79 (m, 6H), 2.74-2.53 (m, 5H), 2.29-2.13 (m, 3H), 2.08 (d, J = 6.9 Hz, 2H), 2.02-1.87 (m, 5H), 1.85-1.57 (m, 11H), 1.47-1.30 (m, 12H), 1.18-1.02 (m, 2H). |

-continued
| Compd No. | Structure Observed MS $[M + 1]^+$ | $^1H$ NMR (400 MHz, DMSO-$d^6$) δ (ppm) |
|---|---|---|
| 57 | 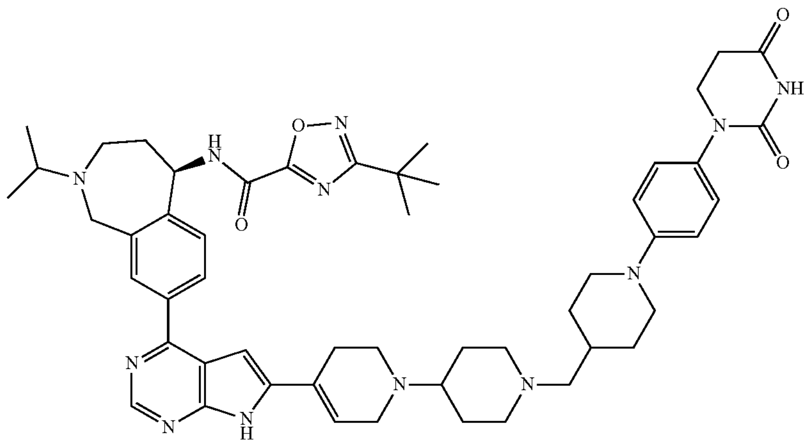 923.6 | 12.30 (s, 1H), 10.25 (s, 1H), 9.68 (d, J = 7.2 Hz, 1H), 8.78 (s, 1H), 8.07-7.91 (m, 2H), 7.42 (d, J = 8.6 Hz, 1H), 7.13 (d, J = 8.9 Hz, 2H), 7.01-6.86 (m, 2H), 6.80 (s, 1H), 6.59 (s, 1H), 5.49-5.36 (m, 1H), 4.07 (d, J = 15.5 Hz, 1H), 3.85 (d, J = 15.2 Hz, 1H), 3.75-3.61 (m, 4H), 3.29-3.22 (m, 2H), 3.14-3.03 (m, 1H), 3.00-2.82 (m, 4H), 2.78-2.60 (m, 6H), 2.57-2.54 (m, 1H), 2.36-2.25 (m, 1H), 2.22-2.10 (m, 3H), 2.04-1.93 (m, 2H), 1.92-1.84 (m, 2H), 1.83-1.73 (m, 4H), 1.71-1.59 (m, 1H), 1.56-1.43 (m, 2H), 1.39-1.37 (m, 9H), 1.23-1.16 (m, 2H), 1.15-1.05 (m, 6H). |
| 60 | 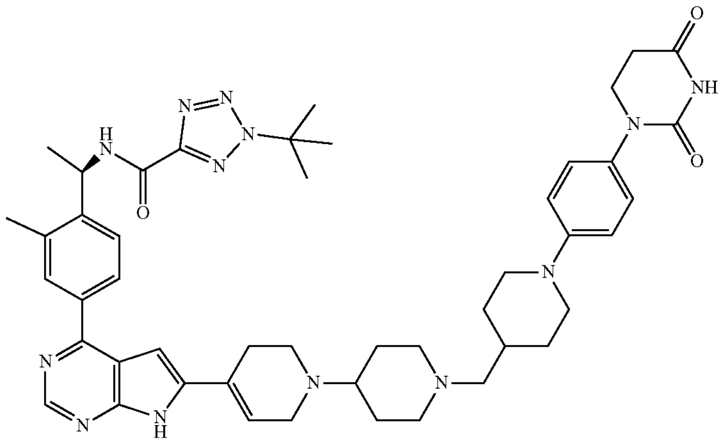 [SMILES: Cc1cc(-c2ncnc3[nH]c(C4=CCN(C5CCN(CC6CCN(c7ccc(N8CCC(=O)NC8=O)cc7)CC6)CC5)CC4)cc23)ccc1[C@@H](C)NC(=O)c1nnn(C(C)(C)C)n1] 854.5 | 12.30 (s, 1H), 10.28 (s, 1H), 9.56 (d, J = 8.0 Hz, 1H), 8.79 (s, 1H), 8.01-7.97 (m, 1H), 7.69 (d, J = 8.0 Hz, 1H), 7.16 (d, J = 8.8 Hz, 2H), 6.97-6.87 (m, 2H), 6.83 (s, 1H), 6.61 (s, 1H), 5.51-5.33 (m, 2H), 3.74-3.70 (m, 4H), 3.32-3.26 (m, 4H), 2.96-2.88 (m, 1H), 2.78-2.66 (m, 8H), 2.61-2.57 (m, 2H), 2.40-2.32 (m, 1H), 2.27-2.13 (m, 2H), 2.05-1.99 (m, 2H), 1.97-1.89 (m, 1H), 1.85-1.79 (m, 2H), 1.76-1.75 (m, 9H), 1.59-1.44 (m, 7H), 1.25-1.19 (m, 2H). |

Example 8: (R)-3-(tert-butyl)-N-(1-(4-(2-(6-H-((1-(4-(2,4-dioxotetrahydropyrimidin-1(2H)-yl)phenyl)piperidin-4-yl)methyl)piperazin-1-yl)pyridin-3-yl)-6-methyl-7-oxo-6,7-dihydro-1H-pyrrolo[2,3-d]pyridazin-4-yl)-2-methylphenyl)ethyl)-1,2,4-oxadiazole-5-carboxamide (Compound No. 6)

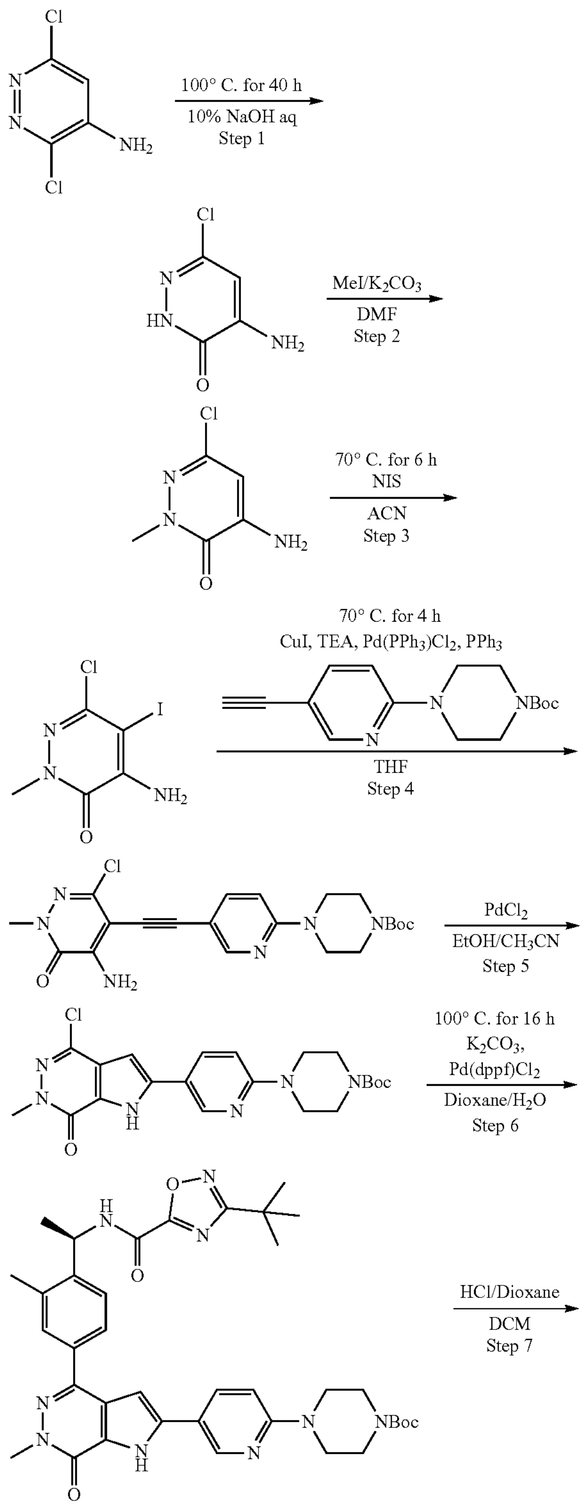

-continued

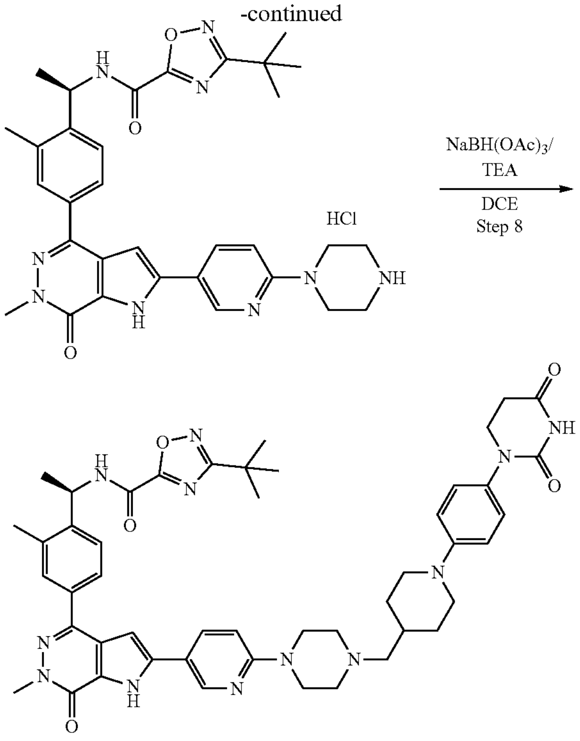

Step 1: 4-amino-6-chloropyridazin-3(2H)-one

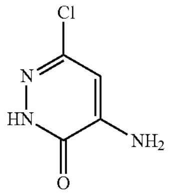

A mixture of 3,6-dichloropyridazin-4-amine (25 g, 152 mmol, 1.0 eq) in 3M NaOH aqueous (200 ml) was stirred at 100° C. for 40 h. Cooled to rt, adjust pH=3-4 using HCl aqueous. Filtered and rinsed with EtOH. Dried in vacuo to give the title compound (18 g, 80%) as a pink solid. LC-MS: 146.7 (M+H+).

Step 2:
4-amino-6-chloro-2-methylpyridazin-3(2H)-one

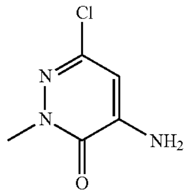

A mixture of 4-amino-6-chloropyridazin-3(2H)-one (5 g, 34.4 mmol, 1.0 eq), iodomethane (5.36 g, 37.8 mmol, 1.1 eq) and $K_2CO_3$ (9.97 g, 72.1 mmol, 2.1 eq) in dry DMF (100 ml)

was stirred at rt for 3 h. Diluted with water, extracted with EA for 3 times. The combined EA layers were washed with brine, dried over anhydrous $Na_2SO_4$ and concentrated in vacuo. The residue was purified by flash chromatography eluted with DCM/MeOH=20:1 to give the title compound (2.2 g, 40.1%) as a pink solid. LC-MS: 160.1 (M+H+).

Step 3: 4-amino-6-chloro-5-iodo-2-methylpyridazin-3(2H)-one

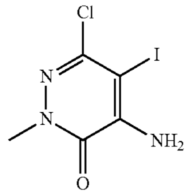

A mixture of 4-amino-6-chloro-2-methylpyridazin-3(2H)-one (1.6 g, 10.0 mmol, 1.0 eq) and NIS (3.38 g, 15.0 mmol, 1.5 eq) in dry $CH_3CN$ (100 ml) was stirred at 80° C. for 6 h. $Na_2S_2O_3$ aqueous was added and extracted with EA for 3 times. The combined EA layers were washed with brine, dried over anhydrous $Na_2SO_4$ and concentrated in vacuo. The residue was purified by flash chromatography eluted with Hex/EA=3:1 to give the title compound (800 mg, 27.9%) as a yellow solid. LC-MS: 286.1 (M+H+).

Step 4: tert-butyl 4-(5-((5-amino-3-chloro-1-methyl-6-oxo-1,6-dihydropyridazin-4-yl)ethynyl)pyridin-2-yl)piperazine-1-carboxylate

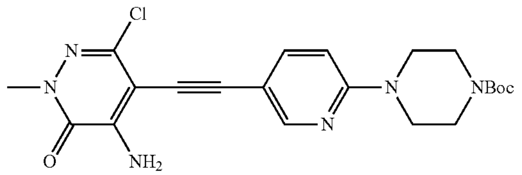 [SMILES: Cn1nc(Cl)c(C#Cc2ccc(N3CCN(C(=O)OC(C)(C)C)CC3)nc2)c(N)c1=O]

To a mixture of 4-amino-6-chloro-5-iodo-2-methylpyridazin-3(2H)-one (500 mg, 1.752 mmol, 1.0 eq), triethylamine (886 mg, 8.76 mmol, 5.0 eq), copper (I) iodide (66.7 mg, 0.35 mmol, 0.2 eq), $PPh_3$ (300 mg, 1.14 mmol, 0.65 eq) and $Pd(PPh_3)_2Cl_2$ (123 mg, 0.175 mmol, 0.1 eq) in dry $CH_3CN$ (15 ml) under Ar was added tert-butyl 4-(5-ethynylpyridine-2-yl)piperazine-1-carboxylate (755 mg, 2.63 mmol, 1.5 eq) at rt. The reaction mixture was stirred at 70° C. under Ar for 4 h. Water was added and extracted with EA for 3 times. The combined EA layers were washed with brine, dried over anhydrous $Na_2SO_4$ and concentrated in vacuo. The residue was purified by flash chromatography eluted with Hex/EA=1:1 to give the title compound (600 mg, 77%) as a yellow solid. LC-MS: 445.6 (M+H+).

Step 5: tert-butyl 4-(5-(4-chloro-6-methyl-7-oxo-6,7-dihydro-1H-pyrrolo[2,3-d]pyridazin-2-yl)pyridin-2-yl)piperazine-1-carboxylate

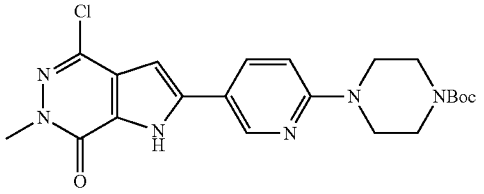 [SMILES: Cn1nc(Cl)c2cc(-c3ccc(N4CCN(C(=O)OC(C)(C)C)CC4)nc3)[nH]c2c1=O]

A mixture of tert-butyl 4-(5-((5-amino-3-chloro-1-methyl-6-oxo-1,6-dihydropyridazin-4-yl)ethynyl)pyridin-2-yl)piperazine-1-carboxylate (300 mg, 0.674 mmol, 1.0 eq) and EtONa (229 mg, 3.37 mmol, 5.0 eq) in EtOH (4 ml) and $CH_3CN$ (4 ml) was stirred at 80° C. under Ar for 6 h. Quenched with $NH_4Cl$ aqueous and concentrated. Filtered and dried in vacuo to give the title compound (200 mg, 66.7%) as a yellow solid. LC-MS: 445.2 (M+H+).

Step 6: tert-butyl (R)-4-(5-(4-(4-(1-(3-(tert-butyl)-1,2,4-oxadiazole-5-carboxamido)ethyl)-3-methylphenyl)-6-methyl-7-oxo-6,7-dihydro-1H-pyrrolo[2,3-d]pyridazin-2-yl)pyridin-2-yl)piperazine-1-carboxylate

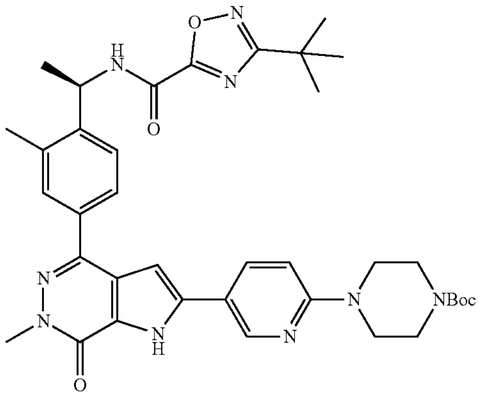 [SMILES: Cc1cc(-c2nn(C)c(=O)c3[nH]c(-c4ccc(N5CCN(C(=O)OC(C)(C)C)CC5)nc4)cc23)ccc1[C@@H](C)NC(=O)c1nc(C(C)(C)C)no1]

A mixture of (R)-3-(tert-butyl)-N-(1-(2-methyl-4-(4,4,5,5-tetramethyl-1,3,2-dioxaborolan-2-yl)phenyl)ethyl)-1,2,4-oxadiazole-5-carboxamide (223 mg, 0.54 mmol, 1.2 eq), above obtained intermediate (200 mg, 0.45 mmol, 1.0 eq), $PdCl_2$ (dppf) (66 mg, 0.09 mmol, 0.2 eq) and $K_2CO_3$ (186 mg, 1.35 mmol, 3.0 eq) in Dioxane/$H_2O$ (10 ml/2 ml) was stirred at 100° C. under Ar for 16 h. Diluted with water, extracted with EA for 3 times. The combined EA layers were washed with brine, dried over anhydrous $Na_2SO_4$ and concentrated in vacuo. The residue was purified by flash chromatography eluted with DCM/EA=1:1-1:3 to give the title compound (120 mg, 38.4%) as a yellow solid. LC-MS: 696.3 (M+H+).

Step 7: (R)-3-(tert-butyl)-N-(1-(2-methyl-4-(6-methyl-7-oxo-2-(6-(piperazin-1-yl)pyridin-3-yl)-6,7-dihydro-1H-pyrrolo[2,3-d]pyridazin-4-yl)phenyl) ethyl)-1,2,4-oxadiazole-5-carboxamide hydrochloride

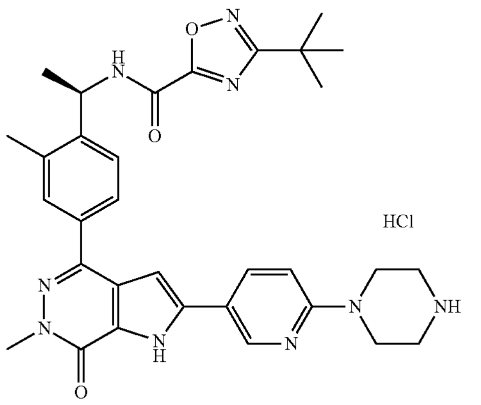 [SMILES: Cc1cc(-c2nn(C)c(=O)c3[nH]c(-c4ccc(N5CCNCC5)nc4)cc23)ccc1[C@@H](C)NC(=O)c1nc(C(C)(C)C)no1 ; Cl]

A mixture of above obtained intermediate (120 mg, 0.172 mmol, 1.0 eq) in 4M HCl/Dioxane (1 ml) and dry DCM (4 ml) was stirred at rt for 2 h. Concentrated in vacuo to give the title compound (110 mg, 100%) as a yellow solid. LC-MS: 596.4 (M+H$^+$).

Step 8: (R)-3-(tert-butyl)-N-(1-(4-(2-(6-(4-((1-(4-(2,4-dioxotetrahydropyrimidin-1(2H)-yl)phenyl)piperidin-4-yl)methyl)piperazin-1-yl)pyridin-3-yl)-6-methyl-7-oxo-6,7-dihydro-1H-pyrrolo[2,3-d]pyridazin-4-yl)-2-methylphenyl)ethyl)-1,2,4-oxadiazole-5-carboxamide

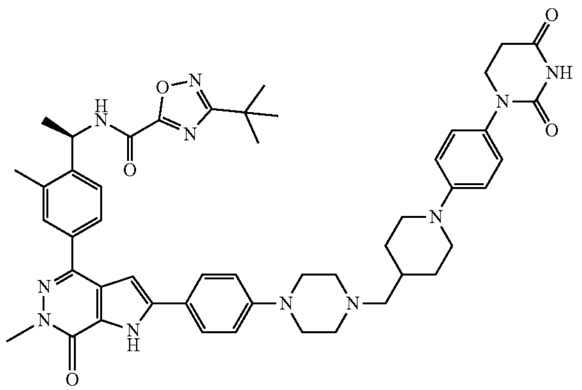 [SMILES: Cc1cc(-c2nn(C)c(=O)c3[nH]c(-c4ccc(N5CCN(CC6CCN(c7ccc(N8CCC(=O)NC8=O)cc7)CC6)CC5)cc4)cc23)ccc1[C@@H](C)NC(=O)c1nc(C(C)(C)C)no1]

To a mixture of above obtained intermediate (100 mg, 0.158 mmol, 1.0 eq), 1-(4-(2,4-dioxotetrahydropyrimidin-1(2H)-yl)phenyl)piperidine-4-carbaldehyde (71.5 mg, 0.237 mmol, 1.5 eq) and TEA (80 mg, 0.791 mmol, 5.0 eq) in dry DCE (5 ml) was added NaBH(OAc) 3 (67 mg, 0.316 mmol, 2.0 eq) in portions. The reaction was stirred at rt under Ar for 16 h. The reaction was quenched with water and extracted with DCM for 3 times. The organic layers were washed with brine, dried over anhydrous $Na_2SO_4$. After concentration in vacuo. The residue was purified by pre-HPLC to give the title compound (54 mg, 38.7%) as a white solid. LC-MS: 881.7 (M+H$^+$). $^1$H NMR (400 MHz, DMSO-d$^6$) δ (ppm) 12.87 (s, 1H), 10.16 (s, 1H), 9.83 (d, J=8.0 Hz, 1H), 8.71 (d, J=2.0 Hz, 1H), 8.15-8.05 (m, 1H), 7.68-7.52 (m, 3H), 7.06 (d, J=8.8 Hz, 2H), 6.95 (s, 1H), 6.88-6.80 (m, 3H), 5.34-5.25 (m, 1H), 3.74 (s, 3H), 3.66-3.58 (m, 4H), 3.55-3.45 (m, 4H), 3.23-3.17 (m, 2H), 2.65-2.55 (m, 4H), 2.43-2.35 (m, 4H), 2.20-2.10 (m, 2H), 1.81-1.60 (m, 3H), 1.46 (d, J=3.2 Hz, 3H), 1.30 (s, 9H), 1.22-1.10 (m, 3H).

Example 9: (R)-2-(tert-butyl)-N-(2-(6-(6-(4-((1-(4-(2,4-dioxotetrahydropyrimidin-1(2H)-yl)phenyl) piperidin-4-yl)methyl)piperazin-1-yl)pyridin-3-yl)-7H-pyrrolo[2,3-d]pyrimidin-4-yl)-6,7,8,9-tetrahydro-5H-benzo[7]annulen-5-yl)-2H-tetrazole-5-carboxamide (Compound No. 12)

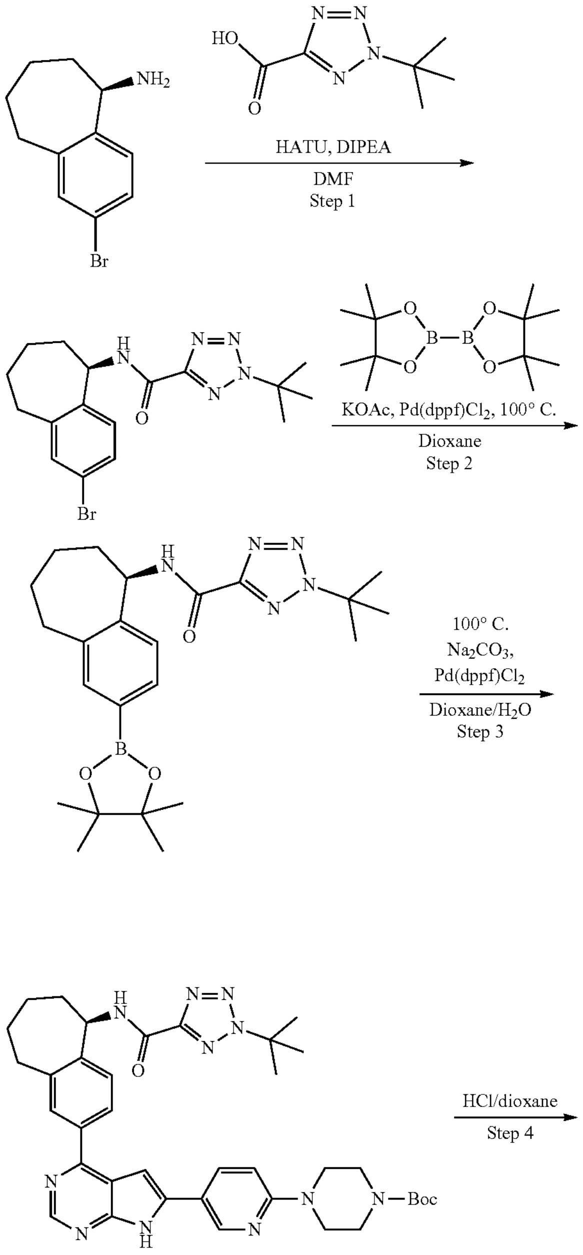

-continued

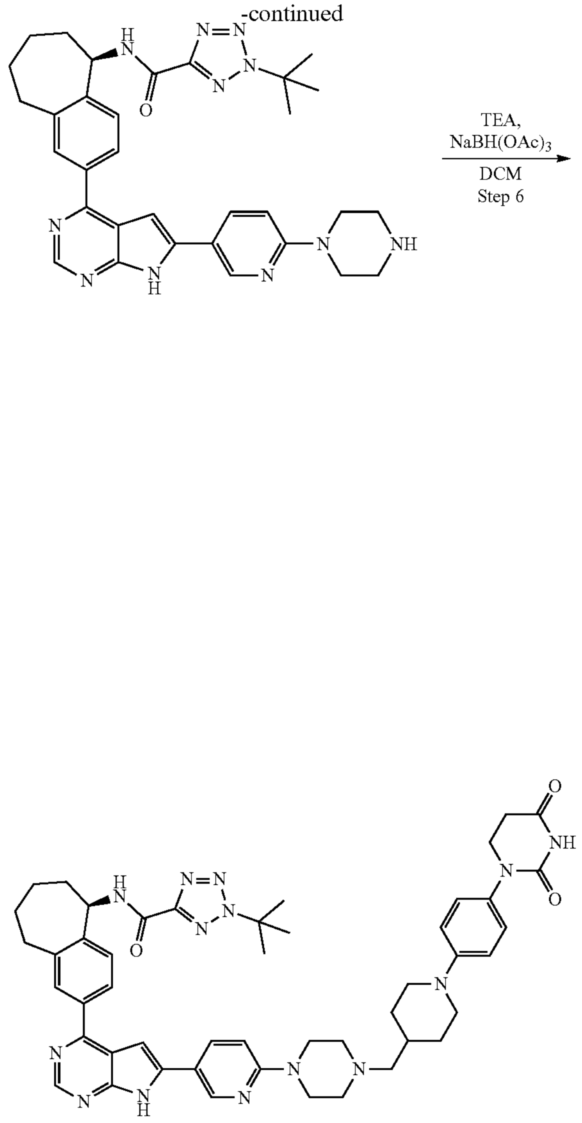

Step 1: (R)—N-(2-bromo-6,7,8,9-tetrahydro-5H-benzo[7]annulen-5-yl)-2-(tert-butyl)-2H-tetrazole-5-carboxamide

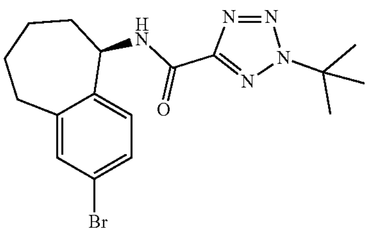 [SMILES: CC(C)(C)n1nnc(C(=O)N[C@@H]2CCCCc3cc(Br)ccc32)n1]

A mixture of (R)-2-bromo-6,7,8,9-tetrahydro-5H-benzo[7]annulen-5-amine (350 mg, 1.457 mmol, 1.0 eq), 2-(tert-butyl)-2H-tetrazole-5-carboxylic acid (273 mg, 1.603 mmol, 1.1 eq), HATU (665 mg, 1.749 mmol, 1.2 eq) and DIEA (565 mg, 4.37 mmol, 3.0 eq) in dry DMF (15 ml) was stirred at rt for 1 h under Ar. Water was added to the reaction mixture followed by extraction with EA for times. The combined organic layers were washed with brine, dried over anhydrous $Na_2SO_4$ and concentrated. The residue was purified by flash chromatography eluted with Hex/EA=3:1 to give the title compound (523 mg, 91%) as a white solid. MS (ESI) m/z 392.1 [M+H$^+$].

Steps 2-4: (R)-2-(tert-butyl)-N-(2-(6-(6-(4-((1-(4-(2,4-dioxotetrahydropyrimidin-1(2H)-yl)phenyl)piperidin-4-yl)methyl)piperazin-1-yl)pyridin-3-yl)-7H-pyrrolo[2,3-d]pyrimidin-4-yl)-6,7,8,9-tetrahydro-5H-benzo[7]annulen-5-yl)-2H-tetrazole-5-carboxamide

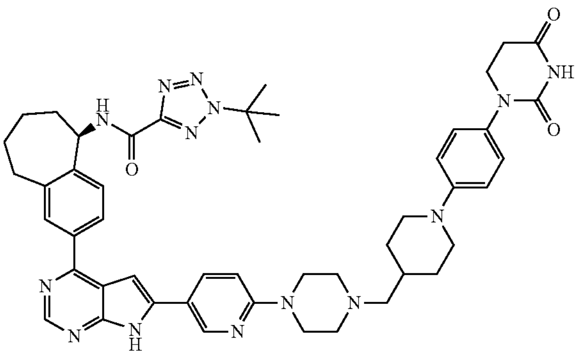 [SMILES: CC(C)(C)n1nnc(C(=O)N[C@@H]2CCCCc3cc(-c4ncnc5[nH]c(-c6ccc(N7CCN(CC8CCN(c9ccc(N%10CCC(=O)NC%10=O)cc9)CC8)CC7)nc6)cc45)ccc32)n1]

Following the synthesis of EXAMPLE 1, the title compound was obtained (35 mg) as a yellow solid. MS (ESI) m/z 877.5 [M+H$^+$]. $^1$H NMR (400 MHz, DMSO-d$^6$) δ (ppm): 12.55 (s, 1H), 10.23 (s, 1H), 9.63 (d, J=8.1 Hz, 1H), 8.78 (d, J=2.2 Hz, 1H), 8.74 (s, 1H), 8.24-8.11 (m, 1H), 8.09-7.95 (m, 2H), 7.41 (d, J=7.9 Hz, 1H), 7.27 (s, 1H), 7.11 (d, J=8.9 Hz, 2H), 6.99-6.83 (m, 3H), 5.45-5.21 (m, 1H), 3.82-3.61 (m, 4H), 3.60-3.48 (m, 4H), 3.13-2.87 (m, 2H), 2.77-2.57 (m, 4H), 2.47-2.33 (m, 4H), 2.19 (d, J=6.8 Hz, 2H), 2.04-1.55 (m, 18H), 1.42-1.28 (m, 1H), 1.20-1.12 (m, 1H).

Following the synthesis of EXAMPLE 9, the following compounds were synthesized and obtained in a similar manner.

| Compd No. | Structure Observed MS [M + 1]+ | $^1H$ NMR (400 MHz, DMSO-d6) δ (ppm) |
|---|---|---|
| 15 | 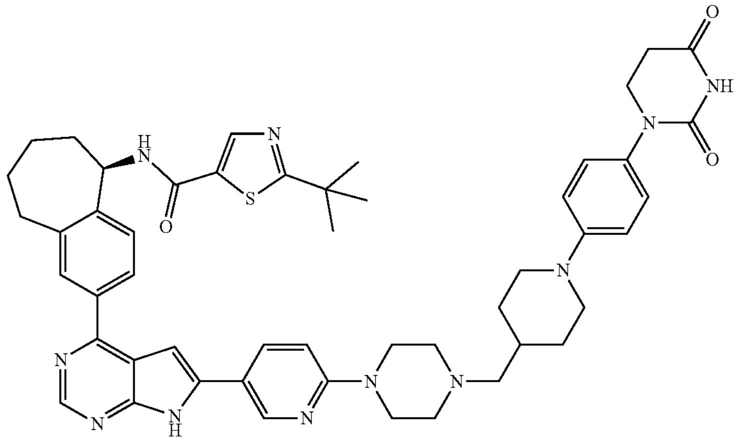 892.5 | 12.53 (s, 1H), 10.22 (s, 1H), 8.84-8.76 (m, 1H), 8.73 (s, 1H), 8.60 (d, J = 8.3 Hz, 1H), 8.25-8.11 (m, 2H), 8.07-7.94 (m, 2H), 7.39 (d, J = 7.9 Hz, 1H), 7.26 (s, 1H), 7.10 (d, J = 8.8 Hz, 2H), 6.97-6.82 (m, 3H), 5.40-5.13 (m, 1H), 3.72-3.60 (m, 4H), 3.59-3.48 (m, 4H), 3.10-2.91 (m, 2H), 2.73-2.55 (m, 4H), 2.46-2.31 (m, 4H), 2.18 (d, J = 6.8 Hz, 2H), 2.05-1.60 (m, 9H), 1.44 (s, 9H), 1.22-1.14 (m, 2H). |
| 18 | 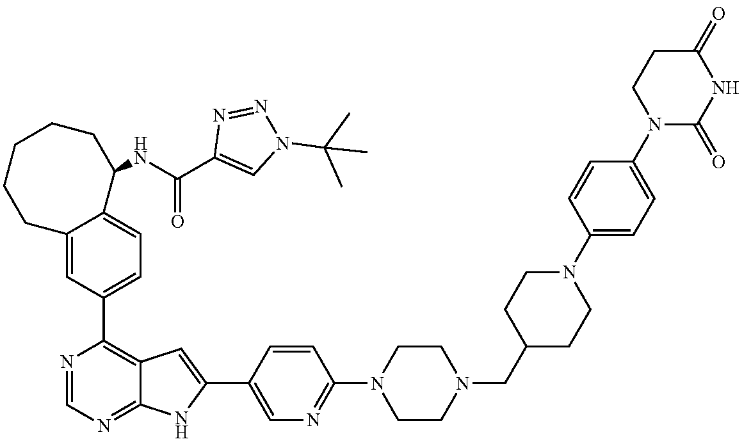 [SMILES: CC(C)(C)n1cc(C(=O)N[C@@H]2CCCCCc3cc(-c4ncnc5[nH]c(-c6ccc(N7CCN(CC8CCN(c9ccc(N%10CCC(=O)NC%10=O)cc9)CC8)CC7)nc6)cc45)ccc32)nn1] 876.5 | 12.53 (s, 1H), 10.22 (s, 1H), 9.00 (d, J = 8.2 Hz, 1H), 8.83-8.64 (m, 3H), 8.23-8.08 (m, 1H), 8.08-7.94 (m, 2H), 7.40 (d, J = 8.2 Hz, 1H), 7.25 (s, 1H), 7.10 (d, J = 8.9 Hz, 2H), 6.97-6.82 (m, 3H), 5.43-5.13 (m, 1H), 3.78-3.48 (m, 8H), 3.13-2.87 (m, 2H), 2.75-2.55 (m, 4H), 2.46-2.35 (m, 4H), 2.28-2.11 (m, 2H), 2.03-1.53 (m, 18H), 1.42-1.27 (m, 1H), 1.20-1.12 (m, 1H). |
| 22 | 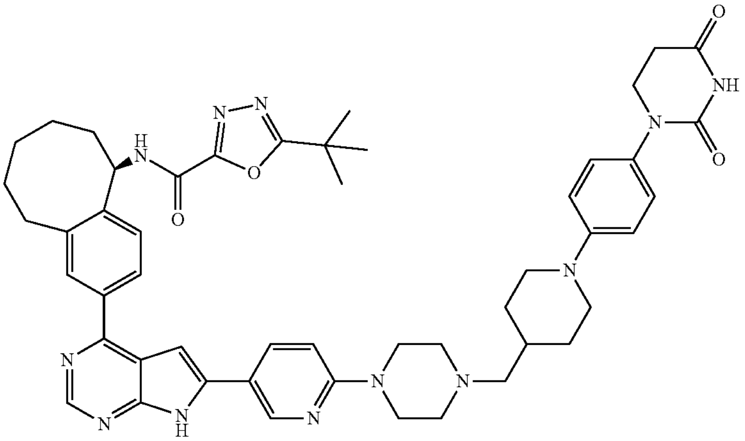 877.5 | 12.55 (s, 1H), 10.23 (s, 1H), 9.92 (d, J = 8.0 Hz, 1H), 8.85-8.66 (m, 2H), 8.23-8.11 (m, 1H), 8.09-7.96 (m, 2H), 7.41 (d, J = 8.0 Hz, 1H), 7.26 (s, 1H), 7.10 (d, J = 8.9 Hz, 2H), 6.95-6.70 (m, 3H), 5.44-5.13 (m, 1H), 3.82-3.47 (m, 8H), 3.15-2.83 (m, 2H), 2.77-2.57 (m, 4H), 2.46-2.34 (m, 4H), 2.28-2.11 (m, 2H), 2.09-1.56 (m, 9H), 1.41 (s, 9H), 1.36-1.28 (m, 1H), 1.20-1.08 (m, 1H). |

-continued
| Compd No. | Structure Observed MS [M + 1]$^+$ | $^1$H NMR (400 MHz, DMSO-d$^6$) δ (ppm) |
|---|---|---|
| 23 | 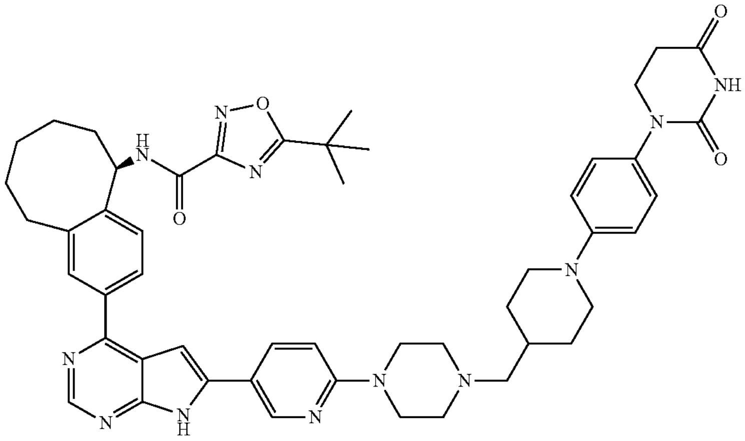 [SMILES: CC(C)(C)c1nc(C(=O)N[C@@H]2CCCCCc3cc(-c4ncnc5[nH]c(-c6ccc(N7CCN(CC8CCN(c9ccc(N%10CCC(=O)NC%10=O)cc9)CC8)CC7)nc6)cc45)ccc32)no1] | 12.55 (s, 1H), 10.23 (s, 1H), 9.59 (d, J = 8.0 Hz, 1H), 8.87-8.68 (m, 2H), 8.25-8.11 (m, 1H), 8.12-7.94 (m, 2H), 7.39 (d, J = 8.0 Hz, 1H), 7.27 (s, 1H), 7.12 (d, J = 8.7 Hz, 2H), 7.00-6.84 (m, 3H), 5.41-5.16 (m, 1H), 3.79-3.49 (m, 8H), 3.14-2.89 (m, 2H), 2.78-2.58 (m, 4H), 2.48-2.37 (m, 4H), 2.20 (d, J = 6.7 Hz, 2H), 2.04-1.62 (m, 9H), 1.45 (s, 9H), 1.39-1.31 (m, 1H), 1.21-1.14 (m, 1H). |
Example 10: (R)-3-(tert-butyl)-N-(1-(4-(6-(6-(4-((1-(4-(2,4-dioxotetrahydropyrimidin-1(2H)-yl)phenyl)piperidin-4-yl)methyl)piperazin-1-yl)pyridin-3-yl)pyrrolo[2,1-f][1,2,4]triazin-4-yl)-2-methylphenyl)ethyl)-1,2,4-oxadiazole-5-carboxamide (Compound No. 19)
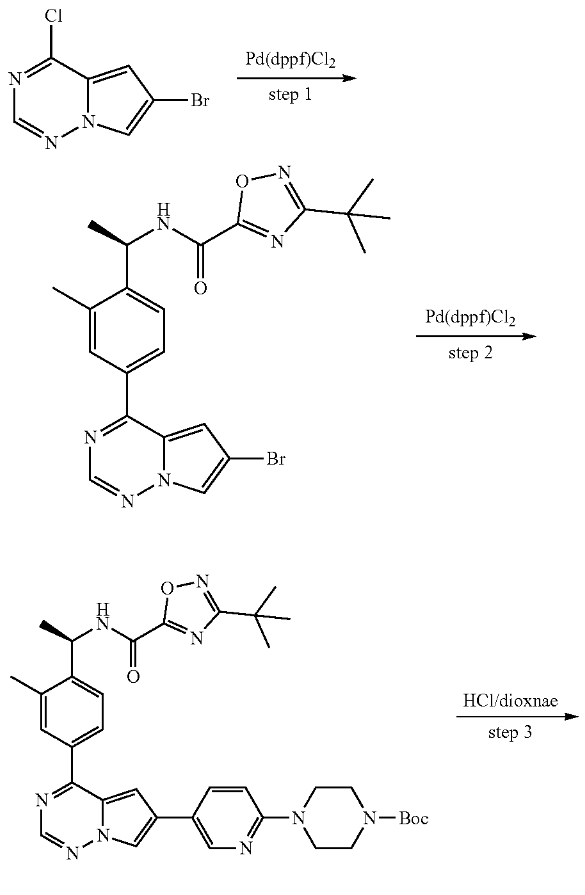
-continued
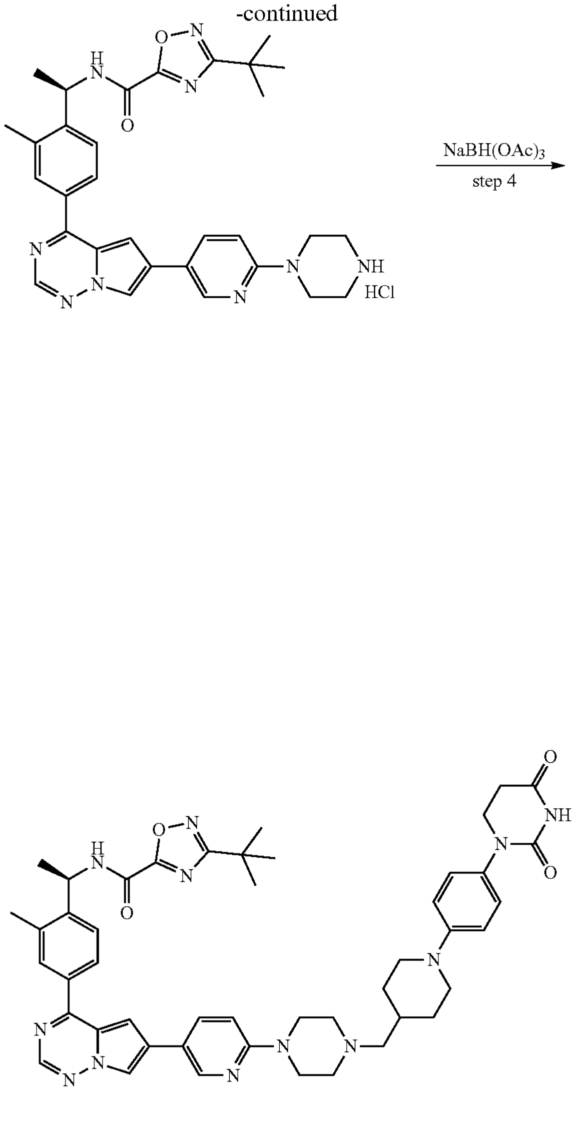

Step 1: (R)—N-(1-(4-(6-bromopyrrolo[2,1-f][1,2,4]triazin-4-yl)-2-methylphenyl)ethyl)-3-(tert-butyl)-1,2,4-oxadiazole-5-carboxamide

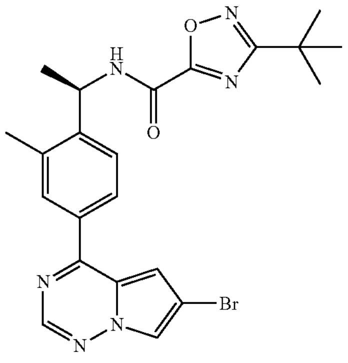 [SMILES: Cc1cc(-c2ncnn3cc(Br)cc23)ccc1[C@@H](C)NC(=O)c1nc(C(C)(C)C)no1]

In a 100 ml round-bottomed flask, (R)-3-(tert-butyl)-N-(1-(2-methyl-4-(4,4,5,5-tetramethyl-1,3,2-dioxaborolan-2-yl)phenyl)ethyl)-1,2,4-oxadiazole-5-carboxamide (273 mg, 0.660 mmol, 1.0 eq), 6-bromo-4-chloropyrrolo[2,1-f][1,2,4]triazine (200 mg, 0.859 mmol, 1.3 eq), $K_2CO_3$ (274 mg, 1.981 mmol, 3.0 eq) and Pd(dppf)$Cl_2$ (48.3 mg, 0.066 mmol, 0.1 eq) were dissolved in Dioxane (5 ml) and Water (0.5 ml) under nitrogen. The mixture was stirred at 100° C. for 16 h. Water was added to the reaction mixture followed by extraction with EA. The combined organic layers were dried $Na_2SO_4$, filtered and concentrated. The crude product was added to a silica gel column and was eluted with PE/EA 0~30% to give the title compound (280 mg, 88%) as a yellow solid. MS (ESI) m/z 483.3 $[M+H]^+$.

Step 2: tert-butyl (R)-4-(5-(4-(4-(1-(3-(tert-butyl)-1,2,4-oxadiazole-5-carboxamido)ethyl)-3-methylphenyl) pyrrolo[2,1-f][1,2,4]triazin-6-yl)pyridin-2-yl) piperazine-1-carboxylate

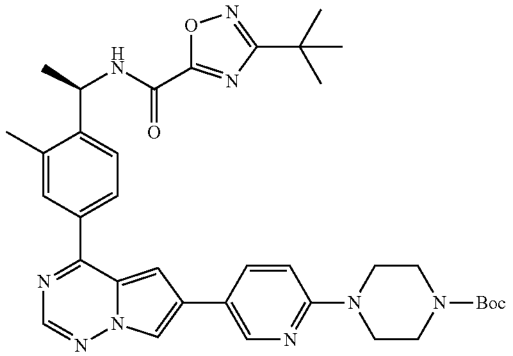 [SMILES: Cc1cc(-c2ncnn3cc(-c4ccc(N5CCN(C(=O)OC(C)(C)C)CC5)nc4)cc23)ccc1[C@@H](C)NC(=O)c1nc(C(C)(C)C)no1]

In a 100 ml round-bottomed flask, above obtained intermediate (280 mg, 0.579 mmol, 1.0 eq), tert-butyl 4-(5-(4,4,5,5-tetramethyl-1,3,2-dioxaborolan-2-yl)pyridin-2-yl)piperazine-1-carboxylate (338 mg, 0.869 mmol, 1.5 eq), Pd(dppf)$Cl_2$ (42.4 mg, 0.058 mmol, 0.1 eq) and $K_2CO_3$ (240 mg, 1.738 mmol, 3.0 eq) were dissolved in Dioxane (10 ml) and Water (1 ml) under argon. The reaction mixture was stirred at 100° C. for 12 h under Ar. Water was added to the reaction mixture followed by extraction with ethyl acetate. The combined organic layers were dried $Na_2SO_4$, filtered and concentrated. The crude product was added to a silica gel column and was eluted with EA/PE from 0% to 40% to give the title compound (300 mg, 78%) as a yellow solid. MS (ESI) m/z 666.6 $[M+H]^+$.

Step 3: (R)-3-(tert-butyl)-N-(1-(2-methyl-4-(6-(6-(piperazin-1-yl)pyridin-3-yl) pyrrolo[2,1-f][1,2,4]triazin-4-yl)phenyl)ethyl)-1,2,4-oxadiazole-5-carboxamide hydrochloride

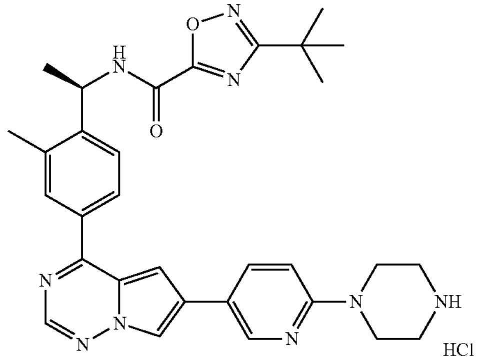 [SMILES: Cc1cc(-c2ncnn3cc(-c4ccc(N5CCNCC5)nc4)cc23)ccc1[C@@H](C)NC(=O)c1nc(C(C)(C)C)no1 ; Cl]

In a 100 ml round-bottomed flask, above obtained intermediate (100 mg, 0.150 mmol, 1.0 eq) was dissolved in DCM (5 ml) and 4M HCl in dioxane (2 ml). The reaction mixture was stirred for 3 h and concentrated to give the title compound (90 mg, 100%) as a yellow solid. MS (ESI) m/z 4566.6 $[M-HCl+H]^+$.

Step 4: (R)-3-(tert-butyl)-N-(1-(4-(6-(6-(4-((1-(4-(2,4-dioxotetrahydropyrimidin-1(2H)-yl)phenyl)piperidin-4-yl)methyl)piperazin-1-yl)pyridin-3-yl) pyrrolo[2,1-f][1,2,4]triazin-4-yl)-2-methylphenyl)ethyl)-1,2,4-oxadiazole-5-carboxamide

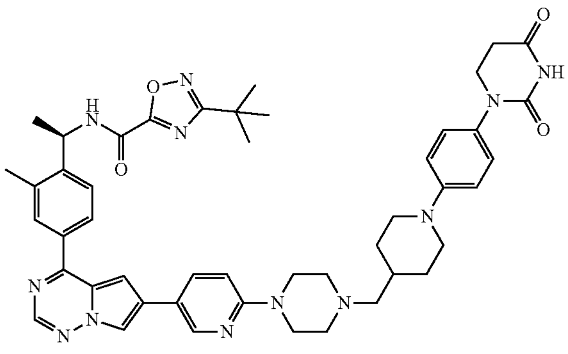 [SMILES: Cc1cc(-c2ncnn3cc(-c4ccc(N5CCN(CC6CCN(c7ccc(N8CCC(=O)NC8=O)cc7)CC6)CC5)nc4)cc23)ccc1[C@@H](C)NC(=O)c1nc(C(C)(C)C)no1]

In a 25 ml round-bottomed flask, above obtained intermediate (90 mg, 0.149 mmol, 1.0 eq), 1-(4-(2,4-dioxotetrahydropyrimidin-1(2H)-yl)phenyl)piperidine-4-carbaldehyde (54.0 mg, 0.179 mmol, 1.2 eq), triethylamine (46 mg, 0.447 mmol, 3.0 eq), and sodium triacetoxyborohydride (47.5 mg, 0.224 mmol, 1.5 eq) were dissolved in DCM (10 ml). The mixture was stirred at rt for 16 h. Water was added to the reaction mixture followed by extraction with dichloromethane. The combined organic layers were dried $Na_2SO_4$, filtered and concentrated. The crude product was added to a Prep HPLC column to give the title compound (45.1 mg, 35.5%) as a light-yellow solid. MS (ESI) m/z 851.6 $[M+H]^+$. $^1$H NMR (400 MHz, DMSO-d$^6$) δ (ppm) 10.27 (s, 1H), 10.01 (d, J=7.7 Hz, 1H), 8.75 (d, J=2.5 Hz, 1H), 8.68 (d, J=1.5 Hz, 1H), 8.60 (s, 1H), 8.15-8.06 (m, 2H), 8.05-8.00 (m, 1H), 7.72 (d, J=8.1 Hz, 1H), 7.62 (d, J=1.6 Hz, 1H), 7.16 (d, J=8.9 Hz, 2H), 6.96 (s, 1H), 6.93 (d, J=11.1 Hz, 2H), 5.41 (p, J=7.1 Hz, 1H), 3.78-3.66 (m, 3H), 3.57 (s, 4H), 3.41-3.33 (m, 3H), 2.75-2.64 (m, 4H), 2.56 (s, 3H), 2.51-2.46 (m, 4H), 2.25 (d, J=7.0 Hz, 2H), 1.78-1.70 (m, 1H), 1.75 (s, 1H), 1.58 (d, J=7.0 Hz, 3H), 1.40 (s, 9H), 1.31-1.20 (m, 2H).

Following the synthesis of EXAMPLE 10, the following compounds were synthesized and obtained in a similar manner.

| Compd No. | Structure Observed MS $[M + 1]^+$ | $^1$H NMR (400 MHz, DMSO-d$^6$) δ (ppm) |
|---|---|---|
| 35 | 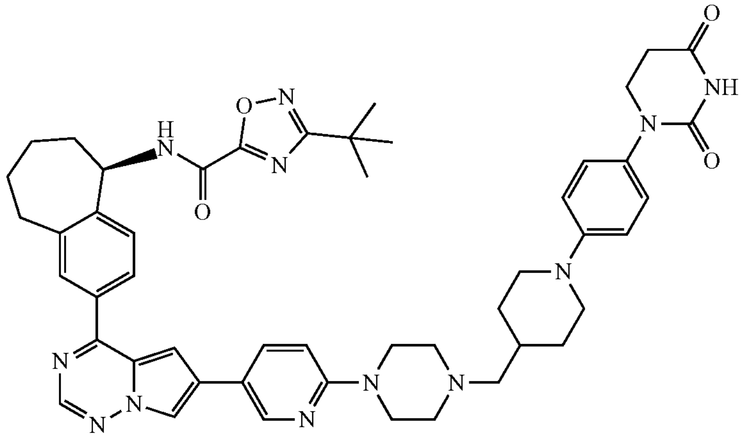 877.8 | 10.28 (s, 1H), 10.10 (d, J = 7.9 Hz, 1H), 8.75 (d, J = 2.5 Hz, 1H), 8.69 (d, J = 1.5 Hz, 1H), 8.60 (s, 1H), 8.15-8.06 (m, 2H), 8.02 (d, J = 1.9 Hz, 1H), 7.62 (d, J = 1.6 Hz, 1H), 7.47 (d, J = 8.1 Hz, 1H), 7.16 (d, J = 8.9 Hz, 2H), 6.94 (dd, J = 11.7, 8.9 Hz, 3H), 5.34 (t, J = 8.7 Hz, 1H), 3.74-3.67 (m, 2H), 3.58-3.50 (m, 4H), 3.44-3.37 (m, 2H), 3.15-2.96 (m, 2H), 2.75-2.64 (m, 3H), 2.51-2.44 (m, 4H), 2.25 (d, J = 7.1 Hz, 2H), 2.10-1.94 (m, 4H), 1.90-1.67 (m, 6H), 1.44 (s, 9H), 1.39-1.20 (m, 2H). |
| 36 | 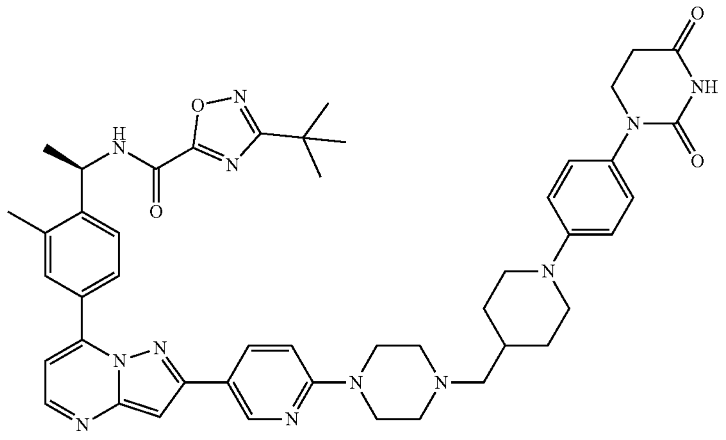 [SMILES: Cc1cc(-c2ccnc3cc(-c4ccc(N5CCN(CC6CCN(c7ccc(N8CCC(=O)NC8=O)cc7)CC6)CC5)nc4)nn23)ccc1[C@@H](C)NC(=O)c1nc(C(C)(C)C)no1] 851.8 | 10.28 (s, 1H), 9.98 (d, J = 7.7 Hz, 1H), 8.80 (d, J = 2.4 Hz, 1H), 8.58 (d, J = 4.4 Hz, 1H), 8.16-8.09 (m, 2H), 8.07 (d, J = 1.9 Hz, 1H), 7.73 (d, J = 8.2 Hz, 1H), 7.27-7.20 (m, 2H), 7.16 (d, J = 8.8 Hz, 2H), 6.96 (dd, J = 9.1, 3.5 Hz, 3H), 5.41 (p, J = 7.0 Hz, 1H), 3.75-3.67 (m, 4H), 3.58-3.51 (m, 4H), 2.75-2.64 (m, 4H), 2.54 (s, 3H), 2.50-2.45 (m, 3H), 2.24 (d, J = 7.0 Hz, 2H), 1.85 (d, J = 12.7 Hz, 2H), 1.80-1.70 (m, 2H), 1.59 (d, J = 6.9 Hz, 3H), 1.40 (s, 9H), 1.31-1.19 (m, 2H). |

-continued
| Compd No. | Structure Observed MS $[M+1]^+$ | $^1H$ NMR (400 MHz, DMSO-$d^6$) δ (ppm) |
|---|---|---|
| 37 | 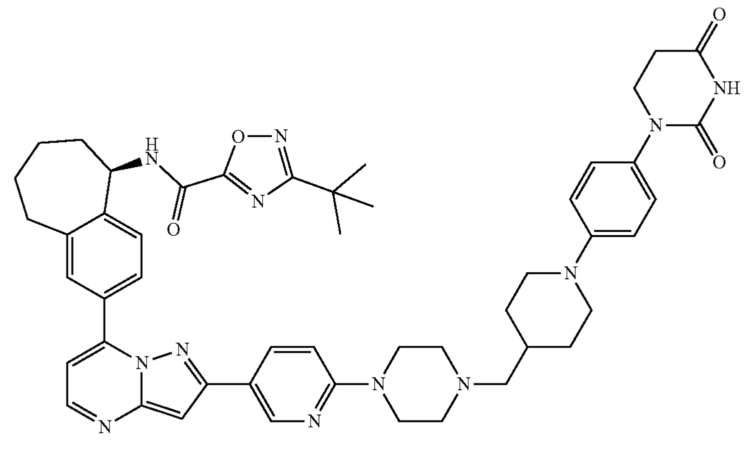 [SMILES: CC(C)(C)c1noc(C(=O)N[C@@H]2CCCCc3cc(-c4ccnc5cc(-c6ccc(N7CCN(CC8CCN(c9ccc(N%10CCC(=O)NC%10=O)cc9)CC8)CC7)nc6)nn45)ccc32)n1] 877.8 | 10.28 (s, 1H), 10.06 (d, J = 7.9 Hz, 1H), 8.80 (d, J = 2.4 Hz, 1H), 8.57 (d, J = 4.4 Hz, 1H), 8.16-8.10 (m, 2H), 8.05 (d, J = 1.9 Hz, 1H), 7.48 (d, J = 8.2 Hz, 1H), 7.24 (d, J = 5.2 Hz, 2H), 7.20-7.13 (m, 2H), 6.99-6.92 (m, 3H), 5.34 (t, J = 8.6 Hz, 1H), 3.75-3.67 (m, 4H), 3.58-3.50 (m, 4H), 3.03 (d, J = 7.5 Hz, 2H), 2.74-2.63 (m, 4H), 2.50-2.41 (m, 4H), 2.24 (d, J = 7.1 Hz, 2H), 2.11-1.93 (m, 4H), 1.92-1.68 (m, 5H), 1.43 (s, 9H), 1.33-1.19 (m, 2H). |
Example 11: (R)-3-(tert-butyl)-N-(1-(4-(6-(6-(4-((1-(4-(2,4-dioxotetrahydropyrimidin-1(2H)-yl)phenyl)piperidin-4-yl)methyl)piperazin-1-yl)pyridin-3-yl)pyrazolo[1,5-a]pyridin-4-yl)-2-methylphenyl)ethyl)-1,2,4-oxadiazole-5-carboxamide (Compound No. 20)
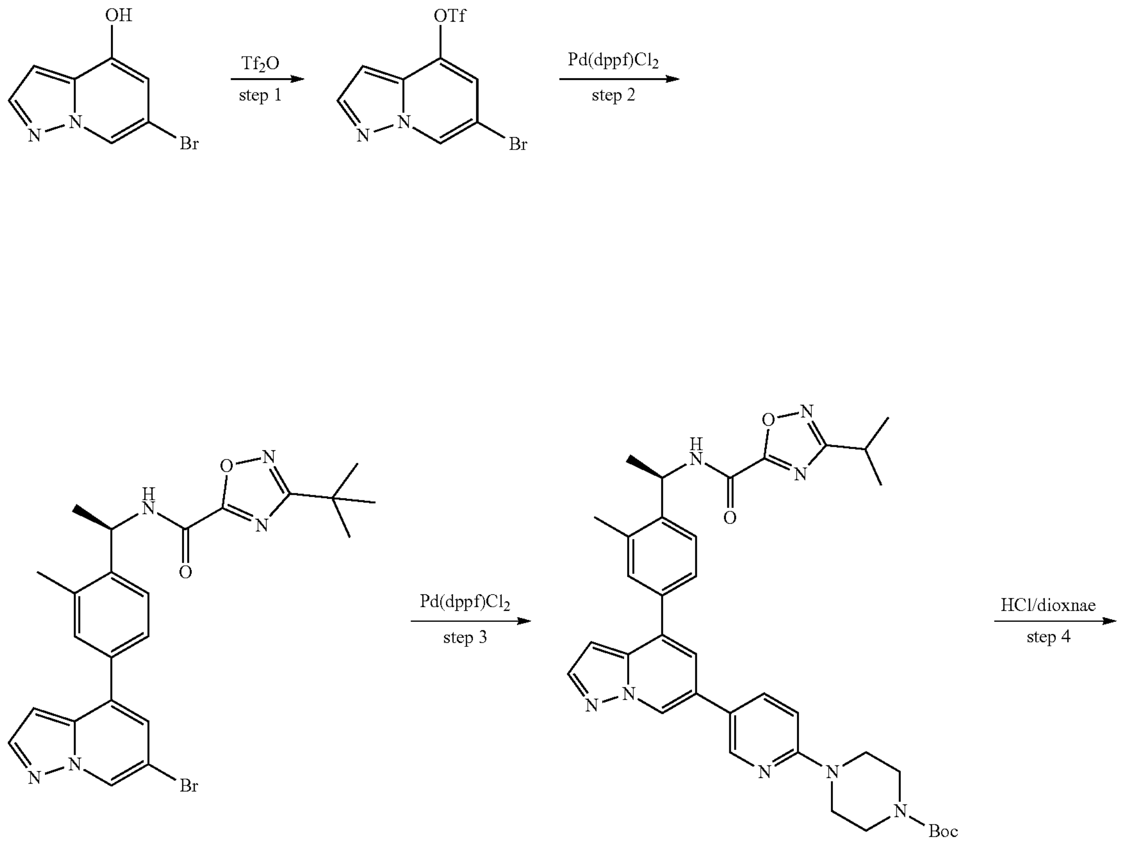

-continued

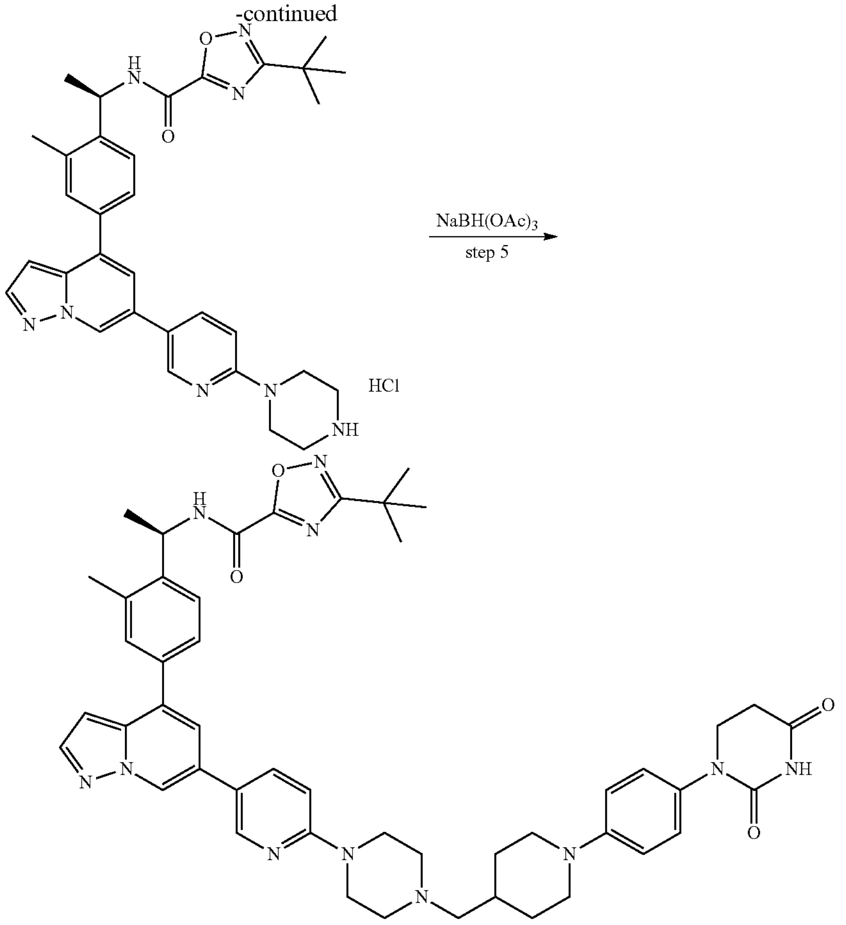

Step 1: 6-bromopyrazolo[1,5-a]pyridin-4-yl trifluoromethanesulfonate

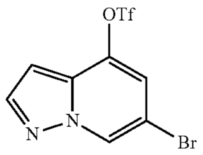 [SMILES: O=S(=O)(Oc1cc(Br)cn2nccc12)C(F)(F)F]

In a 100 ml round-bottomed flask, 6-bromopyrazolo[1,5-a]pyridin-4-ol (500 mg, 2.347 mmol, 1.0 eq) and triethylamine (713 mg, 7.04 mmol, 3.0 eq) were dissolved in DCM (10 ml). $Tf_2O$ (1324 mg, 4.69 mmol, 2.0 eq) was added at 0° C. and stirred for 12 h at RT. Water was added to the reaction mixture followed by extraction with DCM. The combined organic layers were dried $Na_2SO_4$, filtered and concentrated. The crude product was added to a silica gel column and was eluted with PE/EA from 0~ 10% to give the title compound (750 mg, 93%) as a white solid.

Step 2: (R)—N-(1-(4-(6-bromopyrazolo[1,5-a]pyridin-4-yl)-2-methylphenyl)ethyl)-3-(tert-butyl)-1,2,4-oxadiazole-5-carboxamide

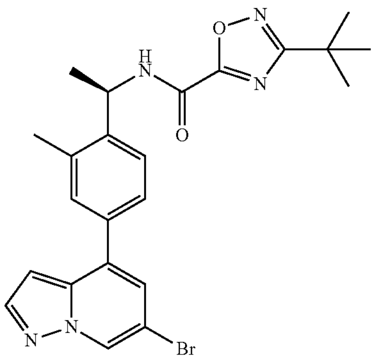 [SMILES: Cc1cc(-c2cc(Br)cn3nccc23)ccc1[C@@H](C)NC(=O)c1nc(C(C)(C)C)no1]

In a 100 ml round-bottomed flask, above obtained intermediate (668 mg, 1.936 mmol, 2.0 eq), (R)-3-(tert-butyl)-N-(1-(2-methyl-4-(4,4,5,5-tetramethyl-1,3,2-dioxaborolan-2-yl)phenyl)ethyl)-1,2,4-oxadiazole-5-carboxamide (400 mg, 0.968 mmol, 1.0 eq), $K_2CO_3$ (401 mg, 2.90 mmol, 3.0 eq) and Pd(dppf)$Cl_2$ (70.8 mg, 0.097 mmol, 0.1 eq) were dissolved in Dioxane (5 ml) and Water (0.5 ml) under nitrogen. The mixture was stirred at 100° C. for 16 h. Water was added to the reaction mixture followed by extraction with EA. The combined organic layers were dried $Na_2SO_4$, filtered and concentrated. The crude product was added to a silica gel column and was eluted with PE/EA 0~30% to give the title compound (400 mg, 86%) as a yellow solid. MS (ESI) m/z 482.3 $[M+H]^+$.

Step 3: tert-butyl (R)-4-(5-(4-(4-(1-(3-(tert-butyl)-1,2,4-oxadiazole-5-carboxamido)ethyl)-3-methylphenyl)pyrazolo[1,5-a]pyridin-6-yl)pyridin-2-yl)piperazine-1-carboxylate

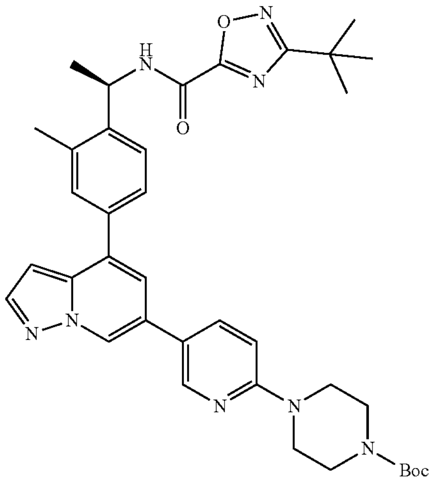 [SMILES: Cc1cc(-c2cc(-c3ccc(N4CCN(C(=O)OC(C)(C)C)CC4)nc3)cn3nccc23)ccc1[C@@H](C)NC(=O)c1nc(C(C)(C)C)no1]

In a 100 ml round-bottomed flask, above obtained intermediate (100 mg, 0.207 mmol, 1.0 eq), tert-butyl 4-(5-(4,4,5,5-tetramethyl-1,3,2-dioxaborolan-2-yl)pyridin-2-yl)piperazine-1-carboxylate (97 mg, 0.249 mmol, 1.2 eq), $Pd(dppf)Cl_2$ (15.17 mg, 0.021 mmol, 0.1 eq) and $K_2CO_3$ (86 mg, 0.622 mmol, 3.0 eq) were dissolved in Dioxane (10 ml) and Water (1 ml) under argon. The reaction mixture was stirred at 100° C. for 12 h under Ar. Water was added to the reaction mixture followed by extraction with EA. The combined organic layers were dried $Na_2SO_4$, filtered and concentrated. The crude product was added to a silica gel column and was eluted with EA/PE from 0% to 40% to give the title compound (110 mg, 80%) as a yellow solid. MS (ESI) m/z 665.6 $[M+H]^+$.

Step 4: (R)-3-(tert-butyl)-N-(1-(2-methyl-4-(6-(6-(piperazin-1-yl)pyridin-3-yl)pyrazolo[1,5-a]pyridin-4-yl)phenyl)ethyl)-1,2,4-oxadiazole-5-carboxamide hydrochloride

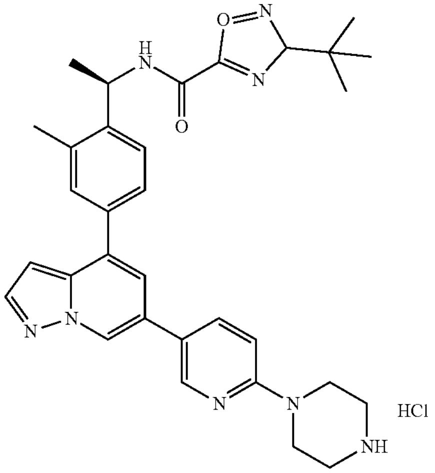

In a 100 ml round-bottomed flask, above obtained intermediate (110 mg, 0.165 mmol, 1.0 eq) was dissolved in DCM (5 ml) and 4M HCl in Dioxane (2 ml). The reaction mixture was stirred for 3 h and concentrated to give the title compound (99 mg, 100%) as a yellow solid. MS (ESI) m/z 565.6 $[M-HCl+H]^+$.

Step 5: (R)-3-(tert-butyl)-N-(1-(4-(6-(6-(4-((1-(4-(2,4-dioxotetrahydropyrimidin-1(2H)-yl)phenyl)piperidin-4-yl)methyl)piperazin-1-yl)pyridin-3-yl)pyrazolo[1,5-a]pyridin-4-yl)-2-methylphenyl)ethyl)-1,2,4-oxadiazole-5-carboxamide

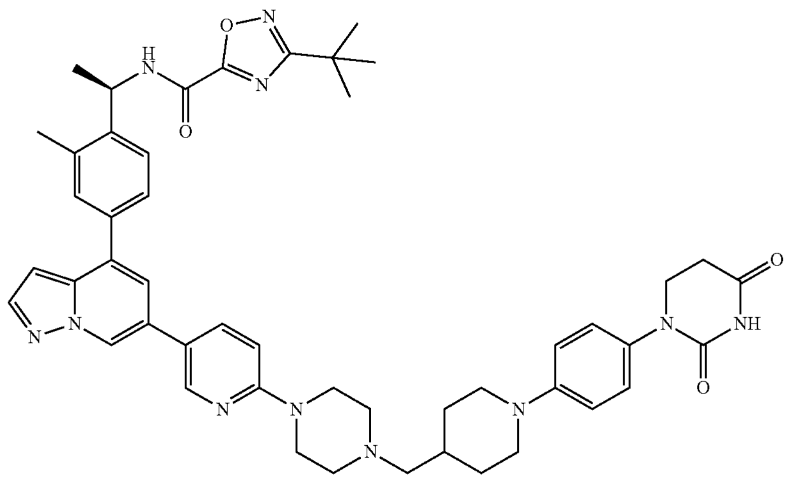

In a 100 ml round-bottomed flask, above obtained intermediate (99 mg, 0.165 mmol, 1.0 eq), 1-(4-(2,4-dioxotetrahydropyrimidin-1(2H)-yl)phenyl)piperidine-4-carbaldehyde (149 mg, 0.494 mmol, 3.0 eq), triethylamine (50 mg, 0.494 mmol, 3.0 eq), and NaBH(OAc) 3 (52.4 mg, 0.247 mmol, 1.5 eq) were dissolved in DCM (10 ml). The mixture was stirred at rt for 16 h. Water was added to the reaction mixture followed by extraction with dichloromethane. The combined organic layers were dried $Na_2SO_4$, filtered and concentrated. The crude product was added to a Prep HPLC column to give the title compound (55.3 mg, 39.5%) as a white solid. MS (ESI) m/z 850.6 $[M+H]^+$. $^1H$ NMR (400 MHz, DMSO-$d^6$) δ (ppm) 10.27 (s, 1H), 9.94 (d, J=7.9 Hz, 1H), 9.01 (t, J=1.1 Hz, 1H), 8.64 (d, J=2.6 Hz, 1H), 8.07 (dd, J=11.2, 2.5 Hz, 2H), 7.73-7.63 (m, 3H), 7.60 (d, J=1.6 Hz, 1H), 7.16 (d, J=8.9 Hz, 2H), 7.00-6.92 (m, 3H), 6.76 (d, J=2.4 Hz, 1H), 5.39 (q, J=7.2 Hz, 1H), 3.72 (t, J=6.7 Hz, 4H), 3.59 (s, 4H), 3.33-3.28 (m, 2H), 2.76-2.62 (m, 3H), 2.51 (s, 3H), 2.50-2.47 (m, 3H), 2.25 (d, J=7.1 Hz, 2H), 1.85 (d, J=12.7 Hz, 2H), 1.80-1.70 (m, 1H), 1.57 (d, J=7.0 Hz, 3H), 1.40 (s, 9H), 1.31-1.20 (m, 2H).

Example 12: (R)-3-(tert-butyl)-N-(1-(4-(6-(1-(1-((1-(4-(2,4-dioxotetrahydropyrimidin-1(2H)-yl)phenyl)piperidin-4-yl)methyl)piperidin-4-yl)-1H-pyrazol-4-yl)pyrazolo[1,5-a]pyridin-4-yl)-2-methylphenyl)ethyl)-1,2,4-oxadiazole-5-carboxamide (Compound No. 21)

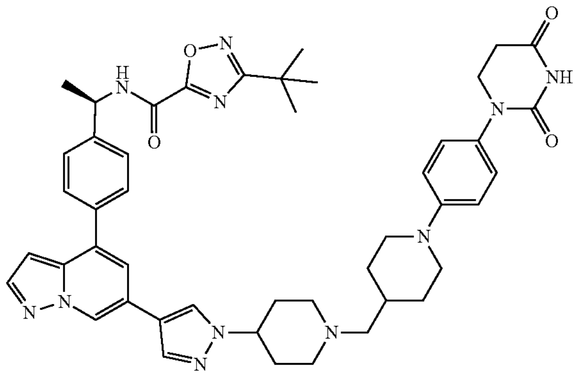 [SMILES: C[C@@H](NC(=O)c1nc(C(C)(C)C)no1)c1ccc(-c2cc(-c3cnn(C4CCN(CC5CCN(c6ccc(N7CCC(=O)NC7=O)cc6)CC5)CC4)c3)cn3nccc23)cc1]

Following the synthesis of EXAMPLE 11, the title compound was obtained as a white solid (36.7 mg). MS (ESI) m/z 838.7 $[M+H]^+$. $^1H$ NMR (400 MHz, DMSO-$d^6$) δ (ppm) 10.28 (s, 1H), 9.95 (d, J=7.8 Hz, 1H), 9.04 (t, J=1.2 Hz, 1H), 8.52 (s, 1H), 8.12 (s, 1H), 8.05 (d, J=2.3 Hz, 1H), 7.71-7.59 (m, 4H), 7.17 (d, J=8.8 Hz, 2H), 6.96 (d, J=9.0 Hz, 2H), 6.73 (dd, J=2.4, 1.0 Hz, 1H), 5.40 (p, J=7.1 Hz, 1H), 4.24-4.13 (m, 1H), 3.78-3.67 (m, 3H), 3.00 (d, J=10.7 Hz, 2H), 2.76-2.65 (m, 4H), 2.56-2.54 (m, 1H), 2.52 (s, 3H), 2.26 (d, J=7.2 Hz, 2H), 2.15-1.98 (m, 6H), 1.84 (d, J=12.7 Hz, 2H), 1.77-1.69 (m, 1H), 1.58 (d, J=7.0 Hz, 3H), 1.41 (s, 9H), 1.32-1.20 (m, 2H).

Example 13: (R)-3-(tert-butyl)-N-(2-(6-((5-(4-((1-(4-(2,4-dioxotetrahydropyrimidin-1(2H)-yl)phenyl)piperidin-4-yl)methyl)piperazin-1-yl)pyridin-2-yl)amino)pyrimidin-4-yl)-6,7,8,9-tetrahydro-5H-benzo[7]annulen-5-yl)-1,2,4-oxadiazole-5-carboxamide (Compound No. 24)

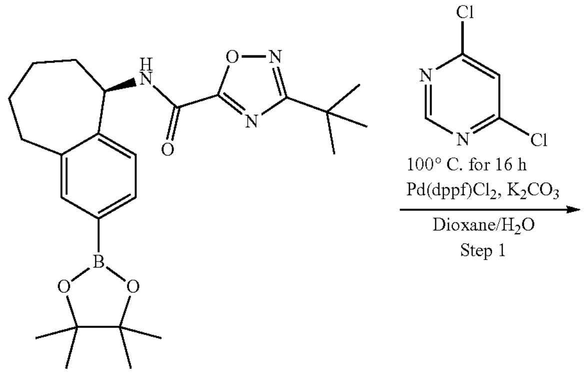

-continued
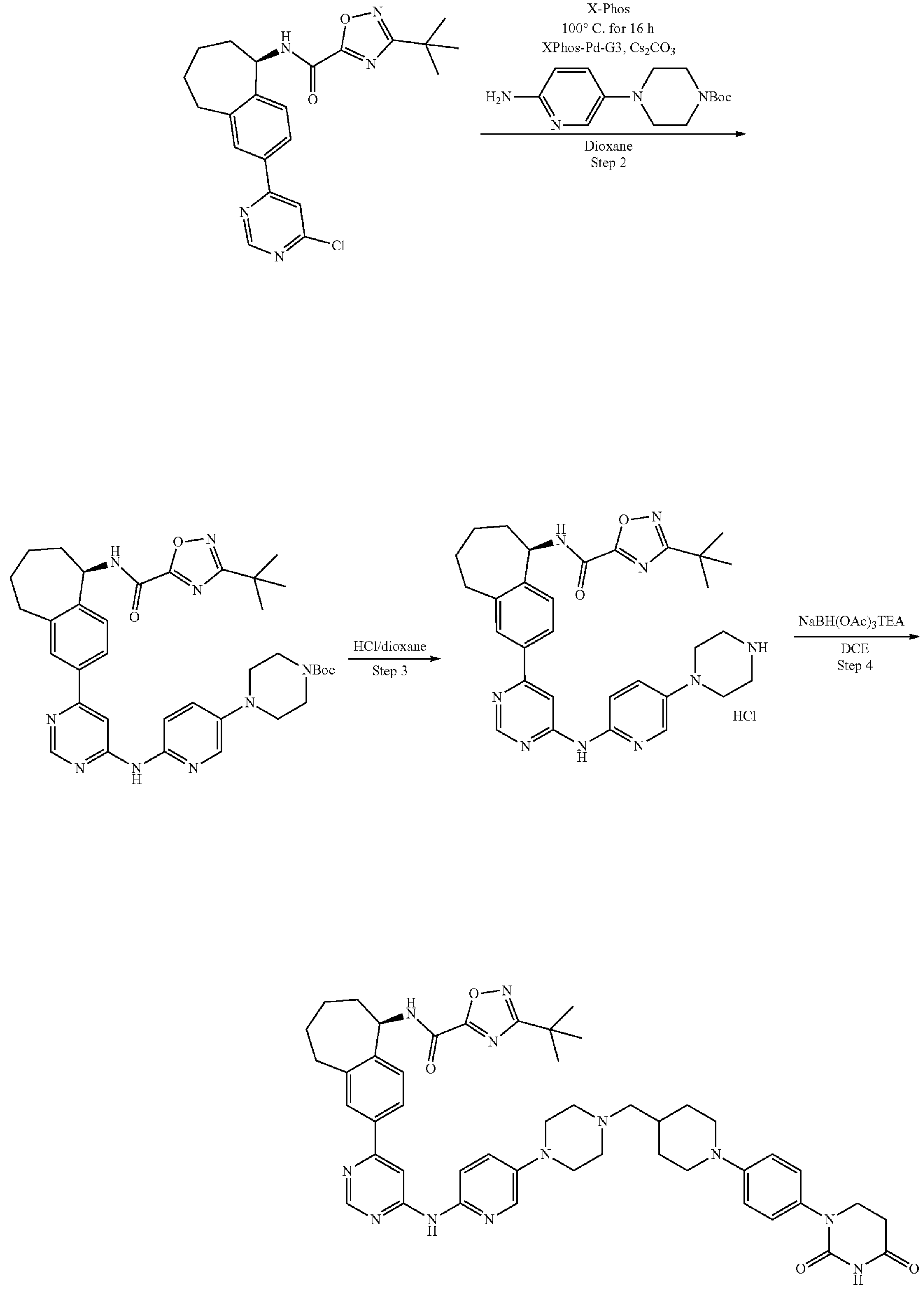

Step 1: (R)-3-(tert-butyl)-N-(2-(6-chloropyrimidin-4-yl)-6,7,8,9-tetrahydro-5H-benzo[7]annulen-5-yl)-1,2,4-oxadiazole-5-carboxamide

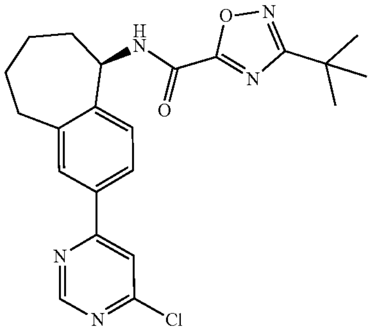 [SMILES: CC(C)(C)c1noc(C(=O)N[C@@H]2CCCCc3cc(-c4cc(Cl)ncn4)ccc32)n1]

A mixture of (R)-3-(tert-butyl)-N-(2-(4,4,5,5-tetramethyl-1,3,2-dioxaborolan-2-yl)-6,7,8,9-tetrahydro-5H-benzo[7]annulen-5-yl)-1,2,4-oxadiazole-5-carboxamide (200 mg, 0.455 mmol, 1.0 eq), 4,6-dichloropyrimidine (136 mg, 0.91 mmol, 2.0 eq), $K_3PO_4$ (290 mg, 1.37 mmol, 3.0 eq) and Pd(dppf)$Cl_2$ (34 mg, 0.046 mmol, 0.1 eq) in dioxane (4 ml) and water (1 ml) was stirred at 100° C. under Ar for 16 h. Diluted with water, extracted with EA for 3 times. Dried over anhydrous $Na_2SO_4$ and concentrated in vacuo. The residue was purified by flash chromatography eluted with Hex/EA=3:1 to give the title compound (90 mg, 46.4%) as yellow oil. LC-MS: 426.1 (M+H$^+$).

Step 2: tert-butyl (R)-4-(6-((6-(5-(3-(tert-butyl)-1,2,4-oxadiazole-5-carboxamido)-6,7,8,9-tetrahydro-5H-benzo[7]annulen-2-yl)pyrimidin-4-yl)amino)pyridin-3-yl)piperazine-1-carboxylate

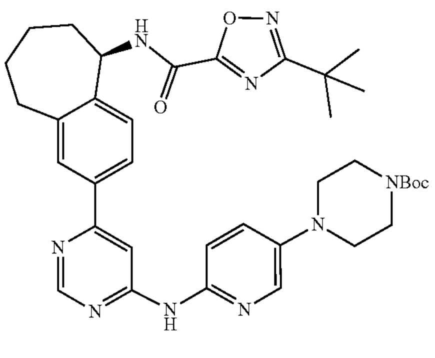 [SMILES: CC(C)(C)OC(=O)N1CCN(c2ccc(Nc3cc(-c4ccc5c(c4)CCCC[C@H]5NC(=O)c4nc(C(C)(C)C)no4)ncn3)nc2)CC1]

A mixture of tert-butyl 4-(6-aminopyridin-3-yl)piperazine-1-carboxylate (65 mg, 0.232 mmol, 1.1 eq). (R)-3-(tert-butyl)-N-(2-(6-chloropyrimidin-4-yl)-6,7,8,9-tetrahydro-5H-benzo[7]annulen-5-yl)-1,2,4-oxadiazole-5-carboxamide (90 mg, 0.211 mmol, 1.0 eq), $CS_2CO_3$ (207 mg, 0.634 mmol, 3.0 eq), dicyclohexyl(2',4',6'-triisopropyl-[1,1'-biphenyl]-2-yl)phosphane (10 mg, 0.021 mmol, 3.0 eq) and Xphos-Pd-G3 (18 mg, 0.021 mmol, 0.1 eq) in dioxane (5 ml) was stirred at 100° C. under Ar for 16 h. Diluted with water, extracted with EA for 3 times. The combined EA layers were washed with brine, dried over anhydrous $Na_2SO_4$ and concentrated in vacuo. The residue was purified by flash chromatography eluted with Hex/EA=1:1 to give the title compound (60 mg, 42.5%) as yellow oil. LC-MS: 668.3 (M+H$^+$).

Step 3: (R)-3-(tert-butyl)-N-(2-(6-((5-(piperazin-1-yl)pyridin-2-yl)amino)pyrimidin-4-yl)-6,7,8,9-tetrahydro-5H-benzo[7]annulen-5-yl)-1,2,4-oxadiazole-5-carboxamide hydrochloride

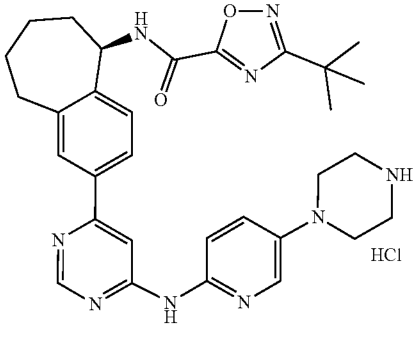 [SMILES: CC(C)(C)c1noc(C(=O)N[C@@H]2CCCCc3cc(-c4cc(Nc5ccc(N6CCNCC6)cn5)ncn4)ccc32)n1 ; Cl]

A mixture of above obtained intermediate (60 mg, 0.09 mmol, 1.0 eq) in DCM (2 ml) and HCl/Dioxane (0.5 ml, 4 M in dioxane) was stirred at rt for 2 h. After concentration in vacuo, the residue was used in next step without further purification (50 mg, 98%) as a yellow solid. LC-MS: 568.5 (M+H$^+$).

Step 4: (R)-3-(tert-butyl)-N-(2-(6-((5-(4-((1-(4-(2,4-dioxotetrahydropyrimidin-1(2H)-yl)phenyl)piperidin-4-yl)methyl)piperazin-1-yl)pyridin-2-yl)amino)pyrimidin-4-yl)-6,7,8,9-tetrahydro-5H-benzo[7]annulen-5-yl)-1,2,4-oxadiazole-5-carboxamide

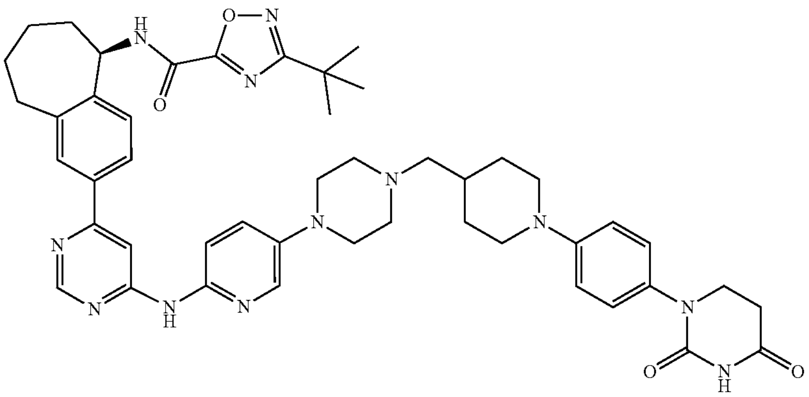 [SMILES: CC(C)(C)c1noc(C(=O)N[C@@H]2CCCCc3cc(-c4cc(Nc5ccc(N6CCN(CC7CCN(c8ccc(N9CCC(=O)NC9=O)cc8)CC7)CC6)cn5)ncn4)ccc32)n1]

To a solution of above obtained intermediate (50 mg, 0.083 mmol, 1.0 eq), 1-(4-(2,4-dioxotetrahydropyrimidin-1(2H)-yl)phenyl)piperidine-4-carbaldehyde (40 mg, 0.132 mmol, 1.6 eq) and TEA (42 mg, 0.414 mmol, 5.0 eq) in dry DCE (3 ml) was added NaBH(OAc) 3 (35 mg, 0.166 mmol, 2.0 eq) in portions. The reaction was stirred at rt for 4 h. The solution was quenched with water and extracted with DCM for 3 times. The organic layers were washed with brine, dried over anhydrous $Na_2SO_4$ and concentrated in vacuo. The residue was purified by pre-HPLC to give the title compound (35 mg, 49.6%) as a white solid. LC-MS: 853.4 $(M+H^+)$. $^1H$ NMR (400 MHz, DMSO-$d^6$) δ (ppm) 10.24 (s, 1H), 10.00-9.90 (m, 2H), 8.69 (s, 1H), 8.04 (d, J=2.8 Hz, 2H), 7.85-7.78 (m, 2H), 7.72-7.67 (m, 1H), 7.47-7.42 (m, 1H), 7.35 (d, J=8.4 Hz, 1H), 7.13 (d, J=8.8 Hz, 2H), 6.92 (d, J=8.4 Hz, 2H), 5.30-5.20 (m, 1H), 3.75-3.62 (m, 4H), 3.20-3.10 (m, 4H), 3.00-2.92 (m, 2H), 2.70-2.60 (m, 4H), 2.55-2.51 (m, 4H), 2.22 (d, J=7.2 Hz, 2H), 2.05-1.65 (m, 8H), 1.40 (s, 9H), 1.35-1.20 (m, 3H).

Example 14: 3-(tert-butyl)-N—((R)-2-(6-((5-((S)-4-((1-(4-(2,4-dioxotetrahydropyrimidin-1(2H)-yl)phenyl)piperidin-4-yl)methyl)-2-methylpiperazin-1-yl)pyridin-2-yl)amino)pyrimidin-4-yl)-6,7,8,9-tetrahydro-5H-benzo[7]annulen-5-yl)-1,2,4-oxadiazole-5-carboxamide (Compound No. 29)

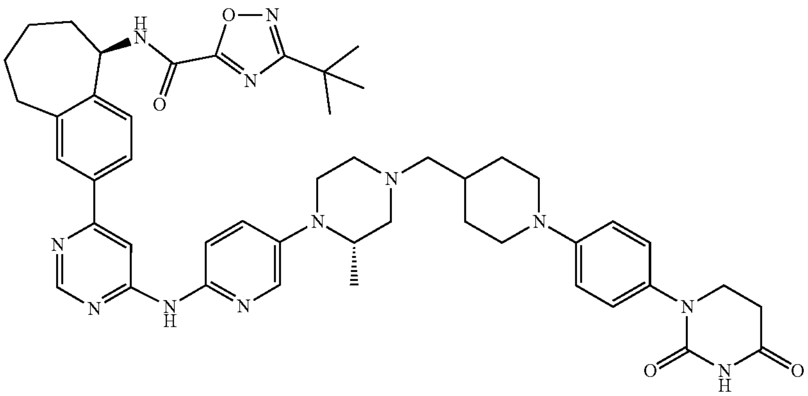 [SMILES: C[C@H]1CN(CC2CCN(c3ccc(N4CCC(=O)NC4=O)cc3)CC2)CCN1c1ccc(Nc2cc(-c3ccc4c(c3)CCCC[C@H]4NC(=O)c3nc(C(C)(C)C)no3)ncn2)nc1]

Following the synthesis of EXAMPLE 13, the title compound was obtained (54 mg) as a white solid. LC-MS: 867.6 ($M+H^+$). $^1H$ NMR (400 MHz, DMSO-$d^6$) δ (ppm) 10.24 (s, 1H), 10.00-9.90 (m, 2H), 8.70 (s, 1H), 8.04 (s, 1H), 7.99 (d, J=2.8 Hz, 1H), 7.84 (s, 1H), 7.80 (d, J=8.0 Hz, 1H), 7.69 (d, J=8.0 Hz, 1H), 7.45-7.40 (m, 1H), 7.35 (d, J=8.0 Hz, 1H), 7.13 (d, J=8.8 Hz, 2H), 6.93 (d, J=8.8 Hz, 2H), 5.30-5.20 (m, 1H), 3.85-3.80 (m, 1H), 3.73-3.65 (m, 4H), 3.24-3.17 (m, 1H), 3.05-2.92 (m, 3H), 2.80-2.73 (m, 1H), 2.71-2.57 (m, 5H), 2.40-2.30 (m, 1H), 2.28-2.13 (m, 3H), 2.05-1.65 (m, 8H), 1.40 (s, 9H), 1.35-1.18 (m, 3H), 1.01 (d, J=6.4 Hz, 3H).

Example 15: 1-(4-(4-((4-(4-(4-(piperidin-1-yl)pyrazolo[1,5-a]pyrazin-6-yl)-1H-pyrazol-1-yl)piperidin-1-yl)methyl)piperidin-1-yl)phenyl)dihydropyrimidine-2,4(1H,3H)-dione (Compound No. 33)

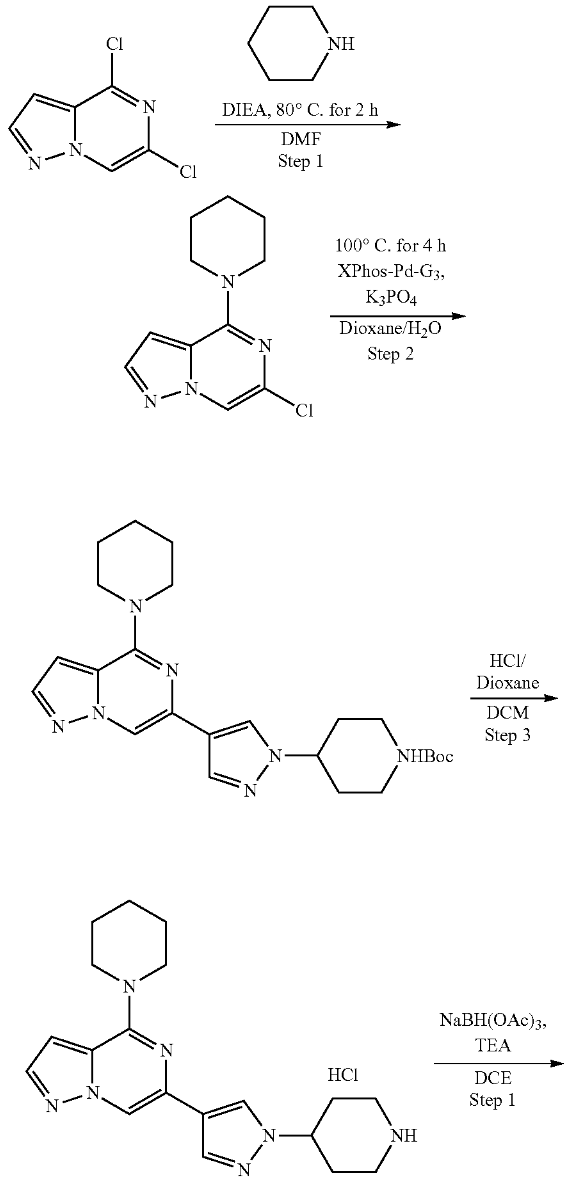

-continued

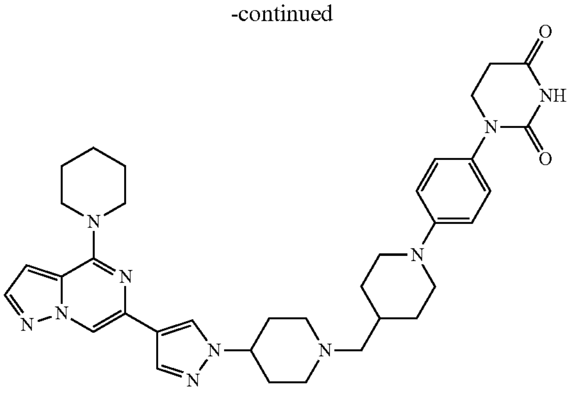

Step 1: 6-chloro-4-(piperidin-1-yl)pyrazolo[1,5-a]pyrazine

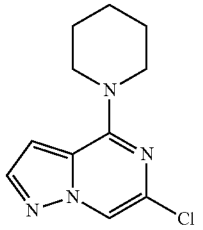 [SMILES: Clc1cn2nccc2c(N2CCCCC2)n1]

A mixture of 4,6-dichloropyrazolo[1,5-a]pyrazine (200 mg, 1.064 mmol, 1.0 eq), piperidine (100 mg, 1.17 mmol, 1.1 eq) and DIEA (412 mg, 3.19 mmol, 3.0 eq) in dry DMF (4 ml) was stirred at 80° C. under Ar for 2 h. Diluted with EA, washed with water, brine, dried over anhydrous $Na_2SO_4$ and concentrated in vacuo. The residue was purified by flash chromatography eluted with Hex/EA=1:1 to give the title compound (240 mg, 95%) as a white solid. LC-MS: 237.4 ($M+H^+$).

Step 2:6-chloro-4-(piperidin-1-yl)pyrazolo[1,5-a]pyrazine

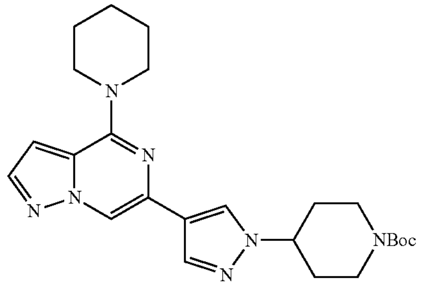 [SMILES: CC(C)(C)OC(=O)N1CCC(n2cc(-c3cn4nccc4c(N4CCCCC4)n3)cn2)CC1]

A mixture of tert-butyl 4-(4-(4,4,5,5-tetramethyl-1,3,2-dioxaborolan-2-yl)-1H-pyrazol-1-yl)piperidine-1-carboxylate (574 mg, 1.521 mmol, 1.5 eq), above obtained intermediate (240 mg, 1.014 mmol, 1.0 eq), $K_3PO_4$ (646 mg, 3.04 mmol, 3.0 eq) and XPhos-Pd-G3 (85 mg, 0.1 mmol, 0.1 eq) in dioxane (20 ml) and water (4 ml) was stirred at 100° C. under Ar for 16 h. The solution was diluted with water, extracted with ethyl acetate for 3 times. The combined organic layers were washed with brine, dried over anhydrous $Na_2SO_4$ and concentrated in vacuo. The residue was purified by flash chromatography eluted with Hex/EA=1:1 to give the title compound (400 mg, 87%) as a yellow solid. LC-MS: 452.6 (M+H$^+$).

Step in 4-(piperidin-1-yl)-6-(1-(piperidin-4-yl)-1H-pyrazol-4-yl)pyrazolo[1,5-a]pyrazine hydrochloride

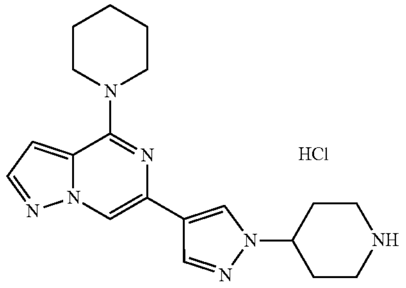 [SMILES: c1cc2c(N3CCCCC3)nc(-c3cnn(C4CCNCC4)c3)cn2n1 ; Cl]

A mixture of above obtained intermediate (200 mg, 0.443 mmol, 1.0 eq) in DCM (6 ml) and HCl/Dioxane (2 ml, 4 M in dioxane) was stirred at rt for 2 h. After concentration in vacuo, the residue was used in next step without further purification (170 mg, 99%) as a yellow solid. LC-MS: 352.3 (M+H$^+$).

Step 4: 1-(4-(4-((4-(4-(4-(piperidin-1-yl)pyrazolo[1,5-a]pyrazin-6-yl)-1H-pyrazol-1-yl)piperidin-1-yl)methyl)piperidin-1-yl)phenyl)dihydropyrimidine-2,4(1H,3H)-dione

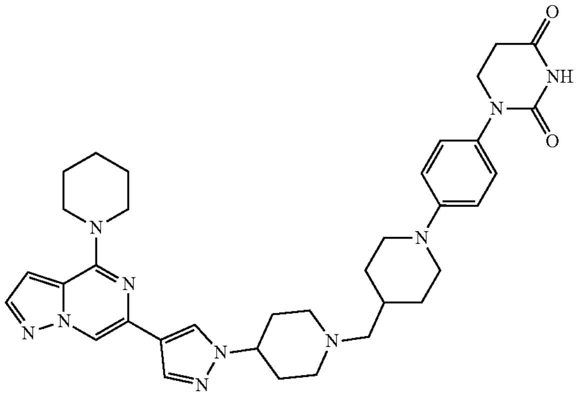 [SMILES: O=C1CCN(c2ccc(N3CCC(CN4CCC(n5cc(-c6cn7nccc7c(N7CCCCC7)n6)cn5)CC4)CC3)cc2)C(=O)N1]

To a solution of above obtained intermediate (170 mg, 0.438 mmol, 1.0 eq), 1-(4-(2,4-dioxotetrahydropyrimidin-1(2H)-yl)phenyl)piperidine-4-carbaldehyde (198 mg, 0.657 mmol, 1.5 eq) and TEA (222 mg, 2.191 mmol, 5.0 eq) in dry DCE (5 ml) was added NaBH(OAc) 3 (186 mg, 0.876 mmol, 2.0 eq) in portions. The reaction was stirred at rt for 4 h. The solution was quenched with water and extracted with DCM for 3 times. The organic layers were washed with brine, dried over anhydrous $Na_2SO_4$ and concentrated in vacuo. The residue was purified by pre-HPLC to give the title compound (90 mg, 32.2%) as a white solid. LC-MS: 637.4 (M+H$^+$). $^1$H NMR (400 MHz, DMSO-d$^6$) δ (ppm) 10.24 (s, 1H), 8.44 (s, 1H), 8.25 (s, 1H), 7.96 (s, 1H), 7.93 (d, J=2.4 Hz, 1H), 7.11 (d, J=8.8 Hz, 2H), 6.92 (d, J=8.8 Hz, 2H), 6.90 (d, J=2.0 Hz, 1H), 4.22-4.10 (m, 1H), 3.83-3.63 (m, 8H), 3.00-2.90 (m, 2H), 2.71-2.59 (m, 4H), 2.22 (d, J=7.2 Hz, 2H), 2.10-1.95 (m, 6H), 1.85-1.75 (m, 2H), 1.73-1.65 (m, 7H), 1.27-1.18 (m, 2H).

Following the synthesis of EXAMPLE 15, the following compounds were synthesized and obtained in a similar manner.

| Compd No. | Structure Observed MS [M + 1]$^+$ | $^1$H NMR (400 MHz, DMSO-d$^6$) δ (ppm) |
|---|---|---|
| 44 | 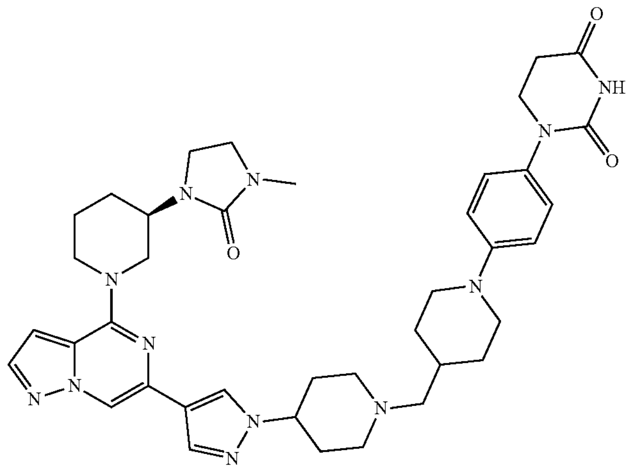 [SMILES: CN1CCN([C@@H]2CCCN(c3nc(-c4cnn(C5CCN(CC6CCN(c7ccc(N8CCC(=O)NC8=O)cc7)CC6)CC5)c4)cn4nccc34)C2)C1=O] | 10.24 (s, 1H), 8.46 (d, J = 8.0 Hz, 2H), 8.00 (s, 1H), 7.95 (d, J = 2.4 Hz, 1H), 7.13 (d, J = 8.8 Hz, 2H), 6.97 (d, J = 2.0 Hz, 1H), 6.92 (d, J = 8.8 Hz, 2H), 4.50-4.35 (m, 2H), 4.20-4.10 (m, 1H), 3.95-3.85 (m, 1H), 3.73-3.63 (m, 4H), 3.40-3.35 (m, 2H), 3.29-3.22 (m, 2H), 3.13-2.90 (m, 4H), 2.71 (s, 3H), 2.70-2.60 (m, 4H), 2.22 (d, J = 7.2 Hz, 2H), 2.10-1.98 (m, 6H), 1.90-1.50 (m, 7H), 1.27-1.15 (m, 2H). |

-continued
| Compd No. | Structure Observed MS $[M + 1]^+$ | $^1$H NMR (400 MHz, DMSO-$d^6$) δ (ppm) |
|---|---|---|
| | 735.8 | |
| 49 | 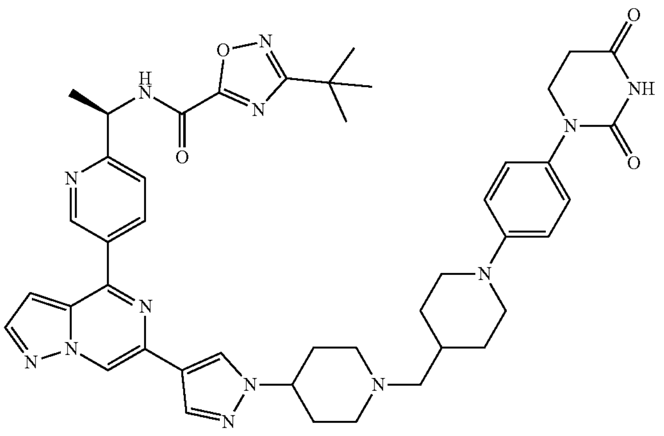 [SMILES: C[C@@H](NC(=O)c1nc(C(C)(C)C)no1)c1ccc(-c2nc(-c3cnn(C4CCN(CC5CCN(c6ccc(N7CCC(=O)NC7=O)cc6)CC5)CC4)c3)cn3nccc23)cn1] 832.3 | |
| 50 | 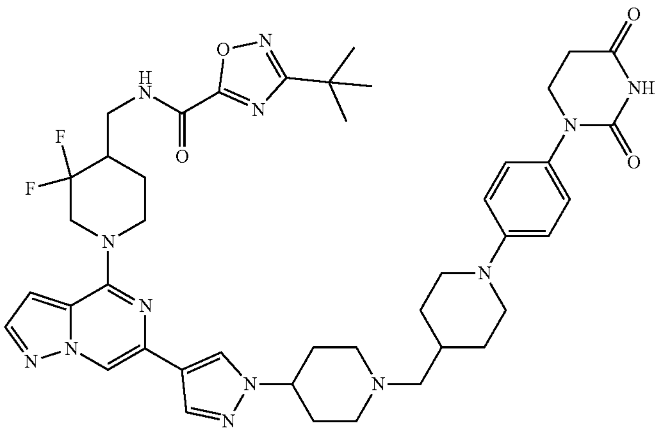 [SMILES: CC(C)(C)c1noc(C(=O)NCC2CCN(c3nc(-c4cnn(C5CCN(CC6CCN(c7ccc(N8CCC(=O)NC8=O)cc7)CC6)CC5)c4)cn4nccc34)CC2(F)F)n1] 854.3 | 10.24 (s, 1H), 9.50-9.44 (m, 1H), 8.56 (s, 1H), 8.30 (s, 1H), 8.02-7.97 (m, 2H), 7.13 (d, J = 8.4 Hz, 2H), 6.99 (d, J = 2.0 Hz, 1H), 6.92 (d, J = 8.4 Hz, 2H), 4.75-4.62 (m, 1H), 4.52 (d, J = 14.0 Hz, 1H), 4.22-4.12 (m, 1H), 3.75-3.52 (m, 6H), 3.40-3.35 (m, 1H), 3.25-3.15 (m, 1H), 3.00-2.90 (m, 2H), 2.70-2.55 (m, 5H), 2.22 (d, J = 7.2 Hz, 2H), 2.12-1.96 (m, 7H), 1.85-1.76 (m, 2H), 1.74-1.63 (m, 2H), 1.37 (s, 9H), 1.28-1.18 (m, 2H). |
| 144 | 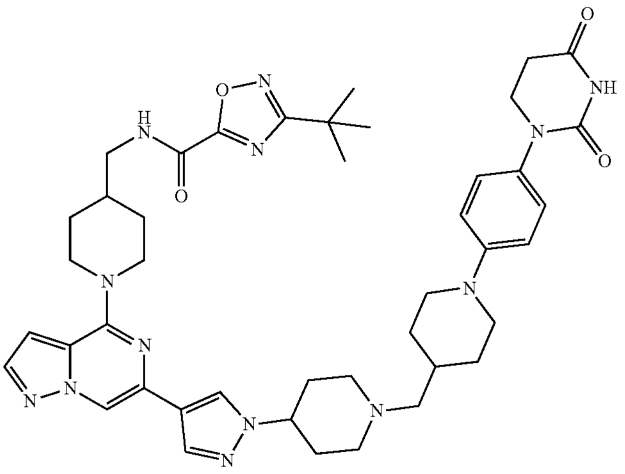 818.6 | 10.24 (s, 1H), 9.39 (t, J = 6.0 Hz, 1H), 8.45 (s, 1H), 8.25 (s, 1H), 7.97 (s, 1H), 7.94 (d, J = 2.4 Hz, 1H), 7.13 (d, J = 8.9 Hz, 2H), 6.92 (d, J = 8.9 Hz, 3H), 4.54 (d, J = 13.5 Hz, 2H), 4.24-4.08 (m, 1H), 3.69 (t, J = 6.7 Hz, 4H), 3.22 (t, J = 6.4 Hz, 2H), 3.07 (t, J = 11.9 Hz, 2H), 2.96 (d, J = 9.7 Hz, 2H), 2.73-2.58 (m, 4H), 2.22 (d, J = 5.8 Hz, 2H), 2.14-1.90 (m, 7H), 1.88-1.75 (m, 4H), 1.72-1.60 (m, 1H), 1.36 (s, 9H), 1.32-1.17 (m, 4H). |

-continued
| Compd No. | Structure Observed MS [M + 1]$^+$ | $^1$H NMR (400 MHz, DMSO-d$^6$) δ (ppm) |
|---|---|---|
| 145 | 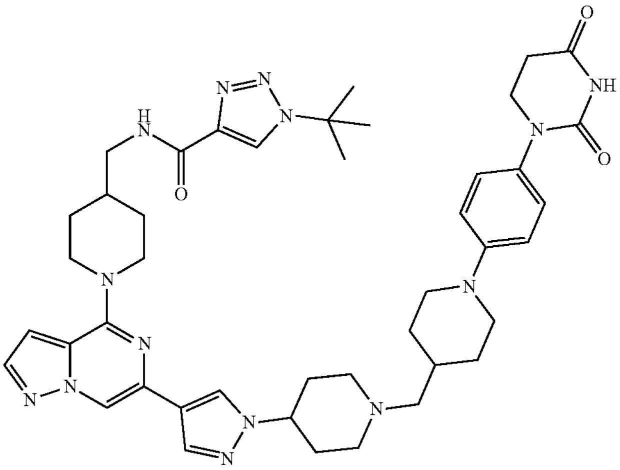 817.6 | 10.24 (s, 1H), 8.63 (s, 1H), 8.54 (t, J = 6.1 Hz, 1H), 8.44 (s, 1H), 8.24 (s, 1H), 7.97 (s, 1H), 7.93 (d, 1H), 7.13 (d, J = 8.9 Hz, 2H), 7.00-6.83 (m, 3H), 4.54 (d, J = 13.3 Hz, 2H), 4.24-4.08 (m, 1H), 3.69 (t, J = 6.7 Hz, 4H), 3.21 (t, J = 6.4 Hz, 2H), 3.06 (t, J = 11.8 Hz, 2H), 2.96 (d, J = 9.8 Hz, 2H), 2.74-2.59 (m, 4H), 2.21 (d, J = 6.5 Hz, 2H), 2.11-1.87 (m, 7H), 1.80 (d, J = 13.4 Hz, 4H), 1.71-1.64 (m, 1H), 1.63 (s, 9H), 1.35-1.14 (m, 4H). |
| 146 | 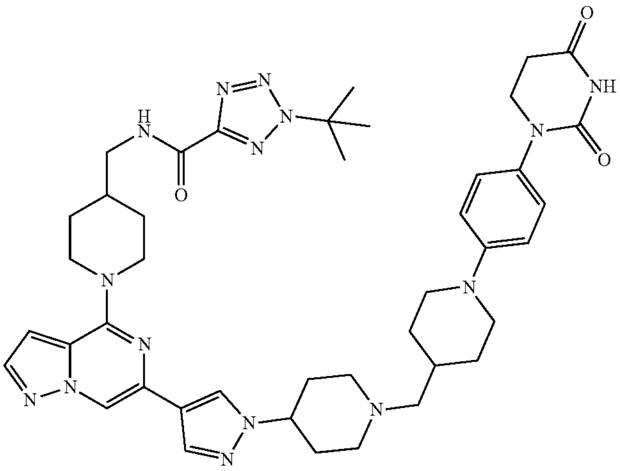 818.6 | 10.24 (s, 1H), 9.05 (t, J = 6.1 Hz, 1H), 8.44 (s, 1H), 8.24 (s, 1H), 7.97 (s, 1H), 7.93 (d, J = 2.4 Hz, 1H), 7.13 (d, J = 9.0 Hz, 2H), 6.92 (d, J = 9.1 Hz, 3H), 4.54 (d, J = 13.2 Hz, 2H), 4.25-4.08 (m, 1H), 3.69 (t, J = 6.7 Hz, 4H), 3.24 (t, J = 6.5 Hz, 2H), 3.07 (t, J = 11.8 Hz, 2H), 2.96 (d, J = 9.9 Hz, 2H), 2.66 (dd, J = 16.3, 9.6 Hz, 4H), 2.21 (d, J = 6.4 Hz, 2H), 2.13-1.90 (m, 7H), 1.81 (s, 4H), 1.75-1.65 (m, 10H), 1.37-1.14 (m, 4H). |
| 169 | 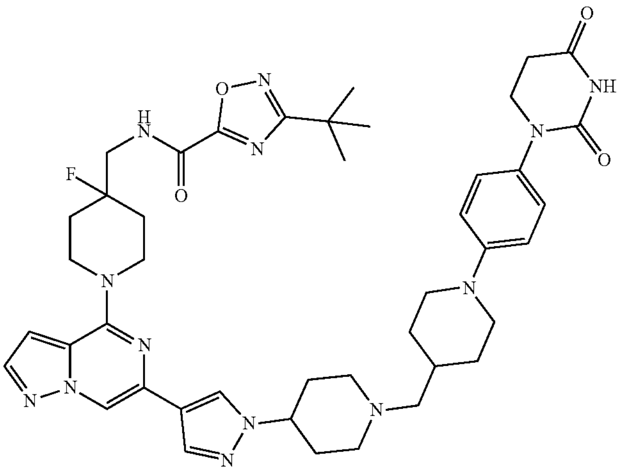 836.7 | 10.25 (s, 1H), 9.49 (t, J = 6.0 Hz, 1H), 8.49 (s, 1H), 8.27 (s, 1H), 7.98 (s, 1H), 7.96 (d, J = 2.4 Hz, 1H), 7.13 (d, J = 9.2 Hz, 2H), 6.97 (d, J = 2.0 Hz, 1H), 6.93 (d, J = 9.2 Hz, 2H), 4.40-4.17 (m, 3H), 3.71-3.54 (m, 6H), 3.44-3.30 (m, 6H), 2.99-2.93 (m, 1H), 2.69-2.64 (m,4H), 2.22-1.79 (m, 12H), 1.36 (s, 9H), 1.26-1.17 (m, 2H). |

-continued
| Compd No. | Structure Observed MS [M + 1]+ | $^1$H NMR (400 MHz, DMSO-d[6]) δ (ppm) |
|---|---|---|
| 170 | 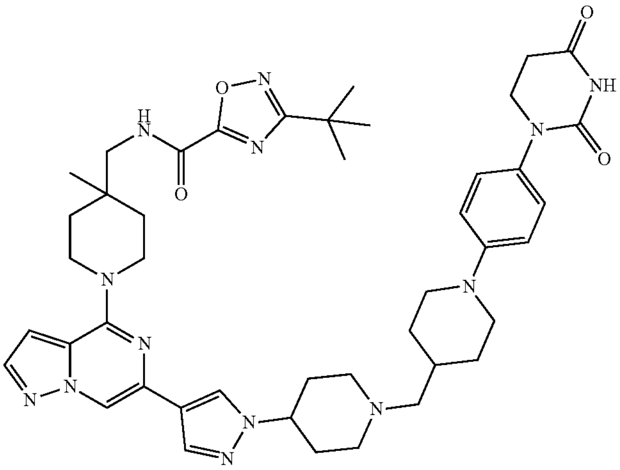 832.7 | 10.25 (s, 1H), 9.31 (t, J = 6.4 Hz, 1H), 8.44 (s, 1H), 8.25 (s, 1H), 7.96-7.93 (m, 2H), 7.13 (d, J = 8.8 Hz, 2H), 6.92 (d, J = 8.8 Hz, 3H), 4.18-4.14 (m, 1H), 4.05-4.01 (m, 2H), 3.71-3.61 (m, 6H), 3.30-3.28 (m, 2H), 2.97-2.94 (m, 2H), 2.69-2.63 (m, 4H), 2.22-2.20 (m, 2H), 2.09-1.96 (m, 6H), 1.82-1.79 (m, 2H), 1.66-1.61 (m, 3H), 1.47-1.43 (m, 2H), 1.35 (s, 9H), 1.27-1.18 (m, 2H), 1.03 (s, 3H). |
| 171 | 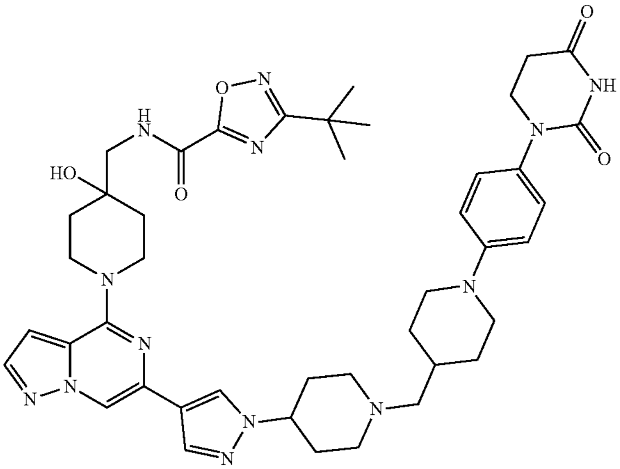 834.7 | 10.25 (s, 1H), 9.02 (t, J = 6.4 Hz, 1H), 8.43 (s, 1H), 8.25 (s, 1H), 7.96 (s, 1H), 7.93 (d, J = 2.4 Hz, 1H), 7.13 (d, J = 8.8 Hz, 2H), 6.94-6.89 (m, 3H), 4.82 (s, 1H), 4.28-4.15 (m,, 3H), 3.71-3.67 (m, 4H), 3.51-3.45 (m, 2H), 3.36-3.29 (m, 3H), 2.98-2.95 (m ,2H), 2.69-2.63 (m, 4H), 2.23-1.62 (m, 14H), 1.35 (s, 9H), 1.26-1.78 (m, 2H). |
| 172 | 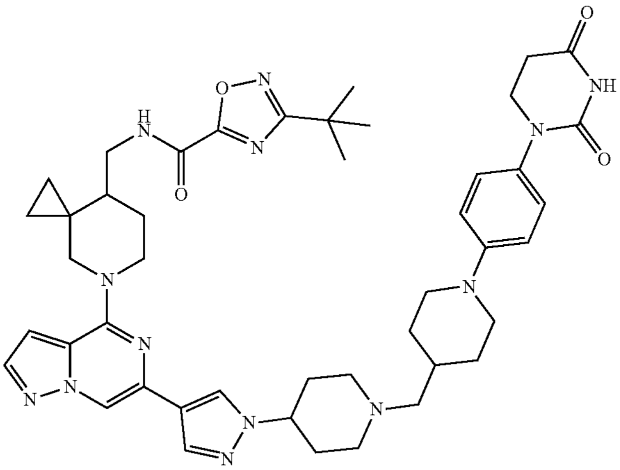 844.8 | 10.25 (s, 1H), 9.37 (t, J = 6.4 Hz, 1H), 8.44 (s, 1H), 8.24 (s, 1H), 7.96 (s, 1H), 7.93 (d, J = 2.4 Hz, 1H), 7.13 (d, J = 8.8 Hz, 2H), 6.92 (d, J = 8.8 Hz, 2H), 6.87 (d, J = 2.4 Hz, 1H), 4.17-4.14 (m, 2H), 3.71-3.52 (m, 8H), 3.41-3.36 (m, 1H), 2.97-2.95 (m, 2H), 2.69-2.63 (m, 4H), 2.22-1.54 (m, 14H), 1.37 (s, 9H), 1.26-1.17 (m, 2H), 0.55-0.36 (m, 4H). |

-continued
| Compd No. | Structure Observed MS [M + 1]+ | $^1$H NMR (400 MHz, DMSO-d$^6$) δ (ppm) |
|---|---|---|
| 173 | 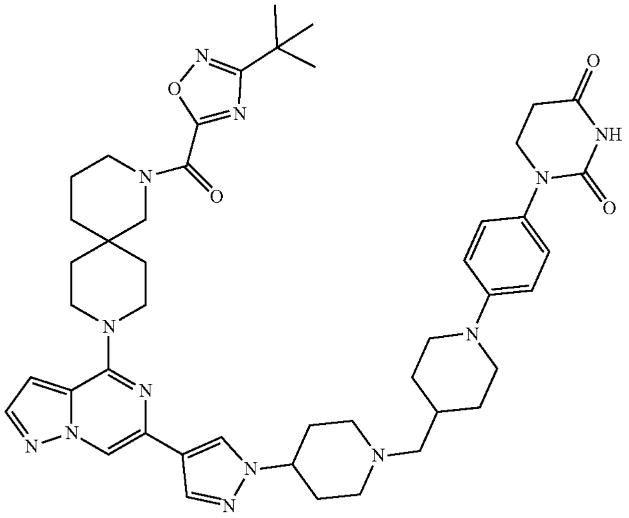 [SMILES: CC(C)(C)c1noc(C(=O)N2CCCC3(CCN(c4nc(-c5cnn(C6CCN(CC7CCN(c8ccc(N9CCC(=O)NC9=O)cc8)CC7)CC6)c5)cn5nccc45)CC3)C2)n1] 858.7 | 10.25 (s, 1H), 8.45 (d, J = 3.6Hz, 1H), 8.27-8.22 (m, 1H), 7.98-7.93 (m, 2H), 7.13 (d, J = 8.8 Hz, 2H), 6.96-6.90 (m, 3H), 4.18-4.00 (m, 2H), 3.83-3.47 (m, 11H), 2.99-2.92 (m, 4H), 2.22-1.52 (m, 20H), 1.36-1.23 (m, 12H). |
| 174 | 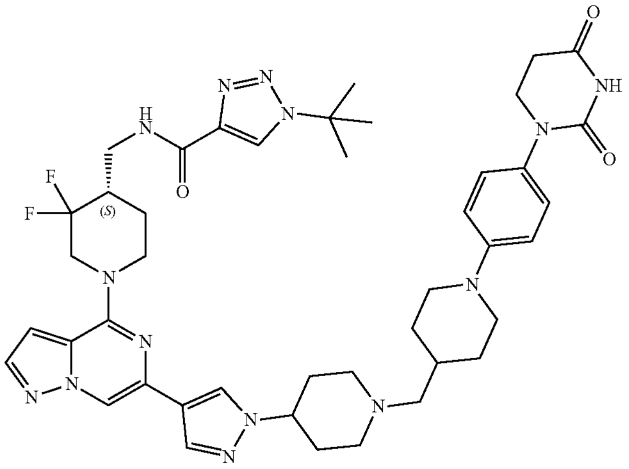 Isomer 1: 853.6 | 10.25 (s, 1H), 8.68 (s, 1H), 8.65-8.60 (m, 1H), 8.56 (s, 1H), 8.30 (s, 1H), 8.00 (s, 1H), 7.98 (d, J = 2.4 Hz, 1H), 7.13 (d, J = 9.2 Hz, 2H), 6.98 (d, J = 2.4 Hz, 1H), 6.92 (d, J = 9.2 Hz, 2H), 4.75-4.62 (m, 1H), 4.55-4.45 (m, 1H), 4.25-4.10 (m, 1H), 3.75-3.50 (m, 6H), 3.40-3.35 (m, 2H), 3.25-3.15 (m, 1H), 3.00-2.90 (m, 2H), 2.70-2.52 (m, 5H), 2.30-2.18 (m, 2H), 2.10-1.90 (m, 6H), 1.85-1.76 (m, 2H), 1.74-1.66 (m, 2H), 1.64 (s, 9H), 1.30-1.15 (m, 2H). |
| 175 | 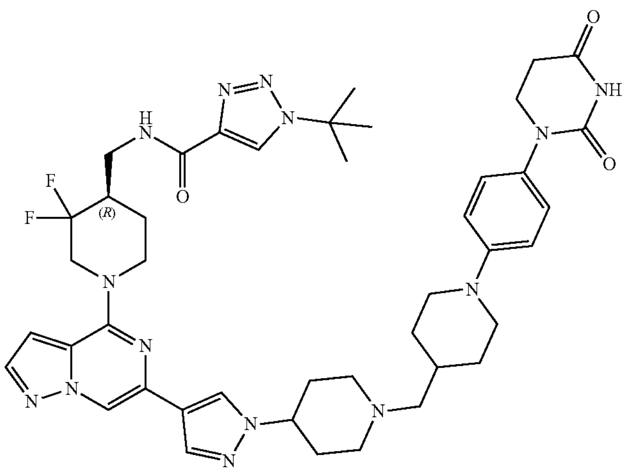 Isomer 2: 853.6 | 10.25 (s, 1H), 8.68 (s, 1H), 8.65-8.60 (m, 1H), 8.56 (s, 1H), 8.30 (s, 1H), 8.00 (s, 1H), 7.98 (d, J = 2.4 Hz, 1H), 7.13 (d, J = 9.2 Hz, 2H), 6.98 (d, J = 2.4 Hz, 1H), 6.92 (d, J = 9.2 Hz, 2H), 4.75-4.62 (m, 1H), 4.55-4.45 (m, 1H), 4.25-4.10 (m, 1H), 3.75-3.50 (m, 6H), 3.40-3.35 (m, 2H), 3.25-3.15 (m, 1H), 3.00-2.90 (m, 2H), 2.70-2.52 (m, 5H), 2.30-2.18 (m, 2H), 2.10-1.90 (m, 6H), 1.85-1.76 (m, 2H), 1.74-1.66 (m, 2H), 1.64 (s, 9H), 1.30-1.15 (m, 2H). |

-continued
| Compd No. | Structure Observed MS $[M + 1]^+$ | $^1H$ NMR (400 MHz, DMSO-$d^6$) δ (ppm) |
|---|---|---|
| 176 | 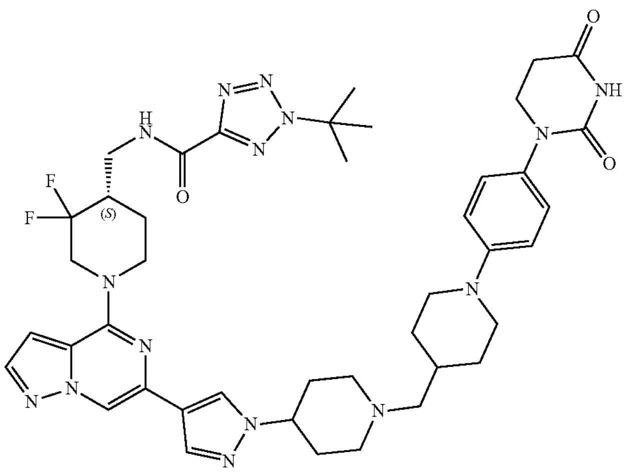 Isomer 1: 854.4 | 10.25 (s, 1H), 9.15-9.10 (m, 1H), 8.56 (s, 1H), 8.31 (s, 1H), 8.00 (s, 1H), 7.98 (d, J = 2.4 Hz, 1H), 7.13 (d, J = 9.2 Hz, 2H), 6.98 (d, J = 2.4 Hz, 1H), 6.92 (d, J = 9.2 Hz, 2H), 4.75-4.65 (m, 1H), 4.55-4.45 (m, 1H), 4.25-4.10 (m, 1H), 3.75-3.50 (m, 6H), 3.40-3.32 (m, 4H), 3.28-3.15 (m, 1H), 3.00-2.90 (m, 2H), 2.70-2.60 (m, 4H), 2.28-2.18 (m, 2H), 2.10-1.95 (m, 6H), 1.85-1.78 (m, 2H), 1.74 (s, 9H), 1.70-1.66 (m, 1H), 1.28-1.15 (m, 2H). |
| 177 | 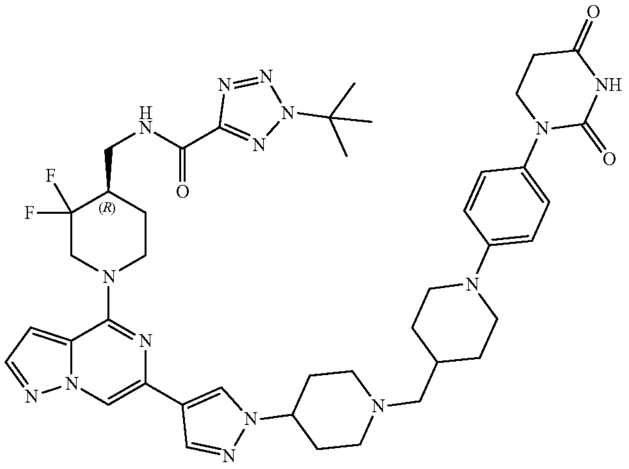 Isomer 2: 854.4 | 10.25 (s, 1H), 9.15-9.10 (m, 1H), 8.56 (s, 1H), 8.31 (s, 1H), 8.00 (s, 1H), 7.98 (d, J = 2.4 Hz, 1H), 7.13 (d, J = 9.2 Hz, 2H), 6.98 (d, J = 2.4 Hz, 1H), 6.92 (d, J = 9.2 Hz, 2H), 4.75-4.65 (m, 1H), 4.55-4.45 (m, 1H), 4.25-4.10 (m, 1H), 3.75-3.50 (m, 6H), 3.40-3.32 (m, 4H), 3.28-3.15 (m, 1H), 3.00-2.90 (m, 2H), 2.70-2.60 (m, 4H), 2.28-2.18 (m, 2H), 2.10-1.95 (m, 6H), 1.85-1.78 (m, 2H), 1.74 (s, 9H), 1.70-1.66 (m, 1H), 1.28-1.15 (m, 2H). |
| 178 | 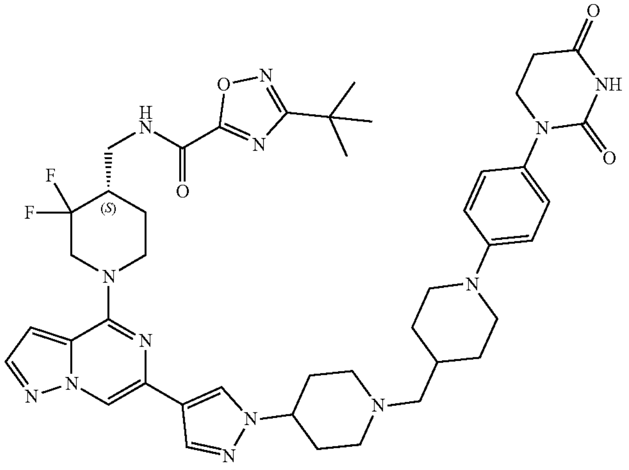 Isomer 1: 854.6 | 10.25 (s, 1H), 9.50-9.45 (m, 1H), 8.56 (s, 1H), 8.31 (s, 1H), 8.00 (s, 1H), 7.98 (d, J = 2.4 Hz, 1H), 7.13 (d, J = 8.8 Hz, 2H), 6.98 (d, J = 2.0 Hz, 1H), 6.92 (d, J = 8.8 Hz, 2H), 4.75-4.65 (m, 1H), 4.56-4.46 (m, 1H), 4.23-4.12 (m, 1H), 3.73-3.55 (m, 6H), 3.25-3.15 (m, 1H), 3.00-2.90 (m, 2H), 2.70-2.55 (m, 5H), 2.21 (d, J = 6.8 Hz, 2H), 2.10-1.95 (m, 7H), 1.85-1.62 (m, 4H), 1.37 (s, 9H), 1.36-1.30 (m, 1H), 1.28-1.15 (m, 2H). |

-continued
| Compd No. | Structure Observed MS $[M + 1]^+$ | $^1H$ NMR (400 MHz, DMSO-$d^6$) δ (ppm) |
|---|---|---|
| 179 | 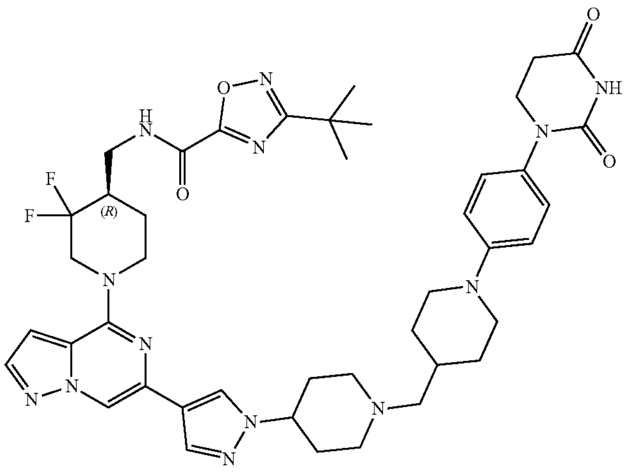 Isomer 2: 854.6 | 10.25 (s, 1H), 9.50-9.45 (m, 1H), 8.56 (s, 1H), 8.31 (s, 1H), 8.00 (s, 1H), 7.98 (d, J = 2.4 Hz, 1H), 7.13 (d, J = 8.8 Hz, 2H), 6.98 (d, J = 2.0 Hz, 1H), 6.92 (d, J = 8.8 Hz, 2H), 4.75-4.65 (m, 1H), 4.56-4.46 (m, 1H), 4.23-4.12 (m, 1H), 3.73-3.55 (m, 6H), 3.25-3.15 (m, 1H), 3.00-2.90 (m, 2H), 2.70-2.55 (m, 5H), 2.21 (d, J = 6.8 Hz, 2H), 2.10-1.95 (m, 7H), 1.85-1.62 (m, 4H), 1.37 (s, 9H), 1.36-1.30 (m, 1H), 1.28-1.15 (m, 2H). |
| 187 | 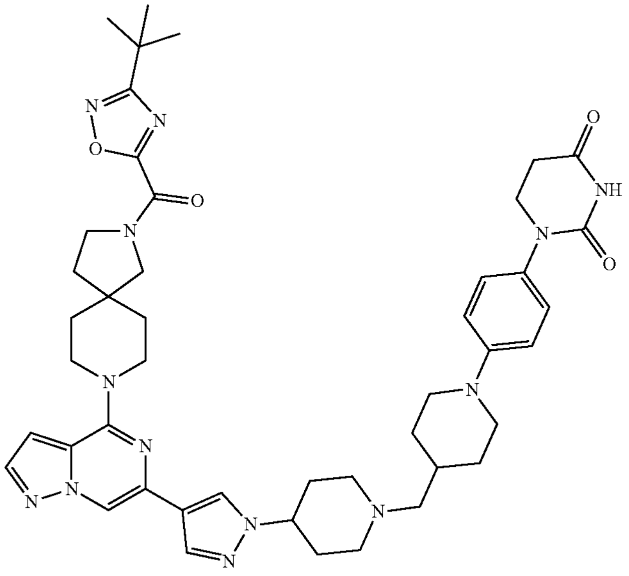 844.8 | 10.25 (s, 1H), 8.46 (s, 1H), 8.25 (d, J = 4.4 Hz, 1H), 8.00-7.94 (m, 2H), 7.13 (d, J = 8.8 Hz, 2H), 6.94-6.91 (m, 3H), 4.17-3.52 (m, 13H), 2.97-2.95 (m, 2H), 2.69-2.63 (m, 4H), 2.22-1.69 (m, 17H), 1.36 (s, 9H), 1.26-1.18(m, 2H). |

-continued

| Compd No. | Structure Observed MS [M + 1]$^+$ | $^1$H NMR (400 MHz, DMSO-d$^6$) δ (ppm) |
|---|---|---|
| 227 | 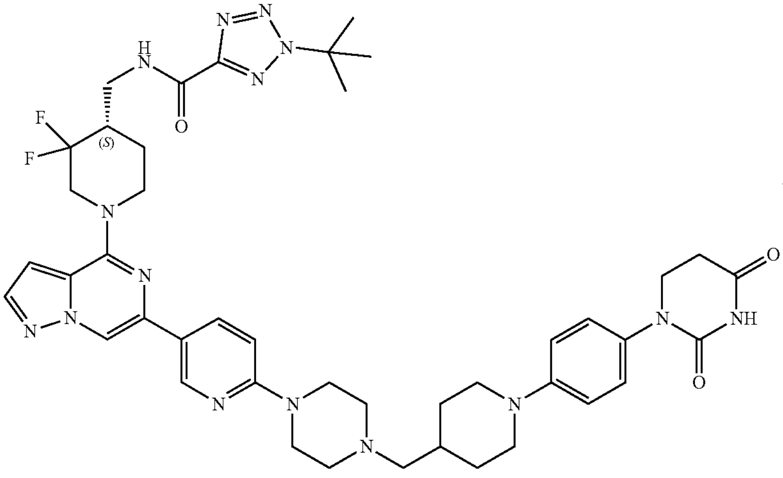 Isomer 1: 866.7 | 10.25 (s, 1H), 9.18-9.10 (m, 1H), 8.83 (d, J = 2.0 Hz, 1H), 8.74 (s, 1H), 8.20-8.15 (m, 1H), 8.02 (d, J = 2.4 Hz, 1H), 7.13 (d, J = 8.8 Hz, 2H), 7.02 (d, J = 2.4 Hz, 1H), 6.95-6.85 (m, 3H), 4.75-4.62 (m, 1H), 4.58-4.47 (m, 1H), 3.75-3.50 (m, 10H), 3.40-3.35 (m, 2H), 3.28-3.18 (m, 1H), 2.70-2.55 (m, 5H), 2.48-2.43 (m, 4H), 2.21 (d, J = 7.2 Hz, 2H), 2.05-1.95 (m, 1H), 1.85-1.78 (m, 2H), 1.73 (s, 9H), 1.70-1.65 (m, 1H), 1.25-1.15 (m, 2H). |
| 228 | 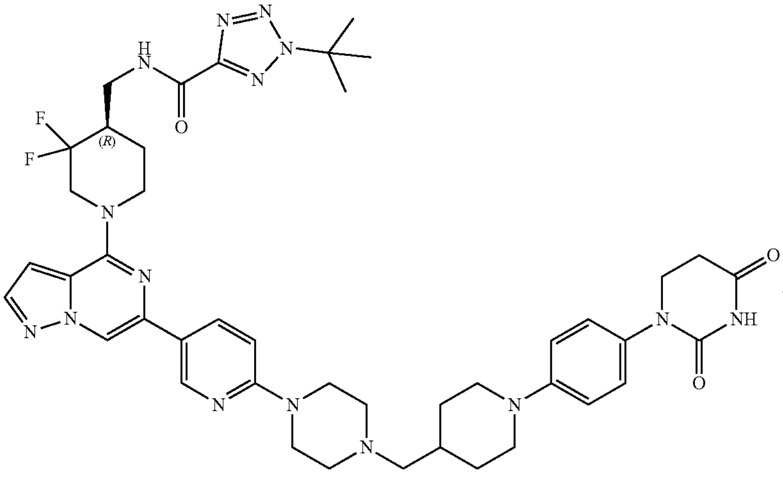 Isomer 2: 866.7 | 10.25 (s, 1H), 9.18-9.10 (m, 1H), 8.83 (d, J = 2.0 Hz, 1H), 8.74 (s, 1H), 8.20-8.15 (m, 1H), 8.02 (d, J = 2.4 Hz, 1H), 7.13 (d, J = 8.8 Hz, 2H), 7.02 (d, J = 2.4 Hz, 1H), 6.95-6.85 (m, 3H), 4.75-4.62 (m, 1H), 4.58-4.47 (m, 1H), 3.75-3.50 (m, 10H), 3.40-3.35 (m, 2H), 3.28-3.18 (m, 1H), 2.70-2.55 (m, 5H), 2.48-2.43 (m, 4H), 2.21 (d, J = 7.2 Hz, 2H), 2.05-1.95 (m, 1H), 1.85-1.78 (m, 2H), 1.73 (s, 9H), 1.70-1.65 (m, 1H), 1.25-1.15 (m, 2H). |

Example 16: (R)-3-(tert-butyl)-N-(8-(6-(1-(1-((1-(4-(2,4-dioxotetrahydropyrimidin-1(2H)-yl)phenyl)piperidin-4-yl)methyl)piperidin-4-yl)-1H-pyrazol-4-yl)pyrazolo[1,5-a]pyrazin-4-yl)-2-methyl-2,3,4,5-tetrahydro-1H-benzo[c]azepin-5-yl)-1,2,4-oxadiazole-5-carboxamide (Compound No. 34)

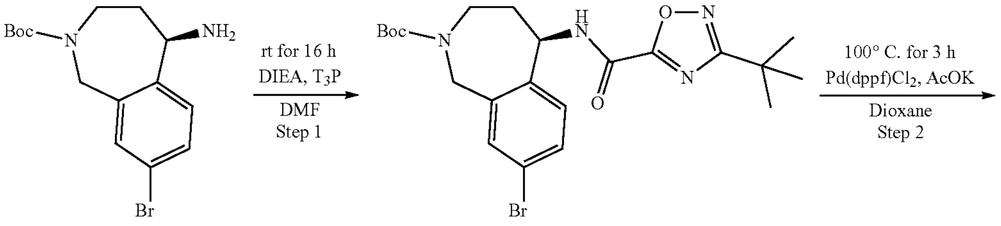

-continued
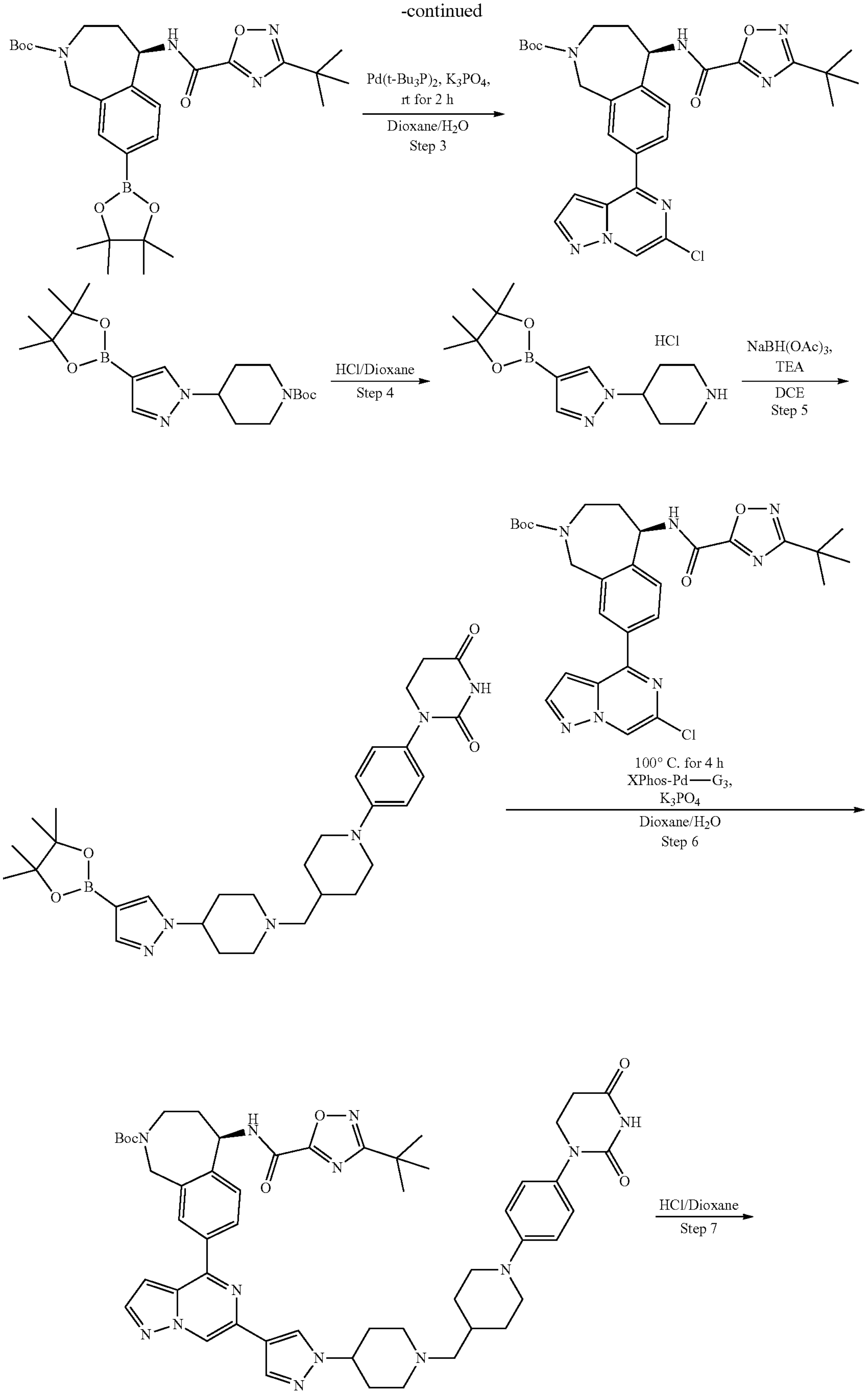

-continued

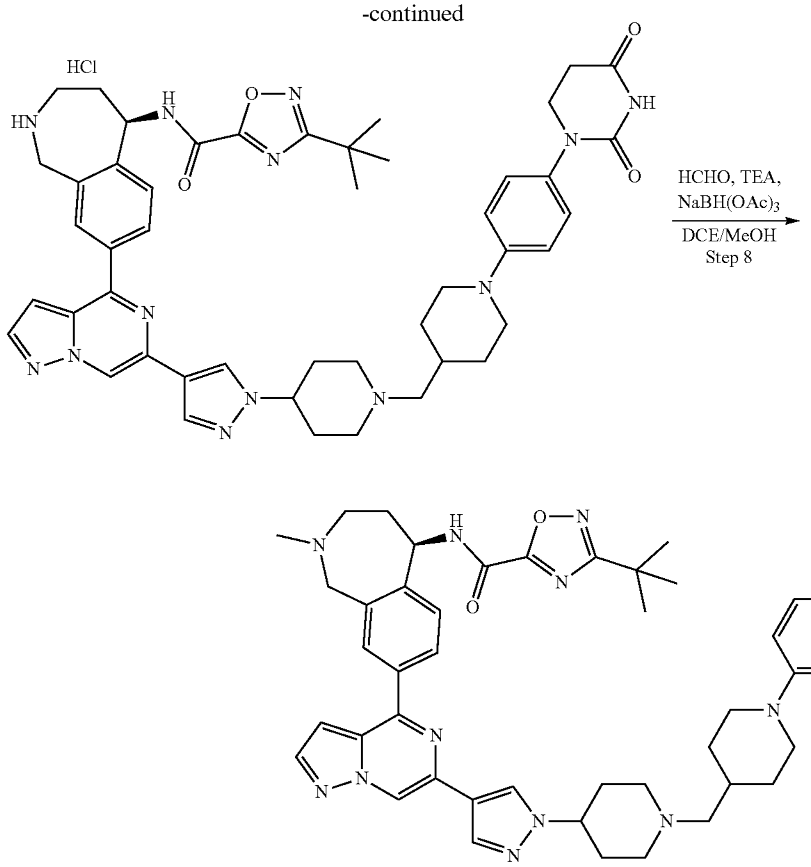

Step 1: tert-butyl (R)-8-bromo-5-(3-(tert-butyl)-1,2,4-oxadiazole-5-carboxamido)-1,3,4,5-tetrahydro-2H-benzo[c]azepine-2-carboxylate

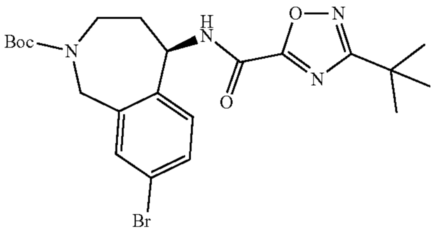 [SMILES: CC(C)(C)OC(=O)N1CC[C@@H](NC(=O)c2nc(C(C)(C)C)no2)c2ccc(Br)cc2C1]

To a mixture of tert-butyl (R)-5-amino-8-bromo-1,3,4,5-tetrahydro-2H-benzo[c]azepine-2-carboxylate (2.0 g, 5.86 mmol, 1.0 eq), 3-(tert-butyl)-1,2,4-oxadiazole-5-carboxylic acid (1.0 g, 5.86 mmol, 1.0 eq) and DIEA (3.0 g, 23.4 mmol, 4.0 eq) in dry DMF (30 ml) was added 2,4,6-tripropyl-1,3,5,2,4,6-trioxatriphosphinane 2,4,6-trioxide (3.73 g, 11.72 mmol, 2.0 eq) at 0° C. The reaction mixture was stirred at rt under Ar for 16 h. Diluted with EA, washed with water, brine, dried over anhydrous $Na_2SO_4$ and concentrated in vacuo. The residue was purified by flash chromatography eluted with Hex/EA=3:1 to give the title compound (1.0 g, 34.6%) as a white solid. LC-MS: 493.4 $(M+H^+)$.

Step 2: tert-butyl (R)-5-(3-(tert-butyl)-1,2,4-oxadiazole-5-carboxamido)-8-(4,4,5,5-tetramethyl-1,3,2-dioxaborolan-2-yl)-1,3,4,5-tetrahydro-2H-benzo[c]azepine-2-carboxylate

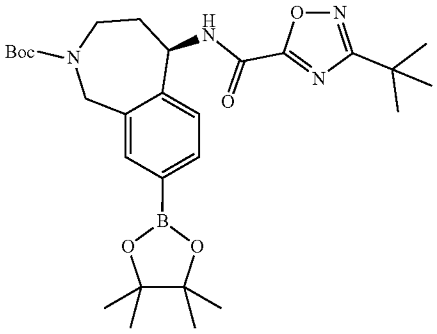 [SMILES: CC(C)(C)OC(=O)N1CC[C@@H](NC(=O)c2nc(C(C)(C)C)no2)c2ccc(B3OC(C)(C)C(C)(C)O3)cc2C1]

A mixture of 4,4,4',4',5,5,5',5'-octamethyl-2,2'-bi (1,3,2-dioxaborolane) (1.03 g, 4.06 mmol, 2.0 eq), potassium acetate (796 mg, 8.12 mmol, 4.0 eq), Pd(dppf)$Cl_2$ (148 mg, 0.203 mmol, 0.1 eq) and above obtained intermediate (1.0 g, 2.03 mmol, 1.0 eq) in dioxane (15 ml) was stirred at 100° C. under Ar for 4 h. Filtered and concentrated in vacuo. The residue was purified by flash chromatography eluted with Hex/EA=4:1 to give the title compound (800 mg, 73%) as a yellow solid. LC-MS: 541.3 $(M+H^+)$.

Step 3: tert-butyl (R)-5-(3-(tert-butyl)-1,2,4-oxadiazole-5-carboxamido)-8-(6-chloropyrazolo[1,5-a]pyrazin-4-yl)-1,3,4,5-tetrahydro-2H-benzo[c]azepine-2-carboxylate

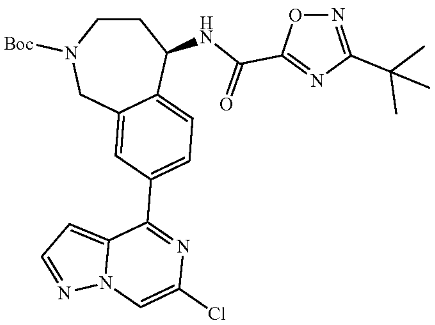 [SMILES: CC(C)(C)OC(=O)N1CC[C@@H](NC(=O)c2nc(C(C)(C)C)no2)c2ccc(-c3nc(Cl)cn4nccc34)cc2C1]

A mixture of above obtained intermediate (700 mg, 1.295 mmol, 1.0 eq), 4,6-dichloropyrazolo[1,5-a]pyrazine (350 mg, 1.862 mmol, 1.44 eq), $K_3PO_4$ (1375 mg, 6.48 mmol, 5.0 eq) and $Pd(t-Bu_3P)_2$ (132 mg, 0.259 mmol, 0.2 eq) in THF (20 ml) and water (4 ml) was stirred at rt under Ar for 16 h. The solution was diluted with water, extracted with ethyl acetate for 3 times. The combined organic layers were washed with brine, dried over anhydrous $Na_2SO_4$ and concentrated in vacuo. The residue was purified by flash chromatography eluted with Hex/EA=2:1 to give the title compound (550 mg, 75%) as a yellow solid. LC-MS: 566.7 ($M+H^+$).

Step 4: 4-(4-(4,4,5,5-tetramethyl-1,3,2-dioxaborolan-2-yl)-1H-pyrazol-1-yl)piperidine hydrochloride

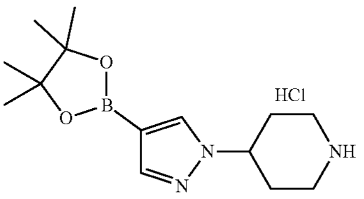 [SMILES: CC1(C)OB(c2cnn(C3CCNCC3)c2)OC1(C)C ; Cl]

A mixture of tert-butyl 4-(4-(4,4,5,5-tetramethyl-1,3,2-dioxaborolan-2-yl)-1H-pyrazol-1-yl)piperidine-1-carboxylate (1.0 g, 2.65 mmol, 1.0 eq) in DCM (20 ml) and HCl/Dioxane (4 ml, 4 M in dioxane) was stirred at rt for 2 h. After concentration in vacuo, the residue was used in next step without further purification (830 mg, 100%) as yellow oil. LC-MS: 278.5 ($M+H^+$).

Step 5: 1-(4-(4-((4-(4-(4,4,5,5-tetramethyl-1,3,2-dioxaborolan-2-yl)-1H-pyrazol-1-yl)piperidin-1-yl)methyl)piperidin-1-yl)phenyl)dihydropyrimidine-2,4(1H,3H)-dione

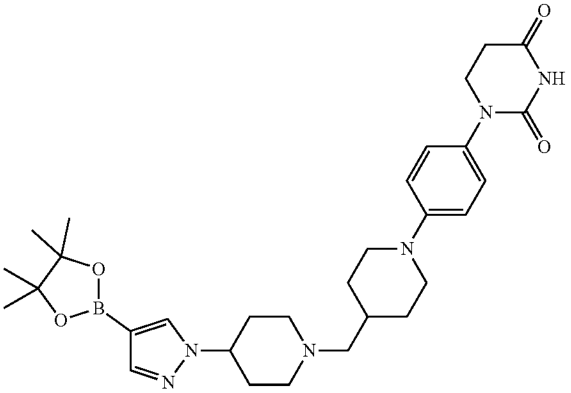 [SMILES: CC1(C)OB(c2cnn(C3CCN(CC4CCN(c5ccc(N6CCC(=O)NC6=O)cc5)CC4)CC3)c2)OC1(C)C]

To a solution of above obtained intermediate (730 mg, 2.33 mmol, 1.0 eq), 1-(4-(2,4-dioxotetrahydropyrimidin-1(2H)-yl)phenyl)piperidine-4-carbaldehyde (700 mg, 2.33 mmol, 1.0 eq) and TEA (942 mg, 9.32 mmol, 4.0 eq) in dry DCE (10 ml) was added NaBH(OAc) 3 (987 mg, 4.66 mmol, 2.0 eq) in portions. The reaction was stirred at rt for 2 h. The solution was quenched with water and extracted with DCM for 3 times. The organic layers were washed with brine, dried over anhydrous $Na_2SO_4$ and concentrated in vacuo. The residue was purified by flash chromatography eluted with DCM/MeOH=20:1 to give the title compound (300 mg, 23%) as a white solid. LC-MS: 563.4 ($M+H^+$).

Step 6: tert-butyl (R)-5-(3-(tert-butyl)-1,2,4-oxadiazole-5-carboxamido)-8-(6-(1-(1-((1-(4-(2,4-dioxotetrahydropyrimidin-1(2H)-yl)phenyl)piperidin-4-yl)methyl)piperidin-4-yl)-1H-pyrazol-4-yl)pyrazolo[1,5-a]pyrazin-4-yl)-1,3,4,5-tetrahydro-2H-benzo[c]azepine-2-carboxylate

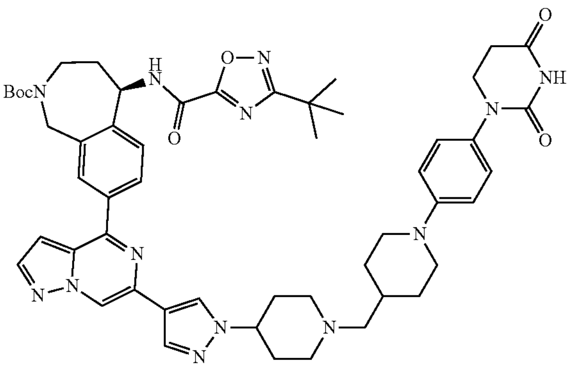 [SMILES: CC(C)(C)OC(=O)N1CC[C@@H](NC(=O)c2nc(C(C)(C)C)no2)c2ccc(-c3nc(-c4cnn(C5CCN(CC6CCN(c7ccc(N8CCC(=O)NC8=O)cc7)CC6)CC5)c4)cn4nccc34)cc2C1]

A mixture of tert-butyl (R)-5-(3-(tert-butyl)-1,2,4-oxadiazole-5-carboxamido)-8-(6-chloropyrazolo[1,5-a]pyrazin-4-yl)-1,3,4,5-tetrahydro-2H-benzo[c]azepine-2-carboxylate (130 mg, 0.231 mmol, 1.0 eq), above obtained intermediate (130 mg, 0.231 mmol, 1.0 eq), $K_3PO_4$ (147 mg, 0.693 mmol, 3.0 eq) and XPhos-Pd-G3 (39 mg, 0.023 mmol, 0.2 eq) in dioxane (8 ml) and water (2 ml) was stirred at 100° C. under Ar for 16 h. The solution was diluted with water, extracted with ethyl acetate for 3 times. The combined organic layers were washed with brine, dried over anhydrous $Na_2SO_4$ and concentrated in vacuo. The residue was purified by flash chromatography eluted with Hex/EA=1:1 to give the title compound (60 mg, 27%) as yellow oil. LC-MS: 966.8 ($M+H^+$).

Step 7: (R)-3-(tert-butyl)-N-(8-(6-(1-(1-((1-(4-(2,4-dioxotetrahydropyrimidin-1(2H)-yl)phenyl)piperidin-4-yl)methyl)piperidin-4-yl)-1H-pyrazol-4-yl)pyrazolo[1,5-a]pyrazin-4-yl)-2,3,4,5-tetrahydro-1H-benzo[c]azepin-5-yl)-1,2,4-oxadiazole-5-carboxamide hydrochloride

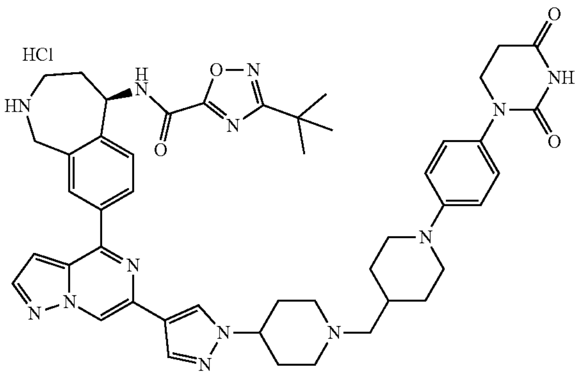 [SMILES: CC(C)(C)c1noc(C(=O)N[C@@H]2CCNCc3cc(-c4nc(-c5cnn(C6CCN(CC7CCN(c8ccc(N9CCC(=O)NC9=O)cc8)CC7)CC6)c5)cn5nccc45)ccc32)n1 ; Cl]

A mixture of above obtained intermediate (60 mg, 0.062 mmol, 1.0 eq) in DCM (4 ml) and HCl/Dioxane (1 ml, 4 M in dioxane) was stirred at rt for 2 h. After concentration in vacuo, the residue was used in next step without further purification (56 mg, 100%) as a yellow solid. LC-MS: 866.5 ($M+H^+$).

Step 8: (R)-3-(tert-butyl)-N-(8-(6-(1-(1-((1-(4-(2,4-dioxotetrahydropyrimidin-1(2H)-yl)phenyl)piperidin-4-yl)methyl)piperidin-4-yl)-1H-pyrazol-4-yl)pyrazolo[1,5-a]pyrazin-4-yl)-2-methyl-2,3,4,5-tetrahydro-1H-benzo[c]azepin-5-yl)-1,2,4-oxadiazole-5-carboxamide

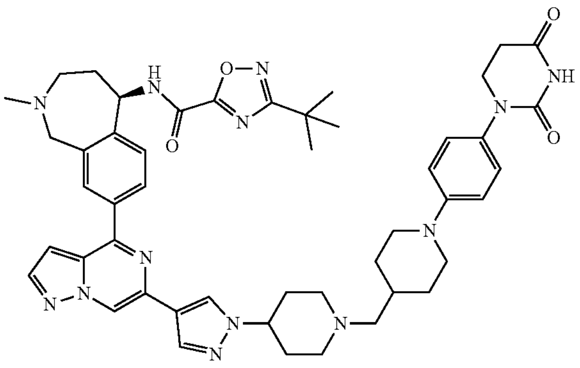 [SMILES: CN1CC[C@@H](NC(=O)c2nc(C(C)(C)C)no2)c2ccc(-c3nc(-c4cnn(C5CCN(CC6CCN(c7ccc(N8CCC(=O)NC8=O)cc7)CC6)CC5)c4)cn4nccc34)cc2C1]

To a solution of above obtained intermediate (50 mg, 0.055 mmol, 1.0 eq), formaldehyde aqueous solution (0.05 ml) and TEA (28 mg, 0.275 mmol, 5.0 eq) in dry DCE (5 ml) was added NaBH(OAc) 3 (35 mg, 0.165 mmol, 3.0 eq) in portions. The reaction was stirred at rt for 2 h. The solution was quenched with water and extracted with DCM for 3 times. The organic layers were washed with brine, dried over anhydrous $Na_2SO_4$ and concentrated in vacuo. The residue was purified by pre-HPLC to give the title compound (8 mg, 16.4%) as a white solid. LC-MS: 880.4 ($M+H^+$). $^1H$ NMR (400 MHz, DMSO-$d^6$) δ (ppm) 10.25 (s, 1H), 9.98 (d, J=8.0 Hz, 1H), 9.13 (s, 1H), 8.45 (s, 1H), 8.19 (d, J=2.4 Hz, 1H), 8.15 (s, 1H), 8.06-8.01 (m, 1H), 7.99 (s, 1H), 7.42 (d, J=8.0 Hz, 1H), 7.17 (d, J=1.6 Hz, 1H), 7.13 (d, J=8.8 Hz, 2H), 6.92 (d, J=8.8 Hz, 2H), 5.45-5.35 (m, 1H), 4.25-4.15 (m, 1H), 4.05-3.90 (m, 2H), 3.73-3.65 (m, 4H), 3.10-2.90 (m, 4H), 2.71-2.60 (m, 4H), 2.27 (s, 3H), 2.25-1.60 (m, 13H), 1.40 (s, 9H), 1.25-1.20 (m, 2H).

Example 17: 1-(4-(4-((4-(4-(4-(2-(7,7-dimethyl-1-oxo-1,3,4,6,7,8-hexahydro-2H-cyclopenta[4,5]pyrrolo[1,2-a]pyrazin-2-yl)-3-(hydroxymethyl)pyridin-4-yl)pyrazolo[1,5-a]pyrazin-6-yl)-1H-pyrazol-1-yl)piperidin-1-yl)methyl)piperidin-1-yl)phenyl)dihydropyrimidine-2,4(1H,3H)-dione (Compound No. 46)

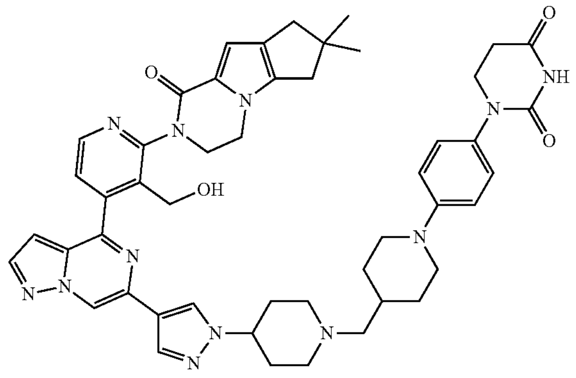 [SMILES: CC1(C)Cc2cc3n(c2C1)CCN(c1nccc(-c2nc(-c4cnn(C5CCN(CC6CCN(c7ccc(N8CCC(=O)NC8=O)cc7)CC6)CC5)c4)cn4nccc24)c1CO)C3=O]

Following the synthesis of EXAMPLE 18, the title compound was obtained (98 mg) as a white solid. LC-MS: 863.3 ($M+H^+$). $^1H$ NMR (400 MHz, DMSO-$d^6$) δ (ppm) 10.24 (s, 1H), 9.20 (s, 1H), 8.61 (d, J=4.8 Hz, 1H), 8.37 (s, 1H), 8.16 (d, J=2.0 Hz, 1H), 8.09 (s, 1H), 7.56 (d, J=4.8 Hz, 1H), 7.13 (d, J=8.8 Hz, 2H), 6.93 (d, J=8.8 Hz, 2H), 6.66 (d, J=2.0 Hz, 1H), 6.60 (s, 1H), 4.70-4.65 (m, 1H), 4.60-4.52 (m, 1H), 4.43-4.30 (m, 2H), 4.25-4.15 (m, 3H), 4.05-3.95 (m, 1H), 3.75-3.65 (m, 4H), 3.00-2.90 (m, 2H), 2.71-2.55 (m, 6H), 2.43 (s, 2H), 2.21 (d, J=7.2 Hz, 2H), 2.13-1.95 (m, 6H), 1.85-1.60 (m, 3H), 1.22 (s, 8H).

Example 18: 1-(4-(4-((4-(4-(4-(3-(6-cyclopropyl-8-fluoro-1-oxoisoquinolin-2(1H)-yl)-2-(hydroxymethyl)phenyl)pyrazolo[1,5-a]pyrazin-6-yl)-1H-pyrazol-1-yl)piperidin-1-yl)methyl)piperidin-1-yl)phenyl)dihydropyrimidine-2,4(1H,3H)-dione (Compound No. 51)
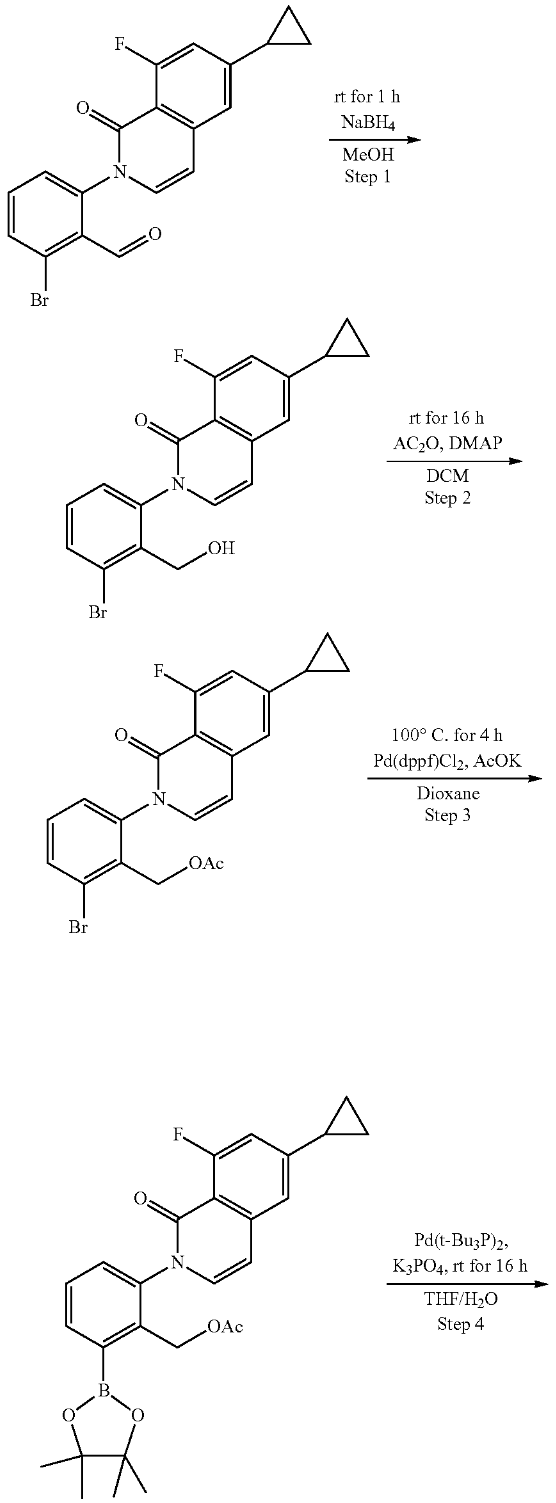
-continued
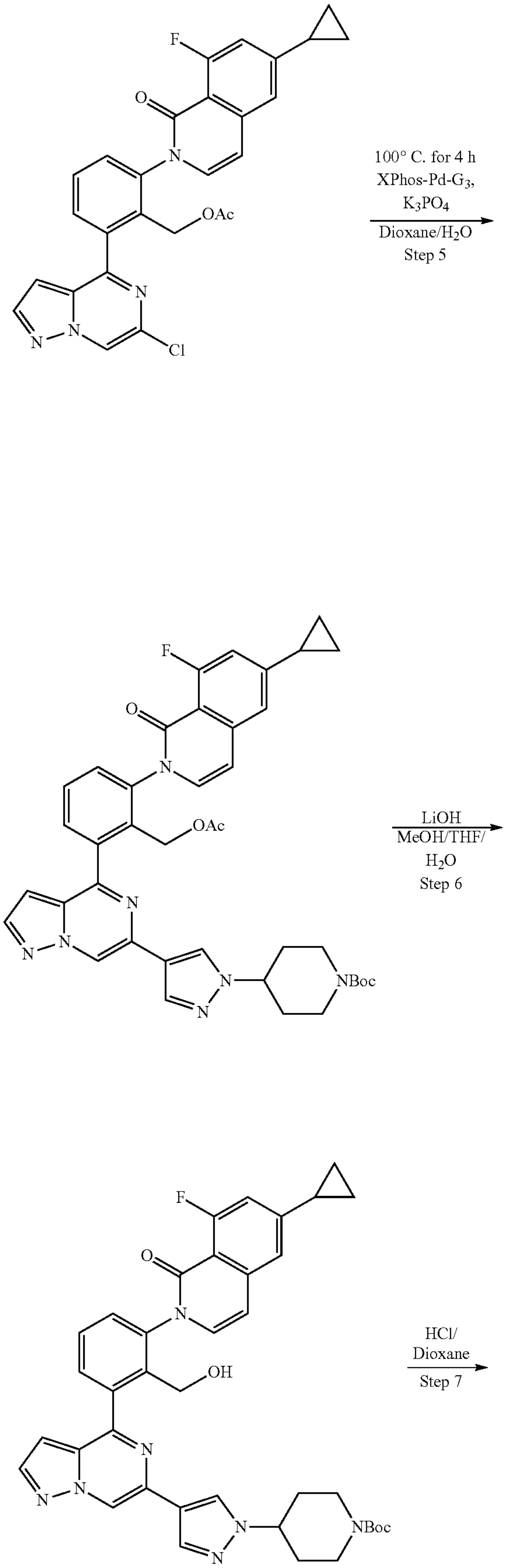

-continued

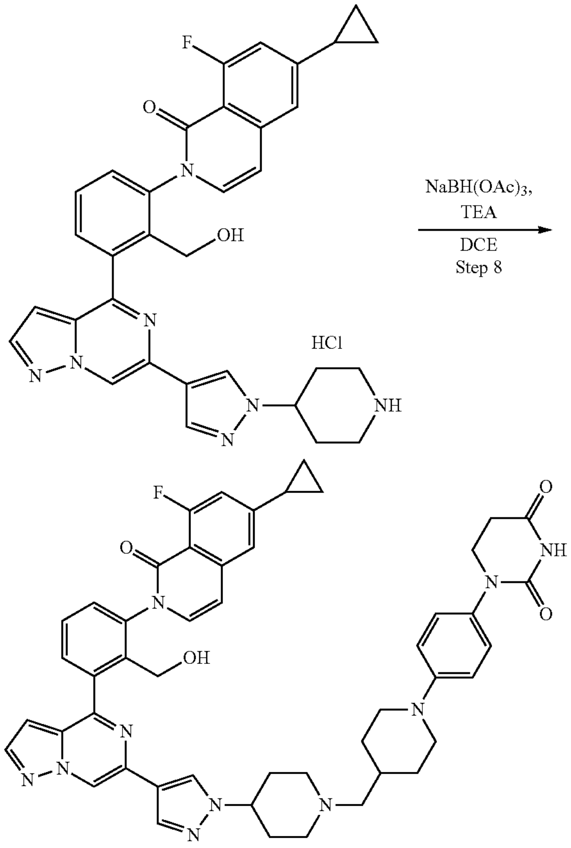

Step 1:4-(piperidin-1-yl)-6-(1-(piperidin-4-yl)-1H-pyrazol-4-yl)pyrazolo[1,5-a]pyrazine hydrochloride

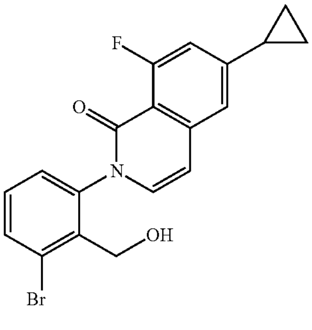 [SMILES: O=c1c2c(F)cc(C3CC3)cc2ccn1-c1cccc(Br)c1CO]

To a solution of 2-bromo-6-(6-cyclopropyl-8-fluoro-1-oxoisoquinolin-2(1H)-yl)benzaldehyde (1.5 g, 3.88 mmol, 1.0 eq) in MeOH (20 ml) was added $NaBH_4$ (420 mg, 11.1 mmol, 2.86 eq) in portions at 0° C. The reaction was stirred at rt for 2 h. The solution was quenched with $NH_4Cl$ aqueous and extracted with EA for 3 times. The combined organic layers were washed with brine, dried over anhydrous $Na_2SO_4$ and concentrated in vacuo. The residue was purified by flash chromatography eluted with Hex/EA=3:1 to give the title compound (850 mg, 56.3%) as a white solid. LC-MS: 388.6 (M+H+).

Step 2: 2-bromo-6-(6-cyclopropyl-8-fluoro-1-oxoisoquinolin-2(1H)-yl)benzyl acetate

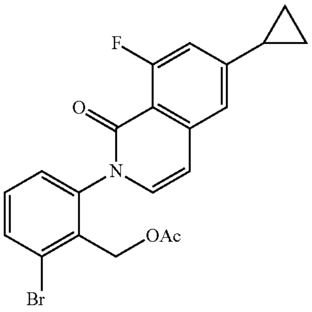 [SMILES: CC(=O)OCc1c(Br)cccc1-n1ccc2cc(C3CC3)cc(F)c2c1=O]

To a solution of 2-(3-bromo-2-(hydroxymethyl)phenyl)-6-cyclopropyl-8-fluoroisoquinolin-1(2H)-one (850 mg, 2.19 mmol, 1.0 eq) and DMAP (300 mg, 2.46 mmol, 1.12 eq) in dry DCM (20 ml) was added acetic anhydride (800 mg, 7.84 mmol, 3.58 eq) in portions at 0° C. The reaction was stirred at rt for 16 h. Water was added and extracted with DCM for 3 times. The combined organic layers were washed with brine, dried over anhydrous $Na_2SO_4$ and concentrated in vacuo. The residue was purified by flash chromatography eluted with Hex/EA=10:1 to give the title compound (500 mg, 53.1%) as a white solid. LC-MS: 430.2 (M+H+).

Step 3: 2-(6-cyclopropyl-8-fluoro-1-oxoisoquinolin-2(1H)-yl)-6-(4,4,5,5-tetramethyl-1,3,2-dioxaborolan-2-yl)benzyl acetate

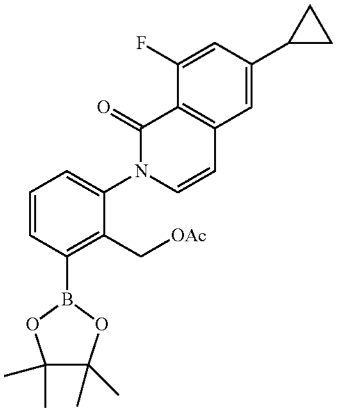 [SMILES: CC(=O)OCc1c(B2OC(C)(C)C(C)(C)O2)cccc1-n1ccc2cc(C3CC3)cc(F)c2c1=O]

A mixture of above obtained intermediate (500 mg, 1.162 mmol, 1.0 eq), 4,4,4',4',5,5,5',5'-octamethyl-2,2'-bi (1,3,2-dioxaborolane) (590 mg, 2.324 mmol, 2.0 eq), KOAc (456 mg, 4.65 mmol, 4.0 eq) and $PdCl_2$ (dppf) (85 mg, 0.116 mmol, 0.1 eq) in dry Dioxane (10 ml) was stirred at 100° C. under Ar for 3 h. Water was added and extracted with EA for 3 times. The combined organic layers were washed with brine, dried over anhydrous $Na_2SO_4$ and concentrated in vacuo. The residue was purified by flash chromatography eluted with Hex/EA=10:1 to give the title compound (400 mg, 72.1%) as a white solid. LC-MS: 478.1 (M+H+).

Step 4: 2-(6-chloropyrazolo[1,5-a]pyrazin-4-yl)-6-(6-cyclopropyl-8-fluoro-1-oxoisoquinolin-2 (1H)-yl) benzyl acetate

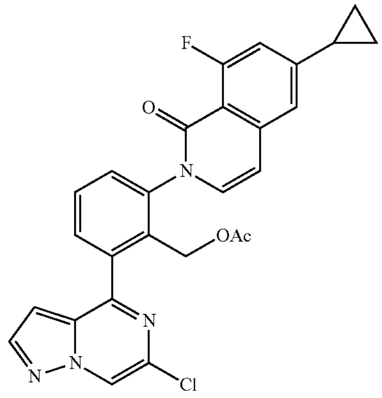 [SMILES: CC(=O)OCc1c(-c2nc(Cl)cn3nccc23)cccc1-n1ccc2cc(C3CC3)cc(F)c2c1=O]

A mixture of above obtained intermediate (400 mg, 0.838 mmol, 1.0 eq), 4,6-dichloropyrazolo[1,5-a]pyrazine (158 mg, 0.838 mmol, 1.0 eq), $K_3PO_4$ (534 mg, 2.51 mmol, 3.0 eq) and $Pd(t\text{-}Bu_3P)_2$ (43 mg, 0.084 mmol, 0.1 eq) in THF (10 ml) and water (2 ml) was stirred at rt under Ar for 16 h. The solution was diluted with water, extracted with ethyl acetate for 3 times. The combined organic layers were washed with brine, dried over anhydrous $Na_2SO_4$ and concentrated in vacuo. The residue was purified by flash chromatography eluted with Hex/EA=2:1 to give the title compound (150 mg, 35.6%) as yellow oil. LC-MS: 503.5 ($M+H^+$).

Step 5: tert-butyl 4-(4-(4-(2-(acetoxymethyl)-3-(6-cyclopropyl-8-fluoro-1-oxoisoquinolin-2(1H)-yl) phenyl)pyrazolo[1,5-a]pyrazin-6-yl)-1H-pyrazol-1-yl)piperidine-1-carboxylate

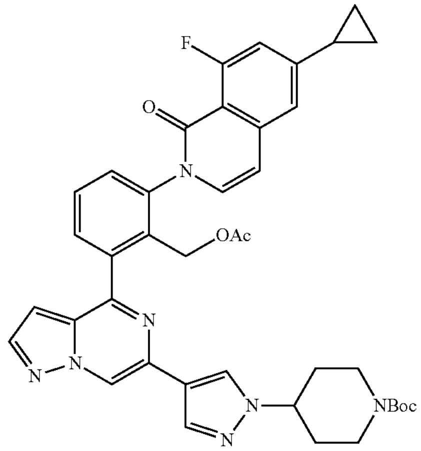 [SMILES: CC(=O)OCc1c(-c2nc(-c3cnn(C4CCN(C(=O)OC(C)(C)C)CC4)c3)cn3nccc23)cccc1-n1ccc2cc(C3CC3)cc(F)c2c1=O]

A mixture of tert-butyl 4-(4-(4,4,5,5-tetramethyl-1,3,2-dioxaborolan-2-yl)-1H-pyrazol-1-yl)piperidine-1-carboxylate (180 mg, 0.477 mmol, 1.5 eq), above obtained intermediate (150 mg, 0.298 mmol, 1.0 eq), $K_3PO_4$ (190 mg, 0.895 mmol, 3.0 eq) and XPhos-Pd-G3 (26 mg, 0.03 mmol, 0.1 eq) in dioxane (8 ml) and water (2 ml) was stirred at 100° C. under Ar for 16 h. The solution was diluted with water, extracted with ethyl acetate for 3 times. The combined organic layers were washed with brine, dried over anhydrous $Na_2SO_4$ and concentrated in vacuo. The residue was purified by flash chromatography eluted with Hex/EA=1:1 to give the title compound (140 mg, 65.4%) as yellow oil. LC-MS: 718.7 ($M+H^+$).

Step 6: tert-butyl 4-(4-(4-(3-(6-cyclopropyl-8-fluoro-1-oxoisoquinolin-2(1H)-yl)-2-(hydroxymethyl)phenyl)pyrazolo[1,5-a]pyrazin-6-yl)-1H-pyrazol-1-yl)piperidine-1-carboxylate

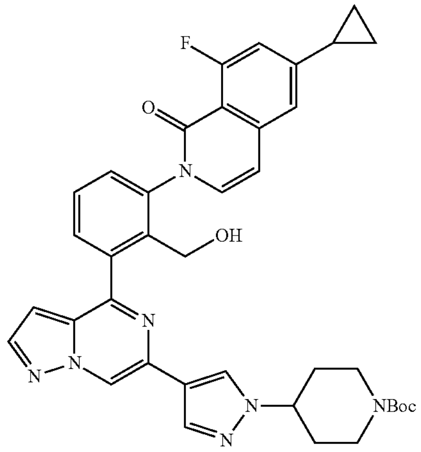 [SMILES: CC(C)(C)OC(=O)N1CCC(n2cc(-c3cn4nccc4c(-c4cccc(-n5ccc6cc(C7CC7)cc(F)c6c5=O)c4CO)n3)cn2)CC1]

A mixture above obtained intermediate (140 mg, 0.195 mmol, 1.0 eq) and LiOH (33 mg, 1.365 mmol, 7.0 eq) in MeOH (2 ml), THF (2 ml) and water (1 ml) was stirred at RT under Ar for 1 h. The solution was diluted with $NH_4Cl$ aqueous, extracted with ethyl acetate for 3 times. The combined organic layers were washed with brine, dried over anhydrous $Na_2SO_4$ and concentrated in vacuo. The residue was purified by flash chromatography eluted with Hex/EA=1:1 to give the title compound (120 mg, 91%) as yellow oil. LC-MS: 676.3 ($M+H^+$).

Step 7: 6-cyclopropyl-8-fluoro-2-(2-(hydroxymethyl)-3-(6-(1-(piperidin-4-yl)-1H-pyrazol-4-yl)pyrazolo[1,5-a]pyrazin-4-yl)phenyl) isoquinolin-1(2H)-one hydrochloride

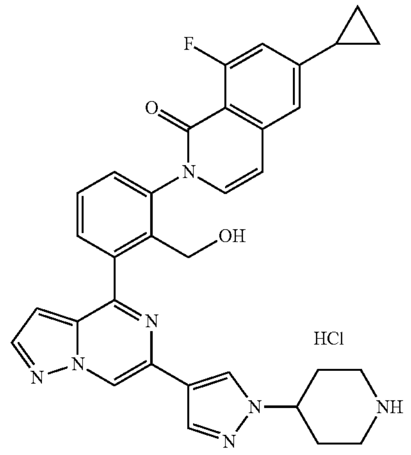 [SMILES: O=c1c2c(F)cc(C3CC3)cc2ccn1-c1cccc(-c2nc(-c3cnn(C4CCNCC4)c3)cn3nccc23)c1CO ; Cl]

A mixture of above obtained intermediate (120 mg, 0.178 mmol, 1.0 eq) in DCM (4 ml) and 4M HCl/Dioxane (1 ml) was stirred at rt for 4 h. After concentration in vacuo, the residue was used in next step without further purification (110 mg, 98%) as a yellow solid. LC-MS: 576.5 (M+H$^+$).

Step 8: 1-(4-(4-((4-(4-(4-(3-(6-cyclopropyl-8-fluoro-1-oxoisoquinolin-2(1H)-yl)-2-(hydroxymethyl)phenyl)pyrazolo[1,5-a]pyrazin-6-yl)-1H-pyrazol-1-yl)piperidin-1-yl)methyl)piperidin-1-yl)phenyl)dihydropyrimidine-2,4(1H,3H)-dione

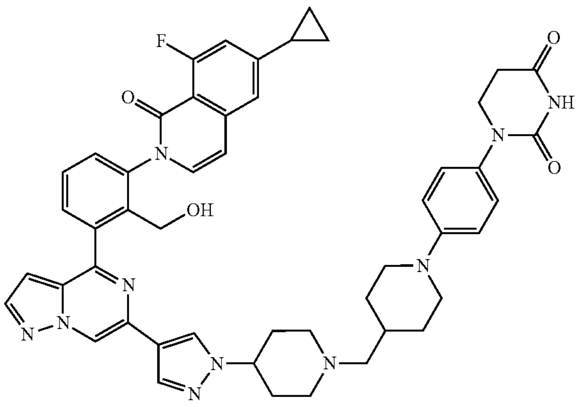 [SMILES: O=C1CCN(c2ccc(N3CCC(CN4CCC(n5cc(-c6cn7nccc7c(-c7cccc(-n8ccc9cc(C%10CC%10)cc(F)c9c8=O)c7CO)n6)cn5)CC4)CC3)cc2)C(=O)N1]

To a solution of above obtained intermediate (100 mg, 0.161 mmol, 1.0 eq), 1-(4-(2,4-dioxotetrahydropyrimidin-1(2H)-yl)phenyl)piperidine-4-carbaldehyde (49 mg, 0.161 mmol, 1.0 eq) and TEA (82 mg, 0.805 mmol, 5.0 eq) in dry DCE (5 ml) was added NaBH(OAc) 3 (68 mg, 0.322 mmol, 2.0 eq) in portions. The reaction was stirred at rt for 2 h. The solution was quenched with water and extracted with DCM for 3 times. The organic layers were washed with brine, dried over anhydrous $Na_2SO_4$ and concentrated in vacuo. The residue was purified by pre-HPLC to give the title compound (62 mg, 44.6%) as a white solid. LC-MS: 861.4 (M+H$^+$). $^1$H NMR (400 MHz, DMSO-d$^6$) δ (ppm) 10.24 (s, 1H), 9.19 (s, 1H), 8.39 (s, 1H), 8.15 (d, J=2.4 Hz, 1H), 8.09 (s, 1H), 7.76 (d, J=8.0 Hz, 1H), 7.68-7.62 (m, 1H), 7.53 (d, J=8.0 Hz, 1H), 7.42 (d, J=7.2 Hz, 1H), 7.28 (d, J=1.2 Hz, 1H), 7.13 (d, J=9.2 Hz, 2H), 7.00 (d, J=13.2 Hz, 1H), 6.93 (d, J=9.2 Hz, 2H), 6.75-6.70 (m, 1H), 6.65-6.60 (m, 1H), 4.70-4.65 (m, 1H), 4.50-4.42 (m, 1H), 4.28-4.15 (m, 2H), 3.75-3.65 (m, 4H), 3.00-2.90 (m, 2H), 2.71-2.58 (m, 4H), 2.21 (d, J=7.2 Hz, 2H), 2.13-1.95 (m, 7H), 1.85-1.60 (m, 3H), 1.28-1.15 (m, 2H), 1.13-1.07 (m, 2H), 0.90-0.85 (m, 2H).

Example 19: (R)-3-(tert-butyl)-N-(8-(6-(1-(1-((1-(4-(2,4-dioxotetrahydropyrimidin-1(2H)-yl)phenyl)piperidin-4-yl)methyl)piperidin-4-yl)-1H-pyrazol-4-yl)pyrazolo[1,5-a]pyrazin-4-yl)-2-ethyl-2,3,4,5-tetrahydro-1H-benzo[c]azepin-5-yl)-1,2,4-oxadiazole-5-carboxamide (Compound No. 52)

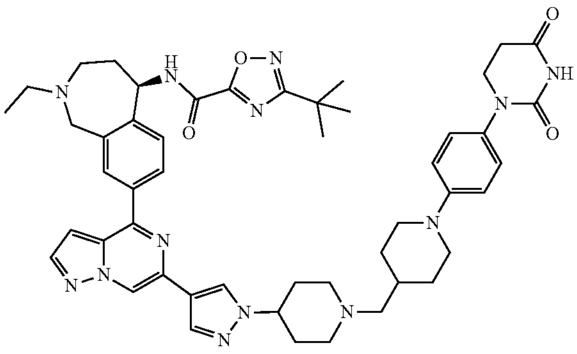 [SMILES: CCN1CC[C@@H](NC(=O)c2nc(C(C)(C)C)no2)c2ccc(-c3nc(-c4cnn(C5CCN(CC6CCN(c7ccc(N8CCC(=O)NC8=O)cc7)CC6)CC5)c4)cn4nccc34)cc2C1]

Following the synthesis of EXAMPLE 20, the title compound was obtained (10 mg) as a white solid. LC-MS: 894.2 (M+H$^+$).

Example 20: (R)-3-(tert-butyl)-N-(8-(6-(1-(1-((1-(4-(2,4-dioxotetrahydropyrimidin-1(2H)-yl)phenyl)piperidin-4-yl)methyl)piperidin-4-yl)-1H-pyrazol-4-yl)pyrazolo[1,5-a]pyrazin-4-yl)-2-isopropyl-2,3,4,5-tetrahydro-1H-benzo[c]azepin-5-yl)-1,2,4-oxadiazole-5-carboxamide (Compound No. 53)

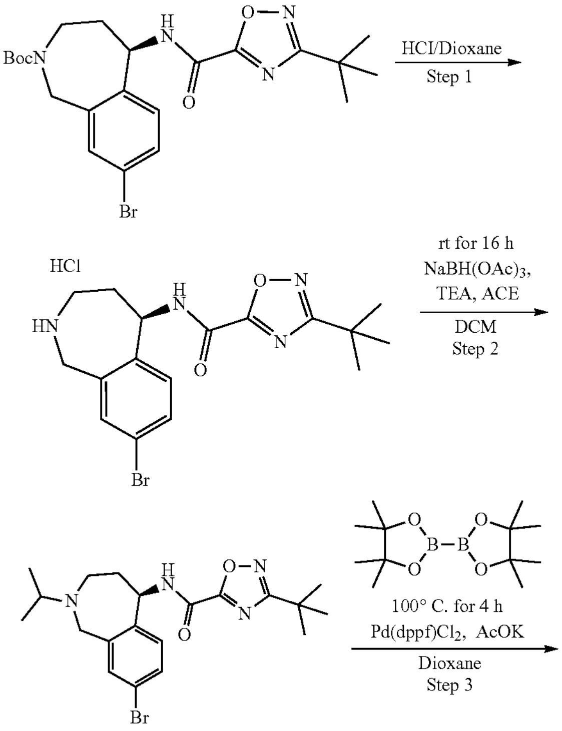

-continued

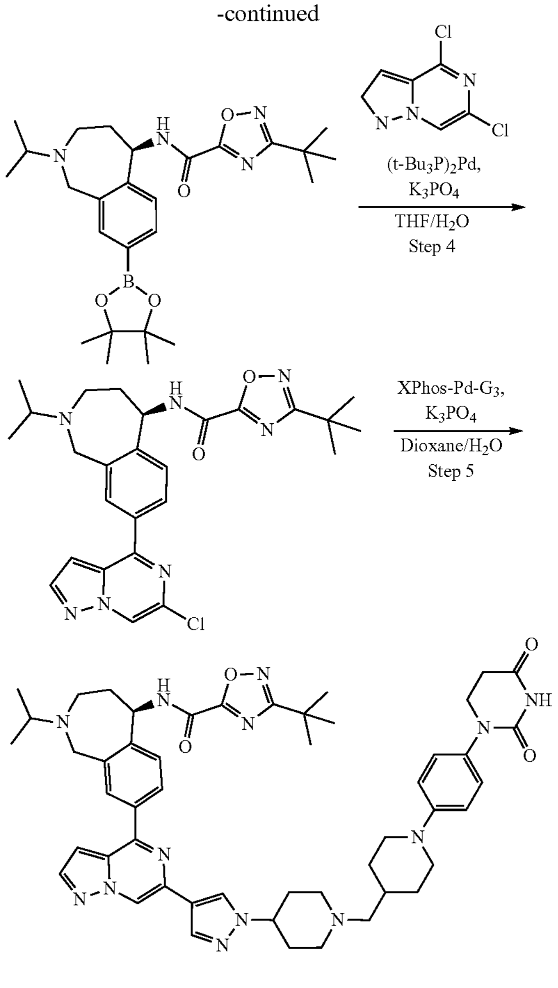

Step 1: (R)—N-(8-bromo-2,3,4,5-tetrahydro-1H-benzo[c]azepin-5-yl)-3-(tert-butyl)-1,2,4-oxadiazole-5-carboxamide hydrochloride A mixture of tert-butyl (R)-8-bromo-5-(3-(tert-butyl)-1,2,4-oxadiazole-5-carboxamido)-1,3,4,5-tetrahydro-2H-benzo[c]azepine-2-carboxylate (7.0 g, 14.19 mmol, 1.0 eq) in DCM (60 ml) and 4M HCl/Dioxane (15 ml) was stirred at rt under Ar for 2 h. After concentration in vacuo, the residue was used in next step without further purification (6.0 g, 98%) as a brown solid. LC-MS: 393.1 (M+H$^+$).

Step 2: (R)—N-(8-bromo-2-isopropyl-2,3,4,5-tetrahydro-1H-benzo[c]azepin-5-yl)-3-(tert-butyl)-1,2,4-oxadiazole-5-carboxamide

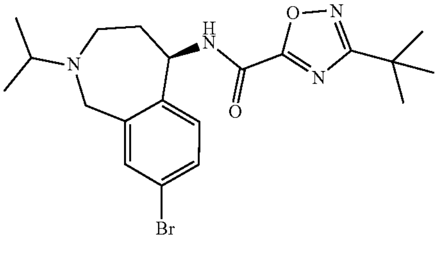 [SMILES: CC(C)N1CC[C@@H](NC(=O)c2nc(C(C)(C)C)no2)c2ccc(Br)cc2C1]

A solution of (R)—N-(8-bromo-2,3,4,5-tetrahydro-1H-benzo[c]azepin-5-yl)-3-(tert-butyl)-1,2,4-oxadiazole-5-carboxamide (700 mg, 1.780 mmol, 1.000), triethylamine (540 mg, 5.34 mmol, 3) and propan-2-one (310 mg, 5.34 mmol, 3) in DCM (25 ml) was stirred at 25° C. under Ar for 30 min, then NaBH(OAc) 3 (566 mg, 2.67 mmol, 1.5) was added and stirred at 25° C. for 16 h. Water was added to the reaction mixture followed by extraction with DCM for 3 times. The combined organic layers were dried $Na_2SO_4$, filtered and concentrated. The crude product was added to a silica gel column and was eluted with DCM/MeOH=20:1 to give the title compound (550 mg, 71.0%) as a yellow solid. LC-MS: 435.7 (M+H$^+$).

Step 3 (R)-3-(tert-butyl)-N-(2-isopropyl-8-(4,4,5,5-tetramethyl-1,3,2-dioxaborolan-2-yl)-2,3,4,5-tetrahydro-1H-benzo[c]azepin-5-yl)-1,2,4-oxadiazole-5-carboxamide

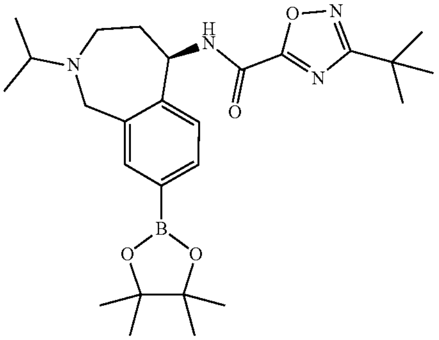 [SMILES: CC(C)N1CC[C@@H](NC(=O)c2nc(C(C)(C)C)no2)c2ccc(B3OC(C)(C)C(C)(C)O3)cc2C1]

A mixture of (R)—N-(8-bromo-2-isopropyl-2,3,4,5-tetrahydro-1H-benzo[c]azepin-5-yl)-3-(tert-butyl)-1,2,4-oxadiazole-5-carboxamide (550 mg, 1.263 mmol, 1.0 eq), 4,4,4',4',5,5,5',5'-octamethyl-2,2'-bi (1,3,2-dioxaborolane) (481 mg, 1.895 mmol, 1.5 eq), potassium acetate (372 mg, 3.79 mmol, 3.0 eq) and $PdCl_2$ (dppf) (92 mg, 0.126 mmol, 0.1 eq) in dry Dioxane (10 ml) was stirred at 100° C. under Ar for 4 h. Water was added to the reaction mixture followed by extraction with EA for 3 times. The combined organic layers were dried $Na_2SO_4$, filtered and concentrated. The crude product was added to a silica gel column and was eluted with DCM/MeOH=20:1 to give the title compound (140 mg, 22.97%) as a white solid. LC-MS: 483.3 (M+H$^+$).

Step 4: (R)-3-(tert-butyl)-N-(8-(6-chloropyrazolo[1,5-a]pyrazin-4-yl)-2-isopropyl-2,3,4,5-tetrahydro-1H-benzo[c]azepin-5-yl)-1,2,4-oxadiazole-5-carboxamide

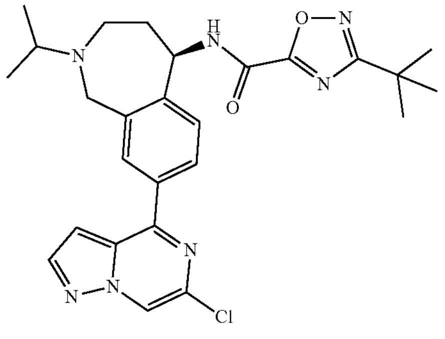 [SMILES: CC(C)N1CC[C@@H](NC(=O)c2nc(C(C)(C)C)no2)c2ccc(-c3nc(Cl)cn4nccc34)cc2C1]

A mixture of above obtained intermediate (140 mg, 0.29 mmol, 1.0 eq), 4,6-dichloropyrazolo[1,5-a]pyrazine (82 mg, 0.435 mmol, 1.5 eq), $K_3PO_4$ (185 mg, 0.871 mmol, 3.0 eq) and $Pd(t\text{-}Bu_3P)_2$ (15 mg, 0.029 mmol, 0.1 eq) in THF (10 ml) and water (2 ml) was stirred at rt under Ar for 16 h. The solution was diluted with water, extracted with EA for 3 times. The combined organic layers were washed with brine, dried over anhydrous $Na_2SO_4$ and concentrated in vacuo. The residue was purified by flash chromatography eluted with DCM/MeOH=20:1 to give the title compound (50 mg, 34%) as a yellow solid. LC-MS: 508.5 ($M+H^+$).

Step 5: (R)-3-(tert-butyl)-N-(8-(6-(1-(1-((1-(4-(2,4-dioxotetrahydropyrimidin-1(2H)-yl)phenyl)piperidin-4-yl)methyl)piperidin-4-yl)-1H-pyrazol-4-yl)pyrazolo[1,5-a]pyrazin-4-yl)-2-isopropyl-2,3,4,5-tetrahydro-1H-benzo[c]azepin-5-yl)-1,2,4-oxadiazole-5-carboxamide

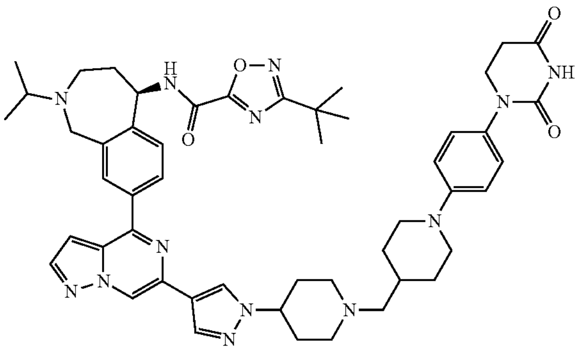 [SMILES: CC(C)N1CC[C@@H](NC(=O)c2nc(C(C)(C)C)no2)c2ccc(-c3nc(-c4cnn(C5CCN(CC6CCN(c7ccc(N8CCC(=O)NC8=O)cc7)CC6)CC5)c4)cn4nccc34)cc2C1]

A mixture of 1-(4-(4-((4-(4-(4,4,5,5-tetramethyl-1,3,2-dioxaborolan-2-yl)-1H-pyrazol-1-yl)piperidin-1-yl)methyl)piperidin-1-yl)phenyl)dihydropyrimidine-2,4(1H,3H)-dione (83 mg, 0.148 mmol, 1.5 eq), above obtained intermediate (50 mg, 0.098 mmol, 1.0 eq), $K_3PO_4$ (63 mg, 0.296 mmol, 3.0 eq) and XPhos-Pd-G3 (16 mg, 0.02 mmol, 0.2 eq) in dioxane (4 ml) and water (1 ml) was stirred at 100° C. under Ar for 16 h. The solution was diluted with water, extracted with ethyl acetate for 3 times. The combined organic layers were washed with brine, dried over anhydrous $Na_2SO_4$ and concentrated in vacuo. The residue was purified by pre- HPLC to give the title compound (14 mg, 15.7%) as a white solid. LC-MS: 908.8 ($M+H^+$).

Example 21: (R)-3-(tert-butyl)-N-(2-cyclopropyl-8-(6-(1-(1-((1-(4-(2,4-dioxotetrahydropyrimidin-1(2H)-yl)phenyl)piperidin-4-yl)methyl)piperidin-4-yl)-1H-pyrazol-4-yl)pyrazolo[1,5-a]pyrazin-4-yl)-2,3,4,5-tetrahydro-1H-benzo[c]azepin-5-yl)-1,2,4-oxadiazole-5-carboxamide (Compound No. 54)

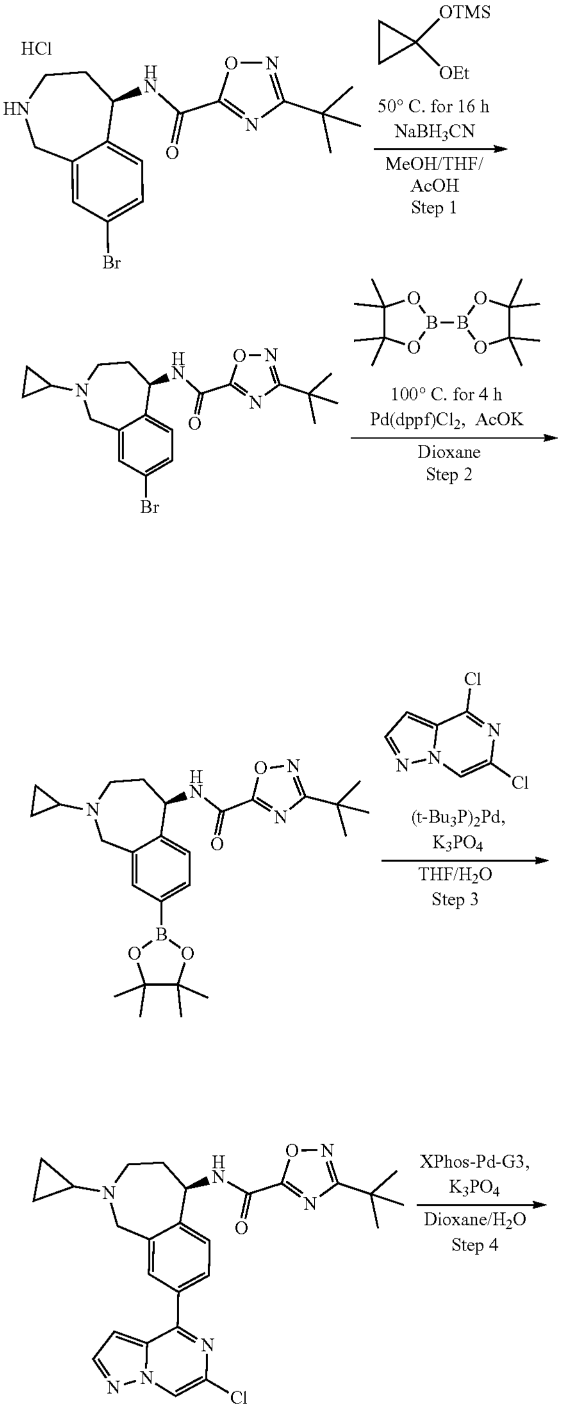

-continued

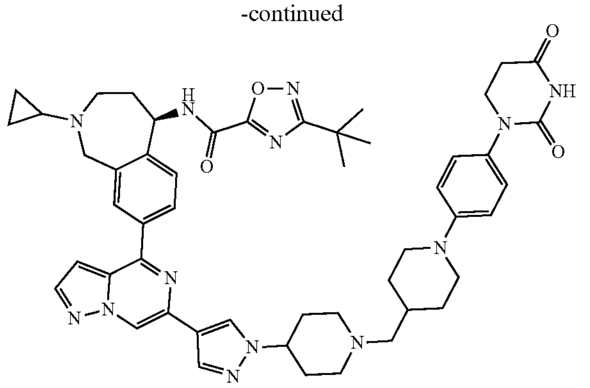

Step 1: (R)—N-(8-bromo-2-cyclopropyl-2,3,4,5-tetrahydro-1H-benzo[c]azepin-5-yl)-3-(tert-butyl)-1,2,4-oxadiazole-5-carboxamide

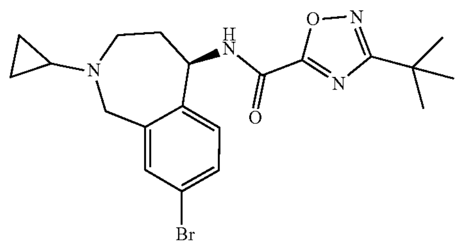 [SMILES: CC(C)(C)c1noc(C(=O)N[C@@H]2CCN(C3CC3)Cc3cc(Br)ccc32)n1]

A mixture of (R)—N-(8-bromo-2,3,4,5-tetrahydro-1H-benzo[c]azepin-5-yl)-3-(tert-butyl)-1,2,4-oxadiazole-5-carboxamide hydrochloride (2178 mg, 5.09 mmol, 1.0 eq), acetic acid (3054 mg, 50.9 mmol, 10.0 eq) and (1-ethoxycyclopropoxy)trimethylsilane (2659 mg, 15.26 mmol, 3.0 eq) were dissolved in MeOH (10 ml)/THF (20 ml) under Ar was stirred at rt for 30 min, then $NaBH_3CN$ (479 mg, 7.63 mmol, 1.5 eq) was added at rt and stirred at 50° C. for 16 h, water (30 ml) was added to the reaction mixture followed by extraction with EA (15 ml×3). The combined organic layers were dried $Na_2SO_4$, filtered and concentrated. The crude product was added to a silica gel column and was eluted with DCM/MeOH=50:1 to give the title compound (800 mg, 36.3%) as a yellow solid. LC-MS: 433.3 ($M+H^+$).

Step 2: (R)—N-(8-bromo-2-cyclopropyl-2,3,4,5-tetrahydro-1H-benzo[c]azepin-5-yl)-3-(tert-butyl)-1,2,4-oxadiazole-5-carboxamide

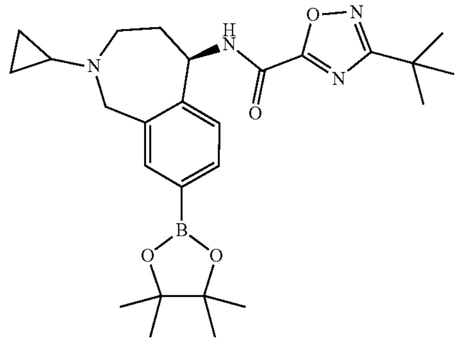 [SMILES: CC(C)(C)c1noc(C(=O)N[C@@H]2CCN(C3CC3)Cc3cc(B4OC(C)(C)C(C)(C)O4)ccc32)n1]

A mixture of above obtained intermediate (800 mg, 1.846 mmol, 1.0 eq), 4,4,4',4',5,5,5',5'-octamethyl-2,2'-bi (1,3,2-dioxaborolane) (703 mg, 2.77 mmol, 1.5 eq), potassium acetate (544 mg, 5.54 mmol, 3.0 eq) and $PdCl_2$ (dppf) (135 mg, 0.185 mmol, 0.1 eq) in dry Dioxane (10 ml) was stirred at 100° C. under Ar for 4 h. Water was added to the reaction mixture followed by extraction with EA for 3 times. The combined organic layers were dried $Na_2SO_4$, filtered and concentrated. The crude product was added to a silica gel column and was eluted with DCM/MeOH=50:1 to give the title compound (140 mg, 22.97%) as a white solid. LC-MS: 481.2 ($M+H^+$).

Step 3: (R)-3-(tert-butyl)-N-(8-(6-chloropyrazolo[1,5-a]pyrazin-4-yl)-2-cyclopropyl-2,3,4,5-tetrahydro-1H-benzo[c]azepin-5-yl)-1,2,4-oxadiazole-5-carboxamide

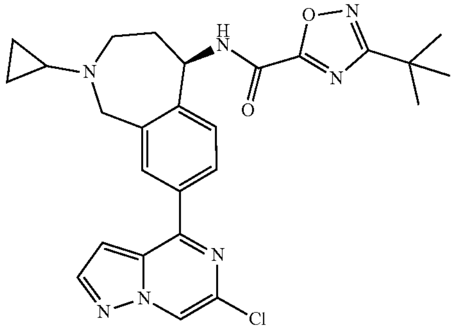 [SMILES: CC(C)(C)c1noc(C(=O)N[C@@H]2CCN(C3CC3)Cc3cc(-c4nc(Cl)cn5nccc45)ccc32)n1]

A mixture of above obtained intermediate (400 mg, 0.833 mmol, 1.0 eq), 4,6-dichloropyrazolo[1,5-a]pyrazine (188 mg, 1.00 mmol, 1.2 eq), $K_3PO_4$ (530 mg, 2.498 mmol, 3.0 eq) and $Pd(t-Bu_3P)_2$ (44 mg, 0.083 mmol, 0.1 eq) in THF (10 ml) and water (2 ml) was stirred at rt under Ar for 16 h. The solution was diluted with water, extracted with EA for 3 times. The combined organic layers were washed with brine, dried over anhydrous $Na_2SO_4$ and concentrated in vacuo. The residue was purified by flash chromatography eluted with DCM/MeOH=20:1 to give the title compound (150 mg, 35.6%) as a yellow solid. LC-MS: 506.5 ($M+H^+$).

Step 4: (R)-3-(tert-butyl)-N-(2-cyclopropyl-8-(6-(1-(1-((1-(4-(2,4-dioxotetrahydropyrimidin-1(2H)-yl)phenyl)piperidin-4-yl)methyl)piperidin-4-yl)-1H-pyrazol-4-yl)pyrazolo[1,5-a]pyrazin-4-yl)-2,3,4,5-tetrahydro-1H-benzo[c]azepin-5-yl)-1,2,4-oxadiazole-5-carboxamide

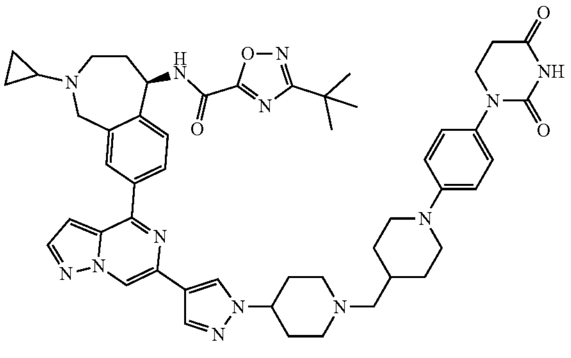 [SMILES: CC(C)(C)c1noc(C(=O)N[C@@H]2CCN(C3CC3)Cc3cc(-c4nc(-c5cnn(C6CCN(CC7CCN(c8ccc(N9CCC(=O)NC9=O)cc8)CC7)CC6)c5)cn5nccc45)ccc32)n1]

A mixture of 1-(4-(4-((4-(4-(4,4,5,5-tetramethyl-1,3,2-dioxaborolan-2-yl)-1H-pyrazol-1-yl)piperidin-1-yl)methyl)piperidin-1-yl)phenyl)dihydropyrimidine-2,4(1H,3H)-dione (83 mg, 0.148 mmol, 1.5 eq), above obtained intermediate (50 mg, 0.098 mmol, 1.0 eq), $K_3PO_4$ (63 mg, 0.296 mmol, 3.0 eq) and XPhos-Pd-G3 (16 mg, 0.02 mmol, 0.2 eq) in dioxane (4 ml) and water (1 ml) was stirred at 100° C. under Ar for 16 h. The solution was diluted with water, extracted with ethyl acetate for 3 times. The combined organic layers were washed with brine, dried over anhydrous $Na_2SO_4$ and concentrated in vacuo. The residue was purified by pre-HPLC to give the title compound (19 mg, 21.2%) as a white solid. LC-MS: 906.6 ($M+H^+$). $^1H$ NMR (400 MHz, DMSO-$d^6$) δ (ppm) 10.25 (s, 1H), 9.83 (d, J=8.0 Hz, 1H), 9.13 (s, 1H), 8.44 (s, 1H), 8.19 (d, J=2.8 Hz, 1H), 8.13 (s, 1H), 8.02-7.98 (m, 1H), 7.95 (d, J=2.0 Hz, 1H), 7.44 (d, J=8.0 Hz, 1H), 7.15-7.11 (m, 3H), 6.93 (d, J=9.2 Hz, 2H), 5.50-5.40 (m, 1H), 4.25-4.05 (m, 3H), 3.75-3.65 (m, 4H), 3.28-3.10 (m, 2H), 2.96 (d, J=11.2 Hz, 2H), 2.71-2.62 (m, 4H), 2.28-2.15 (m, 3H), 2.13-1.60 (m, 11H), 1.39 (s, 9H), 1.25-1.15 (m, 2H), 0.52-0.38 (m, 4H).

Example 22: (R)-3-(tert-butyl)-N-(8-(6-(1-(1-((1-(4-(2,4-dioxotetrahydropyrimidin-1(2H)-yl)phenyl)piperidin-4-yl)methyl)piperidin-4-yl)-1H-pyrazol-4-yl)pyrazolo[1,5-a]pyrazin-4-yl)-2-(2,2,2-trifluoroethyl)-2,3,4,5-tetrahydro-1H-benzo[c]azepin-5-yl)-1,2,4-oxadiazole-5-carboxamide (Compound No. 55)

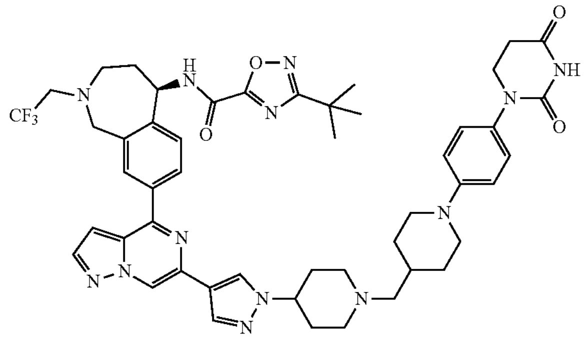 [SMILES: CC(C)(C)c1noc(C(=O)N[C@@H]2CCN(CC(F)(F)F)Cc3cc(-c4nc(-c5cnn(C6CCN(CC7CCN(c8ccc(N9CCC(=O)NC9=O)cc8)CC7)CC6)c5)cn5nccc45)ccc32)n1]

A mixture of 2,2,2-trifluoroethyl trifluoromethanesulfonate (77 mg, 0.333 mmol, 3.0 eq), $K_2CO_3$ (77 mg, 0.555 mmol, 5.0 eq) and (R)-3-(tert-butyl)-N-(8-(6-(1-(1-((1-(4-(2,4-dioxotetrahydropyrimidin-1(2H)-yl)phenyl)piperidin-4-yl)methyl)piperidin-4-yl)-1H-pyrazol-4-yl)pyrazolo[1,5-a]pyrazin-4-yl)-2,3,4,5-tetrahydro-1H-benzo[c]azepin-5-yl)-1,2,4-oxadiazole-5-carboxamide hydrochloride (100 mg, 0.111 mmol, 1.0 eq) in dry Acetonitrile was stirred at 80° C. under Ar for 16 h. Filtered and concentrated in vacuo. The residue was purified by pre-HPLC to give the title compound (18 mg, 17%) as a white solid. LC-MS: 948.3 ($M+H^+$).

Example 23: (R)-3-(tert-butyl)-N-(1-(1-(7-(6-(4-((1-(4-(2,4-dioxotetrahydropyrimidin-1(2H)-yl)phenyl)piperidin-4-yl)methyl)piperazin-1-yl)pyridin-3-yl)imidazo[1,2-c]pyrimidin-5-yl)piperidin-4-yl)ethyl)-1,2,4-oxadiazole-5-carboxamide (Compound No. 64)

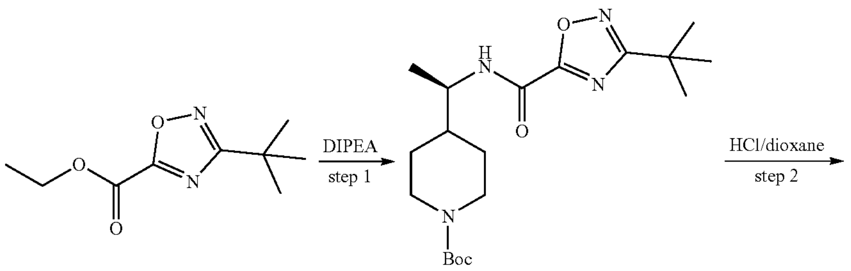

-continued
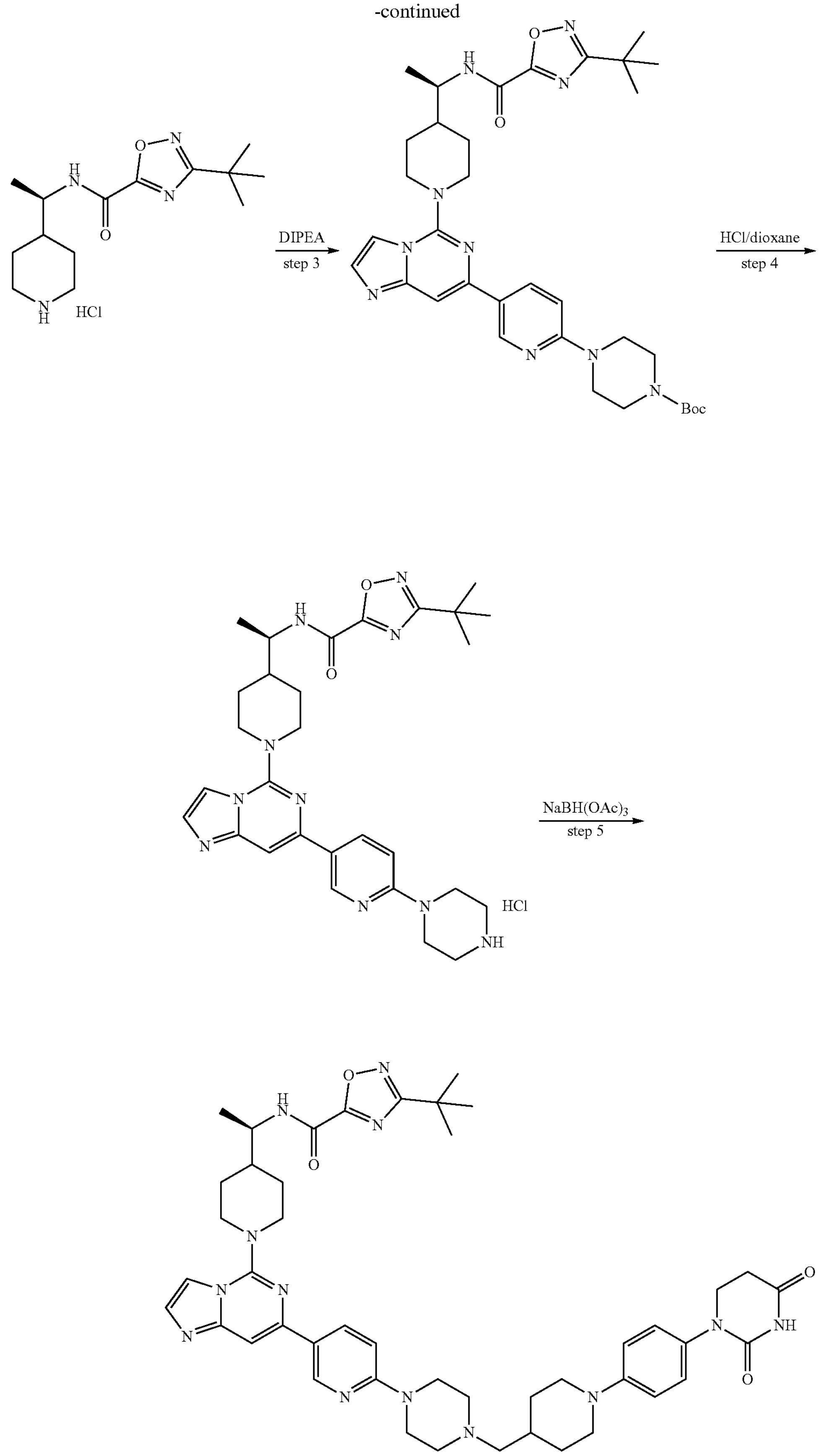

Step 1: tert-butyl (R)-4-(1-(3-(tert-butyl)-1,2,4-oxadiazole-5-carboxamido)ethyl)piperidine-1-carboxylate

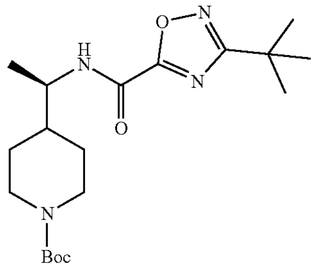 [SMILES: C[C@@H](NC(=O)c1nc(C(C)(C)C)no1)C1CCN(C(=O)OC(C)(C)C)CC1]

In a 100 ml round-bottomed flask, ethyl 3-(tert-butyl)-1,2,4-oxadiazole-5-carboxylate (500 mg, 2.52 mmol, 1.0 eq), tert-butyl (R)-4-(1-aminoethyl)piperidine-1-carboxylate (634 mg, 2.77 mmol, 1.1 eq) and DIPEA (978 mg, 7.57 mmol, 3.0 eq) were dissolved in DMSO (10 ml). The mixture was stirred at 80° C. for 16 h. Water was added to the reaction mixture followed by extraction with EA. The combined organic layers were dried $Na_2SO_4$, filtered and concentrated. The crude product was added to a silica gel column and was eluted with MeOH/DCM 0~3% to give the title compound (450 mg, 46.9%) as a colorless oil. MS (ESI) m/z 381.4 $[M+H]^+$.

Step 2: (R)-3-(tert-butyl)-N-(1-(piperidin-4-yl)ethyl)-1,2,4-oxadiazole-5-carboxamide hydrochloride

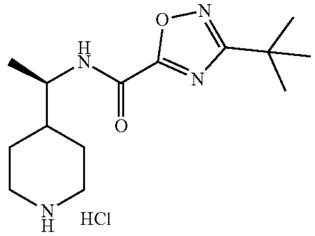 [SMILES: C[C@@H](NC(=O)c1nc(C(C)(C)C)no1)C1CCNCC1 ; Cl]

In a 50 ml round-bottomed flask, above obtained intermediate (450 mg, 1.183 mmol, 1.0 eq) was dissolved in DCM (5 ml) and 2M HCl in Dioxane (1 ml). The mixture was stirred for 2 h and concentrated to give the title compound (375 mg, 100%) as a yellow solid. MS (ESI) m/z 281.4 $[M-HCl+H]^+$.

Step 3: tert-butyl (R)-4-(5-(5-(4-(1-(3-(tert-butyl)-1,2,4-oxadiazole-5-carboxamido)ethyl)piperidin-1-yl)imidazo[1,2-c]pyrimidin-7-yl)pyridin-2-yl)piperazine-1-carboxylate

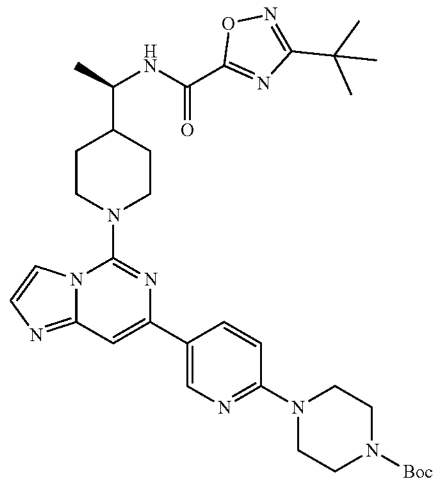 [SMILES: C[C@@H](NC(=O)c1nc(C(C)(C)C)no1)C1CCN(c2nc(-c3ccc(N4CCN(C(=O)OC(C)(C)C)CC4)nc3)cc3nccn23)CC1]

In a 50 ml round-bottomed flask, above obtained intermediate (80 mg, 0.193 mmol, 1.0 eq), (R)-3-(tert-butyl)-N-(1-(piperidin-4-yl)ethyl)-1,2,4-oxadiazole-5-carboxamide hydrochloride (73.3 mg, 0.231 mmol, 1.2 eq) and DIPEA (74.8 mg, 0.578 mmol, 3.0 eq) were dissolved in DMF (5 ml). The mixture was stirred at 60° C. for 6 h. Water was added to the reaction mixture followed by extraction with EA. The combined organic layers were dried $Na_2SO_4$, filtered and concentrated. The crude product was added to a silica gel column and was eluted with MeOH/DCM 0~3% to give the title compound (100 mg, 79%) as a yellow solid. MS (ESI) m/z 659.7 $[M+H]^+$.

Step 4: (R)-3-(tert-butyl)-N-(1-(1-(7-(6-(piperazin-1-yl)pyridin-3-yl)imidazo[1,2-c]pyrimidin-5-yl)piperidin-4-yl)ethyl)-1,2,4-oxadiazole-5-carboxamide hydrochloride

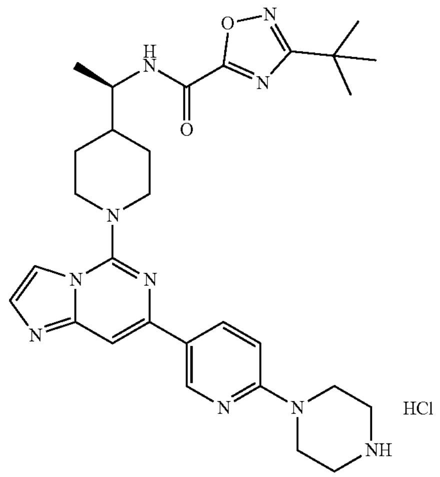 [SMILES: C[C@@H](NC(=O)c1nc(C(C)(C)C)no1)C1CCN(c2nc(-c3ccc(N4CCNCC4)nc3)cc3nccn23)CC1 ; Cl]

In a 50 ml round-bottomed flask, above obtained intermediate (100 mg, 0.152 mmol, 1.0 eq) was dissolved in DCM (5 ml) and 4M HCl/dioxane (2 ml). The reaction mixture was stirred for 3 h and concentrated to give the title compound (90 mg, 100%) as a yellow solid. MS (ESI) m/z 595.7 $[M-HCl+H]^+$.

Step 5: (R)-3-(tert-butyl)-N-(1-(1-(7-(6-(4-((1-(4-(2,4-dioxotetrahydropyrimidin-1(2H)-yl)phenyl)piperidin-4-yl)methyl)piperazin-1-yl)pyridin-3-yl)imidazo[1,2-c]pyrimidin-5-yl)piperidin-4-yl)ethyl)-1,2,4-oxadiazole-5-carboxamide

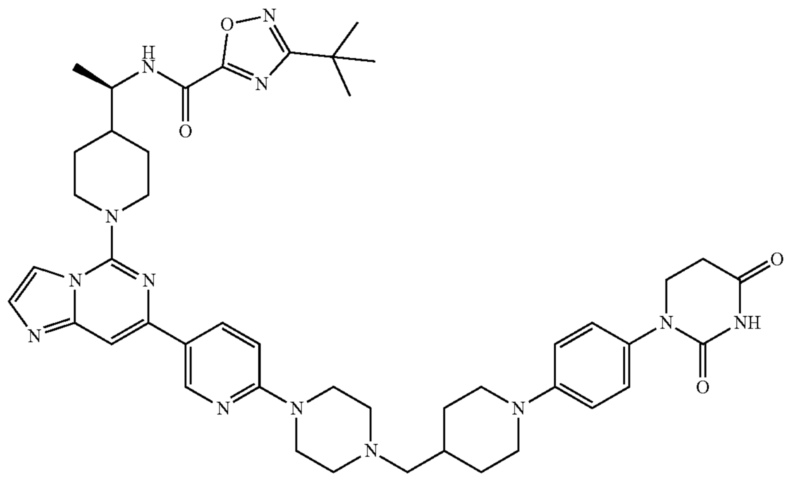 [SMILES: C[C@@H](NC(=O)c1nc(C(C)(C)C)no1)C1CCN(c2nc(-c3ccc(N4CCN(CC5CCN(c6ccc(N7CCC(=O)NC7=O)cc6)CC5)CC4)nc3)cc3nccn23)CC1]

In a 50 ml round-bottomed flask, above obtained intermediate (90 mg, 0.151 mmol, 1.0 eq), triethylamine (45.9 mg, 0.454 mmol, 3.0 eq), 1-(4-(2,4-dioxotetrahydropyrimidin-1(2H)-yl)phenyl)piperidine-4-carbaldehyde (54.7 mg, 0.181 mmol, 1.2 eq) and NaBH(OAc) 3 (49 mg, 0.227 mmol, 1.5 eq) were dissolved in DCM (10 ml). The mixture was stirred for 16 h. Water was added to the reaction mixture followed by extraction with DCM. The combined organic layers were dried $Na_2SO_4$, filtered and concentrated. The crude product was purified by prep-HPLC to give the title compound (36.9 mg, 28.9%) as a yellow solid. MS (ESI) m/z 844.8 $[M+H]^+$. $^1H$ NMR (400 MHz, DMSO-$d^6$) δ (ppm) 10.28 (s, 1H), 9.28 (d, J=8.8 Hz, 1H), 8.94 (d, J=2.6 Hz, 1H), 8.26 (dd, J=8.9, 2.5 Hz, 1H), 7.72 (s, 1H), 7.66 (s, 1H), 7.59 (d, J=1.4 Hz, 1H), 7.16 (d, J=8.8 Hz, 2H), 6.94 (dd, J=11.7, 8.9 Hz, 3H), 4.06-3.89 (m, 3H), 3.74-3.67 (m, 2H), 3.63-3.57 (m, 4H), 3.45-3.40 (m, 2H), 3.01-2.91 (m, 2H), 2.76-2.62 (m, 4H), 2.50-2.44 (m, 4H), 2.24 (d, J=7.0 Hz, 2H), 1.95-1.70 (m, 6H), 1.57-1.47 (m, 2H), 1.39 (s, 9H), 1.32-1.26 (m, 2H), 1.25 (d, J=6.7 Hz, 3H).

Following the synthesis of EXAMPLE 23, the following compounds were synthesized and obtained in a similar manner.

| Compd No. | Structure Observed MS [M + 1]+ | $^1$H NMR (400 MHz, DMSO-$d^6$) δ (ppm) |
|---|---|---|
| 65 | 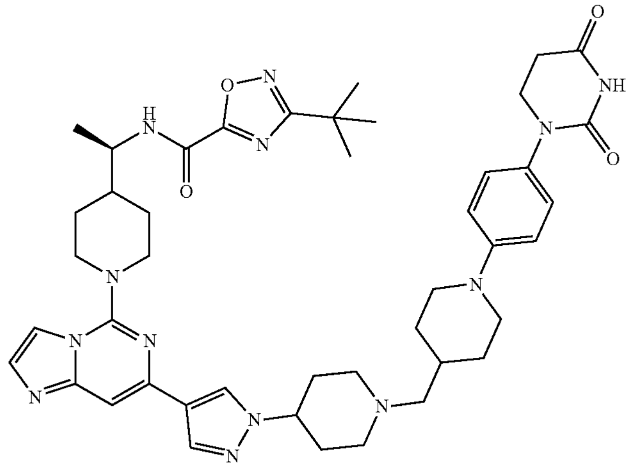 832.7 | 10.27 (s, 1H), 9.27 (d, J = 8.8 Hz, 1H), 8.35 (s, 1H), 8.06 (s, 1H), 7.68 (d, J = 1.3 Hz, 1H), 7.55 (d, J = 1.4 Hz, 1H), 7.44 (s, 1H), 7.19-7.11 (m, 2H), 6.99-6.92 (m, 2H), 4.27-4.09 (m, 1H), 4.01-3.89 (m, 3H), 3.76-3.66 (m, 4H), 3.04-2.86 (m, 4H), 2.73-2.63 (m, 3H), 2.24 (d, J = 7.0 Hz, 2H), 2.15-1.97 (m, 6H), 1.90-1.77 (m, 5H), 1.76-1.62 (m, 1H), 1.57-1.45 (m, 2H), 1.39 (s, 9H), 1.30-1.26 (m, 2H), 1.25 (d, J = 6.6 Hz, 3H). |
| 67 | 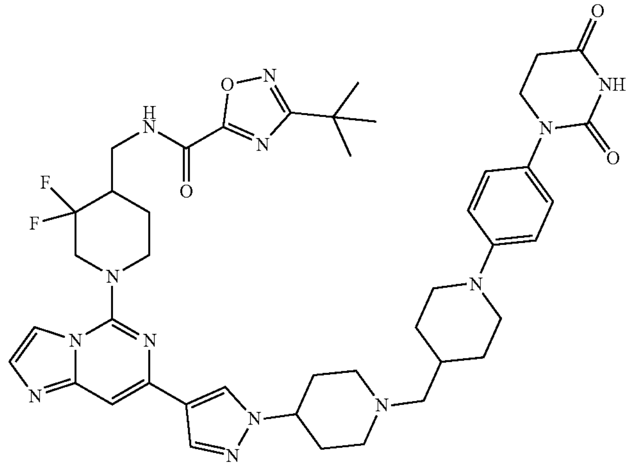 854.7 | 10.27 (s, 1H), 9.52 (t, J = 6.0 Hz, 1H), 8.41 (s, 1H), 8.09 (s, 1H), 7.73 (d, J = 1.4 Hz, 1H), 7.60 (d, J = 1.4 Hz, 1H), 7.52 (s, 1H), 7.16 (d, J = 8.9 Hz, 2H), 6.96 (d, J = 8.9 Hz, 2H), 4.26-4.18 (m, 1H), 4.12-4.06 (m, 1H), 4.02 (d, J = 12.9 Hz, 1H), 3.76-3.68 (m, 5H), 3.66-3.50 (m, 1H), 3.45-3.37 (m, 1H), 3.13-3.02 (m, 1H), 2.99 (d, J = 10.2 Hz, 2H), 2.74-2.64 (m, 4H), 2.24 (d, J = 7.1 Hz, 2H), 2.14-2.01 (m, 7H), 2.00-1.89 (m, 1H), 1.84 (d, J = 12.9 Hz, 2H), 1.75-1.66 (m, 1H), 1.40 (s, 9H), 1.30-1.18 (m, 2H). |
| 181 | 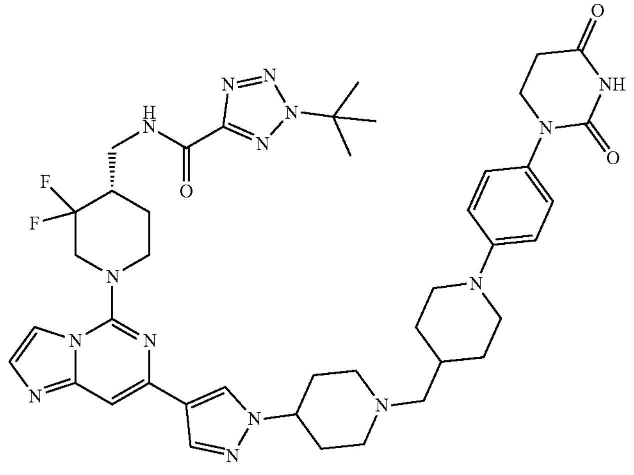 Isomer 1: 854.7 | 10.28 (s, 1H), 9.19 (t, J = 6.1 Hz, 1H), 8.41 (s, 1H), 8.09 (s, 1H), 7.73 (d, J = 1.2 Hz, 1H), 7.60 (d, J = 1.4 Hz, 1H), 7.53 (d, J = 0.7 Hz, 1H), 7.20-7.12 (m, 2H), 6.99-6.92 (m, 2H), 4.30-4.07 (m, 2H), 4.02 (d, J = 13.0 Hz, 1H), 3.77-3.67 (m, 4H), 3.60 (dd, J = 30.0, 13.5 Hz, 1H), 3.51-3.39 (m, 1H), 3.34-3.30 (m, 1H), 3.07 (t, J = 12.0 Hz, 1H), 2.99 (d, J = 9.9 Hz, 2H), 2.75-2.64 (m, 4H), 2.24 (d, J = 7.0 Hz, 2H), 2.15-2.00 (m, 7H), 1.94 (d, J = 11.4 Hz, 1H), 1.88-1.79 (m, 2H), 1.76 (s, 9H), 1.74-1.67 (m, 1H), 1.31-1.18 (m, 3H). |

-continued

| Compd No. | Structure Observed MS [M + 1]+ | $^1$H NMR (400 MHz, DMSO-d$^6$) δ (ppm) |
|---|---|---|
| 182 | 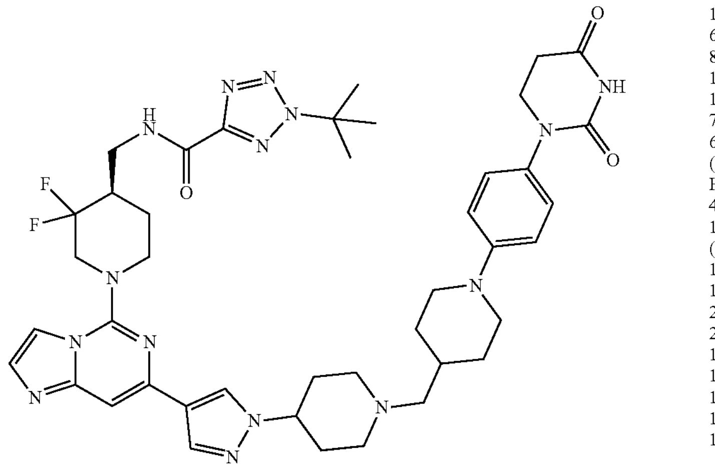 Isomer 2: 854.7 | 10.28 (s, 1H), 9.19 (t, J = 6.0 Hz, 1H), 8.41 (s, 1H), 8.09 (s, 1H), 7.73 (d, J = 1.4 Hz, 1H), 7.60 (d, J = 1.4 Hz, 1H), 7.53 (s, 1H), 7.20-7.12 (m, 2H), 6.99-6.92 (m, 2H), 4.29-4.07 (m, 2H), 4.02 (d, J = 12.9 Hz, 1H), 3.79-3.68 (m, 4H), 3.60 (dd, J = 29.9, 13.6 Hz, 1H), 3.51-3.39 (m, 1H), 3.34-3.30 (m, 1H), 3.08 (t, J = 12.0 Hz, 1H), 2.99 (d, J = 9.8 Hz, 2H), 2.75-2.64 (m, 4H), 2.28-2.19 (m, 2H), 2.15-1.98 (m, 7H), 1.94 (d, J = 10.9 Hz, 1H), 1.84 (d, J = 12.7 Hz, 2H), 1.77 (s, 9H), 1.74-1.67 (m, 1H), 1.31-1.18 (m, 3H). |
| 198 | 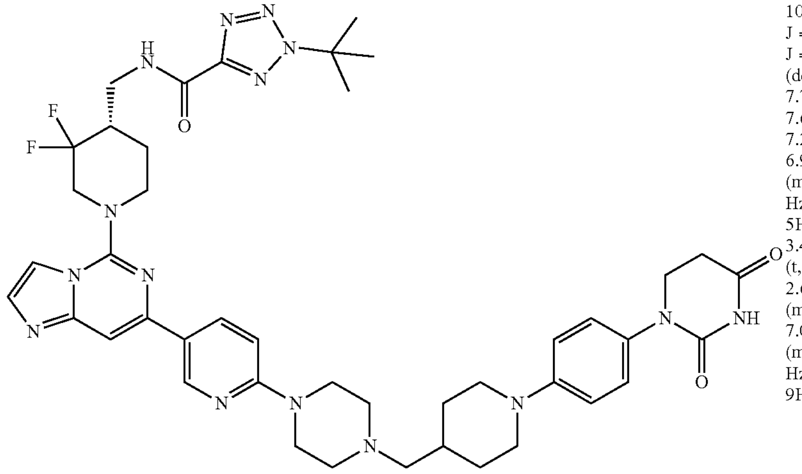 Isomer 1: 866.7 | 10.27 (s, 1H), 9.19 (t, J = 6.0 Hz, 1H), 8.96 (d, J = 2.5 Hz, 1H), 8.28 (dd, J = 9.0, 2.5 Hz, 1H), 7.76 (d, J = 13.0 Hz, 2H), 7.64 (d, J = 1.3 Hz, 1H), 7.20-7.13 (m, 2H), 6.99-6.91 (m, 3H), 4.20-4.11 (m, 1H), 4.07 (d, J = 13.0 Hz, 1H), 3.75-3.67 (m, 5H), 3.65-3.55 (m, 4H), 3.47-3.41 (m, 3H), 3.14 (t, J = 12.1 Hz, 1H), 2.75-2.65 (m, 4H), 2.52-2.45 (m, 4H), 2.25 (d, J = 7.0 Hz, 2H), 2.10-1.90 (m, 2H), 1.85 (d, J = 12.7 Hz, 2H), 1.77 (s, 9H), 1.35-1.18 (m, 3H). |
| 199 | 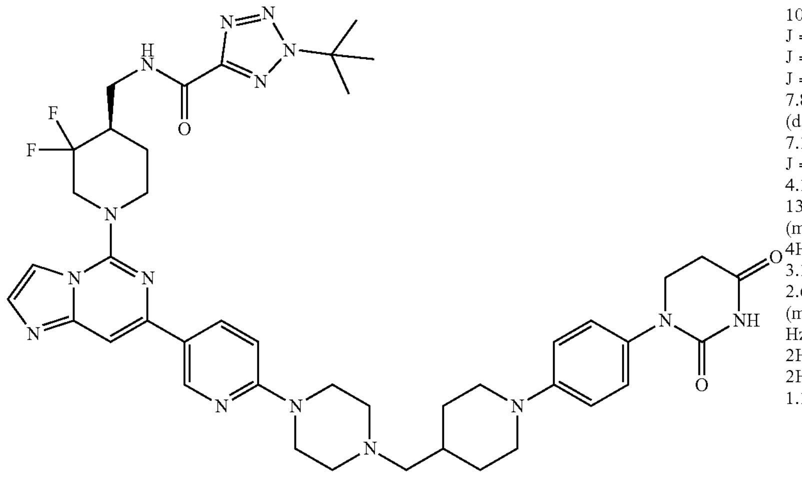 Isomer 2: 866.7 | 10.27 (s, 1H), 9.18 (t, J = 6.0 Hz, 1H), 8.96 (d, J = 2.5 Hz, 1H), 8.28 (dd, J = 9.0, 2.5 Hz, 1H), 7.80-7.72 (m, 2H), 7.64 (d, J = 1.4 Hz, 1H), 7.19-7.12 (m, 2H), 6.95 (dd, J = 9.1, 4.9 Hz, 3H), 4.20-4.11 (m, 1H), 4.07 (d, J = 13.0 Hz, 1H), 3.75-3.67 (m, 5H), 3.65-3.55 (m, 4H), 3.47-3.41 (m, 3H), 3.19-3.08 (m, 1H), 2.74-2.65 (m, 4H), 2.51-2.46 (m, 4H), 2.25 (d, J = 7.1 Hz, 2H), 2.13-1.89 (m, 2H), 1.85 (d, J = 12.4 Hz, 2H), 1.76 (s, 9H), 1.33-1.19 (m, 3H). |

-continued
| Compd No. | Structure Observed MS $[M + 1]^+$ | $^1$H NMR (400 MHz, DMSO-$d^6$) δ (ppm) |
|---|---|---|
| 200 | 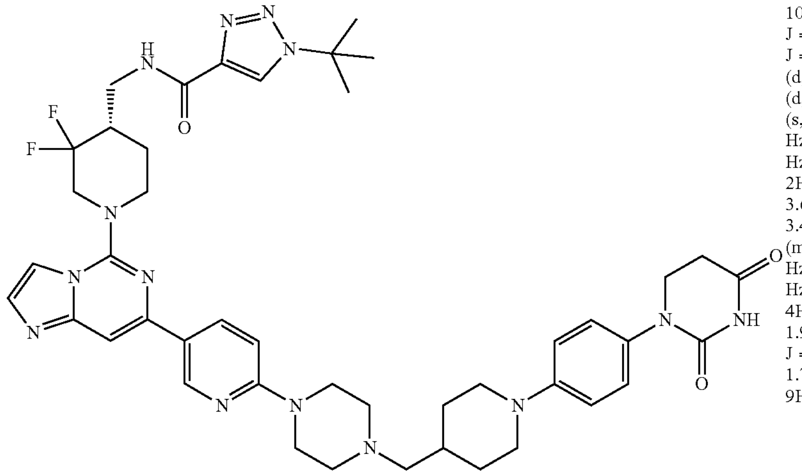 Isomer 1: 865.7 | 10.27 (s, 1H), 8.96 (d, J = 2.3 Hz, 1H), 8.70 (d, J = 12.1 Hz, 2H), 8.29 (d, J = 8.7 Hz, 1H), 7.76 (d, J = 11.2 Hz, 2H), 7.65 (s, 1H), 7.17 (d, J = 8.5 Hz, 2H), 6.96 (d, J = 8.6 Hz, 3H), 4.21-4.00 (m, 2H), 3.76-3.69 (m, 5H), 3.66-3.55 (m, 4H), 3.47-3.40 (m, 1H), 3.33-3.28 (m, 1H), 3.13 (t, J = 12.2 Hz, 1H), 2.72 (d, J = 7.3 Hz, 4H), 2.51-2.45 (m, 4H), 2.25 (s, 2H), 2.10-1.92 (m, 2H), 1.86 (d, J = 13.0 Hz, 2H), 1.79-1.72 (m, 1H), 1.67 (s, 9H), 1.34-1.17 (m, 3H). |
| 201 | 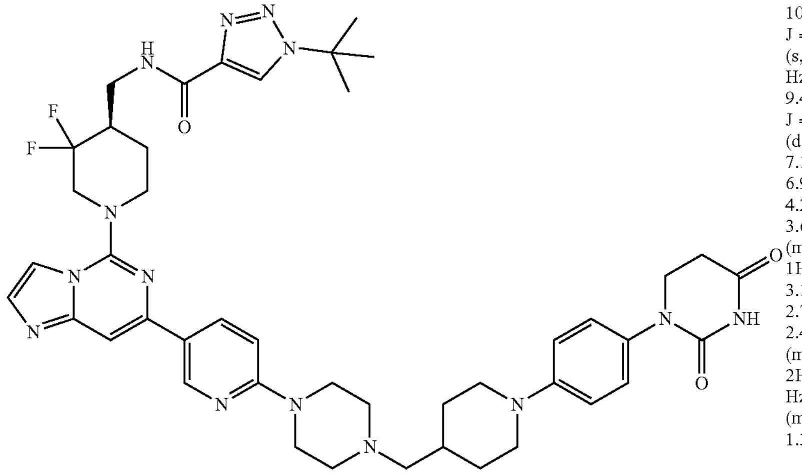 Isomer 2: 865.7 | 10.27 (s, 1H), 8.96 (d, J = 2.5 Hz, 1H), 8.71 (s, 1H), 8.68 (t, J = 6.1 Hz, 1H), 8.28 (d, J = 9.4 Hz, 1H), 7.75 (d, J = 10.8 Hz, 2H), 7.64 (d, J = 1.4 Hz, 1H), 7.16 (d, J = 8.9 Hz, 2H), 6.95 (d, J = 8.9 Hz, 3H), 4.23-3.90 (m, 2H), 3.75-3.66 (m, 4H), 3.65-3.55 (m, 4H), 3.46-3.37 (m, 1H), 3.34-3.29 (m, 1H), 3.13 (t, J = 12.2 Hz, 1H), 2.74-2.64 (m, 4H), 2.51-2.44 (m, 4H), 2.27-2.21 (m, 2H), 2.07-1.91 (m, 2H), 1.85 (d, J = 12.9 Hz, 2H), 1.79-1.71 (m, 1H), 1.66 (s, 9H), 1.32-1.16 (m, 3H). |
| 202 | 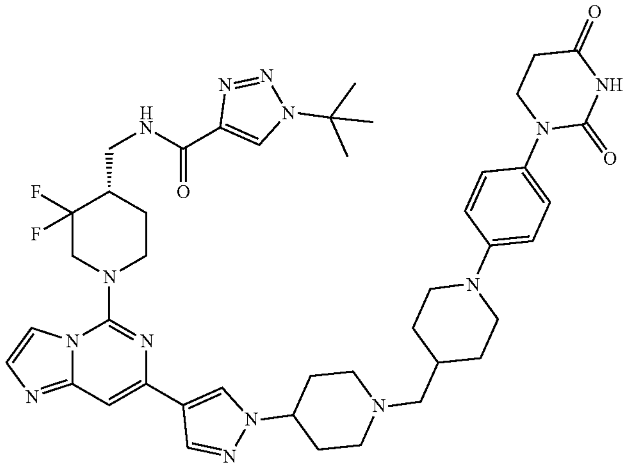 [SMILES: CC(C)(C)n1cc(C(=O)NC[C@@H]2CCN(c3nc(-c4cnn(C5CCN(CC6CCN(c7ccc(N8CCC(=O)NC8=O)cc7)CC6)CC5)c4)cc4nccn34)CC2(F)F)nn1] Isomer 1: 853.7 | |

-continued
| Compd No. | Structure Observed MS [M + 1]+ | $^1$H NMR (400 MHz, DMSO-d$^6$) δ (ppm) |
|---|---|---|
| 203 | 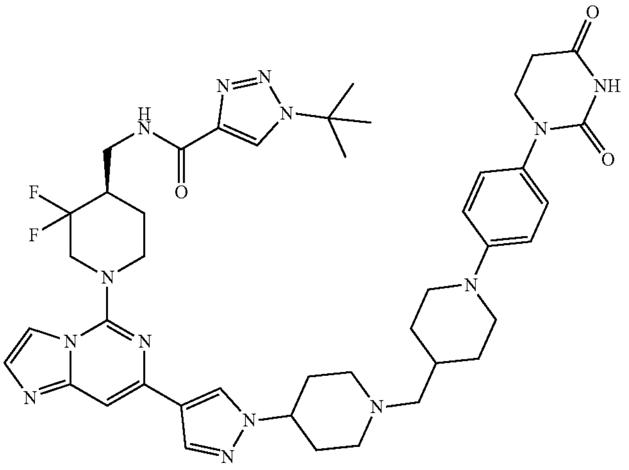 Isomer 2: 853.7 | |
| 204 | 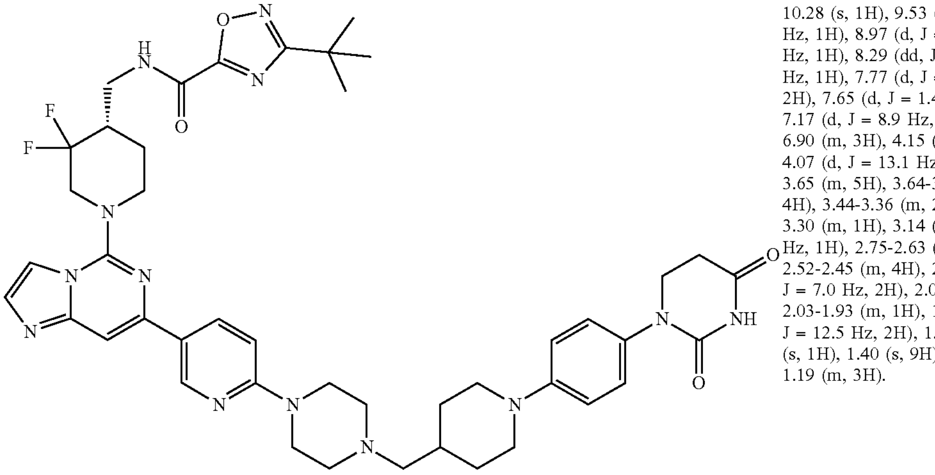 Isomer 1: 866.7 | 10.28 (s, 1H), 9.53 (t, J = 6.1 Hz, 1H), 8.97 (d, J = 2.4 Hz, 1H), 8.29 (dd, J = 9.0, 2.5 Hz, 1H), 7.77 (d, J = 12.7 Hz, 2H), 7.65 (d, J = 1.4 Hz, 1H), 7.17 (d, J = 8.9 Hz, 2H), 6.99-6.90 (m, 3H), 4.15 (s, 1H), 4.07 (d, J = 13.1 Hz, 1H), 3.77-3.65 (m, 5H), 3.64-3.57 (m, 4H), 3.44-3.36 (m, 2H), 3.35-3.30 (m, 1H), 3.14 (t, J = 12.2 Hz, 1H), 2.75-2.63 (m, 3H), 2.52-2.45 (m, 4H), 2.26 (d, J = 7.0 Hz, 2H), 2.09 (s, 1H), 2.03-1.93 (m, 1H), 1.86 (d, J = 12.5 Hz, 2H), 1.76 (s, 1H), 1.40 (s, 9H), 1.30-1.19 (m, 3H). |

-continued
| Compd No. | Structure Observed MS $[M + 1]^+$ | $^1H$ NMR (400 MHz, DMSO-$d^6$) δ (ppm) |
|---|---|---|
| 205 | 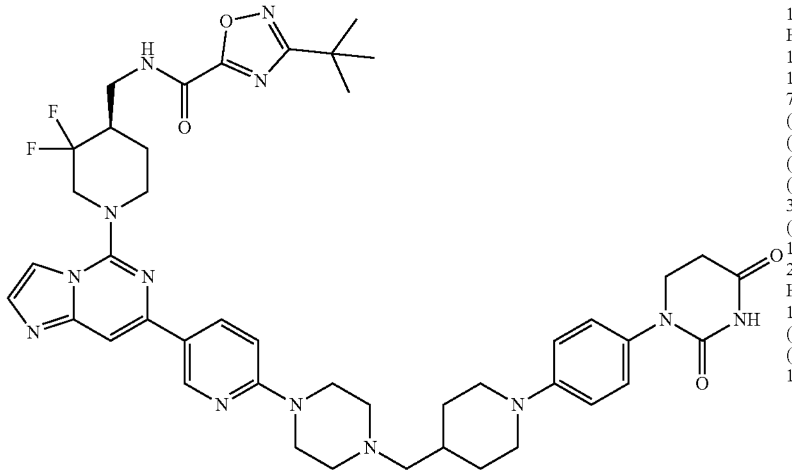 Isomer 2: 866.7 | 10.27 (s, 1H), 9.52 (t, J = 6.0 Hz, 1H), 8.96 (d, J = 2.5 Hz, 1H), 8.29 (dd, J = 9.0, 2.5 Hz, 1H), 7.76 (d, J = 13.2 Hz, 2H), 7.65 (d, J = 1.4 Hz, 1H), 7.16 (d, J = 8.9 Hz, 2H), 7.04-6.83 (m, 3H), 4.15 (s, 1H), 4.07 (d, J = 13.0 Hz, 1H), 3.76-3.65 (m, 5H), 3.64-3.57 (m, 4H), 3.44-3.36 (m, 2H), 3.35-3.30 (m, 1H), 3.14 (t, J = 12.2 Hz, 1H), 2.75-2.63 (m, 3H), 2.52-2.45 (m, 4H), 2.25 (d, J = 7.0 Hz, 2H), 2.14-2.03 (m, 1H), 2.00-1.93 (m, 1H), 1.85 (d, J = 12.5 Hz, 2H), 1.80-1.69 (m, 1H), 1.40 (s, 9H), 1.30-1.19 (m, 3H). |
| 218 | 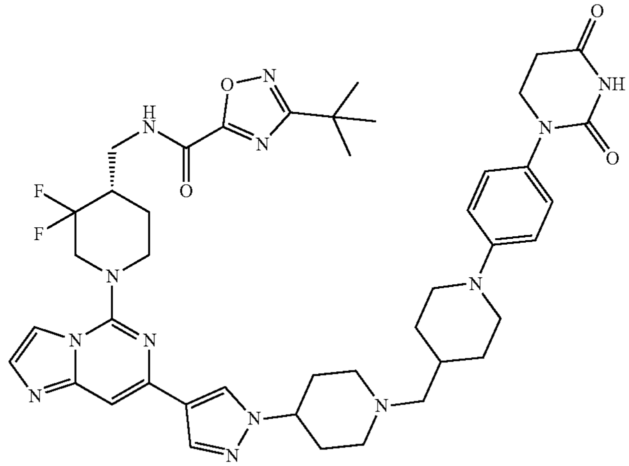 Isomer 1: 854.7 | 10.27 (s, 1H), 9.52 (t, J = 6.2 Hz, 1H), 8.41 (s, 1H), 8.09 (s, 1H), 7.74 (s, 1H), 7.61 (s, 1H), 7.53 (s, 1H), 7.16 (d, J = 8.5 Hz, 2H), 6.96 (d, J = 8.5 Hz, 2H), 4.23 (s, 1H), 4.15-3.96 (m, 2H), 3.76-3.68 (m, 5H), 3.60 (dd, J = 30.0, 13.6 Hz, 1H), 3.38-3.37 (m, 1H), 3.34-3.28 (m, 1H), 3.14-2.95 (m, 3H), 2.75-2.64 (m, 4H), 2.30-2.20 (m, 2H), 2.18-1.99 (m, 6H), 1.93 (d, J = 12.3 Hz, 1H), 1.84 (d, J = 12.8 Hz, 2H), 1.77-1.66 (m, 1H), 1.40 (s, 9H), 1.31-1.18 (m, 3H). |

-continued

| Compd No. | Structure Observed MS $[M + 1]^+$ | $^1H$ NMR (400 MHz, DMSO-$d^6$) δ (ppm) |
|---|---|---|
| 219 | 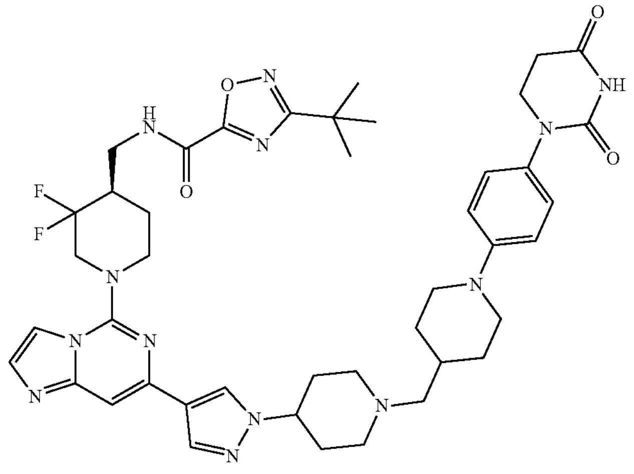 Isomer 2: 854.7 | 10.27 (s, 1H), 9.52 (t, J = 6.0 Hz, 1H), 8.41 (s, 1H), 8.09 (s, 1H), 7.74 (d, J = 1.4 Hz, 1H), 7.61 (d, J = 1.4 Hz, 1H), 7.53 (s, 1H), 7.16 (d, J = 8.5 Hz, 2H), 6.96 (d, J = 9.0 Hz, 2H), 4.29-4.18 (m, 1H), 4.15-4.07 (m, 1H), 4.03 (d, J = 13.1 Hz, 1H), 3.76-3.69 (m, 5H), 3.61 (dd, J = 30.1, 13.5 Hz, 1H), 3.45-3.38 (m, 1H), 3.34-3.28 (m, 1H), 3.08 (t, J = 12.0 Hz, 1H), 3.02-2.95 (m, 2H), 2.75-2.63 (m, 4H), 2.31-2.22 (m, 2H), 2.18-1.99 (m, 6H), 1.93 (d, J = 12.3 Hz, 1H), 1.84 (d, J = 12.8 Hz, 2H), 1.77-1.66 (m, 1H), 1.40 (s, 9H), 1.31-1.17 (m, 3H). |

Example 24: (R)-2-(tert-butyl)-N-(1-(4-(6-(1-(1-(4-(2,4-dioxotetrahydropyrimidin-1(2H)-yl)phenethyl)piperidin-4-yl)-1H-pyrazol-4-yl)pyrazolo[1,5-a]pyrazin-4-yl)-2-methylphenyl)ethyl)-2H-tetrazole-5-carboxamide (Compound No. 81)

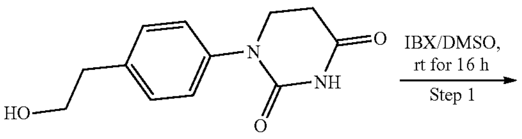

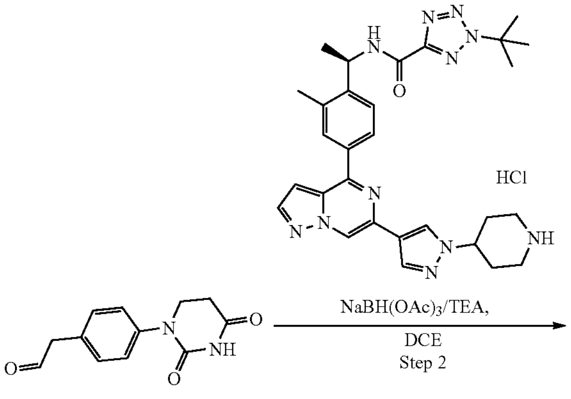

-continued

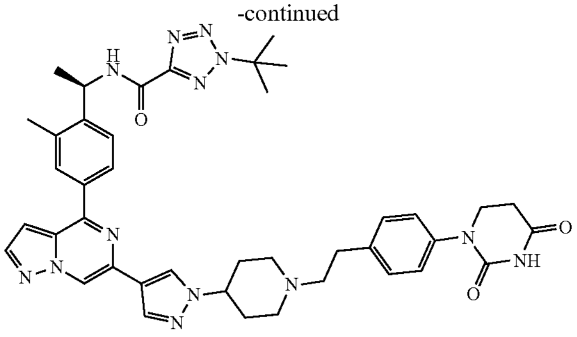

Step 1: 2-(4-(2,4-dioxotetrahydropyrimidin-1(2H)-yl)phenyl) acetaldehyde

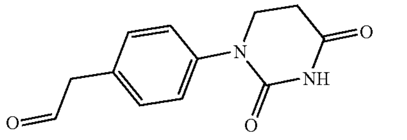 [SMILES: O=CCc1ccc(N2CCC(=O)NC2=O)cc1]

A mixture of 1-(4-(2-hydroxyethyl)phenyl)dihydropyrimidine-2,4(1H,3H)-dione (600 mg, 2.56 mmol, 1.0 eq) and IBX (2.15 g, 7.68 mmol, 3.0 eq) in dry DMSO (10 ml) was stirred at rt for 16 h. Water was added and extracted with EA for 3 times. The combined EA layers were washed with brine, dried over anhydrous $Na_2SO_4$ and concentrated in vacuo. The residue was purified by flash chromatography eluted with DCM/MeOH=50:1 to give the title compound (120 mg, 20.1%) as colorless oil. LC-MS: 233.4 $(M+H^+)$.

Step 2: (R)-2-(tert-butyl)-N-(1-(4-(6-(1-(1-(4-(2,4-dioxotetrahydropyrimidin-1(2H)-yl)phenethyl)piperidin-4-yl)-1H-pyrazol-4-yl)pyrazolo[1,5-a]pyrazin-4-yl)-2-methylphenyl)ethyl)-2H-tetrazole-5-carboxamide

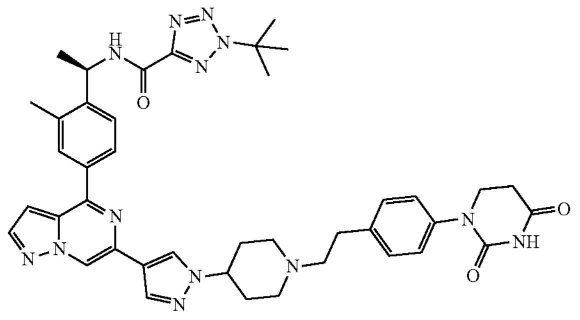 [SMILES: Cc1cc(-c2nc(-c3cnn(C4CCN(CCc5ccc(N6CCC(=O)NC6=O)cc5)CC4)c3)cn3nccc23)ccc1[C@@H](C)NC(=O)c1nnn(C(C)(C)C)n1]

To a solution of above obtained intermediate (80 mg, 0.34 mmol, 2.0 eq), (R)-2-(tert-butyl)-N-(1-(2-methyl-4-(6-(1-(piperidin-4-yl)-1H-pyrazol-4-yl)pyrazolo[1,5-a]pyrazin-4-yl)phenyl)ethyl)-2H-tetrazole-5-carboxamide hydrochloride (100 mg, 0.17 mmol, 1.0 eq) and TEA (69 mg, 0.678 mmol, 4.0 eq) in dry DCE (5 ml) was added NaBH(OAc) 3 (72 mg, 0.34 mmol, 2.0 eq) in portions. The reaction was stirred at rt for 2 h. The solution was quenched with water and extracted with DCM for 3 times. The organic layers were washed with brine, dried over anhydrous $Na_2SO_4$ and concentrated in vacuo. The residue was purified by pre-HPLC to give the title compound (36.6 mg, 28.1%) as a white solid. LC-MS: 770.4 ($M+H^+$). $^1H$ NMR (400 MHz, DMSO-$d^6$) δ (ppm) 10.34 (s, 1H), 9.57 (d, J=8.8 Hz, 1H), 9.11 (s, 1H), 8.44 (s, 1H), 8.17 (d, J=2.4 Hz, 1H), 8.13 (s, 1H), 7.95 (d, J=8.0 Hz, 1H), 7.92 (s, 1H), 7.69 (d, J=8.0 Hz, 1H), 7.30-7.20 (m, 4H), 7.16 (d, J=2.0 Hz, 1H), 5.45-5.40 (m, 1H), 4.25-4.15 (m, 1H), 3.80-3.72 (m, 2H), 3.10-3.02 (m, 2H), 2.80-2.65 (m, 4H), 2.62-2.56 (m, 2H), 2.55 (s, 3H), 2.20-1.95 (m, 6H), 1.73 (s, 9H), 1.55 (d, J=7.2 Hz, 3H).

Example 25: 2-(tert-butyl)-N-((1R)-1-(4-(6-(1-(1-((1-(2-(2,6-dioxopiperidin-3-yl)-6-fluoro-1,3-dioxoisoindolin-5-yl)piperidin-4-yl)methyl)piperidin-4-yl)-1H-pyrazol-4-yl)pyrazolo[1,5-a]pyrazin-4-yl)-2-methylphenyl)ethyl)-2H-tetrazole-5-carboxamide (Compound No. 85)

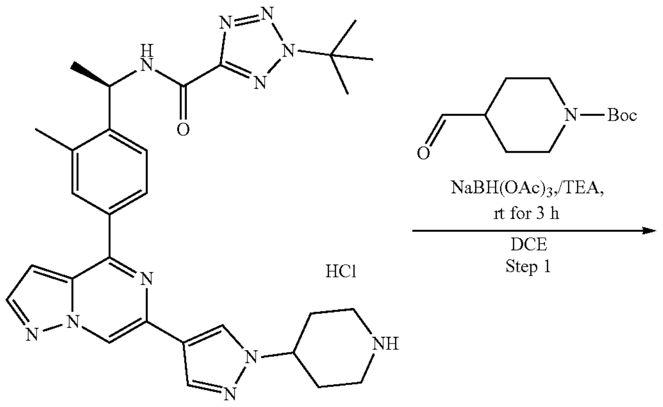

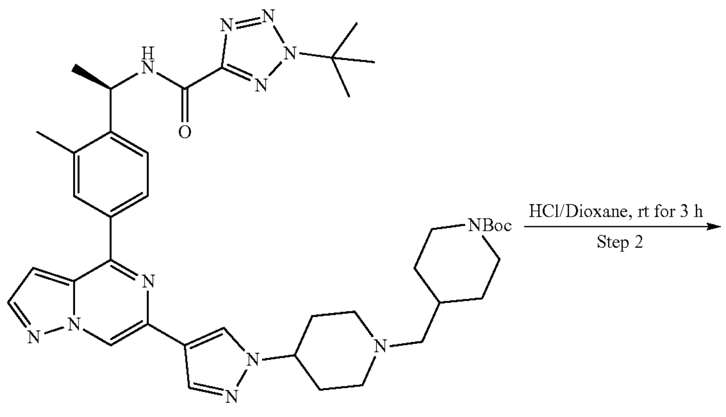

-continued

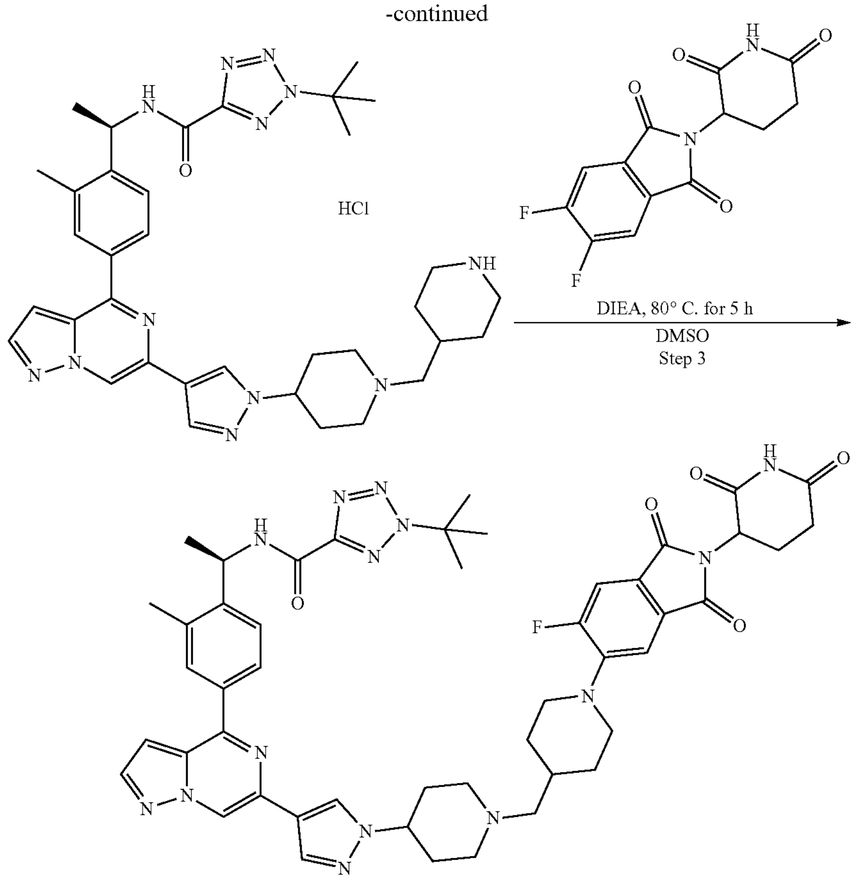

Step 1: tert-butyl (R)-4-((4-(4-(4-(4-(1-(2-(tert-butyl)-2H-tetrazole-5-carboxamido)ethyl)-3-methylphenyl)pyrazolo[1,5-a]pyrazin-6-yl)-1H-pyrazol-1-yl)piperidin-1-yl)methyl)piperidine-1-carboxylate

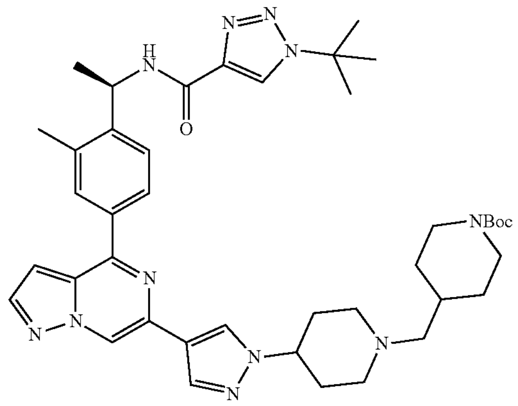 [SMILES: Cc1cc(-c2nc(-c3cnn(C4CCN(CC5CCN(C(=O)OC(C)(C)C)CC5)CC4)c3)cn3nccc23)ccc1[C@@H](C)NC(=O)c1cn(C(C)(C)C)nn1]

To a solution of (R)-2-(tert-butyl)-N-(1-(2-methyl-4-(6-(1-(piperidin-4-yl)-1H-pyrazol-4-yl)pyrazolo[1,5-a]pyrazin-4-yl)phenyl)ethyl)-2H-tetrazole-5-carboxamide hydrochloride (120 mg, 0.203 mmol, 1.0 eq), tert-butyl 4-formylpiperidine-1-carboxylate (65 mg, 0.305 mmol, 1.5 eq) and TEA (105 mg, 1.02 mmol, 5.0 eq) in dry DCE (3 ml) was added NaBH(OAc) 3 (86 mg, 0.407 mmol, 2.0 eq) in portions. The reaction was stirred at rt for 2 h. The solution was quenched with water and extracted with DCM for 3 times. The organic layers were washed with brine, dried over anhydrous $Na_2SO_4$ and concentrated in vacuo. The residue was purified by pre-HPLC to give the title compound (120 mg, 79%) as a white solid. LC-MS: 751.4 (M+H+).

Step 2: (R)-2-(tert-butyl)-N-(1-(2-methyl-4-(6-(1-(1-(piperidin-4-ylmethyl)piperidin-4-yl)-1H-pyrazol-4-yl)pyrazolo[1,5-a]pyrazin-4-yl)phenyl)ethyl)-2H-tetrazole-5-carboxamide hydrochloride

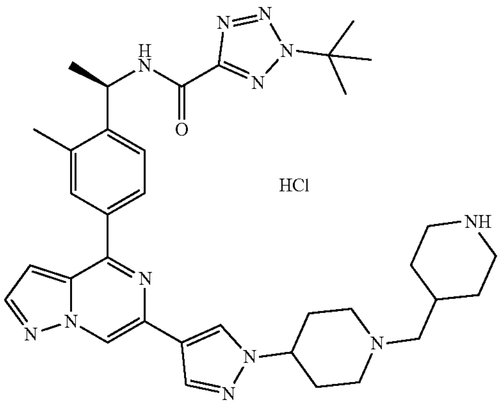 [SMILES: Cc1cc(-c2nc(-c3cnn(C4CCN(CC5CCNCC5)CC4)c3)cn3nccc23)ccc1[C@@H](C)NC(=O)c1nnn(C(C)(C)C)n1 ; Cl]

A mixture of above obtained intermediate (120 mg, 0.16 mmol, 1.0 eq) in DCM (4 ml) and 4M HCl/Dioxane (1 ml)

was stirred at rt for 4 h. After concentration in vacuo, the residue was used in next step without further purification (100 mg, 91%) as a yellow solid. LC-MS: 651.5 ($M+H^+$).

Step 3: 2-(tert-butyl)-N-((1R)-1-(4-(6-(1-(1-((1-(2-(2,6-dioxopiperidin-3-yl)-6-fluoro-1,3-dioxoisoindolin-5-yl)piperidin-4-yl)methyl)piperidin-4-yl)-1H-pyrazol-4-yl)pyrazolo[1,5-a]pyrazin-4-yl)-2-methylphenyl)ethyl)-2H-tetrazole-5-carboxamide

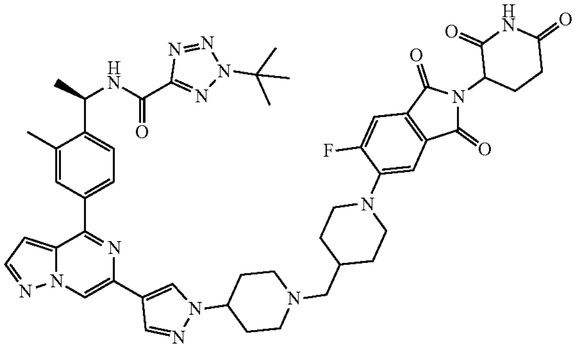 [SMILES: Cc1cc(-c2nc(-c3cnn(C4CCN(CC5CCN(c6cc7c(cc6F)C(=O)N(C6CCC(=O)NC6=O)C7=O)CC5)CC4)c3)cn3nccc23)ccc1[C@@H](C)NC(=O)c1nnn(C(C)(C)C)n1]

A mixture of 2-(2,6-dioxopiperidin-3-yl)-5,6-difluoroisoindoline-1,3-dione (33 mg, 0.113 mmol, 1.3 eq), DIEA (34 mg, 0.262 mmol, 3.0 eq) and above obtained intermediate (60 mg, 0.087 mmol, 1.0 eq) in DMSO (4 ml) was stirred at 80° C. under Ar for 6 h. The mixture was purified by pre-HPLC to give the title compound (30 mg, 37.1%) as a yellow solid. LC-MS: 925.3 ($M+H^+$).

Example 26: (R)-2-(tert-butyl)-N-(1-(4-(6-(1-(1-((1-(3-(2,4-dioxotetrahydropyrimidin-1(2H)-yl)-1-methyl-1H-indazol-6-yl)piperidin-4-yl)methyl)piperidin-4-yl)-1H-pyrazol-4-yl)pyrazolo[1,5-a]pyrazin-4-yl)-2-methylphenyl)ethyl)-2H-tetrazole-5-carboxamide (Compound No. 88)

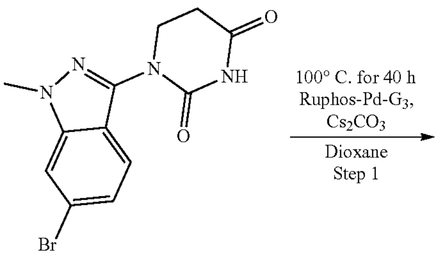

-continued

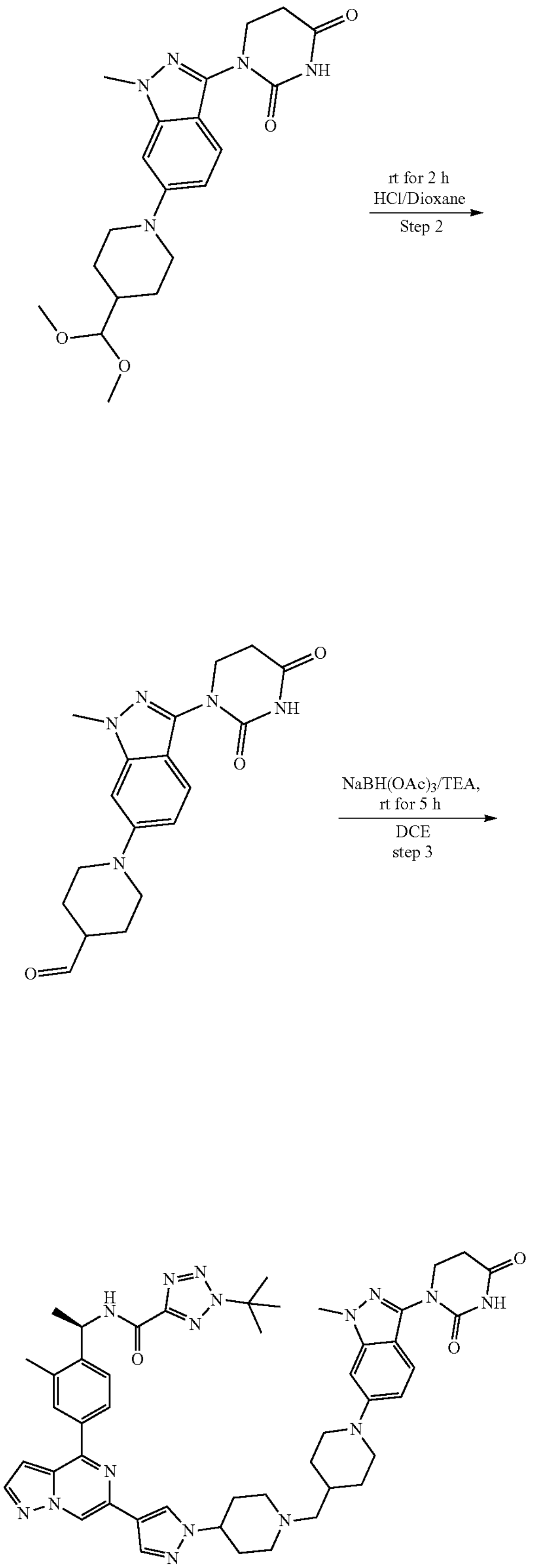

Step 1: 1-(6-(4-(dimethoxymethyl)piperidin-1-yl)-1-methyl-1H-indazol-3-yl)dihydropyrimidine-2,4(1H,3H)-dione

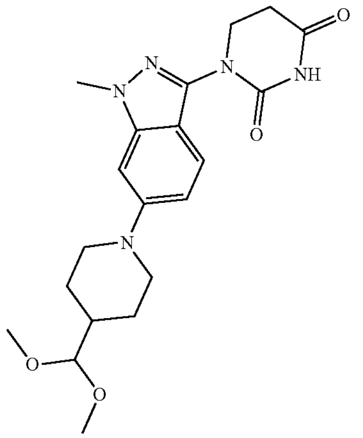 [SMILES: COC(OC)C1CCN(c2ccc3c(N4CCC(=O)NC4=O)nn(C)c3c2)CC1]

A mixture of 1-(6-bromo-1-methyl-1H-indazol-3-yl)dihydropyrimidine-2,4(1H,3H)-dione (600 mg, 1.857 mmol, 1.0 eq), 4-(dimethoxymethyl)piperidine (473 mg, 2.97 mmol, 1.6 eq), $Cs_2CO_3$ (3025 mg, 9.28 mmol, 5.0 eq) and Ruphos-Pd-G3 (360 mg, 0.43 mmol, 0.23 eq) in dry dioxane (10 ml) was stirred at 100° C. for 24 h. Diluted with DCM, filtered and concentrated in vacuo. The residue was purified by flash chromatography eluted with DCM/MeOH=50:1-30:1 to give the title compound (120 mg, 16.1%) as a yellow solid. LC-MS: 402.3 ($M+H^+$).

Step 2:1-(3-(2,4-dioxotetrahydropyrimidin-1(2H)-yl)-1-methyl-1H-indazol-6-yl)piperidine-4-carbaldehyde

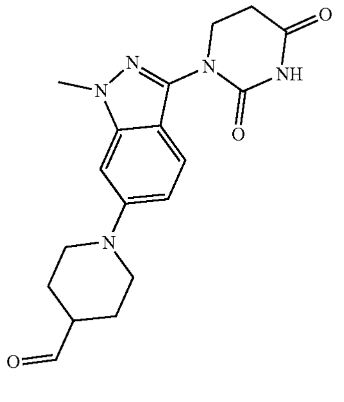 [SMILES: Cn1nc(N2CCC(=O)NC2=O)c2ccc(N3CCC(C=O)CC3)cc21]

A mixture of above obtained intermediate (120 mg, 0.299 mmol, 1.0 eq) in DCM (4 ml) and HCl/Dioxane (1 ml, 4 M in dioxane) was stirred at rt for 4 h. After concentration in vacuo, the residue was used in next step without further purification (106 mg, 94%) as a yellow solid. LC-MS: 356.5 ($M+H^+$).

Step 3: (R)-2-(tert-butyl)-N-(1-(4-(6-(1-(1-((1-(3-(2,4-dioxotetrahydropyrimidin-1(2H)-yl)-1-methyl-1H-indazol-6-yl)piperidin-4-yl)methyl)piperidin-4-yl)-1H-pyrazol-4-yl)pyrazolo[1,5-a]pyrazin-4-yl)-2-methylphenyl)ethyl)-2H-tetrazole-5-carboxamide

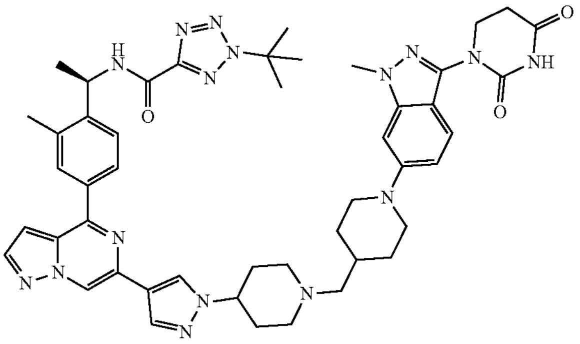 [SMILES: Cc1cc(-c2nc(-c3cnn(C4CCN(CC5CCN(c6ccc7c(N8CCC(=O)NC8=O)nn(C)c7c6)CC5)CC4)c3)cn3nccc23)ccc1[C@@H](C)NC(=O)c1nnn(C(C)(C)C)n1]

To a solution of above obtained intermediate (50 mg, 0.141 mmol, 1.6 eq), (R)-2-(tert-butyl)-N-(1-(2-methyl-4-(6-(1-(piperidin-4-yl)-1H-pyrazol-4-yl)pyrazolo[1,5-a]pyrazin-4-yl)phenyl)ethyl)-2H-tetrazole-5-carboxamide hydrochloride (50 mg, 0.085 mmol, 1.0 eq) and TEA (35 mg, 0.039 mmol, 4.0 eq) in dry DCE (3 ml) was added NaBH (OAc) 3 (36 mg, 0.169 mmol, 2.0 eq) in portions. The reaction was stirred at rt for 2 h. The solution was quenched with water and extracted with DCM for 3 times. The organic layers were washed with brine, dried over anhydrous $Na_2SO_4$ and concentrated in vacuo. The residue was purified by pre-HPLC to give the title compound (21 mg, 28.4%) as a white solid. LC-MS: 893.4 ($M+H^+$).

Following the synthesis of EXAMPLE 26, the following compounds were synthesized and obtained in a similar manner.

| Compd No. | Structure Observed MS $[M + 1]^+$ | $^1H$ NMR (400 MHz, DMSO-$d^6$) δ (ppm) |
|---|---|---|
| 87 | 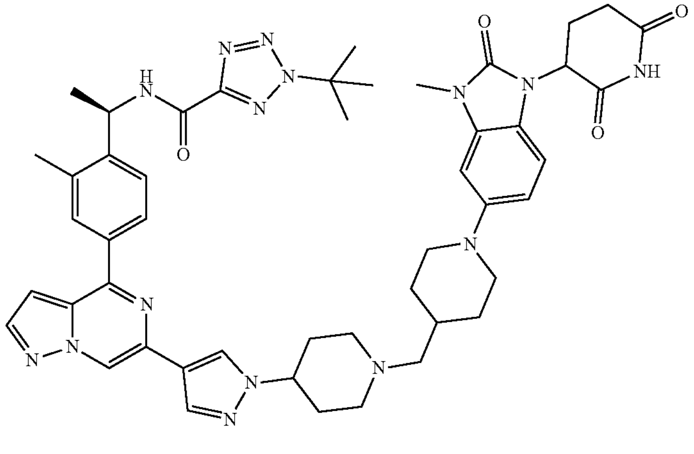 908.2 | |
| 89 | 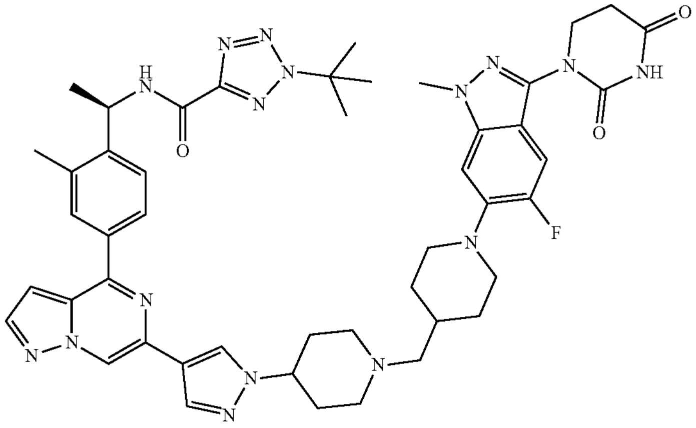 911.2 | |
| 258 | 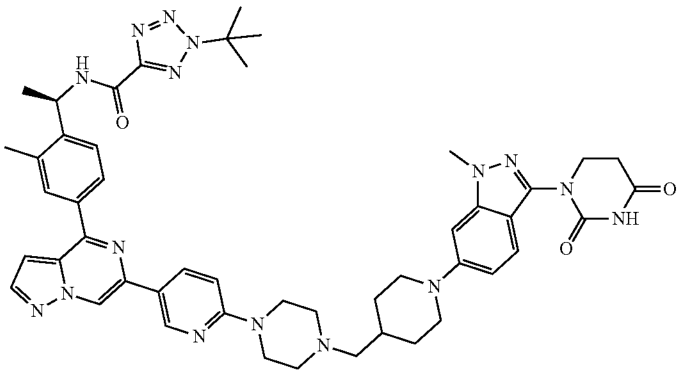 905.7 | 10.48 (s, 1H), 9.55 (d, J = 7.8 Hz, 1H), 9.27 (s, 1H), 8.95 (d, J = 2.4 Hz, 1H), 8.31 (dd, J = 8.9, 2.4 Hz, 1H), 8.21 (d, J = 2.4 Hz, 1H), 8.01-7.91 (m, 2H), 7.71 (d, J = 8.1 Hz, 1H), 7.43 (d, J = 9.0 Hz, 1H), 7.19 (d, J = 2.0 Hz, 1H), 7.02-6.86 (m, 2H), 6.81 (s, 1H), 5.52-5.37 (m, 1H), 3.96-3.73 (m, 7H), 3.67-3.53 (m, 4H), 3.31-3.30 (m, 4H), 2.84-2.70 (m, 4H), 2.55 (s, 3H), 2.29-2.18 (m, 2H), 1.90-1.69 (m, 12H), 1.55 (d, J = 7.0 Hz, 3H), 1.35-1.27 (m, 2H). |

-continued

| Compd No. | Structure Observed MS [M + 1]+ | 1H NMR (400 MHz, DMSO-d6) δ (ppm) |
|---|---|---|
| 263 | 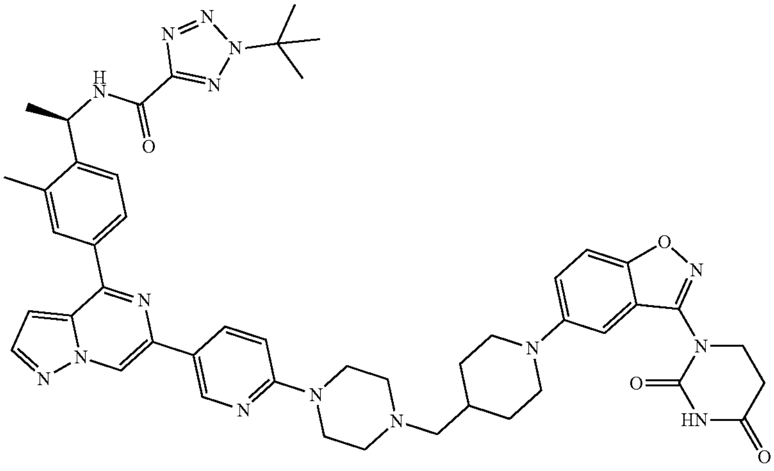 892.7 | 10.82 (s, 1H), 9.57 (d, J = 7.9 Hz, 1H), 9.27 (s, 1H), 9.07-8.86 (m, 1H), 8.38-8.25 (m, 1H), 8.21 (d, J = 2.4 Hz, 1H), 8.06-7.88 (m, 2H), 7.71 (d, J = 8.0 Hz, 1H), 7.56 (d, J = 9.2 Hz, 1H), 7.49-7.32 (m, 1H), 7.19 (d, J = 1.9 Hz, 1H), 7.14 (d, J = 2.2 Hz, 1H), 6.95 (d, J = 9.1 Hz, 1H), 5.55-5.36 (m, 1H), 4.12-3.93 (m, 2H), 3.76-3.50 (m, 6H), 3.32-3.28 (m, 4H), 2.90-2.74 (m, 2H), 2.75-2.59 (m, 2H), 2.55 (s, 3H), 2.30-2.13 (m, 2H), 1.93-1.79 (m, 2H), 1.73 (s, 10H), 1.55 (d, J = 7.0 Hz, 3H), 1.37-1.27 (m, 2H). |

Example 27: (R)-2-(tert-butyl)-N-(1-(4-(6-(1-(1-((1-(3-(2,4-dioxotetrahydropyrimidin-1(2H)-yl)pyrazolo[1,5-a]pyridin-6-yl)piperidin-4-yl)methyl)piperidin-4-yl)-1H-pyrazol-4-yl)pyrazolo[1,5-a]pyrazin-4-yl)-2-methylphenyl)ethyl)-2H-tetrazole-5-carboxamide (Compound No. 91)

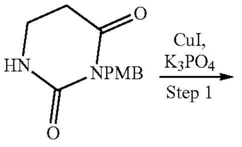

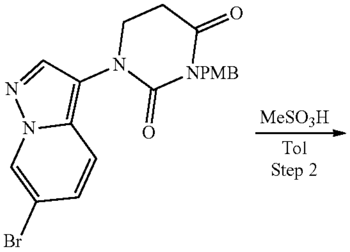

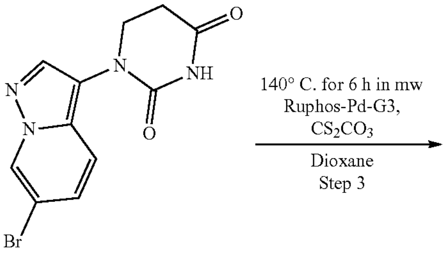

-continued

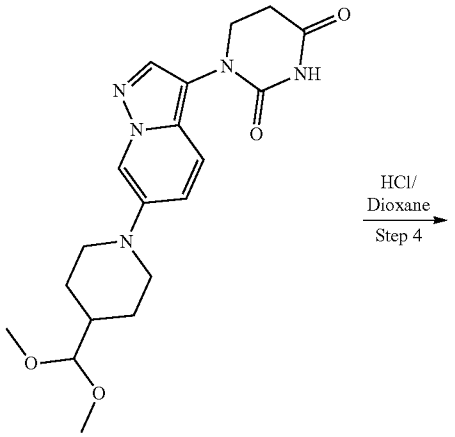

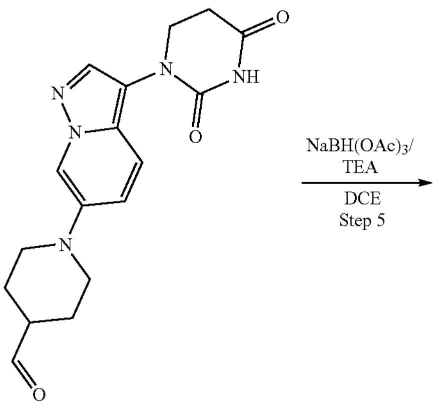

-continued

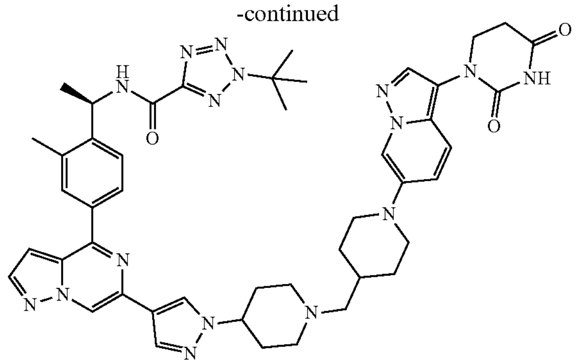

Step 1: 1-(6-bromopyrazolo[1,5-a]pyridin-3-yl)-3-(4-methoxybenzyl)dihydropyrimidine-2,4(1H,3H)-dione

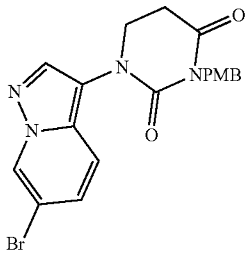

A mixture of 6-bromo-3-iodopyrazolo[1,5-a]pyridine (300 mg, 0.929 mmol, 1.0 eq), copper (I) iodide (30 mg, 0.158 mmol, 0.17 eq), (1S,2S)-cyclohexane-1,2-diamine (30 mg, 0.263 mmol, 0.283 eq), $K_3PO_4$ (592 mg, 2.79 mmol, 3.0 eq) and 3-(4-methoxybenzyl)dihydropyrimidine-2,4(1H,3H)-dione (300 mg, 1.281 mmol, 1.38 eq) in dry DMF (6 ml) was stirred at 80° C. under Ar for 16 h. Concentrated in vacuo. The residue was purified by flash chromatography eluted with Hex/EA=1:1 to give the title compound (200 mg, 50%) as yellow oil. LC-MS: 429.2 $(M+H^+)$.

Step 2: 1-(6-bromopyrazolo[1,5-a]pyridin-3-yl)dihydropyrimidine-2,4(1H,3H)-dione

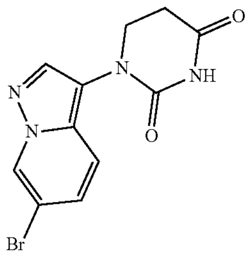 [SMILES: O=C1CCN(c2cnn3cc(Br)ccc23)C(=O)N1]

A mixture of above obtained intermediate (200 mg, 0.466 mmol, 1.0 eq) and methanesulfonic acid (0.5 ml) in Tol (5 ml) was stirred at 110° C. under Ar for 16 h. Concentrated in vacuo, the residue was purified by flash chromatography eluted with DCM/MeOH=20:1 to give the title compound (110 mg, 76.5%) as a white solid. LC-MS: 309.2 $(M+H^+)$.

Step 3: 1-(6-(4-(dimethoxymethyl)piperidin-1-yl)pyrazolo[1,5-a]pyridin-3-yl)dihydropyrimidine-2,4(1H,3H)-dione

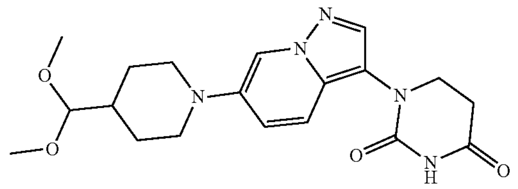 [SMILES: COC(OC)C1CCN(c2ccc3c(N4CCC(=O)NC4=O)cnn3c2)CC1]

A mixture of above obtained intermediate (100 mg, 0.323 mmol, 1.0 eq), 4-(dimethoxymethyl)piperidine (103 mg, 0.646 mmol, 2.0 eq), $Cs_2CO_3$ (316 mg, 0.97 mmol, 3.0 eq) and Ruphos-Pd-G3 (54 mg, 0.065 mmol, 0.2 eq) in dry dioxane (5 ml) was stirred at 130° C. in mw for 8 h. Diluted with DCM, filtered and concentrated in vacuo. The residue was purified by flash chromatography eluted with DCM/MeOH=50:1-30:1 to give the title compound (10 mg, 8%) as a yellow solid. LC-MS: 388.3 $(M+H^+)$.

Step 4: 1-(3-(2,4-dioxotetrahydropyrimidin-1(2H)-yl)pyrazolo[1,5-a]pyridin-6-yl)piperidine-4-carbaldehyde

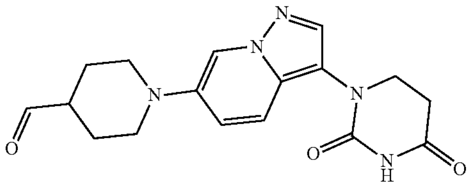 [SMILES: O=CC1CCN(c2ccc3c(N4CCC(=O)NC4=O)cnn3c2)CC1]

A mixture of above obtained intermediate (10 mg, 0.026 mmol, 1.0 eq) in DCM (2 ml) and HCl/Dioxane (0.5 ml, 4 M in dioxane) was stirred at rt for 2 h. After concentration in vacuo, the residue was used in next step without further purification (9 mg, 100%) as a yellow solid. LC-MS: 342.4 $(M+H^+)$.

Step 5: (R)-2-(tert-butyl)-N-(1-(4-(6-(1-(1-((1-(3-(2,4-dioxotetrahydropyrimidin-1(2H)-yl)pyrazolo[1,5-a]pyridin-6-yl)piperidin-4-yl)methyl)piperidin-4-yl)-1H-pyrazol-4-yl)pyrazolo[1,5-a]pyrazin-4-yl)-2-methylphenyl)ethyl)-2H-tetrazole-5-carboxamide

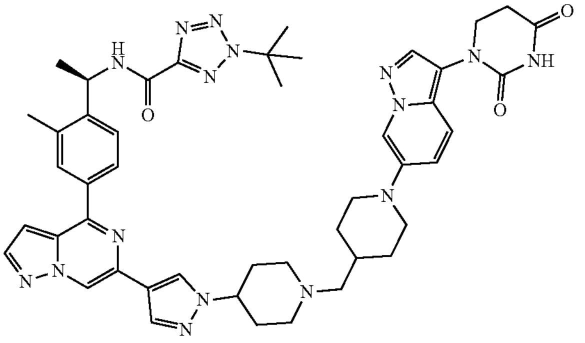 [SMILES: Cc1cc(-c2nc(-c3cnn(C4CCN(CC5CCN(c6ccc7c(N8CCC(=O)NC8=O)cnn7c6)CC5)CC4)c3)cn3nccc23)ccc1[C@@H](C)NC(=O)c1nnn(C(C)(C)C)n1]

To a solution of above obtained intermediate (9 mg, 0.026 mmol, 1.0 eq), (R)-2-(tert-butyl)-N-(1-(2-methyl-4-(6-(1-(piperidin-4-yl)-1H-pyrazol-4-yl)pyrazolo[1,5-a]pyrazin-4-yl)phenyl)ethyl)-2H-tetrazole-5-carboxamide hydrochloride (16 mg, 0.026 mmol, 1.0 eq) and TEA (11 mg, 0.104 mmol, 4.0 eq) in dry DCE (2 ml) was added NaBH(OAc) 3 (11 mg, 0.052 mmol, 2.0 eq) in portions. The reaction was stirred at rt for 2 h. The reaction was quenched with water and extracted with DCM for 3 times. The organic layers were washed with brine, dried over anhydrous $Na_2SO_4$ and concentrated in vacuo. The residue was purified by pre-HPLC to give the title compound (2.2 mg, 10%) as a white solid. LC-MS: 879.6 ($M+H^+$).

Example 28:2-(tert-butyl)-N—((R)-1-(4-(6-(1-(1-((1-(4-(((S)-2,6-dioxopiperidin-3-yl)carbamoyl)-3-fluorophenyl)piperidin-4-yl)methyl)piperidin-4-yl)-1H-pyrazol-4-yl)pyrazolo[1,5-a]pyrazin-4-yl)-2-methylphenyl)ethyl)-2H-tetrazole-5-carboxamide (Compound No. 95)

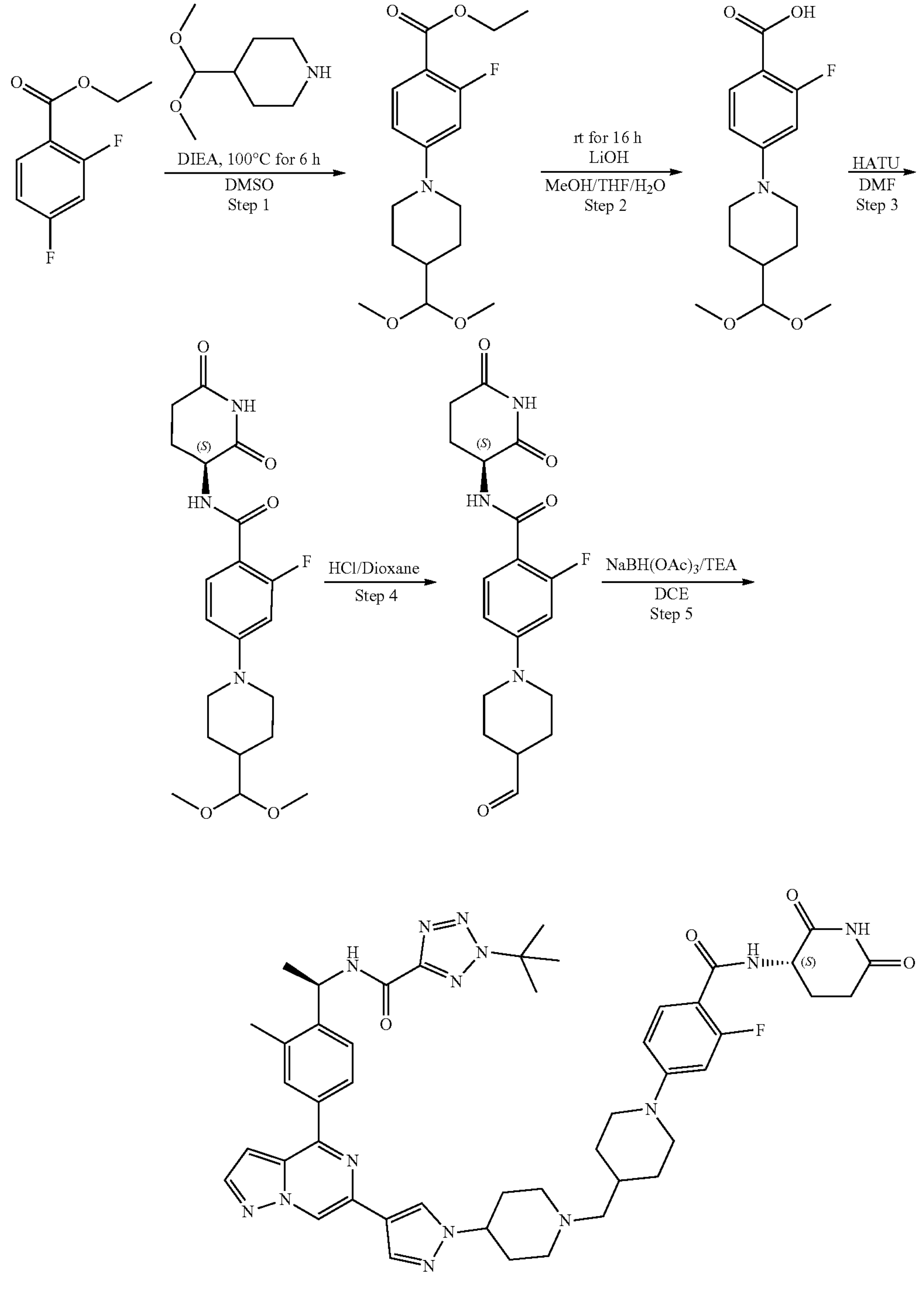

Step 1: ethyl 4-(4-(dimethoxymethyl)piperidin-1-yl)-2-fluorobenzoate

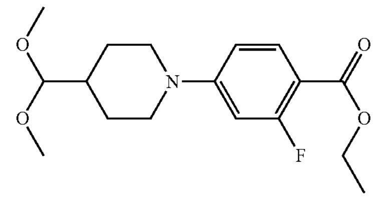 [SMILES: CCOC(=O)c1ccc(N2CCC(C(OC)OC)CC2)cc1F]

A mixture of ethyl 2,4-difluorobenzoate (3.0 g, 16.12 mmol, 1.0 eq), 4-(dimethoxymethyl)piperidine (2.82 g, 17.73 mmol, 1.1 eq) and DIEA (6.25 g, 48.3 mmol, 3.0 eq) in dry DMSO (30 ml) was stirred at 100° C. for 6 h. Diluted with EA, washed with water, brine, dried over anhydrous $Na_2SO_4$ and concentrated in vacuo. The residue was purified by flash chromatography eluted with Hex/EA=5:1 to give the title compound (2.0 g, 38.1%) as yellow oil. LC-MS: 326.3 (M+H$^+$).

Step 2: 4-(4-(dimethoxymethyl)piperidin-1-yl)-2-fluorobenzoic Acid

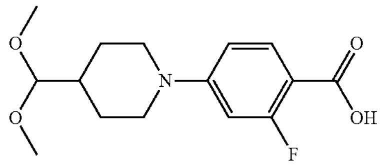 [SMILES: COC(OC)C1CCN(c2ccc(C(=O)O)c(F)c2)CC1]

A mixture of ethyl 4-(4-(dimethoxymethyl)piperidin-1-yl)-2-fluorobenzoate (1.1 g, 3.38 mmol, 1.0 eq) and LiOH (810 mg, 33.8 mmol, 10.0 eq) in MeOH/THF/$H_2O$ (20 ml/20 ml/10 ml) was stirred at rt under Ar for 16 h. Acided with 1N HCl aqueous, extracted with EA for 3 times. The combined EA layers were washed with brine, dried over anhydrous $Na_2SO_4$ and concentrated in vacuo to give the title compound (1.0 g, 100%) as a white solid. LC-MS: 298.3 (M+H$^+$).

Step 3: (S)-4-(4-(dimethoxymethyl)piperidin-1-yl)-N-(2,6-dioxopiperidin-3-yl)-2-fluorobenzamide

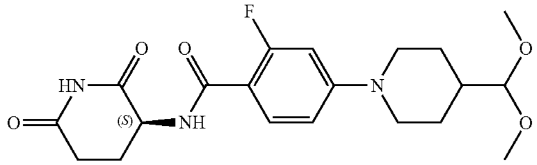

To a mixture of above obtained intermediate (1.0 g, 3.36 mmol, 1.0 eq), (S)-3-aminopiperidine-2,6-dione (430 mg, 3.36 mmol, 1.1 eq) and DIEA (867 mg, 6.72 mmol, 2.0 eq) in dry DMF (15 ml) was added HATU (1.4 g, 3.70 mmol, 1.1 eq). The mixture was stirred at rt under Ar for 3 h. Diluted with EA, washed with water, brine, dried over anhydrous $Na_2SO_4$ and concentrated in vacuo. The residue was purified by flash chromatography eluted with Hex/EA=5:1 to give the title compound (1.0 g, 73%) as yellow oil. LC-MS: 408.2 (M+H$^+$).

Step 4: (S)—N-(2,6-dioxopiperidin-3-yl)-2-fluoro-4-(4-formylpiperidin-1-yl)benzamide

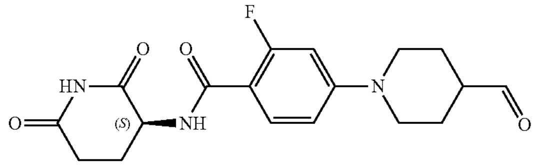

A mixture of above obtained intermediate (120 mg, 0.295 mmol, 1.0 eq) in DCM (4 ml) and HCl/Dioxane (1 ml, 4 M in dioxane) was stirred at rt for 4 h. After concentration in vacuo, the residue was used in next step without further purification (100 mg, 94%) as a yellow solid. LC-MS: 362.4 (M+H$^+$).

Step 5: 2-(tert-butyl)-N—((R)-1-(4-(6-(1-(1-((1-(4-(((S)-2,6-dioxopiperidin-3-yl)carbamoyl)-3-fluorophenyl)piperidin-4-yl)methyl)piperidin-4-yl)-1H-pyrazol-4-yl)pyrazolo[1,5-a]pyrazin-4-yl)-2-methylphenyl)ethyl)-2H-tetrazole-5-carboxamide

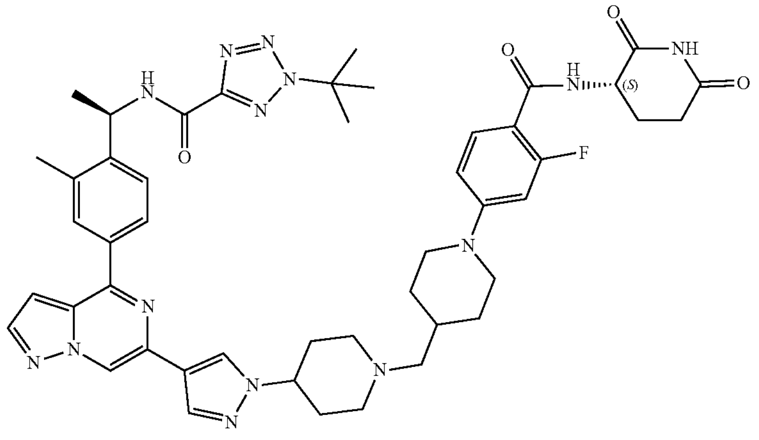

To a solution of above obtained intermediate (100 mg, 0.277 mmol, 1.4 eq), (R)-2-(tert-butyl)-N-(1-(2-methyl-4-(6-(1-(piperidin-4-yl)-1H-pyrazol-4-yl)pyrazolo[1,5-a]pyrazin-4-yl)phenyl)ethyl)-2H-tetrazole-5-carboxamide hydrochloride (100 mg, 0.169 mmol, 1.0 eq) and TEA (86 mg, 0.847 mmol, 4.0 eq) in dry DCE (3 ml) was added NaBH(OAc) 3 (72 mg, 0.34 mmol, 2.0 eq) in portions. The reaction was stirred at rt for 2 h. The solution was quenched with water and extracted with DCM for 3 times. The organic layers were washed with brine, dried over anhydrous $Na_2SO_4$ and concentrated in vacuo. The residue was purified by pre-HPLC to give the title compound (50 mg, 32.8%) as a white solid. LC-MS: 899.6 ($M+H^+$). $^1H$ NMR (400 MHz, DMSO-$d^6$) δ (ppm) 10.84 (s, 1H), 9.57 (d, J=8.0 Hz, 1H), 9.11 (s, 1H), 8.44 (s, 1H), 8.17 (d, J=2.4 Hz, 1H), 8.13 (s, 1H), 8.05-7.92 (m, 3H), 7.69 (d, J=8.0 Hz, 1H), 7.65-7.60 (m, 1H), 7.20-7.14 (m, 1H), 6.84-6.70 (m, 2H), 5.48-5.38 (m, 1H), 4.80-4.68 (m, 1H), 4.25-4.15 (m, 1H), 3.95-3.82 (m, 2H), 3.00-2.90 (m, 2H), 2.88-2.70 (m, 3H), 2.55 (s, 3H), 2.20-1.95 (m, 11H), 1.85-1.75 (m, 3H), 1.73 (s, 9H), 1.55 (d, J=7.2 Hz, 3H), 1.20-1.10 (m, 2H).

Example 29:2-(tert-butyl)-N-((1R)-1-(4-(6-(1-(1-((1-(4-((2,6-dioxopiperidin-3-yl)amino)-2-fluorophenyl)piperidin-4-yl)methyl)piperidin-4-yl)-1H-pyrazol-4-yl)pyrazolo[1,5-a]pyrazin-4-yl)-2-methylphenyl)ethyl)-2H-tetrazole-5-carboxamide (Compound No. 98)

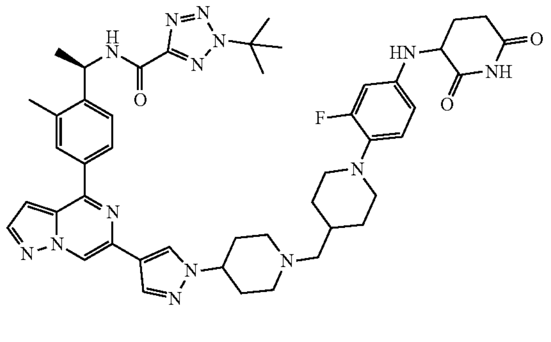 [SMILES: Cc1cc(-c2nc(-c3cnn(C4CCN(CC5CCN(c6ccc(NC7CCC(=O)NC7=O)cc6F)CC5)CC4)c3)cn3nccc23)ccc1[C@@H](C)NC(=O)c1nnn(C(C)(C)C)n1]

To a solution of (R)-2-(tert-butyl)-N-(1-(2-methyl-4-(6-(1-(piperidin-4-yl)-1H-pyrazol-4-yl)pyrazolo[1,5-a]pyrazin-4-yl)phenyl)ethyl)-2H-tetrazole-5-carboxamide hydrochloride (100 mg, 0.169 mmol, 1.0 eq), 1-(4-((2,6-dioxopiperidin-3-yl)amino)-2-fluorophenyl)piperidine-4-carbaldehyde (85 mg, 0.254 mmol, 1.5 eq) and TEA (86 mg, 0.847 mmol, 5.0 eq) in dry DCE (5 ml) was added NaBH (OAc) 3 (72 mg, 0.34 mmol, 2.0 eq) in portions. The reaction was stirred at rt for 2 h. The solution was quenched with water and extracted with DCM for 3 times. The organic layers were washed with brine, dried over anhydrous $Na_2SO_4$ and concentrated in vacuo. The residue was purified by pre-HPLC to give the title compound (60 mg, 40.7%) as a white solid. LC-MS: 871.3 ($M+H^+$). $^1H$ NMR (400 MHz, DMSO-$d^6$) δ (ppm) 10.76 (s, 1H), 9.57 (d, J=8.0 Hz, 1H), 9.11 (s, 1H), 8.44 (s, 1H), 8.17 (d, J=2.4 Hz, 1H), 8.13 (s, 1H), 7.98-7.92 (m, 2H), 7.73-7.68 (m, 2H), 7.18-7.15 (m, 1H), 7.06-7.01 (m, 1H), 6.68 (d, J=8.8 Hz, 2H), 5.48-5.35 (m, 2H), 4.25-4.15 (m, 1H), 4.01 (d, J=12.8 Hz, 2H), 3.00-2.90 (m, 2H), 2.75-2.56 (m, 4H), 2.55 (s, 3H), 2.25-2.00 (m, 9H), 1.90-1.65 (m, 13H), 1.55 (d, J=6.8 Hz, 3H), 1.18-1.06 (m, 2H).

Example 30: (R)-1-(tert-butyl)-N-(1-(4-(6-(1-(1-((1-(4-(2,4-dioxotetrahydropyrimidin-1(2H)-yl)phenyl)piperidin-4-yl)methyl)piperidin-4-yl)-5-methyl-1H-pyrazol-4-yl)pyrazolo[1,5-a]pyrazin-4-yl)-2-methylphenyl)ethyl)-1H-1,2,3-triazole-4-carboxamide (Compound No. 116)

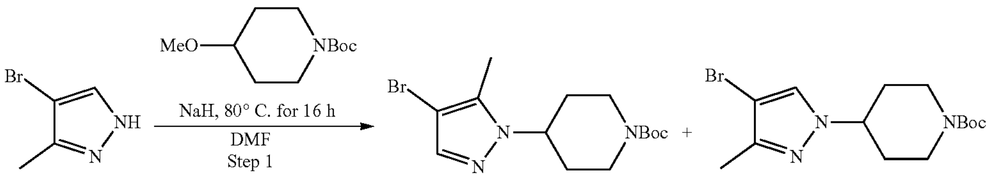

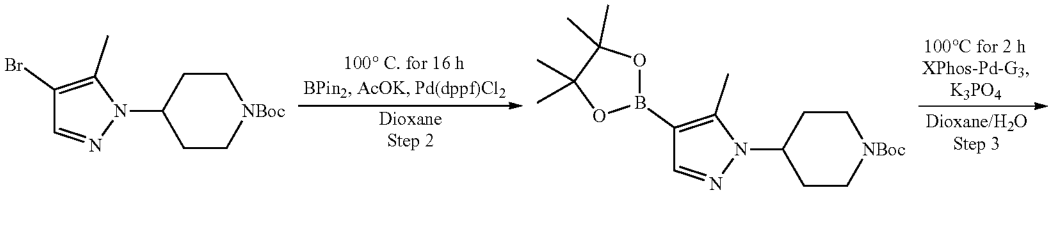

-continued

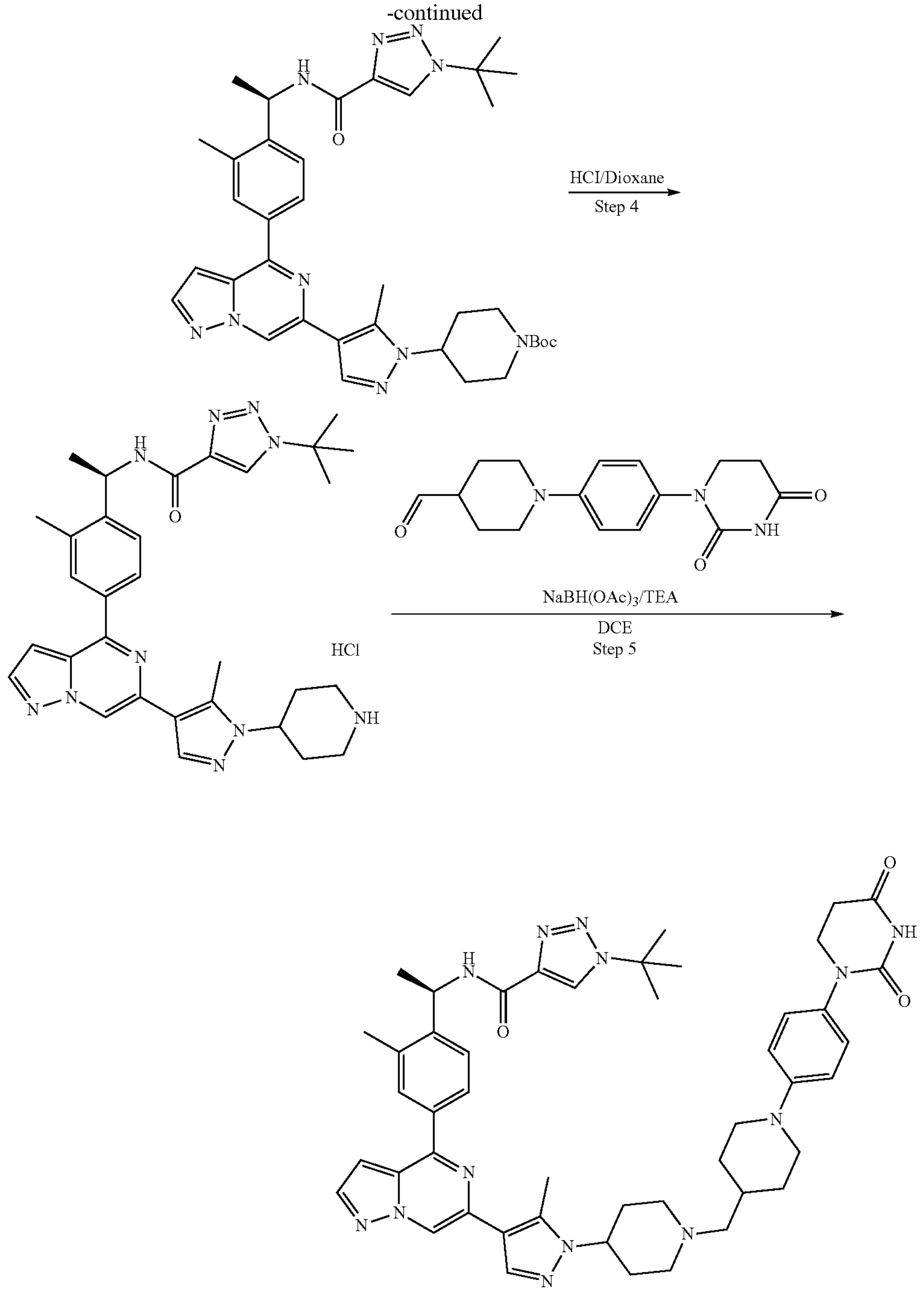

Step 1: tert-butyl 4-(4-bromo-5-methyl-1H-pyrazol-1-yl)piperidine-1-carboxylate

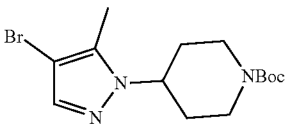 [SMILES: Cc1c(Br)cnn1C1CCN(C(=O)OC(C)(C)C)CC1]

A mixture of NaH (1.12 g, 27.9 mmol, 3.0 eq) and 4-bromo-3-methyl-1H-pyrazole (1.5 g, 9.32 mmol, 1.0 eq) in dry DMF (30 ml) was stirred at rt for 1 h. tert-butyl 4-((methylsulfonyl)oxy) piperidine-1-carboxylate (3.9 g, 13.97 mmol, 1.5 eq) was added and the reaction mixture was stirred at 80° C. under Ar for 16 h. Quenched with water, and diluted with EA. The separated EA layer was washed with water, brine, dried over anhydrous $Na_2SO_4$ and concentrated in vacuo. The residue was purified by flash chromatography eluted with Hex/EA=20:1 to give the title compound (800 mg, 25%) as a white solid and tert-butyl 4-(4-bromo-3-methyl-1H-pyrazol-1-yl) piperidine-1-carboxylate (1.0 g, 31%) as colorless oil. LC-MS: 344.2 ($M+H^+$).

Step 2: tert-butyl 4-(5-methyl-4-(4,4,5,5-tetramethyl-1,3,2-dioxaborolan-2-yl)-1H-pyrazol-1-yl) piperidine-1-carboxylate

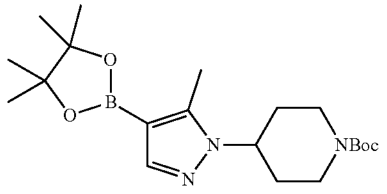 [SMILES: Cc1c(B2OC(C)(C)C(C)(C)O2)cnn1C1CCN(C(=O)OC(C)(C)C)CC1]

A mixture of above obtained intermediate (800 mg, 2.32 mmol, 1.0 eq), 4,4,4',4',5,5,5',5'-octamethyl-2,2'-bi (1,3,2-dioxaborolane) (885 mg, 3.49 mmol, 1.5 eq), KOAc (684 mg, 6.97 mmol, 3.0 eq) and $PdCl_2$ (dppf) (170 mg, 0.23 mmol, 0.1 eq) in dry Dioxane (20 ml) was stirred at 100° C. under Ar for 3 h. Water was added and extracted with EA for 3 times. The combined organic layers were washed with brine, dried over anhydrous $Na_2SO_4$ and concentrated in vacuo. The residue was purified by flash chromatography eluted with Hex/EA=10:1 to give the title compound (350 mg, 38.5%) as colorless oil. LC-MS: 392.3 ($M+H^+$).

Step 3: tert-butyl 4-(5-methyl-4-(4,4,5,5-tetramethyl-1,3,2-dioxaborolan-2-yl)-1H-pyrazol-1-yl) piperidine-1-carboxylate

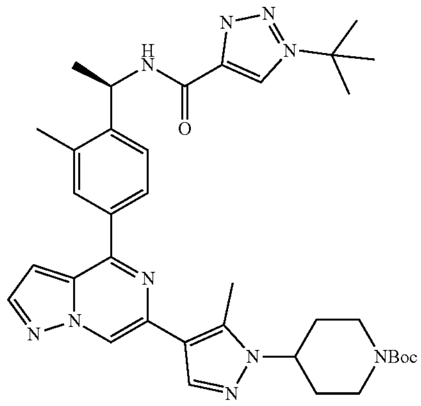

A mixture of (R)-1-(tert-butyl)-N-(1-(4-(6-chloropyrazolo[1,5-a]pyrazin-4-yl)-2-methylphenyl)ethyl)-1H-1,2,3-triazole-4-carboxamide (150 mg, 0.343 mmol, 1.0 eq), above obtained intermediate (350 mg, 0.894 mmol, 2.6 eq), $K_3PO_4$ (218 mg, 1.028 mmol, 3.0 eq) and XPhos-Pd-G3 (30 mg, 0.034 mmol, 0.1 eq) in dioxane (8 ml) and water (2 ml) was stirred at 100° C. under Ar for 3 h. The solution was diluted with water, extracted with ethyl acetate for 3 times. The combined organic layers were washed with brine, dried over anhydrous $Na_2SO_4$ and concentrated in vacuo. The residue was purified by flash chromatography eluted with DCM/EA=1:1 to give the title compound (170 mg, 74.4%) as a white solid. LC-MS: 667.7 ($M+H^+$).

Step 4: (R)-1-(tert-butyl)-N-(1-(2-methyl-4-(6-(5-methyl-1-(piperidin-4-yl)-1H-pyrazol-4-yl)pyrazolo [1,5-a]pyrazin-4-yl)phenyl)ethyl)-1H-1,2,3-triazole-4-carboxamide hydrochloride

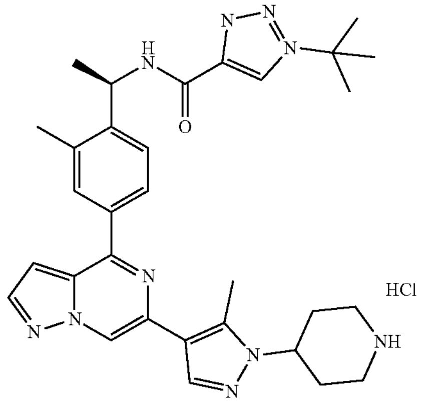

A mixture of above obtained intermediate (170 mg, 0.255 mmol, 1.0 eq) in DCM (4 ml) and HCl/Dioxane (1 ml, 4 M in dioxane) was stirred at rt for 4 h. After concentration in vacuo, the residue was used in next step without further purification (150 mg, 98%) as a yellow solid. LC-MS: 567.5 ($M+H^+$).

Step 5: (R)-1-(tert-butyl)-N-(1-(4-(6-(1-(1-((1-(4-(2,4-dioxotetrahydropyrimidin-1(2H)-yl)phenyl)piperidin-4-yl)methyl)piperidin-4-yl)-5-methyl-1H-pyrazol-4-yl)pyrazolo[1,5-a]pyrazin-4-yl)-2-methylphenyl)ethyl)-1H-1,2,3-triazole-4-carboxamide

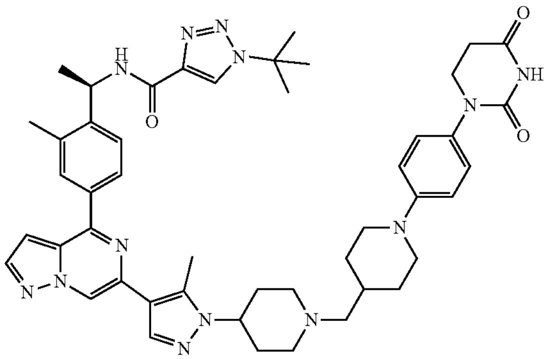 [SMILES: Cc1cc(-c2nc(-c3cnn(C4CCN(CC5CCN(c6ccc(N7CCC(=O)NC7=O)cc6)CC5)CC4)c3C)cn3nccc23)ccc1[C@@H](C)NC(=O)c1cn(C(C)(C)C)nn1]

To a solution of above obtained intermediate (150 mg, 0.25 mmol, 1.4 eq), 1-(4-(2,4-dioxotetrahydropyrimidin-1 (2H)-yl)phenyl)piperidine-4-carbaldehyde (112 mg, 0.375 mmol, 1.5 eq) and TEA (126 mg, 1.25 mmol, 5.0 eq) in dry DCE (4 ml) was added NaBH(OAc) 3 (106 mg, 0.5 mmol, 2.0 eq) in portions. The reaction was stirred at rt for 2 h. The solution was quenched with water and extracted with DCM for 3 times. The organic layers were washed with brine, dried over anhydrous $Na_2SO_4$ and concentrated in vacuo. The residue was purified by pre-HPLC to give the title compound (84.7 mg, 40%) as a white solid. LC-MS: 852.6 ($M+H^+$). $^1H$ NMR (400 MHz, DMSO-$d^6$) δ (ppm) 10.25 (s, 1H), 9.00-8.92 (m, 2H), 8.64 (s, 1H), 8.18 (d, J=2.0 Hz, 1H), 8.00 (s, 1H), 7.95-7.88 (m, 2H), 7.70 (d, J=8.4 Hz, 1H), 7.18-7.10 (m, 3H), 6.93 (d, J=8.8 Hz, 2H), 5.45-5.35 (m, 1H), 4.30-4.15 (m, 1H), 3.75-3.65 (m, 4H), 3.05-2.90 (m, 2H), 2.75-2.62 (m, 7H), 2.52 (s, 3H), 2.22 (d, J=6.8 Hz, 2H), 2.15-2.05 (m, 4H), 1.90-1.65 (m, 5H), 1.62 (s, 9H), 1.52 (d, J=6.8 Hz, 3H), 1.28-1.15 (m, 2H).

Example 31: (R)-1-(tert-butyl)-N-(1-(4-(6-(2-(1-((1-(4-(2,4-dioxotetrahydropyrimidin-1(2H)-yl)phenyl)piperidin-4-yl)methyl)piperidin-4-yl)-2H-1,2,3-triazol-4-yl)pyrazolo[1,5-a]pyrazin-4-yl)-2-methylphenyl)ethyl)-1H-1,2,3-triazole-4-carboxamide formate (Compound No. 120)

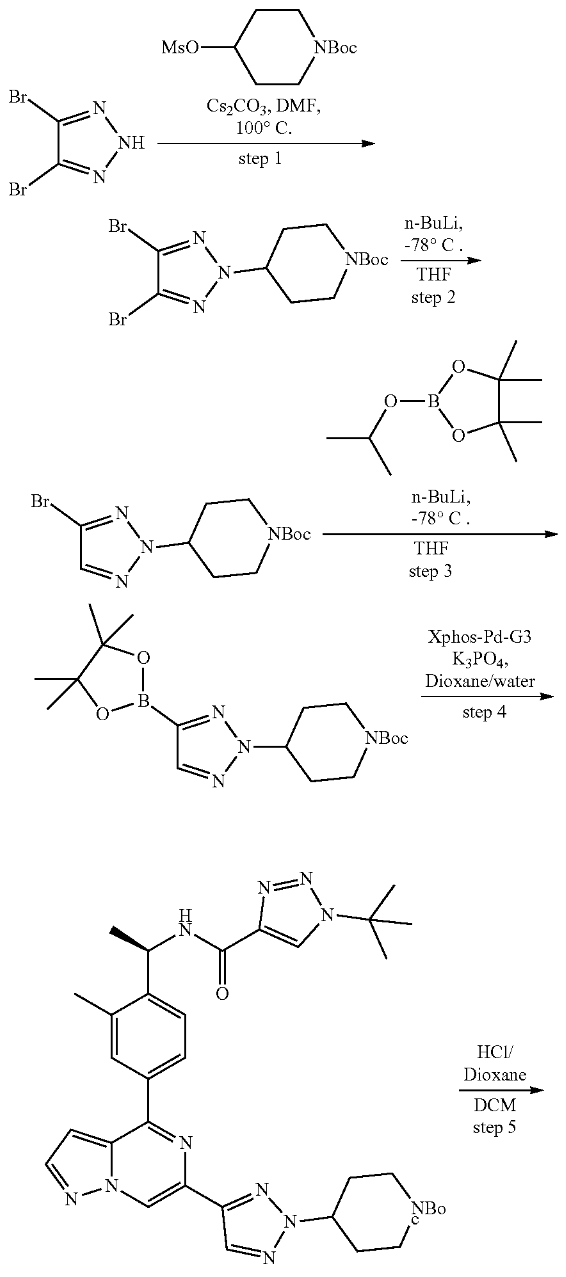

-continued

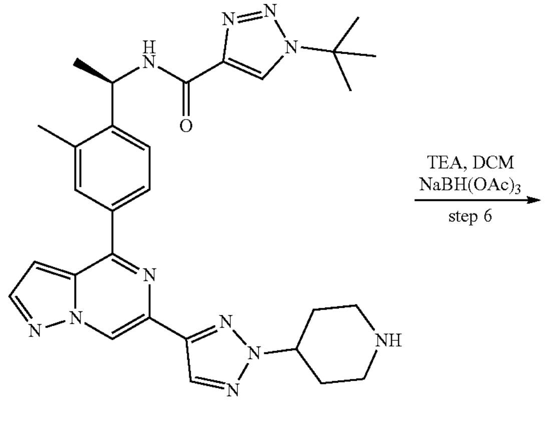

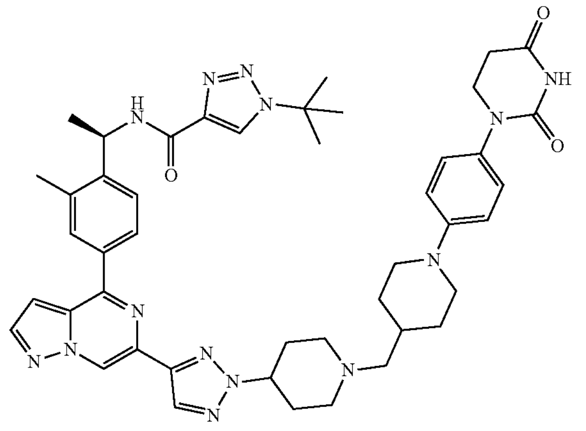

Step 1: tert-butyl 4-(4,5-dibromo-2H-1,2,3-triazol-2-yl)piperidine-1-carboxylate

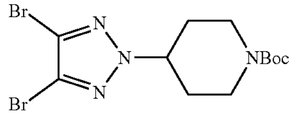 [SMILES: CC(C)(C)OC(=O)N1CCC(n2nc(Br)c(Br)n2)CC1]

A mixture of $Cs_2CO_3$ (3.45 g, 10.58 mmol, 1.2 eq) and 4,5-dibromo-2H-1,2,3-triazole (2 g, 8.82 mmol, 1.0 eq) in DMF (4 ml) was stirred at rt under Ar for 30 min. tert-butyl 4-(methoxysulfonyl)piperidine-1-carboxylate (2.96 g, 10.58 mmol, 1.2 eq) was added in one portion and the mixture was stirred at 100° C. for 20 h under Ar. The reaction mixture was diluted with EA and water. The organic layer was washed with water, brine, dried over anhydrous magnesium sulfate and concentrated in vacuo. The crude product was purified by flash chromatography on silica gel eluting with 10 to 30% of ethyl acetate in petroleum ether to afford the title compound (2.83 g, 78%) as an off-white solid. LC-MS: 411.5 (M+H$^+$).

Step 2: tert-butyl 4-(4-bromo-2H-1,2,3-triazol-2-yl)piperidine-1-carboxylate

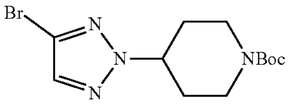 [SMILES: CC(C)(C)OC(=O)N1CCC(n2ncc(Br)n2)CC1]

To a solution of tert-butyl 4-(4,5-dibromo-2H-1,2,3-triazol-2-yl)piperidine-1-carboxylate (1 g, 2.438 mmol, 1.0 eq) in dry THF (15 ml) was added n-BuLi (1.2 ml, 2.93 mmol, 1.2 eq) at −70° C. and the mixture was stirred −70° C. for 3 h. Quenched with $NH_4Cl$ aqueous, extracted with EA for 3 times. The combined EA layers were washed with brine, dried over anhydrous $Na_2SO_4$ and concentrated in vacuo. The residue was purified by flash chromatography eluted with Hex/EA=2:1 to give the title compound (0.537 g, 66.5%) as a yellow solid. LC-MS: 331.2 $(M+H^+)$.

Step 3: tert-butyl 4-(4-(4,4,5,5-tetramethyl-1,3,2-dioxaborolan-2-yl)-2H-1,2,3-triazol-2-yl)piperidine-1-carboxylate

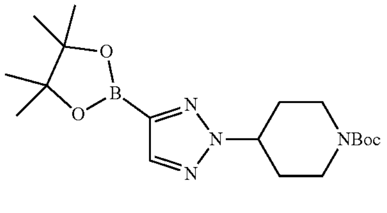 [SMILES: CC(C)(C)OC(=O)N1CCC(n2ncc(B3OC(C)(C)C(C)(C)O3)n2)CC1]

To a solution of above obtained intermediate (0.2 g, 0.604 mmol, 1.0 eq) in dry THF (10 ml) at −70° C. was added n-butyllithium (0.35 ml, 0.876 mmol, 1.5 eq) and the reaction mixture was stirred at −70° C. for 15 min. 2-isopropoxy-4,4,5,5-tetramethyl-1,3,2-dioxaborolane (0.225 g, 1.208 mmol, 2.0 eq) was added and the reaction mixture was stirred while the temperature gradually warmed to room temperature over 2 h. The reaction was quenched with saturated $NH_4Cl$ aqueous. Extracted with EA for 3 times. The combined organic layers were washed with brine, dried over anhydrous $MgSO_4$ and concentrated in vacuo to give the title compound without further purification. LC-MS: 379.6 $(M+H^+)$.

Step 4: tert-butyl (R)-4-(4-(4-(4-(1-(1-(tert-butyl)-1H-1,2,3-triazole-4-carboxamido)ethyl)-3-methylphenyl)pyrazolo[1,5-a]pyrazin-6-yl)-2H-1,2,3-triazol-2-yl)piperidine-1-carboxylate

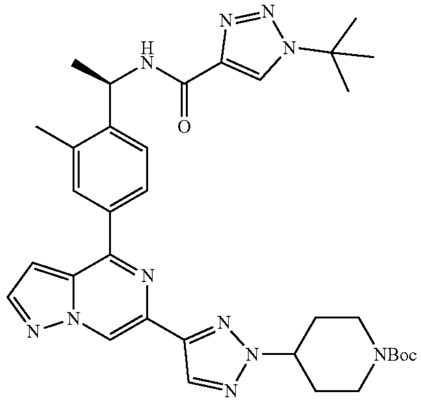 [SMILES: Cc1cc(-c2nc(-c3cnn(C4CCN(C(=O)OC(C)(C)C)CC4)n3)cn3nccc23)ccc1[C@@H](C)NC(=O)c1cn(C(C)(C)C)nn1]

A mixture of (R)-1-(tert-butyl)-N-(1-(4-(6-chloropyrazolo[1,5-a]pyrazin-4-yl)-2-methylphenyl)ethyl)-1H-1,2,3-triazole-4-carboxamide (200 mg, 0.457 mmol, 1.0 eq), above obtained intermediate (225 mg, 0.594 mmol, 1.3 eq), $K_3PO_4$ (291 mg, 1.370 mmol, 3.0 eq) and XPhos-Pd-G3 (38.7 mg, 0.046 mmol, 0.1 eq) in Dioxane (5 ml) and water (1 ml) was stirred at 100° C. under Ar for 3 h. The reaction was diluted with water and extracted with EA for 3 times. The combined EA layers were washed with brine, dried over anhydrous $Na_2SO_4$ and concentrated in vacuo. The residue was purified by flash chromatography eluted with DCM/EA=1:1 to give the title compound (140 mg, 46.9%) as a white solid. LC-MS: 654.7 $(M+H^+)$.

Step 5: (R)-1-(tert-butyl)-N-(1-(2-methyl-4-(6-(2-(piperidin-4-yl)-2H-1,2,3-triazol-4-yl)pyrazolo[1,5-a]pyrazin-4-yl)phenyl)ethyl)-1H-1,2,3-triazole-4-carboxamide

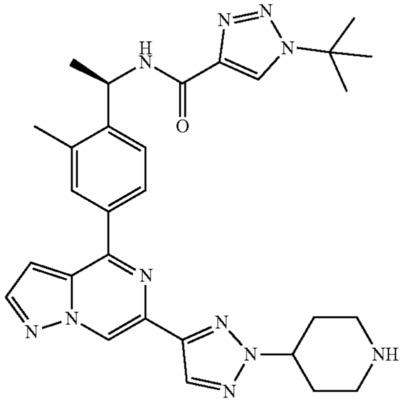 [SMILES: Cc1cc(-c2nc(-c3cnn(C4CCNCC4)n3)cn3nccc23)ccc1[C@@H](C)NC(=O)c1cn(C(C)(C)C)nn1]

A mixture of above obtained intermediate (140 mg, 0.214 mmol, 1.0 eq) and 4M HCl/Dioxane (2 ml) in dry $CH_2Cl_2$ (3 ml) was stirred at rt for 2 h. Concentrated in vacuo to give the title compound without purification. LC-MS: 554.6 $(M+H^+)$.

Step 6: (R)-1-(tert-butyl)-N-(1-(4-(6-(2-(1-((1-(4-(2,4-dioxotetrahydropyrimidin-1(2H)-yl)phenyl)piperidin-4-yl)methyl)piperidin-4-yl)-2H-1,2,3-triazol-4-yl)pyrazolo[1,5-a]pyrazin-4-yl)-2-methylphenyl)ethyl)-1H-1,2,3-triazole-4-carboxamide formate

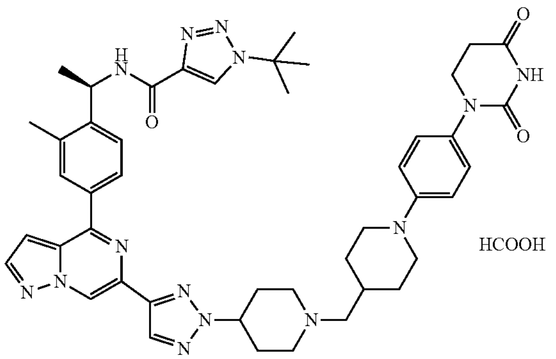 [SMILES: Cc1cc(-c2nc(-c3cnn(C4CCN(CC5CCN(c6ccc(N7CCC(=O)NC7=O)cc6)CC5)CC4)n3)cn3nccc23)ccc1[C@@H](C)NC(=O)c1cn(C(C)(C)C)nn1 ; "HCOOH"]

The titled compound was synthesized in the procedures similar to Example 1. MS (ESI) m/z 839.45 $[M+H]^+$. $^1$H NMR (400 MHz, DMSO-$d^6$) δ (ppm) 10.25 (s, 1H), 9.11 (d, J=1.0 Hz, 1H), 8.98 (d, J=7.9 Hz, 1H), 8.64 (s, 1H), 8.36 (s, 1H), 8.27 (d, J=2.4 Hz, 1H), 7.93 (d, J=10.9 Hz, 2H), 7.71 (d, J=8.1 Hz, 1H), 7.25 (dd, J=2.5, 1.0 Hz, 1H), 7.13 (d, J=8.9 Hz, 2H), 6.93 (d, J=9.0 Hz, 2H), 4.61 (s, 1H), 3.73-3.63 (m, 5H), 2.96 (s, 3H), 2.74-2.65 (m, 5H), 2.38-2.30 (m, 1H), 2.20 (m, 8H), 1.82 (d, J=12.9 Hz, 2H), 1.63 (s, 11H), 1.53 (d, J=7.0 Hz, 3H), 1.20-1.24 (m, 2H).

Example 32: (R)-1-(tert-butyl)-N-(1-(4-(6-(1-(1-((1-(4-(2,4-dioxotetrahydropyrimidin-1(2H)-yl)phenyl)piperidin-4-yl)methyl)piperidin-4-yl)-3-fluoro-1H-pyrazol-4-yl)pyrazolo[1,5-a]pyrazin-4-yl)-2-methylphenyl)ethyl)-1H-1,2,3-triazole-4-carboxamide formate (Compound No. 121/122)

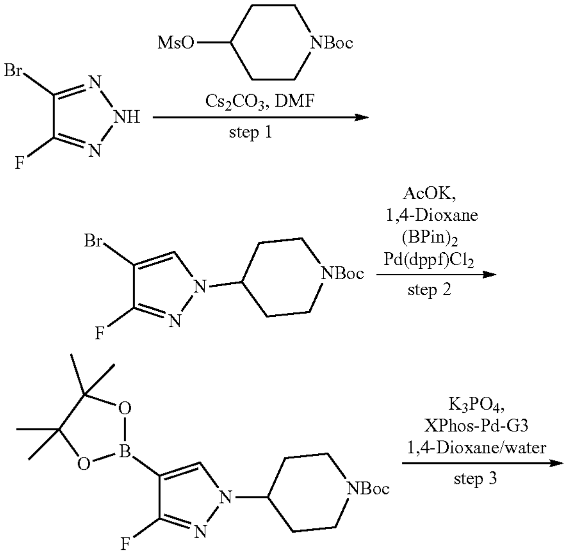

-continued

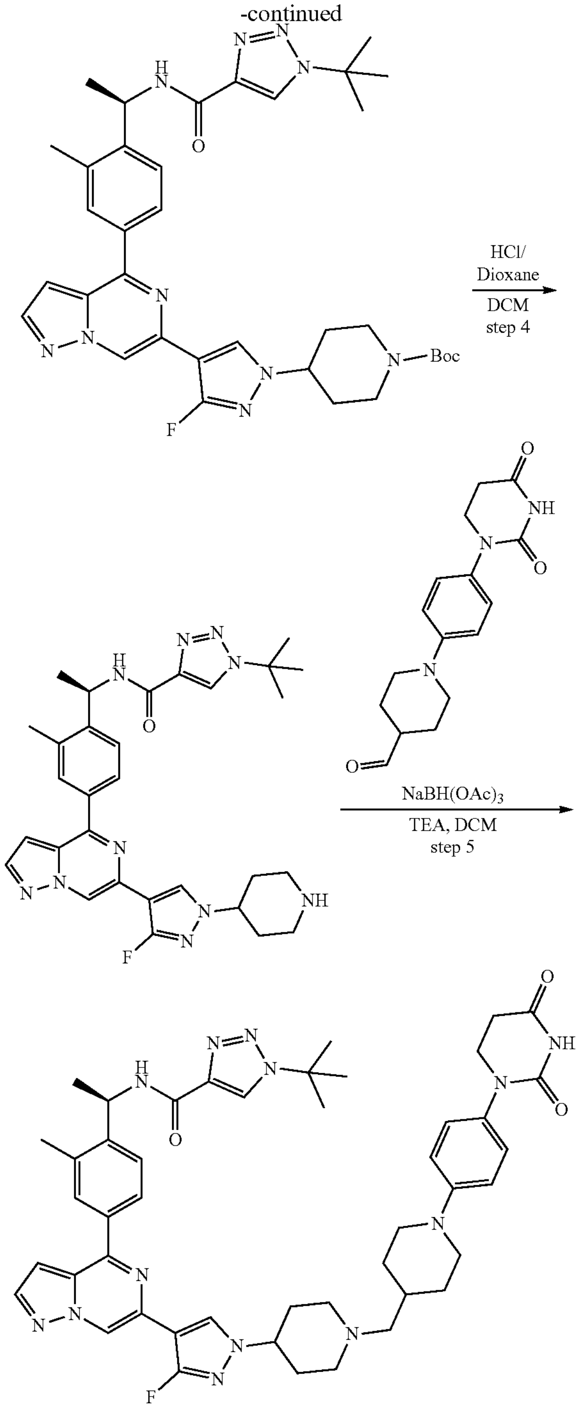

Step 1: tert-butyl 4-(4-bromo-3-fluoro-1H-pyrazol-1-yl)piperidine-1-carboxylate

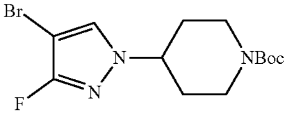 [SMILES: CC(C)(C)OC(=O)N1CCC(n2cc(Br)c(F)n2)CC1]

To a suspension of $Cs_2CO_3$ (5.93 g, 18.19 mmol, 3.0 eq) in DMF (60 ml) was added dropwise 4-bromo-3-fluoro-1H-pyrazole (1.00 g, 6.06 mmol, 1.0 eq). The mixture was stirred for 30 min at rt and then tert-butyl 4-(methoxysulfonyl)piperidine-1-carboxylate (1.69 g, 6.06 mmol, 1.0 eq) was added in one portion and the mixture was stirred at 100° C. for 20 h under Ar. Concentrated in vacuo and the residue was dissolved in ethyl acetate and water. The organic layer was washed with water, brine and dried over anhydrous $MgSO_4$ and concentrated in vacuo. The crude product was purified by flash chromatography on silica gel eluting with Hex/EA=5:1 to give the title compound (1.60 g, 76%) as a yellow oil. LC-MS: 348.2 (M+H+).

Step 2: tert-butyl 4-(3-fluoro-4-(4,4,5,5-tetramethyl-1,3,2-dioxaborolan-2-yl)-1H-pyrazol-1-yl)piperidine-1-carboxylate

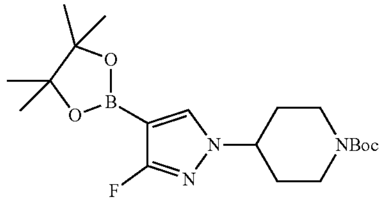 [SMILES: CC(C)(C)OC(=O)N1CCC(n2cc(B3OC(C)(C)C(C)(C)O3)c(F)n2)CC1]

A mixture of tert-butyl 4-(4-bromo-3-fluoro-1H-pyrazol-1-yl)piperidine-1-carboxylate (300 mg, 0.862 mmol, 1.0 eq), 4,4,4',4',5,5,5',5'-octamethyl-2,2'-bi (1,3,2-dioxaborolane) (328 mg, 1.292 mmol, 1.5 eq)), potassium acetate (254 mg, 2.58 mmol, 3.0 eq) and $Pd(dppf)Cl_2$ (63.0 mg, 0.086 mmol, 0.1 eq) in dry Dioxane (6 ml) was stirred at 100° C. for 16 h. The mixture was diluted with water, extracted with EA for 3 times. The combined EA layers were washed with brine, dried over anhydrous $MgSO_4$ and concentrated in vacuo. The residue was purified by flash chromatography eluted with Hex/EA=10:1 to give the title compound (230 mg, 67.5%) as colorless oil. LC-MS: 396.4 (M+H+).

Step 3: tert-butyl (R)-4-(4-(4-(4-(1-(1-(tert-butyl)-1H-1,2,3-triazole-4-carboxamido)ethyl)-3-methylphenyl)pyrazolo[1,5-a]pyrazin-6-yl)-3-fluoro-1H-pyrazol-1-yl)piperidine-1-carboxylate

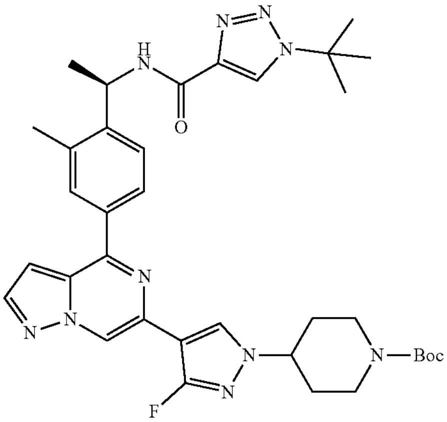 [SMILES: Cc1cc(-c2nc(-c3cn(C4CCN(C(=O)OC(C)(C)C)CC4)nc3F)cn3nccc23)ccc1[C@@H](C)NC(=O)c1cn(C(C)(C)C)nn1]

A mixture of (R)-1-(tert-butyl)-N-(1-(4-(6-chloropyrazolo[1,5-a]pyrazin-4-yl)-2-methylphenyl)ethyl)-1H-1,2,3-triazole-4-carboxamide (200 mg, 0.457 mmol, 1.0 eq), above obtained intermediate (217 mg, 0.548 mmol, 1.2 eq), $K_3PO_4$ (291 mg, 1.370 mmol, 3.0 eq) and XPhos-Pd-G3 (38.7 mg, 0.046 mmol, 0.1 eq) in Dioxane (4 ml) and water (1 ml) was stirred at 100° C. under Ar for 3 h. The mixture was diluted with water, extracted with EA for 3 times. The combined EA layers were washed with brine, dried over anhydrous $Na_2SO_4$ and concentrated in vacuo. The residue was purified by flash chromatography eluted with DCM/EA=1:1 to give the title compound (170 mg, 55.5%) as a yellow solid. LC-MS: 671.2 (M+H+).

Step 4: (R)-1-(tert-butyl)-N-(1-(4-(6-(3-fluoro-1-(piperidin-4-yl)-1H-pyrazol-4-yl)pyrazolo[1,5-a]pyrazin-4-yl)-2-methylphenyl)ethyl)-1H-1,2,3-triazole-4-carboxamide

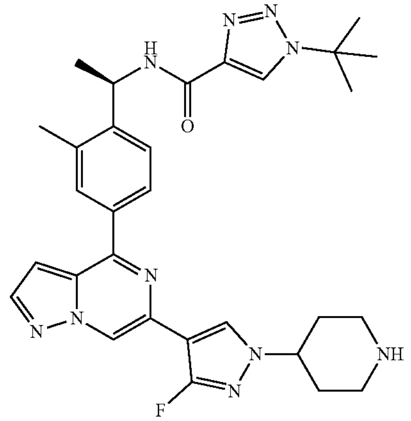 [SMILES: Cc1cc(-c2nc(-c3cn(C4CCNCC4)nc3F)cn3nccc23)ccc1[C@@H](C)NC(=O)c1cn(C(C)(C)C)nn1]

A mixture of above obtained intermediate (160 mg, 0.239 mmol, 1.0 eq) and 4M HCl/Dioxane (2 ml) in dry $CH_2Cl_2$ (3 ml) was stirred at rt for 2 h. Concentrated in vacuo to give the title compound. LC-MS: 571.3 (M+H+).

Step 5: (R)-2-(tert-butyl)-N-(1-(4-(6-(6-(4-((1-(4-(2,4-dioxotetrahydropyrimidin-1(2H)-yl)phenyl)piperidin-4-yl)methyl)piperidin-4-yl)-3-fluoro-1H-pyrazol-4-yl)pyrazolo[1,5-a]pyrazin-4-yl)-2-methylphenyl)ethyl)-1H-1,2,3-triazole-4-carboxamide formate

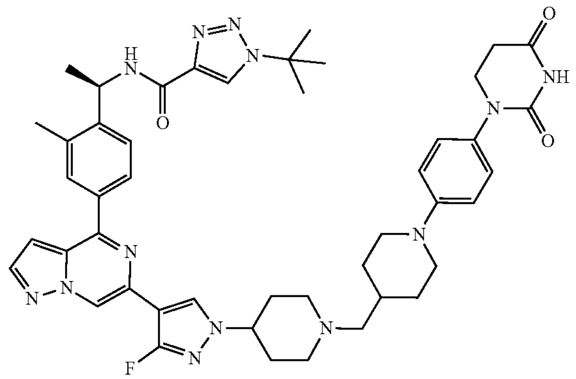 [SMILES: Cc1cc(-c2nc(-c3cn(C4CCN(CC5CCN(c6ccc(N7CCC(=O)NC7=O)cc6)CC5)CC4)nc3F)cn3nccc23)ccc1[C@@H](C)NC(=O)c1cn(C(C)(C)C)nn1]

The titled compound was synthesized in the procedures similar to EXAMPLE 1. MS (ESI) m/z 856.6 ($M+H^+$). $^1$H NMR (400 MHz, DMSO-$d^6$) δ (ppm) 10.25 (s, 1H), 8.98 (d, J=8.0 Hz, 1H), 8.72 (d, J=1.0 Hz, 1H), 8.63 (s, 1H), 8.39 (d, J=2.2 Hz, 1H), 8.21 (d, J=2.5 Hz, 1H), 8.00-7.87 (m, 2H), 7.70 (d, J=8.1 Hz, 1H), 7.21 (dd, J=2.5, 1.0 Hz, 1H), 7.13 (d, J=8.9 Hz, 2H), 6.93 (d, J=9.1 Hz, 2H), 4.12 (s, 1H), 3.69 (t, J=6.7 Hz, 4H), 2.96 (d, J=10.6 Hz, 2H), 2.74-2.64 (m, 4H), 2.54 (s, 3H), 2.21 (d, J=7.1 Hz, 2H), 2.11-1.90 (m, 8H), 1.80 (d, J=12.7 Hz, 2H), 1.63 (s, 9H), 1.52 (d, J=7.0 Hz, 3H), 1.24-1.23 (m, 2H).

Following the synthesis of EXAMPLE 32, the following compounds were synthesized and obtained in a similar manner.

| Compd No. | Structure Observed MS [M + 1]$^+$ | $^1$H NMR (400 MHz, DMSO-$d^6$) δ (ppm) |
|---|---|---|
| 186 | 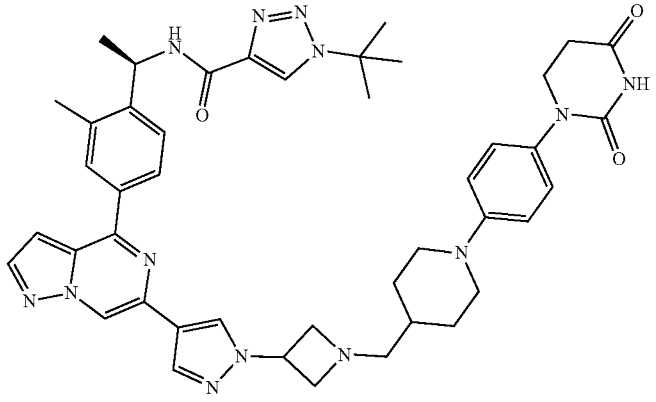 810.43 | 10.25 (s, 1H), 9.14 (d, J = 1.0 Hz, 1H), 8.97 (d, J = 8.0 Hz, 1H), 8.63 (s, 1H), 8.52 (s, 1H), 8.22-8.15 (m, 2H), 7.89 (d, J = 1.9 Hz, 2H), 7.70 (d, J = 8.1 Hz, 1H), 7.18-7.08 (m, 3H), 6.91 (d, J = 9.1 Hz, 2H), 5.40 (p, J = 7.1 Hz, 1H), 5.05 (p, J = 6.9 Hz, 1H), 3.75 (t, J = 7.2 Hz, 2H), 3.71-3.62 (m, 4H), 3.44 (d, J = 7.1 Hz, 2H), 2.71-2.58 (m, 4H), 2.53 (s, 3H), 2.45 (d, J = 6.8 Hz, 2H), 1.78 (dd, J = 10.9, 7.9 Hz, 2H), 1.62 (s, 9H), 1.52 (d, J = 7.0 Hz, 3H), 1.30-1.21 (m, 2H). |
| 195 | 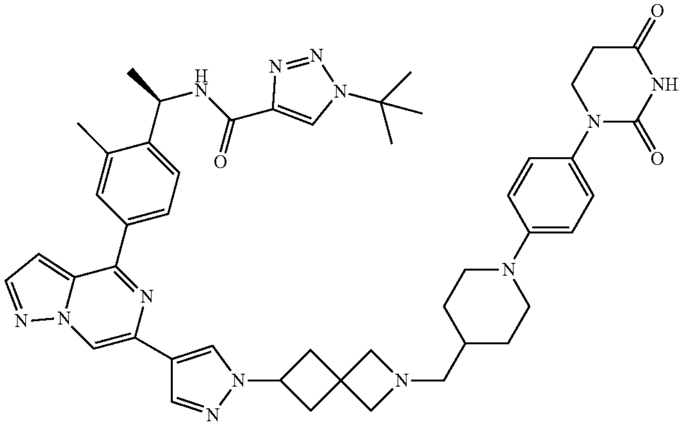 850.05 | 10.25 (s, 1H), 9.11 (d, J = 1.0 Hz, 1H), 8.97 (d, J = 8.0 Hz, 1H), 8.64 (s, 1H), 8.41 (s, 1H), 8.20-8.12 (m, 2H), 7.98-7.84 (m, 2H), 7.69 (d, J = 8.1 Hz, 1H), 7.18-7.07 (m, 3H), 6.91 (d, J = 9.1 Hz, 2H), 4.80 (t, J = 8.1 Hz, 1H), 3.74-3.57 (m, 5H), 2.71-2.60 (m, 11H), 2.39-2.30 (m, 3H), 1.74 (d, J = 12.6 Hz, 2H), 1.63 (s, 10H), 1.52 (d, J = 7.0 Hz, 3H), 1.19-1.27 (m, 2H). |

-continued
| Compd No. | Structure Observed MS $[M + 1]^+$ | $^1H$ NMR (400 MHz, DMSO-$d^6$) δ (ppm) |
|---|---|---|
| 206 | 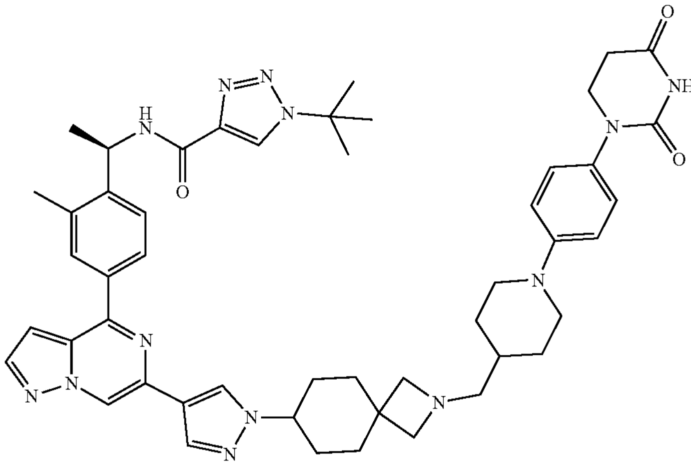 878.10 | 10.24 (s, 1H), 9.09 (s, 1H), 8.96 (d, J = 7.9 Hz, 1H), 8.63 (s, 1H), 8.38 (s, 1H), 8.16 (d, J = 2.4 Hz, 1H), 8.10 (s, 1H), 7.96-7.86 (m, 2H), 7.69 (d, J = 8.1 Hz, 1H), 7.17-7.08 (m, 3H), 6.91 (d, J = 8.7 Hz, 2H), 5.40 (t, J = 7.3 Hz, 1H), 4.16 (d, J = 12.1 Hz, 1H), 3.69 (t, J = 6.8 Hz, 3H), 3.63 (s, 1H), 3.03 (s, 1H), 2.92 (s, 1H), 2.71-2.56 (m, 5H), 2.53 (s, 5H), 2.35 (s, 1H), 2.07 (s, 1H), 2.03-1.93 (m, 4H), 1.81 (d, J = 11.5 Hz, 1H), 1.75 (d, J = 12.7 Hz, 3H), 1.62 (s, 9H), 1.52 (d, J = 7.0 Hz, 3H), 1.25-1.19 (m, 2H). |
| 213 | 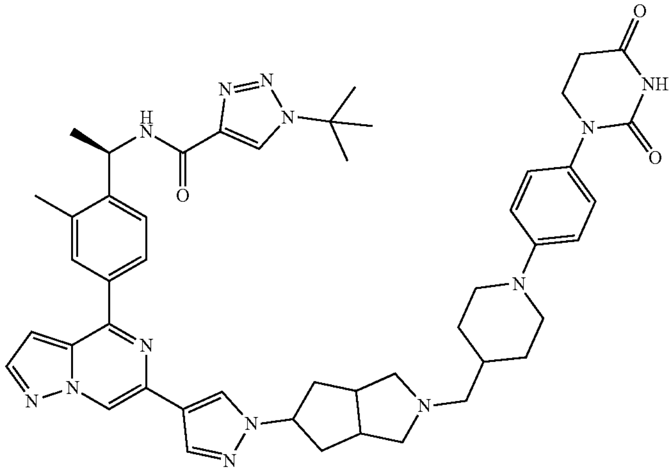 864.81 | 10.25 (s, 1H), 9.12 (d, J = 1.0 Hz, 1H), 8.97 (d, J = 8.0 Hz, 1H), 8.64 (s, 1H), 8.42 (s, 1H), 8.17 (d, J = 2.4 Hz, 1H), 8.11 (s, 1H), 7.97-7.87 (m, 2H), 7.70 (d, J = 8.1 Hz, 1H), 7.18-7.09 (m, 3H), 6.93 (d, J = 8.9 Hz, 2H), 5.40 (p, J = 7.1 Hz, 1H), 4.94-4.86 (m, 1H), 3.73-3.65 (m, 4H), 2.74 (s, 2H), 2.71-2.61 (m, 5H), 2.54 (s, 4H), 2.39 (s, 1H), 2.24 (s, 3H), 1.97 (dd, J = 12.6, 6.2 Hz, 2H), 1.84 (d, J = 12.8 Hz, 2H), 1.62 (s, 9H), 1.53 (d, J = 7.0 Hz, 3H), 1.31-1.28 (m, 2H). |

Example 33: 3-(tert-butyl)-N-((1-(6-(6-(4-((1-(4-(2,4-dioxotetrahydropyrimidin-1(2H)-yl)phenyl)piperidin-4-yl)methyl)piperazin-1-yl)pyridin-3-yl)-7H-pyrrolo[2,3-d]pyrimidin-4-yl)-3,3-difluoropiperidin-4-yl)methyl)-1,2,4-oxadiazole-5-carboxamide (Compound No. 140)

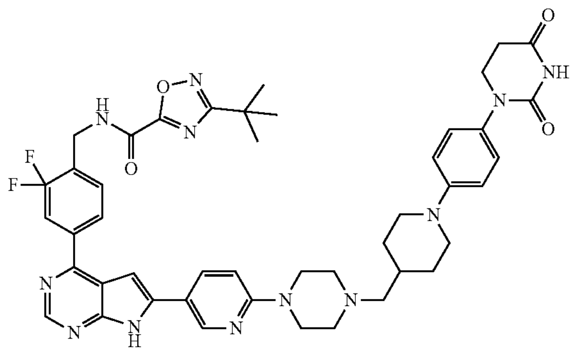

The title compound was obtained after pre-HPLC purification as a white solid. MS (ESI) m/z 866.8 [M+H$^+$]. $^1$H NMR (400 MHz, DMSO-d$^6$) δ (ppm) 12.18 (s, 1H), 10.24 (s, 1H), 9.46 (t, J=6.0 Hz, 1H), 8.68 (d, J=2.4 Hz, 1H), 8.17 (s, 1H), 8.06 (dd, J=8.9, 2.4 Hz, 1H), 7.13 (d, J=8.9 Hz, 2H), 7.02 (s, 1H), 6.97-6.82 (m, 3H), 5.05-4.87 (m, 1H), 4.67 (d, J=13.6 Hz, 1H), 3.73-3.64 (m, 5H), 3.60-3.49 (m, 5H), 2.76-2.59 (m, 5H), 2.46 (s, 4H), 2.22 (d, J=7.0 Hz, 2H), 2.04-1.95 (m, 1H), 1.82 (d, J=12.0 Hz, 2H), 1.78-1.67 (m, 1H), 1.63-1.48 (m, 1H), 1.36 (s, 9H), 1.28-1.17 (m, 4H).

Example 34: 1-(tert-butyl)-N-((1-(6-(6-(4-((1-(4-(2,4-dioxotetrahydropyrimidin-1(2H)-yl)phenyl)piperidin-4-yl)methyl)piperazin-1-yl)pyridin-3-yl)-7H-pyrrolo[2,3-d]pyrimidin-4-yl)-3,3-difluoropiperidin-4-yl)methyl)-1H-1,2,3-triazole-4-carboxamide (Compound No. 141)

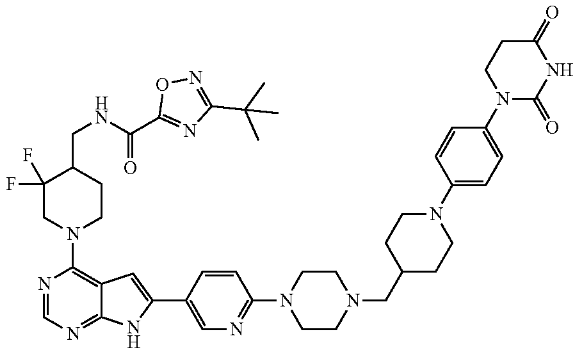 [SMILES: CC(C)(C)c1noc(C(=O)NCC2CCN(c3ncnc4[nH]c(-c5ccc(N6CCN(CC7CCN(c8ccc(N9CCC(=O)NC9=O)cc8)CC7)CC6)nc5)cc34)CC2(F)F)n1]

Following the synthesis of EXAMPLE 33, The title compound was obtained after preparative HPLC purification as a white solid. MS (ESI) m/z 865.7 [M+H$^+$]. $^1$H NMR (400 MHz, DMSO-d$^6$) δ (ppm) 12.18 (s, 1H), 10.24 (s, 1H), 8.70-8.65 (m, 2H), 8.65-8.58 (m, 1H), 8.16 (s, 1H), 8.06 (dd, J=8.9, 2.4 Hz, 1H), 7.13 (d, J=8.9 Hz, 2H), 7.01 (s, 1H), 6.91 (t, J=8.6 Hz, 3H), 5.07-4.85 (m, 1H), 4.66 (d, J=13.2 Hz, 1H), 3.75-3.63 (m, 5H), 3.63-3.48 (m, 6H), 2.68 (t, J=6.7 Hz, 4H), 2.47-2.40 (m, 3H), 2.22 (d, J=7.0 Hz, 2H), 2.03-1.91 (m, 1H), 1.82 (d, J=12.1 Hz, 2H), 1.72 (s, 1H), 1.66-1.45 (m, 12H), 1.30-1.15 (m, 3H).

Example 35: 2-(tert-butyl)-N-((1-(6-(6-(4-((1-(4-(2,4-dioxotetrahydropyrimidin-1(2H)-yl)phenyl)piperidin-4-yl)methyl)piperazin-1-yl)pyridin-3-yl)-7H-pyrrolo[2,3-d]pyrimidin-4-yl)-3,3-difluoropiperidin-4-yl)methyl)-2H-tetrazole-5-carboxamide (Compound No. 142)

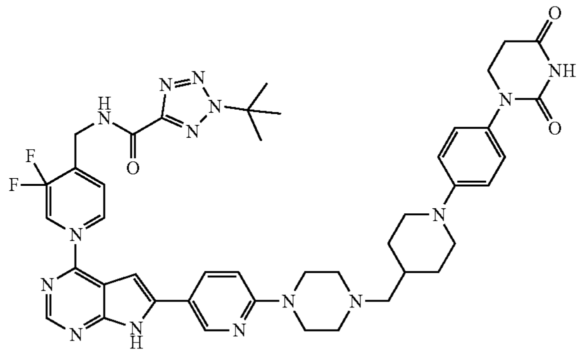

Following the synthesis of EXAMPLE 33, the title compound was obtained after preparative HPLC purification as a white solid. MS (ESI) m/z 866.9 [M+H$^+$]. $^1$H NMR (400 MHz, DMSO-d$^6$) δ (ppm) 12.19 (s, 1H), 10.25 (s, 1H), 9.12 (t, J=6.0 Hz, 1H), 8.68 (d, J=2.3 Hz, 1H), 8.17 (s, 1H), 8.06 (dd, J=8.9, 2.4 Hz, 1H), 7.13 (d, J=8.9 Hz, 2H), 7.02 (s, 1H), 6.97-6.84 (m, 3H), 5.05-4.85 (m, 1H), 4.67 (d, J=13.5 Hz, 1H), 3.76-3.47 (m, 10H), 3.32-3.20 (m, 2H), 2.72-2.55 (m, 5H), 2.48-2.36 (m, 4H), 2.21 (d, J=6.6 Hz, 2H), 2.04-1.91 (m, 1H), 1.81 (d, J=12.1 Hz, 2H), 1.74-1.66 (m, 10H), 1.63-1.48 (m, 1H), 1.29-1.18 (m, 2H).

Example 36: 2-(tert-butyl)-N-((1R)-1-(4-(7-(6-(4-((1-(6-((2,6-dioxopiperidin-3-yl)amino)pyridin-3-yl)piperidin-4-yl)methyl)piperazin-1-yl)pyridin-3-yl)imidazo[1,2-c]pyrimidin-5-yl)-2-methylphenyl)ethyl)-2H-tetrazole-5-carboxamide (Compound No. 166)

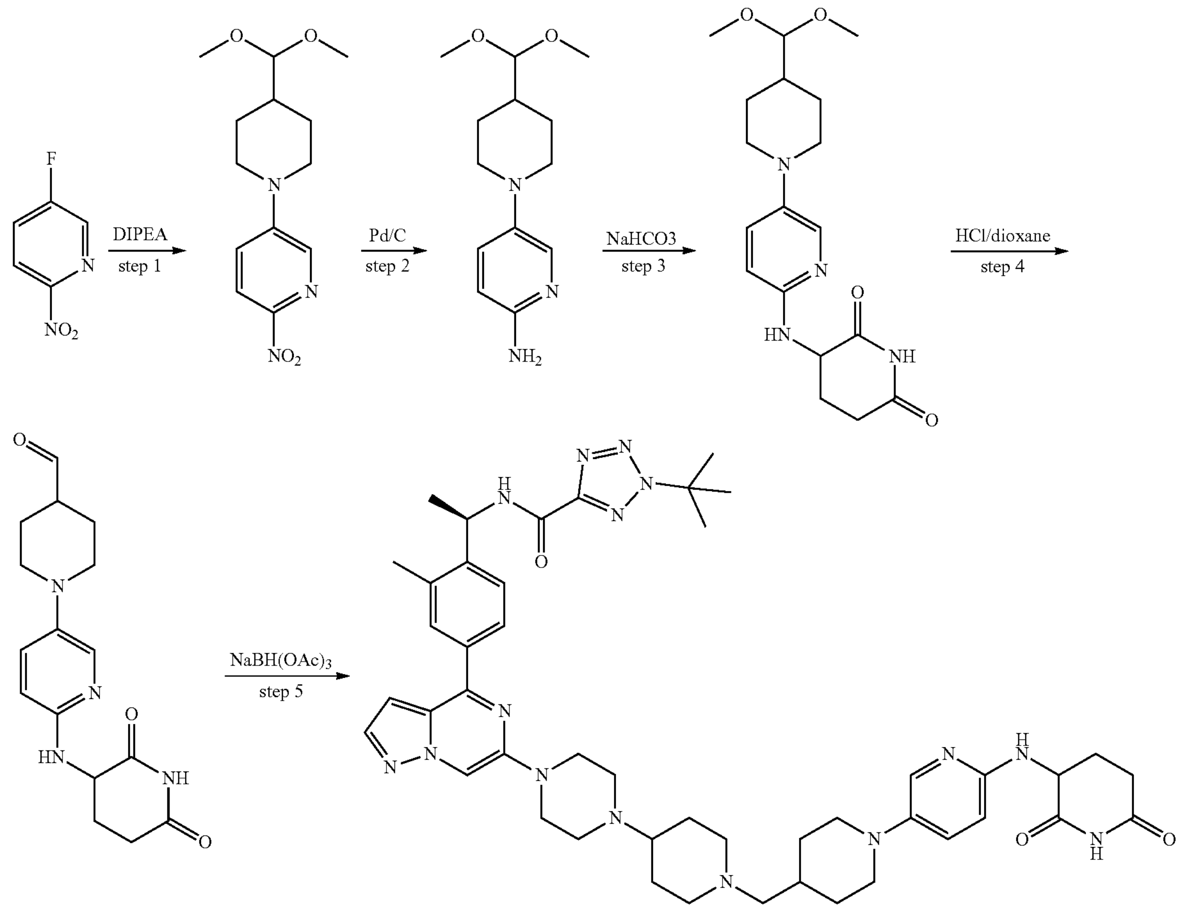

Step 1: 5-(4-(dimethoxymethyl)piperidin-1-yl)-2-nitropyridine

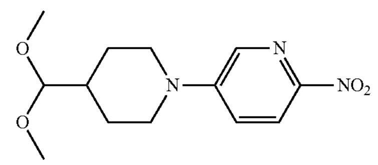

In a 100 ml round-bottomed flask, 5-fluoro-2-nitropyridine (500 mg, 3.52 mmol, 1.0 eq), 4-(dimethoxymethyl)piperidine (728 mg, 4.57 mmol, 1.3 eq) and DIPEA (1364 mg, 10.56 mmol, 3.0 eq) were dissolved in Acetonitrile (10 ml). The mixture was stirred at 80° C. for 16 h and concentrated. The crude product was added to a silica gel column and was eluted with MeOH/DCM 0~3% to give the title compound (900 mg, 91%) as a yellow solid. MS (ESI) m/z 282.0 [M+H]$^+$.

Step 2: give 5-(4-(dimethoxymethyl)piperidin-1-yl)pyridin-2-amine

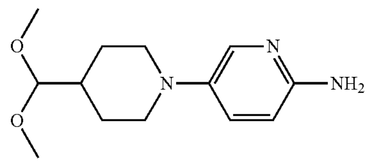 [SMILES: COC(OC)C1CCN(c2ccc([N+](=O)[O-])nc2)CC1]

In a 100 ml round-bottomed flask, above obtained intermediate (500 mg, 1.777 mmol, 1.0 eq) and Pd—C (189 mg, 1.777 mmol, 1.0 eq) were dissolved in MeOH (10 ml) under $H_2$. The reaction was stirred for 12 h. The reaction mixture was filtered and the filter cake was rinsed with MeOH. Concentrated to give the title compound (400 mg, 90%) as a colorless oil. MS (ESI) m/z 252.0 [M+H]$^+$.

Step 3: 3-((5-(4-(dimethoxymethyl)piperidin-1-yl) pyridin-2-yl)amino) piperidine-2,6-dione

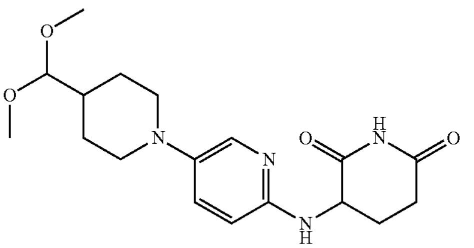 [SMILES: COC(OC)C1CCN(c2ccc(NC3CCC(=O)NC3=O)nc2)CC1]

In a 100 ml round-bottomed flask, above obtained intermediate (400 mg, 1.592 mmol, 1.0 eq), 3-bromopiperidine-2,6-dione (367 mg, 1.910 mmol, 1.2 eq) and sodium bicarbonate (267 mg, 3.18 mmol, 2.0 eq) were dissolved in DMF (5 ml). The mixture was stirred at 60° C. for 16 h. Water was added to the reaction mixture followed by extraction with EA. The combined organic layers were dried $Na_2SO_4$, filtered and concentrated. The crude product was added to a silica gel column and was eluted with MeOH/DCM 0~3% to give the title compound (70 mg, 12.1%) as a brown solid. MS (ESI) m/z 363.1 $[M+H]^+$.

Step 4: 1-(6-((2,6-dioxopiperidin-3-yl)amino)pyridin-3-yl)piperidine-4-carbaldehyde

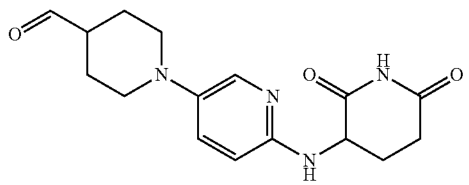 [SMILES: O=CC1CCN(c2ccc(NC3CCC(=O)NC3=O)nc2)CC1]

In a 100 ml round-bottomed flask, above obtained intermediate (70 mg, 0.193 mmol, 1.0 eq) was dissolved in DCM (5 ml) and 4M HCl/dioxane (2 ml). The reaction mixture was stirred for 3 h and concentrated to give the title compound (61 mg, 100%) as a brown oil. MS (ESI) m/z 317.1 $[M+H]^+$.

Step 5: 2-(tert-butyl)-N-((1R)-1-(4-(7-(6-(4-((1-(6-((2,6-dioxopiperidin-3-yl)amino)pyridin-3-yl)piperidin-4-yl)methyl)piperazin-1-yl)pyridin-3-yl)imidazo[1,2-c]pyrimidin-5-yl)-2-methylphenyl)ethyl)-2H-tetrazole-5-carboxamide

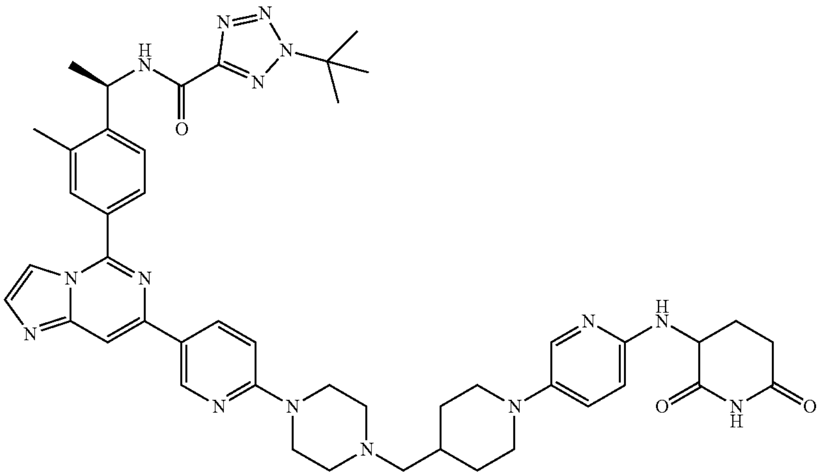 [SMILES: Cc1cc(-c2nc(-c3ccc(N4CCN(CC5CCN(c6ccc(NC7CCC(=O)NC7=O)nc6)CC5)CC4)nc3)cc3nccn23)ccc1[C@@H](C)NC(=O)c1nnn(C(C)(C)C)n1]

In a 100 ml round-bottomed flask, above obtained intermediate (116 mg, 0.193 mmol, 1.0 eq), 1-(6-((2,6-dioxopiperidin-3-yl)amino)pyridin-3-yl)piperidine-4-carbaldehyde (61 mg, 0.193 mmol, 1.0 eq), triethylamine (59 mg, 0.579 mmol, 3.0 eq), and sodium triacetoxyhydroborate (61.3 mg, 0.289 mmol, 1.5 eq) were dissolved in DCM (5 ml). The reaction mixture was stirred for 14 h. The reaction mixture was diluted with DCM, washed with saturated $NaHCO_3$ aqueous, dried $Na_2SO_4$ and concentrated in vacuo. The crude product was added to a pre-HPLC column to give the title compound (35.6 mg, 21.3%) as a yellow solid. MS (ESI) m/z 866.7 $[M+H]^+$. $^1H$ NMR (400 MHz, DMSO-$d^6$) δ (ppm) 10.75 (s, 1H), 9.63 (d, J=7.8 Hz, 1H), 9.00 (d, J=2.5 Hz, 1H), 8.34 (dd, J=9.0, 2.6 Hz, 1H), 8.09-8.01 (m, 2H), 7.92-7.83 (m, 2H), 7.77 (d, J=8.1 Hz, 1H), 7.68 (dd, J=4.2, 2.1 Hz, 2H), 7.25 (dd, J=9.0, 2.9 Hz, 1H), 6.95 (d, J=9.2 Hz, 1H), 6.57 (d, J=8.9 Hz, 1H), 6.40 (d, J=7.6 Hz, 1H), 5.52-5.44 (m, 1H), 4.71-4.63 (m, 1H), 3.62 (s, 4H), 3.43-3.35 (m, 3H), 3.33-3.29 (m, 2H), 2.84-2.67 (m, 1H), 2.57 (s, 3H), 2.51-2.43 (m, 4H), 2.25 (d, J=6.9 Hz, 2H), 2.16-2.07 (m, 1H), 2.06-1.95 (m, 1H), 1.84 (d, J=12.4 Hz, 2H), 1.76 (s, 9H), 1.70-1.63 (m, 1H), 1.59 (d, J=7.1 Hz, 3H), 1.34-1.20 (m, 2H).

Example 37: 2-(tert-butyl)-N-((1R)-1-(4-(7-(6-(4-((1-(5-((2,6-dioxopiperidin-3-yl)amino)pyridin-2-yl)piperidin-4-yl)methyl)piperazin-1-yl)pyridin-3-yl)imidazo[1,2-c]pyrimidin-5-yl)-2-methylphenyl)ethyl)-2H-tetrazole-5-carboxamide (Compound No. 167)

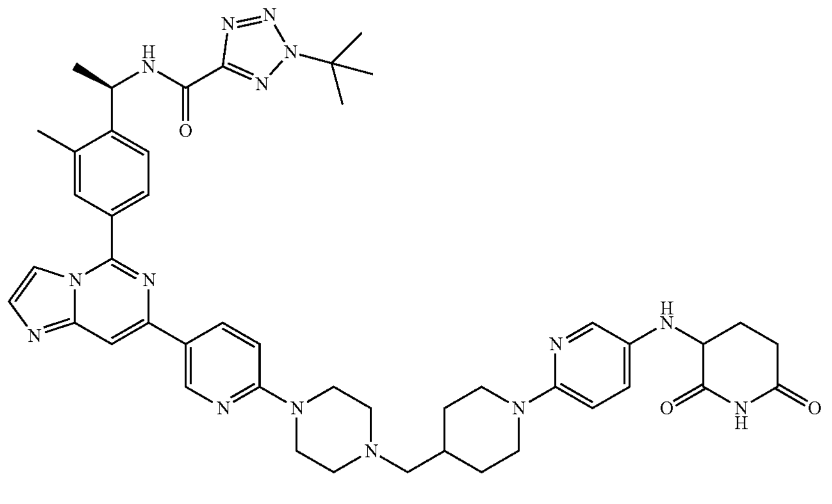 [SMILES: Cc1cc(-c2nc(-c3ccc(N4CCN(CC5CCN(c6ccc(NC7CCC(=O)NC7=O)cn6)CC5)CC4)nc3)cc3nccn23)ccc1[C@@H](C)NC(=O)c1nnn(C(C)(C)C)n1]

Following the synthesis of EXAMPLE 36, the title compound was obtained as a white solid (48.1 mg). MS (ESI) m/z 866.7 $[M+H]^+$. $^1H$ NMR (400 MHz, DMSO-$d^6$) δ (ppm) 10.79 (s, 1H), 9.64 (d, J=7.9 Hz, 1H), 9.01 (d, J=2.5 Hz, 1H), 8.35 (dd, J=9.0, 2.5 Hz, 1H), 8.06 (d, J=15.5 Hz, 2H), 7.93-7.84 (m, 2H), 7.77 (d, J=8.1 Hz, 1H), 7.73 (d, J=3.0 Hz, 1H), 7.69 (d, J=1.5 Hz, 1H), 7.07 (dd, J=9.1, 2.9 Hz, 1H), 6.96 (d, J=9.1 Hz, 1H), 6.71 (d, J=9.0 Hz, 1H), 5.49 (p, J=7.2 Hz, 1H), 5.38 (d, J=7.5 Hz, 1H), 4.27-4.18 (m, 1H), 4.05 (d, J=12.4 Hz, 2H), 3.63 (s, 4H), 3.33-3.20 (m, 2H), 2.82-2.67 (m, 1H), 2.67-2.60 (m, 2H), 2.58 (s, 3H), 2.51-2.46 (m, 4H), 2.26-2.20 (m, 2H), 2.19-2.10 (m, 1H), 1.96-1.85 (m, 1H), 1.81 (d, J=13.3 Hz, 2H), 1.77 (s, 9H), 1.59 (d, J=7.1 Hz, 3H), 1.24-1.14 (m, 2H).

Example 38: 1-(tert-butyl)-N-((1R)-1-(4-(6-(1-(8-((1-(4-(2,4-dioxotetrahydropyrimidin-1(2H)-yl)phenyl)piperidin-4-yl)methyl)-8-azabicyclo[3.2.1]octan-3-yl)-1H-pyrazol-4-yl)pyrazolo[1,5-a]pyrazin-4-yl)-2-methylphenyl)ethyl)-1H-1,2,3-triazole-4-carboxamide formate (Compound No. 184/185)

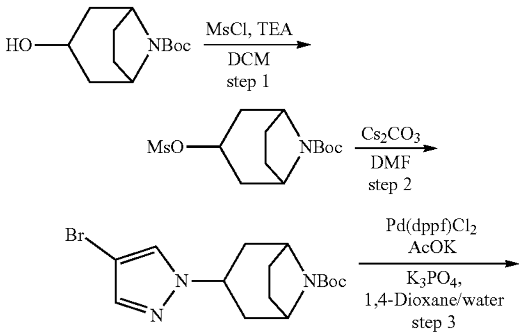

-continued

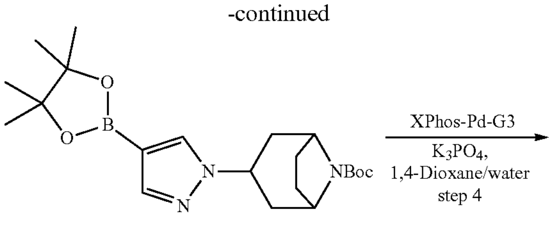

-continued

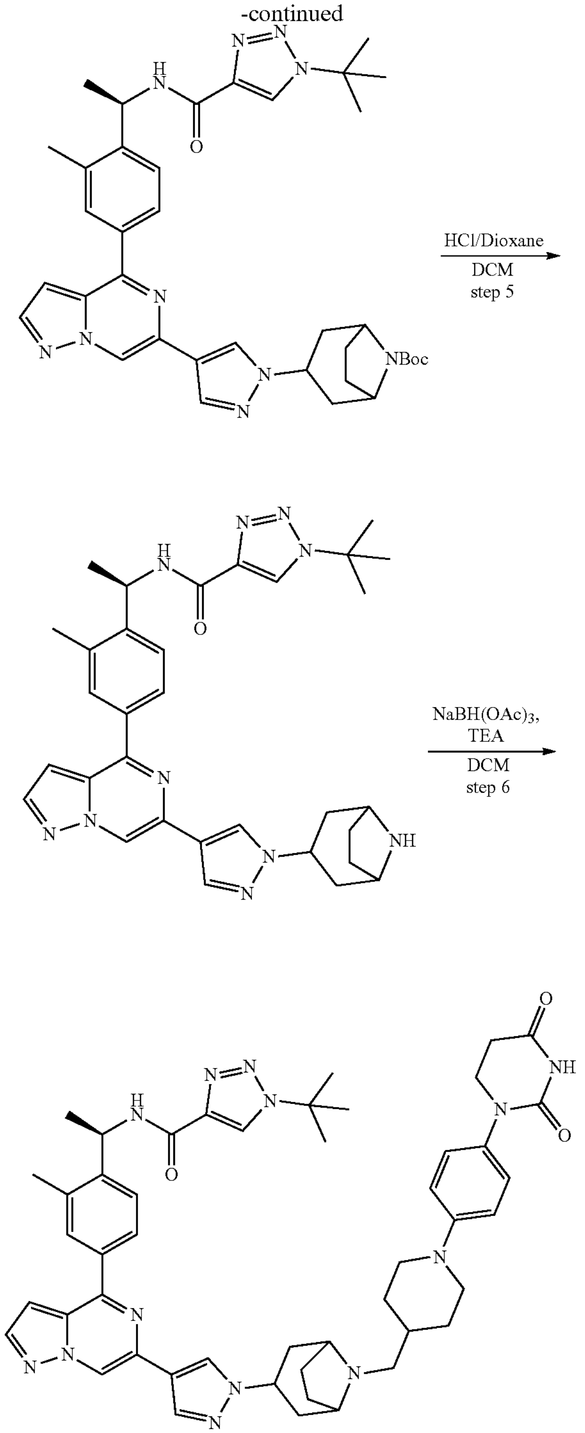

Step 1: tert-butyl 3-((methylsulfonyl)oxy)-8-azabicyclo[3.2.1]octane-8-carboxylate

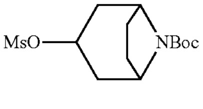

To a stirred solution of tert-butyl 3-hydroxy-8-azabicyclo[3.2.1]octane-8-carboxylate (1.00 g, 4.40 mmol, 1.0 eq) and $Et_3N$ (0.67 g, 6.60 mmol, 1.5 eq) in DCM (15 ml) was added methanesulfonyl chloride (0.60 g, 5.28 mmol, 1.2 eq) at 0° C. The reaction mixture was stirred at this temperature for 3 h. The reaction was quenched by $NaHCO_3$ aqueous and extracted EA for 3 times. The organic phase was washed with water, brine and concentrated in vacuo, the residue was purified by column to give the title compound (1.30 g, 97%) as colorless oi. LC-MS: 306.6 ($M+H^+$).

Step 2: tert-butyl 3-(4-bromo-1H-pyrazol-1-yl)-8-azabicyclo[3.2.1]octane-8-carboxylate

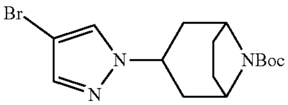 [SMILES: CC(C)(C)OC(=O)N1C2CCC1CC(n1cc(Br)cn1)C2]

To a suspension of $Cs_2CO_3$ (3.20 g, 9.82 mmol, 3.0 eq) in DMF (10 ml) was added dropwise 4-bromo-1H-pyrazole (0.481 g, 3.27 mmol, 1.0 eq). The mixture was stirred for 30 min at room temperature and then above obtained intermediate (1 g, 3.27 mmol, 1.0 eq) was added in one portion. The reaction mixture was stirred at 100° C. for 20 h under Ar. Diluted with in EA, washed with water, brine, dried over anhydrous $MgSO_4$ and concentrated in vacuo. The crude product was purified by flash chromatography on silica gel eluting with 10 to 30% of ethyl acetate in petroleum ether to afford the title compound (0.75 g, 64.3%) as a yellow oil. LC-MS: 356.6 ($M+H^+$).

Step 3: tert-butyl 3-(4-(4,4,5,5-tetramethyl-1,3,2-dioxaborolan-2-yl)-1H-pyrazol-1-yl)-8-azabicyclo[3.2.1]octane-8-carboxylate

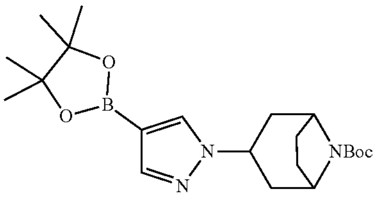 [SMILES: CC(C)(C)OC(=O)N1C2CCC1CC(n1cc(B3OC(C)(C)C(C)(C)O3)cn1)C2]

A mixture of above obtained intermediate (700 mg, 1.965 mmol, 1.0 eq), 4,4,4',4',5,5,5',5'-octamethyl-2,2'-bi (1,3,2-dioxaborolane) (748 mg, 2.95 mmol, 1.5 eq), potassium acetate (579 mg, 5.89 mmol, 3.0 eq) and $Pd(dppf)Cl_2$ (144 mg, 0.196 mmol, 0.1 eq) in dry Dioxane (15 ml) was stirred at 100° C. for 16 h. The reaction mixture was diluted with water, extracted with EA for 3 times. The combined EA layers were washed with brine, dried over anhydrous $MgSO_4$ and concentrated in vacuo. The residue was purified by flash chromatography eluted with Hex/EA=10:1 to give the title compound (720 mg, 91%) as colorless oil. LC-MS: 404.3 ($M+H^+$).

Step 4: tert-butyl 3-(4-(4-(4-((R)-1-(1-(tert-butyl)-1H-1,2,3-triazole-4-carboxamido)ethyl)-3-methylphenyl)pyrazolo[1,5-a]pyrazin-6-yl)-1H-pyrazol-1-yl)-8-azabicyclo[3.2.1]octane-8-carboxylate

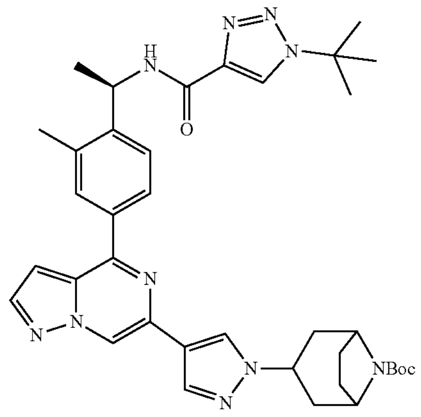 [SMILES: Cc1cc(-c2nc(-c3cnn(C4CC5CCC(C4)N5C(=O)OC(C)(C)C)c3)cn3nccc23)ccc1[C@@H](C)NC(=O)c1cn(C(C)(C)C)nn1]

A mixture of above obtained intermediate (221 mg, 0.548 mmol, 1.2 eq), $K_3PO_4$ (291 mg, 1.370 mmol, 3.0 eq) and XPhos-Pd-G3 (38.7 mg, 0.046 mmol, 0.1 eq) in Dioxane (4 ml) and water (1 ml) was stirred at 100° C. under Ar for 3 h. The reaction mixture was diluted with water, extracted with EA for 3 times. The combined EA layers were washed with brine, dried over anhydrous $Na_2SO_4$ and concentrated in vacuo. The residue was purified by flash chromatography eluted with DCM/EA=1:1 to give the title compound (170 mg, 54.8%) as a yellow solid. LC-MS: 679.6 ($M+H^+$).

Step 5: (R)-1-(tert-butyl)-N-(1-(4-(6-(3-fluoro-1-(piperidin-4-yl)-1H-pyrazol-4-yl)pyrazolo[1,5-a]pyrazin-4-yl)-2-methylphenyl)ethyl)-1H-1,2,3-triazole-4-carboxamide

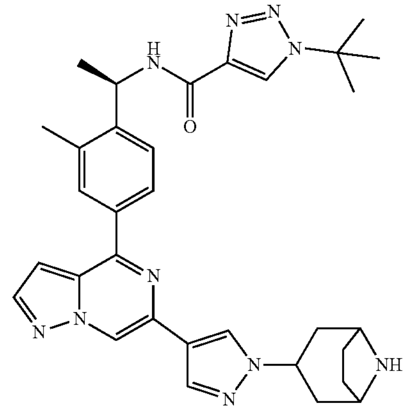 [SMILES: Cc1cc(-c2nc(-c3cnn(C4CC5CCC(C4)N5)c3)cn3nccc23)ccc1[C@@H](C)NC(=O)c1cn(C(C)(C)C)nn1]

A mixture of above obtained intermediate (218 mg, 0.321 mmol) and HCl/Dioxane (2 ml) in dry $CH_2Cl_2$ (3 ml) was stirred at rt for 2 h. Concentrated in vacuo to give the title compound without further purification. LC-MS: 579.4 ($M+H^+$).

Step 6: 1-(tert-butyl)-N-((1R)-1-(4-(6-(1-(8-((1-(4-(2,4-dioxotetrahydropyrimidin-1(2H)-yl)phenyl)piperidin-4-yl)methyl)-8-azabicyclo[3.2.1]octan-3-yl)-1H-pyrazol-4-yl)pyrazolo[1,5-a]pyrazin-4-yl)-2-methylphenyl)ethyl)-1H-1,2,3-triazole-4-carboxamide formate

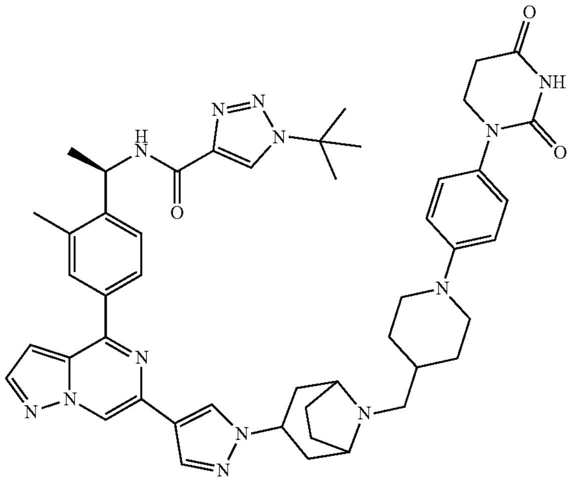 [SMILES: Cc1cc(-c2nc(-c3cnn(C4CC5CCC(C4)N5CC4CCN(c5ccc(N6CCC(=O)NC6=O)cc5)CC4)c3)cn3nccc23)ccc1[C@@H](C)NC(=O)c1cn(C(C)(C)C)nn1]

The titled compound Isomer 1 and Isomer 2 was synthesized in the procedures similar to Example 1. MS (ESI) m/z 864.07 $[M+H]^+$. $^1H$ NMR (400 MHz, DMSO-$d^6$) δ (ppm) 10.25 (s, 1H), 9.10 (s, 1H), 8.97 (d, J=8.0 Hz, 1H), 8.64 (s, 1H), 8.41 (s, 1H), 8.20-8.09 (m, 2H), 7.98-7.85 (m, 2H), 7.70 (d, J=8.1 Hz, 1H), 7.18-7.10 (m, 3H), 6.93 (d, J=9.0 Hz, 2H), 4.57 (s, 1H), 3.75-3.63 (m, 5H), 2.73-2.63 (m, 6H), 2.40-2.29 (m, 4H), 2.14 (s, 3H), 2.07-1.80 (m, 10H), 1.71 (d, J=8.1 Hz, 2H), 1.62 (s, 9H), 1.53 (d, J=7.0 Hz, 3H). 1.24-1.23 (m, 2H).

Example 39: 3-(tert-butyl)-N-(6-(6-(1-(1-((1-(4-(2,4-dioxotetrahydropyrimidin-1(2H)-yl)phenyl)piperidin-4-yl)methyl)piperidin-4-yl)-1H-pyrazol-4-yl)pyrazolo[1,5-a]pyrazin-4-yl)-6-azaspiro[2.5]octan-1-yl)-1,2,4-oxadiazole-5-carboxamide (Compound No. 211)

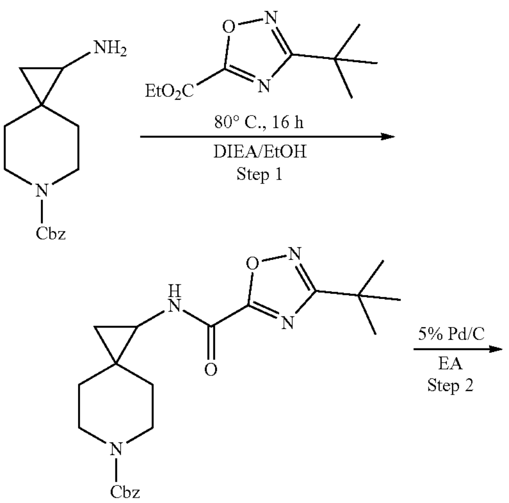

-continued

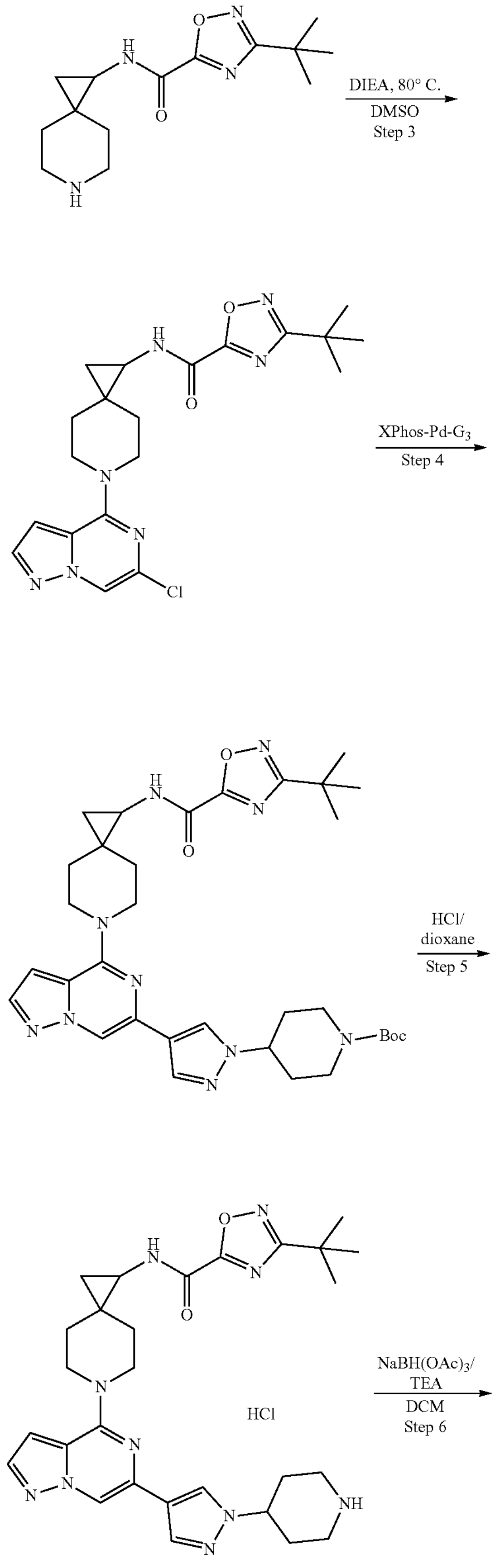

-continued

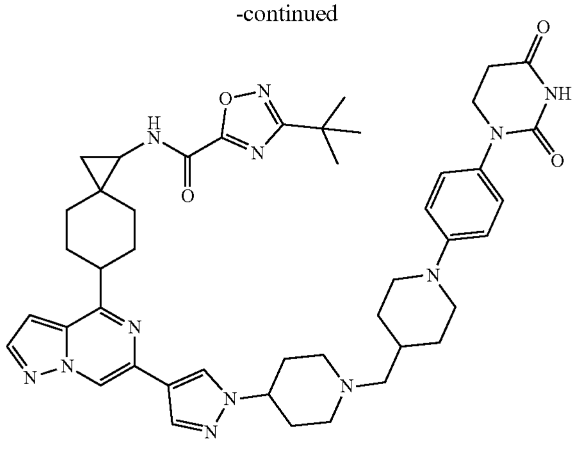

Step 1: benzyl 1-(3-(tert-butyl)-1,2,4-oxadiazole-5-carboxamido)-6-azaspiro[2.5]octane-6-carboxylate

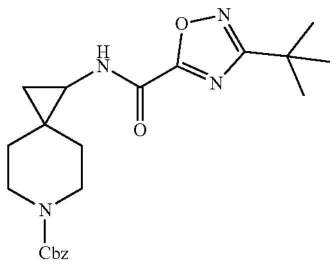 [SMILES: CC(C)(C)c1noc(C(=O)NC2CC23CCN(C(=O)OCc2ccccc2)CC3)n1]

A mixture of benzyl 1-amino-6-azaspiro[2.5]octane-6-carboxylate (1 g, 3.84 mmol, 1.0 eq), ethyl 3-(tert-butyl)-1,2,4-oxadiazole-5-carboxylate (0.846 g, 3.84 mmol, 1.0 eq) and DIEA (1.489 g, 11.52 mmol, 3.0 eq) in EtOH (4 ml) was stirred at 80° C. under Ar for 16 h. Concentrated in vacuo, the residue was purified by flash chromatography eluted with Hex/EA=1:2 to give the title compound (1.27 g, 80%) as a white solid. LC-MS: 413.42 (M+H$^+$).

Step 2:3-(tert-butyl)-N-(6-azaspiro[2.5]octan-1-yl)-1,2,4-oxadiazole-5-carboxamide

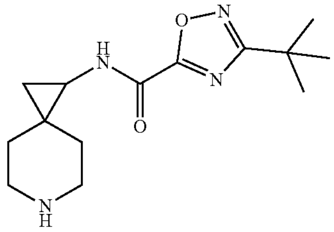 [SMILES: CC(C)(C)c1noc(C(=O)NC2CC23CCNCC3)n1]

A mixture benzyl 1-(3-(tert-butyl)-1,2,4-oxadiazole-5-carboxamido)-6-azaspiro[2.5]octane-6-carboxylate (570 mg, 1.382 mmol, 1.0 eq), Pd/C (147 mg, 1.382 mmol, 1.0 eq) in Ethyl acetate (10 ml) was stirred at rt under $H_2$ for 3 h. Filtered and the filtrate was concentrated in vacuo. The residue was purified by combi-flash eluted with DCM/

MeOH=10:1 to give the title compound (280 mg, 72.8%) as a colorless oil. LC-MS: 279.36 (M+H$^+$).

Steps 3-6: 3-(tert-butyl)-N-(6-(6-(1-(1-((1-(4-(2,4-dioxotetrahydropyrimidin-1(2H)-yl)phenyl)piperidin-4-yl)methyl)piperidin-4-yl)-1H-pyrazol-4-yl)pyrazolo[1,5-a]pyrazin-4-yl)-6-azaspiro[2.5]octan-1-yl)-1,2,4-oxadiazole-5-carboxamide

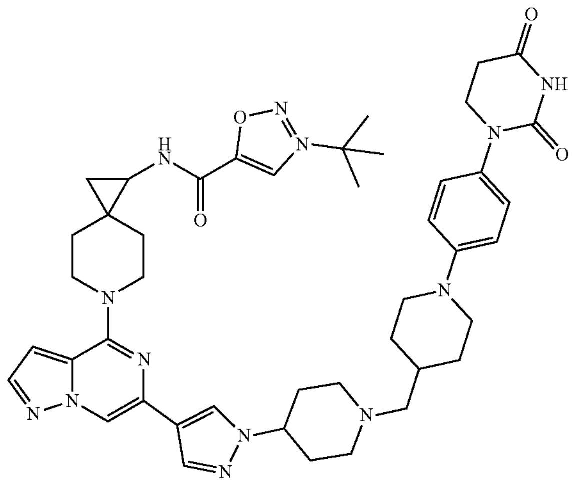

Following the synthesis of EXAMPLE 23, the title compound was obtained after preparative HPLC purification as a white solid. LC-MS: 830.76 (M+H$^+$).

Example 40: (R)-2-(tert-butyl)-N-(1-(4-(6-(1-(1-((1-(4-(2,4-dioxotetrahydropyrimidin-1(2H)-yl)phenyl)piperidin-4-yl)methyl)piperidin-4-yl)-1,2,3,6-tetrahydropyridin-4-yl)pyrazolo[1,5-a]pyrazin-4-yl)-2-methylphenyl)ethyl)-2H-tetrazole-5-carboxamide (Compound No. 217)

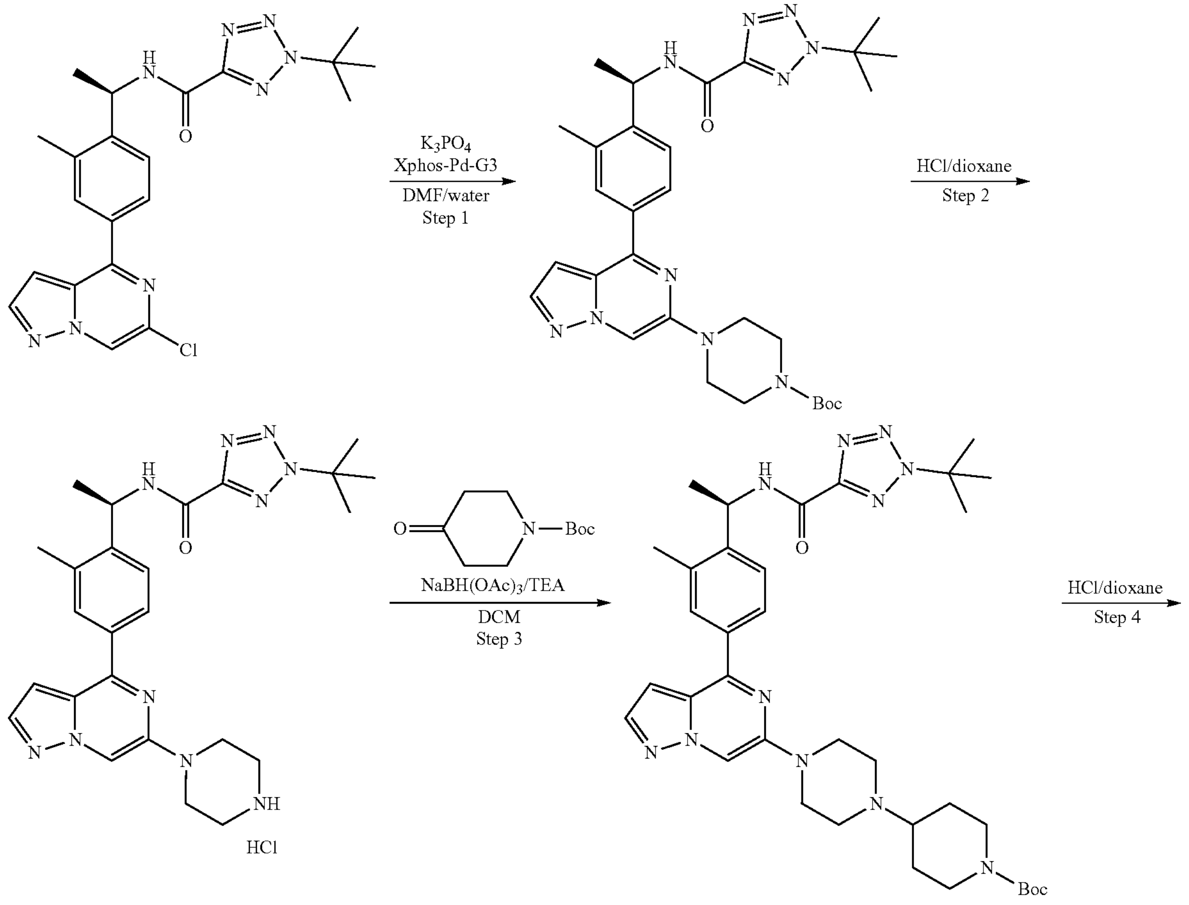

-continued
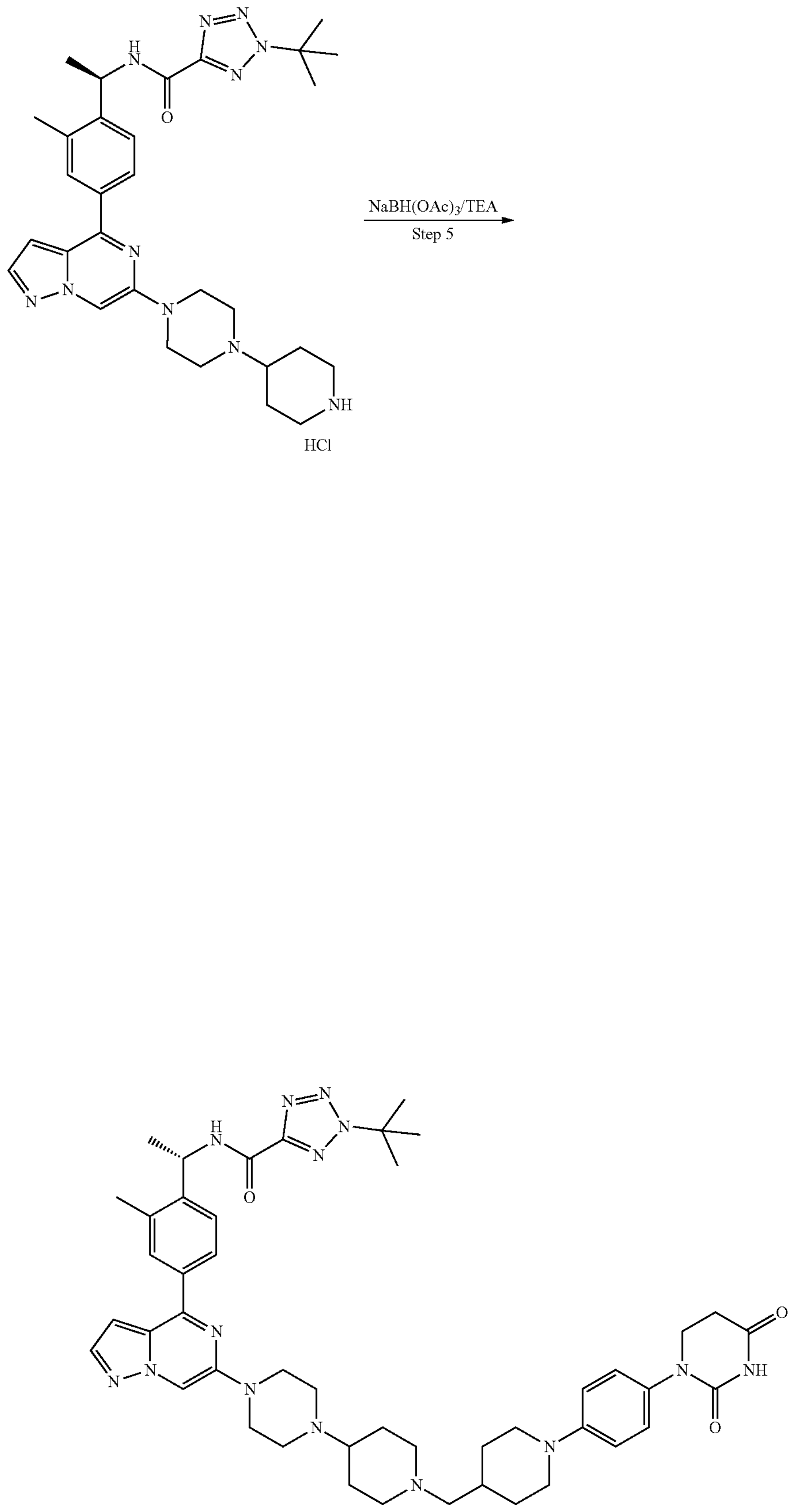

Step 1: tert-butyl (R)-4-(4-(4-(1-(2-(tert-butyl)-2H-tetrazole-5-carboxamido)ethyl)-3-methylphenyl) pyrazolo[1,5-a]pyrazin-6-yl)-3,6-dihydropyridine-1 (2H)-carboxylate

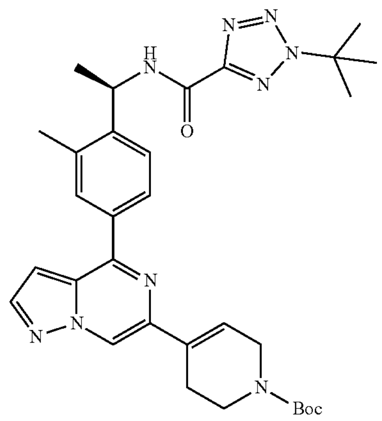 [SMILES: Cc1cc(-c2nc(C3=CCN(C(=O)OC(C)(C)C)CC3)cn3nccc23)ccc1[C@@H](C)NC(=O)c1nnn(C(C)(C)C)n1]

A mixture of (R)-2-(tert-butyl)-N-(1-(4-(6-chloropyrazolo[1,5-a]pyrazin-4-yl)-2-methylphenyl)ethyl)-2H-tetrazole-5-carboxamide (200 mg, 0.455 mmol, 1.0 eq), tert-butyl 4-(4,4,5,5-tetramethyl-1,3,2-dioxaborolan-2-yl)-3,6-dihydropyridine-1(2H)-carboxylate (211 mg, 0.683 mmol, 1.5 eq), $K_3PO_4$ (290 mg, 1.367 mmol, 3.0 eq), XPhos-Pd-G3 (38.6 mg, 0.046 mmol, 0.1 eq) in DMF (6 ml) and Water (1.5 ml) was stirred at 100° C. for 16 h. Concentrated in vacuo and the residue was purified by combi-flash eluted with DCM/MeOH=97:3 to give the title compound (205 mg, 77%) as a yellow solid. LC-MS: 586.57 ($M+H^+$).

Step 2: (R)-2-(tert-butyl)-N-(1-(2-methyl-4-(6-(1,2,3,6-tetrahydropyridin-4-yl)pyrazolo[1,5-a]pyrazin-4-yl)phenyl)ethyl)-2H-tetrazole-5-carboxamide hydrochloride

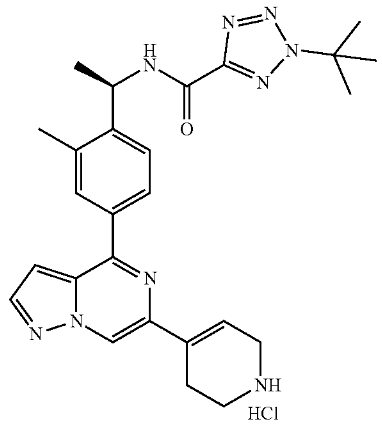 [SMILES: Cc1cc(-c2nc(C3=CCNCC3)cn3nccc23)ccc1[C@@H](C)NC(=O)c1nnn(C(C)(C)C)n1 ; Cl]

To a mixture of above obtained intermediate (205 mg, 0.350 mmol, 1.0 eq) in DCM (4 ml) was added 4M HCl/dioxane (4 ml). The reaction mixture was stirred at rt for 1 h. Concentrated to give the title compound (183 mg, 100%) as a yellow solid. LC-MS: 486.96 ($M+H^+$).

Step 3: tert-butyl (R)-4-(4-(4-(4-(1-(2-(tert-butyl)-2H-tetrazole-5-carboxamido)ethyl)-3-methylphenyl) pyrazolo[1,5-a]pyrazin-6-yl)-3,6-dihydropyridin-1 (2H)-yl)piperidine-1-carboxylate

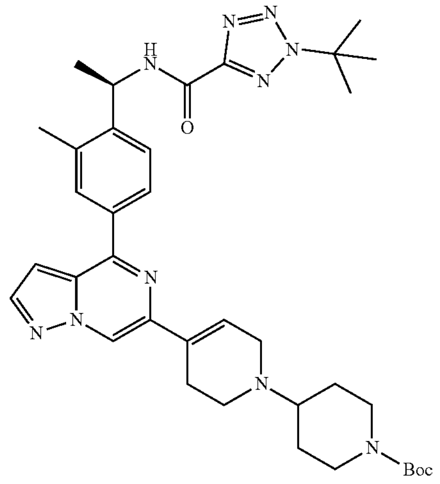 [SMILES: Cc1cc(-c2nc(C3=CCN(C4CCN(C(=O)OC(C)(C)C)CC4)CC3)cn3nccc23)ccc1[C@@H](C)NC(=O)c1nnn(C(C)(C)C)n1]

To a solution of above obtained intermediate (183 mg, 0.351 mmol, 1.0 eq), tert-butyl 4-oxopiperidine-1-carboxylate (69.8 mg, 0.351 mmol, 1.000), TEA (177 mg, 1.753 mmol, 5.0 eq) in DCM (5 ml) was added NaBH(OAc) 3 (223 mg, 1.052 mmol, 3.0 eq). The reaction was stirred at rt for 1 h. Diluted with DCM, washed with water, brine, dried over anhydrous $Na_2SO_4$ and Concentrated in vacuo. The residue was purified by flash chromatography eluted with DCM/MeOH-20:1 to give the title compound (180 mg, 77%) as a yellow solid. LC-MS: 670.29 ($M+H^+$).

Steps 4-5: (R)-2-(tert-butyl)-N-(1-(4-(6-(1-(1-((1-(4-(2,4-dioxotetrahydropyrimidin-1(2H)-yl)phenyl)piperidin-4-yl)methyl)piperidin-4-yl)-1,2,3,6-tetrahydropyridin-4-yl)pyrazolo[1,5-a]pyrazin-4-yl)-2-methylphenyl)ethyl)-2H-tetrazole-5-carboxamide

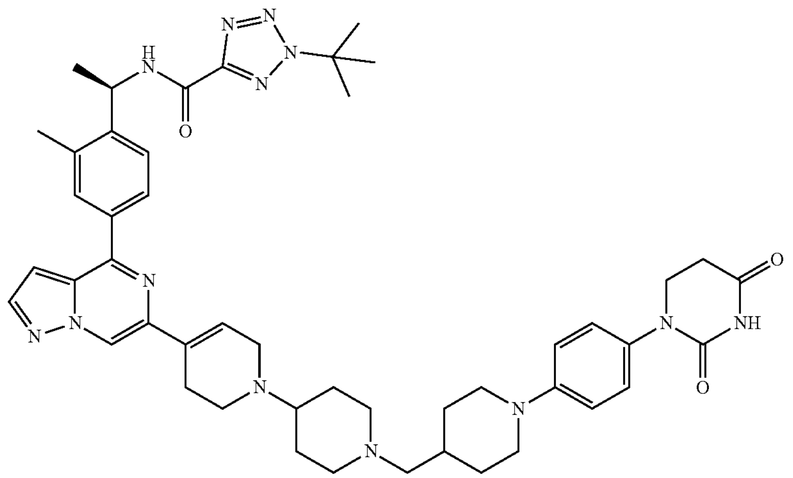

Following the synthesis of EXAMPLE 1, the title compound was obtained after preparative HPLC purification as a white solid. LC-MS: 854.75 (M+H$^+$). $^1$H NMR (400 MHz, DMSO-d$^6$) δ (ppm) 10.24 (s, 1H), 9.55 (s, J=7.6 Hz, 1H), 8.63 (s, 1H), 8.17 (d, J=2.4 Hz, 1H), 7.81-7.87 (m, 2H), 7.68 (d, J=8.4 Hz, 1H), 7.16-7.11 (m, 3H), 6.94-6.90 (m, 3H), 5.46-5.39 (m, 1H), 3.71-3.65 (m, 4H), 2.91-2.88 (m, 2H), 2.77-2.74 (m, 2H), 2.69-2.62 (m, 4H), 2.58-2.54 (m, 2H), 2.53 (s, 3H), 2.34-2.27 (m, 1H), 2.14 (d, J=7.2 Hz, 2H), 1.91-1.62 (m, 18H), 1.55-1.48 (m, 5H), 1.23-1.15 (m, 2H).

Example 41: (R)-3-(tert-butyl)-N-(1-(4-(6-(1-(4-(4-(4-(2,4-dioxotetrahydropyrimidin-1(2H)-yl)phenyl)piperazin-1-yl)cyclohexyl)-1H-pyrazol-4-yl)pyrazolo[1,5-a]pyrazin-4-yl)-2-methylphenyl)ethyl)-1,2,4-oxadiazole-5-carboxamide (Compound No. 230 and Compound No. 231)

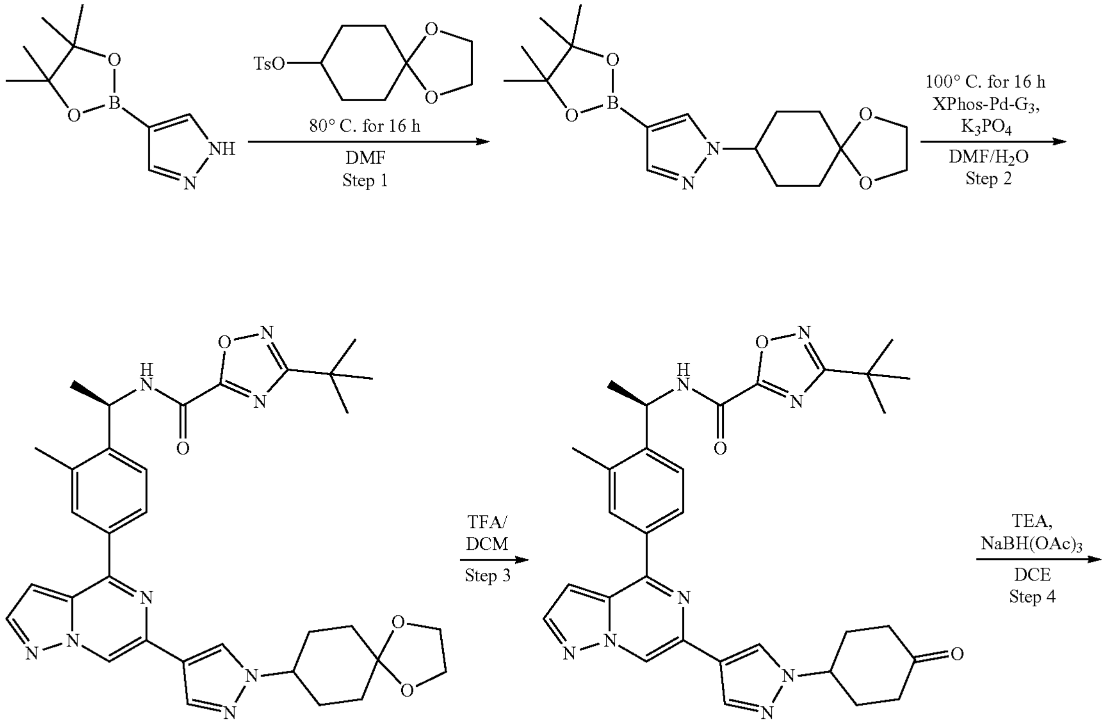

-continued

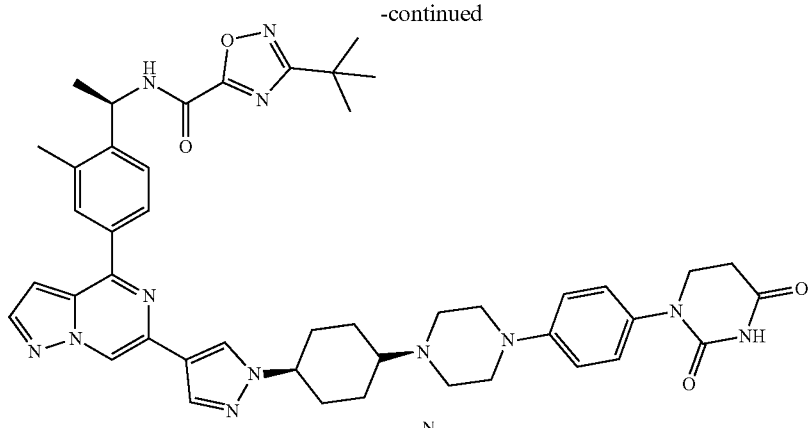

+

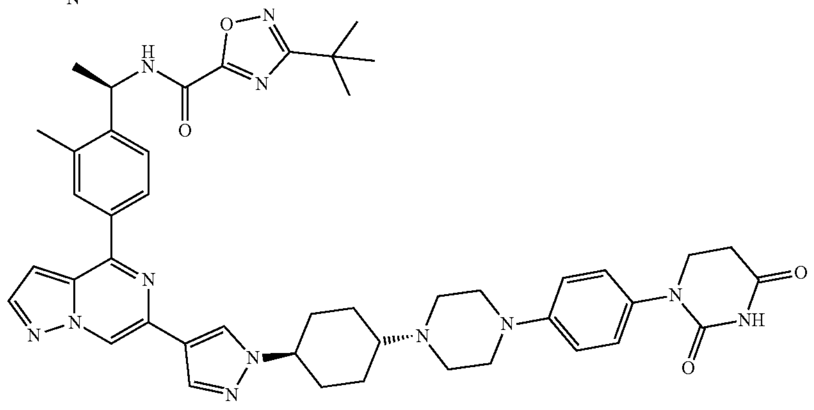

Step 1: 1-(1,4-dioxaspiro[4.5]decan-8-yl)-4-(4,4,5,5-tetramethyl-1,3,2-dioxaborolan-2-yl)-1H-pyrazole

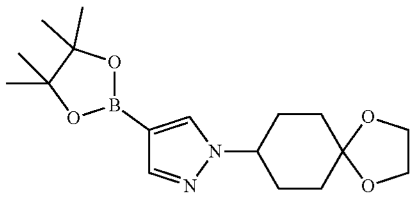 [SMILES: CC1(C)OB(c2cnn(C3CCC4(CC3)OCCO4)c2)OC1(C)C]

A mixture of 4-(4,4,5,5-tetramethyl-1,3,2-dioxaborolan-2-yl)-1H-pyrazole (311 mg, 1.6 mmol, 1.0 eq), 1,4-dioxaspiro[4.5]decan-8-yl 4-methylbenzenesulfonate (500 mg, 1.6 mmol, 1.0 eq) and $CS_2CO_3$ (1565 mg, 4.8 mmol, 3.0 eq) in dry DMF (10 ml) was stirred at 80° C. under Ar for 16 h. Diluted with EA, washed with water, brine, dried over anhydrous $Na_2SO_4$ and concentrated in vacuo. The residue was purified by flash chromatography eluted with Hex/EA=5:1 to give the title compound (100 mg, 18.7%) as a white solid. LC-MS: 335.6 (M+H$^+$).

Step 2 (R)—N-(1-(4-(6-(1-(1,4-dioxaspiro[4.5]decan-8-yl)-1H-pyrazol-4-yl)pyrazolo[1,5-a]pyrazin-4-yl)-2-methylphenyl)ethyl)-3-(tert-butyl)-1,2,4-oxadiazole-5-carboxamide

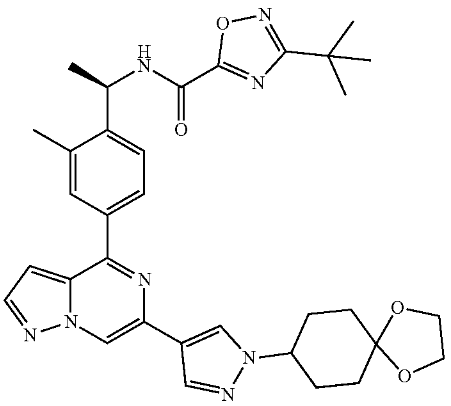 [SMILES: Cc1cc(-c2nc(-c3cnn(C4CCC5(CC4)OCCO5)c3)cn3nccc23)ccc1[C@@H](C)NC(=O)c1nc(C(C)(C)C)no1]

A mixture of tert-butyl (R)-3-(tert-butyl)-N-(1-(4-(6-chloropyrazolo[1,5-a]pyrazin-4-yl)-2-methylphenyl)ethyl)-1,2,4-oxadiazole-5-carboxamide (80 mg, 0.182 mmol, 1.0 eq), above obtained intermediate (97 mg, 0.292 mmol, 1.6 eq), $K_3PO_4$ (116 mg, 0.546 mmol, 3.0 eq) and XPhos-Pd-G3 (15 mg, 0.018 mmol, 0.1 eq) in DMF (4 ml) and water (1 ml) was stirred at 100° C. under Ar for 16 h. The solution was diluted with water, extracted with ethyl acetate for 3 times. The combined organic layers were washed with brine, dried over anhydrous $Na_2SO_4$ and concentrated in vacuo. The residue was purified by flash chromatography eluted with Hex/EA=1:1 to give the title compound (50 mg, 45%) as yellow oil. LC-MS: 611.5 ($M+H^+$).

Step 3: (R)-3-(tert-butyl)-N-(1-(2-methyl-4-(6-(1-(4-oxocyclohexyl)-1H-pyrazol-4-yl)pyrazolo[1,5-a]pyrazin-4-yl)phenyl)ethyl)-1,2,4-oxadiazole-5-carboxamide

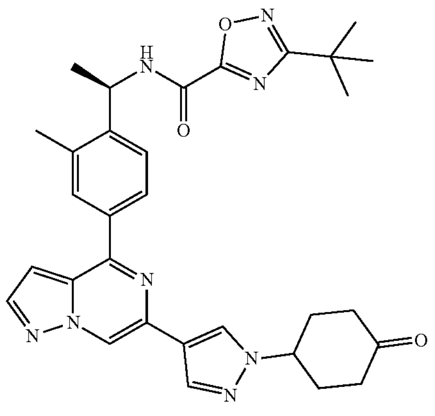 [SMILES: Cc1cc(-c2nc(-c3cnn(C4CCC(=O)CC4)c3)cn3nccc23)ccc1[C@@H](C)NC(=O)c1nc(C(C)(C)C)no1]

A mixture of above obtained intermediate (50 mg, 0.082 mmol, 1.0 eq) in TFA (1 ml) and DCM (4 ml) was stirred at rt under Ar for 16 h. Concentrated in vacuo to give the title compound (46 mg, 99%) as yellow oil. LC-MS: 567.3 ($M+H^+$).

Step 4: (R)-3-(tert-butyl)-N-(1-(4-(6-(1-(4-(4-(4-(2,4-dioxotetrahydropyrimidin-1(2H)-yl)phenyl) piperazin-1-yl)cyclohexyl)-1H-pyrazol-4-yl)pyrazolo[1,5-a]pyrazin-4-yl)-2-methylphenyl)ethyl)-1,2,4-oxadiazole-5-carboxamide

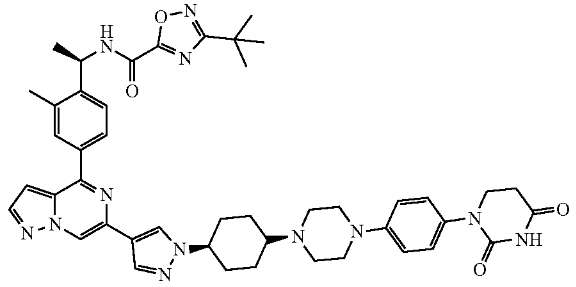

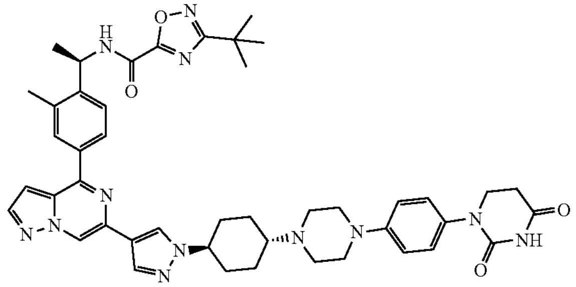

To a solution of above obtained intermediate (46 mg, 0.082 mmol, 1.0 eq), 1-(4-(piperazin-1-yl)phenyl)dihydropyrimidine-2,4(1H,3H)-dione (34 mg, 0.123 mmol, 1.5 eq) and TEA (33 mg, 0.328 mmol, 4.0 eq) in dry DCE (4 ml) was added NaBH(OAc) 3 (35 mg, 0.164 mmol, 2.0 eq) in portions. The reaction was stirred at rt for 16 h. The solution was quenched with water and extracted with DCM for 3 times. The organic layers were washed with brine, dried over anhydrous $Na_2SO_4$ and concentrated in vacuo. The residue was purified by pre-HPLC to give isomer 1 (4.0 mg, 6%) as a white solid and isomer 2 (6.1 mg, 9%) as a white solid. LC-MS: 825.6 ($M+H^+$).

Example 42: (R)-2-(tert-butyl)-N-(1-(4-(6-(4-(1-((1-(4-(2,4-dioxotetrahydropyrimidin-1(2H)-yl)phenyl) piperidin-4-yl)methyl)piperidin-4-yl) piperazin-1-yl) pyrazolo[1,5-a]pyrazin-4-yl)-2-methylphenyl)ethyl)-2H-tetrazole-5-carboxamide (Compound No. 232)

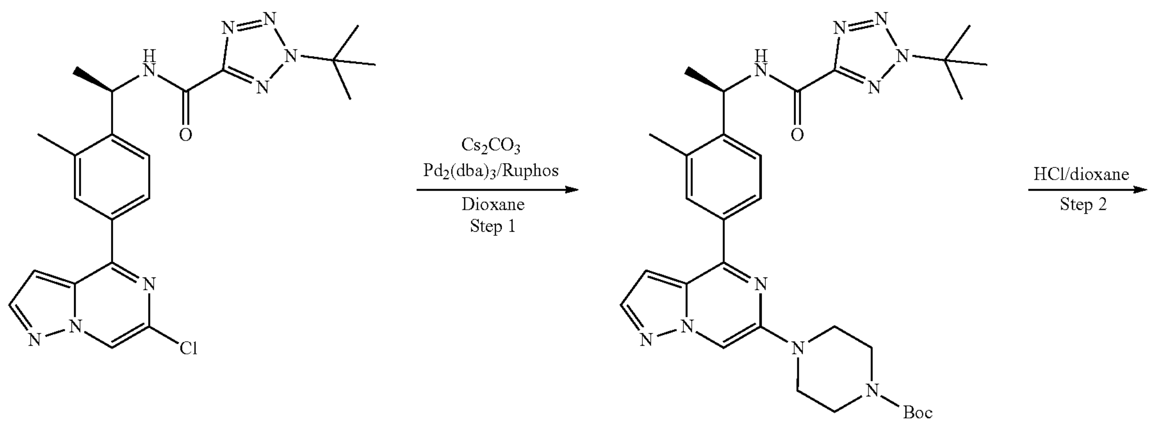

-continued
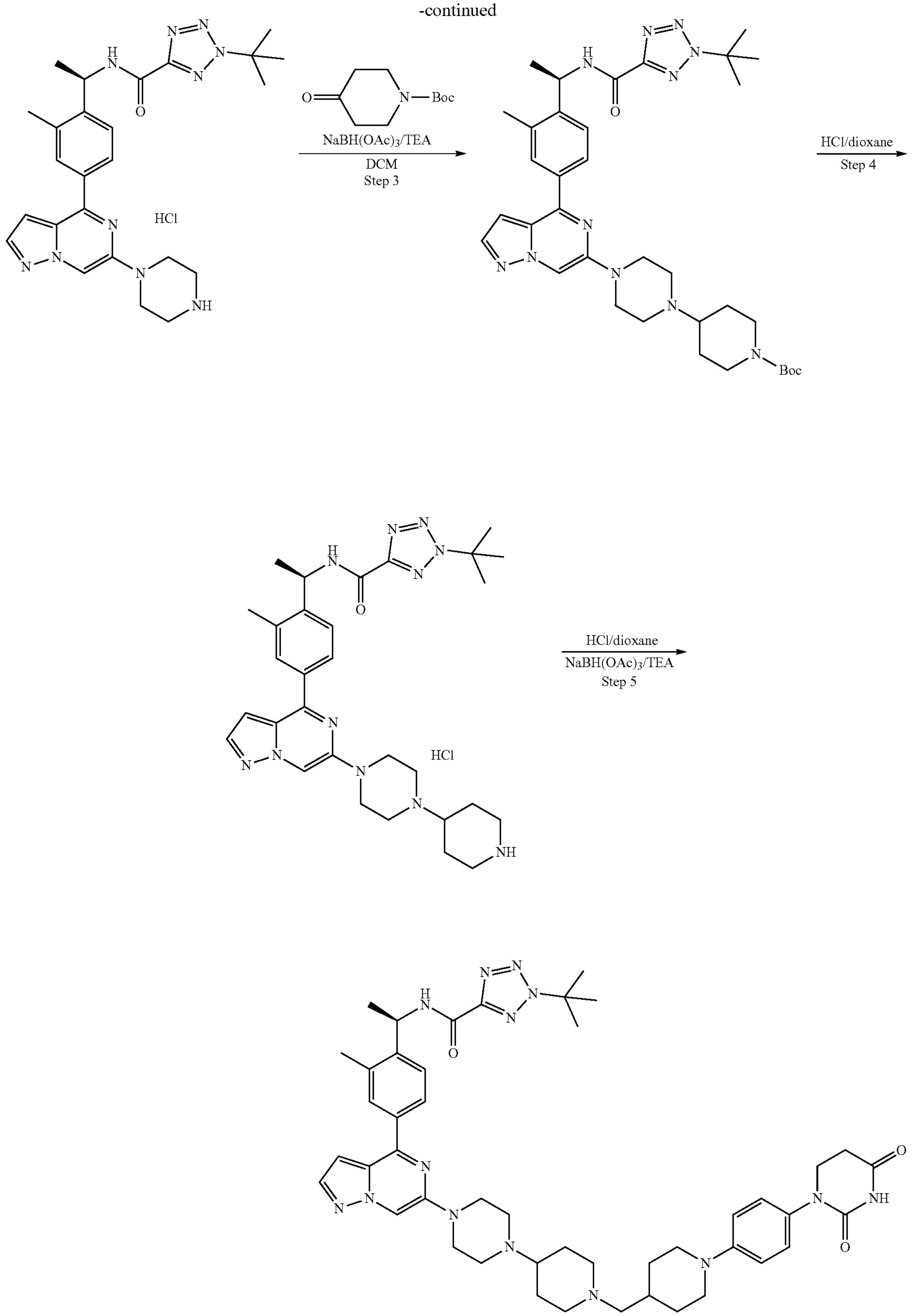

Step 1: tert-butyl (R)-4-(4-(4-(1-(2-(tert-butyl)-2H-tetrazole-5-carboxamido)ethyl)-3-methylphenyl) pyrazolo[1,5-a]pyrazin-6-yl)piperazine-1-carboxylate

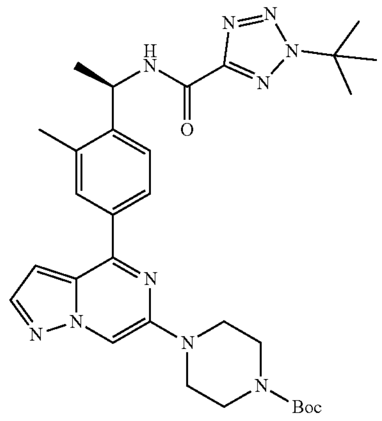 [SMILES: Cc1cc(-c2nc(N3CCN(C(=O)OC(C)(C)C)CC3)cn3nccc23)ccc1[C@@H](C)NC(=O)c1nnn(C(C)(C)C)n1]

A mixture of (R)-2-(tert-butyl)-N-(1-(4-(6-chloropyrazolo[1,5-a]pyrazin-4-yl)-2-methylphenyl)ethyl)-2H-tetrazole-5-carboxamide (200 mg, 0.456 mmol, 1.0 eq), $Pd_2(dba)_3$ (20.86 mg, 0.023 mmol, 0.05 eq), $Cs_2CO_3$ (445 mg, 1.367 mmol, 3.0 eq), tert-butyl piperazine-1-carboxylate (127 mg, 0.683 mmol, 1.5 eq) and RuPhos (21.26 mg, 0.046 mmol, 0.1 eq) in dry dioxane (4 ml) was stirred at 100° C. overnight under Ar. Filtered and concentrated in vacuo, the residue was purified by flash chromatography eluted with DCM/MeOH=20:1 to give the title compound (267 mg, 100%) as a yellow solid. LC-MS: 589.57 ($M+H^+$).

Steps 2-5: (R)-2-(tert-butyl)-N-(1-(4-(6-(4-(1-((1-(4-(2,4-dioxotetrahydropyrimidin-1(2H)-yl)phenyl) piperidin-4-yl)methyl)piperidin-4-yl) piperazin-1-yl) pyrazolo[1,5-a]pyrazin-4-yl)-2-methylphenyl)ethyl)-2H-tetrazole-5-carboxamide

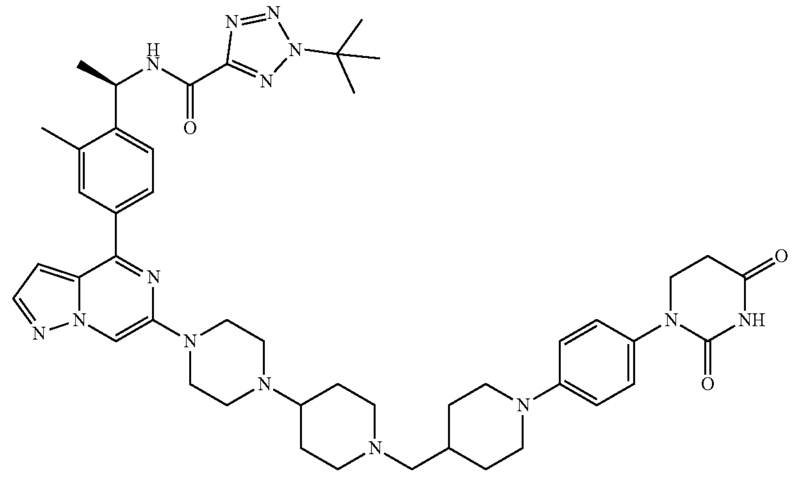

Following the synthesis of EXAMPLE 3, the title compound was obtained after preparative HPLC purification as a white solid. LC-MS: 857.83 ($M+H^+$). $^1H$ NMR (400 MHz, DMSO-$d^6$) δ (ppm) 10.24 (s, 1H), 9.54 (d, J=8.0 Hz, 1H), 8.07 (s, 1H), 7.98 (d, J=2.4 Hz, 1H), 7.87-7.82 (m, 2H), 7.66 (d, J=8.0 Hz, 1H), 7.12 (d, J=8.8 Hz, 2H), 7.01 (d, J=2.4 Hz, 1H), 6.91 (d, J=8.8 Hz, 2H), 5.45-5.38 (m, 1H), 3.70-3.65 (m, 4H), 3.38-3.35 (m, 2H), 2.91-2.88 (m, 2H), 2.69-2.61 (m, 8H), 2.52 (s, 3H), 2.27-2.13 (m, 3H), 1.90-1.62 (m, 18H), 1.56-1.43 (m, 5H), 1.23-1.14 (m, 2H).

Example 43: (R)-3-(tert-butyl)-N-(1-(4-(7-(6-(4-((1-(4-(2,4-dioxotetrahydropyrimidin-1(2H)-yl)phenyl)piperidin-4-yl)methyl)piperazin-1-yl)pyridin-3-yl)imidazo[1,2-c]pyrimidin-5-yl)-2-(hydroxymethyl)phenyl)ethyl)-1,2,4-oxadiazole-5-carboxamide (Compound No. 233)

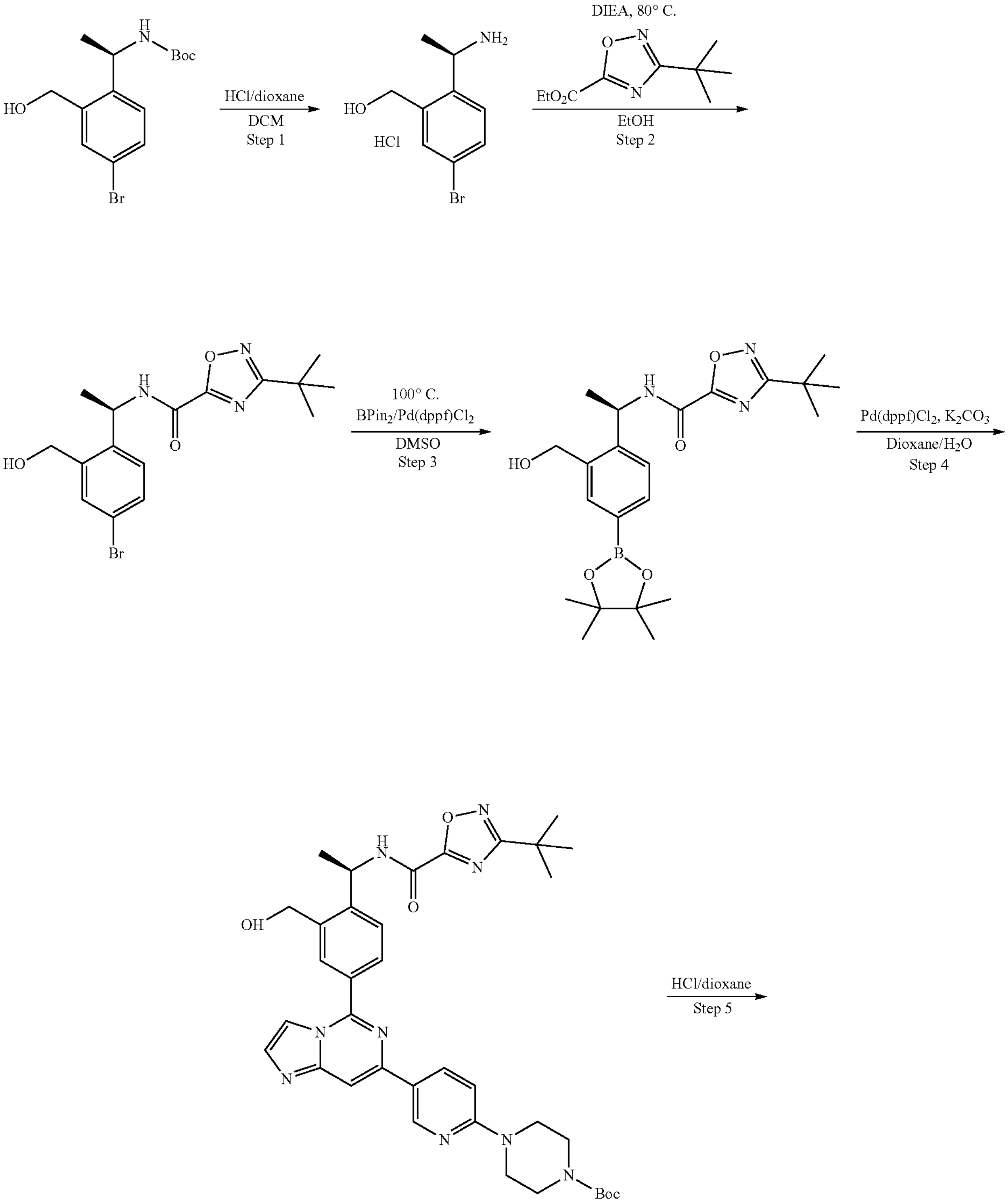

-continued

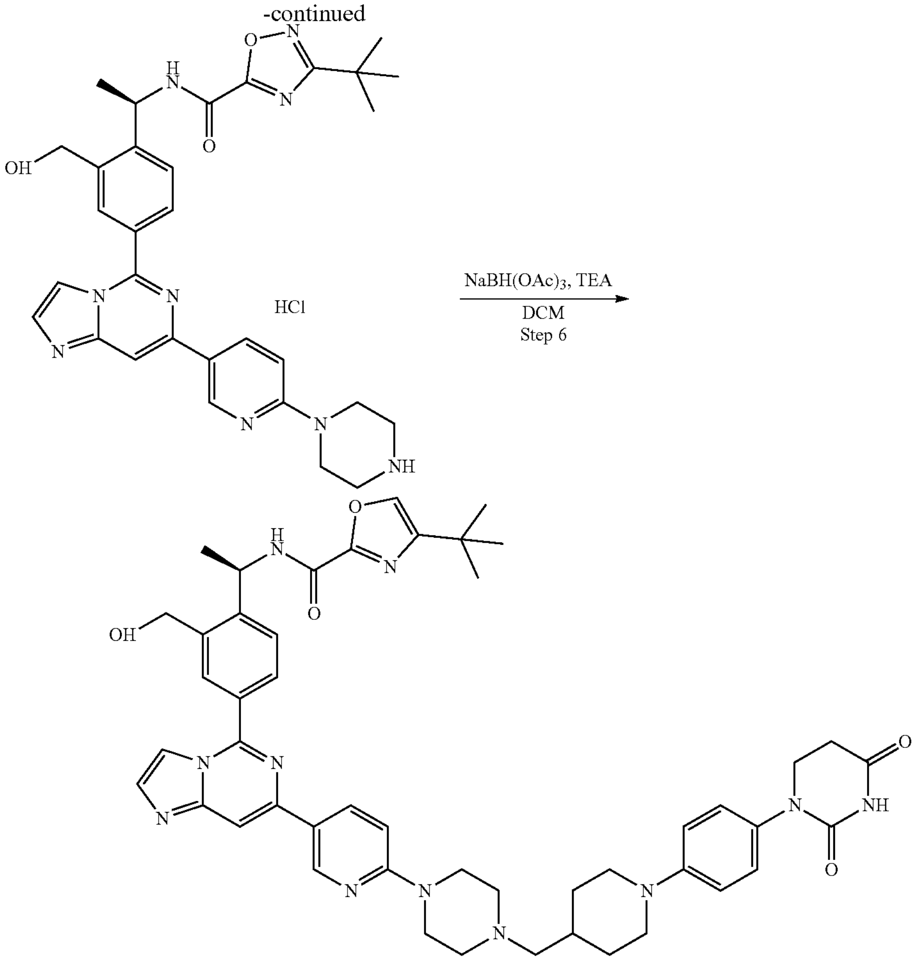

Step 1: (R)-(2-(1-aminoethyl)-5-bromophenyl) methanol hydrochloride

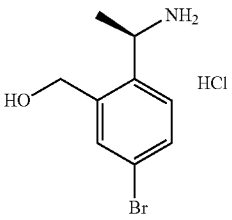

A mixture of tert-butyl (R)-(1-(4-bromo-2-(hydroxymethyl)phenyl)ethyl)carbamate (500 mg, 1.514 mmol, 1.0 eq) in DCM (4 ml) and 4M HCl/dioxane (2 ml) was stirred at rt for 1 h. Concentrated to give the title compound (404 mg, 100%) as a white solid. LC-MS: 230.15 (M+H$^+$).

Step 2: (R)—N-(1-(4-bromo-2-(hydroxymethyl) phenyl)ethyl)-3-(tert-butyl)-1,2,4-oxadiazole-5-carboxamide

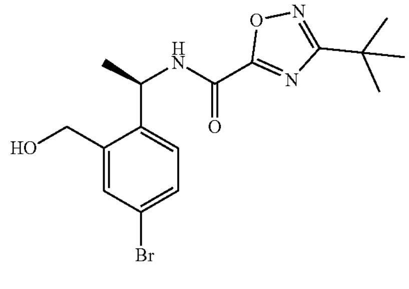 [SMILES: C[C@@H](NC(=O)c1nc(C(C)(C)C)no1)c1ccc(Br)cc1CO]

A mixture of above obtained intermediate (404 mg, 1.516 mmol, 1.0 eq), ethyl 3-(tert-butyl)-1,2,4-oxadiazole-5-carboxylate (316 mg, 1.516 mmol, 1.0 eq) and DIEA (979 mg, 7.58 mmol, 5) in Ethanol (8 ml) was stirred at 80° C. under Ar for 16 h. Concentrated in vacuo, the residue was purified by flash chromatography eluted with DCM/MeOH=19:1 to give the title compound (313 mg, 54.0%) as a white solid. LC-MS: 382.21 (M+H$^+$).

Step 3: (R)-3-(tert-butyl)-N-(1-(2-(hydroxymethyl)-4-(4,4,5,5-tetramethyl-1,3,2-dioxaborolan-2-yl)phenyl)ethyl)-1,2,4-oxadiazole-5-carboxamide

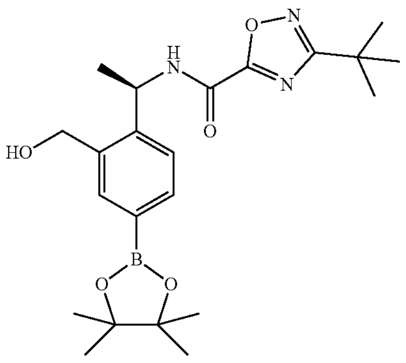 [SMILES: C[C@@H](NC(=O)c1nc(C(C)(C)C)no1)c1ccc(B2OC(C)(C)C(C)(C)O2)cc1CO]

A mixture of above obtained intermediate (313 mg, 0.819 mmol, 1.0 eq), 4,4,4',4',5,5,5',5'-octamethyl-2,2'-bi (1,3,2-dioxaborolane) (270 mg, 1.064 mmol, 1.3 eq), potassium acetate (241 mg, 2.456 mmol, 3.0 eq) and $PdCl_2$(dppf) (59.9 mg, 0.082 mmol, 0.1 eq) in DMSO (10 ml) under Ar was stirred at 100° C. for 4 h. Water was added to the reaction mixture followed by extraction with EA for 3 times. The combined organic layers were washed with brine, dried over anhydrous $Na_2SO_4$ and concentrated. The residue was purified by flash chromatography eluted with DCM/MeOH=20:1 to give the title compound (220 mg, 62.6%) as a black solid. LC-MS: 430.47 ($M+H^+$).

Step 4-6: (R)-3-(tert-butyl)-N-(1-(4-(7-(6-(4-((1-(4-(2,4-dioxotetrahydropyrimidin-1(2H)-yl)phenyl) piperidin-4-yl)methyl)piperazin-1-yl)pyridin-3-yl) imidazo[1,2-c]pyrimidin-5-yl)-2-(hydroxymethyl) phenyl)ethyl)-1,2,4-oxadiazole-5-carboxamide

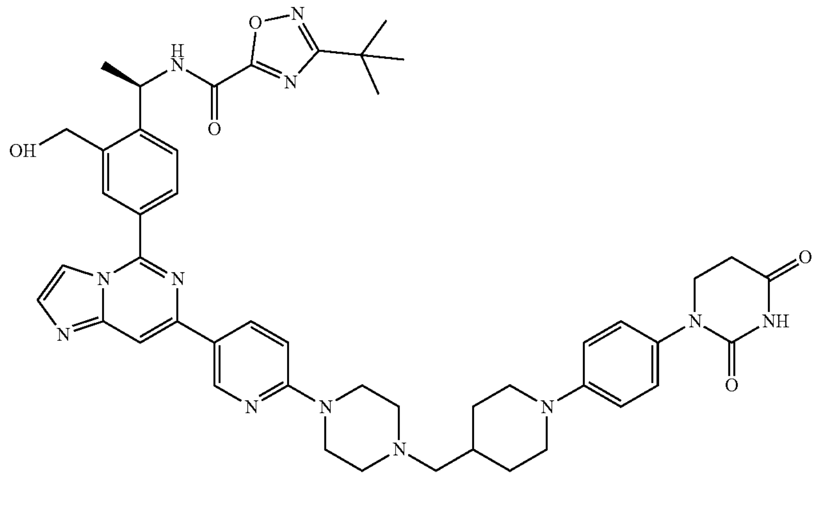 [SMILES: C[C@@H](NC(=O)c1nc(C(C)(C)C)no1)c1ccc(-c2nc(-c3ccc(N4CCN(CC5CCN(c6ccc(N7CCC(=O)NC7=O)cc6)CC5)CC4)nc3)cc3nccn23)cc1CO]

Following the synthesis of EXAMPLE 3, the title compound was obtained after preparative HPLC purification as a white solid. LC-MS: 867.78 ($M+H^+$). $^1H$ NMR (400 MHz, DMSO-$d^6$) δ (ppm) 10.24 (s, 1H), 10.01 (d, J=7.6 Hz, 1H), 8.98 (d, J=2.4 Hz, 1H), 8.32 (dd, J=8.8, 2.4 Hz, 1H), 8.06-7.96 (m, 4H), 7.79 (d, J=8.0 Hz, 1H), 7.68 (d, J=1.2 Hz, 1H), 7.13 (d, J=8.8 Hz, 2H), 6.93 (d, J=8.8 Hz, 3H), 5.46-5.40 (m, 2H), 4.90-4.76 (m, 2H), 3.71-3.60 (m, 8H), 2.69-2.64 (m, 5H), 2.49-2.45 (m, 3H), 2.22 (d, J=7.2 Hz, 2H), 1.84-1.73 (m, 3H), 1.58 (d, J=7.2 Hz, 3H), 1.37 (s, 9H), 1.27-1.17 (m, 2H).

Example 44: (R)-2-(tert-butyl)-N-(1-(4-(3-chloro-6-(6-(4-((1-(4-(2,4-dioxotetrahydropyrimidin-1(2H)-yl)phenyl)piperidin-4-yl)methyl)piperazin-1-yl)pyridin-3-yl)pyrazolo[1,5-a]pyrazin-4-yl)-2-methylphenyl)ethyl)-2H-tetrazole-5-carboxamide (Compound No. 234)

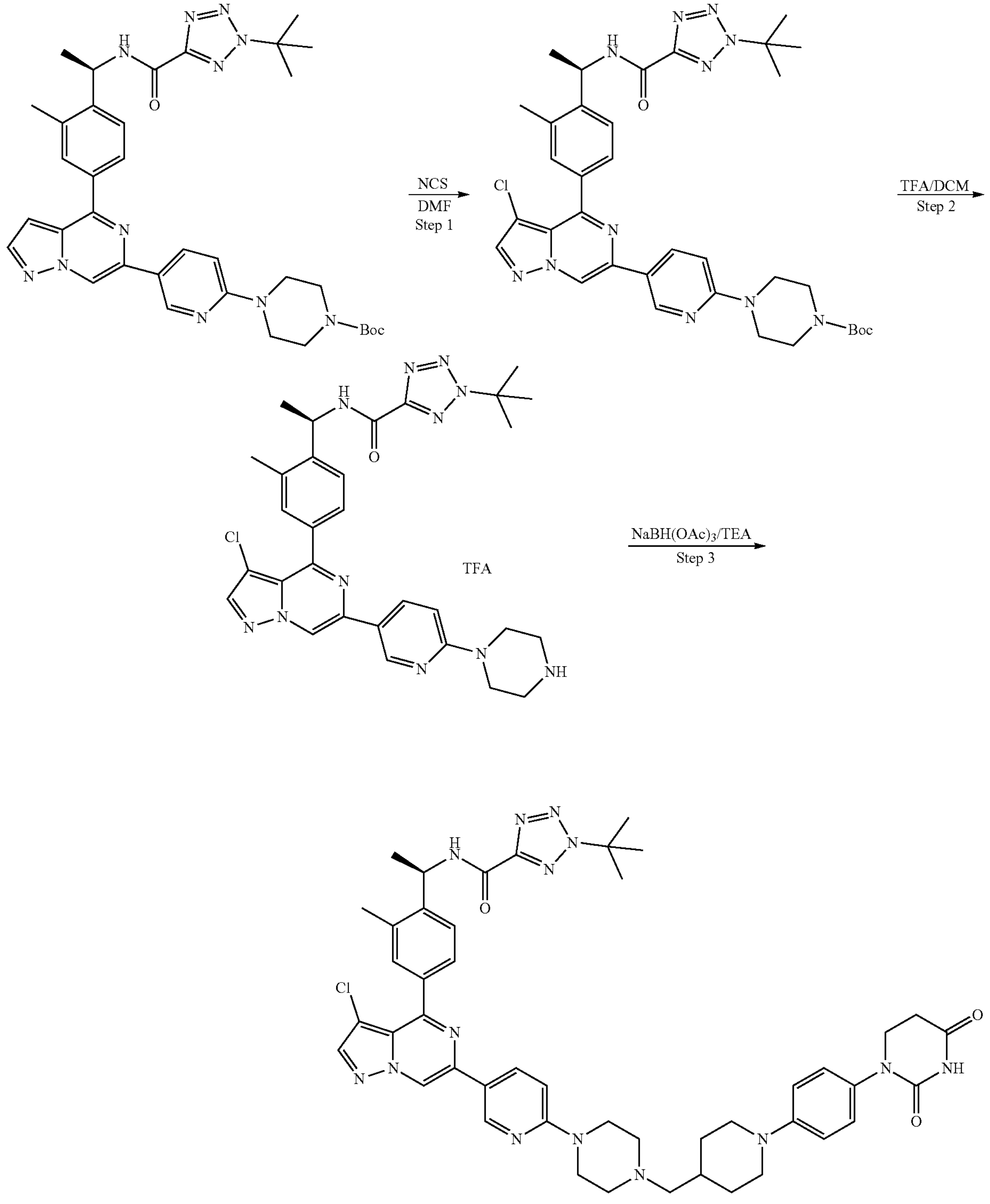

Step 1: tert-butyl (R)-4-(5-(4-(4-(1-(2-(tert-butyl)-2H-tetrazole-5-carboxamido)ethyl)-3-methylphenyl)-3-chloropyrazolo[1,5-a]pyrazin-6-yl)pyridin-2-yl)piperazine-1-carboxylate

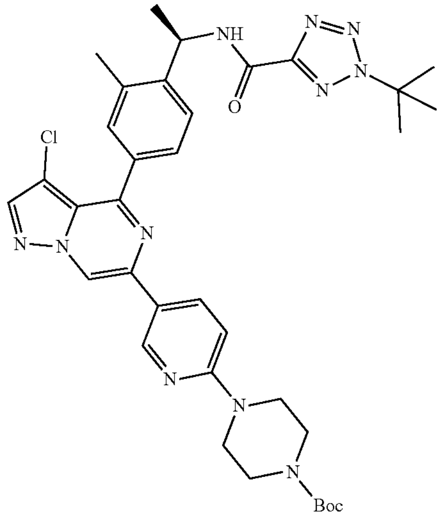 [SMILES: Cc1cc(-c2nc(-c3ccc(N4CCN(C(=O)OC(C)(C)C)CC4)nc3)cn3ncc(Cl)c23)ccc1[C@@H](C)NC(=O)c1nnn(C(C)(C)C)n1]

To a mixture of tert-butyl (R)-4-(5-(4-(4-(1-(2-(tert-butyl)-2H-tetrazole-5-carboxamido)ethyl)-3-methylphenyl)pyrazolo[1,5-a]pyrazin-6-yl)pyridin-2-yl)piperazine-1-carboxylate (150 mg, 0.225 mmol, 1.0 eq) in dry DMF (2 ml) was added NCS (33.1 mg, 0.248 mmol, 1.1 eq). The mixture was stirred at rt overnight under Ar. Diluted with EA, washed with water, brine, dried over anhydrous $Na_2SO_4$ and concentrated in vacuo. The residue was purified by flash chromatography eluted with DCM/MeOH=50:1 to give the title compound (110 mg, 69.7%) as a yellow oil. LC-MS: 701.11 ($M+H^+$).

Step 2-3: (R)-2-(tert-butyl)-N-(1-(4-(3-chloro-6-(6-(4-((1-(4-(2,4-dioxotetrahydropyrimidin-1(2H)-yl)phenyl)piperidin-4-yl)methyl)piperazin-1-yl)pyridin-3-yl)pyrazolo[1,5-a]pyrazin-4-yl)-2-methylphenyl)ethyl)-2H-tetrazole-5-carboxamide

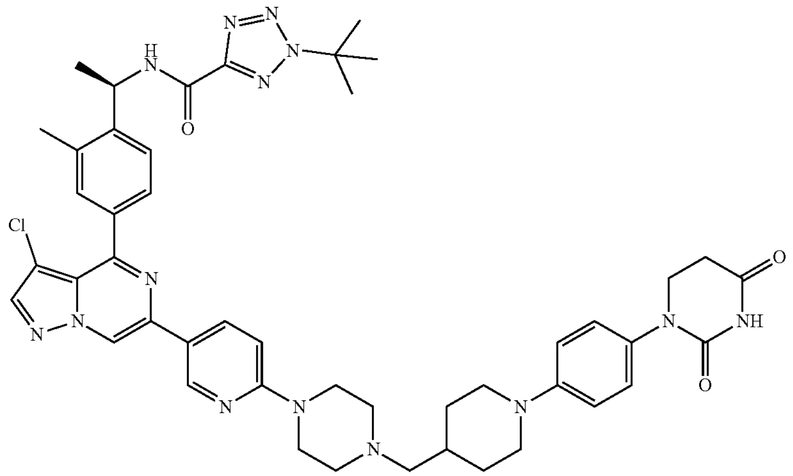 [SMILES: Cc1cc(-c2nc(-c3ccc(N4CCN(CC5CCN(c6ccc(N7CCC(=O)NC7=O)cc6)CC5)CC4)nc3)cn3ncc(Cl)c23)ccc1[C@@H](C)NC(=O)c1nnn(C(C)(C)C)n1]

Following the synthesis of EXAMPLE 3, the title compound was obtained after preparative HPLC purification as a white solid. LC-MS: 885.84 (M+H$^+$). $^1$H NMR (400 MHz, DMSO-d$^6$) δ (ppm) 10.24 (s, 1H), 9.53 (d, J=8.0 Hz, 1H), 9.31 (s, 1H), 8.88 (d, J=2.4 Hz, 1H), 8.34 (s, 1H), 8.26 (dd, J=8.8, 2.4 Hz, 1H), 1.68-1.58 (m, 3H), 7.13 (d, J=8.8 Hz, 2H), 6.92 (d, J=8.8 Hz, 3H), 5.49-5.42 (m, 1H), 3.71-3.58 (m, 8H), 2.69-2.64 (m, 4H), 2.51 (s, 3H), 2.49-2.45 (m, 4H), 2.22 (d, J=7.2 Hz, 2H), 1.83-1.80 (m, 3H), 1.73 (s, 9H), 1.55 (d, J=6.8 Hz, 3H), 1.27-1.19 (m, 2H).

Example 45: (R)-2-(tert-butyl)-N-(1-(4-(6-(4-(4-((1-(4-(2,4-dioxotetrahydropyrimidin-1(2H)-yl)phenyl)piperidin-4-yl)methyl)piperazin-1-yl)piperidin-1-yl)pyrazolo[1,5-a]pyrazin-4-yl)-2-methylphenyl)ethyl)-2H-tetrazole-5-carboxamide (Compound No. 238)

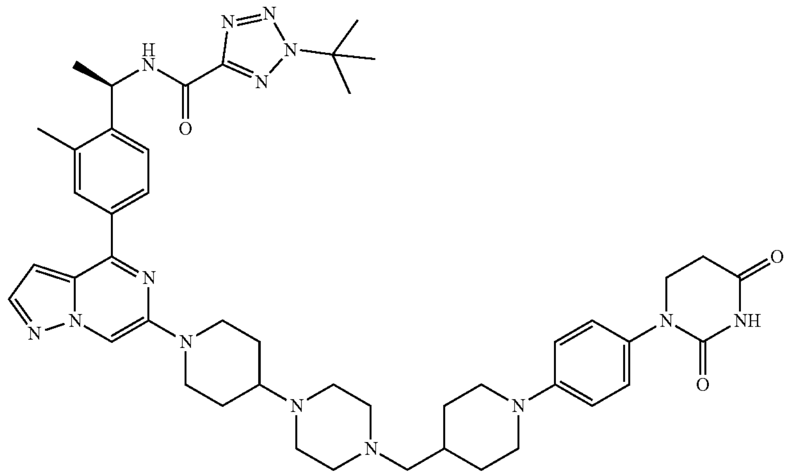

Following the synthesis of EXAMPLE 42, the title compound was obtained after preparative HPLC purification as a white solid. LC-MS: 857.79 (M+H$^+$). $^1$H NMR (400 MHz, DMSO-d$^6$) δ (ppm) 10.24 (s, 1H), 9.53 (d, 7.6 Hz, 1H), 8.09 (s, 1H), 7.97 (d, J=2.0 Hz, 1H), 7.86 (d, J=8.0 Hz, 1H), 7.82 (s, 1H), 7.66 (d, J=8.0 Hz, 1H), 7.12 (d, J=8.4 Hz, 2H), 7.00 (s, 1H), 6.91 (d, J=8.4 Hz, 2H), 5.44-5.37 (m, 1H), 4.16-4.13 (m, 2H), 3.70-3.64 (m, 4H), 2.77-2.38 (m, 16H), 2.17-2.12 (m, 2H), 1.89-1.53 (m, 21H), 1.23-1.14 (m, 2H).

Example 46: (R)-2-(tert-butyl)-N-(1-(4-(6-(6-(4-(4-(4-(2,4-dioxotetrahydropyrimidin-1(2H)-yl)phenyl)piperazin-1-yl)piperidin-1-yl)pyridin-3-yl)pyrazolo[1,5-a]pyrazin-4-yl)-2-methylphenyl)ethyl)-2H-tetrazole-5-carboxamide (Compound No. 239)

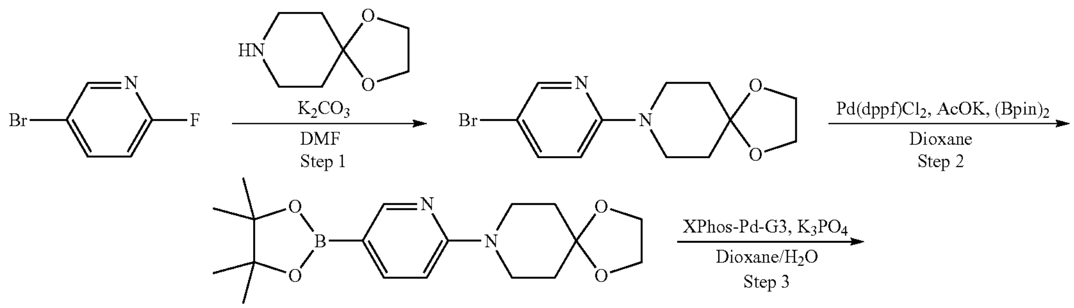

-continued
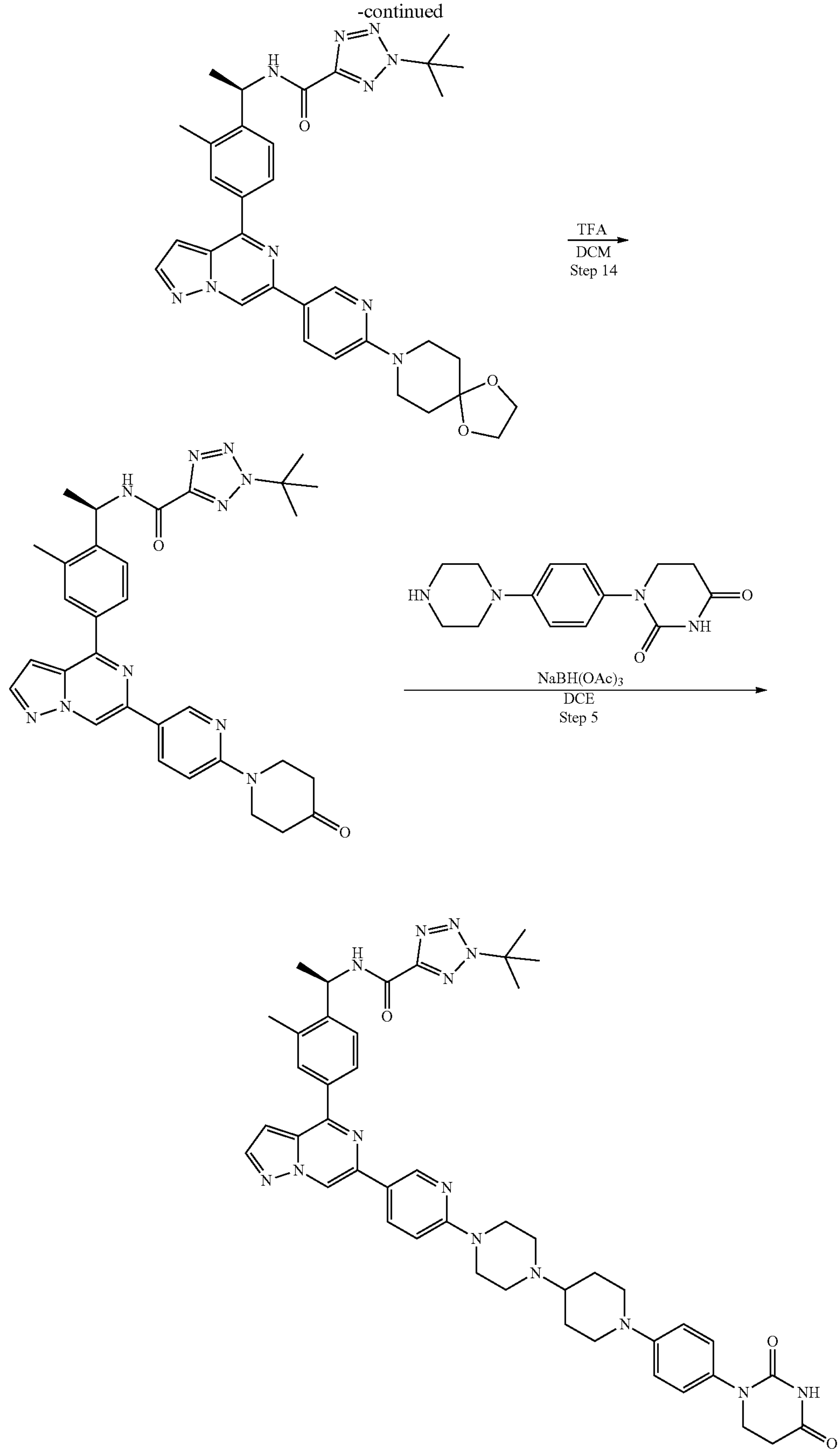

Step 1: 8-(5-bromopyridin-2-yl)-1,4-dioxa-8-azaspiro[4.5]decane

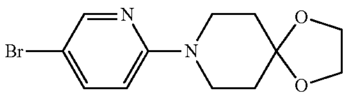 [SMILES: Brc1ccc(N2CCC3(CC2)OCCO3)nc1]

A mixture of 5-bromo-2-fluoropyridine (1.0 g, 5.68 mmol, 1.0 eq), 1,4-dioxa-8-azaspiro[4.5]decane (976 mg, 6.82 mmol, 1.2 eq) and $K_2CO_3$ (2.36 g, 17.05 mmol, 3.0 eq) in dry DMF (15 ml) was stirred at 100° C. under Ar for 16 h. The solution was diluted with water, extracted with ethyl acetate for 3 times. The combined organic layers were washed with brine, dried over anhydrous $Na_2SO_4$ and concentrated in vacuo. The residue was purified by flash chromatography eluted with Hex/EA-3:1 to give the title compound (1.2 g, 70.6%) as yellow oil. LC-MS: 299.2 ($M+H^+$).

Step 2: 8-(5-(4,4,5,5-tetramethyl-1,3,2-dioxaborolan-2-yl)pyridin-2-yl)-1,4-dioxa-8-azaspiro[4.5]decane

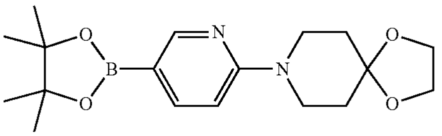 [SMILES: CC1(C)OB(c2ccc(N3CCC4(CC3)OCCO4)nc2)OC1(C)C]

A mixture of above obtained intermediate (500 mg, 1.671 mmol, 1.0 eq), 4,4,4',4',5,5,5',5'-octamethyl-2,2'-bi (1,3,2-dioxaborolane) (637 mg, 2.506 mmol, 1.5 eq), KOAc (491 mg, 5.012 mmol, 3.0 eq) and $PdCl_2$(dppf) (122 mg, 0.167 mmol, 0.1 eq) in dry Dioxane (20 ml) was stirred at 100° C. under Ar for 2 h. Water was added and extracted with EA for 3 times. The combined organic layers were washed with brine, dried over anhydrous $Na_2SO_4$ and concentrated in vacuo. The residue was purified by flash chromatography eluted with Hex/EA=3:1 to give the title compound (400 mg, 69.1%) as yellow oil. LC-MS: 347.3 ($M+H^+$).

Step 3: N-(1-(4-(6-(6-(1,4-dioxa-8-azaspiro[4.5]decan-8-yl)pyridin-3-yl)pyrazolo[1,5-a]pyrazin-4-yl)-2-methylphenyl)ethyl)-2-(tert-butyl)-2H-tetrazole-5-carboxamide

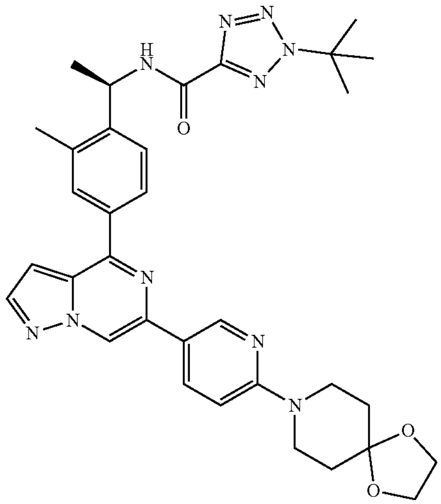 [SMILES: Cc1cc(-c2nc(-c3ccc(N4CCC5(CC4)OCCO5)nc3)cn3nccc23)ccc1[C@@H](C)NC(=O)c1nnn(C(C)(C)C)n1]

A mixture of (R)-2-(tert-butyl)-N-(1-(4-(6-chloropyrazolo[1,5-a]pyrazin-4-yl)-2-methylphenyl)ethyl)-2H-tetrazole-5-carboxamide (420 mg, 0.957 mmol, 1.0 eq), above obtained intermediate (398 mg, 1.148 mmol, 1.2 eq), $K_3PO_4$ (609 mg, 2.87 mmol, 3.0 eq) and XPhos-Pd-G3 (81 mg, 0.096 mmol, 0.1 eq) in DMF (10 ml) and water (2 ml) was stirred at 100° C. under Ar for 3 h. The reaction mixture was diluted with water, extracted with ethyl acetate for 3 times. The combined organic layers were washed with brine, dried over anhydrous $Na_2SO_4$ and concentrated in vacuo. The residue was purified by flash chromatography eluted with Hex/EA=1:1 to give the title compound (400 mg, 45%) as a yellow solid. LC-MS: 623.5 ($M+H^+$).

Step 4: (R)-2-(tert-butyl)-N-(1-(2-methyl-4-(6-(6-(4-oxopiperidin-1-yl)pyridin-3-yl)pyrazolo[1,5-a]pyrazin-4-yl)phenyl)ethyl)-2H-tetrazole-5-carboxamide

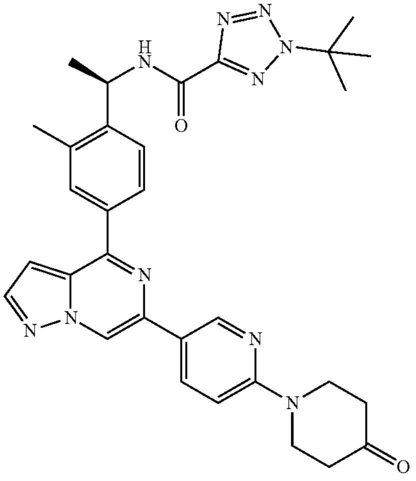 [SMILES: Cc1cc(-c2nc(-c3ccc(N4CCC(=O)CC4)nc3)cn3nccc23)ccc1[C@@H](C)NC(=O)c1nnn(C(C)(C)C)n1]

A mixture of above obtained intermediate (400 mg, 0.642 mmol, 1.0 eq) in TFA (2 ml) and DCM (10 ml) was stirred at rt under Ar for 16 h. Concentrated and based with $NH_3$/MeOH. Concentrated in vacuo, the residue was purified by flash chromatography eluted with DCM/MeOH=20:1 to give the title compound (370 mg, 99%) as a yellow solid. LC-MS: 579.5 (M+H$^+$).

Step 5 (R)-2-(tert-butyl)-N-(1-(2-methyl-4-(6-(6-(4-oxopiperidin-1-yl)pyridin-3-yl)pyrazolo[1,5-a]pyrazin-4-yl)phenyl)ethyl)-2H-tetrazole-5-carboxamide

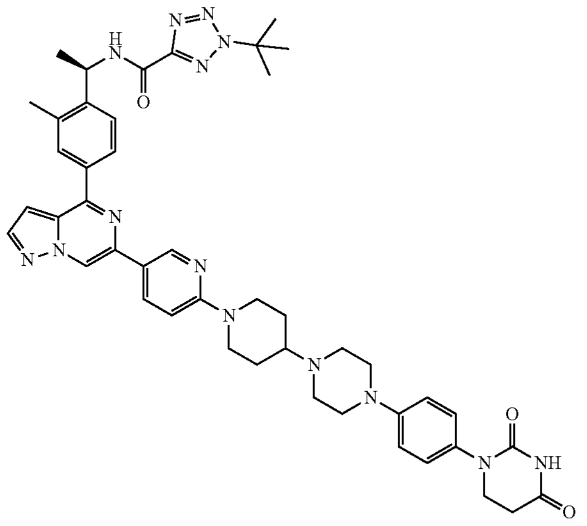 [SMILES: Cc1cc(-c2nc(-c3ccc(N4CCC(N5CCN(c6ccc(N7CCC(=O)NC7=O)cc6)CC5)CC4)nc3)cn3nccc23)ccc1[C@@H](C)NC(=O)c1nnn(C(C)(C)C)n1]

A mixture of 1-(4-(piperazin-1-yl)phenyl)dihydropyrimidine-2,4(1H,3H)-dione (71 mg, 0.259 mmol, 1.0 eq), above obtained intermediate (150 mg, 0.259 mmol, 1.0 eq), AcOH (156 mg, 2.59 mmol, 10.0 eq), anhydrous $Na_2SO_4$ (368 mg, 2.59 mmol, 10.0 eq) and NaBH(OAc) 3 (164 mg, 0.777 mmol, 3.0 eq) in DCE (10 ml) was stirred at 80° C. under Ar for 16 h. The mixture was quenched with water and extracted with DCM for 3 times. The organic layers were washed with brine, dried over anhydrous $Na_2SO_4$ and concentrated in vacuo. The residue was purified by pre-HPLC to give the title compound (19.2 mg, 9%) as a yellow solid. LC-MS: 837.6 (M+H$^+$). $^1$H NMR (400 MHz, DMSO-d$^6$) δ (ppm) 10.25 (s, 1H), 9.57 (d, J=7.6 Hz, 1H), 9.27 (s, 1H), 8.94 (d, J=2.4 Hz, 1H), 8.33-8.25 (m, 1H), 8.20 (d, J=2.0 Hz, 1H), 7.98 (d, J=8.0 Hz, 1H), 7.95 (s, 1H), 7.71 (d, J=8.4 Hz, 1H), 7.19 (d, J=2.0 Hz, 1H), 7.14 (d, J=8.8 Hz, 2H), 6.97 (d, J=8.8 Hz, 1H), 6.92 (d, J=8.8 Hz, 2H), 5.45-5.40 (m, 1H), 4.50-4.38 (m, 2H), 3.75-3.65 (m, 2H), 3.15-3.05 (m, 4H), 2.95-2.85 (m, 2H), 2.70-2.60 (m, 6H), 2.55 (s, 3H), 1.95-1.85 (m, 2H), 1.73 (s, 9H), 1.71-1.67 (m, 1H), 1.55 (d, J=7.2 Hz, 3H), 1.50-1.35 (m, 2H).

Example 47: (R)-2-(tert-butyl)-N-(1-(4-(6-(6-(4-(1-(4-(2,4-dioxotetrahydropyrimidin-1(2H)-yl)phenyl)piperidin-4-yl) piperazin-1-yl)pyridin-3-yl)pyrazolo[1,5-a]pyrazin-4-yl)-2-methylphenyl)ethyl)-2H-tetrazole-5-carboxamide (Compound No. 246)

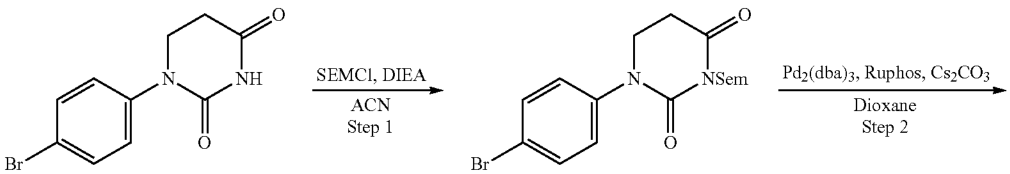

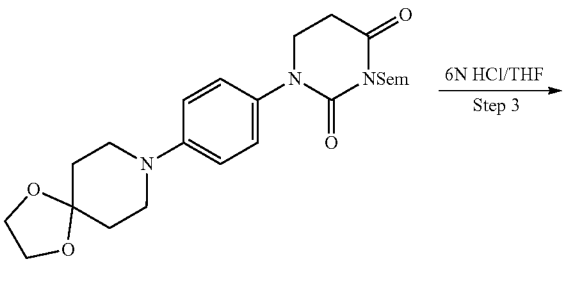

-continued
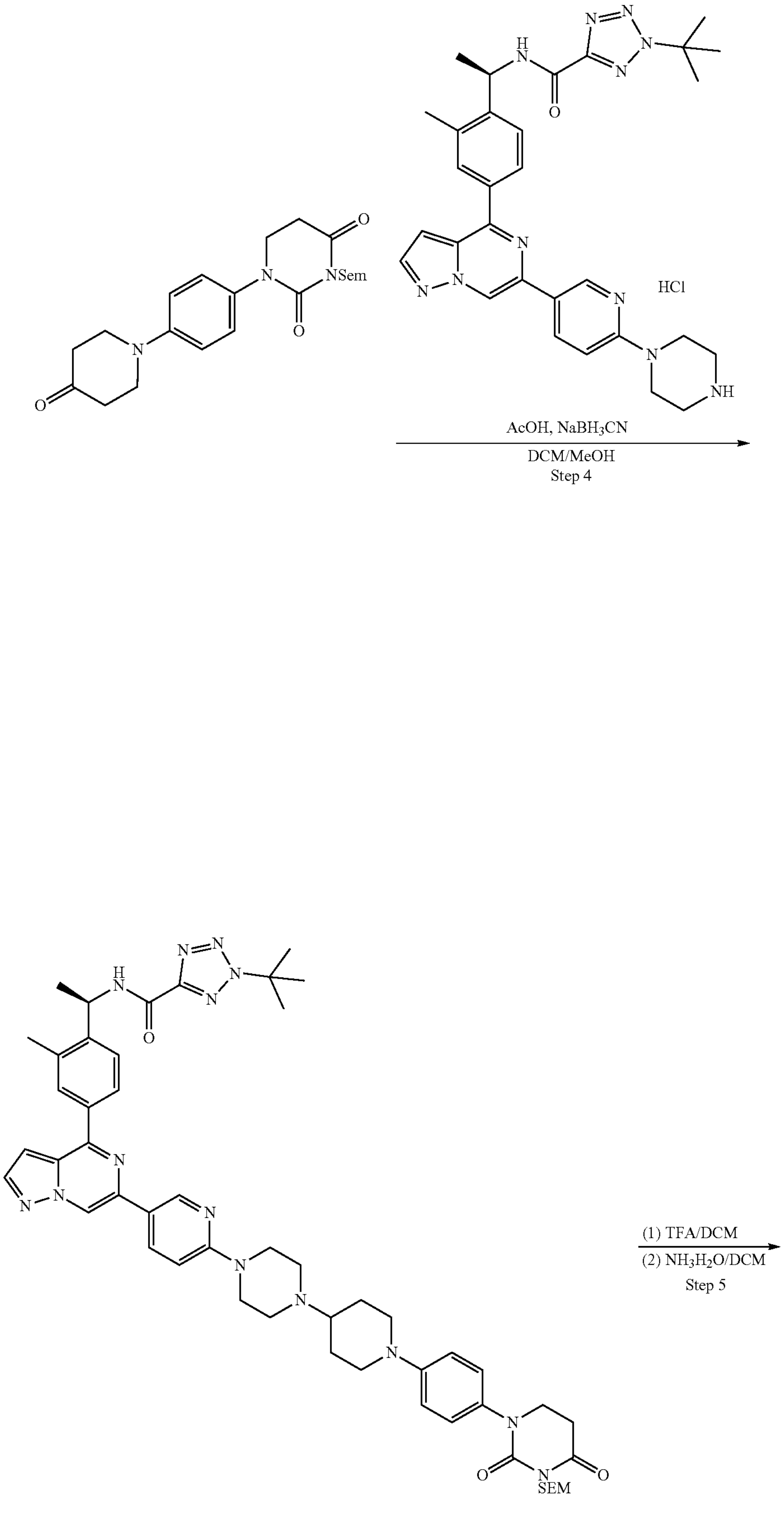

-continued

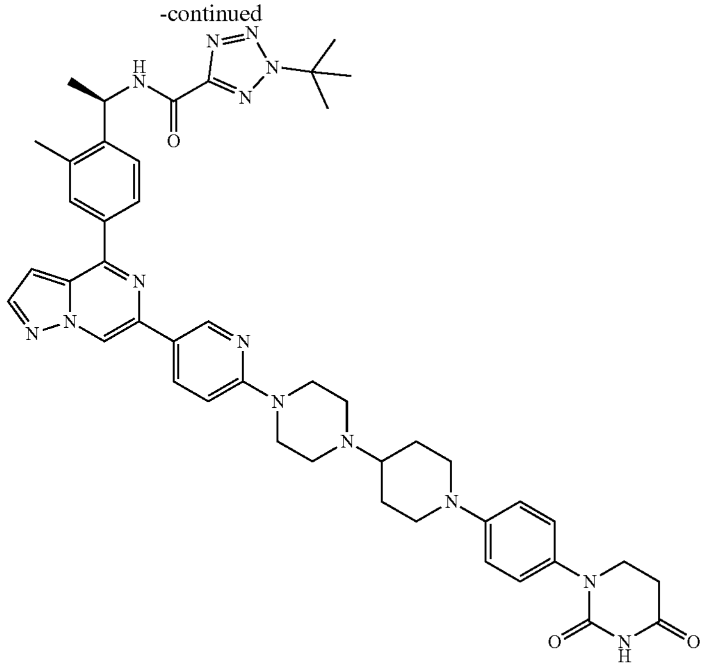

Step 1: 1-(4-bromophenyl)-3-((2-(trimethylsilyl) ethoxy)methyl)dihydropyrimidine-2,4(1H,3H)-dione

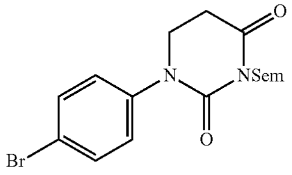

A mixture of 1-(4-bromophenyl)dihydropyrimidine-2,4 (1H,3H)-dione (1.5 g, 5.57 mmol, 1.0 eq), (2-(chloromethoxy)ethyl)trimethylsilane (1.39 g, 8.36 mmol, 1.5 eq) and DIEA (2.16 g, 16.72 mmol, 3.0 eq) in dry Acetonitrile (20 ml) was stirred at 80° C. under Ar for 16 h. Water was added and extracted with EA for 3 times. The combined organic layers were washed with brine, dried over anhydrous $Na_2SO_4$ and concentrated in vacuo. The residue was purified by flash chromatography eluted with Hex/EA-3:1 to give the title compound (1.8 g, 81%) as a white solid. LC-MS: 399.3 (M+H+).

Step 2: 1-(4-(1,4-dioxa-8-azaspiro[4.5]decan-8-yl) phenyl)-3-((2-(trimethylsilyl) ethoxy)methyl)dihydropyrimidine-2,4(1H,3H)-dione

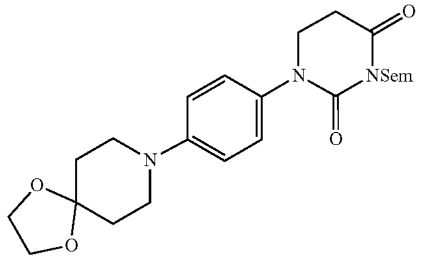

A mixture of 1,4-dioxa-8-azaspiro[4.5]decane (233 mg, 1.628 mmol, 1.3 eq), above obtained intermediate (500 mg, 1.252 mmol, 1.0 eq), $Cs_2CO_3$ (1224 mg, 3.76 mmol, 3.0 eq), $Pd_2(dba)_3$ (115 mg, 0.125 mmol, 0.1 eq) and RuPhos (58 mg, 0.125 mmol, 0.1 eq) in dry dioxane (10 ml) was stirred at 100° C. under Ar for 16 h. The mixture was diluted with water, extracted with ethyl acetate for 3 times. The combined organic layers were washed with brine, dried over anhydrous $Na_2SO_4$ and concentrated in vacuo. The residue was purified by flash chromatography eluted with Hex/EA=3:1 to give the title compound (200 mg, 34.6%) as a white solid. LC-MS: 462.6 (M+H+).

Step 3: 1-(4-(4-oxopiperidin-1-yl)phenyl)-3-((2-(trimethylsilyl) ethoxy)methyl)dihydropyrimidine-2,4(1H,3H)-dione

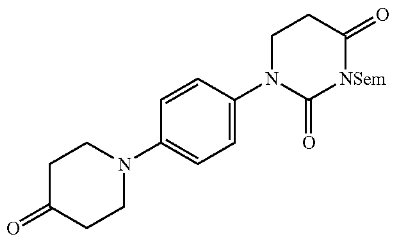

A mixture of above obtained intermediate (200 mg, 0.433 mmol, 1.0 eq) and 6N HCl aqueous (2 ml) in THF (10 ml) was stirred at 60° C. under Ar for 16 h. Quenched with $NaHCO_3$ aqueous, extracted with ethyl acetate for 3 times. The combined organic layers were washed with brine, dried over anhydrous $Na_2SO_4$ and concentrated in vacuo. The residue was purified by flash chromatography eluted with Hex/EA=3:1 to give the title compound (70 mg, 39%) as a white solid. LC-MS: 418.6 ($M+H^+$).

Step 4: (R)-2-(tert-butyl)-N-(1-(4-(6-(6-(4-(1-(4-(2,4-dioxo-3-((2-(trimethylsilyl) ethoxy)methyl)tetrahydropyrimidin-1(2H)-yl)phenyl)piperidin-4-yl) piperazin-1-yl)pyridin-3-yl)pyrazolo[1,5-a]pyrazin-4-yl)-2-methylphenyl)ethyl)-2H-tetrazole-5-carboxamide

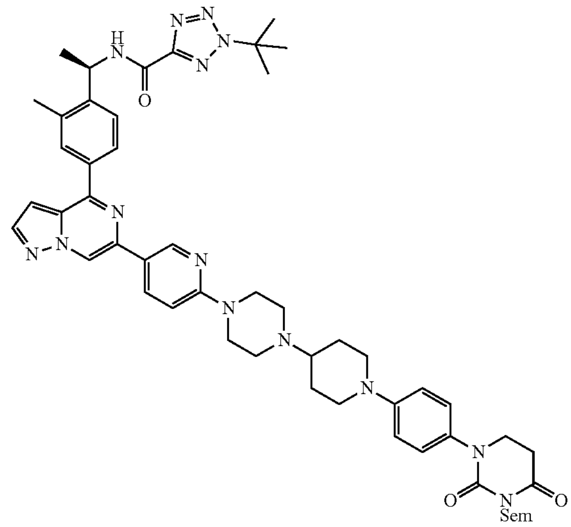

A mixture of (R)-2-(tert-butyl)-N-(1-(2-methyl-4-(6-(6-(piperazin-1-yl)pyridin-3-yl)pyrazolo[1,5-a]pyrazin-4-yl) phenyl)ethyl)-2H-tetrazole-5-carboxamide hydrochloride (126 mg, 0.209 mmol, 1.0 eq), above obtained intermediate (60 mg, 0.209 mmol, 1.0 eq), AcOH (126 mg, 2.09 mmol, 10.0 eq) and $NaBH_3CN$ (40 mg, 0.627 mmol, 3.0 eq) in DCM/MeOH (5 ml/1 ml) was stirred at 60° C. under Ar for 16 h. The mixture was quenched with water and extracted with DCM for 3 times. The organic layers were washed with brine, dried over anhydrous $Na_2SO_4$ and concentrated in vacuo. The residue was purified by flash chromatography eluted with Hex/EA=3:1 to give the title compound (20 mg, 10%) as a white solid. LC-MS: 967.6 ($M+H^+$).

Step 5: (R)-2-(tert-butyl)-N-(1-(4-(6-(6-(4-(1-(4-(2,4-dioxotetrahydropyrimidin-1(2H)-yl)phenyl)piperidin-4-yl) piperazin-1-yl)pyridin-3-yl)pyrazolo[1,5-a] pyrazin-4-yl)-2-methylphenyl)ethyl)-2H-tetrazole-5-carboxamide

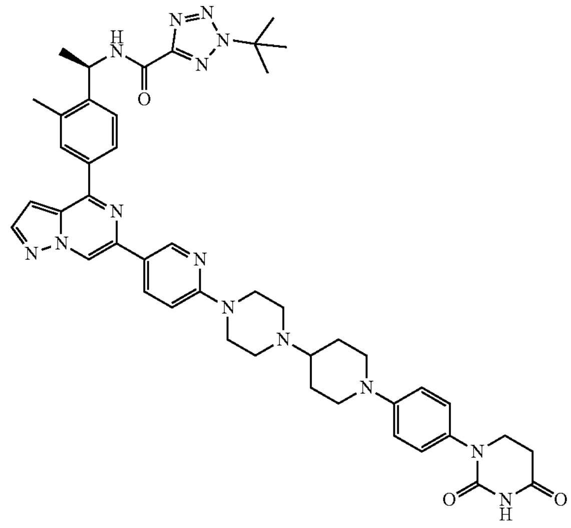 [SMILES: Cc1cc(-c2nc(-c3ccc(N4CCN(C5CCN(c6ccc(N7CCC(=O)NC7=O)cc6)CC5)CC4)nc3)cn3nccc23)ccc1[C@@H](C)NC(=O)c1nnn(C(C)(C)C)n1]

A solution of above obtained intermediate (20 mg, 0.02 mmol, 1.0 eq) in TFA (0.5 ml) and DCM (2 ml) was stirred at rt under Ar for 6 h. Concentrated in vacuo, the residue was dissolved in DCM (3 ml) and $NH_3 \cdot H_2O$ (0.5 ml). The mixture was stirred at rt for 16 h. Diluted with water, extracted with DCM for 3 times. The organic layers were washed with brine, dried over anhydrous $Na_2SO_4$ and concentrated in vacuo. The residue was purified by pre-HPLC to give the title compound (8.1 mg, 46.8%) as a yellow solid. LC-MS: 837.6 ($M+H^+$). $^1H$ NMR (400 MHz, DMSO-$d^6$) δ (ppm) 10.25 (s, 1H), 9.57 (d, J=8.0 Hz, 1H), 9.28 (s, 1H), 8.95 (d, J=2.4 Hz, 1H), 8.33-8.28 (m, 1H), 8.21 (d, J=2.4 Hz, 1H), 7.98 (d, J=8.0 Hz, 1H), 7.95 (s, 1H), 7.70 (d, J=8.0 Hz, 1H), 7.19 (d, J=2.0 Hz, 1H), 7.13 (d, J=8.8 Hz, 2H), 7.00-6.90 (m, 3H), 5.50-5.40 (m, 1H), 3.78-3.65 (m, 4H), 3.63-3.55 (m, 4H), 2.75-2.60 (m, 8H), 2.55 (s, 3H), 2.45-2.35 (m, 1H), 1.93-1.85 (m, 2H), 1.73 (s, 9H), 1.60-1.50 (m, 5H).

Example 48: (R)-2-(tert-butyl)-N-(1-(2-methyl-4-(6-(6-(4-((1-(4-(3-methyl-2,4-dioxotetrahydropyrimidin-1(2H)-yl)phenyl)piperidin-4-yl)methyl)piperazin-1-yl)pyridin-3-yl)pyrazolo[1,5-a]pyrazin-4-yl)phenyl)ethyl)-2H-tetrazole-5-carboxamide (Compound No. 247)

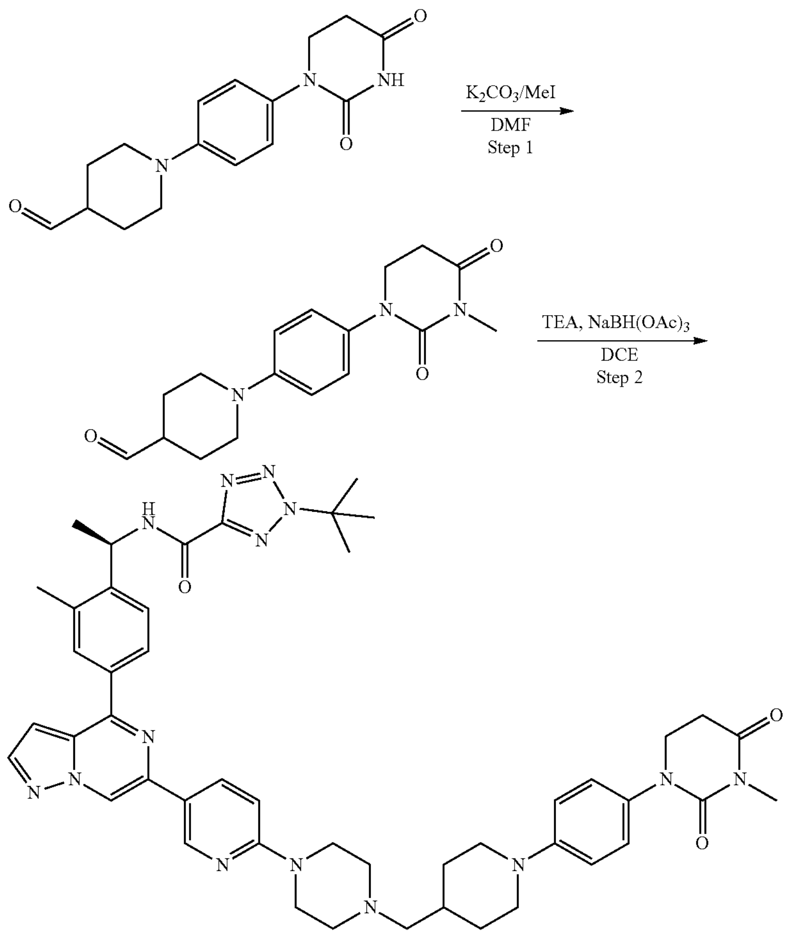

Step 1: 1-(4-(3-methyl-2,4-dioxotetrahydropyrimidin-1(2H)-yl)phenyl)piperidine-4-carbaldehyde

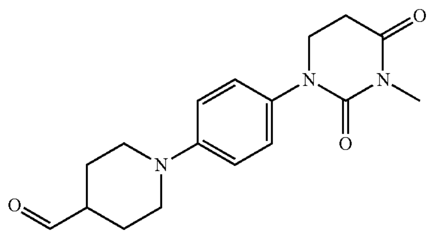 [SMILES: CN1C(=O)CCN(c2ccc(N3CCC(C=O)CC3)cc2)C1=O]

A mixture of 1-(4-(2,4-dioxotetrahydropyrimidin-1(2H)-yl)phenyl)piperidine-4-carbaldehyde (200 mg, 0.664 mmol, 1.0 eq), $K_2CO_3$ (459 mg, 3.32 mmol, 5.0 eq) and iodomethane (141 mg, 0.996 mmol, 1.5 eq) in dry DMF (4 ml) was stirred at rt for 2 h. Diluted with EA, washed with water, brine, dried over anhydrous $Na_2SO_4$ and concentrated in vacuo to give the title compound (90 mg, 43%) as a red solid. LC-MS: 316.6 (M+H$^+$).

Step 2: (R)-2-(tert-butyl)-N-(1-(2-methyl-4-(6-(6-(4-((1-(4-(3-methyl-2,4-dioxotetrahydropyrimidin-1(2H)-yl)phenyl)piperidin-4-yl)methyl)piperazin-1-yl)pyridin-3-yl)pyrazolo[1,5-a]pyrazin-4-yl)phenyl)ethyl)-2H-tetrazole-5-carboxamide

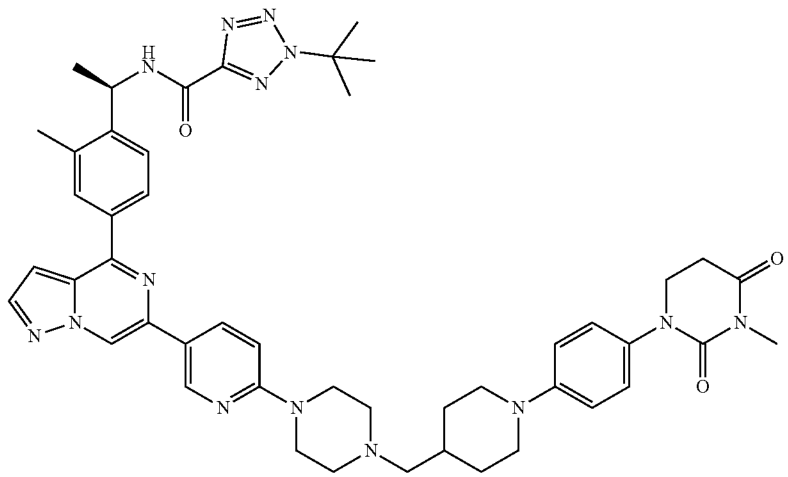 [SMILES: Cc1cc(-c2nc(-c3ccc(N4CCN(CC5CCN(c6ccc(N7CCC(=O)N(C)C7=O)cc6)CC5)CC4)nc3)cn3nccc23)ccc1[C@@H](C)NC(=O)c1nnn(C(C)(C)C)n1]

To a solution of above obtained intermediate (82 mg, 0.259 mmol, 1.3 eq), (R)-2-(tert-butyl)-N-(1-(2-methyl-4-(6-(6-(piperazin-1-yl)pyridin-3-yl)pyrazolo[1,5-a]pyrazin-4-yl)phenyl)ethyl)-2H-tetrazole-5-carboxamide hydrochloride (120 mg, 0.199 mmol, 1.0 eq) and TEA (100 mg, 0.996 mmol, 5.0 eq) in dry DCE (4 ml) was added NaBH(OAc) 3 (84 mg, 0.399 mmol, 2.0 eq) in portions. The reaction was stirred at rt for 2 h. The reaction was quenched with water and extracted with DCM for 3 times. The organic layers were washed with brine, dried over anhydrous $Na_2SO_4$ and concentrated in vacuo. The residue was purified by pre-HPLC to give the title compound (105 mg, 60.9%) as a yellow solid. LC-MS: 865.6 ($M+H^+$). $^1H$ NMR (400 MHz, DMSO-$d^6$) δ (ppm) 9.57 (d, J=8.0 Hz, 1H), 9.27 (s, 1H), 8.95 (d, J=2.4 Hz, 1H), 8.35-8.28 (m, 1H), 8.20 (d, J=2.4 Hz, 1H), 7.98 (d, J=8.4 Hz, 1H), 7.95 (s, 1H), 7.71 (d, J=8.4 Hz, 1H), 7.19 (d, J=2.0 Hz, 1H), 7.13 (d, J=8.8 Hz, 2H), 7.00-6.88 (m, 3H), 5.48-5.40 (m, 1H), 3.73-3.65 (m, 4H), 3.63-3.55 (m, 4H), 3.03 (s, 3H), 2.83-2.75 (m, 2H), 2.73-2.62 (m, 2H), 2.55 (s, 3H), 2.48-2.40 (m, 4H), 2.21 (d, J=6.8 Hz, 2H), 1.85-1.78 (m, 2H), 1.73 (s, 9H), 1.71-1.65 (m, 1H), 1.55 (d, J=6.8 Hz, 3H), 1.28-1.15 (m, 2H).

Example 49: (R)-3-(tert-butyl)-N-(1-(4-(7-(2-(4-((1-(4-(2,4-dioxotetrahydropyrimidin-1(2H)-yl)phenyl)piperidin-4-yl)methyl)piperazin-1-yl)pyrimidin-5-yl)imidazo[1,2-c]pyrimidin-5-yl)-2-methylphenyl)ethyl)-1,2,4-oxadiazole-5-carboxamide (Compound No. 251)

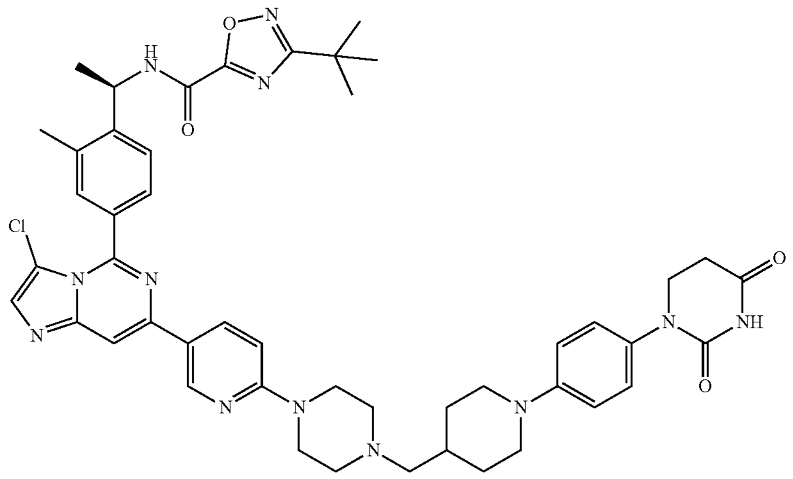 [SMILES: Cc1cc(-c2nc(-c3ccc(N4CCN(CC5CCN(c6ccc(N7CCC(=O)NC7=O)cc6)CC5)CC4)nc3)cc3ncc(Cl)n23)ccc1[C@@H](C)NC(=O)c1nc(C(C)(C)C)no1]

Following the synthesis of EXAMPLE 44, the title compound was obtained after preparative HPLC purification as a white solid. LC-MS: 885.72 (M+H$^+$). $^1$H NMR (400 MHz, DMSO-d$^6$) δ (ppm) 10.24 (s, 1H), 9.92 (d, J=8.0 Hz, 1H), 8.92 (d, J=2.4 Hz, 1H), 8.27 (dd, J=8.8, 2.4 Hz, 1H), 8.11 (s, 1H), 7.73 (s, 1H), 7.64-7.53 (m, 3H), 7.13 (d, J=8.8 Hz, 2H), 6.94-6.89 (m, 3H), 5.43-5.36 (m, 1H), 3.71-3.66 (m, 4H), 3.61-3.57 (m, 4H), 2.69-2.64 (m, 4H), 2.47-2.44 (m, 7H), 2.21 (d, J=6.8 Hz, 2H), 1.83-1.72 (m, 3H), 1.55 (d, J=6.8 Hz, 3H), 1.37 (s, 9H), 1.27-1.18 (m, 2H).

Example 50: (R)-3-(tert-butyl)-N-(1-(4-(7-(6-(4-((1-(4-(2,4-dioxotetrahydropyrimidin-1(2H)-yl)phenyl)piperidin-4-yl)methyl)piperazin-1-yl)pyridin-3-yl)-3-isocyanoimidazo[1,2-c]pyrimidin-5-yl)-2-methylphenyl)ethyl)-1,2,4-oxadiazole-5-carboxamide (Compound No. 252)

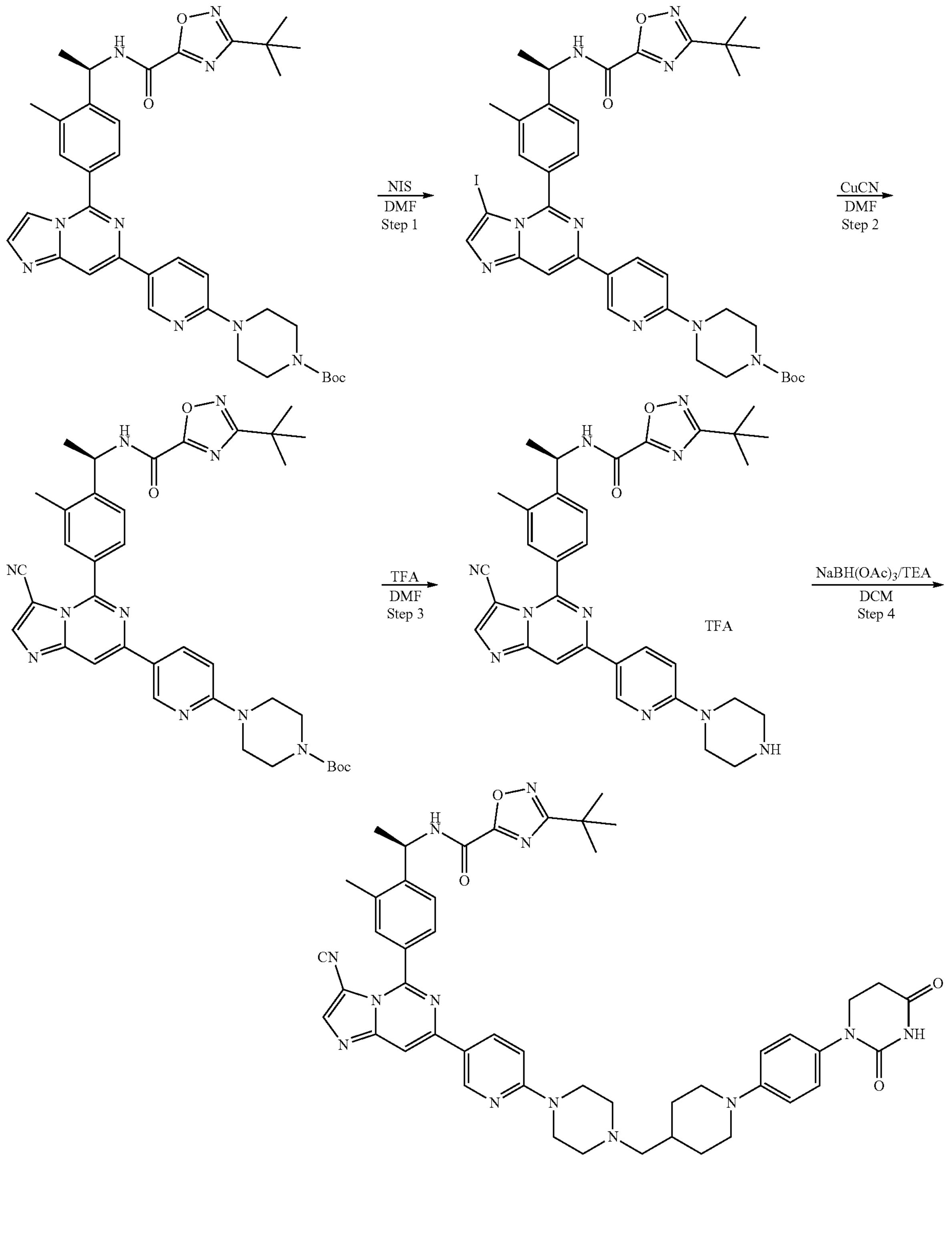

Step 1: tert-butyl (R)-4-(5-(5-(4-(1-(3-(tert-butyl)-1,2,4-oxadiazole-5-carboxamido)ethyl)-3-methylphenyl)-3-iodoimidazo[1,2-c]pyrimidin-7-yl)pyridin-2-yl)piperazine-1-carboxylate

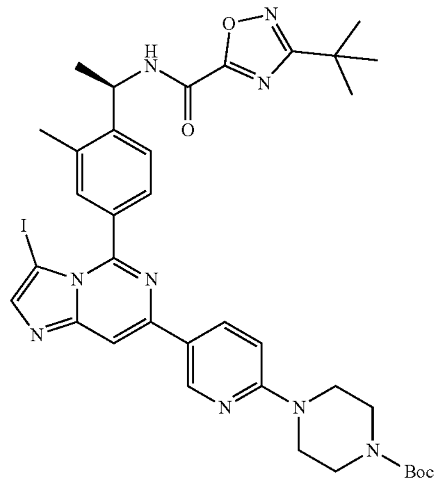 [SMILES: Cc1cc(-c2nc(-c3ccc(N4CCN(C(=O)OC(C)(C)C)CC4)nc3)cc3ncc(I)n23)ccc1[C@@H](C)NC(=O)c1nc(C(C)(C)C)no1]

To a mixture of tert-butyl (R)-4-(5-(5-(4-(1-(3-(tert-butyl)-1,2,4-oxadiazole-5-carboxamido)ethyl)-3-methylphenyl)imidazo[1,2-c]pyrimidin-7-yl)pyridin-2-yl)piperazine-1-carboxylate (500 mg, 0.751 mmol, 1.0 eq) in dry DMF (3 ml) was added NIS (253 mg, 1.126 mmol, 1.5 eq), the mixture was stirred at rt for 3 h. Water was added, extracted with EA, washed with water, brine, dried over anhydrous $Na_2SO_4$ and concentrated. The residue was purified by flash chromatography eluted with DCM/MeOH=20:1 to give the title compound (534 mg, 90%) as a brown solid. LC-MS: 792.48 ($M+H^+$).

Step 2: tert-butyl (R)-4-(5-(5-(4-(1-(3-(tert-butyl)-1,2,4-oxadiazole-5-carboxamido)ethyl)-3-methylphenyl)-3-cyanoimidazo[1,2-c]pyrimidin-7-yl)pyridin-2-yl)piperazine-1-carboxylate

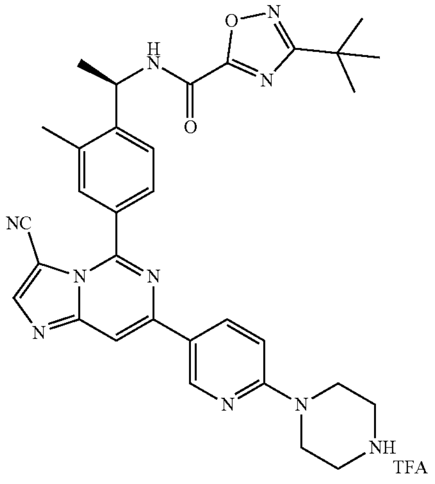 [SMILES: Cc1cc(-c2nc(-c3ccc(N4CCNCC4)nc3)cc3ncc(C#N)n23)ccc1[C@@H](C)NC(=O)c1nc(C(C)(C)C)no1 ; "TFA"]

A mixture of above obtained intermediate (434 mg, 0.548 mmol, 1.0 eq) and CuCN (123 mg, 1.370 mmol, 2.5 eq) in dry DMF (6 ml) was added stirred at 100° C. for 6 h. Filtered and concentrated to dryness. The residue was purified by combi-flash eluted with DCM/MeOH=100:1 to give the title compound (210 mg, 55.5%) as a yellow oil. LC-MS: 691.63 ($M+H^+$).

Step 3: (R)-3-(tert-butyl)-N-(1-(4-(3-cyano-7-(6-(piperazin-1-yl)pyridin-3-yl)imidazo[1,2-c]pyrimidin-5-yl)-2-methylphenyl)ethyl)-1,2,4-oxadiazole-5-carboxamide-2,2,2-trifluoroacetaldehyde

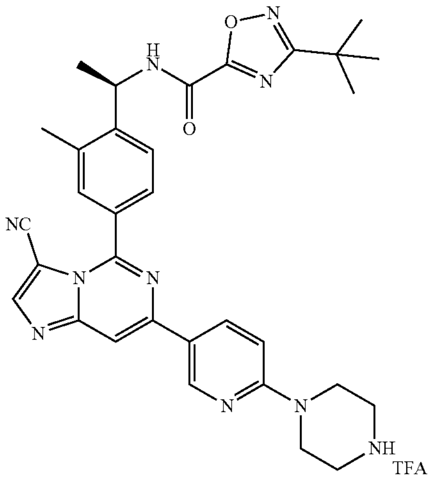 [SMILES: Cc1cc(-c2nc(-c3ccc(N4CCNCC4)nc3)cc3ncc(C#N)n23)ccc1[C@@H](C)NC(=O)c1nc(C(C)(C)C)no1 ; "TFA"]

A mixture of above obtained intermediate (210 mg, 0.304 mmol, 1.0 eq) in DCM (3 ml) and TFA (3 ml) was stirred at rt for 1 h. Concentrated to give the title compound (214 mg, 100%) as a brown solid. LC-MS: 591.52 ($M+H^+$).

Step 4: (R)-3-(tert-butyl)-N-(1-(4-(3-cyano-7-(6-(piperazin-1-yl)pyridin-3-yl)imidazo[1,2-c]pyrimidin-5-yl)-2-methylphenyl)ethyl)-1,2,4-oxadiazole-5-carboxamide-2,2,2-trifluoroacetaldehyde

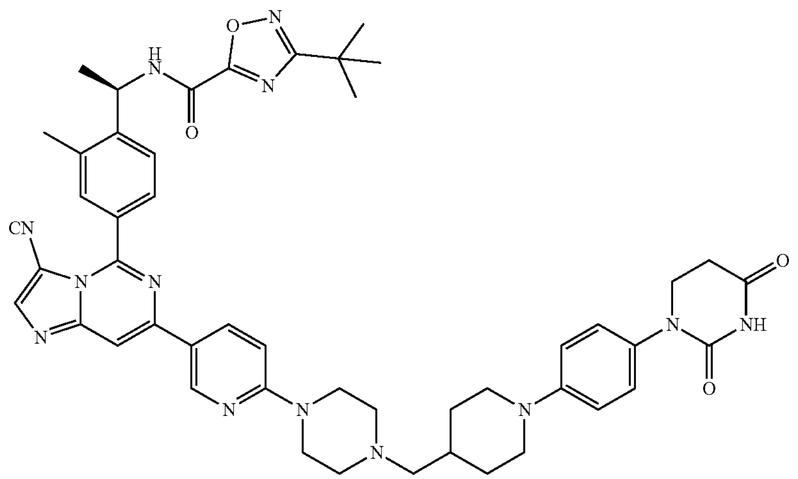

To a solution of above obtained intermediate (214 mg, 0.304 mmol, 1.0 eq), 1-(4-(2,4-dioxotetrahydropyrimidin-1(2H)-yl)phenyl)piperidine-4-carbaldehyde (110 mg, 0.364 mmol, 1.2 eq), TEA (154 mg, 1.518 mmol, 5.0 eq) in DCM (5 ml) was added sodium triacetoxyborohydride (129 mg, 0.607 mmol, 2.0 eq). The reaction was stirred at rt for 1 h. Diluted with DCM, washed with water, brine, dried over anhydrous $Na_2SO_4$ and concentrated to dryness. The residue was purified by pre-HPLC to give the title compound (53 mg, 19.92%) as a yellow solid. LC-MS: 876.75 ($M+H^+$). $^1H$ NMR (400 MHz, DMSO-$d^6$) δ (ppm) 10.24 (s, 1H), 9.94 (d, J=7.6 Hz, 1H), 8.99 (d, J=2.4 Hz, 1H), 8.53 (s, 1H), 8.34-8.31 (m, 2H), 7.72-7.67 (m, 3H), 7.13 (d, J=9.2 Hz, 2H), 6.94-6.91 (m, 3H), 5.44-5.36 (m, 1H), 3.71-3.61 (m, 8H), 2.69-2.64 (m, 4H), 2.51 (s, 3H), 2.47-2.44 (m, 4H), 2.22 (d, J=6.8 Hz, 2H), 1.83-1.80 (m, 2H), 1.53 (d, J=7.2 Hz, 3H), 1.37 (s, 10H), 1.27-1.18 (m, 2H).

Example 51: (R)-3-(tert-butyl)-N-(1-(4-(7-(6-(4-((1-(4-(2,4-dioxotetrahydropyrimidin-1(2H)-yl)phenyl)piperidin-4-yl)methyl)piperazin-1-yl)pyridin-3-yl)-[1,2,4]triazolo[4,3-a]pyridin-5-yl)-2-methylphenyl)ethyl)-1,2,4-oxadiazole-5-carboxamide (Compound No. 253)

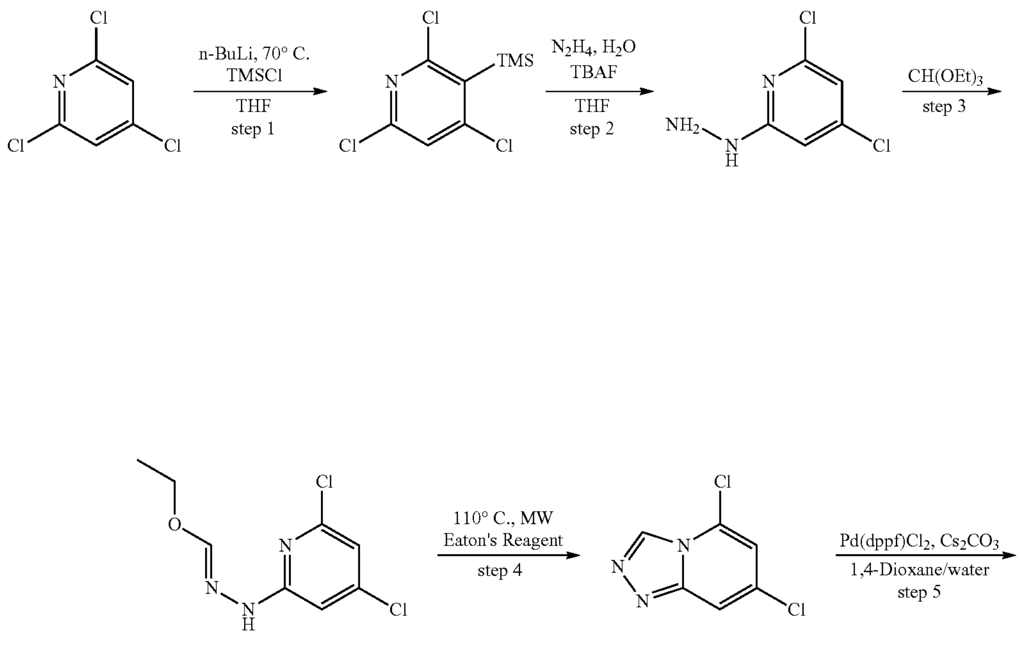

-continued
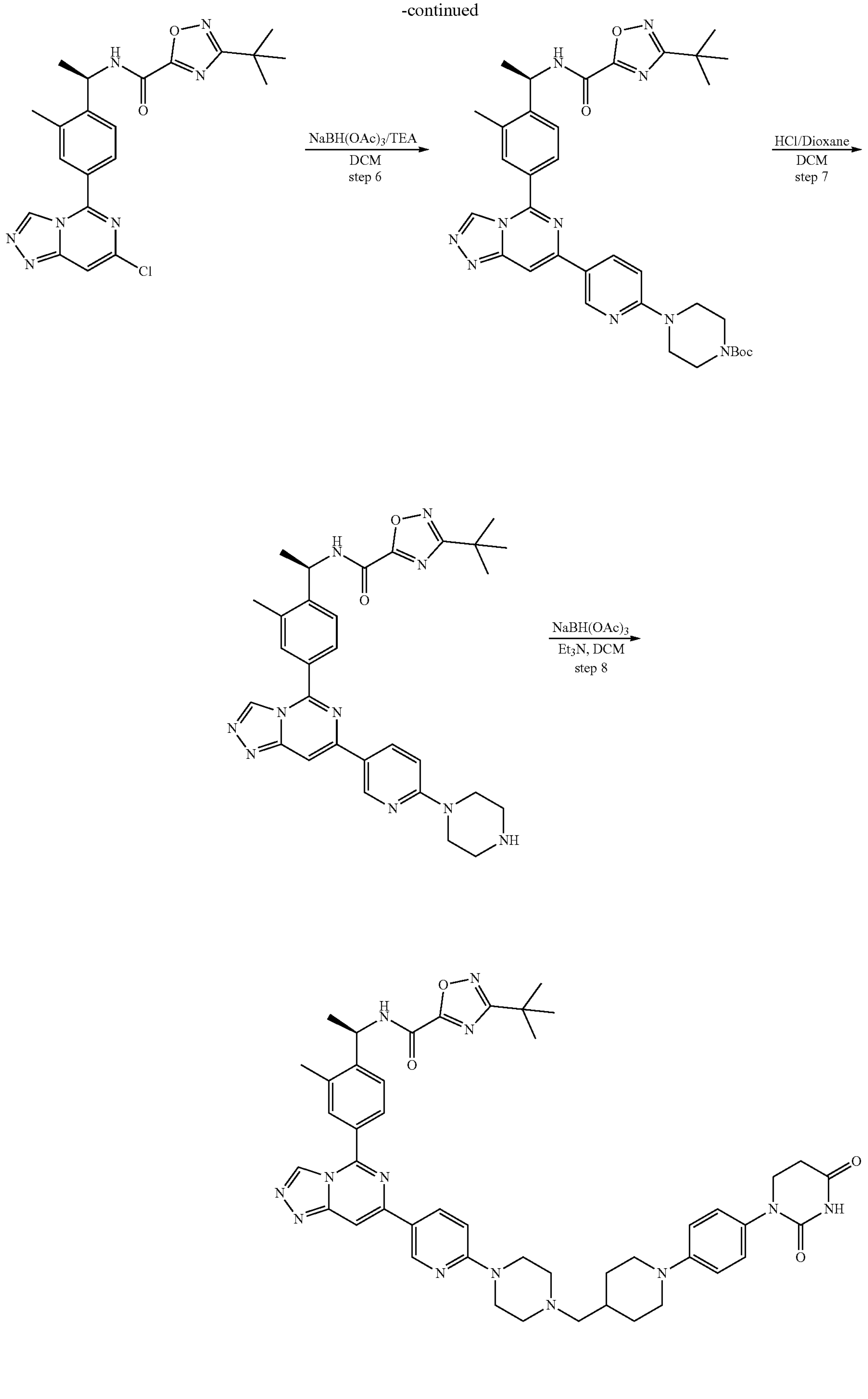

Step 1: 2,4,6-trichloro-3-(trimethylsilyl)pyridine

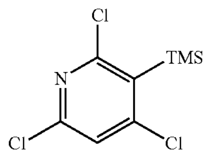 [SMILES: C[Si](C)(C)c1c(Cl)cc(Cl)nc1Cl]

To a solution of 2,4,6-trichloropyridine (9.2 g, 50.4 mmol, 1.0 eq) in dry THF (100 ml) was added n-BuLi (20 ml, 50.4 mmol, 1.0 eq) at −70° C. under Ar. After 45 min at −70° C., the mixture was treated with chlorotrimethylsilane (5.48 g, 50.4 mmol, 1.0 eq). Diluted with water, extracted with EA for 3 times. The combined EA layers were washed with brine, dried over anhydrous $Na_2SO_4$ and concentrated in vacuo. The residue was purified by flash chromatography eluted with Hex/EA=10:1 to give the title compound (11.7 g, 91%) as a colorless oil. LC-MS: 254.4 ($M+H^+$).

Step 2: 2,4-dichloro-6-hydrazineylpyridine

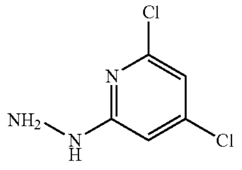

A mixture of 2,4,6-trichloro-3-(trimethylsilyl)pyridine (7 g, 27.5 mmol, 1.0 eq) and hydrazine hydrate (3.44 g, 55.0 mmol, 2.0 eq) in dry THF (100 ml) was stirred at 50° C. under Ar for 20 h. tetrabutylammonium fluoride (7.19 g, 27.5 mmol, 1.0 eq) was added. The reaction mixture was stirred at rt for 2 h. Concentrated in vacuo, the residue was triturated with water and ethyl acetate to give the title compound (4.31 g, 88%) as a white solid. LC-MS: 178.1 ($M+H^+$).

Step 3: ethyl (E)-N-(4,6-dichloropyridin-2-yl)formohydrazonate

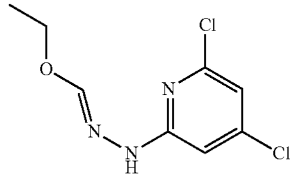

A solution of 2,4-dichloro-6-hydrazinylpyridine (2.4 g, 13.48 mmol, 1.0 eq) in triethyl orthoformate (20 ml) was stirred at 120° C. for 3 h. The reaction solution was concentrated in vacuo and the residue was purified by silica gel column chromatography eluted with Hex/EA=1:1 to give the title compound (1.7 g, 53.9%) as yellow oil. LC-MS: 234.2 ($M+H^+$).

Step 4: 5,7-dichloro-[1,2,4]triazolo[4,3-a]pyridine

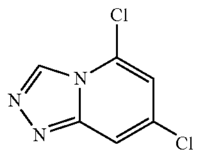 [SMILES: Clc1cc(Cl)n2cnnc2c1]

A mixture of above obtained intermediate (1.3 g, 5.55 mmol, 1.0 eq) in Eaton's reagent (3.0 ml) was stirred at 110° C. for 10 minutes with microwaves. Quenched with $NaHCO_3$ aqueous, extracted with EA for 3 times. The combined EA layers were washed with brine, dried over anhydrous $Na_2SO_4$ and concentrated in vacuo. The residue was purified by flash chromatography eluted with Hex/EA=10:1 to give the title compound (0.3 g, 28.7%) as a yellow solid. LC-MS: 188.3 ($M+H^+$).

Step 5: (R)-3-(tert-butyl)-N-(1-(4-(7-chloro-[1,2,4]triazolo[4,3-a]pyridin-5-yl)-2-methylphenyl)ethyl)-1,2,4-oxadiazole-5-carboxamide

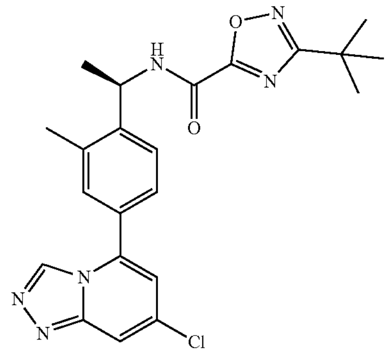 [SMILES: Cc1cc(-c2cc(Cl)cc3nncn23)ccc1[C@@H](C)NC(=O)c1nc(C(C)(C)C)no1]

A mixture of (R)-3-(tert-butyl)-N-(1-(2-methyl-4-(4,4,5,5-tetramethyl-1,3,2-dioxaborolan-2-yl)phenyl)ethyl)-1,2,4-oxadiazole-5-carboxamide (484 mg, 1.170 mmol, 1.1 eq), above obtained intermediate (200 mg, 1.064 mmol, 1.0 eq), $Pd(dppf)Cl_2$ (78 mg, 0.106 mmol, 0.1 eq) and $Cs_2CO_3$ (1040 mg, 3.19 mmol, 3.0 eq) in Dioxane/$H_2O$ (8 ml/2 ml) was stirred at 100° C. under Ar for 2 h. The reaction was diluted with water, extracted with EA for 3 times. The combined EA layers were washed with brine, dried over anhydrous $Na_2SO_4$ and concentrated in vacuo. The residue was purified by flash chromatography eluted with Hex/EA=2:1 to give the title compound (200 mg, 42.8%) as yellow oil. LC-MS: 439.4 ($M+H^+$).

Step 6: tert-butyl (R)-4-(5-(5-(4-(1-(3-(tert-butyl)-1,2,4-oxadiazole-5-carboxamido)ethyl)-3-methylphenyl)-[1,2,4]triazolo[4,3-a]pyridin-7-yl)pyridin-2-yl)piperazine-1-carboxylate

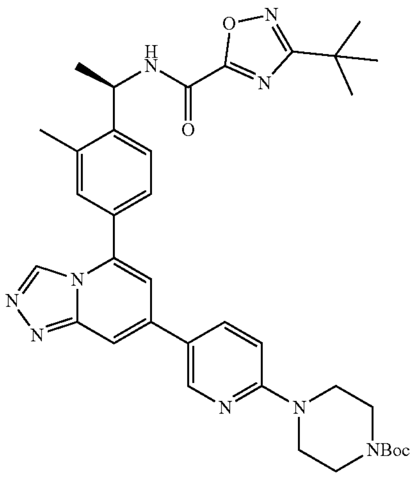 [SMILES: Cc1cc(-c2cc(-c3ccc(N4CCN(C(=O)OC(C)(C)C)CC4)nc3)cc3nncn23)ccc1[C@@H](C)NC(=O)c1nc(C(C)(C)C)no1]

A mixture of above obtained intermediate (0.2 g, 0.456 mmol, 1.0 eq), tert-butyl 4-(5-(4,4,5,5-tetramethyl-1,3,2-dioxaborolan-2-yl)pyridin-2-yl)piperazine-1-carboxylate (0.266 g, 0.684 mmol, 1.5 eq), Pd(dppf)$Cl_2$ (0.033 g, 0.046 mmol, 0.1 eq) and $Cs_2CO_3$ (0.445 g, 1.367 mmol, 3.0 eq) in Dioxane/$H_2O$ (8 ml/2 ml) was stirred at 100° C. under Ar for 16 h. The reaction was diluted with water and extracted with EA for 3 times. The combined EA layers were washed with brine, dried over anhydrous $Na_2SO_4$ and concentrated in vacuo. The residue was purified by flash chromatography eluted with Hex/EA=2:1 to give the title compound (163 mg, 53.7%) as yellow oil. LC-MS: 666.7 (M+H$^+$).

Steps 7-8: (R)-3-(tert-butyl)-N-(1-(4-(7-(6-(4-((1-(4-(2,4-dioxotetrahydropyrimidin-1(2H)-yl)phenyl)piperidin-4-yl)methyl)piperazin-1-yl)pyridin-3-yl)-[1,2,4]triazolo[4,3-a]pyridin-5-yl)-2-methylphenyl)ethyl)-1,2,4-oxadiazole-5-carboxamide

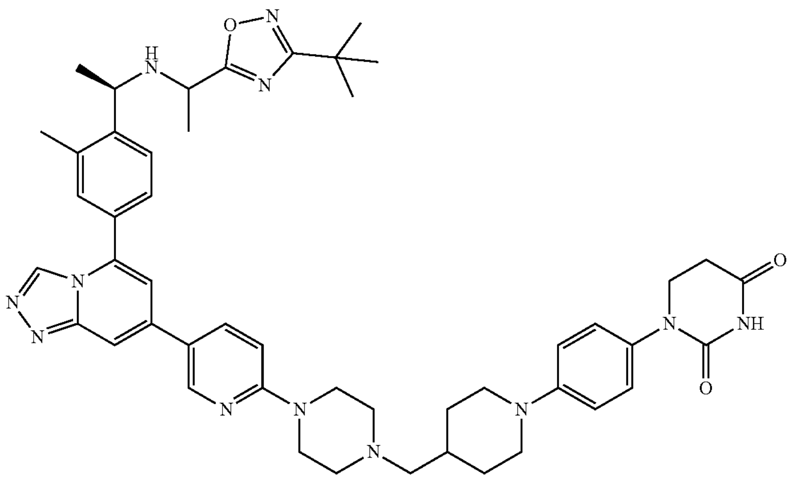

The titled compound was synthesized in the procedures similar to Example 3. MS (ESI) m/z 851.74 $[M+H]^+$. $^1H$ NMR (400 MHz, DMSO-$d^6$) δ (ppm) 10.23 (s, 1H), 9.96 (d, J=7.9 Hz, 1H), 9.17 (d, J=0.9 Hz, 1H), 8.72 (d, J=2.6 Hz, 1H), 8.13 (dd, J=9.0, 2.6 Hz, 1H), 8.05-8.00 (m, 1H), 7.82-7.66 (m, 3H), 7.35 (d, J=1.6 Hz, 1H), 7.17-7.08 (m, 2H), 6.97-6.88 (m, 3H), 5.39 (m, 1H), 3.73-3.64 (m, 5H), 3.59 (t, J=5.0 Hz, 4H), 2.72-2.61 (m, 5H), 2.46 (t, J=4.8 Hz, 4H), 2.22 (d, J=7.1 Hz, 2H), 1.81 (d, J=12.8 Hz, 2H), 1.72 (s, 1H), 1.55 (d, J=7.0 Hz, 3H), 1.37 (s, 9H), 1.26-1.22 (m, 2H).

Example 52: (R)—N-(1-(4-(7-(6-(4-((1-(4-(2,4-dioxotetrahydropyrimidin-1(2H)-yl)phenyl)piperidin-4-yl)methyl)piperazin-1-yl)pyridin-3-yl)imidazo[1,2-c]pyrimidin-5-yl)-2-methylphenyl)ethyl)-5-(1-(trifluoromethyl)cyclopropyl)-1,2,4-oxadiazole-3-carboxamide (Compound No. 255)

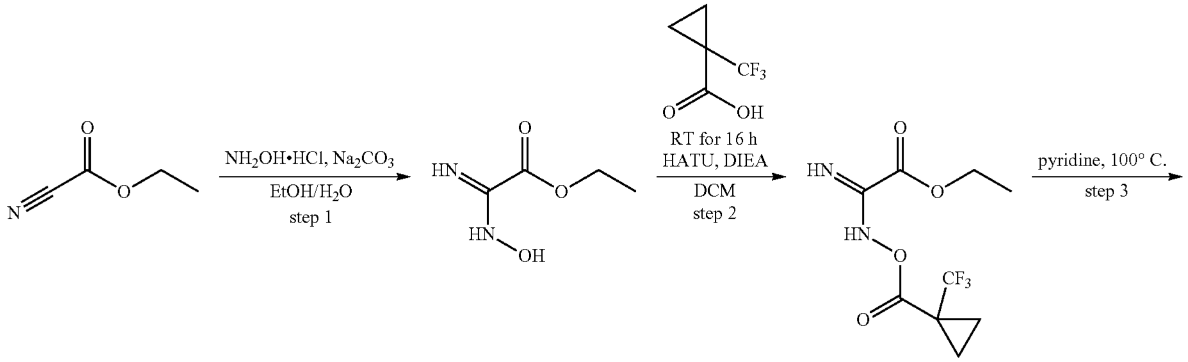

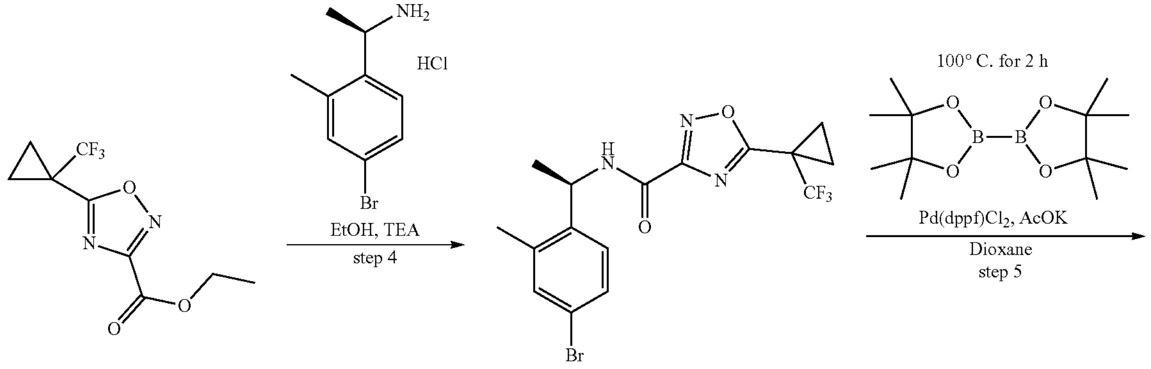

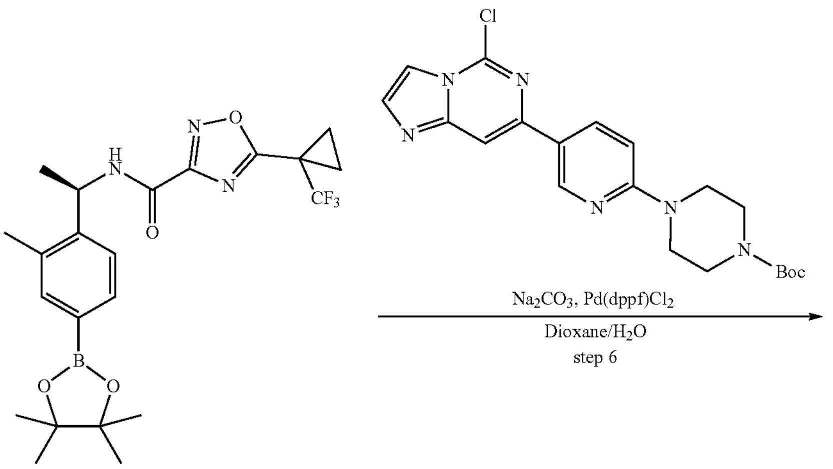

-continued
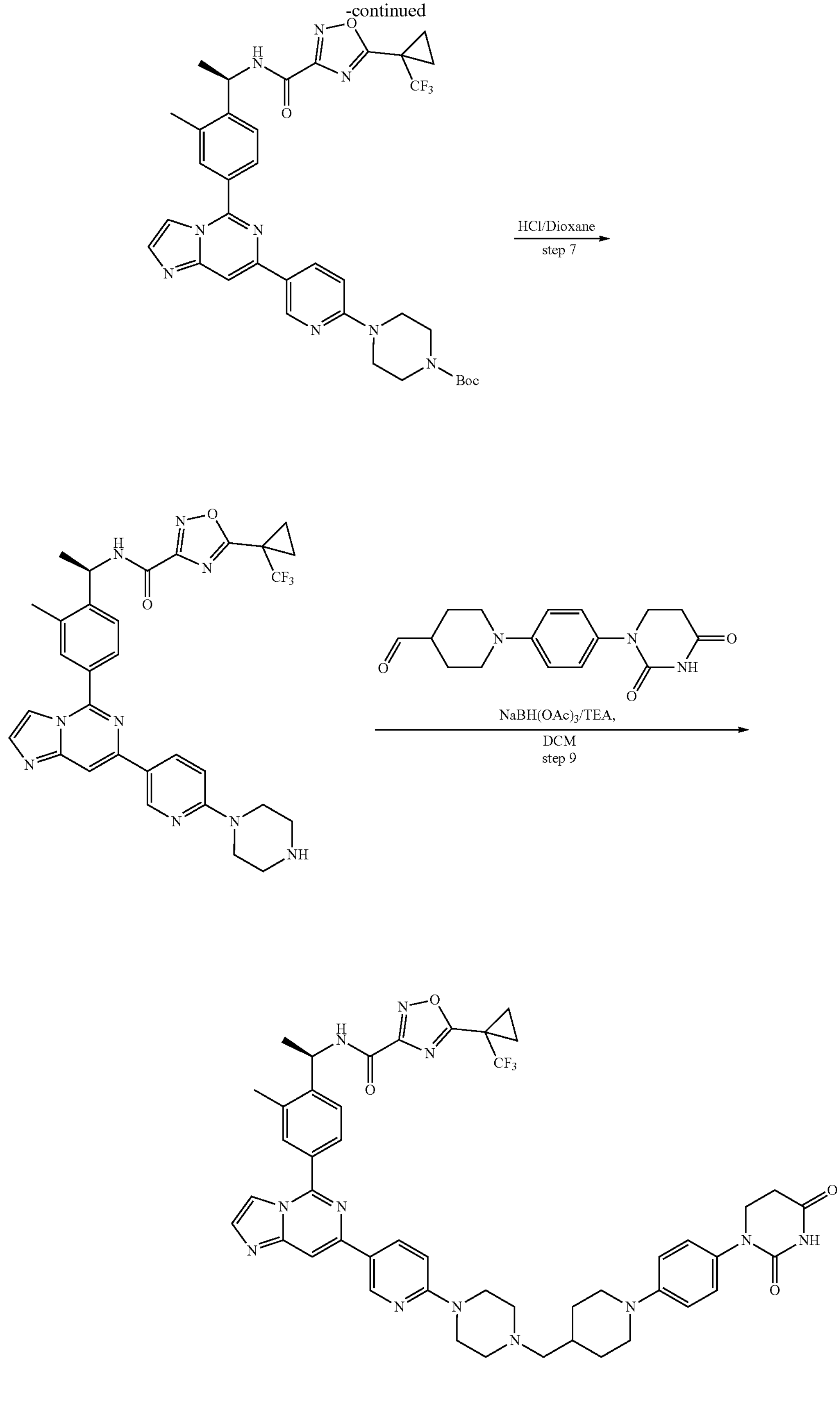

Step 1: ethyl 2-(hydroxyamino)-2-iminoacetate

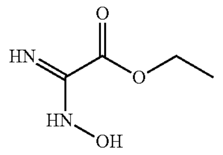

To a mixture of ethyl carbonocyanidate (9.8 g, 99 mmol, 1.0 eq) and hydroxylamine hydrochloride (10.31 g, 148 mmol, 1.5 eq) in EtOH (100 ml) and water (60 ml) was added $Na_2CO_3$ (8.18 g, 77 mmol, 0.78 eq). The reaction mixture was stirred at rt under Ar for 16 h. Diluted with DCM, the reaction was washed with brine, dried over anhydrous $Na_2SO_4$ and concentrated in vacuo. The residue was purified by flash chromatography eluted with DCM/MeOH=50:1 to give the title compound (350 mg, 80%) as a white solid. LC-MS: 133.2 ($M+H^+$).

Step 2: ethyl 2-imino-2-(((1-(trifluoromethyl)cyclopropane-1-carbonyl)oxy)amino)acetate

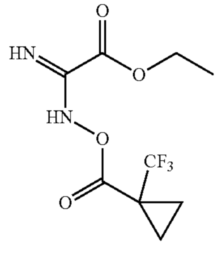 [SMILES: CCOC(=O)C(=N)NOC(=O)C1(C(F)(F)F)CC1]

To a mixture of ethyl 2-(hydroxyamino)-2-iminoacetate (900 mg, 6.81 mmol, 1.0 eq), 1-(trifluoromethyl)cyclopropane-1-carboxylic acid (1050 mg, 6.81 mmol, 1.0 eq) and DIEA (2641 mg, 20.44 mmol, 3.0 eq) in dry DCM (10 ml) was added HATU (2849 mg, 7.49 mmol, 1.1 eq). The reaction mixture was stirred at rt under Ar for 16 h. The solution was diluted with DCM, washed with brine, dried over anhydrous $Na_2SO_4$ and concentrated in vacuo to give the crude compound (1650 mg, 90%) as dark oil. LC-MS: 269.1 ($M+H^+$).

Step 3: ethyl 5-(1-(trifluoromethyl)cyclopropyl)-1,2,4-oxadiazole-3-carboxylate

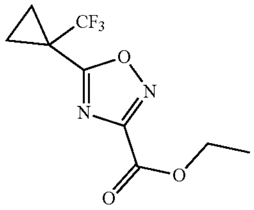 [SMILES: CCOC(=O)c1noc(C2(C(F)(F)F)CC2)n1]

A mixture of above obtained intermediate (1650 mg, 6.15 mmol, 1.0 eq) in pyridine (10 ml) was stirred at 100° C. under Ar for 16 h. The solvent was removed under vacuum, the residue was diluted with ethyl acetate, washed with brine, dried over anhydrous $Na_2SO_4$ and concentrated in vacuo. The residue was purified by flash chromatography eluted with Hex/EA-4:1 to give the title compound (240 mg, 16%) as a colorless oil. LC-MS: 251.2 ($M+H^+$).

Step 4: (R)—N-(1-(4-bromo-2-methylphenyl)ethyl)-5-(1-(trifluoromethyl)cyclopropyl)-1,2,4-oxadiazole-3-carboxamide

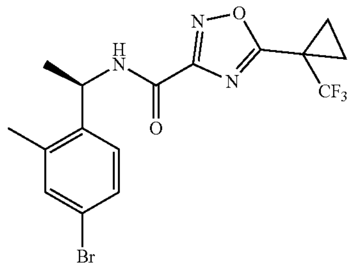 [SMILES: Cc1cc(Br)ccc1[C@@H](C)NC(=O)c1noc(C2(C(F)(F)F)CC2)n1]

To a mixture of above obtained intermediate (240 mg, 0.959 mmol, 1.0 eq), (R)-1-(4-bromo-2-methylphenyl)ethan-1-amine hydrochloride (243 mg, 0.969 mmol, 1.01 eq) in EtOH (10 ml) was added DIEA (372 mg, 2.88 mmol, 3.0 eq). The reaction mixture was stirred at 85° C. under Ar for 16 h. Concentrated and the residue was purified by flash chromatography eluted with Hex/EA=2:1 to give the title compound (120 mg, 30%) as a white solid. LC-MS: 418.1 ($M+H^+$).

Step 5: (R)—N-(1-(2-methyl-4-(4,4,5,5-tetramethyl-1,3,2-dioxaborolan-2-yl)phenyl)ethyl)-5-(1-(trifluoromethyl)cyclopropyl)-1,2,4-oxadiazole-3-carboxamide

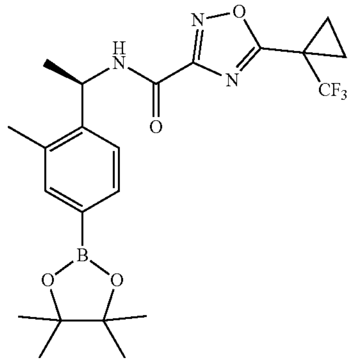 [SMILES: Cc1cc(B2OC(C)(C)C(C)(C)O2)ccc1[C@@H](C)NC(=O)c1noc(C2(C(F)(F)F)CC2)n1]

A mixture of 4,4,4',4',5,5,5',5'-octamethyl-2,2'-bi (1,3,2-dioxaborolane) (111 mg, 0.438 mmol, 1.5 eq), potassium acetate (86 mg, 0.875 mmol, 3.0 eq), $PdCl_2$ (dppf) (21.35 mg, 0.029 mmol, 0.1 eq) and above obtained intermediate (122 mg, 0.292 mmol, 1.0 eq) in dioxane (10 ml) was stirred at 100° C. under Ar for 2 h. Water was added and extracted with ethyl acetate for 3 times. The combined organic layers were washed with brine, dried over anhydrous $Na_2SO_4$. After concentration in vacuo, the residue was purified by flash chromatography eluted with Hex/EA=6:1 to give the title compound (45 mg, 33%) as a white solid. LC-MS: 466.3 ($M+H^+$).

Step 6: tert-butyl (R)-4-(5-(5-(3-methyl-4-(1-(5-(1-(trifluoromethyl)cyclopropyl)-1,2,4-oxadiazole-3-carboxamido)ethyl)phenyl)imidazo[1,2-c]pyrimidin-7-yl)pyridin-2-yl)piperazine-1-carboxylate

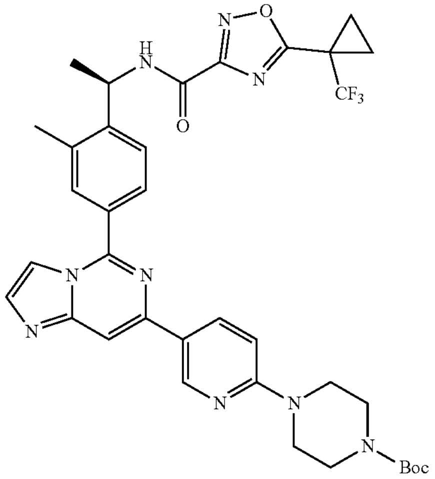 [SMILES: Cc1cc(-c2nc(-c3ccc(N4CCN(C(=O)OC(C)(C)C)CC4)nc3)cc3nccn23)ccc1[C@@H](C)NC(=O)c1noc(C2(C(F)(F)F)CC2)n1]

A mixture of tert-butyl 4-(5-(5-chloroimidazo[1,2-c]pyrimidin-7-yl)pyridin-2-yl)piperazine-1-carboxylate (40 mg, 0.096 mmol, 1.0 eq), $K_2CO_3$ (40.0 mg, 0.289 mmol, 3.0 eq), Pd(dppf)$Cl_2$ (7.05 mg, 9.64 μmol, 0.1 eq) and above obtained intermediate (44.9 mg, 0.096 mmol, 1.0 eq) in dioxane (8 ml) and water (2 ml) was stirred at 100° C. under Ar for 2 h. The solution was diluted with water, extracted with ethyl acetate for 3 times. The combined organic layers were washed with brine, dried over anhydrous $Na_2SO_4$. After concentration in vacuo. The residue was purified by flash chromatography eluted with Hex/EA=2:1 to give the title compound (58 mg, 84%) as a yellow solid. LC-MS: 718.4 (M+H$^+$).

Step 7: (R)—N-(1-(2-methyl-4-(7-(6-(piperazin-1-yl)pyridin-3-yl)imidazo[1,2-c]pyrimidin-5-yl)phenyl)ethyl)-5-(1-(trifluoromethyl)cyclopropyl)-1,2,4-oxadiazole-3-carboxamide

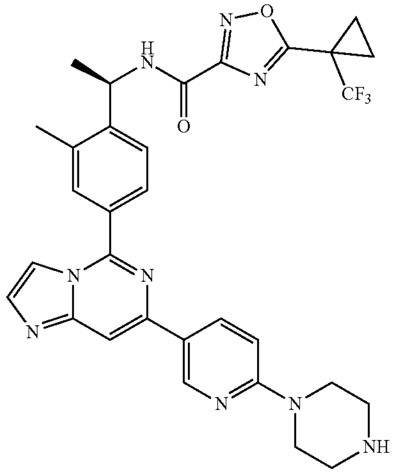 [SMILES: Cc1cc(-c2nc(-c3ccc(N4CCNCC4)nc3)cc3nccn23)ccc1[C@@H](C)NC(=O)c1noc(C2(C(F)(F)F)CC2)n1]

To a solution of above obtained intermediate (58 mg, 0.081 mmol, 1.0 eq) in DCM (3 ml) was added TFA (1 ml). The reaction mixture was stirred at rt under Ar for 1 h. The reaction mixture was concentrated in vacuo to give the title compound (49.9 mg, 100%) as a yellow solid. LC-MS: 618.3 (M+H$^+$).

Step 8: (R)—N-(1-(4-(7-(6-(4-((1-(4-(2,4-dioxotetrahydropyrimidin-1(2H)-yl)phenyl)piperidin-4-yl)methyl)piperazin-1-yl)pyridin-3-yl)imidazo[1,2-c]pyrimidin-5-yl)-2-methylphenyl)ethyl)-5-(1-(trifluoromethyl)cyclopropyl)-1,2,4-oxadiazole-3-carboxamide

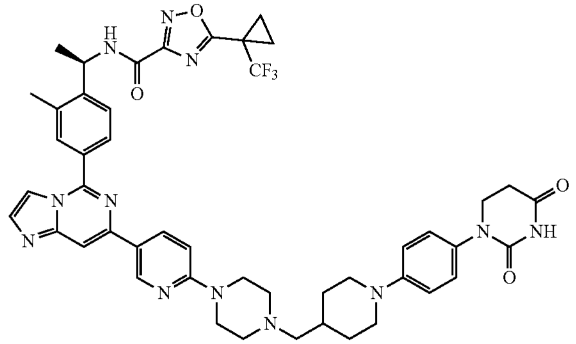 [SMILES: Cc1cc(-c2nc(-c3ccc(N4CCN(CC5CCN(c6ccc(N7CCC(=O)NC7=O)cc6)CC5)CC4)nc3)cc3nccn23)ccc1[C@@H](C)NC(=O)c1noc(C2(C(F)(F)F)CC2)n1]

To a mixture of above obtained intermediate (49 mg, 0.079 mmol, 1.0 eq), 1-(4-(2,4-dioxotetrahydropyrimidin-1(2H)-yl)phenyl)piperidine-4-carbaldehyde (26.3 mg, 0.087 mmol, 1.1 eq) and triethylamine (48.2 mg, 0.476 mmol, 6.0 eq) in DCM (5 ml) was added sodium triacetoxyborohydride (37.0 mg, 0.175 mmol, 2.2 eq) in portions. The reaction was stirred at rt under Ar for 1 h. The reaction was quenched with water and extracted with DCM for 3 times. The organic layers were washed with brine, dried over anhydrous $Na_2SO_4$. After concentration in vacuo. The residue was purified by pre-HPLC to give the title compound (12 mg, 17%) as a yellow solid. LC-MS: 903.4 (M+H$^+$). $^1$H NMR (400 MHz, DMSO-d$^6$) δ (ppm) 10.27 (s, 1H), 9.69 (d, J=7.6 Hz, 1H), 9.00 (d, J=2.4 Hz, 1H), 8.36 (dd, J=8.8, 2.4 Hz, 1H), 8.07 (s, 1H), 8.03 (s, 1H), 7.9 (m, 1H), 7.86 (s, 1H), 7.73 (m, 1H), 7.69 (m, 1H), 7.17 (m, 2H), 6.97 (m, 3H), 5.45 (m, 1H), 3.80-3.74 (m, 4H), 3.68-3.60 (m, 4H), 2.55 (s, 2H), 2.50 (m, 3H), 2.26-2.46 (d, 2H), 2.74-2.65 (m, 3H), 2.55 (s, 3H), 2.51-2.46 (m, 1H), 2.25 (d, J=7.2 Hz, 2H), 1.85 (m, 6H), 1.57 (d, J=7.2 Hz, 3H), 1.27-1.25 (m, 2H).

Example 53: (R)-2-(tert-butyl)-N-(1-(4-(6-(6-(4-(1-(3-(2,4-dioxotetrahydropyrimidin-1(2H)-yl)-4-methoxybenzoyl)piperidin-4-yl) piperazin-1-yl)pyridin-3-yl)pyrazolo[1,5-a]pyrazin-4-yl)-2-methylphenyl)ethyl)-2H-tetrazole-5-carboxamide (Compound No. 256)
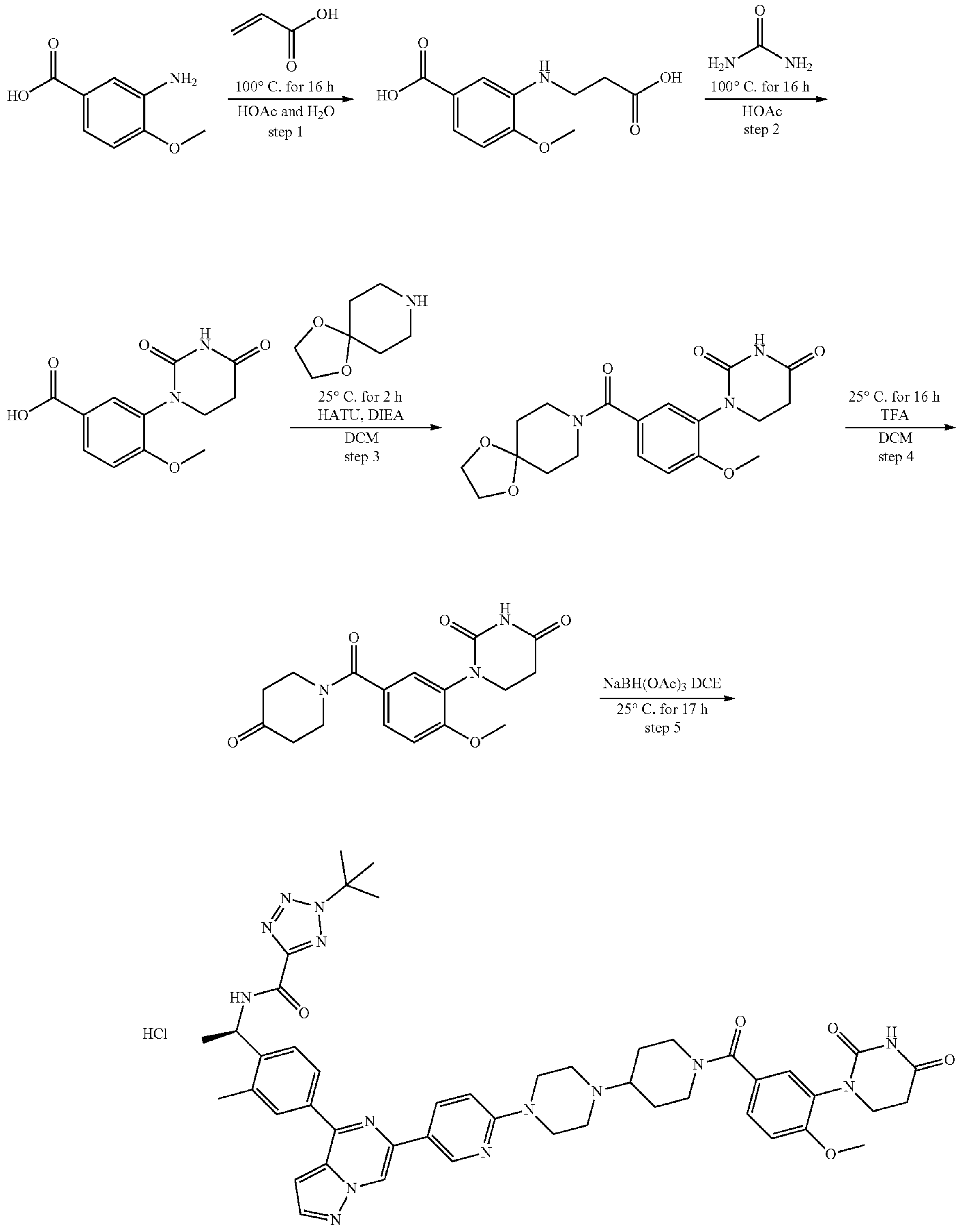

Step 1: 3-((2-carboxyethyl)amino)-4-methoxybenzoic Acid

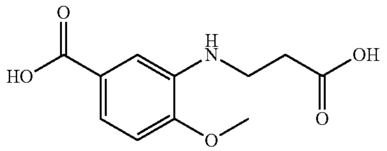 [SMILES: COc1ccc(C(=O)O)cc1NCCC(=O)O]

To a mixture of 3-amino-4-methoxybenzoic acid (1 g, 5.98 mmol, 1.0 eq) in HOAc (16 ml) and water (2 ml) was added acrylic acid (0.625 mg, 8.67 mmol, 1.45 eq). The reaction was stirred at 100° C. under Ar for 16 h. The reaction was cooled and filtered to give the title compound (1.34 g, 94% yield) as a brown solid. LC-MS: 240.2 ($M+H^+$).

Step 2: 3-(2,4-dioxotetrahydropyrimidin-1(2H)-yl)-4-methoxybenzoic acid

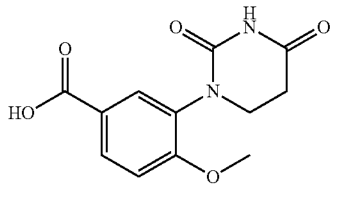 [SMILES: COc1ccc(C(=O)O)cc1N1CCC(=O)NC1=O]

To a mixture of above obtained intermediate (0.785 g, 3.82 mmol, 1.0 eq) in HOAc (12 ml) was added urea (0.985 mg, 16.41 mmol, 5.0 eq). The reaction was stirred at 100° C. under Ar for 16 h. The reaction was concentrated, then quenched with ice water. Adjust pH>7 with NaOH aqueous and extracted with EA for 3 times. The aqueous layer was poured into 4M HCl aqueous. Filtered and dried in vacuo to give the title compound (567 mg, 65% yield) as a yellow solid. LC-MS: 265.2 ($M+H^+$).

Step 3:1-(2-methoxy-5-(1,4-dioxa-8-azaspiro[4.5]decane-8-carbonyl)phenyl)dihydropyrimidine-2,4(1H,3H)-dione

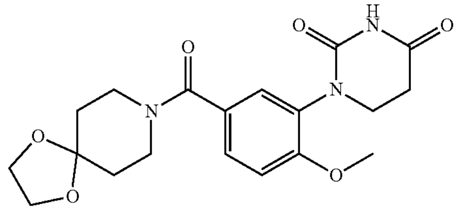 [SMILES: COc1ccc(C(=O)N2CCC3(CC2)OCCO3)cc1N1CCC(=O)NC1=O]

To a mixture of above obtained intermediate (100 mg, 0.378 mmol, 1.0 eq), 1,4-dioxa-8-azaspiro[4.5]decane (81 mg, 0.568 mmol, 1.5 eq), DIEA (196 mg, 1.514 mmol, 4.0 eq) in dry DCM (5 ml) was added HATU (216 mg, 0.568 mmol, 1.5 eq). The reaction was stirred at rt under Ar for 16 h. The reaction was quenched with water and extracted with DCM for 3 times. The organic layers were washed with brine, dried over anhydrous $Na_2SO_4$ and concentration in vacuo. The residue was purified by flash chromatography eluted with DCM/MeOH=15:1 to give the title compound (63 mg, 433% yield) as a yellow oil. LC-MS: 390.4 ($M+H^+$).

Step 4:1-(2-methoxy-5-(4-oxopiperidine-1-carbonyl)phenyl)dihydropyrimidine-2,4(1H,3H)-dione

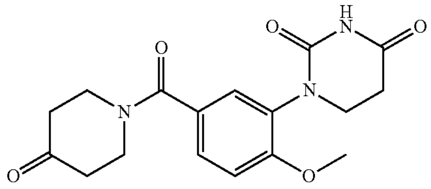 [SMILES: COc1ccc(C(=O)N2CCC(=O)CC2)cc1N1CCC(=O)NC1=O]

To a mixture of above obtained intermediate (295 mg, 0.758 mmol, 1.0 eq) in dry DCM (12 ml) was added TFA (17.28 g, 152 mmol, 200 eq). The reaction was stirred at rt under Ar for 16 h. The reaction was quenched with water and neutralized with $NaHCO_3$ aqueous before extracted with DCM for 3 times. The organic layers were washed with brine, dried over anhydrous $Na_2SO_4$ and concentration in vacuo. The residue was purified by flash chromatography eluted with DCM/MeOH=10:1 to give the title compound (260 mg, 99% yield) as a white solid. LC-MS: 346.3 ($M+H^+$).

Step 5: (R)-2-(tert-butyl)-N-(1-(4-(6-(6-(4-(1-(3-(2,4-dioxotetrahydropyrimidin-1(2H)-yl)-4-methoxy-benzoyl)piperidin-4-yl) piperazin-1-yl)pyridin-3-yl) pyrazolo[1,5-a]pyrazin-4-yl)-2-methylphenyl)ethyl)-2H-tetrazole-5-carboxamide

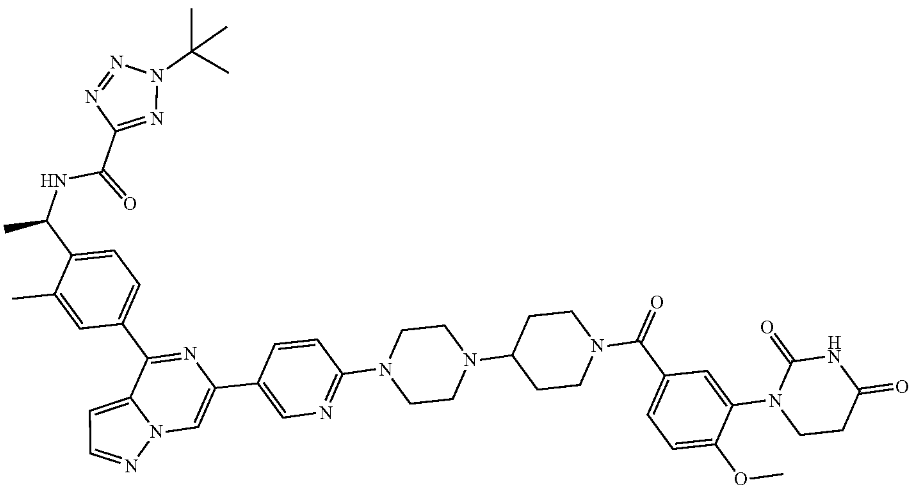 [SMILES: COc1ccc(C(=O)N2CCC(N3CCN(c4ccc(-c5cn6nccc6c(-c6ccc([C@@H](C)NC(=O)c7nnn(C(C)(C)C)n7)c(C)c6)n5)cn4)CC3)CC2)cc1N1CCC(=O)NC1=O]

To a mixture of (R)-2-(tert-butyl)-N-(1-(2-methyl-4-(6-(6-(piperazin-1-yl)pyridin-3-yl)pyrazolo[1,5-a]pyrazin-4-yl)phenyl)ethyl)-2H-tetrazole-5-carboxamide (349 mg, 0.579 mmol, 1.0 eq), TEA (176 mg, 1.737 mmol, 3.0 eq) and above obtained intermediate (200 mg, 0.579 mmol, 1.0 eq) in dry DCE (16 ml) was added NaBH(OAc) 3 (245 mg, 1.158 mmol, 2.0 eq) in portions. The reaction was stirred at rt under Ar for 17 h. The reaction was quenched with water and extracted with DCM for 3 times. The organic layers were washed with brine, dried over anhydrous $Na_2SO_4$ and concentration in vacuo. The residue was purified by pre-HPLC to give the title compound (67 mg, 13% yield) as a yellow solid. LC-MS: 896.3 $(M+H^+)$. $^1H$ NMR (400 MHz, DMSO-$d^6$) δ (ppm) 10.36 (s, 1H), 9.58 (d, J=8.0 Hz, 1H), 9.29 (d, J=2.0 Hz, 1H), 8.96 (s, 1H), 8.35-8.32 (m, 1H), 8.23 (d, J=2.0 Hz, 1H), 8.01-7.97 (m, 2H), 7.72 (d, J=8.0 Hz, 1H), 7.41-7.35 (m, 2H), 7.22-7.18 (m, 2H), 6.96 (d, J=8.0 Hz, 1H), 5.48-5.44 (m, 1H), 3.87 (s, 3H), 3.64-3.60 (m, 6H), 2.73-2.70 (m, 2H), 2.58-2.49 (m, 11H), 2.23 (d, J=8.0 Hz, 2H), 1.91-1.79 (m, 2H), 1.76 (s, 9H), 1.58 (d, J=8.0 Hz, 3H), 1.30-1.09 (m, 3H).

Example 54: (R)-2-(tert-butyl)-N-(1-(4-(6-(6-(4-((1-(3-(2,4-dioxotetrahydropyrimidin-1(2H)-yl)-4-methoxybenzoyl)piperidin-4-yl)methyl)piperazin-1-yl)pyridin-3-yl)pyrazolo[1,5-a]pyrazin-4-yl)-2-methylphenyl)ethyl)-2H-tetrazole-5-carboxamide (Compound No. 257)

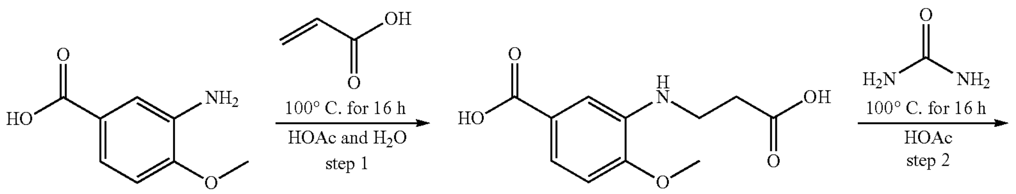

-continued

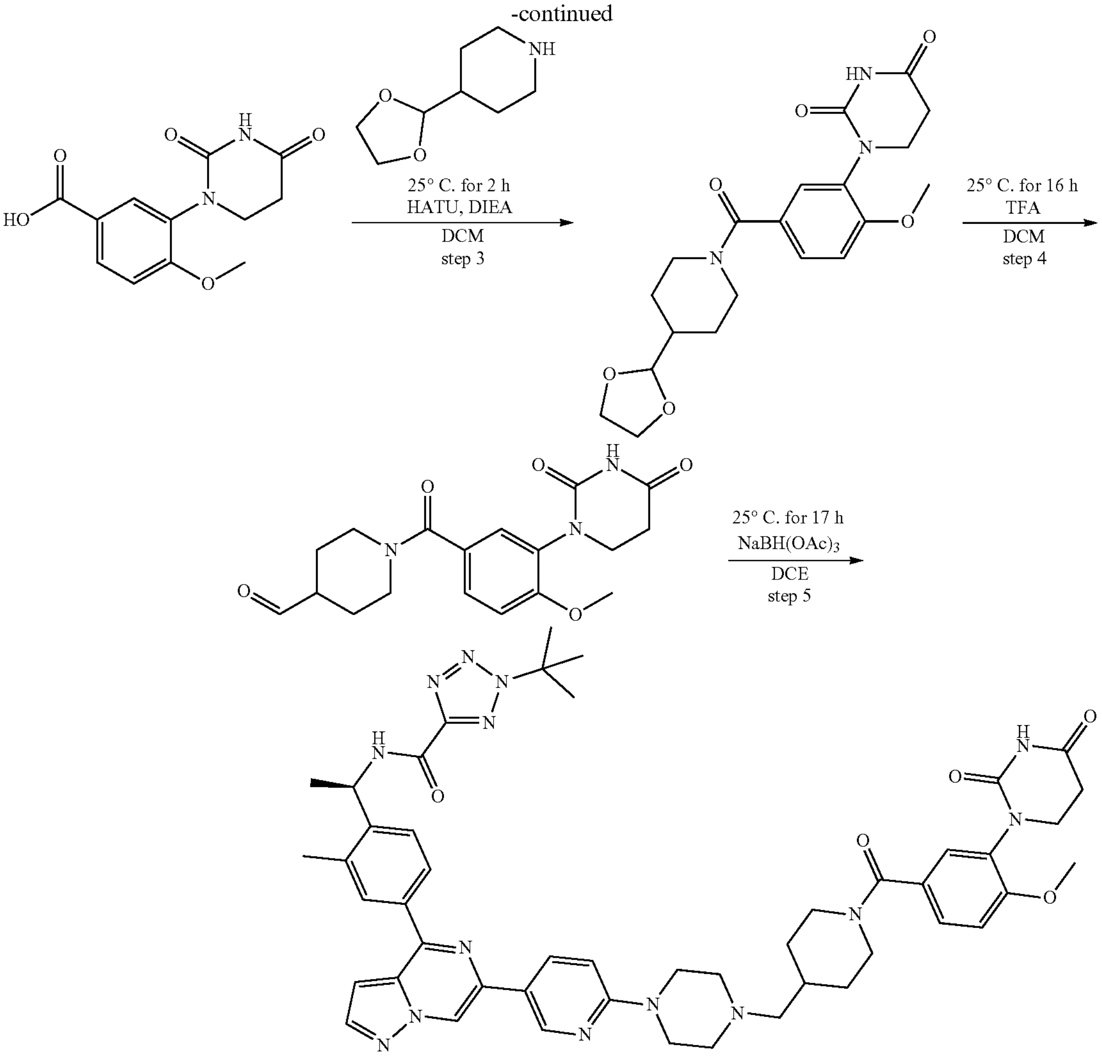

Step 1: 3-((2-carboxyethyl)amino)-4-methoxybenzoic Acid

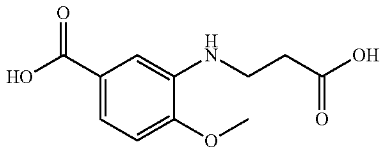 [SMILES: COc1ccc(C(=O)O)cc1NCCC(=O)O]

To a mixture of 3-amino-4-methoxybenzoic acid (1 g, 5.98 mmol, 1.0 eq) in HOAc (16 ml) and water (2 ml) was added acrylic acid (0.625 mg, 8.67 mmol, 1.45 eq). The reaction was stirred at 100° C. under Ar for 16 h. The reaction was cooled and filtered to give the title compound (1.34 g, 94% yield) as a brown solid. LC-MS: 240.2 (M+H$^+$).

Step 2:3-(2,4-dioxotetrahydropyrimidin-1(2H)-yl)-4-methoxybenzoic Acid

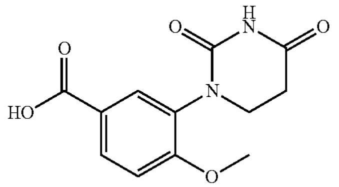 [SMILES: COc1ccc(C(=O)O)cc1N1CCC(=O)NC1=O]

To a mixture of above obtained intermediate (0.785 g, 3.82 mmol, 1.0 eq) in HOAc (12 ml) was added urea (0.985 mg, 16.41 mmol, 5.0 eq). The reaction was stirred at 100° C. under Ar for 16 h. The reaction was concentrated, then quenched with ice water. Adjust pH>7 with NaOH aqueous and extracted with EA for 3 times. The aqueous layer was poured into 4M HCl aqueous. Filtered and dried in vacuo to give the title compound (567 mg, 65% yield) as a yellow solid. LC-MS: 265.2 (M+H$^+$).

Step 3: 1-(5-(4-(1,3-dioxolan-2-yl)piperidine-1-carbonyl)-2-methoxyphenyl)dihydropyrimidine-2,4(1H,3H)-dione

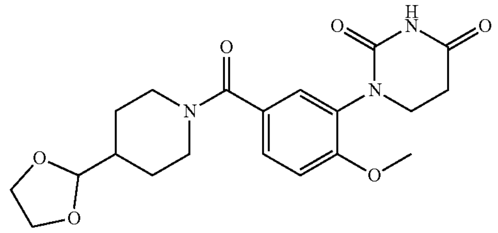 [SMILES: COc1ccc(C(=O)N2CCC(C3OCCO3)CC2)cc1N1CCC(=O)NC1=O]

To a mixture of above obtained intermediate (500 mg, 1.892 mmol, 1.0 eq), 4-(1,3-dioxolan-2-yl)piperidine (446 mg, 2.84 mmol, 1.5 eq), DIEA (978 mg, 7.57 mmol, 4.0 eq) in dry DCM (25 ml) was added HATU (1.079 g, 2.84 mmol, 1.5 eq). The reaction was stirred at rt under Ar for 2 h. The reaction was quenched with water and extracted with DCM for 3 times. The organic layers were washed with brine, dried over anhydrous $Na_2SO_4$ and concentration in vacuo. The residue was purified by flash chromatography eluted with DCM/MeOH=15:1 to give the title compound (560 mg, 73% yield) as a yellow solid. LC-MS: 404.3 (M+H$^+$).

Step 4: 1-(3-(2,4-dioxotetrahydropyrimidin-1(2H)-yl)-4-methoxybenzoyl)piperidine-4-carbaldehyde

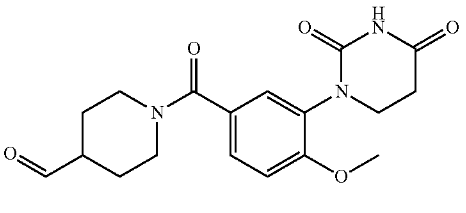 [SMILES: COc1ccc(C(=O)N2CCC(C=O)CC2)cc1N1CCC(=O)NC1=O]

To a mixture of above obtained intermediate (200 mg, 0.496 mmol, 1.0 eq) in dry THF (3 ml) was added 4M HCl/dioxane (3 ml). The reaction was stirred at 70° C. under Ar for 16 h. The reaction was concentrated and neutralized with $NaHCO_3$ aqueous before extracted with DCM for 3 times. The organic layers were washed with brine, dried over anhydrous $Na_2SO_4$ and concentration in vacuo. The residue was purified by flash chromatography eluted with DCM/MeOH=10:1 to give the title compound (180 mg, 58% yield) as a white solid. LC-MS: 360.3 (M+H$^+$).

Step 5: (R)-2-(tert-butyl)-N-(1-(4-(6-(6-(4-((1-(3-(2,4-dioxotetrahydropyrimidin-1(2H)-yl)-4-methoxybenzoyl)piperidin-4-yl)methyl)piperazin-1-yl)pyridin-3-yl)pyrazolo[1,5-a]pyrazin-4-yl)-2-methylphenyl)ethyl)-2H-tetrazole-5-carboxamide

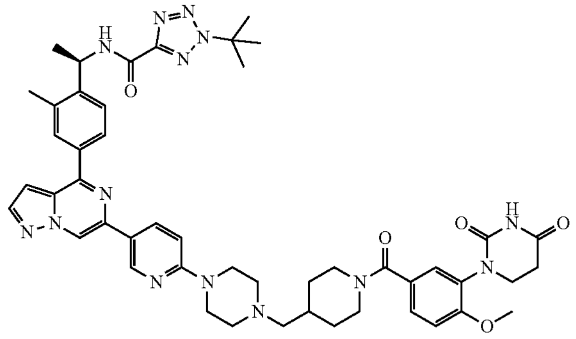 [SMILES: COc1ccc(C(=O)N2CCC(CN3CCN(c4ccc(-c5cn6nccc6c(-c6ccc([C@@H](C)NC(=O)c7nnn(C(C)(C)C)n7)c(C)c6)n5)cn4)CC3)CC2)cc1N1CCC(=O)NC1=O]

To a mixture of (R)-2-(tert-butyl)-N-(1-(2-methyl-4-(6-(6-(piperazin-1-yl)pyridin-3-yl)pyrazolo[1,5-a]pyrazin-4-yl)phenyl)ethyl)-2H-tetrazole-5-carboxamide (151 mg, 0.250 mmol, 1.0 eq), TEA (0.076 mg, 0.751 mmol, 3.0 eq) and above obtained intermediate (90 mg, 0.250 mmol, 1.0 eq) in dry DCE (8 ml) was added NaBH(OAc) 3 (106 mg, 0.501 mmol, 2.0 eq) in portions. The reaction was stirred at rt under Ar for 17 h. The reaction was quenched with water and extracted with DCM for 3 times. The organic layers were washed with brine, dried over anhydrous $Na_2SO_4$. After concentration in vacuo. The residue was purified by pre-HPLC to give the title compound (87 mg, 38% yield) as a yellow solid. LC-MS: 910.8 (M+H$^+$). $^1$H NMR (400 MHz, DMSO-d$^6$) δ (ppm) 10.36 (s, 1H), 9.58 (d, J=8.0 Hz, 1H), 9.29 (s, 1H), 8.97 (d, J=2.0 Hz, 1H), 8.32-8.34 (m, 1H), 8.23 (d, J=2.0 Hz, 1H), 8.01-7.97 (m, 2H), 7.72 (d, J=8.0 Hz, 1H), 7.44-7.37 (m, 2H), 7.22-7.18 (m, 2H), 6.97 (d, J=8.0 Hz, 1H), 5.48-5.39 (m, 1H), 3.87 (s, 3H), 3.73-3.60 (m, 6H), 2.80-2.65 (m, 7H), 2.57 (s, 3H), 2.08-2.02 (m, 1H), 1.91-1.86 (m, 2H), 1.76 (s, 9H), 1.57 (d, J=8.0 Hz, 3H), 1.46-1.44 (m, 2H), 1.26 (s, 3H).

Example 55: (R)-2-(tert-butyl)-N-(1-(4-(6-(6-(4-((1-(4-(2,4-dioxotetrahydropyrimidin-1(2H)-yl)phenyl)piperidin-4-yl)methyl)piperazin-1-yl)pyridin-3-yl)-3-isocyanopyrazolo[1,5-a]pyrazin-4-yl)-2-methylphenyl)ethyl)-2H-tetrazole-5-carboxamide (Compound No. 259)
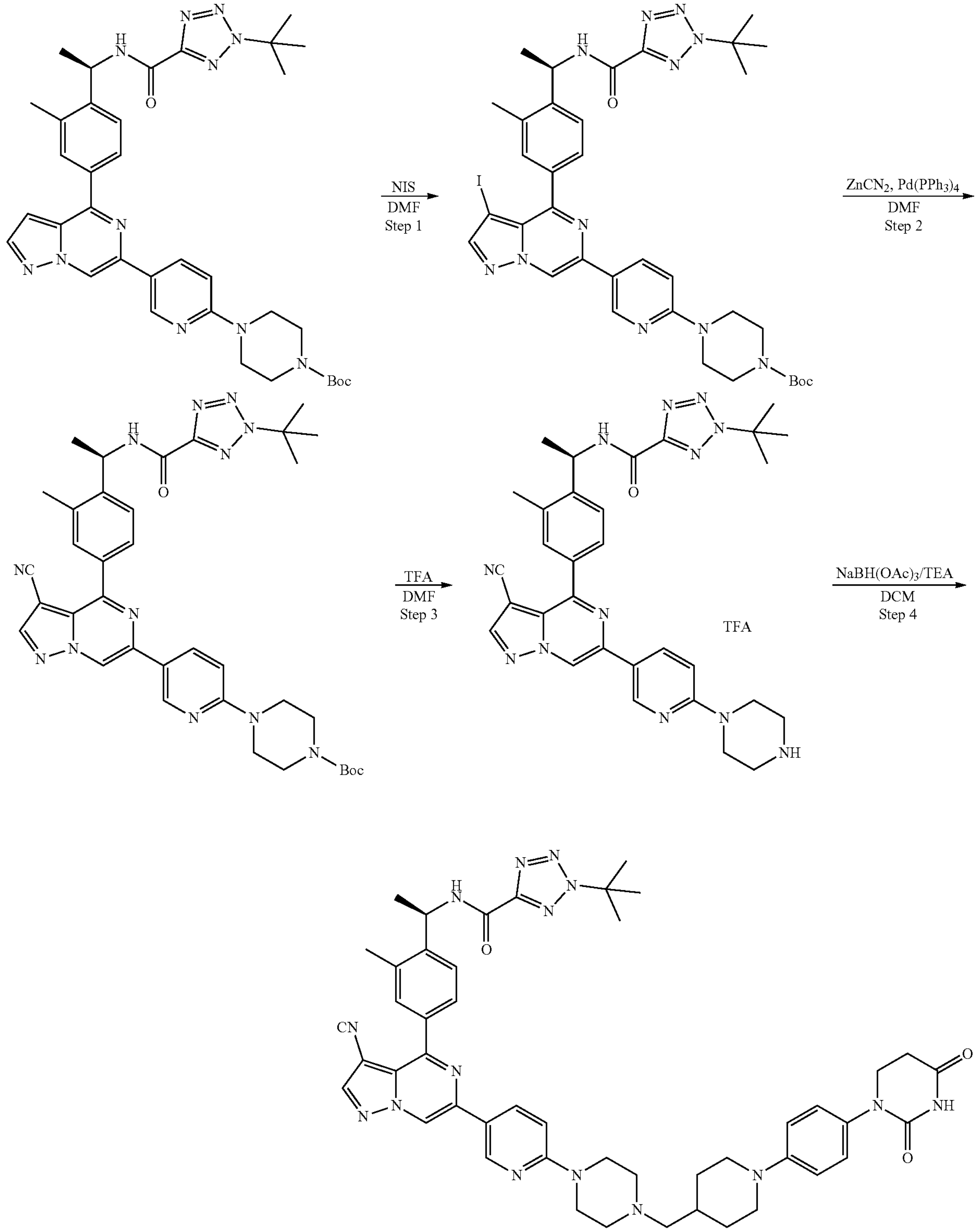

Step 1: tert-butyl (R)-4-(5-(4-(4-(1-(2-(tert-butyl)-2H-tetrazole-5-carboxamido)ethyl)-3-methylphenyl)-3-iodopyrazolo[1,5-a]pyrazin-6-yl)pyridin-2-yl)piperazine-1-carboxylate

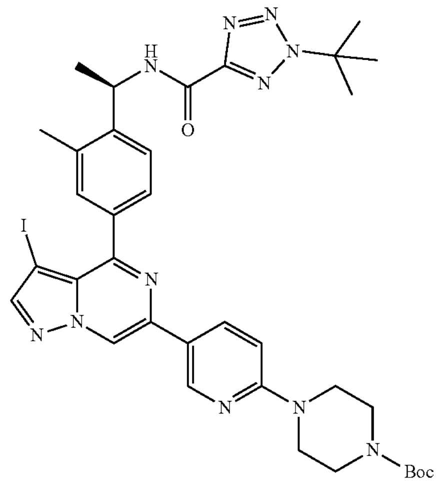

To a solution of tert-butyl (R)-4-(5-(4-(4-(1-(2-(tert-butyl)-2H-tetrazole-5-carboxamido)ethyl)-3-methylphenyl)pyrazolo[1,5-a]pyrazin-6-yl)pyridin-2-yl)piperazine-1-carboxylate (1 g, 1.502 mmol, 1.0 eq) in DMF (3 ml) was added NIS (0.507 g, 2.253 mmol, 1.5 eq). The reaction was stirred at rt overnight. Water was added, extracted with EA, washed with water, brine, dried over anhydrous $Na_2SO_4$ and concentrated to dryness. The residue was purified by combi-flash with 10 DCM/MeOH=19:1 to give the title compound (1.04 g, 87%) as a yellow solid. LC-MS: 792.95 (M+H$^+$).

Step 2: tert-butyl (R)-4-(5-(4-(4-(1-(2-(tert-butyl)-2H-tetrazole-5-carboxamido)ethyl)-3-methylphenyl)-3-cyanopyrazolo[1,5-a]pyrazin-6-yl)pyridin-2-yl)piperazine-1-carboxylate

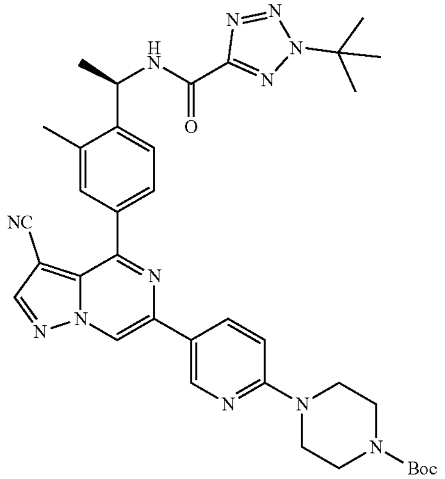 [SMILES: Cc1cc(-c2nc(-c3ccc(N4CCN(C(=O)OC(C)(C)C)CC4)nc3)cn3ncc(C#N)c23)ccc1[C@@H](C)NC(=O)c1nnn(C(C)(C)C)n1]

A mixture of above obtained intermediate (603 mg, 0.762 mmol, 1.0 eq), $ZnCN_2$ (537 mg, 4.57 mmol, 6.0 eq), $Pd(Ph_3P)_4$ (88 mg, 0.076 mmol, 0.1 eq) in dry DMF (6 ml) was stirred at 100° C. under Ar for overnight. Filtered and concentrated to dryness. The residue was purified by cobmi-flash eluted with DCM/MeOH=20:1 to give the title compound (340 mg, 64.6%) as a brown solid. LC-MS: 691.99 (M+H$^+$).

Step 3: (R)-2-(tert-butyl)-N-(1-(4-(3-cyano-6-(6-(piperazin-1-yl)pyridin-3-yl)pyrazolo[1,5-a]pyrazin-4-yl)-2-methylphenyl)ethyl)-2H-tetrazole-5-carboxamide-2,2,2-trifluoroacetaldehyde

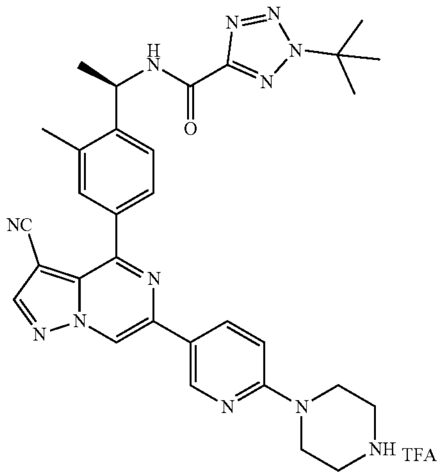 [SMILES: Cc1cc(-c2nc(-c3ccc(N4CCNCC4)nc3)cn3ncc(C#N)c23)ccc1[C@@H](C)NC(=O)c1nnn(C(C)(C)C)n1]

A mixture of above obtained intermediate (340 mg, 0.492 mmol, 1.0 eq) in DCM (5 ml) and TFA (5 ml) was stirred at rt for 1 h. Concentrated to give the title compound (347 mg, 100%) as a brown solid. LC-MS: 592.03 (M+H$^+$).

Step 4: (R)-2-(tert-butyl)-N-(1-(4-(6-(6-(4-((1-(4-(2,4-dioxotetrahydropyrimidin-1(2H)-yl)phenyl)piperidin-4-yl)methyl)piperazin-1-yl)pyridin-3-yl)-3-isocyanopyrazolo[1,5-a]pyrazin-4-yl)-2-methylphenyl)ethyl)-2H-tetrazole-5-carboxamide

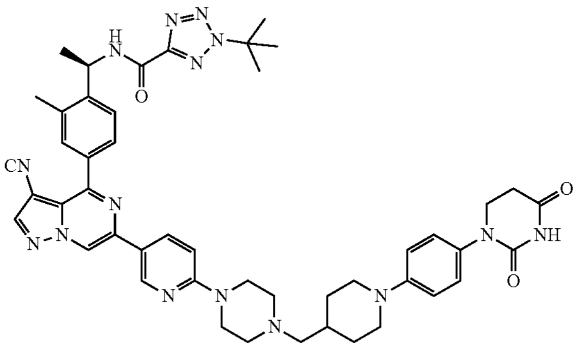

To a solution of above obtained intermediate (347 mg, 0.492 mmol, 1.0 eq), 1-(4-(2,4-dioxotetrahydropyrimidin-1(2H)-yl)phenyl)piperidine-4-carbaldehyde (178 mg, 0.591 mmol, 1.2 eq), TEA (249 mg, 2.462 mmol, 5.0 eq) in DCM (5 ml) was added NaBH(OAc) 3 (209 mg, 0.985 mmol, 2.0 eq). The reaction was stirred at rt for 1 h. Diluted with DCM, the mixture was washed with water, brine, dried over anhydrous $Na_2SO_4$ and concentrated to dryness. The residue was purified by pre-HPLC to give the title compound (35.2 mg, 8.16%) as a yellow solid. LC-MS: 877.02 ($M+H^+$). $^1H$ NMR (400 MHz, DMSO-$d^6$) δ (ppm) 10.25 (s, 1H), 9.57 (d, J=8.0 Hz, 1H), 9.53 (s, 1H), 8.94 (d, J=2.4 Hz, 1H), 8.87 (s, 1H), 8.32-8.30 (dd, J=9.2, 2.4 Hz, 1H), 7.79 (m, 3H), 7.13 (d, J=8.4 Hz, 2H), 6.97-6.92 (m, 3H), 5.50-5.43 (m, 1H), 3.71-3.60 (m, 8H), 2.69-2.64 (m, 4H), 2.53 (s, 3H), 2.47-2.44 (m, 4H), 2.22 (d, J=6.8 Hz, 2H), 1.84-1.80 (m, 2H), 1.73 (s, 10H), 1.54 (d, J=6.8 Hz, 3H), 1.27-1.18 (m, 2H).

Example 56: (R)-2-(tert-butyl)-N-(1-(4-(6-(6-(4-((1-(4-(2,4-dioxotetrahydropyrimidin-1(2H)-yl)phenyl)piperidin-4-yl)methyl)piperazin-1-yl)pyridin-3-yl)-3-fluoropyrazolo[1,5-a]pyrazin-4-yl)-2-methylphenyl)ethyl)-2H-tetrazole-5-carboxamide (Compound No. 260)

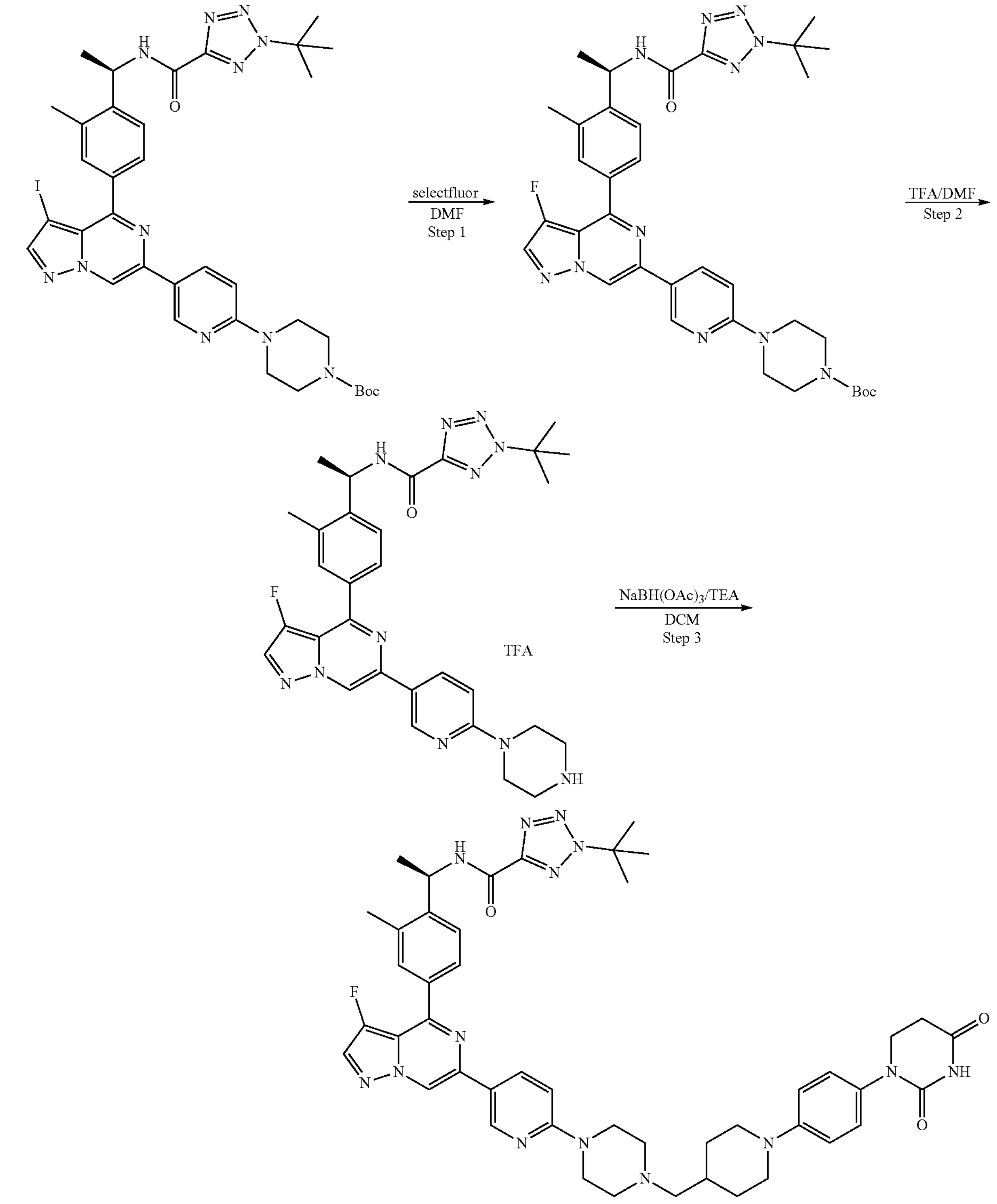

Step 1: (R)-4-(5-(4-(4-(1-(2-(tert-butyl)-2H-tetrazole-5-carboxamido)ethyl)-3-tert-butyl methylphenyl)-3-fluoropyrazolo[1,5-a]pyrazin-6-yl)pyridin-2-yl)piperazine-1-carboxylate

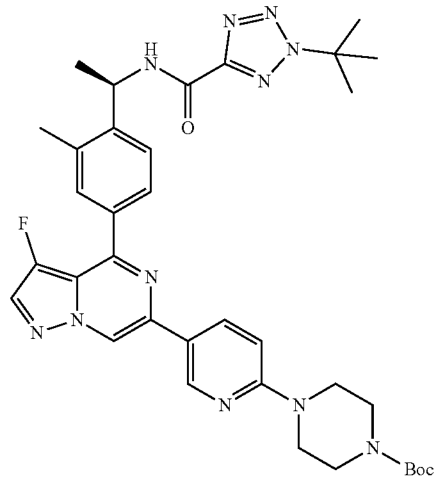 [SMILES: Cc1cc(-c2nc(-c3ccc(N4CCN(C(=O)OC(C)(C)C)CC4)nc3)cn3ncc(F)c23)ccc1[C@@H](C)NC(=O)c1nnn(C(C)(C)C)n1]

To a solution of tert-butyl (R)-4-(5-(4-(4-(1-(2-(tert-butyl)-2H-tetrazole-5-carboxamido)ethyl)-3-methylphenyl) pyrazolo[1,5-a]pyrazin-6-yl)pyridin-2-yl)piperazine-1-carboxylate (1 g, 1.502 mmol, 1.0 eq) in DCM (10 ml) was added select fluor (1.596 g, 4.51 mmol, 3.0 eq). The reaction was stirred at rt overnight. Water was added, the mixture was extracted with DCM for 3 times. The organic layers were washed with brine, dried over anhydrous $Na_2SO_4$ and concentrated to dryness. The residue was purified by combi-flash eluted with DCM/MeOH=97:3 to give the title compound (180 mg, 17.53%) as a brown solid. LC-MS: 684.69 $(M+H^+)$.

Steps 2-3: (R)-2-(tert-butyl)-N-(1-(4-(6-(6-(4-((1-(4-(2,4-dioxotetrahydropyrimidin-1(2H)-yl)phenyl) piperidin-4-yl)methyl)piperazin-1-yl)pyridin-3-yl)-3-fluoropyrazolo[1,5-a]pyrazin-4-yl)-2-methylphenyl) ethyl)-2H-tetrazole-5-carboxamide

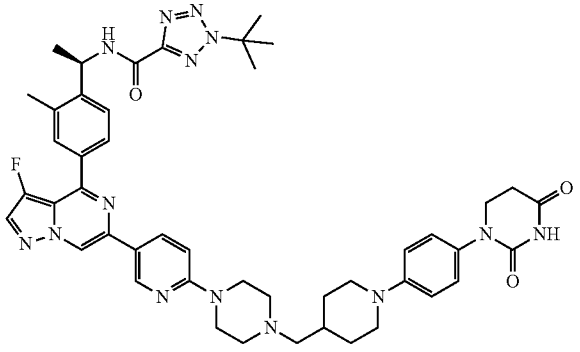 [SMILES: Cc1cc(-c2nc(-c3ccc(N4CCN(CC5CCN(c6ccc(N7CCC(=O)NC7=O)cc6)CC5)CC4)nc3)cn3ncc(F)c23)ccc1[C@@H](C)NC(=O)c1nnn(C(C)(C)C)n1]

Following the synthesis of EXAMPLE 3, the title compound was obtained after preparative HPLC purification as a white solid. (26 mg, 11.60%) as a yellow solid. LC-MS: 869.81 $(M+H^+)$. $^1H$ NMR (400 MHz, DMSO-$d^6$) δ (ppm) 10.25 (s, 1H), 9.58 (d, J=8.0 Hz, 1H), 9.40 (s, 1H), 8.87 (t, d=1.6 Hz, 1H), 8.30-8.24 (m, 2H), 8.00-7.96 (m, 2H), 7.71 (d, J=8.4 Hz, 1H), 7.24-7.22 (m, 1H), 7.13 (d, J=8.8 Hz, 2H), 6.93 (d, J=8.8 Hz, 2H), 5.47-5.40 (m, 1H), 3.71-3.68 (m, 4H), 3.55-3.50 (m, 4H), 2.69-2.64 (m, 4H), 2.55 (m, 3H), 2.54-2.50 (m, 4H), 2.22 (d, J=7.2 Hz, 2H), 1.84-1.80 (m, 2H), 1.74 (s, 10H), 1.55 (d, J=7.2 Hz, 3H), 1.27-1.18 (m, 2H).

Example 57: (R)-3-(tert-butyl)-N-(1-(4-(7-(6-(4-((1-(4-(2,4-dioxotetrahydropyrimidin-1(2H)-yl)phenyl) piperidin-4-yl)methyl)piperazin-1-yl)pyridin-3-yl)-3-fluoroimidazo[1,2-c]pyrimidin-5-yl)-2-methylphenyl)ethyl)-1,2,4-oxadiazole-5-carboxamide (Compound No. 261)

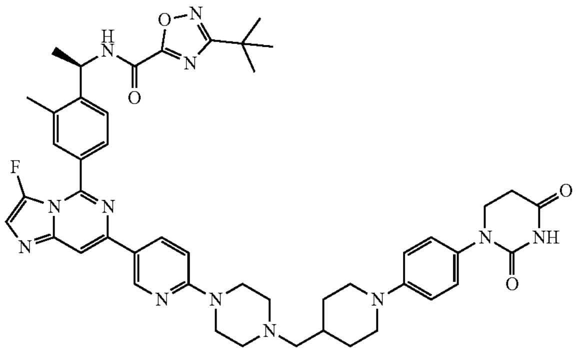

Following the synthesis of EXAMPLE 56, the title compound was obtained after preparative HPLC purification (17.6 mg, 17.44%) as a yellow solid. LC-MS: 869.69 $(M+H^+)$. $^1H$ NMR (400 MHz, DMSO-$d^6$) δ (ppm) 10.25 (s, 1H), 9.99 (d, J=8.0 Hz, 1H), 8.88 (t, J=1.6 Hz, 1H), 8.28-8.24 (m, 1H), 8.19 (s, 1H), 8.06 (s, 1H), 7.91-7.86 (m, 2H), 7.74-7.70 (m, 2H), 7.13 (d, J=9.2 Hz, 2H), 6.92 (d, J=9.2 Hz, 2H), 5.43-5.36 (m, 1H), 3.71-3.67 (m, 4H), 3.55-3.51 (m, 4H), 2.69-2.63 (m, 4H), 2.53-2.49 (m, 7H), 2.22 (d, J=7.2 Hz, 2H), 1.83-1.70 (m, 3H), 1.55 (d, J=6.8 Hz, 3H), 1.37 (s, 9H), 1.27-1.18 (m, 2H).

Example 58: (R)-2-(tert-butyl)-N-(1-(4-(6-(4-(4-((1-(4-(2,4-dioxotetrahydropyrimidin-1(2H)-yl)phenyl)piperidin-4-yl)methyl)piperazin-1-yl)-3-fluorophenyl)pyrazolo[1,5-a]pyrazin-4-yl)-2-methylphenyl)ethyl)-2H-tetrazole-5-carboxamide (Compound No. 262)
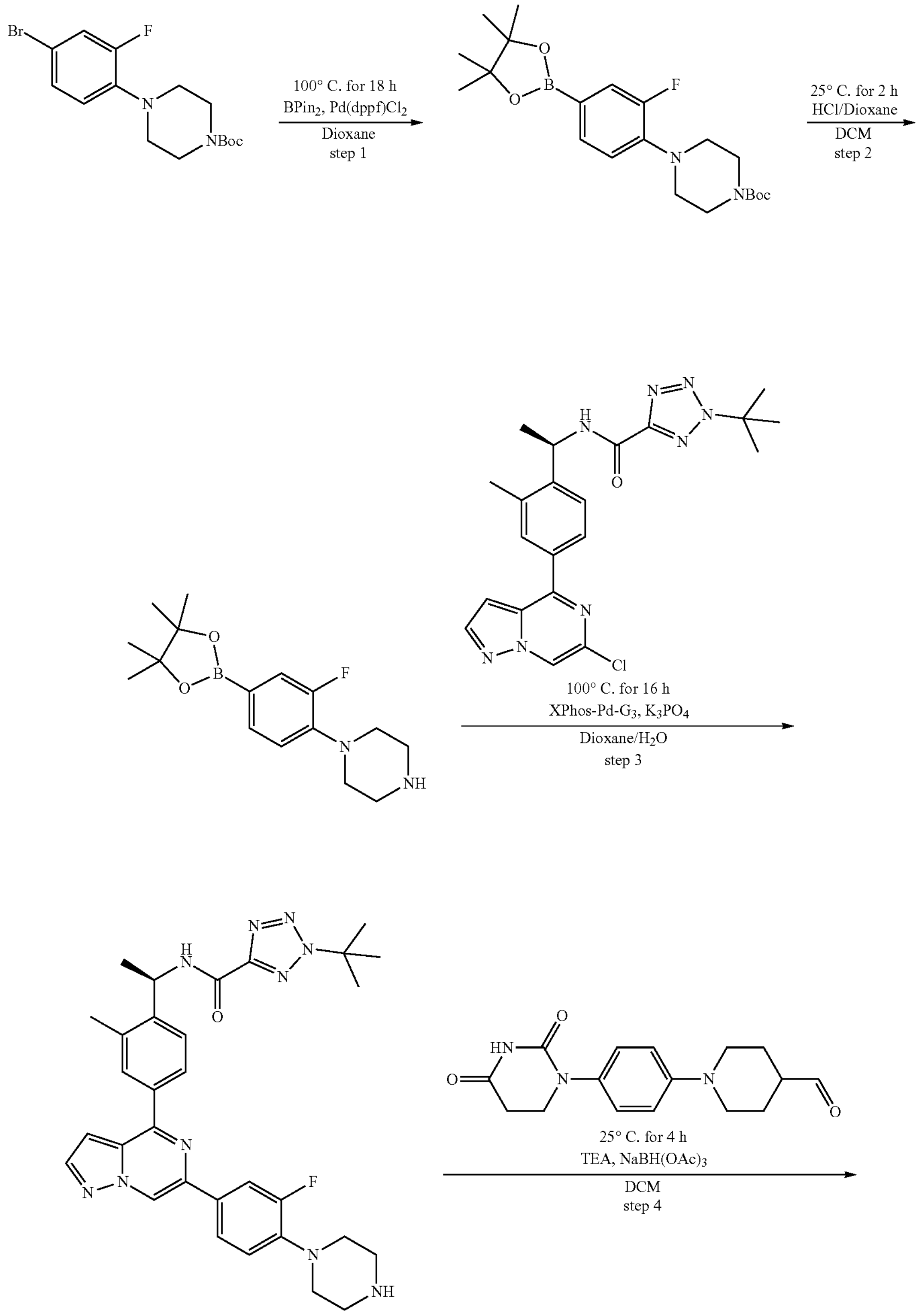

-continued

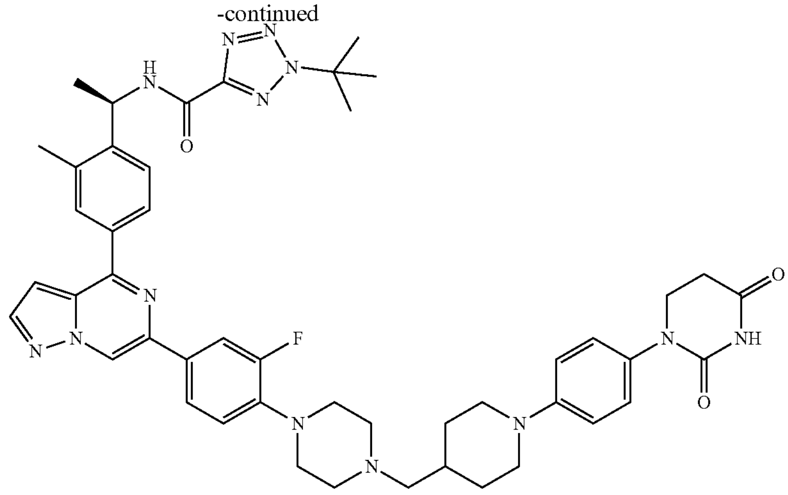

Step 1: tert-butyl 4-(2-fluoro-4-(4,4,5,5-tetramethyl-1,3,2-dioxaborolan-2-yl)phenyl)piperazine-1-carboxylate

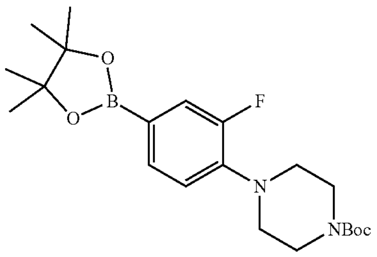 [SMILES: CC(C)(C)OC(=O)N1CCN(c2ccc(B3OC(C)(C)C(C)(C)O3)cc2F)CC1]

A mixture of tert-butyl 4-(4-bromo-2-fluorophenyl)piperazine-1-carboxylate (150 mg, 0.418 mmol, 1.0 eq), $Bpin_2$ (0.212 mg, 0.835 mmol, 2.0 eq), KOAc (0.123 mg, 0.253 mmol, 3.0 eq) and $Pd(dppf)Cl_2$ (0.031 mg, 0.042 mmol, 0.1 eq) in dry dioxane (4 ml) was stirred at 100° C. under Ar for 18 h. The reaction was diluted with water and extracted with DCM for 3 times. The organic layers were washed with brine, dried over anhydrous $Na_2SO_4$ and concentrated in vacuo. The residue was purified by flash chromatography eluted with PE/EA=3:1 to give the title compound (170 mg, 100% yield) as yellow oil. LC-MS: 407.4 ($M+H^+$).

Step 2: 1-(2-fluoro-4-(4,4,5,5-tetramethyl-1,3,2-dioxaborolan-2-yl)phenyl)piperazine

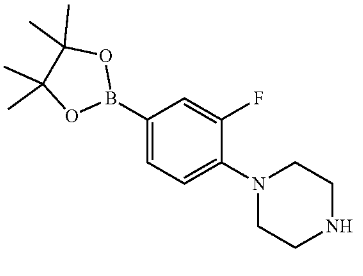 [SMILES: CC1(C)OB(c2ccc(N3CCNCC3)c(F)c2)OC1(C)C]

To a mixture of above obtained intermediate (0.141 g, 0.347 mmol, 1.0 eq) in DCM (4 ml) was added 4M HCl/dioxane (4 ml). The reaction mixture was stirred at rt under Ar for 2 h. After concentration in vacuo, the residue was used in next step without further purification. LC-MS: 306.9 ($M+H^+$).

Step 3: (R)-2-(tert-butyl)-N-(1-(4-(6-(3-fluoro-4-(piperazin-1-yl)phenyl)pyrazolo[1,5-a]pyrazin-4-yl)-2-methylphenyl)ethyl)-2H-tetrazole-5-carboxamide

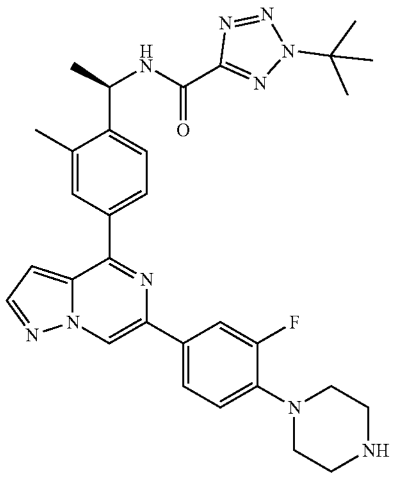 [SMILES: Cc1cc(-c2nc(-c3ccc(N4CCNCC4)c(F)c3)cn3nccc23)ccc1[C@@H](C)NC(=O)c1nnn(C(C)(C)C)n1]

A mixture of above obtained intermediate (100 mg, 0.328 mmol, 1.2 eq), (R)-2-(tert-butyl)-N-(1-(4-(6-chloropyrazolo[1,5-a]pyrazin-4-yl)-2-methylphenyl)ethyl)-2H-tetrazole-5-carboxamide (120 mg, 0.273 mmol, 1.0 eq), $K_3PO_4$ (174 mg, 0.820 mmol, 3.0 eq) and Xphos-Pd-G3 (23 mg, 0.027 mmol, 0.1 eq) in dioxane (4 ml) and water (1 ml) was stirred at 100° C. under Ar for 16 h. The reaction was diluted with water and extracted with DCM for 3 times. The organic layers were washed with brine, dried over anhydrous $Na_2SO_4$ and concentration in vacuo. The residue was purified by flash chromatography eluted with DCM/MeOH=15:1 to give the title compound (64 mg, 40% yield) as a yellow solid. LC-MS: 583.8 ($M+H^+$).

Step 4: (R)-2-(tert-butyl)-N-(1-(4-(6-(4-(4-((1-(4-(2,4-dioxotetrahydropyrimidin-1(2H)-yl)phenyl)piperidin-4-yl)methyl)piperazin-1-yl)-3-fluorophenyl)pyrazolo[1,5-a]pyrazin-4-yl)-2-methylphenyl)ethyl)-2H-tetrazole-5-carboxamide

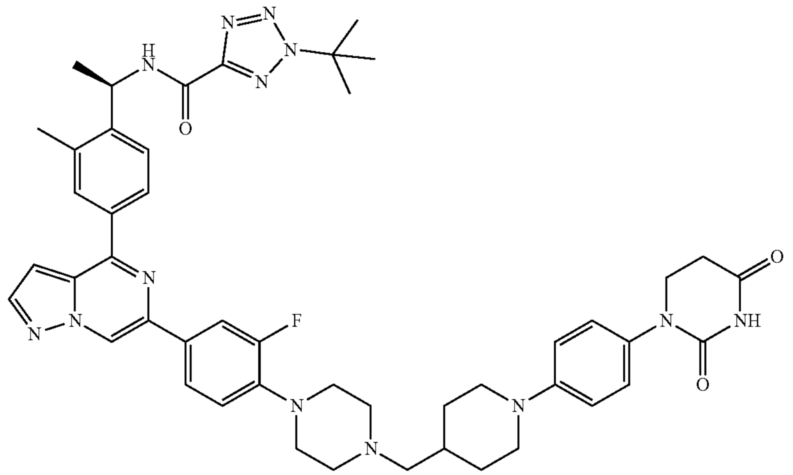 [SMILES: Cc1cc(-c2nc(-c3ccc(N4CCN(CC5CCN(c6ccc(N7CCC(=O)NC7=O)cc6)CC5)CC4)c(F)c3)cn3nccc23)ccc1[C@@H](C)NC(=O)c1nnn(C(C)(C)C)n1]

To a solution of above obtained intermediate (64 mg, 0.110 mmol, 1.0 eq) in DCM (5 ml) were added 1-(4-(2,4-dioxotetrahydropyrimidin-1(2H)-yl)phenyl)piperidine-4-carbaldehyde (40 mg, 0.132 mmol, 1.2 eq) and NaBH(OAc) 3 (47 mg, 0.22 mmol, 2.0 eq). The reaction was stirred at rt under Ar for 4 h. The reaction mixture was quenched with water and extracted with DCM for 3 times. The organic layers were washed with brine, dried over anhydrous $Na_2SO_4$ and concentration in vacuo. The residue was purified by pre-HPLC to give the title compound (41 mg, 43% yield) as a yellow solid. LC-MS: 869.1 ($M+H^+$). $^1H$ NMR (400 MHz, DMSO-$d^6$) δ (ppm) 10.29 (s, 1H), 9.60 (d, J=8.0 Hz, 1H), 9.40 (s, 1H), 8.27 (d, J=2.0 Hz, 1H), 8.04-7.97 (m, 4H), 7.74 (d, J=8.0 Hz, 1H), 7.24 (d, J=2.0 Hz, 1H), 7.19-7.15 (m, 3H), 6.95 (d, J=8.0 Hz, 2H), 5.49-5.45 (m, 1H), 3.74-3.71 (m, 4H), 3.30-3.20 (m, 4H), 3.14 (s, 1H), 2.72-2.67 (m, 4H), 2.59-2.53 (m, 6H), 2.27 (d, J=6.8 Hz, 2H), 1.83 (d, J=8.0 Hz, 2H), 1.76 (s, 9H), 1.74-1.65 (m, 1H), 1.58 (d, J=8.0 Hz, 3H), 1.30-1.26 (m, 2H).

Example 59: (R)-3-(tert-butyl)-N-(1-(2-methyl-4-(7-(6-(4-((1-(4-(3-methyl-2,4-dioxotetrahydropyrimidin-1(2H)-yl)phenyl)piperidin-4-yl)methyl)piperazin-1-yl)pyridin-3-yl)imidazo[1,2-c]pyrimidin-5-yl)phenyl)ethyl)-1,2,4-oxadiazole-5-carboxamide (Compound No. 264)

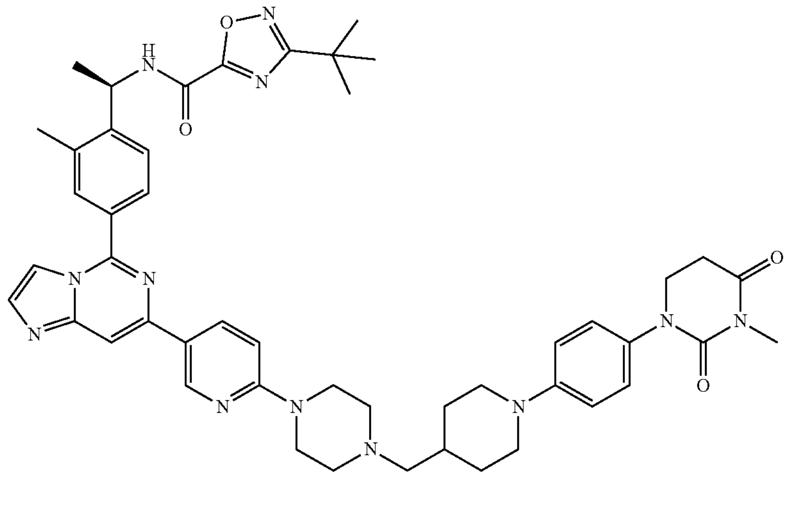 [SMILES: Cc1cc(-c2nc(-c3ccc(N4CCN(CC5CCN(c6ccc(N7CCC(=O)N(C)C7=O)cc6)CC5)CC4)nc3)cc3nccn23)ccc1[C@@H](C)NC(=O)c1nc(C(C)(C)C)no1]

Following the synthesis of EXAMPLE 3, the title compound was obtained after preparative HPLC purification (61 mg, 47.0%) as a yellow solid. LC-MS: 865.71 (M+H$^+$). $^1$H NMR (400 MHz, DMSO-d$^6$) δ (ppm) 9.99 (d, J=7.6 Hz, 1H), 8.97 (d, J=2.4 Hz, 1H), 8.32 (dd, J=8.8, 2.4 Hz, 1H), 8.05 (s, 1H) 8.01 (s, 1H), 7.88 (dd, J=8.0, 1.6 Hz, 1H), 7.84 (s, 1H), 7.72 (d, J=8.0 Hz, 1H), 7.66 (d, J=1.2 Hz, 1H), 7.13 (d, J=8.8 Hz, 2H), 6.94-6.91 (m, 3H), 5.43-5.36 (m, 1H), 3.71-3.60 (m, 8H), 3.03 (s, 3H), 2.82-2.78 (m, 2H), 2.70-2.65 (m, 2H), 2.53 (s, 3H), 2.49-2.45 (m, 4H), 2.22 (d, J=7.2 Hz, 2H), 1.84-1.72 (m, 3H), 1.56 (d, J=6.8 Hz, 3H), 1.37 (s, 9H), 1.27-1.18 (m, 2H).

Example 60: (R)-2-(tert-butyl)-N-(1-(4-(6-(6-(4-((1-(4-(2,4-dioxotetrahydropyrimidin-1(2H)-yl)phenyl)piperidin-4-yl)methyl)piperazin-1-yl)pyridin-3-yl)-3-methylpyrazolo[1,5-a]pyrazin-4-yl)-2-methylphenyl)ethyl)-2H-tetrazole-5-carboxamide (Compound No. 266)

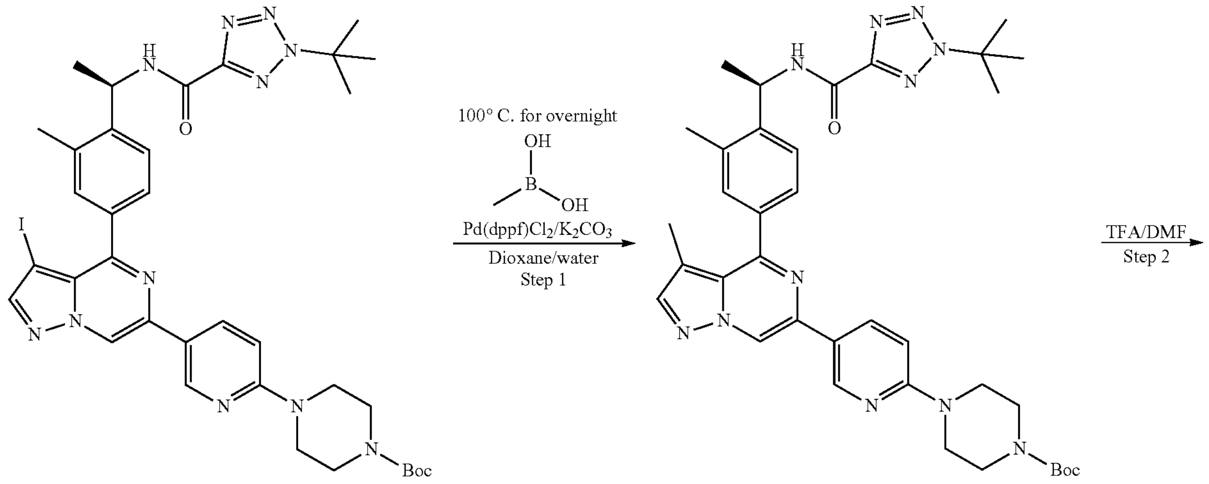

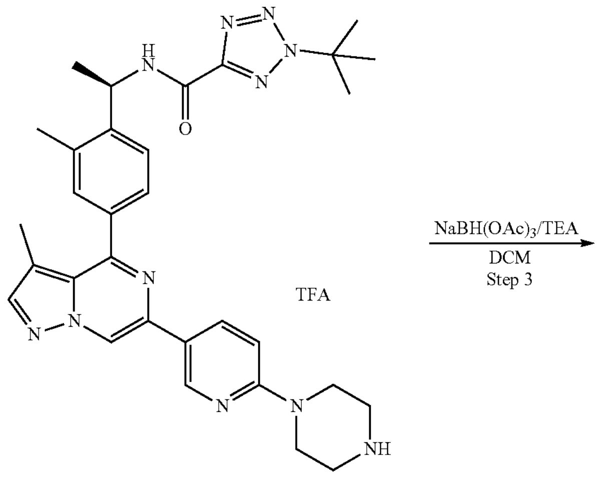

-continued

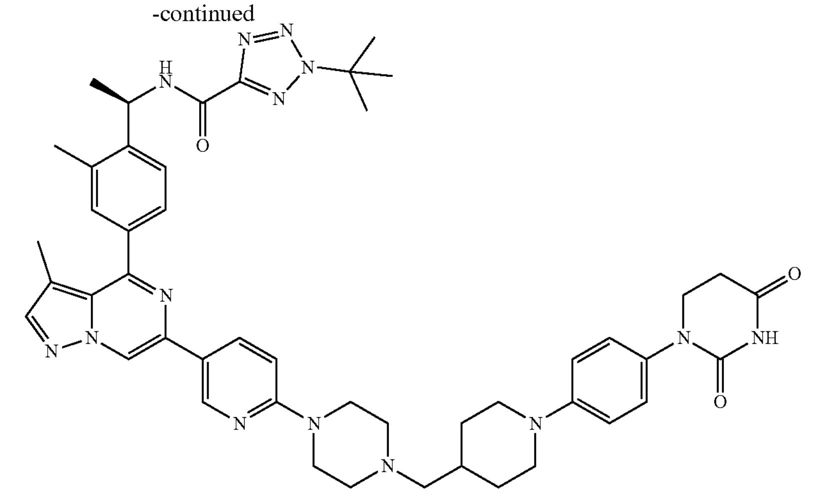

Step 1: tert-butyl (R)-4-(5-(4-(4-(1-(2-(tert-butyl)-2H-tetrazole-5-carboxamido)ethyl)-3-methylphenyl)-3-methylpyrazolo[1,5-a]pyrazin-6-yl)pyridin-2-yl)piperazine-1-carboxylate

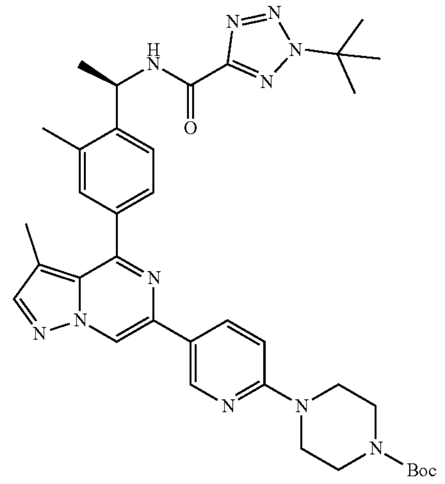 [SMILES: Cc1cc(-c2nc(-c3ccc(N4CCN(C(=O)OC(C)(C)C)CC4)nc3)cn3ncc(C)c23)ccc1[C@@H](C)NC(=O)c1nnn(C(C)(C)C)n1]

A mixture of tert-butyl (R)-4-(5-(4-(4-(1-(2-(tert-butyl)-2H-tetrazole-5-carboxamido)ethyl)-3-methylphenyl)-3-iodopyrazolo[1,5-a]pyrazin-6-yl)pyridin-2-yl)piperazine-1-carboxylate (900 mg, 1.137 mmol, 1.0 eq), methylboronic acid (340 mg, 5.68 mmol, 5.0 eq), $K_2CO_3$ (786 mg, 5.68 mmol, 5.0 eq) and $PdCl_2$(dppf) (83 mg, 0.114 mmol, 0.1 eq) in Dioxane (5 ml) and Water (1 ml) was stirred at 100° C. under Ar for overnight. Filtered and concentrated in vacuo. The residue was purified by combi-flash eluted with DCM/MeOH=19:1 to give the title compound (690 mg, 89%) as a yellow solid. LC-MS: 680.55 ($M+H^+$).

Steps 2-3: (R)-2-(tert-butyl)-N-(1-(4-(6-(6-(4-((1-(4-(2,4-dioxotetrahydropyrimidin-1(2H)-yl)phenyl)piperidin-4-yl)methyl)piperazin-1-yl)pyridin-3-yl)-3-methylpyrazolo[1,5-a]pyrazin-4-yl)-2-methylphenyl)ethyl)-2H-tetrazole-5-carboxamide

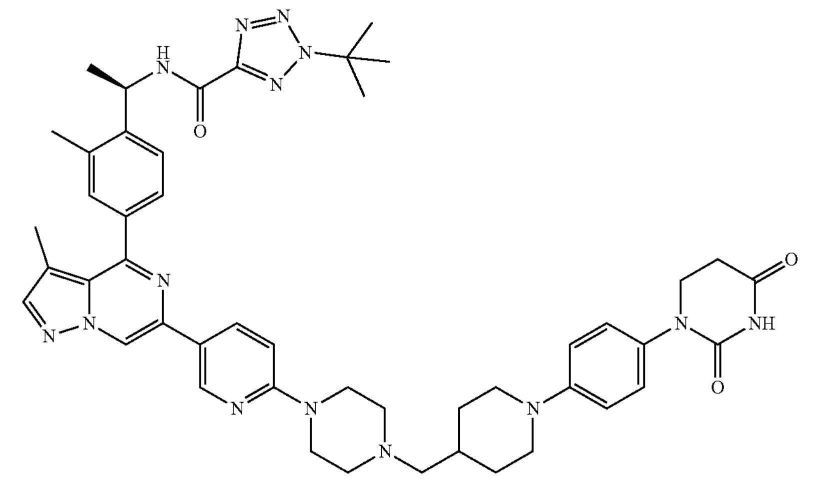 [SMILES: Cc1cc(-c2nc(-c3ccc(N4CCN(CC5CCN(c6ccc(N7CCC(=O)NC7=O)cc6)CC5)CC4)nc3)cn3ncc(C)c23)ccc1[C@@H](C)NC(=O)c1nnn(C(C)(C)C)n1]

Following the synthesis of EXAMPLE 3, the title compound was obtained after preparative HPLC purification (26 mg, 10.22%) as a yellow solid. LC-MS: 865.71 (M+H$^+$). $^1$H NMR (400 MHz, DMSO-d$^6$) δ (ppm) 10.25 (s, 1H), 9.53 (d, J=8.0 Hz, 1H), 9.19 (s, 1H), 8.86 (d, J=2.8 Hz, 1H), 8.22 (dd, J=8.8 Hz, 2.4 Hz, 1H), 8.01 (s, 1H), 7.66 (d, J=8.0 Hz, 1H), 7.55-7.50 (m, 2H), 7.13 (d, J=8.8 Hz, 2H), 6.94-6.90 (m, 3H), 5.49-5.46 (m, 1H), 3.71-3.57 (m, 8H), 2.69-2.64 (m, 4H), 2.51 (s, 3H), 2.49-2.45 (m, 4H), 2.22 (d, J=6.8 Hz, 2H), 2.03 (s, 3H), 1.84-1.80 (m, 2H), 1.73 (s, 10H), 1.55 (d, J=6.8 Hz, 3H), 1.27-1.18 (m, 2H).

II. Biological Evaluation

Cell Proliferation Assay in TMD8 Cells

TMD8 cells at 2000 cells/40 μL/well were seeded into 384 well plate. The compounds were dissolved in DMSO as stock solution, then, 3-fold serial dilution for a total of 10 concentrations were prepared in DMSO. The final concentrations of working solution were 1, 0.33, 0.11, 0.037, 0.012, 0.004, 0.0013, 0.0005, 0.0002, 0 mM. 40 nL of diluted compounds above were added into each well (0.1% DMSO final concentration in cell culture medium) and incubate for 72 h at 37° C. & $CO_2$. 20 μL of CellTiter-Glo reagent was added into each well and shake the plates for 2 min. The plates were incubated at 25° C. for 30 min followed by reading on Envision reader. The dose response curves and IC50 values were generated using Prism.

The results are shown in Table 3 below.

TABLE 3

| Compd No. | TMD-8 cell growth inhibition $GI_{50}$ (nM), 3-day |
|---|---|
| 1 | 11.5 |
| 2 | 11.4 |
| 3 | 2.9 |
| 4 | 0.6 |
| 5 | 8.4 |
| 6 | 10.1 |
| 7 | 0.4 |
| 8 | 4.0 |
| 9 | 0.5 |
| 10 | 8.7 |
| 11 | 1.6 |
| 12 | 1.6 |
| 13 | 6.5 |
| 14 | 6.9 |
| 15 | 34.9 |
| 16 | 1.1 |
| 17 | 0.5 |
| 18 | 2.3 |
| 19 | 2.2 |
| 20 | 5.6 |
| 21 | 1.9 |
| 22 | 1.2 |
| 23 | 2.8 |
| 24 | 0.8 |
| 25 | 0.5 |
| 26 | 0.9 |
| 27 | 1.6 |
| 28 | 1.7 |
| 29 | 1.7 |
| 30 | 2.4 |
| 31 | 2.0 |
| 32 | 0.72 |
| 33 | 965 |
| 34 | 0.61 |
| 35 | 5.2 |
| 36 | 1.7 |
| 37 | 3.5 |
| 38 | 1.4 |
| 39 | >1000 |

TABLE 3-continued

| Compd No. | TMD-8 cell growth inhibition $GI_{50}$ (nM), 3-day |
|---|---|
| 40 | 0.55 |
| 41 | 2.69 |
| 42 | 0.42 |
| 43 | 0.32 |
| 44 | 880 |
| 45 | 408 |
| 46 | 3.85 |
| 47 | 0.34 |
| 48 | 0.31 |
| 49 | 1.3 |
| 50 | 0.67 |
| 51 | 4.6 |
| 52 | 2.5 |
| 53 | 2.8 |
| 54 | 1.8 |
| 55 | 1.5 |
| 56 | 1.6 |
| 57 | 3.2 |
| 58 | 2.0 |
| 59 | 2.2 |
| 60 | 0.3 |
| 61 | 1.7 |
| 62 | 1.6 |
| 63 | 1.1 |
| 64 | 3.9 |
| 65 | 1.6 |
| 66 | 1.1 |
| 67 | 0.27 |
| 70 | 0.23 |
| 74/75 | 0.6 |
| 76 | 0.2 |
| 77 | 0.28 |
| 81 | 0.22 |
| 84 | 0.3 |
| 85 | 4.7 |
| 87 | 1.1 |
| 88 | 0.45 |
| 89 | 0.34 |
| 91 | 0.31 |
| 95 | 0.24 |
| 98 | 0.42 |
| 104 | 0.9 |
| 105 | 0.3 |
| 106 | 1.8 |
| 107 | 0.8 |
| 108 | 3.6 |
| 110 | 1.2 |
| 111 | 3.1 |
| 112 | 0.6 |
| 113 | 1.2 |
| 114 | 1.8 |
| 115 | 0.6 |
| 116 | 0.7 |
| 117 | 0.5 |
| 118 | 2.4 |
| 120 | 3.8 |
| 121/122 | 3.2 |
| 123 | 0.23 |
| 124 | 0.23 |
| 125 | 0.14 |
| 130 | 0.38 |
| 131/134 | 0.83 |
| 135 | 0.8 |
| 136 | 0.8 |
| 138 | 7.3 |
| 139 | 3.2 |
| 140 | 5.2 |
| 142 | 3.8 |
| 143 | 0.45 |
| 144 | 0.38 |
| 145 | 0.5 |
| 146 | 0.35 |
| 161 | 0.28 |
| 162 | 0.1 |
| 163 | 0.86 |
| 164 | 0.87 |
| 165 | 0.34 |

TABLE 3-continued

| Compd No. | TMD-8 cell growth inhibition $GI_{50}$ (nM), 3-day |
|---|---|
| 166 | 1.2 |
| 167 | 0.6 |
| 168 | 1.2 |
| 169 | 1.1 |
| 170 | 2.0 |
| 171 | 0.16 |
| 172 | 1.3 |
| 173 | 5.6 |
| 174 | 0.16 |
| 175 | 2.2 |
| 176 | 0.08 |
| 177 | 0.79 |
| 178 | 0.18 |
| 179 | 1.1 |
| 180 | 0.38 |
| 181 | 0.12 |
| 182 | 1.2 |
| 183 | 0.76 |
| 184 | 0.35 |
| 185 | 0.46 |
| 186 | 0.37 |
| 187 | 13.3 |
| 188 | 4.9 |
| 189 | 38 |
| 190 | 1.5 |
| 191 | 0.97 |
| 192 | 1.5 |
| 193 | 1.3 |
| 194 | 1.3 |
| 195 | 0.33 |
| 196 | 0.7 |
| 197 | 0.7 |
| 198 | 0.4 |
| 199 | 4.4 |
| 200 | 0.7 |
| 201 | 10.2 |
| 202 | 0.4 |
| 203 | 7.5 |
| 204 | 0.7 |
| 205 | 4.1 |
| 206 | 1.4 |
| 207 | 0.1 |
| 208 | 0.08 |
| 209 | 0.8 |
| 210 | 2.3 |
| 211 | 2.0 |
| 212 | 1.3 |
| 213 | 0.9 |
| 214 | 1.8 |
| 215 | 1.1 |
| 216 | 1.6 |
| 217 | 0.8 |
| 218 | 0.2 |
| 219 | 1.6 |
| 220 | 0.6 |
| 221 | 0.7 |
| 222 | 0.7 |
| 223 | 0.4 |
| 224 | 0.7 |
| 225 | 3.9 |
| 226 | 4.8 |
| 227 | 0.7 |
| 228 | 9.8 |
| 229 | 2.8 |
| 230 | 1.2 |
| 231 | 1.1 |
| 232 | 1.2 |
| 233 | 1.5 |
| 234 | 4.0 |
| 235 | 0.9 |
| 236 | 1.3 |
| 237 | 8.1 |
| 238 | 3.1 |
| 239 | 0.9 |
| 240 | 3.6 |
| 241 | 3.4 |
| 242 | 0.5 |

TABLE 3-continued

| Compd No. | TMD-8 cell growth inhibition $GI_{50}$ (nM), 3-day |
|---|---|
| 243 | 2.3 |
| 244 | 1.2 |
| 245 | 1.1 |
| 246 | 0.5 |
| 247 | 41.2 |
| 248 | 4.4 |
| 249 | 1.1 |
| 250 | 1.6 |
| 251 | 3.0 |
| 252 | 1.1 |
| 253 | 4.9 |
| 254 | 2.8 |
| 255 | 1.6 |
| 256 | 0.5 |
| 257 | 0.5 |
| 258 | 3.3 |
| 259 | 11.5 |
| 260 | 0.84 |
| 261 | 4.1 |
| 262 | 5.9 |
| 263 | 5.5 |
| 264 | 8.0 |
| 265 | 290 |
| 266 | 69 |
| 273 | 2.7 |
| 274 | 0.98 |
| 284 | 0.74 |
| 285 | 0.31 |
| 286 | 4.6 |
| 137 | 1.95 |
| 141 | 15.8 |
| 275 | 3.8 |
| 276 | 1.1 |
| 279 | 1.4 |
| 281 | 14.1 |
| 282 | 2.4 |
| 283 | 26.2 |
| 288 | 0.73 |
| 289/290 | 15.2 |
| 292 | 14.9 |
| 293 | 0.97 |
| 294 | 1.1 |
| 295 | 8.1 |
| 297 | 4.7 |
| 298 | 4.0 |
| 302 | 2.8 |
| 303 | 1.0 |
| 304 | 4.7 |
| 305 | 4.3 |
| 306 | 2.9 |
| 307 | 8.6 |
| 308 | 2.1 |
| 309 | 2.1 |

Cell Proliferation Assay in REC-1 Cells

Human MCL cell REC-1 was cultured using standard cell culture conditions in RPMI-1640 supplemented with 10% FBS in humidified incubator at 37° C., 5% CO2. To assess the effect of BTK degraders on cell viability, exponentially growing cells were seeded at a density of 5,000 cells/well in 96-well plates. After cell seeding, serially diluted compound or DMSO was added to the cells (in concentration ranging from 0 to 1 uM, 3-fold serially diluted), and plates were incubated for 6 days. Cell viability was measured using a CellTiter-Glo Luminescent Cell Viability Assay kit (Promega) according to the manufacturer's protocol. The luminescence signal of treated cells was normalized to DMSO control. The dose response curves and IC50 values were generated using Prism.

The results are shown in Table 4 below.

TABLE 4

| Compd No. | Rec-1 cell growth inhibition $GI_{50}$ (nM), 6-day |
|---|---|
| 3 | 0.5 |
| 4 | 0.6 |
| 5 | 1.4 |
| 6 | 1.8 |
| 7 | 0.2 |
| 8 | 0.9 |
| 9 | 0.3 |
| 10 | 1.0 |
| 11 | 1.0 |
| 12 | 0.3 |
| 13 | 0.7 |
| 14 | 0.3 |
| 16 | 1.1 |
| 17 | 0.9 |
| 18 | 0.8 |
| 19 | 0.8 |
| 20 | 0.9 |
| 21 | 0.3 |
| 22 | 0.9 |
| 23 | 1.0 |
| 24 | 0.4 |
| 25 | 0.9 |
| 27 | 2.36 |
| 28 | 2.06 |
| 29 | 0.22 |
| 30 | 0.12 |
| 31 | 0.13 |
| 32 | 0.12 |
| 34 | 0.38 |
| 35 | 0.76 |
| 36 | 0.12 |
| 37 | 0.23 |
| 38 | 8.29 |
| 40 | 0.21 |
| 41 | 0.23 |
| 42 | 0.34 |
| 43 | 0.23 |
| 46 | 44.7 |
| 47 | 0.12 |
| 48 | 0.12 |
| 50 | 0.24 |
| 51 | 5.13 |
| 52 | 0.18 |
| 53 | 0.12 |
| 54 | 0.12 |
| 55 | 0.20 |
| 56 | 5.47 |
| 57 | 1.30 |
| 58 | 4.92 |
| 59 | 11.4 |
| 60 | 0.80 |
| 62 | 0.48 |
| 63 | 0.23 |
| 64 | 0.93 |
| 65 | 1.23 |
| 67 | 0.23 |
| 70 | 0.12 |
| 74/75 | 0.12 |
| 76 | 0.12 |
| 77 | 0.12 |
| 81 | 0.54 |
| 84 | 0.12 |
| 85 | 6.2 |
| 87 | 0.27 |
| 88 | 0.12 |
| 89 | 0.12 |
| 95 | 0.12 |
| 98 | 0.92 |
| 104 | 0.24 |
| 105 | 0.12 |
| 106 | 0.27 |
| 107 | 0.13 |
| 108 | 0.31 |
| 110 | 0.15 |

TABLE 4-continued

| Compd No. | Rec-1 cell growth inhibition $GI_{50}$ (nM), 6-day |
|---|---|
| 111 | 0.12 |
| 112 | 0.12 |
| 113 | 0.12 |
| 114 | 0.12 |
| 115 | 0.12 |
| 116 | 0.14 |
| 117 | 0.12 |
| 118 | 1.08 |
| 120 | 3.7 |
| 121/122 | 0.16 |
| 123 | 0.12 |
| 124 | 0.07 |
| 125 | 0.12 |
| 130 | 0.13 |
| 131/134 | 0.29 |
| 135 | 0.12 |
| 136 | 0.13 |
| 137 | 0.48 |
| 138 | 4.2 |
| 139 | 1.29 |
| 140 | 0.19 |
| 141 | 2.43 |
| 142 | 1.1 |
| 143 | 0.13 |
| 144 | 0.25 |
| 145 | 0.13 |
| 146 | 0.25 |
| 161 | 0.12 |
| 162 | 0.12 |
| 163 | 0.12 |
| 164 | 0.12 |
| 165 | 0.12 |
| 166 | 4.0 |
| 167 | 5.6 |
| 168 | 0.32 |
| 169 | 0.17 |
| 170 | 0.12 |
| 171 | 0.19 |
| 172 | 0.12 |
| 173 | 1.78 |
| 174 | 0.12 |
| 175 | 1.7 |
| 176 | 0.12 |
| 177 | 0.59 |
| 178 | 0.18 |
| 179 | 0.33 |
| 180 | 0.12 |
| 181 | 0.39 |
| 182 | 6.1 |
| 183 | 0.17 |
| 184 | 0.35 |
| 185 | 0.32 |
| 186 | 0.52 |
| 187 | 17.8 |
| 188 | 0.80 |
| 189 | 4.98 |
| 190 | 0.28 |
| 191 | 0.31 |
| 192 | 0.29 |
| 193 | 0.13 |
| 194 | 0.20 |
| 195 | 0.50 |
| 196 | 0.13 |
| 197 | 0.06 |
| 198 | 0.20 |
| 199 | 10.17 |
| 200 | 0.43 |
| 201 | 4.37 |
| 202 | 0.44 |
| 203 | 0.12 |
| 204 | 0.06 |
| 205 | 1.18 |
| 206 | 1.59 |
| 207 | 0.03 |
| 208 | 0.04 |
| 209 | 0.08 |
| 210 | 0.19 |

TABLE 4-continued

| Compd No. | Rec-1 cell growth inhibition $GI_{50}$ (nM), 6-day |
|---|---|
| 211 | 0.57 |
| 212 | 0.12 |
| 213 | 0.17 |
| 214 | 0.58 |
| 215 | 0.05 |
| 216 | 0.05 |
| 217 | 0.08 |
| 218 | 0.15 |
| 219 | 1.33 |
| 220 | 0.06 |
| 221 | 0.06 |
| 222 | 0.08 |
| 223 | 0.04 |
| 224 | 0.04 |
| 225 | 0.09 |
| 226 | 0.09 |
| 227 | 0.01 |
| 228 | 0.18 |
| 229 | 0.05 |
| 230 | 0.03 |
| 231 | 0.08 |
| 232 | 0.10 |
| 233 | 0.18 |
| 234 | 0.05 |
| 235 | 0.02 |
| 236 | 0.04 |
| 237 | 3.61 |
| 238 | 1.14 |
| 239 | 0.05 |
| 240 | 0.24 |
| 241 | 0.36 |
| 242 | 0.08 |
| 243 | 0.38 |
| 244 | 0.30 |
| 245 | 0.35 |
| 246 | 0.05 |
| 247 | 13.8 |
| 248 | 0.53 |
| 249 | 0.19 |
| 250 | 0.33 |
| 251 | 1.01 |
| 252 | 0.28 |
| 253 | 0.33 |
| 254 | 0.37 |
| 255 | 0.35 |
| 256 | 3.16 |
| 257 | 0.98 |
| 258 | 0.20 |
| 259 | 0.10 |
| 260 | 0.57 |
| 261 | 0.53 |
| 262 | 0.45 |
| 263 | 0.51 |
| 264 | 25.3 |
| 265 | 18.7 |
| 266 | 0.41 |
| 273 | 0.21 |
| 274 | 0.13 |
| 275 | 0.32 |
| 276 | 0.12 |
| 279 | 0.13 |
| 281 | 3.3 |
| 282 | 0.13 |
| 283 | 2.82 |
| 284 | 0.08 |
| 285 | 0.08 |
| 288 | 0.12 |
| 291 | 0.34 |
| 292 | 0.50 |
| 293 | 0.13 |
| 294 | 0.70 |
| 302 | 0.23 |
| 303 | 0.12 |
| 304 | 0.58 |
| 305 | 3.47 |

Digital Western Blot Assay in TMD8 Cells

TMD8 cells at 5×105 cells/1 mL/well were seeded into 24-well cell culture plate. The compounds were dissolved in DMSO as stock solution, then, 3-fold serial dilution for a total of 8 concentrations were prepared in DMSO. The final concentrations of working solution were 100, 33.33, 11.11, 3.70, 1.23, 0.41, 0.14, 0 uM. 1 μL of diluted compounds above were added into each well (0.1% DMSO final concentration in cell culture medium). Cells were cultured for 4 hours at 37° C., 5% CO2 incubator. Aspirate medium and wash the cells with cold PBS once, then aspirate the supernatant and directly add 30 μL pre-chilled RIPA Lysis Buffer (Invent, INKLWB1000S) with protease/phosphatase inhibitor (Roche 4693 132001/Roche 4906837001) into the well to lyse the cells for 30 mins on ice. The cell lysates were collected to 1.5 ml EP tubes. Spin the lysates at 14000 rpm for 10 mins at 4° C. to get the supernatant, then transfer 2 μL supernatant for determining the concentration of proteins by BCA methods. Then adjust the rest samples to the same concentration with 1×Sample buffer (From Protein Simple Kit, SM-W004-1). Add 5× loading buffer (From Protein Simple Kit, SM-W004-1) to make the loading samples; heat the samples at 95° C. for 5 mins and cool on ice. Load 3 μg samples, 10 μL primary antibodies (1:50) and 10 μL secondary antibodies in each Jess-plate-well and other required solutions into the Jess plate (From Protein Simple Kit, SM-W004-1) and run Jess (Protein Simple, 004-650). Data was collected after Jess stop.

The results are shown in Table 5 below.

TABLE 5

| Cpd No. | TMD-8 DC50 (nM), 4 h |
|---|---|
| 3 | 3.3 |
| 7 | 0.7 |
| 9 | 0.49 |
| 16 | 0.99 |

In Vivo Single Dose Pharmacokinetic Study in ICR Mice

All procedures related to animal handling, care, and treatment in the study were performed according to the guidelines approved by the Institutional Animal Care and Use Committee. PK studies were performed in 3D BioOptima. Suzhou, China. The animals were divided into two groups (N=9 for each group), with one group receiving an intravenous (IV) dose of 2 mg/kg and the other group receiving an oral dose of 10 mg/kg after fasting. The drug solution was freshly prepared before administration, and the iv group of compounds were formulated in 5% DMSO+5% solutol+90% saline as a clear solution and the blood samples were collected at the following time points: 5 min, 1 h, 8 h for three mice, 15 min, 2 h, 10 h for three mice and 30 min, 4 h, 24 h for three mice post-dose administration The orally dosed compounds were formulated in 10% PEG400+90% (20% HP-β-CD in saline) and blood samples were collected at the following time points: before dose, 1 h, 8 h for three mice, 15 min, 2 h, 10 h for three mice and 30 min, 4 h, 24 h for three mice post-dose administration. 0.10 mL of blood was collected and the samples were placed in tubes containing heparin sodium and stored on ice. The samples were centrifuged at ~6800 G for 6 min at 2-8° C. and the resulting plasma was transferred to appropriately labeled tubes within 1 h of blood collection/centrifugation and then stored frozen at −80° C. Method development and biological sample analysis for the test articles (Sodium heparin anticoagulant) were performed by the testing facility by means of LC-MS/MS. The analytical results were confirmed using quality control samples for intra-assay variation. The accuracy of >66.7% of the quality control samples was between 80 and 120% of the known value(s). Standard set of parameters including $T_{1/2}$ (elimination half-life), $AUC_{0-24\ h}$ (area-under-the-curve), $V_{ss}$ (volume of distribution at steady state), Cl (clearance), $C_{max}$ (maximum drug concentration), F (oral bioavailability) were calculated using Phoenix WinNonlin 7.0 (Pharsight, USA) by the Study Director. The parameters for selected compounds were listed in the following table 6.

TABLE 6

| | IV 2 mpk (N = 9, male) | | | PO 10 mpk (N = 9, male) | | |
|---|---|---|---|---|---|---|
| No | Clearance (mL/min/kg) | $T_{1/2}$ (h) | $V_{ss}$ (L/kg) | $C_{max}$ (ng/mL) | $AUC_{0-24\ h}$ (ng*h/mL) | F (%) |
| NX-5948 | 6.75 | 1.44 | 0.943 | 729 | 4850 | 19.7 |
| 7 | 1.03 | 3.7 | 0.313 | 2630 | 26100 | 16.3 |
| 9 | 1.11 | 14.1 | 1.28 | 2400 | 25800 | 24.2 |
| 16 | 0.373 | 8.33 | 0.255 | 7420 | 109000 | 28.1 |
| 47 | 1.17 | 5.28 | 0.612 | 1340 | 17900 | 13.3 |
| 48 | 2.25 | 3.69 | 0.796 | 1460 | 14600 | 19.9 |
| 104 | 0.746 | 6.72 | 0.376 | 6690 | 94700 | 46.5 |
| 105 | 0.51 | 5.88 | 0.236 | 7750 | 96500 | 31.2 |
| 107 | 0.831 | 4.42 | 0.308 | 6550 | 80000 | 41.2 |
| 112 | 0.54 | 6.76 | 0.30 | 6890 | 97800 | 36.5 |
| 135 | 0.412 | 5.16 | 0.185 | 7950 | 101000 | 26.9 |
| 136 | 1.17 | 2.73 | 0.246 | 5890 | 49000 | 34.5 |
| 178 | 2.54 | 2.35 | 0.489 | 1690 | 14600 | 22.4 |
| 180 | 0.330 | 7.37 | 0.213 | 7500 | 112000 | 25.0 |
| 190 | 0.254 | 10.8 | 0.226 | 12200 | 197000 | 37.9 |
| 192 | 0.115 | 8.92 | 0.089 | 24200 | 403000 | 33.0 |
| 196 | 0.991 | 4.0 | 0.331 | 7320 | 83100 | 52.0 |

iv group of compounds were formulated in 5% DMSO+5% solutol+90% saline as a clear solution and the blood samples were collected at the following time points: before dose, 15 min, 30 min, 1 h, 2 h, 4 h, 8 h, 10 h, 24 h post-dose administration. The orally dosed compounds were formulated in 10% PEG400+90% (20% HP-β-CD in saline) and blood samples were collected at the following time points: 5 min, 15 min, 30 min, 1 h, 2 h, 4 h, 8 h, 10 h and 24 h post-dose administration. 0.15 mL of blood was collected and the samples were placed in tubes containing heparin sodium and stored on ice. The samples were centrifuged at ~6800 G for 6 min at 2-8° C. and the resulting plasma was transferred to appropriately labeled tubes within 1 h of blood collection/centrifugation and then stored frozen at −80° C. Method development and biological sample analysis for the test articles (Sodium heparin anticoagulant) were performed by the testing facility by means of LC-MS/MS. The analytical results were confirmed using quality control samples for intra-assay variation. The accuracy of >66.7% of the quality control samples was between 80 and 120% of the known value(s). Standard set of parameters including $T_{1/2}$ (elimination half-life), $AUC_{0-24\ h}$ (area-under-the-curve), $V_{ss}$ (volume of distribution at steady state), Cl (clearance), $C_{max}$ (maximum drug concentration), F (oral bioavailability) were calculated using Phoenix WinNonlin 7.0 (Pharsight, USA) by the Study Director. The parameters for selected compounds were listed in the following Table 7.

NX-5948

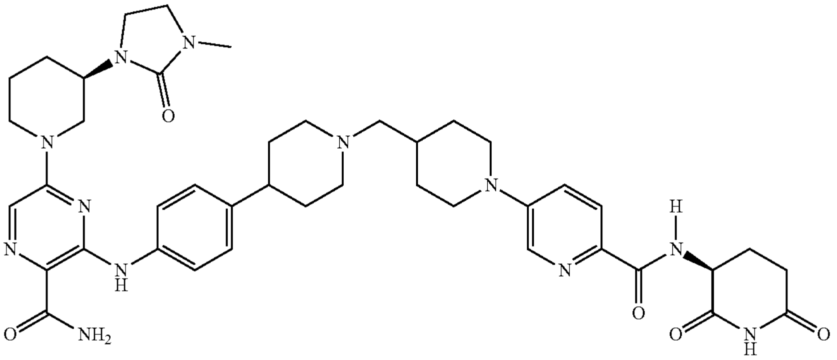

was used as control.

Compared with clinic compound NX-5948, the invented compounds exhibit lower plasma clearance (Cl), longer elimination half-life ($T_{1/2}$) and higher oral plasma exposure ($AUC_{0-24\ h}$) in mouse pharmacokinetic studies.

In Vivo Single Dose Pharmacokinetic Study in SD Rats

All procedures related to animal handling, care, and treatment in the study were performed according to the guidelines approved by the Institutional Animal Care and Use Committee. PK studies were performed in 3D BioOptima. Suzhou, China. The animals were divided into two groups (N=3 for each group), with one group receiving an intravenous (IV) dose of 2 mg/kg and the other group receiving an oral dose of 10 mg/kg after fasting. The drug solution was freshly prepared before administration, and the

TABLE 7

| | IV 2 mpk (N = 3, male) | | | PO 10 mpk (N = 3, male) | | |
|---|---|---|---|---|---|---|
| No | Clearance (mL/min/kg) | $T_{1/2}$ (h) | $V_{ss}$ (L/kg) | $C_{max}$ (ng/mL) | $AUC_{0-24\ h}$ (ng*h/mL) | F (%) |
| NX-5948 | 16.6 | 4.18 | 4.38 | 109 | 1220 | 12.4 |
| 7 | 0.714 | 5.97 | 0.378 | 3430 | 56400 | 26.7 |
| 9 | 4.65 | 5.58 | 2.37 | 361 | 5200 | 15.5 |
| 16 | 0.836 | 10.4 | 0.726 | 3660 | 59700 | 37.3 |
| 47 | 0.477 | 8.44 | 0.337 | 1320 | 22000 | 7.3 |
| 104 | 0.553 | 13.2 | 0.617 | 2810 | 48100 | 23.2 |
| 105 | 0.364 | 11.5 | 0.344 | 5700 | 96900 | 26.2 |
| 107 | 0.324 | 10.8 | 0.277 | 4420 | 67000 | 16.2 |
| 112 | 0.462 | 12.5 | 0.496 | 4370 | 73300 | 28.6 |
| 135 | 0.429 | 12.0 | 0.431 | 4040 | 65800 | 22.5 |
| 136 | 0.717 | 10.3 | 0.613 | 1530 | 59700 | 32.0 |
| 178 | 0.706 | 5.55 | 0.357 | 1610 | 23600 | 11.0 |

TABLE 7-continued

| No | IV 2 mpk (N = 3, male) Clearance (mL/min/kg) | $T_{1/2}$ (h) | $V_{ss}$ (L/kg) | PO 10 mpk (N = 3, male) $C_{max}$ (ng/mL) | $AUC_{0-24\ h}$ (ng*h/mL) | F (%) |
|---|---|---|---|---|---|---|
| 180 | — | — | — | 8840 | 17400 | 26.1 |
| 190 | 0.265 | 13.1 | 0.308 | 11600 | 203000 | 43.2 |
| 192 | 0.394 | 13.3 | 0.425 | 5850 | 110000 | 38.6 |
| 196 | 0.853 | 12.9 | 0.917 | 3920 | 63800 | 42.7 |
| 198 | 0.558 | 8.29 | 0.355 | 4240 | 52600 | 20.0 |

NX-5948

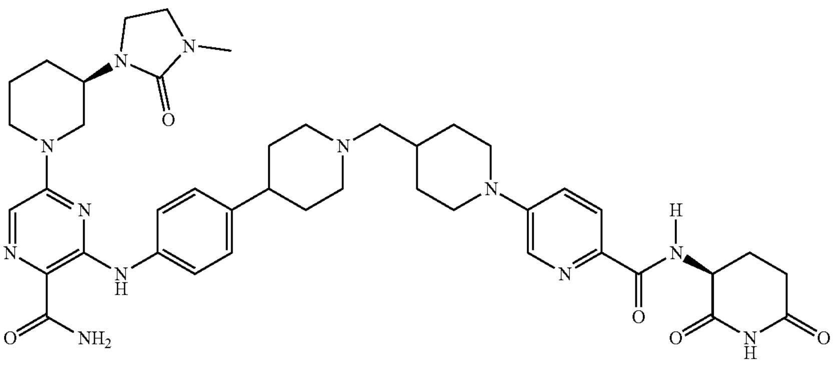

was used as control.

Compared with clinic compound NX-5948, the invented compounds exhibit lower plasma clearance (Cl), longer elimination half-life ($T_{1/2}$) and higher oral plasma exposure ($AUC_{0-24\ h}$) in rat pharmacokinetic studies.

Having now fully described the methods, compounds, and compositions herein, it will be understood by those of skill in the art that the same can be performed within a wide and equivalent range of conditions, formulations, and other parameters without affecting the scope of the methods, compounds, and compositions provided herein or any embodiment thereof.

All patents, patent applications, and publications cited herein are fully incorporated by reference herein in their entirety.

The invention claimed is:

1. A compound selected from

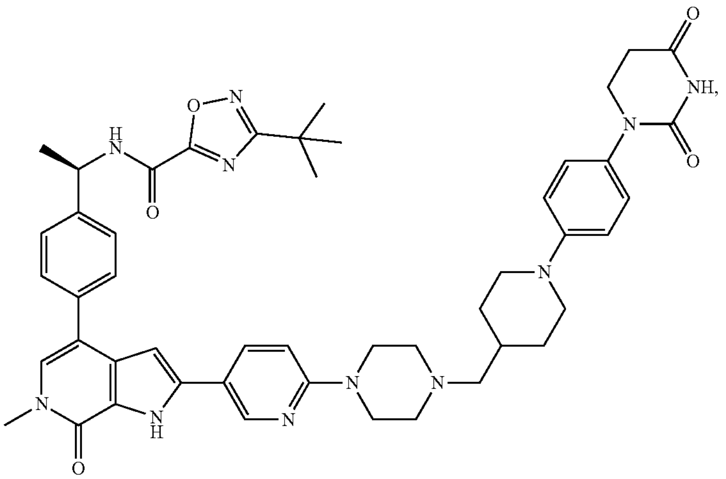

-continued
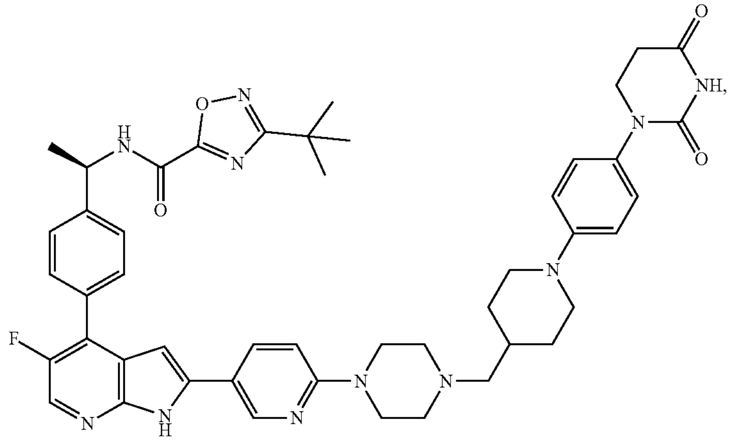
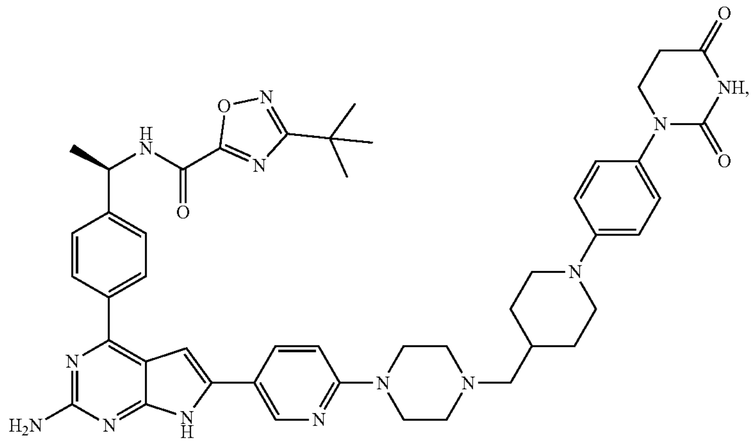
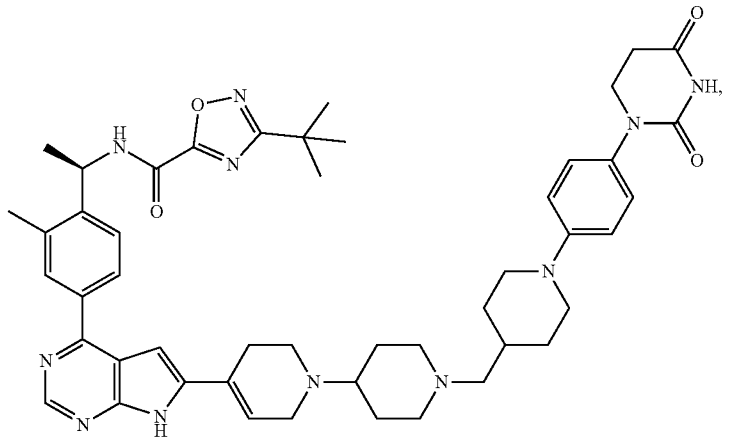

-continued
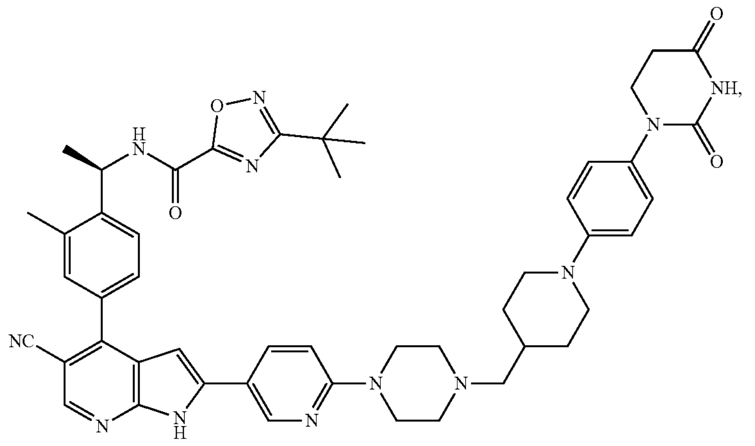
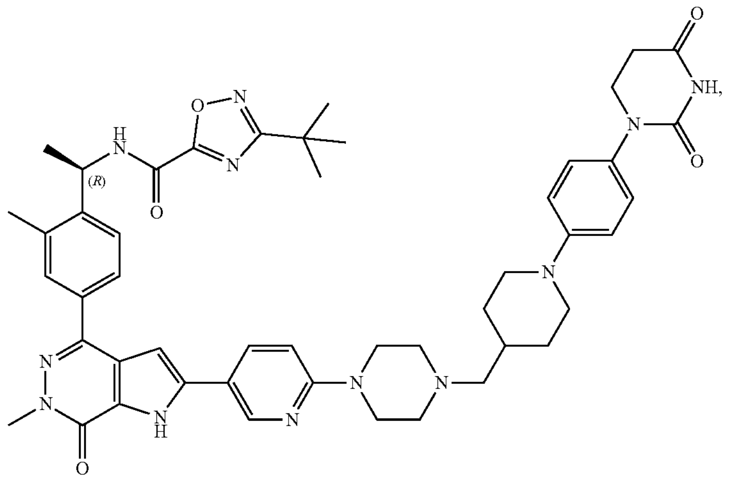
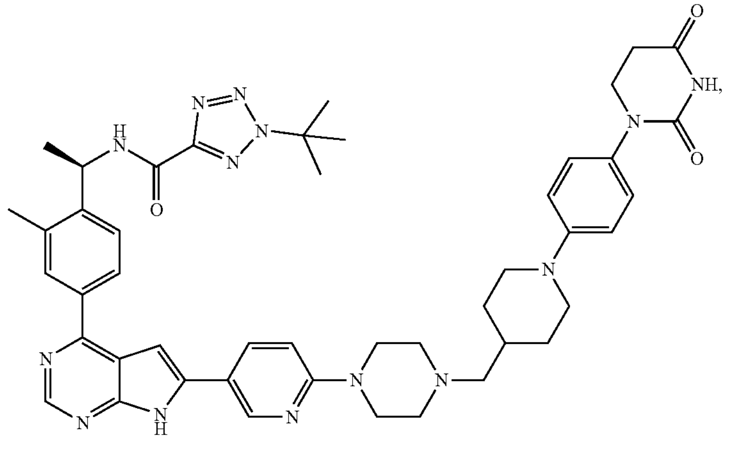

-continued
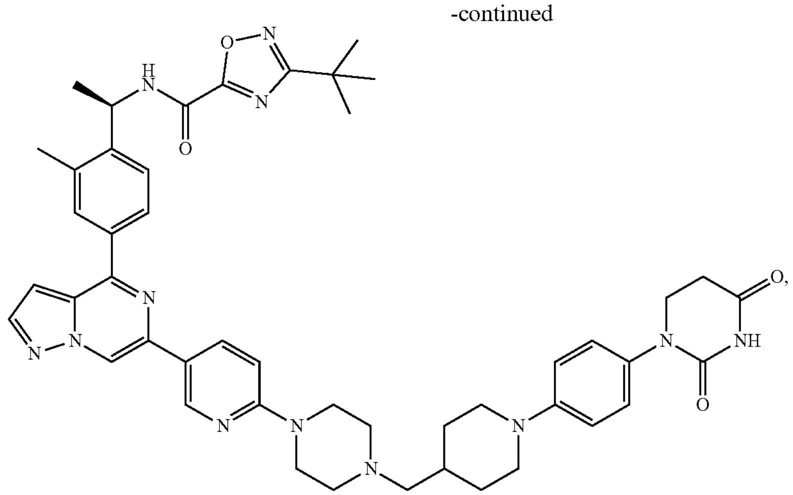
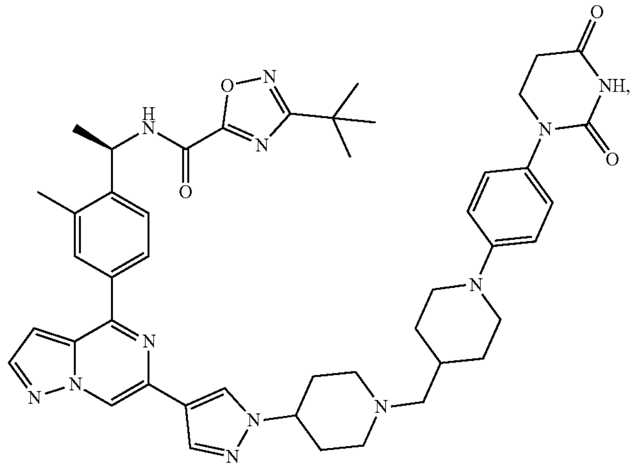
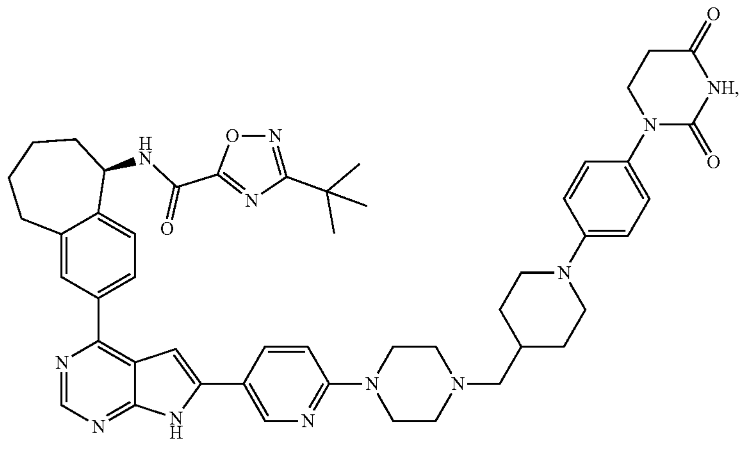

-continued
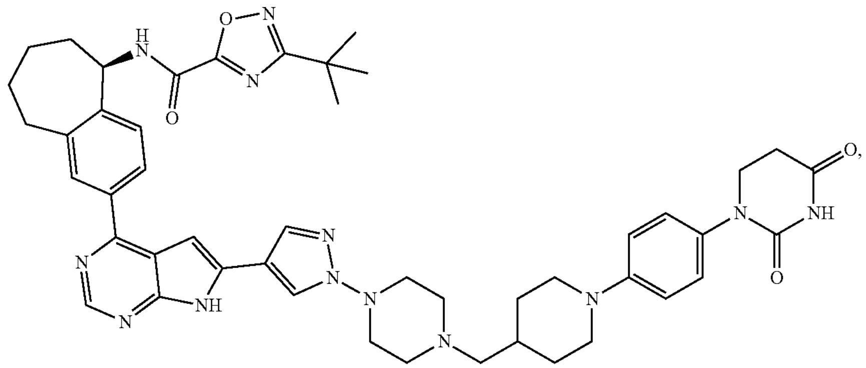
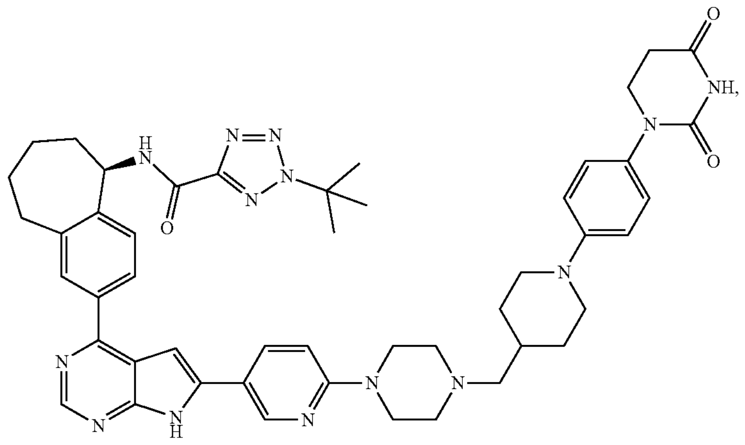
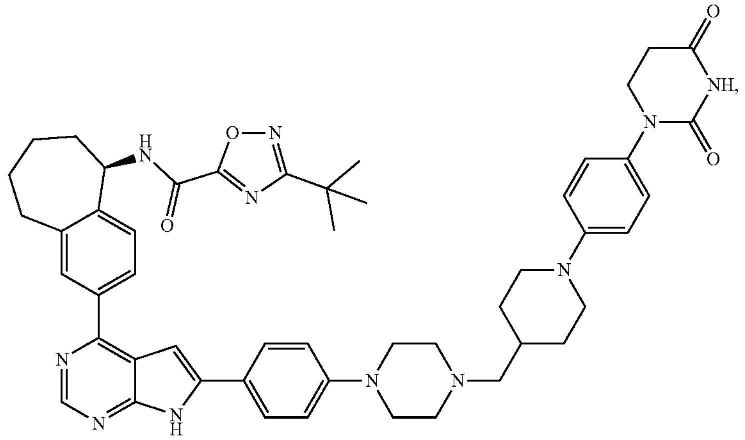
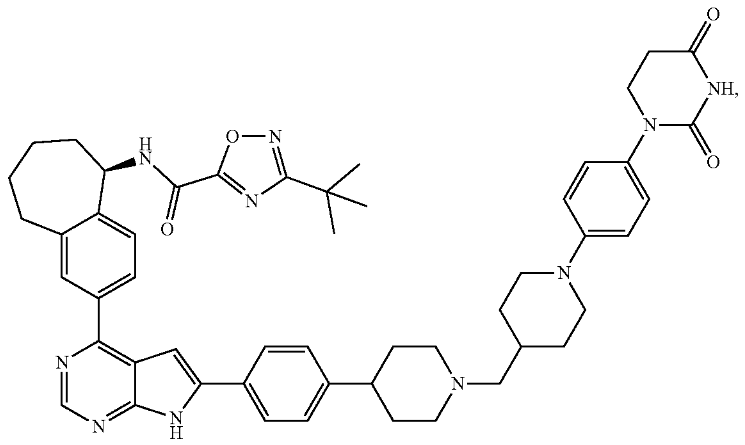

-continued
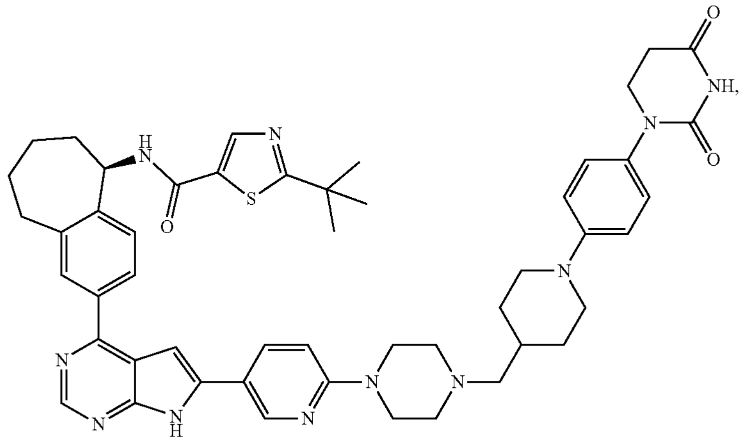
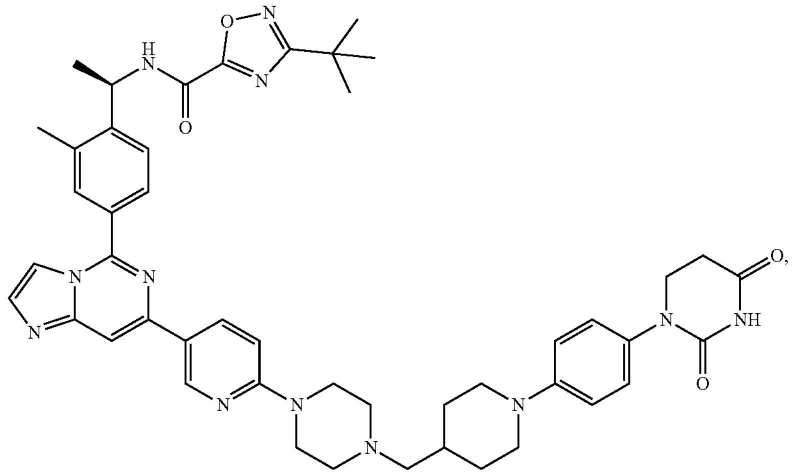
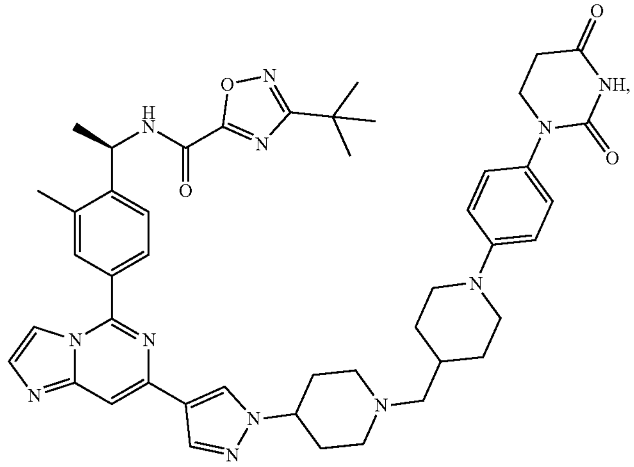

-continued
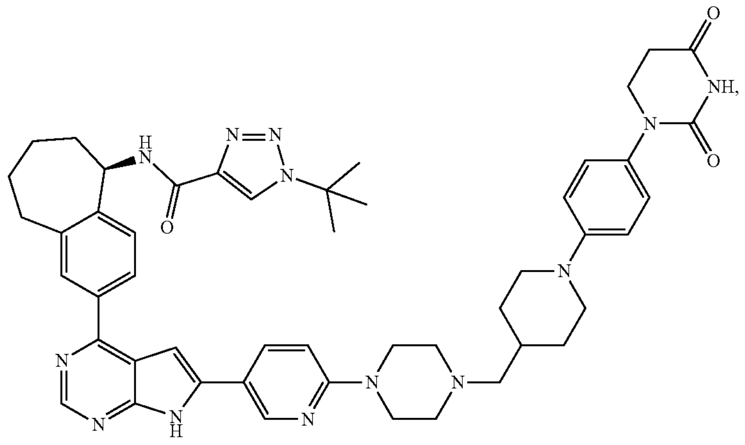
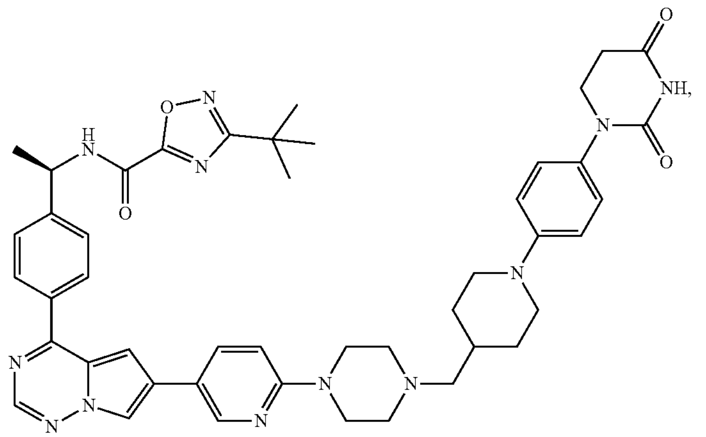
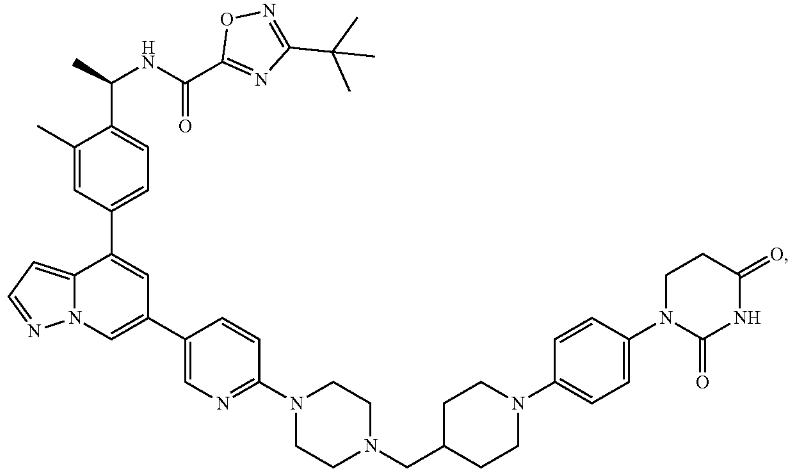

-continued
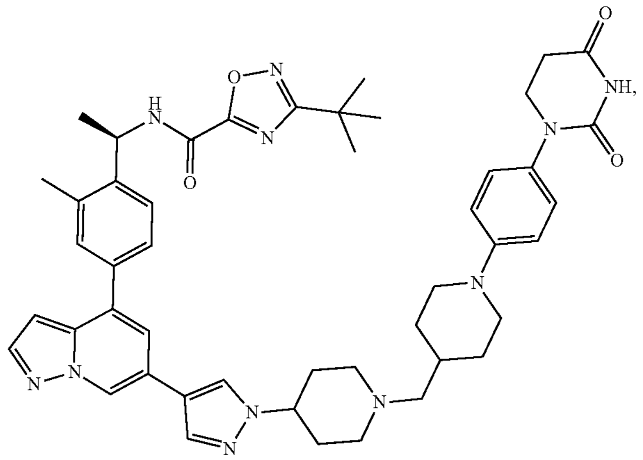
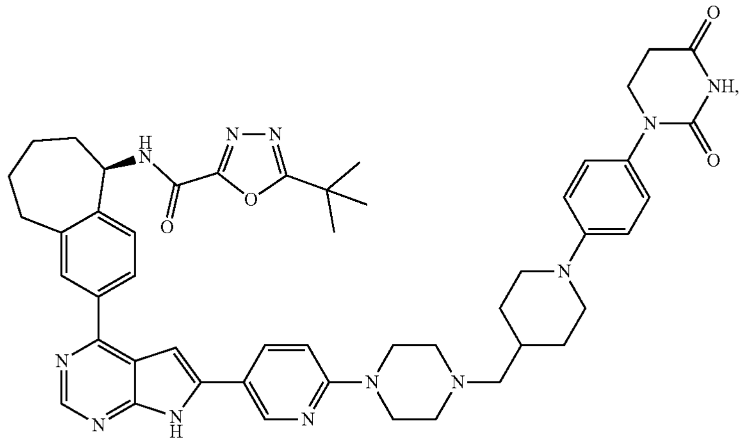
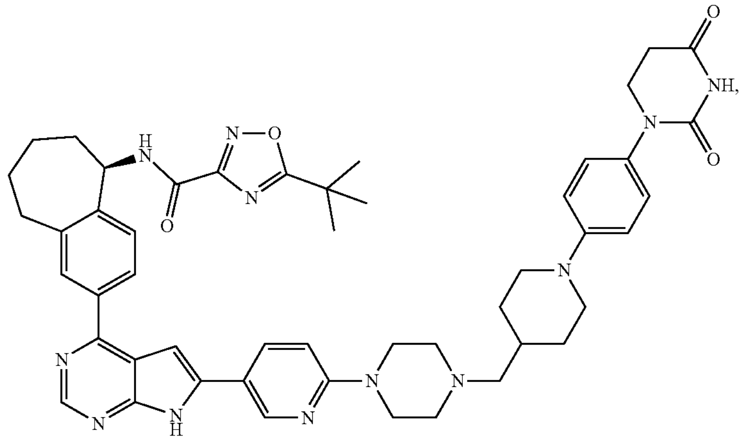
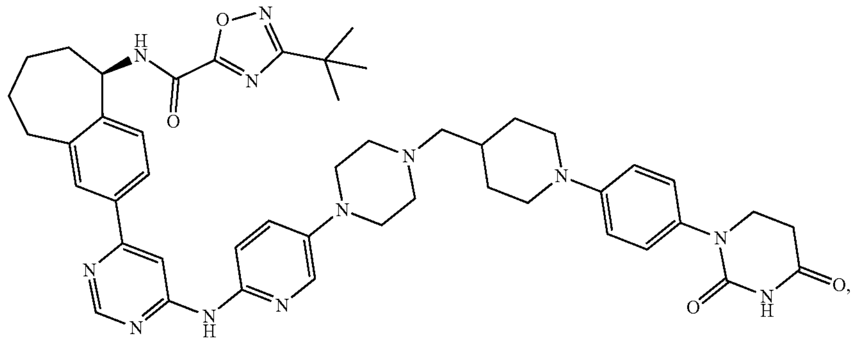

-continued
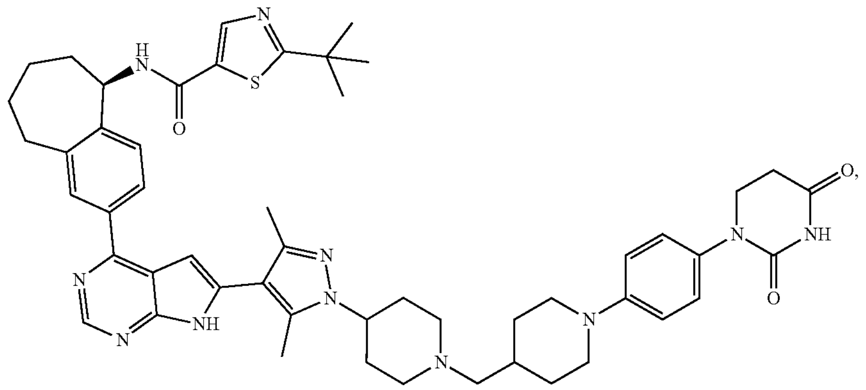
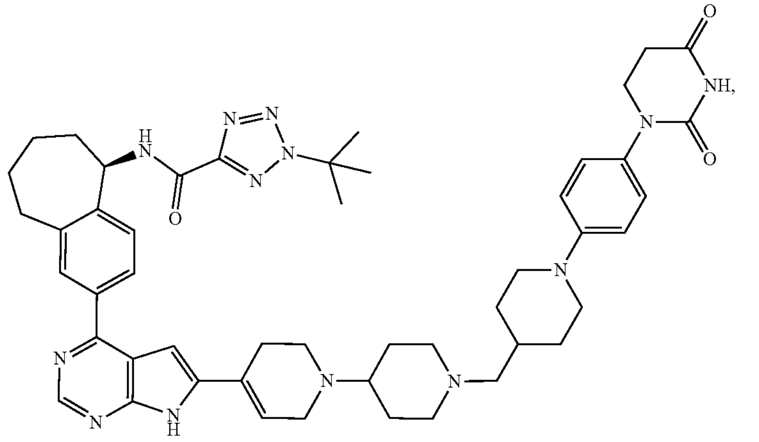
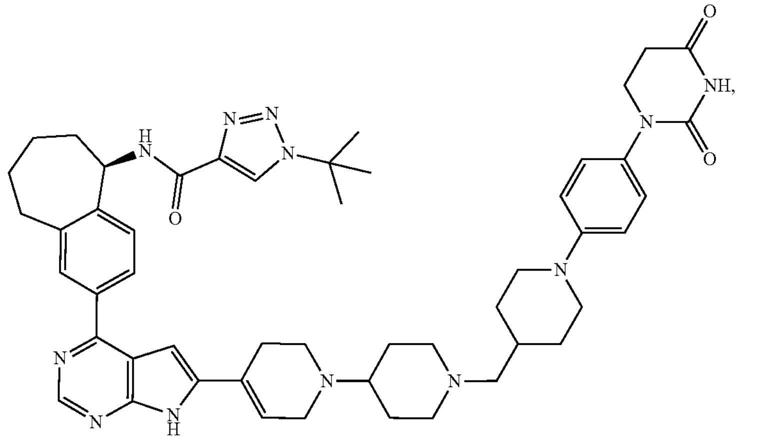
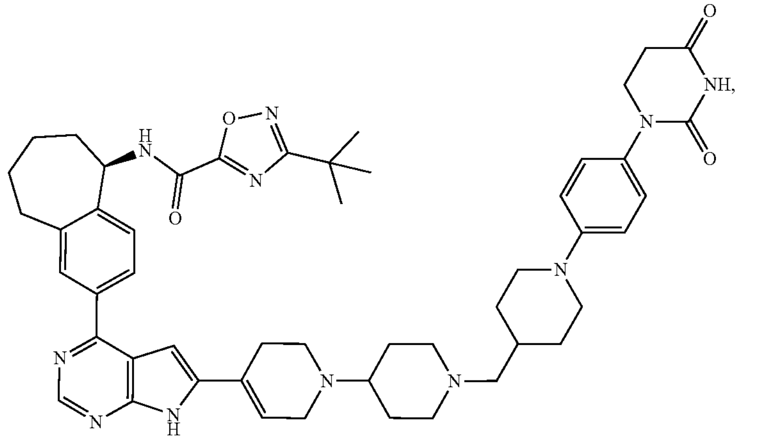

-continued
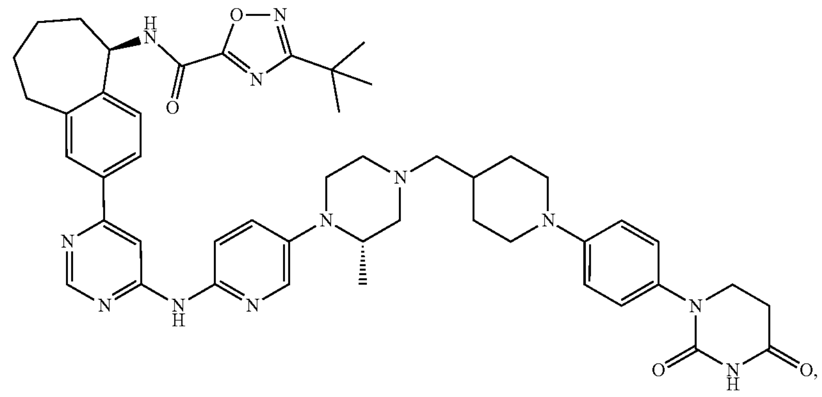
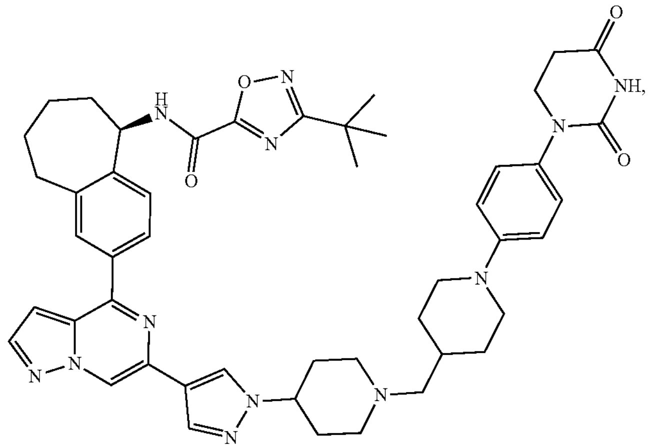
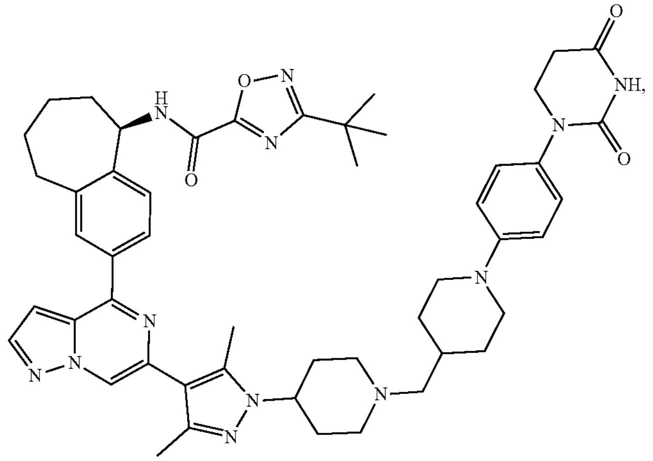

-continued
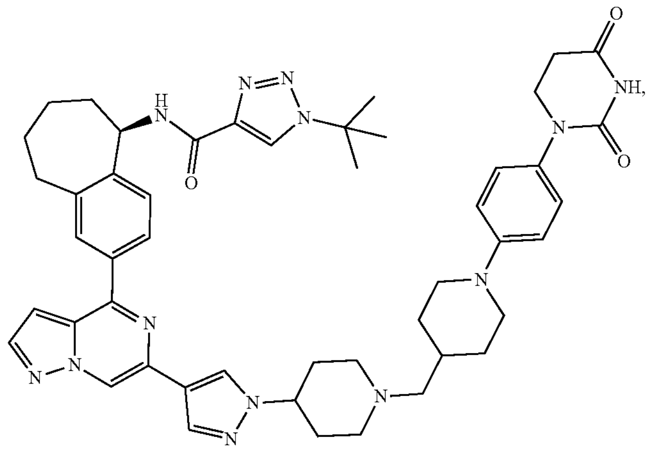
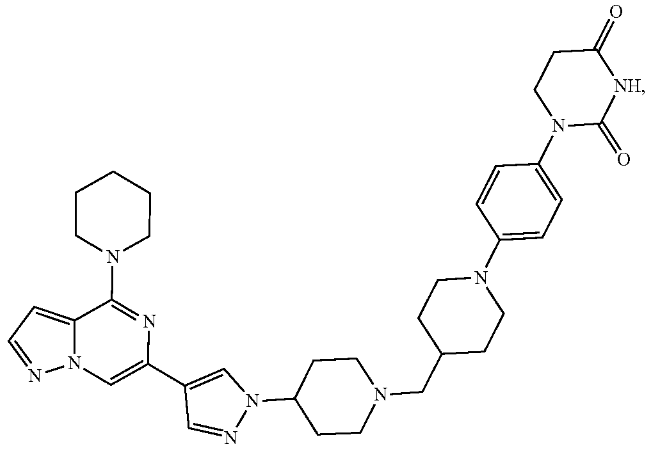
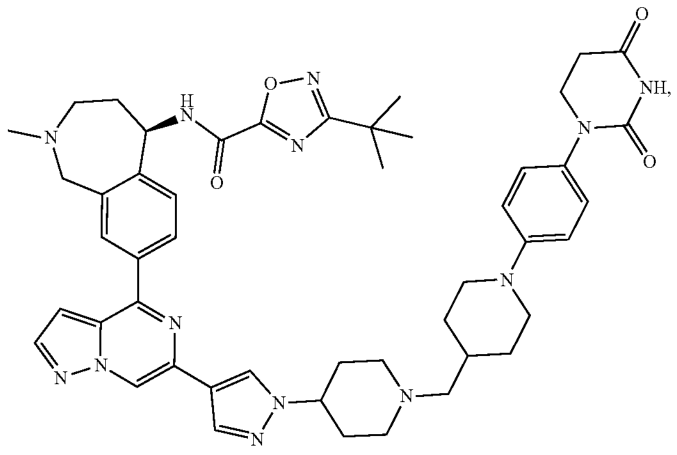

-continued
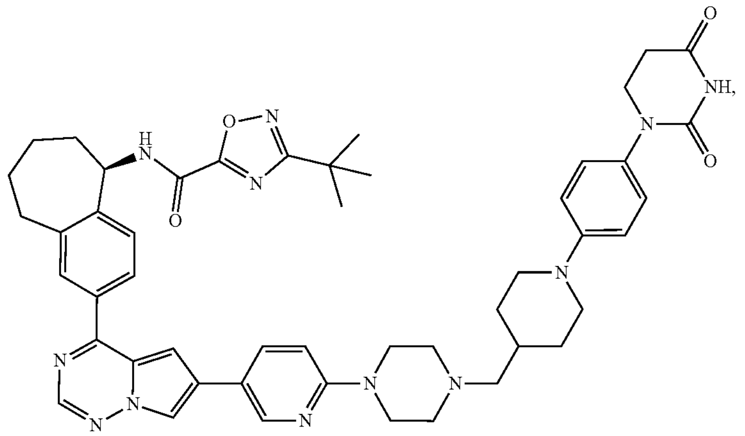
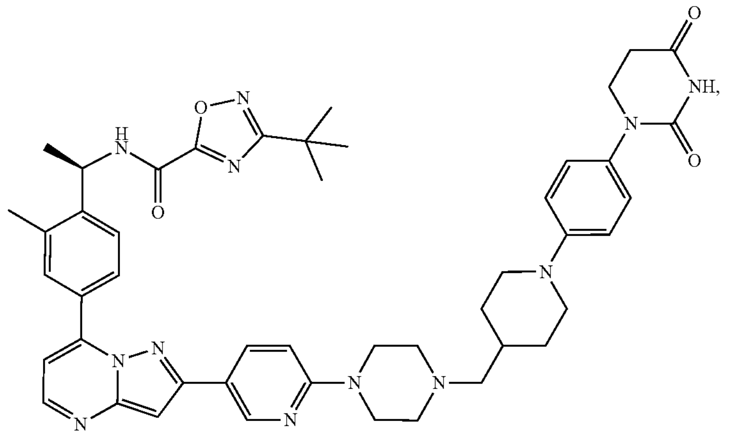
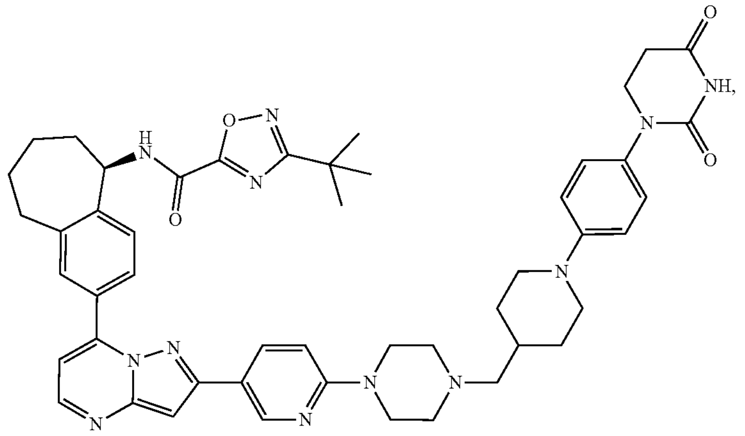

-continued
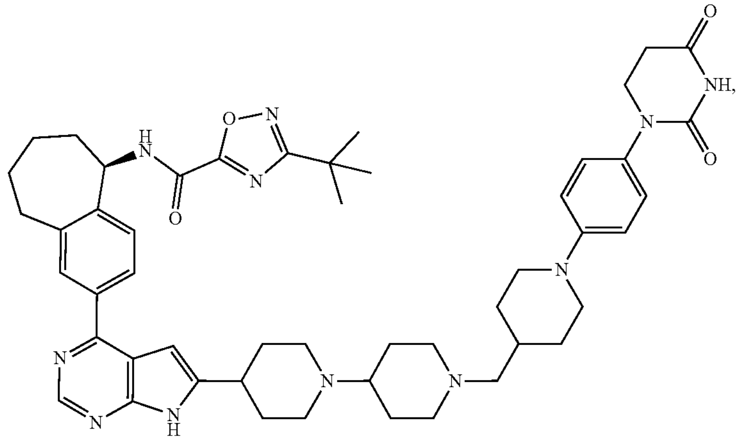
,
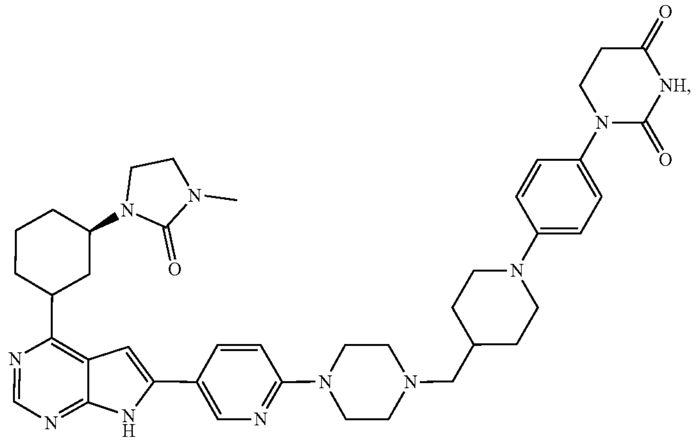
,
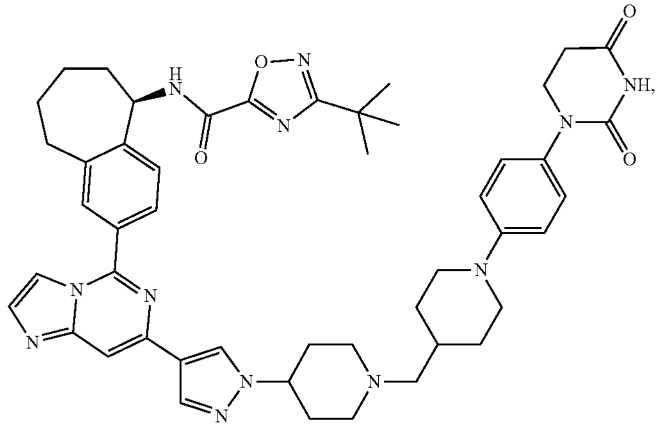
,

-continued
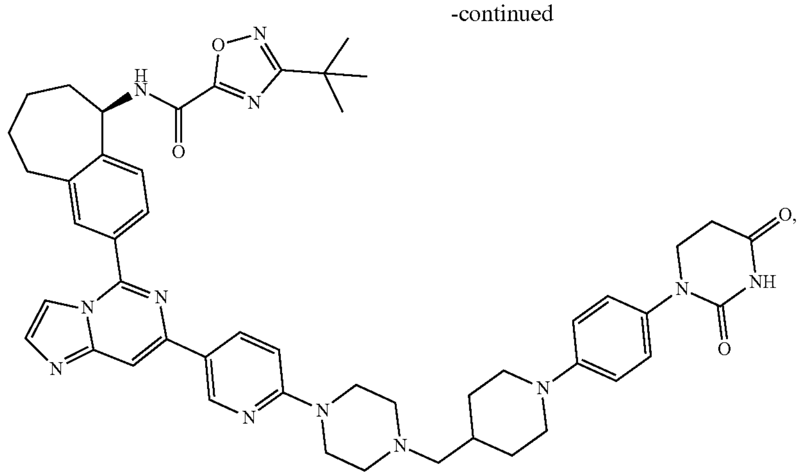
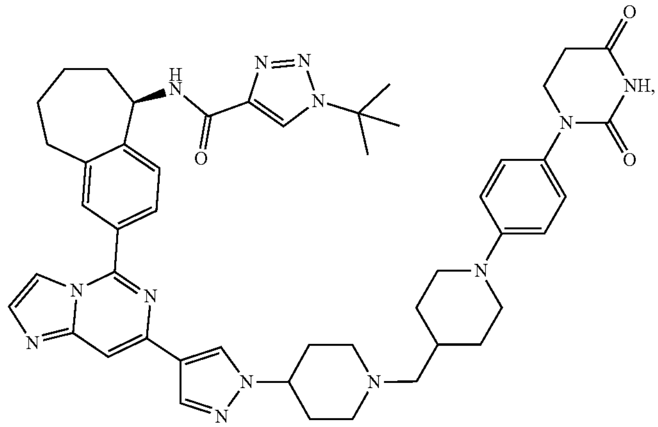
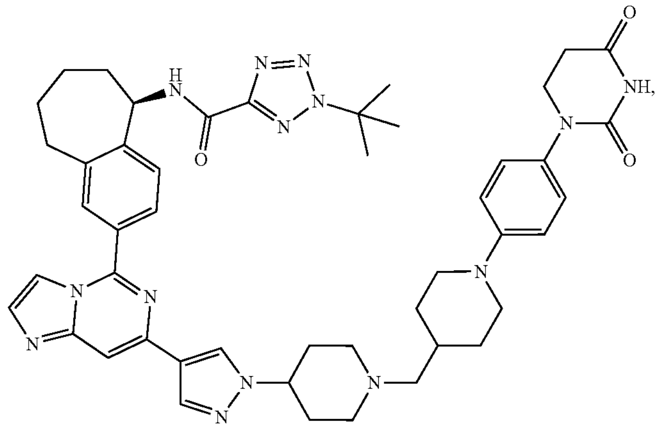

-continued
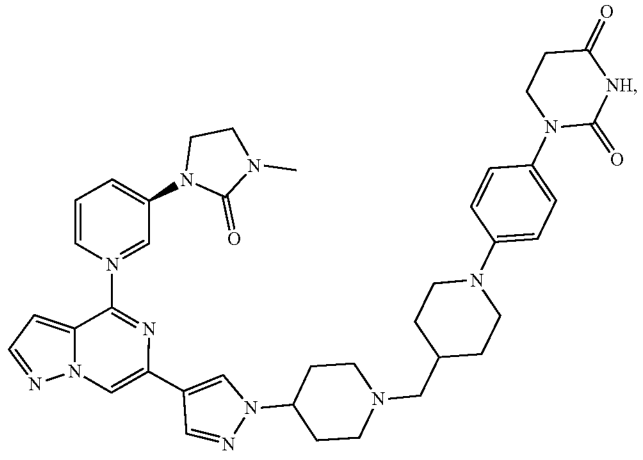
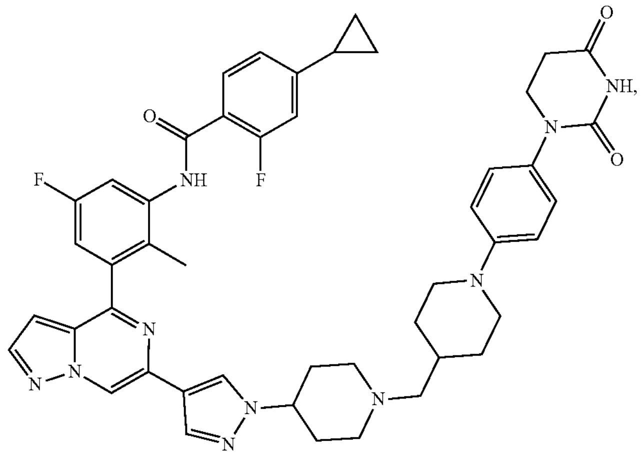
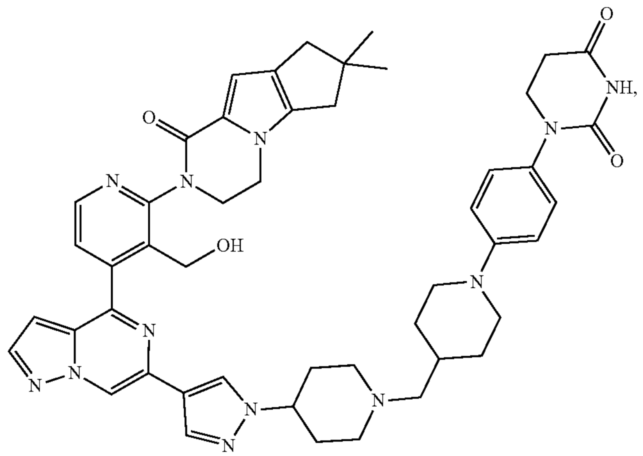

-continued
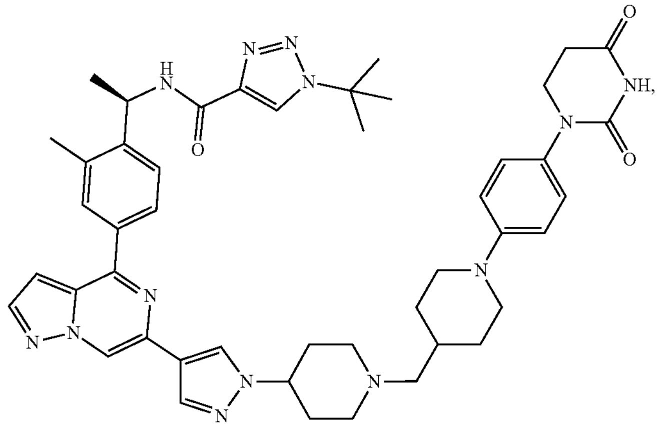
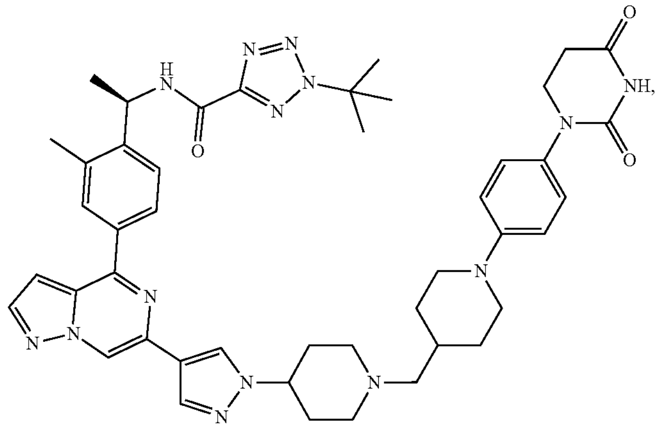
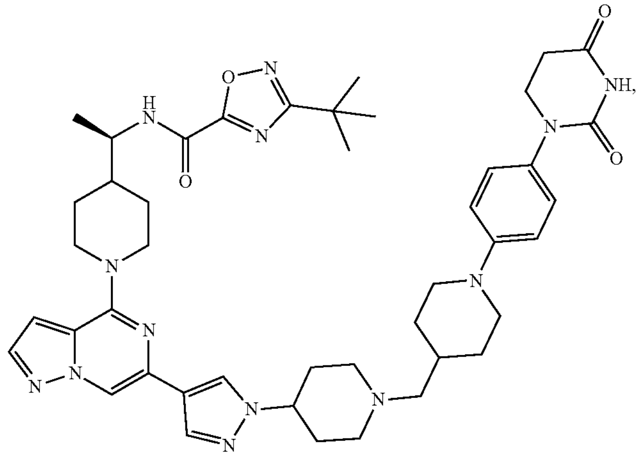

-continued
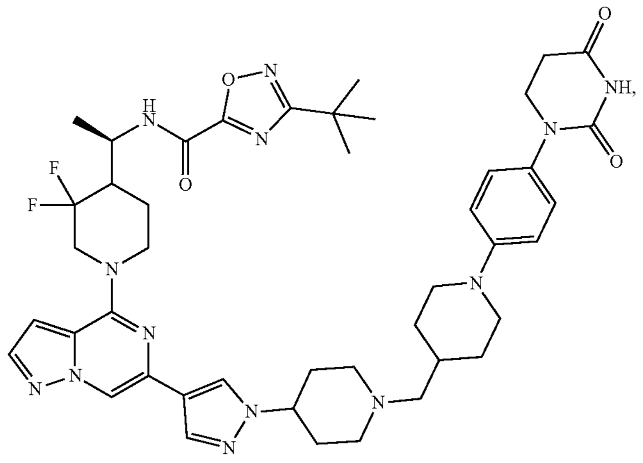
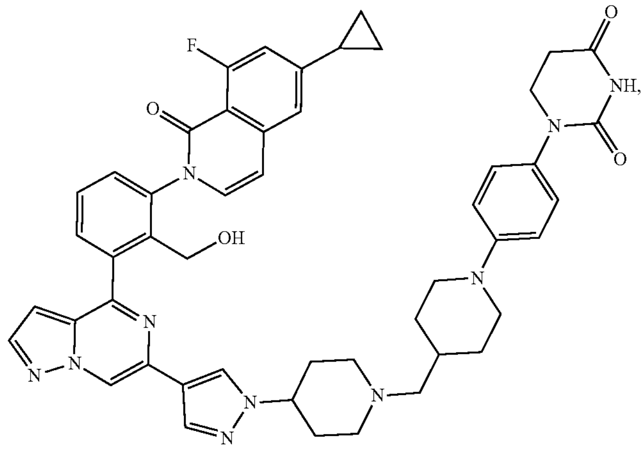
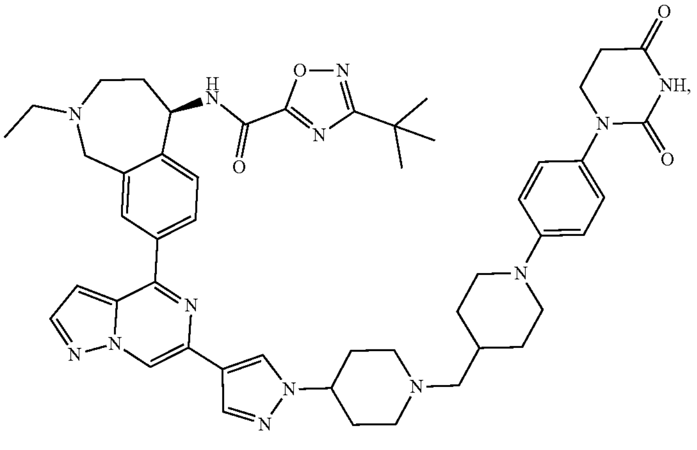

-continued
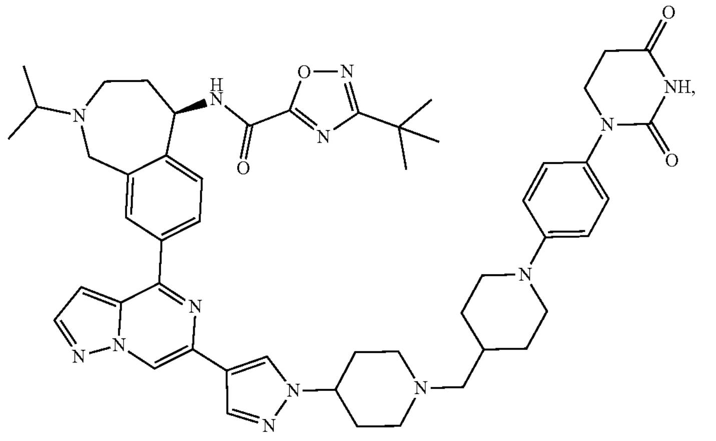
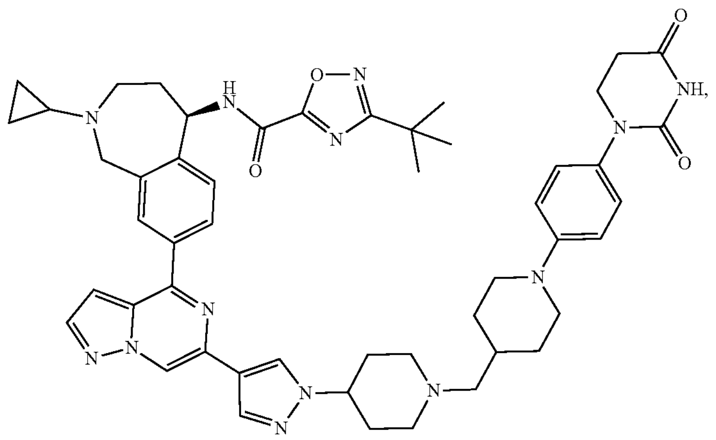
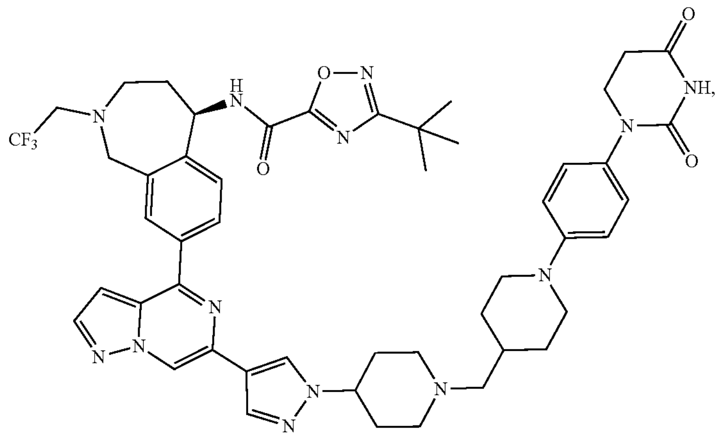

-continued
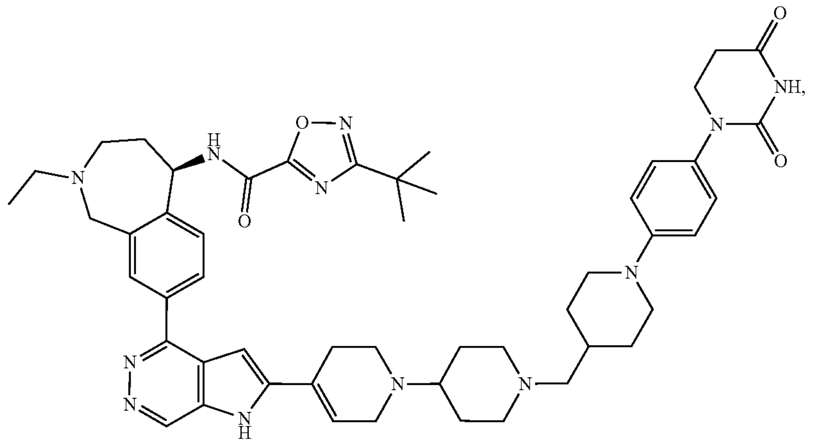
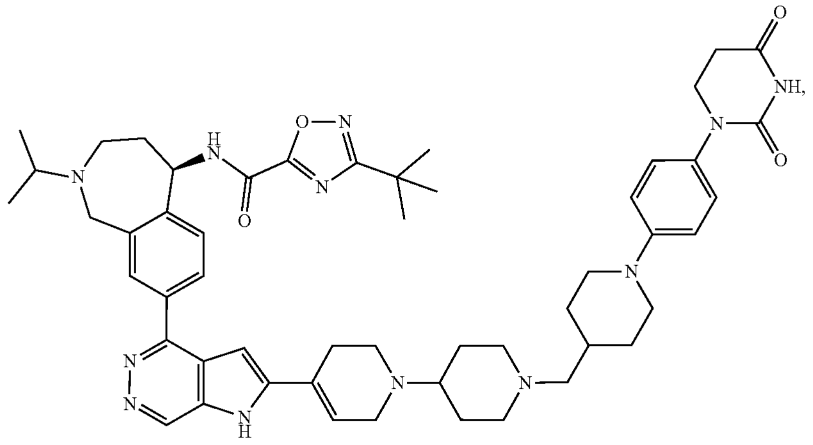
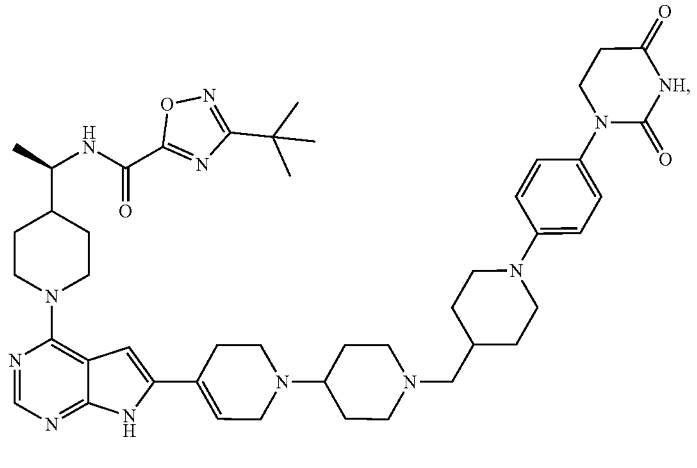

-continued
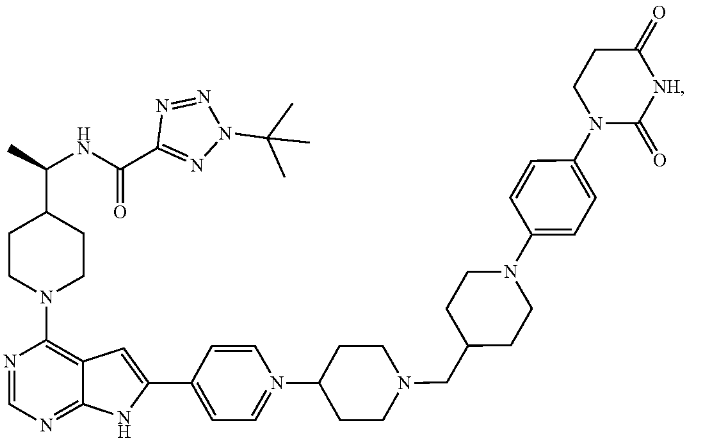
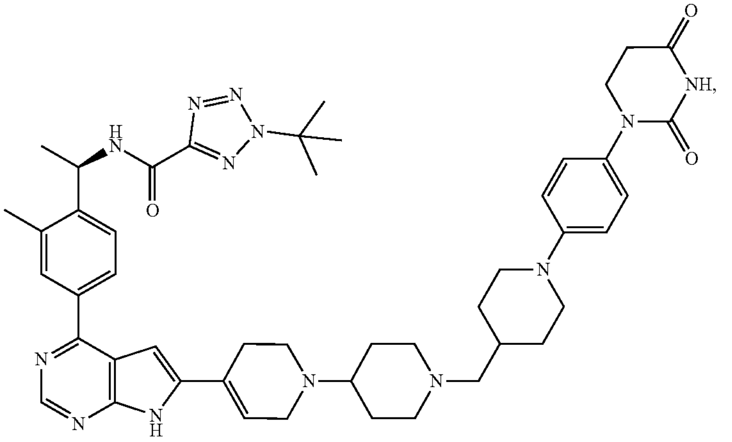
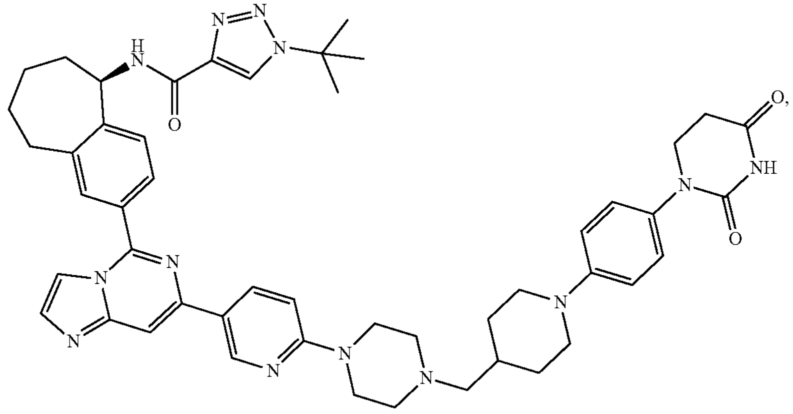
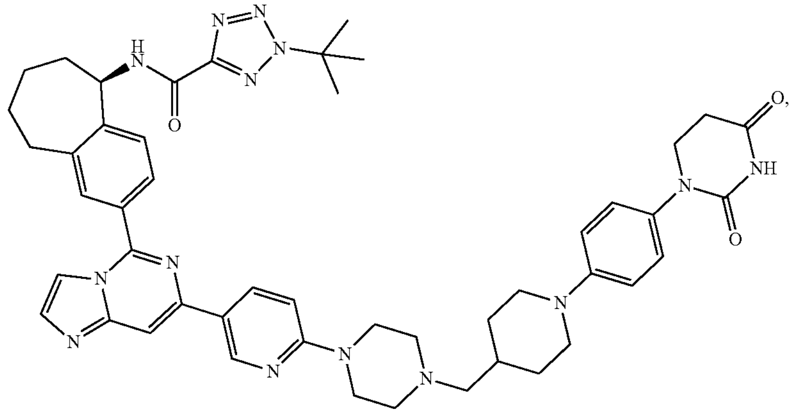

-continued
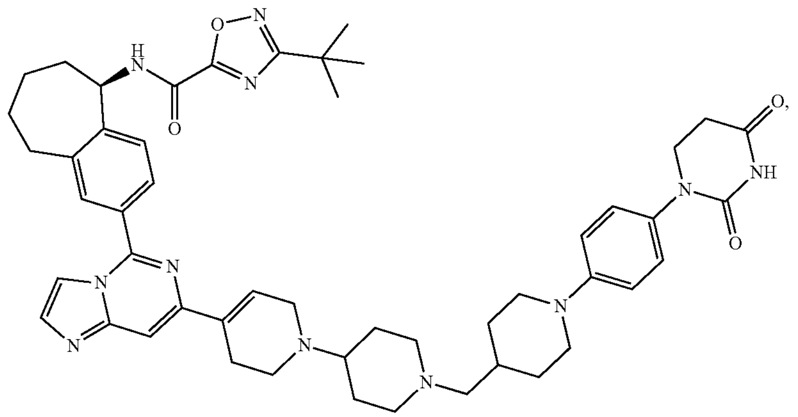
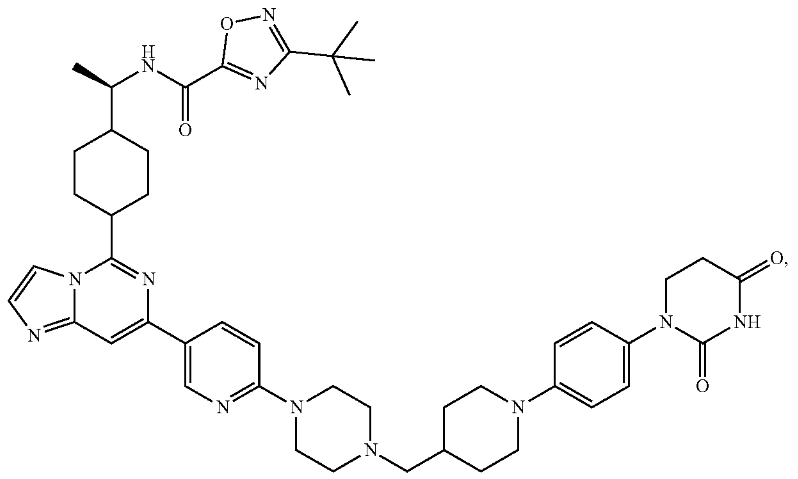
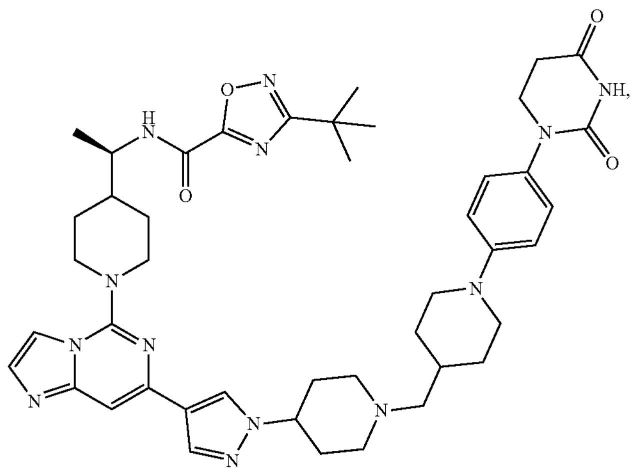

-continued
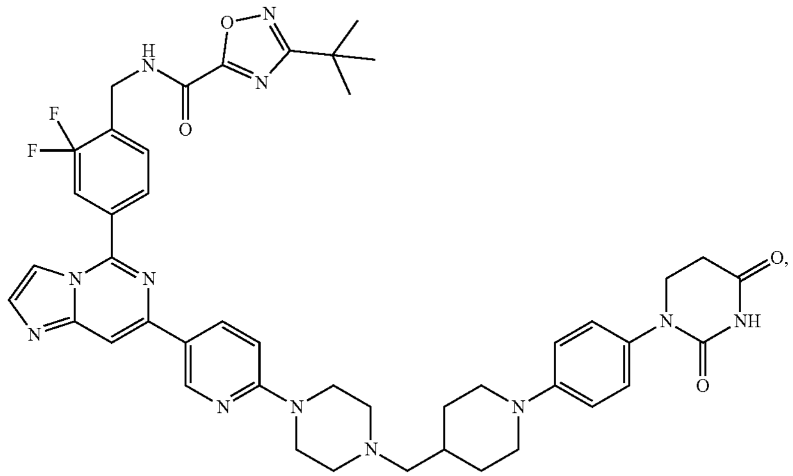
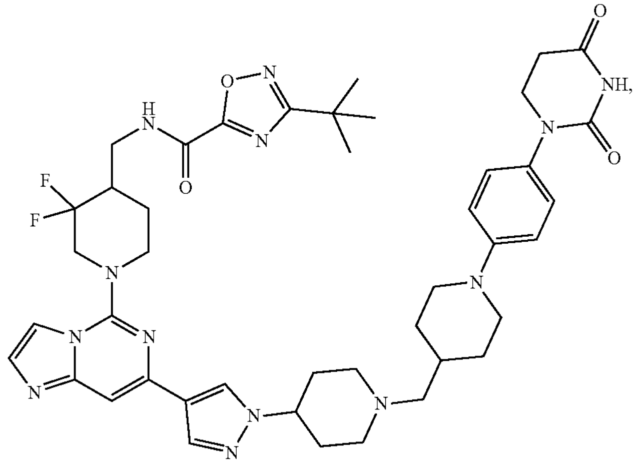
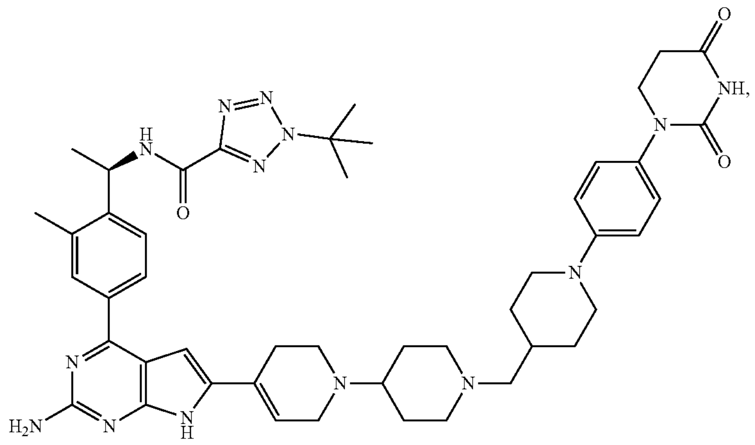

-continued
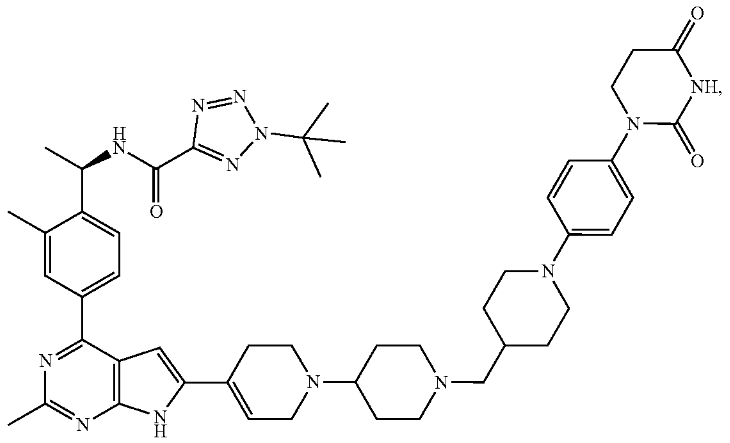
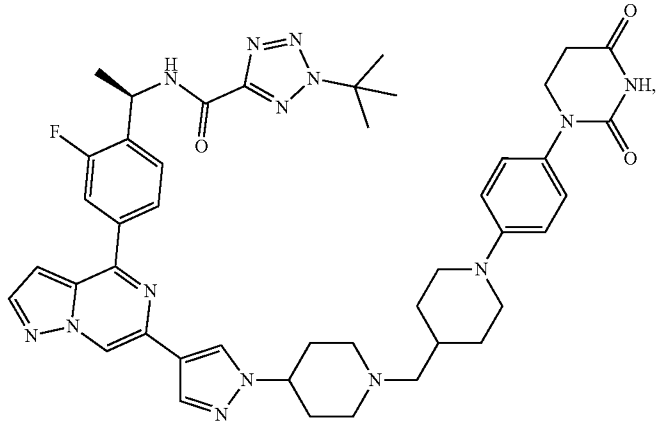
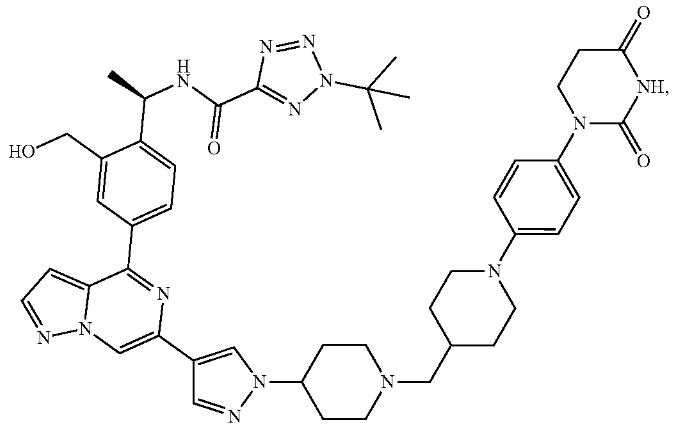
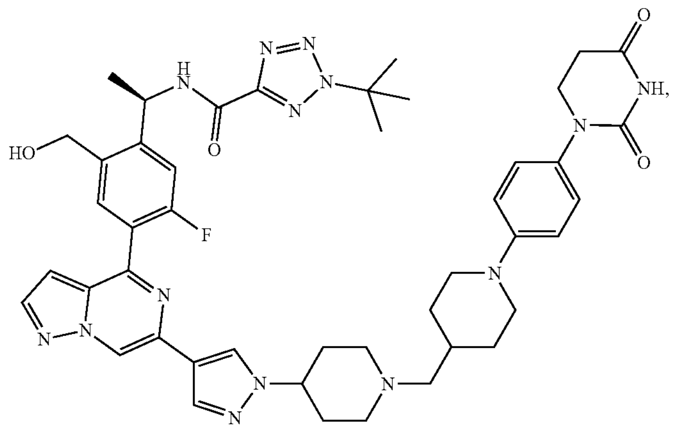

-continued
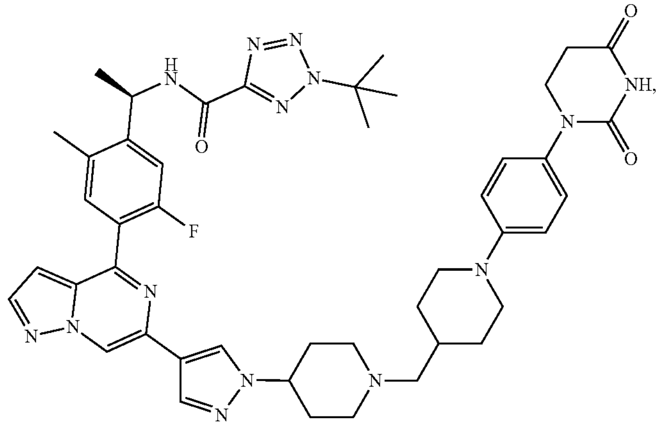
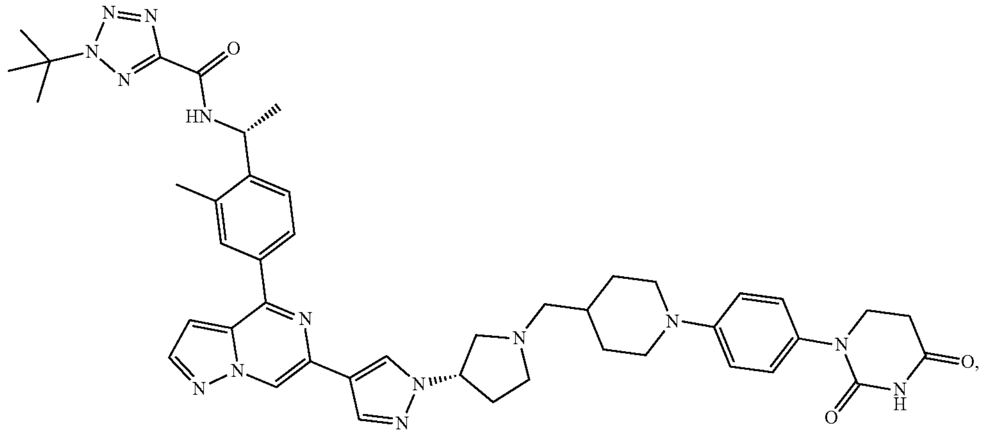
,
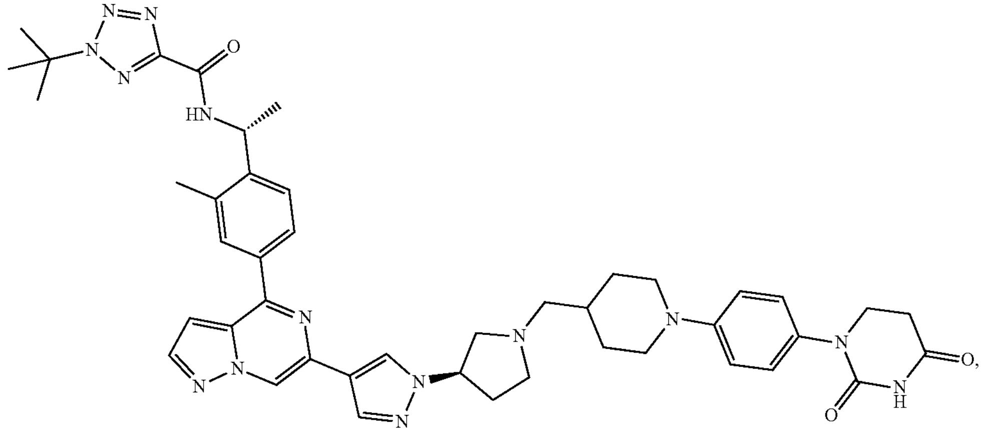
,
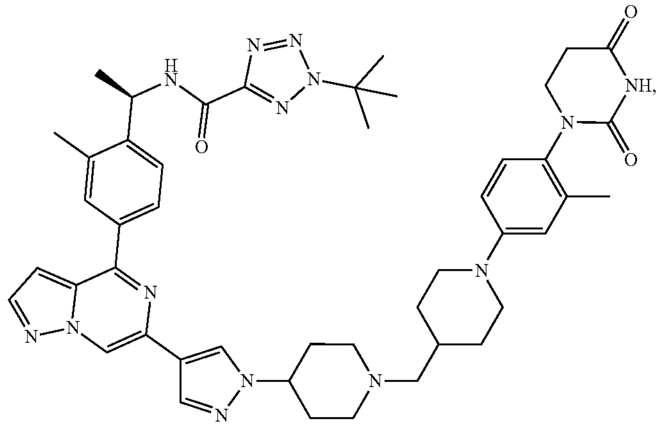

-continued
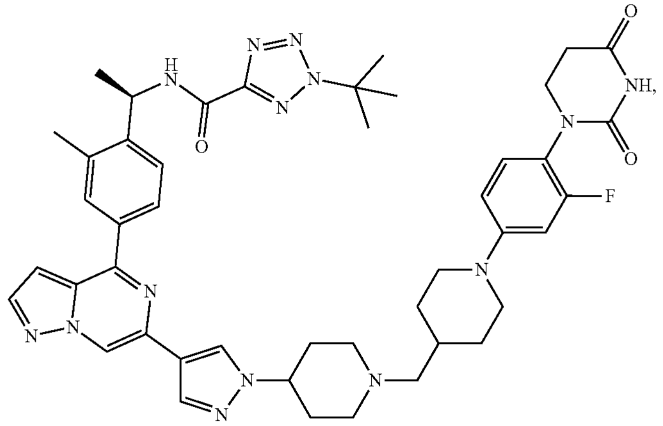
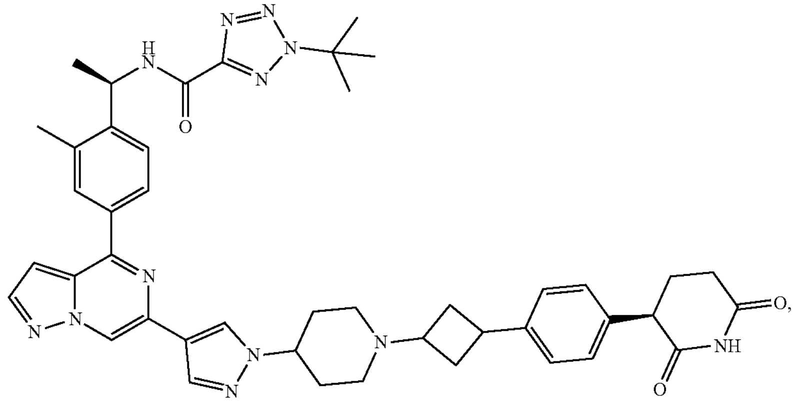
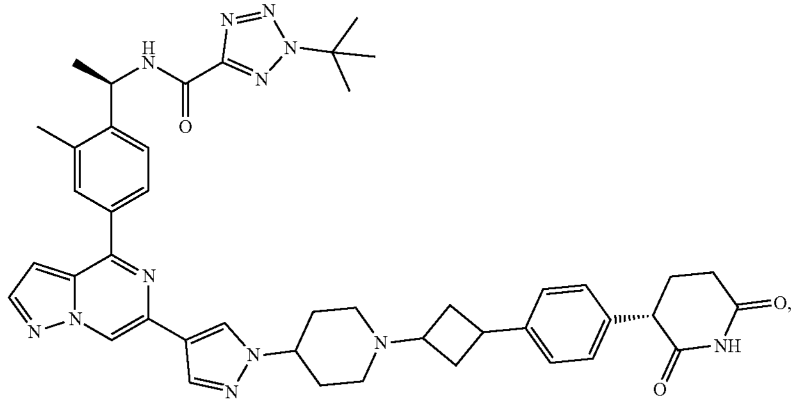
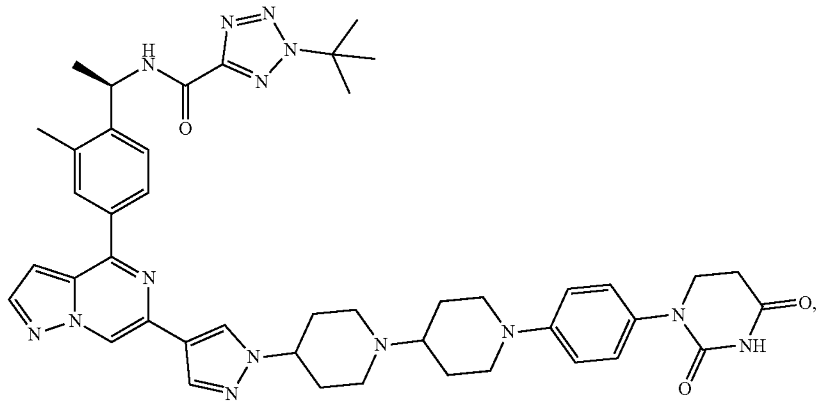

-continued
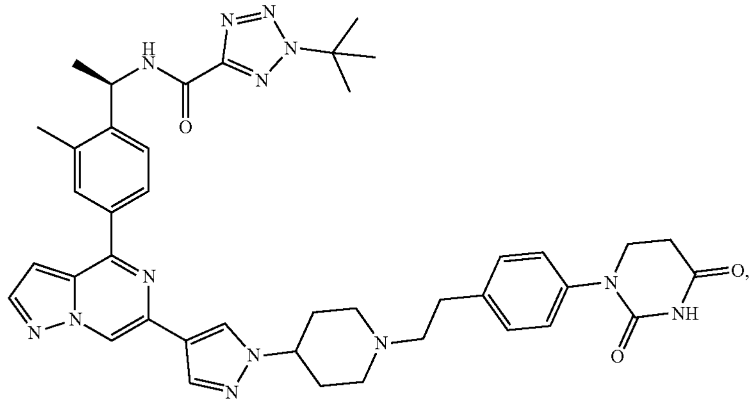
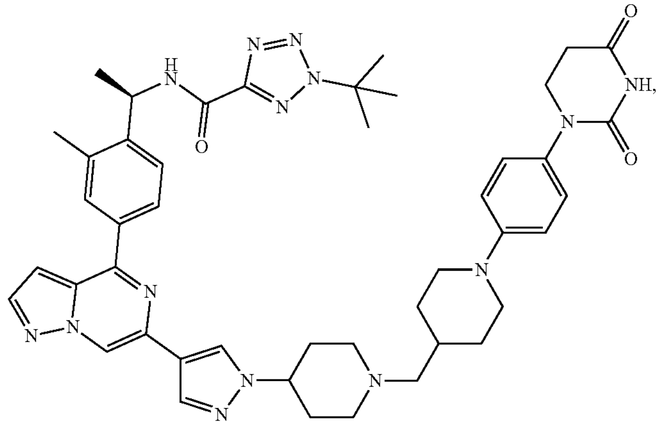
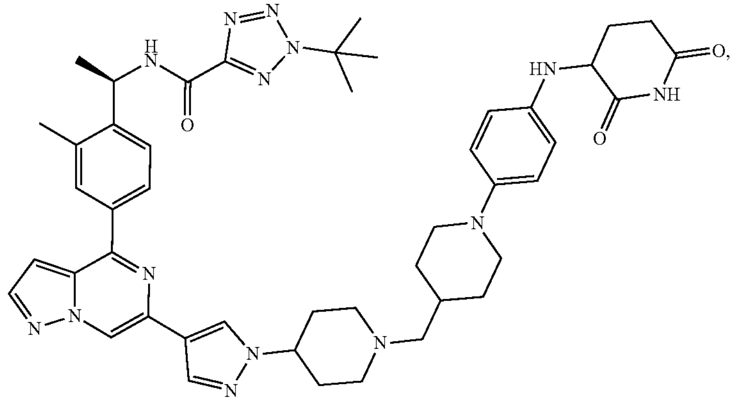
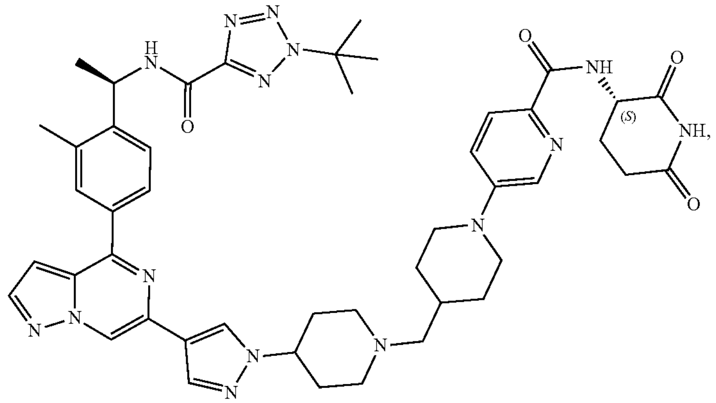

-continued
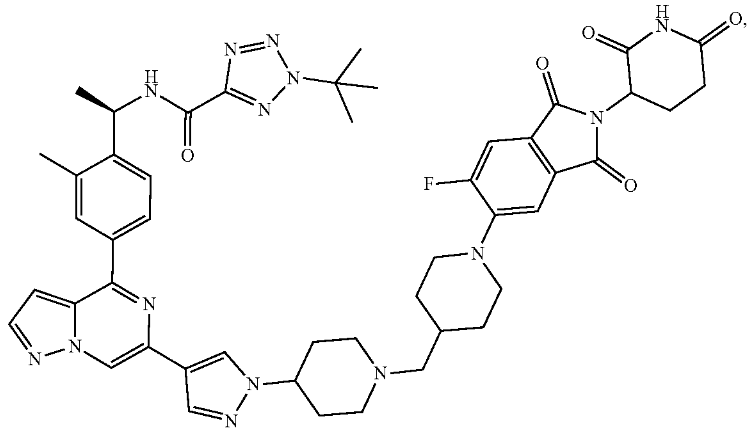
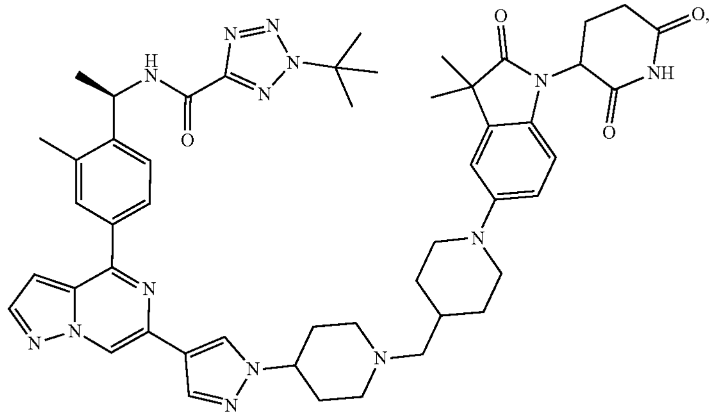
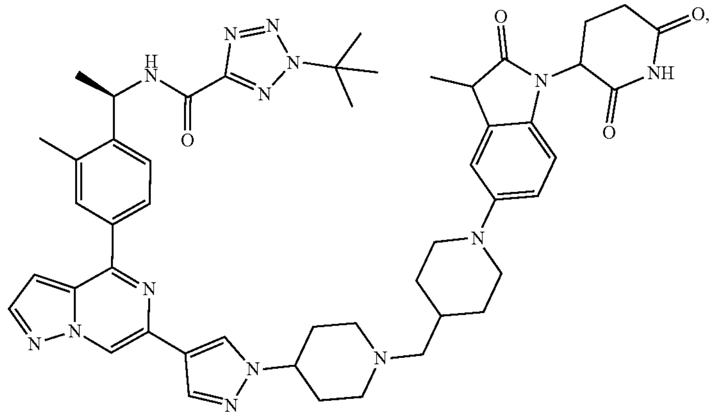
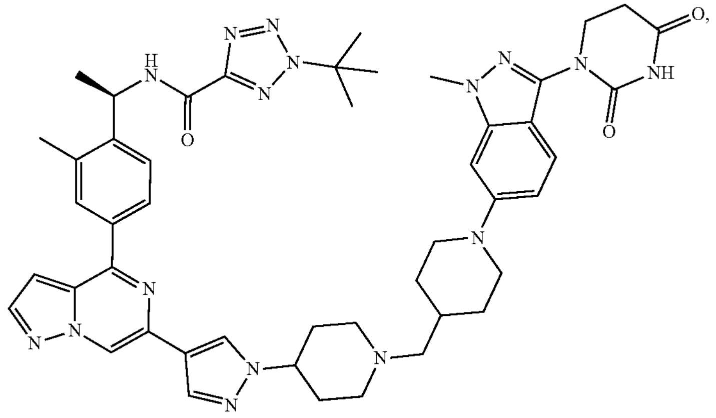

-continued
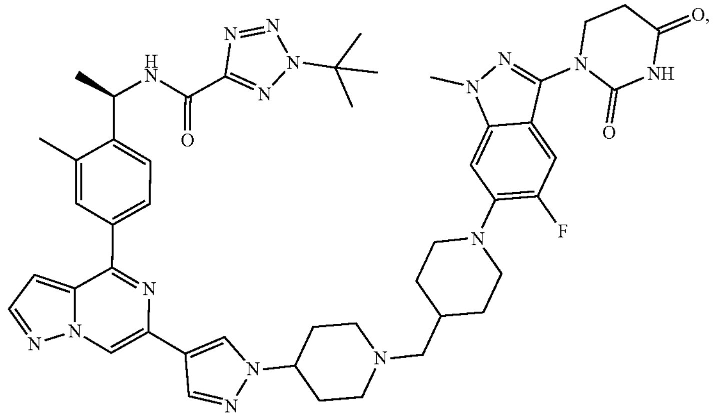
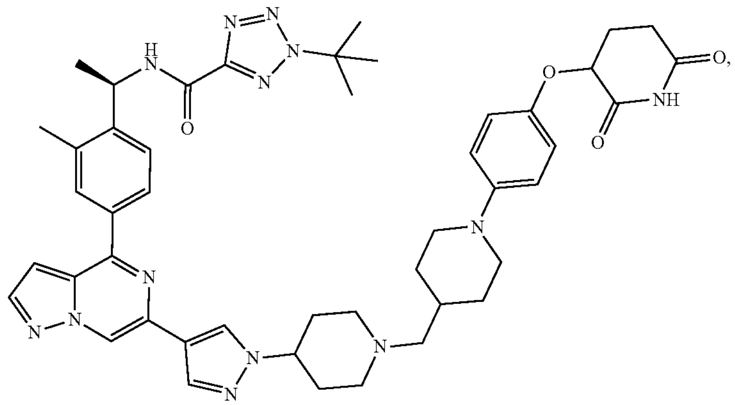
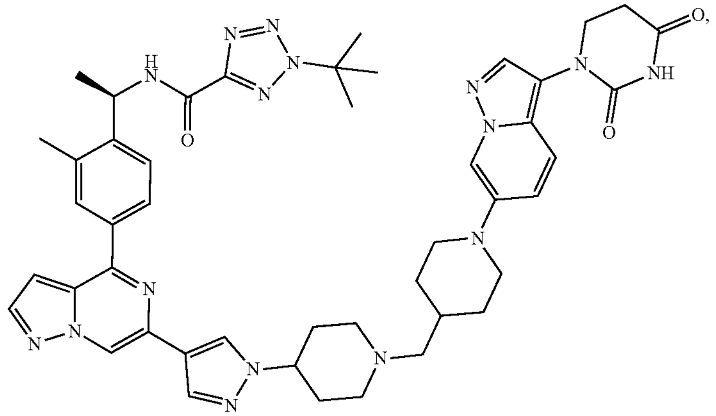
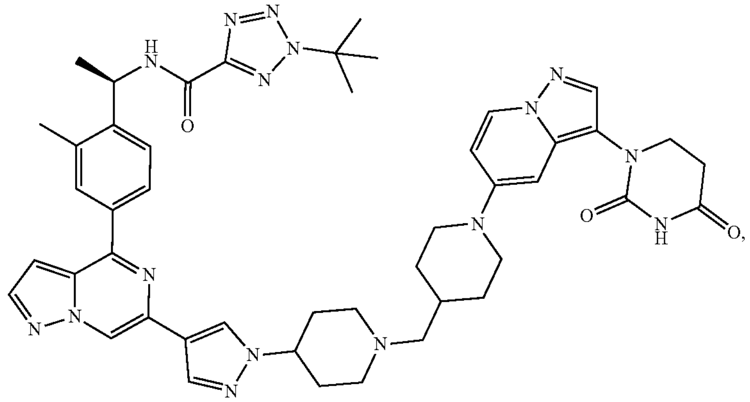

-continued
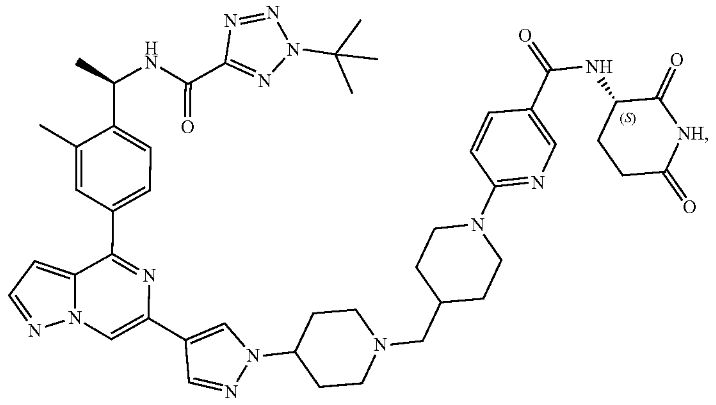
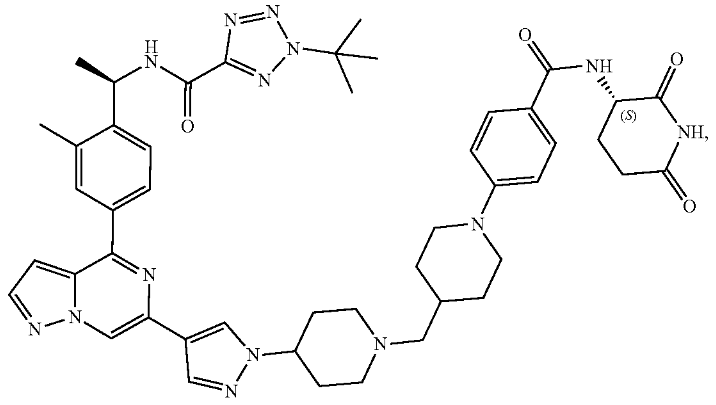
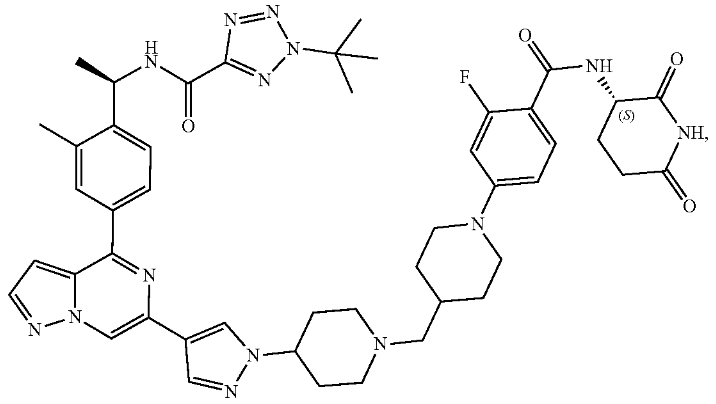
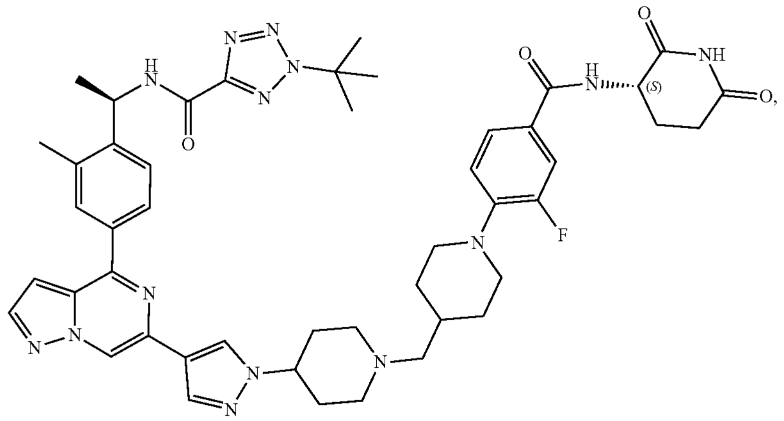

-continued
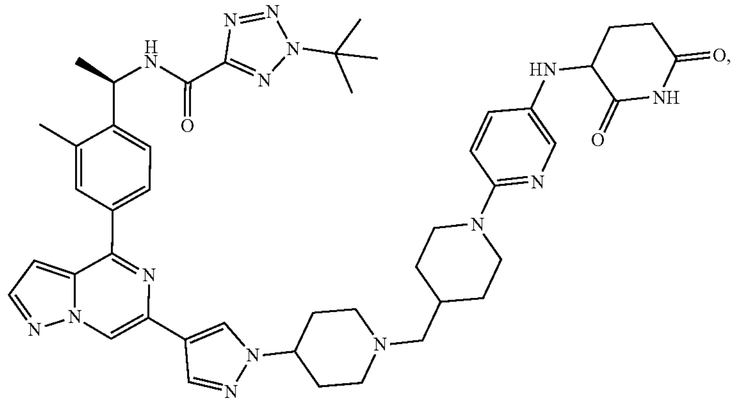
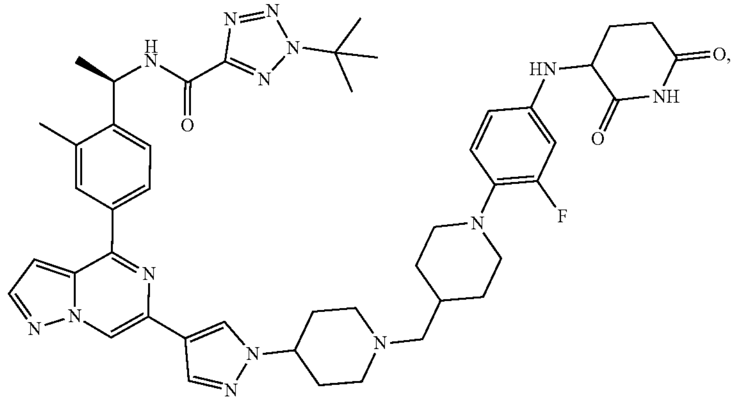
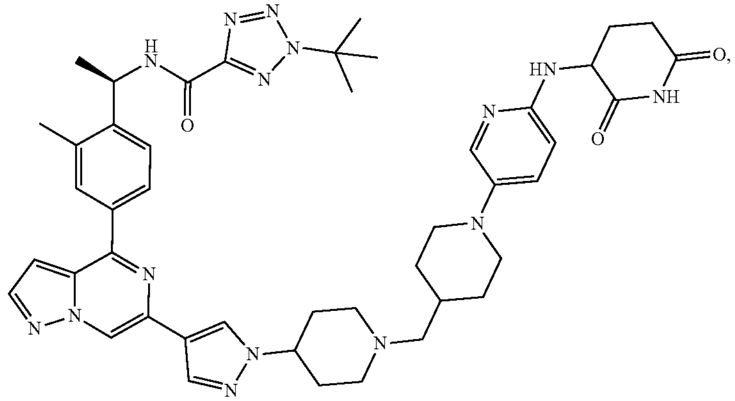
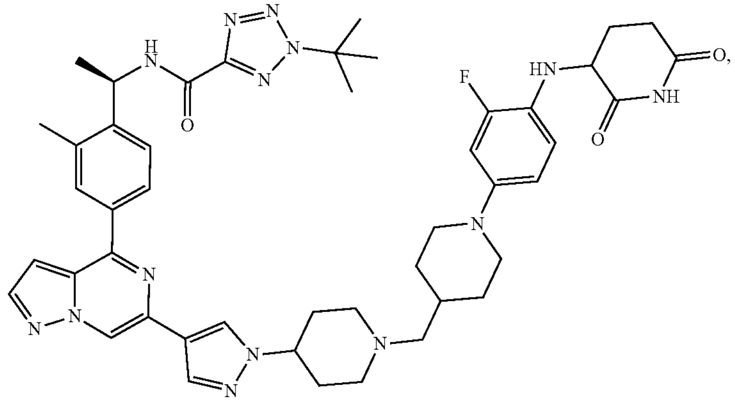

-continued
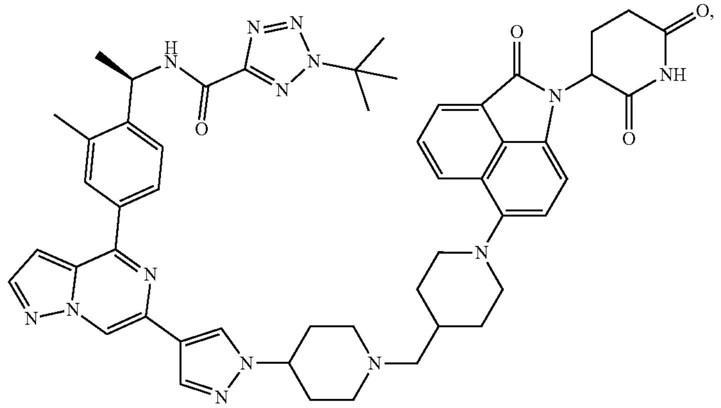
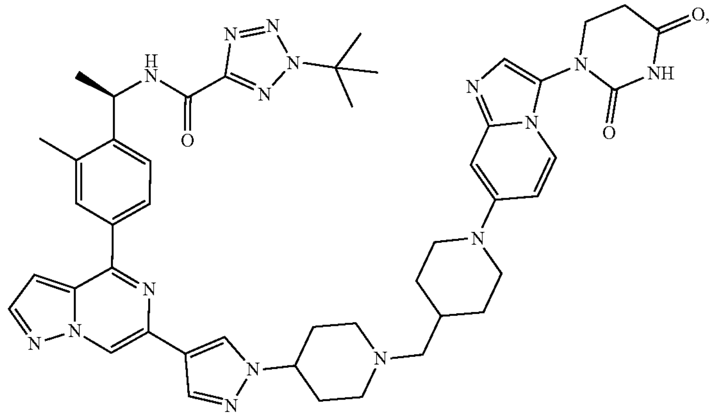
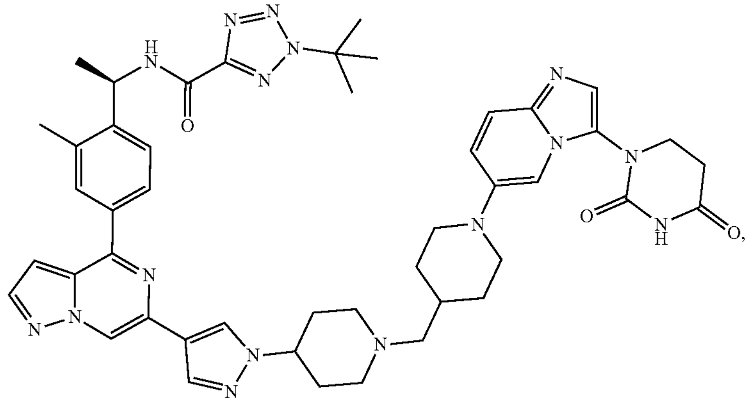
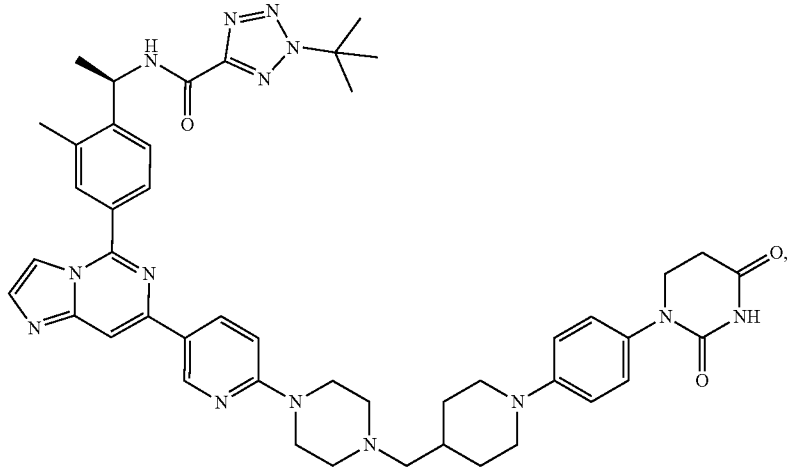

-continued
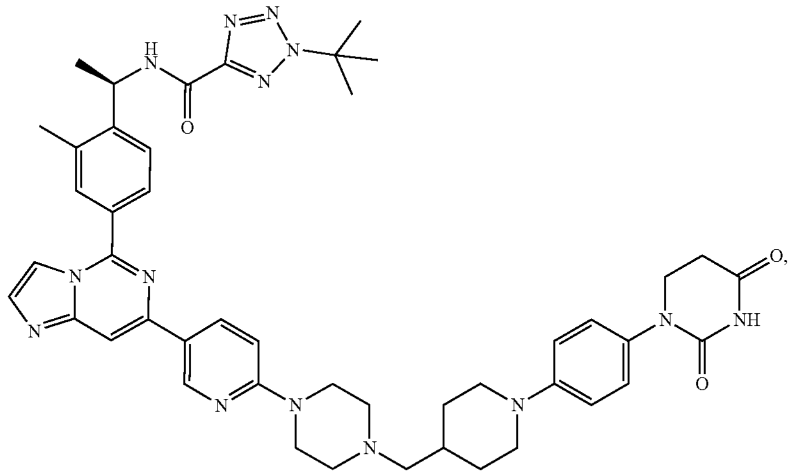
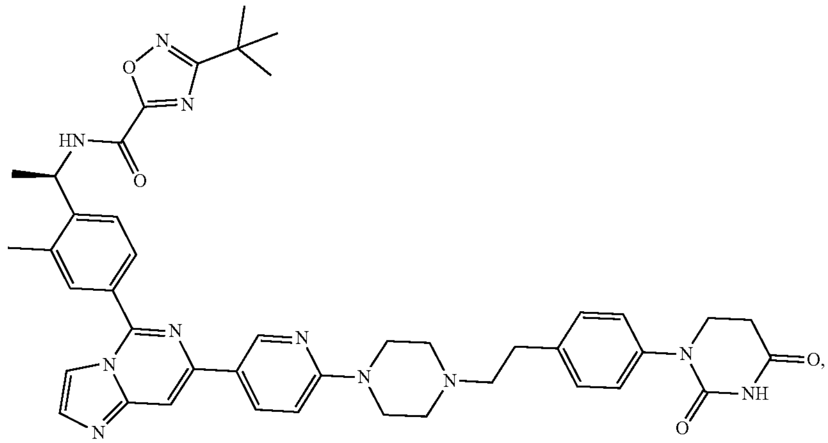
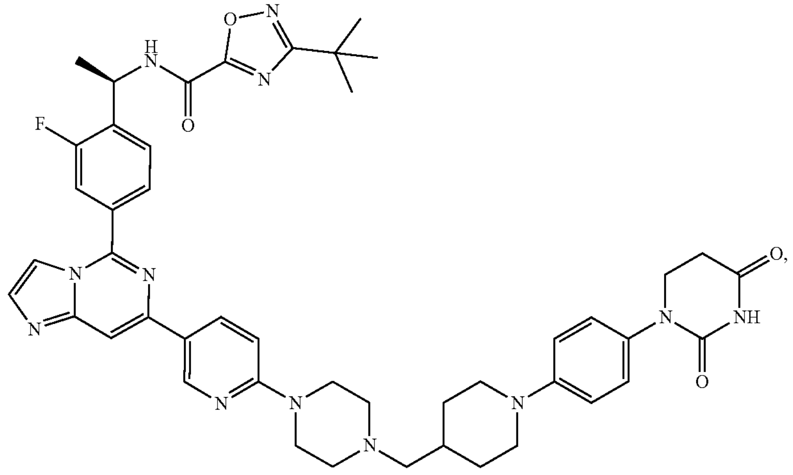

-continued
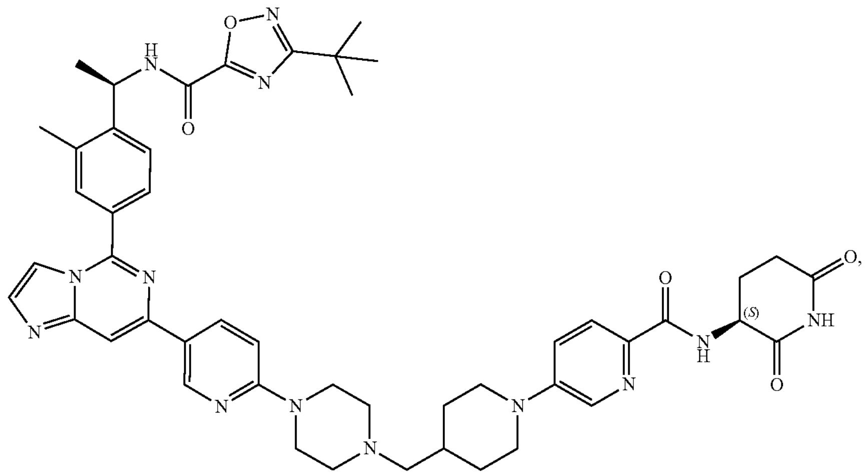
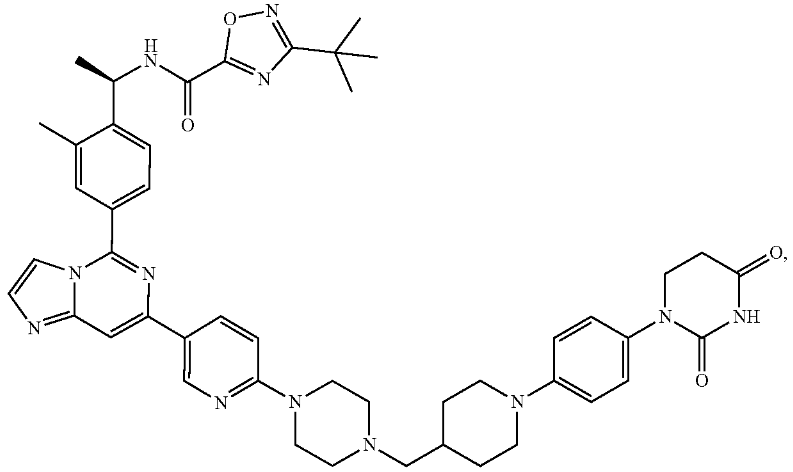
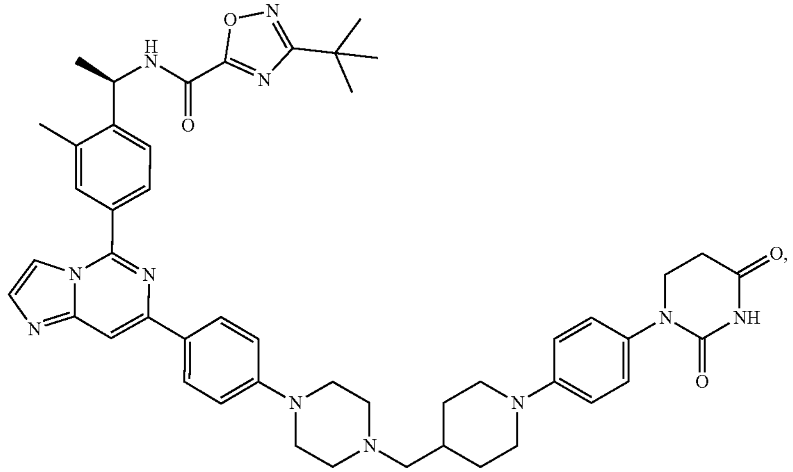

-continued
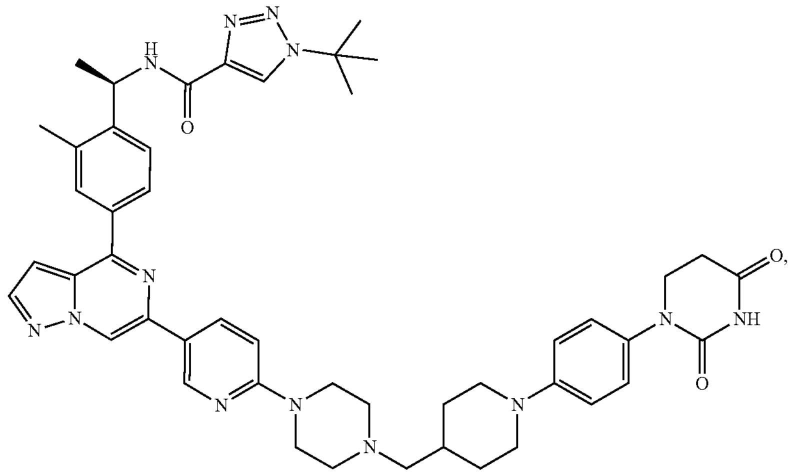
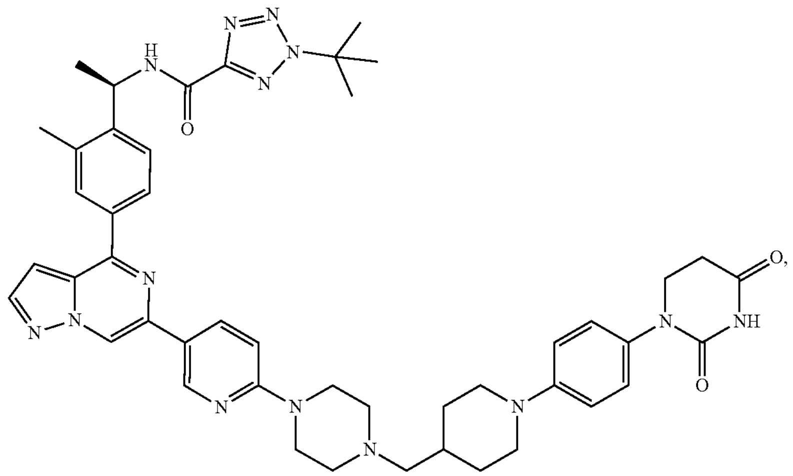
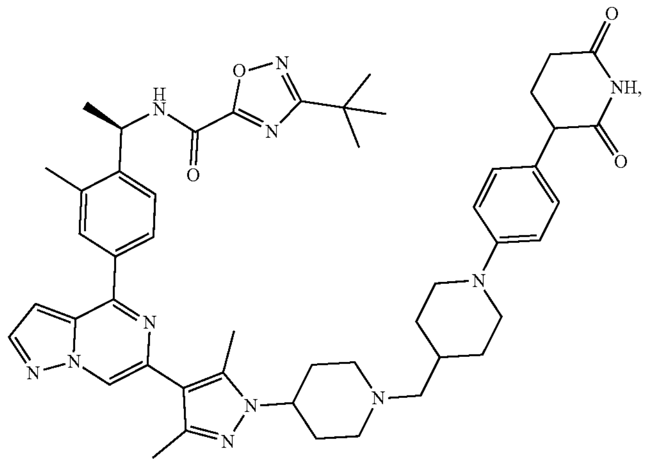

-continued
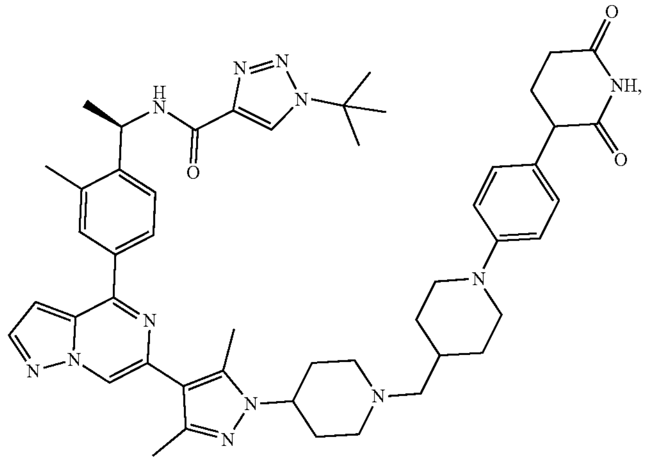 [SMILES: Cc1cc(-c2nc(-c3c(C)nn(C4CCN(CC5CCN(c6ccc(C7CCC(=O)NC7=O)cc6)CC5)CC4)c3C)cn3nccc23)ccc1[C@@H](C)NC(=O)c1cn(C(C)(C)C)nn1]
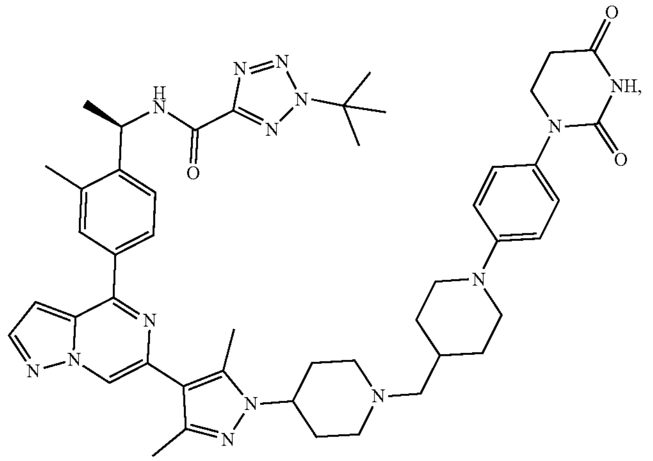
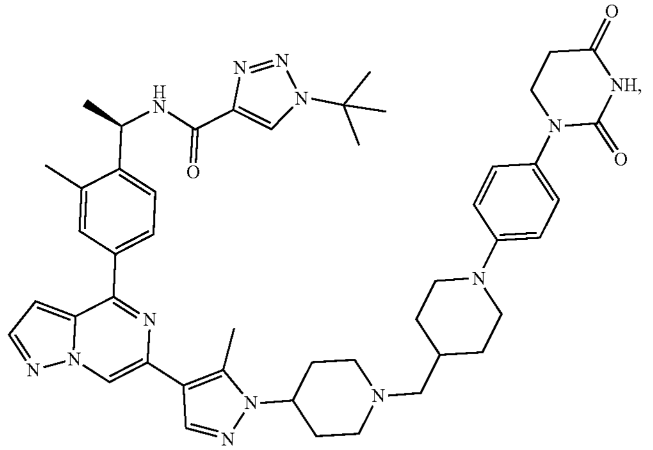

-continued
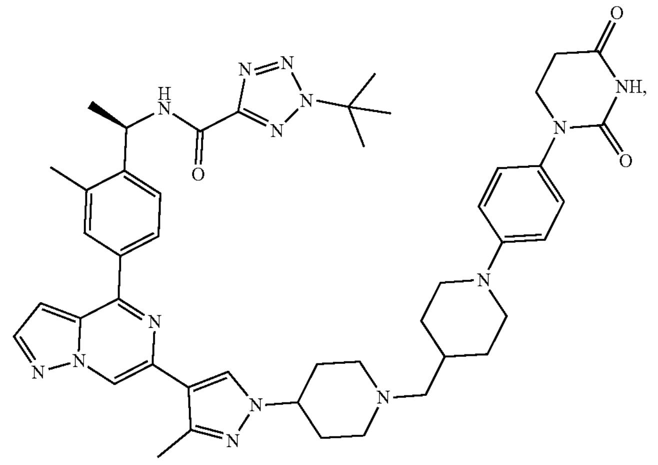
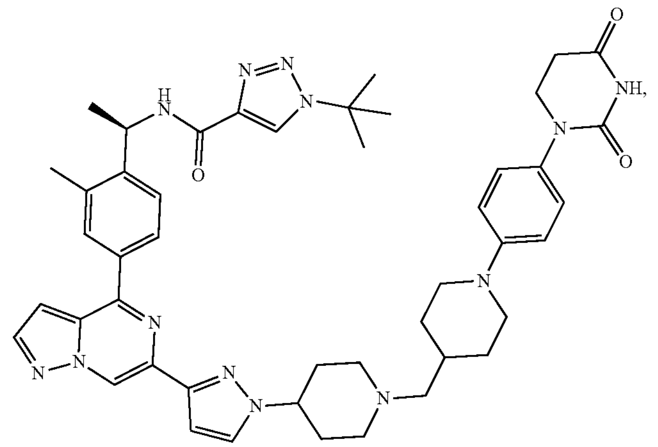
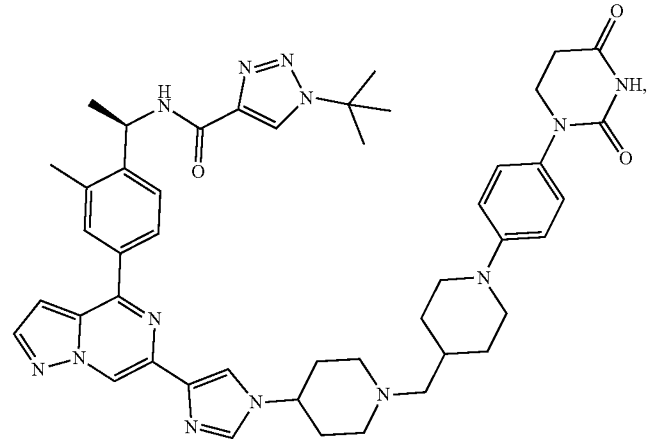
NH,

-continued
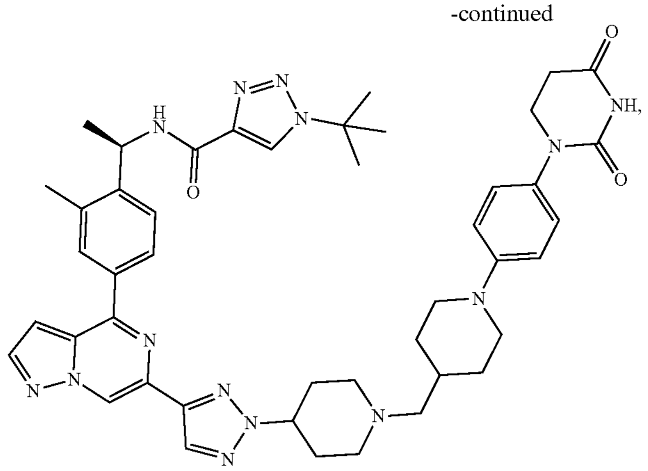
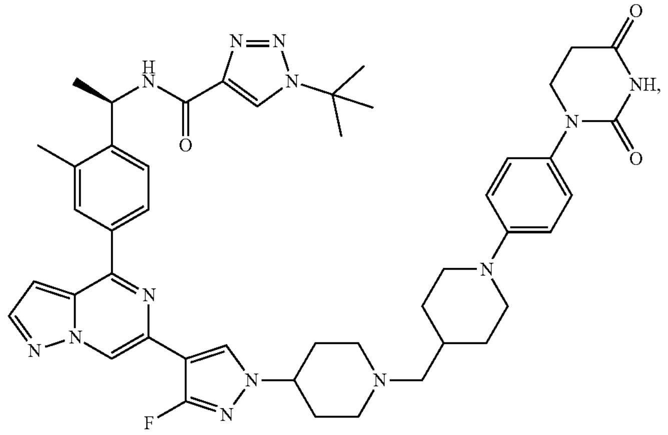
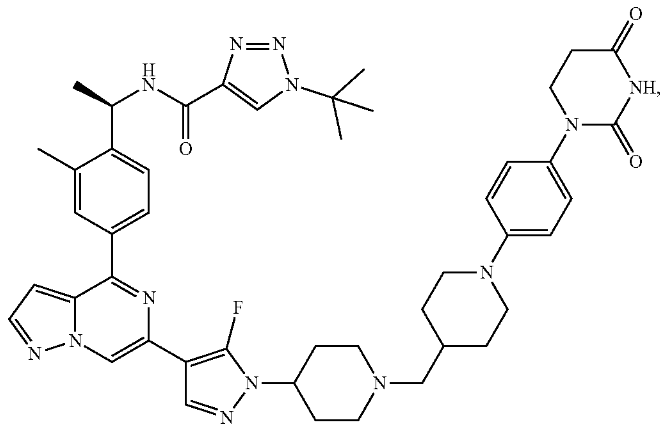

-continued
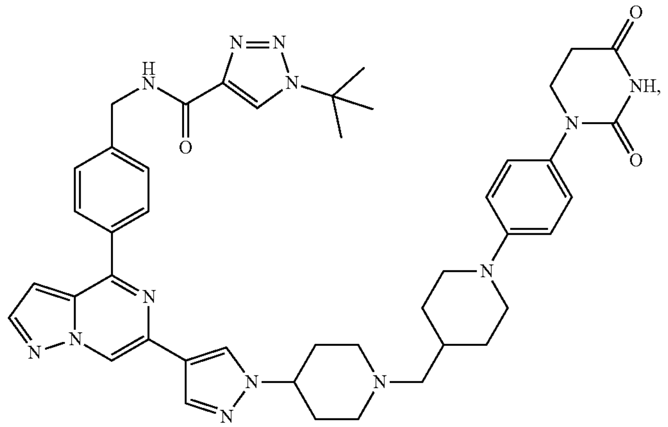
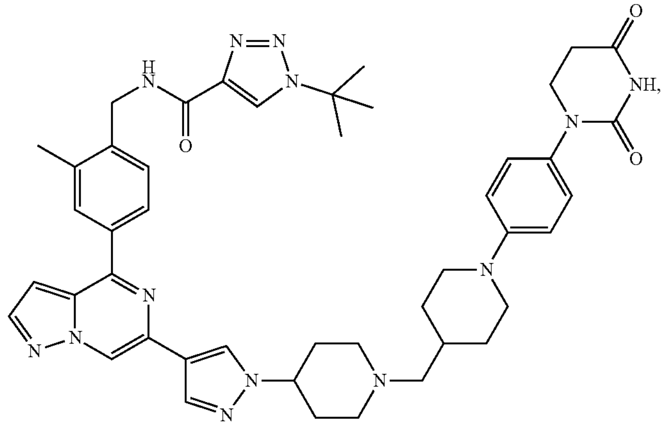
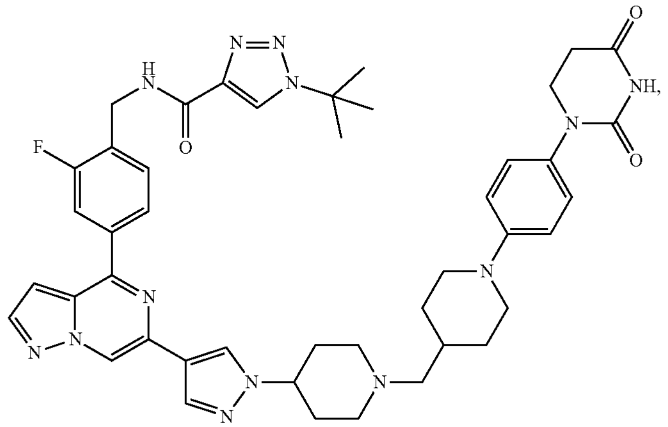
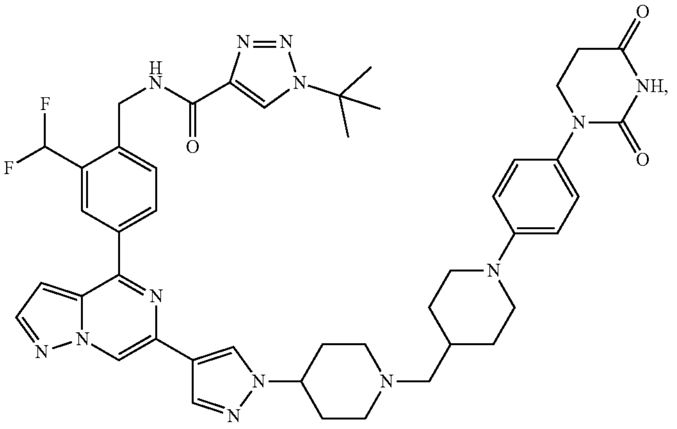

-continued
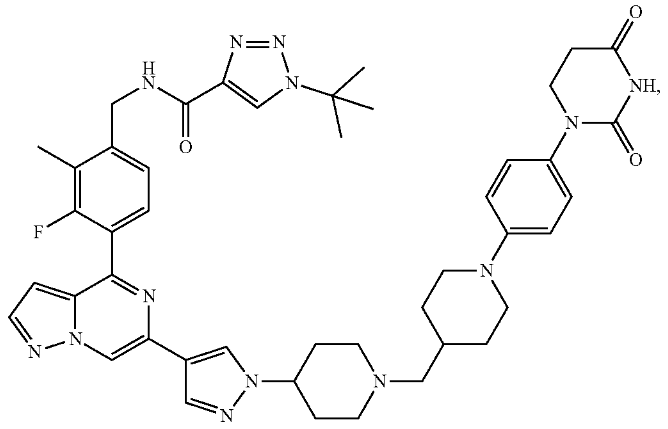
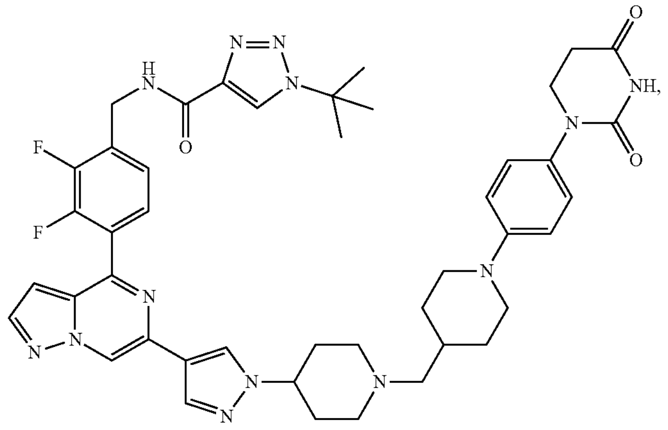
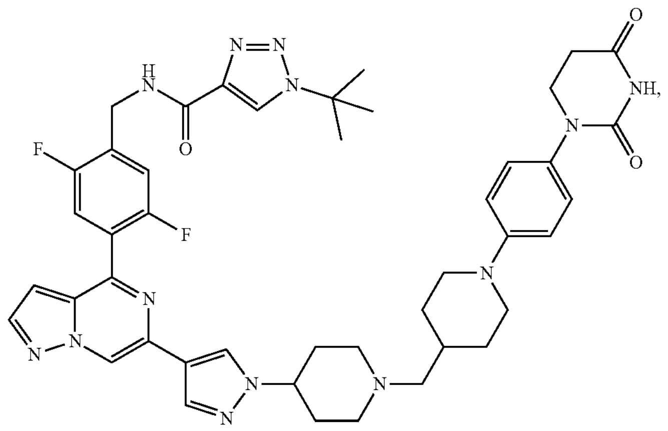
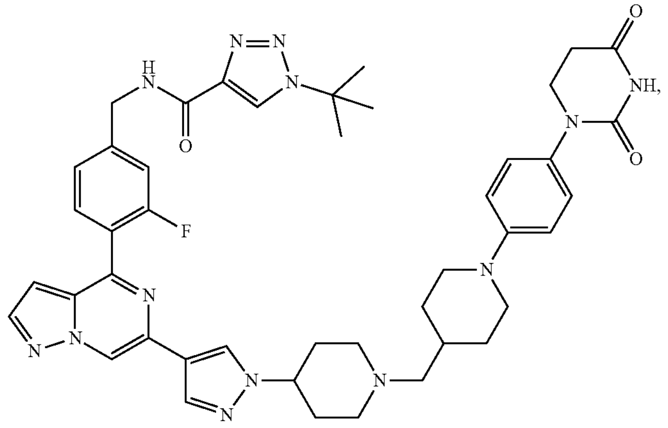

-continued
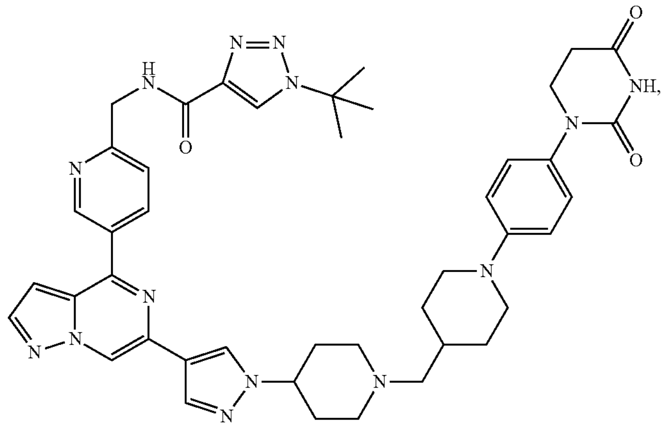
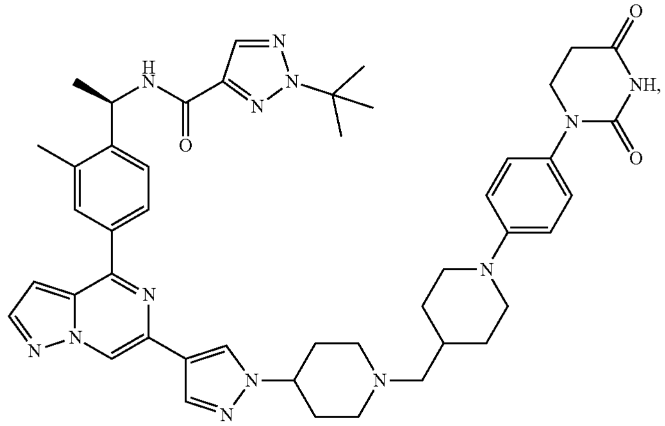
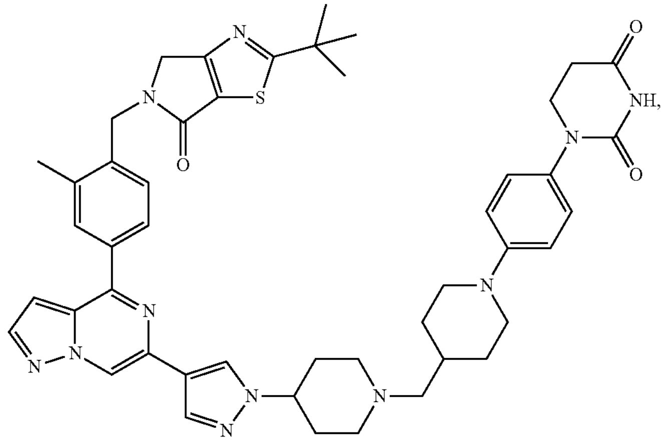
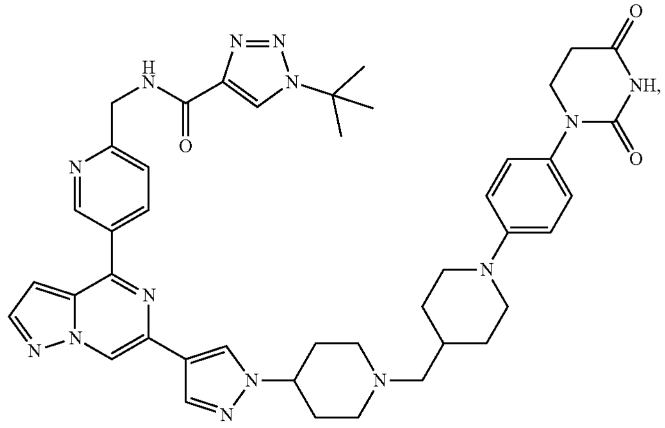

-continued
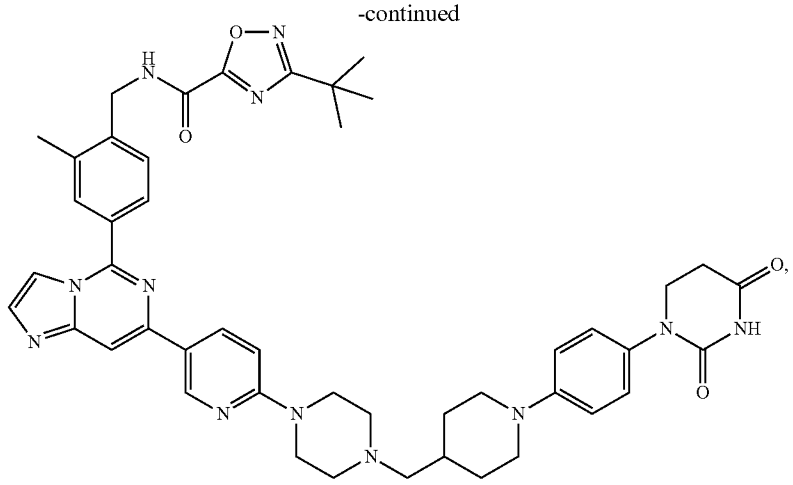
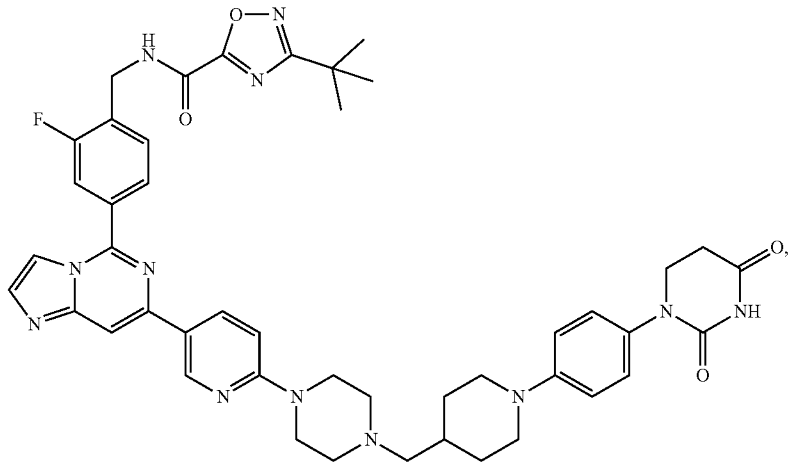
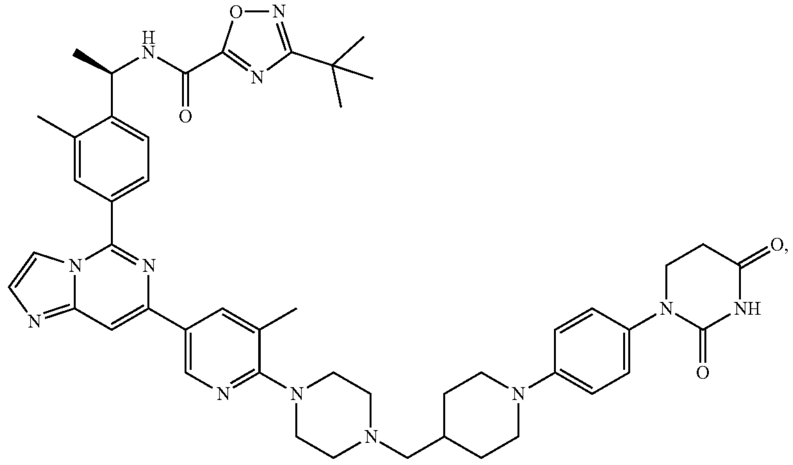

-continued
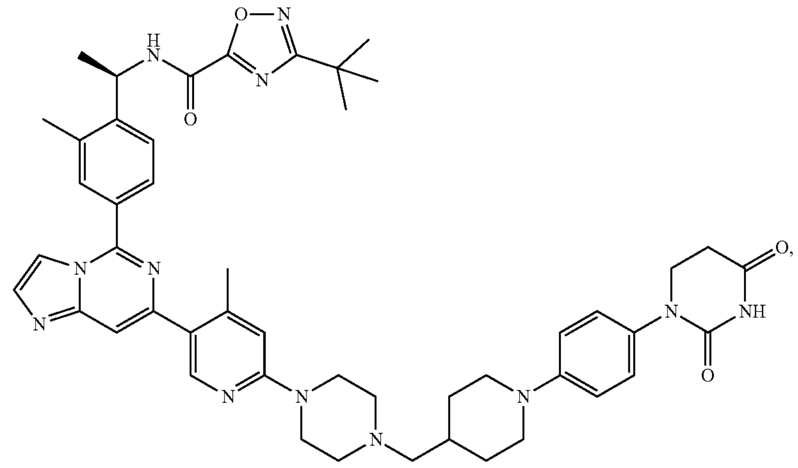
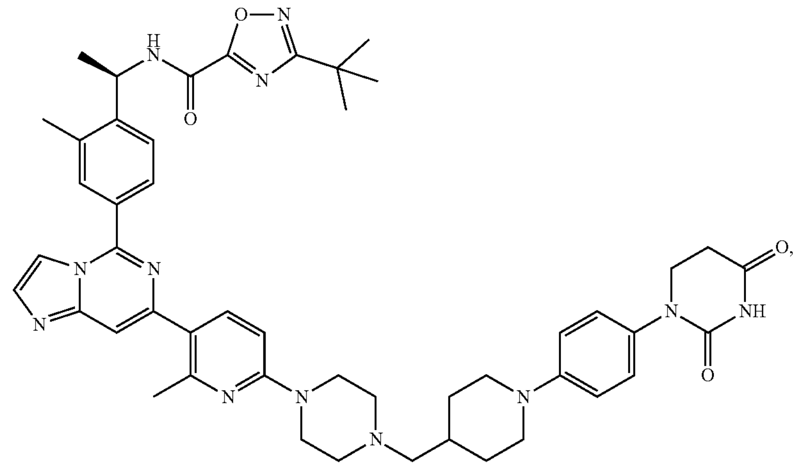
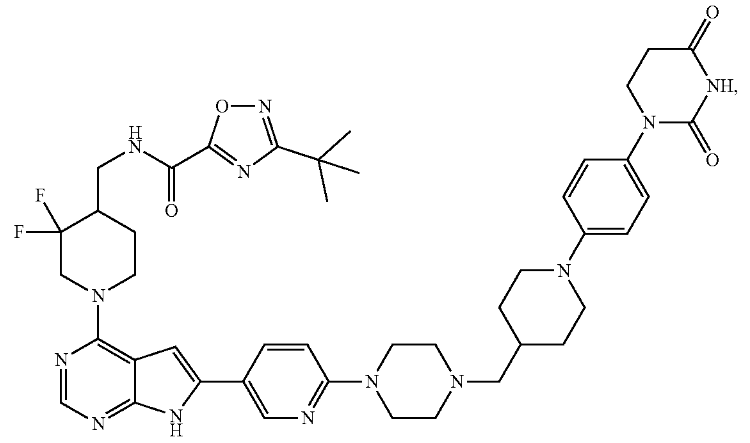

-continued
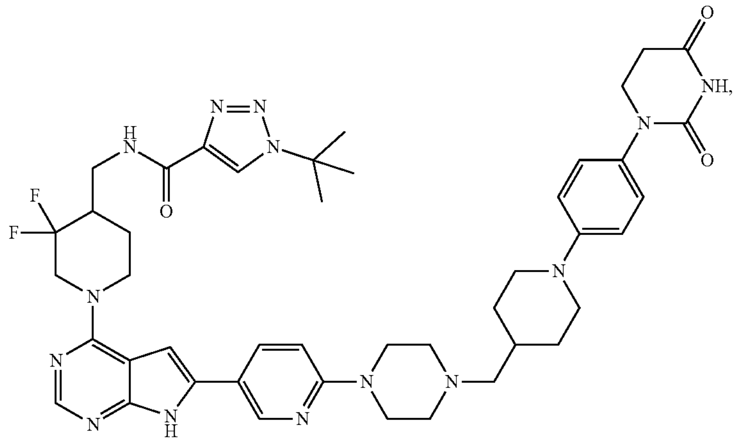
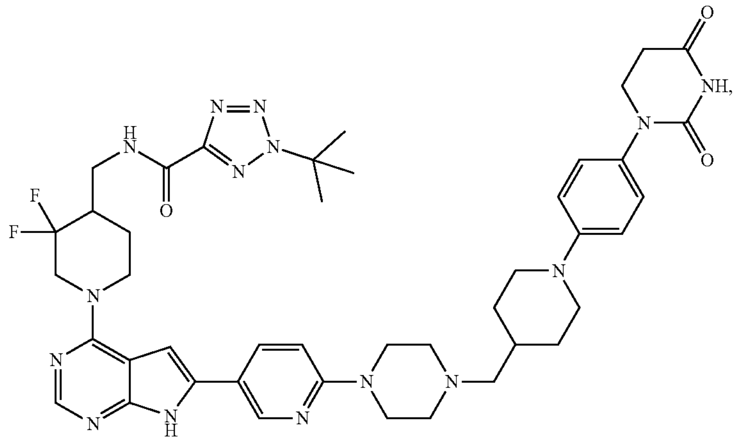
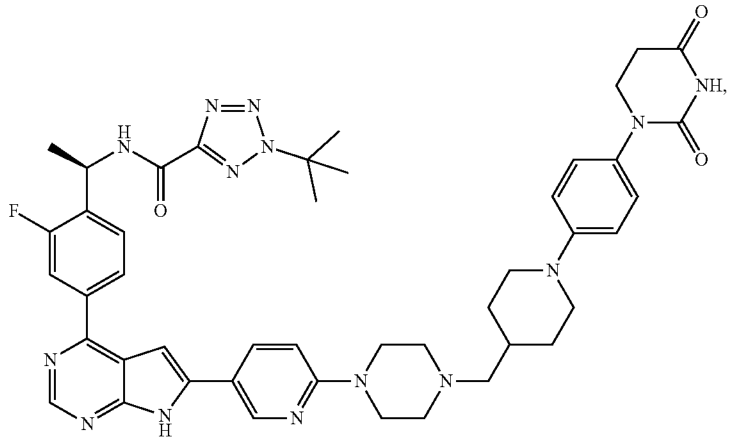

-continued
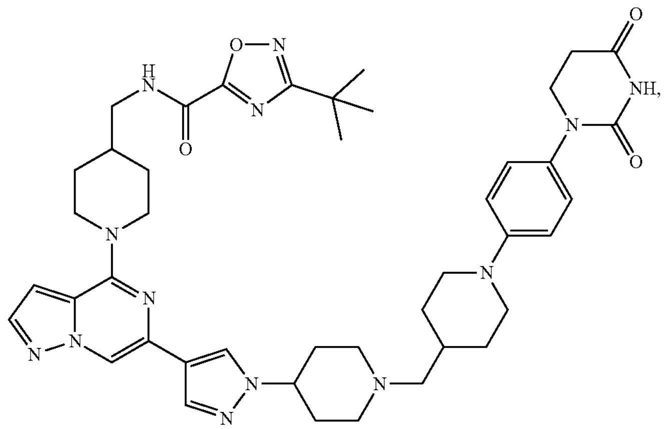
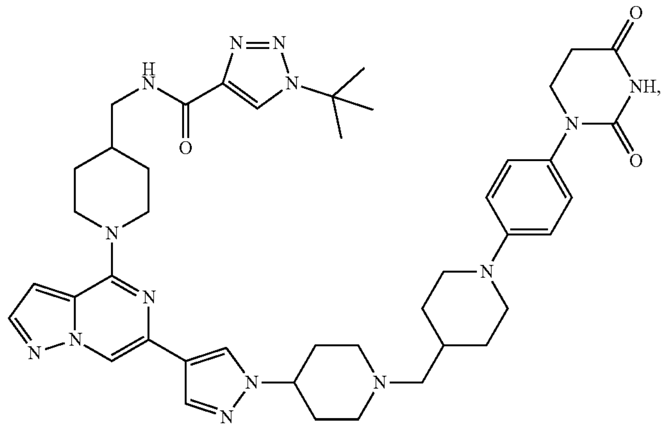
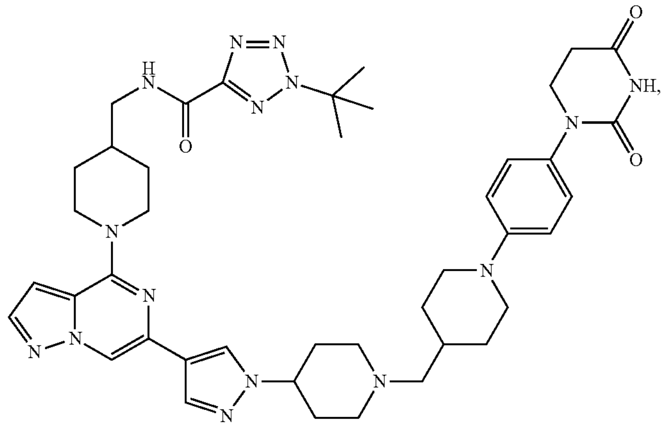
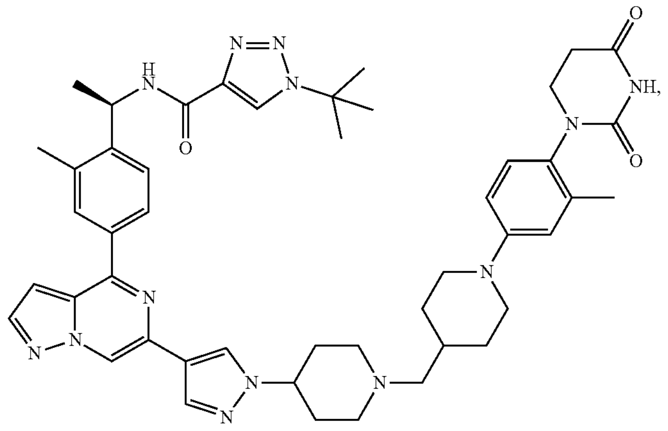

-continued
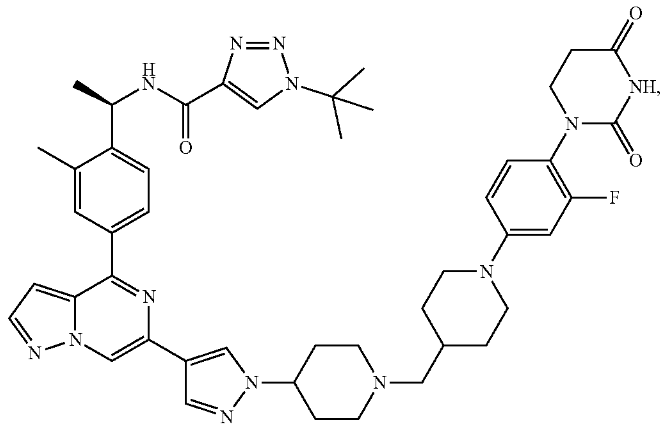
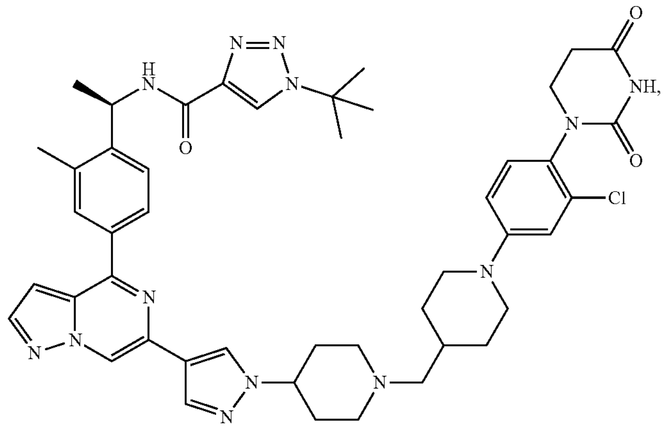
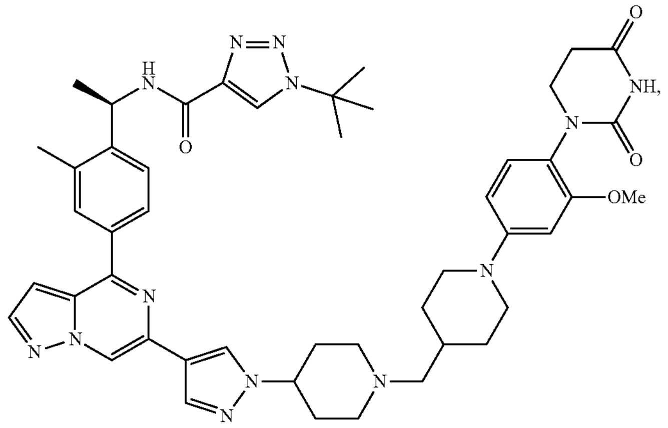
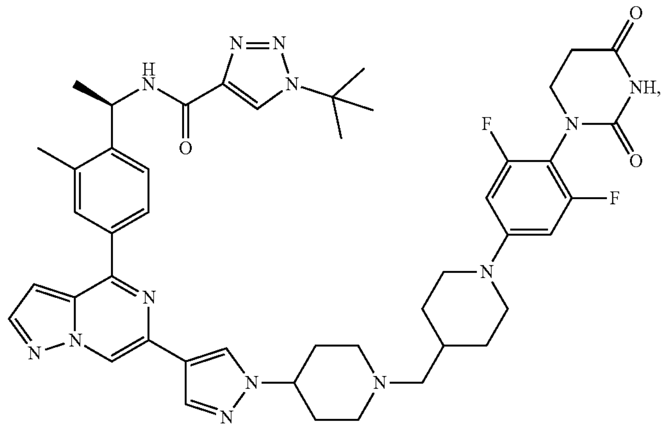

-continued
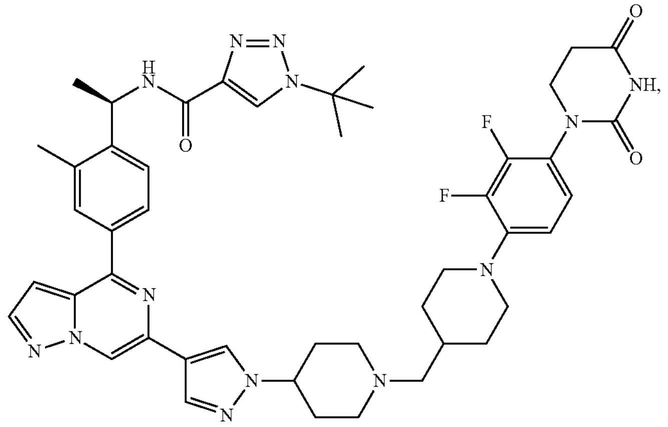
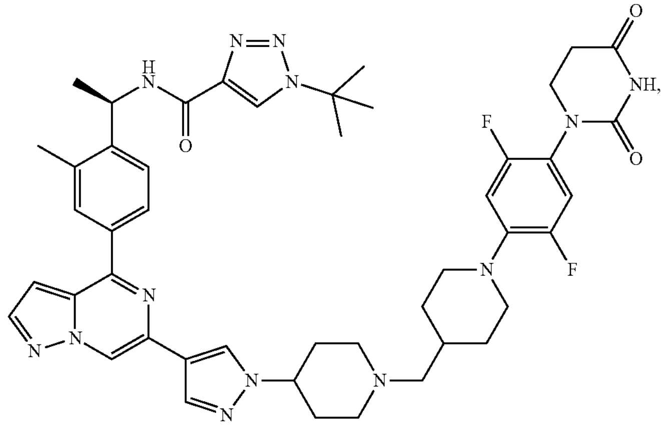
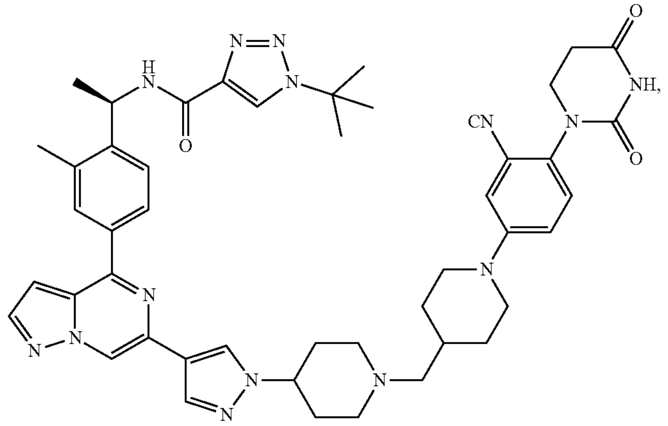
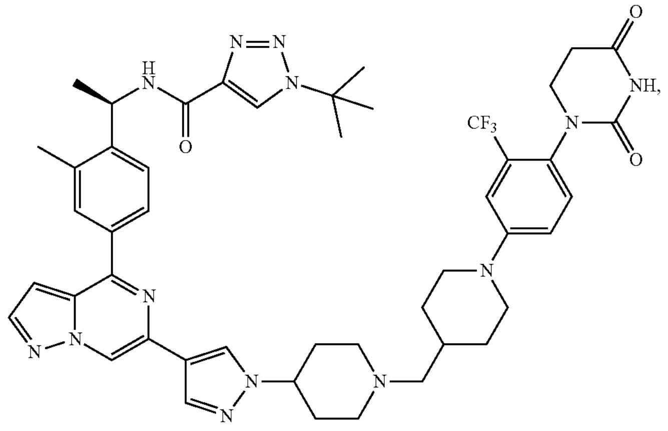

-continued
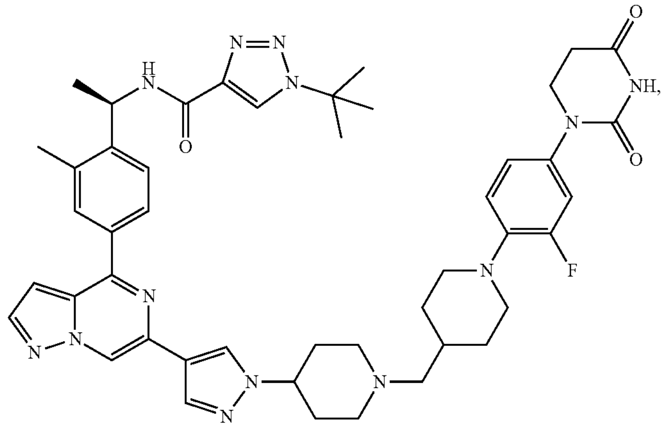
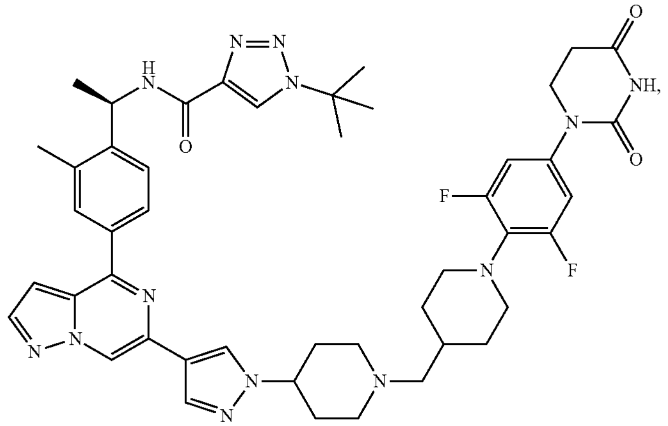
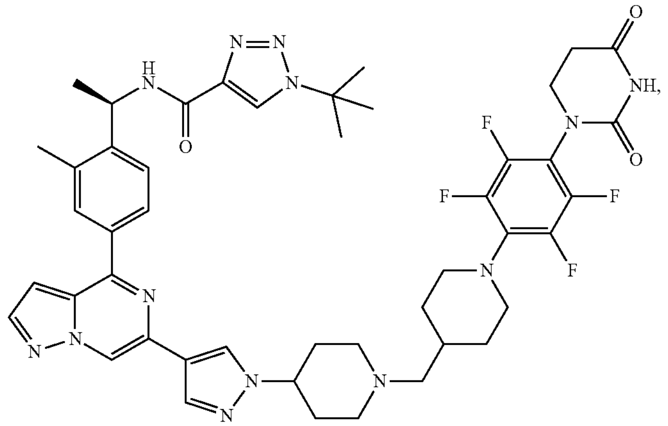
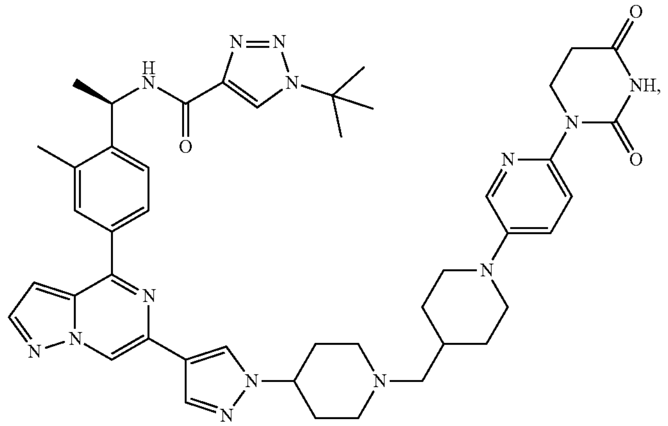 [SMILES: Cc1cc(-c2nc(-c3cnn(C4CCN(CC5CCN(c6ccc(N7CCC(=O)NC7=O)cn6)CC5)CC4)c3)cn3nccc23)ccc1[C@@H](C)NC(=O)c1cn(C(C)(C)C)nn1]

-continued
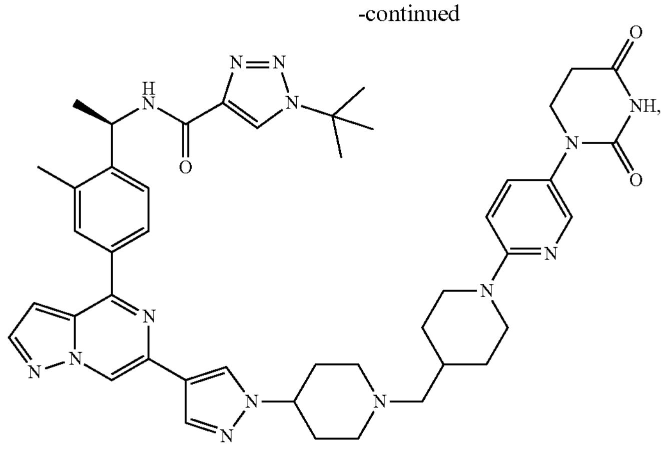
and pharmaceutically acceptable salts and solvates thereof.
2. The compound of claim 1, wherein the compound is
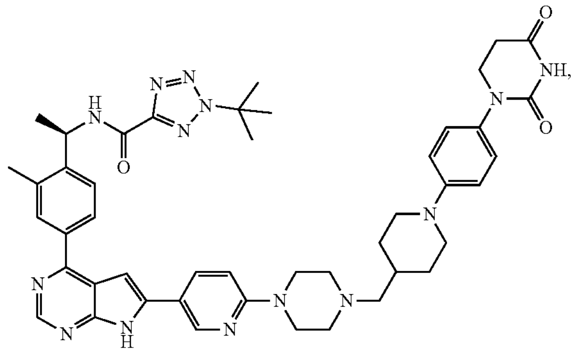 [SMILES: Cc1cc(-c2ncnc3[nH]c(-c4ccc(N5CCN(CC6CCN(c7ccc(N8CCC(=O)NC8=O)cc7)CC6)CC5)nc4)cc23)ccc1[C@@H](C)NC(=O)c1nnn(C(C)(C)C)n1]
or a pharmaceutically acceptable salt or solvate thereof.
3. The compound of claim 1, wherein the compound is
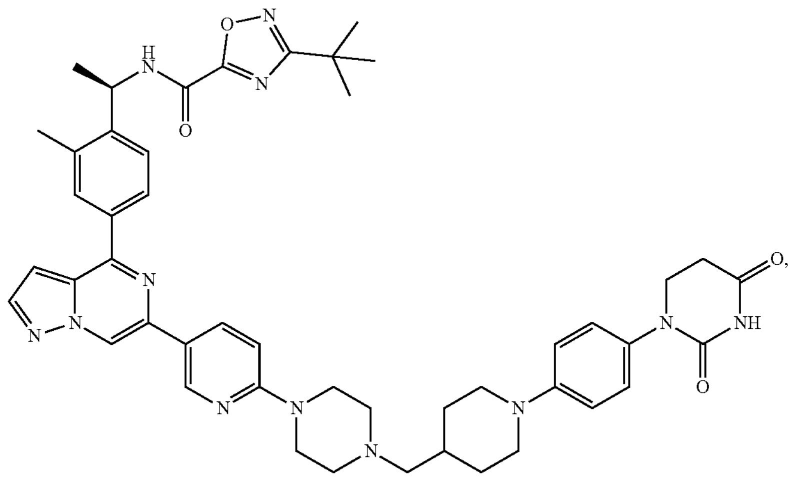 [SMILES: Cc1cc(-c2nc(-c3ccc(N4CCN(CC5CCN(c6ccc(N7CCC(=O)NC7=O)cc6)CC5)CC4)nc3)cn3nccc23)ccc1[C@@H](C)NC(=O)c1nc(C(C)(C)C)no1]
or a pharmaceutically acceptable salt or solvate thereof.

4. The compound of claim 1, wherein the compound is
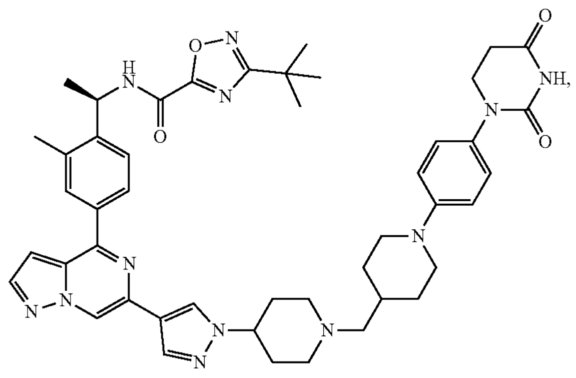 [SMILES: Cc1cc(-c2nc(-c3cnn(C4CCN(CC5CCN(c6ccc(N7CCC(=O)NC7=O)cc6)CC5)CC4)c3)cn3nccc23)ccc1[C@@H](C)NC(=O)c1nc(C(C)(C)C)no1]
or a pharmaceutically acceptable salt or solvate thereof.
5. The compound of claim 1, wherein the compound is
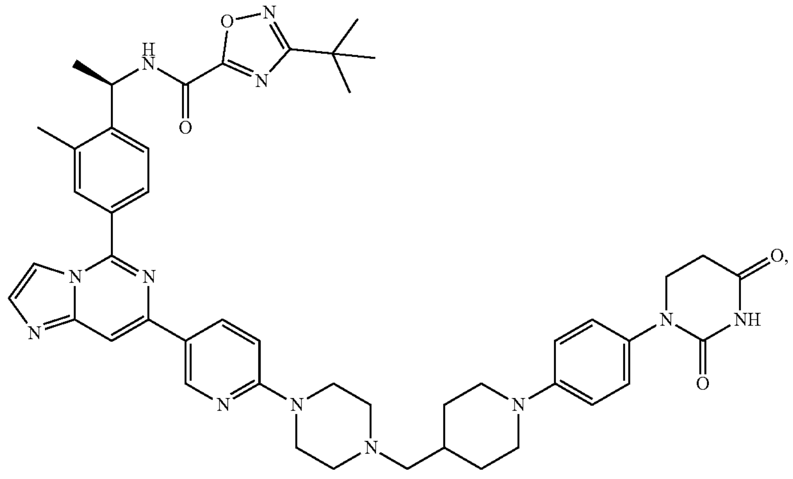 [SMILES: Cc1cc(-c2nc(-c3ccc(N4CCN(CC5CCN(c6ccc(N7CCC(=O)NC7=O)cc6)CC5)CC4)nc3)cc3nccn23)ccc1[C@@H](C)NC(=O)c1nc(C(C)(C)C)no1]
or a pharmaceutically acceptable salt or solvate thereof.
6. The compound of claim 1, wherein the compound is
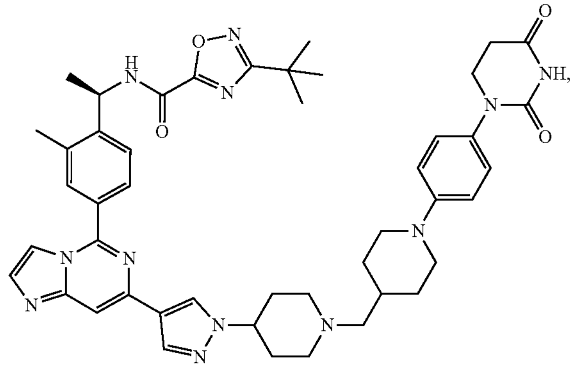 [SMILES: Cc1cc(-c2nc(-c3cnn(C4CCN(CC5CCN(c6ccc(N7CCC(=O)NC7=O)cc6)CC5)CC4)c3)cc3nccn23)ccc1[C@@H](C)NC(=O)c1nc(C(C)(C)C)no1]
or a pharmaceutically acceptable salt or solvate thereof.

7. The compound of claim 1, wherein the compound is

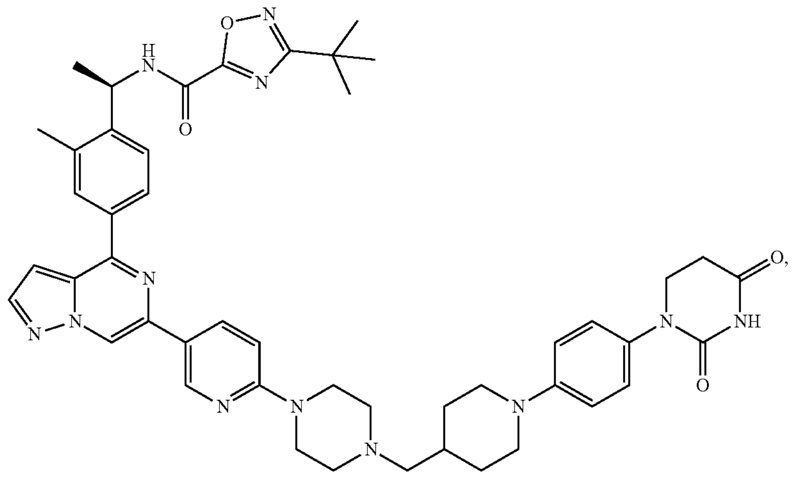 [SMILES: Cc1cc(-c2nc(-c3ccc(N4CCN(CC5CCN(c6ccc(N7CCC(=O)NC7=O)cc6)CC5)CC4)nc3)cn3nccc23)ccc1[C@@H](C)NC(=O)c1nc(C(C)(C)C)no1]

or a pharmaceutically acceptable salt or solvate thereof.

8. The compound of claim 1, wherein the compound is

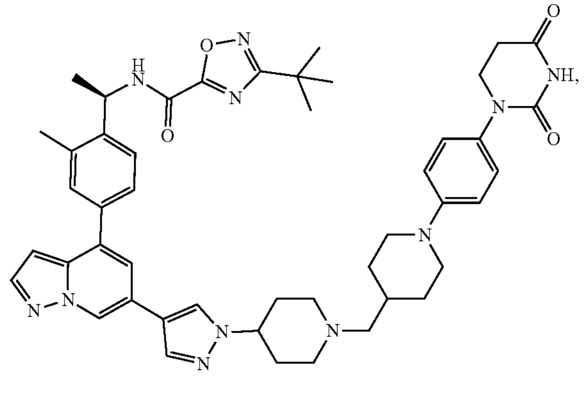 [SMILES: Cc1cc(-c2cc(-c3cnn(C4CCN(CC5CCN(c6ccc(N7CCC(=O)NC7=O)cc6)CC5)CC4)c3)cn3nccc23)ccc1[C@@H](C)NC(=O)c1nc(C(C)(C)C)no1]

or a pharmaceutically acceptable salt or solvate thereof.

9. The compound of claim 1, wherein the compound is

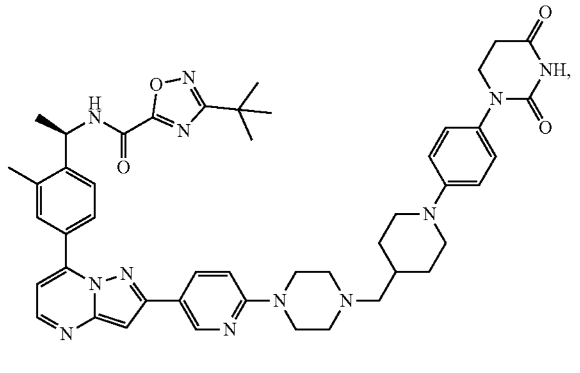 [SMILES: Cc1cc(-c2ccnc3cc(-c4ccc(N5CCN(CC6CCN(c7ccc(N8CCC(=O)NC8=O)cc7)CC6)CC5)nc4)nn23)ccc1[C@@H](C)NC(=O)c1nc(C(C)(C)C)no1]

or a pharmaceutically acceptable salt or solvate thereof.

10. The compound of claim 1, wherein the compound is

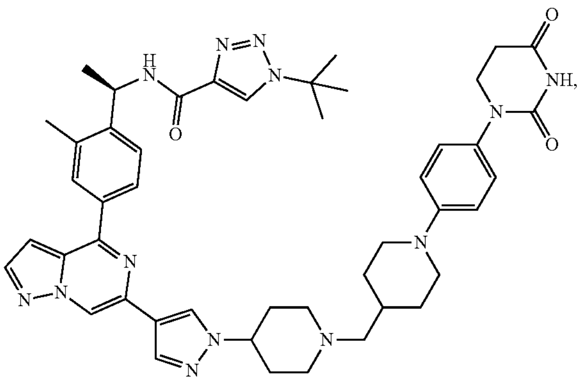 [SMILES: Cc1cc(-c2nc(-c3cnn(C4CCN(CC5CCN(c6ccc(N7CCC(=O)NC7=O)cc6)CC5)CC4)c3)cn3nccc23)ccc1[C@@H](C)NC(=O)c1cn(C(C)(C)C)nn1]

or a pharmaceutically acceptable salt or solvate thereof.

11. The compound of claim 1, wherein the compound is

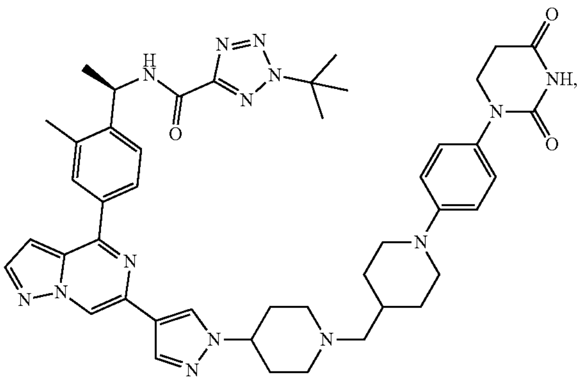 [SMILES: Cc1cc(-c2nc(-c3cnn(C4CCN(CC5CCN(c6ccc(N7CCC(=O)NC7=O)cc6)CC5)CC4)c3)cn3nccc23)ccc1[C@@H](C)NC(=O)c1nnn(C(C)(C)C)n1]

or a pharmaceutically acceptable salt or solvate thereof.

12. The compound of claim 1, wherein the compound is
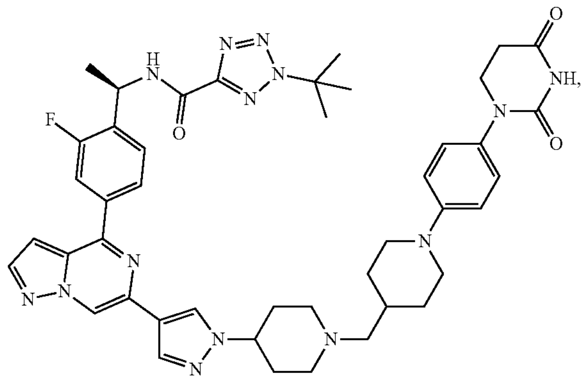 [SMILES: C[C@@H](NC(=O)c1nnn(C(C)(C)C)n1)c1ccc(-c2nc(-c3cnn(C4CCN(CC5CCN(c6ccc(N7CCC(=O)NC7=O)cc6)CC5)CC4)c3)cn3nccc23)cc1F]
or a pharmaceutically acceptable salt or solvate thereof.
13. The compound of claim 1, wherein the compound is
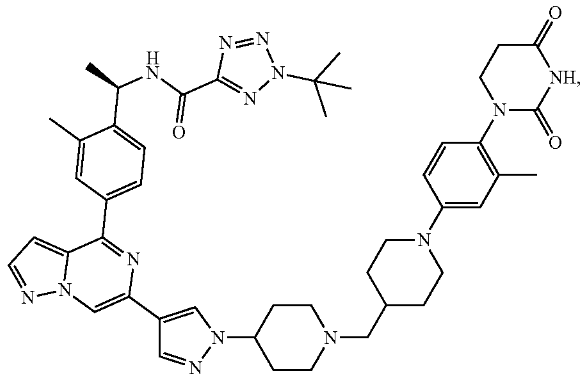 [SMILES: Cc1cc(-c2nc(-c3cnn(C4CCN(CC5CCN(c6ccc(N7CCC(=O)NC7=O)c(C)c6)CC5)CC4)c3)cn3nccc23)ccc1[C@@H](C)NC(=O)c1nnn(C(C)(C)C)n1]
or a pharmaceutically acceptable salt or solvate thereof.
14. The compound of claim 1, wherein the compound is
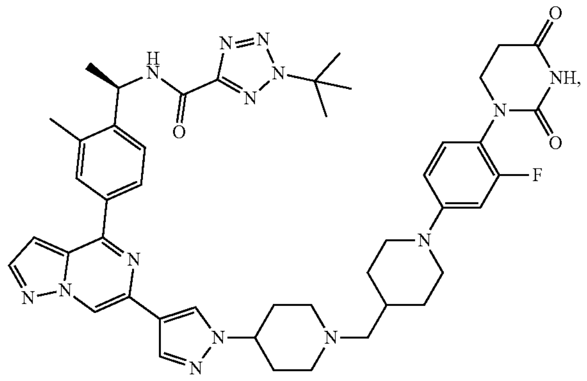 [SMILES: Cc1cc(-c2nc(-c3cnn(C4CCN(CC5CCN(c6ccc(N7CCC(=O)NC7=O)c(F)c6)CC5)CC4)c3)cn3nccc23)ccc1[C@@H](C)NC(=O)c1nnn(C(C)(C)C)n1]
or a pharmaceutically acceptable salt or solvate thereof.

15. The compound of claim 1, wherein the compound is
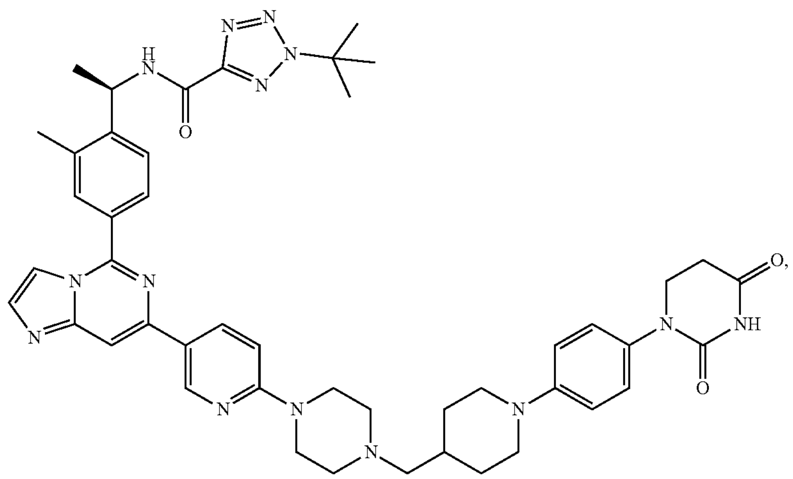 [SMILES: Cc1cc(-c2nc(-c3ccc(N4CCN(CC5CCN(c6ccc(N7CCC(=O)NC7=O)cc6)CC5)CC4)nc3)cc3nccn23)ccc1[C@@H](C)NC(=O)c1nnn(C(C)(C)C)n1]
or a pharmaceutically acceptable salt or solvate thereof.
16. The compound of claim 1, wherein the compound is
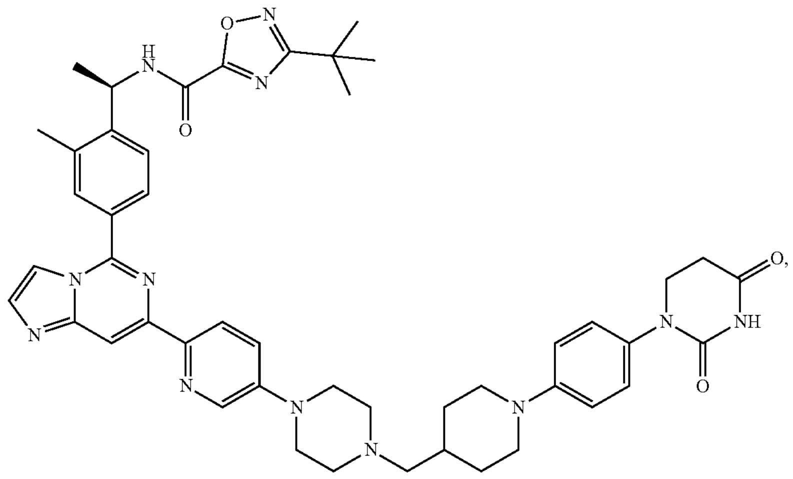 [SMILES: Cc1cc(-c2nc(-c3ccc(N4CCN(CC5CCN(c6ccc(N7CCC(=O)NC7=O)cc6)CC5)CC4)cn3)cc3nccn23)ccc1[C@@H](C)NC(=O)c1nc(C(C)(C)C)no1]
or a pharmaceutically acceptable salt or solvate thereof.

17. The compound of claim 1, wherein the compound is
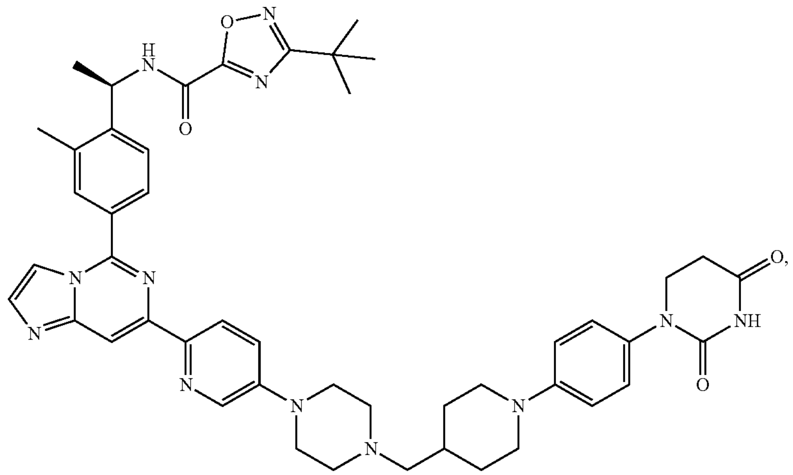 [SMILES: Cc1cc(-c2nc(-c3ccc(N4CCN(CC5CCN(c6ccc(N7CCC(=O)NC7=O)cc6)CC5)CC4)cn3)cc3nccn23)ccc1[C@@H](C)NC(=O)c1nc(C(C)(C)C)no1]
or a pharmaceutically acceptable salt or solvate thereof.
18. The compound of claim 1, wherein the compound is
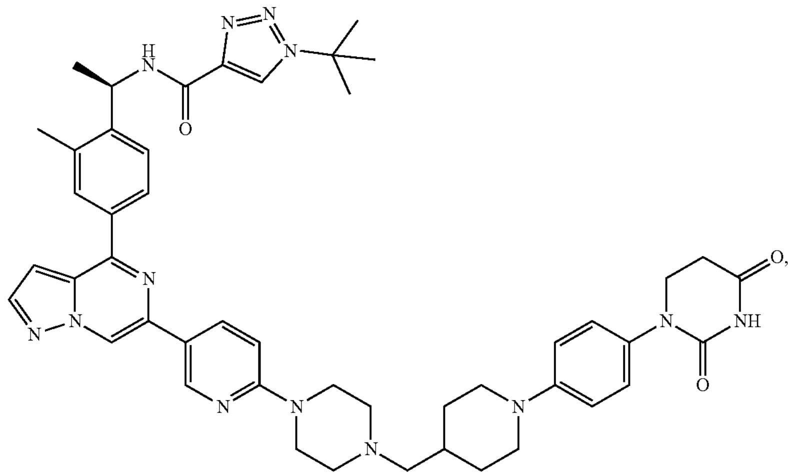
or a pharmaceutically acceptable salt or solvate thereof.

19. The compound of claim 1, wherein the compound is
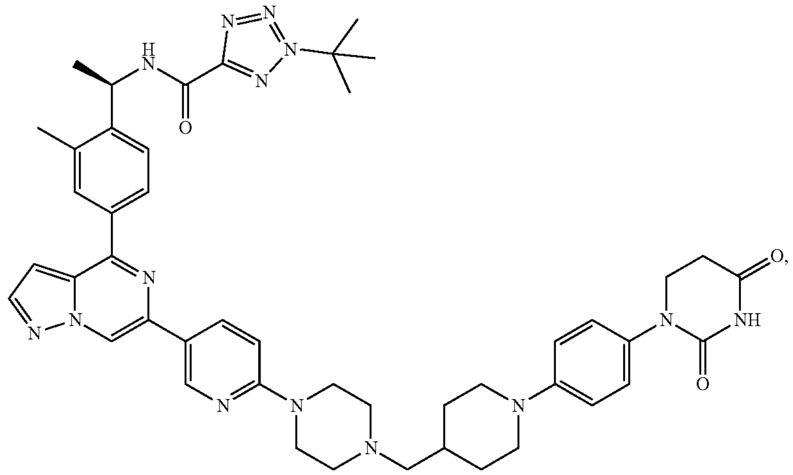
or a pharmaceutically acceptable salt or solvate thereof.
20. The compound of claim 1, wherein the compound is
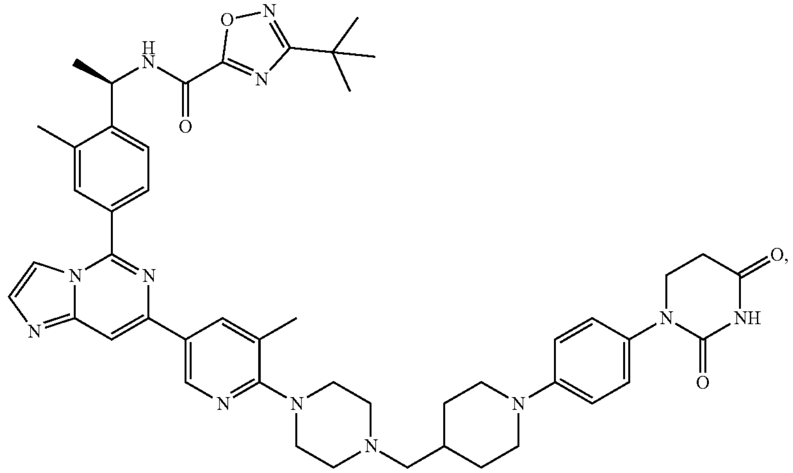 [SMILES: Cc1cc(-c2nc(-c3cnc(N4CCN(CC5CCN(c6ccc(N7CCC(=O)NC7=O)cc6)CC5)CC4)c(C)c3)cc3nccn23)ccc1[C@@H](C)NC(=O)c1nc(C(C)(C)C)no1]
or a pharmaceutically acceptable salt or solvate thereof.

21. The compound of claim 1, wherein the compound is

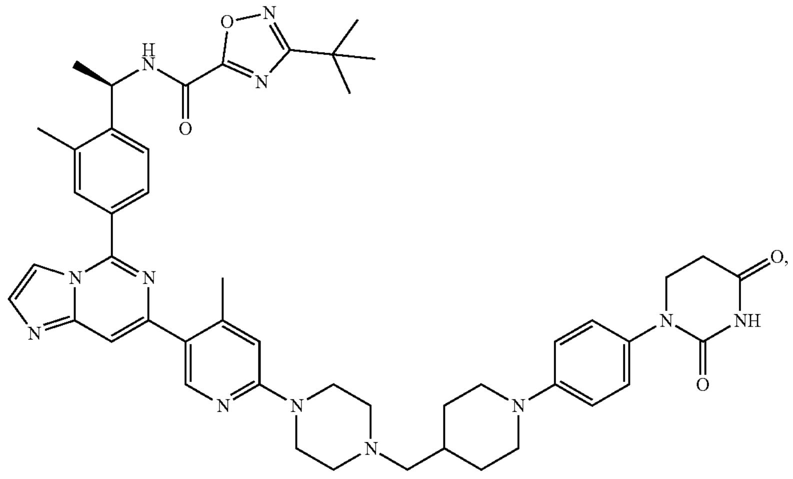 [SMILES: Cc1cc(N2CCN(CC3CCN(c4ccc(N5CCC(=O)NC5=O)cc4)CC3)CC2)ncc1-c1cc2nccn2c(-c2ccc([C@@H](C)NC(=O)c3nc(C(C)(C)C)no3)c(C)c2)n1]

or a pharmaceutically acceptable salt or solvate thereof.

22. The compound of claim 1, wherein the compound is

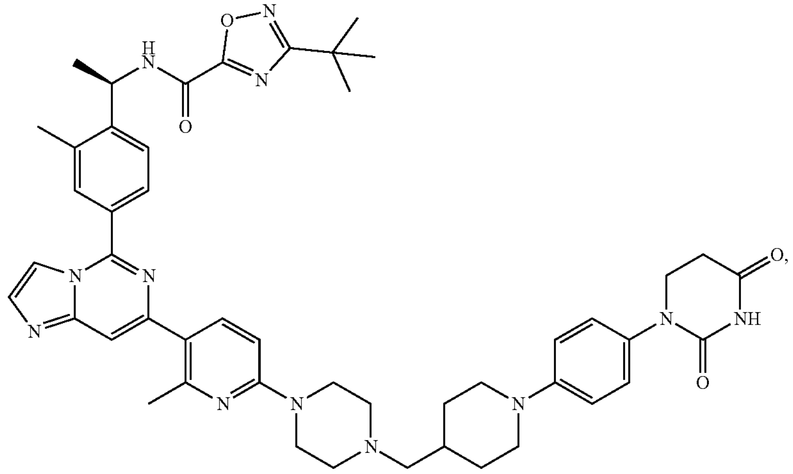 [SMILES: Cc1cc(-c2nc(-c3ccc(N4CCN(CC5CCN(c6ccc(N7CCC(=O)NC7=O)cc6)CC5)CC4)nc3C)cc3nccn23)ccc1[C@@H](C)NC(=O)c1nc(C(C)(C)C)no1]

or a pharmaceutically acceptable salt or solvate thereof.

23. The compound of claim 1, wherein the compound is

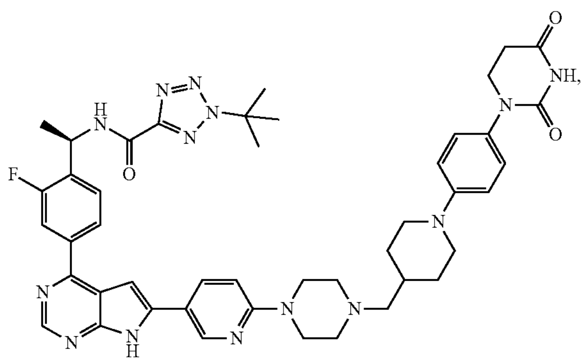 [SMILES: C[C@@H](NC(=O)c1nnn(C(C)(C)C)n1)c1ccc(-c2ncnc3[nH]c(-c4ccc(N5CCN(CC6CCN(c7ccc(N8CCC(=O)NC8=O)cc7)CC6)CC5)nc4)cc23)cc1F]

or a pharmaceutically acceptable salt or solvate thereof.

24. The compound of claim 1, wherein the compound is

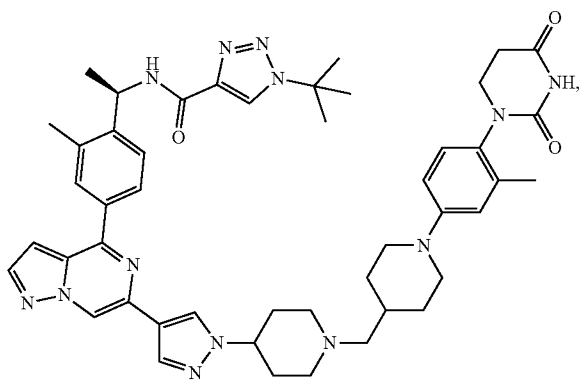 [SMILES: Cc1cc(-c2nc(-c3cnn(C4CCN(CC5CCN(c6ccc(N7CCC(=O)NC7=O)c(C)c6)CC5)CC4)c3)cn3nccc23)ccc1[C@@H](C)NC(=O)c1cn(C(C)(C)C)nn1]

or a pharmaceutically acceptable salt or solvate thereof.

25. A pharmaceutical composition comprising the compound of claim 1 and a pharmaceutically acceptable carrier.

26. A method for inhibiting and/or degrading BTK comprising administering to a patient in need thereof a therapeutically effective amount of a compound of the compound of claim 1.

* * * * *